US011884647B2

(12) United States Patent
Sun et al.

(10) Patent No.: US 11,884,647 B2
(45) Date of Patent: Jan. 30, 2024

(54) COMPOUNDS AND METHODS FOR TARGETING PATHOGENIC BLOOD VESSELS

(71) Applicants: THE REGENTS OF THE UNIVERSITY OF CALIFORNIA, Oakland, CA (US); ATENGEN, INC., Los Angeles, CA (US)

(72) Inventors: Hui Sun, Culver City, CA (US); Pu Sun, San Jose, CA (US); Guo Cheng, Los Angeles, CA (US); Adrian Chichuen Au, Los Angeles, CA (US); Ming Zhong, Nanjing (CN)

(73) Assignees: The Regents of the University of California, Oakland, CA (US); Atengen, Inc., Los Angeles, CA (US)

( * ) Notice: Subject to any disclaimer, the term of this patent is extended or adjusted under 35 U.S.C. 154(b) by 155 days.

(21) Appl. No.: 17/072,844

(22) Filed: Oct. 16, 2020

(65) Prior Publication Data
US 2021/0147385 A1 May 20, 2021

Related U.S. Application Data

(60) Provisional application No. 62/916,983, filed on Oct. 18, 2019.

(51) Int. Cl.
| | | |
|---|---|---|
| *C07D 401/14* | (2006.01) |
| *A61P 35/00* | (2006.01) |
| *C07D 215/42* | (2006.01) |
| *C07D 215/44* | (2006.01) |
| *C07D 215/46* | (2006.01) |
| *C07D 401/04* | (2006.01) |
| *C07D 401/12* | (2006.01) |
| *C07D 405/12* | (2006.01) |
| *C07D 405/14* | (2006.01) |
| *C07D 409/12* | (2006.01) |
| *C07D 417/12* | (2006.01) |
| *C07D 487/08* | (2006.01) |
| *C07D 491/113* | (2006.01) |
| *C07D 498/04* | (2006.01) |
| *C07H 15/26* | (2006.01) |

(52) U.S. Cl.
CPC .......... *C07D 401/14* (2013.01); *A61P 35/00* (2018.01); *C07D 215/42* (2013.01); *C07D 215/44* (2013.01); *C07D 215/46* (2013.01); *C07D 401/04* (2013.01); *C07D 401/12* (2013.01); *C07D 405/12* (2013.01); *C07D 405/14* (2013.01); *C07D 409/12* (2013.01); *C07D 417/12* (2013.01); *C07D 487/08* (2013.01); *C07D 491/113* (2013.01); *C07D 498/04* (2013.01); *C07H 15/26* (2013.01)

(58) Field of Classification Search
CPC ..... A61P 35/00; C07D 215/42; C07D 215/44; C07D 401/04
See application file for complete search history.

(56) References Cited

U.S. PATENT DOCUMENTS

| | | |
|---|---|---|
| 5,342,444 A | 8/1994 | Harnisch et al. |
| 5,374,514 A | 12/1994 | Kirk et al. |
| 5,380,713 A | 1/1995 | Balasubramanian et al. |
| 5,565,408 A | 10/1996 | Hagen et al. |
| 5,576,338 A | 11/1996 | Friesen et al. |
| 5,624,937 A | 4/1997 | Reel et al. |
| 5,939,248 A | 8/1999 | Kirk et al. |
| 6,258,822 B1 | 7/2001 | Geyer et al. |
| 6,262,074 B1 | 7/2001 | Otten et al. |
| 6,284,796 B1 | 9/2001 | Geyer et al. |
| 6,479,436 B1 | 11/2002 | Otten et al. |
| 6,504,031 B1 | 1/2003 | Bruncko et al. |
| 6,576,644 B2 | 6/2003 | Bi et al. |
| 6,583,156 B1 | 6/2003 | Gillespie et al. |
| 6,602,882 B1 | 8/2003 | Davies et al. |
| 6,639,121 B1 | 10/2003 | DePinho et al. |
| 6,803,369 B1 | 10/2004 | Erskine et al. |
| 6,927,214 B1 | 8/2005 | Teng et al. |
| 6,962,917 B2 | 11/2005 | Davies et al. |
| 7,141,564 B2 | 11/2006 | Brooks et al. |

(Continued)

FOREIGN PATENT DOCUMENTS

| | | |
|---|---|---|
| EP | 102008010661 | 9/2009 |
| EP | 2401915 | 1/2012 |

(Continued)

OTHER PUBLICATIONS

Au, Adrian, "Activation Mechanism and Novel Therapeutic Agent of a Membrane Receptor Involved in Pathogenic Angiogenesis", *ProQuest Dissertations Publishing*, 2020.
Bagley et al., "Tumor endothelial marker 7 (TEM-7): a novel target for antiangiogenic therapy", *Microvasc Res.*, 82(3):25-262, 2011.
Beaty et al., "PLXDC1 (TEM7) is identified in a genome-wide expression screen of glioblastoma endothelium." *J Neurooncol.*, 81(3):241-248, 2007.
Cheng et al., "Identification of PLXDC1 and PLXDC2 as the transmembrane receptors for the multifunctional factor PEDF", *eLife*,3:e05401, 2014.
Forest et al., "Optimization of immunostaining on flat-mounted human corneas." *Mol Vis.*, 21:1345-1356, 2015.

(Continued)

*Primary Examiner* — Pancham Bakshi
(74) *Attorney, Agent, or Firm* — Norton Rose Fulbright US LLP

(57) ABSTRACT

The disclosure provides compounds, and compositions, including pharmaceutical compositions, kits that include the compounds, and methods of using (or administering) and making the compounds. The disclosure further provides compounds or compositions thereof for use in a method of modulating PLXDC1 (TEM7) and/or PLXDC2 or killing pathogenic blood vessels. The disclosure further provides compounds or compositions thereof for use in a method of treating a disease, disorder, or condition that is mediated, at least in part, by PEDF receptors or by angiogenesis.

29 Claims, 11 Drawing Sheets

(56) References Cited

U.S. PATENT DOCUMENTS

| | | | |
|---|---|---|---|
| 7,186,730 B2 | 3/2007 | Dartois et al. |
| 7,205,408 B2 | 4/2007 | Davies et al. |
| 7,232,832 B2 | 6/2007 | Axten et al. |
| 7,511,157 B2 | 3/2009 | Bailey et al. |
| 7,576,215 B2 | 8/2009 | Collini et al. |
| 7,592,334 B2 | 9/2009 | Miller et al. |
| 7,605,169 B2 | 10/2009 | Miller et al. |
| 7,648,984 B2 | 1/2010 | Miller et al. |
| 7,692,017 B2 | 4/2010 | Dinsmore et al. |
| 7,705,043 B2 | 4/2010 | Alonso-Alija et al. |
| 7,732,613 B2 | 6/2010 | Kim |
| 7,776,910 B2 | 8/2010 | Lopez-Tapia et al. |
| 7,928,111 B2 | 4/2011 | Tachdjian et al. |
| 7,973,164 B2 | 7/2011 | Jung et al. |
| 7,977,354 B2 | 7/2011 | Marsais et al. |
| 8,008,306 B2 | 8/2011 | Koura et al. |
| 8,063,220 B2 | 11/2011 | Galambos et al. |
| 8,222,297 B2 | 7/2012 | Su et al. |
| 8,278,342 B2 | 10/2012 | Ricciardi |
| 8,623,877 B2 | 1/2014 | Gao et al. |
| 8,642,660 B2 | 2/2014 | Goldfarb |
| 8,772,200 B2 | 7/2014 | Shibayama et al. |
| 8,829,002 B2 | 9/2014 | Ivachtchenko et al. |
| 8,975,259 B2 | 3/2015 | Smrcka et al. |
| 9,000,054 B2 | 4/2015 | Tachdjian et al. |
| 9,127,000 B2 | 9/2015 | Ren et al. |
| 9,573,950 B2 | 2/2017 | Backfisch et al. |
| 9,586,964 B2 | 3/2017 | Lindsley et al. |
| 9,595,683 B2 | 3/2017 | Choi et al. |
| 9,688,635 B2 | 6/2017 | Qian et al. |
| 10,093,628 B2 | 10/2018 | Knape et al. |
| 10,227,350 B2 | 3/2019 | Chandrasekhar et al. |
| 10,244,779 B2 | 4/2019 | Tachdjian et al. |
| 2002/0177121 A1 | 11/2002 | Woltering et al. |
| 2003/0212084 A1 | 11/2003 | Hatton et al. |
| 2004/0053928 A1 | 3/2004 | Davies et al. |
| 2004/0077655 A1 | 4/2004 | Dartois et al. |
| 2004/0077656 A1 | 4/2004 | Markwell et al. |
| 2004/0198756 A1 | 10/2004 | Davies et al. |
| 2005/0261298 A1 | 11/2005 | Solow-Cordero et al. |
| 2006/0040925 A1 | 2/2006 | Davies et al. |
| 2006/0111368 A1 | 5/2006 | Osakada et al. |
| 2006/0189601 A1 | 8/2006 | Hennessy et al. |
| 2007/0254872 A1 | 11/2007 | Miller et al. |
| 2008/0194547 A1 | 8/2008 | Miller et al. |
| 2009/0036485 A1 | 2/2009 | Jung |
| 2009/0042910 A1 | 2/2009 | Jung et al. |
| 2009/0076075 A1 | 3/2009 | Jung et al. |
| 2009/0270371 A1 | 10/2009 | Keseru et al. |
| 2009/0275611 A1 | 11/2009 | Riether et al. |
| 2010/0113513 A1 | 5/2010 | Murphy Kessabi et al. |
| 2010/0255528 A1 | 10/2010 | Zudaire et al. |
| 2011/0065891 A1 | 3/2011 | Fang et al. |
| 2011/0230476 A1 | 9/2011 | Niu et al. |
| 2011/0275643 A1 | 11/2011 | Liou et al. |
| 2012/0071505 A1 | 3/2012 | Gaddam et al. |
| 2013/0079342 A1 | 3/2013 | Dransfield et al. |
| 2013/0090323 A1 | 4/2013 | Dransfield et al. |
| 2013/0274215 A1 | 10/2013 | Thies et al. |
| 2013/0344165 A1 | 12/2013 | Boden et al. |
| 2014/0182680 A1 | 7/2014 | Kawata et al. |
| 2015/0259326 A1 | 9/2015 | Kesari et al. |
| 2016/0155575 A1 | 6/2016 | Yamato et al. |
| 2017/0007610 A1 | 1/2017 | Desai et al. |
| 2017/0174653 A1 | 6/2017 | Sherer et al. |
| 2017/0260278 A1 | 9/2017 | Youngro et al. |
| 2017/0281611 A1 | 10/2017 | Dahl |
| 2018/0086719 A1 | 3/2018 | Chandrasekhar et al. |
| 2018/0179199 A1 | 6/2018 | Dreas et al. |
| 2018/0244995 A1 | 8/2018 | Xia et al. |
| 2019/0010136 A1 | 1/2019 | Danjo et al. |
| 2021/0147385 A1 | 5/2021 | Sun et al. |
| 2021/0147525 A1 | 5/2021 | Sun et al. |

FOREIGN PATENT DOCUMENTS

| | | | |
|---|---|---|---|
| EP | 2402338 | 1/2012 | |
| EP | 102516232 | 6/2012 | |
| GB | 2208862 | 4/1989 | |
| JP | 02262627 | 10/1990 | |
| JP | 05039272 | 2/1993 | |
| JP | 08157461 | 6/1996 | |
| JP | 2005126549 | 5/2005 | |
| JP | 2016153479 | 8/2016 | |
| JP | 2016162983 | 9/2016 | |
| KR | 2011 0136147 A | 12/2011 | |
| KR | 101 748 707 B1 | 6/2017 | |
| WO | WO 95/11592 | 5/1995 | |
| WO | WO 1995/023968 | 9/1995 | |
| WO | WO 98/05652 | 2/1998 | |
| WO | WO 98/12192 | 3/1998 | |
| WO | WO 99/05096 | 2/1999 | |
| WO | WO 2002/042267 | 5/2002 | |
| WO | WO 2006/008644 | 1/2006 | |
| WO | WO 2007/072093 | 6/2007 | |
| WO | WO 2007072093 A1 * | 6/2007 | ......... A61K 37/4706 |
| WO | WO 2007/138112 | 12/2007 | |
| WO | WO 2008/010061 | 1/2008 | |
| WO | WO 2008/049047 | 4/2008 | |
| WO | WO 2008/066691 | 6/2008 | |
| WO | WO 2009/019708 | 2/2009 | |
| WO | WO 2009/153589 | 12/2009 | |
| WO | 2011/143348 | 11/2011 | |
| WO | WO 2011/156557 | 12/2011 | |
| WO | WO 2013/020909 | 2/2013 | |
| WO | WO 2013/158928 | 10/2013 | |
| WO | WO 2017/020030 | 2/2017 | |
| WO | WO 2017/072283 | 5/2017 | |
| WO | WO 2017/189715 | 11/2017 | |
| WO | WO 2018/035138 | 2/2018 | |
| WO | WO 2018/068357 | 4/2018 | |
| WO | WO 2018/130184 | 7/2018 | |
| WO | WO 2018/200498 | 11/2018 | |
| WO | WO 2018/202712 | 11/2018 | |
| WO | WO 2019/037678 | 2/2019 | |
| WO | WO 2019/173482 | 9/2019 | |
| WO | WO 2021/076903 | 4/2021 | |
| WO | WO 2021/076915 | 4/2021 | |
| WO | WO 2021/076930 | 4/2021 | |

OTHER PUBLICATIONS

Galambos et al., "4-Aryl-3-arylsulfonyl-quinolines as negative allosteric modulators of metabotropic GluR5 receptors: From HTS hit to development candidate", *Bioorg Med Chem Lett.*, 26(4): 1249-1252, 2016.

Galambos et al., "Discovery and Preclinical Characterization of 3-((4-(4-Chlorophenyl)-7-fluoroquinoline-3-yl)sulfonyl)benzonitrile, a Novel Non-acetylenic Metabotropic Glutamate Receptor 5 (mGluR5) Negative Allosteric Modulator for Psychiatric Indications", *Journal of Medicinal Chemistry*, 60:2470-2484, 2017.

Galambos et al., "Discovery of 4-amino-3-arylsulfoquinolines, a novel non-acetylenic chemotype of metabotropic glutamate 5(mGlu$_5$) receptor negative allosteric modulators", *European Journal of Medicinal Chemistry*, 113(17):240-254, 2017.

Howat et al., "Tissue fixation and the effect of molecular fixatives on downstream staining procedures." *Methods.*, 70(1):12-19, 2014.

International Search Report and Written Opinion issued in International Application No. PCT/US2020/055979, dated Dec. 22, 2020.

International Search Report and Written Opinion issued in International Application No. PCT/US2020/056003, dated Feb. 17, 2021.

International Search Report and Written Opinion issued in International Application No. PCT/US2020/056020, dated Feb. 4, 2021.

International Search Report and Written Opinion issued in International Application No. PCT/US2020/056039, dated Mar. 26, 2021.

Invitation to Pay Fees issued in corresponding International application No. PCT/US2020/056003, dated Dec. 17, 2020.

Ivachtchenko et al., "5-HT6 Receptor antagonists. I. Screening of the library of various heterocyclic compounds containing an alkysulfonyl moiety", *Pharmaceutical Chemistry Journal*, 46(1): 274-284, 2012.

(56) References Cited

OTHER PUBLICATIONS

Ivachtchenko et al., "Antagonists of Serotonin 5-HT6 Receptors. VI. Substituted 3-(Phenylsulfonyl)Quinolines, Synthesis and Structure-Activity Relationships", *Pharmaceutical Chemistry Journal*, 48(10): 646-660, 2015.

Kang et al., "One-pot Synthesis of Highly Functionalizable 3-(Phenylsulfonyl)-2,3-dihydro-4(1 H)quinolinones via a Cu-catalyzed Aza-Michael Addition/Cyclization Reaction", *Chem. Lett.*, 45:1356-1358, 2016.

Lee et al., "Identification of the basement membrane protein nidogen as a candidate ligand for tumor endothelial marker 7 in vitro and in vivo." *FEBS Lett.*, 580(9):2253-2257, 2006.

Li et al., "Copper-Catalyzed Electrophilic Cyclization of N-Propargylamines with Sodium Sulfinate for the synthesis of 3-Sulfonated Quinolines", *Chem Asian J.*, 14(23):4358-4364, 2019.

Nowak-Sliwinska et al., "Consensus guidelines for the use and interpretation of angiogenesis assays", *Angiogenesis*, 21(3):425-532, 2018.

Shao et al., "Choroid sprouting assay: an ex vivo model of microvascular angiogenesis", *PLoS One.*, 8(7):369552, 2013.

Smusz et al., "Fingerprint-based consensus virtual screening towards structurally new 5-HT(6)R ligands", *Bioorg Med Chem Lett.*, 25(9):1827-1830, 2015.

Sun et al., "Visible-light-induced multicomponent cascase cycloaddition involving N-Propargyl aromatic amines, diaryliodonium salts and sulfur dioxide: rapid access to 3-arylsulfonylquinolines", *Chemical Communications*, 54(11):1335-1338, 2018.

Yamaji et al., "TEM7 (PLXDC1) in neovascular endothelial cells of fibrovascular membranes from patients with proliferative diabetic retinopathy", *Invest Ophthalmol Vis Sci.*, 49(7):3151-3157, 2008.

Yang et al., "An iron delivery pathway mediated by a lipocalin." *Mol Cell.*, 10(5):1045-1056, 2002.

Yang et al., "Discovery of Orally Bioavailable Quinoline-Based Aldehyde Dehydrogenase 1A1 (ALDH1A1) Inhibitors with Potent Cellular Activity", *Journal of Medicinal Chemistry*, 61:4883-4903, 2018.

Zhang et al., "Antiproliferative activities of the second-generation antipsychotic drug sertindole against breast cancers with a potential application for treatment of breast-to-brain metastases", *Sci Rep.*, 8(1):15753, 2018.

Zhang et al., "tert-Butyl Hydroperoxide Mediated Cascade Synthesis of 3-Arylsulfonylquinolines", *Org Lett.*, 18(6):1286-1289, 2016.

Jiang, et al. "A novel peptide isolated from a phage display peptide library with trastuzumab can mimic antigen epitope of HER-2", *J. Biol. Chem*, 280, pp. 4656-5662, 2005.

Office Action issued in corresponding U.S. Appl. No. 17/072,952, dated Dec. 16, 2022.

Stancovski, et al. "Mechanistic aspects of the opposing effects of monoclonal antibodies to the ERBB2 receptor on tumor growth", *Proc. Natl. Acad. Sci.*, vol. 88, pp. 8691-8695, 1991.

\* cited by examiner

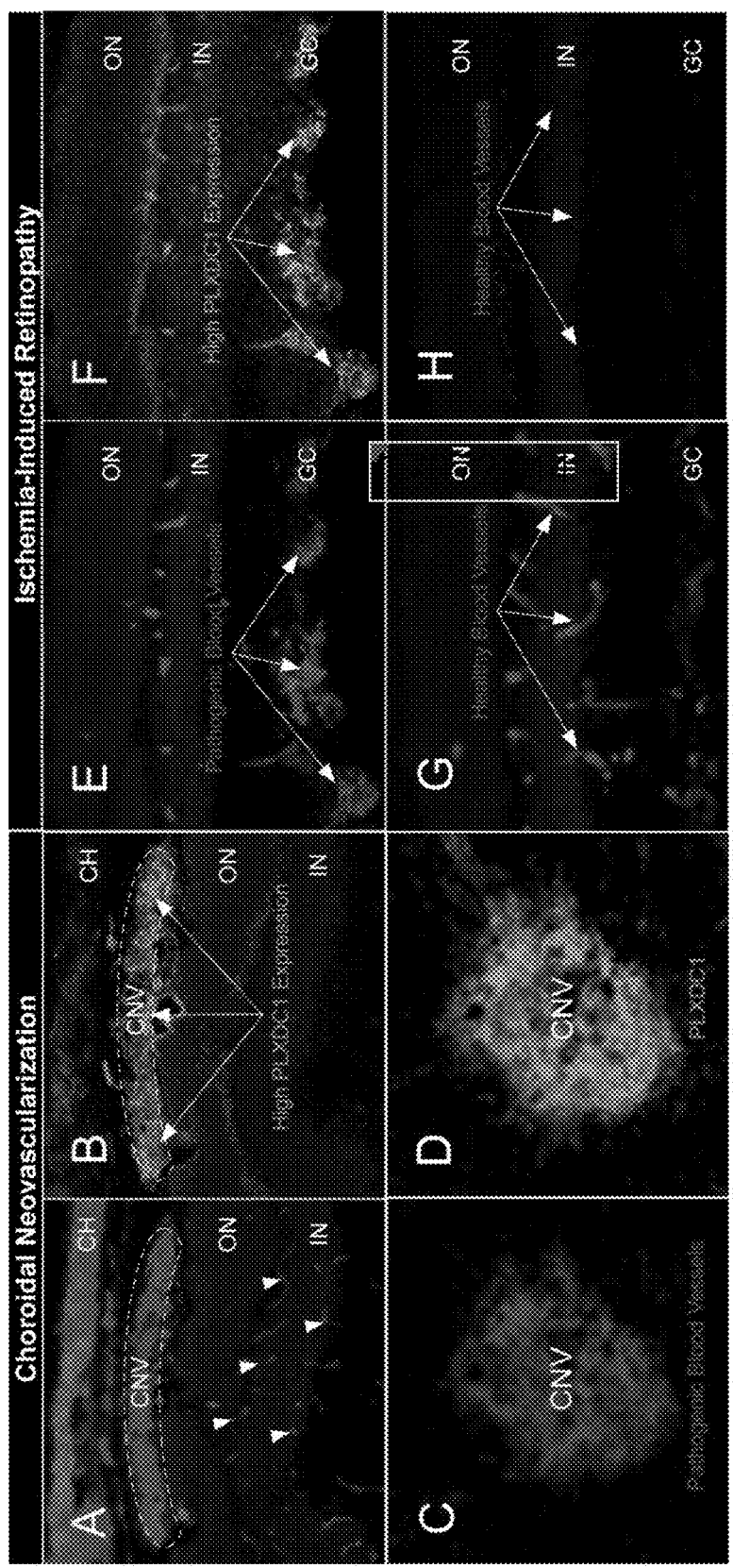
FIG. 1A-H

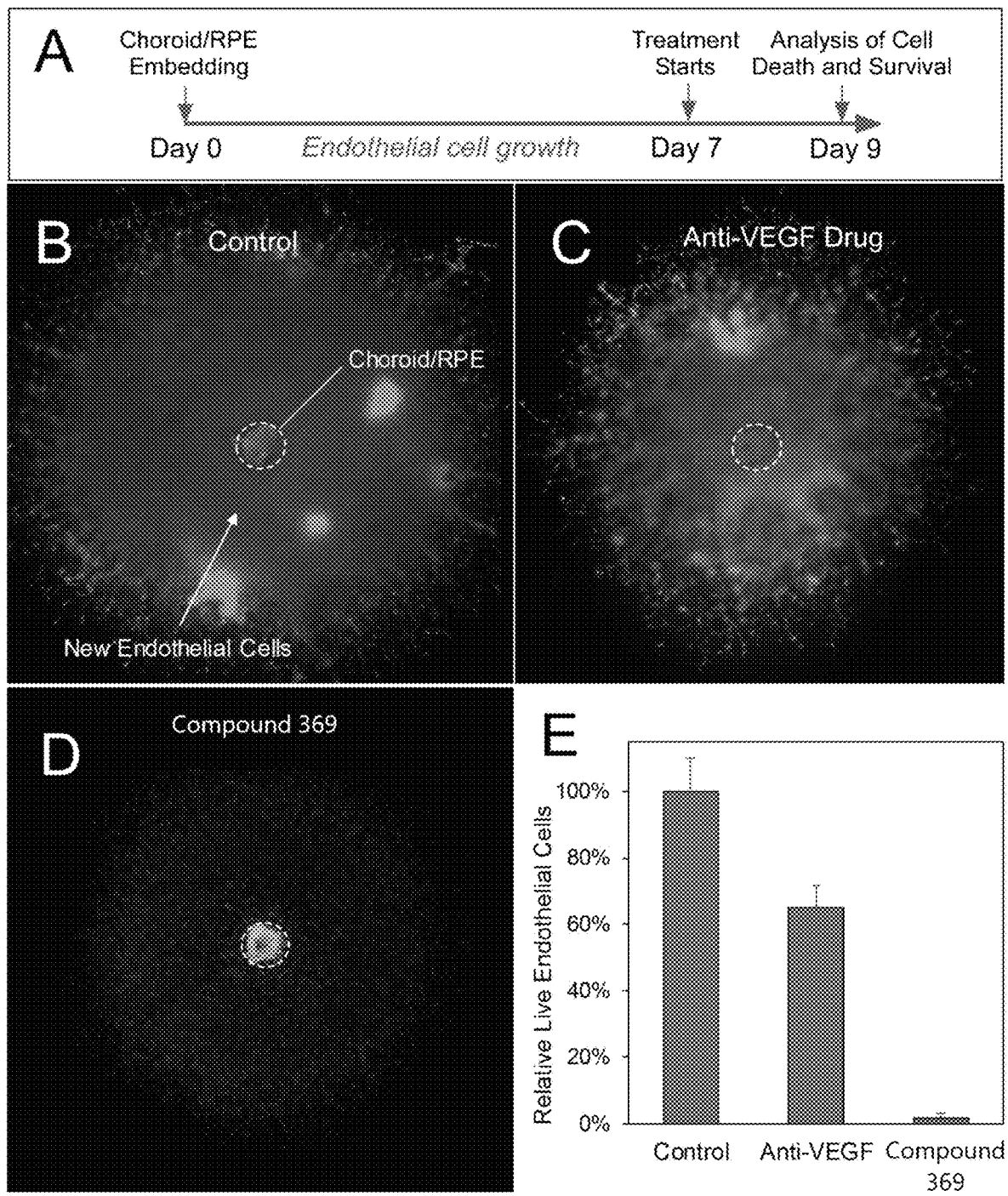
FIG. 2A-E

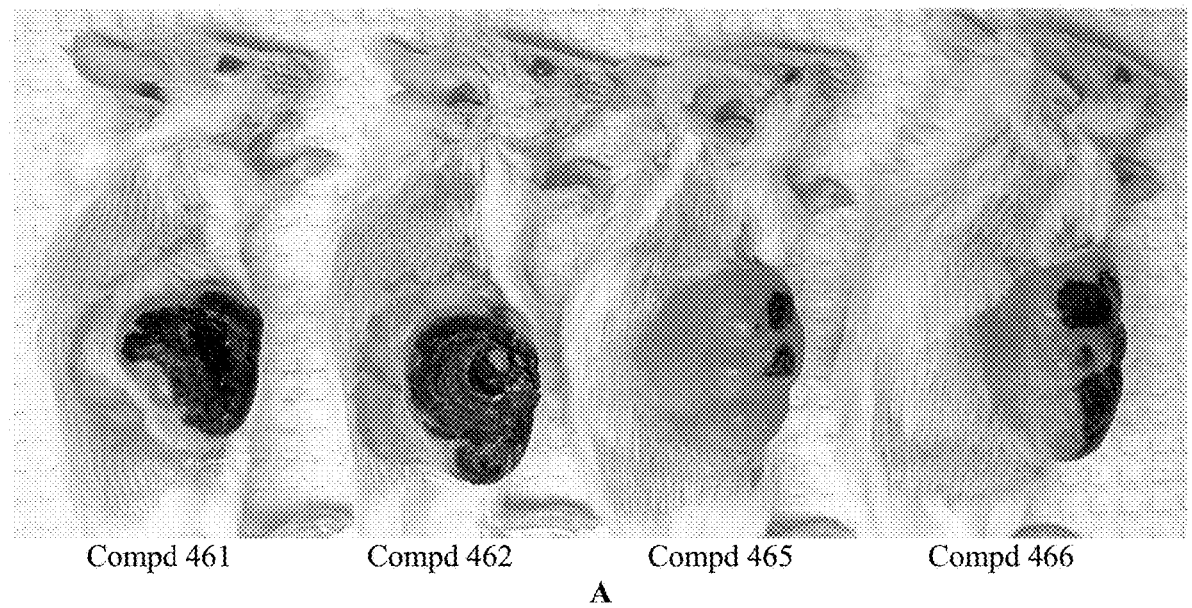
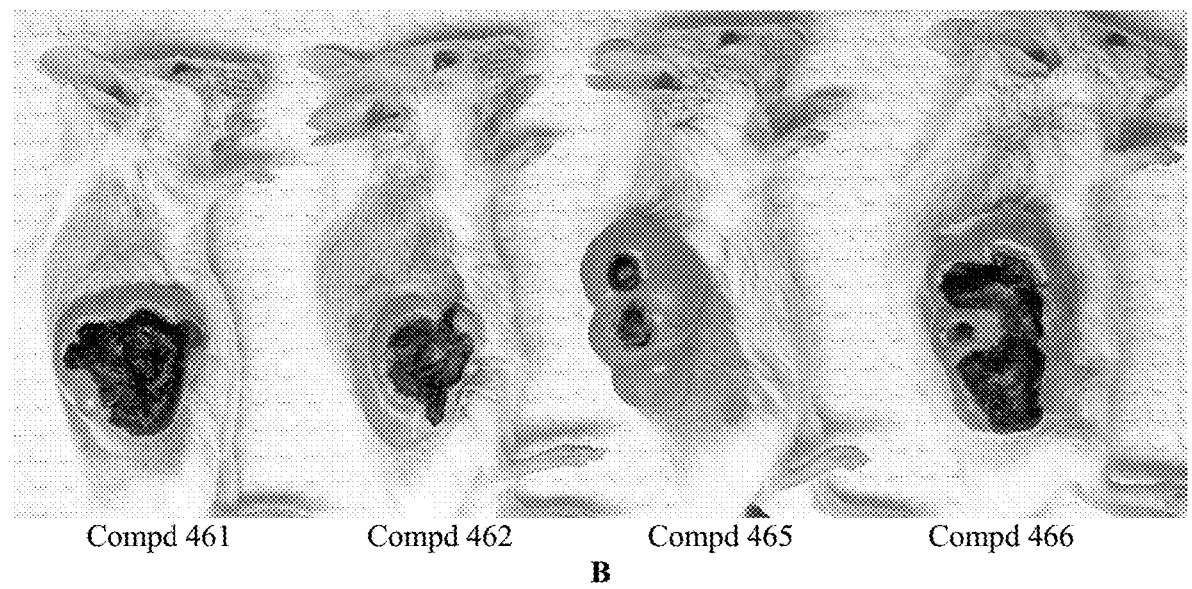
FIG. 3A-B

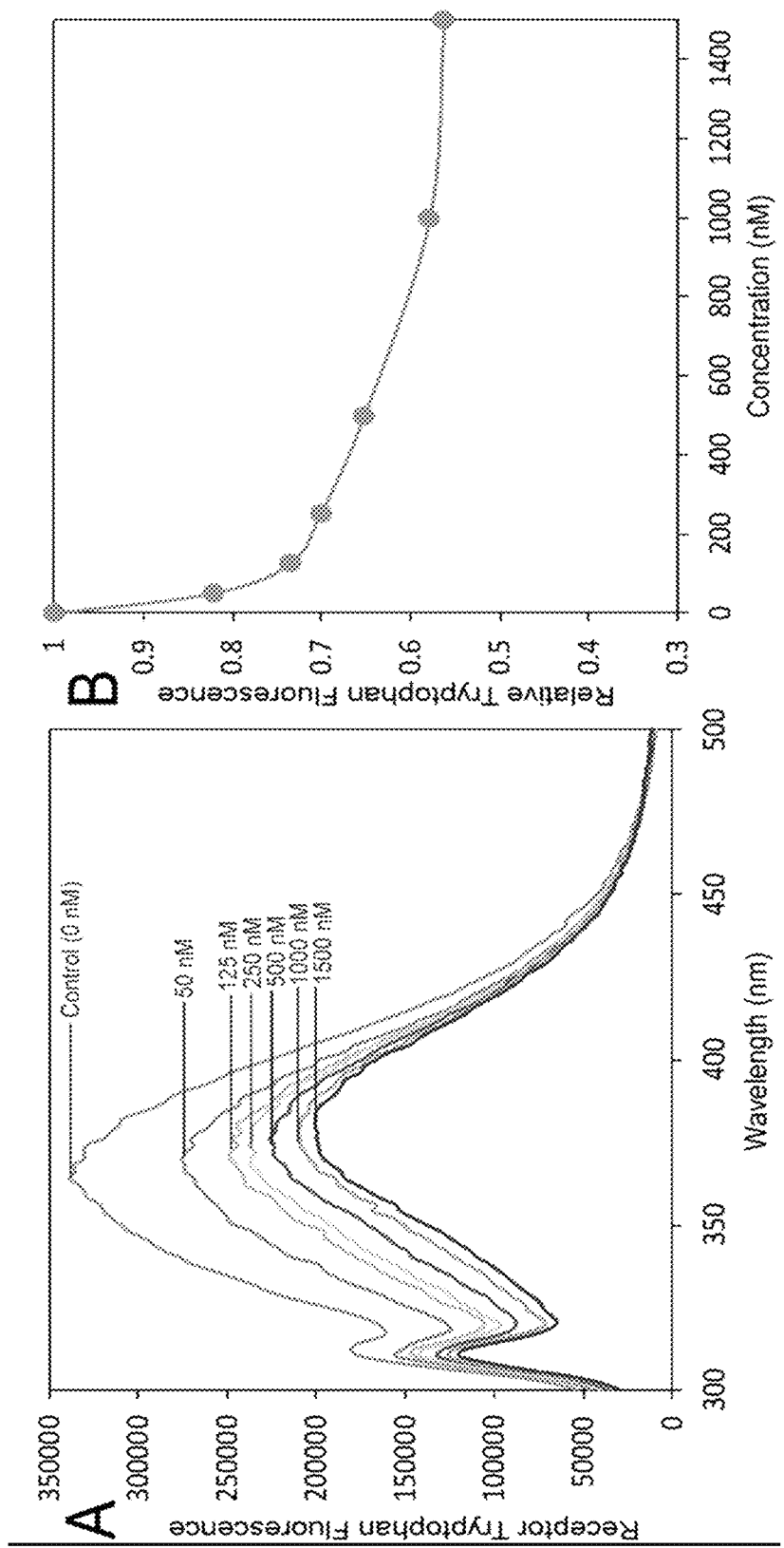
FIG. 4A-B

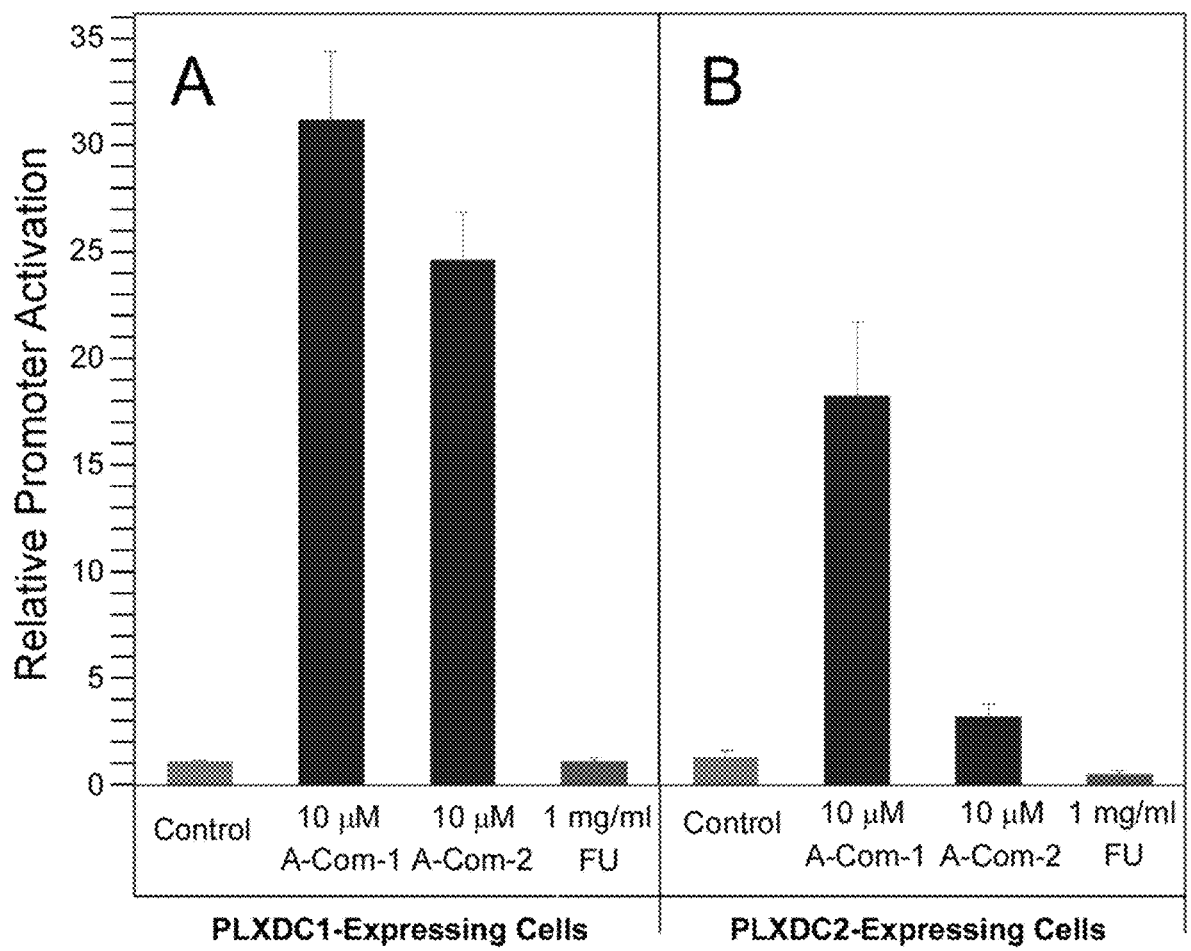
FIG. 5A-B

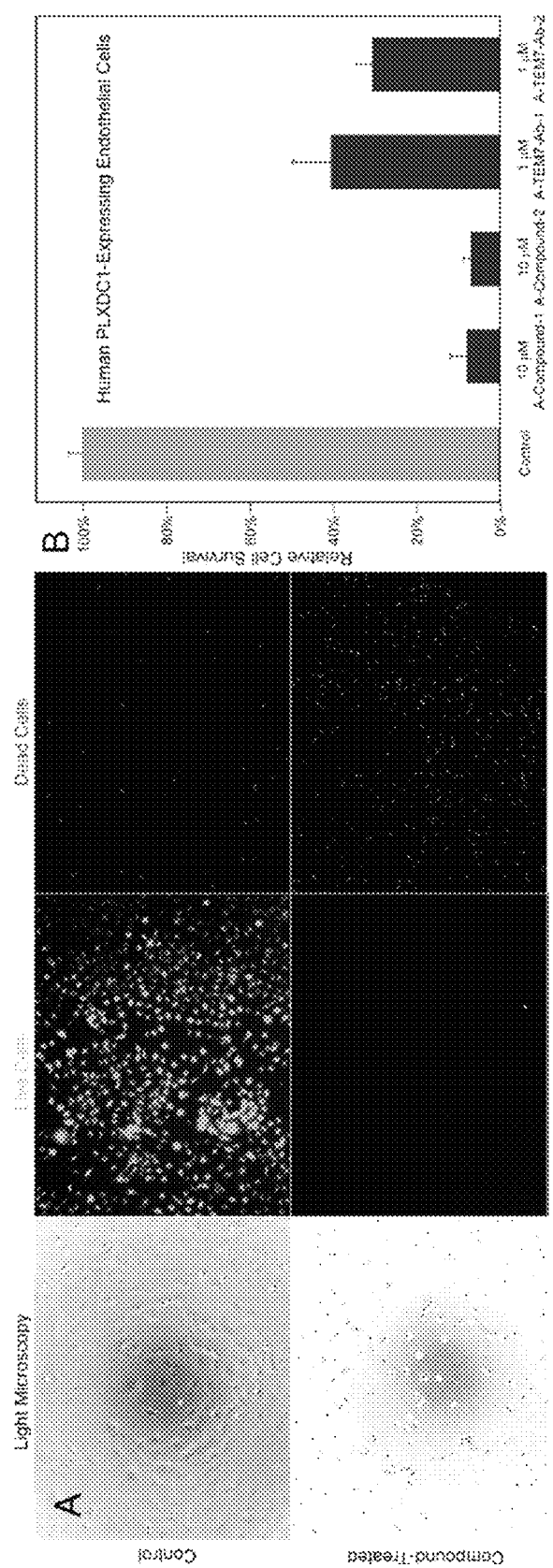
FIG. 6A-B

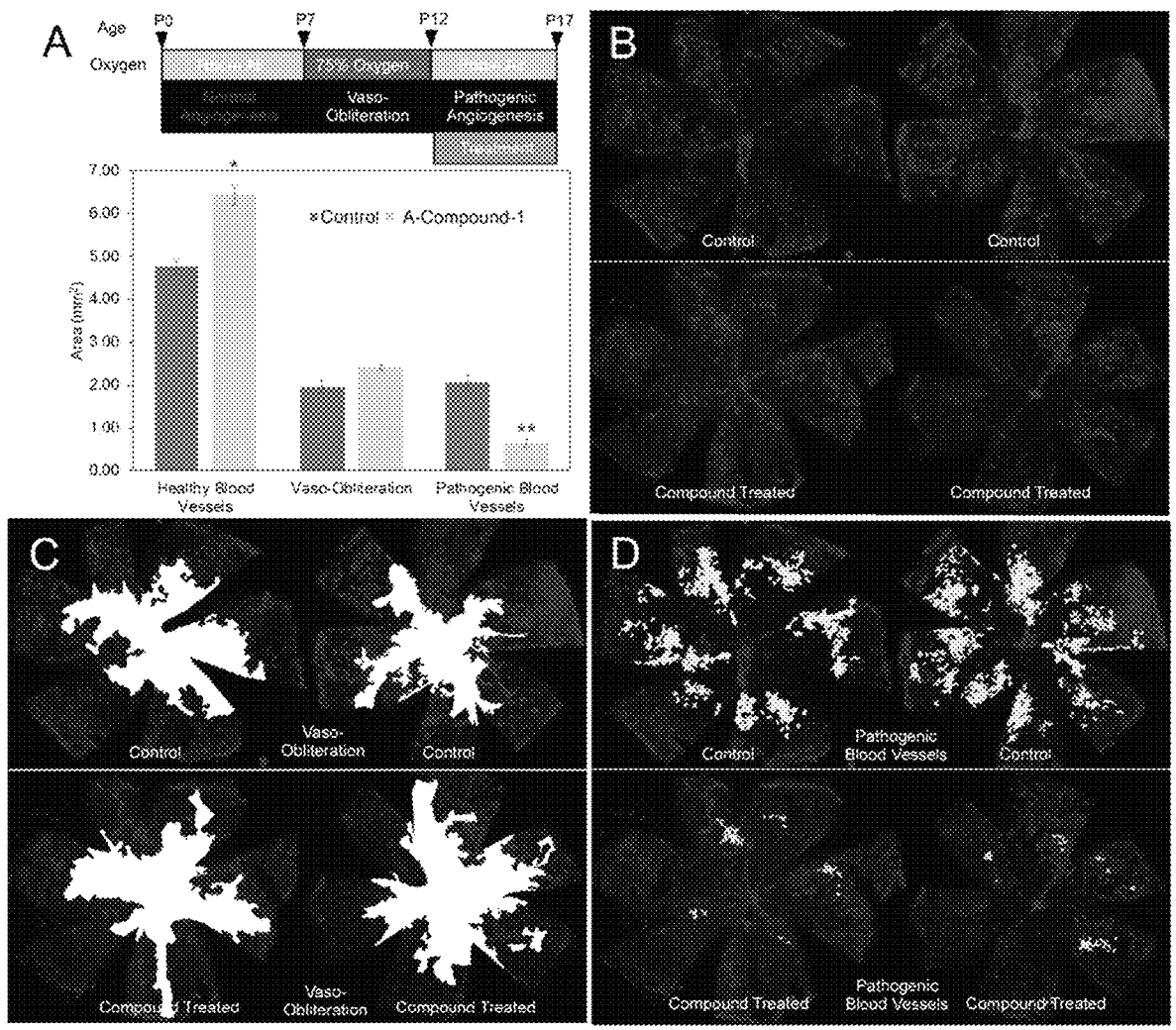
FIG. 7A-D

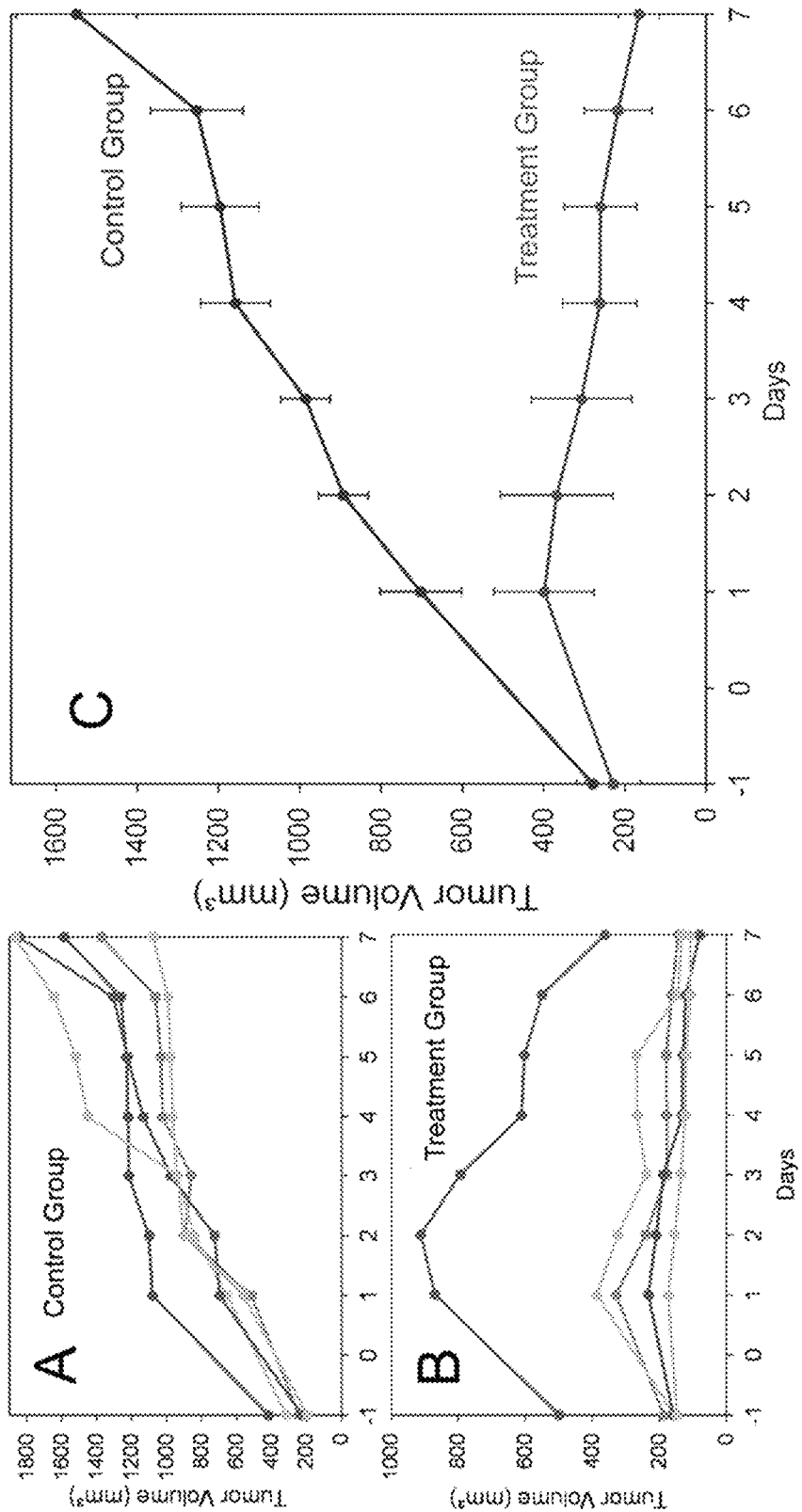
FIG. 8A-C

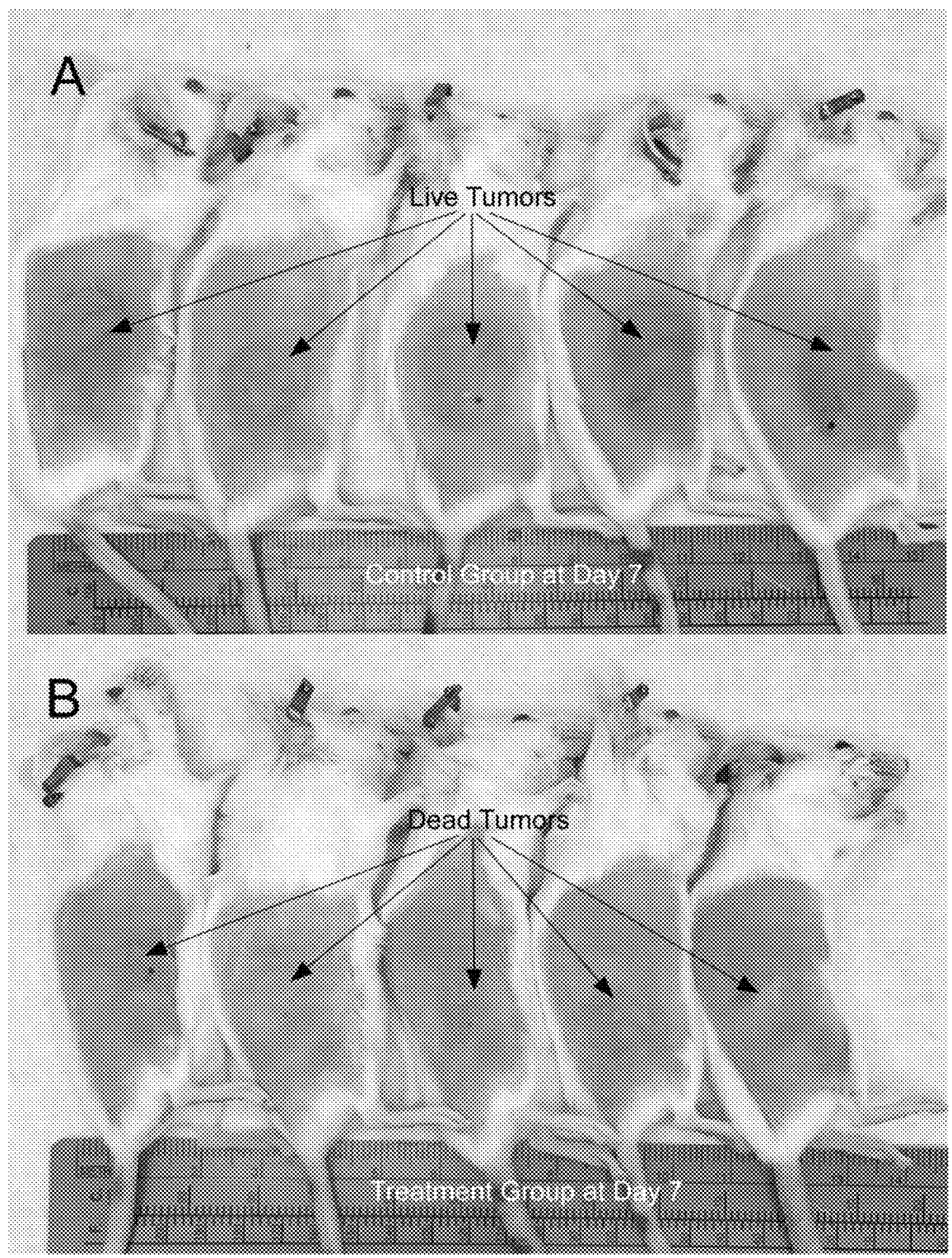
FIG. 10A-B

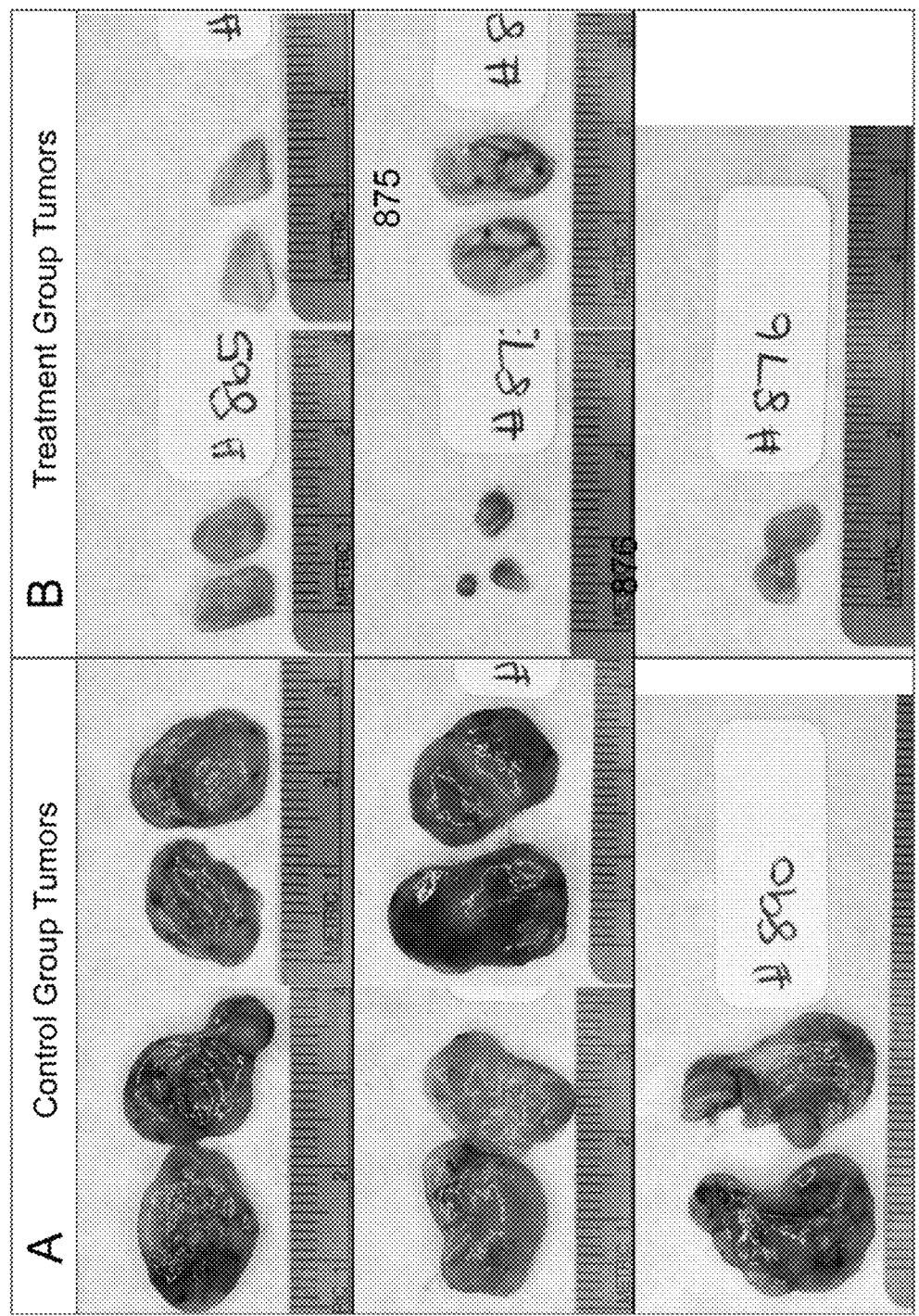
FIG. 11A-B

COMPOUNDS AND METHODS FOR TARGETING PATHOGENIC BLOOD VESSELS

CROSS REFERENCE TO RELATED APPLICATIONS

This application claims priority to U.S. Provisional Application No. 62/916,983 filed on Oct. 18, 2019, which is incorporated herein by reference in its entirety.

FIELD

The present disclosure relates generally to small molecules that target pathogenic blood vessels, compositions comprising the same, and methods of using the compounds and compositions for treating cancer and other pathogenic blood vessel disorders.

BACKGROUND

Angiogenesis plays a key role in the pathogenesis of several major human diseases. In addition to tumor growth and metastasis, angiogenesis is a major driving force in several blinding diseases including diabetic retinopathy, age-related macular degeneration (AMD), and retinopathy of prematurity. AMD and diabetic retinopathy are the leading causes of blindness in the elderly and populations at the working age in the United States, respectively. Retinopathy of prematurity is a common reason that causes the loss of vision for newborn babies.

Angiogenesis also plays a role in pathogenesis of cancer, e.g., tumor development, since newly-formed blood vessels supply the tumor with growth nutrients and signals that allow the tumor to grow and spread. Accordingly, cutting off a tumor's supply of nutrients and primary mechanism for traveling to distant sites is an attractive therapeutic strategy. However, current anti-angiogenic strategies only target newly formed blood vessels, and are unable to target existing blood vessels that contribute to disease progression.

Different disease progression patterns can be induced by anti-angiogenic therapies, which may lead to worse outcomes in terms of drug resistance, invasion, and metastasis. Furthermore, targeting angiogenesis does not treat existing blood vessels that may have, for example, already vascularized a tumor. There is a need in the art for complementary therapies that, in contrast to anti-angiogenic therapies, can target existing blood vessels and treat cancer and other disorders arising from angiogenesis (collectively referred to herein as pathogenic blood vessel disorders).

SUMMARY

The disclosure provides compounds, and compositions, including pharmaceutical compositions, kits that include the compounds, and methods of using (or administering) and making the compounds. The disclosure further provides compounds or compositions thereof for use in a method of modulating PLXDC1 (TEM7) and/or PLXDC2 or killing pathogenic blood vessles. The disclosure further provides compounds or compositions thereof for use in a method of treating a disease, disorder, or condition that is mediated, at least in part, by PEDF receptors or by angiogenesis.

In certain embodiments, provided are compounds of Formula (I) or a pharmaceutically acceptable salt, isotopically enriched analog, stereoisomer, mixture of stereoisomers, or tautomer thereof, wherein Formula (I) is

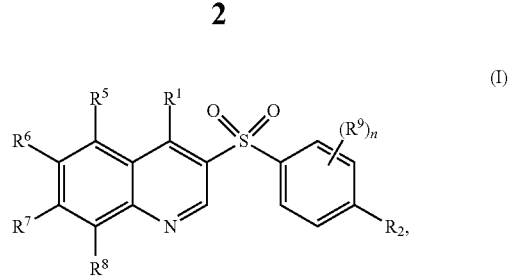

wherein each of n, $R^1$, $R^2$, $R^5$, $R^6$, $R^7$, $R^8$ and $R^9$ is as defined herein.

In certain embodiments, provided is a pharmaceutical composition comprising a compound as described herein, or a pharmaceutically acceptable salt, isotopically enriched analog, stereoisomer, mixture of stereoisomers, or tautomer thereof, and a pharmaceutically acceptable carrier.

In some embodiments, the compound activates the PLXDC (e.g., PLXDC1 and/or PLXDC2) protein. In some embodiments, the compound induces NFκB activation. In some embodiments, the compound induces NFκB activation in pathogenic blood vessels. In some embodiments, the compound increases necrosis of pathogenic blood vessels. In some embodiments, the pathogenic blood vessel-related disorder comprises diabetic retinopathy, age-related macular degeneration (AMD), retinopathy of prematurity, or cancer. In some embodiments, the pathogenic blood vessel-related disorder comprises cancer. In some embodiments, the cancer comprises colon cancer. In some embodiments, the cancer comprises lung cancer. In some embodiments, the cancer comprises a solid tumor. In some embodiments, the cancer comprises a vascularized tumor.

In some embodiments, the pathogenic blood vessel-related disorder comprises cancer and further wherein the patient is one that has a malignant tumor. In some embodiments, the tumor comprises a solid tumor. In some embodiments, the tumor has a diameter of greater than 2 cm. In some embodiments, the tumor has a diameter of at least, or at most 1, 2, 3, 4, 5, 6, 7, or 8 cm (or any range derivable therein).

In some embodiments, the compound specifically induces endothelial cell necrosis in the targeted blood vessels. In some embodiments, the compound does not directly induce tumor cell necrosis. In some embodiments, the compound induces and/or increases coagulative necrosis in a tumor in the patient. In some embodiments, the compound induces and/or increases infarction in the tumor. In some embodiments, the patient has been determined to have pathogenic blood vessels. In some embodiments, the patient has been determined to have PLXDC1 and/or PLXDC1-expressing cells. In some embodiments, the expressing cells comprise endothelial cells. In some embodiments, the expressing cells comprise cell surface expression of PLXDC1 and/or PLXDC2.

In some embodiments, the patient has previously been treated for the pathogenic blood vessel-related disorder with an additional therapy. In some embodiments, the patient has been determined to be non-responsive or have a toxic response to the additional therapy. In some embodiments, the additional therapy comprises an anti-angiogenic therapy. In some embodiments, the additional therapy comprises an immunotherapy. In some embodiments, the patient has not previously been treated for the pathogenic blood vessel-related disorder.

In certain embodiments, provided is a method for treating a disease or disorder that is mediated, at least in part, by PLXDC1 and/or PLXDC2 in a subject in need thereof, the method comprising administering to the subject an effective amount of a compound or a pharmaceutical composition comprising a compound as described herein, or a pharmaceutically acceptable salt, isotopically enriched analog, stereoisomer, mixture of stereoisomers, or tautomer thereof.

The disclosure also provides uses of the compounds, or a pharmaceutically acceptable salt, isotopically enriched analog, stereoisomer, mixture of stereoisomers, or tautomer thereof, in the manufacture of a medicament for modulating PLXDC (e.g., PLXDC1 and/or PLXDC2). Moreover, the disclosure provides uses of the compounds, or a pharmaceutically acceptable salt, isotopically enriched analog, stereoisomer, mixture of stereoisomers, or tautomer thereof, in the manufacture of a medicament for the treatment of a disease, disorder, or condition that is mediated, at least in part, by PLXDC1 and/or PLXDC2.

The disclosure also provides use of the compounds, or a pharmaceutically acceptable salt, isotopically enriched analog, stereoisomer, mixture of stereoisomers, or tautomer thereof, in treating a disease, such as cancer, retinal occlusive vascular disease, retinopathy of prematurity, diabetic retinopathy, and age-related macular degeneration.

These and other aspects of the disclosure is further described in the texts that follow.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-H. Expression of PLXDC1 in pathogenic blood vessels in choroidal neovascularization (CNV) and ischemia-induced retinopathy. Red channel shows blood vessel marker *Griffonia simplicifolia* Lectin I-isolectin B4. Green channel shows anti-PLXDC1 signal. A-D. Highly enriched PLXDC1 expression in pathogenic blood vessels in a mouse model of CNV (laser-induced CNV). A&B, retina sections. Arrowheads indicate examples of normal inner retinal blood vessels (in A) that are negative for PLXDC1 signal (in B). C&D, staining done on flat-mounted eye cup. E-H. High expression of PLXDC1 in pathogenic blood vessels in a mouse model of ischemia-induced retinopathy, but not in blood vessels of healthy retina. E&F. P17 retina of ischemia-induced retinopathy (E and F are the same section stained by endothelial cell marker and PLXDC1 antibody, respectively). Examples of pathogenic blood vessels expressing PLXDC1 are indicated by white arrows. G&H. P17 healthy retina (G and H are the same section stained by endothelial cell marker and PLXDC1 antibody, respectively). Examples of healthy blood vessels showing no detectable PLXDC1 expression are indicated by white arrows in G (there is no corresponding PLXDC1 signals in H). CH, choroid. ON, outer nuclear layer. IN, inner nuclear layer. GC, ganglion cell layer.

FIG. 2A-E. Comparison of compound 369 with the current anti-angiogenic drug in an ex vivo model of choroidal angiogenesis. A. A schematic diagram of the timeframe of the experiment. Treatment does not start until choroidal angiogenesis occurs for 7 days. Treatment lasts for two days before cell death and survival are analyzed. B. Control experiment without any drug treatment at day 7. The white circle in the middle delineates the piece of choroid/RPE that was embedded to initiate neovascularization. C. The most commonly used drug for choroidal neovascularization, Eylea, can inhibit choroidal endothelial cell growth (as expected of an antiangiogenesis drug). Eylea was added at 10 μM. D. Compound 369 that targets PLXDC1/PLXDC2 can kill the new endothelial cells in choroidal angiogenesis. Choroid and RPE are still alive after the treatment, demonstrating the high specificity of the treatment. The compound was added at 10 μM. In B-D, green cells are live cells and red cells are dead cells. E. Quantitation of the experiments described in B-D. The amount of new endothelial cells in the untreated control is defined as 100%.

FIG. 3A-B shows tumor shrinkage and necrosis following treatment with certain compounds described herein. FIG. 3A shows that 3 days after injection, all the tumors were shrinking FIG. 3B shows that the tumor shrinkage was maintained 6 days after injection.

FIG. 4A-B show tumor shrinkage and necrosis following treatment with compounds described herein. FIG. 4A shows that 3 days after injection, all the tumors were shrinking FIG. 4B shows that the tumor shrinkage was maintained 6 days after injection.

FIG. 5A-B show activation of PLXDC1 and PLXDC2 by small molecules. Through RNAseq analysis of PLXDC1-expressing endothelial cells killing by PLXDC1-activating compounds, a transcriptional factor called Gfi1b was found to be induced during PLXDC1-mediated cell killing By linking its promotor to a luciferase reporter gene, this example developed a PLXDC1 receptor activation assay that demonstrates the activation of the receptor by its ligands. A. PLXDC1-activating compounds (A-Com-1 and A-Com-2) highly activated the promotor activity in PLXDC1-expressing cells. B. A-Com-1 and A-Com-2 also activated the promotor activity in PLXDC2-expressing cells. However, both compounds preferentially activate PLXDC1 over PLXDC2. A-Com-2 more strongly differentiates between the two receptors. All compound treatments were done for 1 day. Basal promotor activity of the PLXDC1-expressing cells is defined as 1. Fluorouracil (FU), a chemotherapy drug that kills dividing cells by apoptosis, do not activate this promotor.

FIG. 6A-B show killing of PLXDC1-expressing endothelial cells by PLXDC1-activating small molecules and antibodies. A. Visualization of the killing human PLXDC1-expressing endothelial cells by PLXDC1-activating small molecule (compound). The top three pictures on represent control cells and the lower three pictures represent compound-treated cells, showing light microscopy picture (left), live cell (middle) and dead cell staining (right). Live cells are stained using Fluorescein diacetate (green signal) and dead cells are stained using propidium iodide (red signal). B. Quantitation of the killing of human PLXDC1-expressing endothelial cells by PLXDC1-activating small molecules (A-Compound-1 and A-Compound-2) and antibodies (A-TEM7-Ab-1 and A-TEM7-Ab-2). Incubation time of the compounds and antibodies is 24 hours. Cell survival of the control cells is defined as 100%.

FIG. 7A-D show that PLXDC1-activating compound specifically suppresses pathogenic blood vessels in vivo without affecting healthy blood vessels in ischemia-induced retinopathy. A. Upper graph: Schematic diagram of the experimental design for ischemia-induced retinopathy. The high oxygen environment caused blood vessel loss (vaso-obliteration). In room air, loss of vessels triggered abnormal angiogenesis that generated pathogenic blood vessels on the top of the retina (marked in yellow in D). Treatment was applied during the return to room air by subcutaneous injection. Lower graph: quantitation of healthy blood vessels, vaso-obliteration and pathogenic blood vessels between the control (n=10) and treated retinas (n=10). Treatment by PLXDC1-activating compound (A-Compound-1) highly suppressed pathogenic blood vessels (two asterisks) while improving the amount of healthy blood vessels (one asterisk). B. Representative images of flat-mounted control retinas (upper two images) and retinas from compound treated mice (lower two images). Red signal is blood vessel marker. C. The same retinas in B with vaso-obliteration areas marked in white color. These images illustrate that compound-treated retinas went through vaso-obliteration like the control retinas. D. The same retinas in B with pathogenic blood vessels marked in yellow color. These images illustrate that compound-treated retinas have highly decreased pathogenic blood vessels as compared to the control retinas.

FIG. 8A-C show that PLXDC1-activating compound causes tumor shrinkage in vivo. Treatment was done at day 0 by bolus IV injection. A. Raw data of tumor growth curves of the mice in the control group. B. Raw data of tumor growth curves of the mice in the treatment group. C. Comparison of the combined growth data of the control group and the treatment group.

FIG. 10A-B show tumor morphological changes on live animals due to the treatment by PLXDC1-activating compound. Treatment was done at day 0. While the tumors in the control group have grown to large sizes, tumors in the treatment groups have highly shrunk in size and become yellow in color.

FIG. 11A-B show morphological changes of dissected tumors due to the treatment by PLXDC1-activating compound. Pictures of the dissected tumors in the experiment described in FIG. 11 show tumor morphological and color changes on day 7. While the tumors in the control group are reddish in color, tumors in the treatment groups have highly shrunk in size and become yellow in color, consistent with the lack of tumor blood vessels and tumor necrosis.

DETAILED DESCRIPTION

Figure 9:
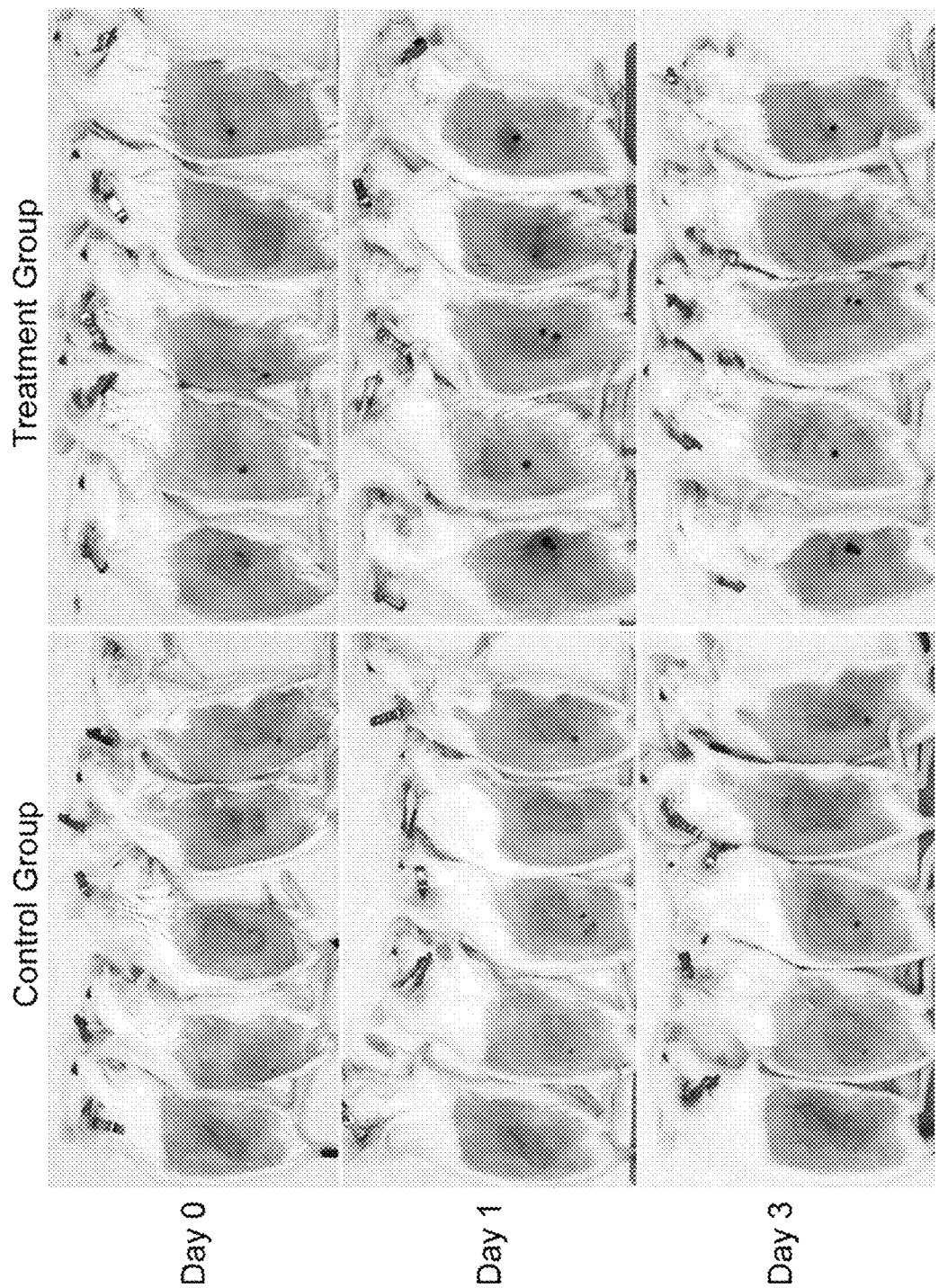
FIG. 9 shows tumor morphological changes on live animals due to the treatment by PLXDC1-activating compound. Pictures of the whole animals in the experiment described in FIG. 11 show tumor morphological and color changes on day 1 and day 3. Treatment was done at day 0. Tumors in the treatment groups becomes darker in color on day 1 due to the destruction of tumor blood vessels and accumulation of blood in the tumors. Tumors in the treatment groups start to become yellower in color on day 3, consistent with the onset of tumor necrosis due to the lack of tumor blood vessels.

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. In some embodiments, alkyl has the indicated number of carbon atoms. In some embodiments, alkyl has 1 to 40 carbon atoms (i.e., $C_{1-40}$ alkyl), 1 to 30 carbon atoms (i.e., $C_{1-30}$ alkyl), 10 to 30 carbon atoms (i.e., $C_{10-30}$ alkyl), 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl, octyl, nonyl, decyl, dodecyl, icosyl, docosyl, tetradecyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group, an "arylene" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond. In some embodiments, alkenyl has the indicated number of carbon atoms. In some embodiments, alkenyl has from 2 to 40 carbon atoms (i.e., $C_{2-40}$ alkenyl), 2 to 30 carbon atoms (i.e., $C_{2-30}$ alkenyl), 10 to 30 carbon atoms (i.e., $C_{10-30}$ alkenyl), 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond. In some embodiments, alkynyl has the indicated number of carbon atoms. In some embodiments, alkynyl has from 2 to 40 carbon atoms (i.e., $C_{2-40}$ alkynyl), 2 to 30 carbon atoms (i.e., $C_{1-30}$ alkynyl), 10 to 30 carbon atoms (i.e., $C_{10-30}$ alkynyl), 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". In some embodiments, alkoxy has from 1 to 40 carbon atoms (i.e., —O—$C_{1-40}$ alkyl), 1 to 30 carbon atoms (i.e., —O—$C_{1-30}$ alkyl), 10 to 30 carbon atoms (i.e., —O—$C_{10-30}$ alkyl, 1 to 20 carbon atoms (i.e., —O—$C_{1-20}$ alkyl), 1 to 12 carbon atoms (i.e., —O—$C_{1-12}$ alkyl), 1 to 8 carbon atoms (i.e., —O—$C_{1-8}$alkyl), 1 to 6 carbon atoms (i.e., —O—$C_{1-6}$ alkyl) or 1 to 4 carbon atoms (i.e., —O—$C_{1-4}$ alkyl). Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkenoxy" refers to the group "alkene-O—". In some embodiments, alkenoxy has from 2 to 40 carbon atoms (i.e., —O—$C_{2-40}$ alkene), 2 to 30 carbon atoms (i.e., —O—$C_{2-30}$ alkene), 10 to 30 carbon atoms (i.e., —O—$C_{10-30}$ alkene), 2 to 20 carbon atoms (i.e., —O—$C_{2-20}$ alkene), 2 to 12 carbon atoms (i.e., —O—$C_{2-12}$ alkene), 2 to 8 carbon atoms (i.e., —O—$C_{2-8}$ alkene), 2 to 6 carbon atoms (i.e., —O—$C_{2-6}$ alkene) or 2 to 4 carbon atoms (i.e., —O—$C_{2-4}$ alkene).

"Alkynoxy" refers to the group "alk2ne-O—". In some embodiments, alkynoxy has from 1 to 40 carbon atoms (i.e., —O—$C_{2-40}$ alkyne), 2 to 30 carbon atoms (i.e., —O—$C_{2-30}$ alkene), 10 to 30 carbon atoms (i.e., —O—$C_{10-30}$ alkyne, 2 to 20 carbon atoms (i.e., —O—$C_{2-20}$ alkyne), 2 to 12 carbon atoms (i.e., —O—$C_{2-12}$ alkyne), 2 to 8 carbon atoms (i.e., —O—$C_{2-8}$ alkyne), 2 to 6 carbon atoms (i.e., —O—$C_{2-6}$ alkyne) or 2 to 4 carbon atoms (i.e., —O—$C_{2-4}$ alkyne).

The term "amido" as used herein refers to both —$NR^gC$(=O)$R^h$ and —C(=O)$NR^gR^h$, wherein each of $R^g$ and $R^h$ is independently hydrogen, alkyl, alkenyl, alkynyl, alkoxy, thioalkyl, aryl, aryl-alkyl, cycloalkyl, cycloalkyl-alkyl, haloalkyl, heterocyclyl, heterocyclyl-alkyl, heteroaryl, or heteroaryl-alkyl, and further wherein each $R^g$ and $R^h$ may be optionally substituted, as defined herein.

"Amino" refers to the group —$NR^yR^z$ wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. In some embodiments, aryl has 6 to 20 ring carbon atoms (i.e., $C_{6-20}$ aryl), 6 to 12 ring carbon atoms (i.e., $C_{6-42}$ aryl), or 6 to 10 ring carbon atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Carboxyl ester" or "ester" refer to both —OC(O)$R^x$ and —C(O)O$R^x$, wherein $R^x$ is alkyl, alkenyl, alkynyl, cycloalkyl, heterocyclyl, aryl, heteroalkyl or heteroaryl; each of which may be optionally substituted, as defined herein.

"Carboxy" as used herein refers to —$CO_2H$, or a salt thereof. Exemplary counter ions which can be used include, but are not limited to, $Na^+$, $K^+$, $Li^+$, $NH_4^+$ and others described herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). In some embodiments, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-40}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic cycloalkyl refers to a cycloalkyl having at least two rings, which may be a fused, bridged or spiro ring system. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. "Spirocycloalkyl" refers to a polycyclic cycloalkyl group wherein at least two rings are linked together by one common atom, for example spiro[2.5]octanyl, spiro[4.5]decanyl, or spiro[5.5]undecanyl. Spirocycloalkyl may contain fused rings in the ring system, but not bridged rings. "Fused cycloalkyl" refers to a polycyclic cycloalkyl group wherein at least two rings are linked together by two common atoms wherein the two common atoms are connected through a covalent bond. Fused cycloalkyl does not contain any spiro or bridged rings in the ring system. "Bridged cycloalkyl" refers to a polycyclic cycloalkyl that contains a bridge—an alkylene (such as $C_{1-4}$ alkylene) group that connect two "bridgehead" atoms. Non-limiting examples of bridged cycloalkyl include bicyclo[2.2.1]heptanyl, bicyclo[2.2.2]octanyl, adamantyl, norbornyl, and 7,7-dimethyl-bicyclo[2.2.1]heptanyl. Bridged cycloalkyl may contain fused and/or spiro rings in the ring system. Further, the term cycloalkyl is intended to encompass any non-aromatic ring which may be fused to an aryl ring, regardless of the attachment to the remainder of the molecule.

"Halogen" or "halo" refers to atoms occupying group VIIA of the periodic table, such as fluoro, chloro, bromo or iodo.

"Haloalkyl" refers to an unbranched or branched alkyl group as defined above, wherein one or more (e.g., 1 to 6, 1 to 5 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6, 1 to 5 or 1 to 3) hydrogen atoms are replaced by a halogen.

"Hydroxyalkyl" refers to an alkyl group as defined above, wherein one or more (e.g., 1 to 6, 1 to 5 or 1 to 3) hydrogen atoms are replaced by a hydroxy group. A non-limiting example of hydroxyalkyl is —$(CH_2)_{1-4}$—OH.

"Heteroalkyl" refers to an alkyl group in which one or more, but not all of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl or heteroaryl; each of which may be optionally substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.) and amines (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, cycloalkyl, heterocyclyl, aryl, heteroalkyl, or heteroaryl; each of which may be optionally substituted, as defined herein). In some embodiments, heteroalkyl includes 1 to 10 carbon atoms (C$_{1-10}$ heteroalkyl), 1 to 8 carbon atoms (C$_{1-8}$ heteroalkyl), or 1 to 4 carbon atoms (C$_{1-4}$ heteroalkyl); and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (=O) or N-oxide (—O$^-$) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., C$_{3-12}$ heterocyclyl), 3 to 8 ring carbon atoms (i.e., C$_{3-8}$ heterocyclyl), or 3 to 6 ring carbon atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. In certain instances, heterocyclyl includes 3- to 10-membered heterocyclyl having 3-10 total ring atoms, 5- to 7-membered heterocyclyl having 5-7 total ring atoms, or 5- or 6-membered heterocyclyl having 5 or 6 total ring atoms. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclyl" also includes "spiroheterocyclyl" when there are at least two rings are linked together by one common atom. Examples of the spiro-heterocyclyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system. Examples of heterocyclyl include sugar moieties such as glucose, mannose, allose, altrose, gulose, idose, galactose, and talose.

The terms "alkylthio" or "thioalkyl" as used herein refer to —S-alkyl, where the term alkyl is as defined herein.

The term "sulfonamido" as used herein refer to both —NR$^g$S(=O)$_2$R$^h$ and —S(=O)$_2$NR$^g$R$^h$, wherein each of R$^g$ and R$^h$ is independently hydrogen, alkyl, alkenyl, alkynyl, alkoxy, thioalkyl, aryl, aryl-alkyl, cycloalkyl, cycloalkyl-alkyl, haloalkyl, heterocyclyl, heterocyclyl-alkyl, heteroaryl, or heteroaryl-alkyl, and further wherein each R$^g$ and R$^h$ may be optionally substituted, as defined herein.

The term "sulfinamido" as used herein refer to both —NR$^g$S(=O)R$^h$ and —S(=O)NR$^g$R$^h$, wherein each of R$^g$ and R$^h$ is independently hydrogen, alkyl, alkenyl, alkynyl, alkoxy, thioalkyl, aryl, aryl-alkyl, cycloalkyl, cycloalkyl-alkyl, haloalkyl, heterocyclyl, heterocyclyl-alkyl, heteroaryl, or heteroaryl-alkyl, and further wherein each $R^g$ and $R^h$ may be optionally substituted, as defined herein.

The term "sulfoxide" or "sulfoxido" refers to the group —S(=O)—$R^g$, wherein $R^g$ is hydrogen, alkyl, alkenyl, alkynyl, alkoxy, thioalkyl, aryl, aryl-alkyl, cycloalkyl, cycloalkyl-alkyl, haloalkyl, heterocyclyl, heterocyclyl-alkyl, heteroaryl, or heteroaryl-alkyl, and further wherein $R^g$ may be optionally substituted, as defined herein.

The term "sulfonyl" refers to the group —S(O)$_2$—$R^g$, wherein $R^g$ is hydrogen, alkyl, alkenyl, alkynyl, alkoxy, thioalkyl, aryl, aryl-alkyl, cycloalkyl, cycloalkyl-alkyl, haloalkyl, heterocyclyl, heterocyclyl-alkyl, heteroaryl, or heteroaryl-alkyl, and further wherein $R^g$ may be optionally substituted, as defined herein. "Sugar moiety" refers to a monovalent radical of a sugar molecule, such as a monosaccharide molecule, including glucose (also known as dextrose), fructose, galactose, mannose, allose, altrose, gulose, idose, and talose. As used herein, a sugar moiety a heterocyclyl substituted with OH and/or hydoxyalkyl groups. However, it is understood that a sugar moiety can exist in a liner form as an alkyl substituted with oxo and OH groups.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5 or 1 to 3) hydrogen atoms on the designated atom or group may or may not be replaced by a moiety other than hydrogen.

In certain embodiments, "substituted" includes any of the above alkyl, heteroalkyl, alkenyl, alkynyl, cycloalkyl, heterocyclyl, aryl or heteroaryl groups in which one or more (e.g., 1 to 5 or 1 to 3) hydrogen atoms are independently replaced with halo, cyano, nitro, azido, oxo, alkyl, alkenyl, alkynyl, haloalkyl, cycloalkyl, heterocyclyl, aryl, heteroaryl, —N$R^gR^h$, —C(N$R^g$)$R^h$, —C(N$R^g$)(N$R^h{}_2$), —N$R^g$C(=O)$R^h$, —N$R^g$C(=O)N$R^gR^h$, —N$R^g$C(=O)O$R^h$, —N$R^g$S(=O)$_{1-2}R^h$, —C(=O)$R^g$, —C(=O)O$R^g$, —OC(=O)O$R^g$, —OC(=O)$R^g$, —C(=O)N$R^gR^h$, —OC(=O)N$R^gR^h$, —O$R^g$, —S$R^g$, —S(=O)$R^g$, —S(=O)$_2R^g$, —OS(=O)$_{1-2}R^g$, —S(=O)$_{1-2}$O$R^g$, —N$R^g$S(=O)$_{1-2}$N$R^gR^h$, =NSO$_2R^g$, =NO$R^g$, —S(=O)$_{1-2}$N$R^gR^h$, —C$R^g$(=NOH), —N$R^g$C(=N$R^h$)(N$R^hR^h$), —SF$_5$, —SCF$_3$ or —OCF$_3$. In certain embodiments, "substituted" also means any of the above groups in which one or more (e.g., 1 to 5 or 1 to 3) hydrogen atoms are replaced with —C(=O)$R^g$, —C(=O)O$R^g$, —C(=O)N$R^gR^h$, —CH$_2$SO$_2R^g$, or —CH$_2$SO$_2$N$R^gR^h$. In the foregoing, each of $R^g$ and $R^h$ is independently hydrogen, alkyl, alkenyl, alkynyl, alkoxy, thioalkyl, aryl, aralkyl, cycloalkyl, cycloalkyl-alkyl, haloalkyl, heterocyclyl, heterocyclyl-alkyl, heteroaryl, and/or heteroaryl-alkyl. In certain embodiments, "substituted" also means any of the above groups in which one or more (e.g., 1 to 5 or 1 to 3) hydrogen atoms are replaced with halo, hydroxy, alkyl, alkylhydroxy, or oxo groups.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl)substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan.

In certain embodiments, as used herein, the phrase "one or more" refers to one to five. In certain embodiments, as used herein, the phrase "one or more" refers to one to three.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Various isotopically labeled compounds of the present disclosure, for example those into which radioactive isotopes such as $^3$H and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects.

The term "isotopically enriched analogs" includes "deuterated analogs" of compounds described herein in which one or more hydrogens is/are replaced by deuterium, such as a hydrogen on a carbon atom. Such compounds may exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, $^{11}$C labeled compound may be useful for PET or SPECT or other imaging studies. Isotopically labeled compounds of this disclosure can generally be prepared by carrying out the procedures disclosed in the schemes or in the examples and preparations described below by substituting a readily available isotopically labeled reagent for a non-isotopically labeled reagent.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when an atom is represented by its name or letter symbol, such as, H, C, O, or N, it is understood that the atom has its natural abundance isotopic composition. For example, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, stereoisomer, and mixture of stereoisomers of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Salts derived from organic acids may be derived from anhydrous organic acids or hydrates thereof. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2(alkyl)$), dialkyl amines (i.e., $HN(alkyl)_2$), trialkyl amines (i.e., $N(alkyl)_3$), substituted alkyl amines (i.e., $NH_2$(substituted alkyl)), di(substituted alkyl) amines (i.e., $HN$(substituted alkyl)$_2$), tri(substituted alkyl) amines (i.e., $N$(substituted alkyl)$_3$), alkenyl amines (i.e., $NH_2$(alkenyl)), dialkenyl amines (i.e., $HN(alkenyl)_2$), trialkenyl amines (i.e., $N(alkenyl)_3$), substituted alkenyl amines (i.e., $NH_2$(substituted alkenyl)), di(substituted alkenyl) amines (i.e., $HN$(substituted alkenyl)$_2$), tri(substituted alkenyl) amines (i.e., $N$(substituted alkenyl)$_3$, mono-, di- or tri-cycloalkyl amines (i.e., $NH_2$(cycloalkyl), $HN$(cycloalkyl)$_2$, $N$(cycloalkyl)$_3$), mono-, di- or tri-arylamines (i.e., $NH_2$(aryl), $HN(aryl)_2$, $N(aryl)_3$) or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise tautomers. Thus, the amide containing compounds are understood to include their imidic acid tautomers. Likewise, the imidic acid containing compounds are understood to include their amide tautomers.

A "stereoisomer" refers to a compound made up of the same atoms bonded by the same bonds but having different three-dimensional structures, which are not interchangeable. The present invention contemplates various stereoisomers and mixtures thereof and includes"

Stereoisomers include enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Stereoisomers also include geometric isomers when the compounds described herein contain olefinic double bonds or other centers of geometric asymmetry. Unless specified otherwise, it is intended that such compounds include both E and Z geometric isomers.

"Enantiomers" are two stereoisomers whose molecules are non-superimposable mirror images of one another. "Diastereomers" are stereoisomers that have at least two asymmetric atoms, but which are not mirror-images of each other.

Relative centers of the compounds as depicted herein are indicated graphically using the "thick bond" style and absolute stereochemistry is depicted using wedge bonds.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the geometry of a disclosed compound is named or depicted by structure, the named or depicted geometrical isomer is at least 60%, 70%, 80%, 90%, 99% or 99.9% by weight pure relative to the other geometrical isomers.

In certain embodiments, where one or more stereocenters are present, a compound disclosed herein may be provided as a racemic mixture. In certain embodiments, where one or more stereocenters are present, a compound disclosed herein may be provided as a single enantiomer. For example, a compound may be provided in a composition having greater than about 30% ee, about 40% ee, about 50% ee, about 60% ee, about 70% ee, about 80% ee, about 90% ee, about 95% ee, about 97% ee, about 98% ee, about 99% ee, or greater.

In certain such embodiments, compounds may be provided in a diastereomerically enriched composition. For example, a diastereomerically enriched composition comprising a compound disclosed herein may have greater than about 30% de, about 40% de, about 50% de, about 60% de, about 70% de, about 80% de, about 90% de, about 95% de, about 97% de, about 98% de, about 99% de, or greater.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. In one embodiment, the subject is human.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" means to decrease, suppress, attenuate, diminish, arrest, or stabilize the development or progression of a disease (e.g., a disease or disorder delineated herein), lessen the severity of the disease or improve the symptoms associated with the disease. Treatment includes treating a symptom of a disease, disorder or condition. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

"Pathogenic blood vessels" are blood vessels that are not involved in the vascularization of normal organs but, instead, are involved in vascularization of diseased tissues, such as the new blood vessels that drive vision diseases or the new blood vessels in tumors that tumors depend on to survive. "Pathogenic blood vessel," in some embodiments, refers to an existing blood vessel that may have vascularized a diseased tissue, for instance, a tumor. In other embodiments, a pathogenic blood vessel may be a blood vessel that is a newly formed blood vessel involved in disease onset and/or progression of, for example, cancer, diabetic retinopathy, age-related macular degeneration (AMD), retinopathy of prematurity and/or any other diseases having etiologies associated with angiogeneis.

Abbreviations

DCM dichloromethane
DIPEA diisopropylethylamine
DMA dimethylacetamide
DMAP dimethylaminopyridine
DMF dimethylformamide
DMSO dimethyl sulfoxide
EDCI 1-ethyl-3-(3-dimethylaminopropyl)carbodiimide
Equiv or eq equivalent
ESI electrospray ionization
EtOAc ethyl acetate
EtOH ethanol
EtONa sodium ethoxide
HOAc or AcOH acetic acid
HOBt 1-hydroxybenzotriazole
HPLC high performance liquid chromatography
HRMS high-resolution mass spectrometry
LC liquid chromatography
LCMS liquid chromatography-mass spectrometry
mCPBA meta-chloroperoxybenzoic acid
MeOH methanol
NMM N-methylmorpholine
NMP N-methyl-2-pyrrolidone
OXONE® Potassium peroxymonosulfate
mPEG methoxypoly(ethylene glycol)
rt room temperature
TEA triethylamine
THF tetrahydrofuran
TLC thin-layer chromatography
TsOH p-toluenesulfonic acid
PPSE Trimethylsilyl polyphosphate 2. Compounds In certain embodiments, provided is a compound of Formula (I):

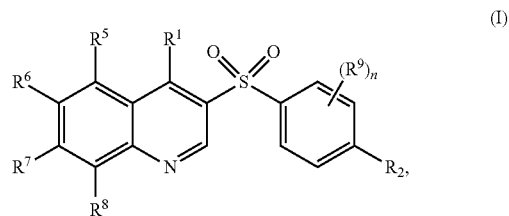

or a pharmaceutically acceptable salt, isotopically enriched analog, stereoisomer, mixture of stereoisomers, or tautomer thereof;
wherein
n is 0, 1, 2, 3 or 4;
$R^1$ is selected from optionally substituted amino, optionally substituted aryl, optionally substituted cycloalklyl, optionally substituted heterocyclyl, and optionally substituted heteroaryl;

$R^2$ is selected from H, halo, alkyl, alkenyl, alkynyl, —OH, alkoxy, —CN, —NO$_2$, alkylthio, sulfoxido, sulfonyl, and amino;

$R^5$, $R^7$ and $R^8$ are each independently selected from H, halo, alkyl, alkenyl, alkynyl, hydroxy, alkoxy, alkenoxy, alkynoxy, alkylthio, sulfoxido, sulfonyl, carboxy, ester, —CN, —NO$_2$, amino, and amido;

$R^6$ is selected from H, halo, alkyl, hydroxy, alkoxy, alkylthio, sulfoxido, sulfonyl, carboxy, ester, —CN, —NO$_2$, amino, amido, sulfinamido, sulfonamido, optionally substituted heterocyclyl, optionally substituted heteroaryl, poly(ethylene glycol), and methoxypoly(ethylene glycol), or $R^6$ and IV together with atoms to which they are attached form an optionally substituted cycloalkyl, optionally substituted heterocyclyl, optionally substituted aryl, or optionally substituted heteroaryl; and each $R^9$ is independently selected from halo, alkyl, —OH, alkoxy, —CN, and amino.

In certain embodiments, when $R^2$ is $C_{1-6}$ alkyl, $R^6$ is not $C_{1-6}$ alkyl or $C_{1-6}$ alkoxy. In other embodiments, when $R^2$ is $C_{1-3}$ alkyl, $R^6$ is not $C_{1-3}$ alkyl or $C_{1-3}$ alkoxy. In certain embodiments, when $R^2$ is ethyl, then $R^6$ is not methyl or methoxy.

In certain embodiments, provided is a compound of Formula (I):

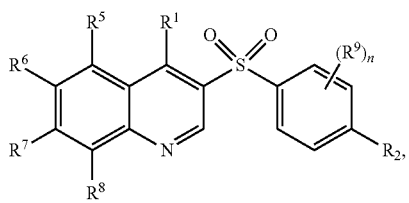

or a pharmaceutically acceptable salt, isotopically enriched analog, stereoisomer, mixture of stereoisomers, or tautomer thereof;
wherein
n is 0, 1, 2, 3 or 4;

$R^1$ is selected from optionally substituted amino, optionally substituted aryl, optionally substituted cycloalkyl, optionally substituted heterocyclyl, and optionally substituted heteroaryl;

$R^2$ is selected from halo, alkyl, alkenyl, alkynyl, alkoxy, alkenoxy, alkynoxy, —CN, and —NO$_2$;

$R^5$, $R^7$ and $R^8$ are each independently selected from H, halo, alkyl, alkenyl, hydroxy, and alkoxy;

$R^6$ is selected from halo, alkyl, alkenyl, alkynyl hydroxy, alkoxy, alkylthio, sulfoxide, sulfonyl, carboxy, ester, —NO$_2$—CN, amino, and amido; and each $R^9$ is independently selected from halo, hydroxy, and alkoxy.

In certain embodiments of Formula (I):
n is 0 or 1;

$R^1$ is selected from optionally substituted amino, optionally substituted heterocyclyl, and optionally substituted heteroaryl;

$R^2$ is selected from alkyl, alkoxy, alkenoxy, alkynoxy, —CN, and —NO$_2$;

$R^5$, $R^7$ and $R^8$ are each independently selected from H and alkoxy;

$R^6$ is selected from halo, alkyl, alkoxy, sulfoxido, sulfonyl, carboxy, ester, —NO$_2$ and amido; and
each $R^9$ is independently halo or alkoxy.

In certain embodiments, provided is a compound of Formula (I):

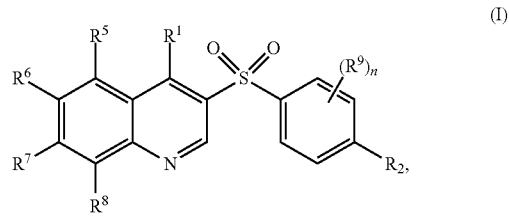

or a pharmaceutically acceptable salt, isotopically enriched analog, stereoisomer, mixture of stereoisomers, or tautomer thereof;
wherein
n is 0 or 1;

$R^1$ is selected from amino, optionally substituted amino heterocyclyl, and optionally substituted amino heteroaryl;

$R^2$ is selected from alkyl, alkoxy, —CN, and —NO$_2$;

$R^5$, $R^7$ and $R^8$ are each independently selected from H and alkoxy;

$R^6$ is selected from halo, alkyl, alkoxy, sulfoxido, sulfonyl, carboxy, ester, —NO$_2$ and amido; and each $R^9$ is independently halo or alkoxy.

In certain embodiments, the compound of Formula (I) described above has at least one of the following:

1) $R^2$ is selected from $C_{2-30}$alkyl, —OH, $C_{1-40}$alkoxy, $C_{1-40}$alkenoxy, $C_{1-40}$alkynoxy, —NO$_2$, alkylthio, sulfoxido, sulfonyl, and amino, where
   a) when $R^2$ is ethyl, then $R^6$ is not methyl or methoxy, and/or
   b) when $R^2$ is methoxy, then $R^6$ is not halo, $C_{1-2}$ alkyl or $C_{1-2}$ alkoxy;

2) $R^1$ is optionally substituted amino heteroaryl, optionally substituted amino bridged heterocyclyl, optionally substituted amino fused heterocyclyl, or optionally substituted amino cycloheptyl;

3) $R^1$ is heterocyclyl optionally substituted with one halo, amino, hydroxy, alkoxy, —CN, —NO$_2$, alkyl, carboxy, alkylthio, sulfoxido, sulfonyl, sulfinamido, sulfonamido, optionally substituted cycloalkyl, optionally substituted heterocyclyl, optionally substituted heteroaryl, poly(ethylene glycol), or methoxypoly(ethylene glycol),
where if the substituent is alkyl, the alkyl is further substituted with one substituent selected from halo, amino, alkoxy, —CN, —NO$_2$, carboxy, ester, alkylthio, sulfoxido, sulfonyl, sulfinamido, sulfonamido, cycloalkyl, heterocyclyl, poly(ethylene glycol), methoxypoly(ethylene glycol), pyrrolidinyl and piperidinyl; or the alkyl is substituted with at least one —OR$^{31}$, wherein R$^{31}$ is poly(ethylene glycol) or methoxypoly(ethylene glycol);

4) $R^1$ is amino substituted with at least one substituent selected from alkyl, cycloalkyl, heterocyclyl, heteroaryl, poly(ethylene glycol) or methoxypoly(ethylene glycol) and amino, where the alkyl is substituted with at least one substituent selected from halo, amino, hydroxy, alkoxy, —CN, —NO$_2$, amido, carboxy, ester, alkylthio, sulfoxido, sulfonyl, sulfinamido, sulfonamido, cycloalkyl, heterocyclyl, and heteroaryl; or 5) R$^6$ is alkyl substituted with at least one substituent selected from halo, amino, hydroxy, alkoxy, cycloalkoxy, heterocycloalkoxy, aryloxy, heteroaryloxy, poly(ethylene glycol)-oxy, methoxypoly(ethylene glycol)-oxy, —CN, —NO$_2$, oxo, amido, carboxy, ester, alkylthio, sulfoxido, sulfonyl, sulfinamido, sulfonamido, heterocyclyl, cycloalkyl, aryl, heteroaryl, poly(ethylene glycol) and methoxypoly(ethylene glycol).

In certain embodiments, provided is a compound of Formula (I'):

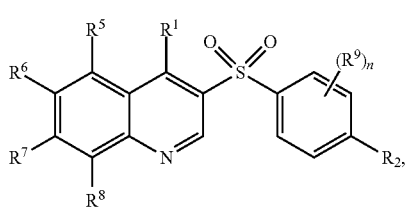

or a pharmaceutically acceptable salt, isotopically enriched analog, stereoisomer, mixture of stereoisomers, or tautomer thereof;
wherein
n is 0, 1, 2, 3 or 4;
R$^1$ is selected from amino, heterocyclyl, and heteroaryl;
R$^2$ is selected from H, halo, alkyl, alkenyl, alkynyl, —OH, alkoxy, —CN, —NO$_2$, alkylthio, sulfoxido, sulfonyl, and amino;
R$^5$, R$^7$ and R$^8$ are each independently selected from H, halo, alkyl, alkenyl, alkynyl, hydroxy, alkoxy, alkylthio, sulfoxido, sulfonyl, carboxy, ester, —CN, —NO$_2$, amino, and amido;
R$^6$ is selected from H, halo, alkyl, hydroxy, alkoxy, alkylthio, sulfoxido, sulfonyl, carboxy, ester, —CN, —NO$_2$, amino, amido, sulfinamido, sulfonamido, heterocyclyl, heteroaryl, poly(ethylene glycol), and methoxypoly(ethylene glycol), or
R$^6$ and R$^7$ together with atoms to which they are attached form a cycloalkyl, heterocyclyl, aryl, or heteroaryl; and
each R$^9$ is independently selected from halo, alkyl, —OH, alkoxy, —CN, and amino.

In certain embodiments, when R$^2$ is C$_{1-6}$ alkyl, R$^6$ is not C$_{1-6}$ alkyl or C$_{1-6}$ alkoxy. In other embodiments, when R$^2$ is C$_{1-3}$ alkyl, R$^6$ is not C$_{1-3}$ alkyl or C$_{1-3}$ alkoxy. In certain embodiments, when R$^2$ is ethyl, then R$^6$ is not methyl or methoxy.

In certain embodiments, provided is a compound of Formula (I'):

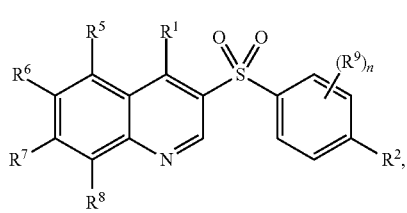

or a pharmaceutically acceptable salt, isotopically enriched analog, stereoisomer, mixture of stereoisomers, or tautomer thereof;
wherein
n is 0, 1, 2, 3 or 4;
R$^1$ is selected from amino, aryl, cycloalkyl, heterocyclyl, and heteroaryl;
R$^2$ is selected from halo, alkyl, alkenyl, alkynyl, alkoxy, —CN, and —NO$_2$;
R$^5$, R$^7$ and R$^8$ are each independently selected from H, halo, alkyl, alkenyl, hydroxy, and alkoxy;
R$^6$ is selected from halo, alkyl, alkenyl, alkynyl hydroxy, alkoxy, alkylthio, sulfoxide, sulfonyl, carboxy, ester, —NO$_2$—CN, amino, and amido; and
each R$^9$ is independently selected from halo, hydroxy, and alkoxy.

In certain embodiments, provided is a compound of Formula (I'):

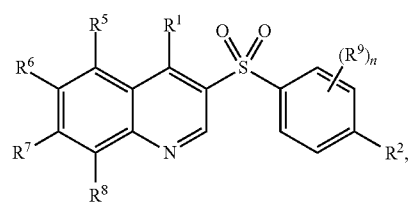

or a pharmaceutically acceptable salt, isotopically enriched analog, stereoisomer, mixture of stereoisomers, or tautomer thereof;
wherein
n is 0 or 1;
R$^1$ is selected from amino, heterocyclyl, and heteroaryl;
R$^2$ is selected from alkyl, alkoxy, —CN, and —NO$_2$;
R$^5$, R$^7$ and R$^8$ are each independently selected from H and alkoxy;
R$^6$ is selected from halo, alkyl, alkoxy, sulfoxido, sulfonyl, carboxy, ester, —NO$_2$ and amido; and
each R$^9$ is independently halo or alkoxy.

In certain embodiments, the compound of Formula (I') described above has at least one of the following:
1) R$^2$ is selected from C$_{2-30}$alkyl, —OH, C$_{1-30}$alkoxy, —NO$_2$, alkylthio, sulfoxido, sulfonyl, and amino, where
   a) when R$^2$ is ethyl, then R$^6$ is not methyl or methoxy, and/or
   b) when R$^2$ is methoxy, then R$^6$ is not halo, C$_{1-2}$ alkyl or C$_{1-2}$ alkoxy;
2) R$^1$ is heteroaryl, bridged heterocyclyl, fused heterocyclyl, or cycloheptyl;
3) R$^1$ is heterocyclyl substituted with one halo, amino, hydroxy, alkoxy, —CN, —NO$_2$, alkyl, carboxy, alkylthio, sulfoxido, sulfonyl, sulfinamido, sulfonamido, cycloalkyl, heterocyclyl, heteroaryl, poly(ethylene glycol), and methoxypoly(ethylene glycol),
   where if the substituent is alkyl, the alkyl is further substituted with one substituent selected from halo, amino, alkoxy, —CN, —NO$_2$, carboxy, ester, alkylthio, sulfoxido, sulfonyl, sulfinamido, sulfonamido, cycloalkyl, heterocyclyl, poly(ethylene glycol), methoxypoly(ethylene glycol), pyrrolidinyl and piperidinyl; or the alkyl is substituted with at least one —OR$^{31}$, wherein R$^{31}$ is poly(ethylene glycol) or methoxypoly(ethylene glycol);

4) $R^1$ is amino substituted with at least one substituent selected from alkyl, cycloalkyl, heterocyclyl, heteroaryl, poly(ethylene glycol) or methoxypoly(ethylene glycol) and amino,
  where the alkyl is substituted with at least one substituent selected from halo, amino, hydroxy, alkoxy, —CN, —NO$_2$, amido, carboxy, ester, alkylthio, sulfoxido, sulfonyl, sulfinamido, sulfonamido, cycloalkyl, heterocyclyl, and heteroaryl; or
5) $R^6$ is alkyl substituted with at least one substituent selected from halo, amino, hydroxy, alkoxy, cycloalkoxy, heterocycloalkoxy, aryloxy, heteroaryloxy, poly(ethylene glycol)-oxy, methoxypoly(ethylene glycol)-oxy, —CN, —NO$_2$, oxo, amido, carboxy, ester, alkylthio, sulfoxido, sulfonyl, sulfinamido, sulfonamido, heterocyclyl, cycloalkyl, aryl, heteroaryl, poly(ethylene glycol) and methoxypoly(ethylene glycol).

In certain embodiments, $R^1$ is heterocyclyl substituted with at least one substituent selected from oxo, —OH, —OR$^{28}$, —N(R$^{28}$)$_2$, alkyl, aryl, and heterocyclyl, wherein the alkyl is substituted with at least one substituent selected from —N(R$^{31}$)$_2$, —S(O)$_{0-2}$NR$^{31}$R$^{31}$, —C(O)N(R$^{31}$)$_2$, heterocyclyl, cycloalkyl, pyrrolidinyl and piperidinyl; or the alkyl is substituted with at least one —OR$^{31a}$, wherein R$^{31a}$ is poly(ethylene glycol) or methoxypoly(ethylene glycol); and each R$^{28}$ and R$^{31}$ are independently H or alkyl.

In certain embodiments, $R^1$ is heterocyclyl substituted with at least one substituent selected from oxo, —OH, —OR$^{28}$, —N(R$^{28}$)$_2$, —C(O)OR$^{28}$, alkyl, aryl, and heterocyclyl, wherein the alkyl is substituted with at least one substituent selected from —OH, —N(R$^{31}$)$_2$, —S(O)$_{0-2}$NR$^{31}$R$^{31}$, —C(O)N(R$^{31}$)$_2$, heterocyclyl, cycloalkyl, pyrrolidinyl and piperidinyl; or the alkyl is substituted with at least one —OR$^{31a}$, wherein R$^{31a}$ is poly(ethylene glycol) or methoxypoly(ethylene glycol); and each R$^{28}$ and R$^{31}$ are independently H or alkyl.

In certain embodiments, $R^1$ is —NR$^3$R$^4$, and $R^3$ is H or alkyl unsubstituted or substituted with at least one substituent selected from —OH, —N(R$^{28}$)$_2$, and heteroaryl, and $R^4$ and R$^{28}$ are each independently H or alkyl.

In certain embodiments, $R^1$ is —NR$^3$R$^4$, and $R^3$ is H or alkyl unsubstituted or substituted with at least one substituent selected from —OH, —N(R$^{28}$)$_2$, aryl, and heteroaryl, and $R^4$ and R$^{28}$ are each independently H or alkyl.

In certain embodiments, a compound of Formula (I), or a compound of Formula I and sub-formulae thereof, refers to a compound of Formula (I), and/or Formula (I'), and/or Formula (II) and/or (Formula III) and/or Formula (IV) and/or (Formula V) and/or Formula (VI) and/or Formula (VII) and/or Formula (VIII) and/or Formula (IX) and/or Formula (X) and/or Formula (XI) and/or Formula (XII), as described herein, or any combination thereof.

In certain embodiments, provided is a compound of Formula (II):

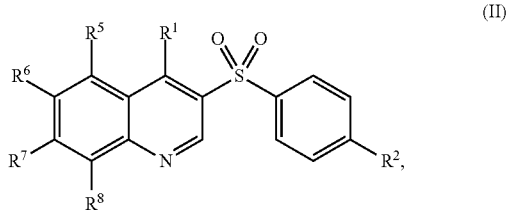

(II)

or a pharmaceutically acceptable salt, isotopically enriched analog, stereoisomer, mixture of stereoisomers, or tautomer thereof, wherein each of $R^1$, $R^2$, $R^5$, $R^6$, $R^7$, and $R^8$ is as defined herein.

In certain embodiments, provided is a compound of Formula (III):

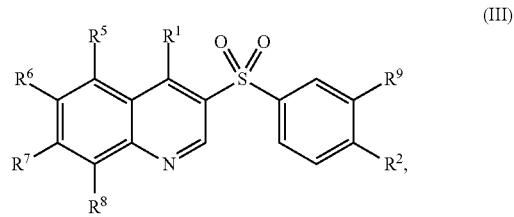

(III)

or a pharmaceutically acceptable salt, isotopically enriched analog, stereoisomer, mixture of stereoisomers, or tautomer thereof, wherein each of $R^1$, $R^2$, $R^5$, $R^6$, $R^7$, $R^8$ and $R^9$ is as defined herein.

In certain embodiments, provided is a compound of Formula (IV):

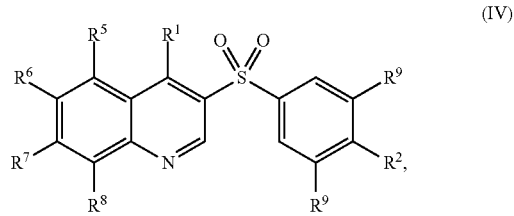

(IV)

or a pharmaceutically acceptable salt, isotopically enriched analog, stereoisomer, mixture of stereoisomers, or tautomer thereof, wherein each of $R^1$, $R^2$, $R^5$, $R^6$, $R^7$, $R^8$ and $R^9$ is as defined herein.

In certain embodiments, $R^1$ is heteroaryl or heterocyclyl, each optionally substituted with a second heterocyclyl, wherein the second heterocyclyl is unsubstituted or substituted with one or more substituents, e.g., selected from —OH, —C(O)Oalkyl, —C(O)NHalkyl, alkyl, aryl, and heterocyclyl;
  wherein the alkyl and heterocyclyl are each unsubstituted or substituted with one or more substituents selected from —OH, alkyl and aryl.

In certain embodiments, $R^1$ is heteroaryl, such as a 5- or 6-membered heteroaryl. In certain embodiments, $R^1$ is heterocyclyl, such as a 5- to 9-membered heterocyclyl, a 5- to 7-membered heterocyclyl, or a 5- to 6-membered heterocyclyl.

In certain embodiments, $R^1$ is heterocyclyl, such as optionally substituted 5- to 7-membered heterocyclyl. In certain embodiments, one of the heterocyclyl substituents is optionally further substituted with a second substituent selected from C$_{3-10}$ cycloalkyl and heterocyclyl. In some embodiments, one heterocyclyl substituent is a sugar moiety, e.g., a hexose. In certain embodiments, one of the second substituents is C$_{3-10}$ cycloalkyl or 5- to 7-membered heterocyclyl. In certain embodiments, one second substituent is 5- to 7-membered heterocyclyl. In some embodiments, one second substituent is a sugar moiety, e.g., a hexose.

In certain embodiments, at least one heterocyclyl substituent is 5- to 7-membered heterocyclyl. In certain embodiments, at least one second substituent is selected from $C_{1-30}$ alkyl, 5- to 7-membered heterocyclyl, and phenyl.

In certain embodiments, $R^1$ is 5- to 7-membered heterocyclyl optionally substituted with one or two substituents, wherein at least one substituent is $C_{1-30}$alkyl. In certain embodiments, $R^1$ is 5- to 7-membered heterocyclyl optionally substituted with one or two substituents, wherein at least one substituent is 5- to 7-membered heterocyclyl. In some embodiments, the 5- to 7-membered heterocyclyl substituent is further substituted with a sugar moiety, e.g., hexose.

In certain embodiments, $R^1$ is

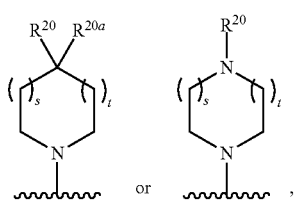

wherein each s and t is independently 0, 1, 2 or 3, provided that the sum of s and t is 1, 2, 3, or 4; $R^{20}$ is selected from alkyl, cycloalkyl, heterocyclyl, aryl, and heteroaryl; and $R^{20a}$ is H, $NH_2$, or OH.

In certain embodiments, $R^1$ is substituted by

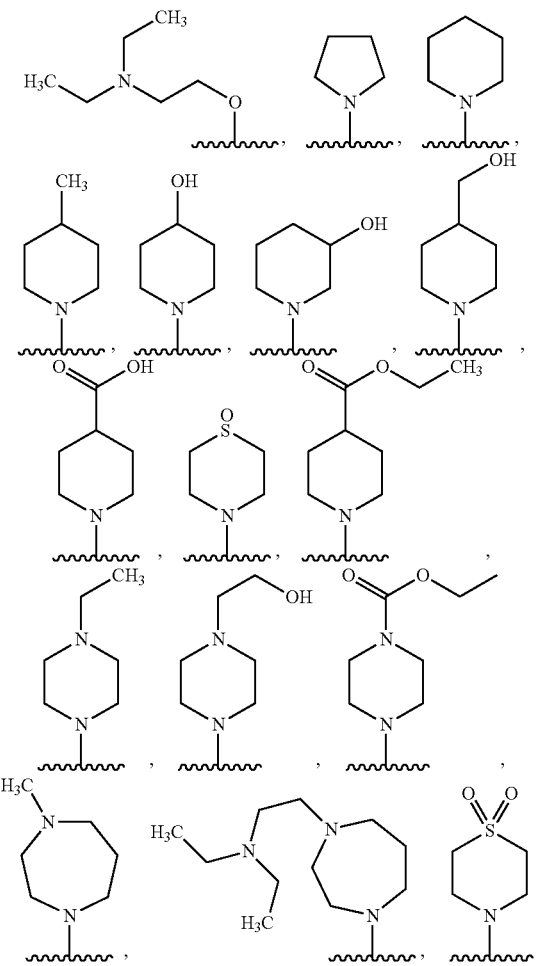

-continued

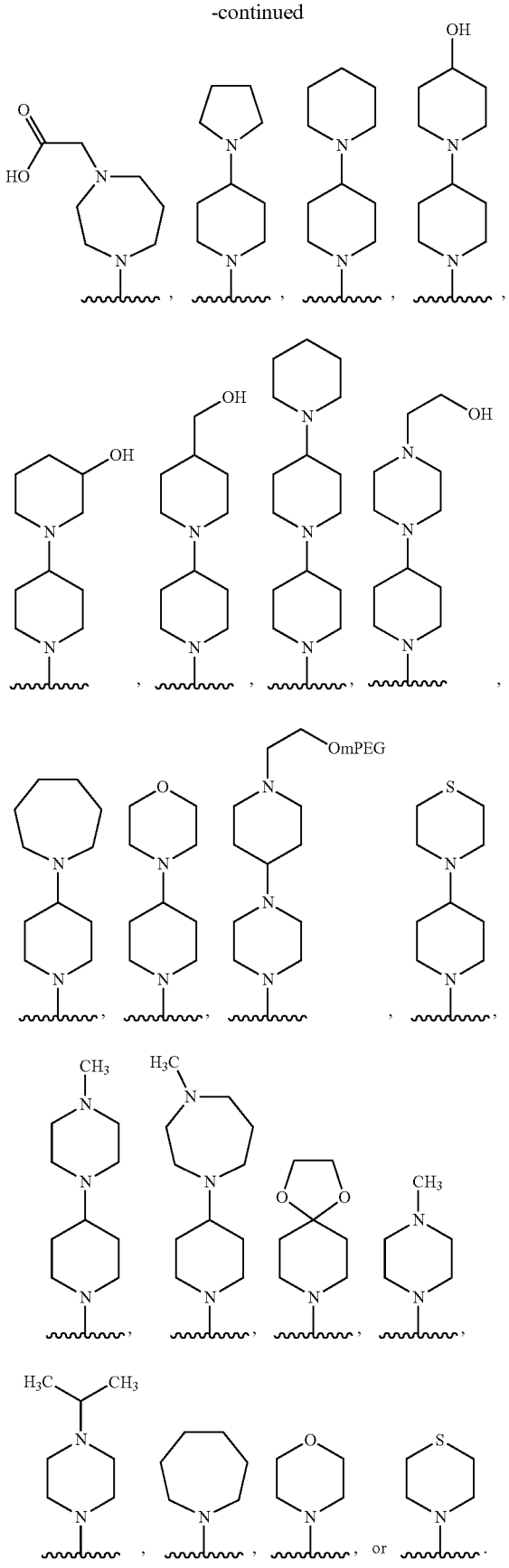

In certain embodiments, $R^1$ is selected from:
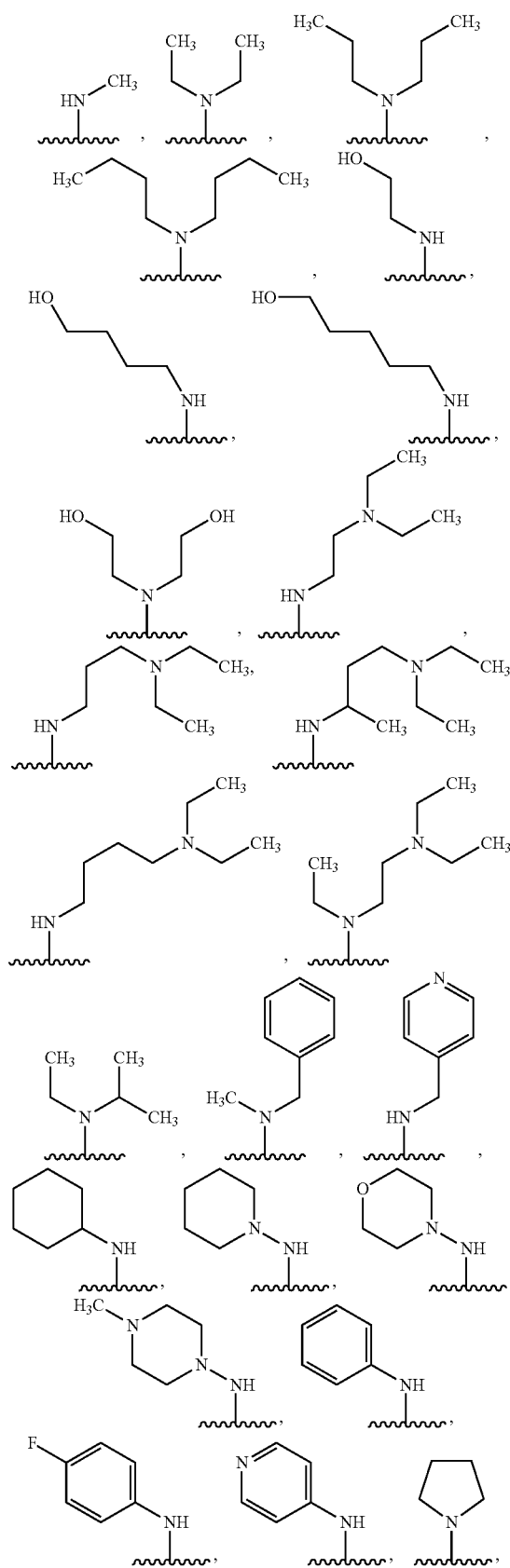
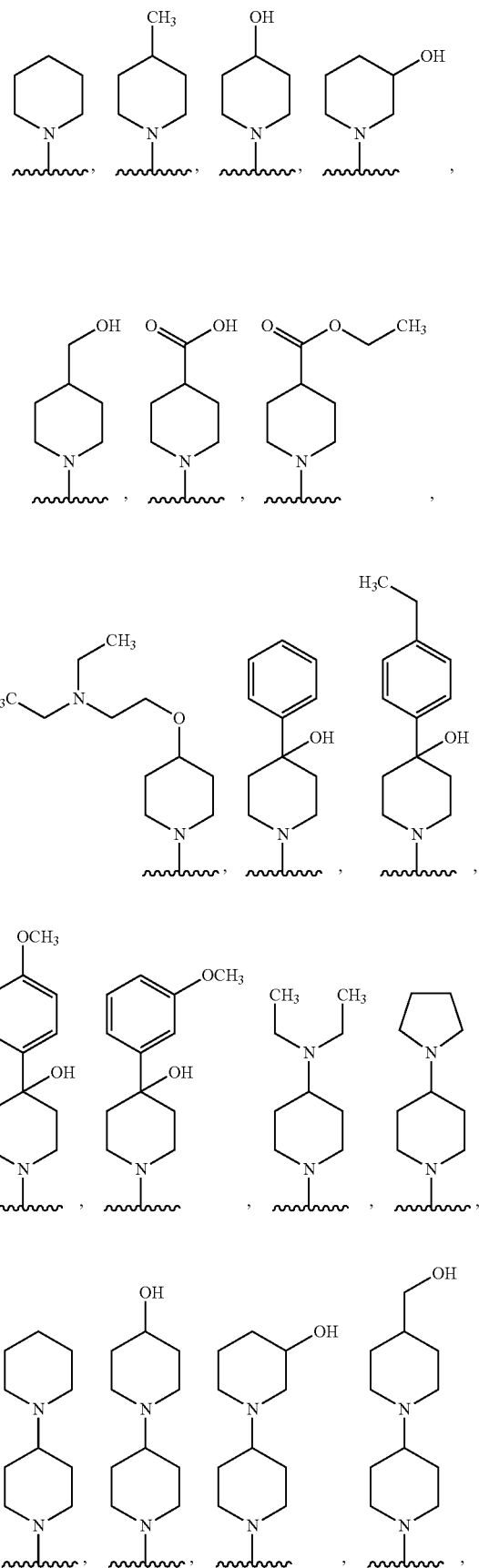

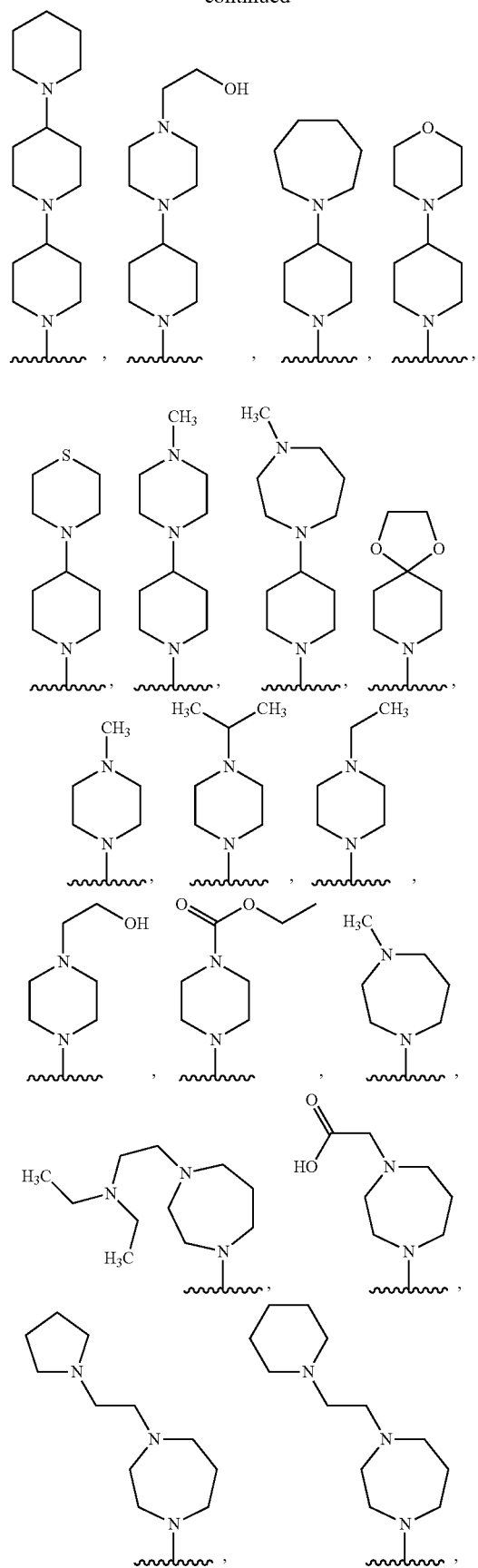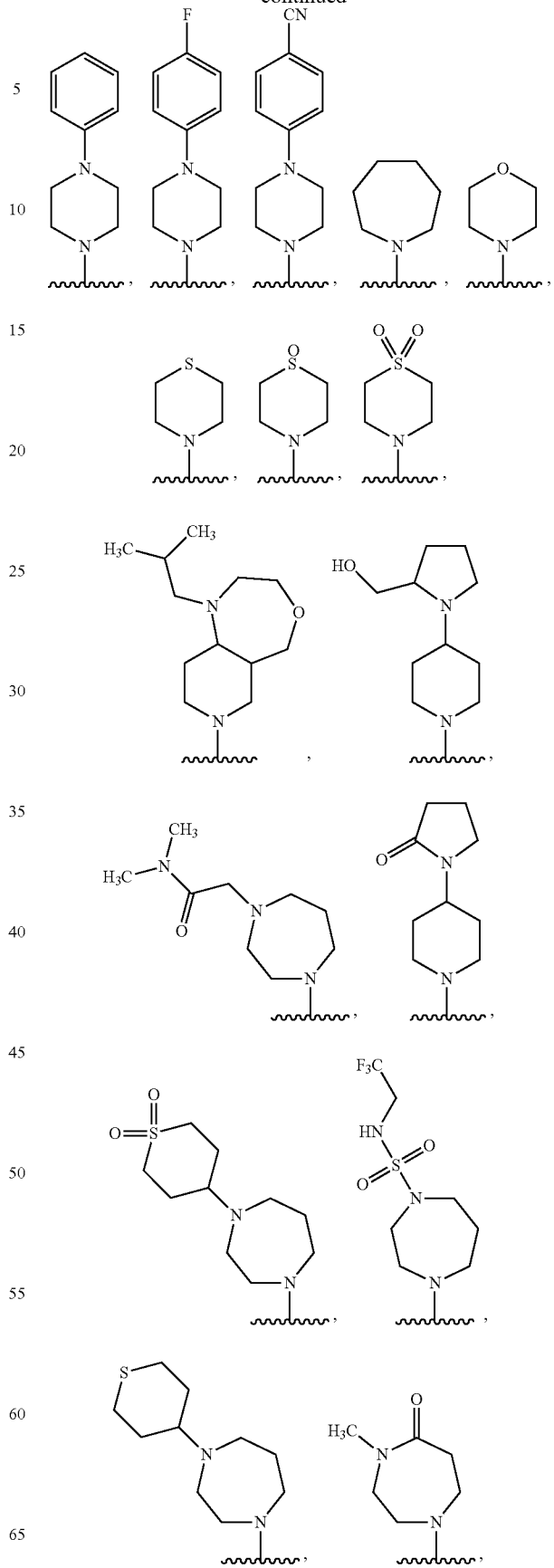

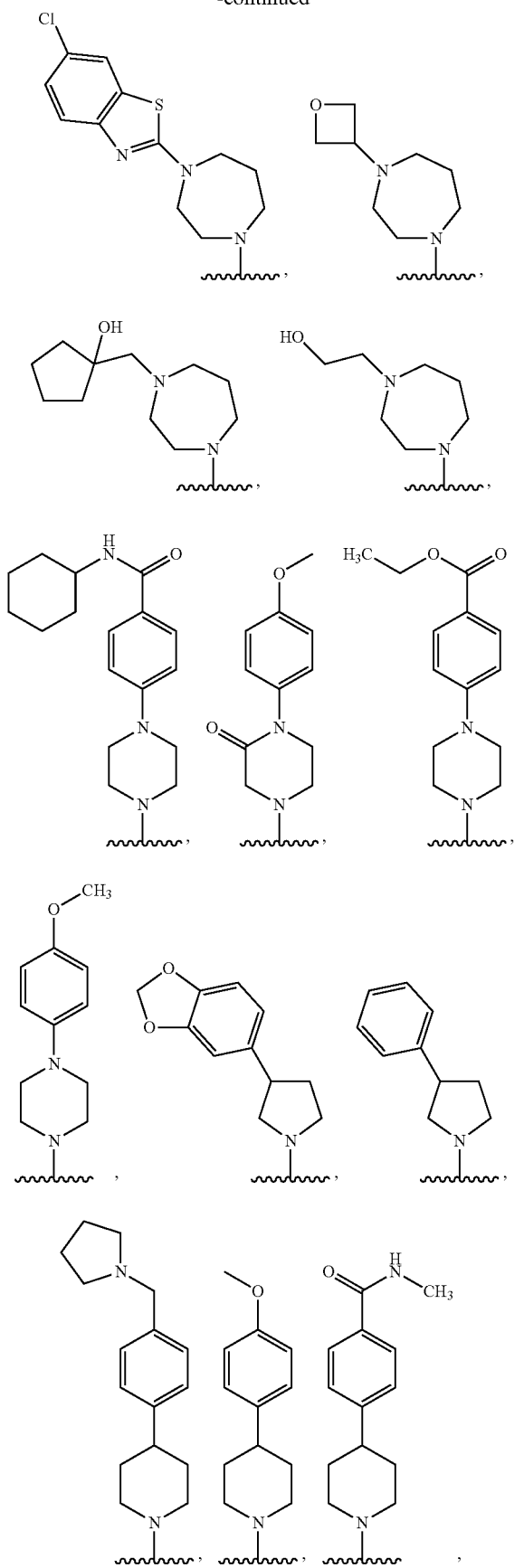
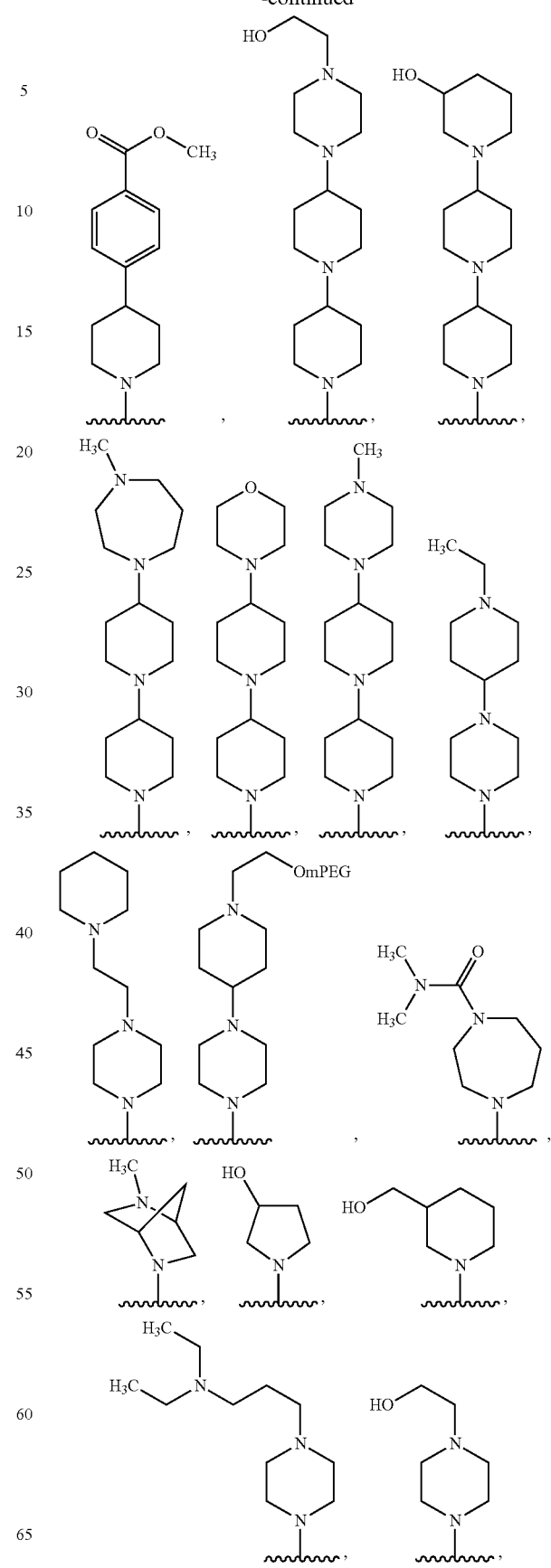

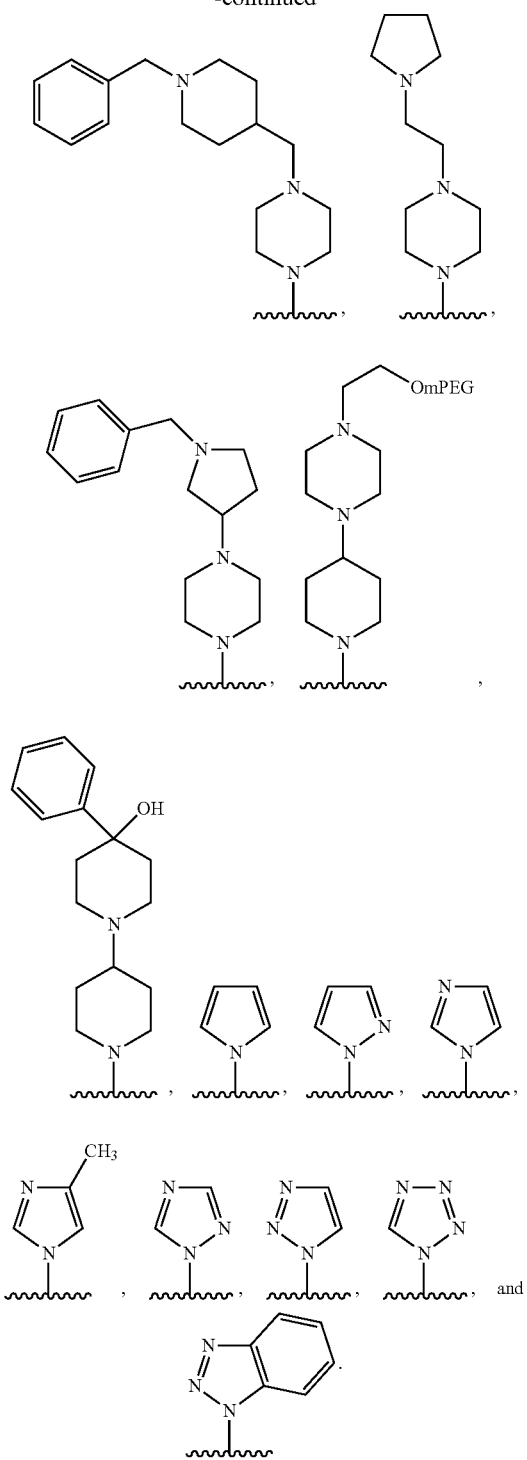
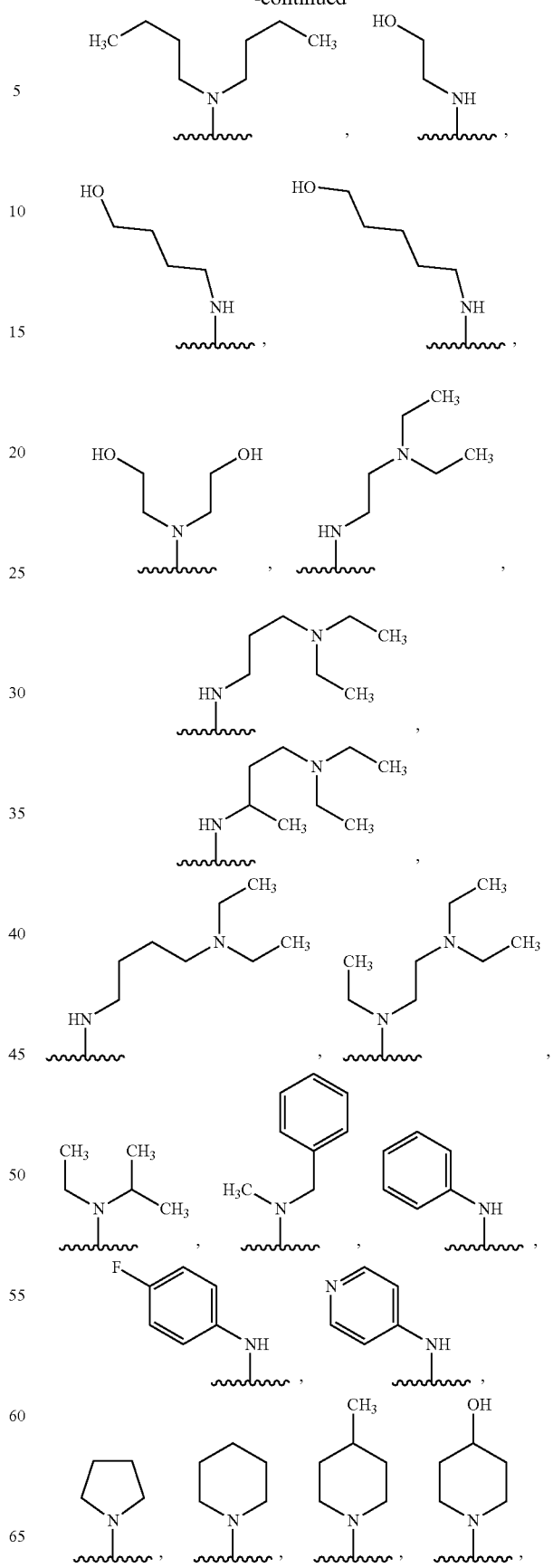
In certain embodiments, R[1] is selected from

-continued
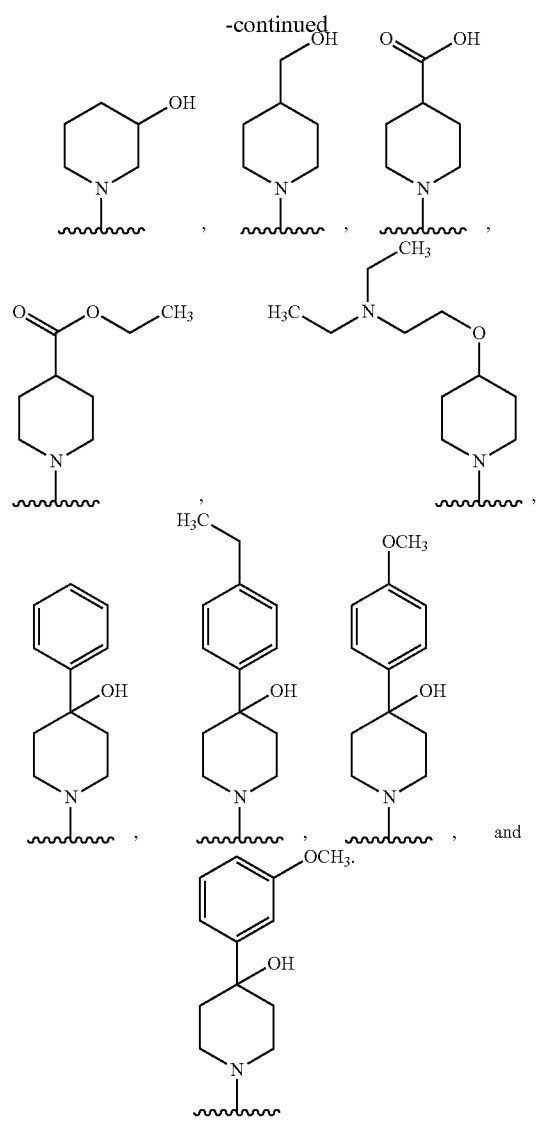
In certain embodiments, R¹ is selected from
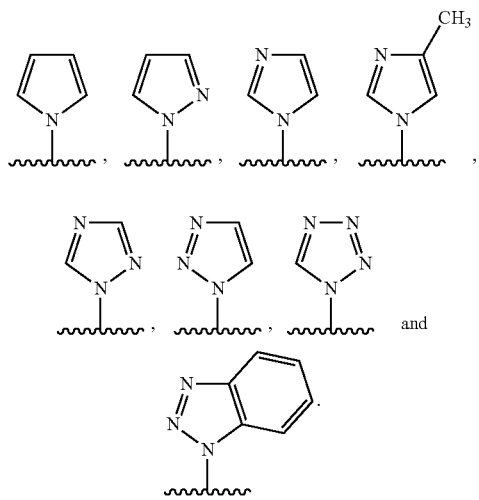
In certain embodiments, R¹ is selected from
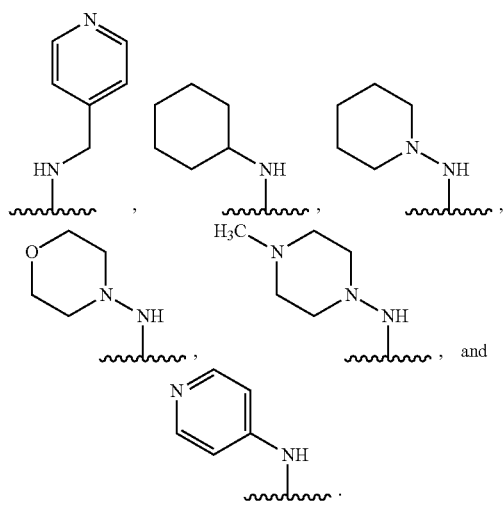
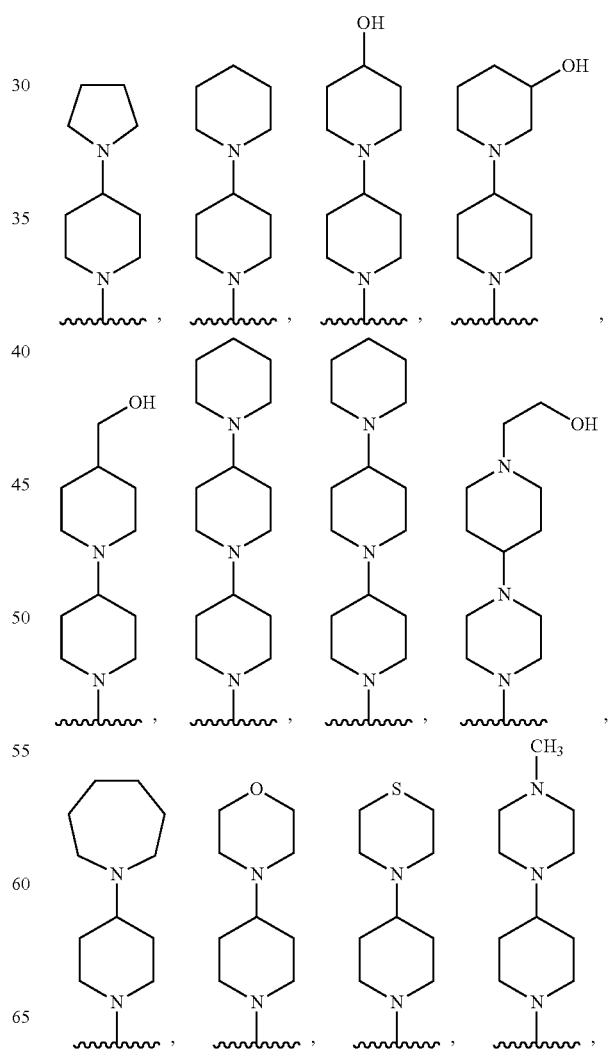

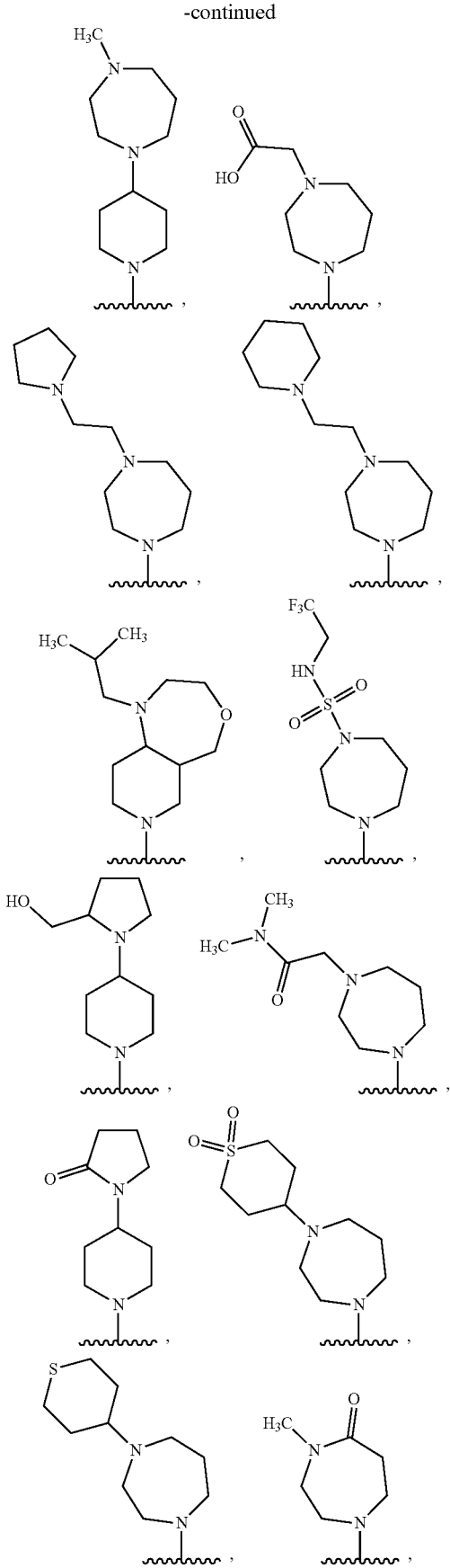
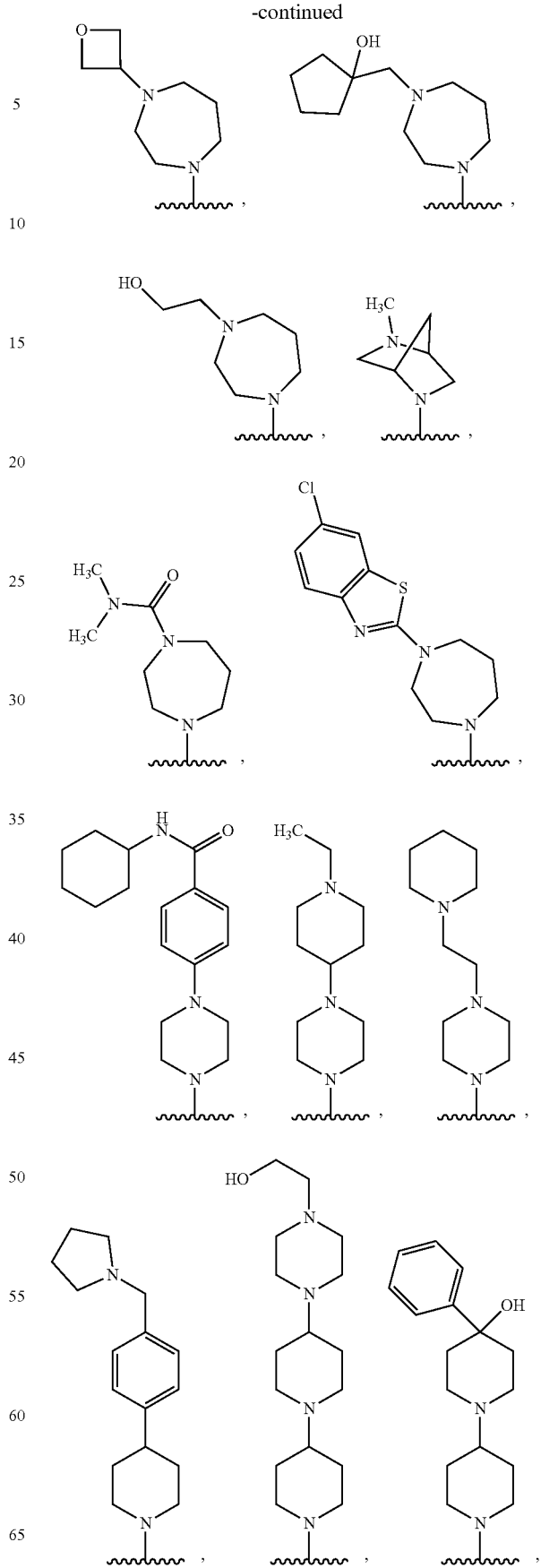

-continued

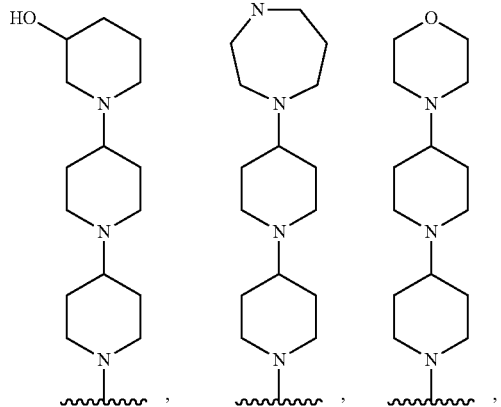

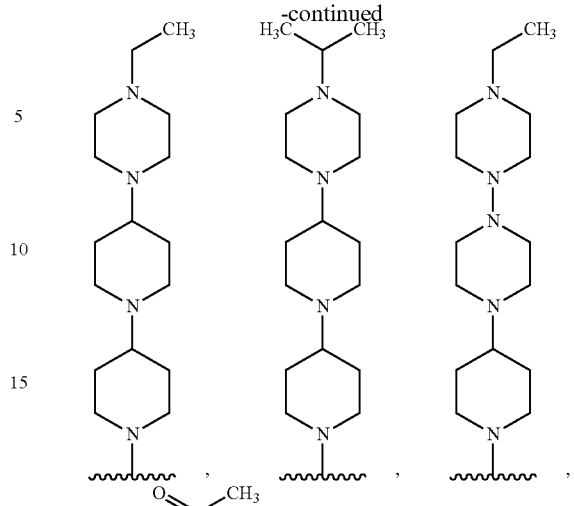

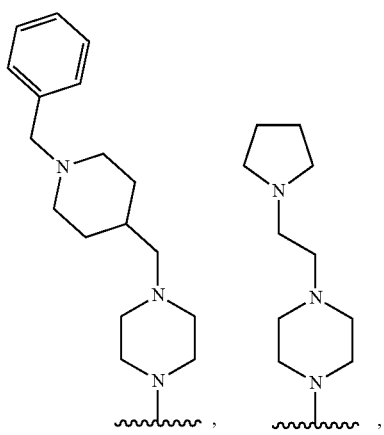

In certain embodiments, $R^2$ is selected from $C_{1-6}$ alkyl, —$NO_2$, —$OR^{18}$, and CN, wherein $R^{18}$ is selected from $C_{1-16}$ alkyl, $C_{1-6}$ haloalkyl, and $C_{1-6}$ aminoalkyl. In certain embodiments, $R^2$ is selected from —$CH_3$, —$CH_2CH_3$, —CN, —$NO_2$, —$OCF_3$, and —$OR^{18}$.

In certain embodiments, $R^2$ is —$O(CH_2)_m CH_3$, wherein m is an integer selected from 1, 2, 3, 4, 5, 6, 7, 8, 9, 10, 11 12, 13, 14, 15, and 16.

In certain embodiments, $R^2$ is amino. In some embodiments, the amino is substituted with one or more substituents selected from alkyl, cycloalkyl, heterocyclyl, aryl, heteroaryl, and amino. In certain embodiments, the amino substituent is selected from cyclohexyl, piperazinyl, piperidinyl, and morpholinyl. In certain embodiments, the amino substituent is alkyl substituted with at least one substituent selected from —C(O)OH, —OH, phenyl and pyridyl, and the phenyl and pyridyl are each independently unsubstituted or substituted with halo, alkyl or OH.

In certain embodiments, $R^6$ is selected from halo, alkyl, $-OR^{17}$, $-S(O)_{0-2}R^{16}$, $-C(O)OR^{15}$, $-NO_2$, and $-C(O)NR^{15}R^{15}$;

$R^{15}$ is selected from H, methyl, ethyl, iPr, $-CH_2CH_2NEt_2$, and $-CH_2CH_2OH$;

$R^{16}$ is methyl; and $R^{17}$ is selected from methyl, trifluoromethyl and butyl.

In certain embodiments, $R^6$ is halo, alkoxy or alkyl. In certain embodiments, $R^6$ is F, alkyl or alkoxy. In certain embodiments, $R^6$ is $-OR^{17}$, and $R^{17}$ is haloalkyl. In certain embodiments, $R^6$ is selected from $-CH_2CN$, $-OCF_3$ and $NO_2$.

In certain embodiments, $R^6$ is $-SCH_3$, $-SOCH_3$, or $-SO_2CH_3$. In certain embodiments, $R^6$ is $-S(O)_{0-2}R^{16}$. In certain embodiments, $R^6$ is $-S(O)R^{16}$. In certain embodiments, $R^6$ is $-S(O)_2R^{16}$. In certain embodiments, $R^6$ is

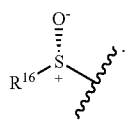

In certain embodiments, $R^6$ is

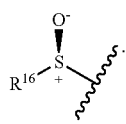

In certain embodiments, $R^6$ is $-C(O)OR^{15}$ where $R^{15}$ is H or alkyl. In certain embodiments, $R^6$ is $-C(O)OH$, $-C(O)OCH_3$ or $-C(O)OCH_2CH_3$.

In certain embodiments, $R^6$ is $-C(O)NR^{15}R^{15}$. In certain embodiments, each $R^{15}$ is independently selected from H, alkyl, and heterocyclyl. In other embodiments, $R^6$ is

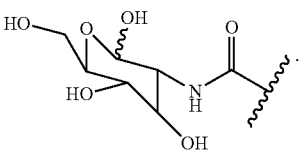 [SMILES: *C(=O)NC1C(O)OC(CO)C(O)C1O]

In certain embodiments, one $R^{15}$ is a sugar moiety. In certain embodiments, one $R^{16}$ is a sugar moiety. In certain embodiments, $R^6$ is a sugar moiety. In certain embodiments, one or more of $R^6$, $R^{15}$, and $R^{16}$ is a hexose.

In certain embodiments, $R^6$ is selected from

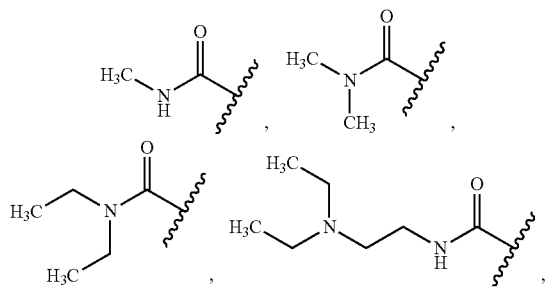

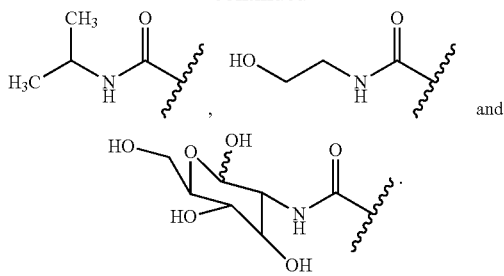

In certain embodiments, provided is a compound of Formula (V):

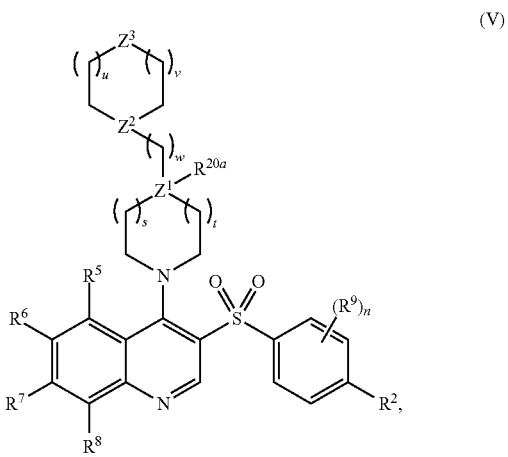

or a pharmaceutically acceptable salt, isotopically enriched analog, stereoisomer, mixture of stereoisomers, or tautomer thereof, wherein each of s, t, u, and v is independently 0, 1, 2, or 3, provided that the sum of s and t is 1, 2, 3 or 4, and the sum of u and v is 1, 2, 3 or 4;

w is 0, 1, 2, or 3;

$Z^1$ is C or N, when $Z^1$ is C, $R^{20a}$ is H, halo, oxo, $-NH_2$, $-OH$, $-CN$, $-NO_2$, $-NHR^{28}$, $-N(R^{28})_2$, $-C(O)R^{28}$, $-C(O)OR^{28}$, $-C(O)OH$, $-OC(O)R^{28}$, $-S(O)_{0-2}R^{28}$, $-NHS(O)_{0-2}R^{28}$, $-S(O)_{0-2}NHR^{28}$, $-NHS(O)_{0-2}NHR^{28}$, $-C(O)NH_2$, $-C(O)NHR^{28}$, $-C(O)N(R^{28})_2$, $-NHC(O)R^{28}$, $-OC(O)NHR^{28}$, $-NHC(O)OR^{28}$, $-OC(O)N(R^{28})_2$, $-NR^{32}C(O)NH_2$, $-NR^{32}C(O)NHR^{28}$, $-NR^{32}C(O)N(R^{28})_2$, poly(ethylene glycol), methoxypoly(ethylene glycol), $C_{1-30}$ alkyl optionally substituted with OH or $-C(O)OH$, or $C_{1-30}$ heteroalkyl optionally substituted with OH or $-C(O)OH$, wherein $R^{32}$ is H or $C_{1-4}$ alkyl, and $R^{28}$ is $C_{1-4}$ alkyl;

when $Z^1$ is N, $R^{20a}$ is absent;

$Z^2$ is C or N;

$Z^3$ is $CH_2$, $CHR^{25}$, $CR^{25}R^{25}$, or $NR^{25}$, O, or $S(O)_{0-2}$ and $R^{25}$ is selected from H and alkyl; and each of n, $R^2$, $R^5$, $R^6$, $R^7$, $R^8$, and $R^9$ is as defined herein.

In certain embodiments, provided is a compound of Formula (V):

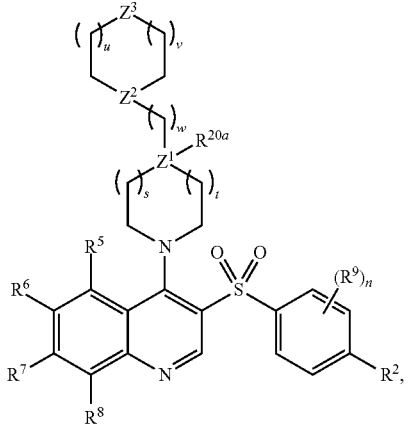

(V)

or a pharmaceutically acceptable salt, isotopically enriched analog, stereoisomer, mixture of stereoisomers, or tautomer thereof,
wherein
each of s, t, u, and v is independently 0, 1, 2, or 3, provided that the sum of s and t is 1, 2, 3 or 4, and the sum of u and v is 1, 2, 3 or 4;
w is 0, 1, 2, or 3;
$Z^1$ is C or N,
when $Z^1$ is C, $R^{20a}$ is H, halo, oxo, —$NH_2$, —OH, —CN, —$NO_2$, —$OR^{28}$, —$NHR^{28}$, —$N(R^{28})_2$, —$C(O)R^{28}$, —$C(O)OR^{28}$, —C(O)OH, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NH_2$, —$C(O)NHR^{28}$, —$C(O)N(R^{28})_2$, —$NHC(O)R^{28}$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, poly(ethylene glycol), methoxypoly(ethylene glycol), $C_{1-30}$ alkyl optionally substituted with OH or —C(O)OH, or $C_{1-30}$ heteroalkyl optionally substituted with OH or —C(O)OH, wherein $R^{32}$ is H or $C_{1-4}$ alkyl, and $R^{28}$ is $C_{1-4}$ alkyl;
when $Z^1$ is N, $R^{20a}$ is absent;
$Z^2$ is C or N;
$Z^3$ is $CH_2$, $CHR^{25}$, $CR^{25}R^{25}$, or $NR^{25}$, O, or $S(O)_{0-2}$ and $R^{25}$ is selected from H and alkyl;
n is 0, 1, 2, 3 or 4;
$R^2$ is selected from H, halo, alkyl, alkenyl, alkynyl, —OH, alkoxy, —CN, —$NO_2$, alkylthio, sulfoxido, sulfonyl, and amino;
$R^5$, $R^7$ and $R^8$ are each independently selected from H, halo, alkyl, alkenyl, alkynyl, hydroxy, alkoxy, alkylthio, sulfoxido, sulfonyl, carboxy, ester, —CN, —$NO_2$, amino, and amido;
$R^6$ is selected from H, halo, alkyl, hydroxy, alkoxy, alkylthio, sulfoxido, sulfonyl, carboxy, ester, —CN, —$NO_2$, amino, amido, sulfinamido, sulfonamido, heterocyclyl, heteroaryl, poly(ethylene glycol), and methoxypoly(ethylene glycol), or
$R^6$ and $R^7$ together with atoms to which they are attached form a cycloalkyl, heterocyclyl, aryl, or heteroaryl; and
each $R^9$ is independently selected from halo, alkyl, —OH, alkoxy, —CN, and amino.
In certain embodiments, s is 0 and t is 0. In certain embodiments, s is 0 and t is 1. In certain embodiments, s is 1 and t is 1. In certain embodiments, s is 2 and t is 1. In certain embodiments, s is 3 and t is 1. In certain embodiments, s is 2 and t is 2.

In certain embodiments, w is 0. In certain embodiments, w is 1. In certain embodiments, w is 2. In certain embodiments, w is 3.

In certain embodiments, u is 0 and v is 0. In certain embodiments, u is 0 and v is 1. In certain embodiments, u is 1 and v is 1. In certain embodiments, u is 2 and v is 1. In certain embodiments, u is 3 and v is 1. In certain embodiments, s is 2 and u is 2.

In certain embodiments, provided is a compound of a formula (VI):

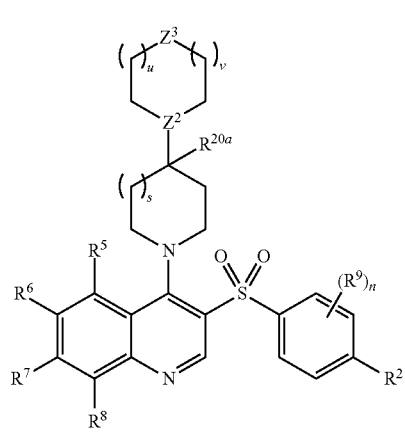

(VI)

or a pharmaceutically acceptable salt, isotopically enriched analog, stereoisomer, mixture of stereoisomers, or tautomer thereof, wherein each of n, s, u, v, $R^2$, $R^5$, $R^6$, $R^7$, $R^8$, $R^9$, $R^{20a}$, $Z^2$, and $Z^3$ is as defined herein.

In certain embodiments, provided is a compound of a formula (VII):

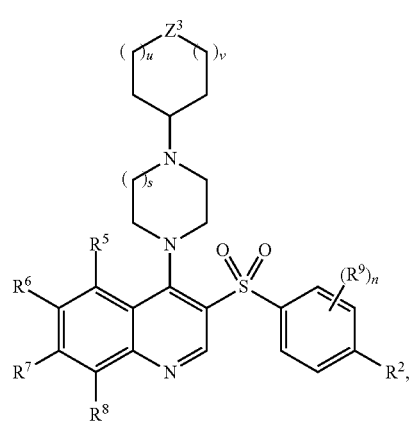

(VII)

or a pharmaceutically acceptable salt, isotopically enriched analog, stereoisomer, mixture of stereoisomers, or tautomer thereof, wherein each of n, s, u, v, $R^2$, $R^5$, $R^6$, $R^7$, $R^8$, $R^9$, and $Z^3$ is as defined herein.

In certain embodiments, provided is a compound of a formula (VIII):

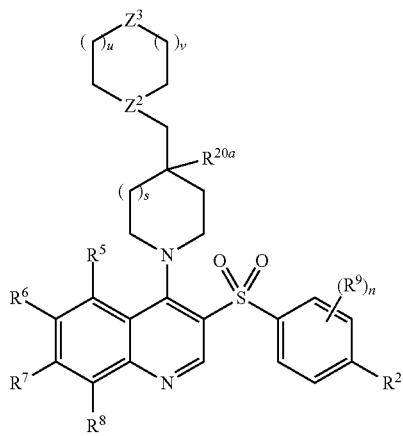

(VIII)

or a pharmaceutically acceptable salt, isotopically enriched analog, stereoisomer, mixture of stereoisomers, or tautomer thereof, wherein each of n, s, u, v, $R^2$, $R^5$, $R^6$, $R^7$, $R^8$, $R^9$, $R^{20a}$, $Z^2$, and $Z^3$ is as defined herein.

In certain embodiments, provided is a compound of a formula (IX):

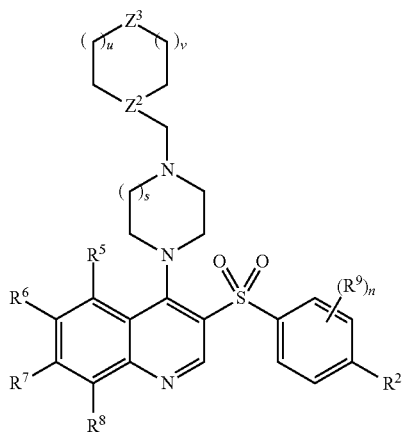

(IX)

or a pharmaceutically acceptable salt, isotopically enriched analog, stereoisomer, mixture of stereoisomers, or tautomer thereof, wherein each of n, s, u, v, $R^2$, $R^5$, $R^6$, $R^7$, $R^8$, $R^9$, $Z^2$, and $Z^3$ is as defined herein.

In certain embodiments, provided is a compound of a formula (X):

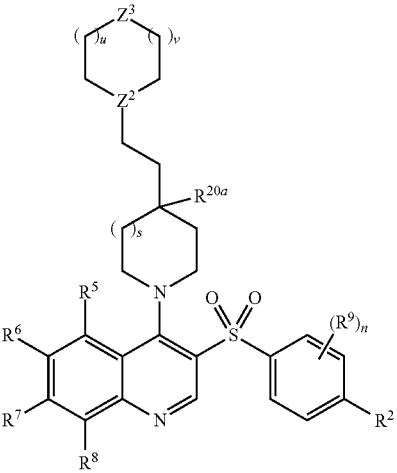

(X)

or a pharmaceutically acceptable salt, isotopically enriched analog, stereoisomer, mixture of stereoisomers, or tautomer thereof, wherein each of n, s, u, v, $R^2$, $R^5$, $R^6$, $R^7$, $R^8$, $R^9$, $R^{20a}$, $Z^2$, and $Z^3$ is as defined herein.

In certain embodiments, provided is a compound of a formula (XI):

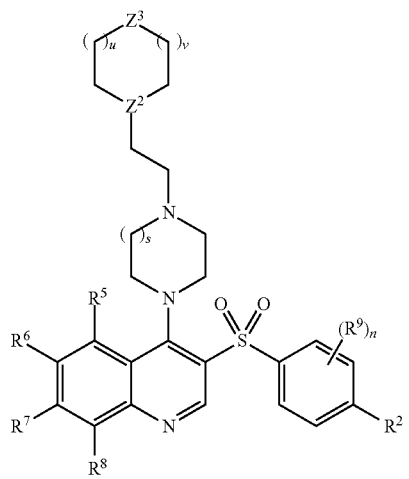

(XI)

or a pharmaceutically acceptable salt, isotopically enriched analog, stereoisomer, mixture of stereoisomers, or tautomer thereof, wherein each of n, s, u, v, $R^2$, $R^5$, $R^6$, $R^7$, $R^8$, $R^9$, $Z^2$, and $Z^3$ is as defined herein.

In certain embodiments, provided is a compound of Formula (I):

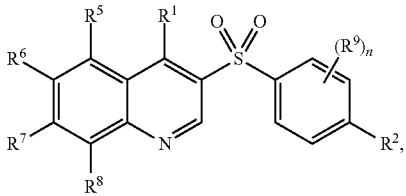

or a pharmaceutically acceptable salt, isotopically enriched analog, stereoisomer, mixture of stereoisomers, or tautomer thereof;
wherein
$R^2$ is —$OC_{4-30}$ alkyl; and
each of n, $R^1$, $R^5$, $R^6$, $R^7$, $R^8$, and $R^9$ is as defined herein.

In certain embodiments, provided is a compound of Formula (I):

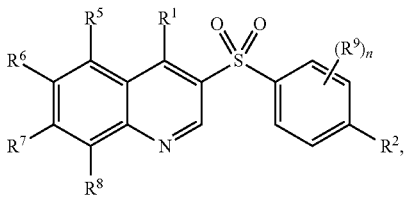

or a pharmaceutically acceptable salt, isotopically enriched analog, stereoisomer, mixture of stereoisomers, or tautomer thereof;
wherein
$R^6$ is —$NO_2$, ester, amido, alkylthio, sulfoxido, or sulfonyl; and
each of n, $R^1$, $R^5$, $R^5$, $R^7$, $R^8$, $R^9$ is as defined herein.

In certain embodiments, $R^9$ is —OH or —O—$C_{1-10}$ alkyl. In certain embodiments, each $R^9$ is independently halo. In certain embodiments, n is 1 or 2 and each $R^9$ is independently halo. In certain embodiments, n is 1 or 2 and each $R^9$ is fluoro.

In certain embodiments, provided is a compound of Formula (I):

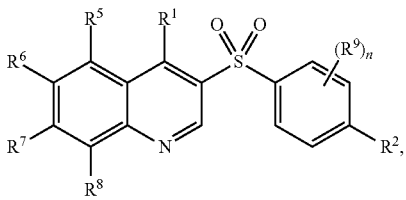

or a pharmaceutically acceptable salt, isotopically enriched analog, stereoisomer, mixture of stereoisomers, or tautomer thereof;
wherein
$R^1$ is selected from —$NR^3R^4$, heterocyclyl optionally substituted with one to five $R^{20}$, and heteroaryl optionally substituted with one to five $R^{21}$;

$R^2$ is selected from H, halo, $C_{1-30}$ alkyl optionally substituted with one to five $R^{19}$, $C_{1-30}$ heteroalkyl optionally substituted with one to five $R^{19}$, —OH, —$OR^{18}$, —CN, —$NO_2$, —$NH_2$, —$S(O)_{0-2}R^{18}$, and —$NR^{11}R^{18}$;

$R^3$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$, $R^4$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), methoxypoly(ethylene glycol), and —$NR^{13}R^{14}$;

$R^5$, $R^7$ and $R^8$ are each independently selected from H, halo, $C_{1-30}$ alkyl optionally substituted with one to five $R^{29}$, $C_{1-30}$ heteroalkyl optionally substituted with one to five $R^{29}$, —$OR^{15}$, —$S(O)_{0-2}R^{16}$, —$C(O)OR^{15}$, —$OC(O)R^{16}$, —CN, —$NO_2$, —$NR^{15}R^{15}$, and —$C(O)NR^{15}R^{15}$;

$R^6$ is selected from H, halo, $C_{1-30}$ alkyl optionally substituted with one to five $R^{29}$, $C_{1-30}$ heteroalkyl optionally substituted with one to five $R^{29}$, —$OR^{17}$, —$S(O)_{0-2}R^{16}$, —$C(O)OR^{15}$, —$OC(O)R^{16}$, —CN, —$NO_2$, —$NR^{15}R^{15}$, —$C(O)NR^{15}R^{15}$, —$NR^{15}C(O)R^{16}$, —$S(O)_{0-2}NR^{15}R^{15}$, —$NR^{15}S(O)_{0-2}R^{16}$, heterocyclyl optionally substituted with one to five $R^{29}$, heteroaryl optionally substituted with one to five $R^{30}$, poly(ethylene glycol), and methoxypoly(ethylene glycol), or $R^6$ and $R^7$ together with atoms to which they are attached form $C_{5-10}$ cycloalkyl optionally substituted with one to five $R^{29}$, heterocyclyl optionally substituted with one to five $R^{29}$, aryl optionally substituted with one to five $R^{30}$, or heteroaryl optionally substituted with one to five $R^{30}$;

$R^9$ is independently selected from halo, $C_{1-8}$ alkyl optionally substituted with one to five $R^{22}$, —OH, —$OR^{10}$, —CN, and —$NR^{11}R^{12}$;

n is 0, 1, 2, 3 or 4;

$R^{10}$ is independently selected from $C_{1-10}$ alkyl optionally substituted with one to five $R^{22}$, and $C_{3-10}$ cycloalkyl optionally substituted with one to five $R^{22}$;

$R^{11}$ and $R^{12}$ are each H or $C_{1-6}$ alkyl optionally substituted with one to five $R^{22}$;

$R^{13}$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$;

$R^{14}$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), and methoxypoly(ethylene glycol);

each $R^{15}$ is independently selected from H, $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);

$R^{16}$ is selected from $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);

$R^{17}$ is selected from H, $C_{1-30}$ alkyl optionally substituted with one to five $R^{27}$, $C_{1-30}$ heteroalkyl optionally substituted with one to five $R^{27}$, $C_{3-10}$ cycloalkyl optionally substituted with one to five $R^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol);

$R^{18}$ is selected from $C_{1-30}$ alkyl optionally substituted with one to five $R^{19}$ and $C_{1-30}$ heteroalkyl optionally substituted with one to five $R^{19}$;

each $R^{20}$ is independently selected from halo, oxo, —$NH_2$, —OH, —CN, —$NO_2$, —$OR^{28}$, —$NHR^{28}$, —$N(R^{28})_2$, —$C(O)R^{28}$, —$C(O)OR^{28}$, —C(O)OH, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NH_2$, —$C(O)NHR^{28}$, —$C(O)N(R^{28})_2$, —$NHC(O)R^{28}$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{21}$ is independently selected from halo, —$NH_2$, —OH, —CN, —$NO_2$, —$OR^{28}$, —$NHR^{28}$, —$N(R^{28})_2$, —$C(O)R^{28}$, —$C(O)OR^{28}$, —C(O)OH, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NHR^{28}$, —$NHC(O)R^{28}$, —$C(O)N(R^{28})_2$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-6}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, and heteroaryl optionally substituted with one to five $R^{26}$, poly(ethylene glycol), and methoxypoly(ethylene glycol);

each $R^{19}$ or $R^{22}$ is independently selected from halo, —$NH_2$, —OH, —CN, —$NO_2$, oxo, $C_{1-4}$ alkyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl)$_2$, —C(O)—$C_{1-4}$ alkyl, —C(O)O—$C_{1-4}$ alkyl, —C(O)OH, —$S(O)_{0-2}$—$C_{1-4}$ alkyl, —$NHS(O)_{0-2}$—$C_{1-4}$ alkyl, —$S(O)_{0-2}NH$—$C_{1-4}$ alkyl, —$NHS(O)_{0-2}NH$—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$ haloalkyl, —N($C_{1-4}$ haloalkyl)$_2$, —C(O)—$C_{1-4}$ haloalkyl, —$S(O)_{0-2}$—$C_{1-4}$ haloalkyl, —$NHS(O)_{0-2}$—$C_{1-4}$ haloalkyl, —$S(O)_{0-2}$NH—$C_{1-4}$ haloalkyl, —$NHS(O)_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl)$_2$, —OC(O)NH—$C_{1-4}$ haloalkyl, —NHC(O)O—$C_{1-4}$ haloalkyl, —OC(O)N($C_{1-4}$ haloalkyl)$_2$, and $C_{3-10}$ cycloalkyl;

each $R^{25}$ is independently selected from halo, —$NH_2$, —OH, —CN, —$NO_2$, oxo, —$NHR^{31}$, —$N(R^{31})_2$, —$C(O)R^{31}$, —$C(O)OR^{31}$, —C(O)OH, —$S(O)_{0-2}R^{31}$, —$NR^{32}S(O)_{0-2}R^{31}$, —$S(O)_{0-2}NR^{32}R^{31}$, —$NR^{32}S(O)_{0-2}NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)OR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_3$ to cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{26}$ is independently selected from halo, —$NH_2$, —OH, —CN, —$NO_2$, —$NHR^{31}$, —$N(R^{31})_2$, —$C(O)R^{31}$, —$C(O)OR^{31}$, —C(O)OH, —$S(O)_{0-2}R^{31}$, —$NR^{32}S(O)_{0-2}R^{31}$, —$S(O)_{0-2}NR^{32}R^{31}$, —$NR^{32}S(O)_{0-2}NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)OR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_3$ to cycloalkyl optionally substituted with one to five $R^{33}$, heterocyclyl optionally substituted with one to five $R^{33}$, aryl optionally substituted with one to five $R^{34}$, and heteroaryl optionally substituted with one to five $R^{34}$, poly(ethylene glycol), and methoxypoly(ethylene glycol);

each $R^{31}$ is independently selected $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol) and methoxypoly(ethylene glycol);

each $R^{32}$ is independently selected H and $C_{1-4}$ alkyl;

each $R^{23}$, $R^{27}$, $R^{29}$ or $R^{33}$ is independently selected from halo, —$NH_2$, —OH, —CN, —$NO_2$, oxo, $C_{1-4}$ alkyl optionally substituted with phenyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl)$_2$, —C(O)—$C_{1-4}$ alkyl, —C(O)O—$C_{1-4}$ alkyl, —C(O)OH, —$S(O)_{0-2}$—$C_{1-4}$ alkyl, —NH$S(O)_{0-2}$—$C_{1-4}$ alkyl, —$S(O)_{0-2}$NH—$C_{1-4}$ alkyl, —$NHS(O)_{0-2}$NH—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$ haloalkyl, —N($C_{1-4}$ haloalkyl)$_2$, —C(O)—$C_{1-4}$ haloalkyl, —$S(O)_{0-2}$—$C_{1-4}$ haloalkyl, —$NHS(O)_{0-2}$—$C_{1-4}$ haloalkyl, —$S(O)_{0-2}$NH—$C_{1-4}$ haloalkyl, —$NHS(O)_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl)$_2$, —OC(O)NH—$C_{1-4}$ haloalkyl, —NHC(O)O—$C_{1-4}$ haloalkyl, —OC(O)N($C_{1-4}$ haloalkyl)$_2$, $C_{3-10}$ cycloalkyl, heterocyclyl, aryl heteroaryl, —$(CH_2)_{1-30}$—C(O)OH, —$(CH_2)_{0-4}$—O-poly(ethylene glycol), methoxypoly(ethylene glycol)-O—$(CH_2)_{0-4}$—, and sugar moiety;

each $R^{24}$, $R^{30}$ or $R^{34}$ is independently selected from halo, —$NH_2$, —OH, —CN, —$NO_2$, $C_{1-4}$ alkyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl)$_2$, —C(O)—$C_{1-4}$ alkyl, —C(O)OH, —C(O)O—$C_{1-4}$ alkyl, —S(O)$_{0-2}$—$C_{1-4}$ alkyl, —NHS(O)$_{0-2}$—$C_{1-40}$ alkyl, —S(O)$_{0-2}$NH—$C_{1-4}$ alkyl, —NHS(O)$_{0-2}$NH—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$ haloalkyl, —N($C_{1-4}$ haloalkyl)$_2$, —C(O)—$C_{1-4}$ haloalkyl, —S(O)$_{0-2}$—$C_{1-4}$ haloalkyl, —NHS(O)$_{0-2}$—$C_{1-40}$ haloalkyl, —S(O)$_{0-2}$NH—$C_{1-4}$ haloalkyl, —NHS(O)$_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl)$_2$, —OC(O)NH—$C_{1-4}$ haloalkyl, —NHC(O)O—$C_{1-4}$ haloalkyl, —OC(O)N($C_{1-4}$ haloalkyl)$_2$, $C_{3-10}$ cycloalkyl, heterocyclyl, aryl, heteroaryl, —(CH$_2$)$_{1-30}$—C(O)OH, —(CH$_2$)$_{0-4}$—O-poly(ethylene glycol), —(CH$_2$)$_{0-4}$—O-methoxypoly(ethylene glycol) and sugar moiety; and each $R^{28}$ is independently selected from $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol).

In certain embodiments, provided is a compound of Formula (I):

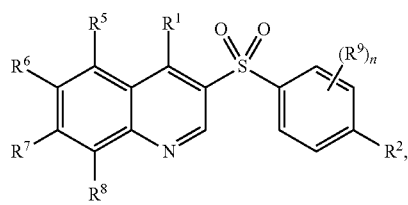

(I)

or a pharmaceutically acceptable salt, isotopically enriched analog, stereoisomer, mixture of stereoisomers, or tautomer thereof;
wherein
n is 0, 1, 2, 3 or 4;
$R^1$ is selected from —NR$^3$R$^4$, heterocyclyl optionally substituted with one to five $R^{20}$, and heteroaryl optionally substituted with one to five $R^{21}$;
$R^2$ is selected from H, halo, $C_{1-30}$ alkyl optionally substituted with one to five $R^{19}$, $C_{1-30}$ heteroalkyl optionally substituted with one to five $R^{19}$, —OH, —OR$^{18}$, —CN, —NO$_2$, —S(O)$_{0-2}$R$^{18}$, and —NR$^{11}$R$^{18}$;
$R^3$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$;
$R^4$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), methoxypoly(ethylene glycol), and —NR$^{13}$R$^{14}$;

$R^5$, $R^7$ and $R^8$ are each independently selected from H, halo, $C_{1-30}$ alkyl optionally substituted with one to five $R^{29}$, $C_{1-30}$ heteroalkyl optionally substituted with one to five $R^{29}$, —OR$^{15}$, —S(O)$_{0-2}$R$^{16}$, —C(O)OR$^{15}$, —OC(O)R$^{16}$, —CN, —NO$_2$, —NR$^{15}$R$^{15}$, and —C(O)NR$^{15}$R$^{15}$;
$R^6$ is selected from H, halo, $C_{1-30}$ alkyl optionally substituted with one to five $R^{29}$, $C_{1-30}$ heteroalkyl optionally substituted with one to five $R^{29}$, —OR$^{17}$, —S(O)$_{0-2}$R$^{16}$, —C(O)OR$^{15}$, —OC(O)R$^{16}$, —CN, —NO$_2$, —NR$^{15}$R$^{15}$, —C(O)NR$^{15}$R$^{15}$, —NR$^{15}$C(O)R$^{16}$, —S(O)$_{0-2}$NR$^{15}$R$^{15}$, —NR$^{15}$S(O)$_{0-2}$R$^{16}$, heterocyclyl optionally substituted with one to five $R^{29}$, heteroaryl optionally substituted with one to five $R^{30}$, poly(ethylene glycol), and methoxypoly(ethylene glycol), or
$R^6$ and $R^7$ together with atoms to which they are attached form $C_{5-10}$ cycloalkyl optionally substituted with one to five $R^{29}$, heterocyclyl optionally substituted with one to five $R^{29}$, aryl optionally substituted with one to five $R^{30}$, or heteroaryl optionally substituted with one to five $R^{30}$;
$R^9$ is independently selected from halo, $C_{1-8}$ alkyl optionally substituted with one to five $R^{22}$, —OH, —OR$^{10}$, —CN, and —NR$^{11}$R$^{12}$;
$R^{10}$ is independently selected from $C_{1-10}$ alkyl optionally substituted with one to five $R^{22}$, and $C_{3-10}$ cycloalkyl optionally substituted with one to five $R^{22}$;
$R^{11}$ and $R^{12}$ are each independently H or $C_{1-6}$ alkyl optionally substituted with one to five $R^{22}$;
$R^{13}$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$;
$R^{14}$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), and methoxypoly(ethylene glycol);
each $R^{15}$ is independently selected from H, $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);
$R^{16}$ is selected from $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);
$R^{17}$ is selected from H, $C_{1-30}$ alkyl optionally substituted with one to five $R^{27}$, $C_{1-30}$ heteroalkyl optionally substituted with one to five $R^{27}$, $C_{3-10}$ cycloalkyl optionally substituted with one to five $R^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol);

$R^{18}$ is selected from $C_{1-30}$ alkyl optionally substituted with one to five $R^{19}$ and $C_{1-30}$ heteroalkyl optionally substituted with one to five $R^{19}$;

each $R^{20}$ is independently selected from halo, oxo, —$NH_2$, —OH, —CN, —$NO_2$, —$NHR^{28}$, —$N(R^{28})_2$, —$C(O)R^{28}$, —$C(O)OR^{28}$, —C(O)OH, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NH_2$, —$C(O)NHR^{28}$, —$C(O)N(R^{28})_2$, —$NHC(O)R^{28}$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{21}$ is independently selected from halo, —$NH_2$, —OH, —CN, —$NO_2$, —$OR^{28}$, —$NHR^{28}$, —$N(R^{28})_2$, —$C(O)R^{28}$, —$C(O)OR^{28}$, —C(O)OH, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NHR^{28}$, —$NHC(O)R^{28}$, —$C(O)N(R^{28})_2$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-6}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, and heteroaryl optionally substituted with one to five $R^{26}$, poly(ethylene glycol), and methoxypoly(ethylene glycol);

each $R^{19}$ or $R^{22}$ is independently selected from halo, —$NH_2$, —OH, —CN, —$NO_2$, oxo, $C_{1-4}$ alkyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl)$_2$, —C(O)—$C_{1-4}$ alkyl, —C(O)O—$C_{1-4}$ alkyl, —C(O)OH, —$S(O)_{0-2}$—$C_{1-4}$ alkyl, —$NHS(O)_{0-2}$—$C_{1-4}$ alkyl, —$S(O)_{0-2}NH$—$C_{1-4}$ alkyl, —$NHS(O)_{0-2}NH$—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$ haloalkyl, —N($C_{1-4}$ haloalkyl)$_2$, —C(O)—$C_{1-4}$ haloalkyl, —$S(O)_{0-2}$—$C_{1-4}$ haloalkyl, —$NHS(O)_{0-2}$—$C_{1-4}$ haloalkyl, —$S(O)_{0-2}NH$—$C_{1-4}$ haloalkyl, —$NHS(O)_{0-2}NH$—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl)$_2$, —OC(O)NH—$C_{1-4}$ haloalkyl, —NHC(O)O—$C_{1-4}$ haloalkyl, —OC(O)N($C_{1-4}$ haloalkyl)$_2$, and $C_{3-10}$ cycloalkyl;

each $R^{25}$ is independently selected from halo, —$NH_2$, —OH, —CN, —$NO_2$, oxo, —$OR^{31}$, —$NHR^{31}$, —$N(R^{31})_2$, —$C(O)R^{31}$, —$C(O)OR^{31}$, —C(O)OH, —$S(O)_{0-2}R^{31}$, —$NR^{32}S(O)_{0-2}R^{31}$, —$S(O)_{0-2}NR^{32}R^{31}$, —$NR^{32}S(O)_{0-2}NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)OR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_3$ to cycloalkyl optionally substituted with one to five $R^{33}$, heterocyclyl optionally substituted with one to five $R^{33}$, aryl optionally substituted with one to five $R^{34}$, and heteroaryl optionally substituted with one to five $R^{34}$, poly(ethylene glycol), and methoxypoly(ethylene glycol);

each $R^{26}$ is independently selected from halo, —$NH_2$, —OH, —CN, —$NO_2$, —$OR^{31}$, —$NHR^{31}$, —$N(R^{31})_2$, —$C(O)R^{31}$, —$C(O)OR^{31}$, —C(O)OH, —$S(O)_{0-2}R^{31}$, —$NR^{32}S(O)_{0-2}R^{31}$, —$S(O)_{0-2}NR^{32}R^{31}$, —$NR^{32}S(O)_{0-2}NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)OR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_3$ to cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{31}$ is independently selected $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol) and methoxypoly(ethylene glycol);

each $R^{32}$ is independently selected H and $C_{1-4}$ alkyl;

each $R^{23}$, $R^{27}$, $R^{29}$ or $R^{33}$ is independently selected from halo, —$NH_2$, —OH, —CN, —$NO_2$, oxo, $C_{1-4}$ alkyl optionally substituted with phenyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl)$_2$, —C(O)—$C_{1-4}$ alkyl, —C(O)O—$C_{1-4}$ alkyl, —C(O)OH, —$S(O)_{0-2}$—$C_{1-4}$ alkyl, —$NHS(O)_{0-2}$—$C_{1-4}$ alkyl, —$S(O)_{0-2}NH$—$C_{1-4}$ alkyl, —$NHS(O)_{0-2}NH$—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$ haloalkyl, —N($C_{1-4}$ haloalkyl)$_2$, —C(O)—$C_{1-4}$ haloalkyl, —$S(O)_{0-2}$—$C_{1-4}$ haloalkyl, —$NHS(O)_{0-2}$—$C_{1-4}$ haloalkyl, —$S(O)_{0-2}NH$—$C_{1-4}$ haloalkyl, —$NHS(O)_{0-2}NH$—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl)$_2$, —OC(O)NH—$C_{1-4}$ haloalkyl, —NHC(O)O—$C_{1-4}$ haloalkyl, —OC(O)N($C_{1-4}$ haloalkyl)$_2$, $C_{3-10}$ cycloalkyl, heterocyclyl, aryl, heteroaryl, —$(CH_2)_{1-30}$—C(O)OH, —$(CH_2)_{0-4}$—O-poly(ethylene glycol), methoxypoly(ethylene glycol)-O—$(CH_2)_{0-4}$—, and sugar moiety;

each $R^{24}$, $R^{30}$ or $R^{34}$ is independently selected from halo, —$NH_2$, —OH, —CN, —$NO_2$, $C_{1-4}$ alkyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl)$_2$, —C(O)—$C_{1-4}$ alkyl, —C(O)OH, —C(O)O—$C_{1-4}$ alkyl, —$S(O)_{0-2}$—$C_{1-4}$ alkyl, —$NHS(O)_{0-2}$—$C_{1-4}$ alkyl, —$S(O)_{0-2}NH$—$C_{1-4}$ alkyl, —$NHS(O)_{0-2}NH$—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$haloalkyl, —N($C_{1-4}$haloalkyl)$_2$, —C(O)—$C_{1-4}$haloalkyl, —$S(O)_{0-2}$—$C_{1-4}$ haloalkyl, —$NHS(O)_{0-2}$—$C_{1-4}$ haloalkyl, —$S(O)_{0-2}NH$—$C_{1-4}$ haloalkyl, —$NHS(O)_{0-2}NH$—$C_{1-4}$haloalkyl, —C(O)NH—$C_{1-4}$ haloalkyl, —NHC(O)—$C_{1-4}$ haloalkyl, —C(O)N($C_{1-4}$haloalkyl)$_2$, —OC(O)NH—$C_{1-4}$haloalkyl, —NHC(O)O—$C_{1-4}$ haloalkyl, —OC(O)N($C_{1-4}$haloalkyl)$_2$, $C_{3-10}$ cycloalkyl, heterocyclyl, aryl, heteroaryl, —(CH$_2$)$_{1-30}$—C(O)OH, —(CH$_2$)$_{0-4}$—O-poly(ethylene glycol), —(CH$_2$)$_{0-4}$—O-methoxypoly(ethylene glycol) and sugar moiety; and each R$^{28}$ is independently selected from C$_{1-30}$ alkyl optionally substituted with one to five R$^{25}$, C$_{1-30}$ heteroalkyl optionally substituted with one to five R$^{25}$, C$_{3-10}$ cycloalkyl optionally substituted with one to five R$^{25}$, heterocyclyl optionally substituted with one to five R$^{25}$, aryl optionally substituted with one to five R$^{26}$, heteroaryl optionally substituted with one to five R$^{26}$, poly(ethylene glycol), and methoxypoly(ethylene glycol).

In certain embodiments, the compound of Formula (I) described above has at least one of the following:

(1) R$^2$ is selected from C$_{2-30}$ alkyl optionally substituted with one to five R$^{19}$, C$_{1-30}$ heteroalkyl optionally substituted with one to five R$^{19}$, —NO$_2$, —OR$^{18}$, —S(O)$_{0-2}$CH$_3$, —S(O)$_{0-2}$R$^{18}$, —NH$_2$, —NHCH$_3$, and —NR$^{11}$R$^{18}$, wherein R$^{18}$ is selected from C$_{1-30}$ haloalkyl, C$_{2-30}$ alkyl optionally substituted with one to five R$^{19}$ and C$_{2-30}$ heteroalkyl optionally substituted with one to five R$^{19}$; wherein when R$^2$ is ethyl, then R$^6$ is not methyl or methoxy;

(2) R$^1$ is heteroaryl optionally substituted with one to five R$^{21}$, or fused heterocyclyl optionally substituted with one to five R$^{20}$;

(3) R$^1$ is heterocyclyl substituted with at least one R$^{20}$ selected from halo, oxo, —NH$_2$, —OH, —CN, —NO$_2$, —NHR$^{28}$, —N(R$^{28}$)$_2$, —C(O)R$^{28}$, —C(O)OR$^{28a}$, —NHS(O)$_{0-2}$R$^{28}$, —OC(O)R$^{28}$, —S(O)$_{0-2}$R$^{28}$, —S(O)$_{0-2}$NHR$^{28}$, —NHS(O)$_{0-2}$NHR$^{28}$, —C(O)NHR$^{28}$, —NHC(O)R$^{28}$, —C(O)N(R$^{28}$)$_2$, —OC(O)NHR$^{28}$, —NHC(O)OR$^{28}$, —OC(O)N(R$^{28}$)$_2$, —NR$^{32}$C(O)NH$_2$, —NR$^{32}$C(O)NHR$^{28}$, —NR$^{32}$C(O)N(R$^{28}$)$_2$, C$_{1-30}$ alkyl substituted with one to five R$^{25}$, C$_{1-30}$ heteroalkyl optionally substituted with one to five R$^{25}$, C$_{3-10}$ cycloalkyl optionally substituted with one to five R$^{25}$, heterocyclyl substituted with one to five R$^{25}$, heteroaryl optionally substituted with one to five R$^{26}$, poly(ethylene glycol), and methoxypoly(ethylene glycol);

wherein
the C$_{1-30}$ alkyl is substituted with at least one R$^{25}$ selected from halo, —NH$_2$, —OH, —CN, —NO$_2$, oxo, —NHR$^{31}$, —N(R$^{31}$)$_2$, —C(O)R$^{31}$, —C(O)OR$^{31}$, —C(O)OH, —S(O)$_{0-2}$R$^{31}$, —NR$^{32}$S(O)$_{0-2}$R$^{31}$, —S(O)$_{0-2}$NR$^{32}$R$^{31}$, —NR$^{32}$S(O)$_{0-2}$NR$^{32}$R$^{31}$, —C(O)NH$_2$, —C(O)NHR$^{31}$, —NR$^{32}$C(O)R$^{31}$, —C(O)N(R$^{31}$)$_2$, —OC(O)NHR$^{31}$, —NR$^{32}$C(O)OR$^{31}$, —OC(O)N(R$^{31}$)$_2$, —NR$^{32}$C(O)NH$_2$, —NR$^{32}$C(O)NHR$^{31}$, —NR$^{32}$C(O)N(R$^{31}$)$_2$, C$_{1-30}$ alkyl optionally substituted with one to five R$^{33}$, C$_{1-30}$ heteroalkyl optionally substituted with one to five R$^{33}$, heterocyclyl substituted with one to five R$^{33}$, poly(ethylene glycol), methoxypoly(ethylene glycol), pyrrolidinyl and piperidinyl; or the C$_{1-30}$ alkyl is substituted with at least one —OR$^{31a}$, wherein R$^{31a}$ is poly(ethylene glycol) or methoxypoly(ethylene glycol);

R$^{28a}$ is selected from C$_{1-30}$ alkyl substituted with one to five R$^{25}$, C$_{1-30}$ heteroalkyl optionally substituted with one to five R$^{25}$, C$_{3-10}$ cycloalkyl optionally substituted with one to five R$^{25}$, heterocyclyl optionally substituted with one to five R$^{25}$, aryl optionally substituted with one to five R$^{26}$, heteroaryl optionally substituted with one to five R$^{26}$, poly(ethylene glycol), and methoxypoly(ethylene glycol);

(4) R$^1$ is —NR$^3$R$^4$, and R$^4$ is selected from C$_{1-30}$ alkyl substituted with one to five R$^{20}$, C$_{1-30}$ heteroalkyl optionally substituted with one to five R$^{20}$, C$_{3-10}$ cycloalkyl optionally substituted with one to five R$^{20}$, heterocyclyl optionally substituted with one to five R$^{20}$, heteroaryl optionally substituted with one to five R$^{21}$, poly(ethylene glycol), methoxypoly(ethylene glycol), and —NR$^{13}$R$^{14}$, wherein
the C$_{1-30}$ alkyl is substituted with at least one R$^{20}$ selected from halo, —NH$_2$, —OH, —CN, —NO$_2$, —NHR$^{28}$, —N(R$^{28}$)$_2$, —C(O)R$^{28}$, —S(O)$_{0-2}$R$^{28}$, —NHS(O)$_{0-2}$R$^{28}$, —S(O)$_{0-2}$NHR$^{28}$, —NHS(O)$_{0-2}$NHR$^{28}$, —C(O)NHR$^{28}$, —NHC(O)R$^{28}$, —C(O)N(R$^{28}$)$_2$, —OC(O)NHR$^{28}$, —NHC(O)OR$^{28}$, —OC(O)N(R$^{28}$)$_2$, C$_{3-10}$ cycloalkyl optionally substituted with one to five R$^{25}$, heterocyclyl optionally substituted with one to five R$^{25}$, and heteroaryl optionally substituted with one to five R$^{26}$; or (5) R$^6$ is selected from C$_{1-6}$ alkyl substituted with one to five R$^{29}$, —OR$^{17}$, —S(O)$_{0-2}$R$^{16}$, C(O)OR$^{15}$, —OC(O)R$^{16}$, —NO$_2$, —NR$^{15}$R$^{15}$, —C(O)NR$^{15}$R$^{15}$, —S(O)$_{0-2}$NHR$^{16}$, —NHS(O)$_{0-2}$R$^{16}$, heterocyclyl optionally substituted with one to five R$^{29}$, heteroaryl optionally substituted with one to five R$^{30}$, poly(ethylene glycol), and methoxypoly(ethylene glycol), wherein R$^{17}$ is selected from C$_{1-30}$ alkyl substituted with one to five R$^{27}$, C$_{1-30}$ heteroalkyl optionally substituted with one to five R$^{27}$, C$_{3-10}$ cycloalkyl optionally substituted with one to five R$^{27}$, heterocyclyl optionally substituted with one to five R$^{27}$, aryl optionally substituted with one to five R$^{24}$, heteroaryl optionally substituted with one to five R$^{24}$, poly(ethylene glycol), and methoxypoly(ethylene glycol).

In certain embodiments, R$^1$ is heteroaryl optionally substituted with one to five R$^{21}$; or R$^1$ is heterocyclyl substituted with at least one R$^{20}$ selected from halo, oxo, —NH$_2$, —OH, —CN, —NO$_2$, —OR$^{28}$, —NHR$^{28}$, —N(R$^{28}$)$_2$, —C(O)R$^{28}$, —C(O)OR$^{28a}$, —NHS(O)$_{0-2}$R$^{28}$, —OC(O)R$^{28}$, —S(O)$_{0-2}$R$^{28}$, —S(O)$_{0-2}$NHR$^{28}$, —NHS(O)$_{0-2}$NHR$^{28}$, —C(O)NHR$^{28}$, —NHC(O)R$^{28}$, —C(O)N(R$^{28}$)$_2$, —OC(O)NHR$^{28}$, —NHC(O)OR$^{28}$, —OC(O)N(R$^{28}$)$_2$, —NR$^{32}$C(O)NH$_2$, —NR$^{32}$C(O)NHR$^{28}$, —NR$^{32}$C(O)N(R$^{28}$)$_2$, C$_{1-30}$ alkyl substituted with one to five R$^{25}$, C$_{1-30}$ heteroalkyl optionally substituted with one to five R$^{25}$, heterocyclyl substituted with one to five R$^{25}$, poly(ethylene glycol), and methoxypoly(ethylene glycol);

wherein
the C$_{1-30}$ alkyl is substituted with at least one R$^{25}$ selected from halo, —NH$_2$, —OH, —CN, —NO$_2$, oxo, —NHR$^{31}$, —N(R$^{31}$)$_2$, —C(O)R$^{31}$, —C(O)OR$^{31}$, —C(O)OH, —S(O)$_{0-2}$R$^{31}$, —NR$^{32}$S(O)$_{0-2}$R$^{31}$, —S(O)$_{0-2}$NR$^{32}$R$^{31}$, —NR$^{32}$S(O)$_{0-2}$NR$^{32}$R$^{31}$, —C(O)NH$_2$, —C(O)NHR$^{31}$, —NR$^{32}$C(O)R$^{31}$, —C(O)N(R$^{31}$)$_2$, —OC(O)NHR$^{31}$, —NR$^{32}$C(O)OR$^{31}$, —OC(O)N(R$^{31}$)$_2$, —NR$^{32}$C(O)NH$_2$, —NR$^{32}$C(O)NHR$^{31}$, —NR$^{32}$C(O)N(R$^{31}$)$_2$, C$_{1-30}$ alkyl optionally substituted with one to five R$^{33}$, C$_{1-30}$ heteroalkyl optionally substituted with one to five R$^{33}$, heterocyclyl substituted with one to five R$^{33}$, poly(ethylene glycol), methoxypoly(ethylene glycol), pyrrolidinyl and piperidinyl; or the $C_{1-30}$ alkyl is substituted with at least one —OR$^{31}$, wherein R$^{31}$ is poly(ethylene glycol) or methoxypoly(ethylene glycol); and R$^{28a}$ is selected from $C_{1-30}$ alkyl substituted with one to five R$^{25}$, $C_{1-30}$ heteroalkyl optionally substituted with one to five R$^{25}$, $C_{3-10}$ cycloalkyl optionally substituted with one to five R$^{25}$, heterocyclyl optionally substituted with one to five R$^{25}$, aryl optionally substituted with one to five R$^{26}$, heteroaryl optionally substituted with one to five R$^{26}$, poly(ethylene glycol), and methoxypoly(ethylene glycol).

In certain embodiments, R$^1$ is heteroaryl optionally substituted with one to five R$^{21}$. In certain embodiments, R$^1$ is 5- or 6-membered heteroaryl optionally substituted with one to five R$^{21}$.

In certain embodiments, R$^1$ is heterocyclyl optionally substituted with one to two R$^{20}$. In certain embodiments, R$^1$ is 5- to 7-membered heterocyclyl optionally substituted with one to two R$^{20}$. In certain embodiments, one of the R$^{20}$ is optionally substituted with one to five R$^{25}$, $C_{1-30}$ heteroalkyl optionally substituted with one to five R$^{25}$, $C_{3-10}$ cycloalkyl optionally substituted with one to five R$^{25}$, or heterocyclyl optionally substituted with one to five R$^{25}$. In some embodiments, one R$^{20}$ is a sugar moiety. In certain embodiments, one of the R$^{25}$ is $C_{3-10}$ cycloalkyl optionally substituted with one to five R$^{33}$, or 5- to 7-membered heterocyclyl optionally substituted with one to five R$^{33}$. In some embodiments, one R$^{25}$ is a sugar moiety. In certain embodiments, one of the R$^{33}$ is 5- to 7-membered heterocyclyl. In some embodiments, one R$^{33}$ is a sugar moiety.

In certain embodiments, at least one R$^{20}$ is 5- to 7-membered heterocyclyl optionally substituted with one to five R$^{25}$. In certain embodiments, at least one R$^{25}$ is selected from $C_{1-30}$ alkyl optionally substituted with one to five R$^{33}$, 5- to 7-membered heterocyclyl optionally substituted with one to five R$^{33}$, and phenyl optionally substituted with one to five R$^{34}$. In some embodiments, one R$^{20}$ is a sugar moiety.

In certain embodiments, R$^1$ is 5- to 7-membered heterocyclyl optionally substituted with one to two R$^{20}$, wherein at least one R$^{20}$ is $C_{1-30}$ alkyl optionally substituted with one to five R$^{25}$. In certain embodiments, R$^1$ is 5- to 7-membered heterocyclyl optionally substituted with one to two R$^{20}$, wherein at least one R$^{20}$ is 5- to 7-membered heterocyclyl optionally substituted with one to five R$^{25}$. In some embodiments, at least one R$^{25}$ is 5- to 7-membered heterocyclyl optionally substituted with one to five R$^{33}$. In some embodiments, one R$^{25}$ is a sugar moiety.

In certain embodiments, R$^1$ is

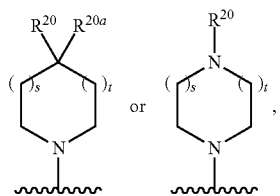

wherein each s and t is independently 0, 1, 2 or 3, provided that the sum of s and t is 1, 2, 3, or 4, R$^{20}$ is $C_{1-30}$ alkyl substituted with one to five R$^{25}$, $C_{1-30}$ heteroalkyl optionally substituted with one to five R$^{25}$, $C_{3-10}$ cycloalkyl optionally substituted with one to five R$^{25}$, heterocyclyl substituted with one to five R$^{25}$, aryl optionally substituted with one to five R$^{26}$, heteroaryl optionally substituted with one to five R$^{26}$, and R$^{20a}$ is H, NH$_2$, or OH.

In certain embodiments, R$^{20}$ is selected from —S(O)$_{0-2}$R$^{28}$, —S(O)$_{0-2}$NHR$^{28}$, —NHS(O)$_{0-2}$NHR$^{28}$, $C_{1-30}$ alkyl substituted with one to five R$^{25}$, heterocyclyl optionally substituted with one to five R$^{25}$, and heteroaryl optionally substituted with one to five R$^{26}$. In some embodiments, one R$^{20}$ is a sugar moiety.

In certain embodiments, one of R$^{25}$ is selected from $C_{1-30}$ alkyl substituted with one to five R$^{33}$, heterocyclyl optionally substituted with one to five R$^{33}$, and heteroaryl optionally substituted with one to five R$^{33}$. In some embodiments, one R$^{25}$ is a sugar moiety. In certain embodiments, one of R$^{26}$ is selected from $C_{1-30}$ alkyl substituted with one to five R$^{33}$, heterocyclyl optionally substituted with one to five R$^{33}$, and heteroaryl optionally substituted with one to five R$^{33}$. In some embodiments, one R$^{26}$ is a sugar moiety.

In certain embodiments, one R$^{21}$ is a sugar moiety. In certain embodiments, one R$^{28}$ is a sugar moiety. In certain embodiments, one R$^{31}$ is a sugar moiety.

In certain embodiments, one R$^{23}$, R$^{24}$, R$^{27}$, R$^{29}$, R$^{30}$, R$^{33}$ or R$^{34}$ is a sugar moiety.

In certain embodiments, both R$^2$ and R$^6$ are other than H. In certain embodiments, when R$^2$ is methyl or ethyl, then R$^6$ is not selected from methyl, ethyl, methoxy or ethoxy.

In certain embodiments, R$^2$ is selected from $C_{2-30}$ alkyl optionally substituted with one to five R$^{19}$, $C_{1-30}$ heteroalkyl optionally substituted with one to five R$^{19}$, —NO$_2$, —S(O)$_{0-2}$R$^{18}$, and —NR$^{11}$R$^{18}$, wherein R$^{18}$ is selected from $C_{1-30}$haloalkyl, $C_{2-30}$ alkyl optionally substituted with one to five R$^{19}$ and $C_{2-30}$ heteroalkyl optionally substituted with one to five R$^{19}$; wherein when R$^2$ is ethyl, then R$^6$ is not methyl or methoxy.

In certain embodiments, R$^2$ is $C_{2-30}$ alkyl substituted with one to five R$^{19}$. In certain embodiments, R$^2$ is $C_{2-30}$ heteroalkyl substituted with one to five R$^{19}$. In certain embodiments, R$^2$ is —O(CH$_2$)$_m$CH$_3$ or —O(CH$_2$)$_m$CH$_2$C(O)OH, wherein m is an integer selected from 1, 2, 3, 4, 5, 6, 7, 8, 9, 10, 11 12, 13, 14, 15, 16, 17, 18, 19, 20, 21, 22, 23, 24, 25, 26, 27, 28, and 29.

In certain embodiments, R$^2$ is —NO$_2$. In certain embodiments, R$^2$ is —CN.

In certain embodiments, R$^2$ is —OR$^{18}$ or —S(O)$_{0-2}$R$^{18}$. In certain embodiments, R$^{18}$ is $C_{1-30}$haloalkyl. In certain embodiments, R$^{18}$ is $C_{2-30}$ alkyl optionally substituted with one to five R$^{19}$. In certain embodiments, R$^{18}$ is $C_{1-30}$ heteroalkyl optionally substituted with one to five R$^{19}$.

In certain embodiments, each R$^{19}$ is independently selected from halo, —NH$_2$, —OH, —CN, —NO$_2$, oxo, $C_{1-4}$ alkoxy, —NH—$C_{1-4}$ alkyl, —N($C_{1-4}$ alkyl)$_2$, —C(O)—$C_{1-4}$ alkyl, and —C(O)OH. In certain embodiments, R$^{19}$ is —C(O)OH.

In certain embodiments, R$^2$ is $C_{1-30}$ alkyl, —CN, —NO$_2$ and —OR$^{18}$. In certain embodiments, R$^2$ is —CH$_3$, —CH$_2$CH$_3$, —NO$_2$, —OCF$_3$, and —OR$^{18}$. In certain embodiments, R$^2$ is —OR$^{18}$, wherein R$^{18}$ is $C_{4-30}$ alkyl optionally substituted with one to five R$^{19}$.

In certain embodiments, R$^6$ is selected from $C_{1-6}$ alkyl substituted with one to five R$^{29}$, —OR$^{17}$, —S(O)$_{0-2}$R$^{16}$, —C(O)OR$^{15}$, —OC(O)R$^{16}$, —NO$_2$, —NR$^{15}$R$^{15}$, —C(O)NR$^{15}$R$^{15}$, —S(O)$_{0-2}$NHR$^{16}$, —NHS(O)$_{0-2}$R$^{16}$, heterocyclyl optionally substituted with one to five R$^{29}$, heteroaryl optionally substituted with one to five R$^{30}$, poly(ethylene glycol), and methoxypoly(ethylene glycol), wherein R$^{17}$ is selected from $C_{1-30}$ alkyl substituted with one to five R$^{27}$, $C_{1-30}$ heteroalkyl optionally substituted with one to five R$^{27}$, $C_{3-10}$ cycloalkyl optionally substituted with one to five R$^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol).

In certain embodiments, $R^6$ is a sugar moiety.

In certain embodiments, $R^6$ is halo, $C_{1-30}$ alkyl optionally substituted with one to five $R^{29}$, $C_{1-30}$ heteroalkyl optionally substituted with one to five $R^{29}$, —$OR^{17}$, —$S(O)_{0-2}R^{16}$, —$C(O)OR^{15}$, —$OC(O)R^{16}$, —$NO_2$, —$NR^{15}R^{15}$, —$C(O)NR^{15}R^{15}$, —$NR^{15}C(O)R^{16}$, —$S(O)_{0-2}NR^{15}R^{15}$, —$NR^{15}S(O)_{0-2}R^{16}$, heterocyclyl optionally substituted with one to five $R^{29}$, heteroaryl optionally substituted with one to five $R^{30}$, poly(ethylene glycol), and methoxypoly(ethylene glycol).

In certain embodiments, $R^6$ is halo, $OR^{17}$, or $C_{1-30}$ alkyl optionally substituted with halo or C(O)OH, wherein $R^{17}$ is $C_{1-30}$ alkyl optionally substituted with halo or C(O)OH. In certain embodiments, $R^6$ is F, $C_1$-$C_4$ alkyl or $C_1$-$C_4$ alkoxy. In certain embodiments, $R^6$ is $OR^{17}$, and $R^{17}$ is $C_1$-$C_4$ haloalkyl. In certain embodiments, $R^6$ is selected from $CH_2CN$, $OCF_3$ and $NO_2$.

In certain embodiments, $R^6$ is $S(O)_{0-2}R^{16}$. In certain embodiments, $R^{16}$ is $C_1$-$C_{30}$ alkyl optionally substituted with halo or C(O)OH. In certain embodiments, $R^6$ is $SCH_3$, $SOCH_3$, and $SO_2CH_3$. In certain embodiments, $R^6$ is —$SCH_3$, —$SOCH_3$, or —$SO_2CH_3$. In certain embodiments, $R^6$ is —$S(O)_{0-2}R^{16}$. In certain embodiments, $R^6$ is —$S(O)R^{16}$. In certain embodiments, $R^6$ is —$S(O)_2R^{16}$. In certain embodiments, $R^6$ is

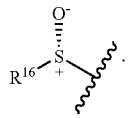

In certain embodiments, $R^6$ is

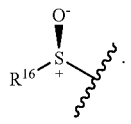

In certain embodiments, $R^6$ is $C(O)OR^{15}$. In certain embodiments, $R^{15}$ is H or $C_{1-30}$ alkyl optionally substituted with halo or C(O)OH. In certain embodiments, $R^6$ is —C(O)OH, —$C(O)OCH_3$ or —$C(O)OCH_2CH_3$.

In certain embodiments, $R^6$ is —$C(O)NR^{15}R^{15}$. In certain embodiments, one $R^{15}$ is H or alkyl. In certain embodiments, one $R^{15}$ is H, $C_{1-30}$ alkyl optionally substituted with one to five $R^{23}$, $C_{1-30}$ heteroalkyl optionally substituted with one to five $R^{20}$, and heterocyclyl optionally substituted with one to five $R^{23}$.

In certain embodiments, one $R^{15}$ is a sugar moiety. In certain embodiments, one $R^{16}$ is a sugar moiety.

In certain embodiments, $R^6$ is a sugar moiety.

In certain embodiments, $R^6$ and $R^7$ together with atoms to which they are attached form $C_{5-10}$ cycloalkyl optionally substituted with one to five $R^{29}$. In certain embodiments, $R^6$ and $R^7$ together with atoms to which they are attached form heterocyclyl optionally substituted with one to five $R^{29}$. In certain embodiments, $R^6$ and $R^7$ together with atoms to which they are attached form aryl optionally substituted with one to five $R^{30}$. In certain embodiments, $R^6$ and $R^7$ together with atoms to which they are attached form heteroaryl optionally substituted with one to five $R^{30}$. In certain embodiments, one $R^{29}$ is a sugar moiety. In certain embodiments, one $R^{30}$ is a sugar moiety.

In certain embodiments, $R^5$, $R^7$ and $R^8$ are each H. In certain embodiments, $R^5$ and $R^8$ are each H, and $R^7$ is $OCH_3$.

In certain embodiments, the compound has no more than one group selected from poly(ethylene glycol), methoxypoly(ethylene glycol) and sugar moiety.

In certain embodiments, both $R^2$ and $R^6$ are other than H. In certain embodiments, when $R^2$ is methyl or ethyl, then $R^6$ is not selected from methyl, ethyl, methoxy or ethoxy.

In certain embodiments, $R^2$ is selected from $C_{2-30}$ alkyl optionally substituted with one to five $R^{19}$, $C_{1-30}$ heteroalkyl optionally substituted with one to five $R^{19}$, —$NO_2$, —$S(O)_{0-2}R^{18}$, and —$NR^{11}R^{18}$, wherein $R^{18}$ is selected from $C_{1-30}$haloalkyl, $C_{2-30}$ alkyl optionally substituted with one to five $R^{19}$ and $C_{2-30}$ heteroalkyl optionally substituted with one to five $R^{19}$; wherein when $R^2$ is ethyl, then $R^6$ is not methyl or methoxy.

In certain embodiments, $R^2$ is $C_{2-30}$ alkyl substituted with one to five $R^{19}$. In certain embodiments, $R^2$ is $C_{2-30}$ heteroalkyl substituted with one to five $R^{19}$. In certain embodiments, $R^2$ is —$O(CH_2)_mCH_3$ or —$O(CH_2)_mCH_2C(O)OH$, wherein m is an integer selected from 1, 2, 3, 4, 5, 6, 7, 8, 9, 10, 11 12, 13, 14, 15, 16, 17, 18, 19, 20, 21, 22, 23, 24, 25, 26, 27, 28, and 29.

In certain embodiments, $R^2$ is —$OR^{18}$, wherein $R^{18}$ is $C_{4-30}$ alkyl optionally substituted with one to five $R^{19}$.

In certain embodiments, $R^2$ is —$NO_2$. In certain embodiments, $R^2$ is —CN.

In certain embodiments, $R^2$ is —$OR^{18}$ or —$S(O)_{0-2}R^{18}$. In certain embodiments, $R^{18}$ is $C_{1-30}$ haloalkyl. In certain embodiments, $R^{18}$ is $C_{2-30}$ alkyl optionally substituted with one to five $R^{19}$. In certain embodiments, $R^{18}$ is $C_{1-30}$ heteroalkyl optionally substituted with one to five $R^{19}$.

In certain embodiments, each $R^{19}$ is independently selected from halo, —$NH_2$, —OH, —CN, —$NO_2$, oxo, $C_{1-4}$ alkoxy, —NH—$C_{1-4}$ alkyl, —N($C_{1-4}$ alkyl)$_2$, —C(O)—$C_{1-4}$ alkyl, and —C(O)OH. In certain embodiments, $R^{19}$ is —C(O)OH.

In certain embodiments, $R^2$ is $C_{1-30}$ alkyl, —CN, —$NO_2$ and —$OR^{18}$. In certain embodiments, $R^2$ is —$CH_3$, —$CH_2CH_3$, —$NO_2$, —$OCF_3$, and —$OR^{18}$. In certain embodiments, $R^2$ is —$OR^{18}$, wherein $R^{18}$ is $C_{4-30}$ alkyl optionally substituted with one to five $R^{19}$.

In certain embodiments, $R^6$ is selected from $C_{1-6}$ alkyl substituted with one to five $R^{29}$, —$OR^{17}$, —$S(O)_{0-2}R^{16}$, —$C(O)OR^{15}$, —$OC(O)R^{16}$, —$NO_2$, —$NR^{15}R^{15}$, —$C(O)NR^{15}R^{15}$, —$S(O)_{0-2}NHR^{16}$, —$NHS(O)_{0-2}R^{16}$, heterocyclyl optionally substituted with one to five $R^{29}$, heteroaryl optionally substituted with one to five $R^{30}$, poly(ethylene glycol), and methoxypoly(ethylene glycol), wherein $R^{17}$ is selected from $C_{1-30}$ alkyl substituted with one to five $R^{27}$, $C_{1-30}$ heteroalkyl optionally substituted with one to five $R^{27}$, $C_{3-10}$ cycloalkyl optionally substituted with one to five $R^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol).

In certain embodiments, $R^6$ is —$NO_2$, —$C(O)OR^{15}$, —$OC(O)R^{16}$, —$C(O)NR^{15}R^{15}$, —$NR^{15}C(O)R^{15}$, —$S(O)_{0-2}R^{16}$, —$S(O)_{0-2}NHR^{16}$, or —$NHS(O)_{0-2}R^{16}$.

In certain embodiments, $R^6$ is a sugar moiety.

In certain embodiments, $R^6$ is halo, $C_{1-30}$ alkyl optionally substituted with one to five $R^{29}$, $C_{1-30}$ heteroalkyl optionally substituted with one to five $R^{29}$, —$OR^{17}$, —$S(O)_{0-2}R^{16}$, —C(O)OR$^{15}$, —OC(O)R$^{16}$, —CN, —NO$_2$, —NR$^{15}$R$^{15}$, —C(O)NR$^{15}$R$^{15}$, —NR$^{15}$C(O)R$^{16}$, S(O)$_{0-2}$NR$^{15}$R$^{15}$, —NR$^{15}$S(O)$_{0-2}$R$^{16}$, heterocyclyl optionally substituted with one to five R$^{29}$, heteroaryl optionally substituted with one to five R$^{30}$, poly(ethylene glycol), and methoxypoly(ethylene glycol).

In certain embodiments, R$^6$ is halo, OR$^{17}$, or C$_{1-30}$ alkyl optionally substituted with halo or C(O)OH, wherein R$^{17}$ is C$_{1-30}$ alkyl optionally substituted with halo or C(O)OH. In certain embodiments, R$^6$ is F, C$_1$-C$_4$ alkyl or C$_1$-C$_4$ alkoxy. In certain embodiments, R$^6$ is OR$^{17}$, and R$^{17}$ is C$_1$-C$_4$ haloalkyl. In certain embodiments, R$^6$ is selected from CH$_2$CN, OCF$_3$ and NO$_2$.

In certain embodiments, R$^6$ is S(O)$_{0-2}$R$^{16}$. In certain embodiments, R$^{16}$ is C$_1$-C$_{30}$ alkyl optionally substituted with halo or C(O)OH. In certain embodiments, R$^6$ is SCH$_3$, SOCH$_3$, and SO$_2$CH$_3$. In certain embodiments, R$^6$ is C(O)OR$^{15}$. In certain embodiments, R$^{15}$ is H or C$_{1-30}$ alkyl optionally substituted with halo or C(O)OH. In certain embodiments, R$^6$ is —C(O)OH, —C(O)OCH$_3$ or —C(O)OCH$_2$CH$_3$.

In certain embodiments, R$^6$ is —C(O)NR$^{15}$R$^{15}$. In certain embodiments, one R$^{15}$ is H or alkyl. In certain embodiments, one R$^{15}$ is H, C$_{1-30}$ alkyl optionally substituted with one to five R$^{23}$, C$_{1-30}$ heteroalkyl optionally substituted with one to five R$^{20}$, and heterocyclyl optionally substituted with one to five R$^{23}$.

In certain embodiments, one R$^{15}$ is a sugar moiety. In certain embodiments, one R$^{16}$ is a sugar moiety.

In certain embodiments, R$^6$ is a sugar moiety.

In certain embodiments, R$^6$ is selected from

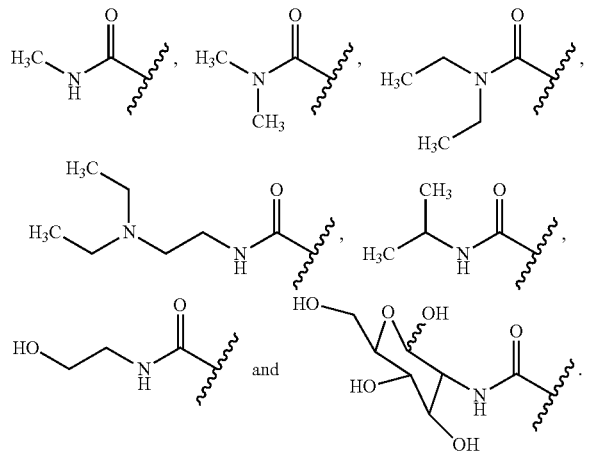

In certain embodiments, R$^6$ and R$^7$ together with atoms to which they are attached form C$_{5-10}$ cycloalkyl optionally substituted with one to five R$^{29}$. In certain embodiments, R$^6$ and IV together with atoms to which they are attached form heterocyclyl optionally substituted with one to five R$^{29}$. In certain embodiments, R$^6$ and IV together with atoms to which they are attached form aryl optionally substituted with one to five R$^{30}$. In certain embodiments, R$^6$ and R$^7$ together with atoms to which they are attached form heteroaryl optionally substituted with one to five R$^{30}$. In certain embodiments, one R$^{29}$ is a sugar moiety. In certain embodiments, one R$^{30}$ is a sugar moiety.

In certain embodiments, R$^5$, R$^7$ and R$^8$ are each H. In certain embodiments, R$^5$ and R$^8$ are each H, and R$^7$ is OCH$_3$.

In certain embodiments, R$^1$, R$^6$ and R$^2$ are each not H. In certain embodiments, R$^1$, R$^6$, R$^1$, and R$^2$ are each not H.

In certain embodiments, R$^2$ is —OR$^{18}$, wherein R$^{18}$ is C$_{4-30}$ alkyl optionally substituted with one to five R$^{19}$; R$^6$ is —NO$_2$, —C(O)OR$^{15}$, —OC(O)R$^{16}$, —C(O)NR$^{15}$R$^{15}$, —NR$^{15}$C(O)R$^{15}$, —S(O)$_{0-2}$R$^{16}$, —S(O)$_{0-2}$NHR$^{16}$, or —NHS(O)$_{0-2}$R$^{16}$; R$^5$, R$^7$ and R$^8$ are each H, or R$^5$ and R$^8$ are each H, and R$^7$ is OCH$_3$.

In certain embodiments, the compound has no more than one group selected from poly(ethylene glycol), methoxypoly (ethylene glycol) and sugar moiety.

Provided herein is a compound of Formula (I):

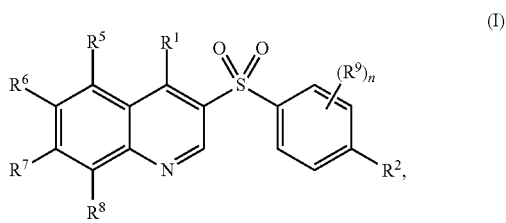

or a pharmaceutically acceptable salt, isotopically enriched analog, stereoisomer, mixture of stereoisomers, or tautomer thereof;

wherein
- R$^1$ is selected from —NR$^3$R$^4$, heterocyclyl optionally substituted with one to five R$^{20}$, and heteroaryl optionally substituted with one to five R$^{21}$;
- R$^2$ is selected from H, halo, C$_{1-30}$ alkyl optionally substituted with one to five R$^{19}$, C$_{1-30}$ heteroalkyl optionally substituted with one to five R$^{19}$, —OH, —OR$^{18}$, —CN, —NO$_2$, —NH$_2$, —S(O)$_{0-2}$R$^{18}$, and —NR$^{11}$R$^{18}$;
- R$^3$ is selected from H, C$_{1-6}$ alkyl optionally substituted with one to five R$^{20}$, C$_{3-10}$ cycloalkyl optionally substituted with one to five R$^{20}$, heterocyclyl optionally substituted with one to five R$^{20}$, aryl optionally substituted with one to five R$^{21}$, and heteroaryl optionally substituted with one to five R$^{21}$,
- R$^4$ is selected from H, C$_{1-30}$ alkyl optionally substituted with one to five R$^{20}$, C$_{1-30}$ heteroalkyl optionally substituted with one to five R$^{20}$, C$_{3-10}$ cycloalkyl optionally substituted with one to five R$^{20}$, heterocyclyl optionally substituted with one to five R$^{20}$, aryl optionally substituted with one to five R$^{21}$, heteroaryl optionally substituted with one to five R$^{21}$, poly(ethylene glycol), methoxypoly(ethylene glycol), and —NR$^{13}$R$^{14}$;
- R$^5$, R$^7$ and R$^8$ are each independently selected from H, halo, C$_{1-30}$ alkyl optionally substituted with one to five R$^{29}$, C$_{1-30}$ heteroalkyl optionally substituted with one to five R$^{29}$, —OR$^{15}$, —S(O)$_{0-2}$R$^{16}$, —C(O)OR$^{15}$, —OC(O)R$^{16}$, —CN, —NO$_2$, —NR$^{15}$R$^{15}$, and —C(O)NR$^{15}$R$^{15}$;
- R$^6$ is selected from H, halo, C$_{1-30}$ alkyl optionally substituted with one to five R$^{29}$, C$_{1-30}$ heteroalkyl optionally substituted with one to five R$^{29}$, —OR$^{17}$, —S(O)$_{0-2}$R$^{16}$, —C(O)OR$^{15}$, —OC(O)R$^{16}$, —CN, —NO$_2$, —NR$^{15}$R$^{15}$, —C(O)NR$^{15}$R$^{15}$, —NR$^{15}$C(O)R$^{16}$, —S(O)$_{0-2}$NR$^{15}$R$^{15}$, —NR$^{15}$S(O)$_{0-2}$R$^{16}$, heterocyclyl optionally substituted with one to five R$^{29}$, heteroaryl optionally substituted with one to five R$^{30}$, poly(ethylene glycol), and methoxypoly(ethylene glycol), or
- R$^6$ and R$^7$ together with atoms to which they are attached form C$_{5-10}$ cycloalkyl optionally substituted with one to five R$^{29}$, heterocyclyl optionally substituted with one to five $R^{29}$, aryl optionally substituted with one to five $R^{30}$, or heteroaryl optionally substituted with one to five $R^{30}$;

$R^9$ is independently selected from halo, $C_{1-8}$ alkyl optionally substituted with one to five $R^{22}$, —OH, —CN, and —$NR^{11}R^{12}$;

n is 0, 1, 2, 3 or 4;

$R^{10}$ is independently selected from $C_{1-10}$ alkyl optionally substituted with one to five $R^{22}$, and $C_{3-10}$ cycloalkyl optionally substituted with one to five $R^{22}$;

$R^{11}$ and $R^{12}$ are each independently H or $C_{1-6}$ alkyl optionally substituted with one to five $R^{22}$;

$R^{13}$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$;

$R^{14}$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), and methoxypoly(ethylene glycol);

each $R^{15}$ is independently selected from H, $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);

$R^{16}$ is selected from $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);

$R^{17}$ is selected from H, $C_{1-30}$ alkyl optionally substituted with one to five $R^{27}$, $C_{1-30}$ heteroalkyl optionally substituted with one to five $R^{27}$, $C_{3-10}$ cycloalkyl optionally substituted with one to five $R^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol);

$R^{18}$ is selected from $C_{1-30}$ alkyl optionally substituted with one to five $R^{19}$ and $C_{1-30}$ heteroalkyl optionally substituted with one to five $R^{19}$;

each $R^{20}$ is independently selected from halo, oxo, —$NH_2$, —OH, —CN, —$NO_2$, —$OR^{28}$, —$NHR^{28}$, —$N(R^{28})_2$, —$C(O)R^{28}$, —$C(O)OR^{28}$, —$C(O)OH$, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NH_2$, —$C(O)NHR^{28}$, —$C(O)N(R^{28})_2$, —$NHC(O)R^{28}$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{21}$ is independently selected from halo, —$NH_2$, —OH, —CN, —$NO_2$, —$OR^{28}$, —$NHR^{28}$, —$N(R^{28})_2$, —$C(O)R^{28}$, —$C(O)OR^{28}$, —$C(O)OH$, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NHR^{28}$, —$NHC(O)R^{28}$, —$C(O)N(R^{28})_2$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-6}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{19}$ or $R^{22}$ is independently selected from halo, —$NH_2$, —OH, —CN, —$NO_2$, oxo, $C_{1-4}$ alkyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl)$_2$, —C(O)—$C_{1-4}$ alkyl, —C(O)O—$C_{1-4}$ alkyl, —C(O)OH, —$S(O)_{0-2}$—$C_{1-4}$ alkyl, —$NHS(O)_{0-2}$—$C_{1-4}$ alkyl, —$S(O)_{0-2}$NH—$C_{1-4}$ alkyl, —$NHS(O)_{0-2}$NH—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$ haloalkyl, —N($C_{1-4}$ haloalkyl)$_2$, —C(O)—$C_{1-4}$ haloalkyl, —$S(O)_{0-2}$—$C_{1-4}$ haloalkyl, —$NHS(O)_{0-2}$—$C_{1-4}$ haloalkyl, —$S(O)_{0-2}$NH—$C_{1-4}$ haloalkyl, —$NHS(O)_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl)$_2$, —OC(O)NH—$C_{1-4}$ haloalkyl, —NHC(O)O—$C_{1-4}$ haloalkyl, —OC(O)N($C_{1-4}$ haloalkyl)$_2$, and $C_{3-10}$ cycloalkyl;

each $R^{25}$ is independently selected from halo, —$NH_2$, —OH, —CN, —$NO_2$, oxo, —$NHR^{31}$, —$N(R^{31})_2$, —$C(O)R^{31}$, —$C(O)OR^{31}$, —$C(O)OH$, —$S(O)_{0-2}R^{31}$, —$NR^{32}S(O)_{0-2}R^{31}$, —$S(O)_{0-2}NR^{32}R^{31}$, —$NR^{32}S(O)_{0-2}NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)OR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{26}$ is independently selected from halo, —$NH_2$, —OH, —CN, —$NO_2$, —$NHR^{31}$, —$N(R^{31})_2$, —$C(O)R^{31}$, —$C(O)OR^{31}$, —$C(O)OH$, —$S(O)_{0-2}R^{31}$, —$NR^{32}S(O)_{0-2}R^{31}$, —$S(O)_{0-2}NR^{32}R^{31}$, —$NR^{32}S(O)_{0-2}NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)OR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{31}$ is independently selected $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol) and methoxypoly(ethylene glycol);

each $R^{32}$ is independently selected H and $C_{1-4}$ alkyl;

each $R^{23}$, $R^{27}$, $R^{29}$ or $R^{33}$ is independently selected from halo, $-NH_2$, $-OH$, $-CN$, $-NO_2$, oxo, $C_{1-4}$ alkyl optionally substituted with phenyl, $C_{1-4}$ haloalkyl, $C_{1-4}$ hydroxyalkyl, $C_{1-4}$ alkoxy, $-NH-C_{1-4}$ alkyl, $-N(C_{1-4}$ alkyl$)_2$, $-C(O)-C_{1-4}$ alkyl, $-C(O)O-C_{1-4}$ alkyl, $-C(O)OH$, $-S(O)_{0-2}-C_{1-4}$ alkyl, $-NHS(O)_{0-2}-C_{1-4}$ alkyl, $-S(O)_{0-2}NH-C_{1-4}$ alkyl, $-NHS(O)_{0-2}NH-C_{1-4}$ alkyl, $-C(O)NH-C_{1-4}$ alkyl, $-NHC(O)-C_{1-4}$ alkyl, $-C(O)N(C_{1-4}$ alkyl$)_2$, $-OC(O)NH-C_{1-4}$ alkyl, $-NHC(O)O-C_{1-4}$ alkyl, $-OC(O)N(C_{1-4}$ alkyl$)_2$, $-NH-C_{1-4}$ haloalkyl, $-N(C_{1-4}$ haloalkyl$)_2$, $-C(O)-C_{1-4}$ haloalkyl, $-S(O)_{0-2}-C_{1-4}$ haloalkyl, $-NHS(O)_{0-2}-C_{1-4}$ haloalkyl, $-S(O)_{0-2}NH-C_{1-4}$ haloalkyl, $-NHS(O)_{0-2}NH-C_{1-4}$ haloalkyl, $-C(O)NH-C_{1-4}$ haloalkyl, $-NHC(O)-C_{1-4}$ haloalkyl, $-C(O)N(C_{1-4}$ haloalkyl$)_2$, $-OC(O)NH-C_{1-4}$ haloalkyl, $-NHC(O)O-C_{1-4}$ haloalkyl, $-OC(O)N(C_{1-4}$ haloalkyl$)_2$, $C_{3-10}$ cycloalkyl, heterocyclyl, aryl heteroaryl, $-(CH_2)_{1-30}-C(O)OH$, $-(CH_2)_{0-4}-$O-poly(ethylene glycol), methoxypoly(ethylene glycol)-O-$(CH_2)_{0-4}-$, and sugar moiety;

each $R^{24}$, $R^{30}$ or $R^{34}$ is independently selected from halo, $-NH_2$, $-OH$, $-CN$, $-NO_2$, $C_{1-4}$ alkyl, $C_{1-4}$ hydroxyalkyl, $C_{1-4}$ haloalkyl, $C_{1-4}$ alkoxy, $-NH-C_{1-4}$ alkyl, $-N(C_{1-4}$ alkyl$)_2$, $-C(O)-C_{1-4}$ alkyl, $-C(O)OH$, $-C(O)O-C_{1-4}$ alkyl, $-S(O)_{0-2}-C_{1-4}$ alkyl, $-NHS(O)_{0-2}-C_{1-40}$ alkyl, $-S(O)_{0-2}NH-C_{1-4}$ alkyl, $-NHS(O)_{0-2}NH-C_{1-4}$ alkyl, $-C(O)NH-C_{1-4}$ alkyl, $-NHC(O)-C_{1-4}$ alkyl, $-C(O)N(C_{1-4}$ alkyl$)_2$, $-OC(O)NH-C_{1-4}$ alkyl, $-NHC(O)O-C_{1-4}$ alkyl, $-OC(O)N(C_{1-4}$ alkyl$)_2$, $-NH-C_{1-4}$ haloalkyl, $-N(C_{1-4}$ haloalkyl$)_2$, $-C(O)-C_{1-4}$ haloalkyl, $-S(O)_{0-2}-C_{1-4}$ haloalkyl, $-NHS(O)_{0-2}-C_{1-4}$ haloalkyl, $-S(O)_{0-2}NH-C_{1-4}$ haloalkyl, $-NHS(O)_{0-2}NH-C_{1-4}$ haloalkyl, $-C(O)NH-C_{1-4}$ haloalkyl, $-NHC(O)-C_{1-4}$ haloalkyl, $-C(O)N(C_{1-4}$ haloalkyl$)_2$, $-OC(O)NH-C_{1-4}$ haloalkyl, $-NHC(O)O-C_{1-4}$ haloalkyl, $-OC(O)N(C_{1-4}$ haloalkyl$)_2$, $C_{3-10}$ cycloalkyl, heterocyclyl, aryl, heteroaryl, $-(CH_2)_{1-30}-C(O)OH$, $-(CH_2)_{0-4}-$O-poly(ethylene glycol), $-(CH_2)_{0-4}-$O-methoxypoly(ethylene glycol) and sugar moiety; and each $R^{28}$ is independently selected from $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

provided at least that the compound has at least one of the following:

(1) $R^2$ is selected from $C_{2-30}$ alkyl optionally substituted with one to five $R^{19}$, $C_{1-30}$ heteroalkyl optionally substituted with one to five $R^{19}$, $-NO_2$, $-OR^{18}$, $-S(O)_{0-2}R^{18}$, and $-NR^{11}R^{18}$, wherein $R^{18}$ is selected from $C_{1-30}$ haloalkyl, $C_{2-30}$ alkyl optionally substituted with one to five $R^{19}$ and $C_{2-30}$ heteroalkyl optionally substituted with one to five $R^{19}$; wherein when $R^2$ is ethyl, then $R^6$ is not methyl or methoxy;

(2) $R^1$ is heteroaryl optionally substituted with one to five $R^{21}$, or fused heterocyclyl optionally substituted with one to five $R^{20}$;

(3) $R^1$ is heterocyclyl substituted with at least one $R^{20}$ selected from halo, oxo, $-NH_2$, $-OH$, $-CN$, $-NO_2$, $-NHR^{28}$, $-N(R^{28})_2$, $-C(O)R^{28}$, $-C(O)OR^{28a}$, $-NHS(O)_{0-2}R^{28}$, $-OC(O)R^{28}$, $-S(O)_{0-2}R^{28}$, $-S(O)_{0-2}NHR^{28}$, $-NHS(O)_{0-2}NHR^{28}$, $-C(O)NHR^{28}$, $-NHC(O)R^{28}$, $-C(O)N(R^{28})_2$, $-OC(O)NHR^{28}$, $-NHC(O)OR^{28}$, $-OC(O)N(R^{28})_2$, $-NR^{32}C(O)NH_2$, $-NR^{32}C(O)NHR^{28}$, $-NR^{32}C(O)N(R^{28})_2$, $C_{1-30}$ alkyl substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl substituted with one to five $R^{25}$, heteroaryl optionally substituted with one to five $R^{26}$, poly(ethylene glycol), and methoxypoly(ethylene glycol);

wherein the $C_{1-30}$ alkyl is substituted with at least one $R^{25}$ selected from halo, $-NH_2$, $-OH$, $-CN$, $-NO_2$, oxo, $-NHR^{31}$, $-N(R^{31})_2$, $-C(O)R^{31}$, $-C(O)OR^{31}$, $-C(O)OH$, $-S(O)_{0-2}R^{31}$, $-NR^{32}S(O)_{0-2}R^{31}$, $-S(O)_{0-2}NR^{32}R^{31}$, $-NR^{32}S(O)_{0-2}NR^{32}R^{31}$, $-C(O)NH_2$, $-C(O)NHR^{31}$, $-NR^{32}C(O)R^{31}$, $-C(O)N(R^{31})_2$, $-OC(O)NHR^{31}$, $-NR^{32}C(O)OR^{31}$, $-OC(O)N(R^{31})_2$, $-NR^{32}C(O)NH_2$, $-NR^{32}C(O)NHR^{31}$, $-NR^{32}C(O)N(R^{31})_2$, $C_{1-30}$ alkyl optionally substituted with one to five $R^{33}$, $C_{1-30}$ heteroalkyl optionally substituted with one to five $R^{33}$, heterocyclyl substituted with one to five $R^{33}$, poly(ethylene glycol), methoxypoly(ethylene glycol), pyrrolidinyl and piperidinyl; or the $C_{1-30}$ alkyl is substituted with at least one $-OR^{31}$, wherein $R^{31}$ is poly(ethylene glycol) or methoxypoly(ethylene glycol);

$R^{28a}$ is selected from $C_{1-30}$ alkyl substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

(4) $R^1$ is $-NR^3R^4$, and $R^4$ is selected from $C_{1-30}$ alkyl substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, heteroaryl optionally substituted with one to five $R^{21}$, poly(ethylene glycol), methoxypoly(ethylene glycol), and $-NR^{13}R^{14}$;

wherein the $C_{1-30}$ alkyl is substituted with at least one $R^{20}$ selected from halo, $-NH_2$, $-OH$, $-CN$, $-NO_2$, $-NHR^{28}$, $-N(R^{28})_2$, $-C(O)R^{28}$, $-S(O)_{0-2}R^{28}$, $-NHS(O)_{0-2}R^{28}$, $-S(O)_{0-2}NHR^{28}$, $-NHS(O)_{0-2}NHR^{28}$, $-C(O)NHR^{28}$, $-NHC(O)R^{28}$, $-C(O)N(R^{28})_2$, $-OC(O)NHR^{28}$, NHC(O)OR$^{28}$, $-OC(O)N(R^{28})_2$, $C_{3-10}$ cycloalkyl optionally substituted with one to five $R^{25}$, heterocyclyl optionally substituted with one to five $R^{25}$, and heteroaryl optionally substituted with one to five $R^{26}$; or (5) $R^6$ is selected from $C_{1-6}$ alkyl substituted with one to five $R^{29}$, $-OR^{17}$, $-S(O)_{0-2}R^{16}$, $C(O)OR^{15}$, $-OC(O)R^{16}$, $-NO_2$, $-NR^{15}R^{15}$, $-C(O)NR^{15}R^{15}$, $-S(O)_{0-2}NHR^{16}$, $-NHS(O)_{0-2}R^{16}$, heterocyclyl optionally substituted with one to five $R^{29}$, heteroaryl optionally substituted with one to five $R^{30}$, poly(ethylene glycol), and methoxypoly(ethylene glycol), wherein $R^{17}$ is selected from $C_{1-30}$ alkyl substituted with one to five $R^{27}$, $C_{1-30}$ heteroalkyl optionally substituted with one to five $R^{27}$, $C_{3-10}$ cycloalkyl optionally substituted with one to five $R^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol).

Provided herein is a compound of Formula (I):

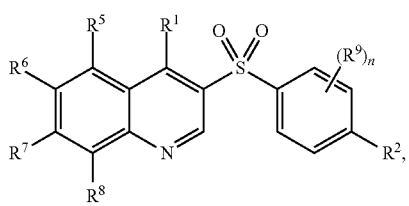

(I)

or a pharmaceutically acceptable salt, isotopically enriched analog, stereoisomer, mixture of stereoisomers, or tautomer thereof;

wherein
- $R^1$ is selected from $-NR^3R^4$, heterocyclyl optionally substituted with one to five $R^{20}$, and heteroaryl optionally substituted with one to five $R^{21}$;
- $R^2$ is selected from $C_{2-30}$ alkyl optionally substituted with one to five $R^{19}$, $C_{1-30}$ heteroalkyl optionally substituted with one to five $R^{19}$, $-NO_2$, $-OR^{18}$, $-S(O)_{0-2}R^{18}$, and $-NR^{11}R^{18}$, wherein $R^{18}$ is selected from $C_{1-30}$ haloalkyl, $C_{2-30}$ alkyl optionally substituted with one to five $R^{19}$ and $C_{2-30}$ heteroalkyl optionally substituted with one to five $R^{19}$; wherein when $R^2$ is ethyl, then $R^6$ is not methyl or methoxy;
- $R^3$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$;
- $R^4$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), methoxypoly(ethylene glycol), and $-NR^{13}R^{14}$;
- $R^5$, $R^7$ and $R^8$ are each independently selected from H, halo, $C_{1-30}$ alkyl optionally substituted with one to five $R^{29}$, $C_{1-30}$ heteroalkyl optionally substituted with one to five $R^{29}$, $-OR^{15}$, $-S(O)_{0-2}R^{16}$, $-C(O)OR^{15}$, $-OC(O)R^{16}$, $-CN$, $-NO_2$, $-NR^{15}R^{15}$, and $-C(O)NR^{15}R^{15}$;
- $R^6$ is selected from H, halo, $C_{1-30}$ alkyl optionally substituted with one to five $R^{29}$, $C_{1-30}$ heteroalkyl optionally substituted with one to five $R^{29}$, $-OR^{17}$, $-S(O)_{0-2}R^{16}$, $-C(O)OR^{15}$, $-OC(O)R^{16}$, $-CN$, $-NO_2$, $-NR^{15}R^{15}$, $-C(O)NR^{15}R^{15}$, $-NR^{15}C(O)R^{16}$, $-S(O)_{0-2}NR^{15}R^{15}$, $-NR^{15}S(O)_{0-2}R^{16}$, heterocyclyl optionally substituted with one to five $R^{29}$, heteroaryl optionally substituted with one to five $R^{30}$, poly(ethylene glycol), and methoxypoly(ethylene glycol), or
- $R^6$ and $R^7$ together with atoms to which they are attached form $C_{5-10}$ cycloalkyl optionally substituted with one to five $R^{29}$, heterocyclyl optionally substituted with one to five $R^{29}$, aryl optionally substituted with one to five $R^{30}$, or heteroaryl optionally substituted with one to five $R^{30}$;
- $R^9$ is independently selected from halo, $C_{1-8}$ alkyl optionally substituted with one to five $R^{22}$, $-OH$, $-OR^{10}$, $-CN$, and $-NR^{11}R^{12}$;
- n is 0, 1, 2, 3 or 4;
- $R^{10}$ is independently selected from $C_{1-10}$ alkyl optionally substituted with one to five $R^{22}$, and $C_{3-10}$ cycloalkyl optionally substituted with one to five $R^{22}$;
- $R^{11}$ and $R^{12}$ are each independently H or $C_{1-6}$ alkyl optionally substituted with one to five $R^{22}$;
- $R^{13}$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$;
- $R^{14}$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), and methoxypoly(ethylene glycol);
- each $R^{15}$ is independently selected from H, $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);
- $R^{16}$ is selected from $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);
- $R^{17}$ is selected from H, $C_{1-30}$ alkyl optionally substituted with one to five $R^{27}$, $C_{1-30}$ heteroalkyl optionally substituted with one to five $R^{27}$, $C_{3-10}$ cycloalkyl optionally substituted with one to five $R^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol);
- $R^{18}$ is selected from $C_{1-30}$ alkyl optionally substituted with one to five $R^{19}$ and $C_{1-30}$ heteroalkyl optionally substituted with one to five $R^{19}$;

each $R^{20}$ is independently selected from halo, oxo, —$NH_2$, —OH, —CN, —$NO_2$, —$OR^{28}$, —$NHR^{28}$, —$N(R^{28})_2$, —$C(O)R^{28}$, —$C(O)OR^{28}$, —C(O)OH, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NH_2$, —$C(O)NHR^{28}$, —$C(O)N(R^{28})_2$, —$NHC(O)R^{28}$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{21}$ is independently selected from halo, —$NH_2$, —OH, —CN, —$NO_2$, —$OR^{28}$, —$NHR^{28}$, —$N(R^{28})_2$, —$C(O)R^{28}$, —$C(O)OR^{28}$, —C(O)OH, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NHR^{28}$, —$NHC(O)R^{28}$, —$C(O)N(R^{28})_2$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-6}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{19}$ or $R^{22}$ is independently selected from halo, —$NH_2$, —OH, —CN, —$NO_2$, oxo, $C_{1-4}$ alkyl, $C_{1-4}$ haloalkyl, $C_{1-4}$ hydroxyalkyl, $C_{1-4}$ alkoxy, —NH—$C_{1-4}$ alkyl, —$N(C_{1-4}$ alkyl$)_2$, —C(O)—$C_{1-4}$ alkyl, —C(O)O—$C_{1-4}$ alkyl, —C(O)OH, —$S(O)_{0-2}$—$C_{1-4}$ alkyl, —$NHS(O)_{0-2}$—$C_{1-4}$ alkyl, —$S(O)_{0-2}$NH—$C_{1-4}$ alkyl, —$NHS(O)_{0-2}$NH—$C_{1-4}$ alkyl, —C(O)NH—$C_{1-4}$ alkyl, —NHC(O)—$C_{1-4}$ alkyl, —C(O)N($C_{1-4}$ alkyl$)_2$, —OC(O)NH—$C_{1-4}$ alkyl, —NHC(O)O—$C_{1-4}$ alkyl, —OC(O)N($C_{1-4}$ alkyl$)_2$, —NH—$C_{1-4}$ haloalkyl, —N($C_{1-4}$ haloalkyl$)_2$, —C(O)—$C_{1-4}$ haloalkyl, —$S(O)_{0-2}$—$C_{1-4}$ haloalkyl, —$NHS(O)_{0-2}$—$C_{1-4}$ haloalkyl, —$S(O)_{0-2}$NH—$C_{1-4}$ haloalkyl, —$NHS(O)_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl$)_2$, —OC(O)NH—$C_{1-4}$ haloalkyl, —NHC(O)O—$C_{1-4}$ haloalkyl, —OC(O)N($C_{1-4}$ haloalkyl$)_2$, and $C_{3-10}$ cycloalkyl;

each $R^{25}$ is independently selected from halo, —$NH_2$, —OH, —CN, —$NO_2$, oxo, —$NHR^{31}$, —$N(R^{31})_2$, —$C(O)R^{31}$, —$C(O)OR^{31}$, —C(O)OH, —$S(O)_{0-2}R^{31}$, —$NR^{32}S(O)_{0-2}R^{31}$, —$S(O)_{0-2}NR^{32}R^{31}$, —$NR^{32}S(O)_{0-2}$ $NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)OR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{26}$ is independently selected from halo, —$NH_2$, —OH, —CN, —$NO_2$, —$NHR^{31}$, —$N(R^{31})_2$, —C(O)$R^{31}$, —$C(O)OR^{31}$, —C(O)OH, —$S(O)_{0-2}R^{31}$, —$NR^{32}S(O)_{0-2}R^{31}$, —$S(O)_{0-2}NR^{32}R^{31}$, —$NR^{32}S(O)_{0-2}$ $NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)NHR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{31}$ is independently selected $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol) and methoxypoly(ethylene glycol);

each $R^{32}$ is independently selected H and $C_{1-4}$ alkyl;

each $R^{23}$, $R^{27}$, $R^{29}$ or $R^{33}$ is independently selected from halo, —$NH_2$, —OH, —CN, —$NO_2$, oxo, $C_{1-4}$ alkyl optionally substituted with phenyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl$)_2$, —C(O)—$C_{1-4}$ alkyl, —C(O)O—$C_{1-4}$ alkyl, —C(O)OH, —$S(O)_{0-2}$—$C_{1-4}$ alkyl, —NHS$(O)_{0-2}$—$C_{1-4}$ alkyl, —$S(O)_{0-2}$NH—$C_{1-4}$ alkyl, —NHS$(O)_{0-2}$NH—$C_{1-4}$ alkyl, —C(O)NH—$C_{1-4}$ alkyl, —NHC(O)—$C_{1-4}$ alkyl, —C(O)N($C_{1-4}$ alkyl$)_2$, —OC(O)NH—$C_{1-4}$ alkyl, —NHC(O)O—$C_{1-4}$ alkyl, —OC(O)N($C_{1-4}$ alkyl$)_2$, —NH—$C_{1-4}$ haloalkyl, —N($C_{1-4}$ haloalkyl$)_2$, —C(O)—$C_{1-4}$ haloalkyl, —$S(O)_{0-2}$—$C_{1-4}$ haloalkyl, —NHS$(O)_{0-2}$—$C_{1-4}$ haloalkyl, —$S(O)_{0-2}$NH—$C_{1-4}$ haloalkyl, —NHS$(O)_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl$)_2$, —OC(O)NH—$C_{1-4}$ haloalkyl, —NHC(O)O—$C_{1-4}$ haloalkyl, —OC(O)N($C_{1-4}$ haloalkyl$)_2$, $C_{3-10}$ cycloalkyl, heterocyclyl, aryl heteroaryl, —$(CH_2)_{1-30}$—C(O)OH, —$(CH_2)_{0-4}$—O-poly(ethylene glycol), methoxypoly(ethylene glycol)-O—$(CH_2)_{0-4}$—, and sugar moiety;

each $R^{24}$, $R^{30}$ or $R^{34}$ is independently selected from halo, —$NH_2$, —OH, —CN, —$NO_2$, $C_{1-4}$ alkyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl$)_2$, —C(O)—$C_{1-4}$ alkyl, —C(O)OH, —C(O)O—$C_{1-4}$ alkyl, —$S(O)_{0-2}$—$C_{1-4}$ alkyl, —NHS$(O)_{0-2}$—$C_{1-4}$ alkyl, —$S(O)_{0-2}$NH—$C_{1-4}$ alkyl, —NHS$(O)_{0-2}$NH—$C_{1-4}$ alkyl, —C(O)NH—$C_{1-4}$ alkyl, —NHC(O)—$C_{1-4}$ alkyl, —C(O)N($C_{1-4}$ alkyl$)_2$, —OC(O)NH—$C_{1-4}$ alkyl, —NHC(O)O—$C_{1-4}$ alkyl, —OC(O)N($C_{1-4}$ alkyl$)_2$, —NH—$C_{1-4}$ haloalkyl, —N($C_{1-4}$ haloalkyl$)_2$, —C(O)—$C_{1-4}$ haloalkyl, —$S(O)_{0-2}$—$C_{1-4}$ haloalkyl, —NHS$(O)_{0-2}$—$C_{1-4}$ haloalkyl, —$S(O)_{0-2}$NH—$C_{1-4}$ haloalkyl, —NHS$(O)_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl$)_2$, —OC(O)NH—$C_{1-4}$ haloalkyl, —NHC(O)O—$C_{1-4}$ haloalkyl, —OC(O)N($C_{1-4}$ haloalkyl$)_2$, $C_{3-10}$ cycloalkyl, heterocyclyl, aryl, heteroaryl, —$(CH_2)_{1-30}$—C(O)OH, —$(CH_2)_{0-4}$—O-poly(ethylene glycol); —$(CH_2)_{0-4}$—O-methoxypoly (ethylene glycol) and sugar moiety; and each $R^{28}$ is independently selected from $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol).

Provided herein is a compound of Formula (I):

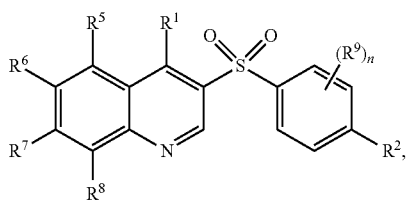

(I)

or a pharmaceutically acceptable salt, isotopically enriched analog, stereoisomer, mixture of stereoisomers, or tautomer thereof;

wherein
- $R^1$ is heteroaryl optionally substituted with one to five $R^{21}$, or fused heterocyclyl optionally substituted with one to five $R^{20}$; or
- $R^1$ is heterocyclyl substituted with at least one $R^{20}$ selected from halo, oxo, —NH$_2$, —OH, —CN, —NO$_2$, —OR$^{28}$, —NHR$^{28}$, —N(R$^{28}$)$_2$, —C(O)R$^{28}$, —C(O)OR$^{28a}$, —NHS(O)$_{0-2}$R$^{28}$, —OC(O)R$^{28}$, —S(O)$_{0-2}$R$^{28}$, —S(O)$_{0-2}$NHR$^{28}$, —NHS(O)$_{0-2}$NHR$^{28}$, —C(O)NHR$^{28}$, —NHC(O)R$^{28}$, —C(O)N(R$^{28}$)$_2$, —OC(O)NHR$^{28}$, —NHC(O)OR$^{28}$, —OC(O)N(R$^{28}$)$_2$, —NR$^{32}$C(O)NH$_2$, —NR$^{32}$C(O)NHR$^{28}$, —NR$^{32}$C(O)N(R$^{28}$)$_2$, $C_{1-30}$ alkyl substituted with one to five $R^{25}$, $C_{1-30}$ heteroalkyl optionally substituted with one to five $R^{25}$, heterocyclyl substituted with one to five $R^{25}$, poly(ethylene glycol), and methoxypoly(ethylene glycol); wherein at least one $R^{25}$ is selected from halo, —NH$_2$, —OH, —CN, —NO$_2$, oxo, —NHR$^{31}$, —N(R$^{31}$)$_2$, —C(O)R$^{31}$, —C(O)OR$^{31}$, —C(O)OH, —S(O)$_{0-2}$R$^{31}$, —NR$^{32}$S(O)$_{0-2}$R$^{31}$, —S(O)$_{0-2}$NR$^{32}$R$^{31}$, —NR$^{32}$S(O)$_{0-2}$ NR$^{32}$R$^{31}$, —C(O)NH$_2$, —C(O)NHR$^{31}$, —NR$^{32}$C(O)R$^{31}$, —C(O)N(R$^{31}$)$_2$, —OC(O)NHR$^{31}$, —NR$^{32}$C(O)OR$^{31}$, —OC(O)N(R$^{31}$)$_2$, —NR$^{32}$C(O)NH$_2$, —NR$^{32}$C(O)NHR$^{31}$, —NR$^{32}$C(O)N(R$^{31}$)$_2$, $C_{1-30}$ alkyl optionally substituted with one to five $R^{33}$, $C_{1-30}$ heteroalkyl optionally substituted with one to five $R^{33}$, heterocyclyl substituted with one to five $R^{33}$, poly(ethylene glycol), methoxypoly(ethylene glycol), pyrrolidinyl and piperidinyl; or the $C_{1-30}$ alkyl is substituted with at least one —OR$^{31a}$, wherein $R^{31a}$ is poly(ethylene glycol) or methoxypoly(ethylene glycol); and $R^{28a}$ is selected from $C_{1-30}$ alkyl substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol); or
- $R^1$ is —NR$^3$R$^4$,
- $R^2$ is selected from H, halo, $C_{1-30}$ alkyl optionally substituted with one to five $R^{19}$, $C_{1-30}$ heteroalkyl optionally substituted with one to five $R^{19}$, —OH, —OR$^{18}$, —CN, —NO$_2$, —NH$_2$, —S(O)$_{0-2}$R$^{18}$, and —NR$^{11}$R$^{18}$;
- $R^3$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$, and
- $R^4$ is selected from $C_{1-30}$ alkyl substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, heteroaryl optionally substituted with one to five $R^{21}$, poly(ethylene glycol), methoxypoly(ethylene glycol), and —NR$^{13}$R$^{14}$, wherein the $C_{1-30}$ alkyl is substituted with at least one $R^{20}$ selected from halo, —NH$_2$, —OH, —CN, —NO$_2$, —OR$^{28}$, —NHR$^{28}$, —N(R$^{28}$)$_2$, —C(O)R$^{28}$, —S(O)$_{0-2}$R$^{28}$, —NHS(O)$_{0-2}$R$^{28}$, —S(O)$_{0-2}$NHR$^{28}$, —NHS(O)$_{0-2}$NHR$^{28}$, —C(O)NHR$^{28}$, —NHC(O)R$^{28}$, —C(O)N(R$^{28}$)$_2$, —OC(O)NHR$^{28}$, —NHC(O)OR$^{28}$, —OC(O)N(R$^{28}$)$_2$, $C_{3-10}$ cycloalkyl optionally substituted with one to five $R^{25}$, heterocyclyl optionally substituted with one to five $R^{25}$, and heteroaryl optionally substituted with one to five $R^{26}$;
- $R^5$, $R^7$ and $R^8$ are each independently selected from H, halo, $C_{1-30}$ alkyl optionally substituted with one to five $R^{29}$, $C_{1-30}$ heteroalkyl optionally substituted with one to five $R^{29}$, —OR$^{15}$, —S(O)$_{0-2}$R$^{16}$, —C(O)OR$^{15}$, —OC(O)R$^{16}$, —CN, —NO$_2$, —NR$^{15}$R$^{15}$, and —C(O)NR$^{15}$R$^{15}$;
- $R^6$ is selected from H, halo, $C_{1-30}$ alkyl optionally substituted with one to five $R^{29}$, $C_{1-30}$ heteroalkyl optionally substituted with one to five $R^{29}$, —OR$^{17}$, —S(O)$_{0-2}$R$^{16}$, —C(O)OR$^{15}$, —OC(O)R$^{16}$, —CN, —NO$_2$, —NR$^{15}$R$^{15}$, —C(O)NR$^{15}$R$^{15}$, —NR$^{15}$C(O)R$^{16}$, —S(O)$_{0-2}$NR$^{15}$R$^{15}$, —NR$^{15}$S(O)$_{0-2}$R$^{16}$, heterocyclyl optionally substituted with one to five $R^{29}$, heteroaryl optionally substituted with one to five $R^{30}$, poly(ethylene glycol), methoxypoly(ethylene glycol), and sugar moiety, or $R^6$ and IV together with atoms to which they are attached form $C_{5-10}$ cycloalkyl optionally substituted with one to five $R^{29}$, heterocyclyl optionally substituted with one to five $R^{29}$, aryl optionally substituted with one to five $R^{30}$, or heteroaryl optionally substituted with one to five $R^{30}$;
- $R^9$ is independently selected from halo, $C_{1-8}$ alkyl optionally substituted with one to five $R^{22}$, —OH, —CN, and —NR$^{11}$R$^{12}$;
- n is 0, 1, 2, 3 or 4;
- $R^{10}$ is independently selected from $C_{1-10}$ alkyl optionally substituted with one to five $R^{22}$, and $C_{3-10}$ cycloalkyl optionally substituted with one to five $R^{22}$;
- $R^{11}$ and $R^{12}$ are each independently H or $C_{1-6}$ alkyl optionally substituted with one to five $R^{22}$;
- $R^{13}$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$;
- $R^{14}$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), and methoxypoly(ethylene glycol);

each $R^{15}$ is independently selected from H, $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, and heterocyclyl optionally substituted with one to five $R^{23}$, aryl optionally substituted with one to five $R^{24}$, heteroaryl optionally substituted with one to five $R^{24}$, poly(ethylene glycol), methoxypoly(ethylene glycol);

$R^{16}$ is selected from $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);

$R^{17}$ is selected from H, $C_{1-30}$ alkyl optionally substituted with one to five $R^{27}$, $C_{1-30}$ heteroalkyl optionally substituted with one to five $R^{27}$, $C_{3-10}$ cycloalkyl optionally substituted with one to five $R^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol);

$R^{18}$ is selected from $C_{1-30}$ alkyl optionally substituted with one to five $R^{19}$ and $C_{1-30}$ heteroalkyl optionally substituted with one to five $R^{19}$;

each $R^{20}$ is independently selected from halo, oxo, —$NH_2$, —OH, —CN, —$NO_2$, —$NHR^{28}$, —$N(R^{28})_2$, —$C(O)R^{28}$, $C(O)R^{28}$, —$C(O)OR^{28}$, —$C(O)OH$, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NH_2$, —$C(O)NHR^{28}$, —$C(O)N(R^{28})_2$, —$NHC(O)R^{28}$, —$OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{21}$ is independently selected from halo, —$NH_2$, —OH, —CN, —$NO_2$, —$NHR^{28}$, —$N(R^{28})_2$, —$C(O)R^{28}$, —$C(O)OR^{28}$, —$C(O)OH$, —$OC(O)R^{28}$, —$S(O)_{0-2}R^{28}$, —$NHS(O)_{0-2}R^{28}$, —$S(O)_{0-2}NHR^{28}$, —$NHS(O)_{0-2}NHR^{28}$, —$C(O)NHR^{28}$, —$NHC(O)R^{28}$, —$C(O)N(R^{28})_2$, $OC(O)NHR^{28}$, —$NHC(O)OR^{28}$, —$OC(O)N(R^{28})_2$, —$NR^{32}C(O)NH_2$, —$NR^{32}C(O)NHR^{28}$, —$NR^{32}C(O)N(R^{28})_2$, $C_{1-6}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{19}$ or $R^{22}$ is independently selected from halo, —$NH_2$, —OH, —CN, —$NO_2$, oxo, $C_{1-4}$ alkyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl)$_2$, —C(O)—$C_{1-4}$ alkyl, —C(O)O—$C_{1-4}$ alkyl, —C(O)OH, —S(O)$_{0-2}$—$C_{1-4}$ alkyl, —NHS(O)$_{0-2}$—$C_{1-4}$ alkyl, —S(O)$_{0-2}$NH—$C_{1-4}$ alkyl, —NHS(O)$_{0-2}$NH—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$ haloalkyl, —N($C_{1-4}$ haloalkyl)$_2$, —C(O)—$C_{1-4}$ haloalkyl, —S(O)$_{0-2}$—$C_{1-4}$ haloalkyl, —NHS(O)$_{0-2}$—$C_{1-4}$ haloalkyl, —S(O)$_{0-2}$NH—$C_{1-4}$ haloalkyl, —NHS(O)$_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl)$_2$, —OC(O)NH—$C_{1-4}$ haloalkyl, —NHC(O)O—$C_{1-4}$ haloalkyl, —OC(O)N($C_{1-4}$ haloalkyl)$_2$, and $C_{3-10}$ cycloalkyl;

each $R^{25}$ is independently selected from halo, —$NH_2$, —OH, —CN, —$NO_2$, oxo, —$NHR^{31}$, —$N(R^{31})_2$, —$C(O)R^{31}$, —$C(O)OR^{31}$, —$C(O)OH$, —$S(O)_{0-2}R^{31}$, —$NR^{32}S(O)_{0-2}R^{31}$, —$S(O)_{0-2}NR^{32}R^{31}$, —$NR^{32}S(O)_{0-2}$ $NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)OR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{26}$ is independently selected from halo, —$NH_2$, —OH, —CN, —$NO_2$, —$NHR^{31}$, —$N(R^{31})_2$, —$C(O)R^{31}$, —$C(O)OR^{31}$, —$C(O)OH$, —$S(O)_{0-2}R^{31}$, —$NR^{32}S(O)_{0-2}R^{31}$, —$S(O)_{0-2}NR^{32}R^{31}$, —$NR^{32}S(O)_{0-2}$ $NR^{32}R^{31}$, —$C(O)NH_2$, —$C(O)NHR^{31}$, —$NR^{32}C(O)R^{31}$, —$C(O)N(R^{31})_2$, —$OC(O)NHR^{31}$, —$NR^{32}C(O)OR^{31}$, —$OC(O)N(R^{31})_2$, —$NR^{32}C(O)NH_2$, —$NR^{32}C(O)NHR^{31}$, —$NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{31}$ is independently selected $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol) and methoxypoly(ethylene glycol);

each $R^{32}$ is independently selected H and $C_{1-4}$ alkyl;

each $R^{23}$, $R^{27}$, $R^{29}$ or $R^{33}$ is independently selected from halo, —$NH_2$, —OH, —CN, —$NO_2$, oxo, $C_{1-4}$ alkyl optionally substituted with phenyl, $C_{1-4}$ haloalkyl, $C_{1-4}$ hydroxyalkyl, $C_{1-4}$ alkoxy, —NH—$C_{1-4}$ alkyl, —N($C_{1-4}$ alkyl)$_2$, —C(O)—$C_{1-4}$ alkyl, —C(O)O—$C_{1-4}$ alkyl, —C(O)OH, —S(O)$_{0-2}$—$C_{1-4}$ alkyl, —NHS(O)$_{0-2}$—$C_{1-4}$ alkyl, —S(O)$_{0-2}$NH—$C_{1-4}$ alkyl, —NHS(O)$_{0-2}$NH—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$ haloalkyl, —N($C_{1-4}$ haloalkyl)$_2$, —C(O)—$C_{1-4}$ haloalkyl, —S(O)$_{0-2}$—$C_{1-4}$ haloalkyl, —NHS(O)$_{0-2}$—$C_{1-4}$ haloalkyl, —S(O)$_{0-2}$NH—$C_{1-4}$ haloalkyl, —NHS(O)$_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl)$_2$, —OC(O)NH—

$C_{1-4}$ haloalkyl, —NHC(O)O—$C_{1-4}$ haloalkyl, —OC(O)N($C_{1-4}$ haloalkyl)$_2$, $C_{3-10}$ cycloalkyl, heterocyclyl, aryl heteroaryl, —(CH$_2$)$_{1-30}$—C(O)OH, —(CH$_2$)$_{0-4}$—O-poly(ethylene glycol), methoxypoly(ethylene glycol)-O—(CH$_2$)$_{0-4}$—, and sugar moiety;

each $R^{24}$, $R^{30}$ or $R^{34}$ is independently selected from halo, —NH$_2$, —OH, —CN, —NO$_2$, $C_{1-4}$ alkyl, $C_{1-4}$ hydroxyalkyl, $C_{1-4}$ haloalkyl, $C_{1-4}$ alkoxy, —NH—$C_{1-4}$ alkyl, —N($C_{1-4}$ alkyl)$_2$, —C(O)—$C_{1-4}$ alkyl, —C(O)OH, —C(O)O—$C_{1-4}$ alkyl, —S(O)$_{0-2}$—$C_{1-4}$ alkyl, —NHS(O)$_{0-2}$—$C_{1-4}$ alkyl, —S(O)$_{0-2}$NH—$C_{1-4}$ alkyl, —NHS(O)$_{0-2}$NH—$C_{1-4}$ alkyl, —C(O)NH—$C_{1-4}$ alkyl, —NHC(O)—$C_{1-4}$ alkyl, —C(O)N($C_{1-4}$ alkyl)$_2$, —OC(O)NH—$C_{1-4}$ alkyl, —NHC(O)O—$C_{1-4}$ alkyl, —OC(O)N($C_{1-4}$ alkyl)$_2$, —NH—$C_{1-4}$ haloalkyl, —N($C_{1-4}$ haloalkyl)$_2$, —C(O)—$C_{1-4}$ haloalkyl, —S(O)$_{0-2}$—$C_{1-4}$ haloalkyl, —NHS(O)$_{0-2}$—$C_{1-4}$ haloalkyl, —S(O)$_{0-2}$NH—$C_{1-4}$ haloalkyl, —NHS(O)$_{0-2}$NH—$C_{1-4}$ haloalkyl, —C(O)NH—$C_{1-4}$ haloalkyl, —NHC(O)—$C_{1-4}$ haloalkyl, —C(O)N($C_{1-4}$ haloalkyl)$_2$, —OC(O)NH—$C_{1-4}$ haloalkyl, —NHC(O)O—$C_{1-4}$ haloalkyl, —OC(O)N($C_{1-4}$ haloalkyl)$_2$, $C_{3-10}$ cycloalkyl, heterocyclyl, aryl, heteroaryl, —(CH$_2$)$_{1-30}$—C(O)OH, —(CH$_2$)$_{0-4}$—O-poly(ethylene glycol), —(CH$_2$)$_{0-4}$—O-methoxypoly(ethylene glycol) and sugar moiety; and each $R^{28}$ is independently selected from $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol).

Provided herein is a compound of Formula (I):

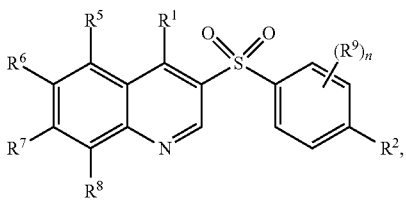

(I)

or a pharmaceutically acceptable salt, isotopically enriched analog, stereoisomer, mixture of stereoisomers, or tautomer thereof;

wherein $R^1$ is selected from —NR$^3$R$^4$, heterocyclyl optionally substituted with one to five $R^{20}$, and heteroaryl optionally substituted with one to five $R^{21}$;

$R^2$ is selected from H, halo, $C_{1-30}$ alkyl optionally substituted with one to five $R^{19}$, $C_{1-30}$ heteroalkyl optionally substituted with one to five $R^{19}$, —OH, —OR$^{18}$, —CN, —NO$_2$, —NH$_2$, —S(O)$_{0-2}$R$^{18}$, and —NR$^{11}$R$^{18}$;

$R^3$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$, $R^4$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), methoxypoly(ethylene glycol), and —NR$^{13}$R$^{14}$;

$R^5$, $R^7$ and $R^8$ are each independently selected from H, halo, $C_{1-30}$ alkyl optionally substituted with one to five $R^{29}$, $C_{1-30}$ heteroalkyl optionally substituted with one to five $R^{29}$, —OR$^{15}$, —S(O)$_{0-2}$R$^{16}$, —C(O)OR$^{15}$, —OC(O)R$^{16}$, —CN, —NO$_2$, —NR$^{15}$R$^{15}$, and —C(O)NR$^{15}$R$^{15}$;

$R^6$ is selected from $C_{1-6}$ alkyl substituted with one to five $R^{29}$, —OR$^{17}$, —S(O)$_{0-2}$R$^{16}$, C(O)OR$^{15}$, —OC(O)R$^{16}$, —NO$_2$, —NR$^{15}$R$^{15}$, —C(O)NR$^{15}$R$^{15}$, —S(O)$_{0-2}$NHR$^{16}$, —NHS(O)$_{0-2}$R$^{16}$, heterocyclyl optionally substituted with one to five $R^{29}$, heteroaryl optionally substituted with one to five $R^{30}$, poly(ethylene glycol), and methoxypoly(ethylene glycol), wherein $R^{17}$ is selected from $C_{1-30}$ alkyl substituted with one to five $R^{27}$, $C_{1-30}$ heteroalkyl optionally substituted with one to five $R^{27}$, $C_{3-10}$ cycloalkyl optionally substituted with one to five $R^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol);

$R^9$ is independently selected from halo, $C_{1-8}$ alkyl optionally substituted with one to five $R^{22}$, —OH, —OR$^{10}$, —CN, and —NR$^{11}$R$^{12}$;

n is 0, 1, 2, 3 or 4;

$R^{10}$ is independently selected from $C_{1-10}$ alkyl optionally substituted with one to five $R^{22}$, and $C_{3-10}$ cycloalkyl optionally substituted with one to five $R^{22}$;

$R^{11}$ and $R^{12}$ are each independently H or $C_{1-6}$ alkyl optionally substituted with one to five $R^{22}$;

$R^{13}$ is selected from H, $C_{1-6}$ alkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, and heteroaryl optionally substituted with one to five $R^{21}$;

$R^{14}$ is selected from H, $C_{1-30}$ alkyl optionally substituted with one to five $R^{20}$, $C_{1-30}$ heteroalkyl optionally substituted with one to five $R^{20}$, $C_{3-10}$ cycloalkyl optionally substituted with one to five $R^{20}$, heterocyclyl optionally substituted with one to five $R^{20}$, aryl optionally substituted with one to five $R^{21}$, heteroaryl optionally substituted with one to five $R^{21}$, poly(ethylene glycol), and methoxypoly(ethylene glycol);

each $R^{15}$ is independently selected from H, $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);

$R^{16}$ is selected from $C_{1-30}$ alkyl optionally substituted with one to five $R^{23}$, $C_{1-30}$ heteroalkyl optionally substituted with one to five $R^{23}$, $C_{3-10}$ cycloalkyl optionally substituted with one to five $R^{23}$, heterocyclyl optionally substituted with one to five $R^{23}$, aryl optionally substituted with one to five $R^{24}$, heteroaryl optionally substituted with one to five $R^{24}$, poly(ethylene glycol), and methoxypoly(ethylene glycol);

$R^{17}$ is selected from H, $C_{1-30}$ alkyl optionally substituted with one to five $R^{27}$, $C_{1-30}$ heteroalkyl optionally substituted with one to five $R^{27}$, $C_{3-10}$ cycloalkyl optionally substituted with one to five $R^{27}$, heterocyclyl optionally substituted with one to five $R^{27}$, aryl optionally substituted with one to five $R^{24}$, heteroaryl optionally substituted with one to five $R^{24}$, poly(ethylene glycol), and methoxypoly(ethylene glycol);

$R^{18}$ is selected from $C_{1-30}$ alkyl optionally substituted with one to five $R^{19}$ and $C_{1-30}$ heteroalkyl optionally substituted with one to five $R^{19}$;

each $R^{20}$ is independently selected from halo, oxo, $-NH_2$, $-OH$, $-CN$, $-NO_2$, $-NHR^{28}$, $-N(R^{28})_2$, $-C(O)R^{28}$, $-C(O)OR^{28}$, $-C(O)OH$, $-OC(O)R^{28}$, $-S(O)_{0-2}R^{28}$, $-NHS(O)_{0-2}R^{28}$, $-S(O)_{0-2}NHR^{28}$, $-NHS(O)_{0-2}NHR^{28}$, $-C(O)NH_2$, $-C(O)NHR^{28}$, $-C(O)N(R^{28})_2$, $-NHC(O)R^{28}$, $-OC(O)NHR^{28}$, $-NHC(O)OR^{28}$, $-OC(O)N(R^{28})_2$, $-NR^{32}C(O)NH_2$, $-NR^{32}C(O)NHR^{28}$, $-NR^{32}C(O)N(R^{28})_2$, $C_{1-30}$ alkyl optionally substituted with one to five $R^{25}$, $C_{1-30}$ heteroalkyl optionally substituted with one to five $R^{25}$, $C_{3-10}$ cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{21}$ is independently selected from halo, $-NH_2$, $-OH$, $-CN$, $-NO_2$, $-OR^{28}$, $-NHR^{28}$, $-N(R^{28})_2$, $-C(O)R^{28}$, $-C(O)OR^{28}$, $-C(O)OH$, $-OC(O)R^{28}$, $-S(O)_{0-2}R^{28}$, $-NHS(O)_{0-2}R^{28}$, $-S(O)_{0-2}NHR^{28}$, $-NHS(O)_{0-2}NHR^{28}$, $-C(O)NHR^{28}$, $-NHC(O)R^{28}$, $-C(O)N(R^{28})_2$, $-OC(O)NHR^{28}$, $-NHC(O)OR^{28}$, $-OC(O)N(R^{28})_2$, $-NR^{32}C(O)NH_2$, $-NR^{32}C(O)NHR^{28}$, $-NR^{32}C(O)N(R^{28})_2$, $C_{1-6}$ alkyl optionally substituted with one to five $R^{25}$, $C_{1-30}$ heteroalkyl optionally substituted with one to five $R^{25}$, $C_3$ to cycloalkyl optionally substituted with one to five $R^{25}$, heterocyclyl optionally substituted with one to five $R^{25}$, aryl optionally substituted with one to five $R^{26}$, heteroaryl optionally substituted with one to five $R^{26}$, poly(ethylene glycol), and methoxypoly(ethylene glycol);

each $R^{22}$ is independently selected from halo, $-NH_2$, $-OH$, $-CN$, $-NO_2$, oxo, $C_{1-4}$ alkyl, $C_{1-4}$ haloalkyl, $C_{1-4}$ hydroxyalkyl, $C_{1-4}$ alkoxy, $-NH-C_{1-4}$ alkyl, $-N(C_{1-4}$ alkyl$)_2$, $-C(O)-C_{1-4}$ alkyl, $-C(O)O-C_{1-4}$ alkyl, $-C(O)OH$, $-S(O)_{0-2}-C_{1-4}$ alkyl, $-NHS(O)_{0-2}-C_{1-4}$ alkyl, $-S(O)_{0-2}NH-C_{1-4}$ alkyl, $-NHS(O)_{0-2}NH-C_{1-4}$ alkyl, $-C(O)NH-C_{1-4}$ alkyl, $-NHC(O)-C_{1-4}$ alkyl, $-C(O)N(C_{1-4}$ alkyl$)_2$, $-OC(O)NH-C_{1-4}$ alkyl, $-NHC(O)O-C_{1-4}$ alkyl, $-OC(O)N(C_{1-4}$ alkyl$)_2$, $-NH-C_{1-4}$ haloalkyl, $-N(C_{1-4}$ haloalkyl$)_2$, $-C(O)-C_{1-4}$ haloalkyl, $-S(O)_{0-2}-C_{1-4}$ haloalkyl, $-NHS(O)_{0-2}-C_{1-4}$ haloalkyl, $-S(O)_{0-2}NH-C_{1-4}$ haloalkyl, $-NHS(O)_{0-2}NH-C_{1-4}$ haloalkyl, $-C(O)NH-C_{1-4}$ haloalkyl, $-NHC(O)-C_{1-4}$ haloalkyl, $-C(O)N(C_{1-4}$ haloalkyl$)_2$, $-OC(O)NH-C_{1-4}$ haloalkyl, $-NHC(O)O-C_{1-4}$ haloalkyl, $-OC(O)N(C_{1-4}$ haloalkyl$)_2$, and $C_{3-10}$ cycloalkyl;

each $R^{25}$ is independently selected from halo, $-NH_2$, $-OH$, $-CN$, $-NO_2$, oxo, $-OR^{31}$, $-NHR^{31}$, $-N(R^{31})_2$, $-C(O)R^{31}$, $-C(O)OR^{31}$, $-C(O)OH$, $-S(O)_{0-2}R^{31}$, $-NR^{32}S(O)_{0-2}R^{31}$, $-S(O)_{0-2}NR^{32}R^{31}$, $-NR^{32}S(O)_{0-2}NR^{32}R^{31}$, $-C(O)NH_2$, $-C(O)NHR^{31}$, $-NR^{32}C(O)R^{31}$, $-C(O)N(R^{31})_2$, $-OC(O)NHR^{31}$, $-NR^{32}C(O)OR^{31}$, $-OC(O)N(R^{31})_2$, $-NR^{32}C(O)$ NH$_2$, $-NR^{32}C(O)NHR^{31}$, $-NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{26}$ is independently selected from halo, $-NH_2$, $-OH$, $-CN$, $-NO_2$, $-OR^{31}$, $-NHR^{31}$, $-N(R^{31})_2$, $-C(O)R^{31}$, $-C(O)OR^{31}$, $-C(O)OH$, $-S(O)_{0-2}R^{31}$, $-NR^{32}S(O)_{0-2}R^{31}$, $-S(O)_{0-2}NR^{32}R^{31}$, $-NR^{32}S(O)_{0-2}$ $NR^{32}R^{31}$, $-C(O)NH_2$, $-C(O)NHR^{31}$, $-NR^{32}C(O)R^{31}$, $-C(O)N(R^{31})_2$, $-OC(O)NHR^{31}$, $-NR^{32}C(O)OR^{31}$, $-OC(O)N(R^{31})_2$, $-NR^{32}C(O)$ NH$_2$, $-NR^{32}C(O)NHR^{31}$, $-NR^{32}C(O)N(R^{31})_2$, $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol), and methoxypoly(ethylene glycol);

each $R^{31}$ is independently selected $C_{1-30}$ alkyl optionally substituted with one to five $R^{33}$, $C_{1-30}$ heteroalkyl optionally substituted with one to five $R^{33}$, $C_{3-10}$ cycloalkyl optionally substituted with one to five $R^{33}$, heterocyclyl optionally substituted with one to five $R^{33}$, aryl optionally substituted with one to five $R^{34}$, heteroaryl optionally substituted with one to five $R^{34}$, poly(ethylene glycol) and methoxypoly(ethylene glycol);

each $R^{32}$ is independently selected H and $C_{1-4}$ alkyl;

each $R^{23}$, $R^{27}$, $R^{29}$ or $R^{33}$ is independently selected from halo, $-NH_2$, $-OH$, $-CN$, $-NO_2$, oxo, $C_{1-4}$ alkyl optionally substituted with phenyl, $C_{1-4}$ haloalkyl, $C_{1-4}$ hydroxyalkyl, $C_{1-4}$ alkoxy, $-NH-C_{1-4}$ alkyl, $-N(C_{1-4}$ alkyl$)_2$, $-C(O)-C_{1-4}$ alkyl, $-C(O)O-C_{1-4}$ alkyl, $-C(O)OH$, $-S(O)_{0-2}-C_{1-4}$ alkyl, $-NHS(O)_{0-2}-C_{1-4}$ alkyl, $-S(O)_{0-2}NH-C_{1-4}$ alkyl, $-NHS(O)_{0-2}NH-C_{1-4}$ alkyl, $-C(O)NH-C_{1-4}$ alkyl, $-NHC(O)-C_{1-4}$ alkyl, $-C(O)N(C_{1-4}$ alkyl$)_2$, $-OC(O)NH-C_{1-4}$ alkyl, $-NHC(O)O-C_{1-4}$ alkyl, $-OC(O)N(C_{1-4}$ alkyl$)_2$, $-NH-C_{1-4}$ haloalkyl, $-N(C_{1-4}$ haloalkyl$)_2$, $-C(O)-C_{1-4}$ haloalkyl, $-S(O)_{0-2}-C_{1-4}$ haloalkyl, $-NHS(O)_{0-2}-C_{1-4}$ haloalkyl, $-S(O)_{0-2}NH-C_{1-4}$ haloalkyl, $-NHS(O)_{0-2}NH-C_{1-4}$ haloalkyl, $-C(O)NH-C_{1-4}$ haloalkyl, $-NHC(O)-C_{1-4}$ haloalkyl, $-C(O)N(C_{1-4}$ haloalkyl$)_2$, $-OC(O)NH-C_{1-4}$ haloalkyl, $-NHC(O)O-C_{1-4}$ haloalkyl, $-OC(O)N(C_{1-4}$ haloalkyl$)_2$, $C_{3-10}$ cycloalkyl, heterocyclyl, aryl heteroaryl, $(CH_2)_{1-30}-C(O)OH$, $-(CH_2)_{0-4}-O-$poly(ethylene glycol), methoxypoly(ethylene glycol)-$O-(CH_2)_{0-4}-$, and sugar moiety;

each $R^{24}$, $R^{30}$ or $R^{34}$ is independently selected from halo, $-NH_2$, $-OH$, $-CN$, $-NO_2$, $C_{1-4}$ alkyl, $C_{1-4}$ haloalkyl, $C_{1-4}$ hydroxyalkyl, $C_{1-4}$ alkoxy, $-NH-C_{1-4}$ alkyl, $-N(C_{1-4}$ alkyl$)_2$, $-C(O)-C_{1-4}$ alkyl, $-C(O)OH$, $-C(O)O-C_{1-4}$ alkyl, $-S(O)_{0-2}-C_{1-4}$ alkyl, $-NHS(O)_{0-2}-C_{1-4}$ alkyl, $-S(O)_{0-2}NH-C_{1-4}$ alkyl, $-NHS(O)_{0-2}NH-C_{1-4}$ alkyl, $-C(O)NH-C_{1-4}$ alkyl, $-NHC(O)-C_{1-4}$ alkyl, $-C(O)N(C_{1-4}$ alkyl$)_2$, $-OC(O)NH-C_{1-4}$ alkyl, $-NHC(O)O-C_{1-4}$ alkyl, $-OC(O)N(C_{1-4}$ alkyl$)_2$, $-NH-C_{1-4}$ haloalkyl, $-N(C_{1-4}$ haloalkyl$)_2$, $-C(O)-C_{1-4}$ haloalkyl, $-S(O)_{0-2}-C_{1-4}$ haloalkyl, —NHS(O)$_{0-2}$—C$_{1-4}$ haloalkyl, —S(O)$_{0-2}$NH—C$_{1-4}$ haloalkyl, —NHS(O)$_{0-2}$NH—C$_{1-4}$ haloalkyl, —C(O)NH—C$_{1-4}$ haloalkyl, —NHC(O)—C$_{1-4}$ haloalkyl, —C(O)N(C$_{1-4}$ haloalkyl)$_2$, —OC(O)NH—C$_{1-4}$ haloalkyl, —NHC(O)O—C$_{1-4}$ haloalkyl, —OC(O)N(C$_{1-4}$ haloalkyl)$_2$, C$_{3-10}$ cycloalkyl, heterocyclyl, aryl, heteroaryl, —(CH$_2$)$_{1-30}$—C(O)OH, —(CH$_2$)$_{0-4}$—O-poly(ethylene glycol), —(CH$_2$)$_{0-4}$—O-methoxypoly(ethylene glycol) and sugar moiety; and each R$^{28}$ is independently selected from C$_{1-30}$ alkyl optionally substituted with one to five R$^{25}$, C$_{1-30}$ heteroalkyl optionally substituted with one to five R$^{25}$, C$_{3-10}$ cycloalkyl optionally substituted with one to five R$^{25}$, heterocyclyl optionally substituted with one to five R$^{25}$, aryl optionally substituted with one to five R$^{26}$, heteroaryl optionally substituted with one to five R$^{26}$, poly(ethylene glycol), and methoxypoly(ethylene glycol).

"Poly(ethylene glycol) refers to a polyether compound of general formula

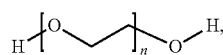

where n varies from 2 to 500,000. In certain embodiments, poly(ethylene glycol) has an average molecular weight of less than 20,000. In certain embodiments, poly(ethylene glycol) has an average molecular weight of less than 15,000. In certain embodiments, poly(ethylene glycol) has an average molecular weight of less than 10,000. In certain embodiments, poly(ethylene glycol) has an average molecular weight of less than 5,000. In certain embodiments, poly(ethylene glycol) has an average molecular weight of less than 2,000. In certain embodiments, poly(ethylene glycol) has an average molecular weight of about 20,000 to about 2,000. In certain embodiments, poly(ethylene glycol) has an average molecular weight of about 10,000 to about 2,000.

"Methoxypoly(ethylene glycol) refers to a polyether compound of general formula

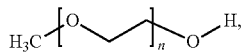

where n varies from 2 to 500,000. In certain embodiments, methoxypoly(ethylene glycol) has an average molecular weight of less than 20,000. In certain embodiments, methoxypoly(ethylene glycol) has an average molecular weight of less than 15,000. In certain embodiments, methoxypoly(ethylene glycol) has an average molecular weight of less than 15,000. In certain embodiments, methoxypoly(ethylene glycol) has an average molecular weight of less than 10,000. In certain embodiments, methoxypoly(ethylene glycol) has an average molecular weight of less than 5,000. In certain embodiments, methoxypoly(ethylene glycol) has an average molecular weight of less than 2,000. In certain embodiments, methoxypoly(ethylene glycol) has an average molecular weight of about 20,000 to about 2,000. In certain embodiments, methoxypoly(ethylene glycol) has an average molecular weight of about 10,000 to about 2,000.

In some embodiments, provided is a compound of Formula (XII):

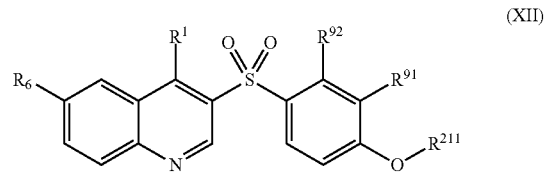

or a pharmaceutically acceptable salt, isotopically enriched analog, stereoisomer, mixture of stereoisomers, or tautomer thereof;

wherein:

R$^1$ is optionally substituted

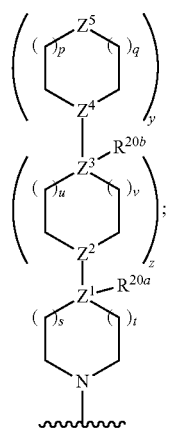

each of s, t, u, v, p and q is independently 0, 1, 2, or 3, provided that the sum of s and t is 1, 2, 3 or 4, the sum of u and v is 1, 2, 3 or 4, and the sum of p and q is 1, 2, 3 or 4;

y is 0 or 1;

z is 0 or 1;

provided that y and z are not both 0;

Z$^1$ is C or N;

when Z$^1$ is C, R$^{20a}$ is H, halo, hydroxy, alkyl, or hydroxyalkyl;

when Z$^1$ is N, R$^{20a}$ is absent;

Z$^2$ is CH or N;

Z$^3$ is C or N;

when Z$^3$ is C, R$^{20b}$ is H, halo, hydroxy, alkyl, or hydroxyalkyl;

when Z$^3$ is N, R$^{20b}$ is absent;

Z$^4$ is CH or N;

Z$^5$ is CH$_2$, CHR$^{25}$, CR$^{25}$R$^{25}$, C(=O), NR$^{25}$, O, or S(O)$_{0-2}$;

each R$^{25}$ is independently H, halo, alkyl or hydroxyalkyl;

R$^{211}$ is C$_{2-40}$ alkyl, C$_{2-40}$ alkenyl, or C$_{2-40}$ alkynyl;

R$^6$ is H, halo, alkyl, haloalkyl, hydroxy, alkoxy, haloalkoxy, alkylthio, sulfoxido, sulfonyl, carboxy, ester, —CN, —NO$_2$, amino, amido, sulfinamido, or sulfonamido; and R$^{91}$ and R$^{92}$ are independently selected from H and halo.

In some embodiments, provided is a pharmaceutical composition comprising a compound of Formula (XII):

(XII)

or a pharmaceutically acceptable salt, isotopically enriched analog, stereoisomer, mixture of stereoisomers, or tautomer thereof;
wherein:
$R^1$ is each of s, t, u, v, p and q is independently 0, 1, 2, or 3, provided that the sum of s and t is 1, 2, 3 or 4, the sum of u and v is 1, 2, 3 or 4, and the sum of p and q is 1, 2, 3 or 4;
y is 0 or 1;
z is 0 or 1;
provided that y and z are not both 0;
$Z^1$ is CH or N;
$Z^2$ is CH or N;
$Z^3$ is CH or N;
$Z^4$ is CH or N;
$Z^5$ is $CH_2$, $CHR^{25}$, $CR^{25}R^{25}$, C(=O), $NR^{25}$, O, or $S(O)_{0-2}$;
each $R^{25}$ is independently H, halo, alkyl or hydroxyalkyl;
$R^{211}$ is $C_{2-40}$ alkyl, $C_{2-40}$ alkenyl, or $C_{2-40}$ alkynyl;
$R^6$ is H, halo, alkyl, haloalkyl, hydroxy, alkoxy, haloalkoxy, alkylthio, sulfoxido, sulfonyl, carboxy, ester, —CN, —$NO_2$, amino, amido, sulfinamido, or sulfonamido; and
$R^{91}$ and $R^{92}$ are independently selected from H and halo.
In some embodiments, in the compound of Formula (XII), $R^{211}$ is $C_{5-40}$ alkyl, $C_{5-40}$ alkenyl, or $C_{5-40}$ alkynyl. In some embodiments, in the compound of Formula (XII), $R^{211}$ is $C_{10-40}$ alkyl, $C_{10-40}$ alkenyl, or $C_{10-40}$ alkynyl. In some embodiments, in the compound of Formula (XII), $R^{211}$ is $C_{10-25}$ alkyl, $C_{10-25}$ alkenyl, or $C_{10-25}$ alkynyl. In some embodiments, in the compound of Formula (XII), $R^{211}$ is $C_{5-40}$ alkyl. In some embodiments, in the compound of Formula (XII), $R^{211}$ is $C_{10-40}$ alkyl. In some embodiments, in the compound of Formula (XII), $R^{211}$ is $C_{10-30}$ alkyl. In some embodiments, in the compound of Formula (XII), $R^{211}$ is $C_{10-25}$ alkyl.

In some embodiments, in the compound of Formula (XII), $R^{91}$ and $R^{92}$ are independently selected from H and F. In some embodiments, in the compound of Formula (XII), $R^{91}$ is H and $R^{92}$ is F. In some embodiments, in the compound of Formula (XII), $R^{91}$ is F and $R^{92}$ is H. In some embodiments, in the compound of Formula (XII), $R^{91}$ and $R^{92}$ are both H. In some embodiments, in the compound of Formula (XII), $R^{91}$ and $R^{92}$ are both F.

In some embodiments, in the compound of Formula (XII), $R^6$ is hydroxy, alkoxy, haloalkoxy, alkylthio, sulfoxido, or sulfonyl. In some embodiments, in the compound of Formula (XII), $R^6$ is hydroxy, or alkoxy. In some embodiments, in the compound of Formula (XII), $R^6$ is alkylthio, sulfoxido, or sulfonyl. In some embodiments, in the compound of Formula (XII), $R^6$ is sulfonyl. In some embodiments, in the compound of Formula (XII), $R^6$ is sulfoxido. In some embodiments, in the compound of Formula (XII), $R^6$ is methylsulfoxido.

In some embodiments, in the compound of Formula (XII), each ring in $R^1$ is independently and optionally further substituted with halo, hydroxy, alkyl, hydroxyalkyl, or oxo. In some embodiments, in the compound of Formula (XII), $R^1$ is wherein $Z^1$, $Z^4$, $Z^5$, s, t, p, q and $R^{20a}$ are as defined herein, and each ring in $R^1$ is independently and optionally further substituted with halo, hydroxy, alkyl, hydroxyalkyl, or oxo. In some embodiments, in the compound of Formula (XII), $R^1$ is wherein $Z^1$, $Z^2$, $Z^3$, $Z^4$, $Z^5$, s, t, u, v, p, q, $R^{20a}$ and $R^{20b}$, are as defined herein, and each ring in $R^1$ is independently and optionally further substituted with halo, hydroxy, alkyl, hydroxyalkyl, or oxo. In some embodiments, in the compound of Formula (XII), $R^1$ is

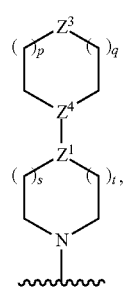
wherein $Z^1$ is CH or N, and $Z^4$, $Z^5$, s, t, p, q are as defined herein. In some embodiments, in the compound of Formula (XII), $R^1$ is
wherein $Z^1$ is CH or N, $Z^3$ is CH or N, and $Z^2$, $Z^4$, $Z^5$, s, t, u, v, p, q are as defined herein.
In some embodiments, in the compound of Formula (XII), $R^1$ is selected from
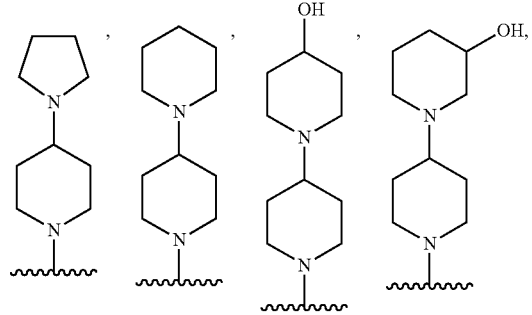
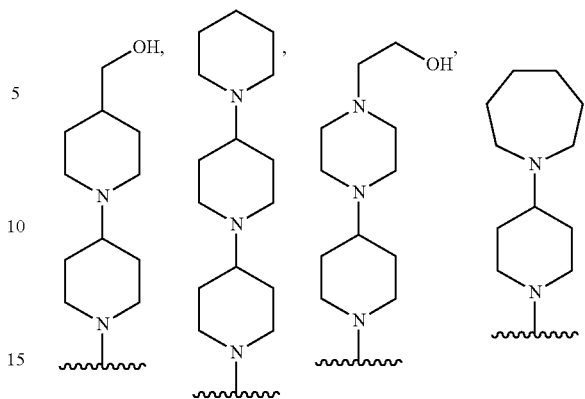
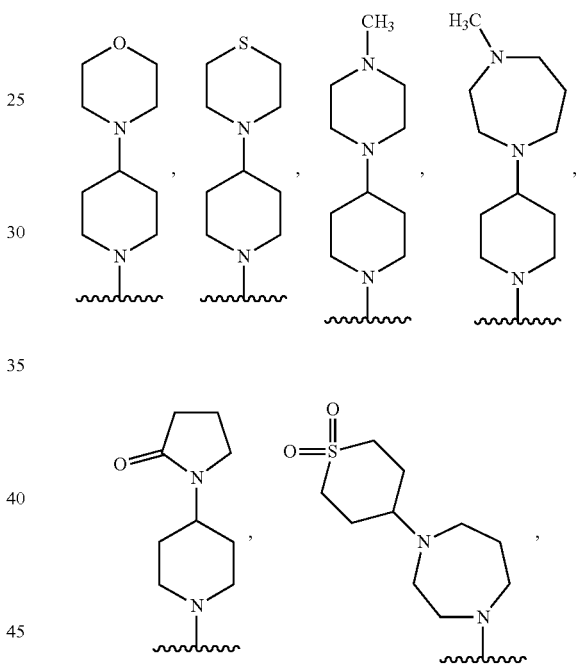

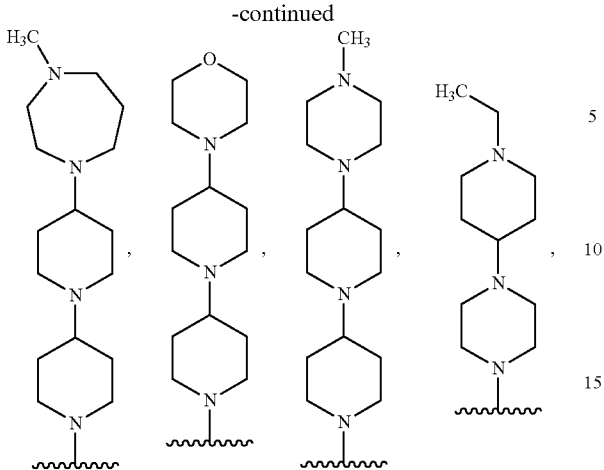
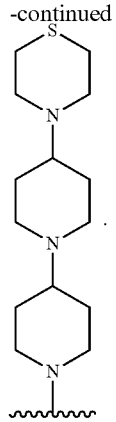
In some embodiments, in the compound of Formula (XII), $R^1$ is selected from
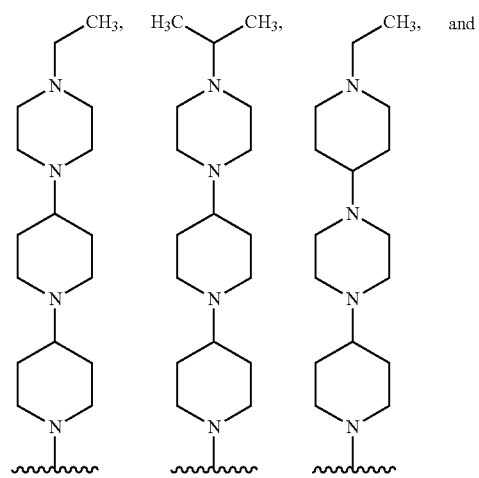
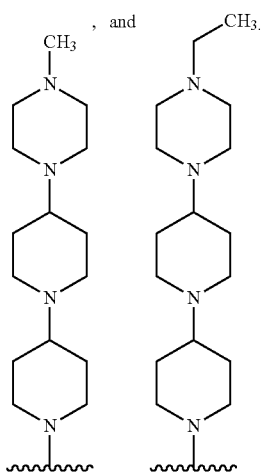 [SMILES: *N1CCC(N2CCC(N3CCN(C)CC3)CC2)CC1 ; *N1CCC(N2CCC(N3CCN(CC)CC3)CC2)CC1]
In some embodiments, the compound of Formula (XII) is selected from
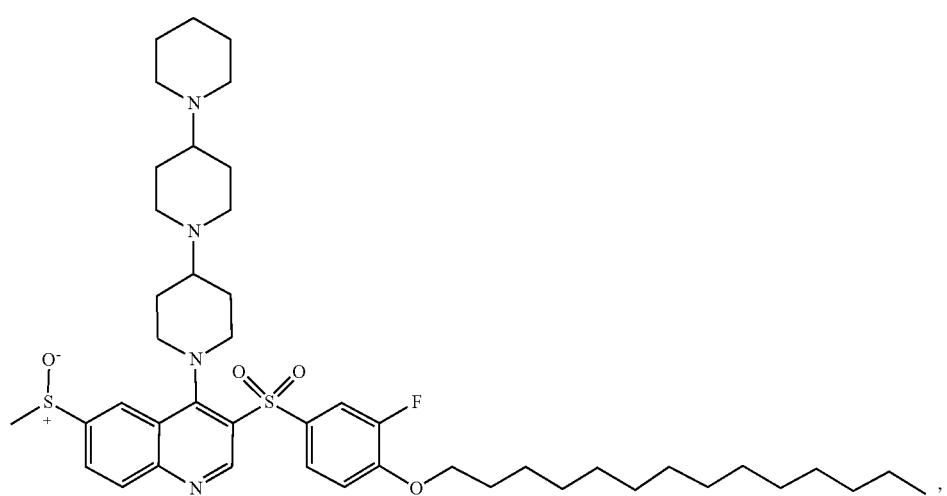

371
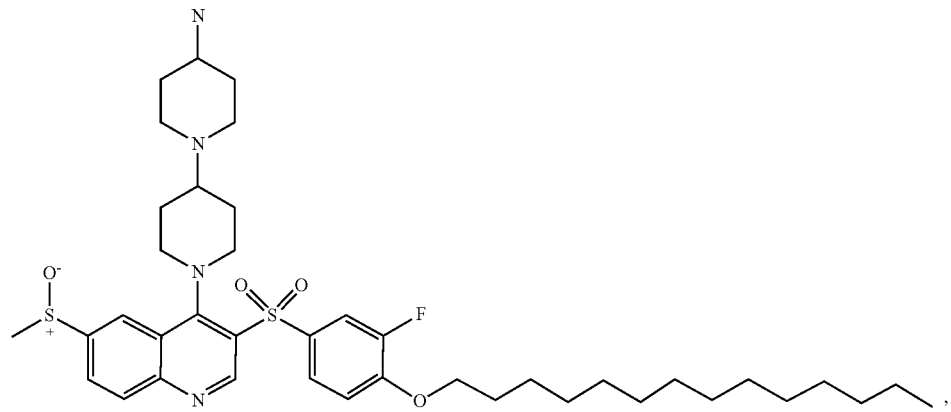
386
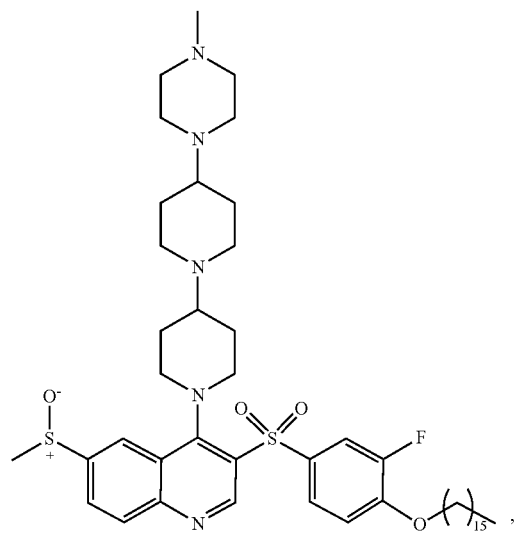
387
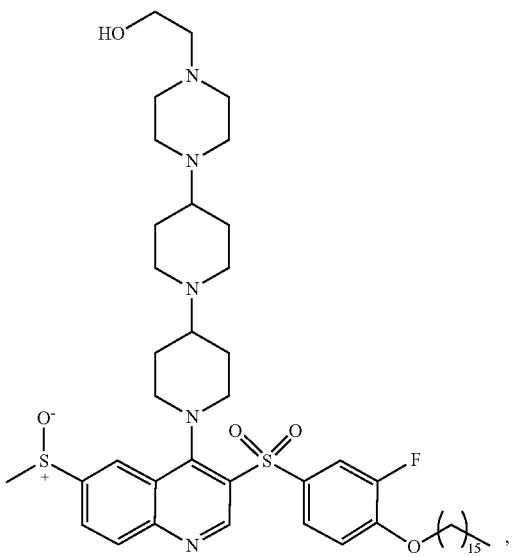
390
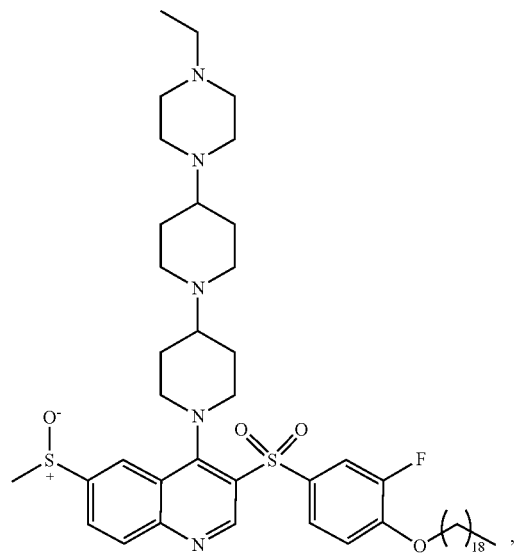
391
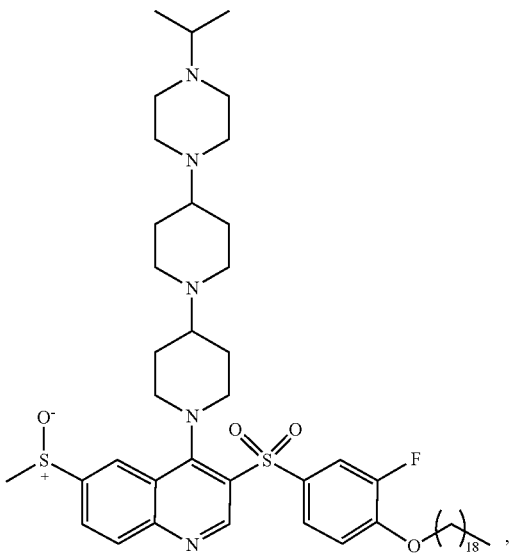

394
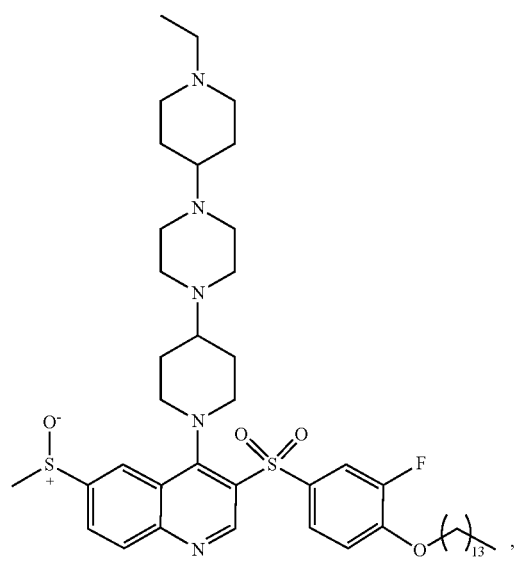
395
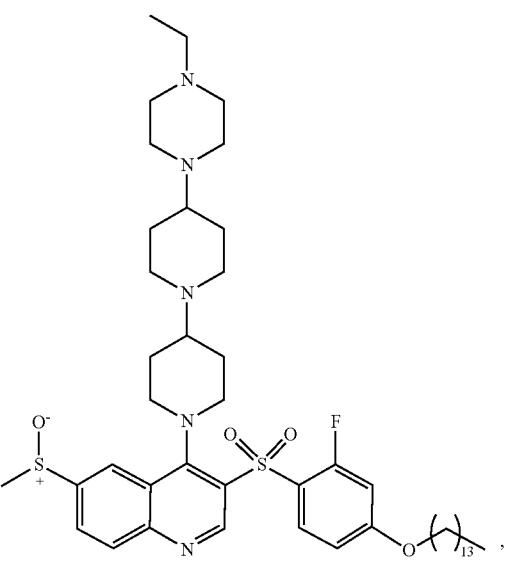
461
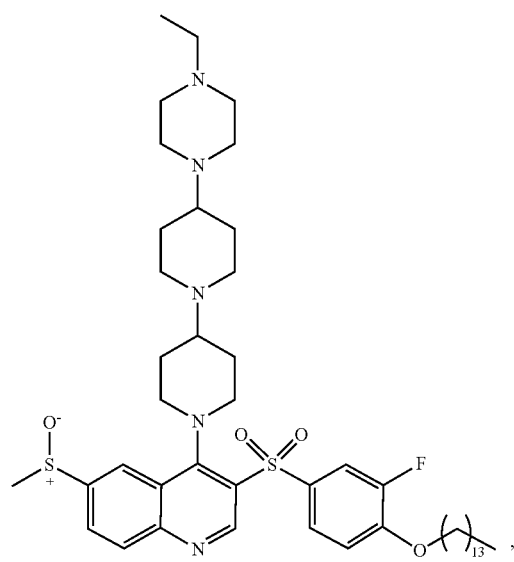
462
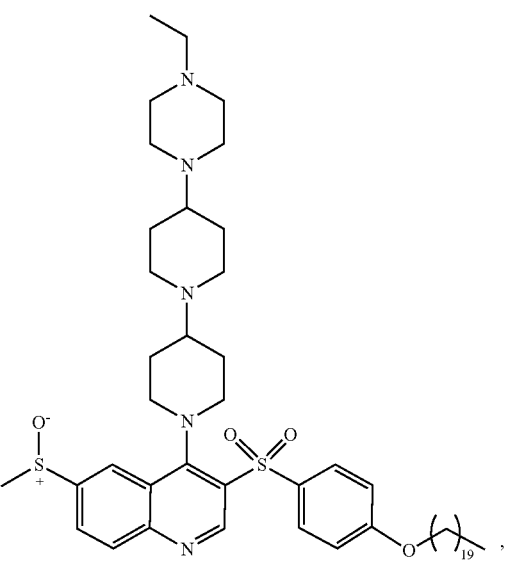
465
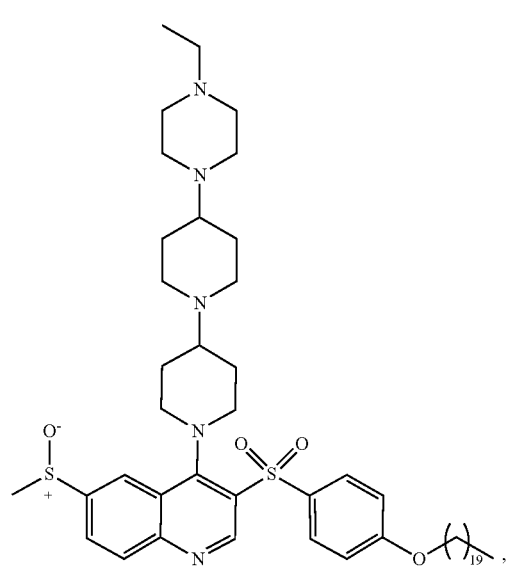
466
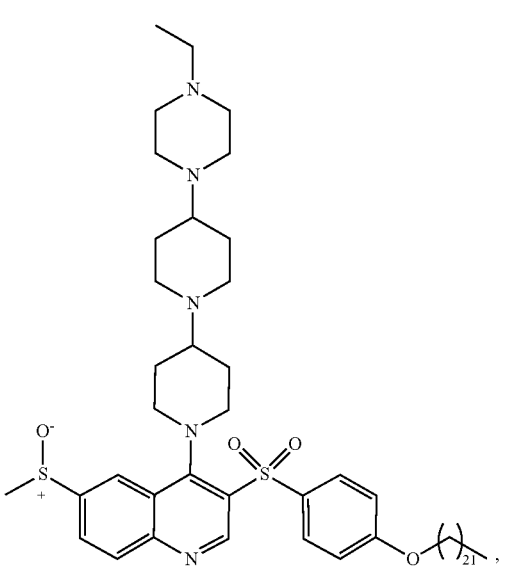

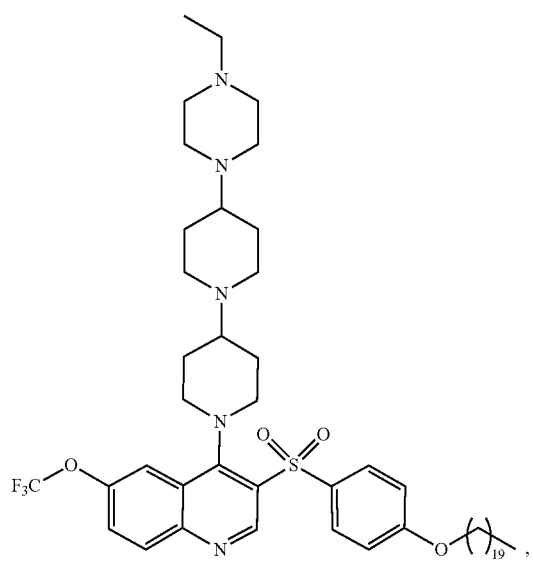

518

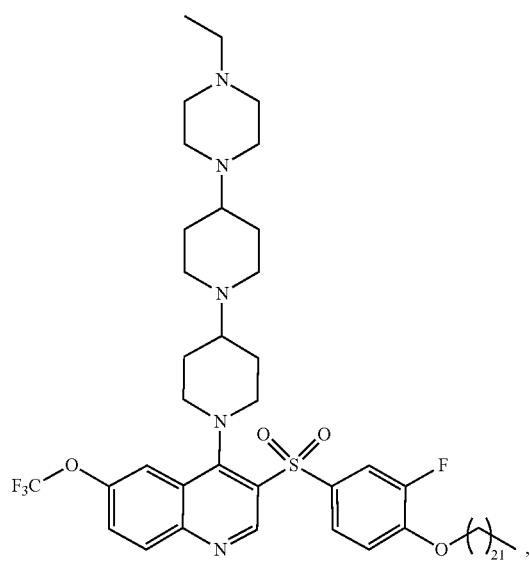

530

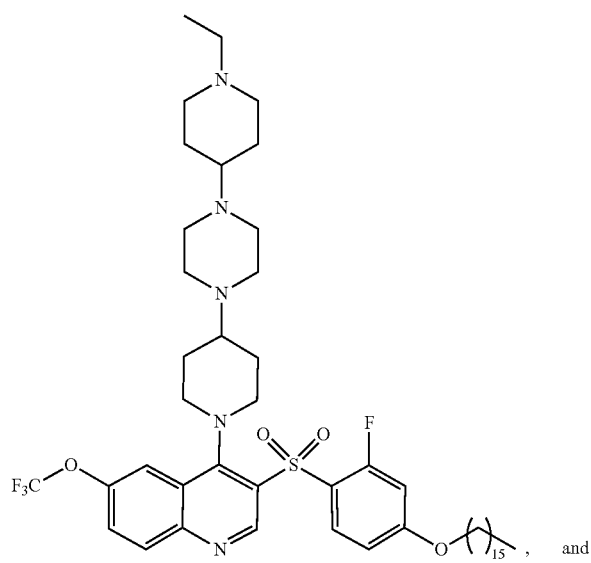

542, and

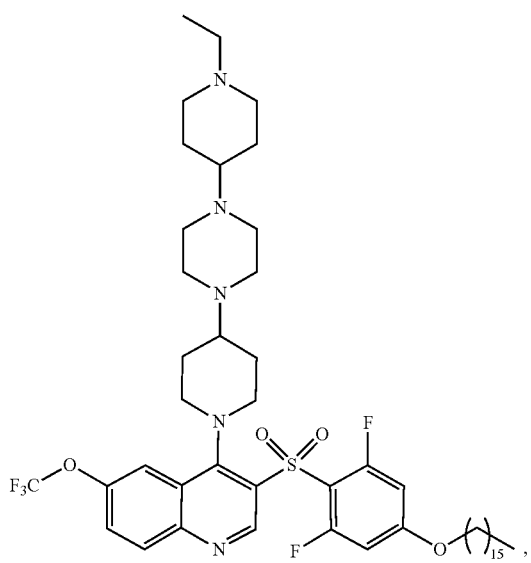

543 or a pharmaceutically acceptable salt, isotopically enriched analog, stereoisomer, mixture of stereoisomers, or tautomer thereof.

In some embodiments, any compound of Formula (I) or sub-formulae thereof, is a salt selected from mono, bis, or tris succinate, oxalate, citrate, maleate, adipate, or fumarate salts thereof. In some embodiments, any compound of Formula (I) or sub-formulae thereof, is a hydrate of a mono, bis or tris succinate, oxalate, citrate, maleate, adipate, or fumarate salt thereof, e.g., a salt of formula

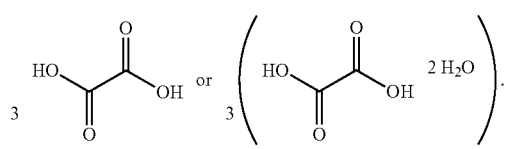

In some embodiments, any compound of Formula (I) or sub-formulae thereof, is a mono, bis, or tris succinate salt. In some embodiments, any compound of Formula (I) or sub-formulae thereof, is a tris succinate salt. In some embodiments, any compound of Formula (I) or sub-formulae thereof, is a tris succinate salt prepared from succinic acid dihydrate.

In some embodiments, any compound of Formula (I) or sub-formulae thereof, is a mono, bis, or tris oxalate salt. In some embodiments, any compound of Formula (I) or sub-formulae thereof, is a tris oxalate salt. In some embodiments, any compound of Formula (I) or sub-formulae thereof, is a tris oxalate salt prepared from oxalic acid dihydrate.

In some embodiments, any compound of Formula (I) or sub-formulae thereof, is a mono, bis, or tris adipate salt. In some embodiments, any compound of Formula (I) or sub-formulae thereof, is a tris adipate salt. In some embodiments, any compound of Formula (I) or sub-formulae thereof, is a tris adipate salt prepared from adipic acid dihydrate.

In certain embodiments, provided is a compound selected from Table 1, or a pharmaceutically acceptable salt, isotopically enriched analog, stereoisomer, mixture of stereoisomers, or tautomer thereof.

TABLE 1

| Ex. | Structure | Name |
| --- | --- | --- |
| 1 | 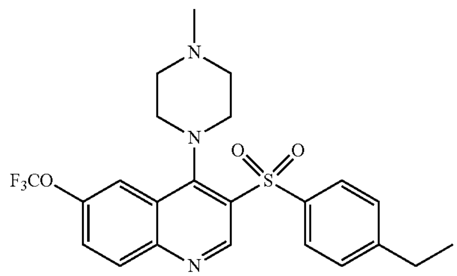 [SMILES: CCc1ccc(S(=O)(=O)c2cnc3ccc(OC(F)(F)F)cc3c2N2CCN(C)CC2)cc1] | 3-((4-ethylphenyl)sulfonyl)-4-(4-methylpiperazin-1-yl)-6-(trifluoromethoxy)quinoline |
| 2 | 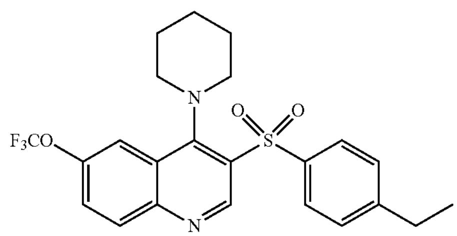 [SMILES: CCc1ccc(S(=O)(=O)c2cnc3ccc(OC(F)(F)F)cc3c2N2CCCCC2)cc1] | 3-((4-ethylphenyl)sulfonyl)-4-(piperidin-1-yl)-6-(trifluoromethoxy)quinoline |
| 3 | 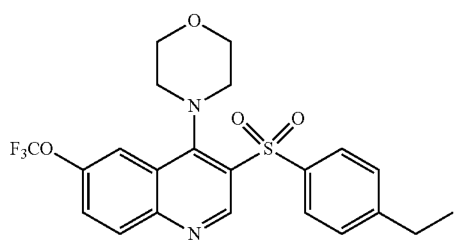 [SMILES: CCc1ccc(S(=O)(=O)c2cnc3ccc(OC(F)(F)F)cc3c2N2CCOCC2)cc1] | 4-(3-((4-ethylphenyl)sulfonyl)-6-(trifluoromethoxy)quinolin-4-yl)morpholine |
| 4 | 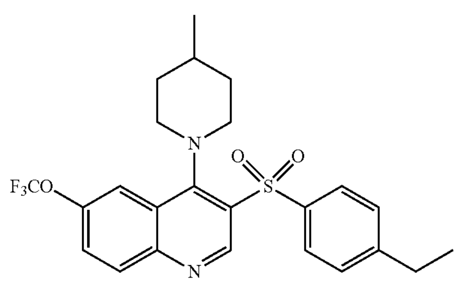 | 3-((4-ethylphenyl)sulfonyl)-4-(4-methylpiperidin-1-yl)-6-(trifluoromethoxy)quinoline |
| 5 | 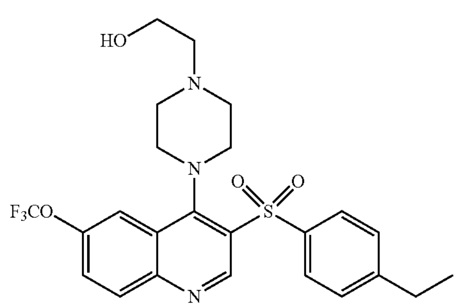 [SMILES: CCc1ccc(S(=O)(=O)c2cnc3ccc(OC(F)(F)F)cc3c2N2CCN(CCO)CC2)cc1] | 2-(4-(3-((4-ethylphenyl)sulfonyl)-6-(trifluoromethoxy)quinolin-4-yl)piperazin-1-yl)ethan-1-ol |

TABLE 1-continued

| Ex. | Structure | Name |
|---|---|---|
| 6 | 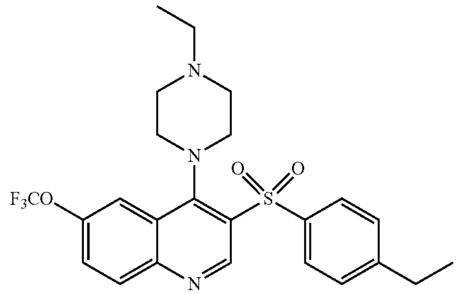 [SMILES: CCc1ccc(S(=O)(=O)c2cnc3ccc(OC(F)(F)F)cc3c2N2CCN(CC)CC2)cc1] | 3-((4-ethylphenyl)sulfonyl)-4-(4-ethylpiperazin-1-yl)-6-(trifluoromethoxy)quinoline |
| 7 | 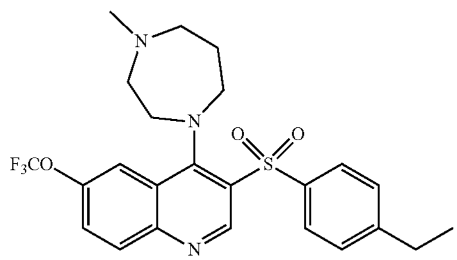 [SMILES: CCc1ccc(S(=O)(=O)c2cnc3ccc(OC(F)(F)F)cc3c2N2CCCN(C)CC2)cc1] | 3-((4-ethylphenyl)sulfonyl)-4-(4-methyl-1,4-diazepan-1-yl)-6-(trifluoromethoxy)quinoline |
| 8 | 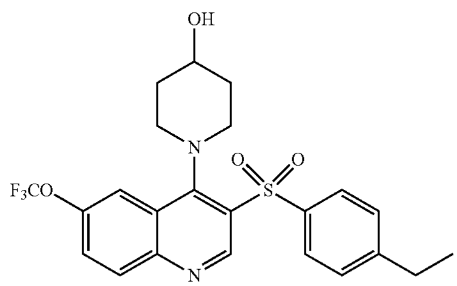 [SMILES: CCc1ccc(S(=O)(=O)c2cnc3ccc(OC(F)(F)F)cc3c2N2CCC(O)CC2)cc1] | 1-(3-((4-ethylphenyl)sulfonyl)-6-(trifluoromethoxy)quinolin-4-yl)piperidin-4-ol |
| 9 | 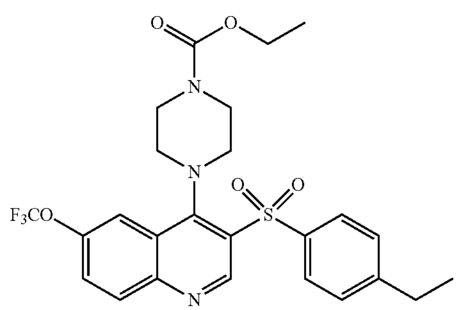 | ethyl 4-(3-((4-ethylphenyl)sulfonyl)-6-(trifluoromethoxy)quinolin-4-yl)piperazine-1-carboxylate |
| 10 | 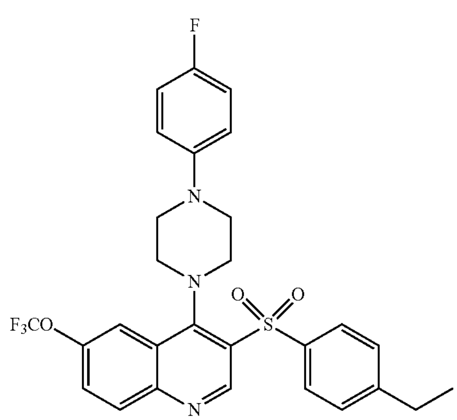 | 3-((4-ethylphenyl)sulfonyl)-4-(4-(4-fluorophenyl)piperazin-1-yl)-6-(trifluoromethoxy)quinoline |

TABLE 1-continued

| Ex. | Structure | Name |
|---|---|---|
| 11 | 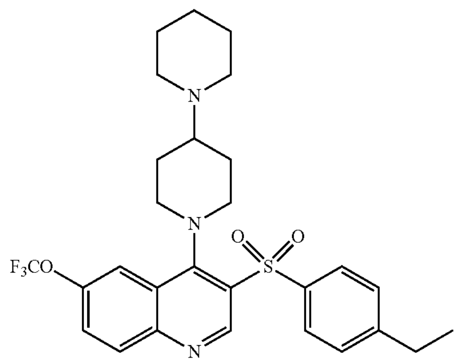 | 4-([1,4'-bipiperidin]-1'-yl)-3-((4-ethylphenyl)sulfonyl)-6-(trifluoromethoxy)quinoline |
| 12 | 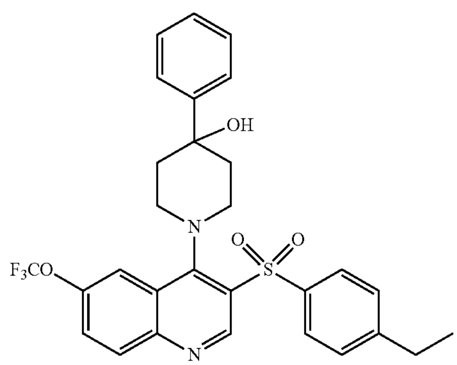 [SMILES: CCc1ccc(S(=O)(=O)c2cnc3ccc(OC(F)(F)F)cc3c2N2CCC(O)(c3ccccc3)CC2)cc1] | 1-(3-((4-ethylphenyl)sulfonyl)-6-(trifluoromethoxy)quinolin-4-yl)-4-phenylpiperidin-4-ol |
| 13 | 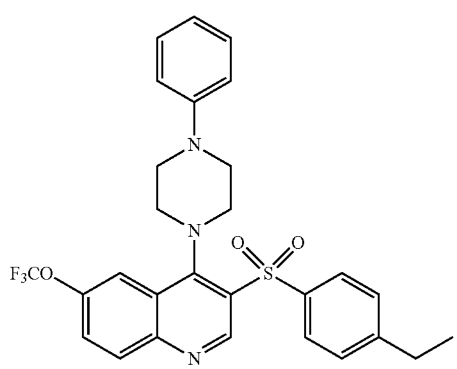 [SMILES: CCc1ccc(S(=O)(=O)c2cnc3ccc(OC(F)(F)F)cc3c2N2CCN(c3ccccc3)CC2)cc1] | 3-((4-ethylphenyl)sulfonyl)-4-(4-phenylpiperazin-1-yl)-6-(trifluoromethoxy)quinoline |
| 14 | 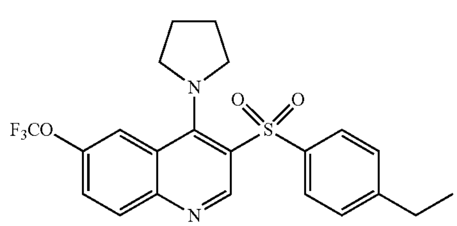 [SMILES: CCc1ccc(S(=O)(=O)c2cnc3ccc(OC(F)(F)F)cc3c2N2CCCC2)cc1] | 3-((4-ethylphenyl)sulfonyl)-4-(pyrrolidin-1-yl)-6-(trifluoromethoxy)quinoline |
| 15 | 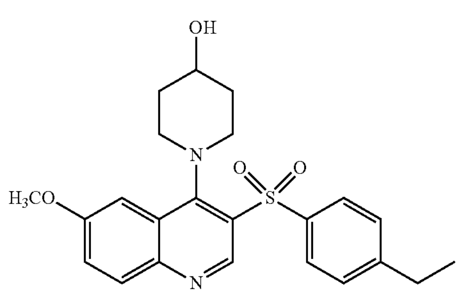 [SMILES: CCc1ccc(S(=O)(=O)c2cnc3ccc(OC)cc3c2N2CCC(O)CC2)cc1] | 1-(3-((4-ethylphenyl)sulfonyl)-6-methoxyquinolin-4-yl)piperidin-4-ol |

TABLE 1-continued

| Ex. | Structure | Name |
|---|---|---|
| 16 | 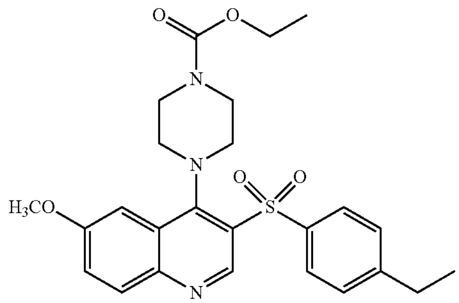 [SMILES: CCOC(=O)N1CCN(c2c(S(=O)(=O)c3ccc(CC)cc3)cnc3ccc(OC)cc23)CC1] | ethyl 4-(3-((4-ethylphenyl)sulfonyl)-6-methoxyquinolin-4-yl)piperazine-1-carboxylate |
| 17 | 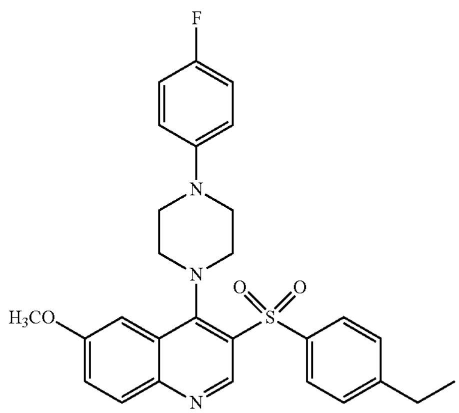 [SMILES: CCc1ccc(S(=O)(=O)c2cnc3ccc(OC)cc3c2N2CCN(c3ccc(F)cc3)CC2)cc1] | 3-((4-ethylphenyl)sulfonyl)-4-(4-(4-fluorophenyl)piperazin-1-yl)-6-methoxyquinoline |
| 18 | 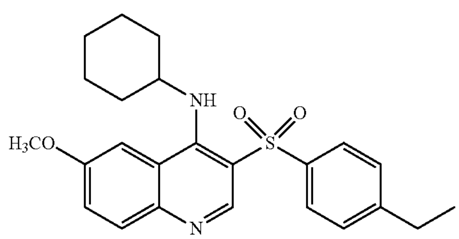 [SMILES: CCc1ccc(S(=O)(=O)c2cnc3ccc(OC)cc3c2NC2CCCCC2)cc1] | N-cyclohexyl-3-((4-ethylphenyl)sulfonyl)-6-methoxyquinolin-4-amine |
| 19 | 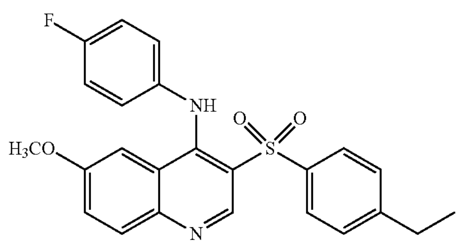 [SMILES: CCc1ccc(S(=O)(=O)c2cnc3ccc(OC)cc3c2Nc2ccc(F)cc2)cc1] | 3-((4-ethylphenyl)sulfonyl)-N-(4-fluorophenyl)-6-methoxyquinolin-4-amine |
| 20 | 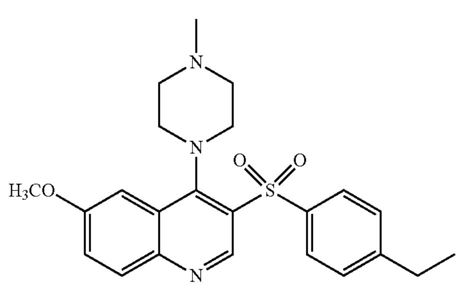 [SMILES: CCc1ccc(S(=O)(=O)c2cnc3ccc(OC)cc3c2N2CCN(C)CC2)cc1] | 3-((4-ethylphenyl)sulfonyl)-6-methoxy-4-(4-methylpiperazin-1-yl)quinoline |

TABLE 1-continued

| Ex. | Structure | Name |
|---|---|---|
| 21 | 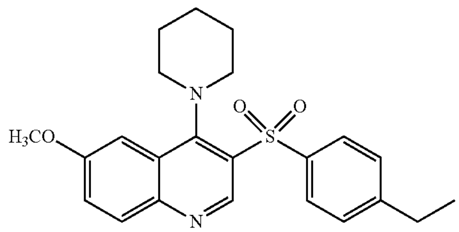 [SMILES: CCc1ccc(S(=O)(=O)c2cnc3ccc(OC)cc3c2N2CCCCC2)cc1] | 3-((4-ethylphenyl)sulfonyl)-6-methoxy-4-(piperidin-1-yl)quinoline |
| 22 | 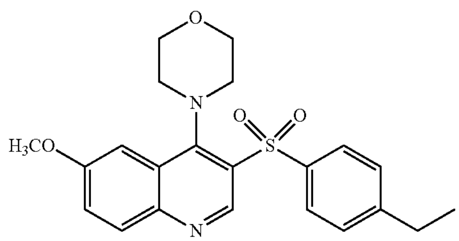 [SMILES: CCc1ccc(S(=O)(=O)c2cnc3ccc(OC)cc3c2N2CCOCC2)cc1] | 4-(3-((4-ethylphenyl)sulfonyl)-6-methoxyquinolin-4-yl)morpholine |
| 23 | 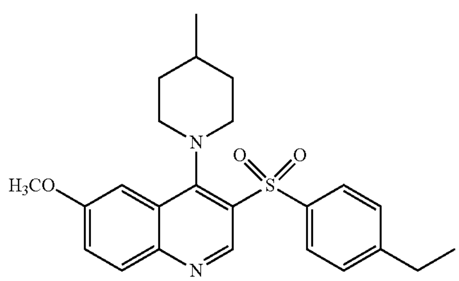 [SMILES: CCc1ccc(S(=O)(=O)c2cnc3ccc(OC)cc3c2N2CCC(C)CC2)cc1] | 3-((4-ethylphenyl)sulfonyl)-6-methoxy-4-(4-methylpiperidin-1-yl)quinoline |
| 24 | 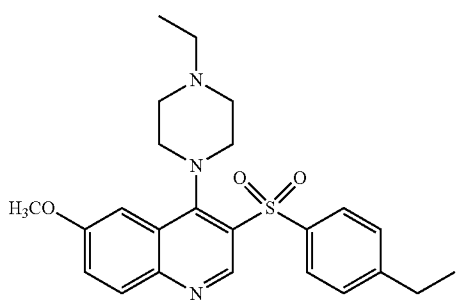 [SMILES: CCc1ccc(S(=O)(=O)c2cnc3ccc(OC)cc3c2N2CCN(CC)CC2)cc1] | 3-((4-ethylphenyl)sulfonyl)-4-(4-ethylpiperazin-1-yl)-6-methoxyquinoline |
| 25 | 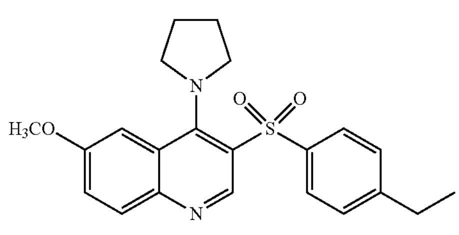 [SMILES: CCc1ccc(S(=O)(=O)c2cnc3ccc(OC)cc3c2N2CCCC2)cc1] | 3-((4-ethylphenyl)sulfonyl)-6-methoxy-4-(pyrrolidin-1-yl)quinoline |

TABLE 1-continued

| Ex. | Structure | Name |
|---|---|---|
| 26 | 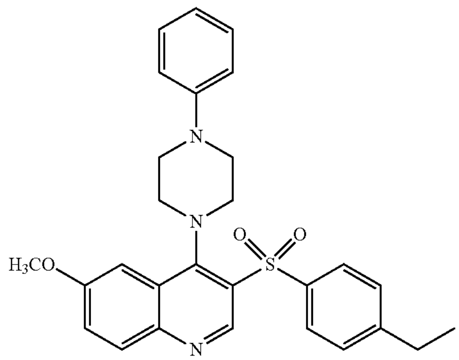 [SMILES: CCc1ccc(S(=O)(=O)c2cnc3ccc(OC)cc3c2N2CCN(c3ccccc3)CC2)cc1] | 3-((4-ethylphenyl)sulfonyl)-6-methoxy-4-(4-phenylpiperazin-1-yl)quinoline |
| 27 | 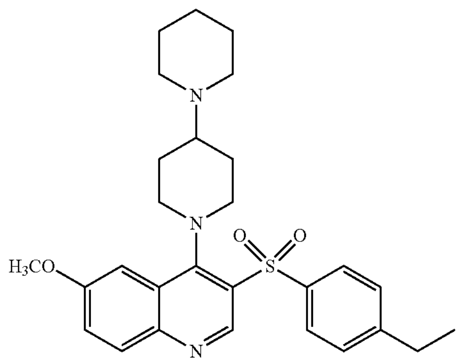 [SMILES: CCc1ccc(S(=O)(=O)c2cnc3ccc(OC)cc3c2N2CCC(N3CCCCC3)CC2)cc1] | 4-([1,4'-bipiperidin]-1'-yl)-3-((4-ethylphenyl)sulfonyl)-6-methoxyquinoline |
| 28 | 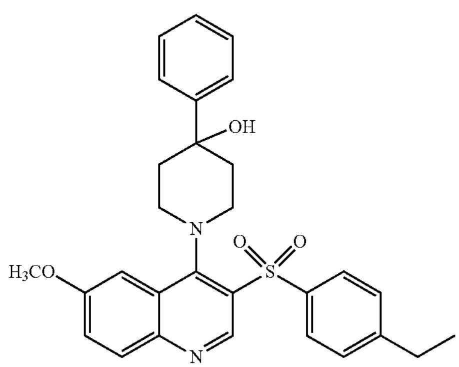 [SMILES: CCc1ccc(S(=O)(=O)c2cnc3ccc(OC)cc3c2N2CCC(O)(c3ccccc3)CC2)cc1] | 1-(3-((4-ethylphenyl)sulfonyl)-6-methoxyquinolin-4-yl)-4-phenylpiperidin-4-ol |
| 29 | 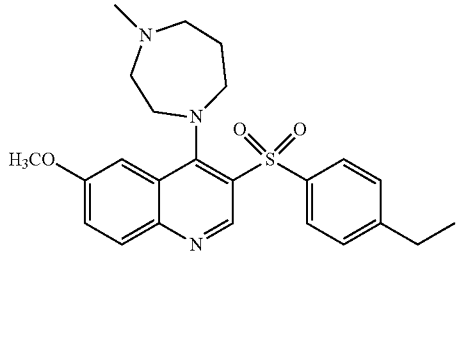 [SMILES: CCc1ccc(S(=O)(=O)c2cnc3ccc(OC)cc3c2N2CCCN(C)CC2)cc1] | 3-((4-ethylphenyl)sulfonyl)-6-methoxy-4-(4-methyl-1,4-diazepan-1-yl)quinoline |

TABLE 1-continued

| Ex. | Structure | Name |
|---|---|---|
| 30 | 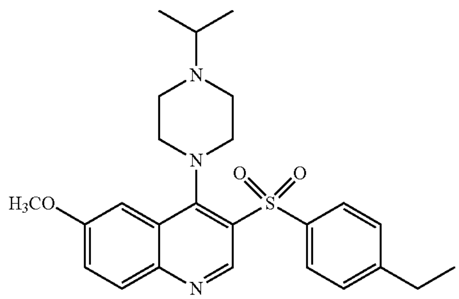 | 3-((4-ethylphenyl)sulfonyl)-4-(4-isopropylpiperazin-1-yl)-6-methoxyquinoline |
| 31 | 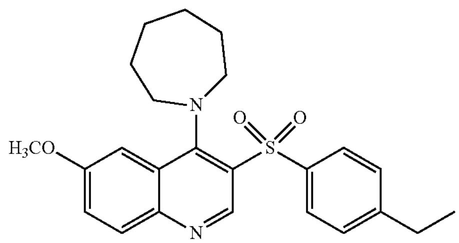 [SMILES: CCc1ccc(S(=O)(=O)c2cnc3ccc(OC)cc3c2N2CCCCCC2)cc1] | 4-(azepan-1-yl)-3-((4-ethylphenyl)sulfonyl)-6-methoxyquinoline |
| 32 | 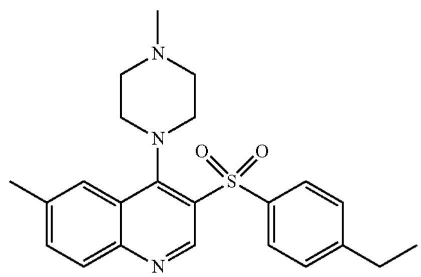 [SMILES: CCc1ccc(S(=O)(=O)c2cnc3ccc(C)cc3c2N2CCN(C)CC2)cc1] | 3-((4-ethylphenyl)sulfonyl)-6-methyl-4-(4-methylpiperazin-1-yl)quinoline |
| 33 | 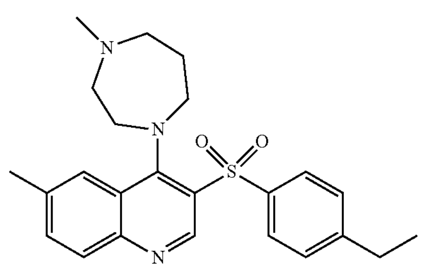 [SMILES: CCc1ccc(S(=O)(=O)c2cnc3ccc(C)cc3c2N2CCCN(C)CC2)cc1] | 3-((4-ethylphenyl)sulfonyl)-6-methyl-4-(4-methyl-1,4-diazepan-1-yl)quinoline |
| 34 | 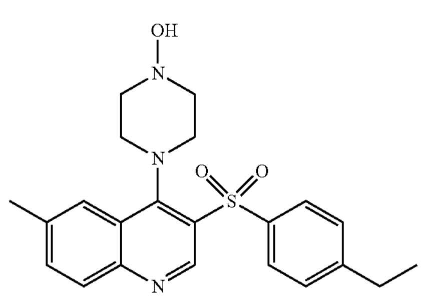 [SMILES: CCc1ccc(S(=O)(=O)c2cnc3ccc(C)cc3c2N2CCN(O)CC2)cc1] | 1-(3-((4-ethylphenyl)sulfonyl)-6-methylquinolin-4-yl)piperidin-4-ol |

TABLE 1-continued

| Ex. | Structure | Name |
|---|---|---|
| 35 | 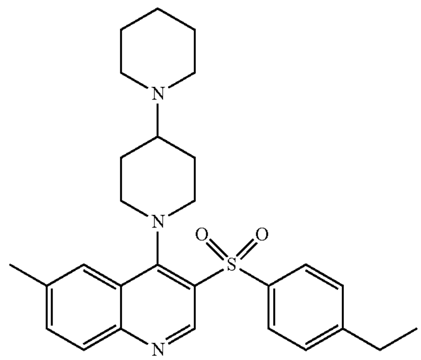 [SMILES: CCc1ccc(S(=O)(=O)c2cnc3ccc(C)cc3c2N2CCC(N3CCCCC3)CC2)cc1] | 4-([1,4'-bipiperidin]-1'-yl)-3-((4-ethylphenyl)sulfonyl)-6-methylquinoline |
| 36 | 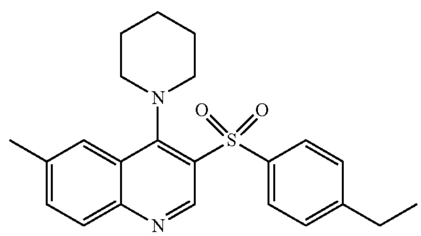 [SMILES: CCc1ccc(S(=O)(=O)c2cnc3ccc(C)cc3c2N2CCCCC2)cc1] | 3-((4-ethylphenyl)sulfonyl)-6-methyl-4-(piperidin-1-yl)quinoline |
| 37 | 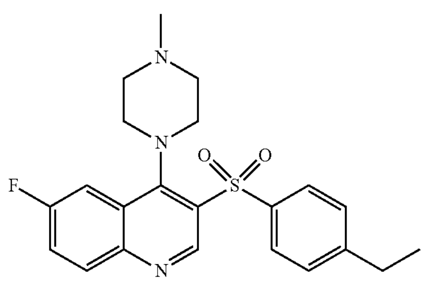 [SMILES: CCc1ccc(S(=O)(=O)c2cnc3ccc(F)cc3c2N2CCN(C)CC2)cc1] | 3-((4-ethylphenyl)sulfonyl)-6-fluoro-4-(4-methylpiperazin-1-yl)quinoline |
| 38 | 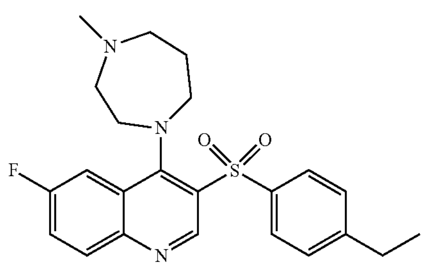 [SMILES: CCc1ccc(S(=O)(=O)c2cnc3ccc(F)cc3c2N2CCCN(C)CC2)cc1] | 3-((4-ethylphenyl)sulfonyl)-6-fluoro-4-(4-methyl-1,4-diazepan-1-yl)quinoline |
| 39 | 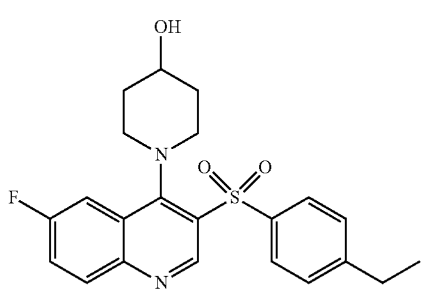 [SMILES: CCc1ccc(S(=O)(=O)c2cnc3ccc(F)cc3c2N2CCC(O)CC2)cc1] | 1-(3-((4-ethylphenyl)sulfonyl)-6-fluoroquinolin-4-yl)piperidin-4-ol |

TABLE 1-continued

| Ex. | Structure | Name |
|---|---|---|
| 40 | 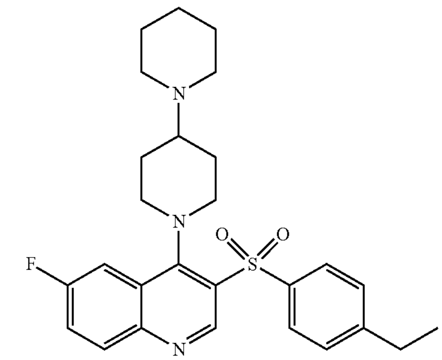 [SMILES: CCc1ccc(S(=O)(=O)c2cnc3ccc(F)cc3c2N2CCC(N3CCCCC3)CC2)cc1] | 4-([1,4'-bipiperidin]-1'-yl)-3-((4-ethylphenyl)sulfonyl)-6-fluoroquinoline |
| 41 | 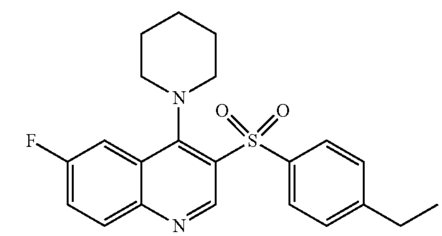 [SMILES: CCc1ccc(S(=O)(=O)c2cnc3ccc(F)cc3c2N2CCCCC2)cc1] | 3-((4-ethylphenyl)sulfonyl)-6-fluoro-4-(piperidin-1-yl)quinoline |
| 42 | 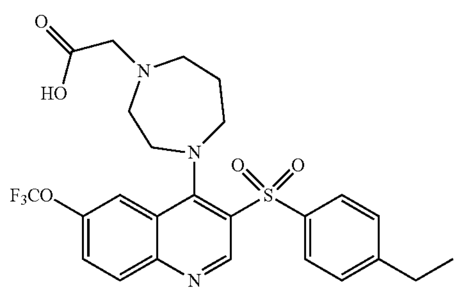 [SMILES: CCc1ccc(S(=O)(=O)c2cnc3ccc(OC(F)(F)F)cc3c2N2CCCN(CC(=O)O)CC2)cc1] | 2-(4-(3-((4-ethylphenyl)sulfonyl)-6-(trifluoromethoxy)quinolin-4-yl)-1,4-diazepan-1-yl)acetic acid |
| 43 | 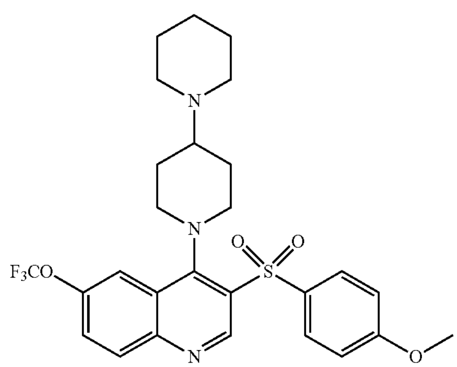 | 4-([1,4'-bipiperidin]-1'-yl)-3-((4-methoxyphenyl)sulfonyl)-6-(trifluoromethoxy)quinoline |
| 44 | 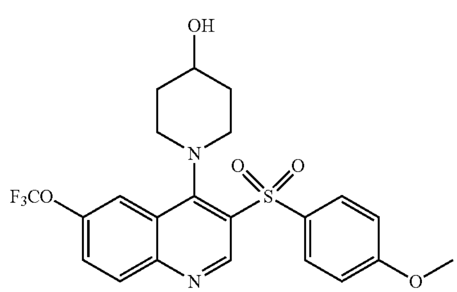 | 1-(3-((4-methoxyphenyl)sulfonyl)-6-(trifluoromethoxy)quinolin-4-yl)piperidin-4-ol |

TABLE 1-continued

| Ex. | Structure | Name |
|---|---|---|
| 45 | 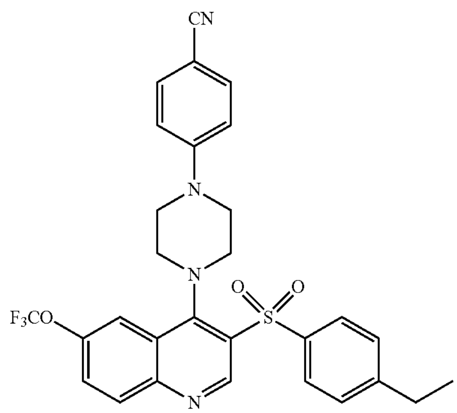 | 4-(4-(3-((4-ethylphenyl)sulfonyl)-6-(trifluoromethoxy)quinolin-4-yl)piperazin-1-yl)benzonitrile |
| 46 | 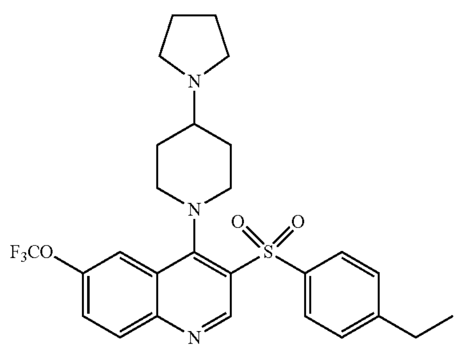 [SMILES: CCc1ccc(S(=O)(=O)c2cnc3ccc(OC(F)(F)F)cc3c2N2CCC(N3CCCC3)CC2)cc1] | 3-((4-ethylphenyl)sulfonyl)-4-(4-(pyrrolidin-1-yl)piperidin-1-yl)-6-(trifluoromethoxy)quinoline |
| 47 | 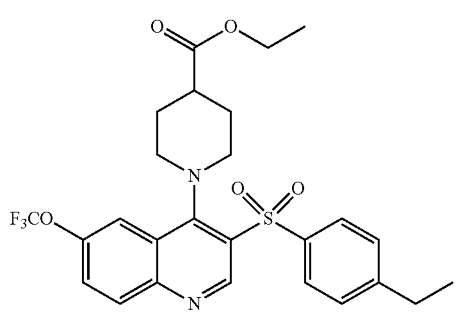 [SMILES: CCOC(=O)C1CCN(c2c(S(=O)(=O)c3ccc(CC)cc3)cnc3ccc(OC(F)(F)F)cc23)CC1] | ethyl 1-(3-((4-ethylphenyl)sulfonyl)-6-(trifluoromethoxy)quinolin-4-yl)piperidine-4-carboxylate |
| 48 | 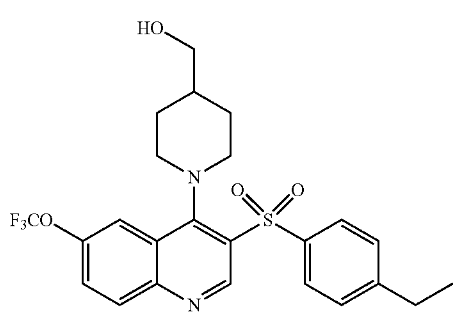 [SMILES: CCc1ccc(S(=O)(=O)c2cnc3ccc(OC(F)(F)F)cc3c2N2CCC(CO)CC2)cc1] | (1-(3-((4-ethylphenyl)sulfonyl)-6-(trifluoromethoxy)quinolin-4-yl)piperidin-4-yl)methanol |

TABLE 1-continued

| Ex. | Structure | Name |
|---|---|---|
| 49 | 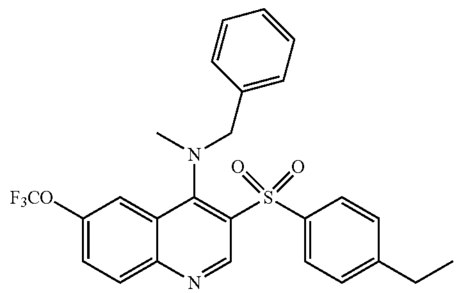 [SMILES: CCc1ccc(S(=O)(=O)c2cnc3ccc(OC(F)(F)F)cc3c2N(C)Cc2ccccc2)cc1] | N-benzyl-3-((4-ethylphenyl)sulfonyl)-N-methyl-6-(trifluoromethoxy)quinolin-4-amine |
| 50 | 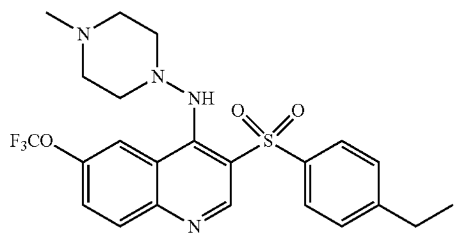 [SMILES: CCc1ccc(S(=O)(=O)c2cnc3ccc(OC(F)(F)F)cc3c2NN2CCN(C)CC2)cc1] | 3-((4-ethylphenyl)sulfonyl)-N-(4-methylpiperazin-1-yl)-6-(trifluoromethoxy)quinolin-4-amine |
| 51 | 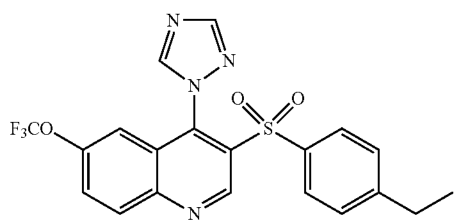 [SMILES: CCc1ccc(S(=O)(=O)c2cnc3ccc(OC(F)(F)F)cc3c2-n2cncn2)cc1] | 3-((4-ethylphenyl)sulfonyl)-4-(1H-1,2,4-triazol-1-yl)-6-(trifluoromethoxy)quinoline |
| 52 | 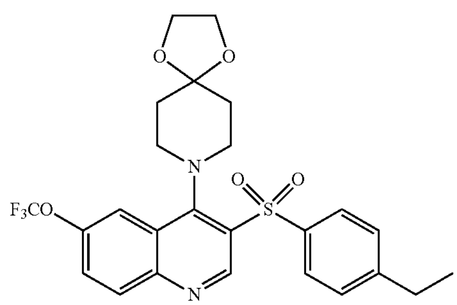 [SMILES: CCc1ccc(S(=O)(=O)c2cnc3ccc(OC(F)(F)F)cc3c2N2CCC3(CC2)OCCO3)cc1] | 8-(3-((4-ethylphenyl)sulfonyl)-6-(trifluoromethoxy)quinolin-4-yl)-1,4-dioxa-8-azaspiro[4.5]decane |
| 53 | 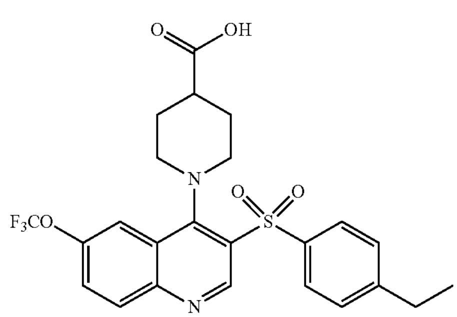 [SMILES: CCc1ccc(S(=O)(=O)c2cnc3ccc(OC(F)(F)F)cc3c2N2CCC(C(=O)O)CC2)cc1] | 1-(3-((4-ethylphenyl)sulfonyl)-6-(trifluoromethoxy)quinolin-4-yl)piperidine-4-carboxlic acid |

TABLE 1-continued

| Ex. | Structure | Name |
|---|---|---|
| 54 | 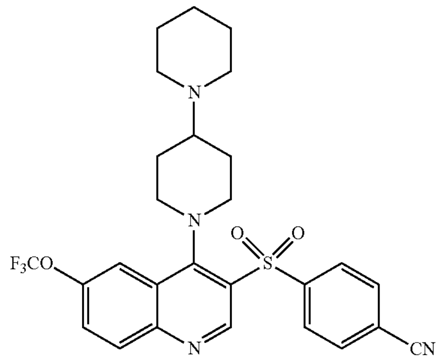 [SMILES: N#Cc1ccc(S(=O)(=O)c2cnc3ccc(OC(F)(F)F)cc3c2N2CCC(N3CCCCC3)CC2)cc1] | 4-((4-([1,4'-bipiperidin]-1'-yl)-6-(trifluoromethoxy)quinolin-3-yl)sulfonyl)benzonitrile |
| 55 | 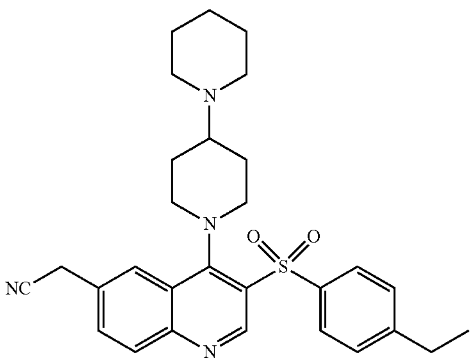 [SMILES: CCc1ccc(S(=O)(=O)c2cnc3ccc(CC#N)cc3c2N2CCC(N3CCCCC3)CC2)cc1] | 2-(4-([1,4'-bipiperidin]-1'-yl)-3-((4-ethylphenyl)sulfonyl)quinolin-6-yl)acetonitrile |
| 56 | 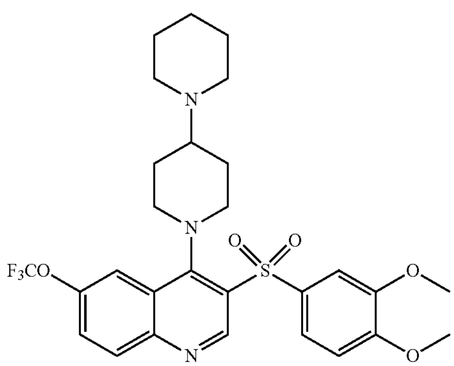 [SMILES: COc1ccc(S(=O)(=O)c2cnc3ccc(OC(F)(F)F)cc3c2N2CCC(N3CCCCC3)CC2)cc1OC] | 4-([1,4'-bipiperidin]-1'-yl)-3-((3,4-dimethoxyphenyl)sulfonyl)-6-(trifluoromethoxy)quinoline |
| 57 | 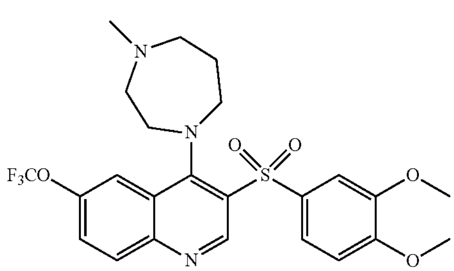 [SMILES: COc1ccc(S(=O)(=O)c2cnc3ccc(OC(F)(F)F)cc3c2N2CCCN(C)CC2)cc1OC] | 3-((3,4-dimethoxyphenyl)sulfonyl)-4-(4-methyl-1,4-diazepan-1-yl)-6-(trifluoromethoxy)quinoline |

TABLE 1-continued

| Ex. | Structure | Name |
|---|---|---|
| 58 | 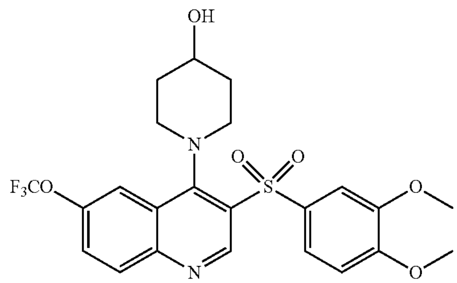 [SMILES: COc1ccc(S(=O)(=O)c2cnc3ccc(OC(F)(F)F)cc3c2N2CCC(O)CC2)cc1OC] | 1-(3-((3,4-dimethoxyphenyl)sulfonyl)-6-(trifluoromethoxy)quinolin-4-yl)piperidin-4-ol |
| 59 | 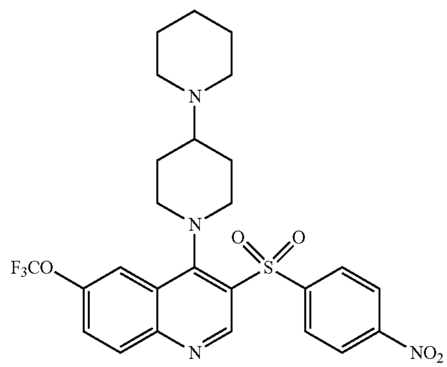 [SMILES: O=[N+]([O-])c1ccc(S(=O)(=O)c2cnc3ccc(OC(F)(F)F)cc3c2N2CCC(N3CCCCC3)CC2)cc1] | 4-([1,4'-bipiperidin]-1'-yl)-3-((4-nitrophenyl)sulfonyl)-6-(trifluoromethoxy)quinoline |
| 60 | 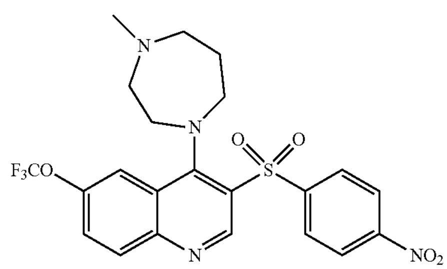 [SMILES: CN1CCCN(c2c(S(=O)(=O)c3ccc([N+](=O)[O-])cc3)cnc3ccc(OC(F)(F)F)cc23)CC1] | 4-(4-methyl-1,4-diazepan-1-yl)-3-((4-nitrophenyl)sulfonyl)-6-(trifluoromethoxy)quinoline |
| 61 | 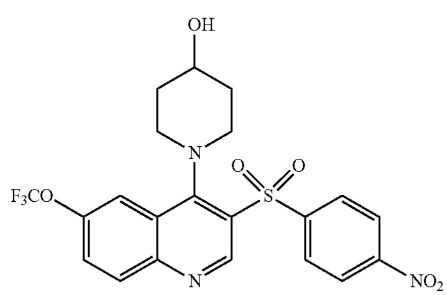 [SMILES: O=[N+]([O-])c1ccc(S(=O)(=O)c2cnc3ccc(OC(F)(F)F)cc3c2N2CCC(O)CC2)cc1] | 1-(3-((4-nitrophenyl)sulfonyl)-6-(trifluoromethoxy)quinolin-4-yl)piperidin-4-ol |
| 62 | 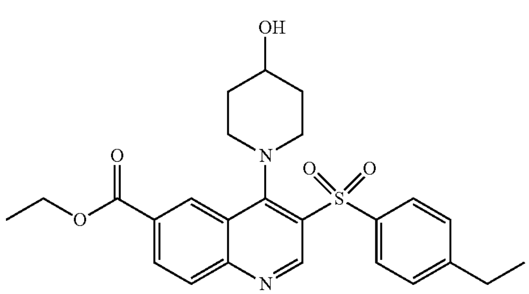 [SMILES: CCOC(=O)c1ccc2ncc(S(=O)(=O)c3ccc(CC)cc3)c(N3CCC(O)CC3)c2c1] | ethyl 3-((4-ethylphenyl)sulfonyl)-4-(4-hydroxypiperidin-1-yl)quinoline-6-carboxylate |

TABLE 1-continued

| Ex. | Structure | Name |
|---|---|---|
| 63 | 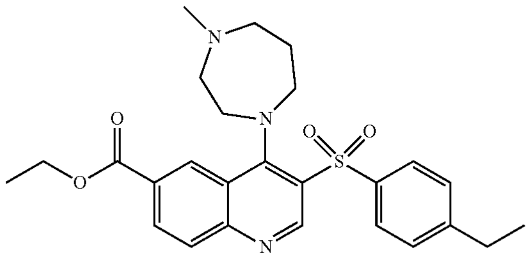 [SMILES: CCOC(=O)c1ccc2ncc(S(=O)(=O)c3ccc(CC)cc3)c(N3CCCN(C)CC3)c2c1] | ethyl 3-((4-ethylphenyl)sulfonyl)-4-(4-methyl-1,4-diazepan-1-yl)quinoline-6-carboxylate |
| 64 | 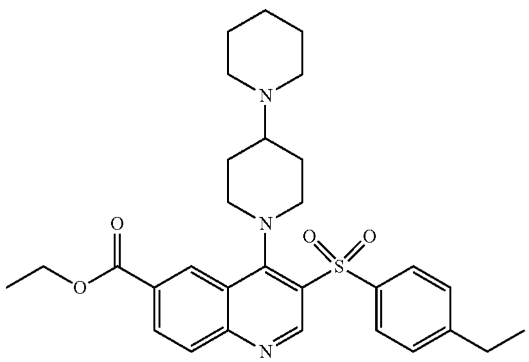 [SMILES: CCOC(=O)c1ccc2ncc(S(=O)(=O)c3ccc(CC)cc3)c(N3CCC(N4CCCCC4)CC3)c2c1] | ethyl 4-([1,4'-bipiperidin]-1'-yl)-3-((4-ethylphenyl)sulfonyl)quinoline-6-carboxylate |
| 65 | 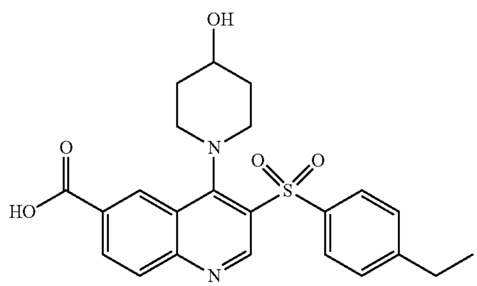 [SMILES: CCc1ccc(S(=O)(=O)c2cnc3ccc(C(=O)O)cc3c2N2CCC(O)CC2)cc1] | 3-((4-ethylphenyl)sulfonyl)-4-(4-hydroxypiperidin-1-yl)quinoline-6-carboxylic acid |
| 66 | 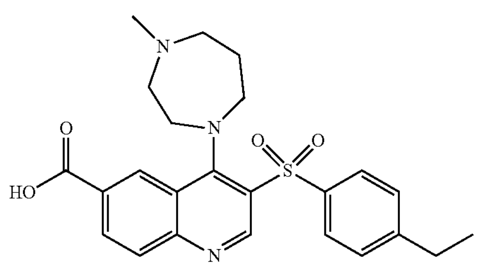 [SMILES: CCc1ccc(S(=O)(=O)c2cnc3ccc(C(=O)O)cc3c2N2CCCN(C)CC2)cc1] | 3-((4-ethylphenyl)sulfonyl)-4-(4-methyl-1,4-diazepan-1-yl)quinoline-6-carboxylic acid |
| 67 | 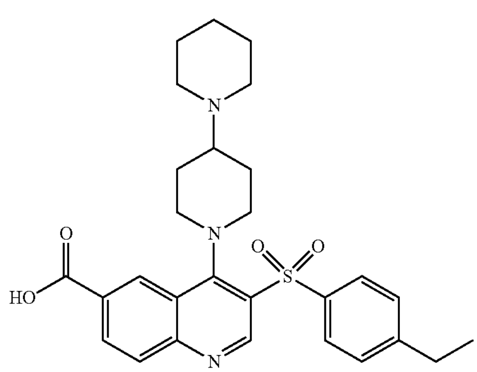 [SMILES: CCc1ccc(S(=O)(=O)c2cnc3ccc(C(=O)O)cc3c2N2CCC(N3CCCCC3)CC2)cc1] | 4-([1,4'-bipiperidin]-1'-yl)-3-((4-ethylphenyl)sulfonyl)quinoline-6-carboxylic acid |

TABLE 1-continued

| Ex. | Structure | Name |
|---|---|---|
| 68 | 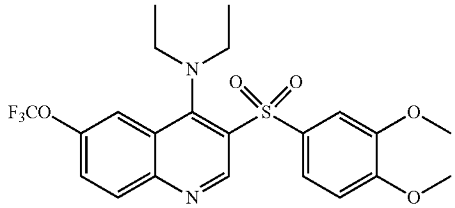 [SMILES: CCN(CC)c1c(S(=O)(=O)c2ccc(OC)c(OC)c2)cnc2ccc(OC(F)(F)F)cc12] | 3-((3,4-dimethoxyphenyl)sulfonyl)-N,N-diethyl-6-(trifluoromethoxy)quinolin-4-amine |
| 69 | 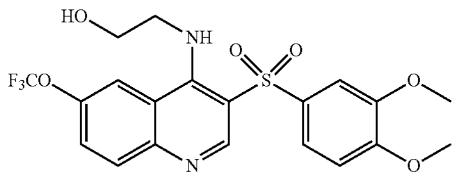 [SMILES: COc1ccc(S(=O)(=O)c2cnc3ccc(OC(F)(F)F)cc3c2NCCO)cc1OC] | 2-((3-((3,4-dimethoxyphenyl)sulfonyl)-6-(trifluoromethoxy)quinolin-4-yl)amino)ethan-1-ol |
| 70 | 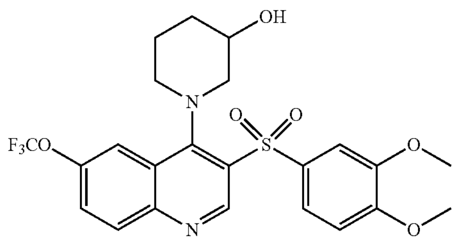 [SMILES: COc1ccc(S(=O)(=O)c2cnc3ccc(OC(F)(F)F)cc3c2N2CCCC(O)C2)cc1OC] | 1-(3-((3,4-dimethoxyphenyl)sulfonyl)-6-(trifluoromethoxy)quinolin-4-yl)piperidin-3-ol |
| 71 | 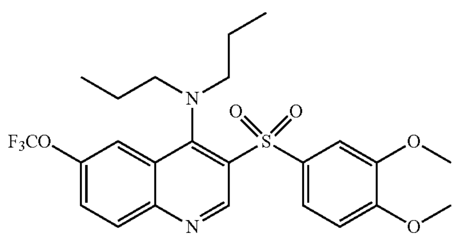 [SMILES: CCCN(CCC)c1c(S(=O)(=O)c2ccc(OC)c(OC)c2)cnc2ccc(OC(F)(F)F)cc12] | 3-((3,4-dimethoxyphenyl)sulfonyl)-N,N-dipropyl-6-(trifluoromethoxy)quinolin-4-amine |
| 72 | 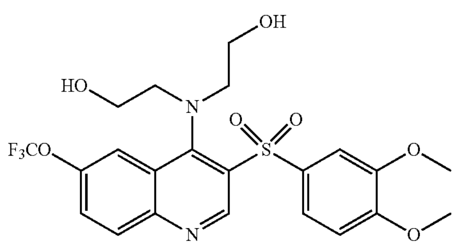 [SMILES: COc1ccc(S(=O)(=O)c2cnc3ccc(OC(F)(F)F)cc3c2N(CCO)CCO)cc1OC] | 2,2'-((3-((3,4-dimethoxyphenyl)sulfonyl)-6-(trifluoromethoxy)quinolin-4-yl)azanediyl)bis(ethan-1-ol) |
| 73 | 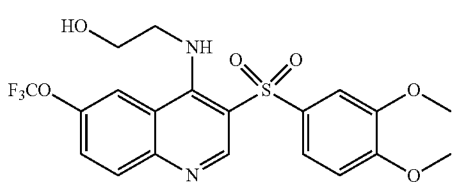 [SMILES: COc1ccc(S(=O)(=O)c2cnc3ccc(OC(F)(F)F)cc3c2NCCO)cc1OC] | 2-((3-((3,4-dimethoxyphenyl)sulfonyl)-6-(trifluoromethoxy)quinolin-4-yl)amino)ethan-1-ol |
| 74 | 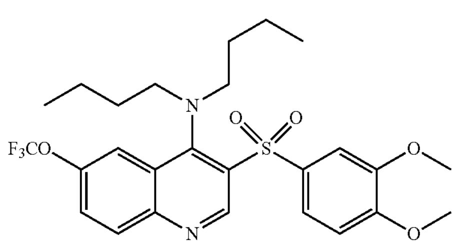 [SMILES: CCCCN(CCCC)c1c(S(=O)(=O)c2ccc(OC)c(OC)c2)cnc2ccc(OC(F)(F)F)cc12] | N,N-dibutyl-3-((3,4-dimethoxyphenyl)sulfonyl)-6-(trifluoromethoxy)quinolin-4-amine |

TABLE 1-continued

| Ex. | Structure | Name |
|---|---|---|
| 75 | 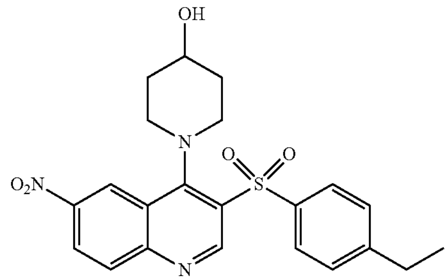 [SMILES: CCc1ccc(S(=O)(=O)c2cnc3ccc([N+](=O)[O-])cc3c2N2CCC(O)CC2)cc1] | 1-(3-((4-ethylphenyl)sulfonyl)-6-nitroquinolin-4-yl)piperidin-4-ol |
| 76 | 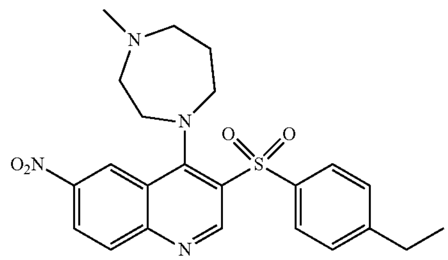 [SMILES: CCc1ccc(S(=O)(=O)c2cnc3ccc([N+](=O)[O-])cc3c2N2CCCN(C)CC2)cc1] | 3-((4-ethylphenyl)sulfonyl)-4-(4-methyl-1,4-diazepan-1-yl)-6-nitroquinoline |
| 77 | 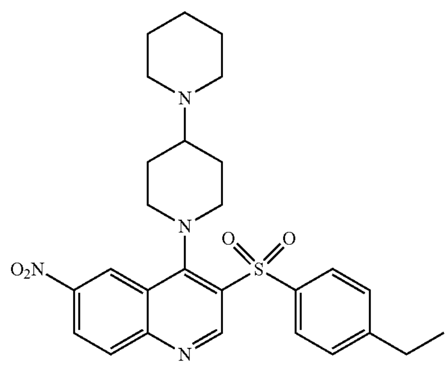 | 4-([1,4'-bipiperidin]-1'-yl)-3-((4-ethylphenyl)sulfonyl)-6-nitroquinoline |
| 78 | 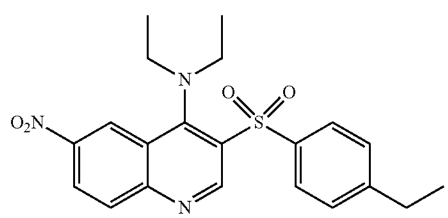 [SMILES: CCc1ccc(S(=O)(=O)c2cnc3ccc([N+](=O)[O-])cc3c2N(CC)CC)cc1] | N,N-diethyl-3-((4-ethylphenyl)sulfonyl)-6-nitroquinolin-4-amine |
| 79 | 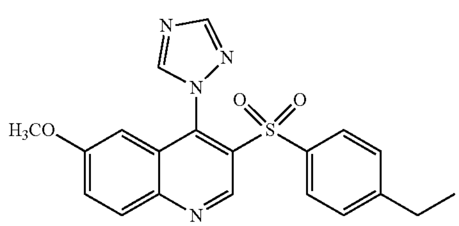 [SMILES: CCc1ccc(S(=O)(=O)c2cnc3ccc(OC)cc3c2-n2cncn2)cc1] | 3-((4-ethylphenyl)sulfonyl)-6-methoxy-4-(1H-1,2,4-triazol-1-yl)quinoline |
| 80 | 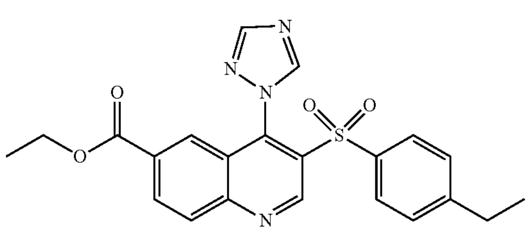 [SMILES: CCOC(=O)c1ccc2ncc(S(=O)(=O)c3ccc(CC)cc3)c(-n3cncn3)c2c1] | ethyl 3-((4-ethylphenyl)sulfonyl)-4-(1H-1,2,4-triazol-1-yl)quinoline-6-carboxylate |

TABLE 1-continued

| Ex. | Structure | Name |
|---|---|---|
| 81 | 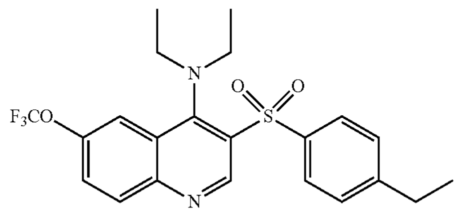 [SMILES: CCc1ccc(S(=O)(=O)c2cnc3ccc(OC(F)(F)F)cc3c2N(CC)CC)cc1] | N,N-diethyl-3-((4-ethylphenyl)sulfonyl)-6-(trifluoromethoxy)quinolin-4-amine |
| 82 | 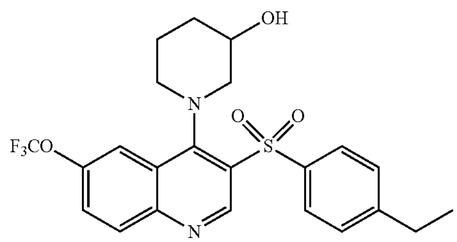 [SMILES: CCc1ccc(S(=O)(=O)c2cnc3ccc(OC(F)(F)F)cc3c2N2CCCC(O)C2)cc1] | 1-(3-((4-ethylphenyl)sulfonyl)-6-(trifluoromethoxy)quinolin-4-yl)piperidin-3-ol |
| 83 | 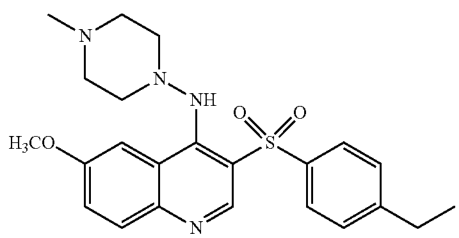 [SMILES: CCc1ccc(S(=O)(=O)c2cnc3ccc(OC)cc3c2NN2CCN(C)CC2)cc1] | 3-((4-ethylphenyl)sulfonyl)-6-methoxy-N-(4-methylpiperazin-1-yl)quinolin-4-amine |
| 84 | 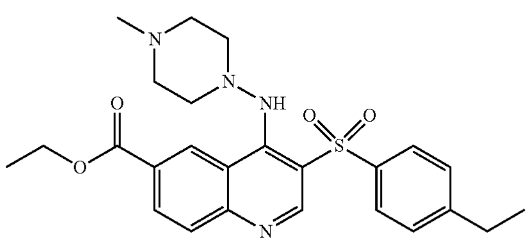 | ethyl 3-((4-ethylphenyl)sulfonyl)-4-((4-methylpiperazin-1-yl)amino)quinoline-6-carboxylate |
| 85 | 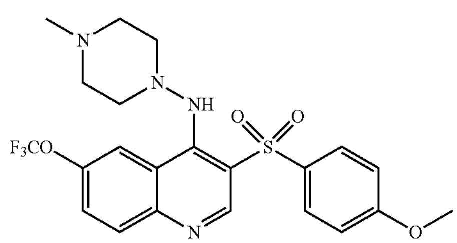 | 3-((4-methoxyphenyl)sulfonyl)-N-(4-methylpiperazin-1-yl)-6-(trifluoromethoxy)quinolin-4-amine |
| 86 | 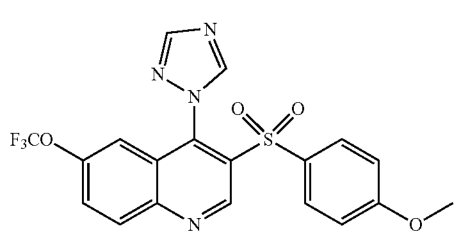 [SMILES: COc1ccc(S(=O)(=O)c2cnc3ccc(OC(F)(F)F)cc3c2-n2cncn2)cc1] | 3-((4-methoxyphenyl)sulfonyl)-4-(1H-1,2,4-triazol-1-yl)-6-(trifluoromethoxy)quinoline |

TABLE 1-continued

| Ex. | Structure | Name |
|---|---|---|
| 87 | 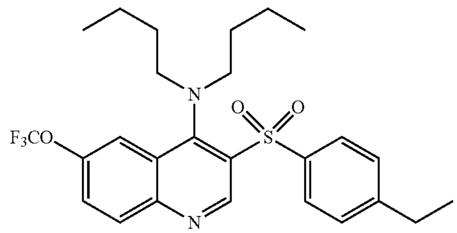 [SMILES: CCCCN(CCCC)c1c(S(=O)(=O)c2ccc(CC)cc2)cnc2ccc(OC(F)(F)F)cc12] | N,N-dibutyl-3-((4-ethylphenyl)sulfonyl)-6-(trifluoromethoxy)quinolin-4-amine |
| 88 | 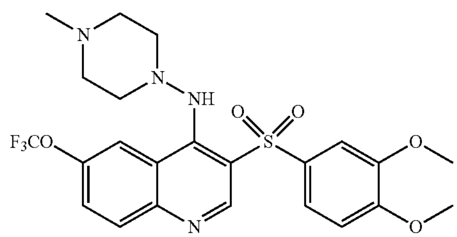 [SMILES: COc1ccc(S(=O)(=O)c2cnc3ccc(OC(F)(F)F)cc3c2NN2CCN(C)CC2)cc1OC] | 3-((3,4-dimethoxyphenyl)sulfonyl)-N-(4-methylpiperazin-1-yl)-6-(trifluoromethoxy)quinolin-4-amine |
| 89 | 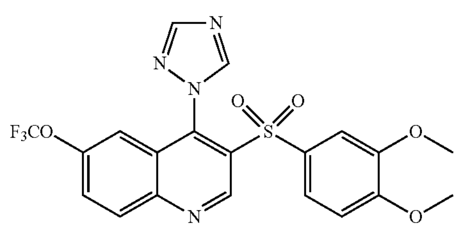 [SMILES: COc1ccc(S(=O)(=O)c2cnc3ccc(OC(F)(F)F)cc3c2-n2cncn2)cc1OC] | 3-((3,4-dimethoxyphenyl)sulfonyl)-4-(1H-1,2,4-triazol-1-yl)-6-(trifluoromethoxy)quinoline |
| 90 | 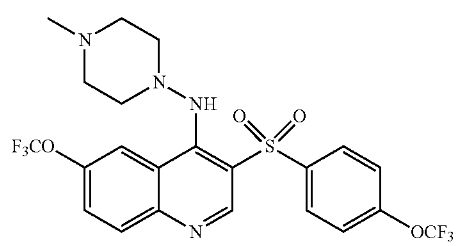 | N-(4-methylpiperazin-1-yl)-6-(trifluoromethoxy)-3-((4-(trifluoromethoxy)phenyl)sulfonyl)quinolin-4-amine |
| 91 | 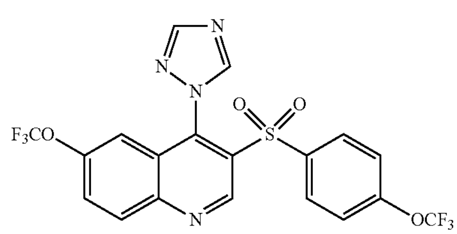 [SMILES: O=S(=O)(c1ccc(OC(F)(F)F)cc1)c1cnc2ccc(OC(F)(F)F)cc2c1-n1cncn1] | 4-(1H-1,2,4-triazol-1-yl)-6-(trifluoromethoxy)-3-((4-(trifluoromethoxy)phenyl)sulfonyl)quinoline |
| 92 | 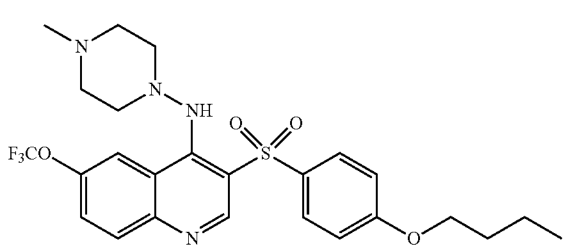 [SMILES: CCCCOc1ccc(S(=O)(=O)c2cnc3ccc(OC(F)(F)F)cc3c2NN2CCN(C)CC2)cc1] | 3-((4-butoxyphenyl)sulfonyl)-N-(4-methylpiperazin-1-yl)-6-(trifluoromethoxy)quinolin-4-amine |

TABLE 1-continued

| Ex. | Structure | Name |
|---|---|---|
| 93 | 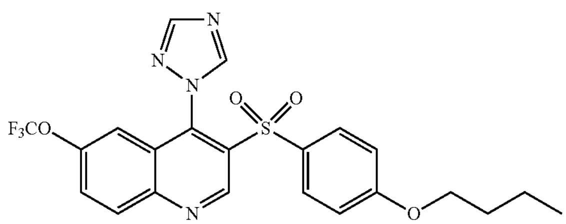 [SMILES: CCCCOc1ccc(S(=O)(=O)c2cnc3ccc(OC(F)(F)F)cc3c2-n2cncn2)cc1] | 3-((4-butoxyphenyl)sulfonyl)-4-(1H-1,2,4-triazol-1-yl)-6-(trifluoromethoxy)quinoline |
| 94 | 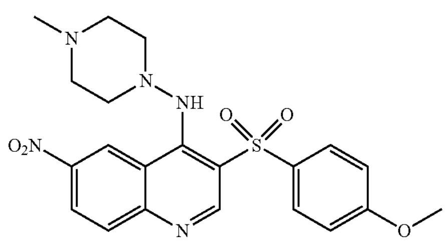 | 3-((4-methoxyphenyl)sulfonyl)-N-(4-methylpiperazin-1-yl)-6-nitroquinolin-4-amine |
| 95 | 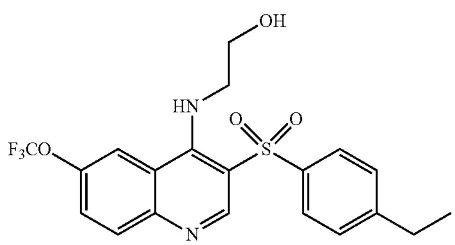 [SMILES: CCc1ccc(S(=O)(=O)c2cnc3ccc(OC(F)(F)F)cc3c2NCCO)cc1] | 2-((3-((4-ethylphenyl)sulfonyl)-6-(trifluoromethoxy)quinolin-4-yl)amino)ethan-1-ol |
| 96 | 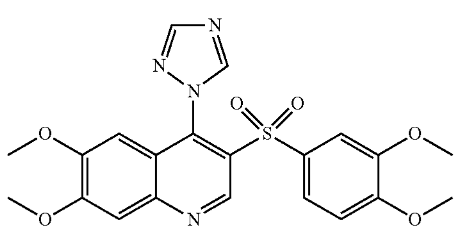 | 3-((3,4-dimethoxyphenyl)sulfonyl)-6,7-dimethoxy-4-(1H-1,2,4-triazol-1-yl)quinoline |
| 97 | 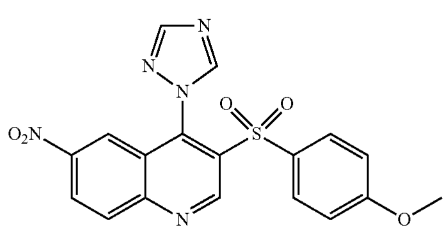 [SMILES: COc1ccc(S(=O)(=O)c2cnc3ccc([N+](=O)[O-])cc3c2-n2cncn2)cc1] | 3-((4-methoxyphenyl)sulfonyl)-6-nitro-4-(1H-1,2,4-triazol-1-yl)quinoline |
| 98 | 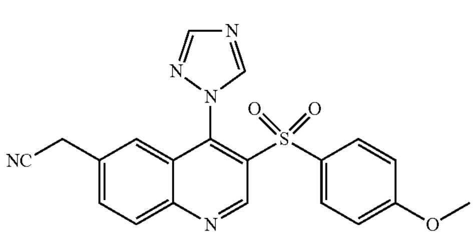 [SMILES: COc1ccc(S(=O)(=O)c2cnc3ccc(CC#N)cc3c2-n2cncn2)cc1] | 2-(3-((4-methoxyphenyl)sulfonyl)-4-(1H-1,2,4-triazol-1-yl)quinolin-6-yl)acetonitrile |

TABLE 1-continued

| Ex. | Structure | Name |
| --- | --- | --- |
| 99 | 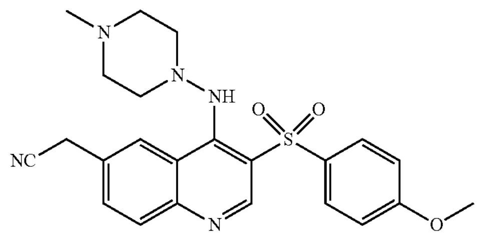 [SMILES: COc1ccc(S(=O)(=O)c2cnc3ccc(CC#N)cc3c2NN2CCN(C)CC2)cc1] | 2-(3-((4-methoxyphenyl)sulfonyl)-4-((4-methylpiperazin-1-yl)amino)quinolin-6-yl)acetonitrile |
| 100 | 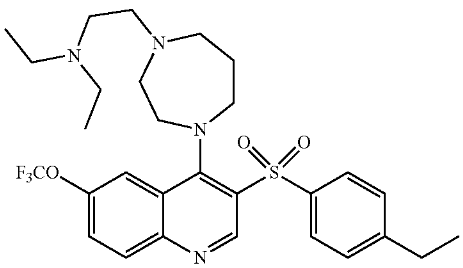 [SMILES: CCc1ccc(S(=O)(=O)c2cnc3ccc(OC(F)(F)F)cc3c2N2CCCN(CCN(CC)CC)CC2)cc1] | N,N-diethyl-2-(4-(3-((4-ethylphenyl)sulfonyl)-6-(trifluoromethoxy)quinolin-4-yl)-1,4-diazepan-1-yl)ethan-1-amine |
| 101 | 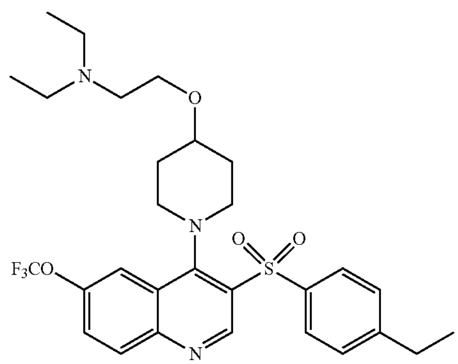 [SMILES: CCc1ccc(S(=O)(=O)c2cnc3ccc(OC(F)(F)F)cc3c2N2CCC(OCCN(CC)CC)CC2)cc1] | N,N-diethyl-2-((1-(3-((4-ethylphenyl)sulfonyl)-6-(trifluoromethoxy)quinolin-4-yl)piperidin-4-yl)oxy)ethan-1-amine |
| 102 | 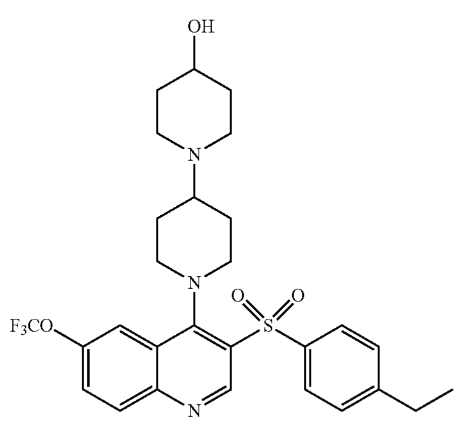 | 1'-(3-((4-ethylphenyl)sulfonyl)-6-(trifluoromethoxy)quinolin-4-yl)-[1,4'-bipiperidin]-4-ol |

TABLE 1-continued

| Ex. | Structure | Name |
|---|---|---|
| 103 | 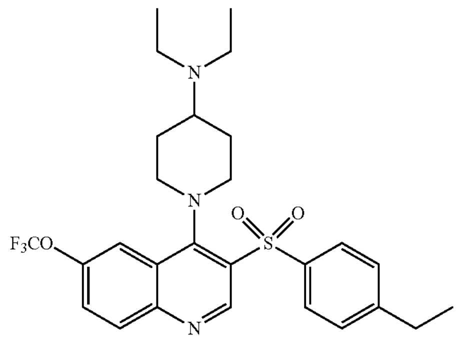 [SMILES: CCc1ccc(S(=O)(=O)c2cnc3ccc(OC(F)(F)F)cc3c2N2CCC(N(CC)CC)CC2)cc1] | N,N-diethyl-1-(3-((4-ethylphenyl)sulfonyl)-6-(trifluoromethoxy)quinolin-4-yl)piperidin-4-amine |
| 104 | 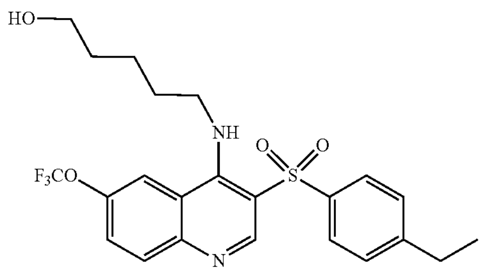 [SMILES: CCc1ccc(S(=O)(=O)c2cnc3ccc(OC(F)(F)F)cc3c2NCCCCCO)cc1] | 5-((3-((4-ethylphenyl)sulfonyl)-6-(trifluoromethoxy)quinolin-4-yl)amino)pentan-1-ol |
| 105 | 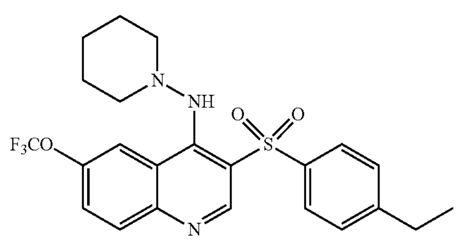 | 3-((4-ethylphenyl)sulfonyl)-N-(piperidin-1-yl)-6-(trifluoromethoxy)quinolin-4-amine |
| 106 | 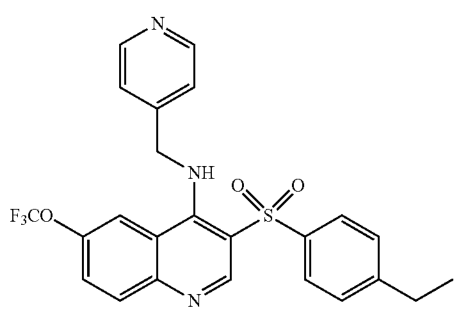 [SMILES: CCc1ccc(S(=O)(=O)c2cnc3ccc(OC(F)(F)F)cc3c2NCc2ccncc2)cc1] | 3-((4-ethylphenyl)sulfonyl)-N-(pyridin-4-ylmethyl)-6-(trifluoromethoxy)quinolin-4-amine |
| 107 | 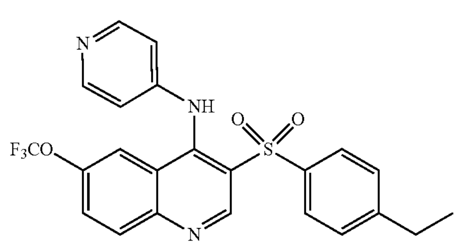 [SMILES: CCc1ccc(S(=O)(=O)c2cnc3ccc(OC(F)(F)F)cc3c2Nc2ccncc2)cc1] | 3-((4-ethylphenyl)sulfonyl)-N-(pyridin-4-yl)-6-(trifluoromethoxy)quinolin-4-amine |

| Ex. | Structure | Name |
| --- | --- | --- |
| 108 | 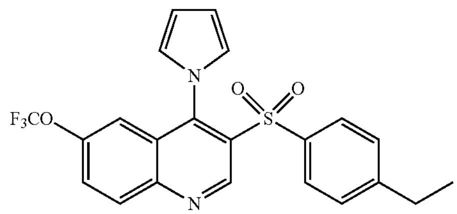 [SMILES: CCc1ccc(S(=O)(=O)c2cnc3ccc(OC(F)(F)F)cc3c2-n2cccc2)cc1] | 3-((4-ethylphenyl)sulfonyl)-4-(1H-pyrrol-1-yl)-6-(trifluoromethoxy)quinoline |
| 109 | 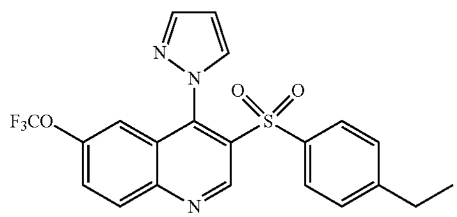 | 3-((4-ethylphenyl)sulfonyl)-4-(1H-pyrazol-1-yl)-6-(trifluoromethoxy)quinoline |
| 110 | 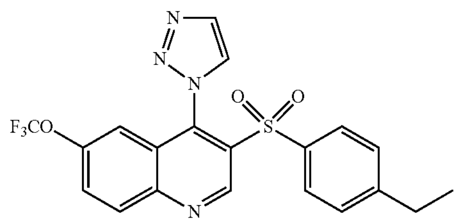 [SMILES: CCc1ccc(S(=O)(=O)c2cnc3ccc(OC(F)(F)F)cc3c2-n2ccnn2)cc1] | 3-((4-ethylphenyl)sulfonyl)-4-(1H-1,2,3-triazol-1-yl)-6-(trifluoromethoxy)quinoline |
| 111 | 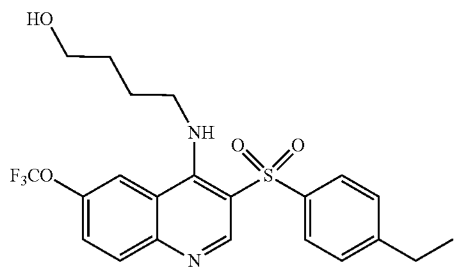 [SMILES: CCc1ccc(S(=O)(=O)c2cnc3ccc(OC(F)(F)F)cc3c2NCCCCO)cc1] | 4-((3-((4-ethylphenyl)sulfonyl)-6-(trifluoromethoxy)quinolin-4-yl)amino)butan-1-ol |
| 112 | 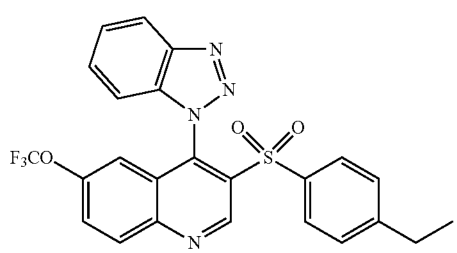 [SMILES: CCc1ccc(S(=O)(=O)c2cnc3ccc(OC(F)(F)F)cc3c2-n2nnc3ccccc32)cc1] | 4-(1H-benzo[d][1,2,3]triazol-1-yl)-3-((4-ethylphenyl)sulfonyl)-6-(trifluoromethoxy)quinoline |
| 113 | 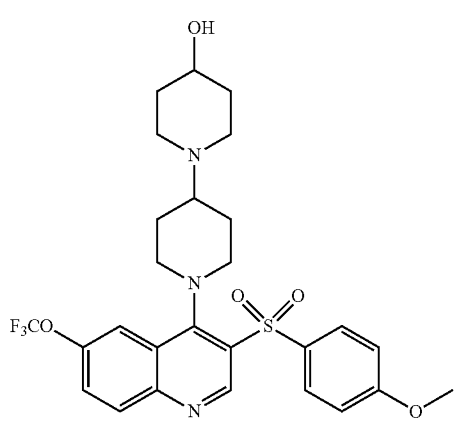 | 1'-(3-((4-methoxyphenyl)sulfonyl)-6-(trifluoromethoxy)quinolin-4-yl)-[1,4'-bipiperidin]-4-ol |

TABLE 1-continued

| Ex. | Structure | Name |
|---|---|---|
| 114 | 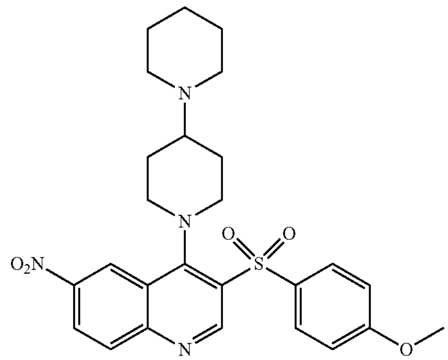 [SMILES: COc1ccc(S(=O)(=O)c2cnc3ccc([N+](=O)[O-])cc3c2N2CCC(N3CCCCC3)CC2)cc1] | 4-([1,4'-bipiperidin]-1'-yl)-3-((4-methoxyphenyl)sulfonyl)-6-nitroquinoline |
| 115 | 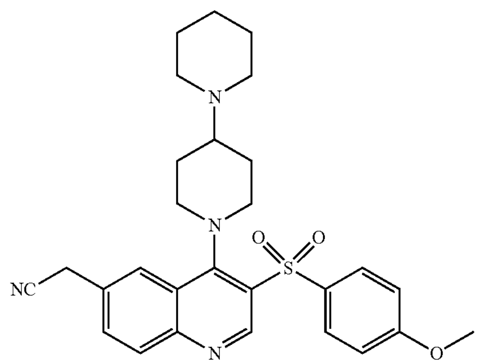 | 2-(4-([1,4'-bipiperidin]-1'-yl)-3-((4-methoxyphenyl)sulfonyl)quinolin-6-yl)acetonitrile |
| 116 | 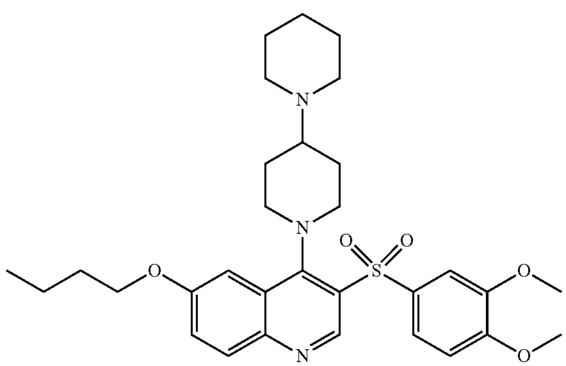 [SMILES: CCCCOc1ccc2ncc(S(=O)(=O)c3ccc(OC)c(OC)c3)c(N3CCC(N4CCCCC4)CC3)c2c1] | 4-([1,4'-bipiperidin]-1'-yl)-6-butoxy-3-((3,4-dimethoxyphenyl)sulfonyl)quinoline |
| 117 | 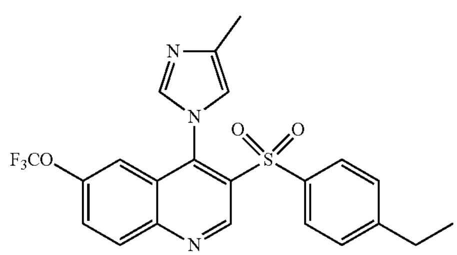 [SMILES: CCc1ccc(S(=O)(=O)c2cnc3ccc(OC(F)(F)F)cc3c2-n2cnc(C)c2)cc1] | 3-((4-ethylphenyl)sulfonyl)-4-(4-methyl-1H-imidazol-1-yl)-6-(trifluoromethoxy)quinoline |
| 118 | 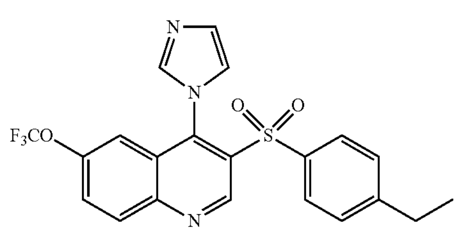 [SMILES: CCc1ccc(S(=O)(=O)c2cnc3ccc(OC(F)(F)F)cc3c2-n2ccnc2)cc1] | 3-((4-ethylphenyl)sulfonyl)-4-(1H-imidazol-1-yl)-6-(trifluoromethoxy)quinoline |

TABLE 1-continued

| Ex. | Structure | Name |
|---|---|---|
| 119 | 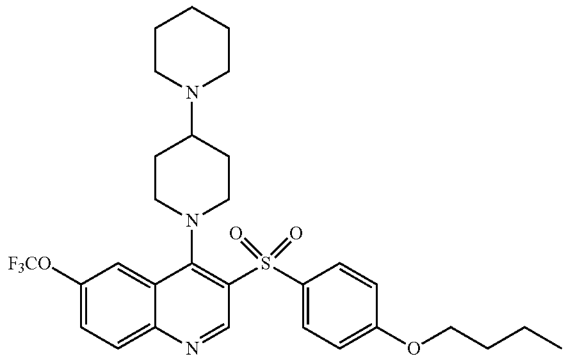 [SMILES: CCCCOc1ccc(S(=O)(=O)c2cnc3ccc(OC(F)(F)F)cc3c2N2CCC(N3CCCCC3)CC2)cc1] | 4-([1,4'-bipiperidin]-1'-yl)-3-((4-butoxyphenyl)sulfonyl)-6-(trifluoromethoxy)quinoline |
| 120 | 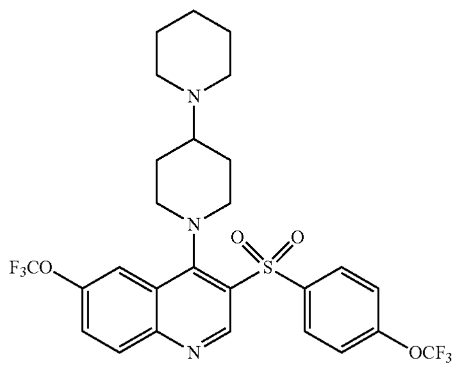 [SMILES: O=S(=O)(c1ccc(OC(F)(F)F)cc1)c1cnc2ccc(OC(F)(F)F)cc2c1N1CCC(N2CCCCC2)CC1] | 4-([1,4'-bipiperidin]-1'-yl)-6-(trifluoromethoxy)-3-((4-(trifluoromethoxy)phenyl)sulfonyl)quinoline |
| 121 | 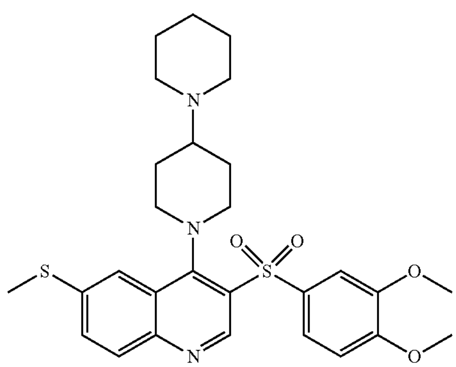 | 4-([1,4'-bipiperidin]-1'-yl)-3-((3,4-dimethoxyphenyl)sulfonyl)-6-(methylthio)quinoline |
| 122 | 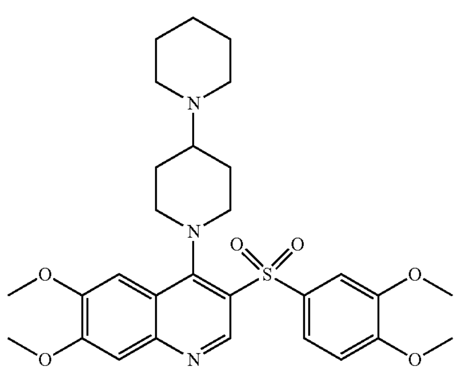 | 4-([1,4'-bipiperidin]-1'-yl)-3-((3,4-dimethoxyphenyl)sulfonyl)-6,7-dimethoxyquinoline |

TABLE 1-continued

| Ex. | Structure | Name |
|---|---|---|
| 123 | 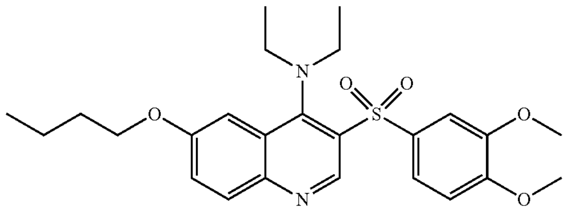 [SMILES: CCCCOc1ccc2ncc(S(=O)(=O)c3ccc(OC)c(OC)c3)c(N(CC)CC)c2c1] | 6-butoxy-3-((3,4-dimethoxyphenyl)sulfonyl)-N,N-diethylquinolin-4-amine |
| 124 | 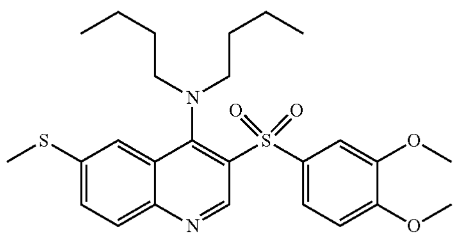 | N,N-dibutyl-3-((3,4-dimethoxyphenyl)sulfonyl)-6-(methylthio)quinolin-4-amine |
| 125 | 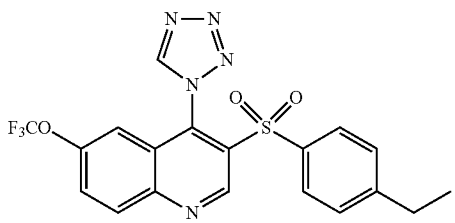 [SMILES: CCc1ccc(S(=O)(=O)c2cnc3ccc(OC(F)(F)F)cc3c2-n2cnnn2)cc1] | 3-((4-ethylphenyl)sulfonyl)-4-(1H-tetrazol-1-yl)-6-(trifluoromethoxy)quinoline |
| 126 | 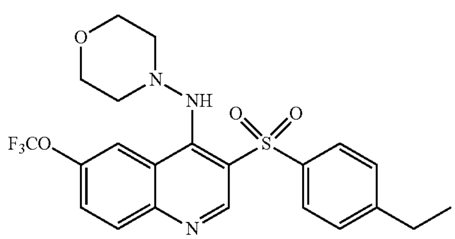 | N-(3-((4-ethylphenyl)sulfonyl)-6-(trifluoromethoxy)quinolin-4-yl)morpholin-4-amine |
| 127 | 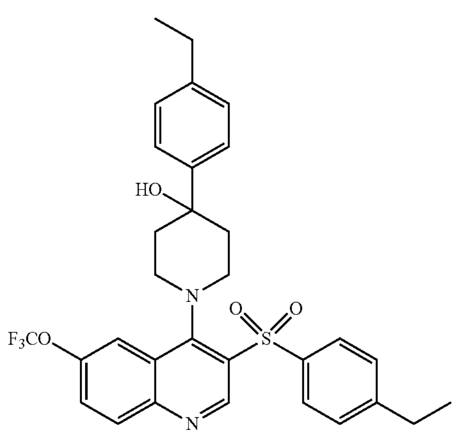 | 4-(4-ethylphenyl)-1-(3-((4-ethylphenyl)sulfonyl)-6-(trifluoromethoxy)quinolin-4-yl)piperidin-4-ol |

TABLE 1-continued

| Ex. | Structure | Name |
|---|---|---|
| 128 | 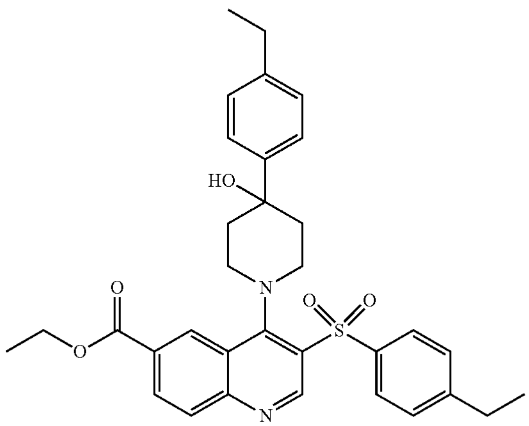 [SMILES: CCOC(=O)c1ccc2ncc(S(=O)(=O)c3ccc(CC)cc3)c(N3CCC(O)(c4ccc(CC)cc4)CC3)c2c1] | ethyl 4-(4-(4-ethylphenyl)-4-hydroxypiperidin-1-yl)-3-((4-ethylphenyl)sulfonyl)quinoline-6-carboxylate |
| 129 | 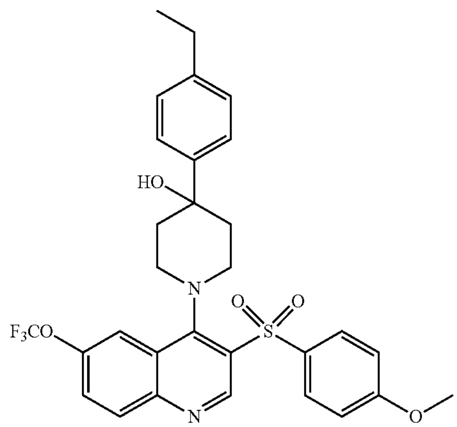 [SMILES: CCc1ccc(C2(O)CCN(c3c(S(=O)(=O)c4ccc(OC)cc4)cnc4ccc(OC(F)(F)F)cc34)CC2)cc1] | 4-(4-ethylphenyl)-1-(3-((4-methoxyphenyl)sulfonyl)-6-(trifluoromethoxy)quinolin-4-yl)piperidin-4-ol |
| 130 | 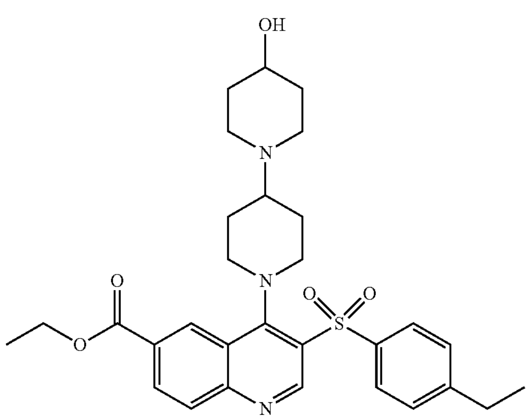 [SMILES: CCOC(=O)c1ccc2ncc(S(=O)(=O)c3ccc(CC)cc3)c(N3CCC(N4CCC(O)CC4)CC3)c2c1] | ethyl 3-((4-ethylphenyl)sulfonyl)-4-(4-hydroxy-[1,4'-bipiperidin]-1'-yl)quinoline-6-carboxylate |
| 131 | 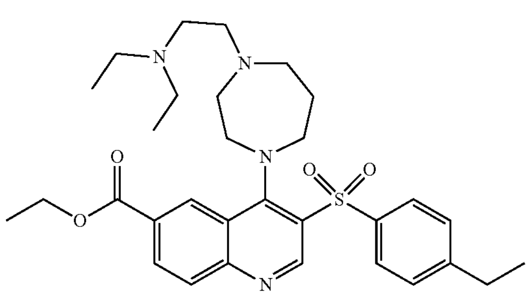 [SMILES: CCOC(=O)c1ccc2ncc(S(=O)(=O)c3ccc(CC)cc3)c(N3CCCN(CCN(CC)CC)CC3)c2c1] | ethyl 4-(4-(2-(diethylamino)ethyl)-1,4-diazepan-1-yl)-3-((4-ethylphenyl)sulfonyl)quinoline-6-carboxylate |

TABLE 1-continued

| Ex. | Structure | Name |
|---|---|---|
| 132 | 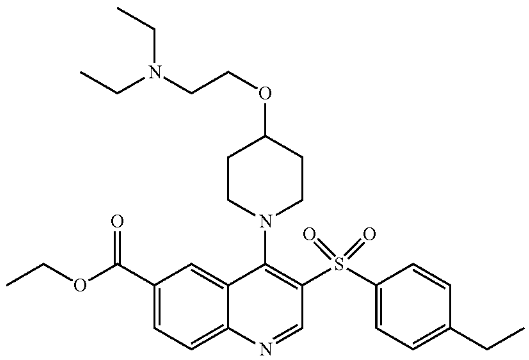 | ethyl 4-(4-(2-(diethylamino)ethoxy)piperidin-1-yl)-3-((4-ethylphenyl)sulfonyl)quinoline-6-carboxylate |
| 133 | 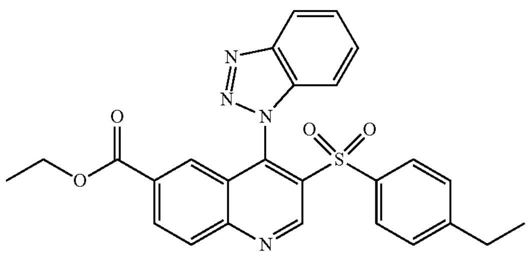 [SMILES: CCOC(=O)c1ccc2ncc(S(=O)(=O)c3ccc(CC)cc3)c(-n3nnc4ccccc43)c2c1] | ethyl 4-(1H-benzo[d][1,2,3]triazol-1-yl)-3-((4-ethylphenyl)sulfonyl)quinoline-6-carboxylate |
| 134 | 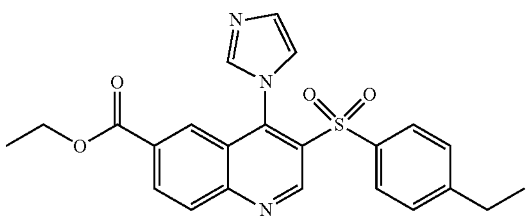 [SMILES: CCOC(=O)c1ccc2ncc(S(=O)(=O)c3ccc(CC)cc3)c(-n3ccnc3)c2c1] | ethyl 3-((4-ethylphenyl)sulfonyl)-4-(1H-imidazol-1-yl)quinoline-6-carboxylate |
| 135 | 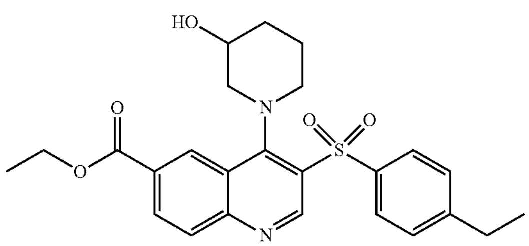 | ethyl 3-((4-ethylphenyl)sulfonyl)-4-(3-hydroxypiperidin-1-yl)quinoline-6-carboxylate |
| 136 | 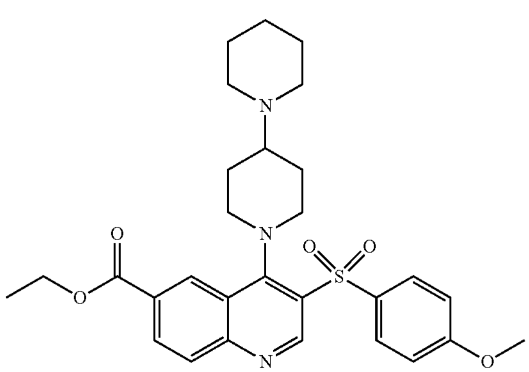 [SMILES: CCOC(=O)c1ccc2ncc(S(=O)(=O)c3ccc(OC)cc3)c(N3CCC(N4CCCCC4)CC3)c2c1] | ethyl 4-([1,4'-bipiperidin]-1'-yl)-3-((4-methoxyphenyl)sulfonyl)quinoline-6-carboxylate |

TABLE 1-continued

| Ex. | Structure | Name |
|---|---|---|
| 137 | 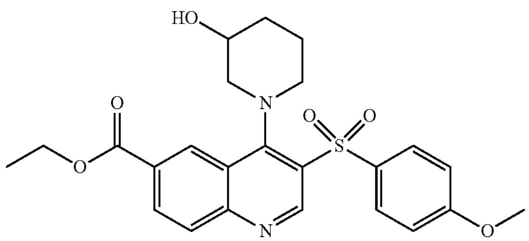 [SMILES: CCOC(=O)c1ccc2ncc(S(=O)(=O)c3ccc(OC)cc3)c(N3CCCC(O)C3)c2c1] | ethyl 4-(3-hydroxypiperidin-1-yl)-3-((4-methoxyphenyl)sulfonyl)quinoline-6-carboxylate |
| 138 | 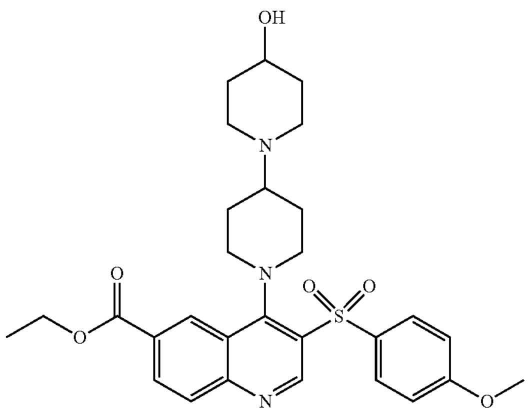 | ethyl 4-(4-hydroxy-[1,4'-bipiperidin]-1'-yl)-3-((4-methoxyphenyl)sulfonyl)quinoline-6-carboxylate |
| 139 | 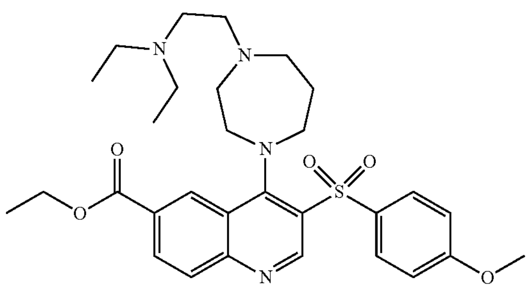 [SMILES: CCOC(=O)c1ccc2ncc(S(=O)(=O)c3ccc(OC)cc3)c(N3CCCN(CCN(CC)CC)CC3)c2c1] | ethyl 4-(4-(2-(diethylamino)ethyl)-1,4-diazepan-1-yl)-3-((4-methoxyphenyl)sulfonyl)quinoline-6-carboxylate |
| 140 | 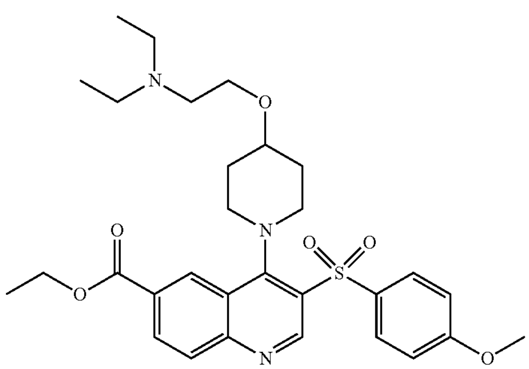 [SMILES: CCOC(=O)c1ccc2ncc(S(=O)(=O)c3ccc(OC)cc3)c(N3CCC(OCCN(CC)CC)CC3)c2c1] | ethyl 4-(4-(2-(diethylamino)ethoxy)piperidin-1-yl)-3-((4-methoxyphenyl)sulfonyl)quinoline-6-carboxylate |
| 141 | 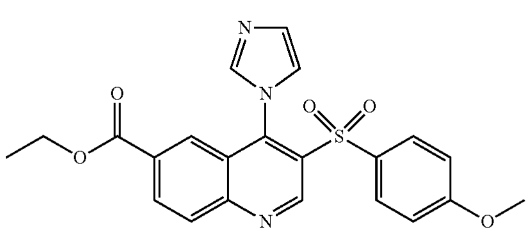 [SMILES: CCOC(=O)c1ccc2ncc(S(=O)(=O)c3ccc(OC)cc3)c(-n3ccnc3)c2c1] | ethyl 4-(1H-imidazol-1-yl)-3-((4-methoxyphenyl)sulfonyl)quinoline-6-carboxylate |

TABLE 1-continued

| Ex. | Structure | Name |
|---|---|---|
| 142 | 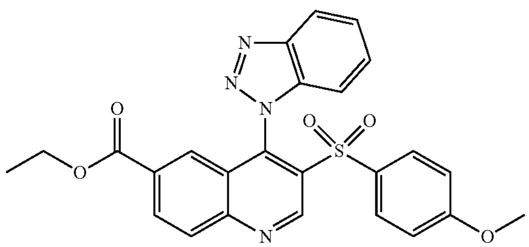 [SMILES: CCOC(=O)c1ccc2ncc(S(=O)(=O)c3ccc(OC)cc3)c(-n3nnc4ccccc43)c2c1] | ethyl 4-(1H-benzo[d][1,2,3]triazol-1-yl)-3-((4-methoxyphenyl)sulfonyl)quinoline-6-carboxylate |
| 143 | 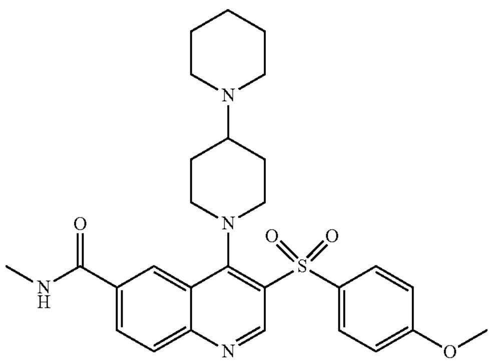 | 4-([1,4'-bipiperidin]-1'-yl)-3-((4-methoxyphenyl)sulfonyl)-N-methylquinoline-6-carboxamide |
| 144 | 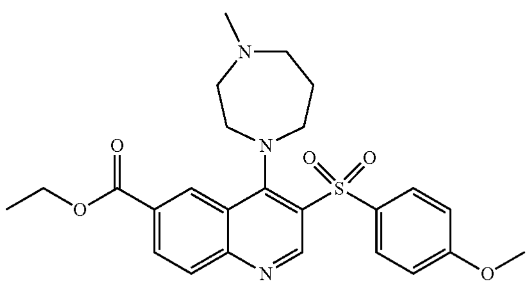 [SMILES: CCOC(=O)c1ccc2ncc(S(=O)(=O)c3ccc(OC)cc3)c(N3CCCN(C)CC3)c2c1] | ethyl 3-((4-methoxyphenyl)sulfonyl)-4-(4-methyl-1,4-diazepan-1-yl)quinoline-6-carboxylate |
| 145 | 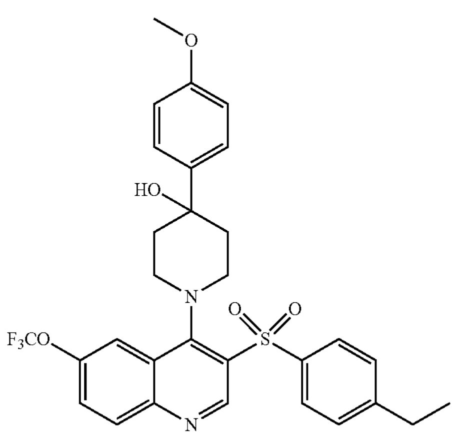 | 1-(3-((4-ethylphenyl)sulfonyl)-6-(trifluoromethoxy)quinolin-4-yl)-4-(4-methoxyphenyl)piperidin-4-ol |

TABLE 1-continued

| Ex. | Structure | Name |
|---|---|---|
| 146 | 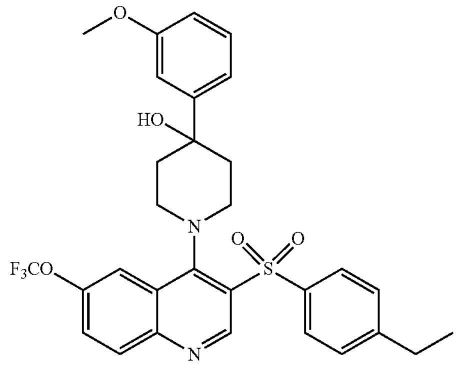 | 1-(3-((4-ethylphenyl)sulfonyl)-6-(trifluoromethoxy)quinolin-4-yl)-4-(3-methoxyphenyl)piperidin-4-ol |
| 147 | 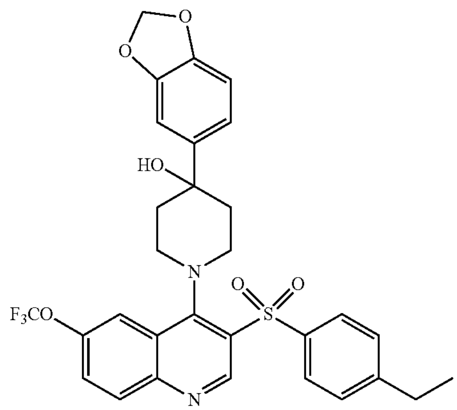 [SMILES: CCc1ccc(S(=O)(=O)c2cnc3ccc(OC(F)(F)F)cc3c2N2CCC(O)(c3ccc4c(c3)OCO4)CC2)cc1] | 4-(benzo[d][1,3]dioxol-5-yl)-1-(3-((4-ethylphenyl)sulfonyl)-6-(trifluoromethoxy)quinolin-4-yl)piperidin-4-ol |
| 148 | 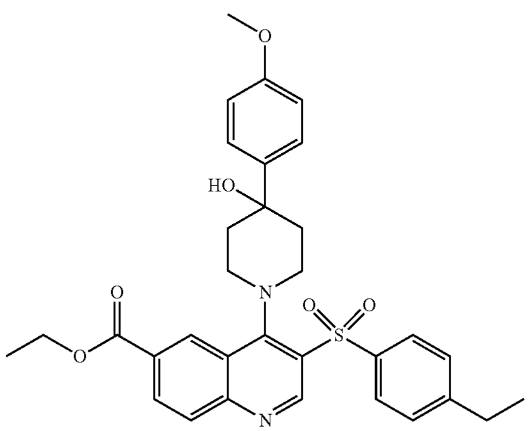 [SMILES: CCOC(=O)c1ccc2ncc(S(=O)(=O)c3ccc(CC)cc3)c(N3CCC(O)(c4ccc(OC)cc4)CC3)c2c1] | ethyl 3-((4-ethylphenyl)sulfonyl)-4-(4-hydroxy-4-(4-methoxyphenyl)piperidin-1-yl)quinoline-6-carboxylate |
| 149 | 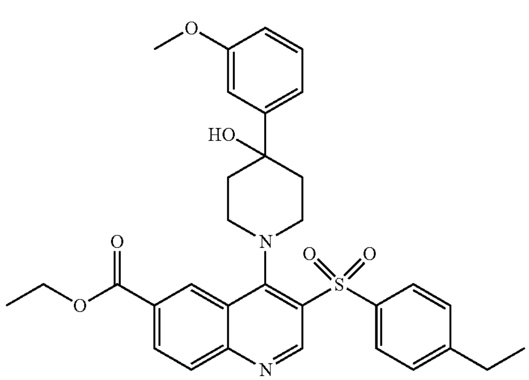 [SMILES: CCOC(=O)c1ccc2ncc(S(=O)(=O)c3ccc(CC)cc3)c(N3CCC(O)(c4cccc(OC)c4)CC3)c2c1] | ethyl 3-((4-ethylphenyl)sulfonyl)-4-(4-hydroxy-4-(3-methoxyphenyl)piperidin-1-yl)quinoline-6-carboxylate |

TABLE 1-continued

| Ex. | Structure | Name |
|---|---|---|
| 150 | 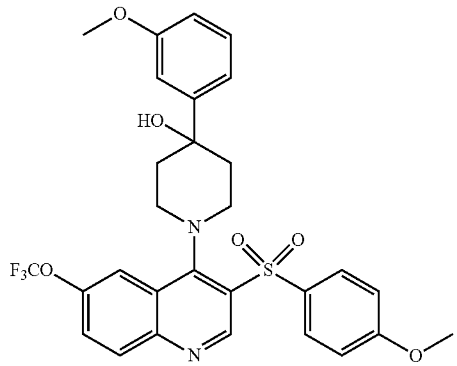 [SMILES: COc1ccc(S(=O)(=O)c2cnc3ccc(OC(F)(F)F)cc3c2N2CCC(O)(c3cccc(OC)c3)CC2)cc1] | 4-(3-methoxyphenyl)-1-(3-((4-methoxyphenyl)sulfonyl)-6-(trifluoromethoxy)quinolin-4-yl)piperidin-4-ol |
| 151 | 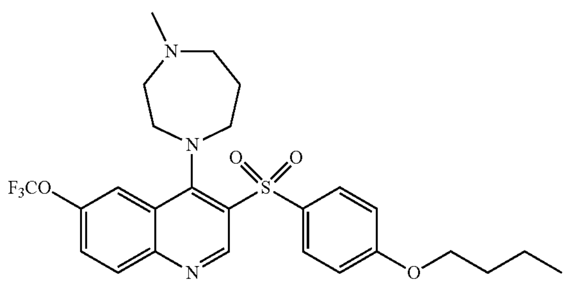 [SMILES: CCCCOc1ccc(S(=O)(=O)c2cnc3ccc(OC(F)(F)F)cc3c2N2CCCN(C)CC2)cc1] | 3-((4-butoxyphenyl)sulfonyl)-4-(4-methyl-1,4-diazepan-1-yl)-6-(trifluoromethoxy)quinoline |
| 152 | 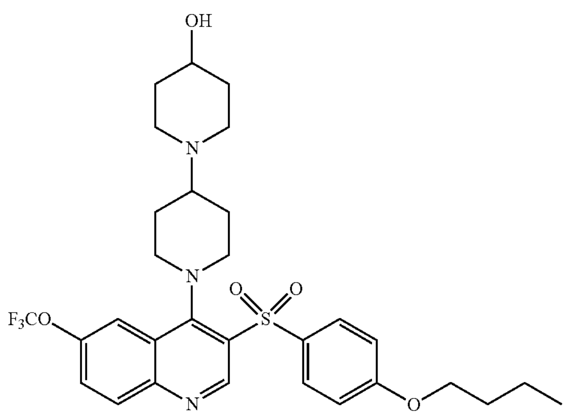 [SMILES: CCCCOc1ccc(S(=O)(=O)c2cnc3ccc(OC(F)(F)F)cc3c2N2CCC(N3CCC(O)CC3)CC2)cc1] | 1'-(3-((4-butoxyphenyl)sulfonyl)-6-(trifluoromethoxy)quinolin-4-yl)-[1,4'-bipiperidin]-4-ol |
| 153 | 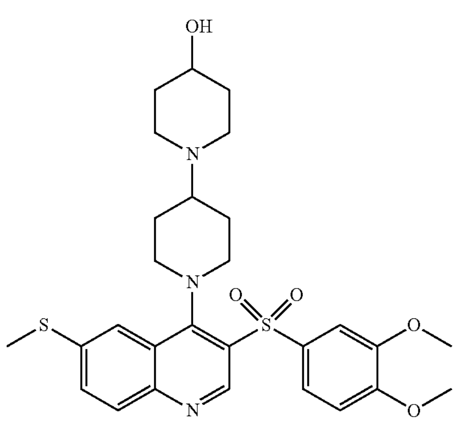 | 1'-(3-((3,4-dimethoxyphenyl)sulfonyl)-6-(methylthio)quinolin-4-yl)-[1,4'-bipiperidin]-4-ol |

TABLE 1-continued

| Ex. | Structure | Name |
|---|---|---|
| 154 | 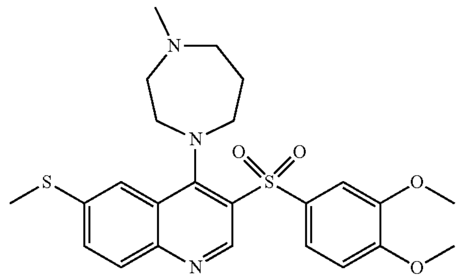 | 3-((3,4-dimethoxyphenyl)sulfonyl)-4-(4-methyl-1,4-diazepan-1-yl)-6-(methylthio)quinoline |
| 155 | 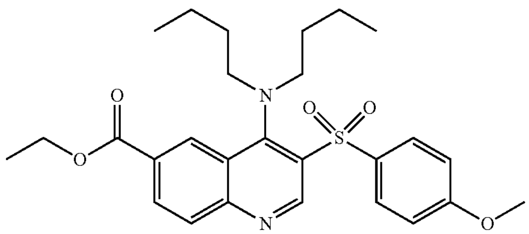 [SMILES: CCCCN(CCCC)c1c(S(=O)(=O)c2ccc(OC)cc2)cnc2ccc(C(=O)OCC)cc12] | ethyl 4-(dibutylamino)-3-((4-methoxyphenyl)sulfonyl)quinoline-6-carboxylate |
| 156 | 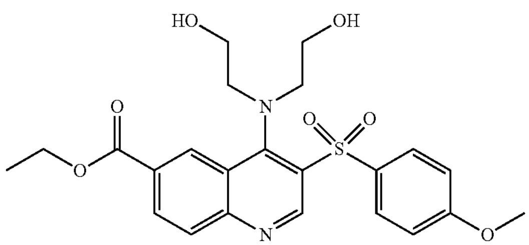 [SMILES: CCOC(=O)c1ccc2ncc(S(=O)(=O)c3ccc(OC)cc3)c(N(CCO)CCO)c2c1] | ethyl 4-(bis(2-hydroxyethyl)amino)-3-((4-methoxyphenyl)sulfonyl)quinoline-6-carboxylate |
| 157 | 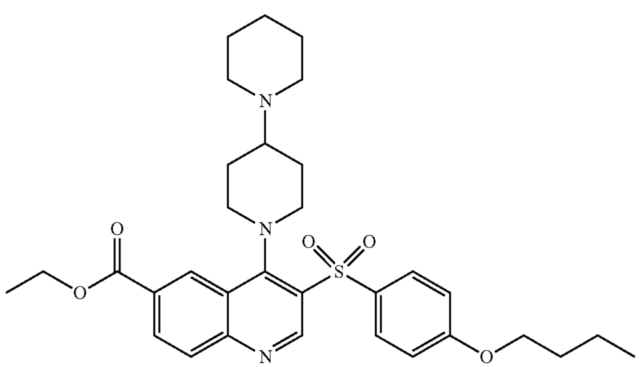 [SMILES: CCCCOc1ccc(S(=O)(=O)c2cnc3ccc(C(=O)OCC)cc3c2N2CCC(N3CCCCC3)CC2)cc1] | ethyl 4-([1,4'-bipiperidin]-1'-yl)-3-((4-butoxyphenyl)sulfonyl)quinoline-6-carboxylate |
| 158 | 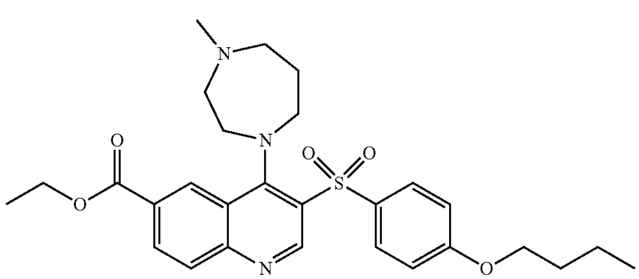 [SMILES: CCCCOc1ccc(S(=O)(=O)c2cnc3ccc(C(=O)OCC)cc3c2N2CCCN(C)CC2)cc1] | ethyl 3-((4-butoxyphenyl)sulfonyl)-4-(4-methyl-1,4-diazepan-1-yl)quinoline-6-carboxylate |

TABLE 1-continued

| Ex. | Structure | Name |
|---|---|---|
| 159 | 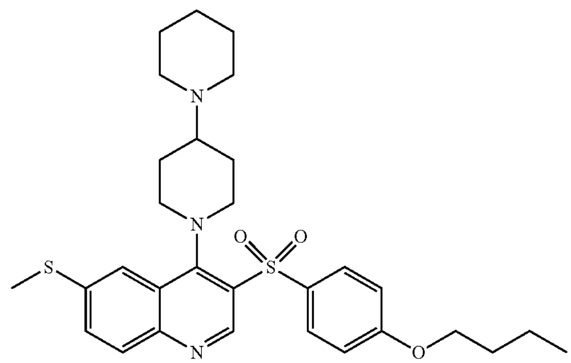 [SMILES: CCCCOc1ccc(S(=O)(=O)c2cnc3ccc(SC)cc3c2N2CCC(N3CCCCC3)CC2)cc1] | 4-([1,4'-bipiperidin]-1'-yl)-3-((4-butoxyphenyl)sulfonyl)-6-(methylthio)quinoline |
| 160 | 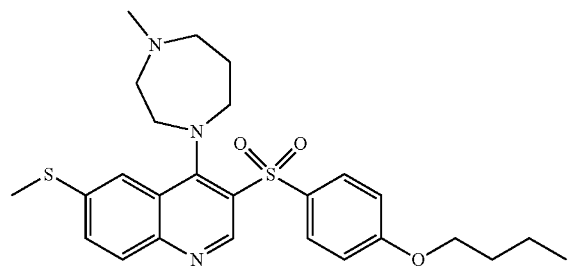 [SMILES: CCCCOc1ccc(S(=O)(=O)c2cnc3ccc(SC)cc3c2N2CCCN(C)CC2)cc1] | 3-((4-butoxyphenyl)sulfonyl)-4-(4-methyl-1,4-diazepan-1-yl)-6-(methylthio)quinoline |
| 161 | 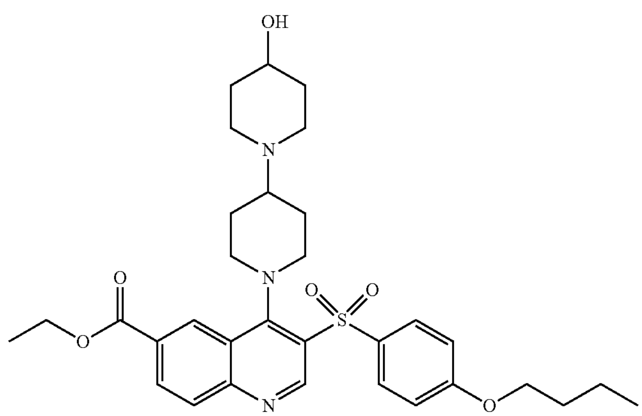 | ethyl 3-((4-butoxyphenyl)sulfonyl)-4-(4-hydroxy-[1,4'-bipiperidin]-1'-yl)quinoline-6-carboxylate |
| 162 | 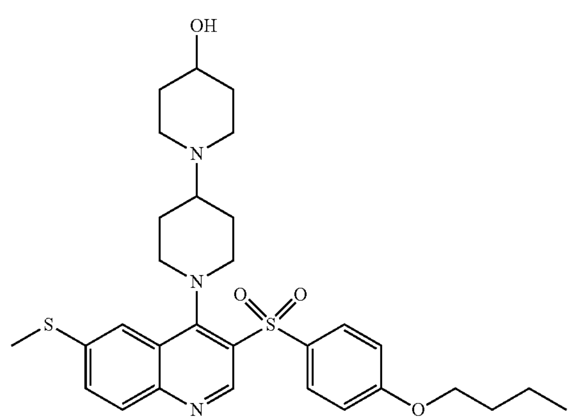 [SMILES: CCCCOc1ccc(S(=O)(=O)c2cnc3ccc(SC)cc3c2N2CCC(N3CCC(O)CC3)CC2)cc1] | 1'-(3-((4-butoxyphenyl)sulfonyl)-6-(methylthio)quinolin-4-yl)-[1,4'-bipiperidin]-4-ol |

TABLE 1-continued

| Ex. | Structure | Name |
|-----|-----------|------|
| 163 | 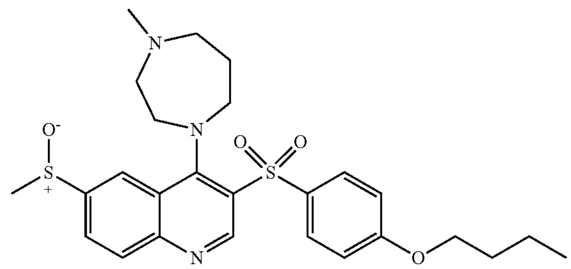 | 3-((4-butoxyphenyl)sulfonyl)-4-(4-methyl-1,4-diazepan-1-yl)-6-(methylsulfinyl)quinoline |
| 164 | 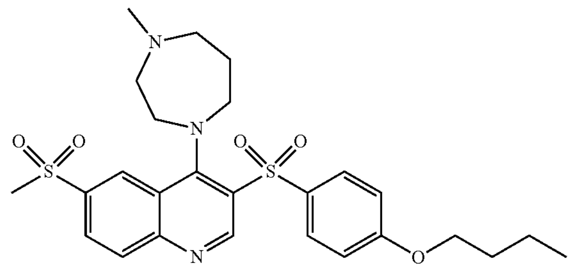 [SMILES: CCCCOc1ccc(S(=O)(=O)c2cnc3ccc(S(C)(=O)=O)cc3c2N2CCCN(C)CC2)cc1] | 3-((4-butoxyphenyl)sulfonyl)-4-(4-methyl-1,4-diazepan-1-yl)-6-(methylsulfonyl)quinoline |
| 165 | 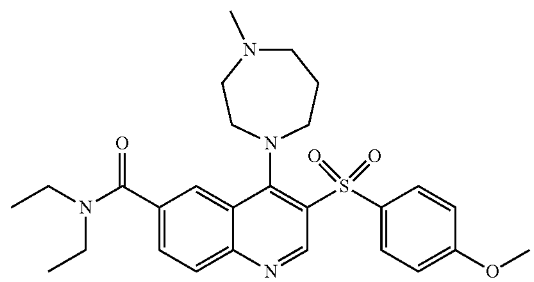 [SMILES: CCN(CC)C(=O)c1ccc2ncc(S(=O)(=O)c3ccc(OC)cc3)c(N3CCCN(C)CC3)c2c1] | N,N-diethyl-3-((4-methoxyphenyl)sulfonyl)-4-(4-methyl-1,4-diazepan-1-yl)quinoline-6-carboxamide |
| 166 | 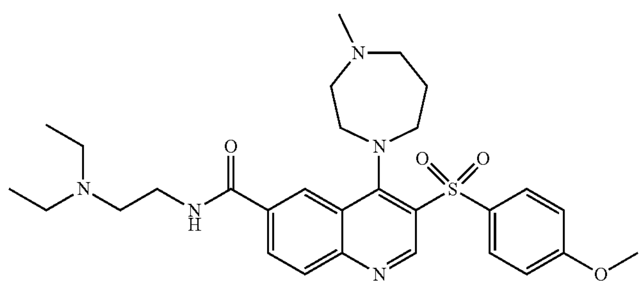 [SMILES: CCN(CC)CCNC(=O)c1ccc2ncc(S(=O)(=O)c3ccc(OC)cc3)c(N3CCCN(C)CC3)c2c1] | N-(2-(diethylamino)ethyl)-3-((4-methoxyphenyl)sulfonyl)-4-(4-methyl-1,4-diazepan-1-yl)quinoline-6-carboxamide |
| 167 | 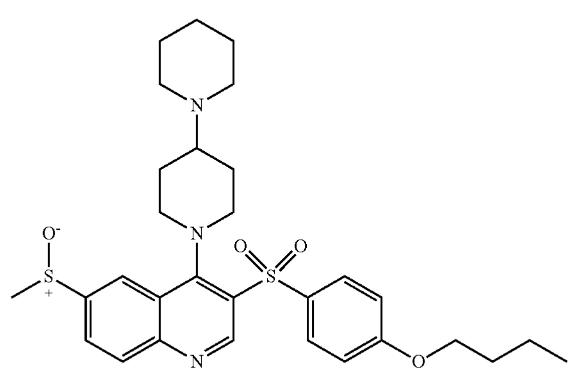 | 4-([1,4'-bipiperidin]-1'-yl)-3-((4-butoxyphenyl)sulfonyl)-6-(methylsulfinyl)quinoline |

TABLE 1-continued

| Ex. | Structure | Name |
|---|---|---|
| 168 | 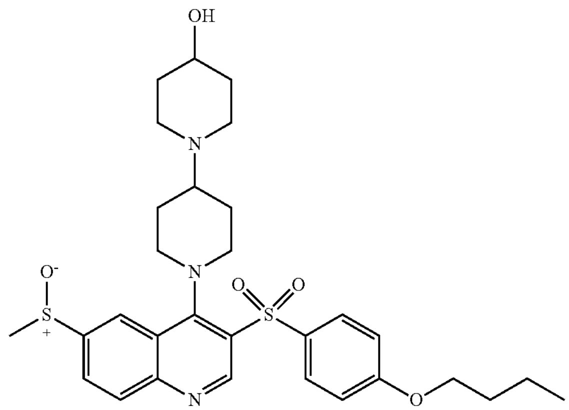 | 1'-(3-((4-butoxyphenyl)sulfonyl)-6-(methylsulfinyl)quinolin-4-yl)-[1,4'-bipiperidin]-4-ol |
| 169 | 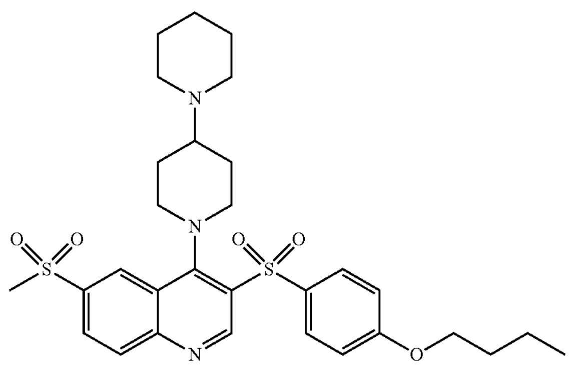 [SMILES: CCCCOc1ccc(S(=O)(=O)c2cnc3ccc(S(C)(=O)=O)cc3c2N2CCC(N3CCCCC3)CC2)cc1] | 4-([1,4'-bipiperidin]-1'-yl)-3-((4-butoxyphenyl)sulfonyl)-6-(methylsulfonyl)quinoline |
| 170 | 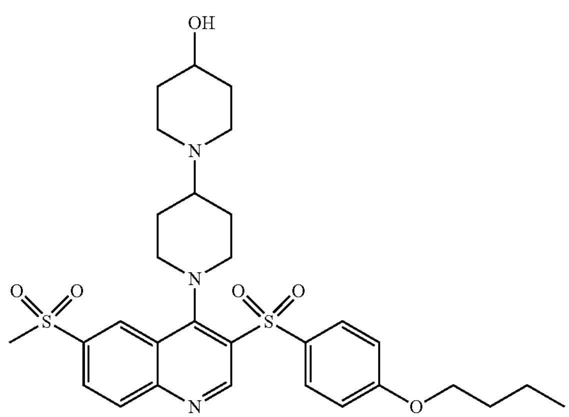 [SMILES: CCCCOc1ccc(S(=O)(=O)c2cnc3ccc(S(C)(=O)=O)cc3c2N2CCC(N3CCC(O)CC3)CC2)cc1] | 1'-(3-((4-butoxyphenyl)sulfonyl)-6-(methylsulfonyl)quinolin-4-yl)-[1,4'-bipiperidin]-4-ol |
| 171 | 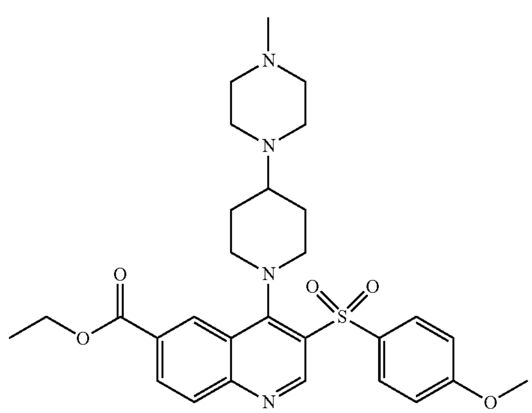 [SMILES: CCOC(=O)c1ccc2ncc(S(=O)(=O)c3ccc(OC)cc3)c(N3CCC(N4CCN(C)CC4)CC3)c2c1] | ethyl 3-((4-methoxyphenyl)sulfonyl)-4-(4-(4-methylpiperazin-1-yl)piperidin-1-yl)quinoline-6-carboxylate |

TABLE 1-continued

| Ex. | Structure | Name |
| --- | --- | --- |
| 172 | 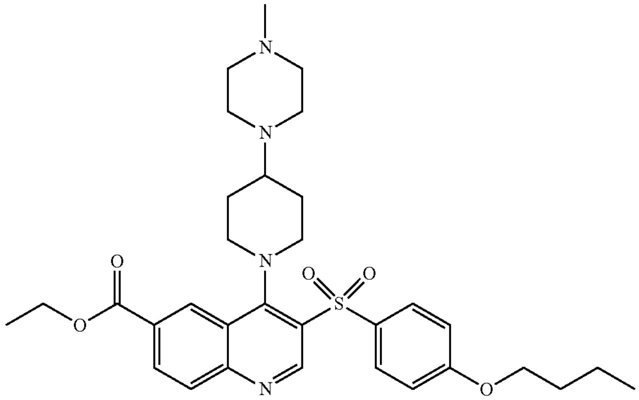 [SMILES: CCCCOc1ccc(S(=O)(=O)c2cnc3ccc(C(=O)OCC)cc3c2N2CCC(N3CCN(C)CC3)CC2)cc1] | ethyl 3-((4-butoxyphenyl)sulfonyl)-4-(4-(4-methylpiperazin-1-yl)piperidin-1-yl)quinoline-6-carboxylate |
| 173 | 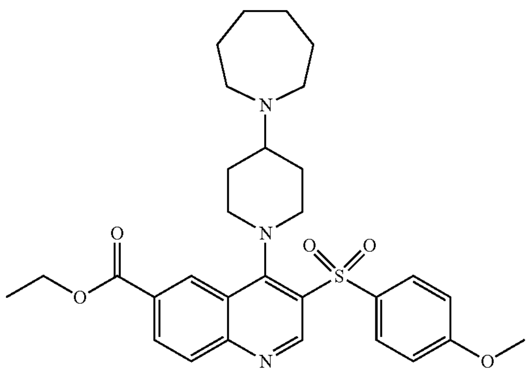 [SMILES: CCOC(=O)c1ccc2ncc(S(=O)(=O)c3ccc(OC)cc3)c(N3CCC(N4CCCCCC4)CC3)c2c1] | ethyl 4-(4-(azepan-1-yl)piperidin-1-yl)-3-((4-methoxyphenyl)sulfonyl)quinoline-6-carboxylate |
| 174 | 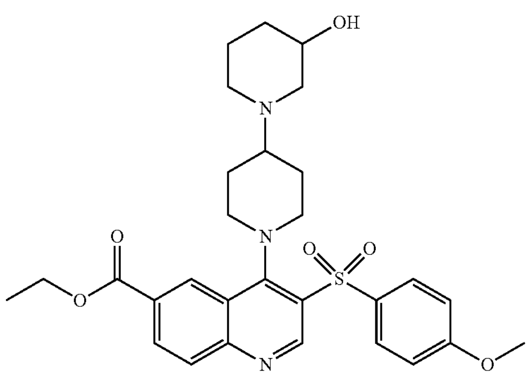 [SMILES: CCOC(=O)c1ccc2ncc(S(=O)(=O)c3ccc(OC)cc3)c(N3CCC(N4CCCC(O)C4)CC3)c2c1] | ethyl 4-(3-hydroxy-[1,4'-bipiperidin]-1'-yl)-3-((4-methoxyphenyl)sulfonyl)quinoline-6-carboxylate |
| 175 | 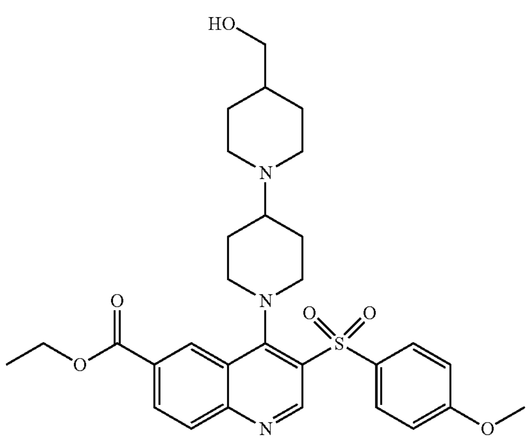 [SMILES: CCOC(=O)c1ccc2ncc(S(=O)(=O)c3ccc(OC)cc3)c(N3CCC(N4CCC(CO)CC4)CC3)c2c1] | ethyl 4-(4-(hydroxymethyl)-[1,4'-bipiperidin]-1'-yl)-3-((4-methoxyphenyl)sulfonyl)quinoline-6-carboxylate |

TABLE 1-continued

| Ex. | Structure | Name |
|---|---|---|
| 176 | 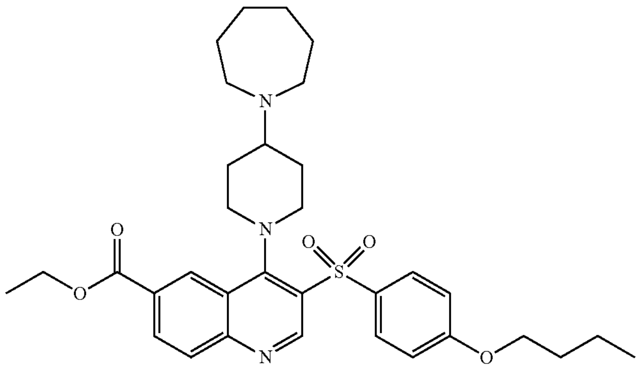 [SMILES: CCCCOc1ccc(S(=O)(=O)c2cnc3ccc(C(=O)OCC)cc3c2N2CCC(N3CCCCCC3)CC2)cc1] | ethyl 4-(4-(azepan-1-yl)piperidin-1-yl)-3-((4-butoxyphenyl)sulfonyl)quinoline-6-carboxylate |
| 177 | 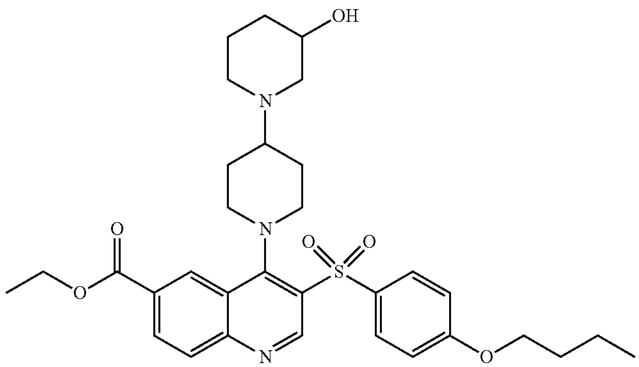 [SMILES: CCCCOc1ccc(S(=O)(=O)c2cnc3ccc(C(=O)OCC)cc3c2N2CCC(N3CCCC(O)C3)CC2)cc1] | ethyl 3-((4-butoxyphenyl)sulfonyl)-4-(3-hydroxy-[1,4'-bipiperidin]-1'-yl)quinoline-6-carboxylate |
| 178 | 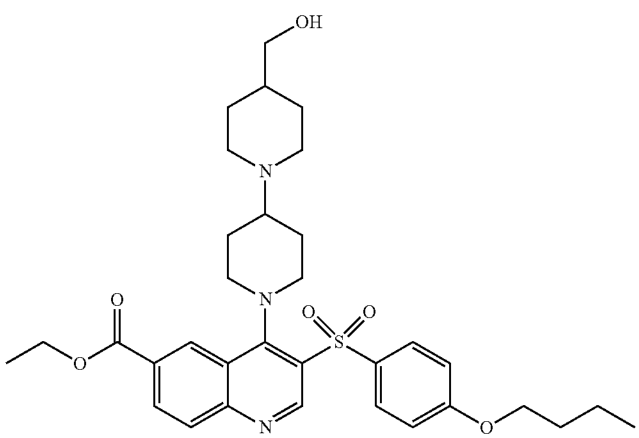 [SMILES: CCCCOc1ccc(S(=O)(=O)c2cnc3ccc(C(=O)OCC)cc3c2N2CCC(N3CCC(CO)CC3)CC2)cc1] | ethyl 3-((4-butoxyphenyl)sulfonyl)-4-(4-(hydroxymethyl)-[1,4'-bipiperidin]-1'-yl)quinoline-6-carboxylate |
| 179 | 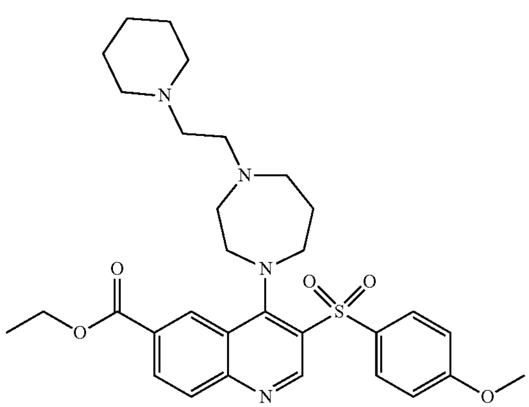 [SMILES: CCOC(=O)c1ccc2ncc(S(=O)(=O)c3ccc(OC)cc3)c(N3CCCN(CCN4CCCCC4)CC3)c2c1] | ethyl 3-((4-methoxyphenyl)sulfonyl)-4-(4-(2-(piperidin-1-yl)ethyl)-1,4-diazepan-1-yl)quinoline-6-carboxylate |

TABLE 1-continued

| Ex. | Structure | Name |
|---|---|---|
| 180 | 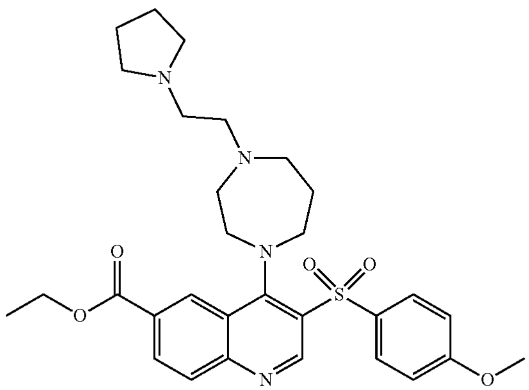 [SMILES: CCOC(=O)c1ccc2ncc(S(=O)(=O)c3ccc(OC)cc3)c(N3CCCN(CCN4CCCC4)CC3)c2c1] | ethyl 3-((4-methoxyphenyl)sulfonyl)-4-(4-(2-(pyrrolidin-1-yl)ethyl)-1,4-diazepan-1-yl)quinoline-6-carboxylate |
| 181 | 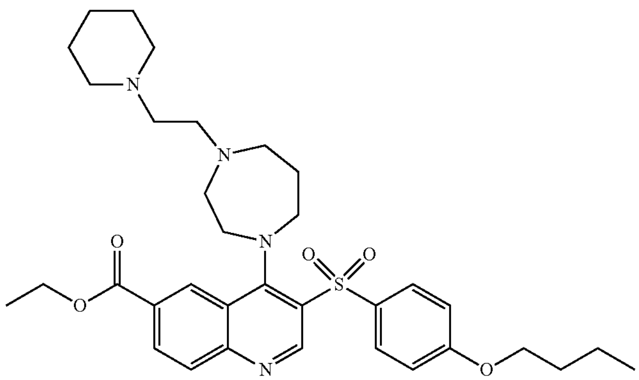 [SMILES: CCCCOc1ccc(S(=O)(=O)c2cnc3ccc(C(=O)OCC)cc3c2N2CCCN(CCN3CCCCC3)CC2)cc1] | ethyl 3-((4-butoxyphenyl)sulfonyl)-4-(4-(2-(piperidin-1-yl)ethyl)-1,4-diazepan-1-yl)quinoline-6-carboxylate |
| 182 | 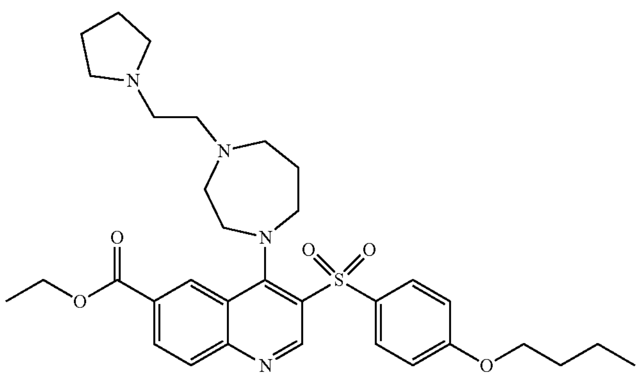 [SMILES: CCCCOc1ccc(S(=O)(=O)c2cnc3ccc(C(=O)OCC)cc3c2N2CCCN(CCN3CCCC3)CC2)cc1] | ethyl 3-((4-butoxyphenyl)sulfonyl)-4-(4-(2-(pyrrolidin-1-yl)ethyl)-1,4-diazepan-1-yl)quinoline-6-carboxylate |
| 183 | 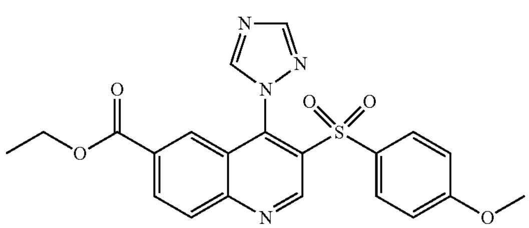 | ethyl 3-((4-methoxyphenyl)sulfonyl)-4-(1H-1,2,4-triazol-1-yl)quinoline-6-carboxylate |
| 184 | 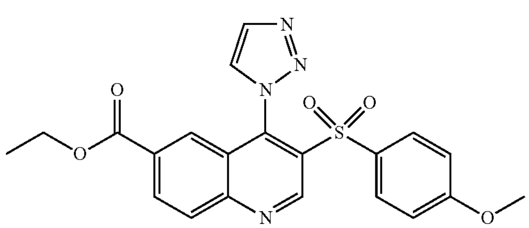 [SMILES: CCOC(=O)c1ccc2ncc(S(=O)(=O)c3ccc(OC)cc3)c(-n3ccnn3)c2c1] | ethyl 3-((4-methoxyphenyl)sulfonyl)-4-(1H-1,2,3-triazol-1-yl)quinoline-6-carboxylate |

TABLE 1-continued

| Ex. | Structure | Name |
|---|---|---|
| 185 | 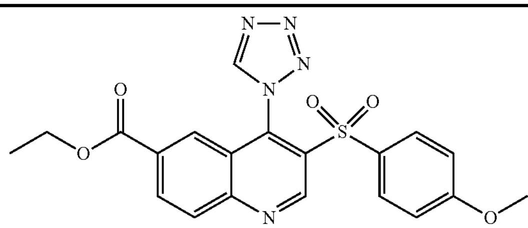 | ethyl 3-((4-methoxyphenyl)sulfonyl)-4-(1H-tetrazol-1-yl)quinoline-6-carboxylate |
| 186 | 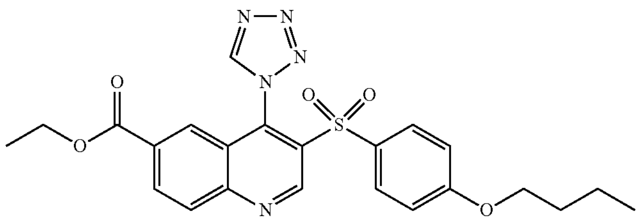 [SMILES: CCCCOc1ccc(S(=O)(=O)c2cnc3ccc(C(=O)OCC)cc3c2-n2cnnn2)cc1] | ethyl 3-((4-butoxyphenyl)sulfonyl)-4-(1H-tetrazol-1-yl)quinoline-6-carboxylate |
| 187 | 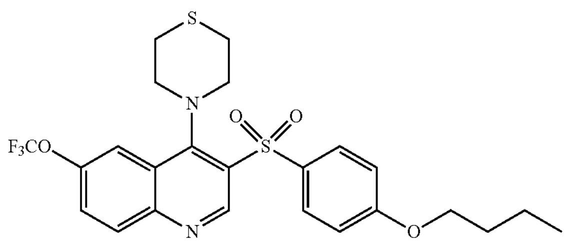 [SMILES: CCCCOc1ccc(S(=O)(=O)c2cnc3ccc(OC(F)(F)F)cc3c2N2CCSCC2)cc1] | 4-(3-((4-butoxyphenyl)sulfonyl)-6-(trifluoromethoxy)quinolin-4-yl)thiomorpholine |
| 188 | 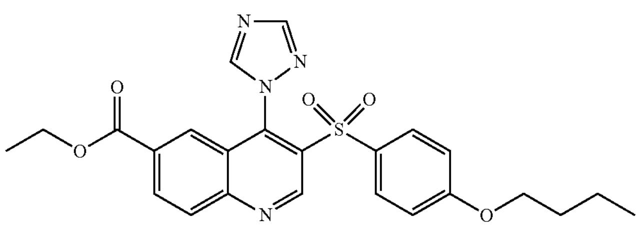 | ethyl 3-((4-butoxyphenyl)sulfonyl)-4-(1H-1,2,4-triazol-1-yl)quinoline-6-carboxylate |
| 189 | 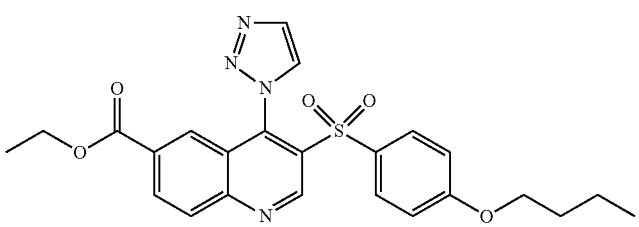 [SMILES: CCCCOc1ccc(S(=O)(=O)c2cnc3ccc(C(=O)OCC)cc3c2-n2ccnn2)cc1] | ethyl 3-((4-butoxyphenyl)sulfonyl)-4-(1H-1,2,3-triazol-1-yl)quinoline-6-carboxylate |
| 190 | 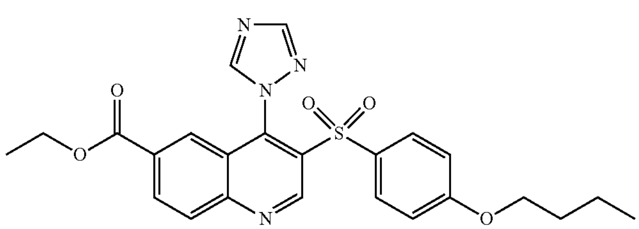 [SMILES: CCCCOc1ccc(S(=O)(=O)c2cnc3ccc(C(=O)OCC)cc3c2-n2cncn2)cc1] | ethyl 3-((4-butoxyphenyl)sulfonyl)-4-(1H-1,2,4-triazol-1-yl)quinoline-6-carboxylate |
| 191 | 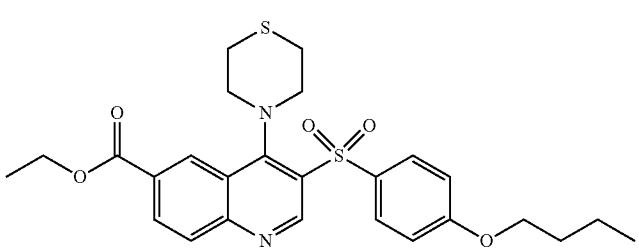 [SMILES: CCCCOc1ccc(S(=O)(=O)c2cnc3ccc(C(=O)OCC)cc3c2N2CCSCC2)cc1] | ethyl 3-((4-butoxyphenyl)sulfonyl)-4-thiomorpholinoquinoline-6-carboxylate |

TABLE 1-continued

| Ex. | Structure | Name |
|---|---|---|
| 192 | 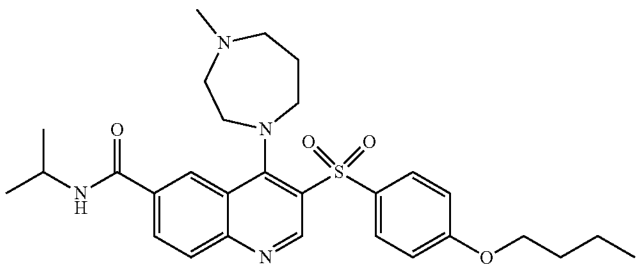 [SMILES: CCCCOc1ccc(S(=O)(=O)c2cnc3ccc(C(=O)NC(C)C)cc3c2N2CCCN(C)CC2)cc1] | 3-((4-butoxyphenyl)sulfonyl)-N-isopropyl-4-(4-methyl-1,4-diazepan-1-yl)quinoline-6-carboxamide |
| 193 | 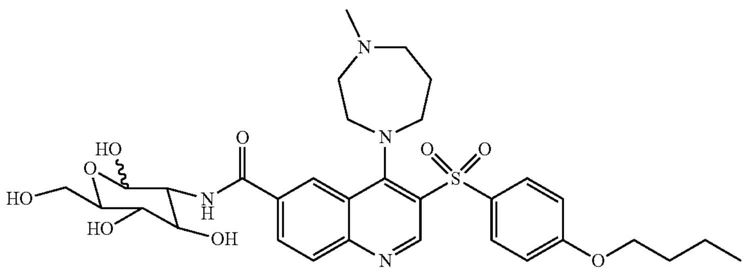 [SMILES: CCCCOc1ccc(S(=O)(=O)c2cnc3ccc(C(=O)NC4C(O)OC(CO)C(O)C4O)cc3c2N2CCCN(C)CC2)cc1] | 3-((4-butoxyphenyl)sulfonyl)-4-(4-methyl-1,4-diazepan-1-yl)-N-((4R,5S,6R)-2,4,5-trihydroxy-6-(hydroxymethyl)tetrahydro-2H-pyran-3-yl)quinoline-6-carboxamide |
| 194 | 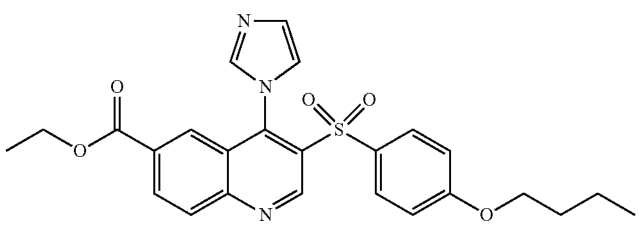 [SMILES: CCCCOc1ccc(S(=O)(=O)c2cnc3ccc(C(=O)OCC)cc3c2-n2ccnc2)cc1] | ethyl 3-((4-butoxyphenyl)sulfonyl)-4-(1H-imidazol-1-yl)quinoline-6-carboxylate |
| 195 | 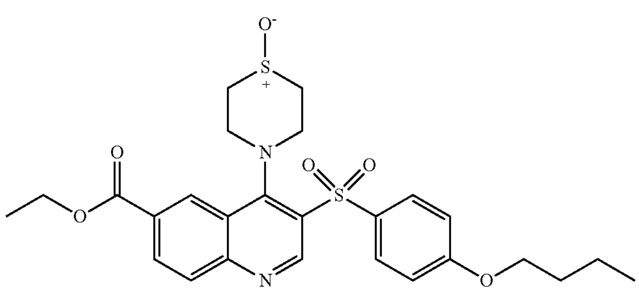 | ethyl 3-((4-butoxyphenyl)sulfonyl)-4-(1-oxidothiomorpholino)quinoline-6-carboxylate |
| 196 | 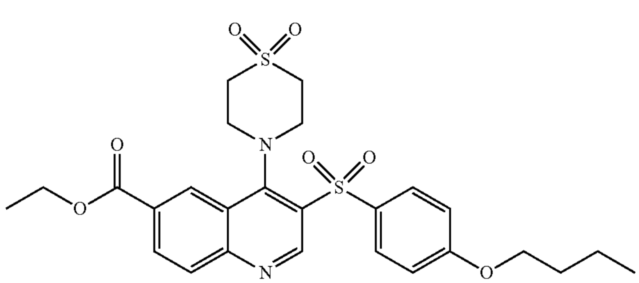 [SMILES: CCCCOc1ccc(S(=O)(=O)c2cnc3ccc(C(=O)OCC)cc3c2N2CCS(=O)(=O)CC2)cc1] | ethyl 3-((4-butoxyphenyl)sulfonyl)-4-(1,1-dioxidothiomorpholino)quinoline-6-carboxylate |

TABLE 1-continued

| Ex. | Structure | Name |
| --- | --- | --- |
| 197 | 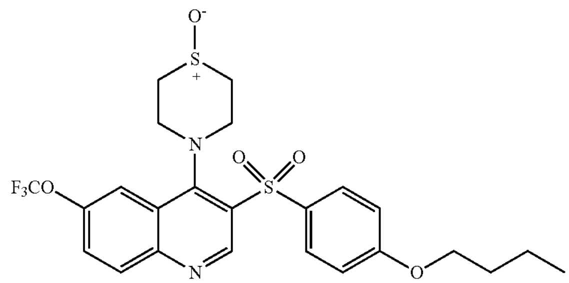 | 4-(3-((4-butoxyphenyl)sulfonyl)-6-(trifluoromethoxy)quinolin-4-yl)thiomorpholine 1-oxide |
| 198 | 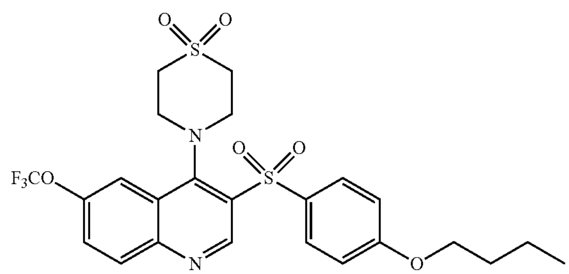 [SMILES: CCCCOc1ccc(S(=O)(=O)c2cnc3ccc(OC(F)(F)F)cc3c2N2CCS(=O)(=O)CC2)cc1] | 4-(3-((4-butoxyphenyl)sulfonyl)-6-(trifluoromethoxy)quinolin-4-yl)thiomorpholine 1,1-dioxide |
| 199 | 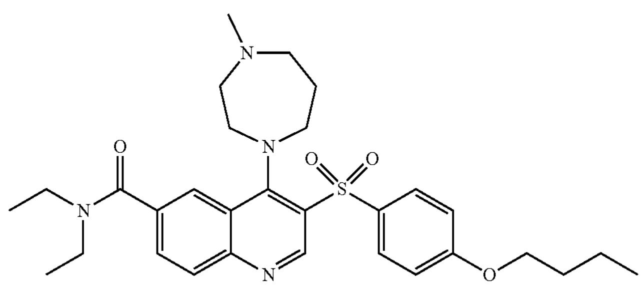 [SMILES: CCCCOc1ccc(S(=O)(=O)c2cnc3ccc(C(=O)N(CC)CC)cc3c2N2CCCN(C)CC2)cc1] | 3-((4-butoxyphenyl)sulfonyl)-N,N-diethyl-4-(4-methyl-1,4-diazepan-1-yl)quinoline-6-carboxamide |
| 200 | 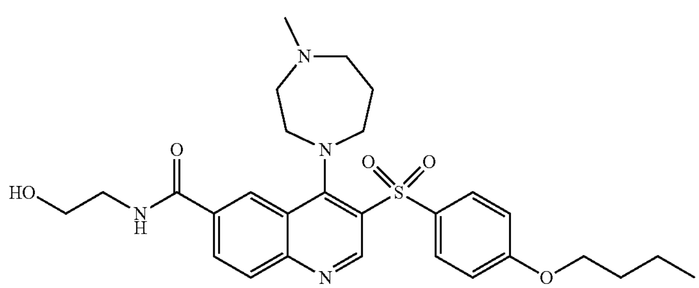 [SMILES: CCCCOc1ccc(S(=O)(=O)c2cnc3ccc(C(=O)NCCO)cc3c2N2CCCN(C)CC2)cc1] | 3-((4-butoxyphenyl)sulfonyl)-N-(2-hydroxyethyl)-4-(4-methyl-1,4-diazepan-1-yl)quinoline-6-carboxamide |
| 201 | 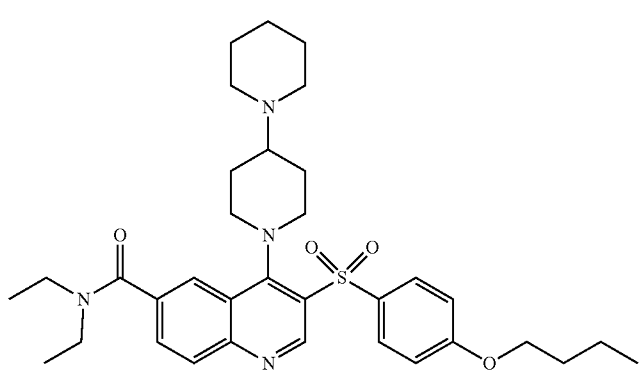 [SMILES: CCCCOc1ccc(S(=O)(=O)c2cnc3ccc(C(=O)N(CC)CC)cc3c2N2CCC(N3CCCCC3)CC2)cc1] | 4-([1,4'-bipiperidin]-1'-yl)-3-((4-butoxyphenyl)sulfonyl)-N,N-diethylquinoline-6-carboxamide |

TABLE 1-continued

| Ex. | Structure | Name |
|---|---|---|
| 202 | 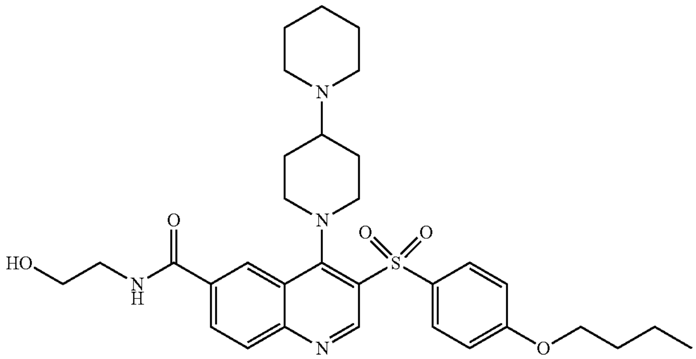 [SMILES: CCCCOc1ccc(S(=O)(=O)c2cnc3ccc(C(=O)NCCO)cc3c2N2CCC(N3CCCCC3)CC2)cc1] | 4-([1,4'-bipiperidin]-1'-yl)-3-((4-butoxyphenyl)sulfonyl)-N-(2-hydroxyethyl)quinoline-6-carboxamide |
| 203 | 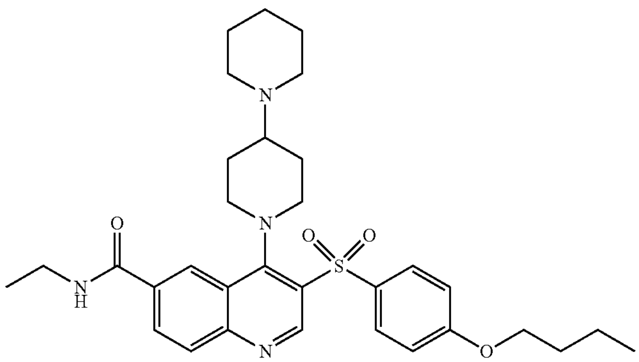 | 4-([1,4'-bipiperidin]-1'-yl)-3-((4-butoxyphenyl)sulfonyl)-N-ethylquinoline-6-carboxamide |
| 204 | 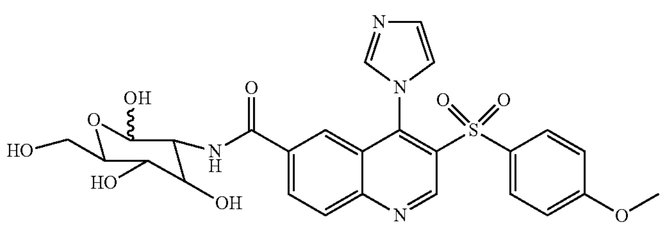 [SMILES: COc1ccc(S(=O)(=O)c2cnc3ccc(C(=O)NC4C(O)OC(CO)C(O)C4O)cc3c2-n2ccnc2)cc1] | 4-(1H-imidazol-1-yl)-3-((4-methoxyphenyl)sulfonyl)-N-((4R,5S,6R)-2,4,5-trihydroxy-6-(hydroxymethyl)tetrahydro-2H-pyran-3-yl)quinoline-6-carboxamide |
| 205 | 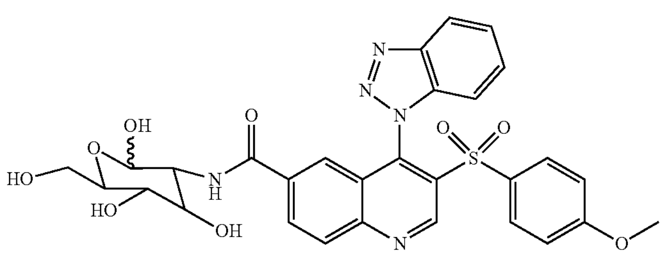 [SMILES: COc1ccc(S(=O)(=O)c2cnc3ccc(C(=O)NC4C(O)OC(CO)C(O)C4O)cc3c2-n2nnc3ccccc32)cc1] | 4-(1H-benzo[d][1,2,3]triazol-1-yl)-3-((4-methoxyphenyl)sulfonyl)-N-((4R,5S,6R)-2,4,5-trihydroxy-6-(hydroxymethyl)tetrahydro-2H-pyran-3-yl)quinoline-6-carboxamide |
| 206 | 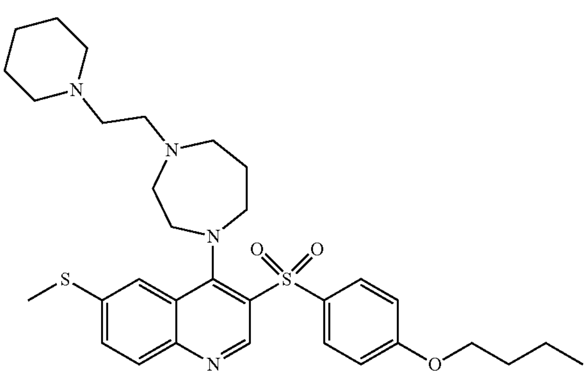 [SMILES: CCCCOc1ccc(S(=O)(=O)c2cnc3ccc(SC)cc3c2N2CCCN(CCN3CCCCC3)CC2)cc1] | 3-((4-butoxyphenyl)sulfonyl)-6-(methylthio)-4-(4-(2-(piperidin-1-yl)ethyl)-1,4-diazepan-1-yl)quinoline |

TABLE 1-continued

| Ex. | Structure | Name |
|---|---|---|
| 207 | 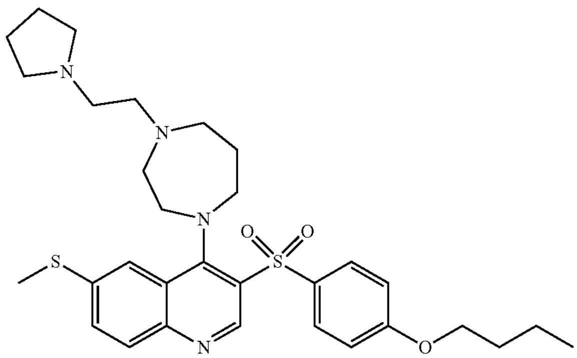 [SMILES: CCCCOc1ccc(S(=O)(=O)c2cnc3ccc(SC)cc3c2N2CCCN(CCN3CCCC3)CC2)cc1] | 3-((4-butoxyphenyl)sulfonyl)-6-(methylthio)-4-(4-(2-(pyrrolidin-1-yl)ethyl)-1,4-diazepan-1-yl)quinoline |
| 208 | 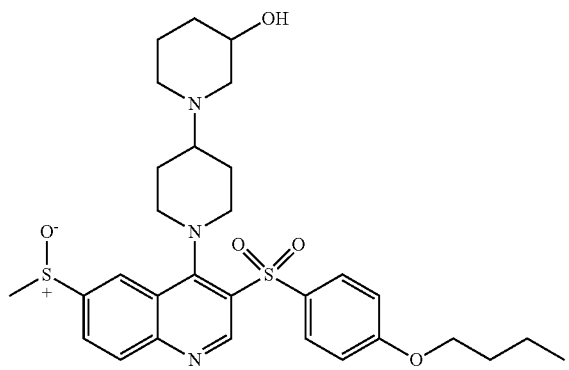 | 1'-(3-((4-butoxyphenyl)sulfonyl)-6-(methylsulfinyl)quinolin-4-yl)-[1,4'-bipiperidin]-3-ol |
| 209 | 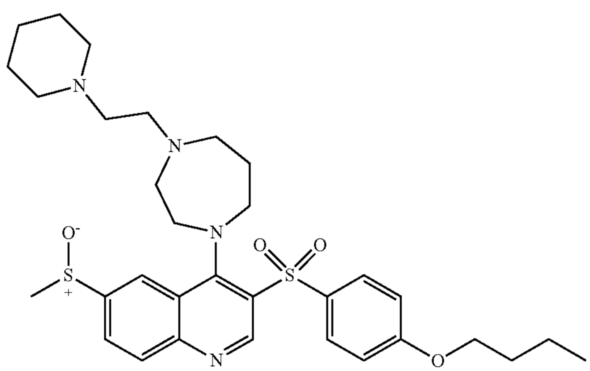 | 3-((4-butoxyphenyl)sulfonyl)-6-(methylsulfinyl)-4-(4-(2-(piperidin-1-yl)ethyl)-1,4-diazepan-1-yl)quinoline |
| 210 | 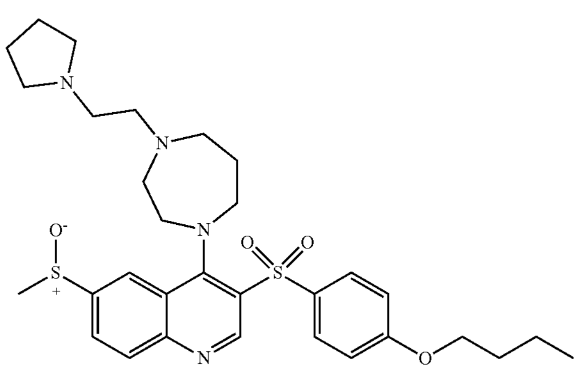 | 3-((4-butoxyphenyl)sulfonyl)-6-(methylsulfinyl)-4-(4-(2-(pyrrolidin-1-yl)ethyl)-1,4-diazepan-1-yl)quinoline |

TABLE 1-continued

| Ex. | Structure | Name |
|---|---|---|
| 211 | 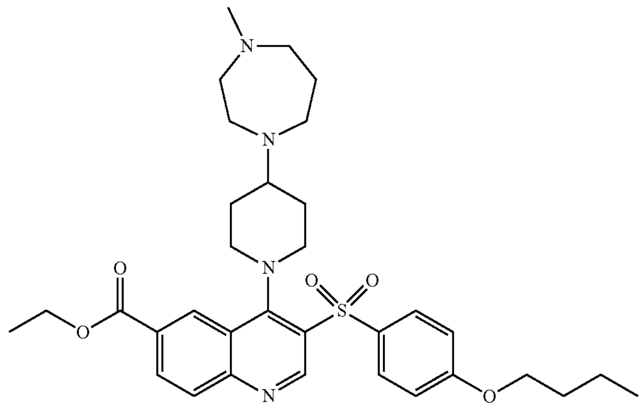 [SMILES: CCCCOc1ccc(S(=O)(=O)c2cnc3ccc(C(=O)OCC)cc3c2N2CCC(N3CCCN(C)CC3)CC2)cc1] | ethyl 3-((4-butoxyphenyl)sulfonyl)-4-(4-(4-methyl-1,4-diazepan-1-yl)piperidin-1-yl)quinoline-6-carboxylate |
| 212 | 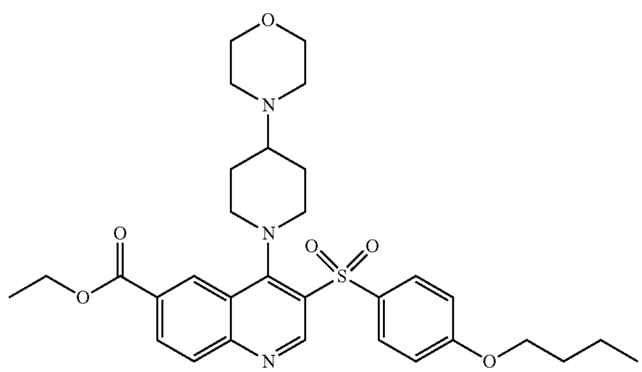 [SMILES: CCCCOc1ccc(S(=O)(=O)c2cnc3ccc(C(=O)OCC)cc3c2N2CCC(N3CCOCC3)CC2)cc1] | ethyl 3-((4-butoxyphenyl)sulfonyl)-4-(4-morpholinopiperidin-1-yl)quinoline-6-carboxylate |
| 213 | 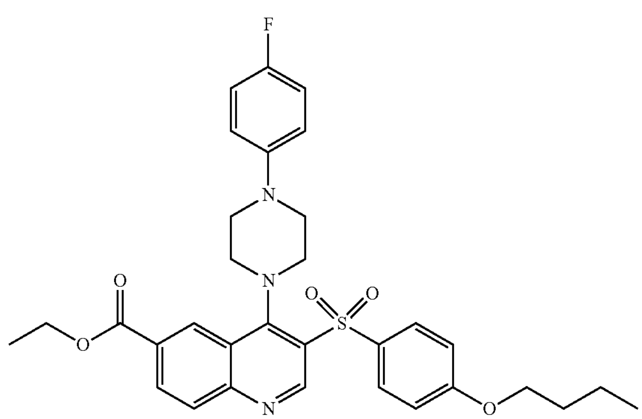 [SMILES: CCCCOc1ccc(S(=O)(=O)c2cnc3ccc(C(=O)OCC)cc3c2N2CCN(c3ccc(F)cc3)CC2)cc1] | ethyl 3-((4-butoxyphenyl)sulfonyl)-4-(4-(4-fluorophenyl)piperazin-1-yl)quinoline-6-carboxylate |
| 214 | 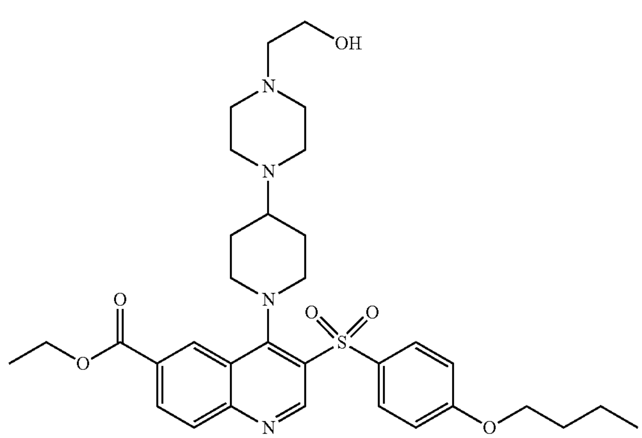 [SMILES: CCCCOc1ccc(S(=O)(=O)c2cnc3ccc(C(=O)OCC)cc3c2N2CCC(N3CCN(CCO)CC3)CC2)cc1] | ethyl 3-((4-butoxyphenyl)sulfonyl)-4-(4-(4-(2-hydroxyethyl)piperazin-1-yl)piperidin-1-yl)quinoline-6-carboxylate |

TABLE 1-continued

| Ex. | Structure | Name |
|---|---|---|
| 215 | 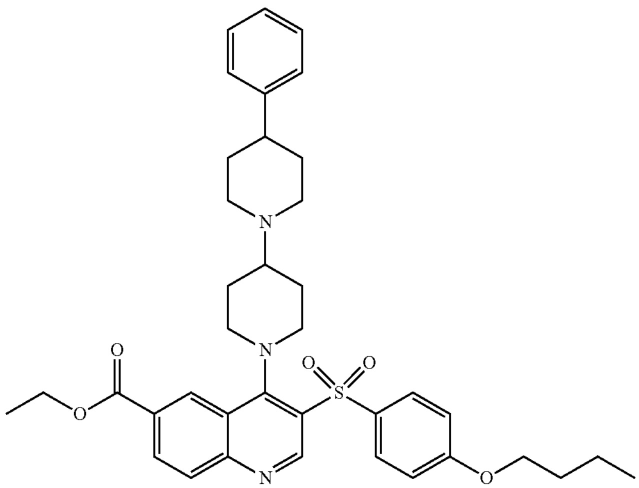 [SMILES: CCCCOc1ccc(S(=O)(=O)c2cnc3ccc(C(=O)OCC)cc3c2N2CCC(N3CCC(c4ccccc4)CC3)CC2)cc1] | ethyl 3-((4-butoxyphenyl)sulfonyl)-4-(4-phenyl-[1,4'-bipiperidin]-1'-yl)quinoline-6-carboxylate |
| 216 | 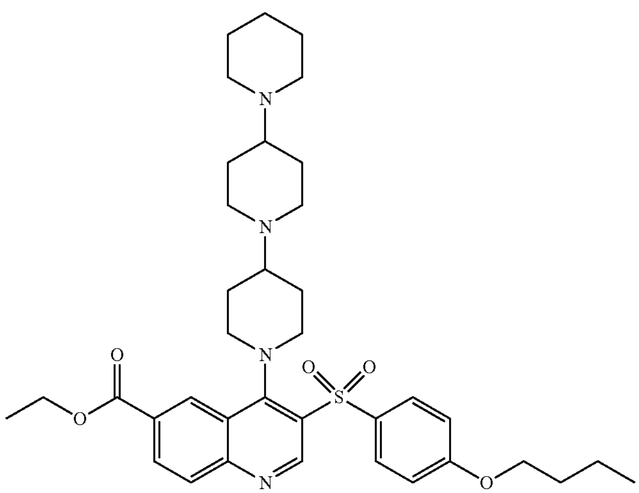 [SMILES: CCCCOc1ccc(S(=O)(=O)c2cnc3ccc(C(=O)OCC)cc3c2N2CCC(N3CCC(N4CCCCC4)CC3)CC2)cc1] | 4-([1,4':1',4''-terpiperidin]-1''-yl)-3-((4-butoxyphenyl)sulfonyl)quinoline-6-carboxylate |
| 217 | 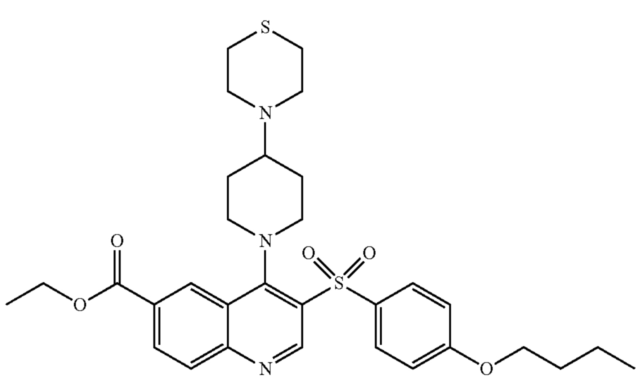 | ethyl 3-((4-butoxyphenyl)sulfonyl)-4-(4-thiomorpholinopiperidin-1-yl)quinoline-6-carboxylate |

TABLE 1-continued

| Ex. | Structure | Name |
|---|---|---|
| 218 | 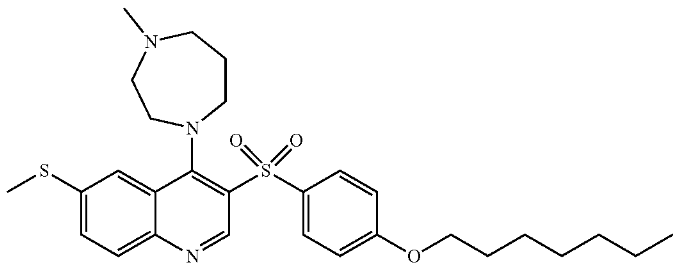 [SMILES: CCCCCCCOc1ccc(S(=O)(=O)c2cnc3ccc(SC)cc3c2N2CCCN(C)CC2)cc1] | 3-((4-(heptyloxy)phenyl)sulfonyl)-4-(4-methyl-1,4-diazepan-1-yl)-6-(methylthio)quinoline |
| 219 | 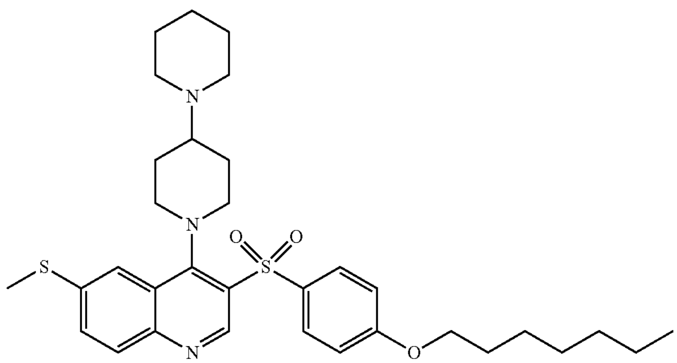 [SMILES: CCCCCCCOc1ccc(S(=O)(=O)c2cnc3ccc(SC)cc3c2N2CCC(N3CCCCC3)CC2)cc1] | 4-([1,4'-bipiperidin]-1'-yl)-3-((4-(heptyloxy)phenyl)sulfonyl)-6-(methylthio)quinoline |
| 220 | 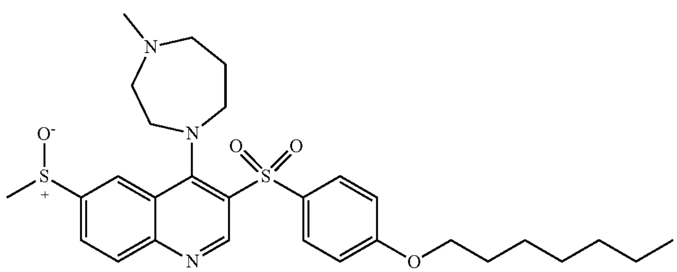 | 3-((4-(heptyloxy)phenyl)sulfonyl)-4-(4-methyl-1,4-diazepan-1-yl)-6-(methylsulfinyl)quinoline |
| 221 | 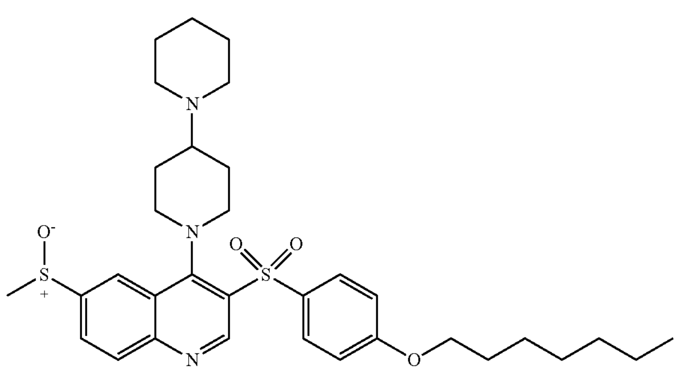 | 4-([1,4'-bipiperidin]-1'-yl)-3-((4-(heptyloxy)phenyl)sulfonyl)-6-(methylsulfinyl)quinoline |

TABLE 1-continued

| Ex. | Structure | Name |
|---|---|---|
| 222 | 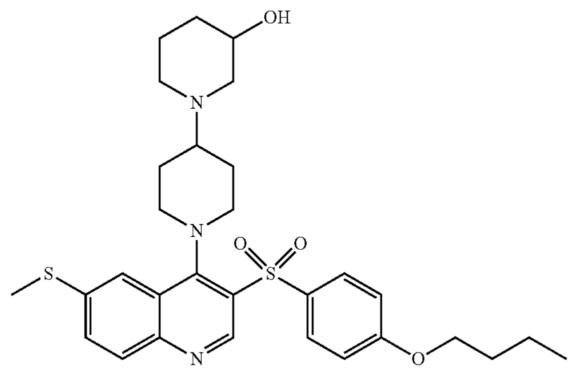 [SMILES: CCCCOc1ccc(S(=O)(=O)c2cnc3ccc(SC)cc3c2N2CCC(N3CCCC(O)C3)CC2)cc1] | 1'-(3-((4-butoxyphenyl)sulfonyl)-6-(methylthio)quinolin-4-yl)-[1,4'-bipiperidin]-3-ol |
| 223 | 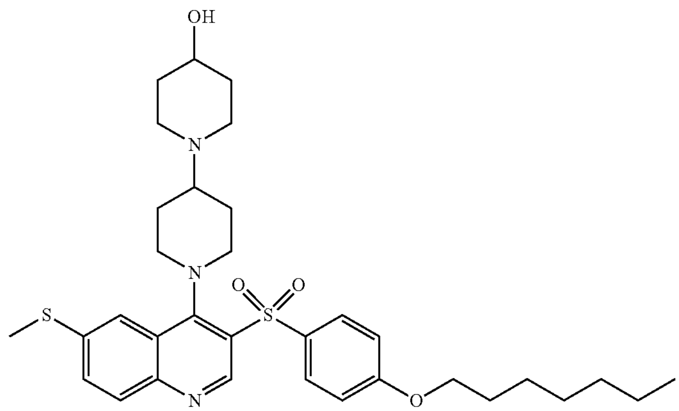 | 1'-(3-((4-(heptyloxy)phenyl)sulfonyl)-6-(methylthio)quinolin-4-yl)-[1,4'-bipiperidin]-4-ol |
| 224 | 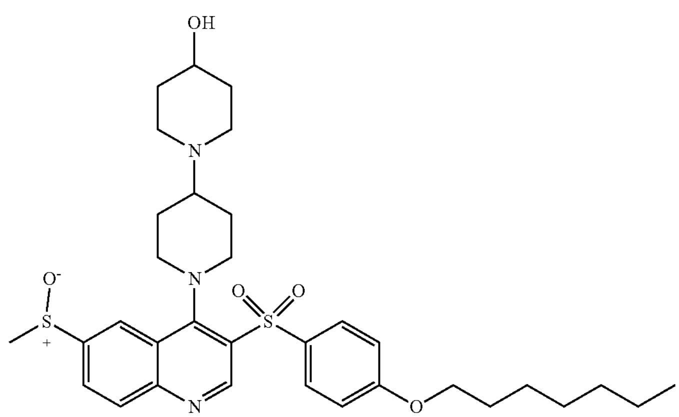 | 1'-(3-((4-(heptyloxy)phenyl)sulfonyl)-6-(methylsulfinyl)quinolin-4-yl)-[1,4'-bipiperidin]-4-ol |
| 225 | 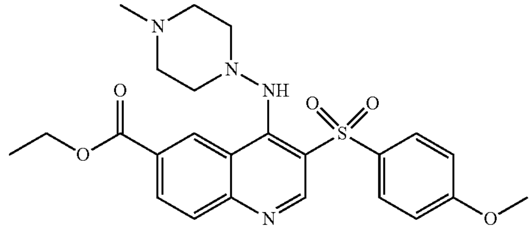 [SMILES: CCOC(=O)c1ccc2ncc(S(=O)(=O)c3ccc(OC)cc3)c(NN3CCN(C)CC3)c2c1] | ethyl 3-((4-methoxyphenyl)sulfonyl)-4-((4-methylpiperazin-1-yl)amino)quinoline-6-carboxylate |

TABLE 1-continued

| Ex. | Structure | Name |
|---|---|---|
| 226 | 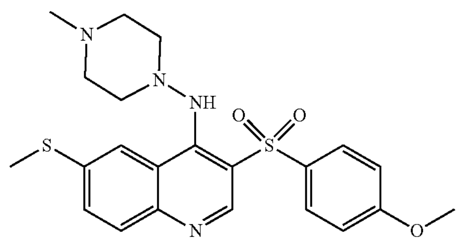 | 3-((4-methoxyphenyl)sulfonyl)-N-(4-methylpiperazin-1-yl)-6-(methylthio)quinolin-4-amine |
| 227 | 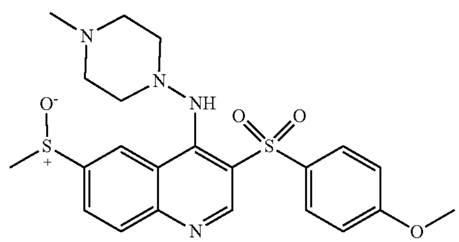 | 3-((4-methoxyphenyl)sulfonyl)-N-(4-methylpiperazin-1-yl)-6-(methylsulfinyl)quinolin-4-amine |
| 228 | 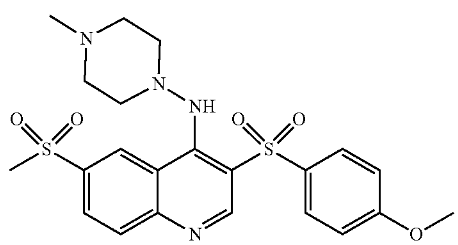 | 3-((4-methoxyphenyl)sulfonyl)-N-(4-methylpiperazin-1-yl)-6-(methylsulfonyl)quinolin-4-amine |
| 229 | 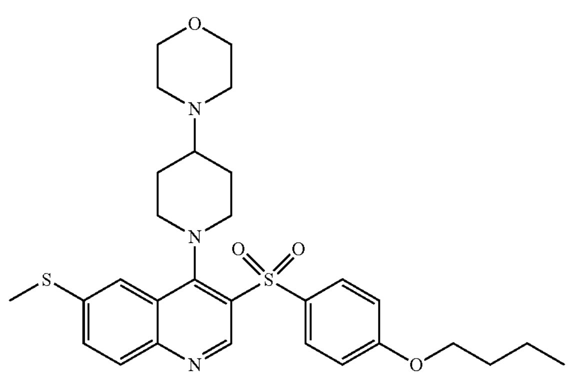 | 4-(1-(3-((4-butoxyphenyl)sulfonyl)-6-(methylthio)quinolin-4-yl)piperidin-4-yl)morpholine |
| 230 | 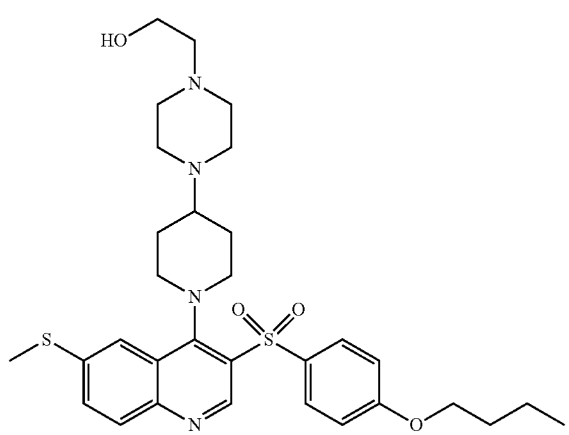 [SMILES: CCCCOc1ccc(S(=O)(=O)c2cnc3ccc(SC)cc3c2N2CCC(N3CCN(CCO)CC3)CC2)cc1] | 2-(4-(1-(3-((4-butoxyphenyl)sulfonyl)-6-(methylthio)quinolin-4-yl)piperidin-4-yl)piperazin-1-yl)ethan-1-ol |

TABLE 1-continued

| Ex. | Structure | Name |
|---|---|---|
| 231 | 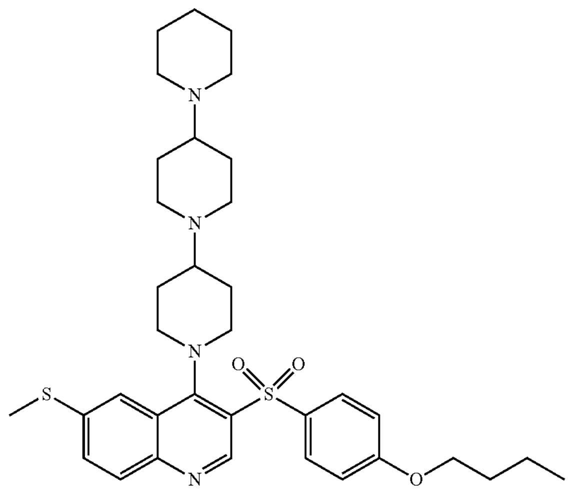 [SMILES: CCCCOc1ccc(S(=O)(=O)c2cnc3ccc(SC)cc3c2N2CCC(N3CCC(N4CCCCC4)CC3)CC2)cc1] | 4-([1,4':1',4''-terpiperidin]-1''-yl)-3-((4-butoxyphenyl)sulfonyl)-6-(methylthio)quinoline |
| 232 | 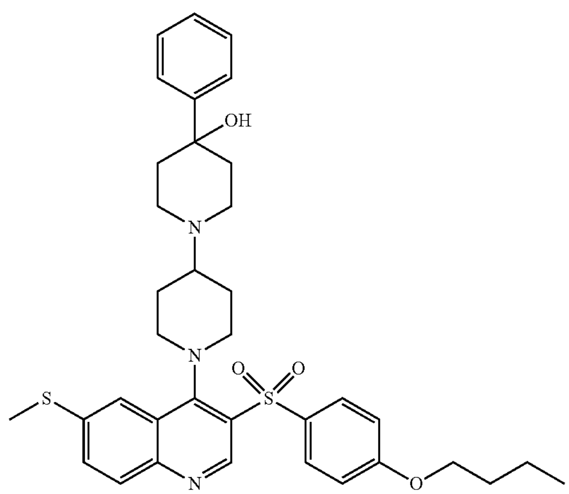 [SMILES: CCCCOc1ccc(S(=O)(=O)c2cnc3ccc(SC)cc3c2N2CCC(N3CCC(O)(c4ccccc4)CC3)CC2)cc1] | 1'-(3-((4-butoxyphenyl)sulfonyl)-6-(methylthio)quinolin-4-yl)-4-phenyl-[1,4'-bipiperidin]-4-ol |
| 233 | 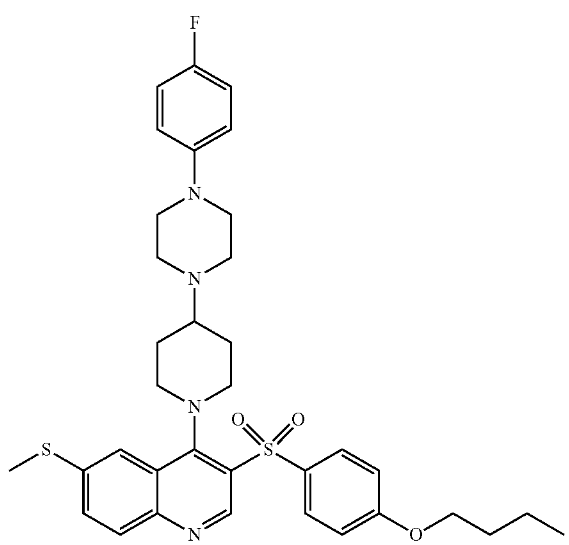 [SMILES: CCCCOc1ccc(S(=O)(=O)c2cnc3ccc(SC)cc3c2N2CCC(N3CCN(c4ccc(F)cc4)CC3)CC2)cc1] | 3-((4-butoxyphenyl)sulfonyl)-4-(4-(4-(4-fluorophenyl)piperazin-1-yl)piperidin-1-yl)-6-(methylthio)quinoline |

TABLE 1-continued

| Ex. | Structure | Name |
| --- | --- | --- |
| 234 | 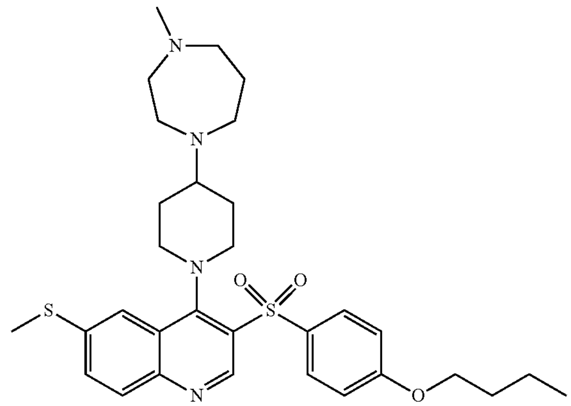 [SMILES: CCCCOc1ccc(S(=O)(=O)c2cnc3ccc(SC)cc3c2N2CCC(N3CCCN(C)CC3)CC2)cc1] | 3-((4-butoxyphenyl)sulfonyl)-4-(4-(4-methyl-1,4-diazepan-1-yl)piperidin-1-yl)-6-(methylthio)quinoline |
| 235 | 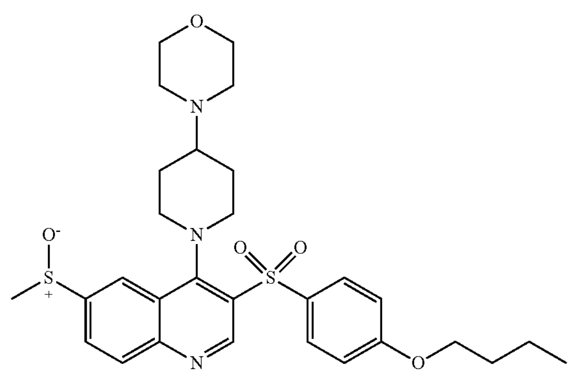 | 4-(1-(3-((4-butoxyphenyl)sulfonyl)-6-(methylsulfinyl)quinolin-4-yl)piperidin-4-yl)morpholine |
| 236 | 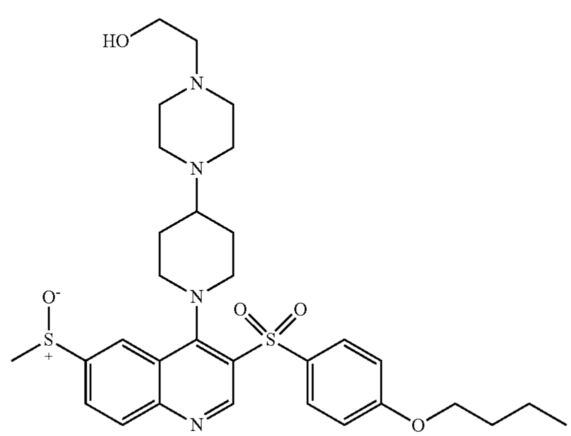 | 2-(4-(1-(3-((4-butoxyphenyl)sulfonyl)-6-(methylsulfinyl)quinolin-4-yl)piperidin-4-yl)piperazin-1-yl)ethan-1-ol |

TABLE 1-continued
| Ex. | Structure | Name |
|---|---|---|
| 237 | 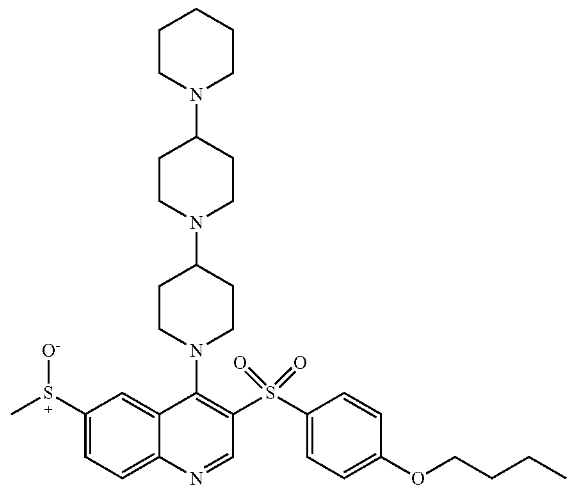 | 4-([1,4':1',4''-terpiperidin]-1''-yl)-3-((4-butoxyphenyl)sulfonyl)-6-(methylsulfinyl)quinoline |
| 238 | 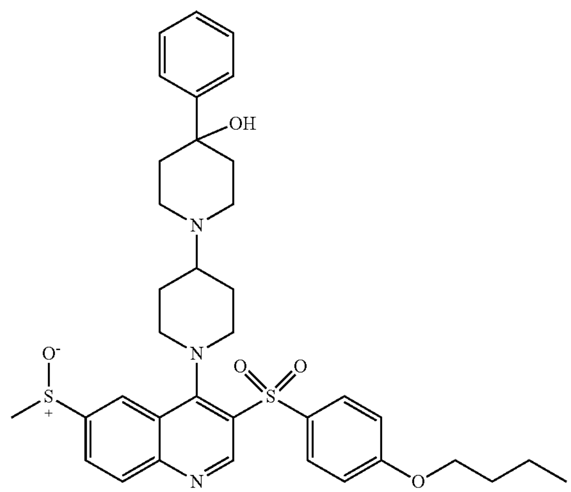 | 1'-(3-((4-butoxyphenyl)sulfonyl)-6-(methylsulfinyl)quinolin-4-yl)-4-phenyl-[1,4'-bipiperidin]-4-ol |
| 239 | 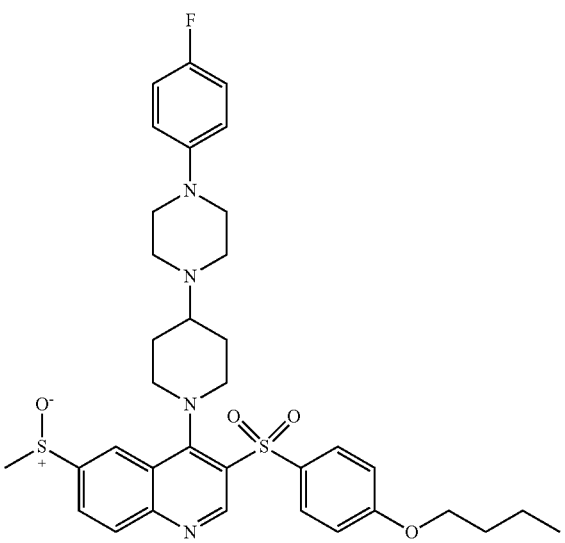 | 3-((4-butoxyphenyl)sulfonyl)-4-(4-(4-(4-fluorophenyl)piperazin-1-yl)piperidin-1-yl)-6-(methylsulfinyl)quinoline |

TABLE 1-continued

| Ex. | Structure | Name |
|---|---|---|
| 240 | 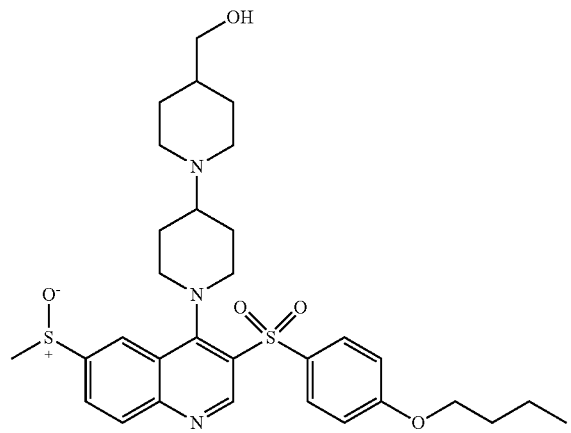 | (1'-(3-((4-butoxyphenyl)sulfonyl)-6-(methylsulfinyl)quinolin-4-yl)-[1,4'-bipiperidin]-4-yl)methanol |
| 241 | 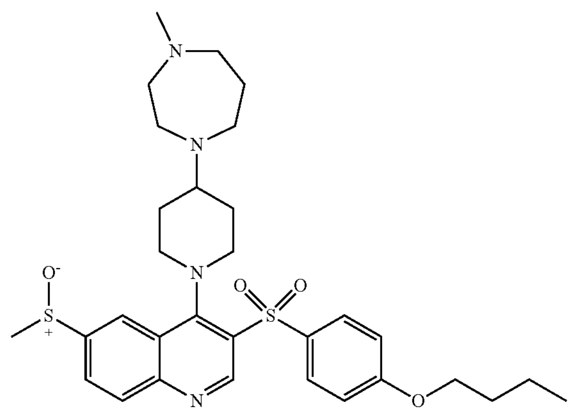 | 3-((4-butoxyphenyl)sulfonyl)-4-(4-(4-methyl-1,4-diazepan-1-yl)piperidin-1-yl)-6-(methylsulfinyl)quinoline |
| 242 | 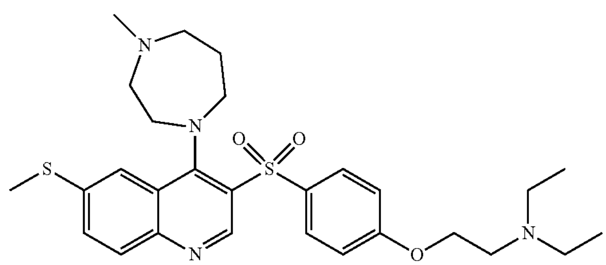 [SMILES: CCN(CC)CCOc1ccc(S(=O)(=O)c2cnc3ccc(SC)cc3c2N2CCCN(C)CC2)cc1] | N,N-diethyl-2-(4-((4-(4-methyl-1,4-diazepan-1-yl)-6-(methylthio)quinolin-3-yl)sulfonyl)phenoxy)ethan-1-amine |
| 243 | 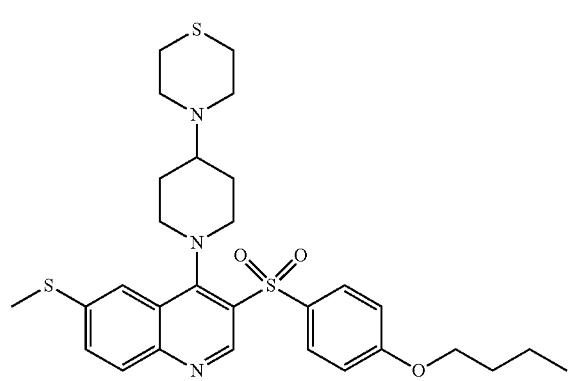 [SMILES: CCCCOc1ccc(S(=O)(=O)c2cnc3ccc(SC)cc3c2N2CCC(N3CCSCC3)CC2)cc1] | 4-(1-(3-((4-butoxyphenyl)sulfonyl)-6-(methylthio)quinolin-4-yl)piperidin-4-yl)thiomorpholine |

TABLE 1-continued

| Ex. | Structure | Name |
|---|---|---|
| 244 | 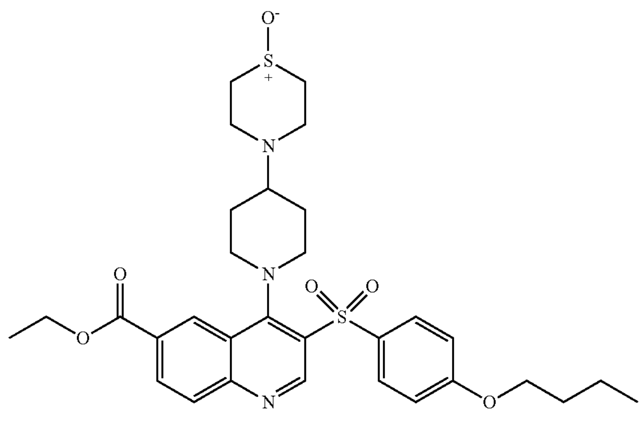 | ethyl 3-((4-butoxyphenyl)sulfonyl)-4-(4-(1-oxidothiomorpholino)piperidin-1-yl)quinoline-6-carboxylate |
| 245 | 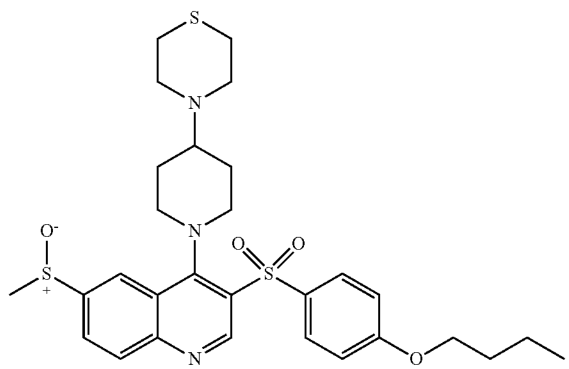 | 4-(1-(3-((4-butoxyphenyl)sulfonyl)-6-(methylsulfinyl)quinolin-4-yl)piperidin-4-yl)thiomorpholine |
| 246 | 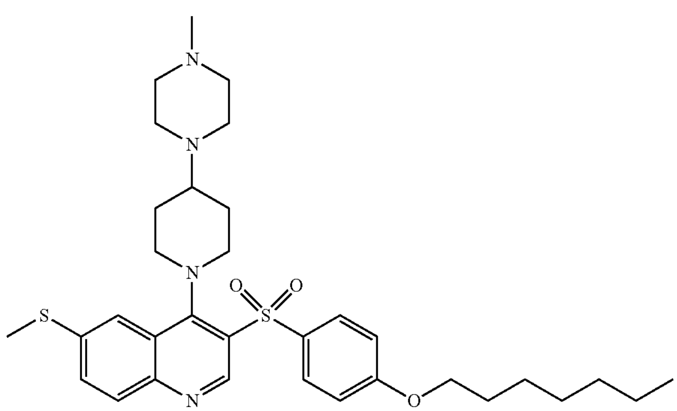 [SMILES: CCCCCCCOc1ccc(S(=O)(=O)c2cnc3ccc(SC)cc3c2N2CCC(N3CCN(C)CC3)CC2)cc1] | 3-((4-(heptyloxy)phenyl)sulfonyl)-4-(4-(4-methylpiperazin-1-yl)piperidin-1-yl)-6-(methylthio)quinoline |
| 247 | 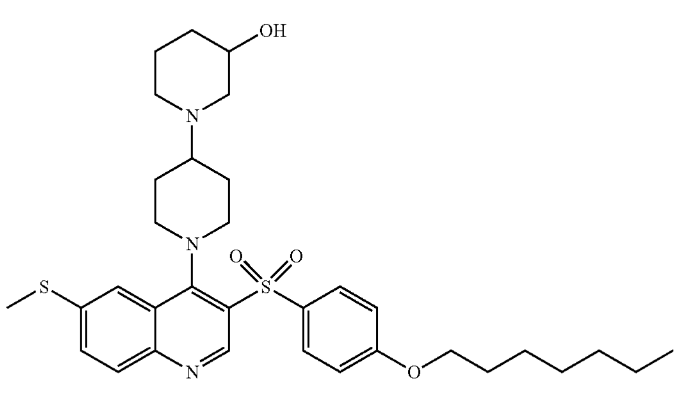 [SMILES: CCCCCCCOc1ccc(S(=O)(=O)c2cnc3ccc(SC)cc3c2N2CCC(N3CCCC(O)C3)CC2)cc1] | 1'-(3-((4-(heptyloxy)phenyl)sulfonyl)-6-(methylthio)quinolin-4-yl)-[1,4'-bipiperidin]-3-ol |

TABLE 1-continued

| Ex. | Structure | Name |
|---|---|---|
| 248 | 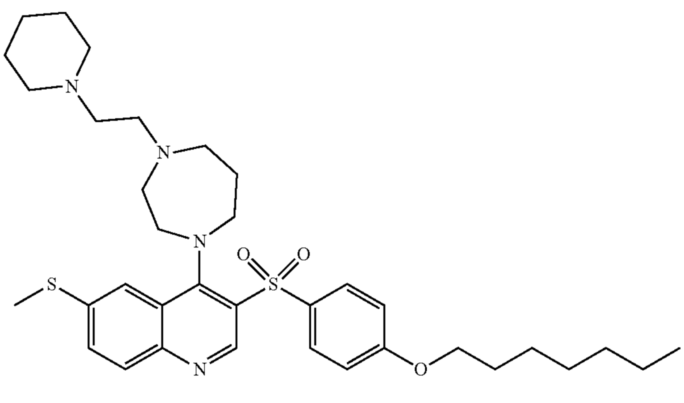 [SMILES: CCCCCCCOc1ccc(S(=O)(=O)c2cnc3ccc(SC)cc3c2N2CCCN(CCN3CCCCC3)CC2)cc1] | 3-((4-(heptyloxy)phenyl)sulfonyl)-6-(methylthio)-4-(4-(2-(piperidin-1-yl)ethyl)-1,4-diazepan-1-yl)quinoline |
| 249 | 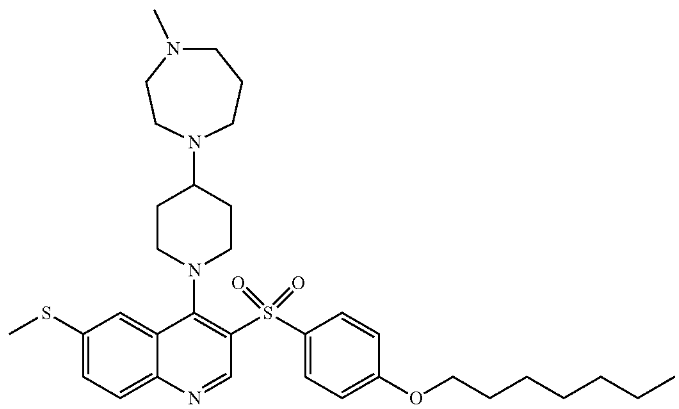 [SMILES: CCCCCCCOc1ccc(S(=O)(=O)c2cnc3ccc(SC)cc3c2N2CCC(N3CCCN(C)CC3)CC2)cc1] | 3-((4-(heptyloxy)phenyl)sulfonyl)-4-(4-(4-methyl-1,4-diazepan-1-yl)piperidin-1-yl)-6-(methylthio)quinoline |
| 250 | 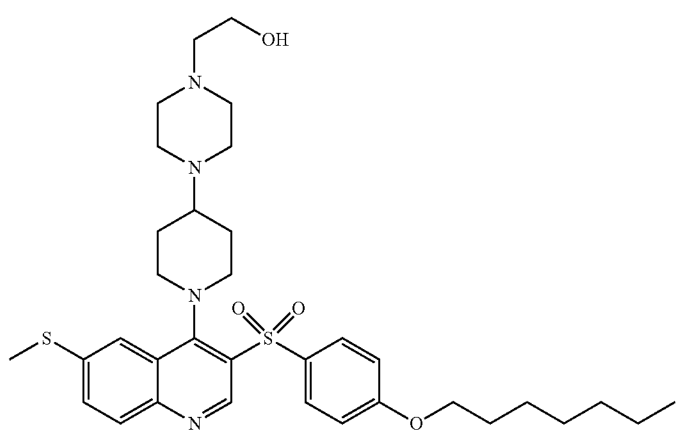 [SMILES: CCCCCCCOc1ccc(S(=O)(=O)c2cnc3ccc(SC)cc3c2N2CCC(N3CCN(CCO)CC3)CC2)cc1] | 2-(4-(1-(3-((4-(heptyloxy)phenyl)sulfonyl)-6-(methylthio)quinolin-4-yl)piperidin-4-yl)piperazin-1-yl)ethan-1-ol |

TABLE 1-continued

| Ex. | Structure | Name |
|---|---|---|
| 251 | 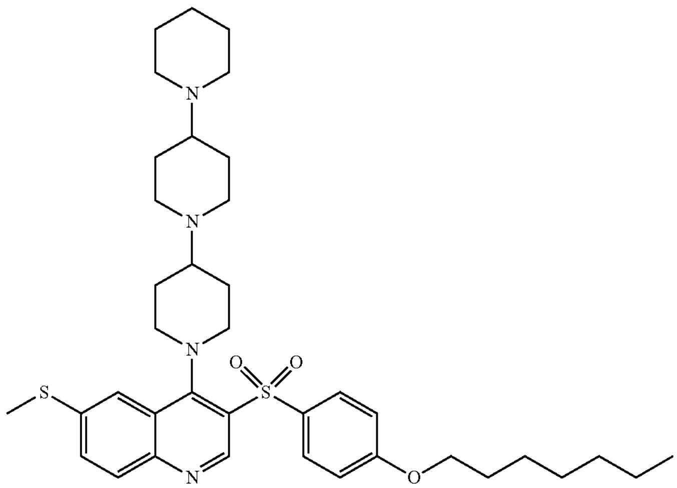 [SMILES: CCCCCCCOc1ccc(S(=O)(=O)c2cnc3ccc(SC)cc3c2N2CCC(N3CCC(N4CCCCC4)CC3)CC2)cc1] | 4-([1,4':1',4''-terpiperidin]-1''-yl)-3-((4-(heptyloxy)phenyl)sulfonyl)-6-(methylthio)quinoline |
| 252 | 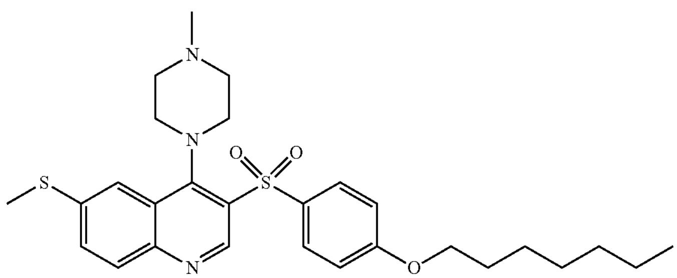 [SMILES: CCCCCCCOc1ccc(S(=O)(=O)c2cnc3ccc(SC)cc3c2N2CCN(C)CC2)cc1] | 3-((4-(heptyloxy)phenyl)sulfonyl)-4-(4-methylpiperazin-1-yl)-6-(methylthio)quinoline |
| 253 | 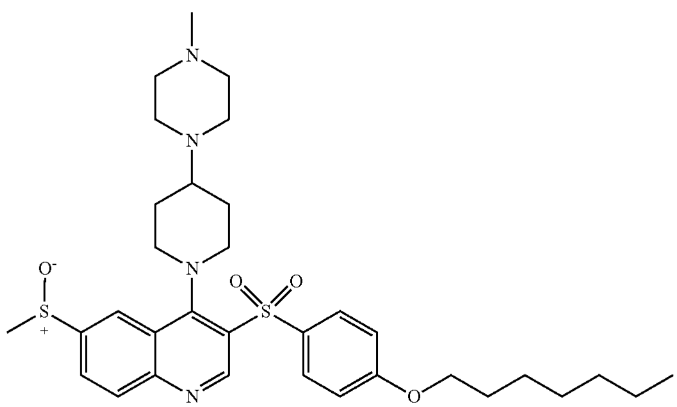 | 3-((4-(heptyloxy)phenyl)sulfonyl)-4-(4-(4-methylpiperazin-1-yl)piperidin-1-yl)-6-(methylsulfinyl)quinoline |
| 254 | 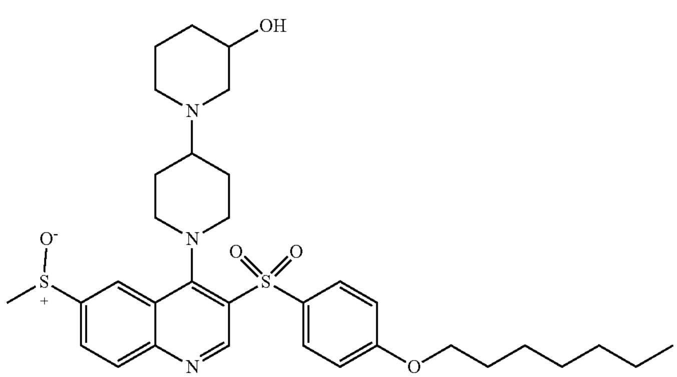 | 1'-(3-((4-(heptyloxy)phenyl)sulfonyl)-6-(methylsulfinyl)quinolin-4-yl)-[1,4'-bipiperidin]-3-ol |

TABLE 1-continued

| Ex. | Structure | Name |
|---|---|---|
| 255 | 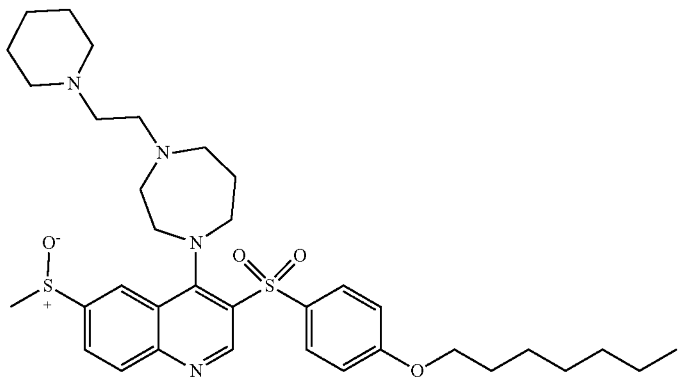 | 3-((4-(heptyloxy)phenyl)sulfonyl)-6-(methylsulfinyl)-4-(4-(2-(piperidin-1-yl)ethyl)-1,4-diazepan-1-yl)quinoline |
| 256 | 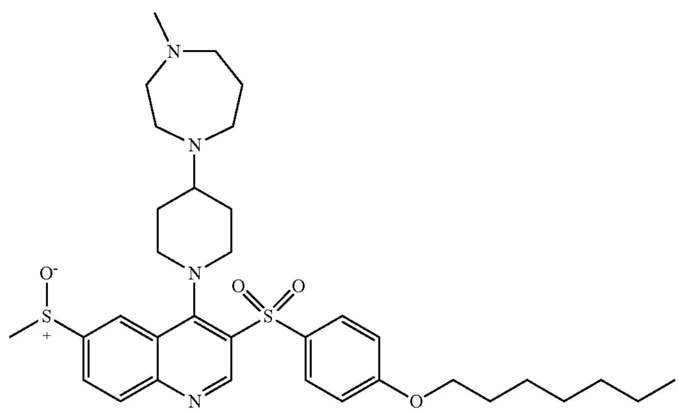 | 3-((4-(heptyloxy)phenyl)sulfonyl)-4-(4-(4-methyl-1,4-diazepan-1-yl)piperidin-1-yl)-6-(methylsulfinyl)quinoline |
| 257 | 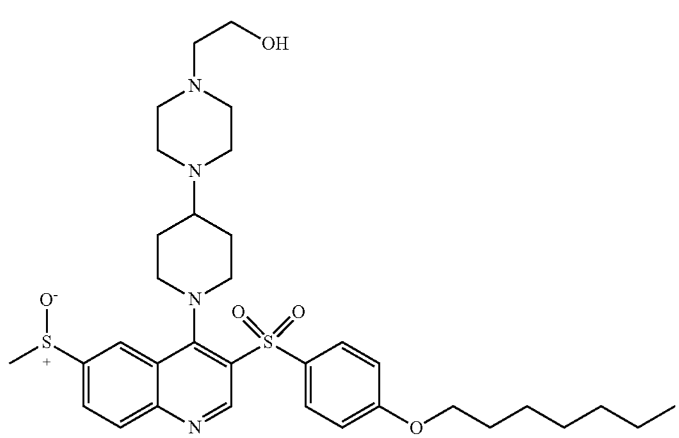 | 2-(4-(1-(3-((4-(heptyloxy)phenyl)sulfonyl)-6-(methylsulfinyl)quinolin-4-yl)piperidin-4-yl)piperazin-1-yl)ethan-1-ol |

TABLE 1-continued

| Ex. | Structure | Name |
|---|---|---|
| 258 | 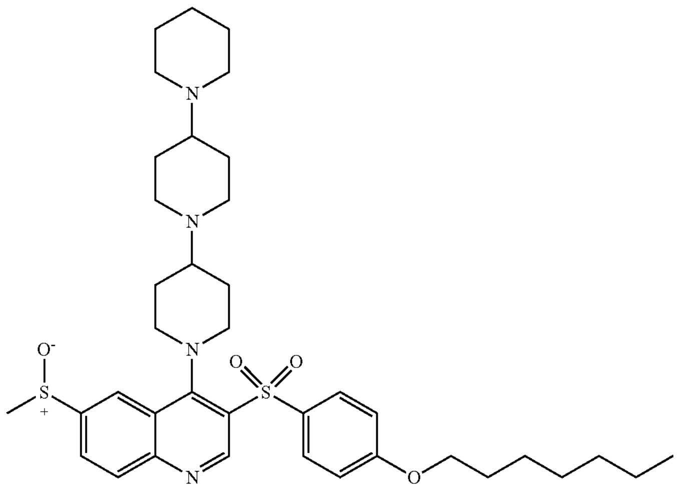 | 4-([1,4':1',4''-terpiperidin]-1''-yl)-3-((4-(heptyloxy)phenyl)sulfonyl)-6-(methylsulfinyl)quinoline |
| 259 | 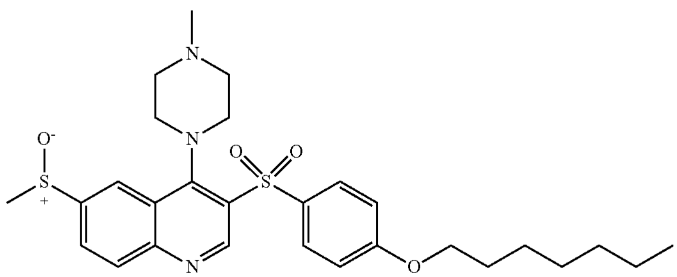 | 3-((4-(heptyloxy)phenyl)sulfonyl)-4-(4-methylpiperazin-1-yl)-6-(methylsulfinyl)quinoline |
| 260 | 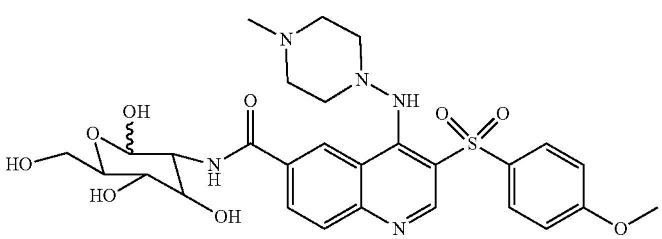 [SMILES: COc1ccc(S(=O)(=O)c2cnc3ccc(C(=O)NC4C(O)OC(CO)C(O)C4O)cc3c2NN2CCN(C)CC2)cc1] | 3-((4-methoxyphenyl)sulfonyl)-4-((4-methylpiperazin-1-yl)amino)-N-((4R,5S,6R)-2,4,5-trihydroxy-6-(hydroxymethyl)tetrahydro-2H-pyran-3-yl)quinoline-6-carboxamide |
| 262 | 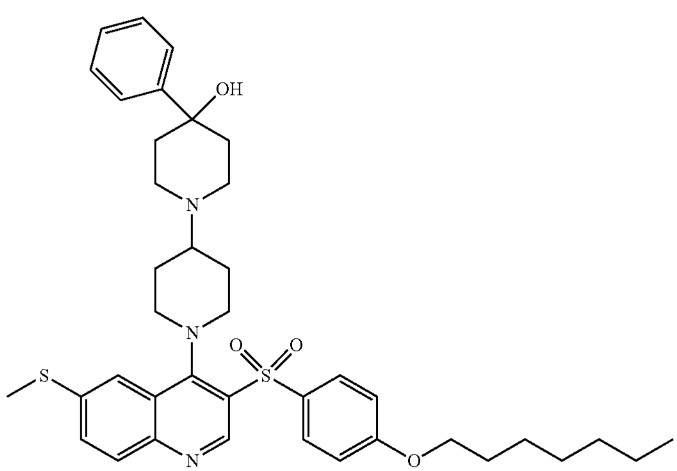 [SMILES: CCCCCCCOc1ccc(S(=O)(=O)c2cnc3ccc(SC)cc3c2N2CCC(N3CCC(O)(c4ccccc4)CC3)CC2)cc1] | 1'-(3-((4-(heptyloxy)phenyl)sulfonyl)-6-(methylthio)quinolin-4-yl)-4-phenyl-[1,4'-bipiperidin]-4-ol |

TABLE 1-continued

| Ex. | Structure | Name |
|---|---|---|
| 263 | 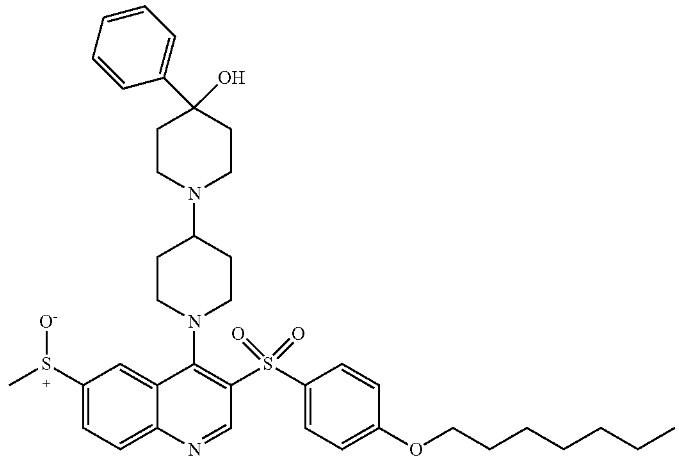 | 1'-(3-((4-(heptyloxy)phenyl)sulfonyl)-6-(methylsulfinyl)quinolin-4-yl)-4-phenyl-[1,4'-bipiperidin]-4-ol |
| 264 | 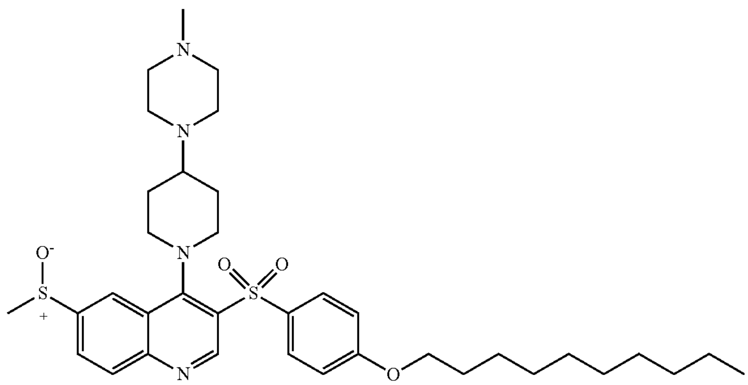 | 3-((4-(decyloxy)phenyl)sulfonyl)-4-(4-(4-methylpiperazin-1-yl)piperidin-1-yl)-6-(methylsulfinyl)quinoline |
| 265 | 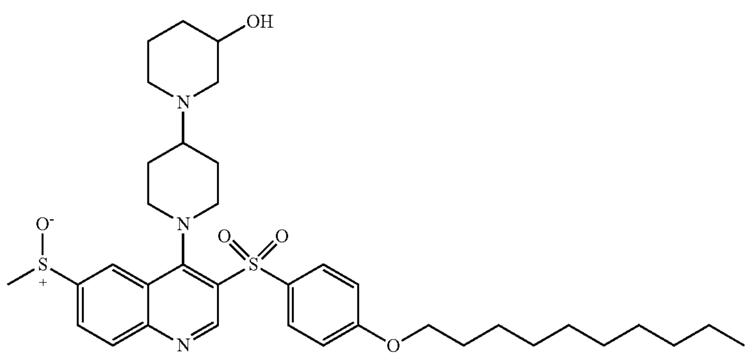 | 1'-(3-((4-(decyloxy)phenyl)sulfonyl)-6-(methylsulfinyl)quinolin-4-yl)-[1,4'-bipiperidin]-3-ol |
| 266 | 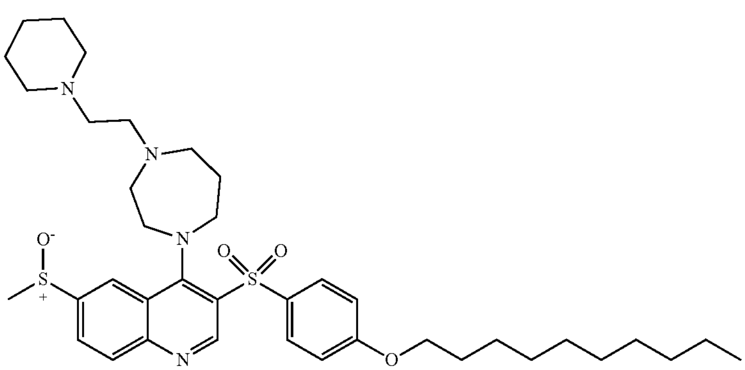 | 3-((4-(decyloxy)phenyl)sulfonyl)-6-(methylsulfinyl)-4-(4-(2-(piperidin-1-yl)ethyl)-1,4-diazepan-1-yl)quinoline |

TABLE 1-continued

| Ex. | Structure | Name |
|---|---|---|
| 267 | 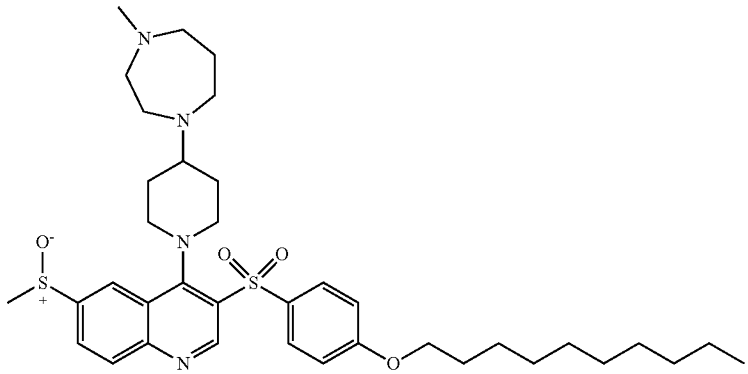 | 3-((4-(decyloxy)phenyl)sulfonyl)-4-(4-(4-methyl-1,4-diazepan-1-yl)piperidin-1-yl)-6-(methylsulfinyl)quinoline |
| 268 | 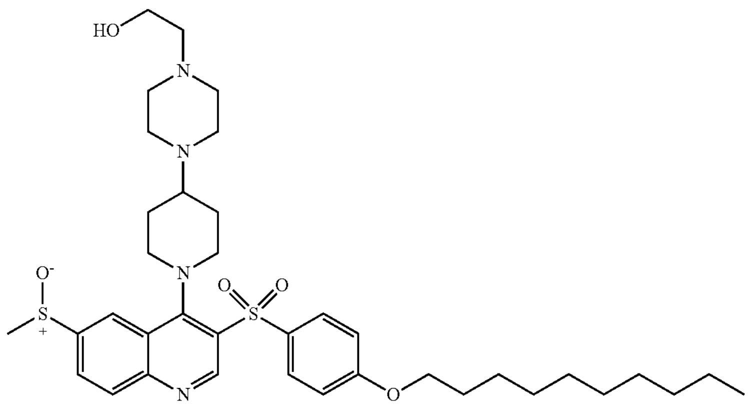 | 2-(4-(1-(3-((4-(decyloxy)phenyl)sulfonyl)-6-(methylsulfinyl)quinolin-4-yl)piperidin-4-yl)piperazin-1-yl)ethan-1-ol |
| 269 | 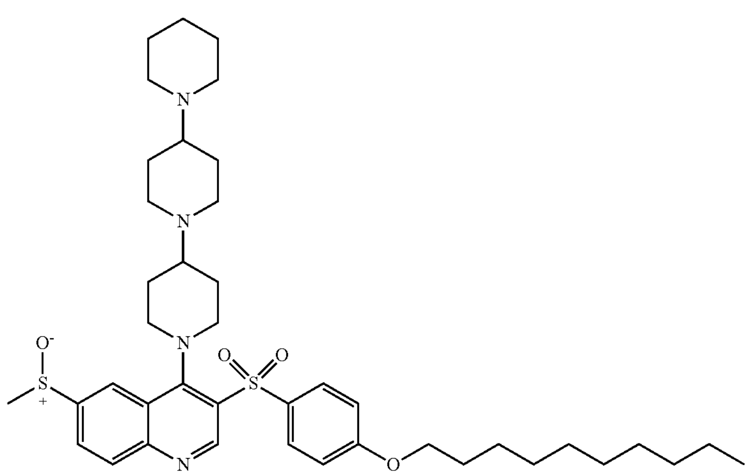 | 4-([1,4':1',4''-terpiperidin]-1''-yl)-3-((4-(decyloxy)phenyl)sulfonyl)-6-(methylsulfinyl)quinoline |

TABLE 1-continued

| Ex. | Structure | Name |
|---|---|---|
| 270 | 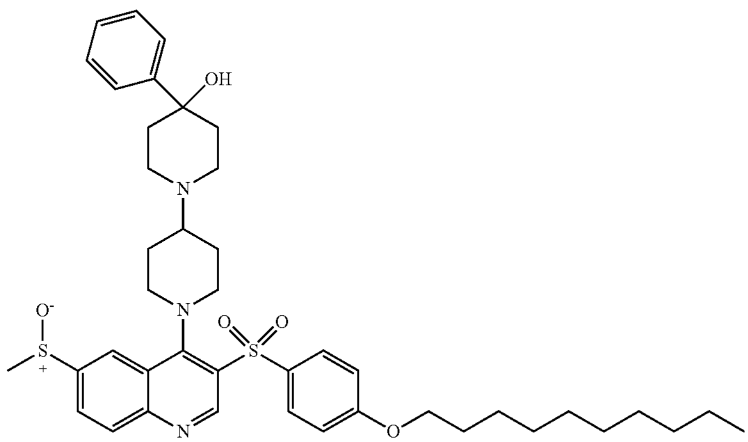 | 1'-(3-((4-(decyloxy)phenyl)sulfonyl)-6-(methylsulfinyl)quinolin-4-yl)-4-phenyl-[1,4'-bipiperidin]-4-ol |
| 271 | 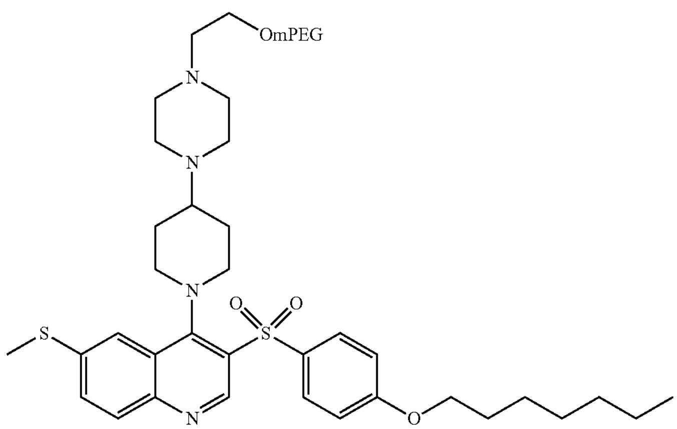 | 3-((4-(heptyloxy)phenyl)sulfonyl)-4-(4-(4-(2-mPEGoxyethyl)piperazin-1-yl)piperidin-1-yl)-6-(methylthio)quinoline |
| 272 | 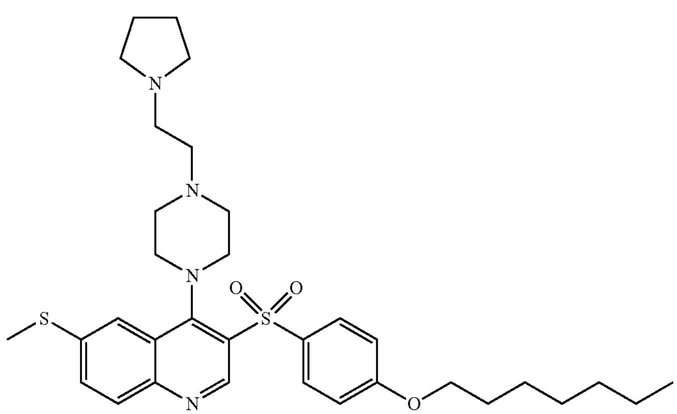 [SMILES: CCCCCCCOc1ccc(S(=O)(=O)c2cnc3ccc(SC)cc3c2N2CCN(CCN3CCCC3)CC2)cc1] | 3-((4-(heptyloxy)phenyl)sulfonyl)-6-(methylthio)-4-(4-(2-(pyrrolidin-1-yl)ethyl)piperazin-1-yl)quinoline |

TABLE 1-continued

| Ex. | Structure | Name |
|---|---|---|
| 273 | 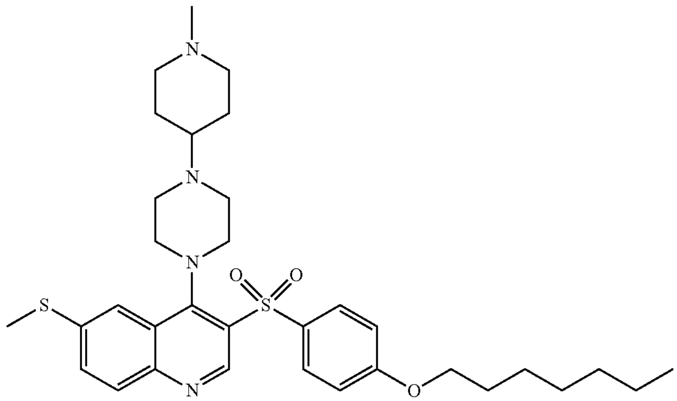 | 3-((4-(heptyloxy)phenyl)sulfonyl)-4-(4-(1-methylpiperidin-4-yl)piperazin-1-yl)-6-(methylthio)quinoline |
| 274 | 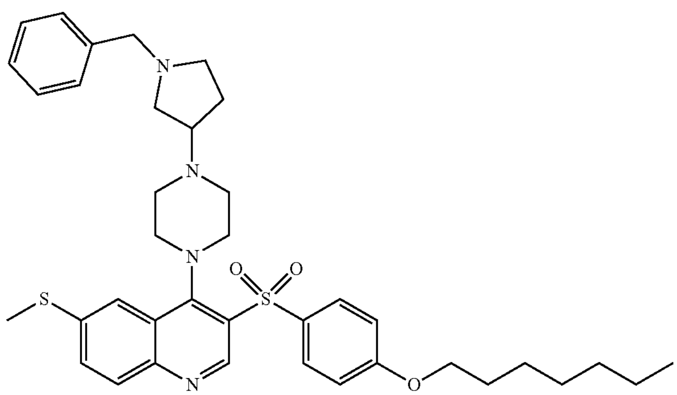 [SMILES: CCCCCCCOc1ccc(S(=O)(=O)c2cnc3ccc(SC)cc3c2N2CCN(C3CCN(Cc4ccccc4)C3)CC2)cc1] | 4-(4-(1-benzylpyrrolidin-3-yl)piperazin-1-yl)-3-((4-(heptyloxy)phenyl)sulfonyl)-6-(methylthio)quinoline |
| 275 | 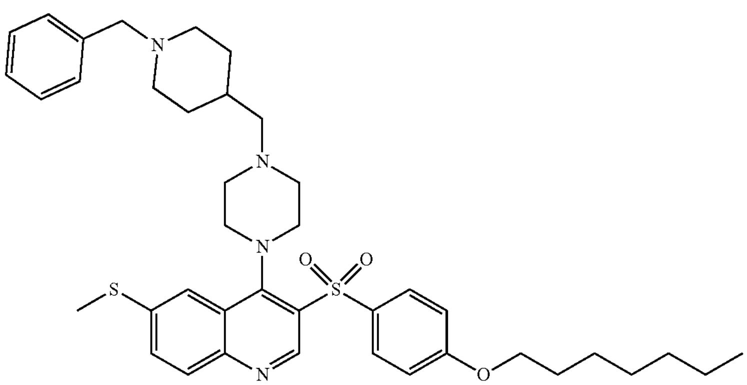 [SMILES: CCCCCCCOc1ccc(S(=O)(=O)c2cnc3ccc(SC)cc3c2N2CCN(CC3CCN(Cc4ccccc4)CC3)CC2)cc1] | 4-(4-((1-benzylpiperidin-4-yl)methyl)piperazin-1-yl)-3-((4-(heptyloxy)phenyl)sulfonyl)-6-(methylthio)quinoline |
| 276 | 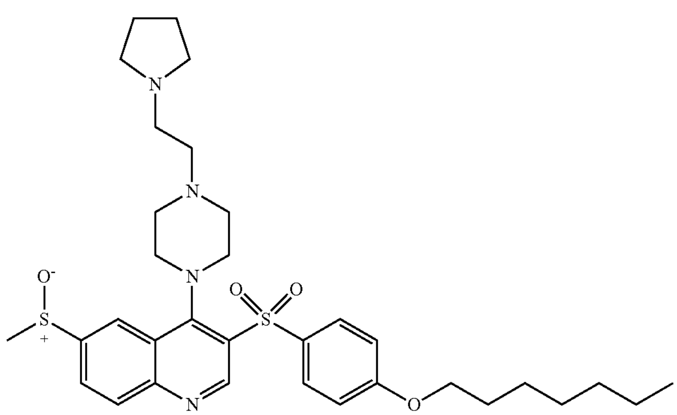 | 3-((4-(heptyloxy)phenyl)sulfonyl)-6-(methylsulfinyl)-4-(4-(2-(pyrrolidin-1-yl)ethyl)piperazin-1-yl)quinoline |

TABLE 1-continued

| Ex. | Structure | Name |
|---|---|---|
| 277 | 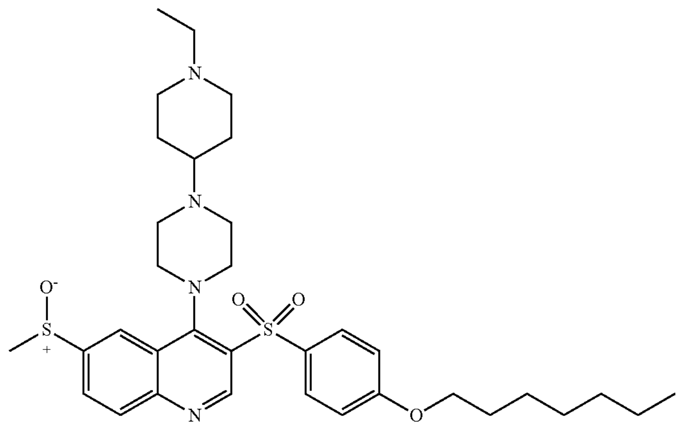 | 4-(4-(1-ethylpiperidin-4-yl)piperazin-1-yl)-3-((4-(heptyloxy)phenyl)sulfonyl)-6-(methylsulfinyl)quinoline |
| 278 | 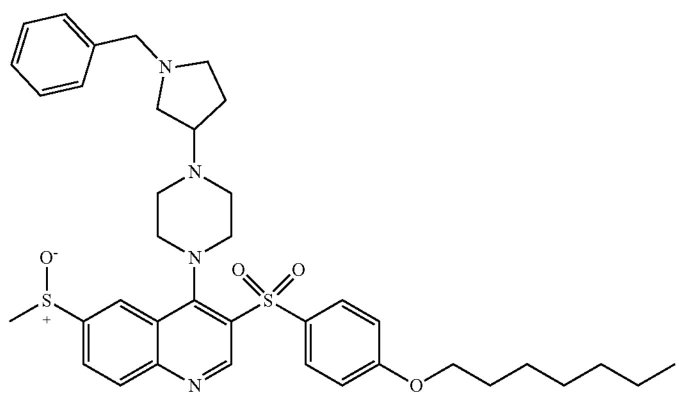 | 4-(4-(1-benzylpyrrolidin-3-yl)piperazin-1-yl)-3-((4-(heptyloxy)phenyl)sulfonyl)-6-(methylsulfinyl)quinoline |
| 279 | 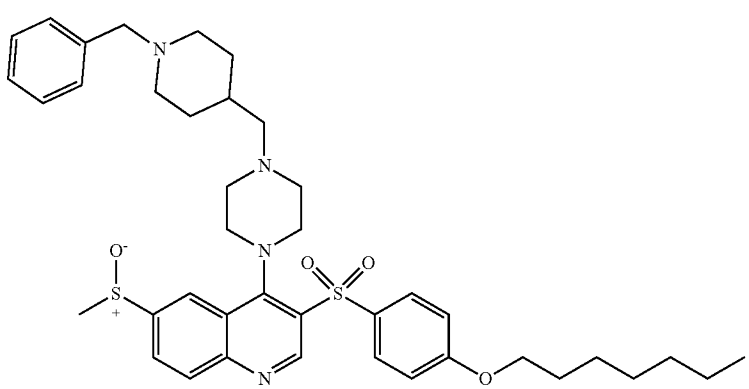 | 4-(4-((1-benzylpiperidin-4-yl)methyl)piperazin-1-yl)-3-((4-(heptyloxy)phenyl)sulfonyl)-6-(methylsulfinyl)quinoline |

TABLE 1-continued

| Ex. | Structure | Name |
|---|---|---|
| 280 | 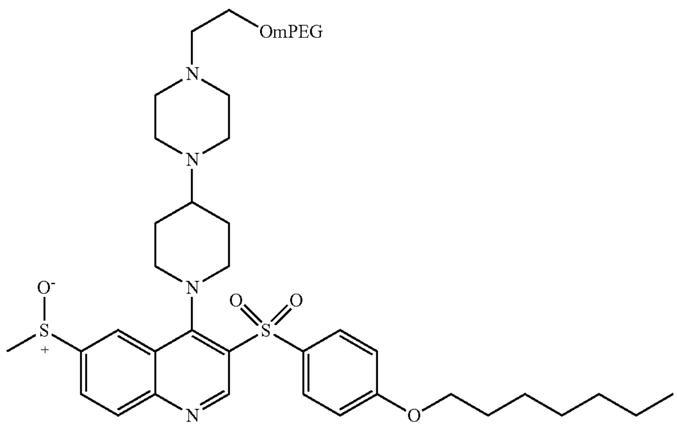 | 3-((4-(heptyloxy)phenyl)sulfonyl)-4-(4-(4-(2-mPEGoxyethyl)piperazin-1-yl)piperidin-1-yl)-6-(methylsulfinyl)quinoline |
| 281 | 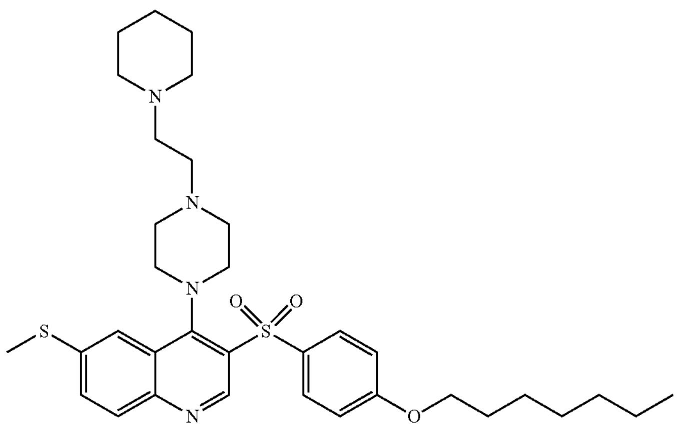 [SMILES: CCCCCCCOc1ccc(S(=O)(=O)c2cnc3ccc(SC)cc3c2N2CCN(CCN3CCCCC3)CC2)cc1] | 3-((4-(heptyloxy)phenyl)sulfonyl)-6-(methylthio)-4-(4-(2-(piperidin-1-yl)ethyl)piperazin-1-yl)quinoline |
| 282 | 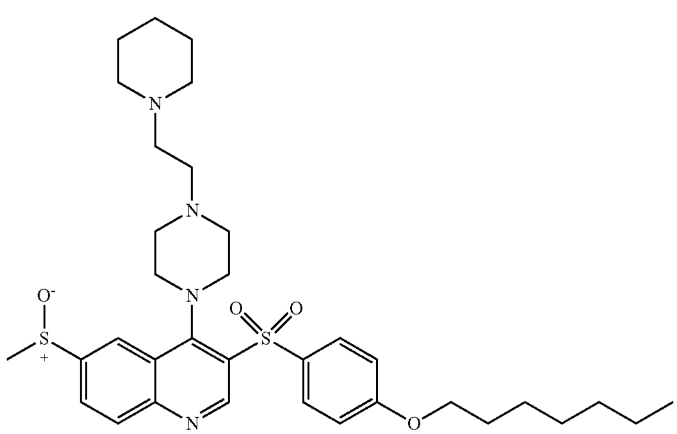 | 3-((4-(heptyloxy)phenyl)sulfonyl)-6-(methylsulfinyl)-4-(4-(2-(piperidin-1-yl)ethyl)piperazin-1-yl)quinoline |

TABLE 1-continued

| Ex. | Structure | Name |
|---|---|---|
| 283 | 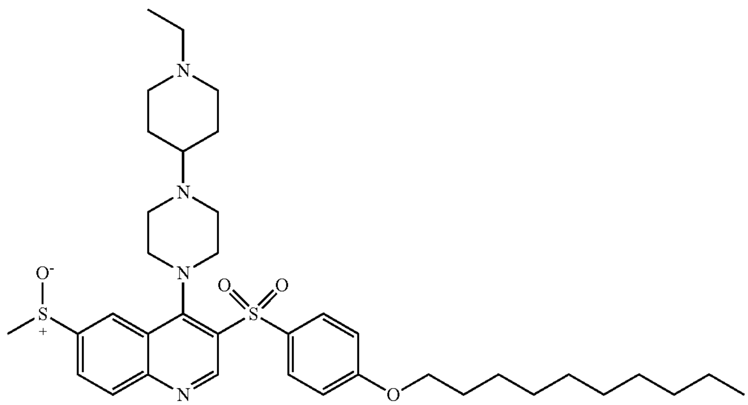 | 3-((4-(decyloxy)phenyl)sulfonyl)-4-(4-(1-ethylpiperidin-4-yl)piperazin-1-yl)-6-(methylsulfinyl)quinoline |
| 284 | 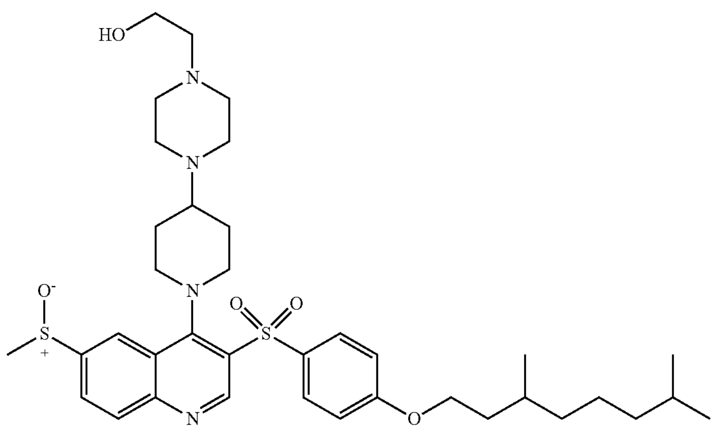 | 2-(4-(1-(3-((4-((3,7-dimethyloctyl)oxy)phenyl)sulfonyl)-6-(methylsulfinyl)quinolin-4-yl)piperidin-4-yl)piperazin-1-yl)ethan-1-ol |
| 285 | 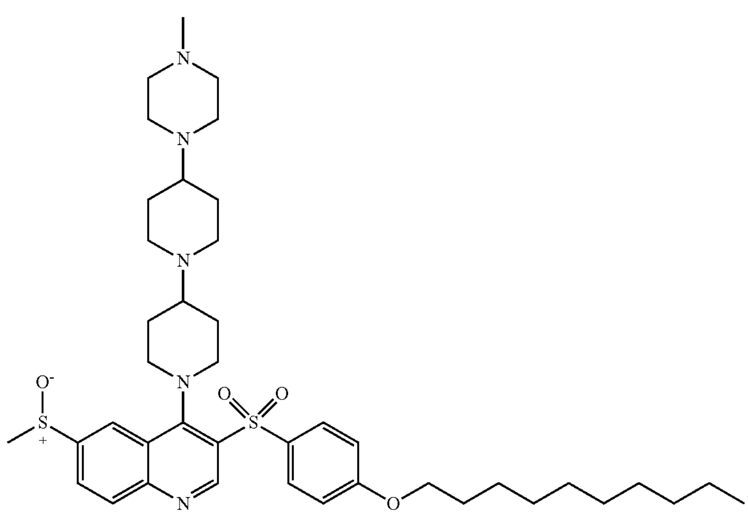 | 3-((4-(decyloxy)phenyl)sulfonyl)-4-(4-(4-methylpiperazin-1-yl)-[1,4'-bipiperidin]-1'-yl)-6-(methylsulfinyl)quinoline |

TABLE 1-continued

| Ex. | Structure | Name |
|---|---|---|
| 286 | 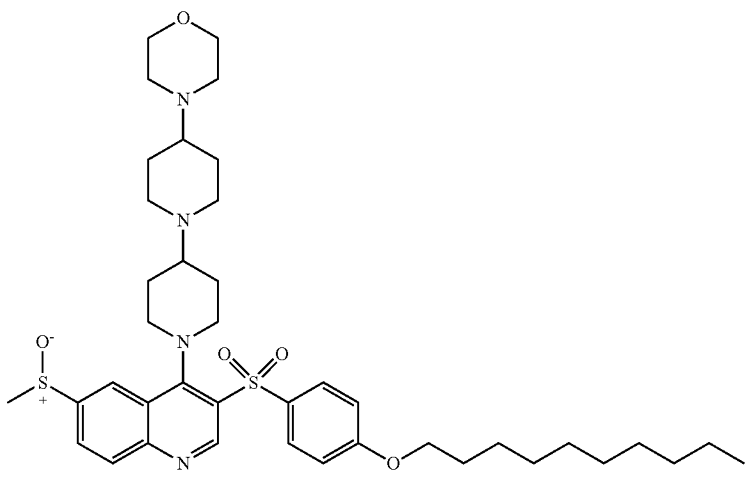 | 4-(1'-(3-((4-(decyloxy)phenyl)sulfonyl)-6-(methylsulfinyl)quinolin-4-yl)-[1,4'-bipiperidin]-4-yl)morpholine |
| 287 | 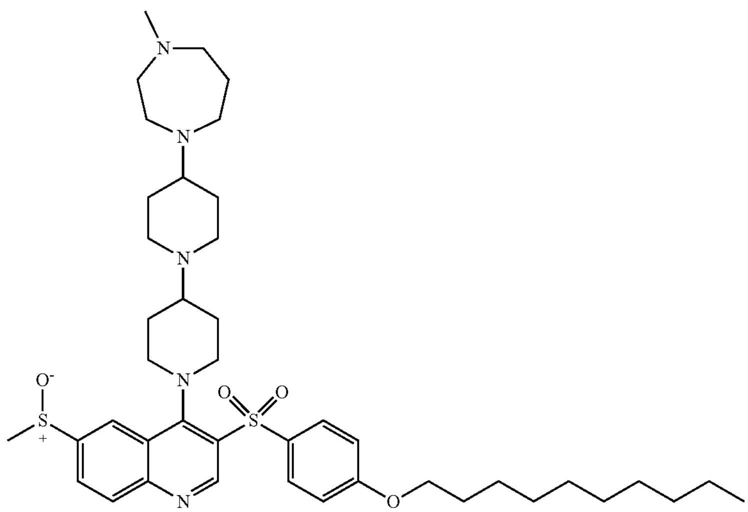 | 3-((4-(decyloxy)phenyl)sulfonyl)-4-(4-(4-methyl-1,4-diazepan-1-yl)-[1,4'-bipiperidin]-1'-yl)-6-(methylsulfinyl)quinoline |
| 288 | 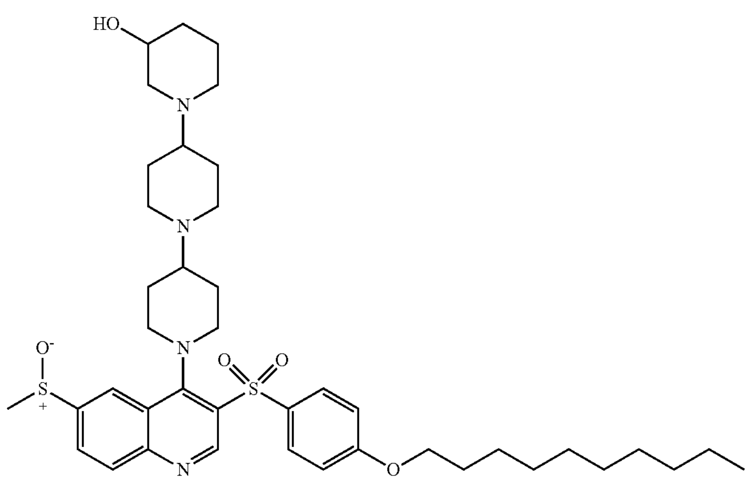 | 1''-(3-((4-(decyloxy)phenyl)sulfonyl)-6-(methylsulfinyl)quinolin-4-yl)-[1,4':1',4''-terpiperidin]-3-ol |

TABLE 1-continued

| Ex. | Structure | Name |
|---|---|---|
| 289 | 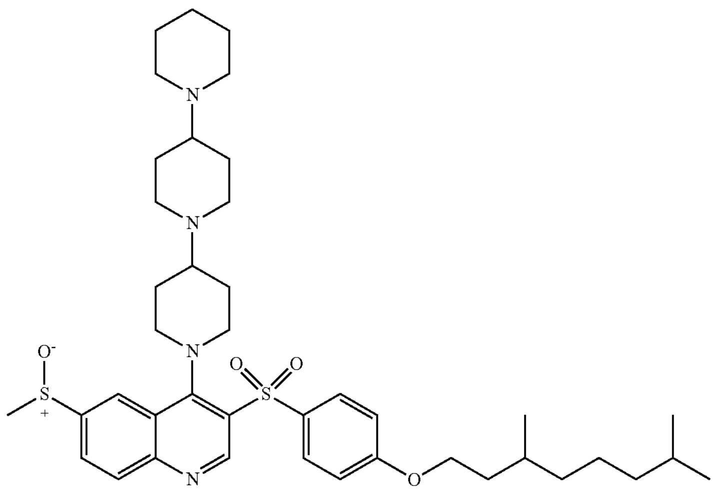 | 4-([1,4':1',4''-terpiperidin]-1''-yl)-3-((4-((3,7-dimethyloctyl)oxy)phenyl)sulfonyl)-6-(methylsulfinyl)quinoline |
| 290 | 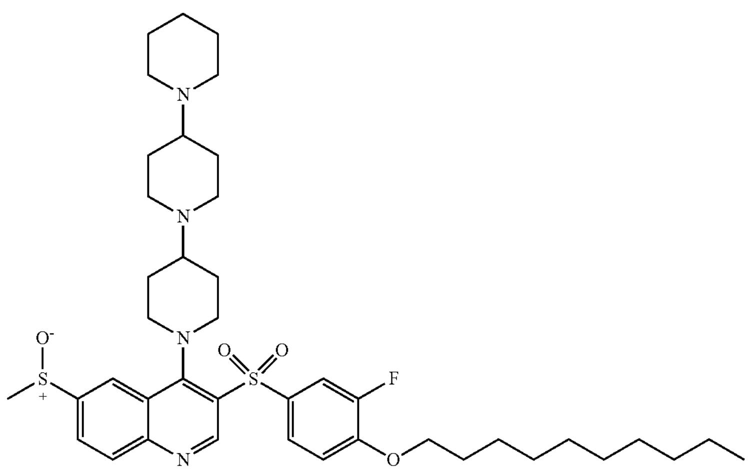 | ([1,4':1',4''-terpiperidin]-1''-yl)-3-((4-(decyloxy)-3-fluorophenyl)sulfonyl)-6-(methylsulfinyl)quinoline |
| 291 | 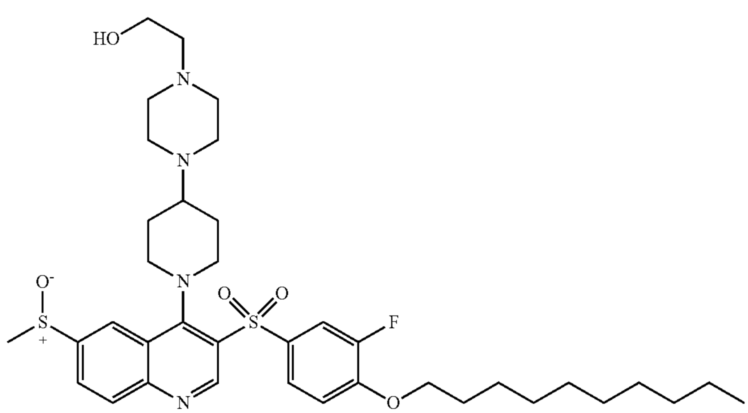 | 2-(4-(1-(3-((4-(decyloxy)-3-fluorophenyl)sulfonyl)-6-(methylsulfinyl)quinolin-4-yl)piperidin-4-yl)piperazin-1-yl)ethan-1-ol |

TABLE 1-continued

| Ex. | Structure | Name |
|---|---|---|
| 292 | 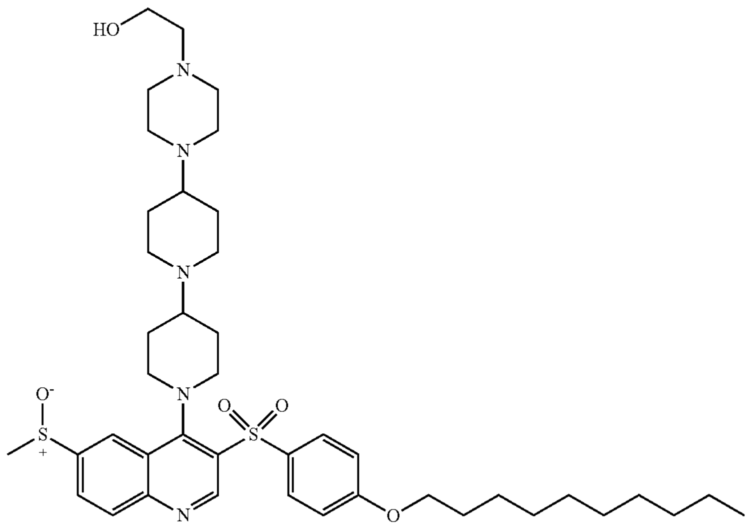 | 2-(4-(1'-(3-((4-(decyloxy)phenyl)sulfonyl)-6-(methylsulfinyl)quinolin-4-yl)-[1,4'-bipiperidin]-4-yl)piperazin-1-yl)ethan-1-ol |
| 293 | 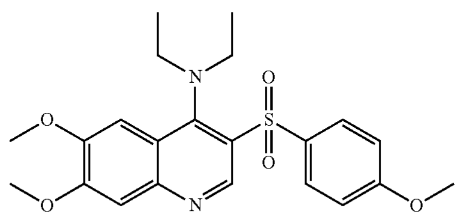 | N,N-diethyl-6,7-dimethoxy-3-((4-methoxyphenyl)sulfonyl)quinolin-4-amine |
| 294 | 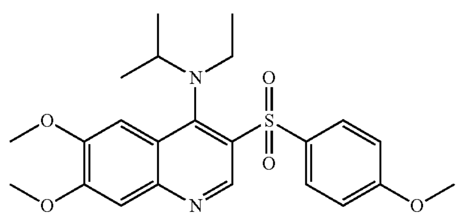 | N-ethyl-N-isopropyl-6,7-dimethoxy-3-((4-methoxyphenyl)sulfonyl)quinolin-4-amine |
| 295 | 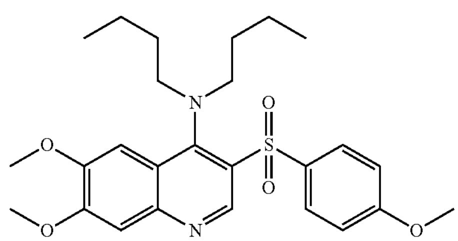 | N,N-dibutyl-6,7-dimethoxy-3-((4-methoxyphenyl)sulfonyl)quinolin-4-amine |
| 296 | 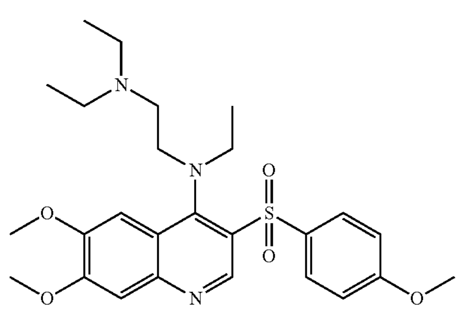 | N1-(6,7-dimethoxy-3-((4-methoxyphenyl)sulfonyl)quinolin-4-yl)-N1,N2,N2-triethylethane-1,2-diamine |

TABLE 1-continued

| Ex. | Structure | Name |
| --- | --- | --- |
| 297 | 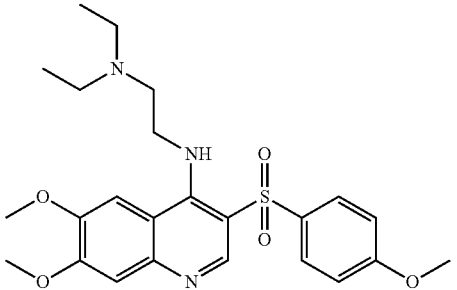 | N1-(6,7-dimethoxy-3-((4-methoxyphenyl)sulfonyl)quinolin-4-yl)-N2,N2-diethylethane-1,2-diamine |
| 298 | 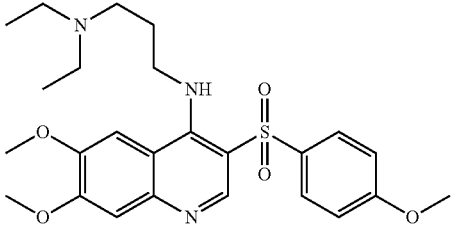 | N1-(6,7-dimethoxy-3-((4-methoxyphenyl)sulfonyl)quinolin-4-yl)-N3,N3-diethylpropane-1,3-diamine |
| 299 | 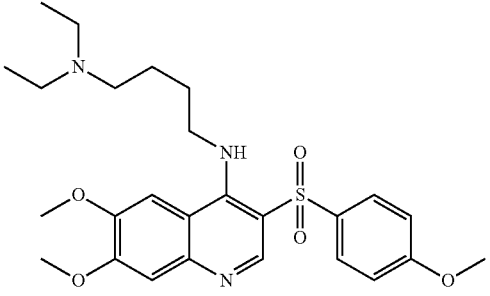 [SMILES: CCN(CC)CCCCNc1c(S(=O)(=O)c2ccc(OC)cc2)cnc2cc(OC)c(OC)cc12] | N1-(6,7-dimethoxy-3-((4-methoxyphenyl)sulfonyl)quinolin-4-yl)-N4,N4-diethylbutane-1,4-diamine |
| 300 | 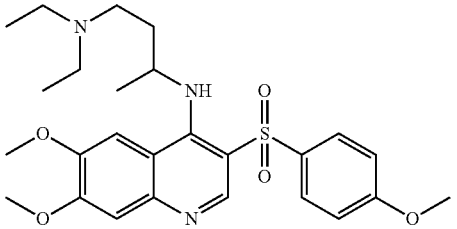 | N3-(6,7-dimethoxy-3-((4-methoxyphenyl)sulfonyl)quinolin-4-yl)-N1,N1-diethylbutane-1,3-diamine |
| 301 | 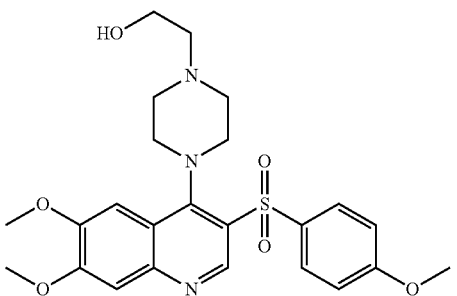 | 2-(4-(6,7-dimethoxy-3-((4-methoxyphenyl)sulfonyl)quinolin-4-yl)piperazin-1-yl)ethan-1-ol |

TABLE 1-continued

| Ex. | Structure | Name |
|---|---|---|
| 302 | 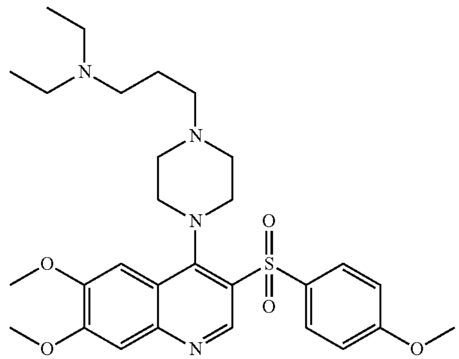 | 3-(4-(6,7-dimethoxy-3-((4-methoxyphenyl)sulfonyl)quinolin-4-yl)piperazin-1-yl)-N,N-diethylpropan-1-amine |
| 303 | 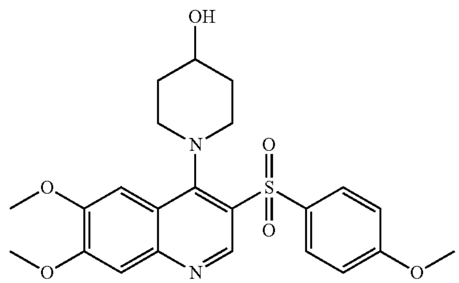 | 1-(6,7-dimethoxy-3-((4-methoxyphenyl)sulfonyl)quinolin-4-yl)piperidin-4-ol |
| 304 | 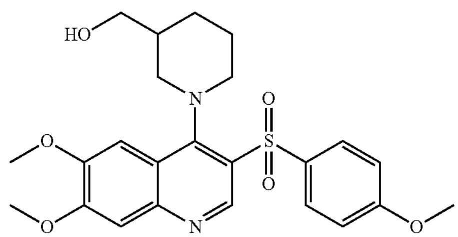 | (1-(6,7-dimethoxy-3-((4-methoxyphenyl)sulfonyl)quinolin-4-yl)piperidin-3-yl)methanol |
| 305 | 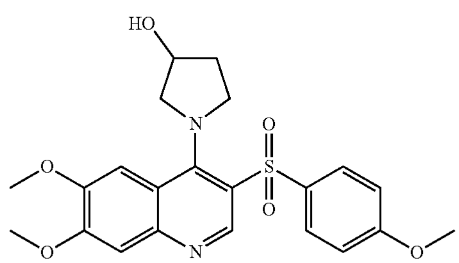 | 1-(6,7-dimethoxy-3-((4-methoxyphenyl)sulfonyl)quinolin-4-yl)pyrrolidin-3-ol |
| 306 | 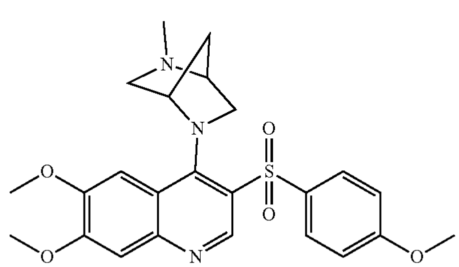 | 6,7-dimethoxy-3-((4-methoxyphenyl)sulfonyl)-4-((1S,4S)-5-methyl-2,5-diazabicyclo[2.2.1]heptan-2-yl)quinoline |

TABLE 1-continued

| Ex. | Structure | Name |
|---|---|---|
| 307 | 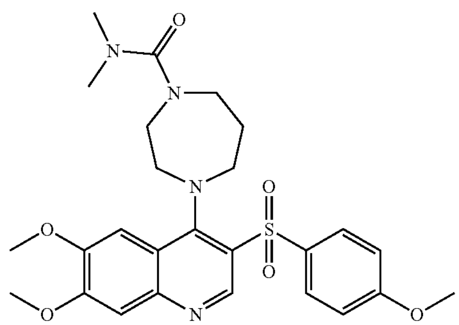 | 4-(6,7-dimethoxy-3-((4-methoxyphenyl)sulfonyl)quinolin-4-yl)-N,N-dimethyl-1,4-diazepane-1-carboxamide |
| 308 | 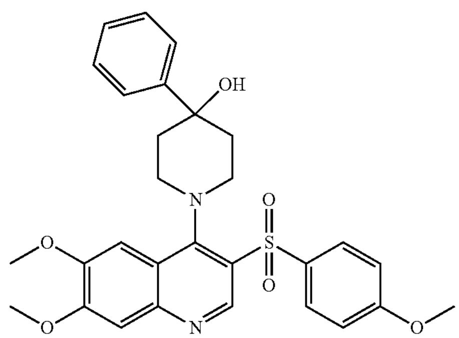 | 1-(6,7-dimethoxy-3-((4-methoxyphenyl)sulfonyl)quinolin-4-yl)-4-phenylpiperidin-4-ol |
| 309 | 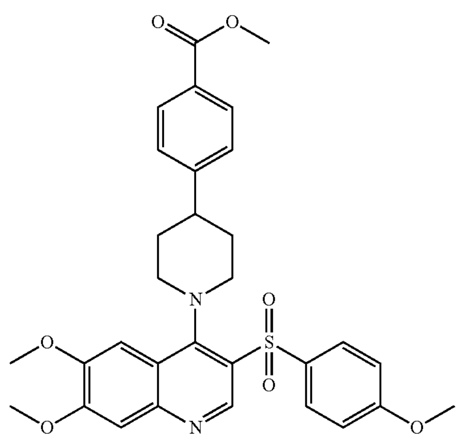 | methyl 4-(1-(6,7-dimethoxy-3-((4-methoxyphenyl)sulfonyl)quinolin-4-yl)piperidin-4-yl)benzoate |
| 310 | 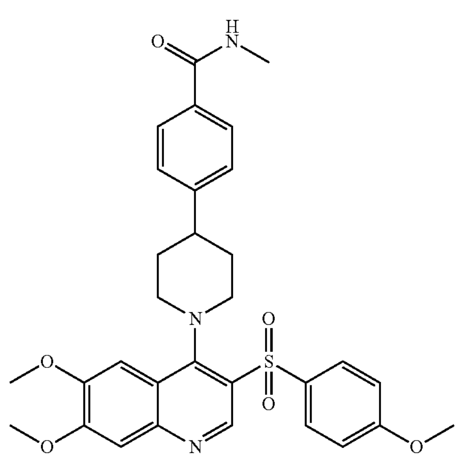 | 4-(1-(6,7-dimethoxy-3-((4-methoxyphenyl)sulfonyl)quinolin-4-yl)piperidin-4-yl)-N-methylbenzamide |

TABLE 1-continued

| Ex. | Structure | Name |
|---|---|---|
| 311 | 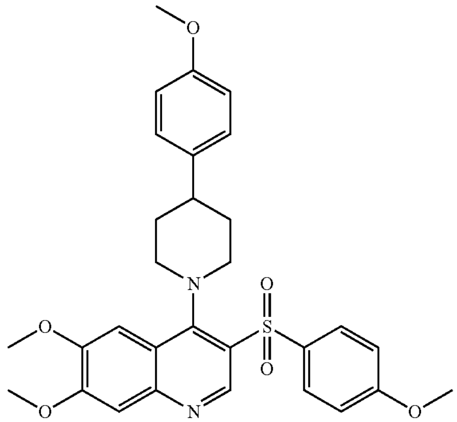 | 6,7-dimethoxy-4-(4-(4-methoxyphenyl)piperidin-1-yl)-3-((4-methoxyphenyl)sulfonyl)quinoline |
| 312 | 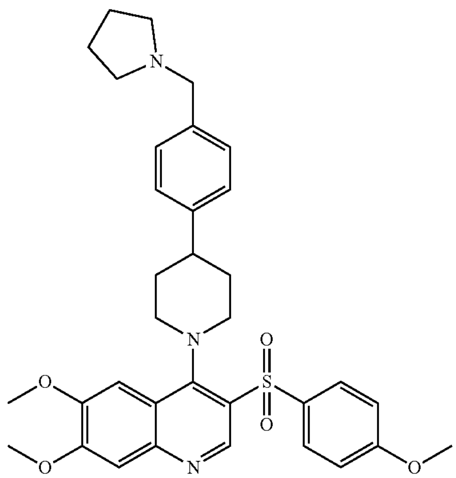 | 6,7-dimethoxy-3-((4-methoxyphenyl)sulfonyl)-4-(4-(4-(pyrrolidin-1-ylmethyl)phenyl)piperidin-1-yl)quinoline |
| 313 | 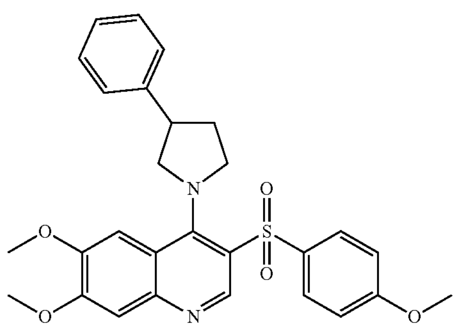 | 6,7-dimethoxy-3-((4-methoxyphenyl)sulfonyl)-4-(3-phenylpyrrolidin-1-yl)quinoline |
| 314 | 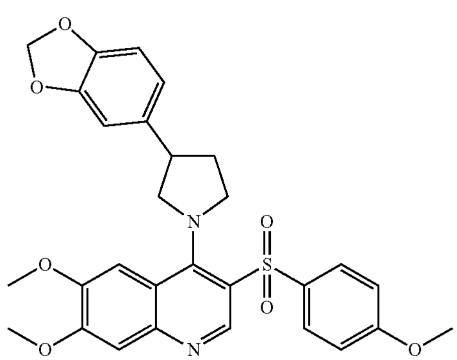 | 4-(3-(benzo[d][1,3]dioxol-5-yl)pyrrolidin-1-yl)-6,7-dimethoxy-3-((4-methoxyphenyl)sulfonyl)quinoline |

TABLE 1-continued

| Ex. | Structure | Name |
|---|---|---|
| 315 | 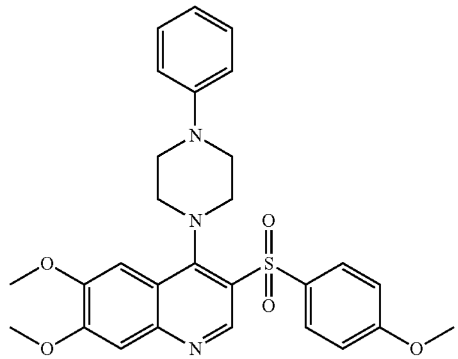 | 6,7-dimethoxy-3-((4-methoxyphenyl)sulfonyl)-4-(4-phenylpiperazin-1-yl)quinoline |
| 316 | 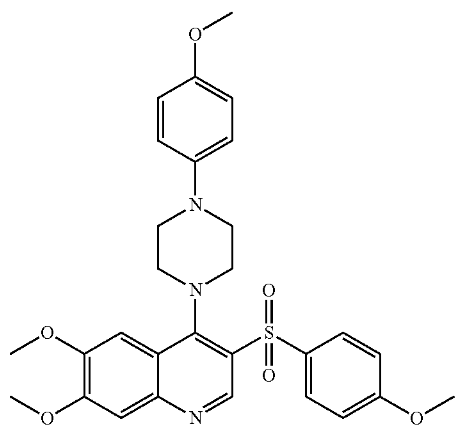 | 6,7-dimethoxy-4-(4-(4-methoxyphenyl)piperazin-1-yl)-3-((4-methoxyphenyl)sulfonyl)quinoline |
| 317 | 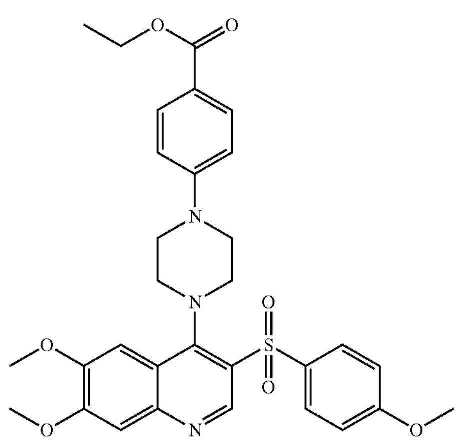 | ethyl 4-(4-(6,7-dimethoxy-3-((4-methoxyphenyl)sulfonyl)quinolin-4-yl)piperazin-1-yl)benzoate |

TABLE 1-continued

| Ex. | Structure | Name |
|---|---|---|
| 318 | 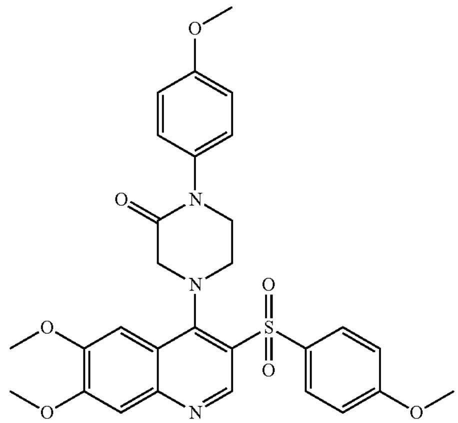 | 4-(6,7-dimethoxy-3-((4-methoxyphenyl)sulfonyl)quinolin-4-1-(4-methoxyphenyl)piperazin-2-one |
| 319 | 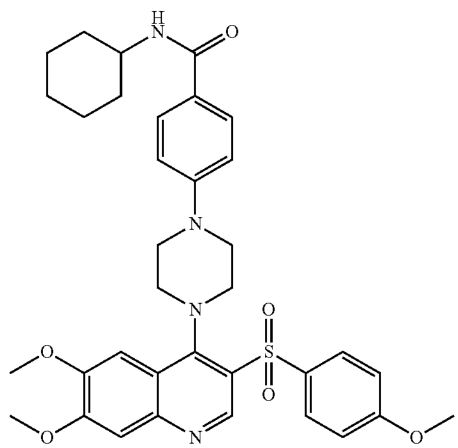 | N-cyclohexyl-4-(4-(6,7-dimethoxy-3-((4-methoxyphenyl)sulfonyl)quinolin-4-yl)piperazin-1-yl)benzamide |
| 320 | 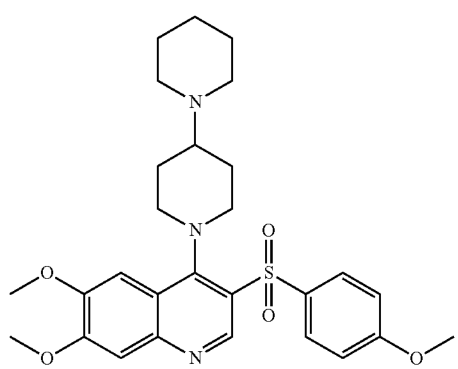 | 4-([1,4'-bipiperidin]-1'-yl)-6,7-dimethoxy-3-((4-methoxyphenyl)sulfonyl)quinoline |
| 321 | 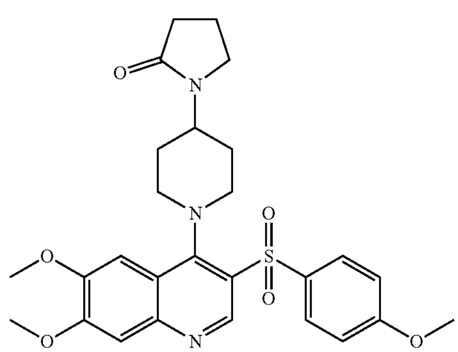 | 1-(1-(6,7-dimethoxy-3-((4-methoxyphenyl)sulfonyl)quinolin-4-yl)piperidin-4-yl)pyrrolidin-2-one |

TABLE 1-continued

| Ex. | Structure | Name |
|---|---|---|
| 322 | 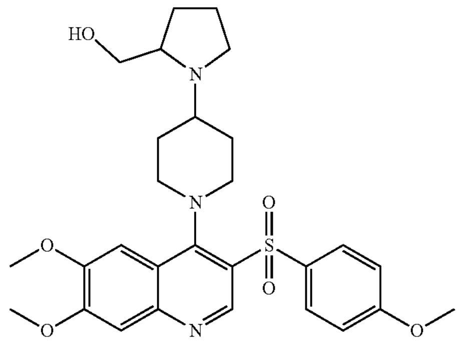 | (1-(1-(6,7-dimethoxy-3-((4-methoxyphenyl)sulfonyl)quinolin-4-yl)piperidin-4-yl)pyrrolidin-2-yl)methanol |
| 323 | 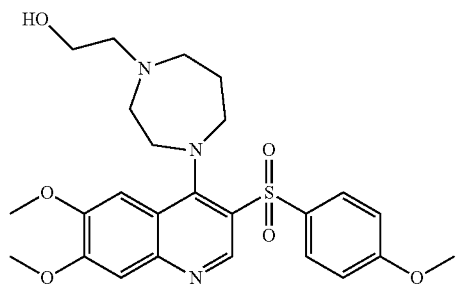 | 2-(4-(6,7-dimethoxy-3-((4-methoxyphenyl)sulfonyl)quinolin-4-yl)-1,4-diazepan-1-yl)ethan-1-ol |
| 324 | 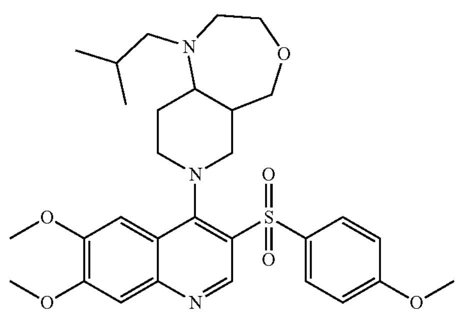 | 7-(6,7-dimethoxy-3-((4-methoxyphenyl)sulfonyl)quinolin-4-yl)-1-isobutyldecahydropyrido[4,3-e][1,4]oxazepine |
| 325 | 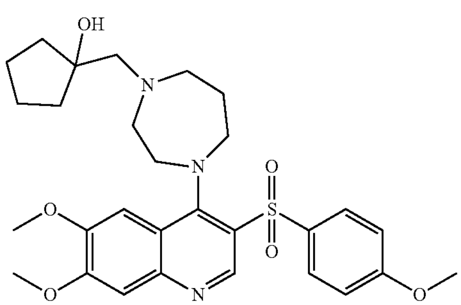 [SMILES: COc1ccc(S(=O)(=O)c2cnc3cc(OC)c(OC)cc3c2N2CCCN(CC3(O)CCCC3)CC2)cc1] | 1-((4-(6,7-dimethoxy-3-((4-methoxyphenyl)sulfonyl)quinolin-4-yl)-1,4-diazepan-1-yl)methyl)cyclopentan-1-ol |
| 326 | 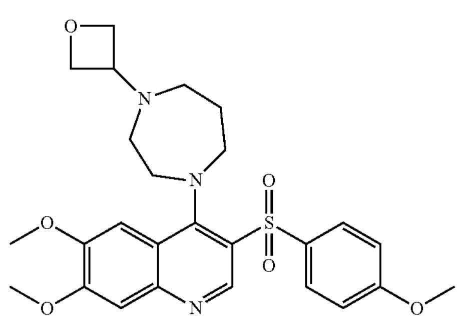 | 6,7-dimethoxy-3-((4-methoxyphenyl)sulfonyl)-4-(4-(oxetan-3-yl)-1,4-diazepan-1-yl)quinoline |

TABLE 1-continued

| Ex. | Structure | Name |
|---|---|---|
| 327 | 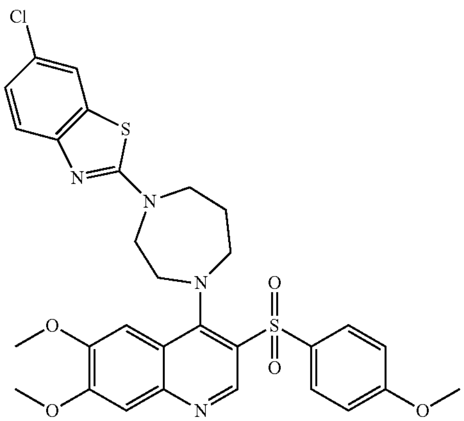 [SMILES: COc1ccc(S(=O)(=O)c2cnc3cc(OC)c(OC)cc3c2N2CCCN(c3nc4ccc(Cl)cc4s3)CC2)cc1] | 6-chloro-2-(4-(6,7-dimethoxy-3-((4-methoxyphenyl)sulfonyl)quinolin-4-yl)-1,4-diazepan-1-yl)benzo[d]thiazole |
| 328 | 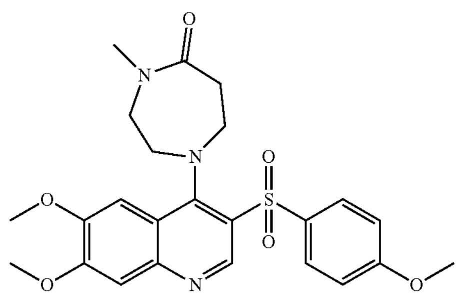 | 1-(6,7-dimethoxy-3-((4-methoxyphenyl)sulfonyl)quinolin-4-yl)-4-methyl-1,4-diazepan-5-one |
| 329 | 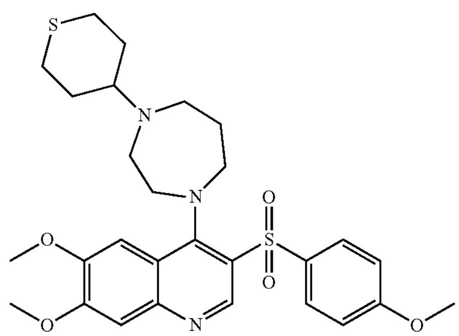 | 6,7-dimethoxy-3-((4-methoxyphenyl)sulfonyl)-4-(4-(tetrahydro-2H-thiopyran-4-yl)-1,4-diazepan-1-yl)quinoline |
| 330 | 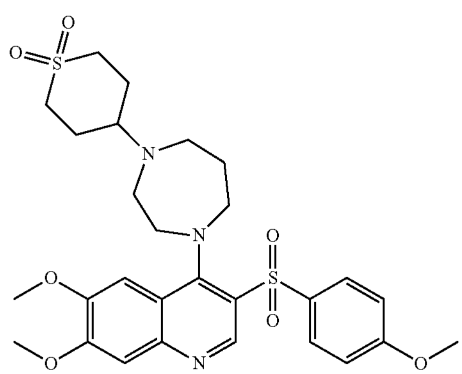 | 4-(4-(6,7-dimethoxy-3-((4-methoxyphenyl)sulfonyl)quinolin-4-yl)-1,4-diazepan-1-yl)tetrahydro-2H-thiopyran 1,1-dioxide |

TABLE 1-continued

| Ex. | Structure | Name |
|---|---|---|
| 331 | 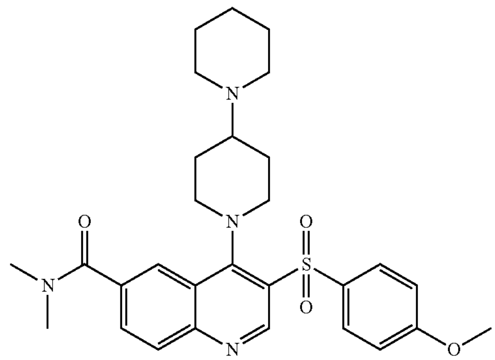 | 4-([1,4'-bipiperidin]-1'-yl)-3-((4-methoxyphenyl)sulfonyl)-N,N-dimethylquinoline-6-carboxamide |
| 332 | 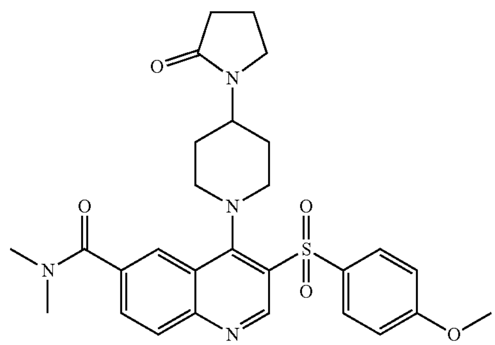 | 3-((4-methoxyphenyl)sulfonyl)-N,N-dimethyl-4-(4-(2-oxopyrrolidin-1-yl)piperidin-1-yl)quinoline-6-carboxamid |
| 333 | 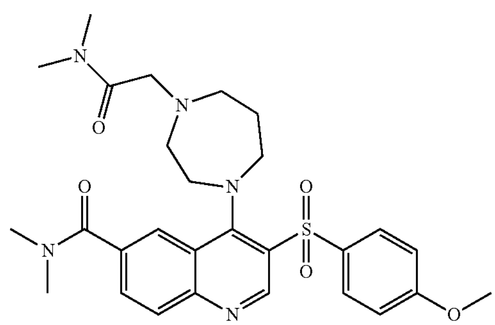 | 4-(4-(2-(dimethylamino)-2-oxoethyl)-1,4-diazepan-1-yl)-3-((4-methoxyphenyl)sulfonyl)-N,N-dimethylquinoline-6-carboxamide |
| 334 | 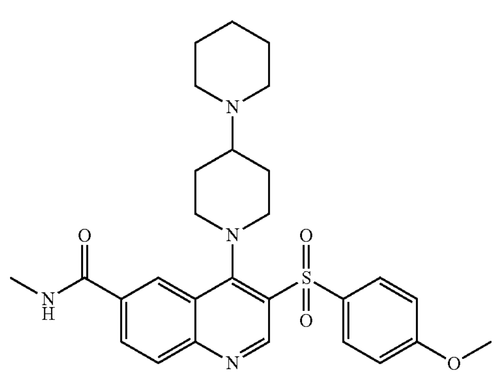 | 4-([1,4'-bipiperidin]-1'-yl)-3-((4-methoxyphenyl)sulfonyl)-N-methylquinoline-6-carboxamide |

TABLE 1-continued

| Ex. | Structure | Name |
|---|---|---|
| 335 | 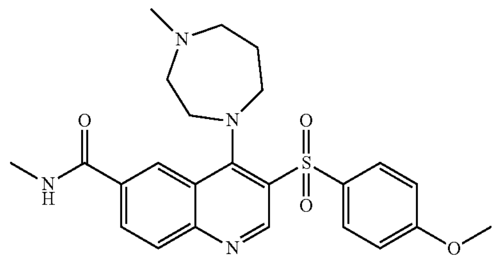 | 3-((4-methoxyphenyl)sulfonyl)-N-methyl-4-(4-methyl-1,4-diazepan-1-yl)quinoline-6-carboxamide |
| 336 | 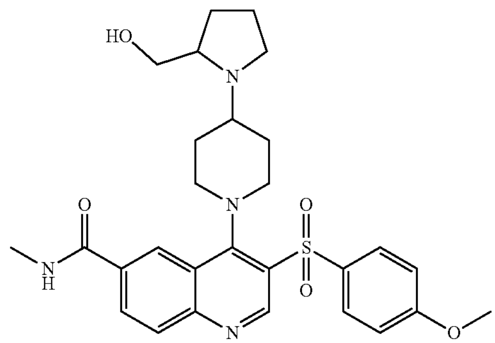 | 4-(4-(2-(hydroxymethyl)pyrrolidin-1-yl)piperidin-1-yl)-3-((4-methoxyphenyl)sulfonyl)-N-methylquinoline-6-carboxamide |
| 337 | 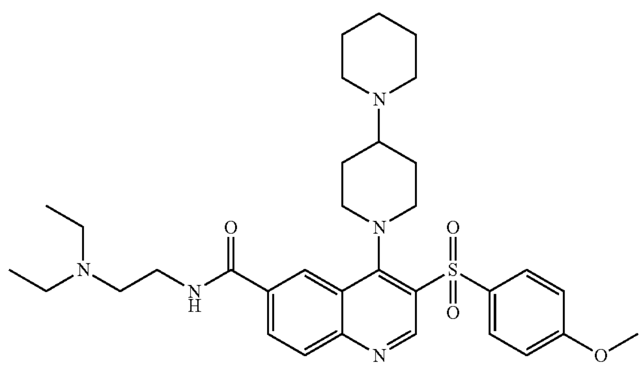 [SMILES: CCN(CC)CCNC(=O)c1ccc2ncc(S(=O)(=O)c3ccc(OC)cc3)c(N3CCC(N4CCCCC4)CC3)c2c1] | 4-([1,4'-bipiperidin]-1'-yl)-N-(2-(diethylamino)ethyl)-3-((4-methoxyphenyl)sulfonyl)quinoline-6-carboxamide |
| 338 | 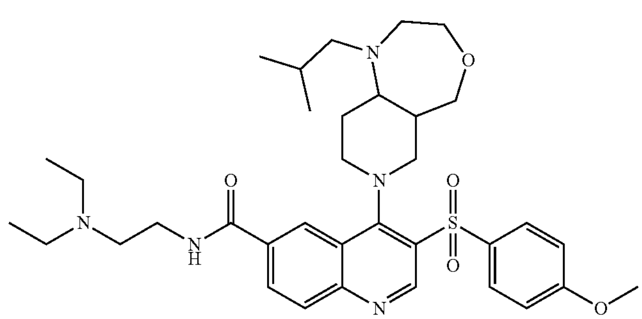 [SMILES: CCN(CC)CCNC(=O)c1ccc2ncc(S(=O)(=O)c3ccc(OC)cc3)c(N3CCC4C(COCCN4CC(C)C)C3)c2c1] | N-(2-(diethylamino)ethyl)-4-(1-isobutyloctahydropyrido[4,3-e][1,4]oxazepin-7(5H)-yl)-3-((4-methoxyphenyl)sulfonyl)quinoline-6-carboxamide |

TABLE 1-continued

| Ex. | Structure | Name |
|---|---|---|
| 339 | 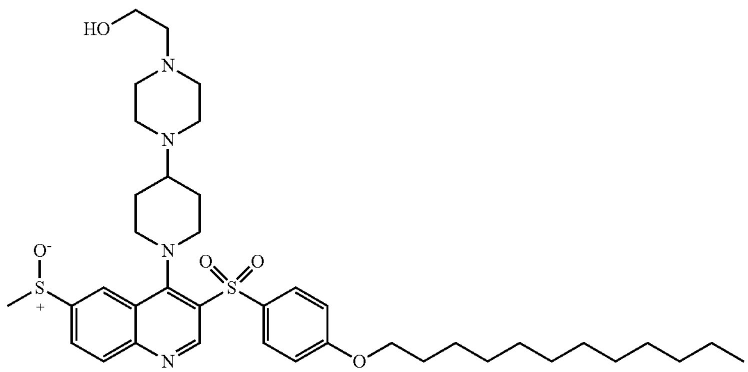 | 2-(4-(1-(3-((4-(dodecyloxy)phenyl)sulfonyl)-6-(methylsulfinyl)quinolin-4-yl)piperidin-4-yl)piperazin-1-yl)ethan-1-ol |
| 340 | 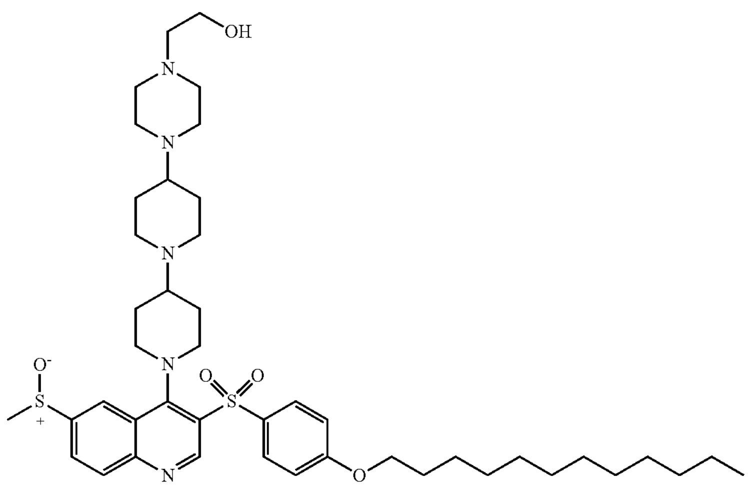 | 2-(4-(1'-(3-((4-(dodecyloxy)phenyl)sulfonyl)-6-(methylsulfinyl)quinolin-4-yl)-[1,4'-bipiperidin]-4-yl)piperazin-1-yl)ethan-1-ol |
| 341 | 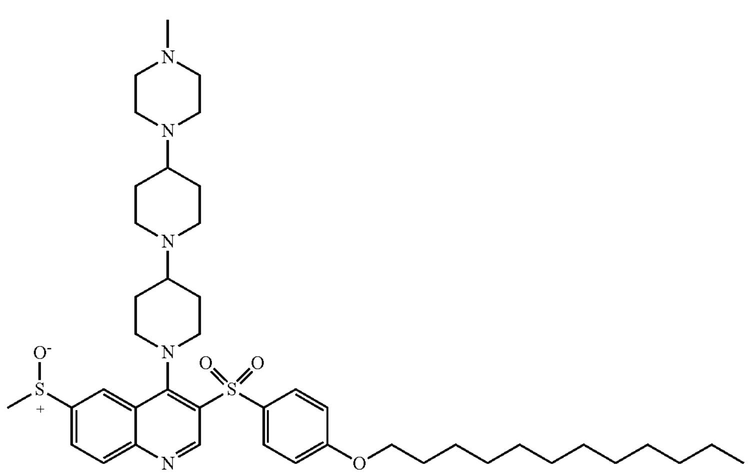 | 3-((4-(dodecyloxy)phenyl)sulfonyl)-4-(4-(4-methylpiperazin-1-yl)-[1,4'-bipiperidin]-1'-yl)-6-(methylsulfinyl)quinoline |

TABLE 1-continued

| Ex. | Structure | Name |
|---|---|---|
| 342 | 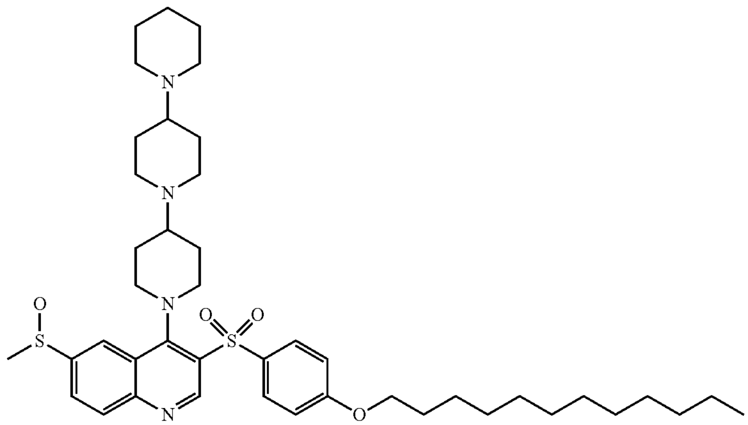 | 4-([1,4':1',4''-terpiperidin]-1''-yl)-3-((4-(dodecyloxy)phenyl)sulfonyl)-6-(methylsulfinyl)quinoline |
| 343 | 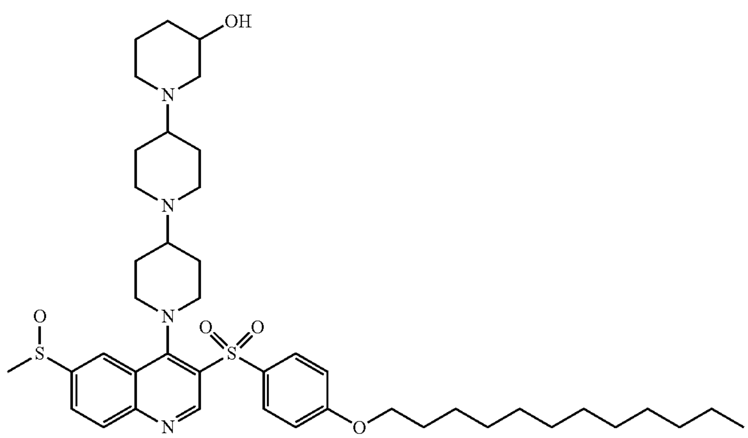 | 1''-(3-((4-(dodecyloxy)phenyl)sulfonyl)-6-(methylsulfinyl)quinolin-4-yl)-[1,4':1',4''-terpiperidin]-3-ol |
| 344 | 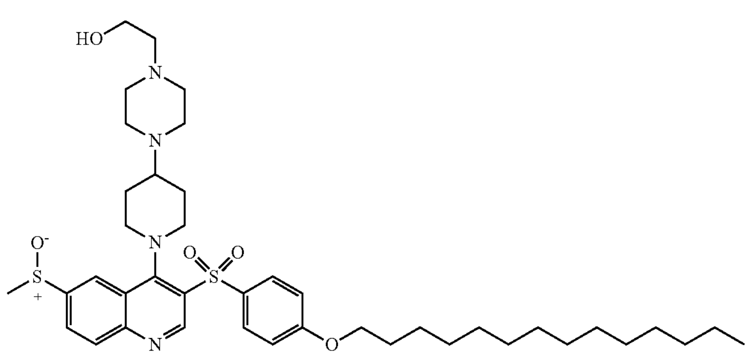 | 2-(4-(1-(6-(methylsulfinyl)-3-((4-(tetradecyloxy)phenyl)sulfonyl)quinolin-4-yl)piperidin-4-yl)piperazin-1-yl)ethan-1-ol |

TABLE 1-continued

| Ex. | Structure | Name |
|---|---|---|
| 345 | 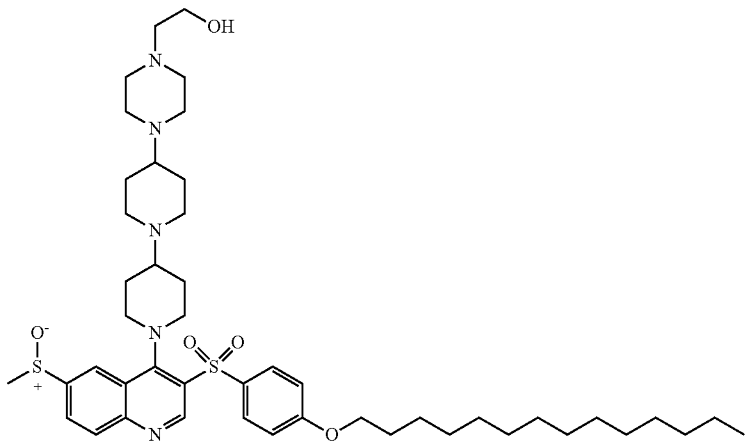 | 2-(4-(1'-(6-(methylsulfinyl)-3-((4-(tetradecyloxy)phenyl)sulfonyl)quinolin-4-yl)-[1,4'-bipiperidin]-4-yl)piperazin-1-yl)ethan-1-ol |
| 346 | 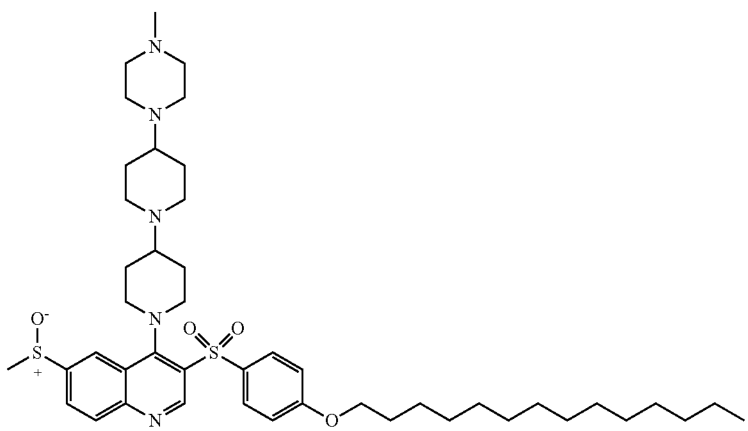 | 4-(4-(4-methylpiperazin-1-yl)-[1,4'-bipiperidin]-1'-yl)-6-(methylsulfinyl)-3-((4-(tetradecyloxy)phenyl)sulfonyl)quinoline |
| 347 | 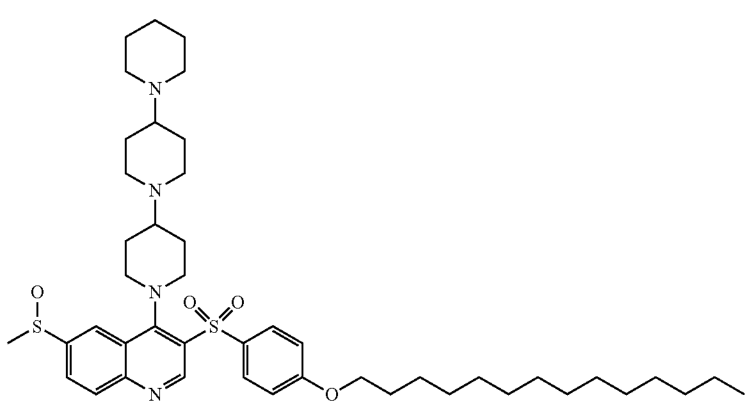 | 4-([1,4':1',4''-terpiperidin]-1''-yl)-6-(methyl($\lambda^1$-oxidanyl)-$\lambda^3$-sulfanyl)-3-((4-(tetradecyloxy)phenyl)sulfonyl)quinoline |

TABLE 1-continued

| Ex. | Structure | Name |
|---|---|---|
| 348 | 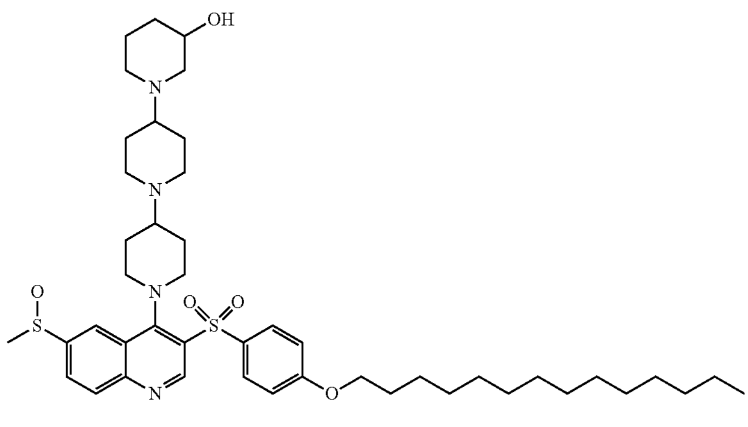 | 1''-(6-(methyl(λ¹-oxidanyl)-λ³-sulfanyl)-3-((4-(tetradecyloxy)phenyl)sulfonyl)quinolin-4-yl)-[1,4':1',4''-terpiperidin]-3-ol |
| 349 | 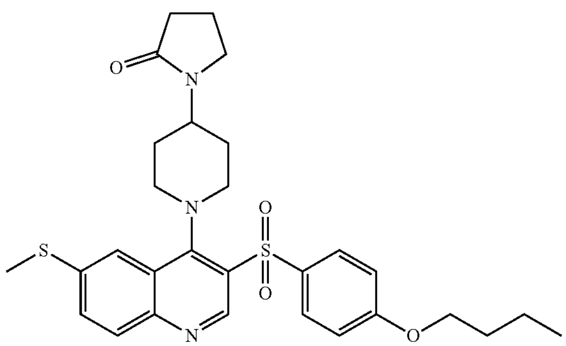 [SMILES: CCCCOc1ccc(S(=O)(=O)c2cnc3ccc(SC)cc3c2N2CCC(N3CCCC3=O)CC2)cc1] | 1-(1-(3-((4-butoxyphenyl)sulfonyl)-6-(methylthio)quinolin-4-yl)piperidin-4-yl)pyrrolidin-2-one |
| 350 | 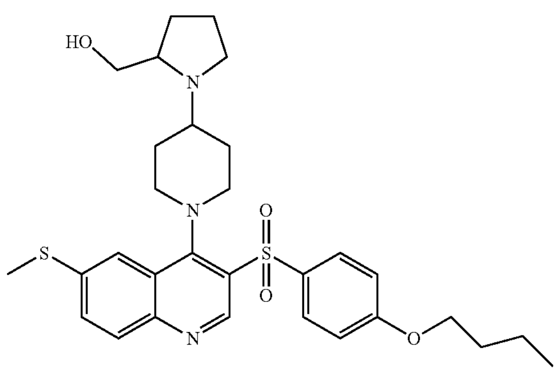 [SMILES: CCCCOc1ccc(S(=O)(=O)c2cnc3ccc(SC)cc3c2N2CCC(N3CCCC3CO)CC2)cc1] | (1-(1-(3-((4-butoxyphenyl)sulfonyl)-6-(methylthio)quinolin-4-yl)piperidin-4-yl)pyrrolidin-2-yl)methanol |
| 351 | 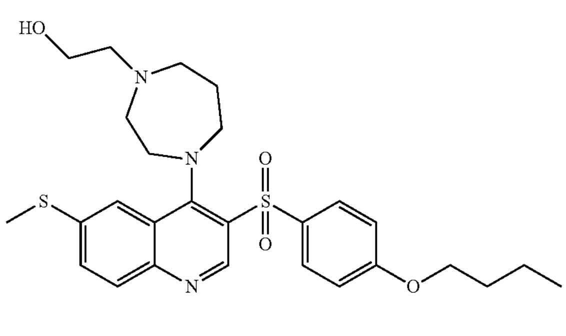 [SMILES: CCCCOc1ccc(S(=O)(=O)c2cnc3ccc(SC)cc3c2N2CCCN(CCO)CC2)cc1] | 2-(4-(3-((4-butoxyphenyl)sulfonyl)-6-(methylthio)quinolin-4-yl)-1,4-diazepan-1-yl)ethan-1-ol |

TABLE 1-continued

| Ex. | Structure | Name |
|---|---|---|
| 352 | 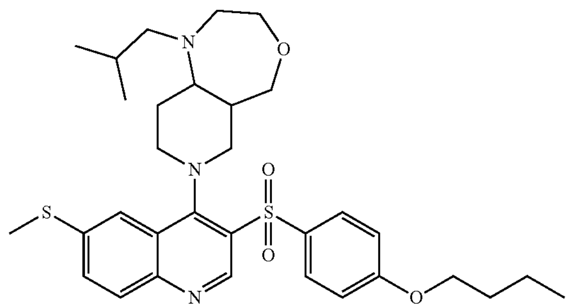 [SMILES: CCCCOc1ccc(S(=O)(=O)c2cnc3ccc(SC)cc3c2N2CCC3C(COCCN3CC(C)C)C2)cc1] | 7-(3-((4-butoxyphenyl)sulfonyl)-6-(methylthio)quinolin-4-yl)-1-isobutyldecahydropyrido[4,3-e][1,4]oxazepine |
| 353 | 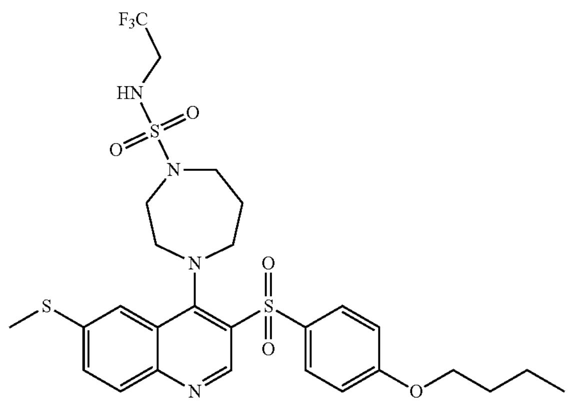 [SMILES: CCCCOc1ccc(S(=O)(=O)c2cnc3ccc(SC)cc3c2N2CCCN(S(=O)(=O)NCC(F)(F)F)CC2)cc1] | 4-(3-((4-butoxyphenyl)sulfonyl)-6-(methylthio)quinolin-4-yl)-N-(2,2,2-trifluoroethyl)-1,4-diazepane-1-sulfonamide |
| 354 | 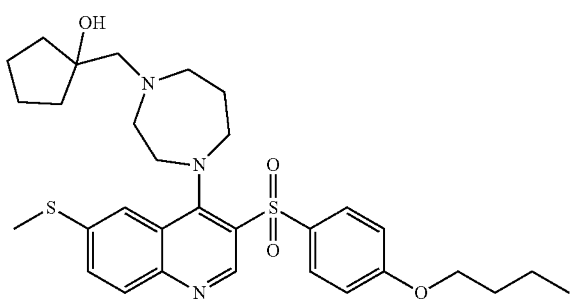 [SMILES: CCCCOc1ccc(S(=O)(=O)c2cnc3ccc(SC)cc3c2N2CCCN(CC3(O)CCCC3)CC2)cc1] | 1-((4-(3-((4-butoxyphenyl)sulfonyl)-6-(methylthio)quinolin-4-yl)-1,4-diazepan-1-yl)methyl)cyclopentan-1-ol |
| 355 | 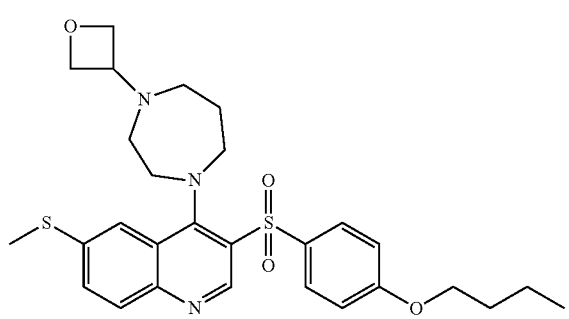 [SMILES: CCCCOc1ccc(S(=O)(=O)c2cnc3ccc(SC)cc3c2N2CCCN(C3COC3)CC2)cc1] | 3-((4-butoxyphenyl)sulfonyl)-6-(methylthio)-4-(4-(oxetan-3-yl)-1,4-diazepan-1-yl)quinoline |

TABLE 1-continued

| Ex. | Structure | Name |
|---|---|---|
| 356 | 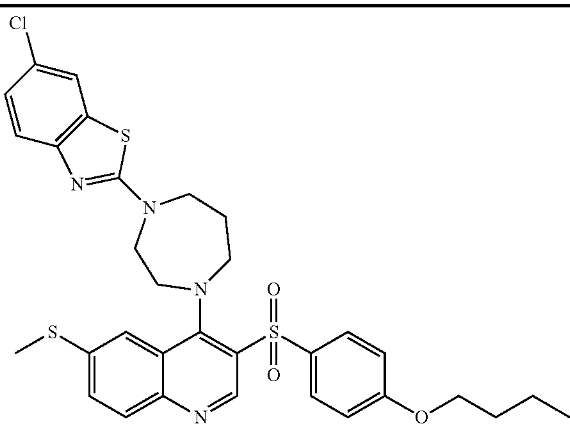 | 2-(4-(3-((4-butoxyphenyl)sulfonyl)-6-(methylthio)quinolin-4-yl)-1,4-diazepan-1-yl)-6-chlorobenzo[d]thiazole |
| 357 | 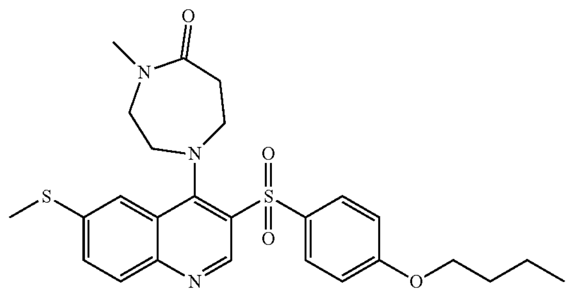 [SMILES: CCCCOc1ccc(S(=O)(=O)c2cnc3ccc(SC)cc3c2N2CCC(=O)N(C)CC2)cc1] | 1-(3-((4-butoxyphenyl)sulfonyl)-6-(methylthio)quinolin-4-yl)-4-methyl-1,4-diazepan-5-one |
| 358 | 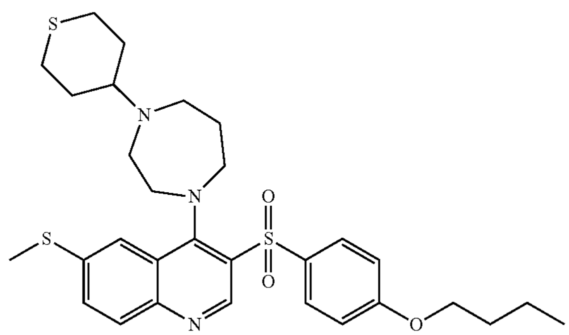 [SMILES: CCCCOc1ccc(S(=O)(=O)c2cnc3ccc(SC)cc3c2N2CCCN(C3CCSCC3)CC2)cc1] | 3-((4-butoxyphenyl)sulfonyl)-6-(methylthio)-4-(4-(tetrahydro-2H-thiopyran-4-yl)-1,4-diazepan-1-yl)quinoline |
| 359 | 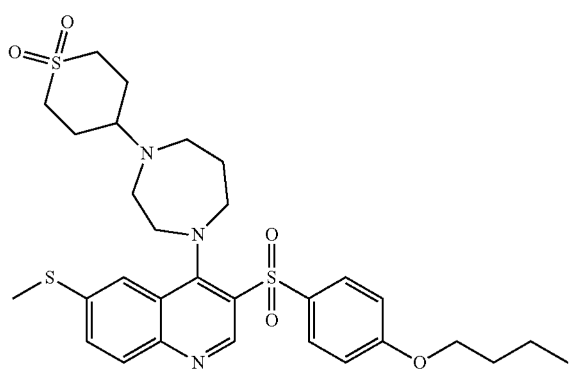 [SMILES: CCCCOc1ccc(S(=O)(=O)c2cnc3ccc(SC)cc3c2N2CCCN(C3CCS(=O)(=O)CC3)CC2)cc1] | 4-(4-(3-((4-butoxyphenyl)sulfonyl)-6-(methylthio)quinolin-4-yl)-1,4-diazepan-1-yl)tetrahydro-2H-thiopyran 1,1-dioxide |
| 360 | 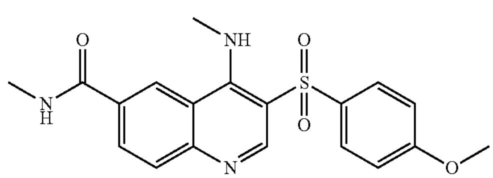 | 3-((4-methoxyphenyl)sulfonyl)-N-methyl-4-(methylamino)quinoline-6-carboxamide |

TABLE 1-continued

| Ex. | Structure | Name |
|---|---|---|
| 361 | 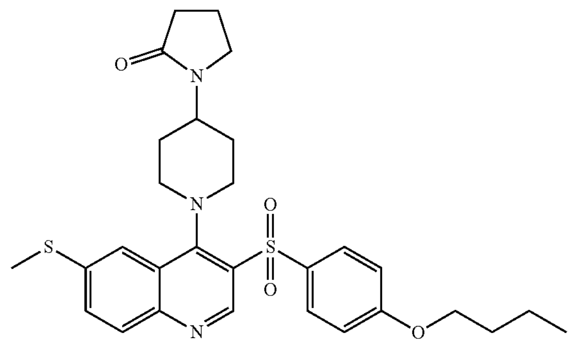 [SMILES: CCCCOc1ccc(S(=O)(=O)c2cnc3ccc(SC)cc3c2N2CCC(N3CCCC3=O)CC2)cc1] | 1-(1-(3-((4-butoxyphenyl)sulfonyl)-6-(methylthio)quinolin-4-yl)piperidin-4-yl)pyrrolidin-2-one |
| 362 | 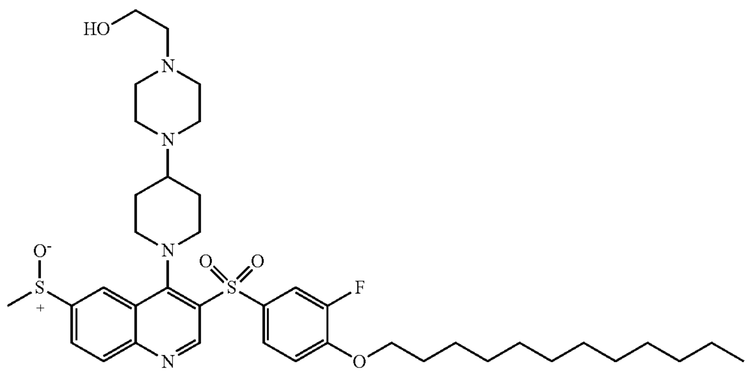 | 2-(4-(1-(3-((4-(dodecyloxy)-3-fluorophenyl)sulfonyl)-6-(methylsulfinyl)quinolin-4-yl)piperidin-4-yl)piperazin-1-yl)ethanol |
| 363 | 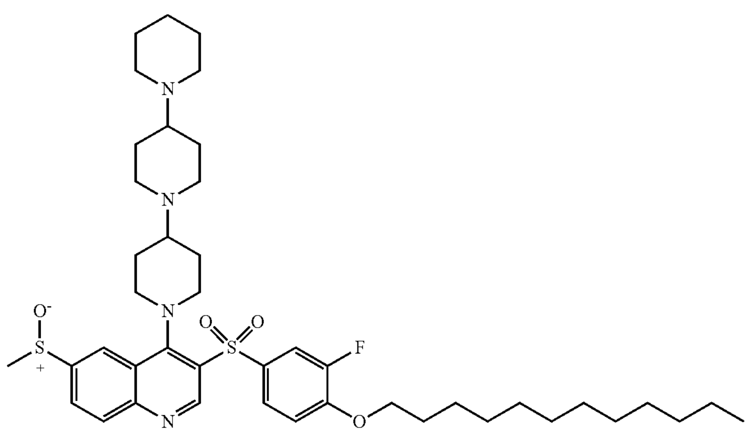 | 4-([1,4':1',4''-terpiperidin]-1''-yl)-3-((4-(dodecyloxy)-3-fluorophenyl)sulfonyl)-6-(methylsulfinyl)quinoline |
| 364 | 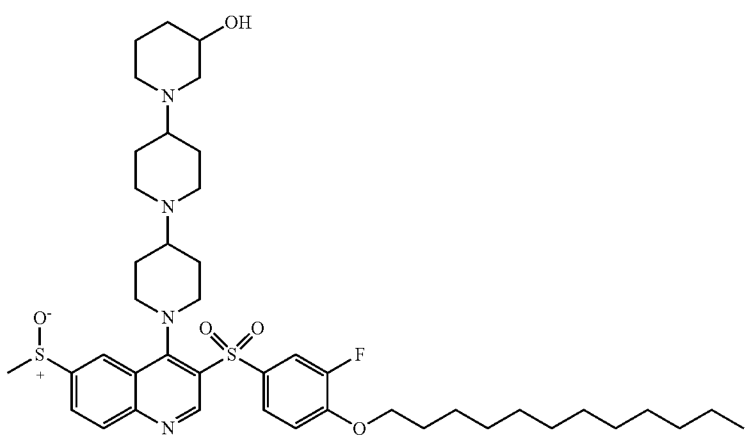 | 1''-(3-((4-(dodecyloxy)-3-fluorophenyl)sulfonyl)-6-(methylsulfinyl)quinolin-4-yl)-[1,4':1',4''-terpiperidin]-3-ol |

TABLE 1-continued

| Ex. | Structure | Name |
|---|---|---|
| 365 | 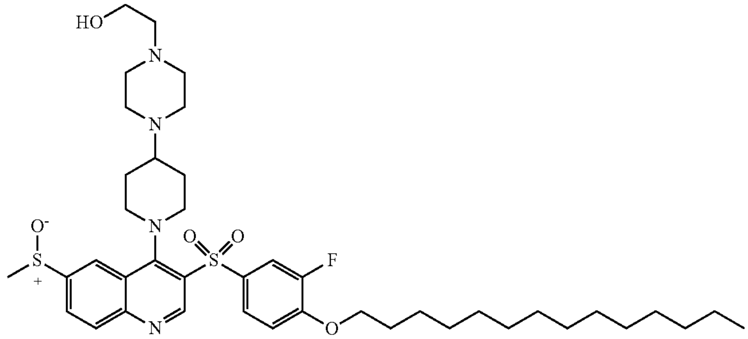 | 2-(4-(1-(3-((3-fluoro-4-(tetradecyloxy)phenyl)sulfonyl)-6-(methylsulfinyl)quinolin-4-yl)piperidin-4-yl)piperazin-1-yl)ethanol |
| 366 | 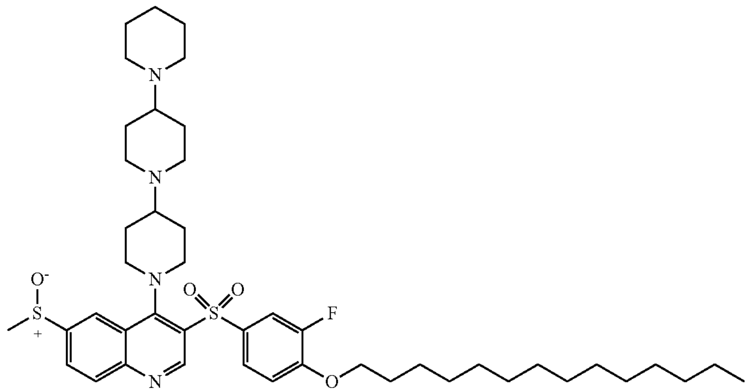 | 4-([1,4':1',4''-terpiperidin]-1''-yl)-3-((3-fluoro-4-(tetradecyloxy)phenyl)sulfonyl)-6-(methylsulfinyl)quinoline |
| 367 | 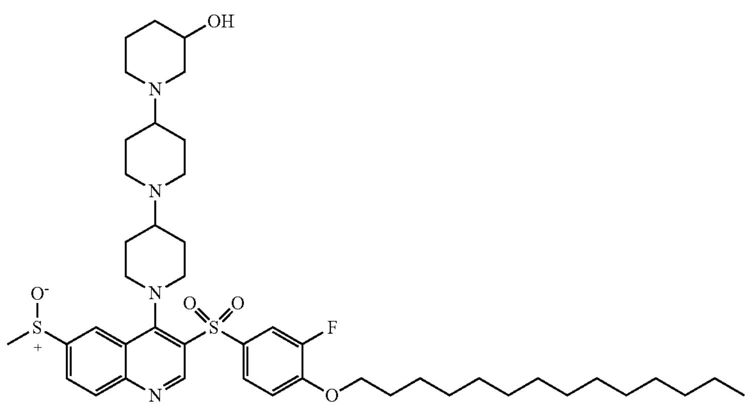 | 1''-(3-((3-fluoro-4-(tetradecyloxy)phenyl)sulfonyl)-6-(methylsulfinyl)quinolin-4-yl)-[1,4':1',4'']-terpiperidin]-3-ol |
| 368 | 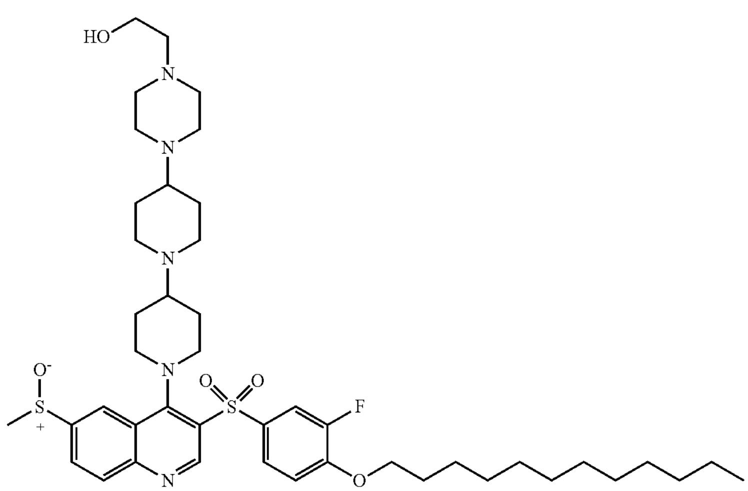 | 2-(4-(1'-(3-((4-(dodecyloxy)-3-fluorophenyl)sulfonyl)-6-(methylsulfinyl)quinolin-4-yl)-[1,4'-bipiperidin]-4-yl)piperazin-1-yl)ethanol |

TABLE 1-continued

| Ex. | Structure | Name |
|---|---|---|
| 369 | 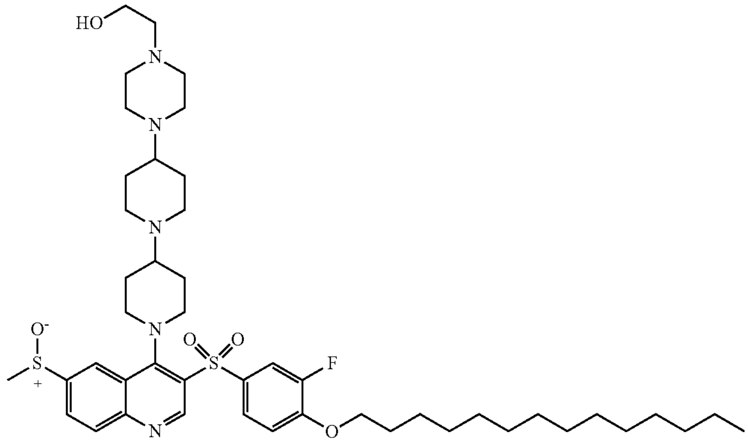 | 2-(4-(1'-(3-((3-fluoro-4-(tetradecyloxy)phenyl)sulfonyl)-6-(methylsulfinyl)quinolin-4-yl)-[1,4'-bipiperidin]-4-yl)piperazin-1-yl)ethanol |
| 370 | 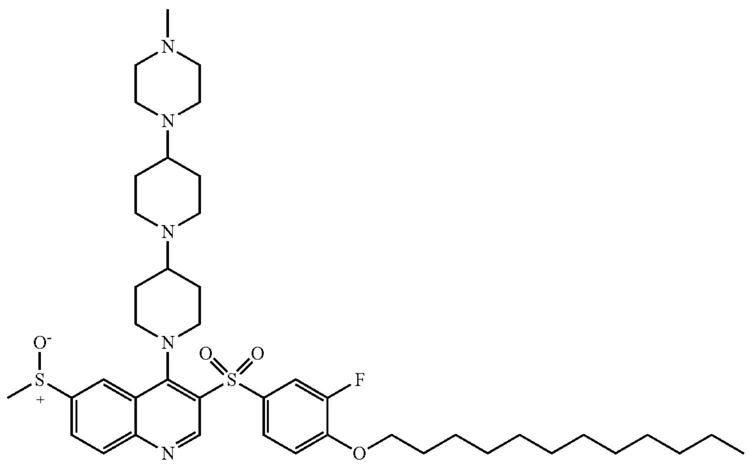 | 3-((4-(dodecyloxy)-3-fluorophenyl)sulfonyl)-4-(4-(4-methylpiperazin-1-yl)-[1,4'-bipiperidin]-1'-yl)-6-(methylsulfinyl)quinoline |
| 371 | 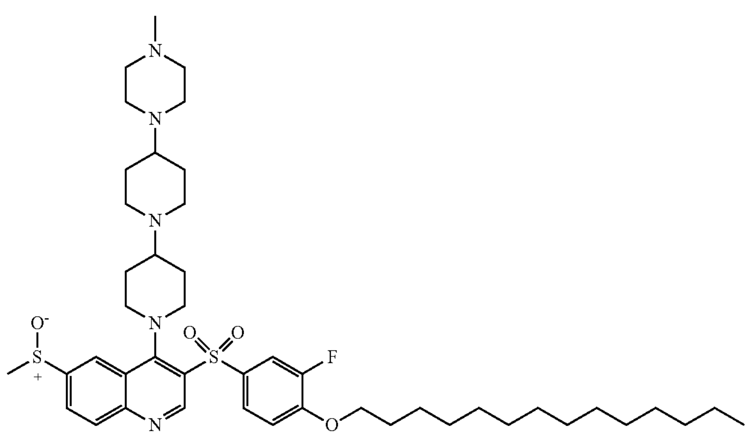 | 3-((3-fluoro-4-(tetradecyloxy)phenyl)sulfonyl)-4-(4-(4-methylpiperazin-1-yl)-[1,4'-bipiperidin]-1'-yl)-6-(methylsulfinyl)quinoline |

TABLE 1-continued
| Ex. | Structure | Name |
|---|---|---|
| 372 | 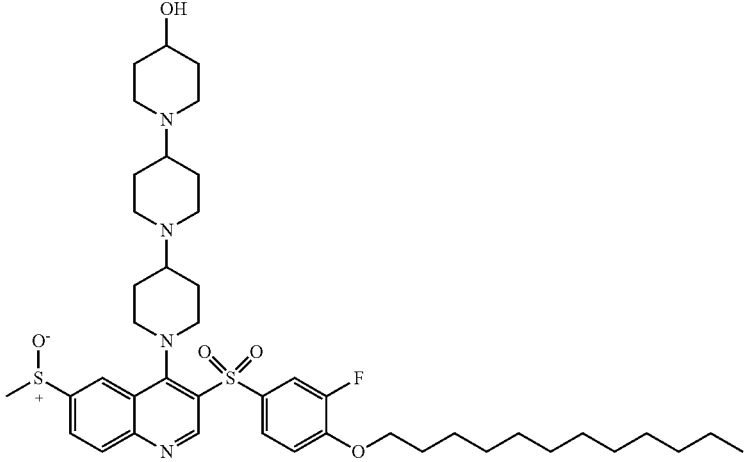 | 1''-(3-((4-(dodecyloxy)-3-fluorophenyl)sulfonyl)-6-(methylsulfinyl)quinolin-4-yl)-[1,4':1',4''-terpiperidin]-4-ol |
| 373 | 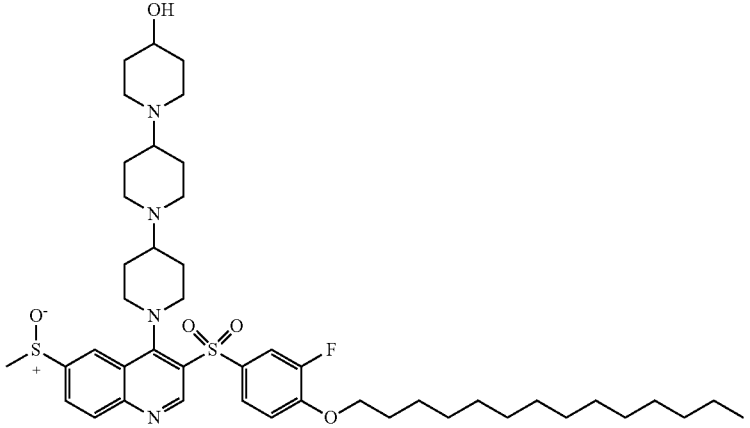 | 1''-(3-((3-fluoro-4-(tetradecyloxy)phenyl)sulfonyl)-6-(methylsulfinyl)quinolin-4-yl)-[1,4':1',4''-terpiperidin]-4-ol |
| 374 | 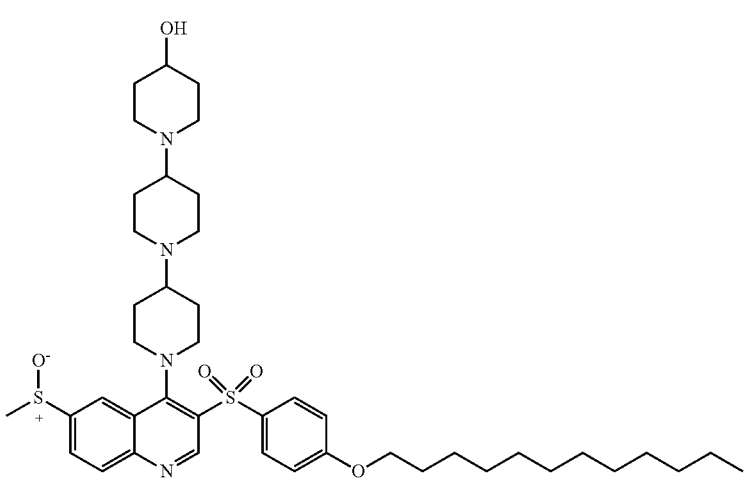 | 1''-(3-((4-(dodecyloxy)phenyl)sulfonyl)-6-(methylsulfinyl)quinolin-4-yl)-[1,4':1',4''-terpiperidin]-4-ol |

TABLE 1-continued

| Ex. | Structure | Name |
|---|---|---|
| 375 | 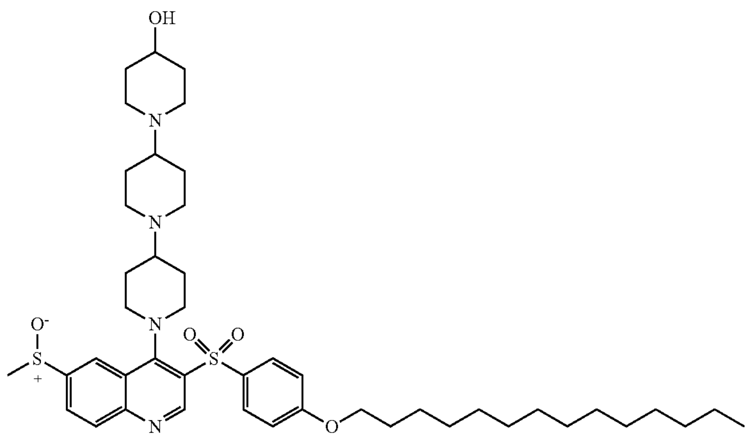 | 1''-(6-(methylsulfinyl)-3-((4-(tetradecyloxy)phenyl)sulfonyl)quinolin-4-yl)-[1,4':1',4''-terpiperidin]-4-ol |
| 376 | 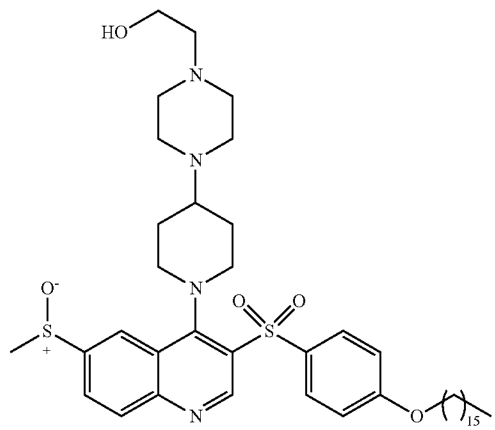 | 2-(4-(1-(3-((4-(hexadecyloxy)phenyl)sulfonyl)-6-(methylsulfinyl)quinolin-4-yl)piperidin-4-yl)piperazin-1-yl)ethanol |
| 377 | 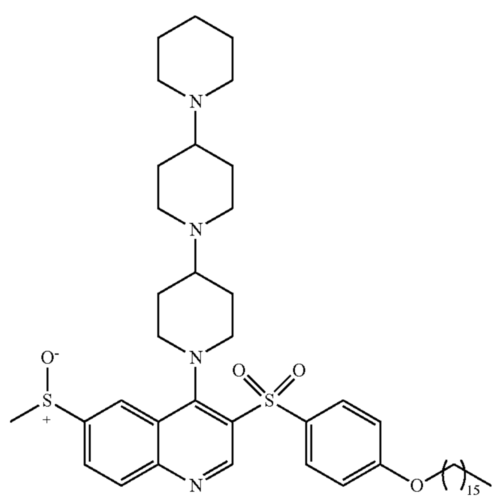 | 4-([1,4':1',4''-terpiperidin]-1''-yl)-3-((4-(hexadecyloxy)phenyl)sulfonyl)-6-(methylsulfinyl)quinoline |

TABLE 1-continued
| Ex. | Structure | Name |
|---|---|---|
| 378 | 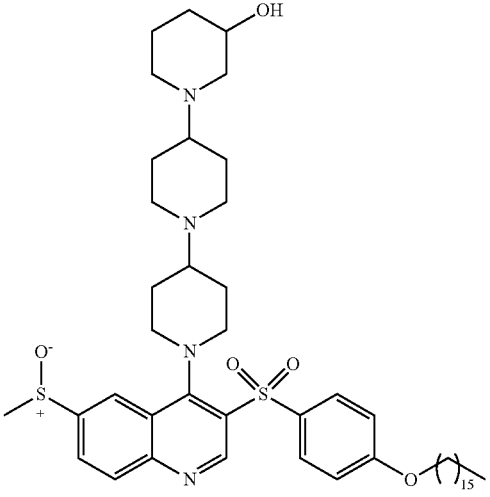 | 1''-(3-((4-(hexadecyloxy)phenyl)sulfonyl)-6-(methylsulfinyl)quinolin-4-yl)-[1,4':1',4''-terpiperidin]-3-ol |
| 379 | 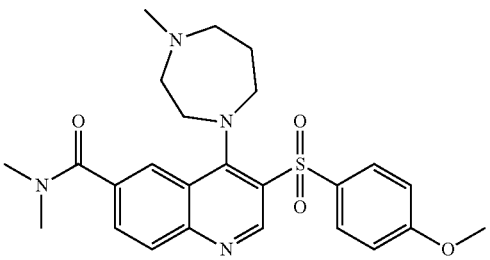 | 3-((4-methoxyphenyl)sulfonyl)-N,N-dimethyl-4-(4-methyl-1,4-diazepan-1-yl)quinoline-6-carboxamide |
| 380 | 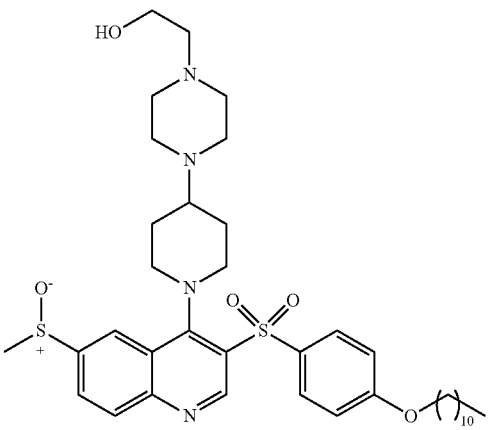 | 2-(4-(1-(6-(methylsulfinyl)-3-((4-(undecyloxy)phenyl)sulfonyl)quinolin-4-yl)piperidin-4-yl)piperazin-1-yl)ethanol |

TABLE 1-continued

| Ex. | Structure | Name |
|---|---|---|
| 381 | 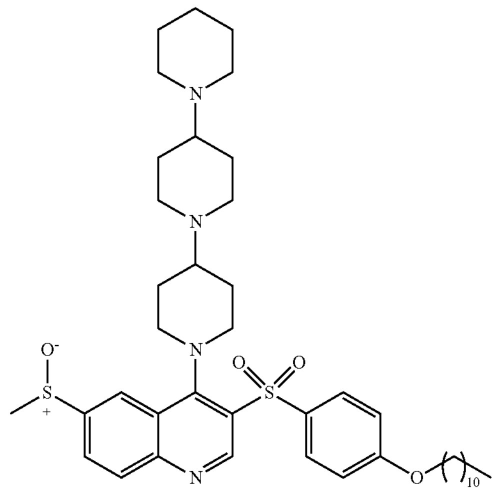 | 4-([1,4':1',4''-terpiperidin]-1''-yl)-6-(methylsulfinyl)-3-((4-(undecyloxy)phenyl)sulfonyl)quinoline |
| 382 | 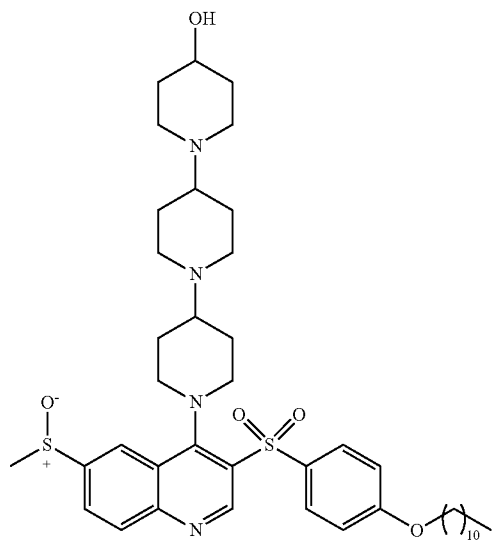 | 1''-(6-(methylsulfinyl)-3-((4-(undecyloxy)phenyl)sulfonyl)quinolin-4-yl)-[1,4':1',4''-terpiperidin]-4-ol |
| 383 | 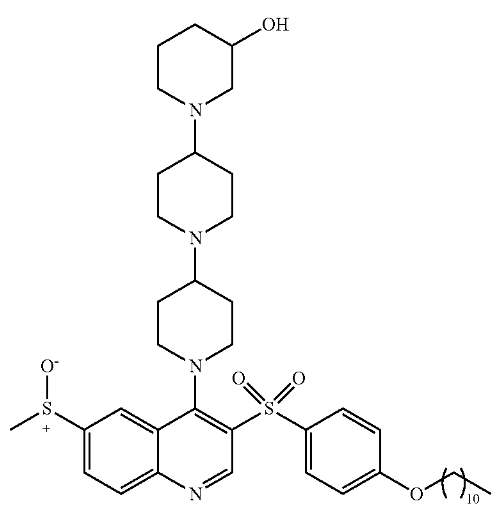 | 1''-(6-(methylsulfinyl)-3-((4-(undecyloxy)phenyl)sulfonyl)quinolin-4-yl)-[1,4':1',4''-terpiperidin]-3-ol |

TABLE 1-continued

| Ex. | Structure | Name |
|---|---|---|
| 384 | 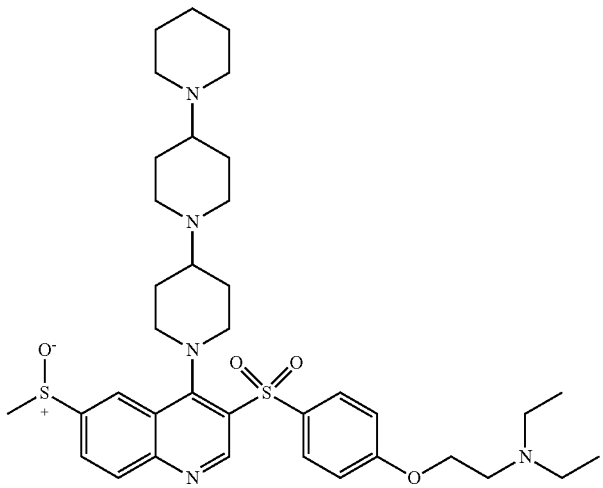 | 2-(4-((4-(([1,4':1',4''-terpiperidin]-1''-yl)-6-(methylsulfinyl)quinolin-3-yl)sulfonyl)phenoxy)-N,N-diethylethanamine |
| 385 | 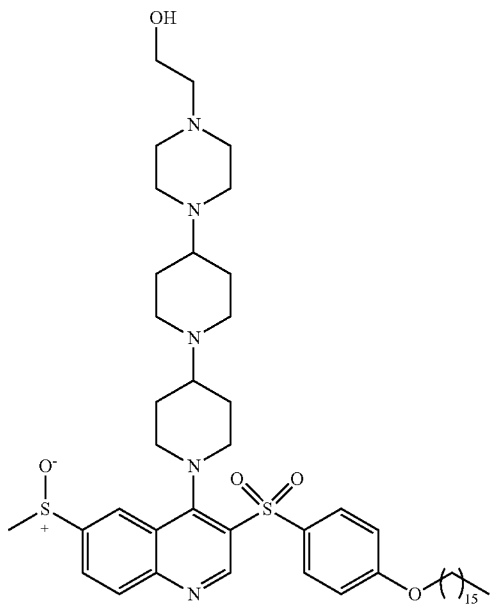 | 2-(4-(1'-(3-((4-(hexadecyloxy)phenyl)sulfonyl)-6-(methylsulfinyl)quinolin-4-yl)-[1,4'-bipiperidin]-4-yl)piperazin-1-yl)ethanol |
| 386 | 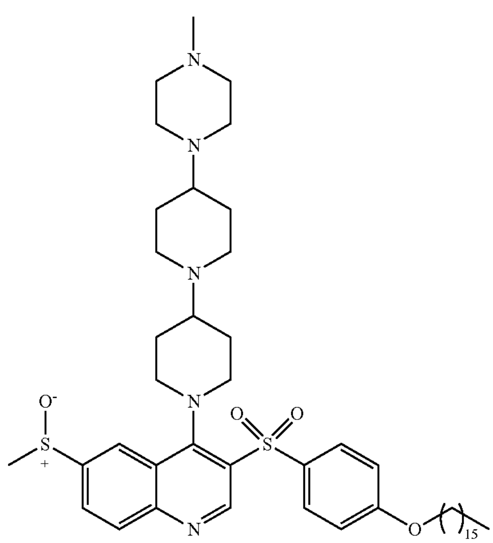 | 3-((4-(hexadecyloxy)phenyl)sulfonyl)-4-(4-(4-methylpiperazin-1-yl)-[1,4'-bipiperidin]-1'-yl)-6-(methylsulfinyl)quinoline |

TABLE 1-continued
| Ex. | Structure | Name |
|---|---|---|
| 387 | 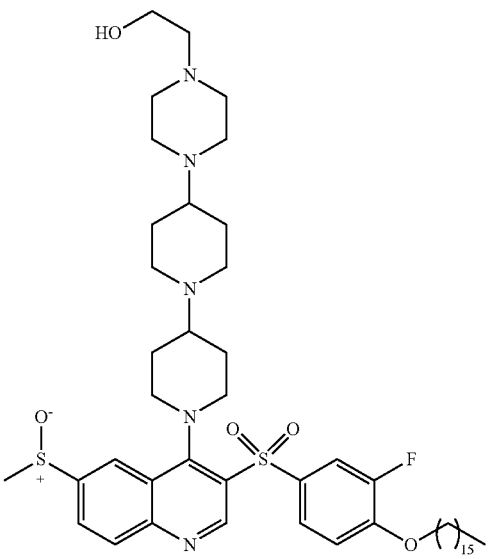 | 2-(4-(1'-(3-((3-fluoro-4-(hexadecyloxy)phenyl)sulfonyl)-6-(methylsulfinyl)quinolin-4-yl)-[1,4'-bipiperidin]-4-yl)piperazin-1-yl)ethanol |
| 388 | 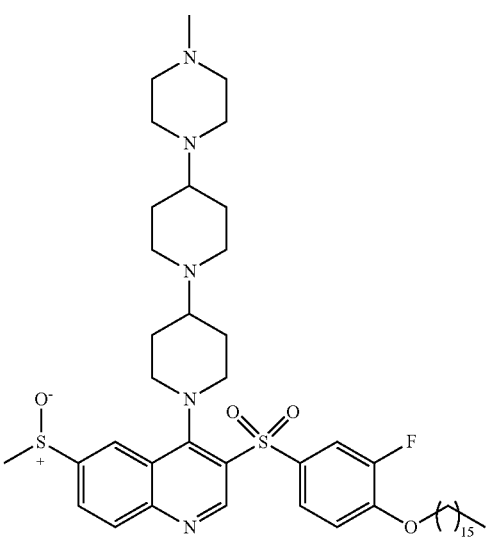 | 3-((3-fluoro-4-(hexadecyloxy)phenyl)sulfonyl)-4-(4-(4-methylpiperazin-1-yl)-[1,4'-bipiperidin]-1'-yl)-6-(methylsulfinyl)quinoline |
| 389 | 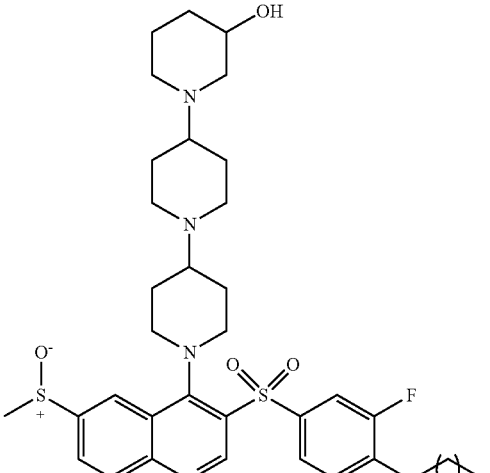 | 1''-(3-((3-fluoro-4-(hexadecyloxy)phenyl)sulfonyl)-6-(methylsulfinyl)quinolin-4-yl)-[1,4':1',4''-terpiperidin]-3-ol |

| Ex. | Structure | Name |
|---|---|---|
| 390 | 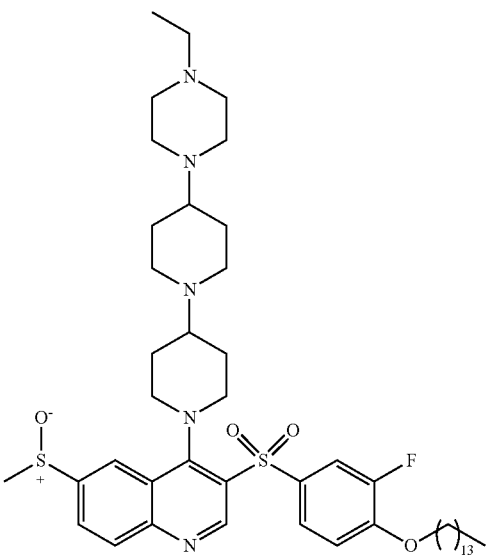 | 4-(4-(4-ethylpiperazin-1-yl)-[1,4'-bipiperidin]-1'-yl)-3-((3-fluoro-4-(tetradecyloxy)phenyl)sulfonyl)-6-(methylsulfinyl)quinoline |
| 391 | 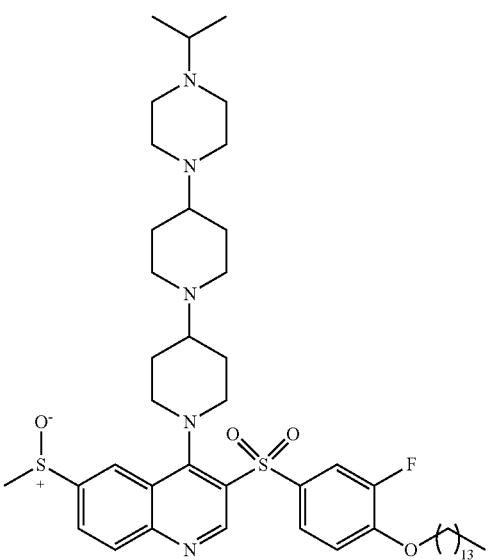 | 3-((3-fluoro-4-(tetradecyloxy)phenyl)sulfonyl)-4-(4-(4-isopropylpiperazin-1-yl)-[1,4'-bipiperidin]-1'-yl)-6-(methylsulfinyl)quinoline |

TABLE 1-continued

| Ex. | Structure | Name |
|---|---|---|
| 392 | 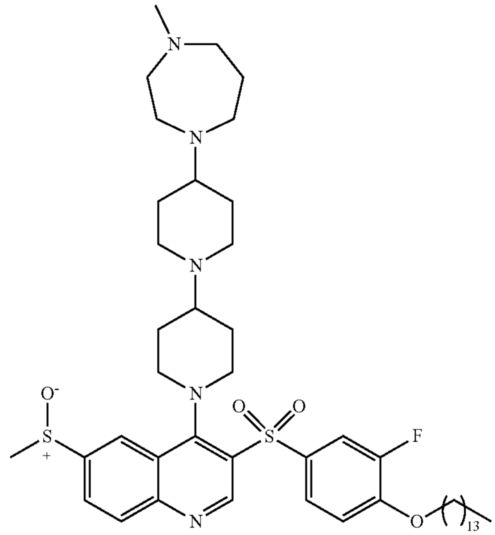 | 3-((3-fluoro-4-(tetradecyloxy)phenyl)sulfonyl)-4-(4-(4-methyl-1,4-diazepan-1-yl)-[1,4'-bipiperidin]-1'-yl)-6-(methylsulfinyl)quinoline |
| 393 | 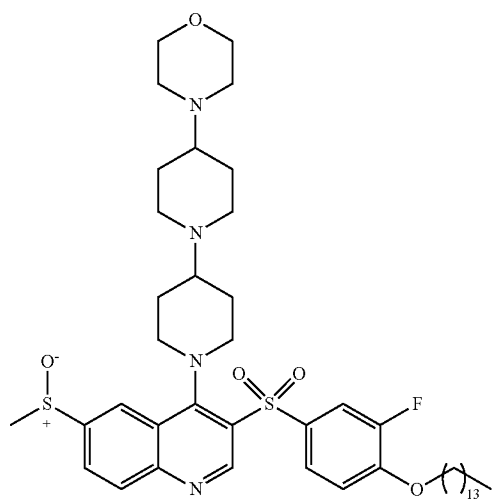 | 4-(1'-(3-((3-fluoro-4-(tetradecyloxy)phenyl)sulfonyl)-6-(methylsulfinyl)quinolin-4-yl)-[1,4'-bipiperidin]-4-yl)morpholine |
| 394 | 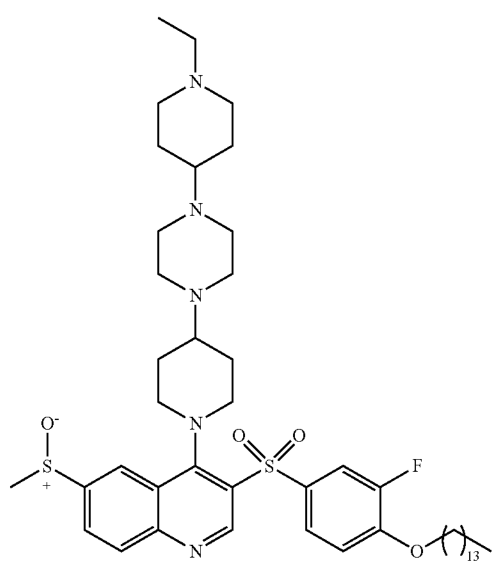 | 4-(4-(4-(1-ethylpiperidin-4-yl)piperazin-1-yl)piperidin-1-yl)-3-((3-fluoro-4-(tetradecyloxy)phenyl)sulfonyl)-6-(methylsulfinyl)quinoline |

TABLE 1-continued
| Ex. | Structure | Name |
|---|---|---|
| 395 | 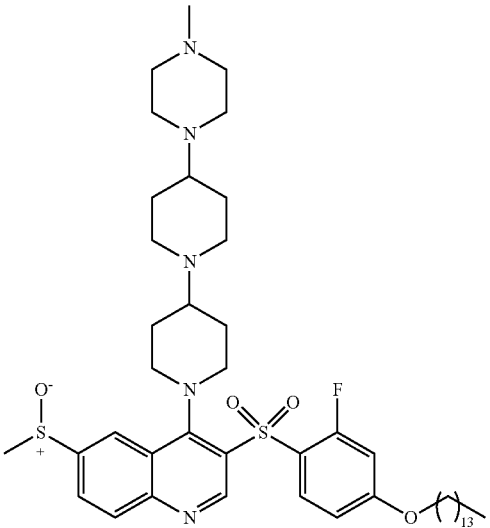 | 3-((2-fluoro-4-(tetradecyloxy)phenyl)sulfonyl)-4-(4-(4-methylpiperazin-1-yl)-[1,4'-bipiperidin]-1'-yl)-6-(methylsulfinyl)quinoline |
| 396 | 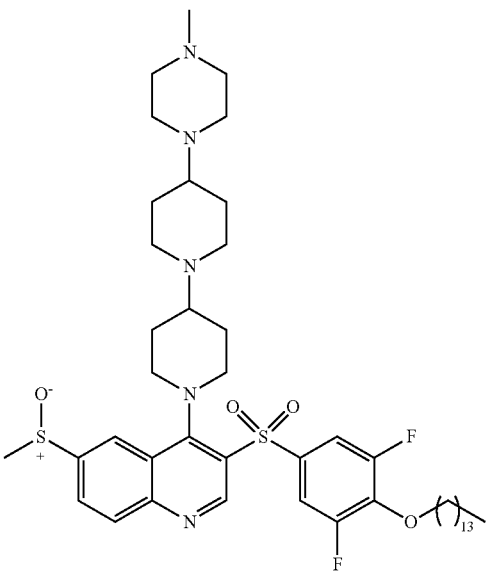 | 3-((3,5-difluoro-4-(tetradecyloxy)phenyl)sulfonyl)-4-(4-(4-methylpiperazin-1-yl)-[1,4'-bipiperidin]-1'-yl)-6-(methylsulfinyl)quinoline |

TABLE 1-continued

| Ex. | Structure | Name |
|---|---|---|
| 397 | 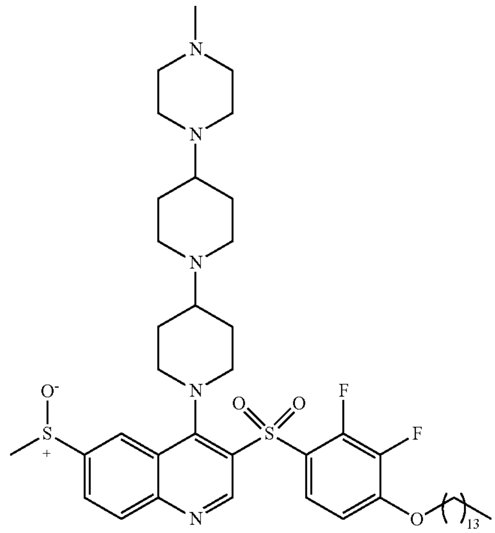 | 3-((2,3-difluoro-4-(tetradecyloxy)phenyl)sulfonyl)-4-(4-(4-methylpiperazin-1-yl)-[1,4'-bipiperidin]-1'-yl)-6-(methylsulfinyl)quinoline |
| 398 | 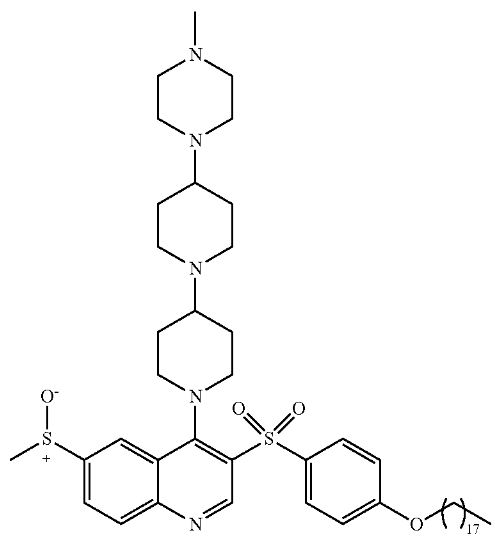 | 4-(4-(4-methylpiperazin-1-yl)-[1,4'-bipiperidin]-1'-yl)-6-(methylsulfinyl)-3-((4-(octadecyloxy)phenyl)sulfonyl)quinoline |
| 399 | 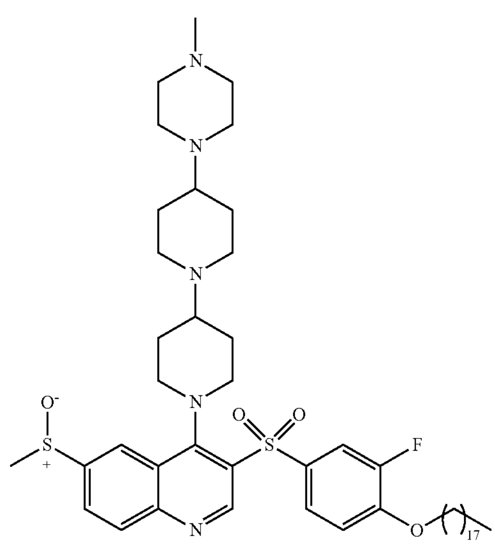 | 3-((3-fluoro-4-(octadecyloxy)phenyl)sulfonyl)-4-(4-(4-methylpiperazin-1-yl)-[1,4'-bipiperidin]-1'-yl)-6-(methylsulfinyl)quinoline |

TABLE 1-continued

| Ex. | Structure | Name |
|---|---|---|
| 400 | 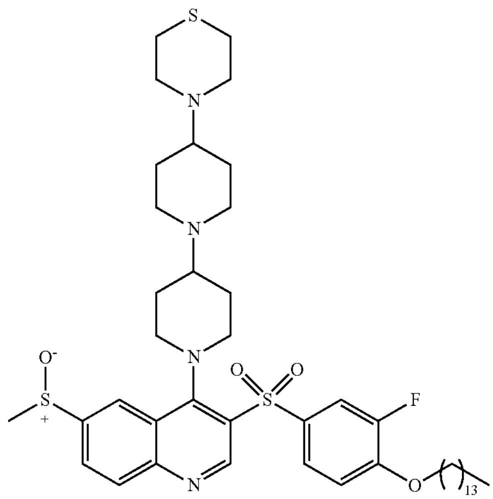 | 4-(1'-(3-((3-fluoro-4-(tetradecyloxy)phenyl)sulfonyl)-6-(methylsulfinyl)quinolin-4-yl)-[1,4'-bipiperidin]-4-yl)thiomorpholine |
| 401 | 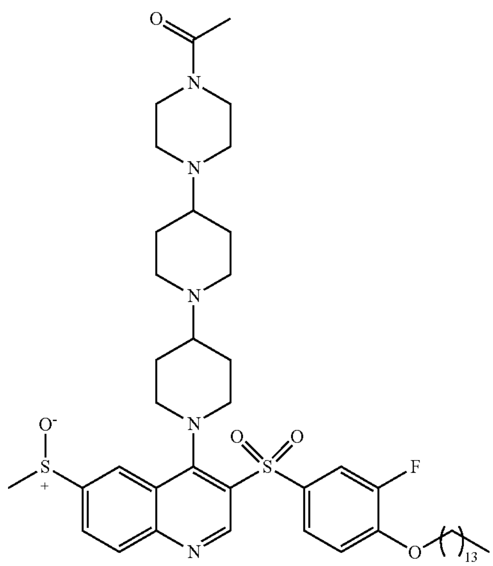 | 1-(4-(1'-(3-((3-fluoro-4-(tetradecyloxy)phenyl)sulfonyl)-6-(methylsulfinyl)quinolin-4-yl)-[1,4'-bipiperidin]-4-yl)piperazin-1-yl)ethanone |
| 402 | 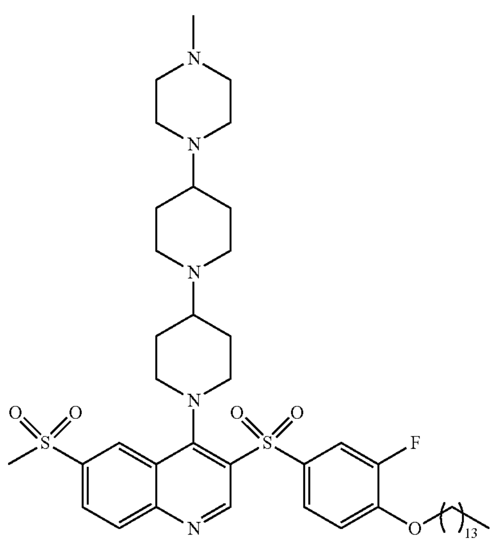 | 3-((3-fluoro-4-(tetradecyloxy)phenyl)sulfonyl)-4-(4-(4-methylpiperazin-1-yl)-[1,4'-bipiperidin]-1'-yl)-6-(methylsulfonyl)quinoline |

TABLE 1-continued
| Ex. | Structure | Name |
|---|---|---|
| 403 | 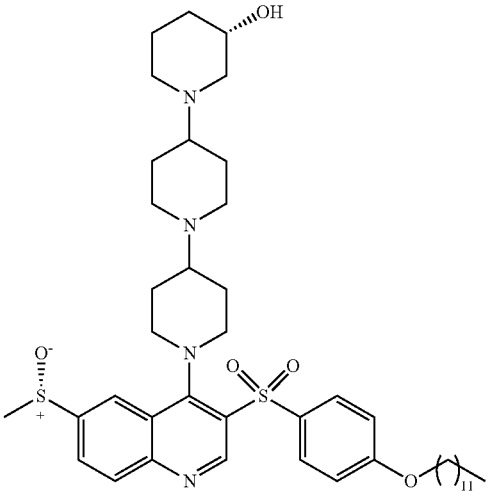 | (S)-1''-(3-((4-(dodecyloxy)phenyl)sulfonyl)-6-((S)-methylsulfinyl)quinolin-4-yl)-[1,4':1',4''-terpiperidin]-3-ol |
| 404 | 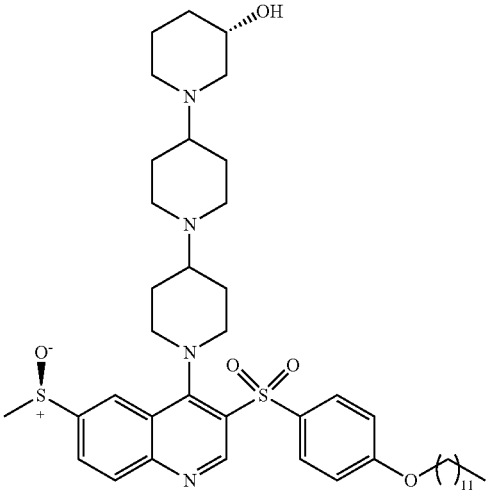 | (S)-1''-(3-((4-(dodecyloxy)phenyl)sulfonyl)-6-((R)-methylsulfinyl)quinolin-4-yl)-[1,4':1',4''-terpiperidin]-3-ol |
| 405 | 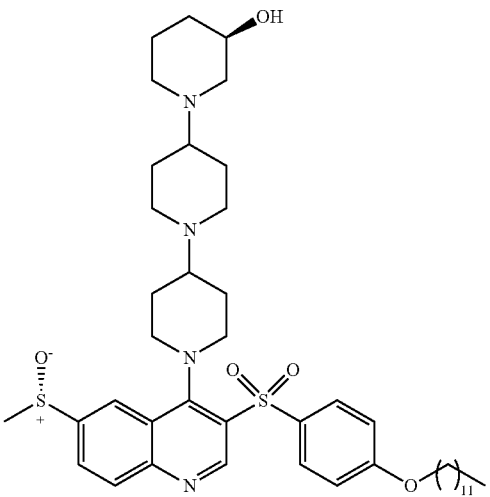 | (R)-1''-(3-((4-(dodecyloxy)phenyl)sulfonyl)-6-((S)-methylsulfinyl)quinolin-4-yl)-[1,4':1',4''-terpiperidin]-3-ol |

TABLE 1-continued
| Ex. | Structure | Name |
|---|---|---|
| 406 | 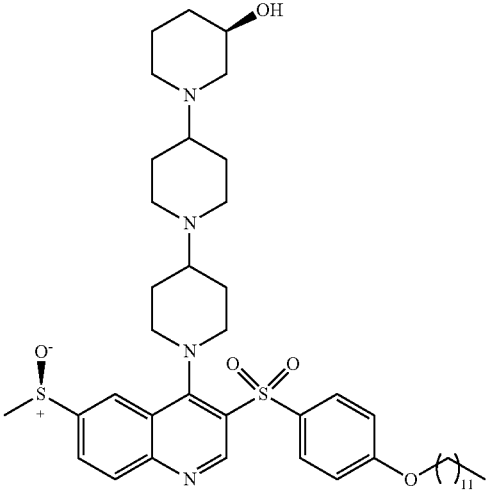 | (R)-1''-(3-((4-(dodecyloxy)phenyl)sulfonyl)-6-((R)-methylsulfinyl)quinolin-4-yl)-[1,4':1',4''-terpiperidin]-3-ol |
| 407 | 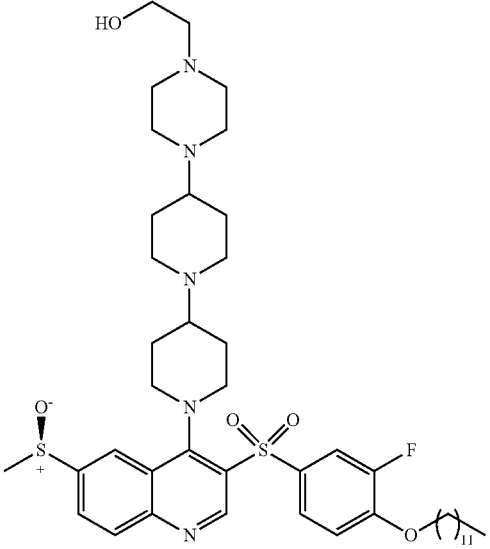 | (R)-2-(4-(1'-(3-((4-(dodecyloxy)-3-fluorophenyl)sulfonyl)-6-(methylsulfinyl)quinolin-4-yl)-[1,4'-bipiperidin]-4-yl)piperazin-1-yl)ethanol |
| 408 | 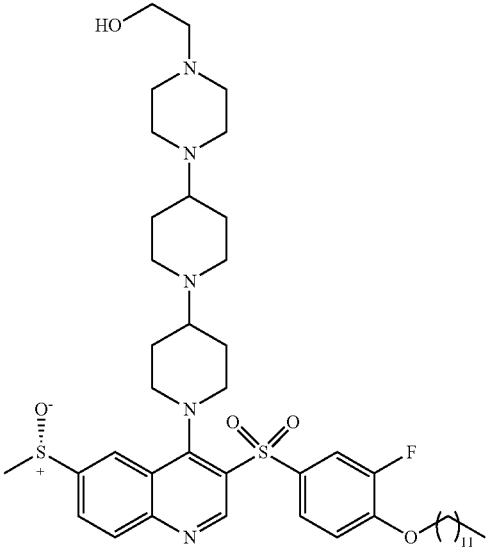 | (S)-2-(4-(1'-(3-((4-(dodecyloxy)-3-fluorophenyl)sulfonyl)-6-(methylsulfinyl)quinolin-4-yl)-[1,4'-bipiperidin]-4-yl)piperazin-1-yl)ethanol |

| Ex. | Structure | Name |
|---|---|---|
| 409 | 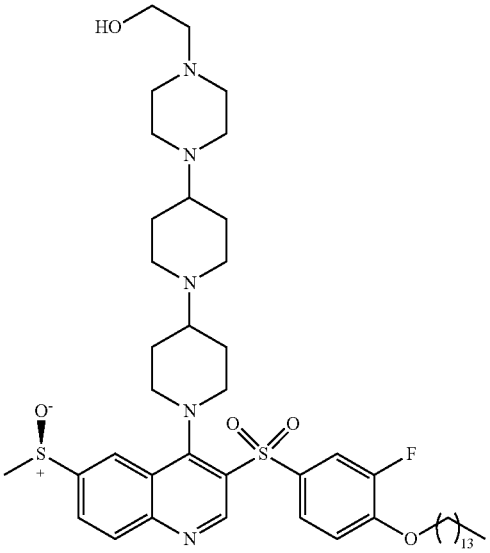 | (R)-2-(4-(1'-(3-((3-fluoro-4-(tetradecyloxy)phenyl)sulfonyl)-6-(methylsulfinyl)quinolin-4-yl)-[1,4'-bipiperidin]-4-yl)piperazin-1-yl)ethanol |
| 410 | 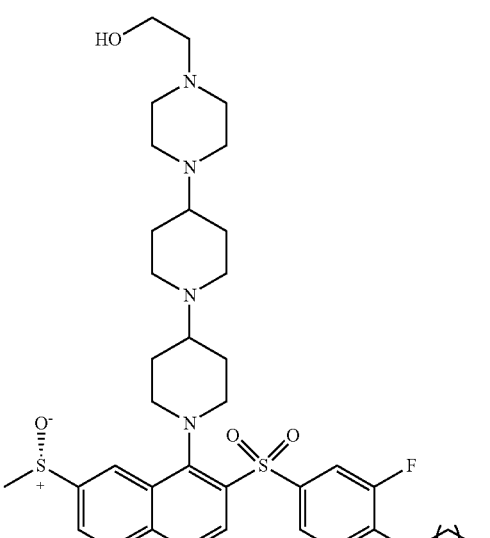 | (S)-2-(4-(1'-(3-((3-fluoro-4-(tetradecyloxy)phenyl)sulfonyl)-6-(methylsulfinyl)quinolin-4-yl)-[1,4'-bipiperidin]-4-yl)piperazin-1-yl)ethanol |

TABLE 1-continued
| Ex. | Structure | Name |
|---|---|---|
| 411 | 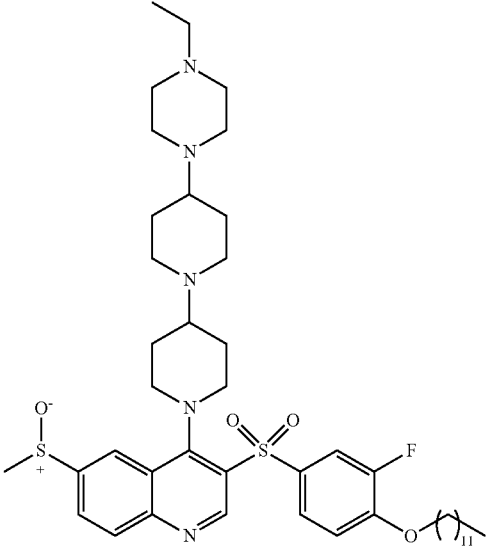 | 3-((4-(dodecyloxy)-3-fluorophenyl)sulfonyl)-4-(4-(4-ethylpiperazin-1-yl)-[1,4'-bipiperidin]-1'-yl)-6-(methylsulfinyl)quinoline |
| 412 | 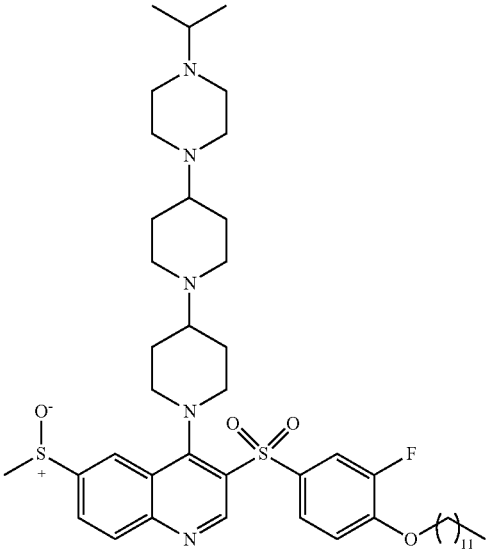 | 3-((4-(dodecyloxy)-3-fluorophenyl)sulfonyl)-4-(4-(4-isopropylpiperazin-1-yl)-[1,4'-bipiperidin]-1'-yl)-6-(methylsulfinyl)quinoline |

TABLE 1-continued
| Ex. | Structure | Name |
|---|---|---|
| 413 | 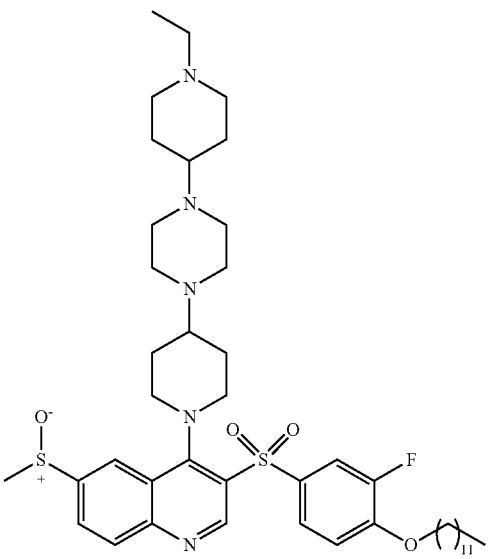 | 3-((4-(dodecyloxy)-3-fluorophenyl)sulfonyl)-4-(4-(4-(1-ethylpiperidin-4-yl)piperazin-1-yl)piperidin-1-yl)-6-(methylsulfinyl)quinoline |
| 414 | 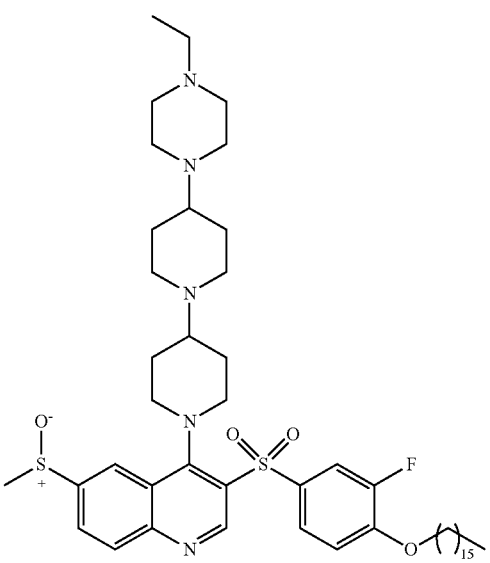 | 4-(4-(4-ethylpiperazin-1-yl)-[1,4'-bipiperidin]-1'-yl)-3-((3-fluoro-4-(hexadecyloxy)phenyl)sulfonyl)-6-(methylsulfinyl)quinoline |

TABLE 1-continued
| Ex. | Structure | Name |
|---|---|---|
| 415 | 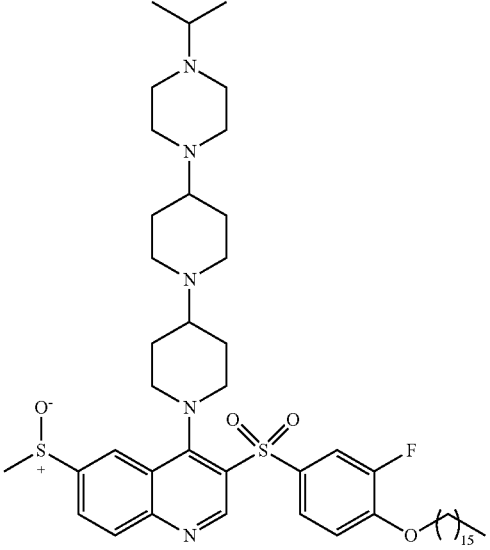 | 3-((3-fluoro-4-(hexadecyloxy)phenyl)sulfonyl)-4-(4-(4-isopropylpiperazin-1-yl)-[1,4'-bipiperidin]-1'-yl)-6-(methylsulfinyl)quinoline |
| 416 | 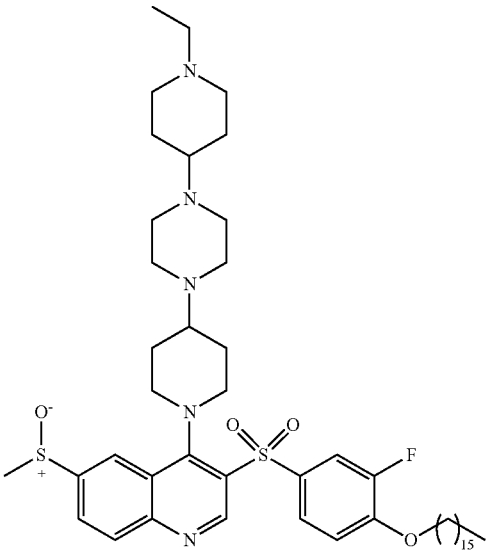 | 4-(4-(4-(1-ethylpiperidin-4-yl)piperazin-1-yl)piperidin-1-yl)-3-((3-fluoro-4-(hexadecyloxy)phenyl)sulfonyl)-6-(methylsulfinyl)quinoline |

TABLE 1-continued
| Ex. | Structure | Name |
|---|---|---|
| 417 | 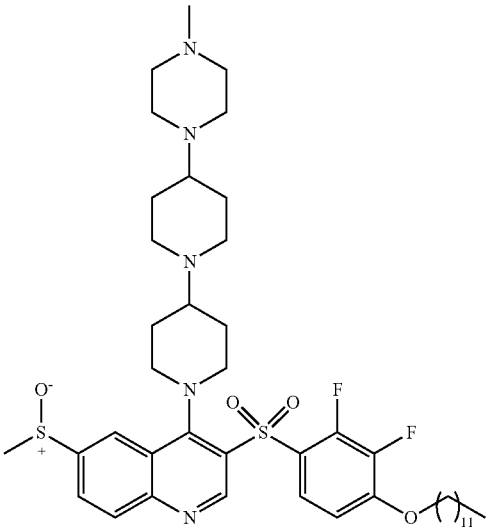 | 3-((4-(dodecyloxy)-2,3-difluorophenyl)sulfonyl)-4-(4-(4-methylpiperazin-1-yl)-[1,4'-bipiperidin]-1'-yl)-6-(methylsulfinyl)quinoline |
| 418 | 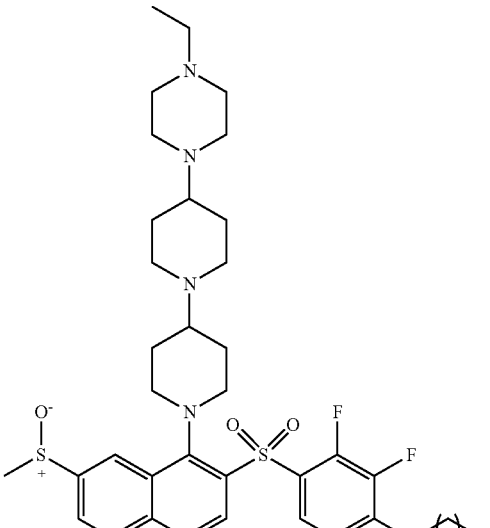 | 3-((4-(dodecyloxy)-2,3-difluorophenyl)sulfonyl)-4-(4-(4-ethylpiperazin-1-yl)-[1,4'-bipiperidin]-1'-yl)-6-(methylsulfinyl)quinoline |

| Ex. | Structure | Name |
|---|---|---|
| 419 | 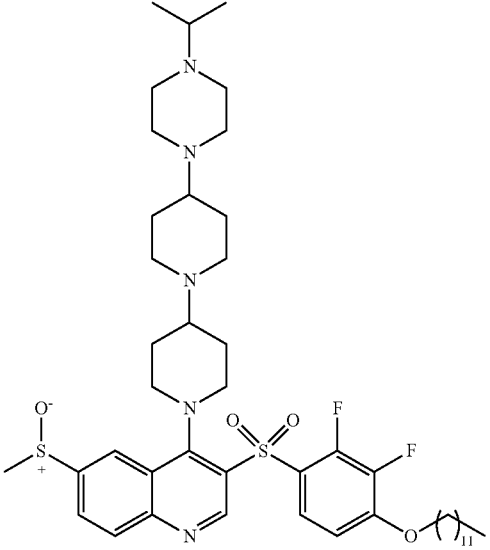 | 3-((4-(dodecyloxy)-2,3-difluorophenyl)sulfonyl)-4-(4-(4-isopropylpiperazin-1-yl)-[1,4'-bipiperidin]-1'-yl)-6-(methylsulfinyl)quinoline |
| 420 | 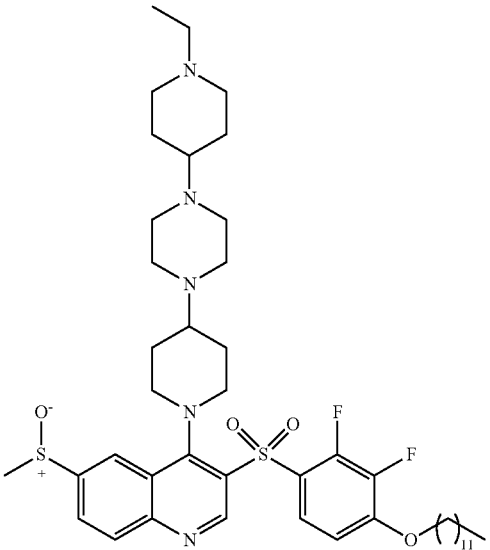 | 3-((4-(dodecyloxy)-2,3-difluorophenyl)sulfonyl)-4-(4-(4-(1-ethylpiperidin-4-yl)piperazin-1-yl)piperidin-1-yl)-6-(methylsulfinyl)quinoline |

TABLE 1-continued
| Ex. | Structure | Name |
|---|---|---|
| 421 | 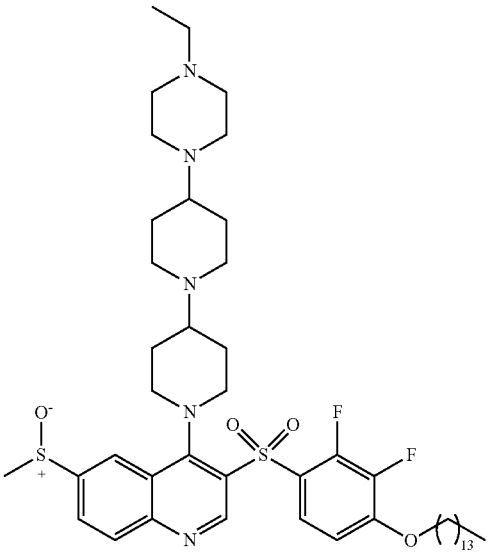 | 3-((2,3-difluoro-4-(tetradecyloxy)phenyl)sulfonyl)-4-(4-(4-ethylpiperazin-1-yl)-[1,4'-bipiperidin]-1'-yl)-6-(methylsulfinyl)quinoline |
| 422 | 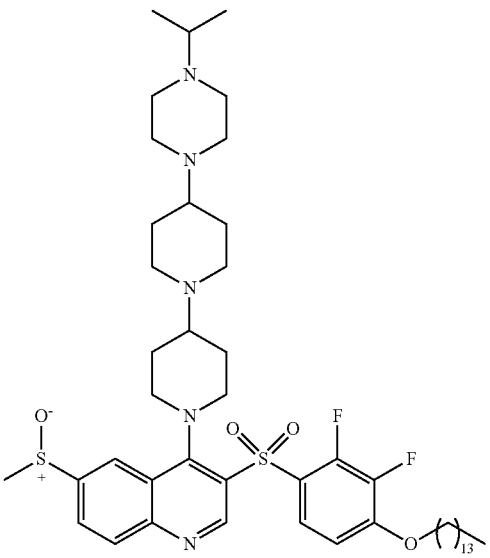 | 3-((2,3-difluoro-4-(tetradecyloxy)phenyl)sulfonyl)-4-(4-(4-isopropylpiperazin-1-yl)-[1,4'-bipiperidin]-1'-yl)-6-(methylsulfinyl)quinoline |

TABLE 1-continued

| Ex. | Structure | Name |
|---|---|---|
| 423 | 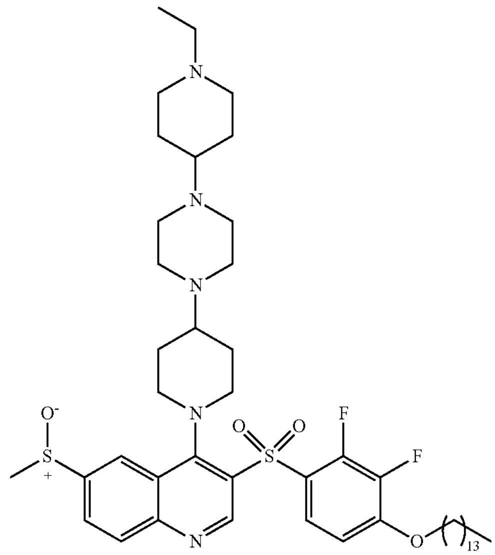 | 3-((2,3-difluoro-4-(tetradecyloxy)phenyl)sulfonyl)-4-(4-(4-(1-ethylpiperidin-4-yl)piperazin-1-yl)piperidin-1-yl)-6-(methylsulfinyl)quinoline |
| 424 | 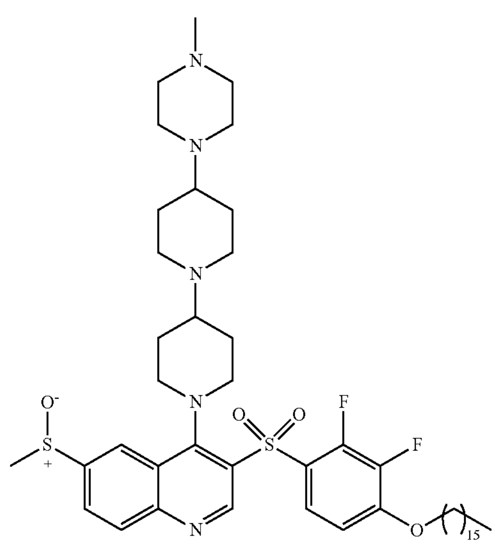 | 3-((2,3-difluoro-4-(hexadecyloxy)phenyl)sulfonyl)-4-(4-(4-methylpiperazin-1-yl)-[1,4'-bipiperidin]-1'-yl)-6-(methylsulfinyl)quinoline |

TABLE 1-continued
| Ex. | Structure | Name |
|---|---|---|
| 425 | 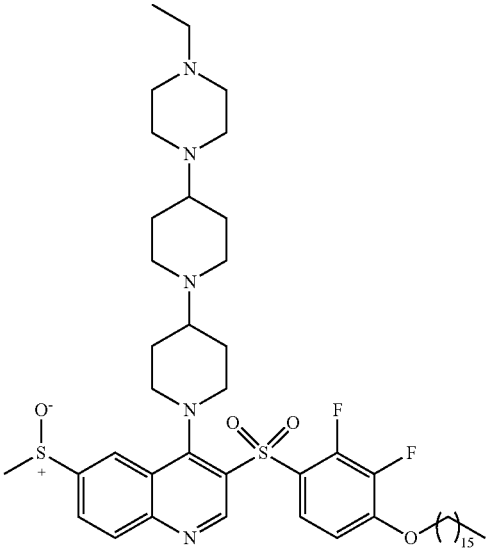 | 3-((2,3-difluoro-4-(hexadecyloxy)phenyl)sulfonyl)-4-(4-(4-ethylpiperazin-1-yl)-[1,4'-bipiperidin]-1'-yl)-6-(methylsulfinyl)quinoline |
| 426 | 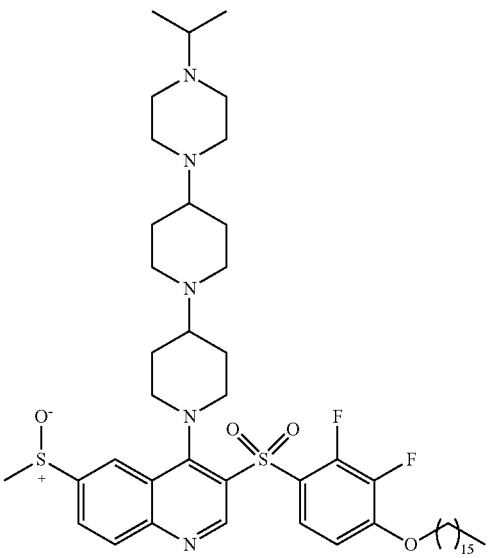 | 3-((2,3-difluoro-4-(hexadecyloxy)phenyl)sulfonyl)-4-(4-(4-isopropylpiperazin-1-yl)-[1,4'-bipiperidin]-1'-yl)-6-(methylsulfinyl)quinoline |

TABLE 1-continued
| Ex. | Structure | Name |
|---|---|---|
| 427 | 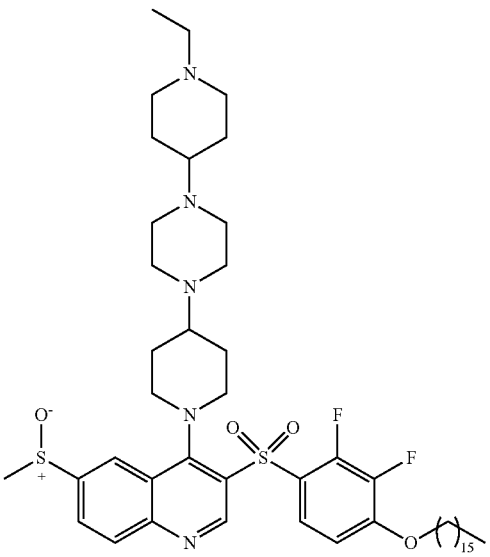 | 3-((2,3-difluoro-4-(hexadecyloxy)phenyl)sulfonyl)-4-(4-(4-(1-ethylpiperidin-4-yl)piperazin-1-yl)piperidin-1-yl)-6-(methylsulfinyl)quinoline |
| 428 | 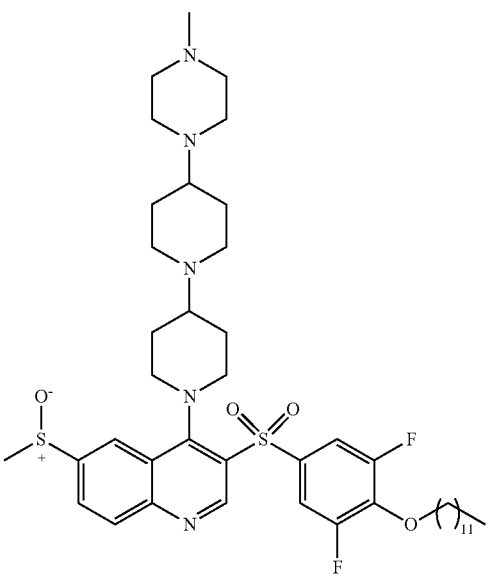 | 3-((4-(dodecyloxy)-3,5-difluorophenyl)sulfonyl)-4-(4-(4-methylpiperazin-1-yl)-[1,4'-bipiperidin]-1'-yl)-6-(methylsulfinyl)quinoline |

TABLE 1-continued
| Ex. | Structure | Name |
|---|---|---|
| 429 | 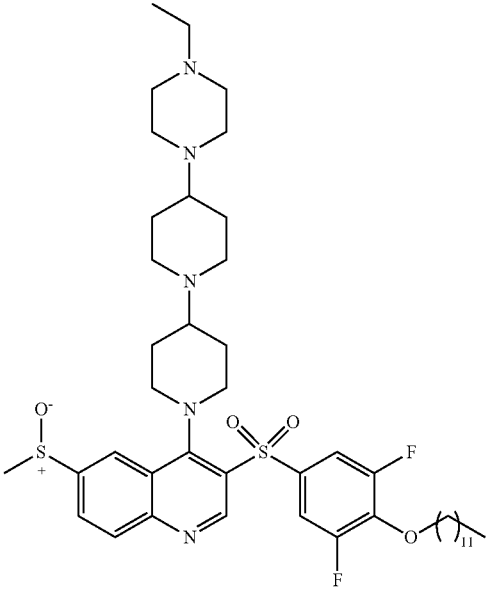 | 3-((4-(dodecyloxy)-3,5-difluorophenyl)sulfonyl)-4-(4-(4-ethylpiperazin-1-yl)-[1,4'-bipiperidin]-1'-yl)-6-(methylsulfinyl)quinoline |
| 430 | 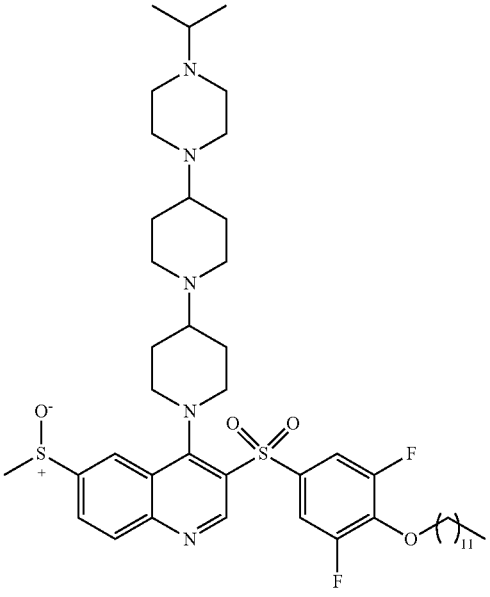 | 3-((4-(dodecyloxy)-3,5-difluorophenyl)sulfonyl)-4-(4-(4-isopropylpiperazin-1-yl)-[1,4'-bipiperidin]-1'-yl)-6-(methylsulfinyl)quinoline |

TABLE 1-continued

| Ex. | Structure | Name |
|---|---|---|
| 431 | 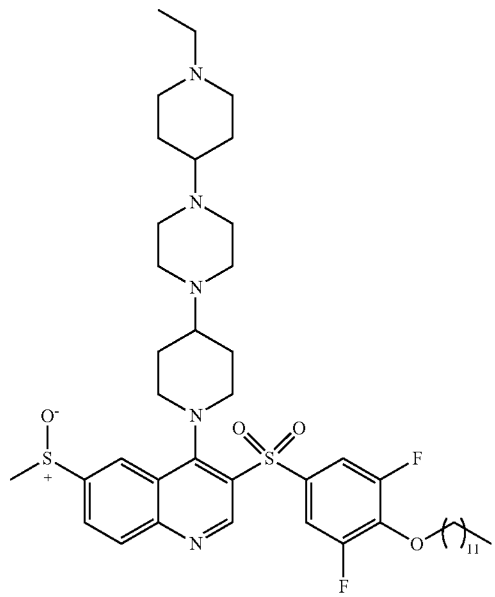 | 3-((4-(dodecyloxy)-3,5-difluorophenyl)sulfonyl)-4-(4-(4-(1-ethylpiperidin-4-yl)piperazin-1-yl)piperidin-1-yl)-6-(methylsulfinyl)quinoline |
| 432 | 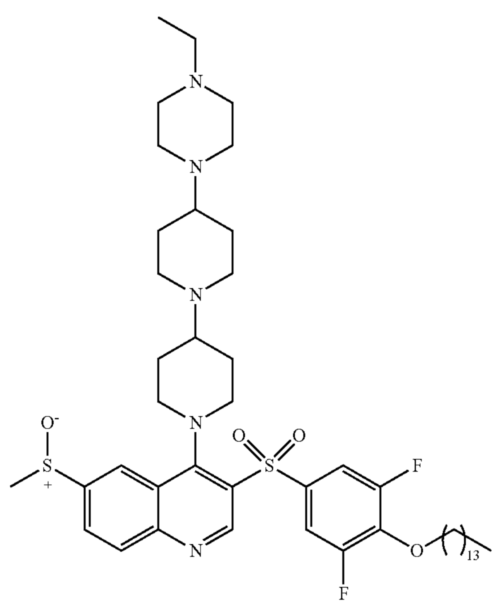 | 3-((3,5-difluoro-4-(tetradecyloxy)phenyl)sulfonyl)-4-(4-(4-ethylpiperazin-1-yl)-[1,4'-bipiperidin]-1'-yl)-6-(methylsulfinyl)quinoline |

TABLE 1-continued
| Ex. | Structure | Name |
|---|---|---|
| 433 | 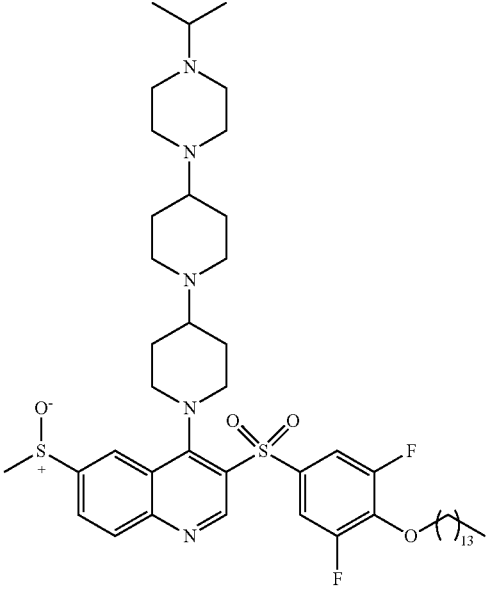 | 3-((3,5-difluoro-4-(tetradecyloxy)phenyl)sulfonyl)-4-(4-(4-isopropylpiperazin-1-yl)-[1,4'-bipiperidin]-1'-yl)-6-(methylsulfinyl)quinoline |
| 434 | 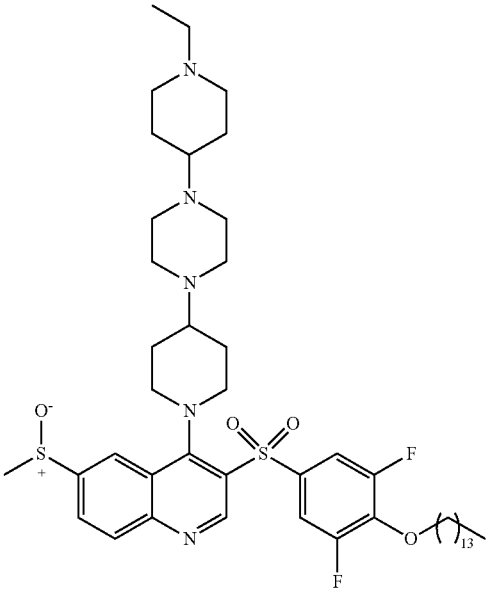 | 3-((3,5-difluoro-4-(tetradecyloxy)phenyl)sulfonyl)-4-(4-(4-(1-ethylpiperidin-4-yl)piperazin-1-yl)piperidin-1-yl)-6-(methylsulfinyl)quinoline |

TABLE 1-continued
| Ex. | Structure | Name |
|---|---|---|
| 435 | 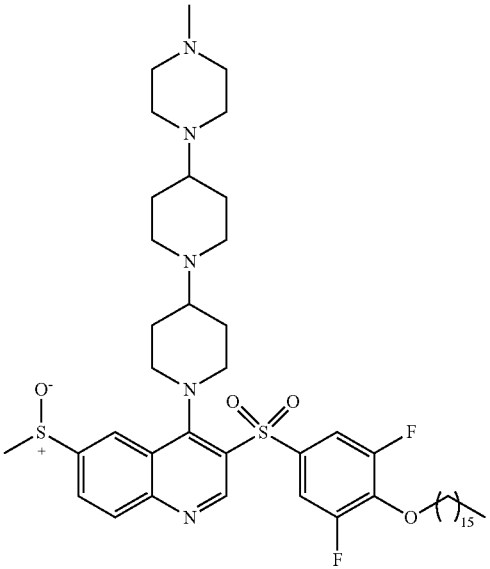 | 3-((3,5-difluoro-4-(hexadecyloxy)phenyl)sulfonyl)-4-(4-(4-methylpiperazin-1-yl)-[1,4'-bipiperidin]-1'-yl)-6-(methylsulfinyl)quinoline |
| 436 | 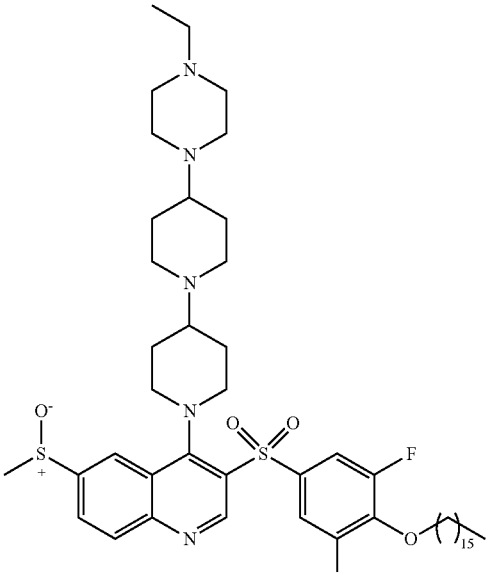 | 3-((3,5-difluoro-4-(hexadecyloxy)phenyl)sulfonyl)-4-(4-(4-ethylpiperazin-1-yl)-[1,4'-bipiperidin]-1'-yl)-6-(methylsulfinyl)quinoline |

TABLE 1-continued
| Ex. | Structure | Name |
|---|---|---|
| 437 | 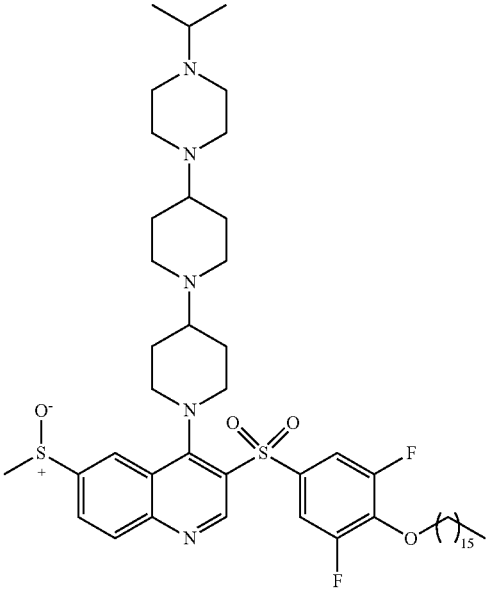 | 3-((3,5-difluoro-4-(hexadecyloxy)phenyl)sulfonyl)-4-(4-(4-isopropylpiperazin-1-yl)-[1,4'-bipiperidin]-1'-yl)-6-(methylsulfinyl)quinoline |
| 438 | 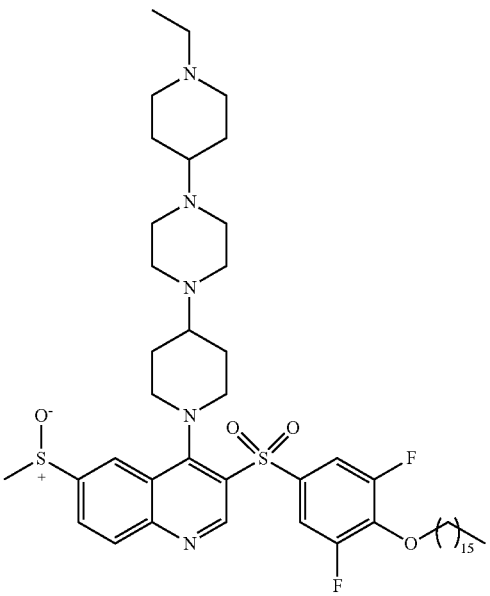 | 3-((3,5-difluoro-4-(hexadecyloxy)phenyl)sulfonyl)-4-(4-(4-(1-ethylpiperidin-4-yl)piperazin-1-yl)piperidin-1-yl)-6-(methylsulfinyl)quinoline |

TABLE 1-continued
| Ex. | Structure | Name |
|---|---|---|
| 439 | 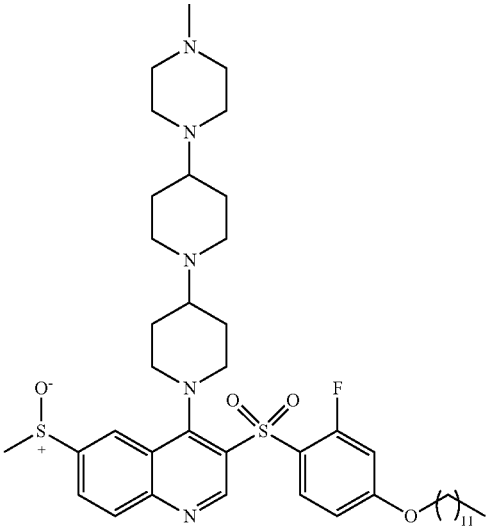 | 3-((4-(dodecyloxy)-2-fluorophenyl)sulfonyl)-4-(4-(4-methylpiperazin-1-yl)-[1,4'-bipiperidin]-1'-yl)-6-(methylsulfinyl)quinoline |
| 440 | 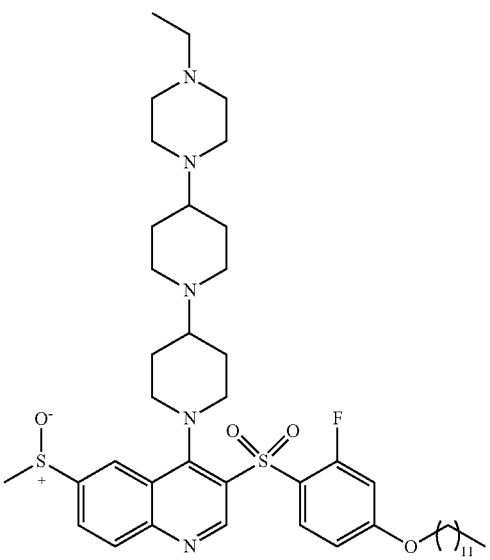 | 3-((4-(dodecyloxy)-2-fluorophenyl)sulfonyl)-4-(4-(4-ethylpiperazin-1-yl)-[1,4'-bipiperidin]-1'-yl)-6-(methylsulfinyl)quinoline |

TABLE 1-continued
| Ex. | Structure | Name |
|---|---|---|
| 441 | 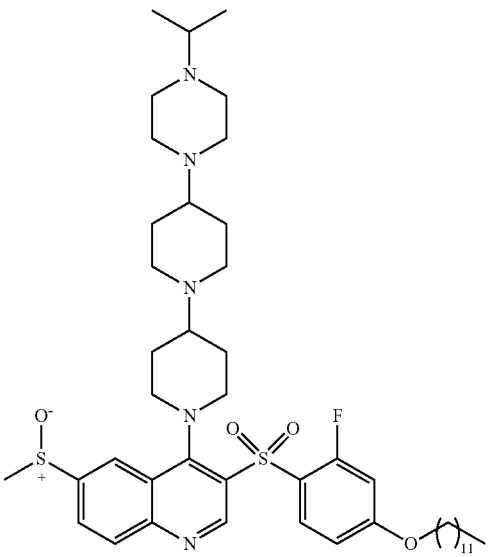 | 3-((4-(dodecyloxy)-2-fluorophenyl)sulfonyl)-4-(4-(4-isopropylpiperazin-1-yl)-[1,4'-bipiperidin]-1'-yl)-6-(methylsulfinyl)quinoline |
| 442 | 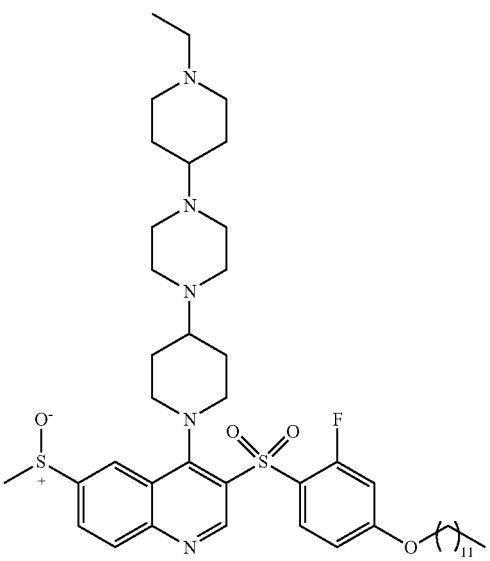 | 3-((4-(dodecyloxy)-2-fluorophenyl)sulfonyl)-4-(4-(4-(1-ethylpiperidin-4-yl)piperazin-1-yl)piperidin-1-yl)-6-(methylsulfinyl)quinoline |

TABLE 1-continued
| Ex. | Structure | Name |
|---|---|---|
| 443 | 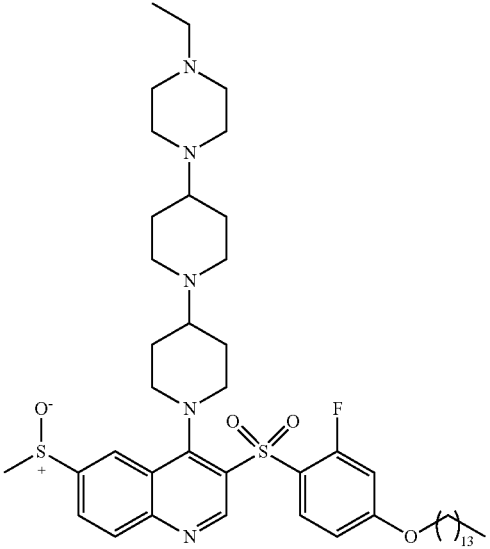 | 4-(4-(4-ethylpiperazin-1-yl)-[1,4'-bipiperidin]-1'-yl)-3-((2-fluoro-4-(tetradecyloxy)phenyl)sulfonyl)-6-(methylsulfinyl)quinoline |
| 444 | 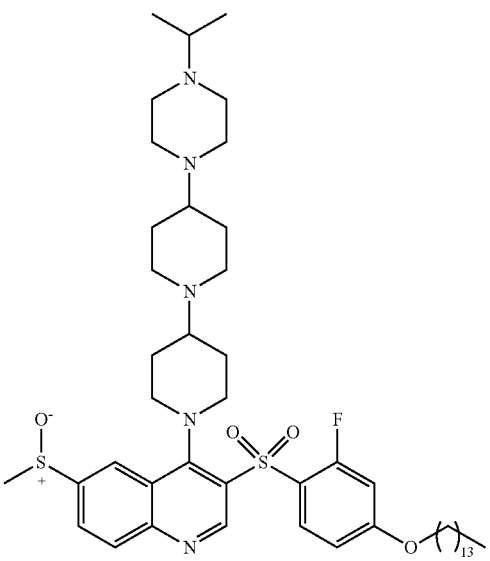 | 3-((2-fluoro-4-(tetradecyloxy)phenyl)sulfonyl)-4-(4-(4-isopropylpiperazin-1-yl)-[1,4'-bipiperidin]-1'-yl)-6-(methylsulfinyl)quinoline |

TABLE 1-continued
| Ex. | Structure | Name |
|---|---|---|
| 445 | 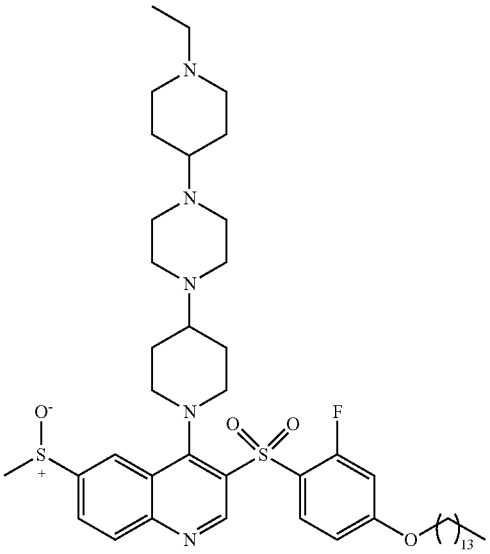 | 4-(4-(4-(1-ethylpiperidin-4-yl)piperazin-1-yl)piperidin-1-yl)-3-((2-fluoro-4-(tetradecyloxy)phenyl)sulfonyl)-6-(methylsulfinyl)quinoline |
| 446 | 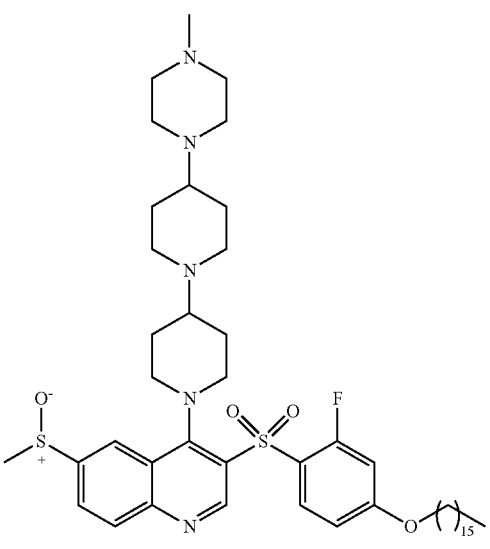 | 3-((2-fluoro-4-(hexadecyloxy)phenyl)sulfonyl)-4-(4-(4-methylpiperazin-1-yl)-[1,4'-bipiperidin]-1'-yl)-6-(methylsulfinyl)quinoline |

TABLE 1-continued
| Ex. | Structure | Name |
|---|---|---|
| 447 | 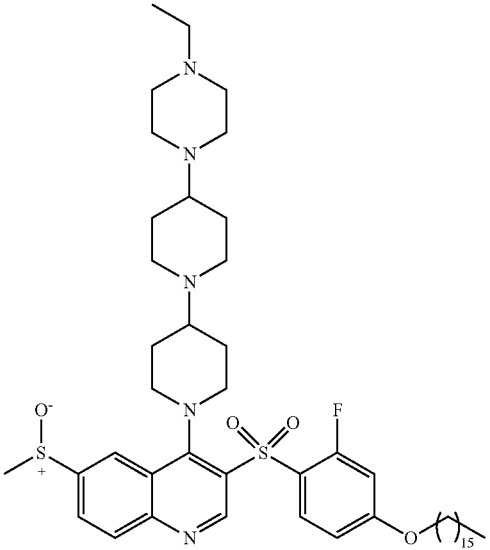 | 4-(4-(4-ethylpiperazin-1-yl)-[1,4'-bipiperidin]-1'-yl)-3-((2-fluoro-4-(hexadecyloxy)phenyl)sulfonyl)-6-(methylsulfinyl)quinoline |
| 448 | 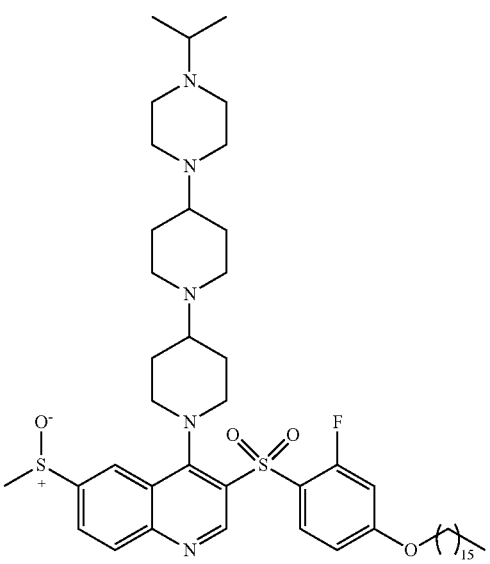 | 3-((2-fluoro-4-(hexadecyloxy)phenyl)sulfonyl)-4-(4-(4-isopropylpiperazin-1-yl)-[1,4'-bipiperidin]-1'-yl)-6-(methylsulfinyl)quinoline |

TABLE 1-continued

| Ex. | Structure | Name |
|---|---|---|
| 449 | 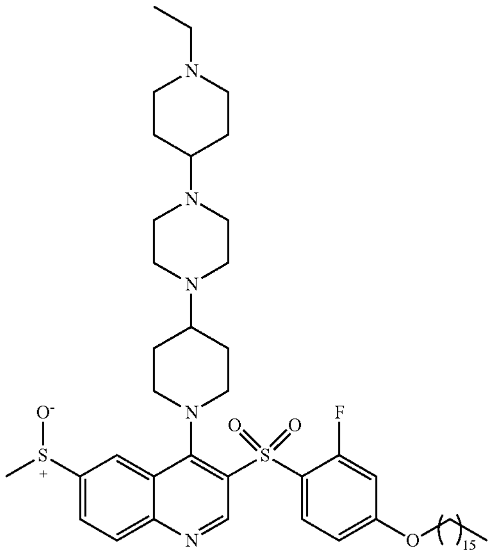 | 4-(4-(4-(1-ethylpiperidin-4-yl)piperazin-1-yl)piperidin-1-yl)-3-((2-fluoro-4-(hexadecyloxy)phenyl)sulfonyl)-6-(methylsulfinyl)quinoline |
| 450 | 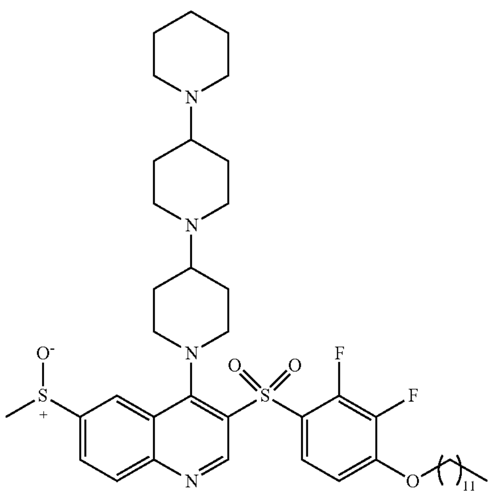 | 4-([1,4':1',4''-terpiperidin]-1''-yl)-3-((4-(dodecyloxy)-2,3-difluorophenyl)sulfonyl)-6-(methylsulfinyl)quinoline |
| 451 | 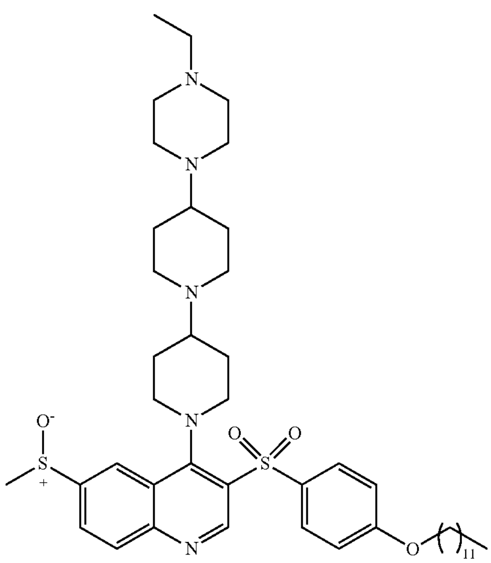 | 3-((4-(dodecyloxy)phenyl)sulfonyl)-4-(4-(4-ethylpiperazin-1-yl)-[1,4'-bipiperidin]-1'-yl)-6-(methylsulfinyl)quinoline |

TABLE 1-continued
| Ex. | Structure | Name |
|---|---|---|
| 452 | 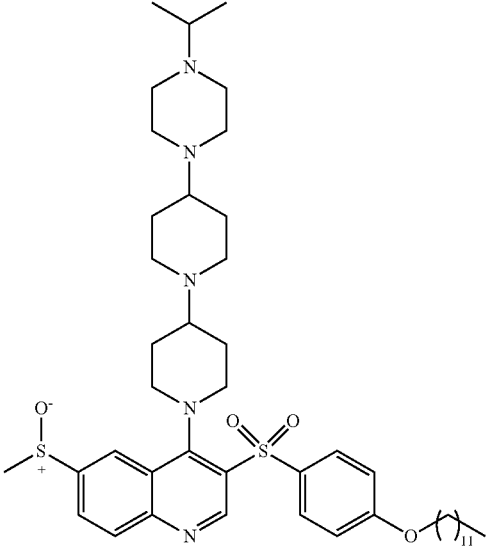 | 3-((4-(dodecyloxy)phenyl)sulfonyl)-4-(4-(4-isopropylpiperazin-1-yl)-[1,4'-bipiperidin]-1'-yl)-6-(methylsulfinyl)quinoline |
| 453 | 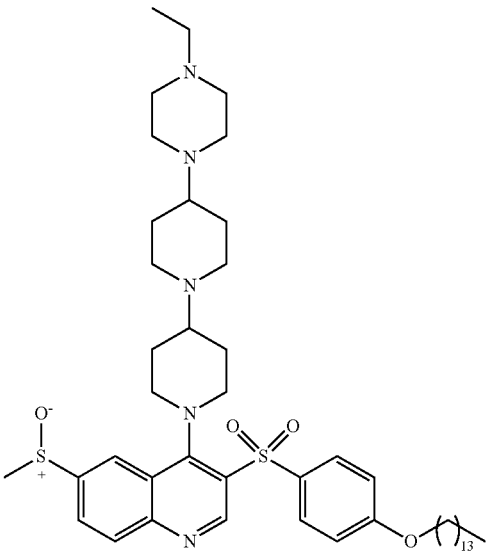 | 4-(4-(4-ethylpiperazin-1-yl)-[1,4'-bipiperidin]-1'-yl)-6-(methylsulfinyl)-3-((4-(tetradecyloxy)phenyl)sulfonyl)quinoline |

TABLE 1-continued

| Ex. | Structure | Name |
|---|---|---|
| 454 | 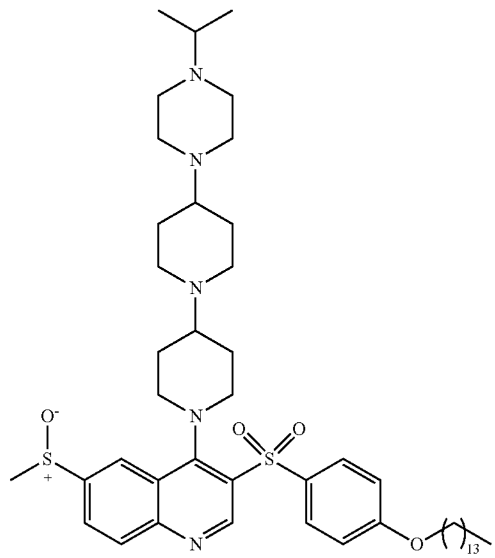 | 4-(4-(4-isopropylpiperazin-1-yl)-[1,4'-bipiperidin]-1'-yl)-6-(methylsulfinyl)-3-((4-(tetradecyloxy)phenyl)sulfonyl)quinoline |
| 455 | 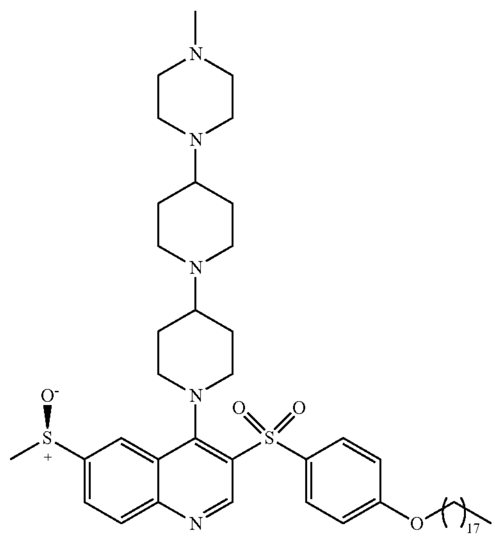 | (R)-4-(4-(4-methylpiperazin-1-yl)-[1,4'-bipiperidin]-1'-yl)-6-(methylsulfinyl)-3-((4-(octadecyloxy)phenyl)sulfonyl)quinoline |
| 456 | 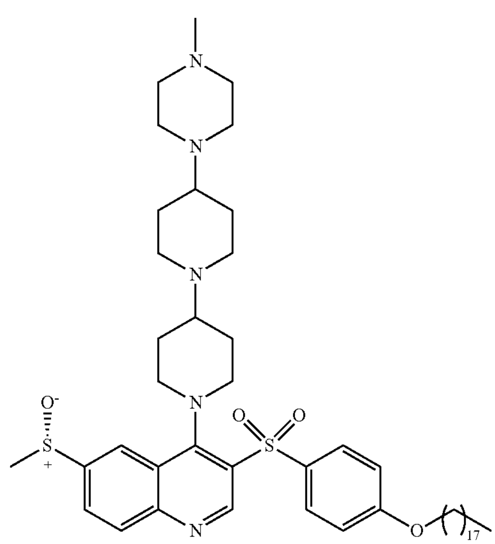 | (S)-4-(4-(4-methylpiperazin-1-yl)-[1,4'-bipiperidin]-1'-yl)-6-(methylsulfinyl)-3-((4-(octadecyloxy)phenyl)sulfonyl)quinoline |

TABLE 1-continued
| Ex. | Structure | Name |
|---|---|---|
| 457 | 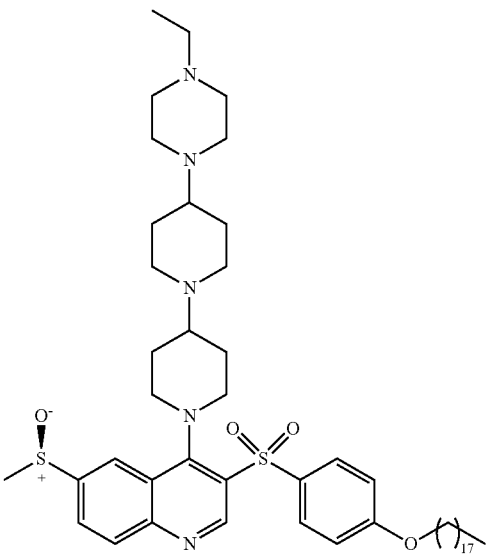 | (R)-4-(4-(4-ethylpiperazin-1-yl)-[1,4'-bipiperidin]-1'-yl)-6-(methylsulfinyl)-3-((4-(octadecyloxy)phenyl)sulfonyl)quinoline |
| 458 | 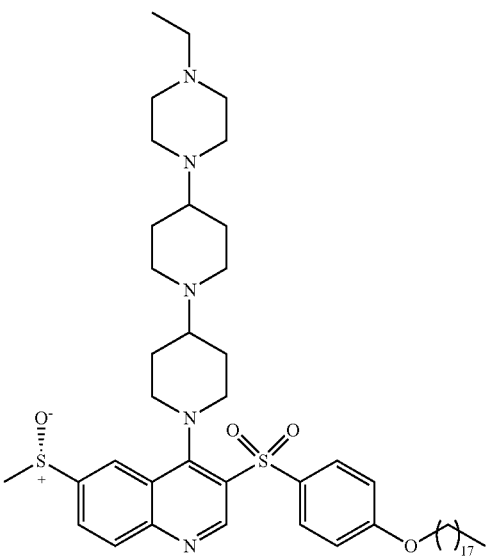 | (S)-4-(4-(4-ethylpiperazin-1-yl)-[1,4'-bipiperidin]-1'-yl)-6-(methylsulfinyl)-3-((4-(octadecyloxy)phenyl)sulfonyl)quinoline |

TABLE 1-continued
| Ex. | Structure | Name |
|---|---|---|
| 459 | 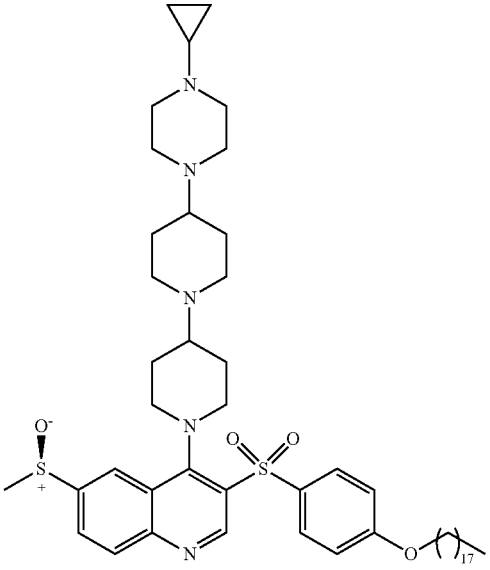 | (R)-4-(4-(4-cyclopropylpiperazin-1-yl)-[1,4'-bipiperidin]-1'-yl)-6-(methylsulfinyl)-3-((4-(octadecyloxy)phenyl)sulfonyl)quinoline |
| 460 | 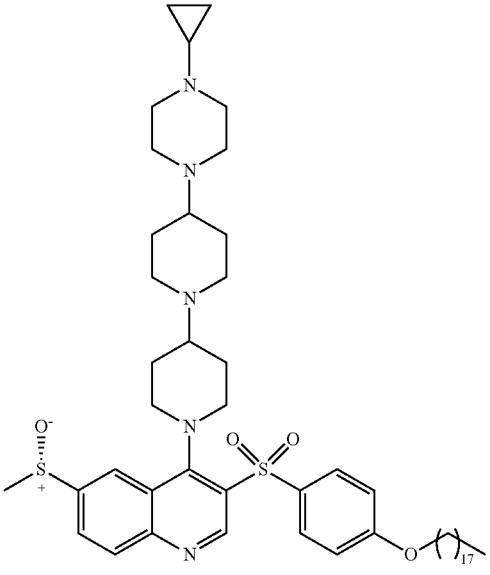 | (S)-4-(4-(4-cyclopropylpiperazin-1-yl)-[1,4'-bipiperidin]-1'-yl)-6-(methylsulfinyl)-3-((4-(octadecyloxy)phenyl)sulfonyl)quinoline |

TABLE 1-continued
| Ex. | Structure | Name |
|---|---|---|
| 461 | 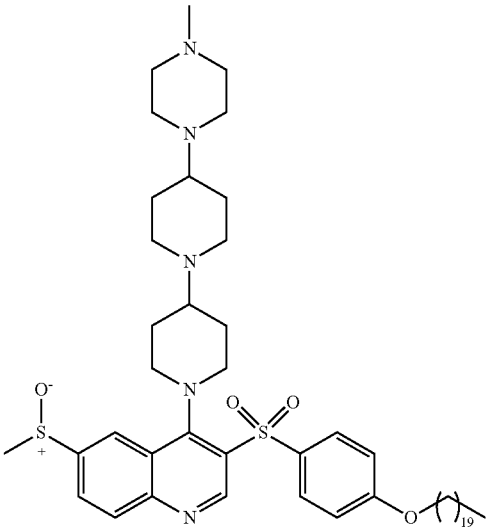 | 3-((4-(icosyloxy)phenyl)sulfonyl)-4-(4-(4-methylpiperazin-1-yl)-[1,4'-bipiperidin]-1'-yl)-6-(methylsulfinyl)quinoline |
| 462 | 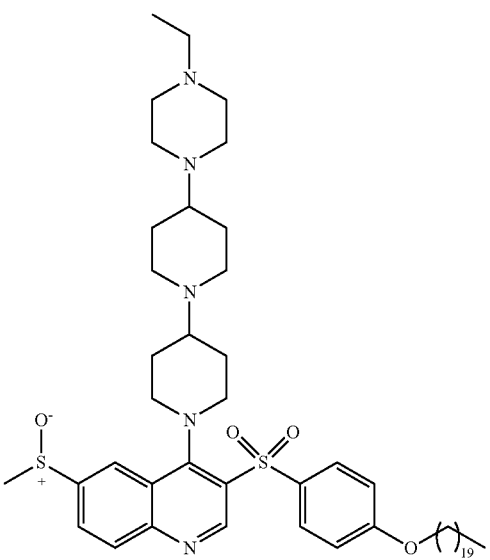 | 4-(4-(4-ethylpiperazin-1-yl)-[1,4'-bipiperidin]-1'-yl)-3-((4-(icosyloxy)phenyl)sulfonyl)-6-(methylsulfinyl)quinoline |

TABLE 1-continued
| Ex. | Structure | Name |
|---|---|---|
| 463 | 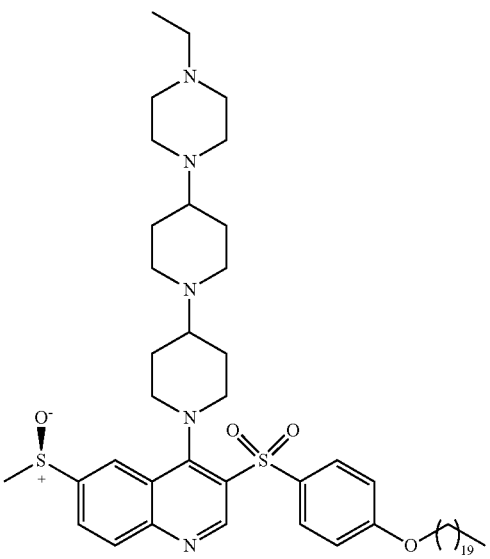 | (R)-4-(4-(4-ethylpiperazin-1-yl)-[1,4'-bipiperidin]-1'-yl)-3-((4-(icosyloxy)phenyl)sulfonyl)-6-(methylsulfinyl)quinoline |
| 464 | 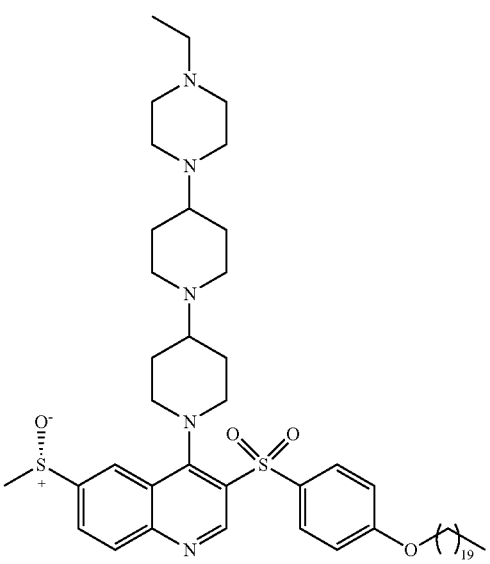 | (S)-4-(4-(4-ethylpiperazin-1-yl)-[1,4'-bipiperidin]-1'-yl)-3-((4-(icosyloxy)phenyl)sulfonyl)-6-(methylsulfinyl)quinoline |

TABLE 1-continued
| Ex. | Structure | Name |
|---|---|---|
| 465 | 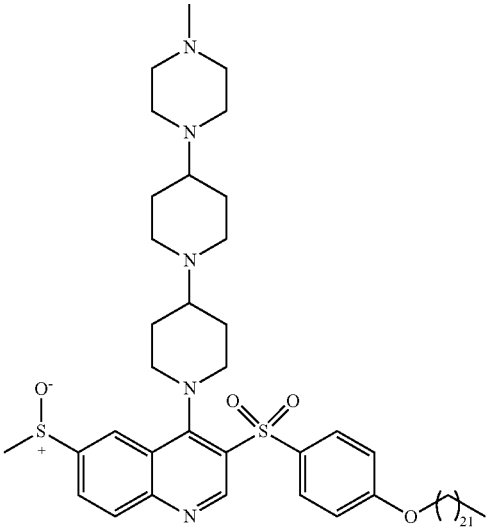 | 3-((4-(docosyloxy)phenyl)sulfonyl)-4-(4-(4-methylpiperazin-1-yl)-[1,4'-bipiperidin]-1'-yl)-6-(methylsulfinyl)quinoline |
| 466 | 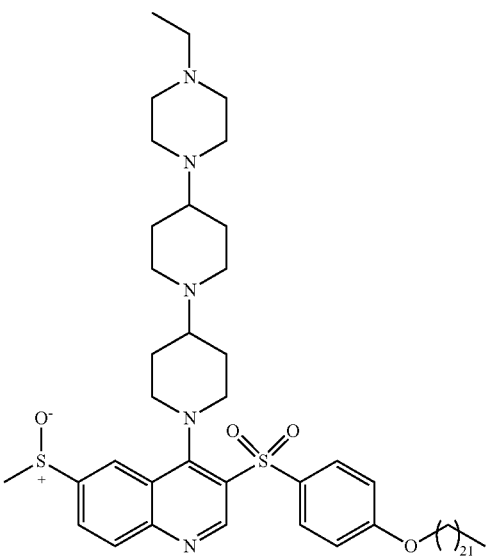 | 3-((4-(docosyloxy)phenyl)sulfonyl)-4-(4-(4-ethylpiperazin-1-yl)-[1,4'-bipiperidin]-1'-yl)-6-(methylsulfinyl)quinoline |

TABLE 1-continued
| Ex. | Structure | Name |
|---|---|---|
| 467 | 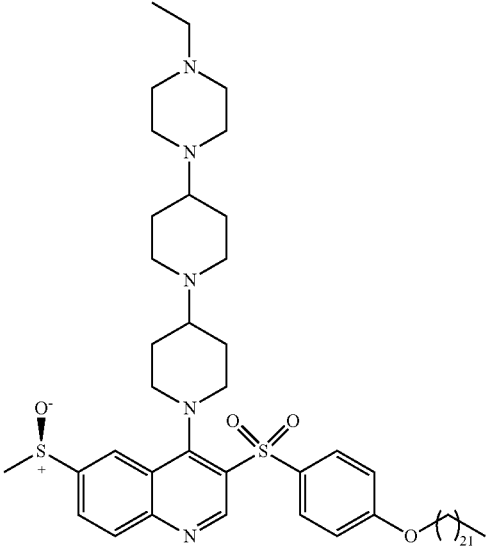 | (R)-3-((4-(docosyloxy)phenyl)sulfonyl)-4-(4-(4-ethylpiperazin-1-yl)-[1,4'-bipiperidin]-1'-yl)-6-(methylsulfinyl)quinoline |
| 468 | 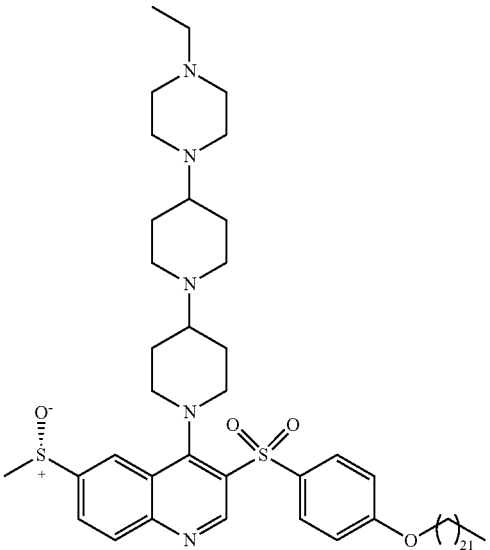 | (S)-3-((4-(docosyloxy)phenyl)sulfonyl)-4-(4-(4-ethylpiperazin-1-yl)-[1,4'-bipiperidin]-1'-yl)-6-(methylsulfinyl)quinoline |

TABLE 1-continued
| Ex. | Structure | Name |
|---|---|---|
| 469 | 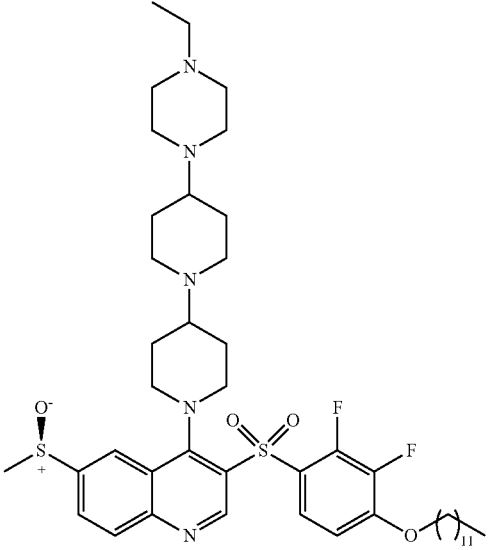 | (R)-3-((4-(dodecyloxy)-2,3-difluorophenyl)sulfonyl)-4-(4-(4-ethylpiperazin-1-yl)-[1,4'-bipiperidin]-1'-yl)-6-(methylsulfinyl)quinoline |
| 470 | 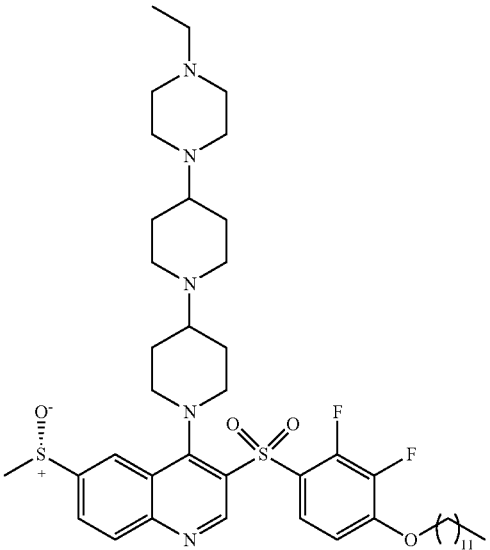 | (S)-3-((4-(dodecyloxy)-2,3-difluorophenyl)sulfonyl)-4-(4-(4-ethylpiperazin-1-yl)-[1,4'-bipiperidin]-1'-yl)-6-(methylsulfinyl)quinoline |

TABLE 1-continued
| Ex. | Structure | Name |
|---|---|---|
| 471 | 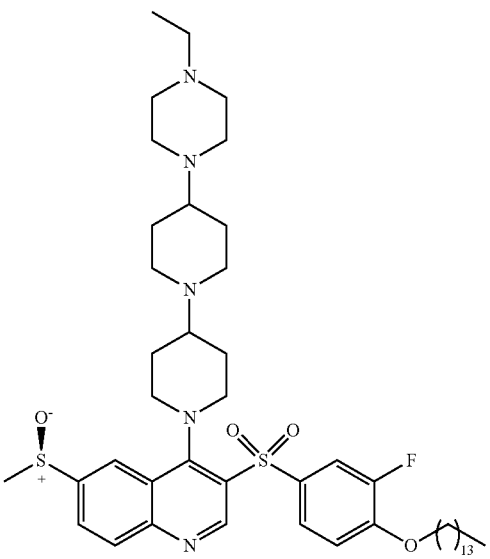 | (R)-4-(4-(4-ethylpiperazin-1-yl)-[1,4'-bipiperidin]-1'-yl)-3-((3-fluoro-4-(tetradecyloxy)phenyl)sulfonyl)-6-(methylsulfinyl)quinoline |
| 472 | 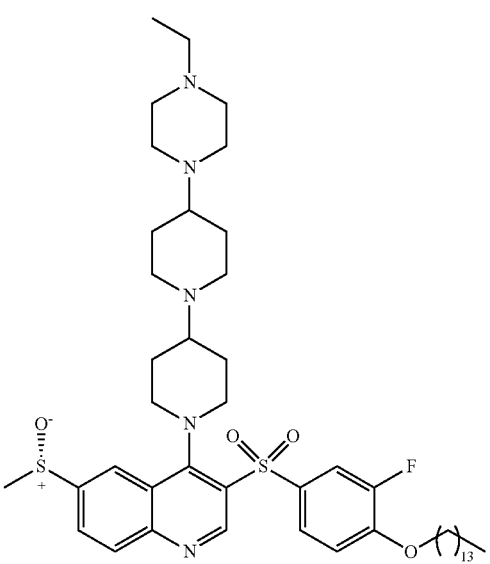 | (S)-4-(4-(4-ethylpiperazin-1-yl)-[1,4'-bipiperidin]-1'-yl)-3-((3-fluoro-4-(tetradecyloxy)phenyl)sulfonyl)-6-(methylsulfinyl)quinoline |

TABLE 1-continued
| Ex. | Structure | Name |
|---|---|---|
| 473 | 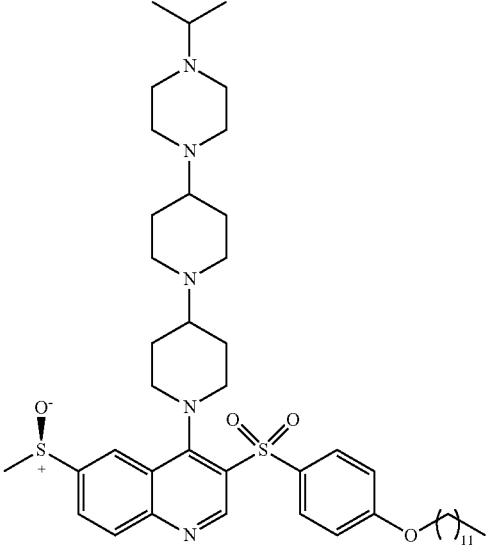 | (R)-3-((4-(dodecyloxy)phenyl)sulfonyl)-4-(4-(4-isopropylpiperazin-1-yl)-[1,4'-bipiperidin]-1'-yl)-6-(methylsulfinyl)quinoline |
| 474 | 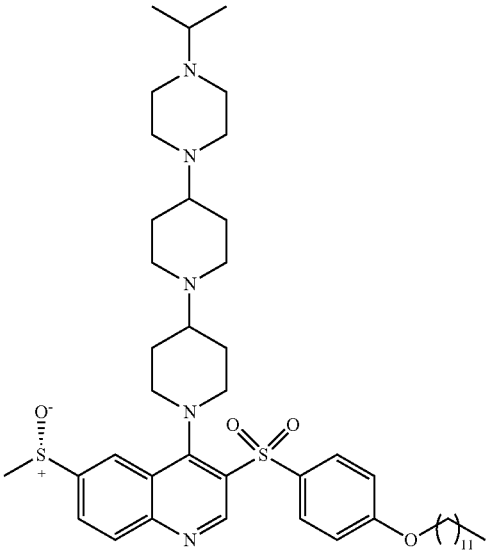 | (S)-3-((4-(dodecyloxy)phenyl)sulfonyl)-4-(4-(4-isopropylpiperazin-1-yl)-[1,4'-bipiperidin]-1'-yl)-6-(methylsulfinyl)quinoline |

TABLE 1-continued
| Ex. | Structure | Name |
|---|---|---|
| 475 | 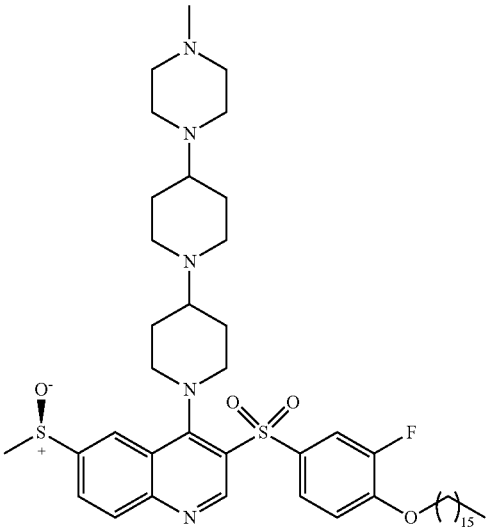 | (R)-3-((3-fluoro-4-(hexadecyloxy)phenyl)sulfonyl)-4-(4-(4-methylpiperazin-1-yl)-[1,4'-bipiperidin]-1'-yl)-6-(methylsulfinyl)quinoline |
| 476 | 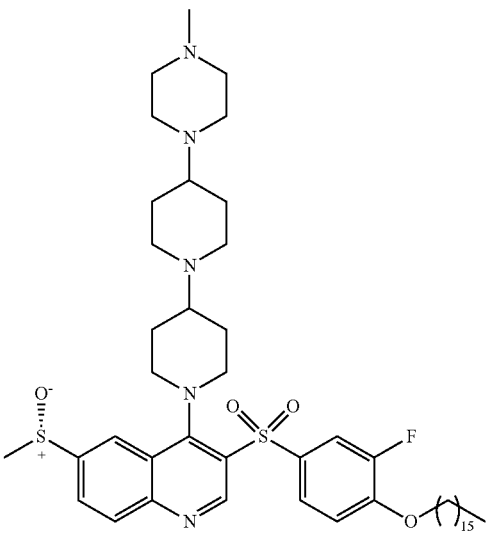 | (S)-3-((3-fluoro-4-(hexadecyloxy)phenyl)sulfonyl)-4-(4-(4-methylpiperazin-1-yl)-[1,4'-bipiperidin]-1'-yl)-6-(methylsulfinyl)quinoline |
| 477 | 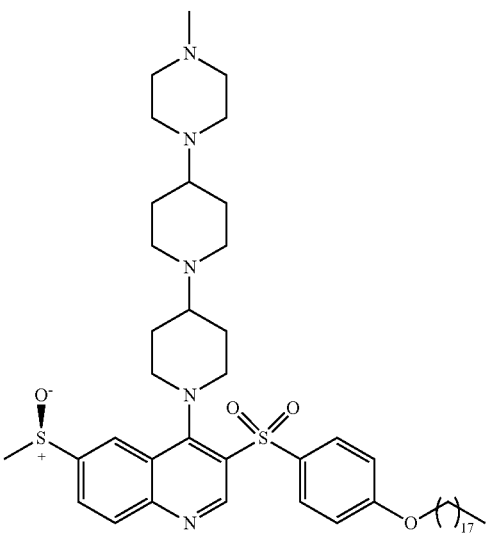 | (R)-4-(4-(4-methylpiperazin-1-yl)-[1,4'-bipiperidin]-1'-yl)-6-(methylsulfinyl)-3-((4-(octadecyloxy)phenyl)sulfonyl)quinoline |

TABLE 1-continued

| Ex. | Structure | Name |
| --- | --- | --- |
| 478 | 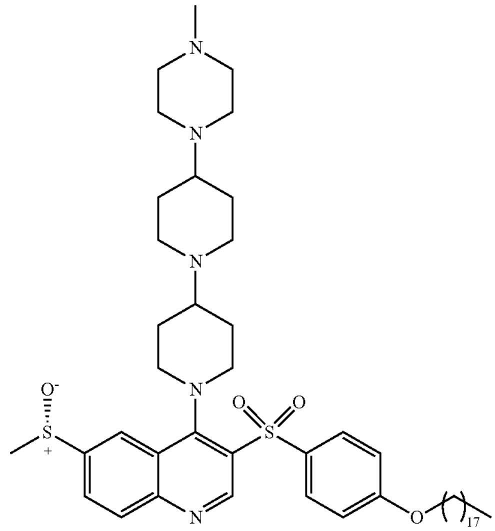 | (S)-4-(4-(4-methylpiperazin-1-yl)-[1,4'-bipiperidin]-1'-yl)-6-(methylsulfinyl)-3-((4-(octadecyloxy)phenyl)sulfonyl)quinoline |
| 479 | 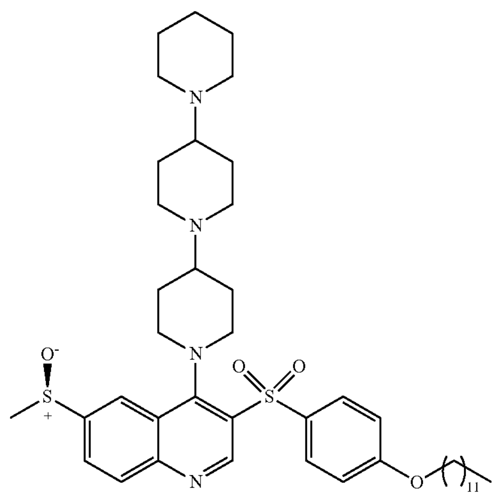 | (R)-4-([1,4':1',4''-terpiperidin]-1''-yl)-3-((4-(dodecyloxy)phenyl)sulfonyl)-6-(methylsulfinyl)quinoline |
| 480 | 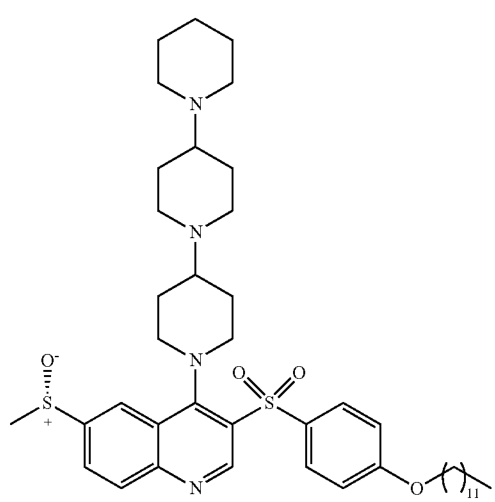 | (S)-4-([1,4':1',4''-terpiperidin]-1''-yl)-3-((4-(dodecyloxy)phenyl)sulfonyl)-6-(methylsulfinyl)quinoline |

TABLE 1-continued

| Ex. | Structure | Name |
|---|---|---|
| 481 | 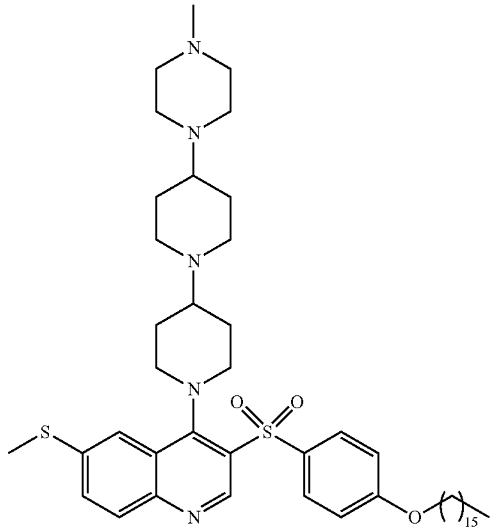 | 3-((4-(hexadecyloxy)phenyl)sulfonyl)-4-(4-(4-methylpiperazin-1-yl)-[1,4'-bipiperidin]-1'-yl)-6-(methylthio)quinoline |
| 482 | 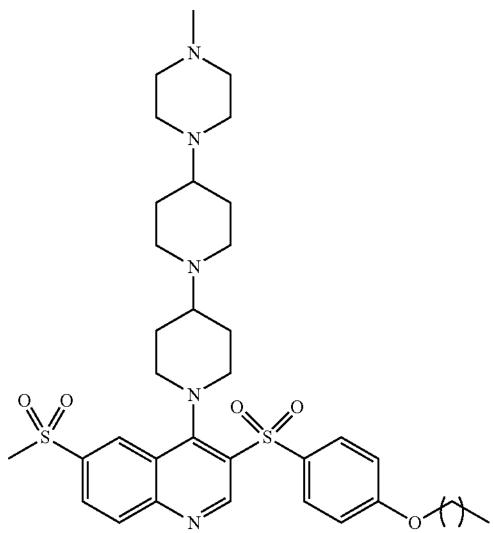 | 3-((4-(hexadecyloxy)phenyl)sulfonyl)-4-(4-(4-methylpiperazin-1-yl)-[1,4'-bipiperidin]-1'-yl)-6-(methylsulfonyl)quinoline |
| 483 | 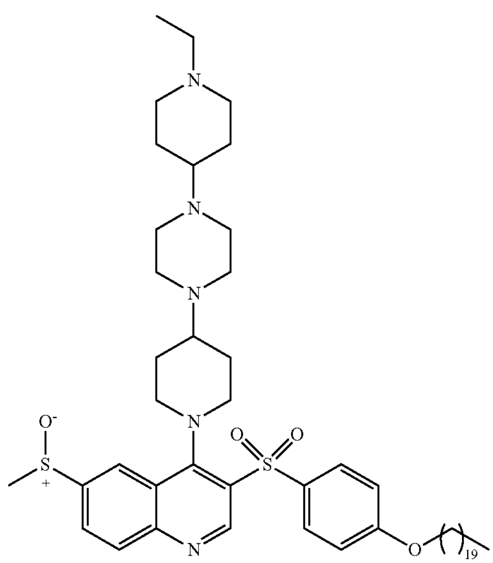 | 4-(4-(4-(1-ethylpiperidin-4-yl)piperazin-1-yl)piperidin-1-yl)-3-((4-(icosyloxy)phenyl)sulfonyl)-6-(methylsulfinyl)quinoline |

TABLE 1-continued

| Ex. | Structure | Name |
|---|---|---|
| 484 | 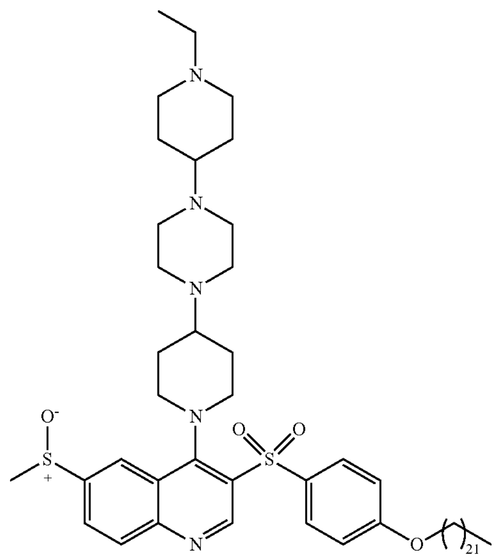 | 3-((4-(docosyloxy)phenyl)sulfonyl)-4-(4-(4-(1-ethylpiperidin-4-yl)piperazin-1-yl)piperidin-1-yl)-6-(methylsulfinyl)quinoline |
| 485 | 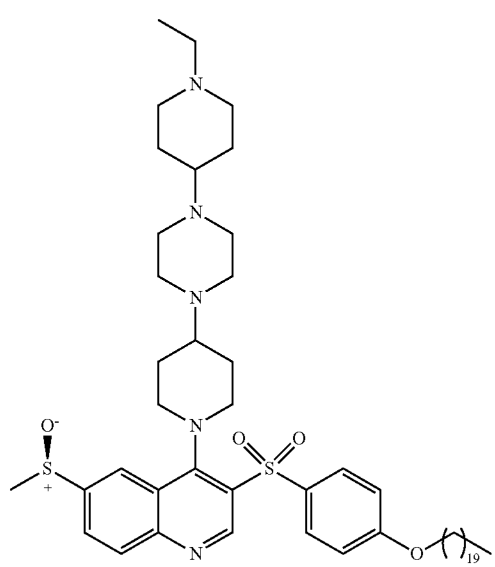 | (R)-4-(4-(4-(1-ethylpiperidin-4-yl)piperazin-1-yl)piperidin-1-yl)-3-((4-(icosyloxy)phenyl)sulfonyl)-6-(methylsulfinyl)quinoline |

TABLE 1-continued
| Ex. | Structure | Name |
|---|---|---|
| 486 | 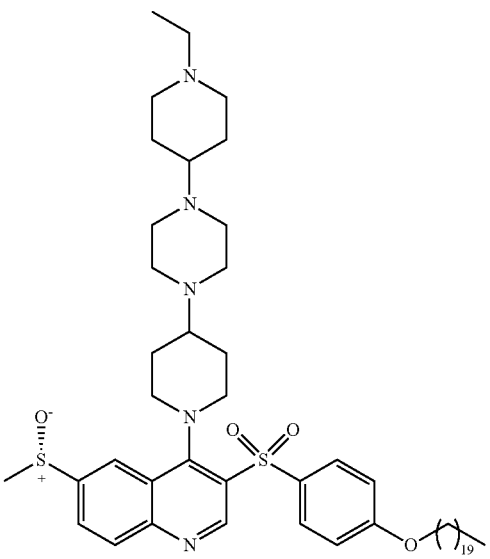 | (S)-4-(4-(4-(1-ethylpiperidin-4-yl)piperazin-1-yl)piperidin-1-yl)-3-((4-(icosyloxy)phenyl)sulfonyl)-6-(methylsulfinyl)quinoline |
| 487 | 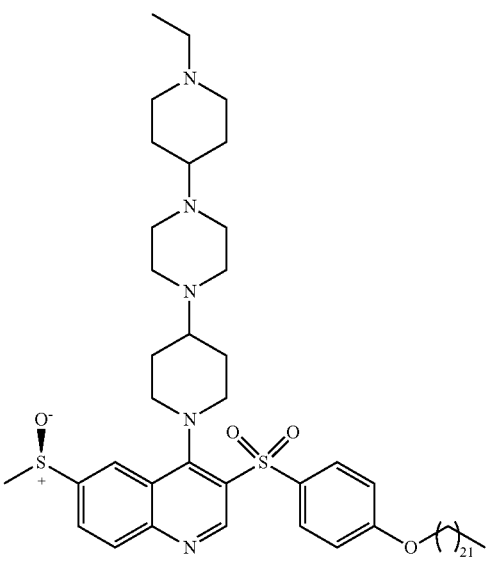 | (R)-3-((4-(docosyloxy)phenyl)sulfonyl)-4-(4-(4-(1-ethylpiperidin-4-yl)piperazin-1-yl)piperidin-1-yl)-6-(methylsulfinyl)quinoline |

TABLE 1-continued
| Ex. | Structure | Name |
|---|---|---|
| 488 | 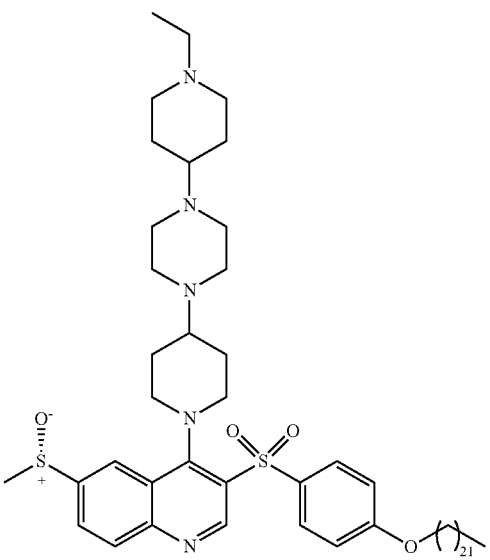 | (S)-3-((4-(docosyloxy)phenyl)sulfonyl)-4-(4-(4-(1-ethylpiperidin-4-yl)piperazin-1-yl)piperidin-1-yl)-6-(methylsulfinyl)quinoline |
| 489 | 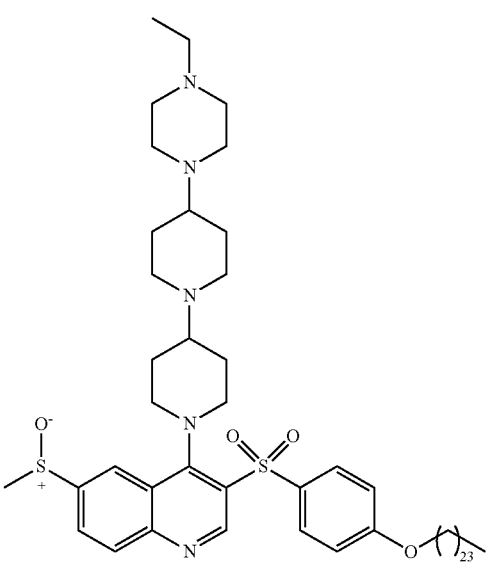 | 4-(4-(4-ethylpiperazin-1-yl)-[1,4'-bipiperidin]-1'-yl)-6-(methylsulfinyl)-3-((4-(tetracosyloxy)phenyl)sulfonyl)quinoline |

TABLE 1-continued
| Ex. | Structure | Name |
|---|---|---|
| 490 | 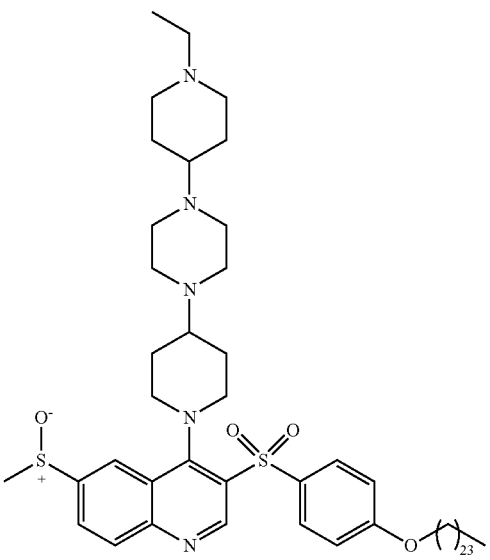 | 4-(4-(4-(1-ethylpiperidin-4-yl)piperazin-1-yl)piperidin-1-yl)-6-(methylsulfinyl)-3-((4-(tetracosyloxy)phenyl)sulfonyl)quinoline |
| 491 | 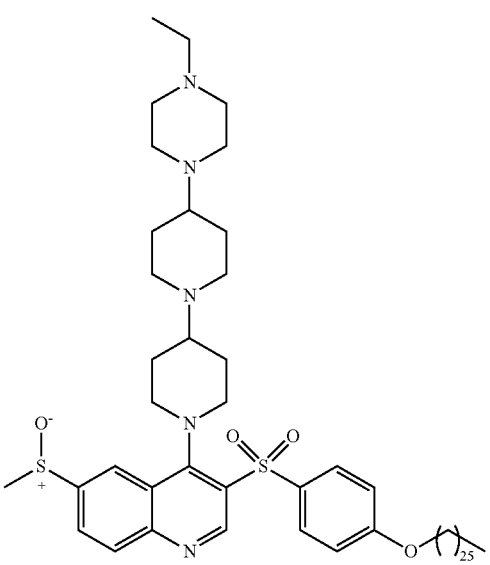 | 4-(4-(4-ethylpiperazin-1-yl)-[1,4'-bipiperidin]-1'-yl)-3-((4-(hexacosyloxy)phenyl)sulfonyl)-6-(methylsulfinyl)quinoline |

TABLE 1-continued
| Ex. | Structure | Name |
|---|---|---|
| 492 | 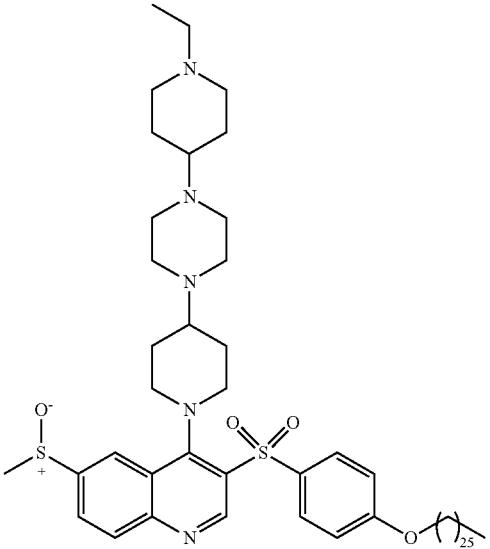 | 4-(4-(4-(1-ethylpiperidin-4-yl)piperazin-1-yl)piperidin-1-yl)-3-((4-(hexacosyloxy)phenyl)sulfonyl)-6-(methylsulfinyl)quinoline |
| 493 | 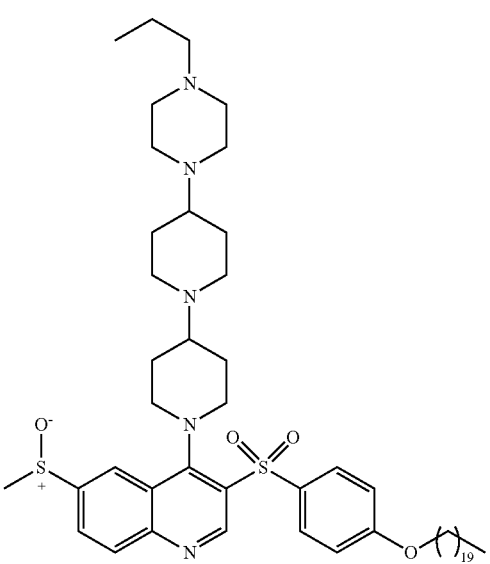 | 3-((4-(icosyloxy)phenyl)sulfonyl)-6-(methylsulfinyl)-4-(4-(4-propylpiperazin-1-yl)-[1,4'-bipiperidin]-1'-yl)quinoline |

TABLE 1-continued
| Ex. | Structure | Name |
|---|---|---|
| 494 | 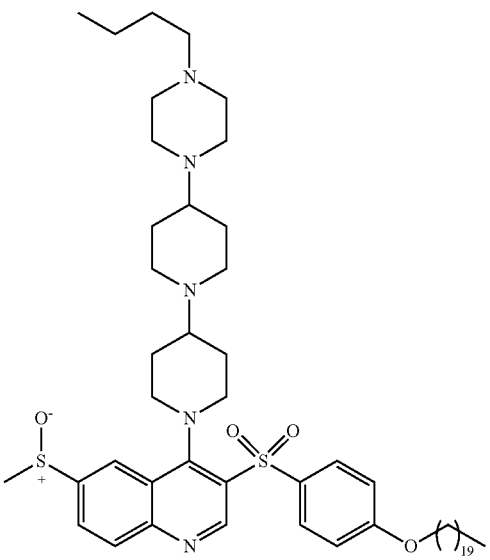 | 4-(4-(4-butylpiperazin-1-yl)-[1,4'-bipiperidin]-1'-yl)-3-((4-(icosyloxy)phenyl)sulfonyl)-6-(methylsulfinyl)quinoline |
| 495 | 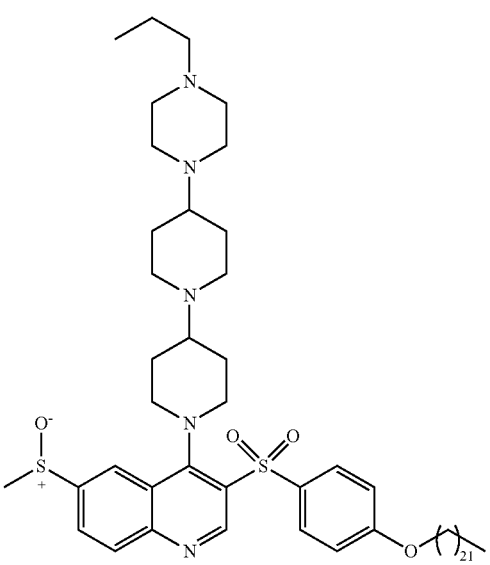 | 3-((4-(docosyloxy)phenyl)sulfonyl)-6-(methylsulfinyl)-4-(4-(4-propylpiperazin-1-yl)-[1,4'-bipiperidin]-1'-yl)quinoline |

TABLE 1-continued

| Ex. | Structure | Name |
|---|---|---|
| 496 | 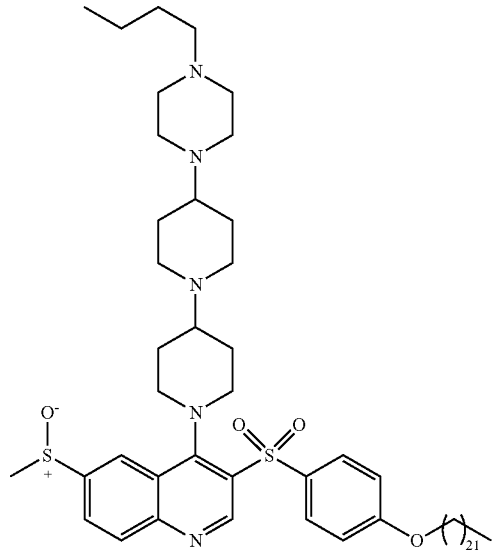 | 4-(4-(4-butylpiperazin-1-yl)-[1,4'-bipiperidin]-1'-yl)-3-((4-(docosyloxy)phenyl)sulfonyl)-6-(methylsulfinyl)quinoline |
| 497 | 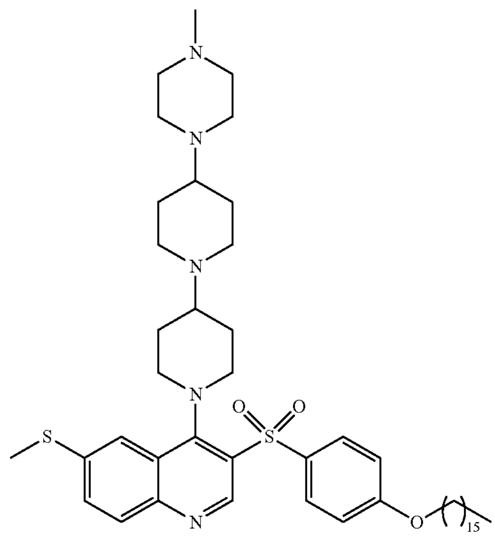 | 3-((4-(hexadecyloxy)phenyl)sulfonyl)-4-(4-(4-methylpiperazin-1-yl)-[1,4'-bipiperidin]-1'-yl)-6-(methylthio)quinoline |
| 498 | 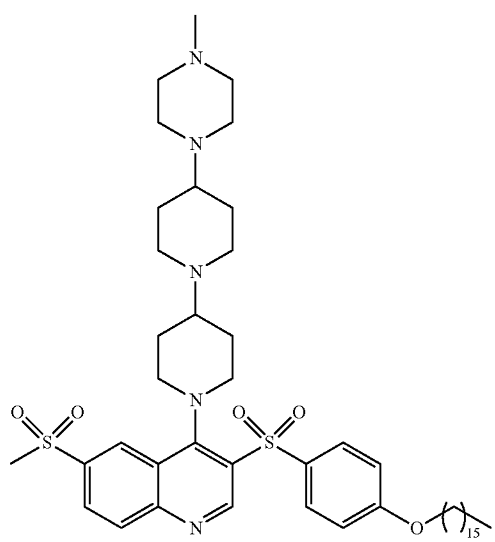 | 3-((4-(hexadecyloxy)phenyl)sulfonyl)-4-(4-(4-methylpiperazin-1-yl)-[1,4'-bipiperidin]-1'-yl)-6-(methylsulfonyl)quinoline |

TABLE 1-continued
| Ex. | Structure | Name |
|---|---|---|
| 499 | 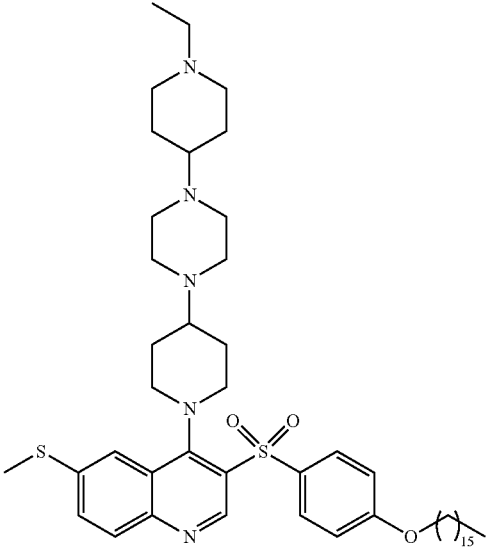 | 4-(4-(4-(1-ethylpiperidin-4-yl)piperazin-1-yl)piperidin-1-yl)-3-((4-(hexadecyloxy)phenyl)sulfonyl)-6-(methylthio)quinoline |
| 500 | 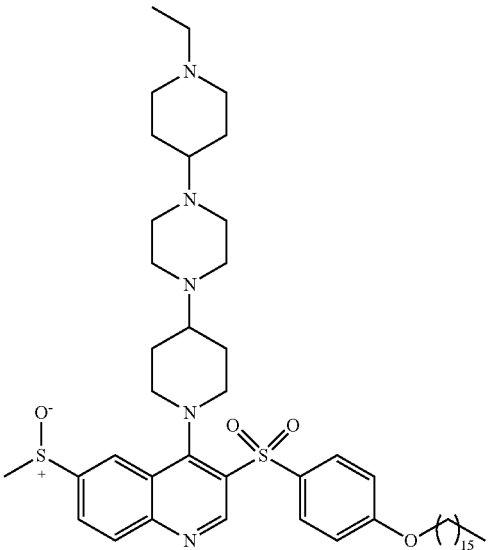 | 4-(4-(4-(1-ethylpiperidin-4-yl)piperazin-1-yl)piperidin-1-yl)-3-((4-(hexadecyloxy)phenyl)sulfonyl)-6-(methylsulfinyl)quinoline |

TABLE 1-continued
| Ex. | Structure | Name |
|---|---|---|
| 501 | 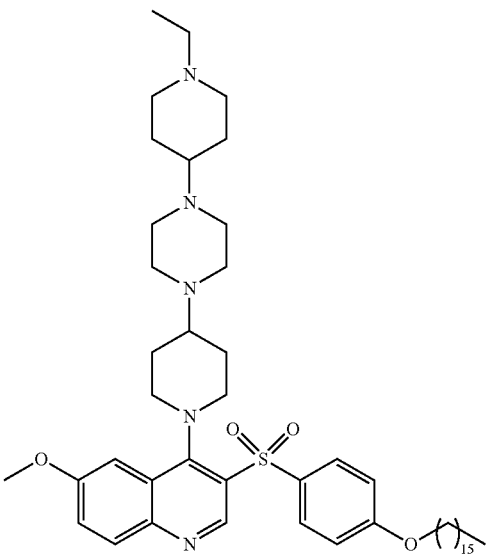 | 4-(4-(4-(1-ethylpiperidin-4-yl)piperazin-1-yl)piperidin-1-yl)-3-((4-(hexadecyloxy)phenyl)sulfonyl)-6-methoxyquinoline |
| 502 | 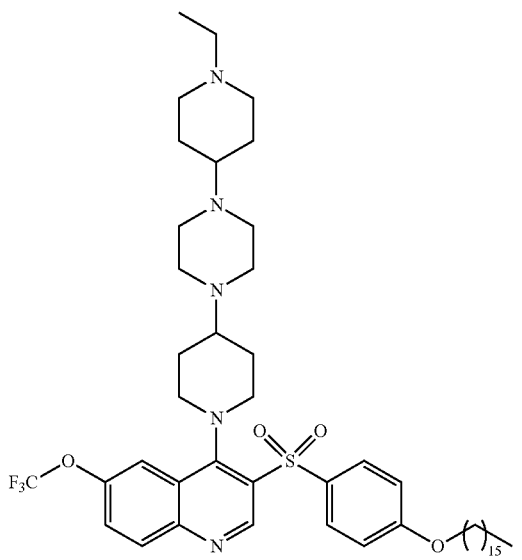 | 4-(4-(4-(1-ethylpiperidin-4-yl)piperazin-1-yl)piperidin-1-yl)-3-((4-(hexadecyloxy)phenyl)sulfonyl)-6-(trifluoromethoxy)quinoline |

TABLE 1-continued
| Ex. | Structure | Name |
|---|---|---|
| 503 | 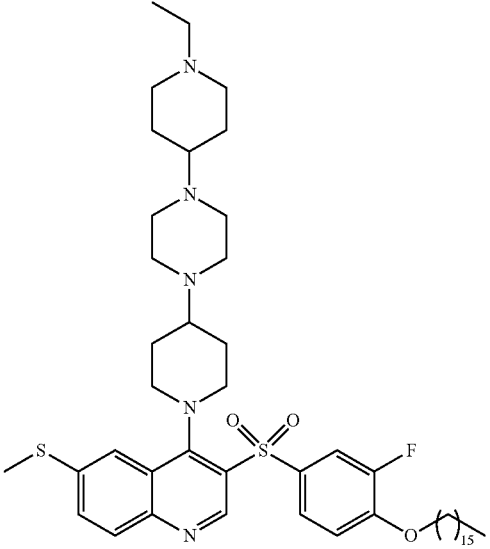 | 4-(4-(4-(1-ethylpiperidin-4-yl)piperazin-1-yl)piperidin-1-yl)-3-((3-fluoro-4-(hexadecyloxy)phenyl)sulfonyl)-6-(methylthio)quinoline |
| 504 | 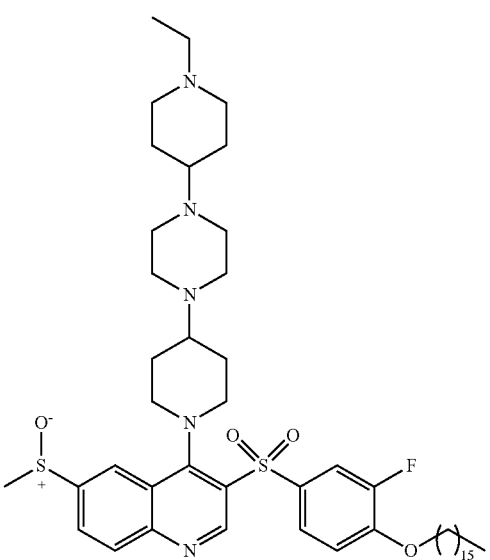 | 4-(4-(4-(1-ethylpiperidin-4-yl)piperazin-1-yl)piperidin-1-yl)-3-((3-fluoro-4-(hexadecyloxy)phenyl)sulfonyl)-6-(methylsulfinyl)quinoline |

TABLE 1-continued
| Ex. | Structure | Name |
|---|---|---|
| 505 | 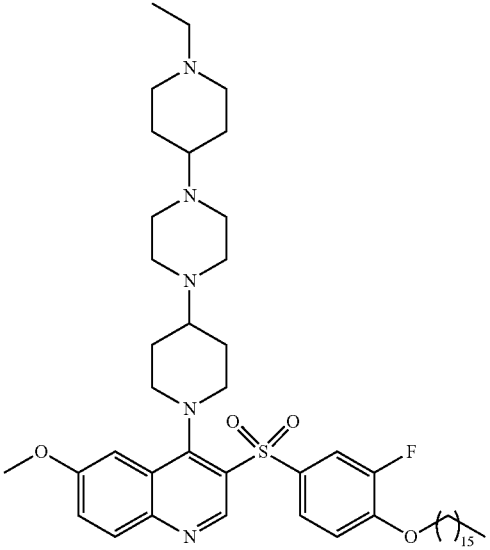 | 4-(4-(4-(1-ethylpiperidin-4-yl)piperazin-1-yl)piperidin-1-yl)-3-((3-fluoro-4-(hexadecyloxy)phenyl)sulfonyl)-6-methoxyquinoline |
| 506 | 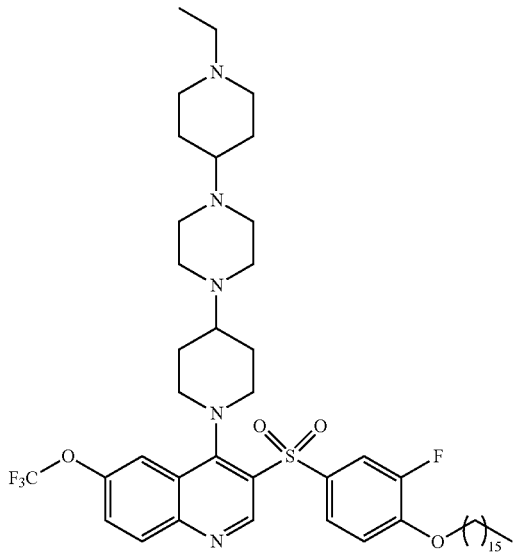 | 4-(4-(4-(1-ethylpiperidin-4-yl)piperazin-1-yl)piperidin-1-yl)-3-((3-fluoro-4-(hexadecyloxy)phenyl)sulfonyl)-6-(trifluoromethoxy)quinoline |

TABLE 1-continued
| Ex. | Structure | Name |
|---|---|---|
| 507 | 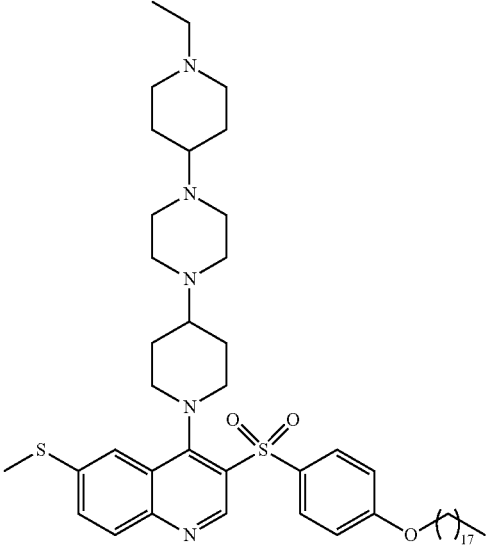 | 4-(4-(4-(1-ethylpiperidin-4-yl)piperazin-1-yl)piperidin-1-yl)-6-(methylthio)-3-((4-(octadecyloxy)phenyl)sulfonyl)quinoline |
| 508 | 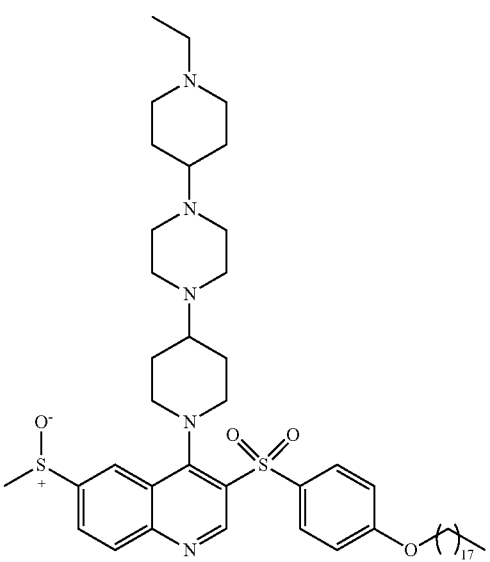 | 4-(4-(4-(1-ethylpiperidin-4-yl)piperazin-1-yl)piperidin-1-yl)-6-(methylsulfinyl)-3-((4-(octadecyloxy)phenyl)sulfonyl)quinoline |

TABLE 1-continued

| Ex. | Structure | Name |
|---|---|---|
| 509 | 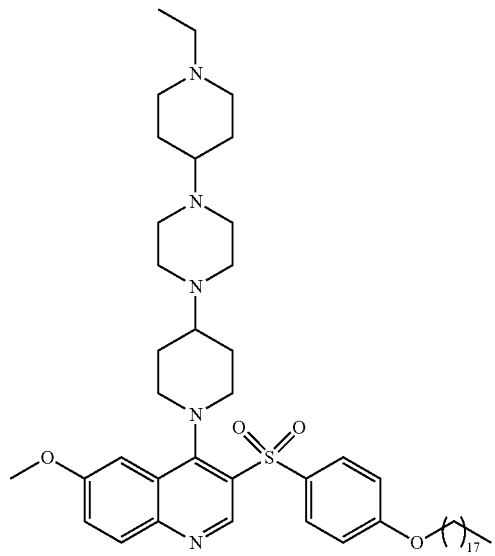 | 4-(4-(4-(1-ethylpiperidin-4-yl)piperazin-1-yl)piperidin-1-yl)-6-methoxy-3-((4-(octadecyloxy)phenyl)sulfonyl)quinoline |
| 510 | 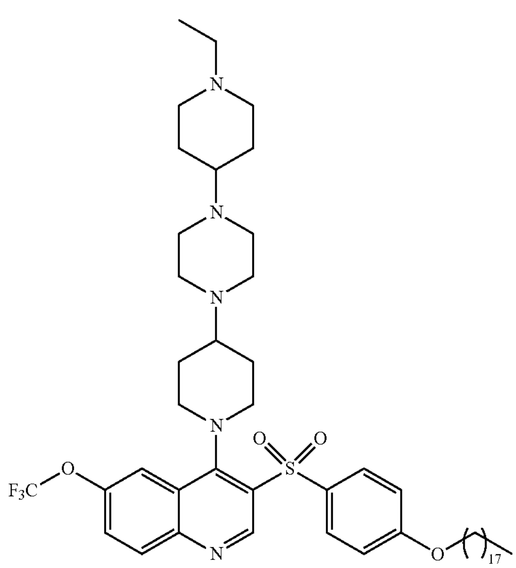 | 4-(4-(4-(1-ethylpiperidin-4-yl)piperazin-1-yl)piperidin-1-yl)-3-((4-(octadecyloxy)phenyl)sulfonyl)-6-(trifluoromethoxy)quinoline |

TABLE 1-continued
| Ex. | Structure | Name |
|---|---|---|
| 511 | 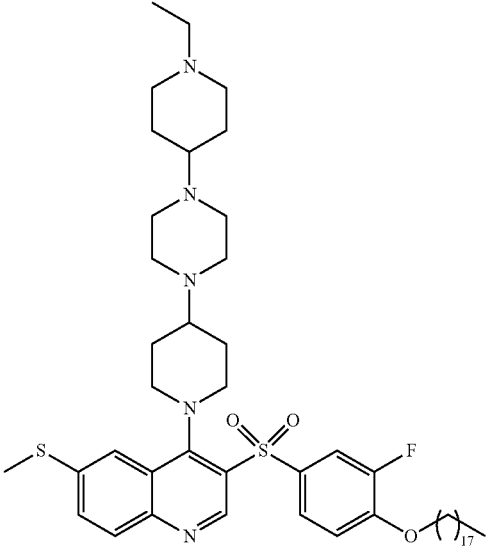 | 4-(4-(4-(1-ethylpiperidin-4-yl)piperazin-1-yl)piperidin-1-yl)-3-((3-fluoro-4-(octadecyloxy)phenyl)sulfonyl)-6-(methylthio)quinoline |
| 512 | 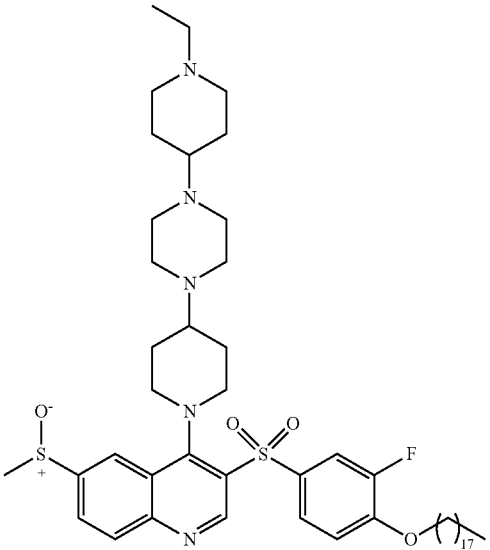 | 4-(4-(4-(1-ethylpiperidin-4-yl)piperazin-1-yl)piperidin-1-yl)-3-((3-fluoro-4-(octadecyloxy)phenyl)sulfonyl)-6-(methylsulfinyl)quinoline |

TABLE 1-continued
| Ex. | Structure | Name |
|---|---|---|
| 513 | 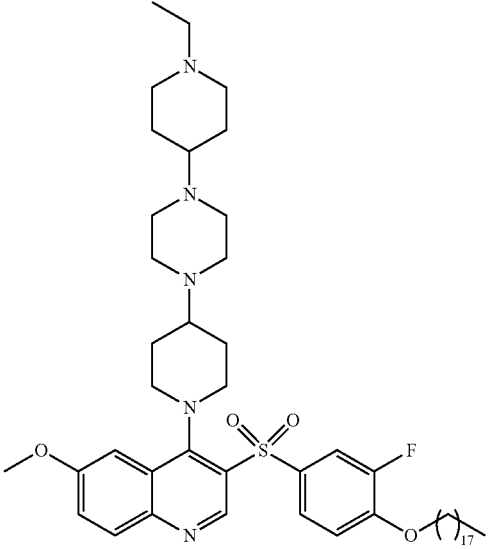 | 4-(4-(4-(1-ethylpiperidin-4-yl)piperazin-1-yl)piperidin-1-yl)-3-((3-fluoro-4-(octadecyloxy)phenyl)sulfonyl)-6-methoxyquinoline |
| 514 | 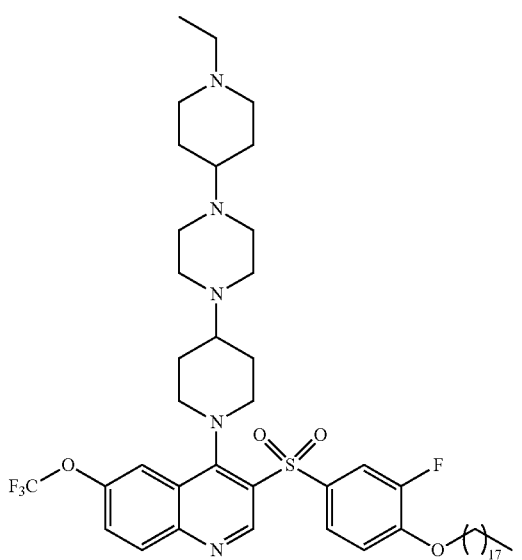 | 4-(4-(4-(1-ethylpiperidin-4-yl)piperazin-1-yl)piperidin-1-yl)-3-((3-fluoro-4-(octadecyloxy)phenyl)sulfonyl)-6-methoxyquinoline |

TABLE 1-continued
| Ex. | Structure | Name |
|---|---|---|
| 515 | 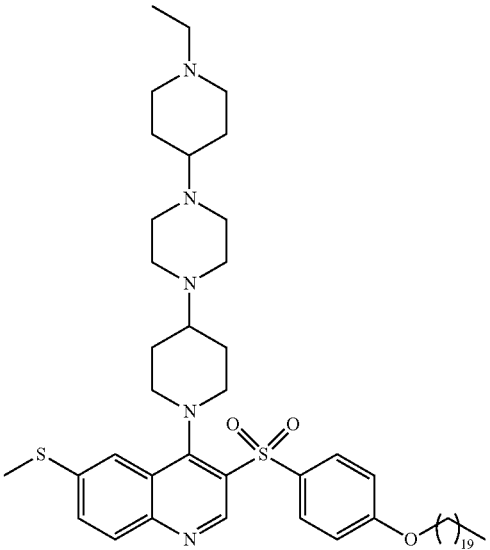 | 4-(4-(4-(1-ethylpiperidin-4-yl)piperazin-1-yl)piperidin-1-yl)-3-((4-(icosyloxy)phenyl)sulfonyl)-6-(methylthio)quinoline |
| 516 | 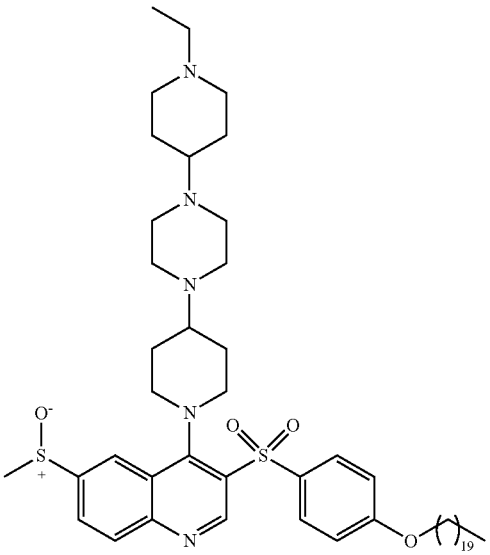 | 4-(4-(4-(1-ethylpiperidin-4-yl)piperazin-1-yl)piperidin-1-yl)-3-((4-(icosyloxy)phenyl)sulfonyl)-6-(methylsulfinyl)quinoline |

TABLE 1-continued
| Ex. | Structure | Name |
|---|---|---|
| 517 | 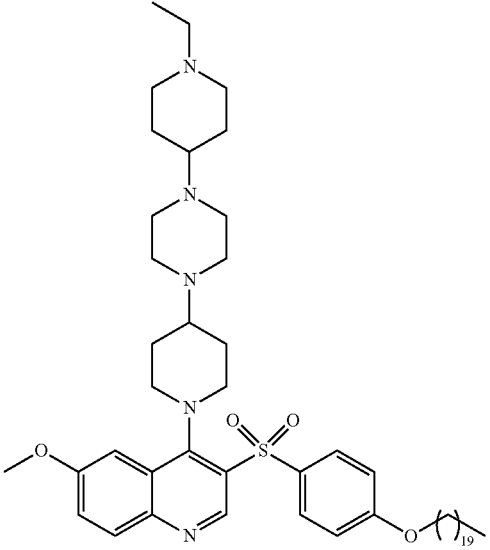 | 4-(4-(4-(1-ethylpiperidin-4-yl)piperazin-1-yl)piperidin-1-yl)-3-((4-(icosyloxy)phenyl)sulfonyl)-6-methoxyquinoline |
| 518 | 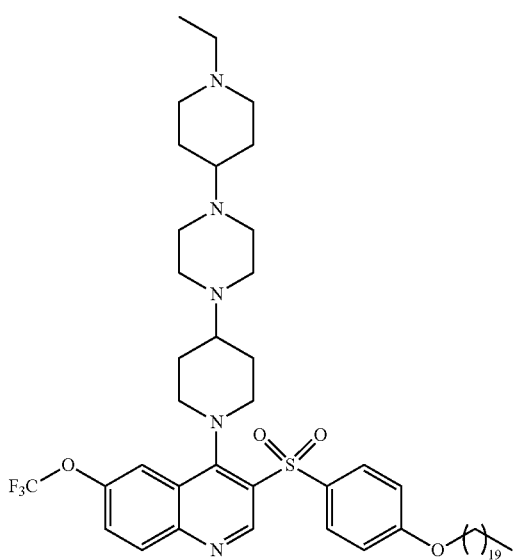 | 4-(4-(4-(1-ethylpiperidin-4-yl)piperazin-1-yl)piperidin-1-yl)-3-((4-(icosyloxy)phenyl)sulfonyl)-6-(trifluoromethoxy)quinoline |

TABLE 1-continued

| Ex. | Structure | Name |
|---|---|---|
| 519 | 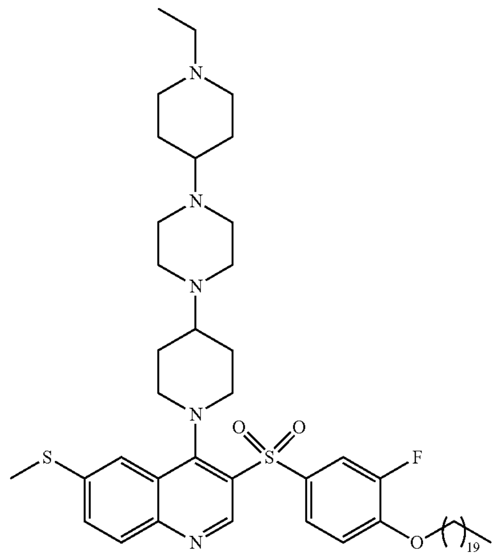 | 4-(4-(4-(1-ethylpiperidin-4-yl)piperazin-1-yl)piperidin-1-yl)-3-((3-fluoro-4-(icosyloxy)phenyl)sulfonyl)-6-(methylthio)quinoline |
| 520 | 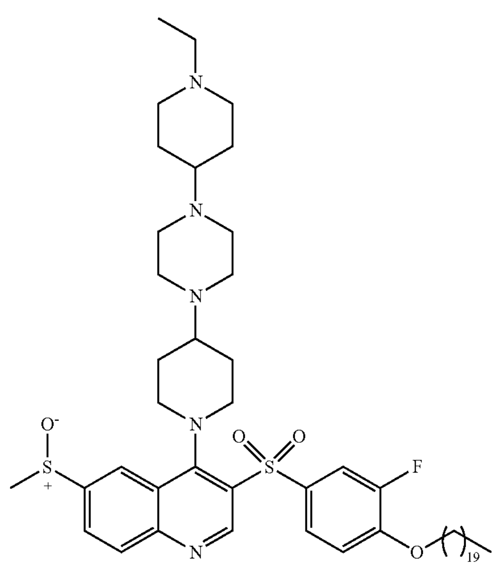 | 4-(4-(4-(1-ethylpiperidin-4-yl)piperazin-1-yl)piperidin-1-yl)-3-((3-fluoro-4-(icosyloxy)phenyl)sulfonyl)-6-(methylsulfinyl)quinoline |

TABLE 1-continued
| Ex. | Structure | Name |
|---|---|---|
| 521 | 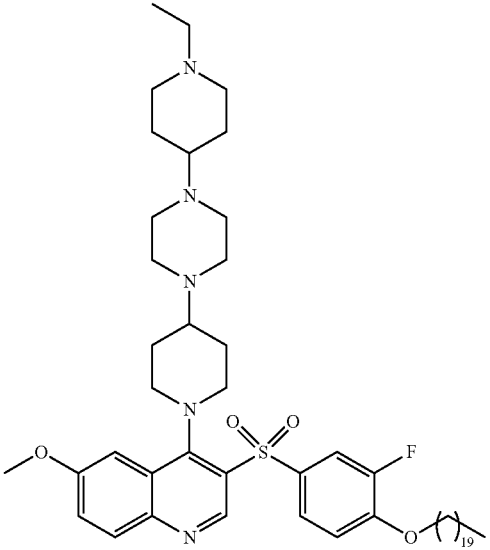 | 4-(4-(4-(1-ethylpiperidin-4-yl)piperazin-1-yl)piperidin-1-yl)-3-((3-fluoro-4-(icosyloxy)phenyl)sulfonyl)-6-methoxyquinoline |
| 522 | 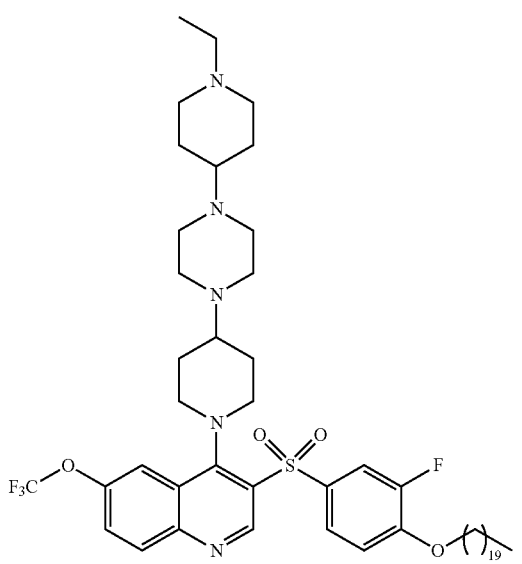 | 4-(4-(4-(1-ethylpiperidin-4-yl)piperazin-1-yl)piperidin-1-yl)-3-((3-fluoro-4-(icosyloxy)phenyl)sulfonyl)-6-(trifluoromethoxy)quinoline |

TABLE 1-continued
| Ex. | Structure | Name |
|---|---|---|
| 523 | 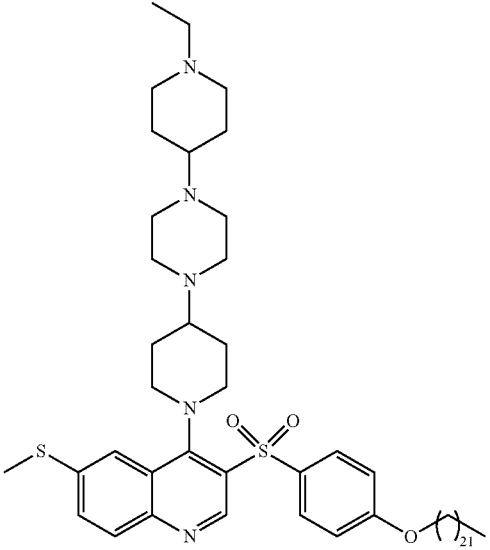 | 3-((4-(docosyloxy)phenyl)sulfonyl)-4-(4-(4-(1-ethylpiperidin-4-yl)piperazin-1-yl)piperidin-1-yl)-6-(methylthio)quinoline |
| 524 | 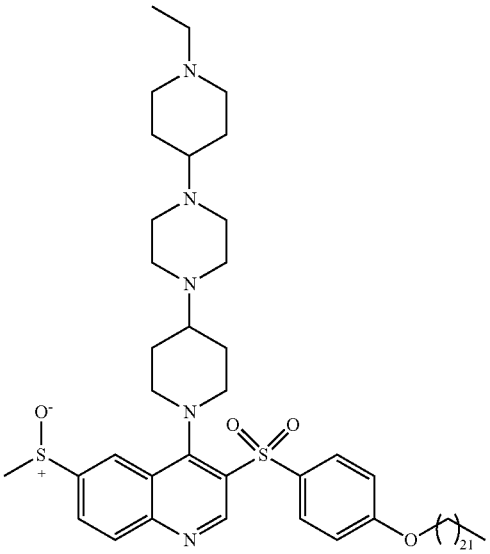 | 3-((4-(docosyloxy)phenyl)sulfonyl)-4-(4-(4-(1-ethylpiperidin-4-yl)piperazin-1-yl)piperidin-1-yl)-6-(methylsulfinyl)quinoline |

TABLE 1-continued

| Ex. | Structure | Name |
|---|---|---|
| 525 | 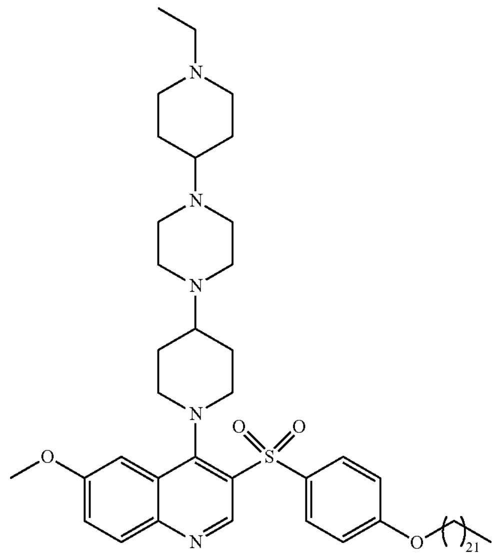 | 3-((4-(docosyloxy)phenyl)sulfonyl)-4-(4-(4-(1-ethylpiperidin-4-yl)piperazin-1-yl)piperidin-1-yl)-6-methoxyquinoline |
| 526 | 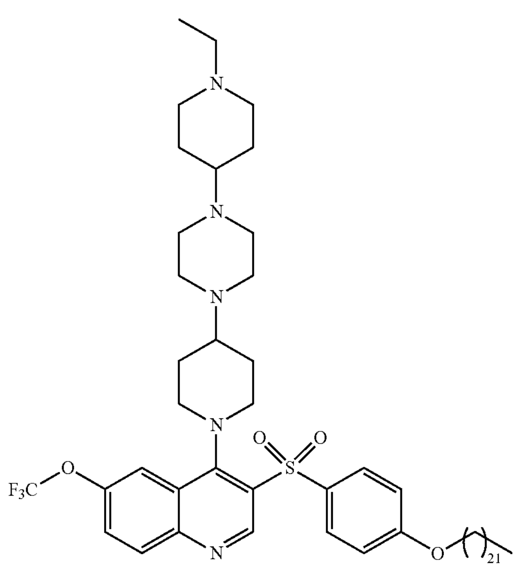 | 3-((4-(docosyloxy)phenyl)sulfonyl)-4-(4-(4-(1-ethylpiperidin-4-yl)piperazin-1-yl)piperidin-1-yl)-6-(trifluoromethoxy)quinoline |

TABLE 1-continued
| Ex. | Structure | Name |
|---|---|---|
| 527 | 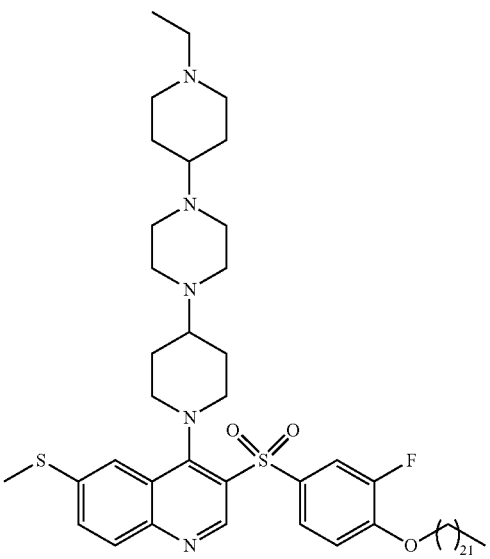 | 3-((4-(docosyloxy)-3-fluorophenyl)sulfonyl)-4-(4-(4-(1-ethylpiperidin-4-yl)piperazin-1-yl)piperidin-1-yl)-6-(methylthio)quinoline |
| 528 | 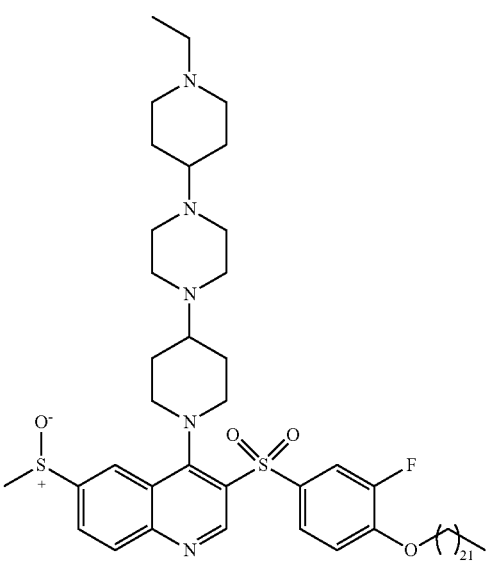 | 3-((4-(docosyloxy)-3-fluorophenyl)sulfonyl)-4-(4-(4-(1-ethylpiperidin-4-yl)piperazin-1-yl)piperidin-1-yl)-6-(methylsulfinyl)quinoline |

TABLE 1-continued
| Ex. | Structure | Name |
|---|---|---|
| 529 | 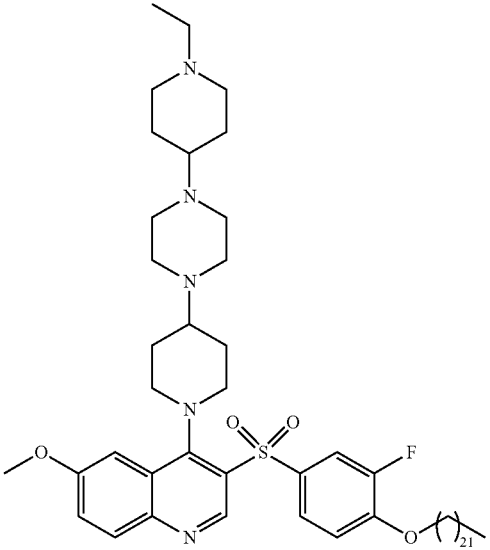 | 3-((4-(docosyloxy)-3-fluorophenyl)sulfonyl)-4-(4-(4-(1-ethylpiperidin-4-yl)piperazin-1-yl)piperidin-1-yl)-6-methoxyquinoline |
| 530 | 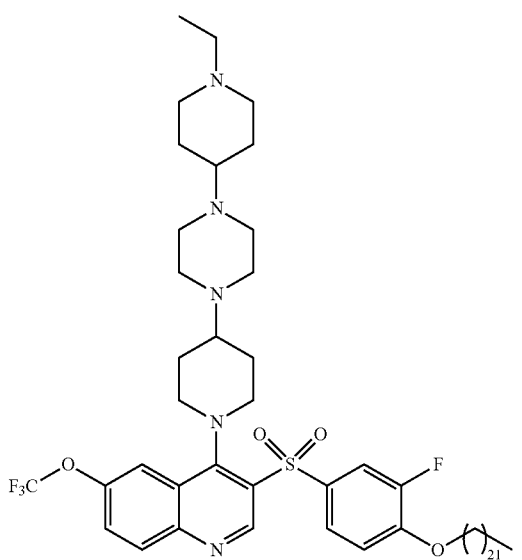 | 3-((4-(docosyloxy)-3-fluorophenyl)sulfonyl)-4-(4-(4-(1-ethylpiperidin-4-yl)piperazin-1-yl)piperidin-1-yl)-6-(trifluoromethoxy)quinoline |

TABLE 1-continued
| Ex. | Structure | Name |
|---|---|---|
| 531 | 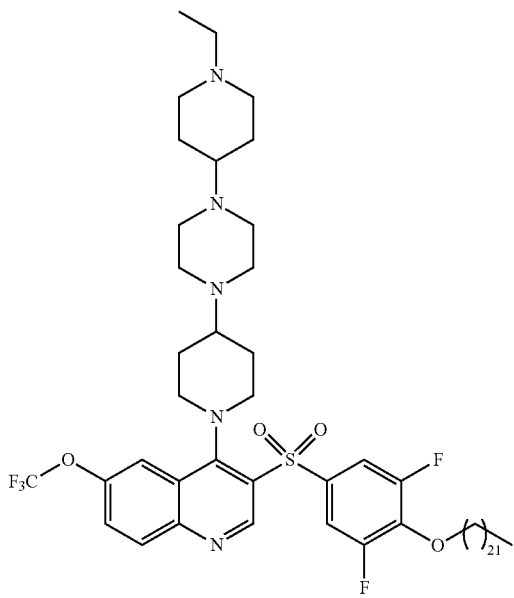 | 3-((4-(docosyloxy)-3,5-difluorophenyl)sulfonyl)-4-(4-(4-(1-ethylpiperidin-4-yl)piperazin-1-yl)piperidin-1-yl)-6-(trifluoromethoxy)quinoline |
| 532 | 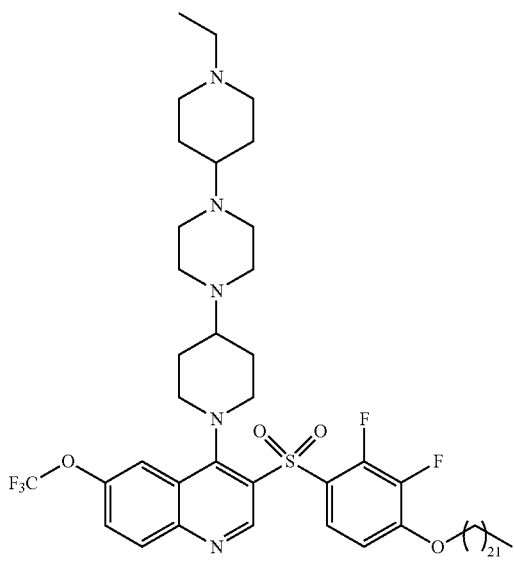 | 3-((4-(docosyloxy)-2,3-difluorophenyl)sulfonyl)-4-(4-(4-(1-ethylpiperidin-4-yl)piperazin-1-yl)piperidin-1-yl)-6-(trifluoromethoxy)quinoline |

TABLE 1-continued

| Ex. | Structure | Name |
|---|---|---|
| 533 | 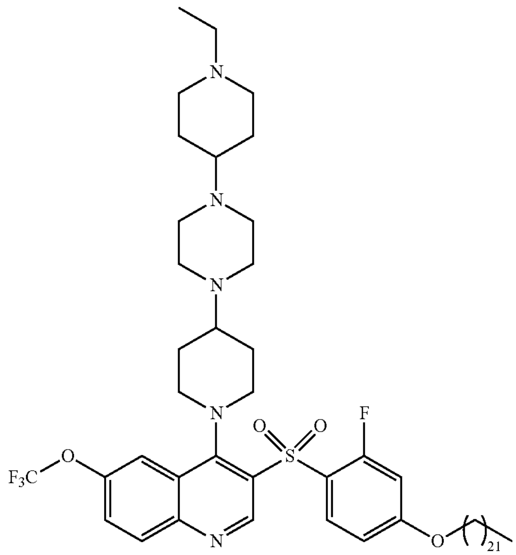 | 3-((4-(docosyloxy)-2-fluorophenyl)sulfonyl)-4-(4-(4-(1-ethylpiperidin-4-yl)piperazin-1-yl)piperidin-1-yl)-6-(trifluoromethoxy)quinoline |
| 534 | 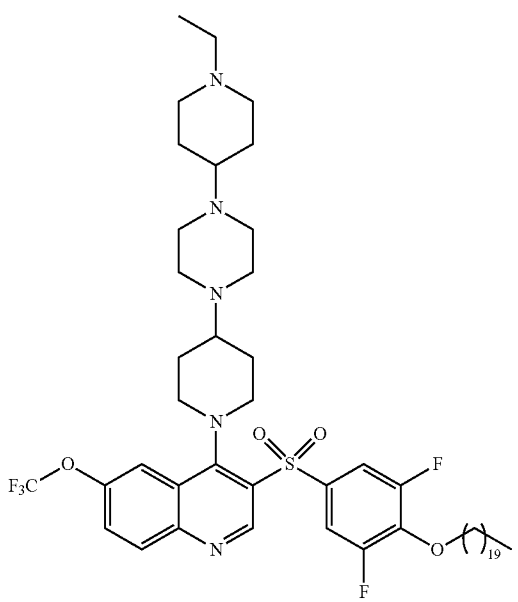 | 3-((3,5-difluoro-4-(icosyloxy)phenyl)sulfonyl)-4-(4-(4-(1-ethylpiperidin-4-yl)piperazin-1-yl)piperidin-1-yl)-6-(trifluoromethoxy)quinoline |

TABLE 1-continued

| Ex. | Structure | Name |
|---|---|---|
| 535 | 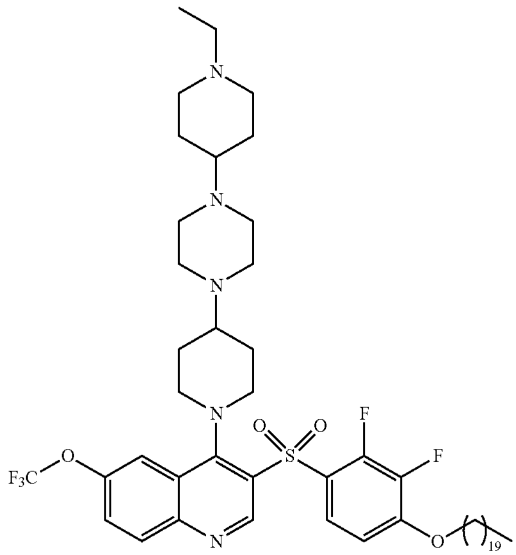 | 3-((2,3-difluoro-4-(icosyloxy)phenyl)sulfonyl)-4-(4-(4-(1-ethylpiperidin-4-yl)piperazin-1-yl)piperidin-1-yl)-6-(trifluoromethoxy)quinoline |
| 536 | 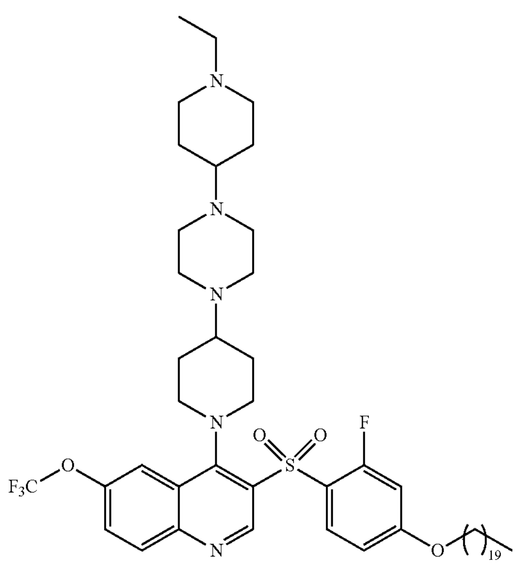 | 4-(4-(4-(1-ethylpiperidin-4-yl)piperazin-1-yl)piperidin-1-yl)-3-((2-fluoro-4-(icosyloxy)phenyl)sulfonyl)-6-(trifluoromethoxy)quinoline |

//
TABLE 1-continued
| Ex. | Structure | Name |
|---|---|---|
| 537 | 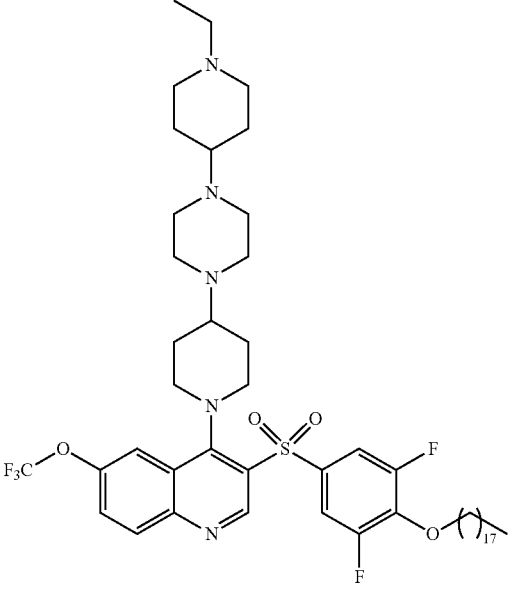 | 3-((3,5-difluoro-4-(octadecyloxy)phenyl)sulfonyl)-4-(4-(4-(1-ethylpiperidin-4-yl)piperazin-1-yl)piperidin-1-yl)-6-(trifluoromethoxy)quinoline |
| 538 | 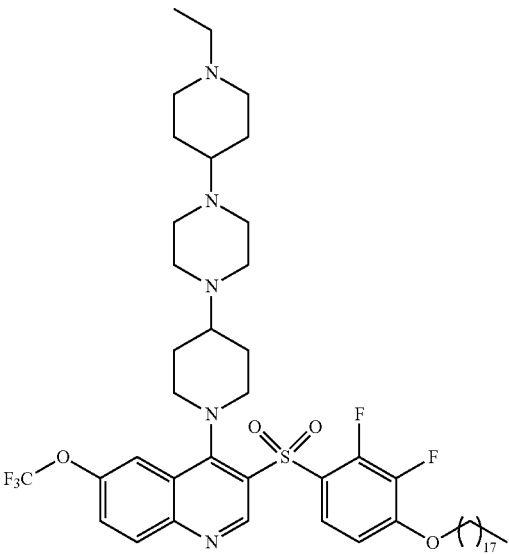 | 3-((2,3-difluoro-4-(octadecyloxy)phenyl)sulfonyl)-4-(4-(4-(1-ethylpiperidin-4-yl)piperazin-1-yl)piperidin-1-yl)-6-(trifluoromethoxy)quinoline |

TABLE 1-continued

| Ex. | Structure | Name |
|---|---|---|
| 539 | 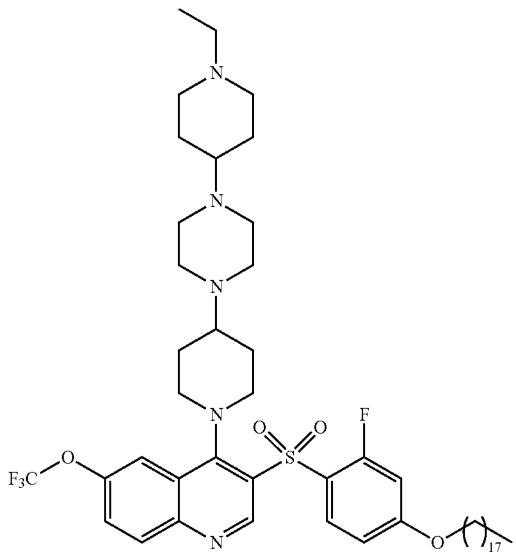 | 4-(4-(4-(1-ethylpiperidin-4-yl)piperazin-1-yl)piperidin-1-yl)-3-((2-fluoro-4-(octadecyloxy)phenyl)sulfonyl)-6-(trifluoromethoxy)quinoline |
| 540 | 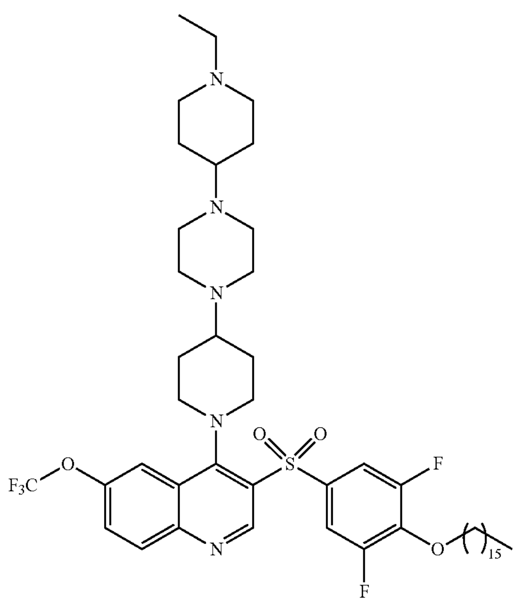 | 3-((3,5-difluoro-4-(hexadecyloxy)phenyl)sulfonyl)-4-(4-(4-(1-ethylpiperidin-4-yl)piperazin-1-yl)piperidin-1-yl)-6-(trifluoromethoxy)quinoline |

TABLE 1-continued
| Ex. | Structure | Name |
|---|---|---|
| 541 | 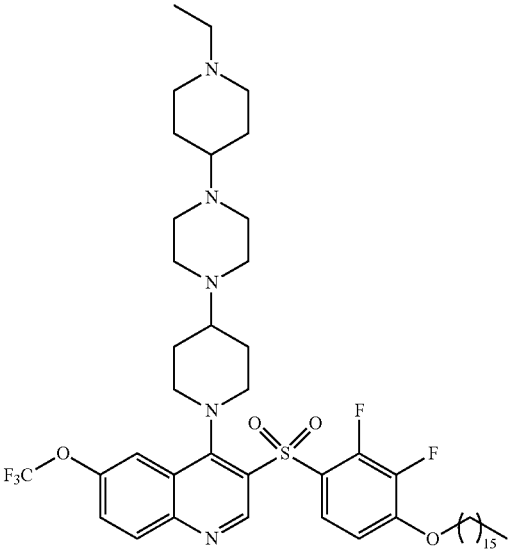 | 3-((2,3-difluoro-4-(hexadecyloxy)phenyl)sulfonyl)-4-(4-(4-(1-ethylpiperidin-4-yl)piperazin-1-yl)piperidin-1-yl)-6-(trifluoromethoxy)quinoline |
| 542 | 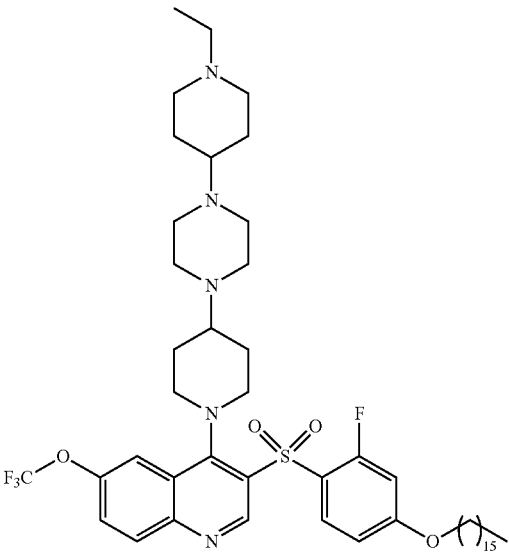 | 4-(4-(4-(1-ethylpiperidin-4-yl)piperazin-1-yl)piperidin-1-yl)-3-((2-fluoro-4-(hexadecyloxy)phenyl)sulfonyl)-6-(trifluoromethoxy)quinoline |

TABLE 1-continued

| Ex. | Structure | Name |
|---|---|---|
| 543 | 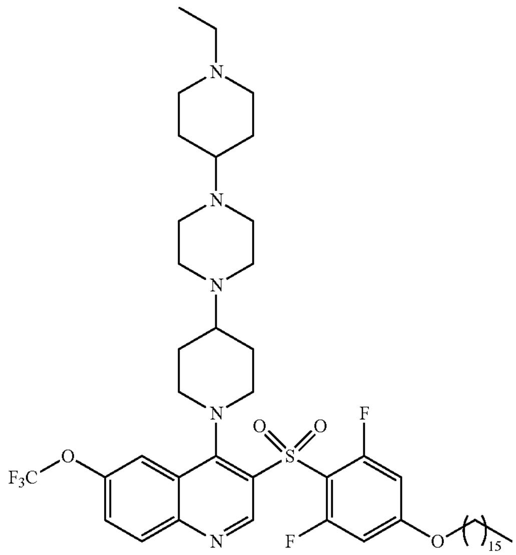 | 3-((2,6-difluoro-4-(hexadecyloxy)phenyl)sulfonyl)-4-(4-(4-(1-ethylpiperidin-4-yl)piperazin-1-yl)piperidin-1-yl)-6-(trifluoromethoxy)quinoline |
| 544 | 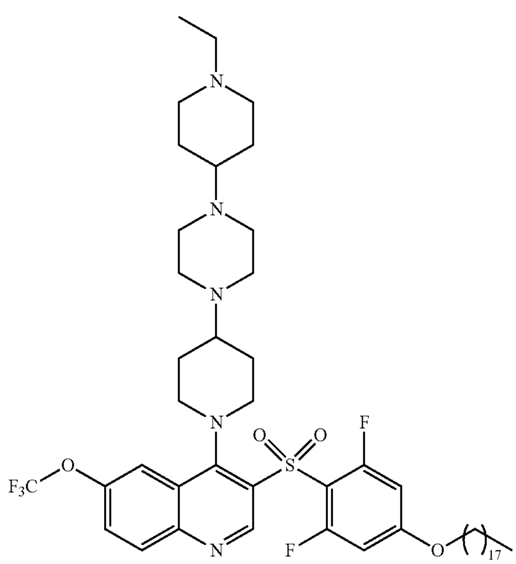 | 3-((2,6-difluoro-4-(octadecyloxy)phenyl)sulfonyl)-4-(4-(4-(1-ethylpiperidin-4-yl)piperazin-1-yl)piperidin-1-yl)-6-(trifluoromethoxy)quinoline |

TABLE 1-continued

| Ex. | Structure | Name |
|---|---|---|
| 545 | 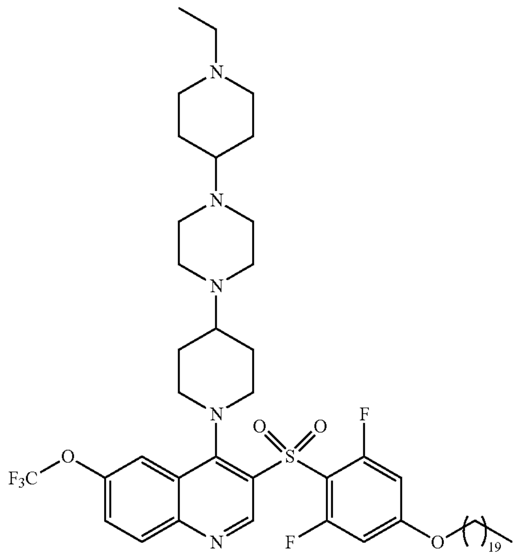 | 3-((2,6-difluoro-4-(icosyloxy)phenyl)sulfonyl)-4-(4-(4-(1-ethylpiperidin-4-yl)piperazin-1-yl)piperidin-1-yl)-6-(trifluoromethoxy)quinoline |
| 546 | 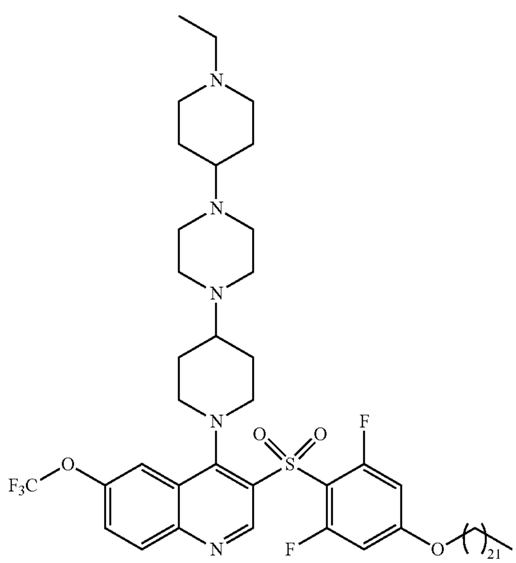 | 3-((4-(docosyloxy)-2,6-difluorophenyl)sulfonyl)-4-(4-(4-(1-ethylpiperidin-4-yl)piperazin-1-yl)piperidin-1-yl)-6-(trifluoromethoxy)quinoline |

//
TABLE 1-continued
| Ex. | Structure | Name |
|---|---|---|
| 547 | 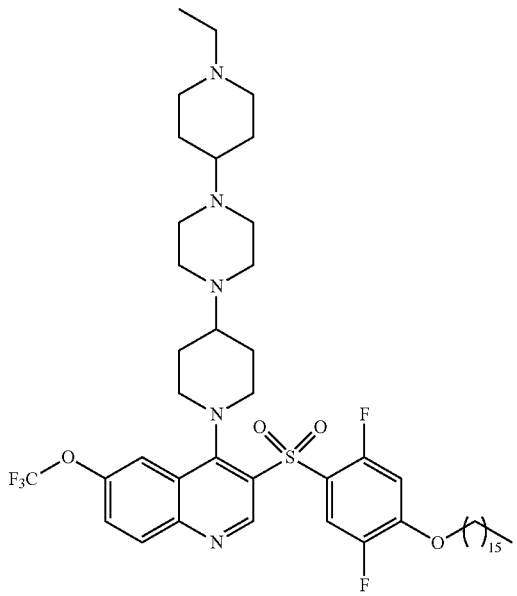 | 3-((2,5-difluoro-4-(hexadecyloxy)phenyl)sulfonyl)-4-(4-(4-(1-ethylpiperidin-4-yl)piperazin-1-yl)piperidin-1-yl)-6-(trifluoromethoxy)quinoline |
| 548 | 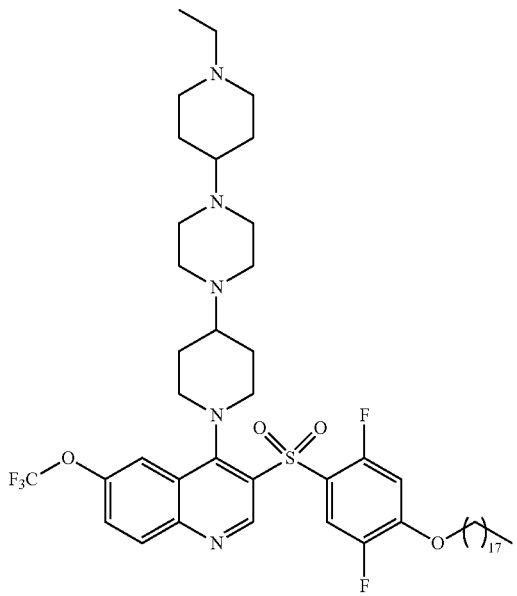 | 3-((2,5-difluoro-4-(octadecyloxy)phenyl)sulfonyl)-4-(4-(4-(1-ethylpiperidin-4-yl)piperazin-1-yl)piperidin-1-yl)-6-(trifluoromethoxy)quinoline |

| Ex. | Structure | Name |
|---|---|---|
| 549 | 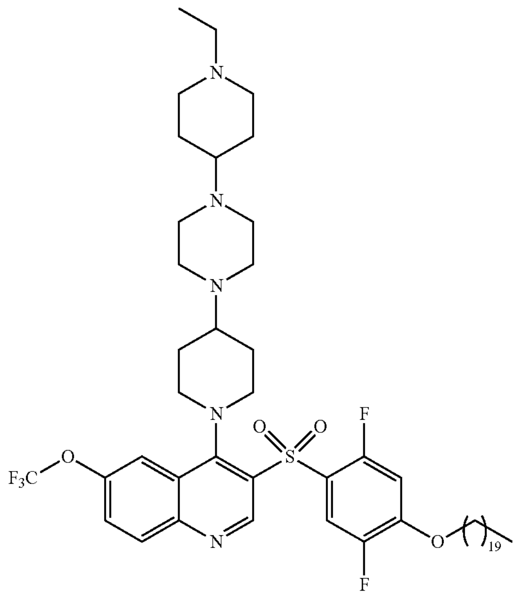 | 3-((2,5-difluoro-4-(icosyloxy)phenyl)sulfonyl)-4-(4-(4-(1-ethylpiperidin-4-yl)piperazin-1-yl)piperidin-1-yl)-6-(trifluoromethoxy)quinoline |
| 550 | 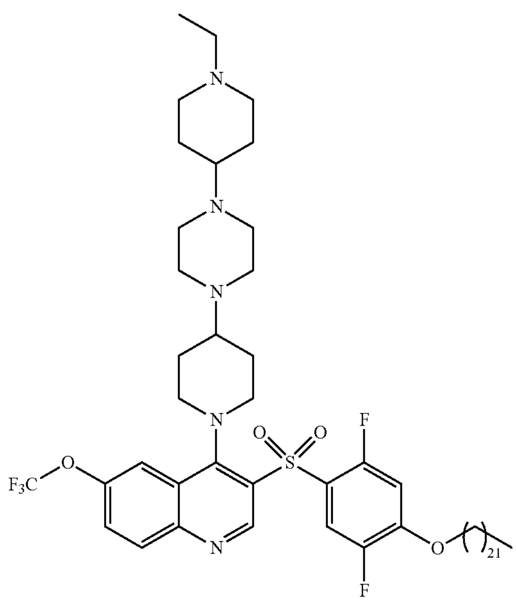 | 3-((4-(docosyloxy)-2,5-difluorophenyl)sulfonyl)-4-(4-(4-(1-ethylpiperidin-4-yl)piperazin-1-yl)piperidin-1-yl)-6-(trifluoromethoxy)quinoline |

In certain embodiments, provided is a salt of a compound of this disclosure. In certain embodiments, the salt is salt of a compound of this disclosure formed with hydrochloric acid, hydrochloric acid, phosphoric acid, methanesulfonic acid (mesylate salt), malic acid, malonic acid, maleic acid, fumaric acid, tartaric acid, citric acid, acetic acid, or oxalic acid. In certain embodiments, the salt is a salt of a compound of this disclosure formed with methanesulfonic acid (mesylate salt). In certain embodiments, the salt is a salt of a compound of this disclosure formed with oxalic acid. In any of these embodiments, the salt is a salt of a compound of this disclosure formed with oxalic acid dihydrate. In any of these embodiments, the salt is a tris(oxalic acid dihydrate) salt.

3. Methods

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art.

The present disclosure provides compounds and compositions for treating pathogenic blood vessel disorders such as diabetic retinopathy, age-related macular degeneration (AMD), retinopathy of prematurity, or cancer. The treatment can be through killing tumor blood vessels. In some embodiments, a tumor patient that can be suitably treated by the present technology expresses a plexin domain-containing protein (e.g., PLXDC1 or PLXDC2). The expression may be on a tumor blood epithelial cell.

As noted, the present technology not only can inhibit growth of new tumor blood vessels, but can also kill existing tumor blood vessels, thereby treating the tumor. In some embodiments, therefore, a tumor patient that can benefit from the present treatment is one that has a tumor that has undergone tumor angiogenesis. In some embodiments, the tumor comprises a vascularized tumor. In some embodiments, the tumor being treat has a diameter that is greater than about 0.1, 0.2, 0.3, 0.4, 0.5, 1, 1.5, 2, 2.5, 3, 4, 5, 6, 7, 8, 9 or 10 cm (or any derivable range therein). In some embodiments, the tumor already contains tumor blood vessels.

In some embodiments, the tumor does not have a known tumor surface marker as target for immunotherapy. In some embodiments, the tumor does not contain a mutant gene that serves as a target for tumor therapy. In some embodiments, the therapy of the present disclosure does not include inducing antibody-dependent cell-mediated cytotoxicity (ADCC). In some embodiments, a therapeutic agent of the present disclosure does not induce ADCC.

In some embodiments, the patient suffers from a cancer such as, polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

In some embodiments, the compounds and compositions described herein may be used to treat any cancerous or pre-cancerous tumor, such as a solid tumor. Cancers that may be treated by compounds and compositions provided herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometrioid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; mammary paget's disease; acinar cell carcinoma; adenosquamous carcinoma; adenocarcinoma w/squamous metaplasia; malignant thymoma; malignant ovarian stromal tumor; malignant thecoma; malignant granulosa cell tumor; and malignant roblastoma; sertoli cell carcinoma; malignant leydig cell tumor; malignant lipid cell tumor; malignant paraganglioma; malignant extra-mammary paraganglioma; pheochromocytoma; glomangiosarcoma; malignant melanoma; amelanotic melanoma; superficial spreading melanoma; malignant melanoma in giant pigmented nevus; epithelioid cell melanoma; malignant blue nevus; sarcoma; fibrosarcoma; malignant fibrous histiocytoma; myxosarcoma; liposarcoma; leiomyosarcoma; rhabdomyosarcoma; embryonal rhabdomyosarcoma; alveolar rhabdomyosarcoma; stromal sarcoma; malignant mixed tumor; mullerian mixed tumor; nephroblastoma; hepatoblastoma; carcinosarcoma; malignant mesenchymoma; malignant brenner tumor; malignant phyllodes tumor; synovial sarcoma; malignant mesothelioma; dysgerminoma; embryonal carcinoma; malignant teratoma; malignant struma ovarii; choriocarcinoma; malignant mesonephroma; hemangiosarcoma; malignant hemangioendothelioma; kaposi's sarcoma; malignant hemangiopericytoma; lymphangiosarcoma; osteosarcoma; juxtacortical osteosarcoma; chondrosarcoma; malignant chondroblastoma; mesenchymal chondrosarcoma; giant cell tumor of bone; ewing's sarcoma; malignant odontogenic tumor; ameloblastic odontosarcoma; malignant ameloblastoma; ameloblastic fibrosarcoma; malignant pinealoma; chordoma; malignant glioma; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; malignant meningioma; neurofibrosarcoma; malignant neurilemmoma; malignant granular cell tumor; malignant lymphoma; Hodgkin's disease; Hodgkin's lymphoma; paragranuloma; small lymphocytic malignant lymphoma; diffuse large cell malignant lymphoma; follicular malignant lymphoma; mycosis fungoides; other specified non-Hodgkin's lymphomas; malignant histiocytosis; multiple myeloma; mast cell sarcoma or immunoproliferative small intestinal disease.

In some embodiments, the subject has cancer, optionally comprising a solid tumor. An agent disclosed herein may be administered locally to the tumor. In some embodiments, the tumor is an adenocarcinoma, an adrenal tumor, an anal tumor, a bile duct tumor, a bladder tumor, a bone tumor, a blood born tumor, a brain/CNS tumor, a breast tumor, a cervical tumor, a colorectal tumor, an endometrial tumor, an esophageal tumor, an Ewing tumor, an eye tumor, a gallbladder tumor, a gastrointestinal, a kidney tumor, a laryngeal or hypopharyngreal tumor, a liver tumor, a lung tumor, a mesothelioma tumor, a multiple myeloma tumor, a muscle tumor, a nasopharyngeal tumor, a neuroblastoma, an oral tumor, an osteosarcoma, an ovarian tumor, a pancreatic tumor, a penile tumor, a pituitary tumor, a primary tumor, a prostate tumor, a retinoblastoma, a Rhabdomyosarcoma, a salivary gland tumor, a soft tissue sarcoma, a melanoma, a metastatic tumor, a basal cell carcinoma, a Merkel cell tumor, a testicular tumor, a thymus tumor, a thyroid tumor, a uterine tumor, a vaginal tumor, a vulvar tumor, or a Wilms tumor. In some embodiments, a compound and/or composition described herein may be administered parenterally, at or near the site of a tumor, or distant from the site of the tumor.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds employed in the pharmaceutical composition at levels lower than that required in order to achieve the desired therapeutic effect and gradually increase the dosage until the desired effect is achieved.

The administration of one or more compounds as described herein may result in at least a 10% decrease (e.g., at least 15%, 20%, 25%, 30%, 35%, 40%, 45%, 50%, 55%, 60%, 65%, 70%, 75%, 80%, 85%, 90% or even 100% decrease in one or more symptoms of a disease or condition, such as a decrease in tumor size.

Compounds described herein can be used in methods for agonizing Pigment-Epithelium-Derived Factor (PEDF) receptors. Compounds described herein can also be used in methods for inhibiting angiogenesis.

The PEDF receptors have been identified as two homologous membrane proteins called plexin domain containing 1 (PLXDC1) and plexin domain containing 2 (PLXDC2). They belong to a new type of cell-surface receptors and are the only proteins that are known to confer cell-surface binding to PEDF and to transduce PEDF signal into the target cells. Consistent with the ability of PEDF to suppress pathogenic angiogenesis in blinding diseases and in cancer without affecting healthy blood vessels, the PEDF receptors are highly expressed in pathogenic blood vessels in many diseases, including tumor blood vessels and diabetic retinopathy. The PEDF receptors are not detected in healthy blood vessels. One of the PEDF receptors (TEM7, PLXDC1) was well studied in the past as a tumor endothelial marker that is enriched in tumor blood vessels of diverse types of human cancer including colon, liver, lung, breast, pancreatic, brain, bladder, ovarian, kidney, esophagus, gastric and endometrial cancer and Kaposi sarcoma, liposarcoma and synovial sarcoma. In blinding diseases, PEDF receptor TEM7 (PLXDC1) is highly expressed in pathogenic blood vessels of diabetic retinopathy, retinal occlusive vascular disease, retinopathy of prematurity, and choroidal neovascularization (pathogenic angiogenesis in AMD). This is consistent with the role of PEDF in suppressing pathogenic angiogenesis in these diseases without affecting healthy blood vessels.

The compounds and methods described herein can therefore be used in treating disease mediated by PEDF receptors or associated with angiogenesis, such as cancer, retinal occlusive vascular disease, retinopathy of prematurity, diabetic retinopathy, and age-related macular degeneration.

In certain embodiments, provided herein are methods for agonizing Pigment-Epithelium-Derived Factor (PEDF) receptors in a patient in need thereof comprising administering to said patient a therapeutically effective amount of a compound of the disclosure, or a pharmaceutically acceptable salt, isotopically enriched analog, stereoisomer, mixture of stereoisomers, or tautomer thereof.

In certain embodiments, provided herein are methods for inhibiting angiogenesis in a patient in need thereof comprising administering to said patient a therapeutically effective amount of a compound of the disclosure, or a pharmaceutically acceptable salt, isotopically enriched analog, stereoisomer, mixture of stereoisomers, or tautomer thereof. In certain embodiments, the angiogenesis is pathogenic angiogenesis.

Also provided herein are methods for treating a disease or disorder mediated by PEDF receptors in a patient in need thereof comprising administering to said patient a therapeutically effective amount of a compound of the disclosure, or a pharmaceutically acceptable salt, isotopically enriched analog, stereoisomer, mixture of stereoisomers, or tautomer thereof.

Also provided herein are methods for treating a disease or disorder associated with angiogenesis in a patient in need thereof comprising administering to said patient a therapeutically effective amount of a compound of the disclosure, or a pharmaceutically acceptable salt, isotopically enriched analog, stereoisomer, mixture of stereoisomers, or tautomer thereof.

Also provided herein are methods for treating a disease or disorder selected from a cancer, retinal occlusive vascular disease, retinopathy of prematurity, diabetic retinopathy, and age-related macular degeneration comprising administering to said patient a therapeutically effective amount of a compound of the disclosure, or a pharmaceutically acceptable salt, isotopically enriched analog, stereoisomer, mixture of stereoisomers, or tautomer thereof. In certain embodiments, the cancer is selected from colon, liver, lung, breast, pancreatic, brain, bladder, ovarian, kidney, esophagus, gastric and endometrial cancer and Kaposi sarcoma, liposarcoma and synovial sarcoma. In certain embodiments, the disease is a blinding disease. In certain embodiments, the disease is diabetic retinopathy, retinal occlusive vascular disease, retinopathy of prematurity, or choroidal neovascularization (pathogenic angiogenesis in AMD).

In certain embodiments, provided herein is use of a compound of the disclosure, or a pharmaceutically acceptable salt, isotopically enriched analog, stereoisomer, mixture of stereoisomers, or tautomer thereof in a method for agonizing Pigment-Epithelium-Derived Factor (PEDF) receptors in a patient in need thereof comprising administering to said patient a therapeutically effective amount of the compound, or a pharmaceutically acceptable salt, isotopically enriched analog, stereoisomer, mixture of stereoisomers, or tautomer thereof.

In certain embodiments, provided herein is use of a compound of the disclosure, or a pharmaceutically acceptable salt, isotopically enriched analog, stereoisomer, mixture of stereoisomers, or tautomer thereof in a method for inhibiting angiogenesis in a patient in need thereof comprising administering to said patient a therapeutically effective amount of the compound, or a pharmaceutically acceptable salt, isotopically enriched analog, stereoisomer, mixture of stereoisomers, or tautomer thereof. In certain embodiments, the angiogenesis is pathogenic angiogenesis.

Also provided herein is use of a compound of the disclosure, or a pharmaceutically acceptable salt, isotopically enriched analog, stereoisomer, mixture of stereoisomers, or tautomer thereof in a method for treating a disease or disorder mediated by PEDF receptors in a patient in need thereof comprising administering to said patient a therapeutically effective amount of the compound, or a pharmaceutically acceptable salt, isotopically enriched analog, stereoisomer, mixture of stereoisomers, or tautomer thereof.

Also provided herein is use of a compound of the disclosure, or a pharmaceutically acceptable salt, isotopically enriched analog, stereoisomer, mixture of stereoisomers, or tautomer thereof in a method for treating a disease or disorder associated with angiogenesis in a patient in need thereof comprising administering to said patient a therapeutically effective amount of the compound, or a pharmaceutically acceptable salt, isotopically enriched analog, stereoisomer, mixture of stereoisomers, or tautomer thereof.

Also provided herein is use of a compound of the disclosure, or a pharmaceutically acceptable salt, isotopically enriched analog, stereoisomer, mixture of stereoisomers, or tautomer thereof in a method for treating a disease or disorder selected from a cancer, retinal occlusive vascular disease, retinopathy of prematurity, diabetic retinopathy, and age-related macular degeneration comprising administering to said patient a therapeutically effective amount of the compound, or a pharmaceutically acceptable salt, isotopically enriched analog, stereoisomer, mixture of stereoisomers, or tautomer thereof. In certain embodiments, the cancer is selected from colon, liver, lung, breast, pancreatic, brain, bladder, ovarian, kidney, esophagus, gastric and endometrial cancer and Kaposi sarcoma, liposarcoma and synovial sarcoma. In certain embodiments, the disease is a blinding disease. In certain embodiments, the disease is diabetic retinopathy, retinal occlusive vascular disease, retinopathy of prematurity, or choroidal neovascularization (pathogenic angiogenesis in AMD).

In certain embodiments, provided herein is use of a compound of the disclosure, or a pharmaceutically acceptable salt, isotopically enriched analog, stereoisomer, mixture of stereoisomers, or tautomer thereof in the manufacture of a medicament for agonizing Pigment-Epithelium-Derived Factor (PEDF) receptors in a patient in need thereof.

In certain embodiments, provided herein is use of a compound of the disclosure, or a pharmaceutically acceptable salt, isotopically enriched analog, stereoisomer, mixture of stereoisomers, or tautomer thereof in the manufacture of a medicament for inhibiting angiogenesis in a patient in need thereof. In certain embodiments, the angiogenesis is pathogenic angiogenesis.

Also provided herein is use of a compound of the disclosure, or a pharmaceutically acceptable salt, isotopically enriched analog, stereoisomer, mixture of stereoisomers, or tautomer thereof in the manufacture of a medicament for treating a disease or disorder mediated by PEDF receptors in a patient in need thereof.

Also provided herein is use of a compound of the disclosure, or a pharmaceutically acceptable salt, isotopically enriched analog, stereoisomer, mixture of stereoisomers, or tautomer thereof in the manufacture of a medicament for treating a disease or disorder associated with angiogenesis in a patient in need thereof.

Also provided herein is use of a compound of the disclosure, or a pharmaceutically acceptable salt, isotopically enriched analog, stereoisomer, mixture of stereoisomers, or tautomer thereof in the manufacture of a medicament for treating a disease or disorder selected from a cancer, retinal occlusive vascular disease, retinopathy of prematurity, diabetic retinopathy, and age-related macular degeneration. In certain embodiments, the cancer is selected from colon, liver, lung, breast, pancreatic, brain, bladder, ovarian, kidney, esophagus, gastric and endometrial cancer and Kaposi sarcoma, liposarcoma and synovial sarcoma. In certain embodiments, the disease is a blinding disease. In certain embodiments, the disease is diabetic retinopathy, retinal occlusive vascular disease, retinopathy of prematurity, or choroidal neovascularization (pathogenic angiogenesis in AMD).

4. Kits

Provided herein are also kits that include a compound of the disclosure, or a pharmaceutically acceptable salt, isotopically enriched analog, stereoisomer, mixture of stereoisomers, or tautomer thereof, and suitable packaging. In certain embodiments, a kit further includes instructions for use. In one aspect, a kit includes a compound of the disclosure, or a pharmaceutically acceptable salt, isotopically enriched analog, stereoisomer, mixture of stereoisomers, or tautomer thereof, and a label and/or instructions for use of the compounds in the treatment of the indications, including the diseases or conditions, described herein.

Provided herein are also articles of manufacture that include a compound described herein or a pharmaceutically acceptable salt, isotopically enriched analog, stereoisomer, mixture of stereoisomers, or tautomer thereof in a suitable container. The container may be a vial, jar, ampoule, preloaded syringe and intravenous bag.

5. Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, isotopically enriched analog, stereoisomer, mixture of stereoisomers, or tautomer thereof (collectively and individually, the "active ingredient") and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). About 0.1% to about 90% of the total weight of the composition may be the active ingredient.

The therapeutic agents of the disclosure may be administered by the same route of administration or by different routes of administration. In some embodiments, the cancer therapy is administered intravenously, intramuscularly, subcutaneously, topically, orally, transdermally, intraperitoneally, intraorbitally, by implantation, by inhalation, intrathecally, intraventricularly, or intranasally. In some embodiments, the antibiotic is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, isotopically enriched analog, stereoisomer, mixture of stereoisomers, or tautomer thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include, e.g., lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The formulations can additionally include lubricating agents such as talc, magnesium stearate and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, isotopically enriched analog, stereoisomer, mixture of stereoisomers, or tautomer thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. Such patches may be constructed for continuous, pulsatile, or on demand delivery of pharmaceutical agents.

For preparing solid compositions such as tablets, the active ingredient may be mixed with a pharmaceutical excipient to form a solid preformulation composition containing a homogeneous mixture of a compound described herein or a pharmaceutically acceptable salt, isotopically enriched analog, stereoisomer, mixture of stereoisomers, or tautomer thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral route, or by the nasal respiratory route for rapid delivery to blood/blood vessels via the lungs, for local and/or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

6. Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

The quantity to be administered, both according to number of treatments and unit dose, depends on the treatment effect desired. An effective dose is understood to refer to an amount necessary to achieve a particular effect. In the practice in certain embodiments, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 µg/kg, mg/kg, µg/day, or mg/day or any range derivable therein. Furthermore, such doses can be administered at multiple times during a day, and/or on multiple days, weeks, or months.

In certain embodiments, the effective dose of the pharmaceutical composition is one which can provide a blood level of about 1 µM to 150 µM. In another embodiment, the effective dose provides a blood level of about 4 µM to 100 µM; or about 1 µM to 100 µM; or about 1 µM to 50 µM; or about 1 µM to 40 µM; or about 1 µM to 30 µM; or about 1 µM to 20 µM; or about 1 µM to 10 µM; or about 10 µM to 150 µM; or about 10 µM to 100 µM; or about 10 µM to 50 µM; or about 25 µM to 150 µM; or about 25 µM to 100 µM; or about 25 µM to 50 µM; or about 50 µM to 150 µM; or about 50 µM to 100 µM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µM or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. In some embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

7. Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents and starting materials may be purchased commercially, e.g., from Sigma Aldrich or other chemical suppliers.

It will be appreciated that where specific process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

General Synthesis

In certain embodiments, provided is a method of preparing a compound of Formula (I):

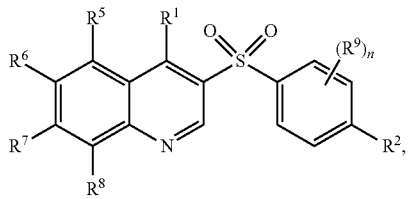
(I)

wherein $R^1$, $R^2$, $R^5$, $R^6$, $R^7$, $R^8$, $R^9$ and n are as described herein.

In certain embodiments, the method comprises contacting $R^1$—H, optionally in the presence of a base, with a compound of Formula (I-A):

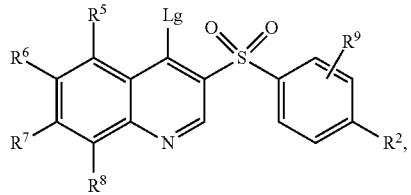
(I-A)

wherein Lg is a leaving group, such as halo, e.g., Cl or Br, to form the compound of Formula (I) or a pharmaceutically acceptable salt, isotopically enriched analog, stereoisomer, mixture of stereoisomers, or tautomer thereof.

In certain embodiments, the compound of Formula (I-A) is prepared by a method comprising converting a compound of Formula (I-B) to the compound of Formula (I-A)

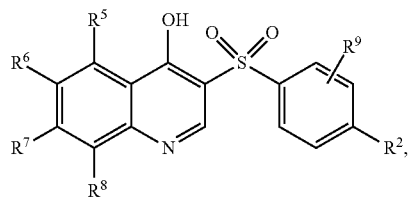
(I-B)

In certain embodiments, the compound of Formula (I-B) is prepared by a method comprising cyclizing a compound of Formula (I-C) (wherein $R^{41}$ is a $C_{1-4}$ alkyl) to the compound of Formula (I-B)

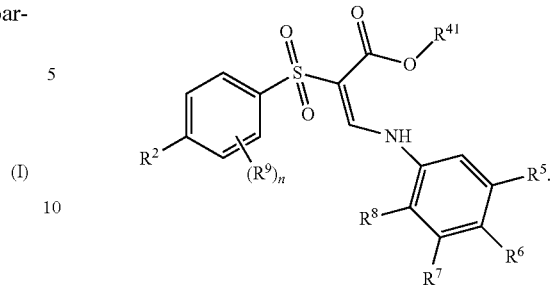
(I-C)

In certain embodiments, the compound of Formula (I-C) is prepared by a method comprising contacting an optionally substituted aniline of Formula (I-D) with a compound of Formula (I-E) (wherein $R^{42}$ is a $C_{1-4}$ alkyl) to form the compound of Formula (I-C)

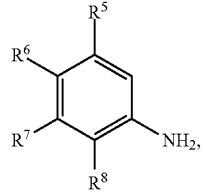
(I-D)

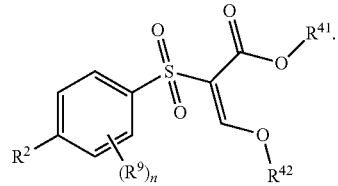
(I-E)

In certain embodiments, the compound of Formula (I-E) is prepared by a method comprising contacting trialkyl orthoformate with a compound of Formula (I-F)

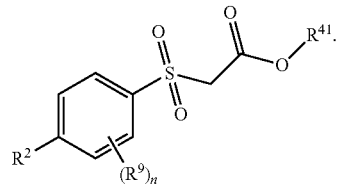
(I-F)

Scheme I illustrates a general method which can be employed for the synthesis of compounds described herein.

Scheme I

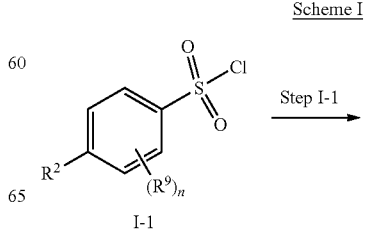

Step I-1

I-1

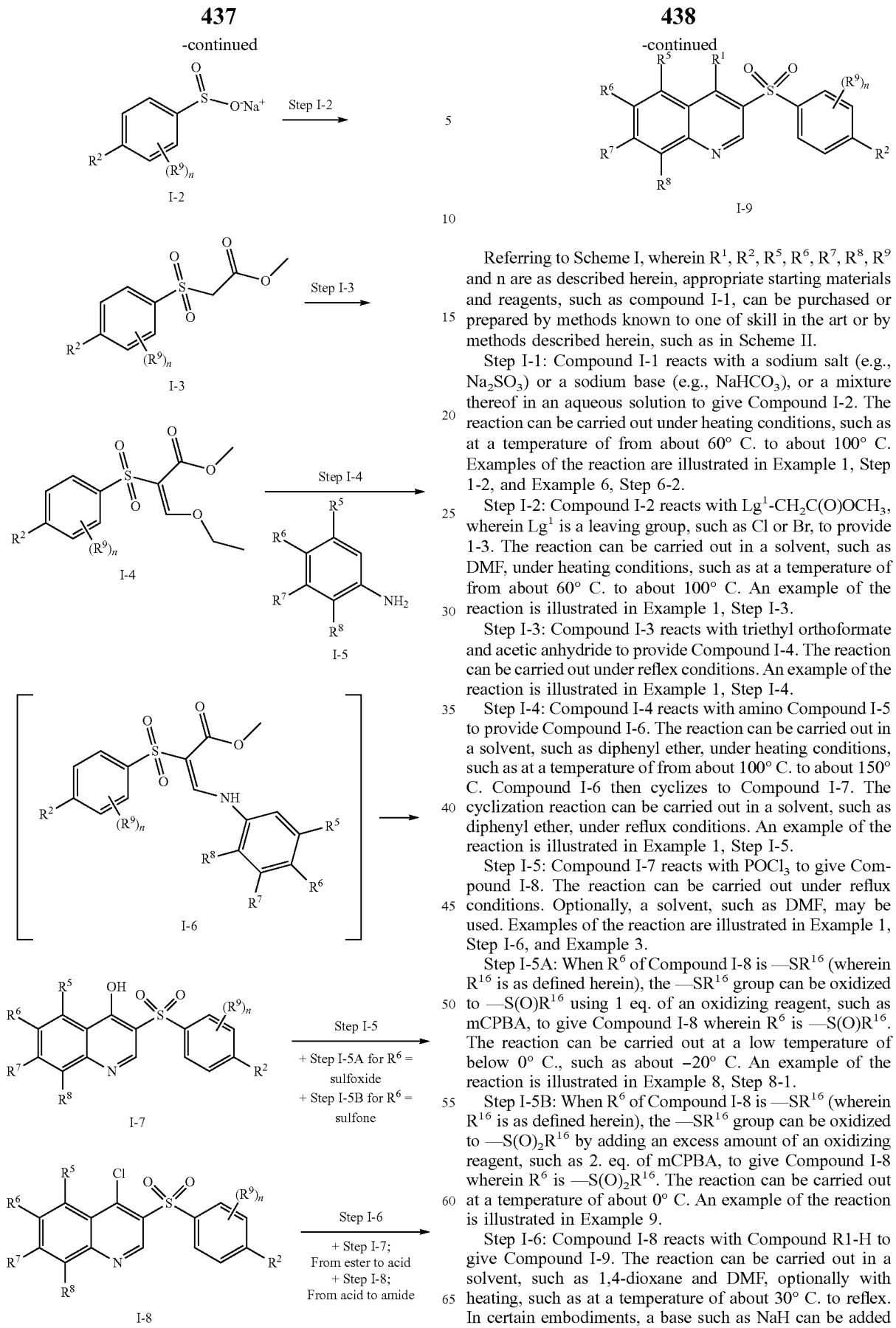

Referring to Scheme I, wherein $R^1$, $R^2$, $R^5$, $R^6$, $R^7$, $R^8$, $R^9$ and n are as described herein, appropriate starting materials and reagents, such as compound I-1, can be purchased or prepared by methods known to one of skill in the art or by methods described herein, such as in Scheme II.

Step I-1: Compound I-1 reacts with a sodium salt (e.g., $Na_2SO_3$) or a sodium base (e.g., $NaHCO_3$), or a mixture thereof in an aqueous solution to give Compound I-2. The reaction can be carried out under heating conditions, such as at a temperature of from about 60° C. to about 100° C. Examples of the reaction are illustrated in Example 1, Step 1-2, and Example 6, Step 6-2.

Step I-2: Compound I-2 reacts with $Lg^1$-$CH_2C(O)OCH_3$, wherein $Lg^1$ is a leaving group, such as Cl or Br, to provide 1-3. The reaction can be carried out in a solvent, such as DMF, under heating conditions, such as at a temperature of from about 60° C. to about 100° C. An example of the reaction is illustrated in Example 1, Step I-3.

Step I-3: Compound I-3 reacts with triethyl orthoformate and acetic anhydride to provide Compound I-4. The reaction can be carried out under reflex conditions. An example of the reaction is illustrated in Example 1, Step I-4.

Step I-4: Compound I-4 reacts with amino Compound I-5 to provide Compound I-6. The reaction can be carried out in a solvent, such as diphenyl ether, under heating conditions, such as at a temperature of from about 100° C. to about 150° C. Compound I-6 then cyclizes to Compound I-7. The cyclization reaction can be carried out in a solvent, such as diphenyl ether, under reflux conditions. An example of the reaction is illustrated in Example 1, Step I-5.

Step I-5: Compound I-7 reacts with $POCl_3$ to give Compound I-8. The reaction can be carried out under reflux conditions. Optionally, a solvent, such as DMF, may be used. Examples of the reaction are illustrated in Example 1, Step I-6, and Example 3.

Step I-5A: When $R^6$ of Compound I-8 is —$SR^{16}$ (wherein $R^{16}$ is as defined herein), the —$SR^{16}$ group can be oxidized to —$S(O)R^{16}$ using 1 eq. of an oxidizing reagent, such as mCPBA, to give Compound I-8 wherein $R^6$ is —$S(O)R^{16}$. The reaction can be carried out at a low temperature of below 0° C., such as about −20° C. An example of the reaction is illustrated in Example 8, Step 8-1.

Step I-5B: When $R^6$ of Compound I-8 is —$SR^{16}$ (wherein $R^{16}$ is as defined herein), the —$SR^{16}$ group can be oxidized to —$S(O)_2R^{16}$ by adding an excess amount of an oxidizing reagent, such as 2. eq. of mCPBA, to give Compound I-8 wherein $R^6$ is —$S(O)_2R^{16}$. The reaction can be carried out at a temperature of about 0° C. An example of the reaction is illustrated in Example 9.

Step I-6: Compound I-8 reacts with Compound R1-H to give Compound I-9. The reaction can be carried out in a solvent, such as 1,4-dioxane and DMF, optionally with heating, such as at a temperature of about 30° C. to reflux. In certain embodiments, a base such as NaH can be added to deprotonate Compound $R^1$—H before reaction with Compound I-8. Examples of 1-6 are illustrated in Example 1, Step 1-7 (I-6A), Example 2 (I-6B), and Example 5 (I-6C).

Step I-7: When $R^6$ of Compound I-9 is an ester —C(O)OR$^{15}$ (wherein R$^{15}$ is as defined herein but is not H), —C(O)OR$^{15}$ can be hydrolyzed to —C(O)OH with a base such as LiOH, in an aqueous solution, to give Compound I-9 wherein $R^6$ is —C(O)OH. An example of the reaction is illustrated in Example 3, conversion of Compound 63 to Compound 66. Similarly, an ester group at other positions of a compound can be hydrolyzed to an acid group.

Step I-8: Compound I-9 wherein $R^6$ is —C(O)OH can be converted to Compound I-9 wherein $R^6$ is —C(O)NR$^{15}$R$^{15}$ by reacting with an amine HNR$^{15}$R$^{15}$ under amide coupling reaction conditions. Amide coupling reaction conditions can include a solvent, such as NMP, DMF, DCM, a coupling reagent, such as EDCI, optionally an additional agent, such as HOBt, and optionally a base, such as triethylamine. The reaction can be carried out at about 0° C. to room temperature. An example of the reaction is illustrated in Example 7.

Scheme II shows a method of preparing starting material I-1 used in Scheme I from compound II-1.

In certain embodiments, Compound II-1 reacts with phosphorus oxychloride and concentrated sulfuric acid to give Compound I-1 (II-A). The reaction may be carried out at an elevated temperature, such as about 60° C. to about 100° C. An example of the reaction is illustrated in Example 1, Step I-1.

In certain embodiments, Compound II-1 reacts with chlorosulfonic acid to give Compound I-1 (II-B). The reaction may be carried out at a low temperature, such as about −10° C. to about 10° C. An example of the reaction is illustrated in Example 6, Step 6-1.

Scheme III

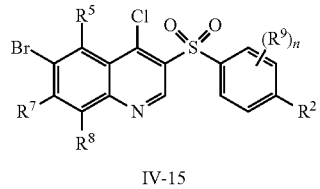

Scheme III shows a method of preparing starting material II-1. Phenol Compound II-1 react with Lg$^2$-R$^{18}$ to give Compound II-2, wherein $R^2$ is —OR$^{18}$, $R^9$ and $R^{18}$ are as defined herein, and Lg$^2$ is a leaving group, such as a halo. The reaction can be carried out in a solvent, such as acetone in the presence of a base such as K$_2$CO$_3$, and a phase transfer catalyst, such as tetra-n-butylammonium iodide. An example of the reaction is illustrated in Example 10.

Scheme II

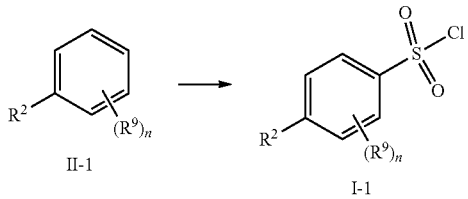

Scheme IV

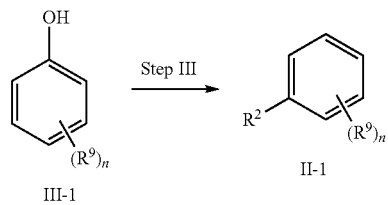

IV-15

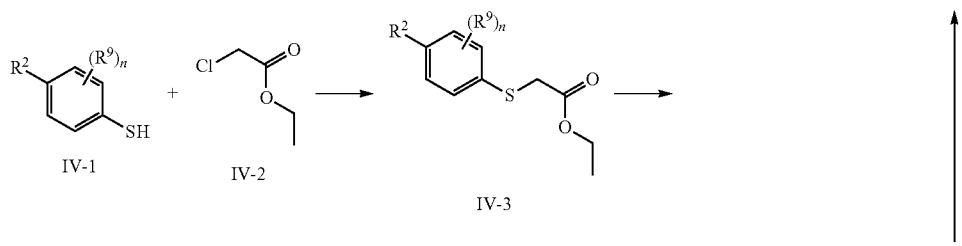

441
442
-continued
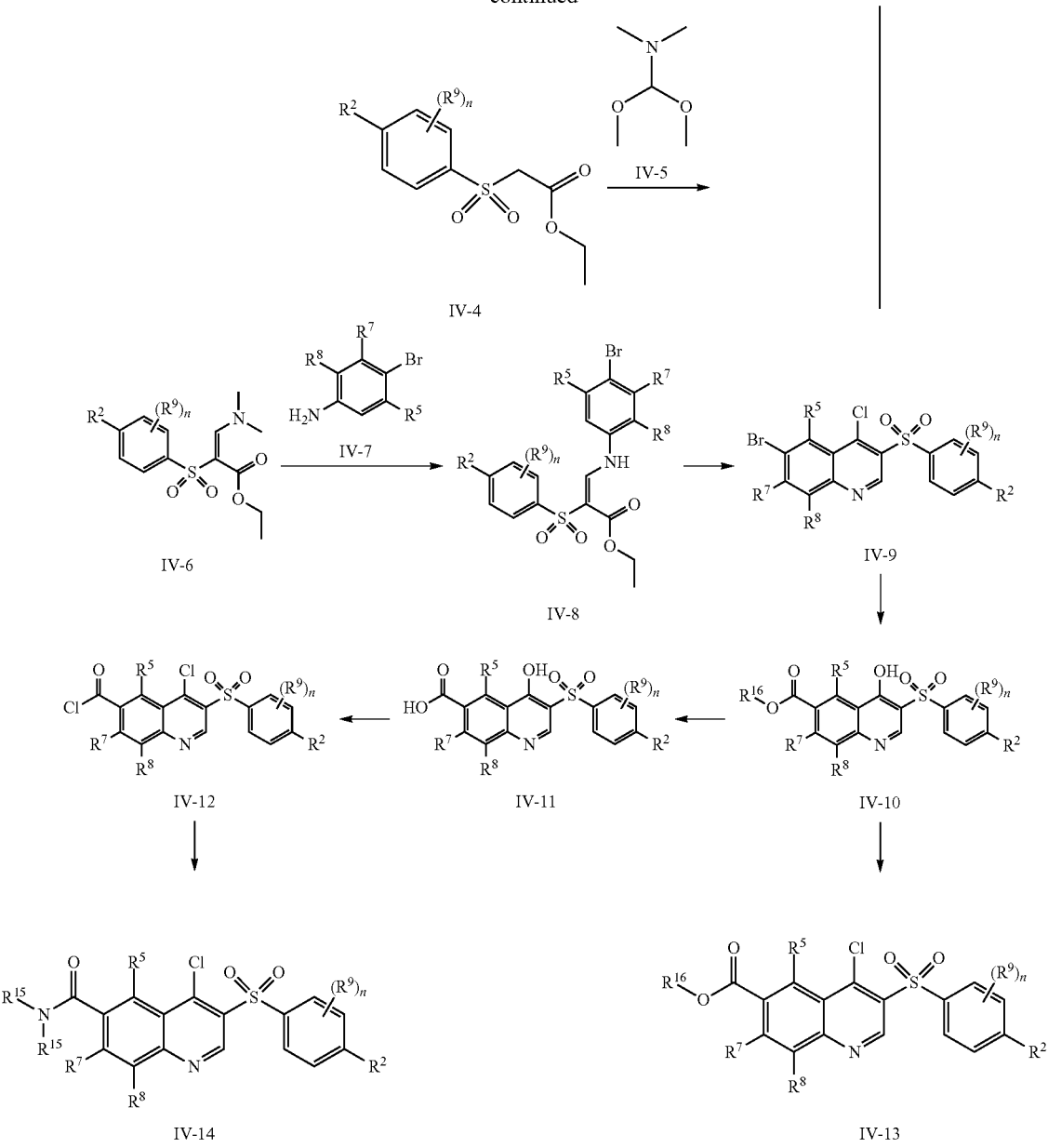
Scheme IV shows a method of preparing Intermediates such as IV-13, IV-14, and IV-15, wherein $R^2$, $R^5$, $R^6$, $R^7$, $R^8$, $R^9$, $R^{15}$, $R^{16}$, and n are as defined herein. An example of the method is illustrated in Example 18.
Scheme IA illustrates a general method which can be employed for the synthesis of compounds described herein.
Scheme IA
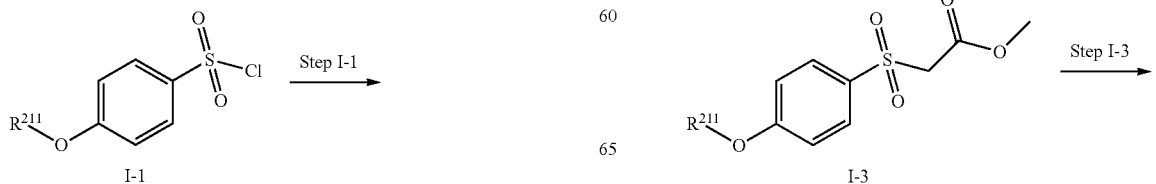
-continued
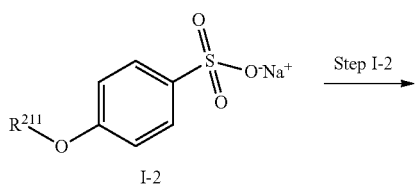

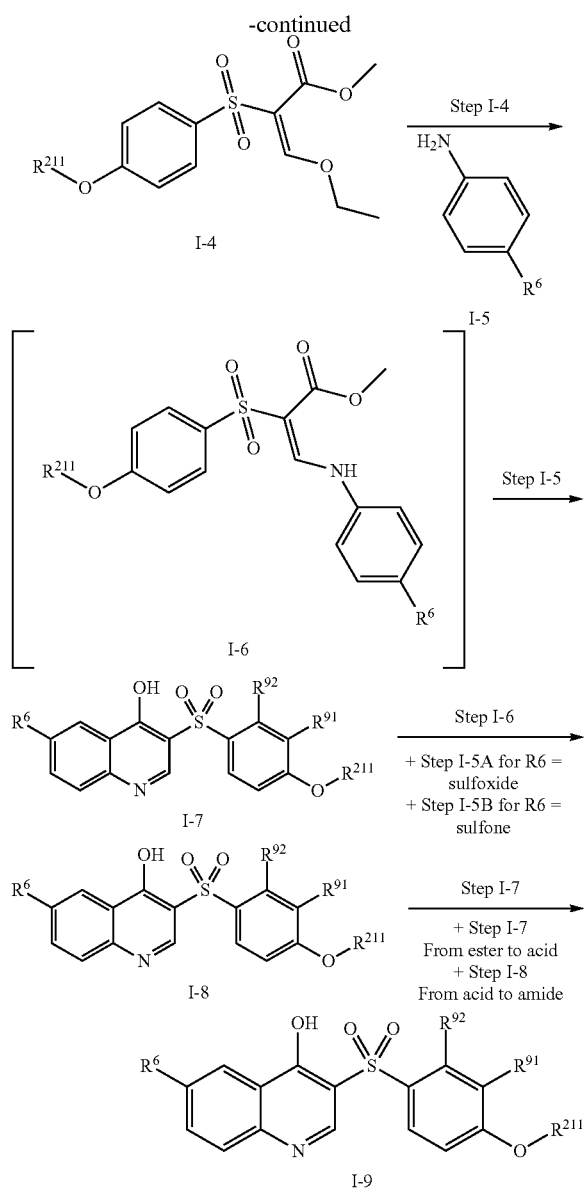

a solvent, such as diphenyl ether, under heating conditions, such as at a temperature of from about 100° C. to about 150° C. Compound I-6 then cyclizes to Compound I-7. The cyclization reaction can be carried out in a solvent, such as diphenyl ether, under reflux conditions.

Step I-5: Compound I-7 reacts with $POCl_3$ to give Compound I-8. The reaction can be carried out under reflux conditions. Optionally, a solvent, such as DMF, may be used.

Step I-5A: When $R^6$ of Compound I-8 is —$SR^{16}$ (wherein $R^{16}$ is alkyl), the —$SR^{16}$ group can be oxidized to —$S(O)R^{16}$ using 1 eq. of an oxidizing reagent, such as mCPBA, to give Compound I-8 wherein $R^6$ is —$S(O)R^{16}$. The reaction can be carried out at a low temperature of below 0° C., such as about −20° C.

Step I-5B: When $R^6$ of Compound I-8 is —$SR^{16}$ (wherein $R^{16}$ is alkyl), the —$SR^{16}$ group can be oxidized to —$S(O)_2R^{16}$ by adding an excess amount of an oxidizing reagent, such as 2. eq. of mCPBA, to give Compound I-8 wherein $R^6$ is —$S(O)_2R^{16}$. The reaction can be carried out at a temperature of about 0° C.

Step I-6: Compound I-8 reacts with Compound $R^1$—H to give Compound I-9. The reaction can be carried out in a solvent, such as 1,4-dioxane and DMF, optionally with heating, such as at a temperature of about 30° C. to reflux. In certain embodiments, a base such as NaH can be added to deprotonate Compound $R^1$—H before reaction with Compound I-8.

Step I-7: When $R^6$ of Compound I-9 is an ester —$C(O)OR^{15}$ (wherein $R^{15}$ is alkyl), —$C(O)OR^{15}$ can be hydrolyzed to —$C(O)OH$ with a base such as LiOH, in an aqueous solution, to give Compound I-9 wherein $R^6$ is —$C(O)OH$.

Step I-8: Compound I-9 wherein $R^6$ is —$C(O)OH$ can be converted to Compound I-9 wherein $R^6$ is —$C(O)NR^{15}R^{15}$ by reacting with an amine $HNR^{15}R^{15}$ (each $R^{15}$ is independently selected from H, alkyl, —$CH_2CH_2NEt_2$, —$CH_2CH_2OH$ and heterocyclyl) under amide coupling reaction conditions. Amide coupling reaction conditions can include a solvent, such as NMP, DMF, DCM, a coupling reagent, such as EDCI, optionally an additional agent, such as HOBt, and optionally a base, such as triethylamine. The reaction can be carried out at about 0° C. to room temperature.

Referring to Scheme IA, wherein $R^1$, $R^{211}$, $R^6$, $R^{91}$, and $R^{92}$ are as described herein, appropriate starting materials and reagents, such as compound I-1, can be purchased or prepared by methods known to one of skill in the art or by methods described herein, such as in Scheme IIA.

Step I-1: Compound I-1 reacts with a sodium salt (e.g., $Na_2SO_3$) or a sodium base (e.g., $NaHCO_3$), or a mixture thereof in an aqueous solution to give Compound I-2. The reaction can be carried out under heating conditions, such as at a temperature of from about 60° C. to about 100° C.

Step I-2: Compound I-2 reacts with $LG^1$-$CH_2C(O)OCH_3$, wherein Lg1 is a leaving group, such as Cl or Br, to provide 1-3. The reaction can be carried out in a solvent, such as DMF, under heating conditions, such as at a temperature of from about 60° C. to about 100° C.

Step I-3: Compound I-3 reacts with triethyl orthoformate and acetic anhydride to provide Compound I-4. The reaction can be carried out under reflex conditions.

Step I-4: Compound I-4 reacts with amino Compound I-5 to provide Compound I-6. The reaction can be carried out in Scheme IIA

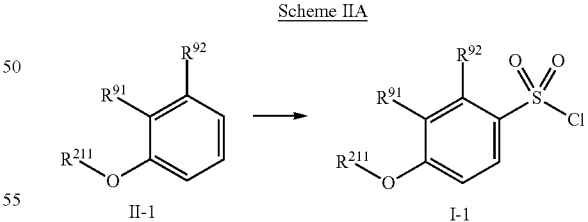

Scheme IIA shows a method of preparing starting material I-1 used in Scheme IA from compound II-1.

In certain embodiments, Compound II-1 reacts with phosphorus oxychloride and concentrated sulfuric acid to give Compound I-1 (II-A). The reaction may be carried out at an elevated temperature, such as about 60° C. to about 100° C.

In certain embodiments, Compound II-1 reacts with chlorosulfonic acid to give Compound I-1 (II-B). The reaction may be carried out at a low temperature, such as about −10° C. to about 10° C.

Scheme IIIA

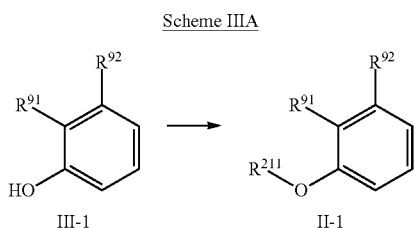

Scheme IIIA shows a method of preparing starting material II-1. Phenol Compound II-1 reacts with $LG^2\text{-}R^{18}$ to give Compound II-2, wherein $R^{18}$ is selected from $C_{1-6}$ alkyl, $C_{1-6}$ haloalkyl, and $C_{1-6}$ aminoalkyl, and $R^{211}$, $R^{91}$ and $R^{92}$ are as defined herein, and $LG^2$ is a leaving group, such as a halo. The reaction can be carried out in a solvent, such as acetone in the presence of a base such as $K_2CO_3$, and a phase transfer catalyst, such as tetra-n-butylammonium iodide.

Scheme IVA

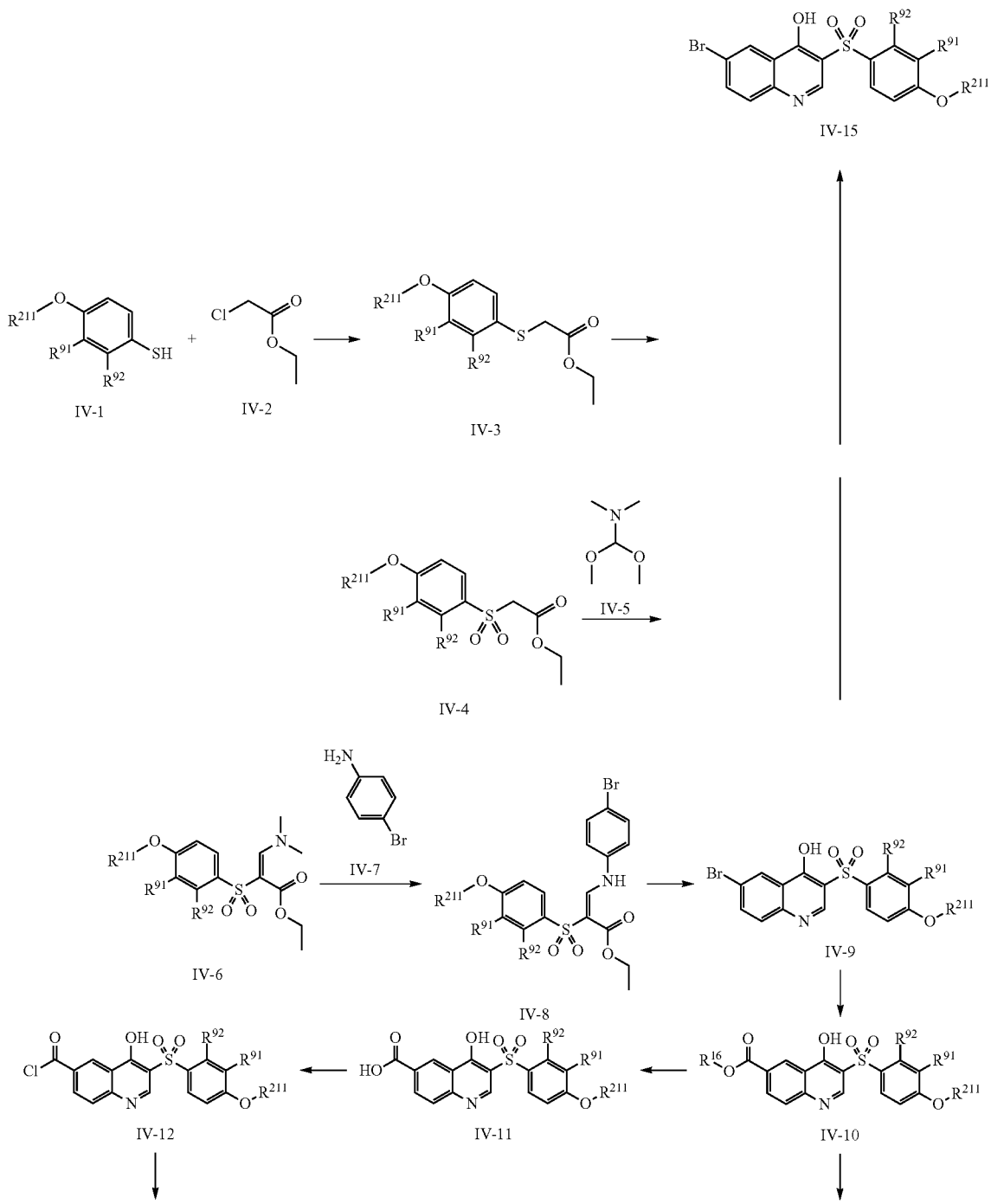

447

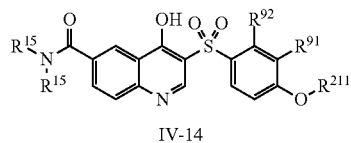

IV-14

448

-continued

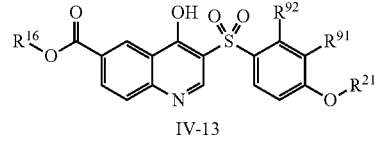

IV-13

Scheme IVA shows a method of preparing Intermediates such as IV-13, IV-14, and IV-15, wherein $R^{211}$, $R^{91}$, $R^{92}$, $R^{15}$, and $R^{16}$, are as defined herein.

For any of the preceding schemes, a poly(ethylene glycol) group or a methoxypoly(ethylene glycol) group can be attached to any compound described herein via the terminal hydroxy group of PEG or mPEG, and by any suitable poly-ol conjugation reaction (e.g., Mitsunobu ether synthesis, halogen displacement, ester formation, and the like).

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

SYNTHETIC EXAMPLES

Example 1. Synthesis of Compound 1

Step I-1

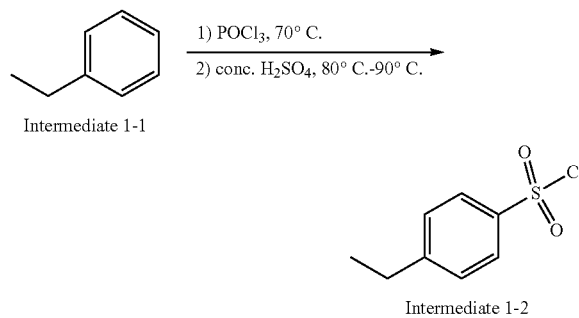

To a solution of ethylbenzene (96.5 g, 0.91 mol, 1.3 eq.) was added phosphorus oxychloride (65 mL, 0.7 mol, 1.0 eq.) at 70° C. After stirring for 20 min at this temperature, concentrated sulfuric acid (48 mL, 0.91 mol, 1.0 eq.) was added dropwise into the mixture. The resulting solution was then incrementally heated to 80° C. for 2 hours, then to 90° C. for 3 hours. After cooling to room temperature, the mixture was washed twice with ice water (2×200 mL). The organic extract was separated and concentrated under reduced pressure to obtain 150 g (81%) of the crude product. The crude product as oil was used without further purification.

Step I-2

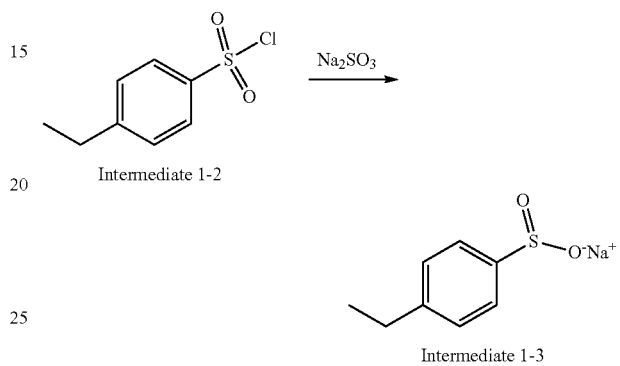

To a mixture of $Na_2SO_3$ (173 g, 1.37 mol, 1.87 eq.) and $NaHCO_3$ (121 g, 1.44 mol, 1.96 eq.) in $H_2O$ (700 mL) was added portion-wise 4-ethylbenzenesulfonyl chloride (150 g, 0.73 mol, 1 eq.) at 75° C.

After addition, the reaction mixture was kept at this temperature for 1 hour before cooling. The crude product was washed with t-butyl methyl ether, dried (75 g, 53%) and used without further purification.

Step I-3

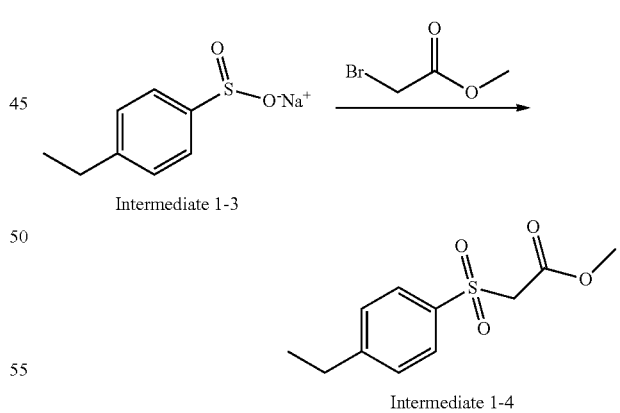

To a mixture of sodium 4-ethylbenzenesulfinate (5 g, 26 mmol, 1.1 eq.) in DMF (22 mL) was added methyl 2-bromoacetate (2.3 mL, 24 mmol, 1 eq.) at room temperature. The resulting mixture was heated to 80° C. and kept this temperature with stirring for 2 hours. After cooling to room temperature, the mixture was diluted with water (44 mL). The aqueous layer was extracted with $CH_2Cl_2$ (2×25 mL). The combined organic extracts were washed with water 4 times (4×20 mL) to remove DMF, dried and concentrated Step I-4

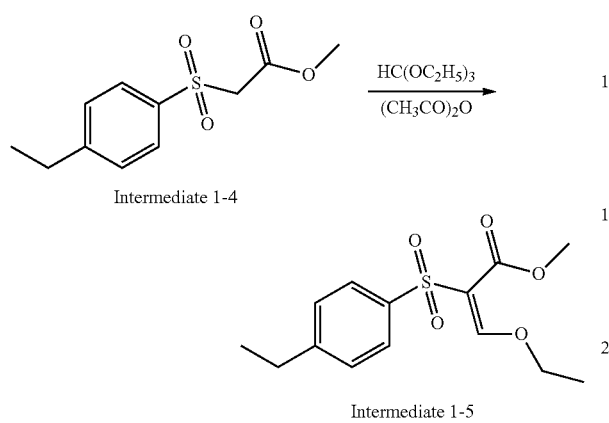

Intermediate 1-4

Intermediate 1-5

The mixture of crude methyl 2-((4-ethylphenyl)sulfonyl) acetate (23.6 g, 97 mmol, 1.0 eq.), triethyl orthoformate (39 mL, 233 mmol, 2.4 eq.) and acetic anhydride (20 mL, 214 mmol, 2.21 eq.) was reflux for 3 hours with simultaneous distillation of ethyl acetate, triethyl orthoformate and acetic anhydride and then evaporated to dryness. The crude product as oil (23.7 g, 82%) was used for the next step without purification: $^1$HNMR (600 MHz, CDCl$_3$, 25° C.): 1.25 (t, 3H, J=7.8 Hz), 1.44 (t, 3H, J=7.2 Hz), 2.71 (q, 2H, J=7.8 Hz), 3.70 (s, 3H), 4.36 (q, 2H, J=7.2 Hz), 7.31-7.33 (m, 2H), 7.83-7.85 (m, 2H), 8.13 (s, 1H).

Step I-5

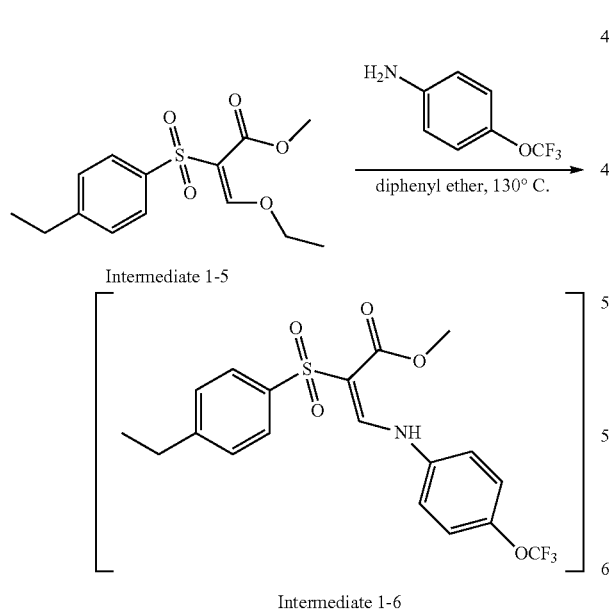

Intermediate 1-5

Intermediate 1-6

The mixture of crude ethyl (E)-3-ethoxy-2-((4-ethylphenyl)sulfonyl)acrylate (87.6 g, 0.29 mol, 1 eq.) and 4-(trifluoromethoxy)-aniline (39 mL, 0.29 mol, 1.0 eq.) in diphenyl ether (120 mL) was heated at 130° C. for 4 hours. After cooling to room temperature, the product was collected by filtration or purified by flash chromatography (EtOAc:Petroleum ether; 1:5) to afford Intermediate 1-6 (74.6 g, 59%) as white solid.

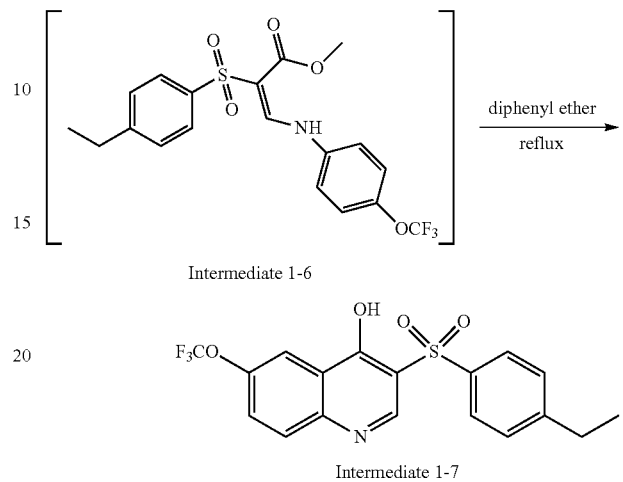

Intermediate 1-6

Intermediate 1-7

The Intermediate 1-6 (31.3 g, 0.17 mol) in diphenyl ether (180 mL) was heated at reflux for 4 hours before cooling to room temperature to give Intermediate 1-7. The solid was collected by filtration, dried (27 g, 55%) and used without further purification.

Step I-6

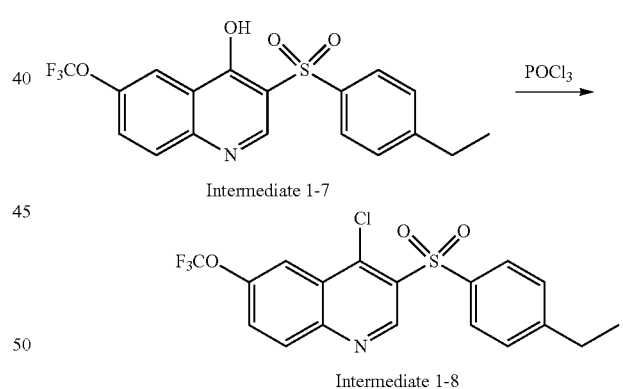

Intermediate 1-7

Intermediate 1-8

A mixture of 3-((R1-)sulfonyl)-6-(R2-)quinolin-4-ol (Intermediate 1-7) (8 g, 20 mmol) and POCl$_3$ (50 mL) was heated to reflux until all the start material was consumed (~3 hours). The resulting mixture was concentrated to followed by the addition of CH$_2$Cl$_2$ (100 mL) and ice water (100 mL). The organic phase was adjusted to pH 9~10 by using 25% NH$_3$·H$_2$O. The organic phase was then separated, concentrated and purified by flash chromatography (EtOAc:Petroleum ether; 1:5) to afford 8.1 g (97%) of the desired Intermediate 1-8 as white solid: $^1$HNMR (600 MHz, CDCl$_3$, 25° C.): 1.27 (t, 3H, J=7.8 Hz), 2.74 (q, 2H, J=7.8 Hz), 7.39 (d, 2H, J=8.4 Hz), 7.77 (dd, 1H, J=6.6, 2.4 Hz), 7.97-7.99 (m, 2H), 8.16 (s, 1H), 8.28 (d, 1H, J=9 Hz), 9.66 (s, 1H).

Step I-7

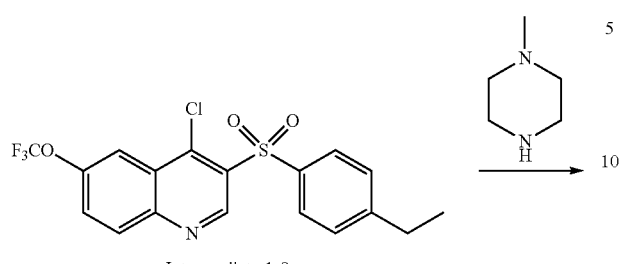

A solution of Intermediate 1-8 (800 mg, 1.9 mmol, 1.0 eq.) and 1-methylpiperazine (213 µL, 4.2 mmol, 2.2 eq.) in CH₃CN (20 mL) was heated to 45° C. and kept at this temperature with stirring for 4 hours (until all the start material was consumed). The mixture was then concentrated under reduced pressure and purified by flash chromatography (EtOAc:Petroleum ether; 1:2) to afford the desired Compound 1 (801 mg, 89%) as a light yellow solid: ¹HNMR (600 MHz, CDCl₃, 25° C.): 1.24 (t, 3H, J=7.8 Hz), 2.37 (s, 3H), 2.42 (m, 4H), 2.73 (q, 2H, J=9 Hz), 3.29 (m, 4H), 5.25 (s, 2H), 7.34 (d, 2H, J=8.4 Hz), 7.67 (dd, 1H, J=9, 1.8 Hz), 7.78 (d, 2H, J=7.8 Hz), 8.10 (s, 1H), 8.22 (d, 1H, J=9.6 Hz), 9.41 (s, 1H). MS (m/z): 480.

Example 2. Synthesis of Compound 51

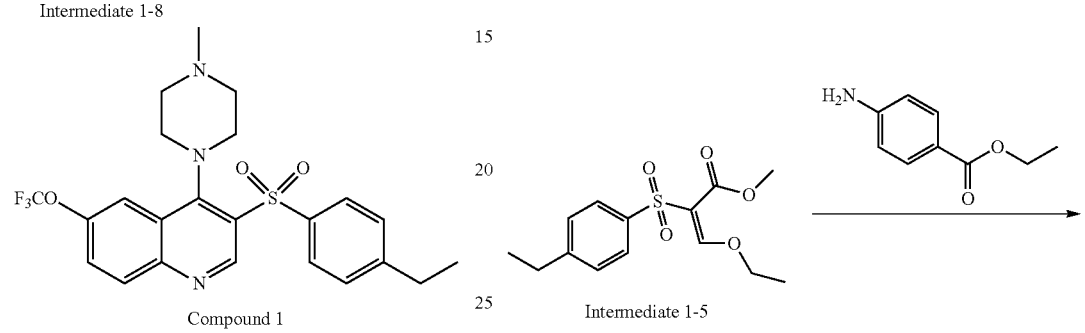

A solution of Intermediate 1-8 (300 mg, 0.72 mmol, 1.0 eq.) and 1H-1,2,4-triazole (55 mg, 0.79 mmol, 1.1 eq.) in 1,4-dioxane (9 mL) was heated to reflux for 24 hours (until all the start material was consumed). The mixture was then concentrated under reduced pressure and purified by flash chromatography (EtOAc:Petroleum ether; 1:5) to afford Compound 51 (270 mg, 84%) as a while solid: ¹HNMR (600 MHz, D₆-DMSO, 25° C.): 1.20 (t, 3H, J=7.8 Hz), 2.65 (q, 2H, J=15.6 Hz), 6.96 (m, 1H), 7.23 (d, 2H, J=8.4 Hz), 7.41 (d, 2H, J=8.4 Hz), 7.75 (dd, 1H, J=9, 1.8 Hz), 8.0 (s, 1H), 8.32 (d, 1H, J=9 Hz), 8.65 (s, 1H), 9.78 (s, 1H).

Example 3. Synthesis of Compound 63 and Compound 66

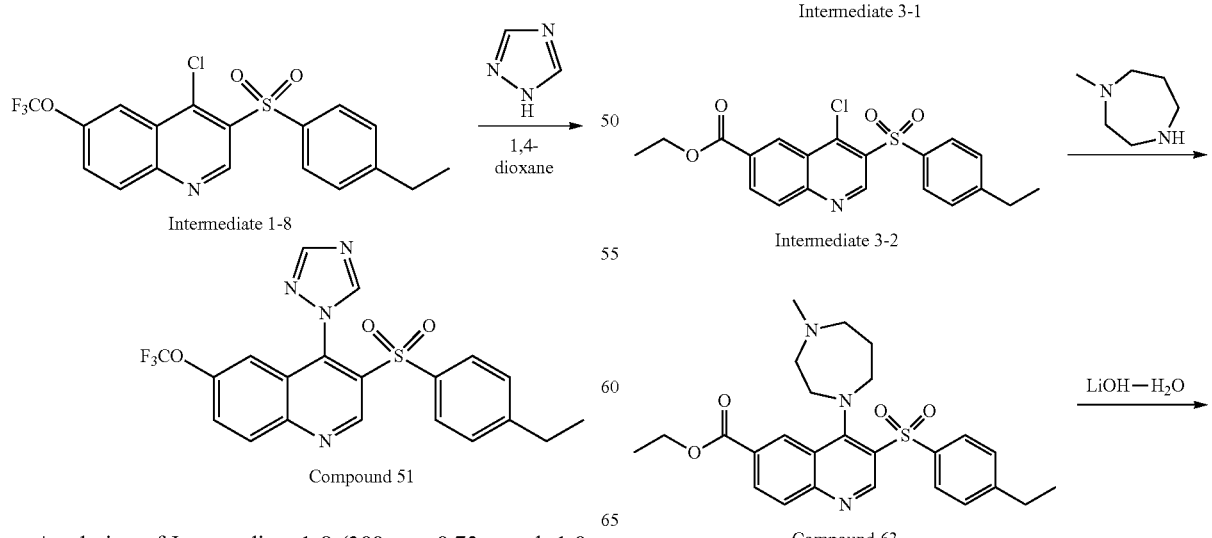

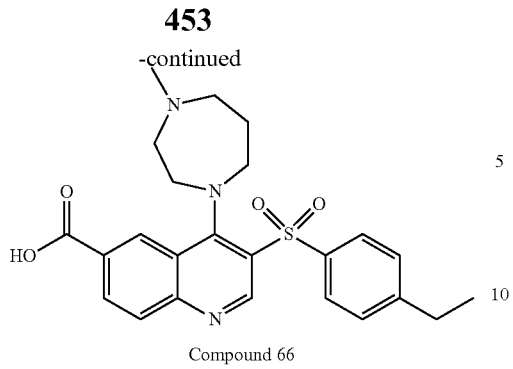

Compound 66

Ethyl 3-((4-ethylphenyl)sulfonyl)-4-hydroxyquinoline-6-carboxylate (Intermediate 3-1) was prepared from Intermediate 1-5 and ethyl 4-aminobenzoate according to a procedure similar to that described in Example 1, Step 6.

A mixture ethyl 3-((4-ethylphenyl)sulfonyl)-4-hydroxyquinoline-6-carboxylate (2 g, 5.2 mmol) and $POCl_3$ (2.9 mL, 31 mmol, 6 eq.) in DMF (40 mL) was heated to reflux until all the start material was consumed (~3 hours). After cooling, the resulting mixture was quenched by addition of 70 mL of ice water. The organic phase was adjusted to pH 9–10 by using 25% $NH_3 \cdot H_2O$. The organic phase was then separated, concentrated and purified by flash chromatography (EtOAc:Petroleum ether; 1:5) to afford 1.5 g (71%) of Intermediate 3-2 as a white solid.

Compound 63 was prepared using Intermediate 3-2 according to a procedure similar to that described in Example 1 (Step I-1 to 1-7).

To a solution of Compound 63 (720 mg, 1.5 mmol) in MeOH (60 mL) was added $LiOH \cdot H_2O$ (126 mg, 3 mmol, 2.0 eq.) in water (2 mL). After the resulting solution was heated to 45° C. and stirred the same temperature for 5 hours, the pH was adjusted to 5-6 by using 2N HCl solution. The product was filtered, concentrated under reduced pressure and purified by flash chromatograph ($CH_2Cl_2$:MeOH; 1:3) to afford Compound 66 (640 mg, 94%) as a yellow solid: $^1HNMR$ (600 MHz, $D_6$-DMSO, 25° C.): 1.17 (t, 3H, J=7.8 Hz), 2.07 (m, 2H), 2.64 (s, 3H), 2.70 (q, 2H, J=15 Hz), 3.13 (m, 8H), 7.15 (d, 2H, J=8.4 Hz), 7.87 (d, 2H, J=8.4 Hz), 8.18 (d, 1H, J=8.4 Hz), 8.38 (dd, 1H, J=9, 1.2 Hz), 8.75 (s, 1H), 9.36 (s, 1H).

Example 4. Synthesis of Compound 102

Synthesis of Intermediate 4-4

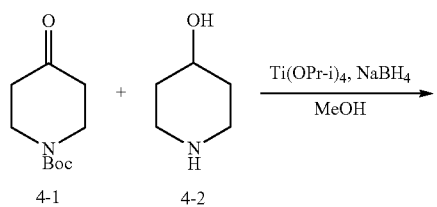

Titanium(IV) isopropoxide (36.2 g, 127 mmol) was added dropwise to a solution of amine 4-2 (7.7 g, 76.4 mmol) in 130 mL of MeOH. It was then followed by the addition of ketone 4-1 (12.7 g, 63.7 mmol). The reaction mixture was stirred at room temperature for 5 hours, followed by addition of sodium borohydride (2.4 g, 63.7 mmol). After additional 2 hours of stirring, the resulting mixture was quenched by water (13 mL). Inorganic precipitate was filtered and washed with ethyl acetate. The combined organic phases were concentrated under reduced pressure and the residue was purified by column chromatography on silica gel (petroleum ether/ethyl acetate=1:1) to give BOC-protected compound 4-3 as pale yellow oil (12 g, 67%).

A solution of BOC-protected compound 4-3 (8 g, 28 mmol) in 50 mL of ethanol was added dropwise to HCl/EtOH (4M, 100 mL) at room temperature while stirring. After 4 hours, the solvent was evaporated, and remaining residue was redissolved by using a mixture of 20 mL of MeOH and 100 mL of $CH_2Cl_2$, followed by the addition of 5 g of $K_2CO_3$. The resulting mixture was filtered through a pad of Celite after 16 hours of stirring. The filtrate was concentrate under reduced pressure to give Intermediate 4-4 as brown oil (5 g, 97%).

Synthesis of Compound 102

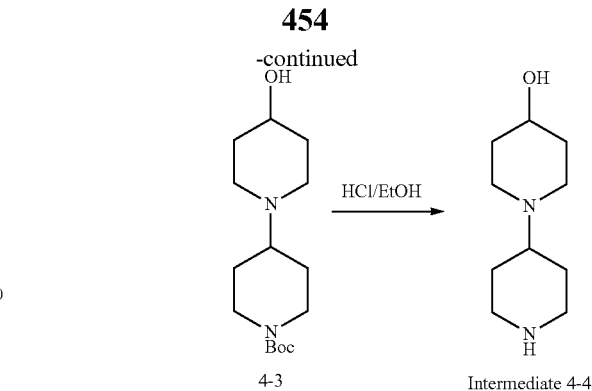

Intermediate 1-8

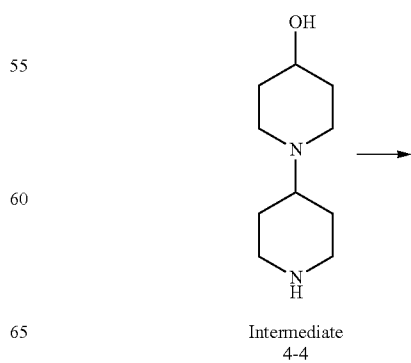

Intermediate 4-4

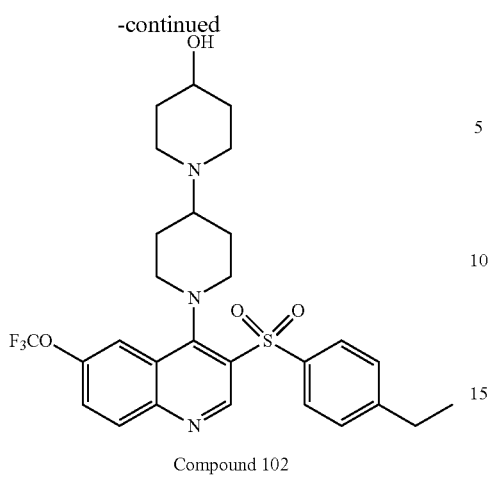

Compound 102

Compound 102 was prepared from Intermediates 1-8 and 4-4 according to a method similar to that described in Step I-8 of Example 1.

Example 5. Synthesis of Compound 108

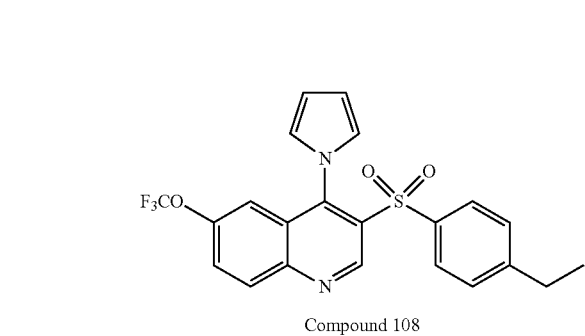

Intermediate 1-8

Compound 108

To a slurry of NaH (43 mg, 60% in mineral oil, 1.08 mmol, 1.5 eq.) in DMF (13 mL) was added 1H-pyrrole (60 µL, 0.86 mmol, 1.2 eq.) at room temperature. After 30 min, Intermediate 1-8 (300 mg, 0.72 mmol, 1.0 eq.) was added to the mixture and the resulting reaction was heated at 45° C. for 4 hours (until all the start material was consumed). After cooling to room temperature, the reaction mixture was diluted with water (39 mL) and CH$_2$Cl$_2$. The organic extracts was then concentrated and purified by flash chromatography (EtOAc:Petroleum ether; 1:5) to afford Compound 108 (40 mg, 12%) as a while solid: $^1$HNMR (600 MHz, CDCl$_3$, 25° C.): 1.19 (t, 3H, J=7.8 Hz), 2.63 (q, 2H, J=15 Hz), 6.33 (m, 2H), 6.53 (m, 2H), 6.87 (m, 1H), 7.15 (d, 2H, J=8.4 Hz), 7.39 (d, 2H, J=7.8 Hz), 7.68 (d, 1H, J=7.8 Hz), 8.26 (d, 1H, J=9 Hz), 9.78 (s, 1H).

Example 6. Synthesis of Compound 144

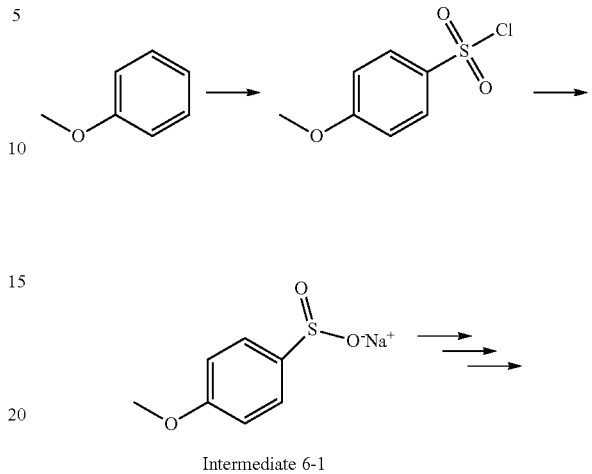

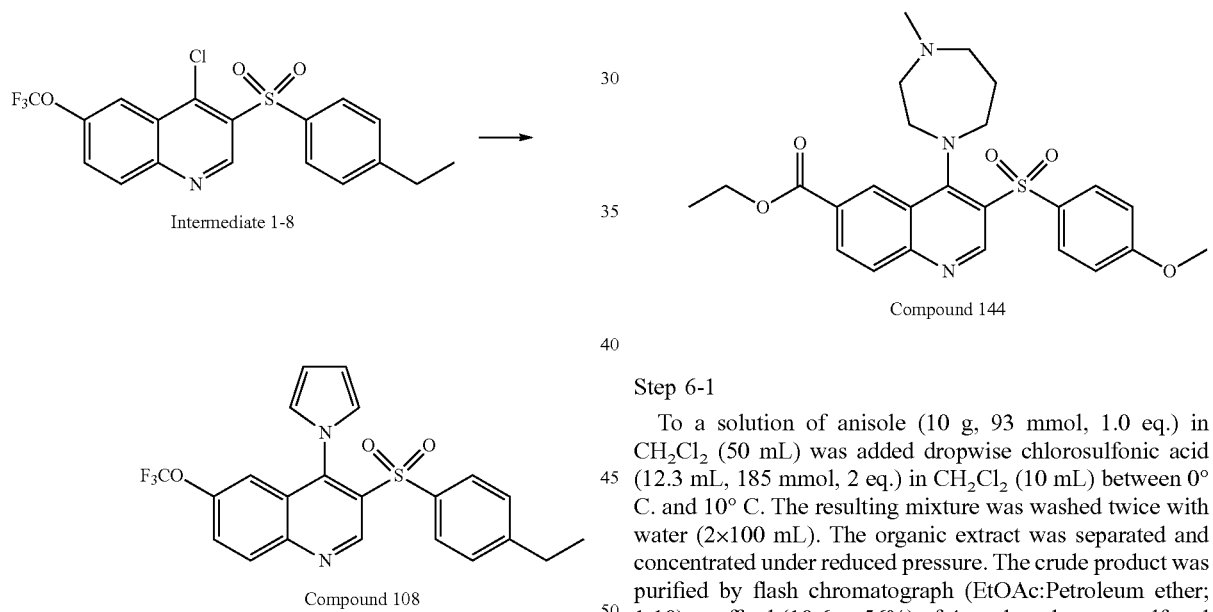

Intermediate 6-1

Compound 144

Step 6-1

To a solution of anisole (10 g, 93 mmol, 1.0 eq.) in CH$_2$Cl$_2$ (50 mL) was added dropwise chlorosulfonic acid (12.3 mL, 185 mmol, 2 eq.) in CH$_2$Cl$_2$ (10 mL) between 0° C. and 10° C. The resulting mixture was washed twice with water (2×100 mL). The organic extract was separated and concentrated under reduced pressure. The crude product was purified by flash chromatograph (EtOAc:Petroleum ether; 1:10) to afford (10.6 g, 56%) of 4-methoxybenzenesulfonyl chloride as a white solid.

Step 6-2

To a mixture of Na$_2$SO$_3$ (7.2 g, 57 mmol, 1.87 eq.) and NaHCO$_3$ (5.1 g, 61 mmol, 1.96 eq.) in H$_2$O (60 mL) was added portion-wise 4-methoxybenzenesulfonyl chloride (6.32 g, 31 mmol, 1 eq.) at 75° C. After addition, the reaction mixture was kept at this temperature for 1 hour before cooling. 20 mL of EtOH was then added followed by filtration to remove all inorganic salts. The crude organic phase was concentrated under reduced pressure to give Intermediate 6-1 which was used without further purification.

Compound 144 was prepared using Intermediate 6-1 according to a procedure similar to that described in Example 1 and Example 3 to prepare Compound 63.

Example 7. Synthesis of Compound 165

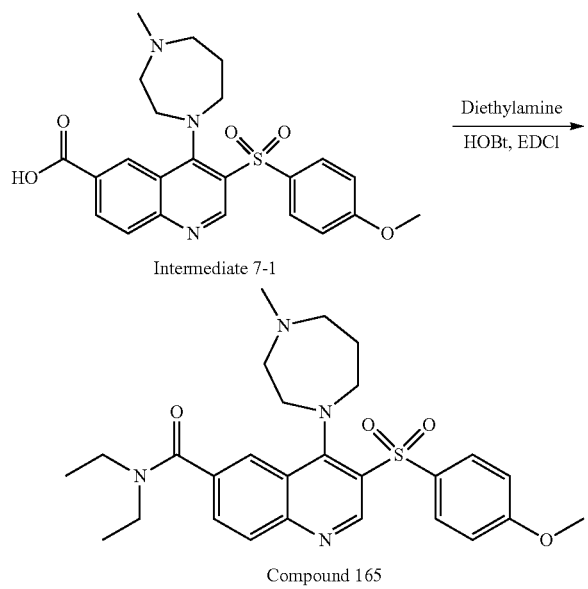

Intermediate 7-1 (300 mg, 0.66 mmol, prepared from Compound 144 according to a procedure similar to that described in Example 3 to prepare Compound 66) in NMP (12 mL) was added sequentially HOBt (101 mg, 0.66 mmol, 1.5 eq.), EDCI (102 mg, 0.66 mmol, 1.5 eq.), triethylamine (184 μL, 1.32 mmol, 3.0 eq.) then finally diethylamine (136 μL, 1.32 mmol, 2.0 eq.) at room temperature. After stirring for overnight, the reaction mixture was quenched by water and extracted by $CH_2Cl_2$, purified by flash chromatography ($CH_2Cl_2$:MeOH; 1:3) to afford Compound 165 (50 mg, 22%) as a yellow solid: $^1$HNMR (600 MHz, $CDCl_3$, 25° C.): 1.24 (m, 6H), 2.04 (m, 4H), 2.56 (s, 3H), 2.93 (m, 2H), 3.43 (m, 8H), 3.89 (s, 3H), 7.03 (d, 2H, J=7.8 Hz), 7.77 (dd, 1H, J=8.4, 1.8 Hz), 7.87 (d, 2H, J=9 Hz), 8.16 (d, 1H, J=9 Hz), 8.22 (m, 1H), 9.08 (s, 1H).

Example 8. Synthesis of Compound 168

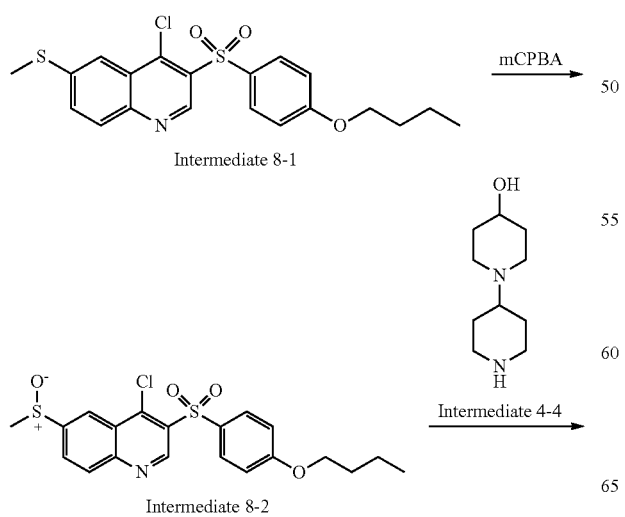

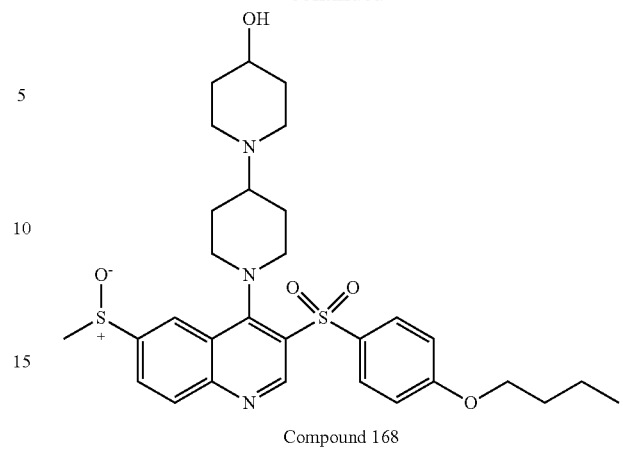

Step 8-1

To a solution of Intermediate 8-1 (200 mg, 0.47 mmol, prepared according to a method similar to that described in Example 1) in $CH_2Cl_2$ (20 mL) was added mCPBA (82 mg, 0.47 mmol, 1.0 eq.) at −20° C. The reaction was slowly warmed to room temperature over 0.5 hours. The reaction was quenched with $Na_2CO_3/H_2O$. The organic extract was separated and purified by flash chromatograph (100% EtOAc) to afford Intermediate 9-2 (200 mg, 97%) as white solid.

Step 8-2

Compound 168 was prepared from Intermediates 8-2 and 4-4 according to a procedure similar to that described in Example 1, Step I-7.

Example 9. Synthesis of Compound 169

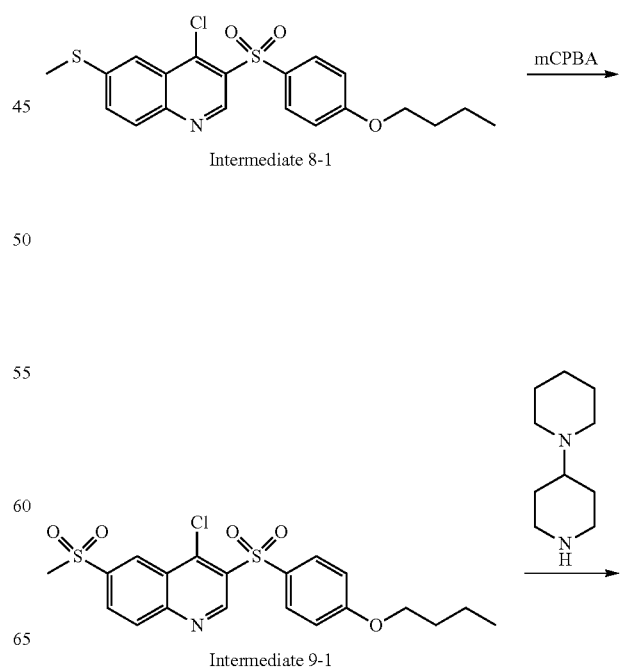

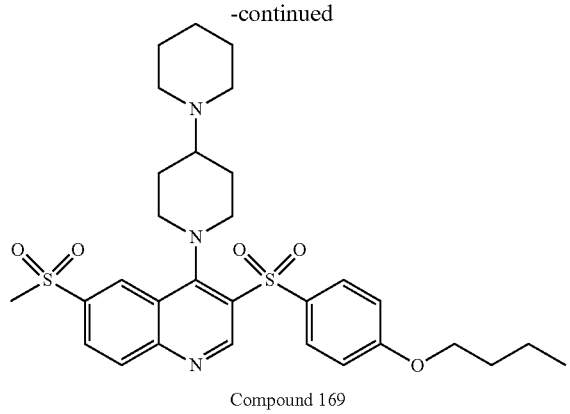

Compound 169

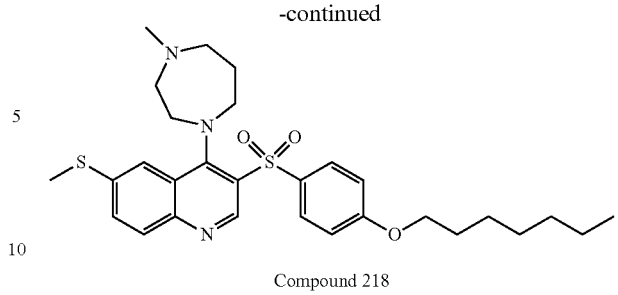

Compound 218

To a solution of Intermediate 8-2 (200 mg, 0.47 mmol) in CH$_2$Cl$_2$ (20 mL) was added mCPBA (164 mg, 0.94 mmol, 2.0 eq.) at 0° C. The reaction was slowly warmed to room temperature over 0.5 hours. The reaction was quenched with Na$_2$CO$_3$/H$_2$O. The organic extract was separated and purified by flash chromatograph (EtOAc:Petroleum ether; 1:2) to afford Intermediate 9-1 (120 mg, 56%) as white solid.

Compound 168 was prepared from Intermediate 10-1 and 1,4'-bipiperidine according to a procedure similar to that described in Example 1, Step I-7.

Example 10. Synthesis of Compound 218

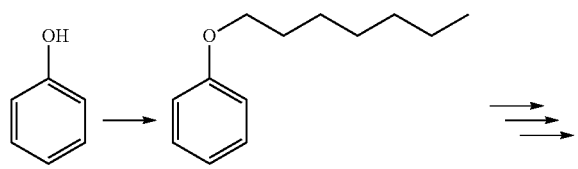

To a solution of phenol (111 g, 1.18 mol, 1.05 eq.) in acetone (1300 mL) was added 1-bromoheptane (200 g, 1.12 mol, 1.0 eq.), K$_2$CO$_3$ (307 g, 2.2 mol, 2 eq.), and tetra-n-butylammonium iodide (2 g, 5 mmol, 0.5%) at room temperature. The resulting mixture was heated to 60° C. and kept at this temperature with stirring for 26 h. After cooling, the reaction was filtered and the solid wash with acetone (600 mL). The combined organic phases were concentrated to dryness, redissolved in CH$_2$Cl$_2$ (500 mL), washed with 2N sodium hydroxide solution (200 mL), the water (3*200 mL) before concentrated under reduced pressure. The crude product (heptyloxy)benzene (207 g, 97%) as a colorless oil, was used for the next step without any purification.

Compound 218 was prepared from (heptyloxy)benzene according to a method similar to that described in Step I-8 of Example 1.

Example 11. Synthesis of Compound 242

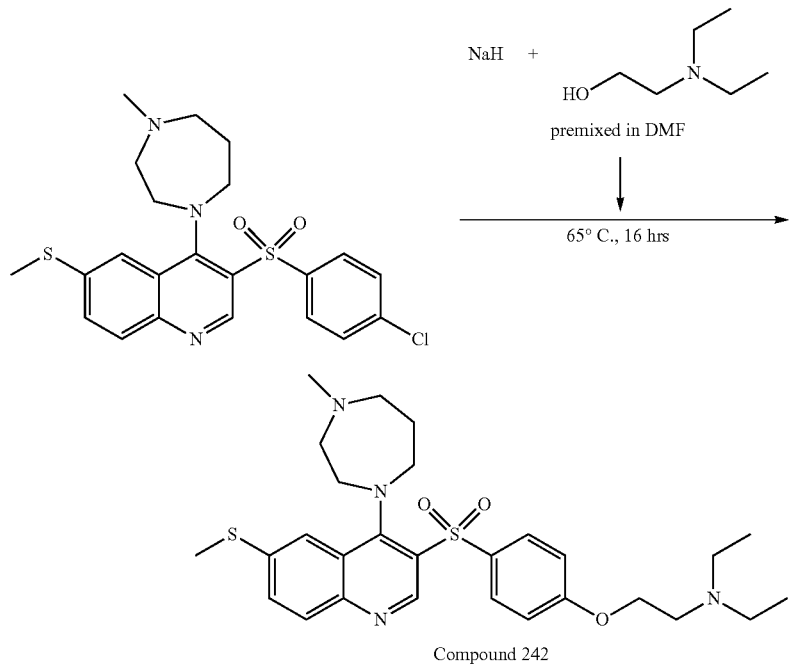

Compound 242

To a mixture of NaH (0.04 g, 0.974 mmol, 1.5 eq) in 16 mL of DMF was added 2-(diethylamino)ethan-1-ol (0.1 g, 0.844 mmol, 1.3 eq). After stirring at rt for 15 minutes, chloride starting material (0.3 g, 0.649 mmol, 1 eq) was added to the mixture and resulting reaction was heated to 65° C. and kept at the same temperature for 16 hours with stirring. After cooling to room temperature, the reaction was concentrated and residues purified by flash chromatography (DCM:MeOH=10:1) that afforded Compound 242 (0.05 g, 14%) as yellow solid.

Example 12. Synthesis of Intermediate 12-4 Useful in Preparing Compounds Described Herein Such as Compound 250

Preparation of Intermediate 12-3

Titanium(IV) isopropoxide (11.4 g, 40 mmol) was added dropwise to a solution of amine 12-2 (2.86 g, 22 mmol) in 40 mL of MeOH, followed by the addition of ketone 12-1 (4.0 g, 20 mmol). The reaction mixture was stirred at rt for 5 hours, then followed by addition of sodium borohydride (0.76 g, 20 mmol) at 0° C. After 2 hours of additional stirring at 0° C., the resulting mixture was quenched by water (4 mL). Inorganic precipitate was filtered and washed with ethyl acetate. The combined organic phases were concentrated under reduced pressure and the residue was purified by column chromatography on silica gel (petroleum ether/ethyl acetate=1:1) to give BOC-protected Intermediate 12-3 as pale yellow oil (3.6 g, 57%).

Preparation of Intermediate 12-4

A solution of Boc-protected Intermediate 12-3 (3.6 g, 11.5 mmol) in 20 mL of methanol was added dropwise to HCl/EtOH (4M, 40 mL) at rt. After 4 hours of stirring at rt, reaction was concentrated and remaining residue was redissolved in a mixture of 10 mL of MeOH and 50 mL of $CH_2Cl_2$, followed by the addition of 5 g of $K_2CO_3$. After 16 hours of stirring, the resulting mixture was filtered through a pad of Celite. The filtrate was concentrate under reduced pressure to give Intermediate 12-4 as pale yellow solid (2.4 g, 100%).

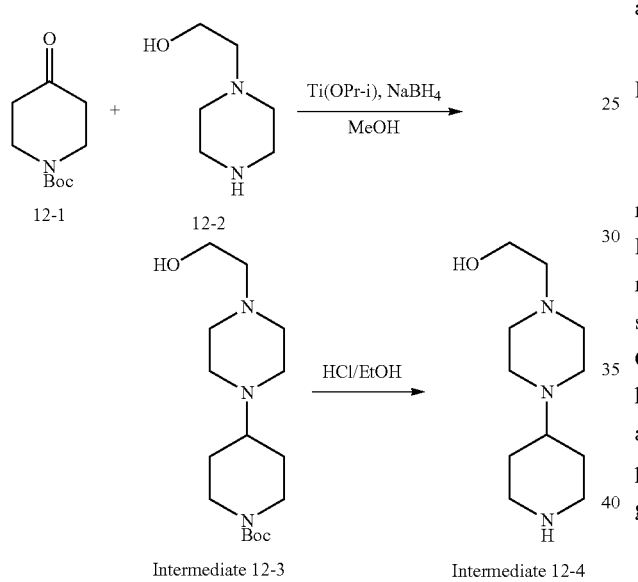

Example 13. Synthesis of Compound 271

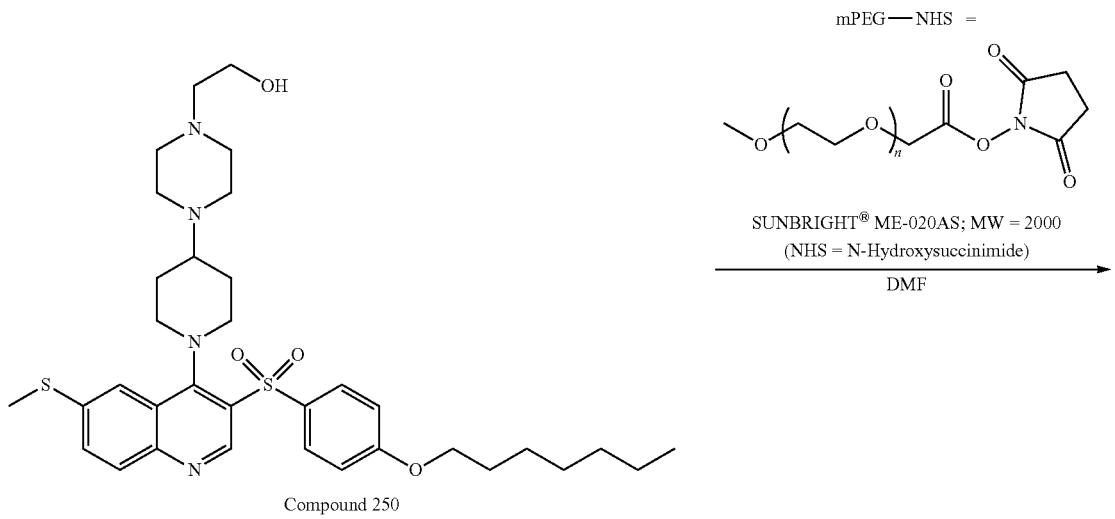

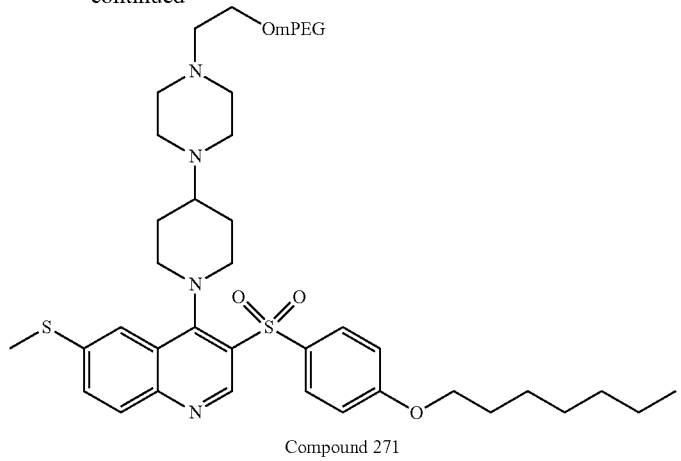

Compound 271

Compound 250 (0.1 g, 0.156 mmol, prepared according to a procedure similar to those described herein using Intermediate 12-4) was dissolved by 9 ml of DMF followed by addition of mPEG-NHS (0.35 g, ~0.156 mmol, obtained from NOF America Corporation (Catalog #: SUN-BRIGHT® ME-020AS)) at rt. After stirring at rt for 8 hours, the reaction mixture was concentrated to dryness, followed by purification using flash chromatography (DCM:MeOH=10:1). The crude product (Compound 271, 0.1 g, 22%) was obtained as yellow solid.

Example 14. Synthesis of Intermediate 14-2 Useful in Preparing Compounds Described Herein Such as Compound 292

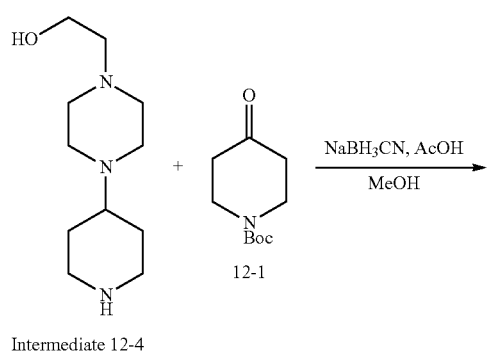

Intermediate 12-4

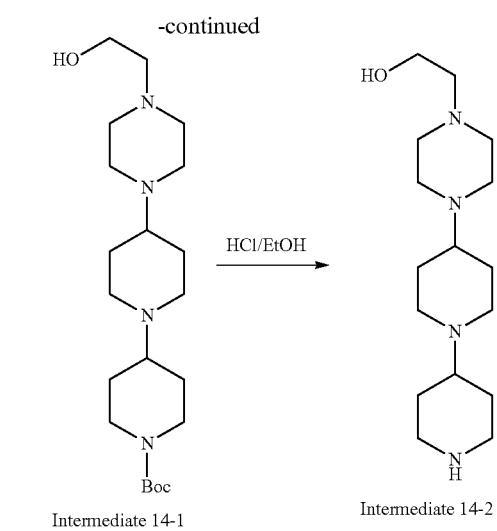

Intermediate 14-1

Intermediate 14-2

Preparation of Intermediate 14-1

After stirring a mixture of Intermediate 12-4 (1.5 g, 7 mmol), ketone 12-1 (2.8 g, 14 mmol) and AcOH (2 mL) in 30 mL of methanol was stirred at rt for 1 hour, NaBH$_3$CN (1.32 g, 21 mmol) was added. The resulting mixture was stirred at 60° C. After 7 hours, the reaction was cooled to ambient temperature, followed by the addition of additional ketone 12-1 (2.8 g, 14 mmol). After another 1 hour of stirring at rt, additional NaBH$_3$CN (1.32 g, 21 mmol) was added. After stirring at 60° C. for another 7 hours, the resulting mixture was concentrated and purified by column chromatography on silica gel (petroleum ether/ethyl acetate=1:2, ethyl acetate/methanol=10:1 to 3:1) to give BOC-protected Intermediate 14-1 as pale yellow solid (1.5 g, 54%).

Preparation of Intermediate 14-2

A solution of Boc-protected Intermediate 14-1 (1.5 g, 3.8 mmol) in 15 mL of methanol was added dropwise to HCl/EtOH (4M, 30 mL) at rt. After stirring at rt for 4 hours, the reaction was concentrated, and remaining residue was redissolved by in a mixture of 10 mL of MeOH and 50 mL of CH$_2$Cl$_2$, followed by the addition of 2 g of K$_2$CO$_3$. The resulting mixture was filtered through a pad of Celite after 16 hours of stirring, concentrate under reduced pressure to give Intermediate 14-2 as pale yellow solid (1 g, 90%).

Example 15. Synthesis of Intermediates 15-4 and 15-2 Useful in Preparing Compounds Described Herein Such as Compounds 276 and 281

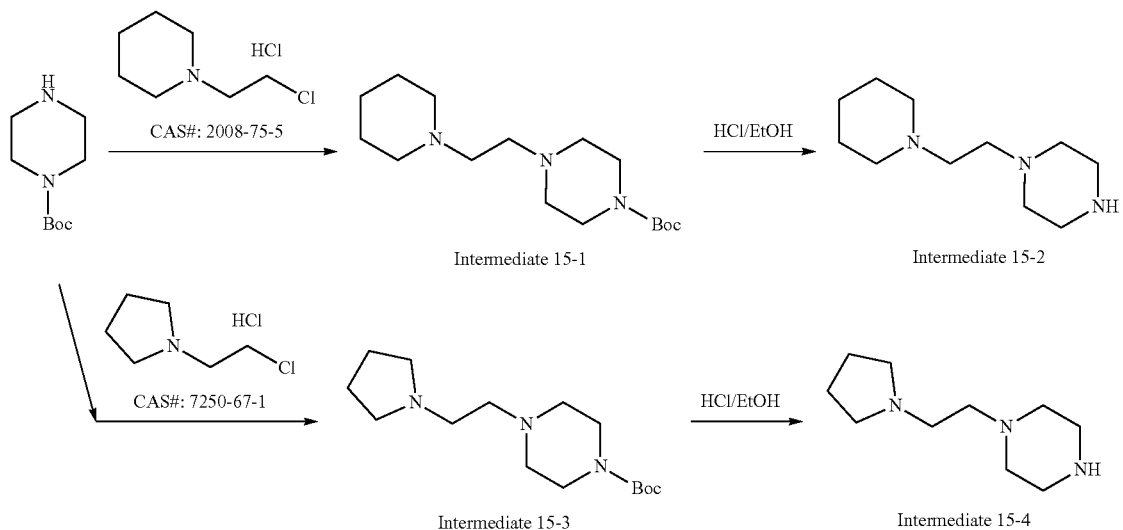

Preparation of Intermediate 15-2

To a solution of 1-Boc-piperazine (4 g, 21.5 mmol) in DMF (60 mL) was added NaH (3.44 g, 86 mmol) portionwise at 5° C. The suspension was subsequently heated to 50° C. After stirring at 50° C. for 5 hours, the reaction mixture was cooled to 5° C., followed by the addition of amine chloride (CAS #: 2008-75-5) (5.6 g, 30 mmol). After stirring at ambient temperature for 16 hours, the reaction was quenched with water (60 mL) and extracted by ethyl acetate (3×50 mL). The organic layers were collected, concentrated and purified by column chromatography on silica gel (petroleum ether/ethyl acetate=1:1 to ethyl acetate) to give Boc-protected Intermediate 15-1 as yellow oil (4.3 g, 67%).

A solution of Boc-protected Intermediate 15-1 (4.3 g, 14.5 mmol) in 20 mL of methanol was added dropwise HCl/EtOH (4M, 50 mL) at rt. After 4 hours of stirring at rt, the reaction mixture was concentrated, and the remaining residue was redissolved by using a mixture of 10 mL of MeOH and 50 mL of $CH_2Cl_2$, followed by the addition of 6 g of $K_2CO_3$. The resulting mixture was filtered through a pad of Celite after 16 hours of stirring. The filtrate was concentrate under reduced pressure to give crude Intermediate 15-2 as pale yellow solid (2.8 g, 100%).

Preparation of Intermediate 15-4

To a solution of 1-Boc-piperazine (4 g, 21.5 mmol) in DMF (60 mL) was added NaH (3.44 g, 86 mmol) portionwise at 5° C. The suspension was subsequently heated to 50° C. After stirring at 50° C. for 5 hours, the reaction mixture was cooled to 5° C., followed by the addition of amine chloride (CAS #: 7250-67-1) (5.5 g, 32.2 mmol). After stirring at ambient temperature for 16 hour, the reaction was quenched with water (60 mL) and extracted by ethyl acetate (3×50 mL). The organic layers were collected, concentrated and purified by column chromatography on silica gel (petroleum ether/ethyl acetate=1:1 to ethyl acetate) to give Boc-protected Intermediate 15-3 as yellow oil (2.6 g, 43%).

A solution of Boc-protected Intermediate 15-3 (2.6 g, 9.2 mmol) in 10 mL of methanol was added dropwise HCl/EtOH (4M, 30 mL) at rt. After 4 hours of stirring at rt, the reaction mixture was concentrated, and remaining residue was redissolved in a mixture of 10 mL of MeOH and 50 mL of $CH_2Cl_2$, followed by the addition of 4 g of $K_2CO_3$. The resulting mixture was filtered through a pad of Celite after 16 hours of stirring. The filtrate was concentrate under reduced pressure to give crude Boc-protected Intermediate 15-4 as pale brown solid (1.1 g, 65%).

Example 16. Synthesis of Intermediate 16-2 Useful in Preparing Compounds Described Herein Such as Compound 277

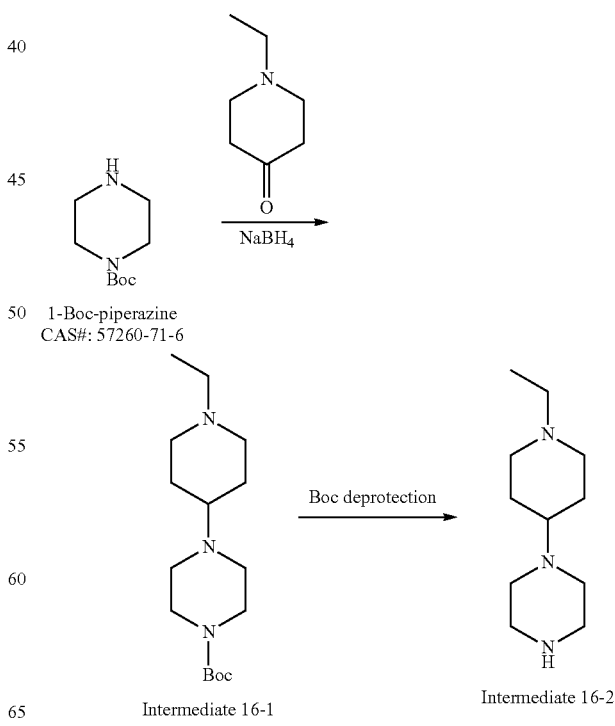

Titanium(IV) isopropoxide (10.2 g, 35.8 mmol) was added dropwise to a solution of 1-Boc-piperazine (4 g, 21.5 mmol) in 40 mL of MeOH. It was then followed by the addition of 1-ethylpiperidin-4-one (2.3 g, 17.9 mmol) at rt. The reaction mixture was stirred at rt for 5 hours, followed by addition of sodium borohydride (0.68 g, 17.9 mmol). The resulting mixture was quenched by water (4 mL) after additional 2 hours of stirring. Inorganic precipitate was filtered and washed with ethyl acetate. The combined organic phases were concentrated under reduced pressure and the residue was purified by column chromatography on silica gel (petroleum ether/ethyl acetate=1:1) to give Boc-protected Intermediate 16-1 as pale yellow oil (3.1 g, 58%).

A solution of Boc-protected Intermediate 16-1 (3.1 g, 10.4 mmol) in 20 mL of methanol was added dropwise to HCl/EtOH (4M, 30 mL) at rt. After 4 hrs of stirring at rt, the reaction was concentrated and remaining residue was redissolved in a mixture of 10 mL of MeOH and 50 mL of CH$_2$Cl$_2$, followed by the addition of 4 g of K$_2$CO$_3$. The resulting mixture was filtered through a pad of Celite after 16 hours of stirring. The filtrate was concentrate under reduced pressure to give Intermediate 16-2 as yellow solid (2 g, 100%).

Example 17. Synthesis of Intermediate 17-2 Useful in Preparing Compounds Described Herein Such as Compound 279

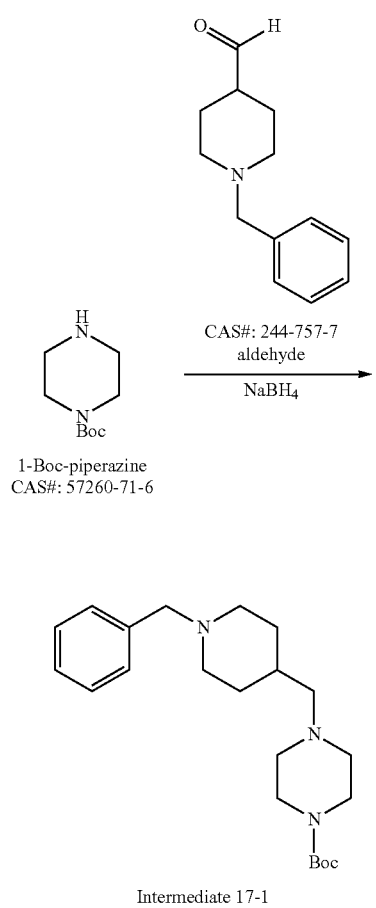

Intermediate 17-1

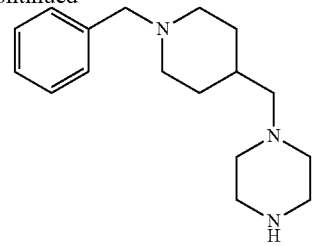

Intermediate 17-2

Titanium(IV) isopropoxide (10.2 g, 35.8 mmol) was added dropwise to a solution of 1-Boc-piperazine (4 g, 21.5 mmol) in 40 mL of MeOH. It was then followed by the addition of aldehyde (CAS #: 244-757-7) (3.6 g, 17.9 mmol) at rt. The reaction mixture was stirred at rt for 5 hours, followed by addition of sodium borohydride (0.68 g, 17.9 mmol). After additional 2 hours of stirring, the resulting mixture was quenched by water (4 mL). Inorganic precipitate was filtered and washed with ethyl acetate. The combined organic phases were concentrated under reduced pressure and the residue was purified by column chromatography on silica gel (petroleum ether/ethyl acetate=1:1) to give Boc-protected Intermediate 17-1 as pale yellow waxy solid (5.6 g, 67%).

A solution of Boc-protected Intermediate 17-1 (5.6 g, 15 mmol) in 80 mL of methanol was added dropwise to HCl/EtOH (4M, 120 mL) at rt while stirring. After 4 hours, the reaction was concentrated and remaining residue was redissolved in a mixture of 20 mL of MeOH and 100 mL of CH$_2$Cl$_2$, followed by the addition of 8 g of K$_2$CO$_3$. The resulting mixture was filtered through a pad of Celite after 16 hours of stirring. The filtrate was concentrate under reduced pressure to give Intermediate 17-2 as brown oil (4.1 g, 100%).

Example 18. Synthesis of Intermediates 18-13, 18-14 and 18-15 Useful in Preparing Compounds Described Herein

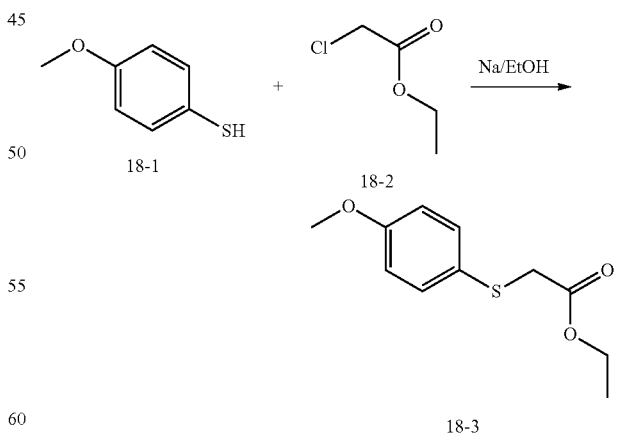

A solution of EtONa was prepared by dissolving Na (2.3 g) in absolute EtOH (250 ml). Starting material 18-1 (14 g, 0.1 mol) was added drop wise to the solution of EtONa (0.1 mol). After stirring the at rt for 1 hour Starting material 18-2 (12.2 g, 0.1 mol) was added in one portion and the reaction mixture was brought to reflux and stirred under reflux for 3 hours. After cooling to rt, the reaction mixture was concentrated in vacuo and the residue was triturated with water (250 ml) followed by extraction with diethyl ether (4×125 mL). Combined organic layer was washed water (2×150 mL), brine (2×150 mL) and dried over Na₂SO₄, filtered and evaporated in vacuo to give Intermediate 18-3 which was used without further purification (22 g, 95%).

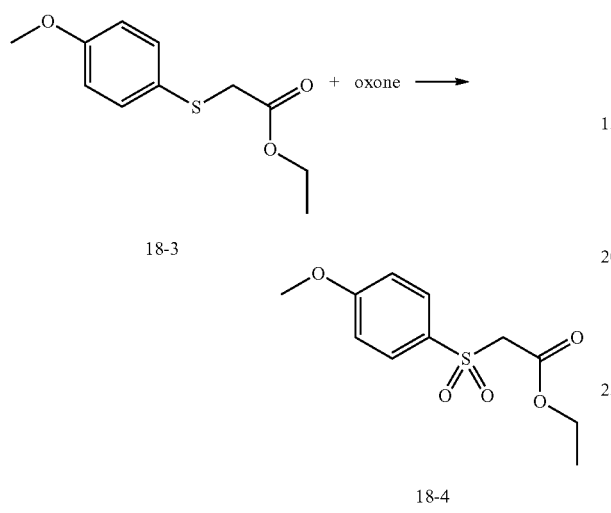

A solution of oxone (95 g, 0.625 mol) in water (400 mL) was added drop-wise at rt to a solution of Intermediate 18-3 (22 g, 0.097 mol) in a mixture of MeOH (200 ml) and THF (200 ml). After stirring at rt for 24 hours, the reaction mixture was filtered and the filtrate was evaporated in vacuo. The residue was extracted with DCM (2×200 mL). The combined organic layers were washed with water (3×100 mL), brine (3×100 mL), dried over Na₂SO₄, filtered and evaporated in vacuo. The product was dried in vacuo and was used without additional purification (22.3 g, 89%).

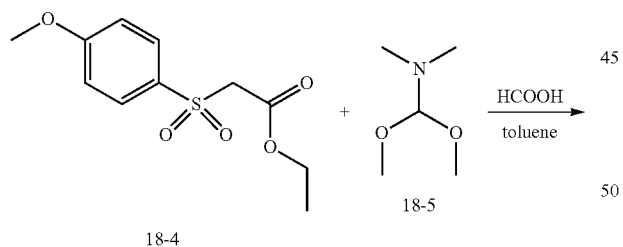

A solution of 18-4 (43 g, 0.167 mol), 18-5 (61 g, 0.51 mol) and HCOOH (2 mL) in toluene (150 mL) was stirred under reflux for 8 hours. The reaction mixture was cooled down to rt, the precipitate formed was filtered off and washed with toluene (2×50 mL) and dried in vacuo (42.3 g, 81%).

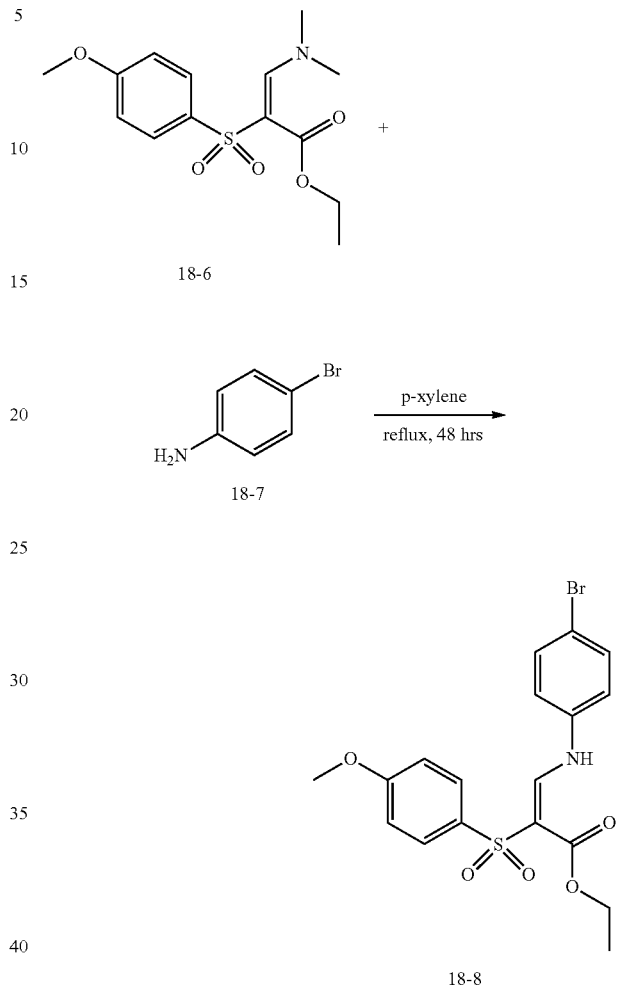

A solution of 18-6 (21.3 g, 67.9 mmol) and 18-7 (11.7 g, 67.9 mmol) in p-xylene (75 mL) was stirred under reflux for 48 hours. The reaction mixture was cooled down to rt. The precipitate was filtered off, washed with p-xylene and recrystallized from benzene (17.3 g, 58%).

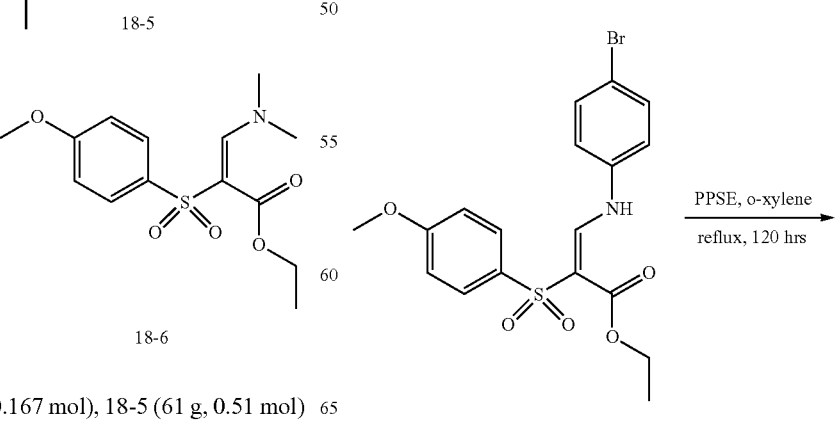

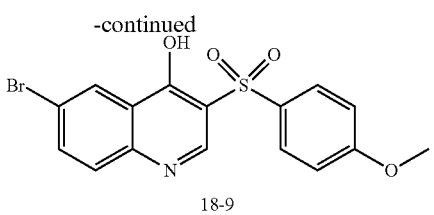

18-9

Trimethylsilyl polyphosphate (PPSE, 230 g) was added to a solution of 18-8 (22.85 g, 52 mmol) in o-xylene (230 ml) and the reaction mixture was stirred under reflux for 120 hours. The reaction was then concentrated under vacuo and the residue was triturated with water (250 mL). The precipitate was filtered off and was triturated with boiling i-PrOH (250 mL). The precipitate was filtered off and dried in vacuo (8.8 g, 43%).

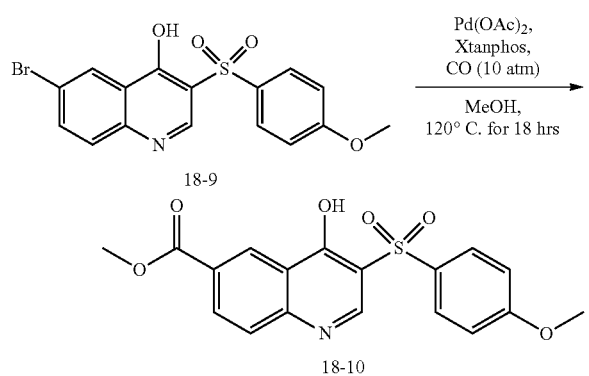

A solution of 18-9 (8.8 g, 22.3 mmol), Et$_3$N (5.6 g, 55.8 mmol), Xantphos (1.03 g, 1.8 mmol), Pd(OAc)$_2$ (0.3 g, 1.3 mol) in MeOH (150 mL) was kept in a pressure reactor for 18 hours at 120° C. and 10 atm of CO. The reaction mixture was cooled down, the precipitate was filtered off and washed with MeOH (50 mL). The filtrate was evaporated in vacuo, and the residue was vacuum dried (7.6 g, 91%).

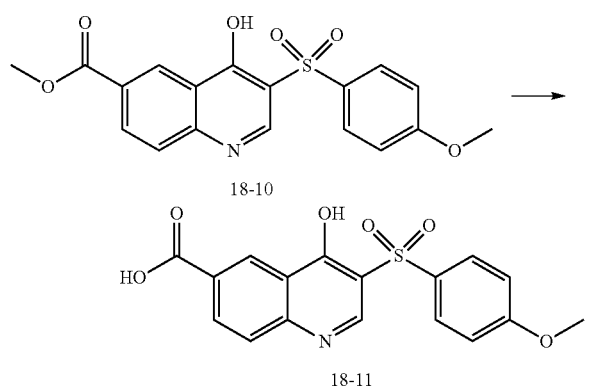

Ester 18-10 (7.6 g, 20 mmol) was dissolved upon heating in i-PrOH (25 mL). To this solution was added KOH (3.41 g, 60 mmol) in i-PrOH (75 mL). After stirring for 45 minutes, the reaction mixture was cooled down to rt and concentrated under vacuo. The residue was stirred with charcoal suspended in water (50 mL) for 15 minutes. The charcoal was filtered off and the filtrate was acidified with concentrated HCl to pH=1. The precipitate was filtered off and dried in vacuo (7.0 g, 98%).

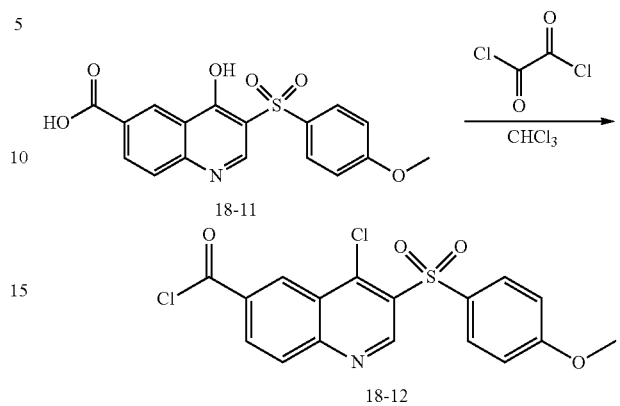

Oxalyl chloride (39.4 mL, 0.46 mol) was carefully added in one portion to a suspension of 18-11 (6.6 g, 18.4 mmol) in anhydrous CHCl$_3$ (250 mL). The reaction mixture was stirred under reflux until all stating material was dissolved (6 hours). The reaction mixture was cooled down and evaporated and dried in vacuo. Acid chloride 18-12 was further used without additional purification.

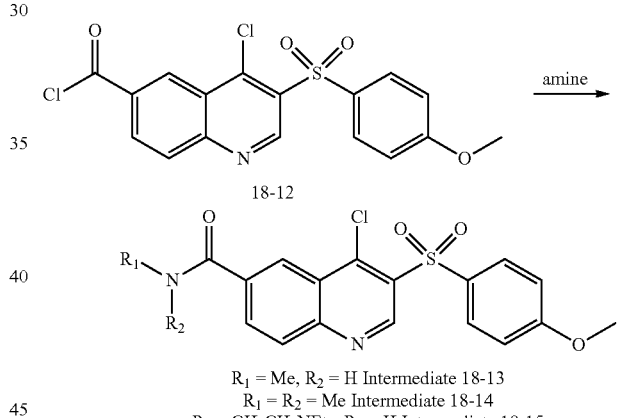

$R_1$ = Me, $R_2$ = H Intermediate 18-13
$R_1$ = $R_2$ = Me Intermediate 18-14
$R_1$ = CH$_2$CH$_2$NEt$_2$, $R_2$ = H Intermediate 18-15

A solution of amine (15.25 mmol) in anhydrous toluene (20 mL) was added slowly drop wise to a solution of 18-12 (2.4 g, 6.1 mmol) in anhydrous CH$_2$Cl$_2$ (100 mL) while maintaining reaction temperature at −20° C.). It was then followed by addition of N,N-diethylethylenediamine (0.78 g, 6.71 mmol) and Et$_3$N (1.23 g, 12.2 mmol) in 10 mL of toluene. The reaction mixture was stirred for 15 minutes at −20° C., the reaction was stopped by adding water (100 mL). The organic layer was washed with water (2×100 mL), brine (100 mL), dried over Na$_2$SO$_4$ filtered and evaporated/dried in vacuo.

Intermediate 18-13 was recrystallized from toluene (3.46 g, 58%).

Intermediate 18-14 was purified by preparative column chromatography (CH$_2$Cl$_2$, MeOH (2.5%) followed by CH$_2$Cl$_2$ acetone (gradient 8-15%)) (Yield: 2.65 g, 43%).

Intermediate 18-15 was purified by preparative column chromatography CH$_2$Cl$_2$ MeOH (gradient 3-6%) (2.2 g, 30%).

Example 19. Synthesis of Intermediate 19-4 Useful in Preparing Compounds Described Herein

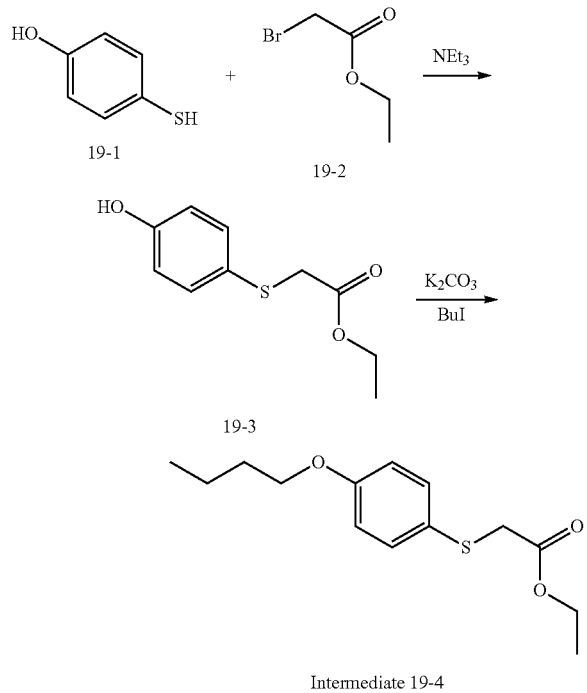

Intermediate 19-4

A mixture of Et₃N (2.5 g, 25 mmol) and 19-2 (3.3 g, 20 mmol) was added drop-wise to a solution of 19-1 (2.52 g, 20 mmol) in CHCl₃ (50 mL) at 25° C. The reaction mixture was stirred at 25° C. for 2 hours and was washed with water (2×50 mL), organic layer was separated, dried over Na₂SO₄, filtered and evaporated/dried in vacuo (4.0 g, 95%). The product was used without additional purification.

A solution of n-butyliodide (1.52 g, 8.3 mmol) in acetone (10 mL) was added drop-wise to a suspension of K₂CO₃ in a solution of 19-3 (1.6 g, 7.5 mmol) in acetone (30 mL). The reaction mixture was stirred under reflux for 48 hours and after cooling down to room temperature the solvent was removed in vacuo. The residue was triturated with water (50 mL) and the product was extracted with CH₂Cl₂ (2×50 mL). The combined organic layer was separated, washed with water (2×50 mL), the organic phase was separated dried over Na₂SO₄, filtered and evaporated/dried in vacuo to give Intermediate 19-4 (1.8 g, 92%).

Example 20. Synthesis of Chiral Sulfoxides

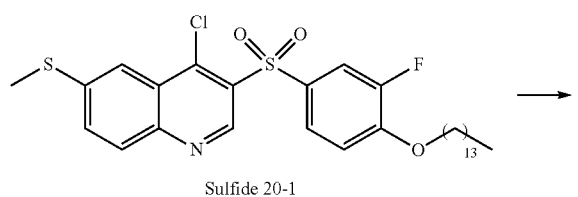

Sulfide 20-1

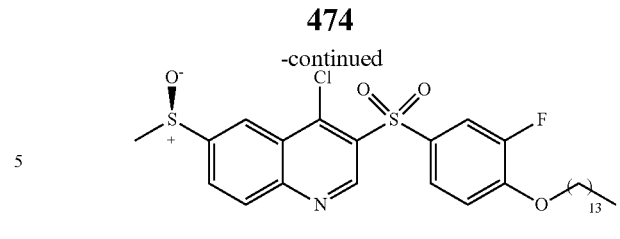

Sulfoxide 20-2-R

To a stirred solution of Sulfide 20-1 (600 mg, 1.03 mmol, 1. eq.) in dichloromethane (18 mL, 30 volumes) was added (−)-Diisopropyl d-tartrate (484 mg, 2.07 mmol, 2.00 equiv) at around 20° C. This solution was yellow in appearance after short mixing. Titanium isopropoxide (294 mg, 1.03 mmol, 1.00 equiv) was then added dropwise. The reaction mixture was then cooled to 0° C. and cumeme hydroperoxide (197 mg, 1.03 mmol, 80% w/w solution, 1 equiv) added dropwise while maintaining the temperature at 0° C. After stirring at 0° C. for 3 h, the reaction mixture was quenched by adding 10 mL of 5% Na₂CO₃ and 5% Na₂SO₃ aqueous solution. The organic layer was separated and purified by flash chromatography to obtain Sulfoxide 20-2-R (500 mg, 81% yield, 88% ee).

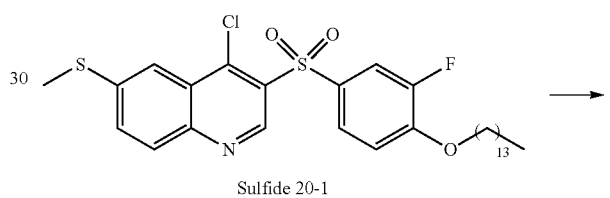

Sulfide 20-1

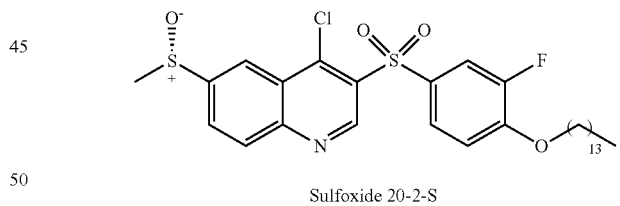

Sulfoxide 20-2-S

To a stirred solution of Sulfide 20-1 (600 mg, 1.03 mmol, 1. eq.) in dichloromethane (18 mL, 30 volumes) was added (+)-Diisopropyl d-tartrate (484 mg, 2.07 mmol, 2.00 equiv) at around 20° C. This solution was yellow in appearance after short mixing. Titanium isopropoxide (294 mg, 1.03 mmol, 1.00 equiv) was then added dropwise. The reaction mixture was then cooled to 0° C. and cumeme hydroperoxide (197 mg, 1.03 mmol, 80% w/w solution, 1 equiv) added dropwise while maintaining the temperature at 0° C. After stirring at 0° C. for 3 h, the reaction mixture was quenched by adding 10 mL of 5% Na₂CO₃ and 5% Na₂SO₃ aqueous solution. The organic layer was separated and purified by flash chromatography to obtain Sulfoxide 20-2-S (510 mg, 83% yield, 85% ee).

Example 21. Synthesis of Intermediate 21-1 and 21-2

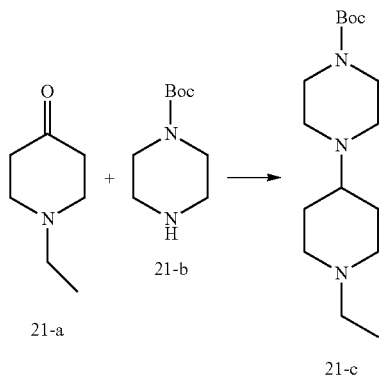

To a stirred solution of 21-b (16.5 g, 88.6 mmol, 1.00 eq.) in 160 mL of MeOH was added Titanium(IV) isopropoxide (50.5 g, 177.7 mmol, 2.00 eq.) at rt. It was then followed by the addition of 21-a (11.3 g, 88.8 mmol, 1.00 eq.). The reaction mixture was stirred at 30° C. for 6 hrs, followed by addition of sodium borohydride (3.4 g, 89.6 mmol) after cooling reaction mixture to 5° C. After additional 14 hrs of stirring at rt, the resulting mixture was quenched by water (20 mL). Inorganic precipitate was filtered and washed with ethyl acetate. The combined organic phases were concentrated under reduced pressure and the residue was diluted with 200 mL ethyl acetate. Inorganic precipitate was filtered again and the filtrate was washed with water 4×50 mL. The aqueous phase was extracted with EtOAc 3×100 mL. The combined organic phases were concentrated under reduced pressure to give crude 21-c as yellow oil (~24 g, crude). The yellow oil was dissolved in EtOAc (150 mL) and $H_2O$ (150 mL). The mixture was stirred and $CH_3COOH$ was added dropwise to adjust the pH of aqueous layer to 7. The aqueous layer was separated and the pH was adjusted to 9 by $K_2CO_3$. DCM (200 mL) was added to extract Compound 1. The DCM layer was separated and concentrated to afford Compound 21-c as yellow oil (20.2 g, 76.5% yield).

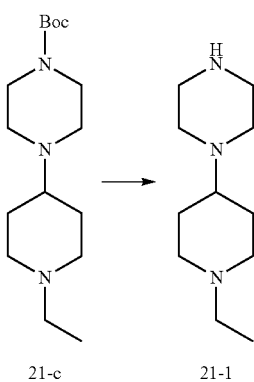 [SMILES: CCN1CCC(N2CCN(C(=O)OC(C)(C)C)CC2)CC1 ; CCN1CCC(N2CCNCC2)CC1]

A solution of Compound 21-c (20.2 g, 67.9 mmol) in 30 mL of EtOAc was added dropwise to HCl/EtOH (4M, 150 mL) at 30° C. After it was stirred at 30° C. for 12 hrs, the reaction mixture was filtered and the filter cake was washed by 20 mL of ethanol and 100 mL of EtOAc. The obtained filter cake was re-dissolved in a mixture of 25 mL of MeOH and 125 mL of $CH_2Cl_2$, followed by the addition of $K_2CO_3$ (18 g, 130 mmol). The resulting mixture was filtered through a pad of Celite after 2 hrs of stirring. The filtrate was concentrated under reduced pressure to give 21-1 as light-yellow oil (11 g, 82.1% yield).

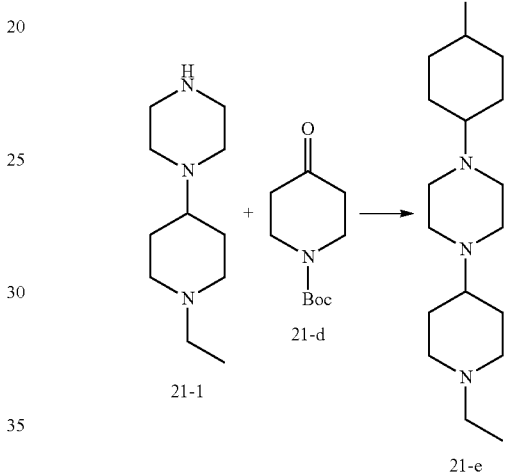

To a solution of 21-1 (11 g, 55.7 mmol, 1.00 eq.) in 150 mL of MeOH was added 21-d (11.1 g, 55.7 mmol, 1.00 eq.) After the resulting reaction mixture was stirred at 60° C. for 5 hrs, it was cooled to 5° C., followed by addition of sodium borohydride (2.1 g, 55.3 mmol, 1.00 eq.). After additional 12 hrs of stirring at rt, the resulting mixture was quenched by water (16 mL). Inorganic precipitate was filtered and washed with 100 mL of ethyl acetate. The combined organic phases were concentrated under reduced pressure and the residue was diluted with 150 mL ethyl acetate. Inorganic precipitate was filtered again and the filtrate was washed with water 4×50 mL. The aqueous phase was extracted with EtOAc 3×100 mL. The combined organic phases were concentrated to about in 150 mL total volume and additional 150 mL of $H_2O$ was add to the mixture. The mixture was stirred and $CH_3COOH$ was added dropwise to adjust the pH of aqueous layer to 7. The aqueous layer was separated and the pH was adjusted to 9 by $K_2CO_3$, followed by addition of 200 mL of DCM. The DCM layer was separated and concentrated to afford 21-e as light-yellow solid (10 g, 47.1% yield).

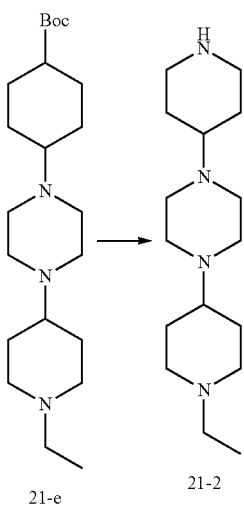 [SMILES: CCN1CCC(N2CCN(C3CCC(C(=O)OC(C)(C)C)CC3)CC2)CC1 ; CCN1CCC(N2CCN(C3CCNCC3)CC2)CC1]

21-e    21-2

To a solution of 21-e (10 g, 26.3 mmol) in 20 mL of EtOAc was added dropwise 70 mL of 4 M HCl/EtOH at 30° C. After it was stirred at 30° C. for 14 hrs, the reaction mixture was filtered and the filter cake was washed by 20 mL ethanol and 30 mL EtOAc. The obtained white filter cake was re-dissolved in a mixture of 25 mL of MeOH and 75 mL of $CH_2Cl_2$, followed by the addition of $K_2CO_3$ (10 g, 72.5 mmol). The resulting mixture was filtered through a pad of Celite after 2 hrs of stirring. The filtrate was concentrated under reduced pressure to give a light-yellow solid. The solid was dissolved in $CH_3CN$ (8 mL), followed by sonication for 3 mins. The mixture was filtered and the filtercake was dried to afford 21-2 as a white solid (6.4 g, 86.8% yield).

Using the procedures described above, other amines corresponding to the substituent $R^1$ can be prepared by using suitable starting materials.

Compounds shown in Table 2 were or may be synthesized according to the procedures described herein from starting materials or intermediates described herein or starting materials known in the art or can be prepared by methods known in the art. For example, Compounds 2-41 were prepared according to procedures similar to those described in II-2A, I-1 to 1-5, I-6A; Compound 42 was prepared according to procedures similar to those described in II-2A, I-1 to 1-5, I-6A, 1-7; Compounds 43, 44, 54, 68, 69, 71-74 and 113-115 were prepared according to procedures similar to those described in II-B, I-1 to I-5, I-6A in the General Synthesis.

TABLE 2

| No | MS (m/z) | $^1$H NMR |
|---|---|---|
| 1 | 480 | $^1$HNMR (600 MHz, CDCl$_3$, 25° C.): 1.24 (t, 3H, J = 7.8 Hz), 2.37 (s, 3H), 2.42 (m, 4H), 2.73 (q, 2H, J = 9 Hz), 3.29 (m, 4H), 5.25 (s, 2H), 7.34 (d, 2H, J = 8.4 Hz), 7.67 (dd, 1H, J = 9, 1.8 Hz), 7.78 (d, 2H, J = 7.8 Hz), 8.10 (s, 1H), 8.22 (d, 1H, J = 9.6 Hz), 9.41 (s, 1H) |
| 2 | 465 | $^1$HNMR (600 MHz, CDCl$_3$, 25° C.): 1.24 (t, 3H, J = 7.8, 7.8 Hz), 1.61 (m, 4H), 1.67 (m, 2H), 2.73 (q, 2H, J = 9 Hz), 3.26 (m, 4H), 5.26 (s, 2H), 7.35 (d, 2H, J = 8.4 Hz), 7.67 (dd, 1H, J = 9, 2.4 Hz), 7.78 (d, 2H, J = 8.4 Hz), 8.04 (s, 1H), 8.16 (d, 1H, J = 9 Hz), 9.28 (s, 1H) |
| 3 | 467 | $^1$HNMR (600 MHz, CDCl$_3$, 25° C.): 1.24 (t, 3H, J = 7.2, 7.8 Hz), 2.73 (q, 2H, J = 9 Hz), 3.26 (m, 2H), 3.67 (m, 4H), 7.35 (d, 2H, J = 8.4 Hz), 7.68 (dd, 1H, J = 9.6, 1.8 Hz), 7.80 (d, 2H, J = 8.4 Hz), 8.04 (s, 1H), 8.26 (d, 1H, J = 7.8 Hz), 9.46 (s, 1H) |
| 4 | 479 | $^1$HNMR (600 MHz, CDCl$_3$, 25° C.): 1.0 (d, 3H, J = 6.6 Hz), 1.22 (m, 1H), 1.24 (t, 3H, J = 7.8, 7.8 Hz), 1.62 (m, 3H), 2.72 (q, 2H, J = 9 Hz), 3.17 (m, 2H), 3.38 (m, 2H), 7.35 (d, 2H, J = 8.4 Hz), 7.64 (dd, 1H, J = 9, 2.4 Hz), 7.77 (d, 2H, J = 8.4 Hz), 8.00 (s, 1H), 8.17 (d, 1H, J = 9.6 Hz), 9.28 (s, 1H) |
| 5 | 510 | $^1$HNMR (600 MHz, CDCl$_3$, 25° C.): 1.27 (t, 3H, J = 7.8, 7.8 Hz), 2.69 (m, 4H), 2.75 (m, 4H), 3.42 (m, 4H), 3.75 (t, 2H, J = 4.8, 4.8 Hz), 7.38 (d, 2H, J = 8.4 Hz), 7.69 (dd, 1H, J = 9, 1.8 Hz), 7.81 (d, 2H, J = 8.4 Hz), 8.09 (d, 1H, J = 0.6 Hz), 8.35 (d, 1H, J = 9.6 Hz), 9.31 (s, 1H) |
| 6 | 494 | $^1$HNMR (600 MHz, CDCl$_3$, 25° C.): 1.13 (t, 3H, J = 7.2 Hz), 1.24 (t, 3H, J = 7.8, 7.2 Hz), 2.45 (m, 4H), 2.51 (m, 2H), 2.72 (q, 2H, J = 9 Hz), 3.32 (m, 4H), 7.35 (d, 2H, J = 8.4 Hz), 7.68 (dd, 1H, J = 9, 1.8 Hz), 8.12 (d, 2H, J = 1.8 Hz), 8.23 (d, 1H, J = 9 Hz), 9.44 (s, 1H) |
| 7 | 494 | $^1$HNMR (600 MHz, CDCl$_3$, 25° C.): 1.23 (t, 3H, J = 7.2, 7.8 Hz), 1.88 (m, 2H), 2.46 (s, 3H), 2.64 (m, 2H), 2.71 (m, 4H), 3.31 (m, 4H), 7.36 (d, 2H, J = 8.4 Hz), 7.63 (dd, 1H, J = 9, 2.4 Hz), 7.82 (d, 2H, J = 8.4 Hz), 8.19 (d, 1H, J = 3.6 Hz), 8.39 (s, 1H), 9.40 (s, 1H) |
| 8 | 481 | $^1$HNMR (600 MHz, CDCl$_3$, 25° C.): 1.26 (t, 3H, J = 7.8 Hz), 1.63 (m, 2H), 1.89 (m, 2H), 2.72 (q, 2H, J = 9.6 Hz), 3.27 (m, 2H), 3.39 (m, 2H), 7.37 (d, 2H, J = 8.4 Hz), 7.68 (d, 1H, J = 2.4 Hz), 7.80 (d, 2H, J = 8.4 Hz), 8.02 (s, 1H), 8.23 (d, 1H, J = 9 Hz), 9.32 (s, 1H) |
| 9 | 538 | $^1$HNMR (600 MHz, CDCl$_3$, 25° C.): 1.26 (t, 3H, J = 7.8 Hz), 1.32 (t, 3H, J = 7.2 Hz), 2.72 (q, 2H, J = 10.8, 9 Hz), 3.24 (m, 4H), 3.48 (m, 4H), 4.19 (q, 2HJ = 13.8 Hz), 7.35 (d, 2H, J = 8.4 Hz), 7.71 (d, 1H, J = 1.8 Hz), 7.77 (d, 2H, J = 8.4 Hz), 7.95 (m, 1H, J = 0.6 Hz), 8.27 (d, 1H, J = 9 Hz), 9.43 (s, 1H) |
| 10 | 560 | $^1$HNMR (600 MHz, CDCl$_3$, 25° C.): 1.24 (t, 3H, J = 7.8 Hz), 2.73 (q, 2H, J = 9 Hz), 3.15 (m, 4H), 3.45 (m, 4H), 6.95 (m, 2H, J = 9 Hz), 7.0 (m, 2H), 7.35 (d, 2H, J = 8.4 Hz), 7.70 (dd, 1H, J = 9, 1.8 Hz), 7.80 (d, 2H, J = 8.4 Hz), 8.10 (s, 1H), 8.26 (d, 1H, J = 9 Hz), 9.44 (s, 1H) |
| 11 | 548 | $^1$HNMR (600 MHz, D$_6$-DMSO, 25° C.): 1.17 (t, 3H, J = 7.8 Hz), 1.87 (m, 6H), 2.70 (q, 2H, J = 9 Hz), 2.89 (m, 4H), 3.35 (m, 2H), 3.33 (m, 2H), 3.45 (m, 4H), 7.48 (d, 2H, J = 9 Hz), 7.83 (d, 2H, J = 8.4 Hz), 7.99 (d, 1H, J = 9 Hz), 8.18 (s, 1H), 8.35 (d, 1H, J = 9.6 Hz), 9.44 (s, 1H) |
| 12 | 557 | $^1$HNMR (600 MHz, CDCl$_3$, 25° C.): 1.20 (t, 3H, J = 7.8 Hz), 1.70 (m, 2H), 2.00 (m, 2H), 2.69 (q, 2H, J = 15, 15.6 Hz), 2.94 (m, 2H), 3.89 (q, 2H, |

TABLE 2-continued

| No | MS (m/z) | ¹H NMR |
|---|---|---|
| | | J = 11.4 Hz), 7.34 (m, 3H), 7.35 (m.2H), 7.45 (d, 2H, J = 7.2 Hz), 7.69 (dd, 2H, J = 9, 1.8 Hz), 7.82 (d, 1H, 8.4 Hz), 8.18 (s, 1H), 8.28 (d, 1H, J = 9 Hz), 9.49 (s, 1H) |
| 13 | 542 | ¹HNMR (600 MHz, CDCl₃, 25° C.): 1.25 (t, 3H, J = 7.8 Hz), 2.72 (q, 2H, J = 9.6 Hz), 3.20 (m, 4H), 3.45 (m, 4H), 6.95 (m, 3H), 7.28 (m, 4H), 7.70 (d, 1H, J = 8.4 Hz), 7.80 (d, 2H, J = 7.8 Hz), 8.11 (s, 1H), 8.26 (d, 1H, J = 9 Hz), 9.47 (s, 1H) |
| 14 | 451 | ¹HNMR (600 MHz, CDCl₃, 25° C.): 1.23 (t, 3H, J = 7.8 Hz), 2.04 (m, 4H), 2.71 (q, 2H, J = 9.6 Hz), 3.18 (m, 4H), 7.33 (d, 2H, J = 8.4 Hz), 7.64 (dd, 1H, J = 9, 2.4 Hz), 7.67 (m, 1H)7.80 (d, 2H, J = 8.4 Hz), 8.22 (d, 1H, J = 9 Hz), 9.43 (s, 1H) |
| 15 | 427 | ¹HNMR (600 MHz, CDCl₃, 25° C.): 1.24 (t, 3H, J = 7.8, 7.2 Hz), 1.59 (m, 2H), 1.81 (m, 2H), 2.70 (q, 2H, J = 9.6 Hz), 3.20 (m, 2H), 3.55 (m, 2H), 3.94 (s, 3H), 7.34 (d, 2H, J = 8.4 Hz), 7.41 (m, 1H), 7.47 (dd, 1H, J = 9, 2.4 Hz), 7.78 (d, 1H, J = 8.4 Hz), 8.10 (d, 1H, J = 9 Hz), 9.23 (s, 1H) |
| 16 | 484 | ¹HNMR (600 MHz, CDCl₃, 25° C.): 1.23 (t, 3H, J = 7.8 Hz), 1.28 (t, 3H, J = 6.6.7.2 Hz), 2.70 (q, 2H, J = 9 Hz), 3.21 (m, 6H), 3.44 (m.2H), 3.92 (s, 3H), 4.16 (q, 2H, J = 7.8 Hz), 7.28 (d, 1H, J = 3 Hz), 7.33 (d, 2H, J = 8.4 Hz), 7.49 (dd, 1H, J = 9.6, 2.4 Hz), 7.75 (d, 2H, J = 8.4 Hz), 8.14 (d, 1H, J = 8.4 Hz), 9.29 (s, 1H) |
| 17 | 506 | ¹HNMR (600 MHz, CDCl₃, 25° C.): 1.22 (t, 3H, J = 7.8 Hz), 2.69 (q, 2H, J = 15 Hz), 3.04 (m, 4H), 3.37 (m, 4H), 3.90 (s, 3H), 6.88 (m, 2H), 7.00 (m, 2H), 7.31 (d, 2H, J = 6.6 Hz), 7.41 (m, 1H), 7.48 (dd, 1H, J = 9, 3 Hz), 7.77 (d, 2H, J = 7.2 Hz), 8.11 (d, 1H, J = 9 Hz), 9.32 (s, 1H) |
| 18 | 425 | ¹HNMR (600 MHz, CDCl₃, 25° C.): 1.22 (t, 3H, J = 7.2, 7.8 Hz), 1.26 (m, 4H), 1.61 (m, 2H), 1.76 (m, 2H), 1.95 (m, 2H)2.66 (q, 2H, J = 9.6 Hz), 3.87 (m, 4H), 7.10 (m, 1H), 7.30 (d, 2H.J = 9 Hz)7.32 (d, 2H, J = 3 Hz), 7.35 (dd, 1H, J = 9, 2.4 Hz), 7.81 (d, 2H, J = 8.4 Hz), 7.88 (d, 1H, J = 9 Hz), 8.93 (s, 1H) |
| 19 | 437 | ¹HNMR (600 MHz, CDCl₃, 25° C.): 1.27 (t, 3H, J = 7.8, 7.2 Hz), 2.59 (q, 2H, J = 9.6 Hz), 3.41 (s, 3H), 6.67 (m, 2H), 6.75 (d, 1H, J = 3 Hz), 6.89 (m, 2H)7.16 (d, 2H, J = 8.4 Hz), 7.30 (dd, 1H, J = 9.6, 3 Hz), 7.75 (d, 2H, J = 8.4 Hz), 7.92 (d, 1H, J = 9 Hz), 8.55 (s, 1H), 9.14 (s, 1H) |
| 20 | 426 | ¹HNMR (600 MHz, CDCl₃, 25° C.): 1.25 (t, 3H, J = 9 Hz), 2.74 (q, 2H.J = 9 Hz)2.79 (s, 3H), 2.92 (m, 4H), 3.27 (m, 2H), 4.10 (s, 3H), 4.52 (m, 2H), 7.40 (d, 2H, J = 8.4 Hz)7.46 (d, 2H, J = 9 Hz), 7.48 (dd, 1H, J = 9, 2.4 Hz), 7.92 (d, 2H, J = 10.8 Hz), 8.06 (d, 1H, J = 9 Hz), 8.83 (s, 1H) |
| 21 | 411 | ¹HNMR (600 MHz, CDCl₃, 25° C.): 1.22 (t, 3H, J = 7.8, 7.2 Hz), 1.52 (m, 4H), 1.60 (m, 2H), 2.69 (q, 2H, J = 15 Hz), 3.20 (m, 4H), 3.94 (s, 3H), 7.31 (d, 2H, J = 8.4 Hz), 7.43 (m, 2H), 7.77 (d, 1H, J = 8.4 Hz), 8.06 (d, 1H, J = 9 Hz), 9.19 (s, 1H) |
| 22 | 413 | ¹HNMR (600 MHz, CDCl₃, 25° C.): 1.22 (t, 3H, J = 7.2, 7.8 Hz), 2.69 (q, 2H, J = 15 Hz), 3.19 (m, 4H), 3.60 (m, 4H), 3.94 (s, 3H), 7.33 (d, 2H, J = 8.4 Hz), 7.38 (d, 1H, J = 2.4 Hz), 7.48 (dd, 1H, J = 9.6, 3 Hz), 7.78 (d, 2H, J = 8.4 Hz), 8.13 (d, 1H, J = 9 Hz), 9.35 (s, 1H) |
| 23 | 425 | ¹HNMR (600 MHz, CDCl₃, 25° C.): 0.97 (d, 3H, J = 9 Hz), 1.13 (m, 2H), 1.22 (t, 3H, J = 7.2, 7.8 Hz), 1.54 (m, 3H), 2.69 (q, 2H, J = 15.6 Hz), 3.06 (m, 2H), 3.35 (t, 2H, J = 11.4 Hz), 7.31 (d, 2H, J = 8.4 Hz), 7.39 (d, 1H, J = 2.4 Hz), 7.44 (dd, 1H, J = 9, 2.4 Hz), 7.76 (d, 2H, J = 8.4 Hz), 8.06 (d, 1H, J = 9 Hz), 9.21 (s, 1H) |
| 24 | 440 | ¹HNMR (600 MHz, CDCl₃, 25° C.): 1.14 (m, 2H), 1.23 (t, 3H, J = 7.8 Hz), 2.07 (m, 2H), 2.42 (m, 6H), 2.71 (q, 2H, J = 15.6 Hz), 3.31 (m, 4H), 3.96 (s, 3H), 7.31 (d, 2H, J = 8.4 Hz), 7.44 (d, 2H, J = 2.4 Hz), 7.45 (dd, 1H, J = 9, 2.4 Hz), 7.75 (d, 2H, J = 8.4 Hz), 8.08 (d, 1H, J = 9 Hz), 9.28 (s, 1H) |
| 25 | 397 | ¹HNMR (600 MHz, CDCl₃, 25° C.): 1.20 (t, 3H, J = 7.8, 7.2 Hz), 2.0 (m, 4H), 2.68 (q, 2H, J = 15 Hz), 3.0 (m, 4H), 3.87 (s, 3H), 6.99 (s, 1H), 7.29 (d, 2H, J = 8.4 Hz), 7.43 (dd, 1H, J = 9, 2.4 Hz), 7.78 (d, 2H, J = 8.4 Hz), 8.12 (d, 1H, J = 9 Hz), 9.42 (s, 1H) |
| 26 | 488 | ¹HNMR (600 MHz, CDCl₃, 25° C.): 1.22 (t, 3H, J = 7.2, 7.8 Hz), 2.69 (q, 2H, J = 15, 7.2 Hz), 3.14 (m, 4H), 3.35 (m, 4H), 6.88 (m, 3H), 7.29 (m, 4H), 7.38 (m, 1H), 7.46 (dd, 1H, J = 15, 2.4 Hz), 7.75 (d, 2H, .8 Hz), 8.10 (d, 1H, J = 15 Hz), 9.36 (s, 1H) |
| 27 | 494 | ¹HNMR (600 MHz, D6-DMSO, 25° C.): 1.16 (t, 3H, J = 7.8, 7.2 Hz), 1.39 (m, 8H), 2.41 (m, 4H), 2.67 (q, 2H, J = 15 Hz), 2.92 (m, 2H), 3.27 (m, 6H), 3.94 (s, 3H), 7.38 (d, 1H, J = 1.8 Hz), 7.44 (d, 2H, J = 8.4 Hz), 7.61 (dd, 2H, J = 15, 2.4 Hz), 7.74 (d, 2H, J = 7.8 Hz), 8.16 (d, 1H, J = 9.6 Hz)), 923 (s, 1H) |
| 28 | 503 | ¹HNMR (600 MHz, D₆-DMSO, 25° C.): 1.08 (t, 3H, J = 7.2, 7.8 Hz), 1.41 (m, 2H), 1.56 (m, 2H), 2.56 (m, 2H), 2.64 (q, 2H, J = 15 Hz), 3.82 (m, 2H), 3.94 (s, 1H), 5.19 (s, 1H), 7.24 (m, 1H), 7.38 (m, 2H), 7.46 (m, 4H), 7.63 (m, 2H), 7.85 (d, 2H, J = 7.8 Hz), 8.14 (d, 1H, J = 9.6 Hz), 9.30 (s, 1H) |

TABLE 2-continued

| No | MS (m/z) | ¹H NMR |
|---|---|---|
| 29 | 440 | ¹HNMR (600 MHz, CDCl$_3$, 25° C.):<br>1.22 (t, 3H, J = 7.2, 7.8 Hz), 2.02 (m, 2H), 3.14 (s, 3H), 2.70 (q, 2H, J = 15.6 Hz), 2.79 (m, 2H), 2.91 (m2H), 3.31 (m, 4H), 3.93 (s, 3H), 7.35 (d, 2H, J = 8.4 Hz), 7.43 (dd, 1H, J = 9, 3 Hz), 7.53 (s, 1H), 7.81 (d, 2H, J = 8.4 Hz), 8.02 (d, 1H, J = 9.6 Hz), 9.01 (s, 1H) |
| 30 | 454 | ¹HNMR (600 MHz, CDCl$_3$, 25° C.):<br>1.09 (m, 6H), 1.25 (t, 3H, J = 7.8, 7.2 Hz), 1.83 (m, 3H), 2.43 (m, 3H), 2.72 (q, 2H, J = 15 Hz), 3.23 (m, 3H), 4.00 (s, 3H), 7.32 (d, 2H, J = 7.8 Hz), 7.47 (m, 2H), 7.74 (d, 2H, J = 8.4 Hz), 8.08 (d, 1H, J = 9.6 Hz), 9.28 (m, 1H) |
| 31 | 425 | ¹HNMR (600 MHz, CDCl$_3$, 25° C.):<br>1.21 (t, 3H, J = 7.8 Hz), 1.68 (m, 8H), 2.71 (q, 2H, J = 9.6 Hz), 3.26 (m, 4H), 3.93 (s, 3H), 7.32 (d, 2H, J = 8.4 Hz), 7.40 (d, 1H, J = 2.4 Hz), 7.43 (dd, 1H, J = 9, 3 Hz), 7.80 (d, 2H, J = 8.4 Hz), 8.05 (d, 1H, J = 9 Hz), 9.19 (s, 1H) |
| 32 | 410 | ¹HNMR (600 MHz, CDCl$_3$, 25° C.):<br>1.21 (t, 3H, J = 7.8 Hz), 2.34 (m, 8H), 2.53 (s, 3H), 2.69 (q, 2H, J = 15 Hz), 3.26 (s, 3H), 7.31 (d, 2H, J = 7.8 Hz), 7.63 (dd, 1H, J = 9, 1.8 Hz), 7.76 (d, 2H, J = 8.4 Hz), 8.0 (s, 1H), 8.09 (d, 1H, J = 8.4 Hz), 9.43 (s, 1H) |
| 33 | 424 | ¹HNMR (600 MHz, CDCl$_3$, 25° C.):<br>1.22 (t, 3H, J = 7.8 Hz), 2.19 (m, 2H), 2.55 (s, 6H), 2.69 (m, 2H), 2.84 (m, 2H), 3.03 (m, 2H), 3.30 (m.2H), 3.54 (m, 2H), 7.36 (d, 2H, J = 8.4 Hz), 7.61 (dd, 1H, J = 9, 1.2 Hz), 7.80 (d, 2H, J = 7.8 Hz), 7.87 (s, 1H), 8.03 (dd, 1H, J = 9 Hz), 9.00 (m, 1H) |
| 34 | 411 | ¹HNMR (600 MHz, CDCl$_3$, 25° C.):<br>1.21 (t, 3H, J = 7.8 Hz), 1.52 (m, 2H), 1.78 (m, 2H), 2.55 (s, 3H), 2.69 (q, 2H, J = 9 Hz), 3.21 (m, 2H), 3.31 (m, 2H), 3.91 (m, 1H), 7.31 (d, 2H, J = 8.4 Hz), 7.63 (dd, 1H, J = 8.4, 1.2 Hz), 7.75 (d, 2H, J = 8.4 Hz), 7.90 (m, 1H), 8.08 (d, 1H, J = 9.6 Hz), 9.33 (s, 1H) |
| 35 | 478 | ¹HNMR (600 MHz, D$_6$-DMSO, 25° C.):<br>1.16 (t, 3H, J = 7.2 Hz), 1.40 (m, 4H), 1.52 (m, 4H), 2.39 (m, 4H), 2.55 (s, 3H), 2.67 (q, 2H, J = 14.4 Hz), 2.88 (m, 2H), 3.30 (m, 4H), 7.42 (d, 2H, J = 7.8 Hz), 7.74 (d, 2H.J = 7.8 Hz), 7.78 (d, 1H, J = 9 Hz), 8.04 (m, 1H), 8.08 (d, 1H, J = 3 Hz), 9.33 (s, 1H) |
| 36 | 395 | ¹HNMR (600 MHz, CDCl$_3$, 25° C.):<br>1.21 (t, 3H, J = 7.2 Hz), 1.50 (m, 4H), 1.61 (m, 2H), 2.69 (q, 2H, J = 15 Hz), 3.19 (m, 2H), 7.30 (d, 2H, J = 7.8 Hz), 7.61 (dd, 1H, J = 8.4, 1.2 Hz), 7.76 (d, 2H, J = 8.4 Hz), 7.94 (m, 1H), 8.05 (d, 1H, J = 8.4 Hz), 9.32 (s, 1H) |
| 37 | 414 | ¹HNMR (600 MHz, CDCl$_3$, 25° C.):<br>1.24 (t, 3H, J = 7.8 Hz), 2.35 (s, 3H), 2.39 (m, 4H), 2.70 (q, 2H, J = 15 Hz), 3.25 (m, 4H), 7.30 (d, 2H, J = 7.8 Hz), 7.57 (m, 1H), 7.78 (d, 2H, J = 8.4 Hz), 7.87 (dd, 1H, J = 9.6, 2.4 Hz), 8.18 (q, 1H, J = 9 Hz), 9.40 (s, 1H) |
| 38 | 428 | ¹HNMR (600 MHz, CDCl$_3$, 25° C.):<br>1.23 (t, 3H, J = 7.2 Hz), 1.97 (m, 2H), 2.48 (s, 3H), 2.70 (m, 4H), 2.82 (m, 2H), 3.30 (m, 2H), 3.37 (m.2H), 7.35 (d, 2H, J = 7.8 Hz), 7.54 (m, 1H), 7.81 (d, 2H, J = 8.4 Hz), 7.93 (d, 1H, J = 9 Hz), 8.14 (q, 1H, J = 9 Hz), 9.20 (m, 1H) |
| 39 | 415 | ¹HNMR (600 MHz, CDCl$_3$, 25° C.):<br>1.22 (t, 3H, J = 7.8 Hz)1.56 (m, 2H), 1.81 (m, 2H), 2.69 (q, 2H, J = 15 Hz), 3.19 (m, 2H), 3.32 (m, 2H), 3.92 (m, 1H), 7.36 (d, 2H, J = 8.4 Hz), 7.56 (m, 1H), 7.76 (m, 3H), 8.11 (m, 1H), 9.30 (s, 1H) |
| 40 | 482 | ¹HNMR (600 MHz, D$_6$-DMSO, 25° C.):<br>1.16 (t, 3H, J = 7.2, 7.8 Hz), 1.40 (m, 8H), 2.39 (m, 5H), 2.68 (q, 2H, J = 15 Hz), 2.90 (m, 2H), 3.32 (m, 4H), 7.44 (d, 2H, J = 7.8 Hz), 7.78 (d, 2H.J = 7.2 Hz), 7.78 (m, 1H), 8.02 (d, 1H, J = 8.4 Hz), 8.26 (m, 1H), 9.36 (s, 1H) |
| 41 | 399 | ¹HNMR (600 MHz, CDCl$_3$, 25° C.):<br>1.23 (t, 3H, J = 7.8 Hz), 1.58 (m, 4H), 1.65 (m, 2H), 2.70 (q, 2H, J = 15.6 Hz), 3.25 (m, 2H), 7.33 (d, 2H, J = 8.4 Hz), 7.51 (m, 1H), 7.78 (m, 3H), 8.19 (m, 1H), 9.25 (s, 1H) |
| 42 | 538 | ¹HNMR (600 MHz, D$_6$-DMSO, 25° C.): 1.16 (t, 3H, J = 7.8 Hz), 1.66 (m, 2H), 2.67 (q, 2H, J = 9 Hz), 2.76 (m, 2H), 2.90 (m, 2H), 3.03 (m, 2H), 3.24 (m, 2H), 3.34 (s, 2H), 7.47 (d, 2H, J = 8.4 Hz), 7.84 (d, 2H, J = 8.4 Hz), 7.92 (dd, 1H, J = 9, 2.4 Hz), 8.277 (d, 1H, J = 9.6 Hz), 8.53 (s, 1H), 9.39 (s, 1H) |
| 43 | 550 | ¹HNMR (600 MHz, D$_6$-DMSO, 25° C.): 1.41 (m, 4H), 1.53 (m, 6H), 2.45 (m, 4H), 3.07 (m, 2H), 3.20 (m, 2H), 3.32 (m, 1H), 3.84 (s, 3H), 7.12 (d, 2H, J = 9 Hz), 7.84 (d, 2H, J = 9 Hz), 7.93 (d, 1H, J = 9 Hz), 8.15 (s, 1H), 8.28 (d, 1H, J = 7.8 Hz), 9.35 (s, 1H) |
| 44 | 483 | ¹HNMR (600 MHz, CDCl$_3$, 25° C.): 1.43 (m, 2H), 1.61 (m, 4H), 1.68 (m, 2H), 3.06 (m, 2H), 3.20 (m, 2H), 3.72 (m, 1H), 3.85 (s, 3H), 4.77 (d, 1H, J = 4.2 Hz), 7.13 (d, 2H, J = 9 Hz), 7.85 (d, 2H, J = 9 Hz), 7.92 (dd, 1H, J = 9.6, 2.4 Hz)8.10 (s, 1H), 8.26 (d, 1H, J = 9.6 Hz), 9.31 (s, 1H) |
| 45 | 566 | ¹HNMR (600 MHz, CDCl$_3$, 25° C.): 1.24 (t, 3H, J = 7.8 Hz), 2.72 (q, 2H, J = 15 Hz)), 3.35 (m, 4H), 3.37 (m, 4H), 6.90 (d, 2H, J = 9 Hz), 7.35 (d, 2H, J = 7.8 Hz), 7.55 (d, 2H, J = 9 Hz), 7.70 (dd, 1H, J = 9, 1.8 Hz), 7.78 (d, 2H, J = 8.4 Hz), 7.99 (s, 1 Hz), 8.34 (d, 1H, J = 9.6 Hz), 9.28 (s, 1H) |

TABLE 2-continued

| No | MS (m/z) | ¹H NMR |
|---|---|---|
| 46 | 534 | ¹HNMR (600 MHz, D$_6$-DMSO, 25° C.): 1.66 (t, 3H, J = 7.8 Hz), 1.46 (m, 2H), 1.75 (m, 6H), 2.51 (m, 2H), 2.68 (q, 2H, J = 15 Hz), 2.97 (m, 4H), 3.33 (m, 5H), 7.47 (d, 2H, J = 7.8 Hz), 7.84 (d, 2H, J = 6.6 Hz), 7.86 (d, 1H, J = 9 Hz), 8.16 (s, 1H), 8.32 (d, 1H, J = 9 Hz), 9.41 (s, 1H) |
| 47 | 537 | ¹HNMR (600 MHz, CDCl$_3$, 25° C.): 1.22 (t, 3H, J = 7.8 Hz), 1.29 (t, 3H, J = 7.2 Hz), 1.70 (m, 2H), 1.87 (m, 2H), 2.50 (m, 1H), 2.70 (q, 2H, J = 15.6 Hz)), 3.21 (m, 2H), 3.34 (m, 2H), 4.17 (q, 2H, J = 9.6 Hz), 7.64 (dd, 1H, J = 9, 1.8 Hz), 7.77 (d, 2H, J = 8.4 Hz), 7.95 (s, 1 Hz), 8.21 (d, 1H, J = 9 Hz), 9.33 (s, 1H) |
| 48 | 495 | ¹HNMR (600 MHz, CDCl$_3$, 25° C.): 1.22 (t, 3H, J = 7.2 Hz), 1.28 (m, 2H), 1.71 (m, 3H), 2.70 (q, 2H, J = 15 Hz), 3.19 (m, 2H), 3.97 (m, 2H), 3.57 (d, 2H, J = 6 Hz), 7.33 (d, 2H, J = 8.4 Hz), 7.62 (dd, 1H, J = 9, 2.4 Hz), 7.77 (d, 2H, J = 8.4 Hz), 7.96 (s, 1H), 8.18 (d, 1H, J = 9.6 Hz), 9.29 (s, 1H) |
| 49 | 501 | ¹HNMR (600 MHz, CDCl$_3$, 25° C.): 1.21 (t, 3H, J = 7.8 Hz), 2.58 (s, 3H), 2.68 (q, 2H, J = 15 Hz), 4.53 (s, 2H), 7.19 (m, 2H), 7.30 (m, 3H), 7.33 (d, 2H, J = 7.8 Hz), 7.46 (s, 1H), 7.58 (dd, 1H, J = 9, 1.8 Hz), 7.82 (d, 2H, J = 8.4 Hz), 8.16 (d, 1H, J = 9 Hz), 9.36 (s, 1H) |
| 50 | 495 | ¹HNMR (600 MHz, D$_6$-DMSO, 25° C.): 1.14 (t, 3H, J = 7.8 Hz), 2.13 (s, 3H), 2.32 (m, 2H), 2.64 (m, 4H), 2.81 (m, 4H), 3.33 (s, 1H), 7.45 (d, 2H, J = 7.8 Hz), 7.79 (m, 2H), 7.92 (m, 1H), 7.96 (m, 2H), 8.97 (s, 1H) |
| 51 | 449 | ¹HNMR (600 MHz, D$_6$-DMSO, 25° C.): 1.20 (t, 3H, J = 7.8 Hz), 2.65 (q, 2H, J = 15.6 Hz), 6.96 (m, 1H), 7.23 (d, 2H, J = 8.4 Hz), 7.41 (d, 2H, J = 8.4 Hz), 7.75 (dd, 1H, J = 9, 1.8 Hz), 8.0 (s, 1H), 8.32 (d, 1H, J = 9 Hz), 8.65 (s, 1H), 9.78 (s, 1H) |
| 52 | 523 | ¹HNMR (600 MHz, D$_6$-DMSO, 25° C.): 1.22 (t, 3H, J = 7.2 Hz), 1.67 (t, 3H, J = 5.4 Hz), 2.69 (q, 2H, J = 16.8 Hz), 3.33 (m, 4H), 4.01 (m, 4H), 7.34 (d, 2H, J = 7.8 Hz), 7.66 (dd, 1H, J = 9, 1.8 Hz), 7.77 (d, 2H, 7.8 Hz), 8.01 (m, 1H), 8.27 (d, 1H, J = 9 Hz), 9.43 (s, 1H) |
| 53 | 509 | ¹HNMR (600 MHz, D$_6$-DMSO, 25° C.): 1.16 (t, 3H, J = 7.2 Hz), 1.37 (m, 2H), 1.66 (m, 2H), 2.67 (q, 2H, J = 15 Hz), 3.0 (m, 2H), 3.24 (m, 2H), 7.43 (d, 2H, J = 8.4 Hz), 7.78 (d, 2H, J = 8.4 Hz), 7.95 (dd, 1H, J = 9, 1.2 Hz), 8.13 (m, 1H), 8.30 (d, 1H, J = 9 Hz), 9.38 (s, 1H), 12.22 (s, 1H) |
| 54 | 545 | ¹HNMR (600 MHz, D$_6$-DMSO, 25° C.): 1.15 (m, 2H), 1.23 (m, 3H), 1.41 (m, 8H), 2.39 (m, 2H), 2.99 (m, 2H), 3.19 (m, 2H), 8.0 (d, 1H, J = 9 Hz), 8.11 (m, 4H), 8.20 (s, 1H), 8.35 (d, 1H, J = 9 Hz), 9.45 (s, 1H) |
| 55 | 503 | ¹HNMR (600 MHz, D$_6$-DMSO, 25° C.): 1.17 (t, 3H, J = 7.2 Hz), 1.39 (m, 6H), 1.88 (m, 4H), 2.41 (m, 4H), 2.68 (q, 2H, J = 15 Hz), 2.93 (m, 3H), 3.34 (m, 3H), 4.34 (s, 1H), 7.45 (m, 2H), 7.78 (m, 2H), 7.91 (m, 1H), 8.21 (m, 2H), 9.36 (s, 1H) |
| 56 | 580 | ¹HNMR (600 MHz, D$_6$-DMSO, 25° C.): 1.41 (m, 4H), 1.53 (m, 6H), 2.43 (m, 4H), 3.07 (m, 2H), 3.20 (m, 5H), 3.79 (s, 3H), 3.84 (s, 3H), 7.17 (m, 1H), 7.32 (m, 1H), 7.47 (m, 1H), 7.95 (d, 1H, J = 7.2 Hz), 8.15 (s, 1H), 8.29 (d, 1H, J = 3 Hz), 9.34 (s, 1H) |
| 57 | 526 | ¹HNMR (600 MHz, CDCl$_3$, 25° C.): 1.95 (m, 2H), 2.46 (s, 3H), 2.72 (m, 4H), 3.38 (m, 4H), 3.91 (s, 3H), 3.93 (s, 3H), 6.95 (d, 1H, J = 9 Hz), 7.38 (d, 2H, J = 1.2 Hz), 7.51 (d, 1H, J = 8.4 Hz), 7.61 (d, 1H, J = 7.8 Hz), 8.15 (d, 1H, J = 9 Hz), 8.36 (s, 1H), 9.24 (s, 1H) |
| 58 | 513 | ¹HNMR (600 MHz, D$_6$-DMSO, 25° C.): 1.43 (m, 2H), 1.69 (m, 2H), 1.68 (m, 2H), 3.16 (m, 2H), 3.21 (m, 2H), 3.73 (m, 1H), 3.82 (s, 3H), 3.84 (s, 3H), 4.79 (d, 1H, J = 3 Hz), 7.15 (d, 1H, J = 9 Hz), 7.38 (d, 1H, J = 1.2 Hz), 7.46 (dd, 1H, J = 8.4, .2 Hz), 7.92 (dd, 1H, J = 9, 1.2 Hz), 8.10 (s, 1H), 8.26 (d, 1H, J = 9.6 Hz), 9.30 (s, 1H) |
| 59 | 565 | ¹HNMR (600 MHz, D$_6$-DMSO, 25° C.): 1.18 (m, 4H), 1.47 (m, 2H), 1.72 (m, 6H), 2.74 (m, 3H), 2.97 (m, 2H), 3.45 (m, 2H), 8.01 (d, 1H, J = 9.6 Hz), 8.20 (m, 3H), 8.37 (d, 1H, J = 9.6 Hz), 8.41 (d, 2H, J = 9 Hz), 9.49 (s, 1H) |
| 60 | 511 | ¹HNMR (600 MHz, CDCl$_3$, 25° C.): 1.85 (m, 2H), 2.43 (s, 3H), 2.62 (m, 2H), 2.68 (m, 2H), 3.19 (m, 2H), 3.27 (m, 2H), 7.67 (dd, 1H, J = 9.6, 2.4 Hz), 8.09 (d, 2H, J = 3.6 Hz), 8.23 (d, 1H, J = 9 Hz), 8.37 (m, 3H), 9.45 (s, 1H) |
| 61 | 498 | ¹HNMR (600 MHz, D$_6$-DMSO, 25° C.): 1.18 (m, 2H), 1.52 (m, 2H), 3.04 (m, 2H), 3.15 (m, 2H), 3.61 (m, 1H), 4.71 (d, 1H, J = 4.2 Hz), 7.99 (dd, 1H, J = 9.6, 1.8 Hz), 8.14 (s, 1H), 8.17 (d, 2H, J = 9 Hz), 8.34 (d, 1H, J = 9 Hz), 8.39 (d, 2H, J = 3 Hz), 9.44 (s, 1H) |
| 62 | 469 | 1HNMR (600 MHz, D$_6$-DMSO, 25° C.): 1.17 (t, 3H, J = 7.2 Hz), 1.36 (t, 3H, J = 6.6 Hz), 1.45 (m, 2H), 1.69 (m, 2H), 2.69 (q, 2H, J = 15 Hz), 3.09 (m, 2H), 3.71 (m, 1H), 4.73 (q, 2H, J = 14.4 Hz), 4.80 (d, 1H, J = 3.6 Hz), 7.46 (d, 2H, J = 8.4 Hz), 7.83 (d, 2H, J = 7.8 Hz), 8.18 (d, 1H, J = 8.4 Hz), 8.31 (d, 1H, J = 8.4 Hz), 8.90 (s, 1H), 9.34 (s, 1H) |

TABLE 2-continued

| No | MS (m/z) | ¹H NMR |
|---|---|---|
| 63 | 482 | ¹HNMR (600 MHz, CDCl$_3$, 25° C.): 1.22 (t, 3H, J = 7.8 Hz), 1.43 (t, 3H, J = 7.2 Hz), 1.99 (m, 2H), 2.47 (s, 3H), 2.70 (m, 4H), 2.85 (m, 2H), 3.32 (m, 2H), 3.51 (m, 2H), 4.43 (q, 2H, J = 14.4 Hz), 7.56 (d, 2H, J = 8.4 Hz), 7.82 (d, 2H, J = 7.8 Hz), 8.16 (d, 1H, J = 8.4 Hz), 8.35 (dd, 1H, J = 8.4, 1.2 Hz), 9.00 (s, 1H), 9.36 (s, 1H) |
| 64 | 536 | ¹HNMR (600 MHz, D$_6$-DMSO, 25° C.): 1.17 (t, 3H, J = 7.8 Hz), 1.37 (t, 3H, J = 7.2 Hz), 1.46 (m, 8H), 1.87 (m, 2H), 2.46 (m, 2H), 2.69 (q, 2H, J = 15 Hz), 3.18 (m, 4H), 3.35 (m, 3H), 4.38 (q, 2H, J = 13.8 Hz), 7.47 (d, 2H, J = 7.2 Hz), 7.83 (m, 2H), 8.21 (m, 1H), 8.33 (m, 1H), 9.36 (m, 1H), 9.77 (m, 1H) |
| 65 | 441 | ¹HNMR (600 MHz, D$_6$-DMSO, 25° C.):<br>1.17 (t, 3H, J = 7.2 Hz), 1.37 (t, 3H, J = 6.6 Hz), 1.62 (m, 2H), 2.66 (q, 2H, J = 31 Hz), 3.09 (m, 2H), 3.24 (m, 3H), 3.66 (m, 1H), 4.80 (d, 1H, J = 3.6 Hz), 7.45 (d, 2H, J = 8.4 Hz), 7.80 (d, 2H, J = 8.4 Hz), 8.14 (d, 1H, J = 8.4 Hz), 8.34 (dd, 1H, J = 9, 1.2 Hz), 8.85 (d, 1H, J = 1.2 Hz), 9.34 (s, 1H) |
| 66 | 454 | ¹HNMR (600 MHz, D$_6$-DMSO, 25° C.):<br>1.17 (t, 3H, J = 7.8 Hz), 2.07 (m, 2H), 2.64 (s, 3H), 2.70 (q, 2H, J = 15 Hz), 3.13 (m, 8H), 7.15 (d, 2H, J = 8.4 Hz), 7.87 (d, 2H, J = 8.4 Hz), 8.18 (d, 1H, J = 8.4 Hz), 8.38 (dd, 1H, J = 9, 1.2 Hz), 8.75 (s, 1H), 9.36 (s, 1H) |
| 67 | 508 | ¹HNMR (600 MHz, D$_6$-DMSO, 25° C.):<br>1.15 (t, 3H, J = 7.2 Hz), 1.26 (m, 2H), 1.50 (m, 2H), 1.75 (m, 6H), 2.66 (q, 2H, J = 15 Hz), 2.83 (m, 4H), 3.02 (m, 3H), 3.82 (m, 2H), 7.45 (d, 2H, J = 7.2 Hz), 7.79 (d, 2H, J = 8.4 Hz), 8.16 (d, 1H, J = 9 Hz), 8.36 (d, 1H, J = 9 Hz), 8.77 (m, 1H), 9.40 (m, 1H) |
| 68 | 485 | 1HNMR (400 MHz, CDCl3, 25° C.):<br>0.95 (t, 6H, J = 6.8 Hz), 3.53 (q, 4H, J = 13.6 Hz), 3.91 (s, 3H), 3.94 (s, 3H), 6.95 (d, 1H, J = 9.2 Hz), 7.38 (d, 1H, J = 2.4 Hz), 7.53 (dd, 1H, J = 8.4, 2 Hz), 7.63 (dd, 1H, J = 8.8, 2 Hz), 7.88 (d, 1H, J = 0.8 Hz), 8.29 (d, 1H, J = 8.4 Hz), 9.26 (s, 1H) |
| 69 | 487 | ¹HNMR (400 MHz, D$_6$-DMSO, 25° C.):<br>1.74 (m, 2H), 3.50 (q, 2H, J = 10.8 Hz), 3.82 (m, 8H), 4.79 (t, 1H, J = 4.4 Hz), 7.15 (d, 1H, J = 8.4 Hz), 7.57 (t, 1H, J = 5.2 Hz), 7.62 (dd, 1H, J = 8.4, 2.4 Hz), 7.77 (dd, 1H, J = 9.2, 1.6 Hz), , 7.96 (d, 1H, J = 5.2 Hz), 8.19 (d, 1H, J = 2 Hz), 8.95 (s, 1H) |
| 70 | 513 | ¹HNMR (400 MHz, CDCl$_3$, 25° C.):<br>1.55 (m, 1H), 1.85 (m, 2H), 2.05 (m, 1H), 3.20 (m, 1H), 3.33 (m, 2H), 3.62 (m, 1H), 3.91 (s, 3H), 3.96 (s, 3H), 4.01 (m, 1H), 6.98 (d, 1H, J = 8.4 Hz), 7.42 (d, 1H, J = 2 Hz), 7.53 (dd, 1H, J = 8.8, 2.4 Hz), 7.64 (dd, 1H, J = 9.2, 2 Hz), 8.06 (s, 1H), 8.19 (d, 1H, J = 10 Hz), 8.96 (s, 1H) |
| 71 | 513 | ¹HNMR (400 MHz, CDCl$_3$, 25° C.):<br>0.73 (t, 6H, J = 8.8 Hz), 1.37 (m, 4H), 3.37 (m, 4H), 3.91 (s, 3H), 3.93 (s, 3H), 6.94 (d, 1H, J = 8.4 Hz), 7.38 (d, 1H, J = 2 Hz), 7.52 (dd, 1H, J = 8.4, 2 Hz), 7.59 (dd, 1H, J = 10, 3.2 Hz), 7.93 (d, 1H, J = 1.2 Hz), 8.13 (d, 1H, J = 8.8 Hz), 9.20 (s, 1H) |
| 72 | 517 | ¹HNMR (400 MHz, D$_6$-DMSO, 25° C.):<br>3.33 (m, 10H), 3.82 (d, 6H), 7.13 (d, 2H, J = 9 Hz), 7.11 (d, 1H, J = 8.4 Hz), 7.53 (d, 1H, J = 2 Hz), 7.62 (dd, 1H, J = 10.4, 2.4 Hz), 7.75 (dd, 1H, J = 8.4, 1.6 Hz), 7.82 (d, 1H, J = 8.8 Hz), 7.91 (d, 1H, J = 1.2 Hz), 8.79 (s, 1H) |
| 73 | 473 | ¹HNMR (400 MHz, D$_6$-DMSO, 25° C.):<br>3.60 (q, 2H, J = 10 Hz), 3.82 (m, 8H), 5.33 (t, 1H, J = 4.8 Hz), 7.14 (d, 1H, J = 8.4 Hz), 7.52 (d, 1H, J = 6 Hz), 7.65 (dd, 1H, J = 8.4, 2.4 Hz), 7.77 (dd, 1H, J = 9.2, 1.6 Hz), 7.82 (t, 1H, J = 4.8 Hz), 7.95 (d, 1H, J = 8.8 Hz), 8.23 (d, 1H, J = 2.4 Hz), 8.95 (s, 1H) |
| 74 | 541 | ¹HNMR (400 MHz, CDCl$_3$, 25° C.):<br>0.77 (t, 6H, J = 11.2 Hz), 1.12 (m, 4H), 1.32 (m, 4H), 3.44 (m, 4H), 3.92 (s, 3H), 3.93 (s, 3H), 6.95 (d, 1H, J = 8.4 Hz), 7.37 (d, 1H, J = 2.4 Hz), 7.51 (dd, 1H, J = 8.8, 2.4 Hz), 7.61 (dd, 1H, J = 8.8, 2 Hz), 7.91 (d, 1H, J = 1.2 Hz), 8.25 (s, 1H), 9.24 (s, 1H) |
| 75 | 442 | ¹HNMR (400 MHz, CDCl$_3$, 25° C.):<br>1.25 (t, 3H, J = 11.4 Hz), 1.78 (m, 2H), 2.04 (m, 2H), 2.41 (m, 4H), 2.72 (q, 2H, J = 15.2 Hz), 3.47 (m, 2H), 3.63 (m, 2H), 4.08 (m, 1H), 7.39 (d, 2H, J = 5.6 Hz), 7.80 (d, 2H, J = 12.6 Hz), 8.37 (d, 1H, J = 8.8 Hz), 8.53 (dd, 1H, J = 9.2, 2.4 Hz), 9.15 (d, 1H, J = 2.4 Hz), 9.21 (s, 1H) |
| 76 | 455 | ¹HNMR (400 MHz, CDCl$_3$, 25° C.):<br>1.22 (t, 3H, J = 7.6 Hz), 1.94 (m, 2H), 2.54 (s, 3H), 2.70 (m, 4H), 2.85 (m, 2H), 3.40 (m, 2H), 3.48 (m, 2H), 7.37 (d, 2H, J = 8 Hz), 7.82 (d, 2H, J = 8.4 Hz), 8.22 (d, 1H, J = 9.2 Hz), 8.49 (dd, 1H, J = 8.4, 2.4 Hz), 9.37 (s, 1H), 9.65 (s, 1H) |
| 77 | 509 | ¹HNMR (400 MHz, D$_6$-DMSO, 25° C.):<br>1.17 (t, 3H, J = 7.6 Hz), 1.44 (m, 4H), 1.57 (m, 6H), 2.41 (m, 4H), 2.68 (q, 2H, J = 15.2 Hz), 3.28 (m, 5H), 7.47 (d, 2H, J = 8.4 Hz), 7.84 (d, 2H, J = 8 Hz), 8.30 (d, 1H, J = 9.2 Hz), 8.58 (dd, 1H, J = 9.2, 2.4 Hz), 9.10 (d, 1H, J = 1.2 Hz), 9.42 (s, 1H) |
| 78 | 414 | ¹HNMR (400 MHz, CDCl$_3$, 25° C.):, 0.93 (t, 6H, J = 6.4 Hz), 1.22 (t, 3H, J = 7.6 Hz), 2.70 (q, 2H, J = 15.2 Hz), 3.59 (q, 2H, J = 14.4 Hz), 7.35 (d, 2H, J = 8.4 Hz), 7.82 (d, 2H, J = 8 Hz), 8.27 (d, 1H, J = 9.2 Hz), 8.49 (dd, 1H, J = 9.2, 2.4 Hz), 8.99 (d, 1H, J = 2.4 Hz), 9.40 (s, 1H) |

TABLE 2-continued

| No | MS (m/z) | ¹H NMR |
|---|---|---|
| 79 | 395 | 1HNMR (600 MHz, CDCl₃, 25° C.):<br>1.20 (t, 3H, J = 7.8 Hz), 2.65 (q, 2H, J = 15 Hz), 3.71 (s, 3H), 6.28 (d, 1H, J = 2.4 Hz), 7.23 (d, 2H, J = 15 Hz), 7.42 (d, 2H, J = 8.4 Hz), 7.54 (dd, 1H, J = 9, 2.4 Hz), 8.07 (s, 1H), 8.18 (d, 1H, J = 9 Hz), 8.59 (s, 1H), 9.59 (s, 1H) |
| 80 | 437 | ¹HNMR (600 MHz, CDCl₃, 25° C.): 1.20 (t, 3H, J = 7.2 Hz), 1.33 (t, 3H, J = 7.2 Hz), 2.65 (q, 2H, J = 9.6 Hz), 4.34 (q, 2H, HJ = 20.4 Hz), 7.24 (d, 2H, J = 8.4 Hz), 7.43 (d, 2H, J = 8.4 Hz), 7.90 (d, 1H, J = 1.8 Hz), 8.10 (s, 1H), 8.31 (d, 1H, J = 9 Hz), 8.37 (dd, 1H, J = 9, 1.8 Hz), 8.65 (s, 1H), 9.83 (s, 1H) |
| 81 | 453 | ¹HNMR (600 MHz, CDCl₃, 25° C.):<br>0.79 (t, 6H, J = 7.2 Hz), 1.21 (t, 3H, J = 7.8 Hz), 2.69 (q, 2H, J = 14.4 Hz), 3.42 (q, 4H, J = 14.4 Hz), 7.33 (d, 2H, J = 8.4 Hz), 7.60 (dd, 1H, J = 9.6, 2.4 Hz), 7.82 (d, 2H, J = 8.4 Hz), 7.86 (d, 1H, J = 0.6 Hz)), 8.18 (d, 1H, J = 9 Hz), 9.41 (s, 1H) |
| 82 | 481 | ¹HNMR (600 MHz, CDCl₃, 25° C.):<br>1.26 (t, 3H, J = 7.8 Hz), 1.50 (m, 1H), 1.81 (m, 2H), 1.96 (m, 1H), 2.74 (q, 2H, J = 15.6 Hz), 3.12 (m, 1H), 3.27 (m, 1H), 3.36 (m, 1H), 3.58 (dd, J = 11.4, 1.8 Hz), 3.95 (m, 1H), 7.38 (d, 2H, J = 8.4 Hz), 7.66 (dd, 1H, J = 9.6, 2.4 Hz), 7.82 (d, 2H, 8.4 Hz), 8.09 (m, 1H), 8.27 (d, 1H, J = 9 Hz), 9.13 (s, 1H) |
| 83 | 442 | ¹HNMR (600 MHz, D₆-DMSO, 25° C.):<br>1.17 (t, 3H, J = 7.8 Hz), 2.18 (s, 3H), 2.69 (m, 2H), 3.10 (m, 4H), 3.31 (s, 1H), 3.92 (s, 3H), 7.45 (d, 2H, J = 8.4 Hz), 7.77 (m, 2H), 7.91 (m, 1H), 7.95 (m, 1H), 8.09 (d, 1H, J = 9 Hz), 9.21 (s, 1H) |
| 84 | 483 | ¹HNMR (600 MHz, D₆-DMSO, 25° C.):<br>1.14 (t, 3H, J = 7.8 Hz), 1.38 (t, 3H, J = 7.2 Hz), 2.17 (m, 5H), 2.65 (m, 4H), 2.86 (m, 4H), 4.36 (q, 2H, J = 13.2 Hz), 7.36 (m, 1H), 7.46 (m, 2H), 7.82 (m, 1H), 7.89 (m, 1H), 7.93 (m, 1H), 8.21 (d, 1H, J = 9 Hz), 8.99 (s, 1H) |
| 85 | 497 | ¹HNMR (600 MHz, D₆-DMSO, 25° C.): 2.18 (s, 3H), 2.34 (m, 2H), 2.86 (m, 4H), 3.30 (m, 2H), 3.91 (s, 1H), 7.13 (d, 2H, J = 7.8 Hz), 7.78 (dd, 1H, J = 9, 2.4 Hz), 7.85 (d, 1H, J = 9 Hz), 7.96 (m, 2H), 8.26 (d, 1H, J = 9.6 Hz), 8.31 (m, 1H), 8.96 (s, 1H) |
| 86 | 451 | 1HNMR (600 MHz, CDCl₃, 25° C.): 3.83 (s, 3H), 6.87 (d, 2H, J = 9 Hz), 6.97 (d, 1H, J = 0.6 Hz), 7.43 (d, 2H, J = 8.4 Hz), 7.75 (d, 1H, J = 9, 2.4 Hz), 8.14 (s, 1H), 8.32 (d, 1H, J = 9.6 Hz), 8.66 (s, 1H) |
| 87 | 509 | ¹HNMR (600 MHz, CDCl₃, 25° C.):<br>0.74 (t, 6H, J = 7.2 Hz), 1.08 (m, 4H), 1.23 (m, 7H), 2.69 (q, 2H, J = 15.6 Hz), 3.35 (m, 4H), 7.33 (d, 2H, J = 7.8 Hz), 7.60 (dd, 1H, J = 9, 2.4 Hz), 7.81 (d, 2H, J = 7.8 Hz), 7.89 (m, 1H), 8.17 (d, 1H, J = 9 Hz), 9.36 (s, 1H) |
| 88 | 527 | ¹HNMR (400 MHz, D₆-DMSO, 25° C.):<br>2.18 (m, 5H), 234 (m, 2H), 2.89 (m, 4H), 3.31 (s, 1H), 3.82 (s, 3H), 3.84 (s, 3H), 7.15 (d, 1H, J = 9 Hz), 7.48 (m, 1H), 7.62 (m, 1H), 7.78 (dd, 1H, J = 9, 2.4 Hz), 7.95 (d, 1H, J = 9 Hz), 8.40 (s, 1H), 8.97 (s, 1H) |
| 89 | 481 | ¹HNMR (400 MHz, CDCl₃, 25° C.):<br>3.86 (s, 3H), 3.90 (s, 3H), 6.83 (d, 1H, J = 8.4 Hz), 6.94 (dd, 2H, J = 11.4, 1.8 Hz), 7.15 (dd, 1H, J = 14.4, 2.4 Hz), 7.57 (dd, 1H, J = 9, 1.8 Hz), 8.14 (s, 1H), 8.32 (d, 1H, J = 9 Hz), 8.68 (s, 1H), 9.76 (s, 1H) |
| 90 | 535 | ¹HNMR (600 MHz, D₆-DMSO, 25° C.):<br>2.01 (m, 5H), 2.61 (m, 2H), 2.78 (m, 4H), 7.42 (m, 1H), 7.84 (m, 1H), 7.96 (m, 4H), 8.12 (m, 2H), 9.00 (s, 1H) |
| 91 | 489 | ¹HNMR (600 MHz, CDCl₃, 25° C.):<br>6.95 (d, 1H, J = 1.8 Hz), 7.65 (q, 4H, J = 24 Hz), 7.79 (dd, 1H, J = 9, 2.4 Hz), 8.08 (s, 1H), 8.36 (d, 1H, J = 9 Hz), 8.66 (s, qH), 9.80 (s, 1H) |
| 92 | 539 | ¹HNMR (600 MHz, D₆-DMSO, 25° C.):<br>0.89 (t, 3H, J = 7.2 Hz), 1.38 (m, 2H), 1.67 (m, 2H), 2.18 (m, 5H), 2.85 (m, 4H), 3.31 (m, 2H), 4.03 (t, 3H, J = 6.6 Hz), 7.11 (d, 2H, J = 9 Hz), 7.78 (dd, 1H, J = 9, 2.4 Hz), 7.95 (m, 3H), 8.29 (m, 1H), 8.96 (s, 1H) |
| 93 | 493 | 1HNMR (600 MHz, CDCl3, 25° C.):<br>0.94 (t, 3H, J = 7.2 Hz)), 1.45 (m, 2H), 1.74 (m, 2H), 2.29 (q, 2H, J = 5.4 Hz), 6.84 (dd, 2H, J = 6.6, 1.8 Hz), 6.96 (d, 1H, J = 1.2 Hz), 7.40 (d, 2H, J = 9 Hz), 7.74 (dd, 1H, J = 9, 1.8 Hz), 8.14 (s, 1H), 8.32 (d, 1H, J = 3 Hz), 8.66 (s, 1H), 9.76 (s, 1H) |
| 94 | 458 | ¹HNMR (600 MHz, D₆-DMSO, 25° C.):<br>2.21 (m, 2H), 2.71 (m, 2H), 2.94 (m, 4H), 3.83 (s, 3H), 7.13 (m, 2H), 7.89 (m, 1H), 7.96 (m, 1H), 8.48 (s, 1H), 8.25 (m, 1H), 8.45 (m, 1 Hz), 9.03 (s, 1H) |
| 95 | 441 | ¹HNMR (600 MHz, D₆-DMSO, 25° C.):<br>1.16 (t, 3H, J = 7.8 Hz), 2.66 (q, 2H, J = 15 Hz), 3.58 (q, 2H, J = 9.6 Hz), 3.81 (q, 2H, J = 10.2 Hz), 5.31 (t, 1H, J = 4.8 Hz), 7.45 (d, 2H, J = 9 Hz), 7.78 (dd, 1H, J = 9, 1.8 Hz), 7.84 (m, 1H), 7.96 (d, 1H, J = 9.6 Hz), 7.98 (d, 2H, J = 1.8 Hz), 8.22 (d, 1H, J = 2.4 Hz), 8.92 (s, 1H) |
| 96 | 457 | ¹HNMR (600 MHz, D₆-DMSO, 25° C.):<br>3.68 (s, 3H), 3.79 (s, 3H), 3.82 (s, 3H), 4.02 (s, 3H), 6.19 (s, 1H), 7.06 (dd, 2H, J = 21.6 Hz), 7.28 (dd, 1H, J = 8.4, 1.8 Hz), 7.63 (s, 1H), 8.39 (s, 1H), 8.96 (s, 1H), 9.42 (s, 1H) |

TABLE 2-continued

| No | MS (m/z) | ¹H NMR |
|---|---|---|
| 97 | 412 | ¹HNMR (600 MHz, D₆-DMSO, 25° C.):<br>3.84 (s, 3H), 7.09 (d, 2H, J = 9 Hz), 7.83 (d, 2H, J = 9 Hz), 7.91 (d, 1H, J = 2.4 Hz), 8.48 (s, 1H), 8.50 (d, 1H, J = 9.6 Hz), 8.70 (dd, 1H, J = 9, 2.4 Hz), 9.03 (s, 1H), 9.85 (s, 1H) |
| 98 | 406 | ¹HNMR (600 MHz, D₆-DMSO, 25° C.):<br>3.83 (s, 3H), 4.17 (s, 2H), 7.08 (dd, 1H, J = 7.2, 1.8 Hz), 7.14 (d, 4H, J = 1.2 Hz), 7.62 (dd, 2H, J = 7.2, 1.8 Hz), 8.01 (dd, 1H, J = 9, 1.8 Hz), 8.32 (d, 1H, J = 3 Hz), 8.40 (s, 1H), 9.01 (s, 1H), 9.66 (s, 1H) |
| 99 | 452 | ¹HNMR (600 MHz, D₆-DMSO, 25° C.):<br>2.19 (m, 5H), 2.66 (m, 2H), 2.89 (m, 8H), 3.82 (s, 3H), 4.24 (s, 2H), 7.12 (d, 2H, J = 7.8 Hz), 7.68 (d, 1H, J = 7.2 Hz), 7.85 (d, 1H, J = 8.4 Hz), 7.95 (d, 2H, J = 8.4 Hz), 8.23 (s, 1H), 8.92 (s, 1H) |
| 100 | 579 | ¹HNMR (600 MHz, D₆-DMSO, 25° C.): 1.17 (m, 9H), 1.73 (m, 2H), 2.67 (m, 4H), 2.82 (m, 4H), 3.20 (m, 5H), 3.39 (m, 6H), 7.48 (d, 2H, J = 8.4 Hz), 7.84 (d, 2H, J = 7.8 Hz), 7.96 (dd, 1H, J = 9.6, 1.8 Hz), 8.17 (m, 1H), 8.30 (d, 1H, J = 9.6 Hz), 9.34 (s, 1H) |
| 101 | 581 | ¹HNMR (600 MHz, D₆-DMSO, 25° C.): 1.16 (t, 3H, J = 7.8 Hz), 1.21 (m, 6H), 1.36 (m, 2H), 1.70 (m, 2H), 2.67 (q, 2H, J = 15 Hz), 3.09 (m, 10H), 3.59 (m, 2H), 3.74 (m, 2H), 7.44 (d, 2H, J = 8.4 Hz), 7.79 (d, 2H, J = 7.8 Hz), 7.95 (d, 1H, J = 15 Hz), 8.05 (m, 1H), 8.30 (d, 1H, J = 9.6 Hz), 9.35 (s, 1H) |
| 102 | 565 | ¹HNMR (600 MHz, D₆-DMSO, 25° C.): 1.17 (t, 3H, J = 7.8 Hz), 1.23 (m, 3H), 1.76 (m, 6H), 2.68 (q, 2H, J = 15 Hz), 2.97 (m, 2H), 3.07 (m, 2H), 3.34 (m, 6H), 7.46 (d, 2H, J = 7.8 Hz), 7.81 (d, 2H, J = 7.8 Hz), 7.98 (d, 1H, J = 3 Hz), 8.14 (m, 1H), 8.33 (d, 1H, J = 9.6 Hz), 9.41 (s, 1H) |
| 103 | 536 | ¹HNMR (600 MHz, D₆-DMSO, 25° C.): 1.16 (m, 9H), 1.73 (m, 2H), 2.68 (q, 2H, J = 15 Hz), 2.92 (m, 4H), 3.34 (m, 6H), 7.45 (d, 2H, J = 8.4 Hz), 7.81 (d, 2H, J = 7.8 Hz), 7.99 (d, 1H, J = 9 Hz), 8.21 (m, 1H), 8.34 (d, 1H, J = 9 Hz), 9.43 (s, 1H) |
| 104 | 483 | ¹HNMR (600 MHz, D₆-DMSO, 25° C.):<br>1.14 (t, 3H, J = 7.8 Hz), 1.25 (m, 2H), 1.35 (m, 2H), 1.51 (m, 2H), 1.96 (m, 1H), 2.65 (q, 2H, J = 15 Hz), 3.34 (m, 2H), 3.70 (q, 2H, J = 12.6 Hz), 4.38 (t, 1H, J = 1.8 Hz), 7.38 (t, 1H, J = 5.4 Hz), 7.46 (d, 2H, J = 8.4 Hz), 7.79 (dd, 1H, J = 9, 1.2 Hz), 7.92 (d, 2H, J = 8.4 Hz), 7.97 (d, 1H, J = 9.6 Hz), 8.18 (d, 1H, J = 1.8 Hz), 8.93 (s, 1H) |
| 105 | 480 | ¹HNMR (600 MHz, D₆-DMSO, 25° C.):<br>1.13 (t, 3H, J = 7.2 Hz), 1.56 (m, 5H), 2.59 (m, 2H), 2.644 (q, 2H, J = 9 Hz), 2.90 (m, 2H), 7.45 (d, 2H, J = 7.8 Hz), 7.78 (dd, 1H, J = 9, 3.6 Hz), 7.92 (m, 2H), 7.95 (d, 1H, J = 9 Hz), 8.36 (m, 1H), 8.96 (s, 1H) |
| 106 | 488 | ¹HNMR (600 MHz, CDCl₃, 25° C.):<br>1.22 (t, 3H, J = 7.8 Hz), 2.69 (q, 2H, J = 15 Hz), 4.84 (d, 2H, J = 6 Hz), 7.27 (m, 2H), 7.30 (d, 1H, J = 7.8 Hz), 7.55 (d, 1H, J = 8.4 Hz), 7.73 (m, 3H), 7.85 (m, 1H), 8.70 (d, 1H, J = 9 Hz), 8.65 (d, 1H, J = 4.8 Hz), 9.08 (s, 1H) |
| 107 | 474 | ¹HNMR (600 MHz, CDCl₃, 25° C.):<br>1.24 (t, 3H, J = 7.8 Hz), , 2.74 (q, 2H, J = 15 Hz), 7.08 (s, 1H), 7.34 (d, 2H, J = 6.6 Hz), 7.40 (d, 2H, J = 8.4 Hz), 7.54 (d, 2H, J = 6.6 Hz), 7.59 (d, 2H, J = 9.6 Hz), 7.83 (d, 1H, J = 9.6 Hz), 8.39 (d, 1H, J = 9 Hz), 9.69 (s, 1H), 10.03 (m, 2H) |
| 108 | 447 | ¹HNMR (600 MHz, CDCl₃, 25° C.):<br>1.19 (t, 3H, J = 7.8 Hz), 2.63 (q, 2H, J = 15 Hz), 6.33 (m, 2H), 6.53 (m, 2H), 6.87 (m, 1H), 7.15 (d, 2H, J = 8.4 Hz), 7.39 (d, 2H, J = 7.8 Hz), 7.68 (d, 1H, J = 7.8 Hz), 8.26 (d, 1H, J = 9 Hz), 9.78 (s, 1H) |
| 109 | 448 | ¹HNMR (600 MHz, D₆-DMSO, 25° C.):<br>1.13 (t, 3H, J = 7.8 Hz), 2.63 (q, 2H, J = 15.6 Hz), 6.70 (t, 1H, J = 2.4 Hz), 6.77 (m, 1H), 7.35 (d, 2H, J = 8.4 Hz), 7.54 (d, 2H, J = 7.8 Hz), 7.83 (d, 1H, J = 1.8 Hz), 8.03 (dd, 1H, J = 9.6, 2.4 Hz)), 8.18 (d, 1H, J = 2.4 Hz), 8.41 (d, 1H, J = 9 Hz), 9.71 (s, 1H) |
| 110 | 449 | ¹HNMR (600 MHz, CDCl₃, 25° C.):<br>1.19 (t, 3H, J = 7.8 Hz), 2.65 (q, 2H, J = 15 Hz), 6.73 (d, 1H, J = 1.8 Hz), 7.27 (m, 2H), 7.41 (d, 2H, J = 9 Hz), 7.75 (dd, 1H, J = 8.4, 1.8 Hz), 8.06 (d, 1H, J = 1.2 Hz), 8.19 (d, 1H, J = 1.2 Hz), 8.32 (d, 1H, J = 9 Hz), 9.77 (s, 1H) |
| 111 | 469 | ¹HNMR (600 MHz, D₆-DMSO, 25° C.):<br>1.14 (t, 3H, J = 7.8 Hz), 1.39 (m, 2H), 1.57 (m, 2H), 2.65 (q, 2H, J = 9 Hz), 3.73 (q, 2H, J = 12 Hz), 4.48 (t, 1H, J = 5.4 Hz), 7.41 (t, 1H, J = 4.8 Hz), 7.46 (d, 2H, J = 7.8 Hz), 7.79 (d, 1H, J = 3 Hz), 7.92 (d, 2H, J = 8.4 Hz), 7.97 (d, 1H, J = 9 Hz), 8.18 (s, 1H), 8.93 (s, 1H) |
| 112 | 499 | ¹HNMR (600 MHz, CDCl₃, 25° C.):<br>1.19 (t, 3H, J = 7.8 Hz), 1.50 (m, 1H), 2.57 (q, 2H, J = 15 Hz), 6.57 (d, 1H, J = 1.8 Hz), 7.13 (m, 1H), 7.20 (d, 2H, J = 8.4 Hz), 7.43 (d, 2H, J = 8.4 Hz), 7.51 (m, 2H), 7.75 (dd, 1H, J = 9, 1.8 Hz), 8.23 (m, 1H), 8.37 (d, 1H, J = 9 Hz), 9.85 (s, 1H) |
| 113 | 567 | ¹HNMR (600 MHz, D₆-DMSO, 25° C.):<br>1.47 (m, 4H), 1.89 (m, 4H), 3.04 (m, 2H), 3.36 (m, 4H), 3.43 (m, 2H), 3.85 (s, 3H), 7.14 (d, 2H, J = 9 Hz), 7.86 (d, 2H, J = 6.6 Hz), 7.96 (m, 1H), 8.13 (s, 1H), 8.30 (d, 1H, J = 9 Hz), 9.35 (s, 1H) |

TABLE 2-continued

| No | MS (m/z) | $^1$H NMR |
|---|---|---|
| 114 | 511 | $^1$HNMR (600 MHz, D$_6$-DMSO, 25° C.):<br>1.65 (m, 10H), 2.61 (m, 2H), 3.35 (m, 4H), 3.85 (s, 3H), 7.16 (d, 2H, J = 7.8 Hz), 7.90 (d, 2H, J = 7.2 Hz), 8.29 (d, 1H, J = 7.2 Hz), 8.56 (d, 1H, J = 7.8 Hz), 9.0 (m, 1H), 9.38 (s, 1H) |
| 115 | 506 | $^1$HNMR (600 MHz, D$_6$-DMSO, 25° C.):<br>1.55 (m, 12H), 2.96 (m, 2H), 3.45 (m, 4H), 3.84 (s, 3H), 4.35 (s, 2H), 7.15 (d, 2H, J = 8.4 Hz), 7.86 (d, 2H, J = 5.4 Hz), 7.90 (d, 1H, J = 7.8 Hz), 8.19 (d, 1H, J = 2.4 Hz), 8.25 (s, 1H), 9.33 (s, 1H) |
| 116 | 568 | $^1$HNMR (600 MHz, D$_6$-DMSO, 25° C.):<br>0.93 (t, 3H, J = 7.8 Hz), 1.42 (m, 4H), 1.47 (m, 2H), 1.58 (m, 6H), 1.75 (m, 2H), 2.41 (m, 2H), 3.0 (m, 2H), 3.33 (m, 4H), 3.78 (s, 3H), 3.83 (s, 3H), 4.14 (t, 3H, J = 6 Hz), 7.16 (d, 1H, J = 7.8 Hz), 7.31 (s, 1H), 7.38 (s, 1H), 7.44 (m, 1H), 7.57 (dd, 1H, J = 9, 1.8 Hz), 8.05 (d, 1H, J = 9 Hz), 9.15 (s, 1H) |
| 117 | 462 | $^1$HNMR (600 MHz, CDCl$_3$, 25° C.):<br>1.20 (t, 3H, J = 7.2 Hz), 2.28 (s, 3H), 2.66 (q, 2H, J = 15.6 Hz), 6.41 (d, 1H, J = 0.6 Hz), 6.97 (s, 1H), 7.22 (d, 2H, J = 6.6 Hz), 7.33 (s, 1H), 7.40 (d, 2H, J = 8.4 Hz), 7.73 (dd, 1H, J = 15, 2.4 Hz), 8.30 (d, 1H, J = 9 Hz), 9.79 (s, 1H) |
| 118 | 448 | $^1$HNMR (600 MHz, CDCl$_3$, 25° C.):<br>1.18 (t, 3H, J = 7.8 Hz), 2.64 (q, 2H, J = 15), 6.84 (s, 1H), 6.87 (d, J = 1.2 Hz), 7.21 (s, 1H), 7.22 (s, 1H), 7.24 (s, 1H), 7.36 (s, 1H), 7.37 (s, 1H), 7.39 (s, 1H), 7.73 (dd, 1H, J = 9, 1.8 Hz), 8.31 (d, 1H, J = 9.6 Hz), 9.79 (s, 1H) |
| 119 | 593 | $^1$HNMR (600 MHz, D$_6$-DMSO, 25° C.):<br>0.91 (t, 3H, J = 7.2 Hz)), 1.39 (m, 2H), 1.55 (m, 10H), 1.68 (m, 2H), 2.45 (m, 4H), 3.06 (m, 2H), 3.22 (m, 2H), 4.05 (t, 2H, J-6.6 Hz), 7.12 (d, 2H, J = 9 Hz), 7.82 (d, 2H, J = 8.4 Hz), 7.94 (d, 1H, J = 8.4 Hz), 8.15 (s, 1H), 8.29 (d, 1H, J = 3 Hz), 9.36 (s, 1H) |
| 120 | 588 | $^1$HNMR (600 MHz, D$_6$-DMSO, 25° C.):<br>1.39 (m, 6H), 1.84 (m, 6H), 2.83 (m, 1H), 2.96 (m, 2H), 3.27 (m, 2H), 3.45 (m, 2H), 8.02 (m, 3H), 8.17 (m, 2H), 8.21 (s, 1H), 8.37 (d, 1H, J = 9 Hz), 9.49 (s, 1H) |
| 121 | 542 | $^1$HNMR (600 MHz, D$_6$-DMSO, 25° C.):<br>1.42 (m, 10H), 2.39 (m, 2H), 2.65 (s, 3H), 3.05 (m, 2H), 3.34 (m, 4H), 3.78 (s, 3H), 7.17 (d, 1H, J = 7.2 Hz), 7.30 (s, 1H), 7.48 (m, 1H), 7.78 (d, 1H, J = 1.2 Hz), 7.81 (dd, 1H, J = 9, 1.8 Hz), 8.04 (d, 1H, J = 9 Hz), 9.19 (s, 1H) |
| 122 | 556 | $^1$HNMR (600 MHz, D$_6$-DMSO, 25° C.):<br>1.55 (m, 8H), 2.55 (m, 4H), 3.12 (m, 2H), 3.51 (m, 5H), 3.83 (s, 6H), 3.96 (s, 3H), 3.98 (s, 3H), 7.15 (d, 1H, J = 9 Hz), 7.28 (m, 2H), 7.34 (m, 1H), 7.51 (s, 1H), 9.14 (s, 1H) |
| 123 | 473 | $^1$HNMR (600 MHz, CDCl$_3$, 25° C.):<br>0.77 (t, 6H, J = 7.2 Hz), 0.97 (t, 3H, J = 7.2 Hz), 1.51 (m, 2H), 1.80 (m, 2H), 3.36 (q, 2H, J = 13.8 Hz), 3.90 (s, 3H), 3.92 (s, 3H), 4.02 (t, 3H, J = 6 Hz), 6.92 (d, 1H, J = 8.4 Hz), 7.23 (d, 1H, J = 9 Hz), 7.41 (dd, 2H, J = 8.4, 3 Hz), 7.54 (dd, 1H, J = 8.4, 1.8 Hz), 8.01 (dd, 1H, J = 9.6, 3 Hz), 9.29 (s, 1H) |
| 124 | 503 | $^1$HNMR (600 MHz, CDCl$_3$, 25° C.):<br>0.77 (t, 6H, J = 7.2 Hz), 1.01 (m, 4H), 1.20 (m, 4H), 2.55 (s, 3H), 3.32 (t, 4H, J = 7.2 Hz), 3.90 (s, 3H), 3.91 (s, 3H), , 6.92 (d, 1H, J = 8.4 Hz), 7.39 (d, 1H, J = 1.8 Hz), 7.51 (dd, 1H, J = 8.4, 1.8 Hz), 7.60 (dd, 1H, J = 8.4, 1.8 Hz), 7.71 (d, 1H, J = 2.4 Hz), 7.79 (d, 1H, J = 8.4 Hz), 9.26 (s, 1H) |
| 125 | 452 | $^1$HNMR (600 MHz, CDCl$_3$, 25° C.): 1.20 (t, 3H, J = 7.8 Hz), 2.28 (s, 3H), 2.66 (q, 2H, J = 15 Hz), 6.76 (d, 1H, J = 1.2 Hz), 7.27 (d, 2H, J = 8.4 Hz), 7.35 (d, 2H, J = 8.4 Hz), 7.81 (dd, 1H, J = 9.6, 1.8 Hz), 8.01 (s, 1H), 8.38 (d, 1H, J = 9 Hz), 9.18 (s, 1H), 9.79 (s, 1H) |
| 126 | 482 | $^1$HNMR (600 MHz, CDCl$_3$, 25° C.):<br>1.20 (t, 3H, J = 7.8 Hz), 2.67 (q, 2H, J = 15 Hz), 2.90 (m, 4H), 3.83 (m, 4H), 7.33 (d, 2H, J = 8.4 Hz), 7.54 (dd, 1H, J = 9, 1.8 Hz), 7.82 (d, 2H, J = 8.4 Hz), 8.00 (d, 1H, J = 8.4 Hz), 8.50 (m, 1H), 9.04 (s, 1H), 9.47 (s, 1H) |
| 127 | 425 | $^1$HNMR (600 MHz, CDCl$_3$, 25° C.):<br>0.96 (t, 3H, J = 7.2 Hz), 1.17 (t, 3H, J = 7.2 Hz), 1.64 (m, 4H), 1.76 (m, 1H), 1.96 (m, 2H), 2.60 (t, 3H, J = 7.8 Hz), 2.67 (q, 2H, J = 15 Hz), 2.93 (m, 2H), 3.86 (m, 2H), 7.23 (d, 2H, J = 7.8 Hz), 7.31 (d, 2H, J = 8.4 Hz), 7.40 (d, 2H, J = 7.8 Hz), 7.66 (dd, 1H, J = 9, 1.8 Hz), 7.79 (d, 2H, J = 9 Hz), 8.16 (s, 1H), 8.26 (d, 1H, J = 9.6 Hz), 9.47 (s, 1H) |
| 128 | 587 | $^1$HNMR (600 MHz, CDCl$_3$, 25° C.):<br>0.95 (t, 3H, J = 7.8 Hz), 1.18 (t, 3H, J = 7.2 Hz), 1.40 (t, 3H, J = 7.2 Hz), 1.63 (m, 2H), 1.72 (m, 2H), 2.04 (m, 2H), 2.60 (t, 2H, J = 7.8 Hz), 2.67 (q, 2H, J = 15 Hz), 3.06 (m, 2H), 3.97 (t, 2H, J = 11.4 Hz), 4.41 (q, 2H, J = 14.4 Hz), 7.22 (d, 2H, J = 8.4 Hz), 7.32 (d, 2H, J = 8.4 Hz), 7.42 (d, 2H, J = 8.4 Hz), 7.80 (d, 2H, J = 8.4 Hz), 8.22 (d, 1H, J = 8.4 Hz), 8.37 (dd, 1H, J = 9, 1.8 Hz), 9.11 (d, 1H, J = 1.2 Hz), 9.45 (s, 1H) |

TABLE 2-continued

| No | MS (m/z) | $^1$H NMR |
|---|---|---|
| 129 | 601 | $^1$HNMR (600 MHz, CDCl$_3$, 25° C.):<br>0.96 (t, 3H, J = 7.2 Hz), 1.64 (m, 3H), 1.77 (m, 2H), 2.10 (m, 2H), 2.60 (t, 2H, J = 7.8 Hz), 3.02 (m, 2H), 3.84 (s, 3H), 3.91 (m, 2H), 6.97 (d, 2H, J = 9 Hz), 7.24 (d, 2H, J = 8.4 Hz), 7.44 (d, 2H, J = 8.4 Hz), 7.66 (dd, 1H, J = 9, 1.8 Hz), 7.85 (d, 2H, J = 8.4 Hz), 8.16 (s, 1H), 8.28 (m, 1H), 9.38 (s, 1H) |
| 130 | 552 | $^1$HNMR (600 MHz, CDCl$_3$, 25° C.):<br>0.83 (m, 2H), 1.23 (t, 3H, J = 7.2 Hz), 1.43 (t, 3H, J = 7.2 Hz), 1.75 (m, 11H), 2.71 (q, 2H, J = 15 Hz), 3.02 (m, 2H), 3.32 (m, 2H), 349 (m, 2H), 4.43 (m, 2H), 7.35 (d, 2H, J = 7.2 Hz), 7.77 (d, 2H, J = 7.8 Hz), 8.15 (m, 1H), 8.35 (d, 1H, J = 9 Hz), 8.88 (s, 1H), 9.30 (s, 1H) |
| 131 | 567 | $^1$HNMR (600 MHz, CDCl$_3$, 25° C.):<br>1.22 (m, 9H), 1.42 (t, 3H, J = 7.2 Hz), 1.90 (m, 2H), 2.70 (q, 2H, J = 15 Hz), 2.81 (m, 2H), 2.92 (m, 2H), 2.97 (m, 6H), 3.05 (m, 2H), 3.42 (m, 2H), 4.41 (q, 2H, J = 13.8 Hz), 7.35 (d, 2H, J = 8.4 Hz), 7.80 (d, 2H, J = 8.4 Hz), 8.14 (d, 1H, J = 8.4 Hz), 8.34 (dd, 1H, J = 9, 1.8 Hz), 9.00 (d, 1H, J = 1.2 Hz), 9.31 (s, 1H) |
| 132 | 568 | $^1$HNMR (600 MHz, CDCl$_3$, 25° C.):<br>1.23 (t, 3H, J = 7.8 Hz), 1.43 (t, 3H, J = 7.2 Hz), 1.51 (t, 6H, J = 7.2 Hz), 1.79 (m, 2H), 1.88 (m, 2H), 2.71 (q, 2H, J = 15 Hz), 3.31 (m, 2H), 3.34 (m, 2H), 3.41 (m, 4H), 3.57 (m, 2H), 3.78 (m, 1H), 4.13 (m, 2H), 4.42 (q, 2H, J = 14.4 Hz), 7.37 (d, 2H, J = 8.4 Hz), 7.79 (d, 2H, J = 8.4 Hz), 8.18 (d, 1H, J = 8.4 Hz), 8.34 (dd, 1H, J = 9, 1.8 Hz), 8.93 (d, 1H, J = 1.8 Hz), 9.32 (s, 1H) |
| 133 | 487 | $^1$HNMR (600 MHz, CDCl$_3$, 25° C.):<br>1.18 (t, 3H, J = 7.2 Hz), 1.22 (t, 3H, J = 6.6 Hz), 2.61 (q, 2H, J = 15 Hz), 4.23 (m, 2H), 7.11 (m, 1H), 7.19 (d, 2H, J = 8.4 Hz), 7.44 (d, 2H, J = 8.4 Hz), 7.50 (m, 2H), 7.55 (d, 1H, J = 1.2 Hz), 8.23 (m, 1H), 8.36 (d, 1H, J = 8.4 Hz), 8.47 (dd, 1H, J = 9, 1.8 Hz), 9.90 (s, 1H) |
| 134 | 436 | $^1$HNMR (600 MHz, CDCl$_3$, 25° C.):<br>1.17 (t, 3H, J = 7.2 Hz), 1.31 (t, 3H, J = 7.2 Hz)2.63 (q, 2H, J = 15.6 Hz), 4.32 (q, 2H, J = 10.8 Hz), 6.85 (s, 1H), 7.21 (d, 2H, J = 7.8 Hz), 7.24 (s, 1H), 7.38 (d, 2H, J = 8.4 Hz), 7.43 (m, 1H), 7.82 (d, 1H, J = 2.4 Hz), 8.28 (d, 1H, J = 9 Hz), 8.44 (dd, 1H, J = 9, 1.8 Hz), 9.83 (s, 1H) |
| 135 | 469 | $^1$HNMR (600 MHz, CDCl$_3$, 25° C.):<br>1.23 (m, 3H), 1.43 (m, 3H), 1.81 (m, 4H), 2.72 (m, 2H), 3.14 (m, 2H), 3.31 (m, 2H), 3.65 (m, 1H), 3.95 (m, 1H), 4.44 (m, 2H), 7.38 (m, 2H), 7.81 (m, 2H), 8.16 (m, 1H), 8.34 (m, 1H), 8.97 (m, 1H), 9.19 (m, 1H) |
| 136 | 538 | 1HNMR (600 MHz, CDCl$_3$, 25° C.):<br>1.42 (t, 3H, J = 7.2 Hz), 1.56 (m, 2H), 1.87 (m, 6H), 2.05 (m, 2H), 2.85 (m, 5H), 3.34 (m, 2H), 3.53 (m, 2H), 3.87 (s, 3H), 4.43 (q, 2H, J = 8.4 Hz), 6.99 (d, 2H, J = 9 Hz), 7.80 (d, 2H, J = 9 Hz), 8.12 (d, 1H, J = 9 Hz), 8.33 (dd, 1H, J = 8.4, 0.6 Hz), 8.86 (s, 1H), 9.21 (s, 1H) |
| 137 | 471 | $^1$HNMR (600 MHz, CDCl$_3$, 25° C.):<br>1.44 (t, 3H, J = 6.6 Hz), 1.61 (m, 2H), 1.84 (m, 2H), 3.21 (m, 2H), 3.42 (m, 2H), 3.72 (m, 1H), 3.89 (s, 3H), 4.44 (q, 2H, J = 13.8 Hz), 7.02 (d, 2H, J = 9 Hz), 7.87 (d, 2H, J = 12, 3 Hz), 8.22 (m, 1H), 8.35 (d, 1H, J = 9 Hz), 9.01 (m, 1H), 9.08 (m, 1H) |
| 138 | 554 | $^1$HNMR (600 MHz, CDCl$_3$, 25° C.):<br>1.44 (t, 3H, J = 6.6 Hz), 2.02 (m, 10H), 2.23 (m, 2H), 2.50 (m, 2H), 3.19 (m, 2H), 3.38 (m, 3H), 3.89 (s, 3H), 4.45 (q, 2H, J = 13.8 Hz), 7.03 (d, 2H, J = 8.4 Hz), 7.82 (d, 2H, J = 8.4 Hz), 8.17 (d, 1H, J = 8.4 Hz), 8.36 (d, 1H, J = 9 Hz), 8.81 (m, 1H), 9.17 (s, 1H) |
| 139 | 569 | $^1$HNMR (600 MHz, CDCl$_3$, 25° C.):<br>1.32 (m, 6H), 1.43 (t, 3H, J = 7.2 Hz), 1.97 (m, 2H), 2.89 (m, 2H), 2.98 (m, 2H), 3.05 (m, 8H), 3.41 (m, 2H), 3.46 (m, 2H), 3.88 (s, 3H), 4.42 (q, 2H, J = 8.4 Hz), 7.01 (d, 2H, J = 9 Hz), 7.85 (d, 2H, J = 9 Hz), 8.14 (d, 1H, J = 9 Hz), 8.33 (dd, 1H, J = 9, 1.8 Hz), 9.02 (d, 1H, J = 1.8 Hz), 9.25 (s, 1H) |
| 140 | 570 | $^1$HNMR (600 MHz, CDCl$_3$, 25° C.):<br>1.43 (m, 9H), 1.68 (m, 2H), 1.81 (m, 2H), 1.94 (m, 2H)3.17 (m, 2H), 3.29 (m, 4H), 3.55 (m, 2H), 3.75 (m, 1H), 3.87 (s, 3H), 4.07 (q, J = 4.2 Hz), 4.42 (q, 2H, J = 14.4 Hz), 7.01 (d, 2H, J = 9 Hz), 7.83 (d, 2H, J = 9 Hz), 8.14 (d, 1H, J = 8.4 Hz), 8.33 (dd, 1H, J = 8.4, 1.2 Hz), 8.94 (d, 1H, J = 1.2 Hz), 9.27 (s, 1H) |
| 141 | 438 | $^1$HNMR (600 MHz, CDCl$_3$, 25° C.):<br>1.33 (t, 3H, J = 6.6 Hz), 3.82 (s, 3H), 4.34 (q, 2H, J = 14.4 Hz), 6.86 (d, 2H, J = 9 Hz), 6.92 (m, 1H), 7.29 (m, 1H), 7.41 (d, 2H, J = 8.4 Hz), 7.46 (m, 1H), 7.84 (d, 1H, J = 1.2 Hz), 8.30 (d, 1H, J = 9 Hz), 8.46 (m, 1H), 9.85 (s, 1H) |
| 142 | 489 | $^1$HNMR (600 MHz, CDCl$_3$, 25° C.):<br>1.25 (t, 3H, J = 7.2 Hz), 3.82 (s, 3H), 4.26 (m, 2H), 6.85 (m, 2H), 7.47 (m, 4H), 7.93 (m, 2H), 8.26 (m, 1H), 8.38 (d, 1H, J = 9 Hz), 8.49 (dd, 1H, J = 9, 1.2 Hz), 9.92 (s, 1H) |
| 143 | 525 | $^1$HNMR (600 MHz, CDCl$_3$, 25° C.):<br>1.85 (m, 12H), 2.80 (m, 4H), 3.34 (m, 2H), 3.53 (m, 2H), 3.88 (s, 3H), 4.01 (s, 3H), 7.00 (d, 2H, J = 9 Hz), 7.81 (d, 2H, J = 8.4 Hz), 8.14 (d, 1H, J = 8.4 Hz), 8.34 (d, 1H, J = 8.4 Hz), 8.87 (m, 1H), 9.23 (s, 1H) |

TABLE 2-continued

| No | MS (m/z) | ¹H NMR |
|---|---|---|
| 144 | 484 | ¹HNMR (600 MHz, CDCl$_3$, 25° C.):<br>1.44 (t, 3H, J = 7.2 Hz), 1.62 (m, 2H), 2.16 (m, 2H), 2.57 (s, 3H), 2.92 (m, 4H), 3.42 (m, 2H), 3.89 (s, 3H), 4.45 (q, 2H, J = 13.8 Hz), 7.03 (d, 2H, J = 9 Hz), 7.88 (d, 2H, J = 8.4 Hz), 8.16 (d, 1H, J = 9 Hz), 8.36 (dd, 1H, J = 8.4, 1.2 Hz), 8.94 (m, 1H), 9.15 (m, 1H) |
| 145 | 619 | ¹HNMR (600 MHz, CDCl$_3$, 25° C.):<br>1.19 (t, 3H, J = 7.8 Hz), 2.53 (m, 2H), 2.64 (m, 4H), 3.45 (m, 2H), 3.59 (m, 2H), 3.85 (s, 3H), 6.92 (d, 2H, J = 15 Hz), 7.24 (d, 2H, J = 8.4 Hz), 7.36 (d, 2H, J = 8.4 Hz), 7.63 (dd, 1H, J = 9, 1.8 Hz), 7.76 (d, 2H, J = 8.4 Hz), 7.87 (s, 1H), 8.23 (d, 1H, J = 9.6 Hz), 9.57 (s, 1H) |
| 146 | 587 | ¹HNMR (600 MHz, CDCl$_3$, 25° C.):<br>1.18 (t, 3H, J = 7.8 Hz), 1.68 (m, 3H), 1.97 (m, 2H), 2.68 (q, 2H, J = 15 Hz), 2.97 (m, 2H), 3.86 (s, 3H), 3.90 (m, 2H), 6.85 (dd, 1H, J = 8.4, 2.4 Hz), 7.06 (m, 2H), 7.33 (m, 3H), 7.67 (dd, 1H, J = 9, 1.8 Hz), 7.80 (d, 2H, J = 8.4 Hz), 8.14 (s, 1H), 8.30 (d, 1H, J = 9 Hz), 9.45 (s, 1H) |
| 147 | 601 | |
| 148 | 575 | ¹HNMR (600 MHz, CDCl$_3$, 25° C.):<br>1.22 (t, 3H, J = 7.8 Hz), 1.27 (t, 3H, J = 7.2 Hz), 1.45 (m, 2H), 2.55 (m, 2H), 2.69 (m, 4H), 3.87 (s, 3H), 4.34 (q, 2H, J = 14.4 Hz), 6.94 (d, 2H, J = 9 Hz), 7.26 (d, 2H, J = 8.4 Hz), 7.41 (d, 2H, J = 8.4 Hz), 7.79 (d, 2H, J = 7.8 Hz), 8.23 (d, 1H, J = 9 Hz), 8.37 (dd, 1H, J = 9, 1.8 Hz), 8.83 (d, 1H, J = 1.8 Hz), 9.65 (m, 1H) |
| 149 | 575 | ¹HNMR (600 MHz, CDCl$_3$, 25° C.):<br>1.19 (t, 3H, J = 7.8 Hz), 1.41 (t, 3H, J = 7.2 Hz), 1.72 (m, 2H), 2.09 (m, 2H), 2.68 (q, 2H, J = 15.6 Hz), 3.09 (m, 2H), 3.81 (s, 1H), 3.98 (m, 2H), 4.42 (q, 2H, J = 14.4 Hz), 6.85 (dd, 1H, J = 7.8, 1.8 Hz), 7.08 (d, 1H, J = 7.8 Hz), 7.11 (m, 1H), 7.33 (m, 3H), 7.81 (d, 2H, J = 8.4 Hz), 8.29 (m, 1H), 8.38 (dd, 1H, J = 9.6, 1.8 Hz), 9.11 (s, 1H), 9.45 (m, 1H) |
| 150 | 589 | ¹HNMR (600 MHz, CDCl$_3$, 25° C.):<br>1.75 (m, 2H), 2.11 (m, 2H), 3.04 (m, 2H), 3.85 (s, 3H), 3.86 (s, 3H), 3.94 (m, 2H), 6.86 (m, 1H), 6.98 (d, 2H, J = 8.4 Hz), 7.10 (m, 2H), 7.34 (t, 1H, J = 8.4 Hz), 7.67 (d, 1H, J = 9 Hz), 7.85 (d, 1H, J = 9 Hz), 8.15 (m, 1H), 8.30 (m, 1H), 9.37 (s, 1H) |
| 151 | 538 | ¹HNMR (600 MHz, CDCl$_3$, 25° C.):<br>0.97 (t, 3H, J = 7.2 Hz)), 1.48 (m, 2H), 1.77 (m, 2H), 2.18 (m, 2H), 2.62 (s, 3H), 3.08 (m, 4H), 3.50 (m, 4H), 4.03 (t, 2H, J = 6.6 Hz), 7.02 (d, 2H, J = 9 Hz), 7.64 (dd, 1H, J = 7.8, 1.2 Hz), 7.85 (d, 2H, J = 9 Hz), 8.16 (d, 2H, J = 9 Hz), 8.96 (m, 1H) |
| 152 | 608 | ¹HNMR (600 MHz, CDCl$_3$, 25° C.):<br>1.44 (t, 3H, J = 6.6 Hz), 1.92 (m, 2H), 2.22 (m, 2H), 3.28 (m, 4H), 3.36 (m, 1H), 3.87 (s, 3H), 4.06 (m, 4H), 4.45 (q, 2H, J = 14.4 Hz), 7.03 (dd, 2H, J = 9.6, 3 Hz), 7.81 (m, 2H), 8.17 (d, 1H, J = 9 Hz), 8.35 (dd, 1H, J = 14.4, 1.2 Hz), 8.81 (m, 1H), 9.17 (s, 1H) |
| 153 | 558 | ¹HNMR (600 MHz, CDCl$_3$, 25° C.):<br>1.88 (m, 4H), 2.05 (m, 4H), 2.29 (m, 2H), 2.62 (s, 3H), 2.89 (m, 1H), 3.05 (m, 1H), 3.18 (m, 2H), 3.32 (m, 2H), 3.51 (m, 2H), 3.88 (s, 3H), 3.96 (s, 3H), 6.98 (d, 1H, J = 8.4 Hz), 7.32 (d, 1H, J = 7.8 Hz), 7.49 (dd, 1H, J = 9, 2.4 Hz), 7.66 (dd, 1H, J = 9, 1.8 Hz), 7.74 (m, 1H), 8.00 (d, 1H, J = 8.4 Hz), 8.89 (s, 1H) |
| 154 | 488 | ¹HNMR (600 MHz, CDCl$_3$, 25° C.):<br>2.19 (m, 2H), 2.60 (s, 3H), 2.61 (s, 3H), 3.02 (m, 4H), 3.44 (m, 2H), 3.56 (m, 2H), 3.91 (s, 3H), 3.96 (s, 3H), 6.99 (d, 1H, J = 8.4 Hz), 7.39 (d, 1H, J = 1.8 Hz), 7.54 (dd, 1H, J = 9, 2.4 Hz), 7.63 (dd, 1H, J = 9, 1.8 Hz), 7.82 (m, 1H), 7.99 (d, 1H, J = 3 Hz), 8.76 (m, 1H) |
| 155 | 582 | ¹HNMR (600 MHz, CDCl$_3$, 25° C.):<br>0.99 (t, 6H, J = 7.2 Hz), 1.37 (t, 3H, J = 7.2 Hz), 1.40 (m, 8H), 1.90 (m, 4H), 3.00 (m, 4H), 3.07 (q, 4H, J = 15 Hz), 3.43 (m, 1H), 3.87 (s, 3H), 4.44 (q, 2H, J = 12.6 Hz), 7.02 (dd, 2H, J = 12, 3 Hz), 7.82 (m, 2H), 8.16 (d, 1H, J = 9 Hz), 8.35 (dd, 1H, J = 8.4, 1.8 Hz), 8.80 (m, 1H), 9.20 (s, 1H) |
| 156 | 558 | ¹HNMR (600 MHz, CDCl$_3$, 25° C.):<br>1.44 (t, 3H, J = 6.6 Hz), 1.92 (m, 2H), 2.22 (m, 2H), 3.28 (m, 4H), 3.36 (m, 1H), 3.87 (s, 3H), 4.06 (m, 4H), 4.45 (q, 2H, J = 14.4 Hz), 7.03 (dd, 2H, J = 9.6, 3 Hz), 7.81 (m, 2H), 8.17 (d, 1H, J = 9 Hz), 8.35 (dd, 1H, J = 14.4, 1.2 Hz), 8.81 (m, 1H), 9.17 (s, 1H) |
| 157 | 580 | ¹HNMR (600 MHz, CDCl$_3$, 25° C.):<br>0.95 (t, 3H, J = 7.2 Hz), 1.42 (t, 3H, J = 7.2 Hz), 1.46 (q, 2H, J = 9 Hz), 1.57 (m, 2H), 1.75 (m, 2H), 1.80 (m, 6H), 2.06 (m, 2H), 2.86 (m, 5H), 3.34 (m, 2H), 3.51 (t, 2H, J = 7.2 Hz), 4.00 (t, 2H, J = 6.6 Hz), 4.31 (q, 2H, J = 14.4 Hz), 6.97 (m, 2H), 7.78 (m, 2H), 8.12 (d, 1H, J = 8.4 Hz), 8.32 (dd, 1H, J = 8.4, 1.2 Hz), 8.85 (s, 1H), 9.20 (s, 1H) |
| 158 | 526 | ¹HNMR (600 MHz, CDCl$_3$, 25° C.):<br>0.95 (t, 3H, J = 7.2 Hz), 1.43 (t, 3H, J = 7.2 Hz), 1.46 (m, 2H), 1.75 (m, 2H), 2.14 (m, 2H), 2.55 (s, 3H), 2.86 (m, 4H), 3.39 (t, 2H, J = 6.6 Hz), 3.62 (m, 2H), 4.01 (t, 2H, J = 6.6 Hz), 4.43 (q, 2H, J = 14.4 Hz), 7.00 (d, 2H, J = 9 Hz), 7.84 (m, 2H), 8.14 (d, 1H, J = 8.4 Hz), 8.34 (dd, 1H, J = 8.4, 1.2 Hz), 8.95 (s, 1H), 9.15 (m, 1H) |

TABLE 2-continued

| No | MS (m/z) | ¹H NMR |
|---|---|---|
| 159 | 554 | ¹HNMR (600 MHz, CDCl₃, 25° C.):<br>0.96 (t, 3H, J = 7.2 Hz), 1.45 (m, 4H), 1.73 (m, 10H), 2.55 (s, 3H), 2.70 (m, 5H), 3.21 (m, 2H), 3.42 (t, 2H, J = 10.8 Hz), 3.99 (t, 2H, J = 6.6 Hz), 6.95 (d, 2H, J = 9 Hz), 7.63 (dd, 1H, J = 9, 1.8 Hz), 7.77 (dd, 3H, J = 7.2, 2.4 Hz), 7.99 (d, 1H, J = 9 Hz), 9.11 (m, 1H) |
| 160 | 501 | ¹HNMR (600 MHz, CDCl₃, 25° C.):<br>0.96 (t, 3H, J = 7.2 Hz), 1.47 (m, 2H), 1.76 (m, 2H), 2.08 (m, 2H), 2.54 (s, 3H), 2.61 (s, 3H), 2.87 (m, 4H), 3.36 (m, 4H), 6.99 (d, 2H, J = 9 Hz), 7.62 (dd, 1H, J = 9, 1.8 Hz), 7.84 (d, 2H, J = 8.4 Hz), 7.89 (m, 1H), 7.98 (d, 1H, J = 9 Hz), 8.99 (m, 1H) |
| 161 | 596 | ¹HNMR (600 MHz, CDCl₃, 25° C.):<br>0.95 (t, 3H, J = 7.2 Hz), 1.42 (t, 3H, J = 6.6 Hz), 1.46 (m, 2H), 1.75 (m, 2H), 1.85 (m, 4H), 2.00 (m, 4H), 2.03 (m, 2H), 2.61 (m, 2H), 3.21 (m, 2H), 3.31 (m, 3H), 3.51 (t, 2H, J = 11.4 Hz), 4.00 (t, 2H, J = 6.6 Hz), 4.44 (q, 2H, J = 14.4 Hz), 6.97 (m, 2H), 7.78 (m, 2H), 8.12 (d, 1H, J = 8.4 Hz), 8.32 (dd, 1H, J = 8.4, 1.2 Hz), 8.85 (s, 1H), 9.20 (s, 1H) |
| 162 | 570 | ¹HNMR (600 MHz, CDCl₃, 25° C.):<br>0.96 (t, 3H, J = 7.8 Hz), 1.47 (m, 2H), 1.76 (m, 9H), 2.00 (m, 2H), 2.24 (m, 2H), 3.21 (m, 4H), 3.38 (m, 2H), 3.52 (m, 2H), 4.02 (m, 2H), 6.99 (d, 2H, J = 9 Hz), 7.66 (d, 2H, J = 8.4 Hz), 7.75 (d, 2H, J = 9 Hz), 8.03 (d, 1H, J = 9 Hz), 9.05 (m, 1H) |
| 163 | 516 | ¹HNMR (600 MHz, CDCl₃, 25° C.):<br>0.97 (t, 3H, J = 7.2 Hz), 1.47 (m, 2H), 1.78 (m, 2H), 2.29 (m, 2H), 2.59 (s, 3H), 2.80 (s, 3H), 3.07 (m, 2H), 3.22 (m, 2H), 3.47 (m, 2H), 3.70 (m, 2H), 4.04 (t, 2H, J = 6.6 Hz), 7.04 (d, 2H, J = 9 Hz), 7.86 (d, 2H, J = 9 Hz), 8.00 (d, 1H, J = 8.4 Hz), 8.28 (d, 1H, J = 9 Hz), 8.54 (m, 1H), 8.94 (m, 1H) |
| 164 | 532 | ¹HNMR (600 MHz, CDCl₃, 25° C.):<br>0.96 (t, 3H, J = 7.2 Hz), 1.46 (m, 2H), 1.76 (m, 2H), 2.14 (m, 2H), 2.60 (s, 3H), 2.97 (m, 2H), 3.05 (m, 2H), 3.16 (s, 3H), 3.50 (m, 2H), 3.60 (m, 2H), 4.02 (t, 2H, J = 6.6 Hz), 7.01 (d, 2H, J = 9 Hz), 7.84 (m, 2H), 8.19 (dd, 1H, J = 9, 1.8 Hz), 8.27 (d, 1H, J = 9 Hz), 9.08 (m, 1H), 9.18 (m, 1H) |
| 165 | 511 | ¹HNMR (600 MHz, CDCl₃, 25° C.):<br>1.24 (m, 6H), 2.04 (m, 4H), 2.56 (s, 3H), 2.93 (m, 2H), 3.43 (m, 8H), 3.89 (s, 3H), 7.03 (d, 2H, J = 7.8 Hz), 7.77 (dd, 1H, J = 8.4, 1.8 Hz), 7.87 (d, 2H, J = 9 Hz), 8.16 (d, 1H, J = 9 Hz), 8.22 (m, 1H), 9.08 (s, 1H) |
| 166 | 554 | ¹HNMR (600 MHz, D₆DMSO, 25° C.):<br>0.96 (t, 6H, J = 7.2 Hz), 1.22 (m, 2H), 1.81 (m, 2H), 2.33 (s, 3H), 2.53 (m, 4H), 2.58 (t, 2H, J = 6.6 Hz), 2.63 (t, 2H, J = 5.4 Hz), 3.22 (m, 2H), 3.26 (m, 2H), 3.37 (m, 2H), 3.84 (s, 3H), 7.15 (d, 2H, J = 9 Hz), 7.87 (m, 2H, J = 9 Hz), 8.18 (d, 1H, J = 8.4 Hz), 8.25 (dd, 1H, J = 9, 1.8 Hz)8.64 (t, 1H, J = 5.4 Hz), 8.74 (d, 1H, J = 1.2 Hz), 9.36 (s, 1H) |
| 167 | 570 | ¹HNMR (600 MHz, CDCl₃, 25° C.):<br>0.96 (t, 3H, J = 7.2 Hz), 1.47 (m, 2H), 1.77 (m, 2H), 2.01 (brm, 14H), 2.78 (m, 2H), 2.82 (s, 3H), 3.34 (m, 2H), 3.54 (m, 2H), 4.02 (t, 2H, J = 5.4 Hz), 7.07 (d, 2H, J = 9 Hz), 7.80 (m, 3H), 8.24 (d, 1H, J = 9 Hz), 8.53 (s, 1H), 9.25 (s, 1H) |
| 168 | 586 | ¹HNMR (600 MHz, CDCl₃, 25° C.):<br>0.96 (t, 3H, J = 7.2 Hz), 1.47 (m, 2H), 1.76 (m, 2H), 2.07 (brm, 8H), 2.29 (m, 2H), 2.84 (s, 3H), 3.08 (m, 2H), 3.35 (m, 4H), 3.59 (m, 2H), 4.02 (t, 2H, J = 7.2 Hz), 7.02 (d, 2H, J = 9 Hz), 7.79 (m, 3H), 8.25 (d, 1H, J = 7.8 Hz), 8.51 (m, 1H), 9.23 (s, 1H) |
| 169 | 586 | ¹HNMR (600 MHz, CDCl₃, 25° C.):<br>0.96 (t, 3H, J = 7.2 Hz), 1.47 (m, 2H), 1.58 (m, 2H), 1.76 (m, 2H), 1.94 (m, 6H), 2.11 (m, 2H), 2.87 (m, 5H), 3.15 (s, 3H), 3.41 (m, 2H), 3.55 (m, 2H), 4.01 (t, 2H, J = 6.6 Hz), 6.99 (d, 2H, J = 8.4 Hz), 7.80 (d, 2H, J = 9 Hz), 8.16 (dd, 1H, J = 8.4, 1.8 Hz), 8.25 (d, 1H, J = 8.4 Hz), 8.79 (d, 1H, J = 1.8 Hz), 9.20 (s, 1H) |
| 170 | 603 | ¹HNMR (600 MHz, CDCl₃, 25° C.):<br>0.98 (t, 3H, J = 7.2 Hz), 1.49 (m, 2H), 1.77 (m, 2H), 2.02 (m, 2H), 2.14 (m, 2H), 2.25 (m, 2H), 2.38 (m, 2H), 3.15 (s, 3H), 3.26 (m, 2H), 3.40 (m, 2H), 3.63 (m, 2H), 4.01 (t, 2H, J = 6 Hz), 6.98 (d, 2H, J = 9 Hz), 7.79 (d, 2H, J = 9 Hz), 8.16 (dd, 1H, J = 9, 1.8 Hz), 8.27 (d, 1H, J = 9 Hz), 8.76 (d, 1H, J = 0.6 Hz), 9.17 (m, 1H) |
| 171 | 553 | ¹HNMR (600 MHz, CDCl₃, 25° C.):<br>1.42 (t, 3H, J = 7.2 Hz), 1.74 (m, 2H), 1.85 (m, 2H), 2.49 (s, 3H), 2.60 (m, 1H), 2.76 (m, 8H), 3.37 (m, 4H), 3.87 (s, 3H), 4.42 (q, 2H, J = 13.2 Hz), 6.99 (d, 2H, J = 9 Hz), 7.81 (dd, 2H, J = 7.2, 2.4 Hz), 8.13 (d, 1H, J = 8.4 Hz), 8.32 (dd, 1H, J = 9, 1.8 Hz), 8.94 (d, 1H, J = 1.8 Hz), 9.29 (m, 1H) |
| 172 | 595 | ¹HNMR (600 MHz, CDCl₃, 25° C.):<br>0.96 (t, 3H, J = 7.2 Hz), 1.43 (t, 3H, J = 7.2 Hz), 1.48 (m, 2H), 1.76 (m, 4H), 1.87 (m, 2H), 2.38 (s, 3H), 2.59 (m, 4H), 2.73 (m, 4H), 3.33 (m, 2H), 3.46 (m, 2H), 4.0 (t, 2H, J = 6.6 Hz), 4.27 (q, 2H, J = 14.4 Hz), 6.96 (d, 2H, J = 9 Hz), 7.80 (dd, 2H, J = 7.2, 1.8 Hz), 78.11 (d, 1H, J = 9 Hz), 8.32 (dd, 1H, J = 9, 1.8 Hz), 8.94 (d, 1H, J = 1.2 Hz), 9.25 (m, 1H) |
| 173 | 552 | ¹HNMR (600 MHz, CDCl₃, 25° C.):<br>1.44 (t, 3H, J = 7.2 Hz), 1.75 (m, 14H), 3.36 (m, 2H), 3.53 (m, 2H), 3.88 (s, 3H), 4.45 (q, 2H, J = 13.8 Hz), 7.01 (d, 2H, J = 8.4 Hz), 7.81 (d, 2H, |

TABLE 2-continued

| No | MS (m/z) | ¹H NMR |
|---|---|---|
| | | J = 9 Hz), 8.15 (d, 1H, J = 9 Hz), 8.35 (dd, 1H, J = 9, 1.8 Hz), 8.84 (s, 1H), 9.18 (s, 1H) |
| 174 | 554 | ¹HNMR (600 MHz, CDCl₃, 25° C.): 1.44 (t, 3H, J = 6.6 Hz), 1.65 (m, 4H), 1.77 (m, 6H), 2.55 (m, 1H), 2.74 (m, 3H), 3.36 (m, 2H), 3.48 (m, 2H), 3.88 (s, 3H), 4.44 (q, 2H, J = 14.4 Hz), 7.00 (d, 2H, J = 8.4 Hz), 7.82 (d, 2H, J = 9 Hz), 8.13 (d, 1H, J = 9 Hz), 8.34 (dd, 1H, J = 9, 1.8 Hz), 8.91 (s, 1H), 9.24 (s, 1H) |
| 175 | 568 | ¹HNMR (600 MHz, CDCl₃, 25° C.): 1.44 (t, 3H, J = 7.2 Hz), 1.78 (m, 6H), 2.03 (m, 4H), 2.17 (m, 2H), 2.30 (m, 2H), 2.85 (m, 2H), 3.39 (m, 2H), 3.57 (m, 3H), 3.89 (s, 3H), 4.46 (q, 2H, J = 14.4 Hz), 7.04 (d, 2H, J = 9 Hz), 7.82 (d, 2H, J = 9 Hz), 8.18 (d, 1H, J = 9 Hz), 8.36 (dd, 1H, J = 9, 1.8 Hz), 8.79 (m, 1H), 9.18 (m, 1H) |
| 176 | 594 | ¹HNMR (600 MHz, CDCl₃, 25° C.): 0.97 (t, 3H, J = 7.2 Hz), 1.44 (t, 3H, J = 7.2 Hz), 1.49 (m, 2H), 2.00 (brm, 17H), 3.37 (m, 2H), 3.53 (m, 2H), 4.02 (t, 2H, J = 6.6 Hz), 4.45 (q, 2H, J = 14.4 Hz), 6.99 (d, 2H, J = 9 Hz), 7.79 (d, 2H, J = 9 Hz), 8.15 (d, 1H, J = 9 Hz), 8.35 (dd, 1H, J = 8.4, 1.2 Hz), 8.83 (m, 1H), 9.16 (m, 1H) |
| 177 | 596 | ¹HNMR (600 MHz, CDCl₃, 25° C.): 0.96 (t, 3H, J = 7.8 Hz), 1.44 (t, 3H, J = 6.6 Hz), 1.47 (m, 2H), 1.76 (m, 10H), 2.55 (m, 1H), 2.73 (m, 3H), 3.35 (m, 8H), 3.50 (m, 2H), 3.93 (m, 1H), 4.01 (t, 2H, J = 6.6 Hz), 4.43 (q, 2H, J = 14.4 Hz), 6.97 (d, 2H, J = 9 Hz), 7.80 (d, 2H, J = 9 Hz), 8.12 (d, 1H, J = 8.4 Hz), 8.33 (dd, 1H, J = 8.4, 1.8 Hz), 8.92 (m, 1H), 9.22 (s, 1H) |
| 178 | 610 | |
| 179 | 581 | 1HNMR (600 MHz, CDCl3, 25° C.): 1.44 (t, 6H, J = 7.2 Hz), 1.62 (m, 2H), 2.00 (m, 6H), 2.93 (m, 2H), 3.02 (m, 2H), 3.07 (m, 7H), 3.16 (m, 3H), 3.42 (m, 2H), 3.48 (m, 2H), 3.89 (s, 3H), 4.42 (q, 2H, J = 14.4 Hz), 7.02 (dd, 2H, J = 7.8, 1.8 Hz), 7.85 (dd, 2H, J = 7.2, 1.8 Hz), 8.14 (d, 1H, J = 9 Hz), 8.33 (dd, 1H, J = 8.4, 1.8 Hz), 8.99 (d, 1H, J = 1.28 Hz), 9.20 (s, 1H) |
| 180 | 567 | ¹HNMR (600 MHz, CDCl₃, 25° C.): 1.43 (t, 6H, J = 7.2 Hz), 1.99 (m, 2H), 2.13 (m, 4H), 2.92 (m, 2H), 3.02 (m, 2H), 3.18 (m, 2H), 3.27 (m, 2H), 3.38 (m, 4H), 3.43 (m, 2H), 3.48 (m, 2H), 3.88 (s, 3H), 4.22 (q, 2H, J = 14.4 Hz), 7.02 (d, 2H, J = 9 Hz), 7.84 (m, 2H), 8.14 (d, 1H, J = 8.4 Hz), 8.33 (dd, 1H, J = 9, 1.8 Hz), 9.00 (s, 1H), 9.21 (s, 1H) |
| 181 | 623 | ¹HNMR (600 MHz, CDCl₃, 25° C.): 0.96 (t, 3H, J = 7.8 Hz), 1.44 (t, 3H, 7.2 Hz), 1.47 (m, 2H), 1.64 (m, 2H), 1.77 (m, 2H), 2.00 (m, 6H), 3.00 (m, 2H), 3.21 (m, 8H), 3.24 (m, 2H), 3.44 (m, 2H), 3.53 (m, 2H), 4.02 (t, 2H, J = 6.6 Hz), 4.28 (q, 2H, J = 14.4 Hz), 7.01 (d, 2H, J = 9 Hz), 7.83 (d, 2H, J = 9 Hz), 8.13 (d, 1H, J = 9 Hz), 8.33 (dd, 1H, J = 8.4, 1.2 Hz), 8.96 (s, 1H), 9.14 (s, 1H) |
| 182 | 609 | ¹HNMR (600 MHz, CDCl₃, 25° C.): 0.96 (t, 6H, J = 7.2 Hz), 1.43 (t, 3H, J = 7.2 Hz), 1.46 (m, 2H), 1.73 (m, 2H), 1.96 (m, 2H), 2.11 (m, 4H), 2.89 (m, 2H), 2.97 (m, 2H), 3.14 (m, 2H), 3.23 (m, 2H), 3.55 (m, 4H), 3.42 (m, 2H), 3.47 (m, 2H), 4.01 (t, 2H, J = 6.6 Hz), 4.20 (q, 2H, J = 1.8 Hz), 6.99 (d, 2H, J = 8.4 Hz), 7.82 (d, 2H, J = 8.4 Hz), 8.13 (d, 1H, J = 8.4 Hz), 8.33 (dd, 1H, J = 9, 1.2 Hz)9.02 (s, 1H), 9.22 (s, 1H) |
| 183 | 439 | ¹HNMR (600 MHz, CDCl₃, 25° C.): 1.33 (t, 3H, J = 7.2 Hz), 3.82 (s, 3H), 4.34 (q, 2H, J = 14.4 Hz), 6.86 (dd, 2H, J = 7.2, 2.4 Hz), 7.43 (dd, 2H, J = 7.2, 1.2 Hz), 7.90 (d, 1H, J = 1.8 Hz), 8.15 (s, 1H), 8.03 (d, 1H, J = 9 Hz), 8.46 (dd, 1H, J = 9, 1.8 Hz), 8.66 (s, 1H), 9.81 (s, 1H) |
| 184 | 439 | ¹HNMR (600 MHz, CDCl₃, 25° C.): 1.32 (t, 3H, J = 7.2 Hz), 3.82 (s, 3H), 4.34 (q, 2H, J = 14.4 Hz), 6.89 (dd, 2H, J = 7.2, 2.4 Hz), 7.45 (dd, 2H, J = 7.2, 1.2 Hz), 7.68 (d, 1H, J = 1.2 Hz), 8.07 (d, 1H, J = 1.2 Hz), 8.20 (d, 1H, J = 1.2 Hz), 8.30 (d, 1H, J = 9 Hz), 8.46 (dd, 1H, J = 8.4, 1.8 Hz), 9.79 (s, 1H) |
| 185 | 440 | ¹HNMR (600 MHz, D₆-DMSO, 25° C.): 1.27 (t, 3H, J = 7.2 Hz), 3.84 (s, 3H), 4.31 (q, 2H, J = 13.2 Hz), 7.15 (dd, 2H, J = 9, 1.8 Hz), 7.51 (d, 1H, J = 1.2 Hz), 7.69 (dd, 2H, J = 7.2, 1.8 Hz), 8.45 (d, 1H, J = 3 Hz), 8.50 (dd, 1H, J = 9, 1.8 Hz), 9.83 (s, 1H), 10.01 (s, 1H) |
| 186 | 482 | ¹HNMR (600 MHz, D₆-DMSO, 25° C.): 0.90 (t, 3H, J = 7.8 Hz), 1.27 (t, 3H, J = 7.2 Hz), 1.39 (m, 2H), 1.68 (m, 2H), 4.06 (t, 2H, J = 7.2 Hz)), 4.31 (q, 2H, J = 14.4 Hz), 7.14 (dd, 2H, J = 6.6, 1.8 Hz), 7.51 (d, 1H, J = 1.8 Hz), 7.69 (dd, 2H, J = 7.2, 2.4 Hz), 8.45 (d, 1H, J = 9 Hz), 8.50 (dd, 1H, J = 9, 1.8 Hz), 9.83 (s, 1H), 10.01 (s, 1H) |
| 187 | N/A | ¹HNMR (600 MHz, CDCl₃, 25° C.): 0.96 (t, 3H, J = 7.2 Hz), 1.46 (m, 2H), 1.77 (m, 2H), 2.62 (m, 4H), 3.47 (m, 4H), 4.01 (q, 2H, J = 6.6 Hz), 6.99 (m, 2H), 7.66 (dd, 1H, J = 9, 2.4 Hz), 7.78 (m, 2H), 8.03 (m, 1H), 8.23 (d, 1H, J = 9.6 Hz), 9.35 (s, 1H) |
| 188 | 481 | ¹HNMR (600 MHz, CDCl₃, 25° C.): 0.94 (t, 3H, J = 7.2 Hz), 1.33 (t, 3H, J = 7.2 Hz), 1.43 (m, 2H), 1.73 (m, 2H), 3.57 (t, 2H, J = 6.6 Hz), 4.34 (q, 2H, J = 14.4 Hz), 6.84 (d, 2H, J = 9 Hz), 7.42 (d, 2H, J = 9 Hz), 7.90 (d, 1H, J = 1.8 Hz), 8.15 (s, 1H), 8.30 (d, 1H, J = 9 Hz), 8.46 (dd, 1H, J = 9, 1.8 Hz), 8.67 (s, 1H), 9.17 (s, 1H) |

TABLE 2-continued

| No | MS (m/z) | ¹H NMR |
|---|---|---|
| 189 | 481 | ¹HNMR (600 MHz, CDCl₃, 25° C.): 0.93 (t, 3H, J = 7.2 Hz), 1.33 (t, 3H, J = 7.2 Hz), 1.42 (m, 2H), 1.72 (m, 2H), 3.95 (t, 2H, J = 6.6 Hz), 4.33 (q, 2H, J = 14.4 Hz), 6.87 (d, 2H, J = 9 Hz), 7.44 (d, 2H, J = 9 Hz), 7.69 (d, 1H, J = 1.2 Hz), 7.63 (s, 1H), 8.08 (s, 1H), 8.20 (s, 1H), 8.30 (d, 1H, J = 9 Hz), 8.47 (dd, 1H, J = 8.4, 1.8 Hz), 9.80 (s, 1H) |
| 190 | 494 | ¹HNMR (600 MHz, CDCl₃, 25° C.): 0.94 (t, 3H, J = 7.2 Hz), 1.34 (t, 3H, J = 7.2 Hz), 1.45 (m, 2H), 1.73 (m, 2H), 2.31 (s, 3H), 3.95 (m), 4.35 (q, 2H, J = 14.4 Hz), 6.51 (s, 1H), 6.83 (d, 2H, J = 9 Hz), 7.38 (d, 1H, J = 0.6 Hz), 7.41 (d, 2H, J = 9 Hz), 7.92 (d, 1H, J = 1.2 Hz), 8.28 (d, 1H, J = 9 Hz), 8.44 (dd, 1H, J = 8.4, 1.8 Hz), 9.84 (s, 1H) |
| 191 | 515 | ¹HNMR (600 MHz, CDCl₃, 25° C.): 0.95 (t, 3H, J = 7.8 Hz), 1.44 (t, 3H, J = 7.2 Hz)1.47 (m, 2H), 1.77 (m, 2H), 2.66 (m, 4H), 3.56 (m, 4H), 4.01 (t, 2H, J = 6.6 Hz), 4.45 (q, 2H, J = 14.4 Hz), 6.99 (dd, 2H, J = 7.2, 1.8 Hz), 7.79 (dd, 2H, J = 7.2, 2.4 Hz), 8.19 (d, 1H, J = 8.4 Hz), 8.36 (dd, 1H, J = 9, 1.8 Hz), 8.97 (d, 1H, J = 1.2 Hz), 9.38 (s, 1H) |
| 192 | 540 | ¹HNMR (600 MHz, CDCl₃, 25° C.): 0.96 (t, 3H, J = 7.8 Hz), 1.33 (d, 6H, J = 6.6 Hz), 1.47 (m, 2H), 1.77 (m, 2H), 2.16 (m, 2H), 2.68 (m, 2H), 2.83 (s, 3H), 3.09 (m, 3H), 3.58 (m, 3H), 4.02 (t, 2H, J = 6.6 Hz), 4.37 (m, 1H), 7.01 (d, 2H, J = 9 Hz), 7.84 (d, 2H, J = 8.4 Hz), 8.15 (d, 1H, J = 9 Hz), 8.30 (d, 1H, J = 8.4 Hz), 8.80 (s, 1H), 9.02 (m, 1H) |
| 194 | 481 | ¹HNMR (600 MHz, CDCl₃, 25° C.): 0.93 (t, 3H, J = 7.2 Hz), 1.32 (t, 3H, J = 7.2 Hz), 1.43 (m, 2H), 1.72 (m, 2H), 3.95 (m, 2H), 4.33 (q, 2H, J = 14.4 Hz), 6.82 (d, 2H, J = 8.4 Hz), 6.90 (s, 1H), 7.27 (s, 1H), 7.38 (d, 2H, J = 2.4 Hz), 7.44 (s, 1H), 7.83 (s, 1H), 8.29 (d, 1H, J = 9 Hz), 8.44 (d, 1H, J = 9 Hz), 9.83 (m, 1H) |
| 195 | 531 | ¹HNMR (600 MHz, CDCl₃, 25° C.): 0.97 (t, 3H, J = 7.8 Hz), 1.44 (t, 3H, J = 7.2 Hz), 1.48 (m, 2H), 1.78 (m, 2H), 2.86 (m, 4H), 3.24 (m, 2H), 4.03 (t, 2H, J = 6.6 Hz), 4.29 (m, 2H), 4.45 (q, 2H, J = 13.8 Hz), 7.02 (d, 2H, J = 8.4 Hz), 7.80 (d, 2H, J = 9 Hz), 8.24 (d, 1H, J = 9 Hz), 8.41 (dd, 1H, J = 9, 1.8 Hz), 8.95 (s, 1H), 9.21 (s, 1H) |
| 196 | 547 | ¹HNMR (600 MHz, CDCl₃, 25° C.): 0.97 (t, 3H, J = 7.2 Hz), 1.45 (t, 3H, J = 7.2 Hz), 1.48 (m, 2H), 1.78 (m, 2H), 3.13 (m, 4H), 3.78 (m, 4H), 4.04 (t, 2H, J = 6.6 Hz), 4.46 (q, 2H, J = 14.4 Hz), 7.05 (d, 2H, J = 9 Hz), 7.81 (d, 2H, J = 8.4 Hz), 8.26 (d, 1H, J = 9 Hz), 8.43 (dd, 1H, J = 9, 1.8 Hz), 8.77 (d, 1H, J = 1.2 Hz), 9.17 (s, 1H) |
| 197 | 543 | ¹HNMR (600 MHz, CDCl₃, 25° C.): 0.97 (t, 3H, J = 7.2 Hz), 1.48 (m, 2H), 1.77 (m, 2H), 2.84 (m, 4H), 3.10 (m, 2H), 4.02 (q, 2H, J = 6.6 Hz), 4.24 (m, 2H), 7.01 (d, 2H, J = 9 Hz), 7.71 (dd, 1H, J = 9, 1.2 Hz), 7.78 (m, 2H), 8.04 (s, 1H), 8.26 (d, 1H, J = 9.6 Hz), 9.16 (s, 1H) |
| 198 | 559 | ¹HNMR (600 MHz, CDCl₃, 25° C.): 0.96 (t, 3H, J = 7.8 Hz), 1.48 (m, 2H), 1.79 (m, 2H), 3.06 (m, 4H), 3.75 (m, 4H), 4.04 (q, 2H, J = 6.6 Hz), 7.05 (dd, 2H, J = 7.2, 2.4 Hz), 7.73 (dd, 1H, J = 9, 1.2 Hz), 7.80 (m, 3H), 8.27 (d, 1H, J = 9 Hz), 9.10 (s, 1H) |
| 199 | 553 | ¹HNMR (600 MHz, CDCl₃, 25° C.): 0.95 (t, 6H, J = 7.2 Hz), 1.16 (m, 3H), 1.28 (m, 3H), 1.47 (m, 2H), 1.77 (m, 2H), 2.08 (m, 2H), 2.54 (s, 3H), 3.00 (m, 4H), 3.25 (m, 2H), 3.40 (m, 2H), 3.59 (m, 4H), 4.01 (t, 2H, J = 6 Hz), 7.00 (d, 2H, J = 9 Hz), 7.75 (dd, 1H, J = 8.4, 1.2 Hz), 7.83 (d, 2H, J = 9 Hz), 8.14 (d, 1H, J = 8.4 Hz), 8.23 (s, 1H), 9.02 (m, 1H) |
| 200 | 542 | ¹HNMR (600 MHz, CDCl₃, 25° C.): 0.96 (t, 6H, J = 7.2 Hz), 1.47 (m, 2H), 1.76 (m, 2H), 2.10 (m, 2H), 2.62 (s, 3H), 3.53 (m, 4H), 3.68 (m, 2H), 3.85 (m, 2H), 4.01 (t, 2H, J = 6 Hz), 7.0 (d, 2H, J = 9 Hz), 7.83 (d, 2H, J = 9 Hz), 7.96 (m, 1H), 8.15 (d, 1H, J = 9 Hz), 8.37 (dd, 1H, J = 9, 1.8 Hz), 8.94 (s, 1H), 9.10 (s, 1H) |
| 201 | 608 | ¹HNMR (600 MHz, CDCl₃, 25° C.): 0.96 (t, 3H, J = 7.2 Hz), 1.13 (m, 3H), 1.30 (m, 3H), 1.49 (m, 2H), 1.73 (m, 16H), 2.74 (m, 1H), 3.26 (m, 4H), 3.50 (m, 2H), 3.61 (m, 2H), 4.01 (t, 2H, J = 6.6 Hz), 6.98 (d, 2H, J = 9 Hz), 7.75 (dd, 1H, J = 8, 1.8 Hz), 7.78 (d, 2H, J = 9 Hz), 8.09 (s, 1H), 8.17 (d, 1H, J = 8.4 Hz), 9.21 (m, 1H) |
| 202 | 597 | ¹HNMR (600 MHz, CDCl₃, 25° C.): 0.94 (t, 3H, J = 7.2 Hz), 1.24 (m, 2H), 1.45 (m, 4H), 1.61 (m, 2H), 1.75 (m, .2H), 1.94 (m, 6H), 2.19 (m, 3H), 2.81 (m, 2H), 2.94 (m, 2H), 3.62 (m, 2H), 3.83 (m, 2H), 3.94 (t, 2H, J = 6.6 Hz), 4.22 (m, 1H), 6.88 (d, 2H, J = 9 Hz), 7.74 (d, 2H, J = 7.8 Hz), 8.13 (m, 1H), 8.41 (d, 1H, J = 8.4 Hz), 8.99 (s, 1H), 9.47 (m, 1H) |
| 206 | 597 | ¹HNMR (600 MHz, CDCl₃, 25° C.): 0.96 (t, 3H, J = 7.2 Hz), 1.49 (m, 2H), 1.60 (m, 2H), 1.78 (m, 2H), 1.92 (m, 4H), 2.20 (m, 2H), 2.62 (s, 3H), 3.01 (m, 4H), 3.15 (m, 4H), 3.31 (m, 4H), 3.95 (m, 2H), 3.63 (m, 2H), 4.03 (t, 2H, J = 6.6 Hz), 7.03 (d, 2H, J = 9 Hz), 7.64 (dd, 1H, J = 9, 1.8 Hz), 7.73 (s, 1H), 7.82 (d, 2H, J = 9 Hz), 7.99 (d, 1H, J = 9 Hz), 8.76 (s, 1H) |

TABLE 2-continued

| No | MS (m/z) | ¹H NMR |
|---|---|---|
| 207 | 583 | ¹HNMR (600 MHz, CDCl₃, 25° C.): 0.96 (t, 3H, J = 7.2 Hz), 1.47 (m, 2H), 1.76 (m, 2H), 1.83 (m, 6H), 2.05 (m, 2H), 2.59 (s, 3H), 2.80 (m, 10H), 3.29 (m, 4H), 3.99 (t, 2H, J = 6.6 Hz), 6.96 (d, 2H, J = 9 Hz), 7.63 (dd, 1H, J = 8.4, 1.8 Hz), 7.82 (d, 2H, J = 9 Hz), 7.97 (d, 1H, J = 1.2 Hz), 8.00 (d, 1H, J = 9 Hz), 9.21 (s, 1H) |
| 208 | 587 | ¹HNMR (600 MHz, CDCl₃, 25° C.): 0.96 (t, 3H, J = 7.2 Hz), 1.47 (m, 2H), 1.50 (m, 3H), 1.71 (m, 10H), 2.43 (m, 1H), 2.59 (m, 4H), 2.80 (s, 3H), 3.30 (m, 2H), 3.42 (m, 2H), 3.86 (m, 1H), 4.01 (t, 2H, J = 6.6 Hz), 6.96 (d, 2H, J = 7.2 Hz), 7.75 (dt, 1H, J = 9, 1.8 Hz), 7.79 (dd, 2H, J = 9, 1.8 Hz), 8.22 (dd, 1H, J = 9, 1.8 Hz), 8.58 (dd, 1H, J = 11.4, 1.2 Hz), 9.31 (d, 1H, J = 9.6 Hz) |
| 209 | 613 | ¹HNMR (600 MHz, CDCl₃, 25° C.): 0.96 (t, 3H, J = 7.8 Hz), 1.48 (m, 4H), 1.77 (m, 6H), 1.91 (m, 2H), 2.50 (m, 2H), 2.74 (m, 4H), 2.80 (s, 3H), 2.85 (m, 6H), 3.36 (m, 2H), 3.41 (m, 2H), 4.00 (t, 2H, J = 6.6 Hz), 6.98 (d, 2H, J = 9 Hz), 7.83 (d, 2H, J = 9 Hz), 7.89 (dd, 1H, J = 9.6, 1.8 Hz), 8.25 (d, 1H, J = 8.4 Hz), 8.77 (d, 1H, J = 1.2 Hz), 9.33 (s, 1H) |
| 210 | 599 | ¹HNMR (600 MHz, CDCl₃, 25° C.): 0.95 (t, 2H, J = 7.2 Hz), 1.46 (m, 2H), 1.76 (m, 2H), 1.83 (m, 4H), 2.72 (m, 2H), 2.80 (, s, 3H), 2.82 (m, 6H), 3.55 (m, 2H), 3.42 (m, 2H), 4.00 (t, 2H, J = 6.6 Hz), 6.97 (dd, 2H, J = 6.6, 1.8 Hz), 7.82 (dd, 2H, J = 7.2, 3 Hz), 7.91 (dd, 1H, J = 8.4, 1.8 Hz), 8.25 (d, 1H, J = 9 Hz), 8.78 (d, 1H, J = 1.8 Hz), 9.36 (s, 1H). |
| 211 | 609 | ¹HNMR (600 MHz, CDCl₃, 25° C.): 0.94 (t, 6H, J = 7.2 Hz), 1.42 (t, 3H, J = 7.2 Hz), 1.46 (m, 2H), 1.76 (m, 6H), 2.75 (m, 2H), 2.79 (s, 3H), 2.82 (m, 2H), 2.95 (m, 2H), 3.08 (m, 2H), 3.17 (m, 2H), 3.29 (m, 2H), 3.39 (m, 2H), 3.45 (m, 2H), 4.00 (t, 2H, J = 6 Hz), 4.41 (d, 2H, J = 14.4 Hz), 6.97 (d, 2H, J = 9 Hz), 7.77 (d, 2H, J = 7.2, 2.4 Hz), 8.11 (d, 1H, J = 9 Hz), 8.32 (dd, 1H, J = 8.4, 1.2 Hz), 8.89 (d, 1H, J = 1.2 Hz), 9.18 (s, 1H) |
| 212 | 582 | ¹HNMR (600 MHz, CDCl₃, 25° C.): 0.96 (t, 3H, J = 7.8 Hz), 1.40 (t, 3H, J = 7.8 Hz), 1.48 (m, 2H), 1.72 (m, 4H), 1.87 (m, 2H), 2.53 (m, 1H), 2.62 (m, 4H), 3.38 (m, 2H), 3.47 (m, 2H), 3.77 (m, 4H), 4.01 (t, 2H, J = 6.6 Hz), 4.27 (q, 2H, J = 14.4 Hz), 6.96 (dd, 2H, J = 6.6, 1.8 Hz), 7.80 (dd, 2H, J = 7.2, 2.4 Hz), 8.10 (d, 1H, J = 8.4 Hz), 8.32 (dd, 1H, J = 8.4, 1.8 Hz), 8.94 (dd, 1H, J = 1.2 Hz), 9.21 (s, 1H). |
| 213 | 675 | ¹HNMR (600 MHz, CDCl₃, 25° C.): 0.96 (t, 3H, J = 7.2 Hz), 1.43 (t, 3H, J = 6.6 Hz), 1.48 (m, 2H), 1.72 (m, 4H), 1.83 (m, 2H), 2.66 (m, 1H), 2.82 (m, 3H), 3.19 (m, 3H), 3.40 (m, 2H), 3.51 (m, 2H), 4.00 (t, 2H, J = 6.6 Hz), 4.42 (q, 2H, J = 14.4 Hz), 6.89 (m, 2H), 6.96 (m, 4H), 7.82 (dd, 2H, J = 7.2, 1.8 Hz), 8.11 (d, 1H, J = 8.4 Hz), 8.33 (dd, 1H, J = 9, 1.8 Hz), 8.96 (s, 1H), 9.21 (s, 1H) |
| 214 | 625 | ¹HNMR (600 MHz, CDCl₃, 25° C.): 0.96 (t, 6H, J = 7.2 Hz), 1.43 (t, 2H, J = 7.2 Hz), 1.46 (m, 2H), 1.75 (m, 4H), 1.88 (m, 2H), 2.62 (m, 2H), 2.69 (m, 2H), 2.77 (m, 7H), 3.38 (m, 4H), 3.70 (m, 2H), 4.00 (t, 2H, J = 6.6 Hz), 4.42 (q, 2H, J = 13.2 Hz), 6.97 (d, 2H, J = 9 Hz), 7.90 (dd, 2H, J = 11.4, 2.4 Hz), 8.11 (d, 1H, J = 9 Hz), 8.32 (dd, 1H, J = 8.4, 1.8 Hz), 8.94 (d, 1H, J = 1.2 Hz), 9.24 (s, 1H). |
| 215 | 672 | ¹HNMR (600 MHz, CDCl₃, 25° C.): 0.96 (t, 3H, J = 7.2 Hz), 1.43 (t, 3H, J = 6.6 Hz), 1.47 (m, 2H), 1.76 (m, 2H), 1.85 (m, 4H), 1.98 (m, 2H), 2.34 (m, 2H), 2.83 (m, 5H), 3.35 (m, 2H), 3.51 (m, 2H), 4.00 (t, 2H, J = 6.6 Hz), 4.43 (q, 2H, J = 13.8 Hz), 6.97 (d, 2H, J = 9 Hz), 7.27 (d, 1H, J = 7.2 Hz), 7.35 (d, 2H, J = 7.8 Hz), 7.54 (d, 2H, J = 7.2 Hz), 7.80 (m, 2H), 8.12 (d, 1H, J = 8.4 Hz), 8.33 (dd, 1H, J = 9, 1.8 Hz), 8.94 (s, 1H), 9.22 (s, 1H) |
| 216 | 663 | ¹HNMR (600 MHz, CDCl₃, 25° C.): 0.92 (t, 6H, J = 7.8 Hz), 1.39 (t, 3H, J = 7.2 Hz), 1.43 (m, 2H), 1.61 (m, 2H), 1.72 (m, 4H), 1.84 (m, 2H), 1.95 (m, 6H), 2.24 (m, 2H), 2.45 (m, 2H), 2.72 (m, 1H), 3.07 (m, 6H), 3.20 (m, 2H), 3.31 (m, 2H), 3.41 (m, 2H), 3.97 (t, 2H, J = 6.6 Hz), 4.39 (q, 2H, J = 13.8 Hz), 6.95 (d, 2H, J = 9 Hz), 7.76 (d, 2H, J = 9 Hz), 8.09 (d, 1H, J = 8.4 Hz), 8.29 (dd, 1H, J = 8.4, 1.8 Hz), 8.86 (d, 1H, J = 1.8 Hz), 9.19 (s, 1H). |
| 217 | 598 | ¹HNMR (600 MHz, CDCl₃, 25° C.): 0.97 (t, 3H, J = 7.2 Hz), 1.43 (t, 3H, J = 7.2 Hz), 1.46 (m, 2H), 1.76 (m, 8H), 2.72 (m, 3H), 3.03 (m, 4H), 3.37 (m, 2H), 3.54 (m, 2H), 4.01 (t, 2H, J = 6.6 Hz), 4.44 (1, 2H, J = 14.4 Hz), 6.98 (d, 2H, J = 9 Hz), 7.79 (m, 2H), 8.13 (d, 1H, J = 9 Hz), 8.34 (dd, 1H, J = 9, 1.8 Hz), 8.88 (m, 1H), 9.17 (m, 1H) |
| 218 | 543 | ¹HNMR (600 MHz, CDCl₃, 25° C.): 0.88 (t, 3H, J = 7.2 Hz), 1.29 (m, 4H), 1.33 (m, 4H), 1.44 (m, 2H), 1.79 (m, 3H), 2, 13 (m, 2H), 2.62 (s, 6H), 2.95 (m, 3H), 3.40 (m, 4H), 4.01 (t, 2H, J = 6 Hz), 7.01 (d, 2H, J = 9 Hz), 7.63 (d, 1H, J = 9, 2.4 Hz), 7.85 (d, 3H, J = 9 Hz), 7.99 (d, 1H, J = 9 Hz), 8.96 (m, 1H) |

TABLE 2-continued

| No | MS (m/z) | ¹H NMR |
|---|---|---|
| 219 | 596 | ¹HNMR (600 MHz, CDCl₃, 25° C.): 0.85 (t, 3H, J = 6.6 Hz), 1.26 (m, 6H), 1.40 (m, 2H), 1.51 (m, 2H), 1.69 (m, 8H), 1.87 (m, 2H), 2.58 (s, 3H), 2.69 (m, 5H), 3.19 (m, 2H), 3.40 (m, 2H), 3.97 (t, 2H, J = 6.6 Hz), 6.93 (m, 2H), 7.62 (dd, 1H, J = 8.4, 1.8 Hz), 7.76 (m, 3H), 7.98 (d, 1H, J = 8.4 Hz), 9.11 (s, 1H). |
| 220 | 558 | ¹HNMR (600 MHz, CDCl₃, 25° C.): 0.86 (t, 3H, J = 6.6 Hz), 1.26 (m, 4H), 1.35 (m, 2H), 1.42 (m, 2H), 1.79 (m, 2H), 2, 43 (m, 2H), 2.80 (s, 3H), 2.84 (s, 3H), 3.34 (m, 2H), 3.52 (m, 4H), 3.82 (m, 2H), 4.03 (t, 2H, J = 6 Hz), 7.06 (dd, 2H, J = 7.2, 2.4 Hz), 7.86 (dd, 2H, J = 6.6, 1.8 Hz), 7.98 (dd1H, J = 9, 1.8 Hz), 8.27 (d, 1H, J = 9 Hz), 8.43 (d, 1H, J = 1.8 Hz), 8.72 (s, 1H). |
| 221 | 612 | ¹HNMR (600 MHz, CDCl₃, 25° C.): 0.86 (t, 3H, J = 6.6 Hz), 1.26 (m, 6H), 1.41 (m, 2H), 1.55 (m, 2H), 1.77 (m, 2H), 1.86 (m, 6H), 2.02 (m, 2H), 2.81 (m, 8H), 3.32 (m, 2H), 3.49 (m, 2H), 3.99 (t, 2H, J = 6.6 Hz), 6.99 (d, 2H, J = 9 Hz), 7.79 (dd, 3H, J = 9, 1.8 Hz), 8.22 (d, 1H, J = 9 Hz), 8.53 (d, 1H, J = 81.2 Hz), 9.26 (s, 1H). |
| 222 | 570.3 | ¹HNMR (600 MHz, CDCl₃, 25° C.): 0.96 (t, 3H, J = 7.2 Hz), 1.46 (m, 2H), 1.52 (m, 6H), 1.78 (m, 4H), 1.90 (m, 2H), 2.55 (s, 3H), 2.65 (m, 4H), 3.21 (m, 2H), 3.42 (m, 2H), 3.95 (m, 1H), 4.01 (t, 2H, J = 6.6 Hz), 6.96 (d, 2H, J = 9 Hz), 7.64 (dd, 1H, J = 9, 1.8 Hz), 7.78 (m, 3H), 8.01 (d, 1H, J = 9 Hz), 9.13 (s, 1H) |
| 223 | 612.3 | ¹HNMR (600 MHz, CDCl₃, 25° C.): 0.87 (t, 3H, J = 7.2 Hz), 1.28 (m, 6H), 1.43 (m, 2H), 1.78 (m, 6H), 1.95 (m, 2H), 2.19 (m, 4H), 2.60 (s, 3H), 2.73 (m, 2H), 3.10 (m, 2H), 3.24 (m, 2H), 3.45 (t, 2H, J = 11.4 Hz), 3.92 (m, 1H), 3.99 (t, 2H, J = 6.6 Hz), 6.97 (d, 2H, J = 8.4 Hz), 7.65 (dd, 1H, J = 8.4, 1.2 Hz), 7.77 (m, 3H), 8.01 (dd, 1H, J = 8.4 Hz), 9.07 (s, 1H). |
| 225 | 485.1 | ¹HNMR (600 MHz, CDCl₃, 25° C.): 1.43 (t, 3H, J = 7.2 Hz), 2.38 (s, 3H), 2.89 (m, 8H), 3.82 (s, 3H), 4.41 (q, 2H, J = 14.4 Hz), 6.94 (d, 2H, J = 9 Hz), 7.83 (dd, 2H, J = 6.6, 1.8 Hz), 7.90 (d, 1H, J = 9 Hz), 8.26 (dd, 1H, J = 9, 1.8 Hz), 8.49 (s, 1H), 9.08 (s, 1H), 10.29 (d, 1H, J = 1.8 Hz). |
| 226 | 459.1 | ¹HNMR (600 MHz, CDCl₃, 25° C.): 2.37 (s, 3H), 2.56 (s, 3H), 2.67 (m, 4H), 2.94 (m, 4H), 3.82 (s, 3H), 6.93 (dd, 2H, J = 8.4, 1.8 Hz), 7.56 (dd, 1H, J = 9, 2.4 Hz), 7.82 (d, 3H, J = 9 Hz), 8.26 (m, 1H), 8.94 (s, 1H), 9.18 (d, 1H, J = 1.8 Hz). |
| 227 | 475.1 | ¹HNMR (600 MHz, CDCl₃, 25° C.): 2.35 (s, 3H), 2.56 (m, 2H), 2.74 (s, 3H), 2.87 (m, 6H), 3.81 (s, 3H), 6.93 (d, 2H, J = 9 Hz), 7.72 (dd, 1H, J = 9, 2.4 Hz), 7.82 (d, 2H, J = 9 Hz), 7.99 (d, 1H, J = 9 Hz), 8.44 (s, 1H), 9.05 (s, 1H), 9.94 (d, 1H, J = 1.8 Hz). |
| 228 | 491.1 | ¹HNMR (600 MHz, CDCl₃, 25° C.): 2.41 (s, 3H), 2.59 (m, 2H), 2.91 (m, 6H), 3.09 (s, 3H), 3.83 (s, 3H), 6.95 (dd, 2H, J = 7.2, 2.4 Hz), 7.84 (dd, 2H, J = 7.2, 1.8 Hz), 8.04 (dd, 2H, J = 17.4, 8.4 Hz)8.59 (s, 1H), 9.12 (s, 1H), 10.34 (d, 1H, J = 1.8 Hz). |
| 229 | 556.2 | ¹HNMR (600 MHz, CDCl₃, 25° C.): 0.96 (t, 3H, J = 7.8 Hz), 1.45 (m, 2H), 1.62 (m, 2H), 1.75 (m, 2H), 1.81 (m, 2H), 2.44 (m, 1H), 2.59 (m, 7H), 3.25 (m, 2H), 3.35 (m, 2H), 3.77 (m, 4H), 3.99 (t, 2H, J = 6.6 Hz), 6.95 (d, 2H, J = 9 Hz), 7.64 (dd, 1H, J = 9, 1.8 Hz), 7.79 (m, 2H), 7.86 (m, 1H), 8.00 (d, 1H, J = 8.4 Hz), 9.15 (s, 1H). |
| 230 | 596.2 | ¹HNMR (600 MHz, CDCl₃, 25° C.): 0.96 (t, 3H, J = 7.8 Hz), 1.45 (m, 2H), 1.62 (m, 2H), 1.75 (m, 2H), 1.81 (m, 2H), 2.47 (m, 1H), 2.57 (m, 12H), 3.23 (m, 2H), 3.38 (m, 2H), 3.64 (t, 2H, J = 9 Hz), 4.01 (t, 2H, J = 6.6 Hz), 6.95 (d, 2H, J = 9 Hz), 7.64 (dd, 1H, J = 9, 1.8 Hz), 7.79 (d, 2H, J = 8.4 Hz), 7.85 (d, 1H, J = 1.2 Hz), 8.00 (d, 1H, J = 9 Hz), 9.15 (m, 1H). |
| 231 | 637 | ¹HNMR (600 MHz, CDCl₃, 25° C.): 0.95 (t, 3H, J = 7.8 Hz), 1.46 (m, 2H), 1.62 (m, 4H), 1.75 (m, 6H), 1.93 (m, 4H), 2.13 (m, 2H), 2.31 (m, 2H), 2.73 (m, 1H), 2.89 (m, 3H), 3.09 (m, 2H), 3.18 (m, 2H), 3.92 (m, 2H), 3.99 (t, 2H, J = 6 Hz), 6.94 (dd, 2H, J = 11.4, 3 Hz), 7.63 (dd, 1H, J = 9, 1.8 Hz), 7.76 (m, 3H), 7.99 (d, 1H, J = 2.4 Hz), 9.12 (m, 1H). |
| 232 | 646.3 | ¹HNMR (600 MHz, CDCl₃, 25° C.): 0.96 (t, 3H, J = 7.2 Hz), 1.41 (m, 2H), 1.63 (m, 4H), 1.71 (m, 2H), 1.83 (m, 4H), 2.21 (m, 2H), 2.60 (s, 3H), 2.76 (m, 2H), 2.88 (m, 2H), 3.24 (m, 2H), 3.42 (m, 2H), 4.00 (t, 3H, J = 6.6 Hz), 6.95 (m, 2H), 7.28 (m, 1H), 7.36 (t, 2H, J = 8.4 Hz), 7.54 (m, 2H), 7.64 (dd, 1H, J = 9, 1.8 Hz), 7.80 (m, 2H), 7.87 (m, 1H), 8.01 (d, 1H, J = 8.4 Hz), 9.16 (m, 1H). |
| 233 | 649.2 | ¹HNMR (600 MHz, CDCl₃, 25° C.): 0.96 (t, 3H, J = 7.2 Hz), 1.46 (m, 2H), 1.68 (m, 2H), 1.77 (m, 2H), 1.80 (m, 2H), 2.56 (m, 1H), 2.59 (s, 3H), 2.78 (m, 4H), 3.18 (m, 4H), 3.26 (m, 2H), 3.39 (m, 2H), 4.00 (t, 2H, J = 6.6 Hz).6.89 (m, 2H), 6.96 (m, 3H), 7.64 (d, 1H, J = 9 Hz), 7.80 (d, 2H, J = 9 Hz), 7.87 (s, 1H), 8.00 (d, 1H, J = 9 Hz), 9.15 (s, 1H). |

TABLE 2-continued

| No | MS (m/z) | ¹H NMR |
|---|---|---|
| 234 | 583.2 | ¹HNMR (600 MHz, CDCl₃, 25° C.):<br>0.95 (t, 3H, J = 7.2 Hz), 1.46 (m, 2H), 1.58 (m, 2H), 1.75 (m, 4H), 2.10 (m, 2H), 2.58 (s, 3H), 2.61 (s, 3H), 2.91 (m, 7H), 3.18 (m, 2H), 3.40 (m, 2H), 4.00 (t, 2H, J = 6.6 Hz), 6.95 (d, 2H, J = 8.4 Hz), 7.63 (dd, 1H, J = 8.4, 1.8 Hz), 7.76 (d, 3H, J = 9 Hz), 8.00 (d, 1H, J = 9 Hz), 9.10 (m, 1H). |
| 235 | 572.2 | ¹HNMR (600 MHz, CDCl₃, 25° C.):<br>0.96 (t, 3H, J = 7.8 Hz), 1.46 (m, 2H), 1.70 (m, 2H), 1.75 (m, 2H), 1.86 (m, 2H), 2.50 (m, 1H), 2.61 (m, 4H), 2.80 (s, 3H), 3.31 (m, 2H), 3.48 (m, 2H), 3.75 (m, 4H), 4.00 (t, 2H, J = 6.6 Hz), 6.96 (dd, 2H, J = 7.2, 1.8 Hz), 7.77 (m, 3H), 8.21 (d, 1H, J = 9 Hz), 8.58 (d, 1H, J = 1.8 Hz), 9.27 (s, 1H). |
| 236 | 615.3 | ¹HNMR (600 MHz, CDCl₃, 25° C.):<br>0.96 (t, 3H, J = 7.2 Hz), 1.48 (m, 2H), 1.73 (m, 4H), 1.85 (m, 2H), 2.05 (m, 4H), 2.52 (m, 1H), 2.58 (m, 6H), 2.80 (s, 3H), 3.34 (m, 2H), 3.45 (m, 2H), 3.63 (t, 2H, J = 5.4 Hz), 4.00 (t, 2H, J = 6.6 Hz), 6.96 (d, 2H, J = 8.4 Hz), 7.77 (m, 3H), 8.21 (d, 1H, J = 8.4 Hz), 8.58 (d, 1H, J = 1.8 Hz), 9.27 (s, 1H). |
| 237 | 653.3 | ¹HNMR (600 MHz, CDCl₃, 25° C.):<br>0.94 (t, 3H, J = 7.2 Hz), 1.44 (m, 4H), 1.65 (m, 12H), 1.93 (m, 2H), 2.44 (m, 1H), 2.54 (m, 1H), 2.65 (m, 4H), 2.79 (m, 3H), 3.05 (m, 2H), 3.29 (m, 2H), 3.43 (m, 2H), 3.99 (t, 2H, J = 6.6 Hz), 6.95 (d, 2H, J = 9 Hz), 7.76 (m, 3H), 8.20 (d, 1H, J = 9 Hz), 8.55 (d, 1H, J = 1.8 Hz), 9.27 (s, 1H). |
| 238 | 662.2 | ¹HNMR (600 MHz, CDCl₃, 25° C.):<br>0.96 (t, 6H, J = 7.2 Hz), 1.46 (m, 2H), 1.75 (m, 6H), 1.91 (m, 2H), 2.03 (m, 2H), 2.19 (m, 2H), 2.67 (m, 1H), 2.76 (m, 1H), 2.79 (s, 3H), 2.90 (m, 2H), 3.32 (m, 2H), 3.49 (m, 2H), 4.00 (t, 2H, J = 6 Hz), 6.97 (d, 2H, J = 9 Hz), 7.25 (m, 1H), 7.33 (m, 2H), 7.53 (m, 2H), 7.78 (m, 3H), 8.21 (d, 1H, J = 8.4 Hz), 8.58 (d, 1H, 1.8 Hz), 9.27 (s, 1H). |
| 239 | 665.2 | ¹HNMR (600 MHz, CDCl₃, 25° C.):<br>0.95 (t, 3H, J = 7.8 Hz), 1.24 (m, 2H), 1.75 (m, 4H), 1.89 (m, 2H), 2.59 (m, 1H), 2.79 (m, 6H), 3.13 (m, 4H), 3.25 (m, 2H), 3.49 (m, 2H), 3.99 (t, 2H, J = 6.6 Hz), 6.87 (m, 2H), 6.94 (m, 4H), 7.77 (m, 3H), 8.21 (d, 1H, J = 9 Hz), 8.59 (d, 1H, J = 1.8 Hz), 9.26 (s, 1H). |
| 240 | 599.2 | ¹HNMR (600 MHz, CDCl₃, 25° C.):<br>0.95 (t, 3H, J = 7.2 Hz), 1.46 (m, 2H), 1.64 (m, 2H), 1.75 (m, 4H), 1.90 (m, 2H), 2.44 (m, 2H), 2.37 (m, 2H), 2.76 (m, 2H), 2.79 (s, 3H), 2.85 (m, 4H), 3.26 (m, 2H), 3.46 (m, 2H), 3.99 (t, 2H, J = 6.6 Hz), 6.95 (m, 2H), 7.75 (m, 3H), 8.21 (d, 1H, J = 9 Hz), 8.57 (d, 1H, J = 1.8 Hz), 9.30 (s, 1H). |
| 241 | 599.3 | ¹HNMR (600 MHz, CDCl₃, 25° C.):<br>0.96 (t, 3H, J = 7.2 Hz), 1.47 (m, 2H), 1.63 (m, 2H), 1.76 (m, 4H), 1.84 (m, 2H), 2.40 (s, 3H), 2.65 (m, 4H), 2.72 (m, 1H), 2.80 (s, 3H), 2.83 (m, 4H), 3.24 (m, 2H), 3.46 (m, 2H), 4.00 (t, 2H, J = 6.6 Hz), 6.95 (d, 2H, J = 9 Hz), 7.77 (m, 3H), 8.23 (d, 1H, J = 8.4 Hz), 8.57 (d, 1H, J = 1.8 Hz), 9.33 (s, 1H). |
| 242 | 543.2 | ¹HNMR (600 MHz, CDCl₃, 25° C.):<br>1.05 (t, 6H, J = 7.2 Hz), 2.15 (m, 2H), 2.58 (s, 3H), 2.60 (s, 3H), 2.63 (q, 4H, J = 14.4 Hz), 2.86 (m, 2H), 2.98 (m, 2H), 3.07 (m, 2H), 3.35 (m, 2H), 3.53 (m, 2H), 3.76 (t, 2H, J = 7.2 Hz), 4.11 (t, 2H, J = 6 Hz), 7.02 (d, 2H, J = 9 Hz), 7.62 (dd, 1H, J = 8.4, 1.8 Hz), 7.81 (m, 3H), 7.98 (d, 1H, J = 2.4 Hz), 8, 87 (s, 1H). |
| 243 | 572.2 | ¹HNMR (600 MHz, CDCl₃, 25° C.):<br>0.95 (t, 3H, J = 7.2 Hz), 1.47 (m, 2H), 1.61 (m, 2H), 1.76 (m, 2H), 2.58 (s, 3H), 2.69 (m, 4H), 2.88 (m, 5H), 3.17 (m, 4H), 3.39 (m, 2H), 3.99 (t, 2H, J = 6.6 Hz), 6.94 (d, 2H, J = 9 Hz), 7.63 (dd, 1H, J = 9, 1.8 Hz), 7.77 (m, 3H), 7.99 (d, 1H, J = 9 Hz), 9.14 (m, 1H). |
| 244 | 630.2 | ¹HNMR (600 MHz, CDCl₃, 25° C.):<br>0.96 (t, 3H, J = 7.2 Hz), 1.43 (t, 3H, J = 7.2 Hz), 1.47 (m, 2H), 1.76 (m, 2H), 2.05 (m, 2H), 2.46 (m, 2H), 2.91 (m, 2H), 3.31 (m, 2H), 3.46 (m, 2H), 3.55 (m, 4H), 3.82 (m, 2H), 4.00 (m, 2H), 4.20 (t, 2H, J = 12 Hz), 4.43 (q, 2H, J = 14.4 Hz), 6.98 (d, 2H, J = 3 Hz), 7.79 (d, 2H, J = 3 Hz), 8.16 (d, 1H, J = 9 Hz), 8.35 (dd, 1H, J = 8.4, 1.2 Hz), 8.83 (s, 1H), 9.17 (s, 1H). |
| 245 | 588.1 | ¹HNMR (600 MHz, CDCl₃, 25° C.):<br>0.95 (t, 3H, J = 7.2 Hz), 1.46 (m, 2H), 1.74 (m, 2H), 1.96 (m, 2H), 2.80 (s, 3H), 2.69 (m, 4H), 2.92 (m, 3H), 3.28 (m, 2H), 3.34 (m, 2H), 3.43 (m, 2H), 3.48 (m, 2H), 4.00 (t, 2H, J = 6.6 Hz), 6.97 (d, 2H, J = 9 Hz), 7.75 (dd, 1H, J = 9, 1.8 Hz), 7.77 (m, 2H), 8.23 (d, 1H, J = 9 Hz), 8.59 (d, 1H, J = 1.2 Hz), 9.30 (m, 1H). |
| 246 | 611.3 | ¹HNMR (600 MHz, CDCl₃, 25° C.):<br>0.87 (t, 3H, J = 7.2 Hz), 1.27 (m, 7H), 1.41 (m, 2H), 1.64 (m, 2H), 1.76 (m, 4H), 2.34 (s, 3H), 2.49 (m, 4H), 2.55 (s, 3H), 2.68 (m, 4H), 3.21 (m, 2H), 3.37 (m, 2H), 3.98 (t, 2H, J = 6.6 Hz), 6.94 (d, 2H, J = 9 Hz), 7.63 (dd, 1H, J = 8.4, 1.8 Hz), 7.78 (d, 2H, J = 8.4 Hz), 7.83 (d, 1H, J = 1.2 Hz), 7.99 (d, 1H, J = 3 Hz), 9.15 (m, 1H). |
| 247 | 612.3 | ¹HNMR (600 MHz, CDCl₃, 25° C.):<br>0.87 (t, 3H, J = 6.6 Hz), 1.29 (m, 7H), 1.41 (m, 2H), 1.57 (m, 5H), 1.70 (m, 6H), 2.47 (m, 2H), 2.59 (s, 3H), 2.63 (m, 3H), 3.20 (m, 2H), 3.40 |

TABLE 2-continued

| No | MS (m/z) | ¹H NMR |
|---|---|---|
| | | (m, 2H), 3.87 (m, 1H), 3.99 (t, 2H, J = 6.6 Hz), 6.95 (d, 2H, J = 9 Hz), 7.63 (d, 1H, J = 10.2 Hz), 7.76 (m, 3H), 8.00 (d, 1H, J = 9 Hz), 9.16 (m, 1H). |
| 248 | 639.3 | ¹HNMR (600 MHz, CDCl₃, 25° C.): 0.87 (t, 3H, J = 6.6 Hz), 1.30 (m, 9H), 1.43 (m, 2H), 1.53 (m, 2H), 1.79 (m, 6H), 2.04 (m, 2H), 2.61 (s, 3H), 2.78 (m, 5H), 2.98 (m, 6H), 3.34 (m, 2H), 4.00 (t, 2H, J = 6.6 Hz), 6.99 (d, 2H, J = 9 Hz), 7.63 (dd, 1H, J = 8.4, 1.2 Hz), 7.82 (m, 3H), 7.99 (d, 1H, J = 9 Hz), 8.96 (m, 1H). |
| 249 | 625.3 | ¹HNMR (600 MHz, CDCl₃, 25° C.): 0.86 (t, 3H, J = 6.6 Hz), 1.21 (m, 6H), 1.41 (m, 2H), 1.59 (m, 2H), 1.75 (m, 4H), 2.04 (m, 2H), 2.56 (s, 3H), 2.58 (s, 3H), 2.73 (m, 1H), 2.88 (m, 8H), 3.18 (m, 2H), 3.04 (m, 2H), 3.98 (t, 2H, J = 6 Hz), 6.94 (d, 2H, J = 9 Hz), 7.63 (dd, 1H, J = 8.4, 1.8 Hz), 7.76 (m, 3H), 8.00 (d, 1H, J = 9 Hz), 9.11 (m, 1H). |
| 250 | 641 | ¹HNMR (600 MHz, CDCl₃, 25° C.): 0.87 (t, 3H, J = 6.6 Hz), 1.29 (m, 6H), 1.42 (m, 2H), 1.64 (m, 2H), 1.77 (m, 6H), 2.46 (m, 1H), 2.57 (m, 11H), 3.23 (m, 2H), 3.37 (t, 2H, J = 10.8 Hz), 3.63 (t, 2H, J = 11.4 Hz), 3.98 (t, 2H, J = 6.6 Hz), 6.95 (d, 2H, J = 9 Hz), 7.63 (dd, 1H, J = 9, 2.4 Hz), 7.79 (d, 2H, J = 9 Hz), 7.85 (d, 1H, J = 1.8 Hz), 7.99 (d, 1H, J = 8.4 Hz), 9.14 (s, 1H). |
| 251 | 680 | ¹HNMR (600 MHz, CDCl₃, 25° C.): 0.86 (t, 3H, J = 6.6 Hz), 1.25 (m, 6H), 1.40 (m, 2H), 1.58 (m, 4H), 1.76 (m, 6H), 1.91 (m, 4H), 2.12 (m, 2H), 2.28 (m, 2H), 2.56 (m, 1H), 2.58 (s, 3H), 2.76 (m, 5H), 3.08 (m, 2H), 3.19 (m, 2H), 3.39 (t, 2H, J = 10.8 Hz), 3.98 (t, 2H, J = 6.6 Hz), 6.94 (d, 2H, J = 9 Hz), 7.63 (dd, 1H, J = 9, 1.8 Hz), 7.77 (m, 3H), 7.99 (d, 1H, J = 3 Hz), 9.11 (s, 1H). |
| 252 | 529.2 | ¹HNMR (600 MHz, CDCl₃, 25° C.): 0.87 (t, 3H, J = 7.2 Hz), 1.28 (m, 6H), 1.41 (m, 2H), 1.77 (m, 2H), 2.35 (s, 3H), 2.44 (m, 4H), 2.59 (s, 3H), 3.29 (m, 4H), 3.98 (t, 2H, J = 6.6 Hz), 6.94 (dd, 2H, J = 7.2, 2.4 Hz), 7.65 (dd, 1H, J = 8.4, 1.8 Hz), 7.79 (dd, 2H, J = 7.2, 1.8 Hz), 7.92 (d, 1H, J = 1.8 Hz), 8.03 (d, 1H, J = 9 Hz), 9.26 (s, 1H). |
| 253 | 627.3 | ¹HNMR (600 MHz, CDCl₃, 25° C.): 0.85 (t, 3H, J = 7.2 Hz), 1.27 (m, 7H), 1.40 (m, 2H), 1.75 (m, 4H), 1.84 (m, 2H), 2.49 (s, 3H), 2.59 (m, 1H), 2.78 (s, 3H), 2.82 (m, 6H), 3.34 (m, 4H), 3.98 (t, 2H, J = 6.6 Hz), 6.95 (d, 2H, J = 9 Hz), 7.73 (dd, 1H, J = 8.4, 1.8 Hz), 7.78 (d, 2H, J = 8.4 Hz), 8.21 (d, 1H, J = 8.4 Hz), 8.58 (d, 1H, J = 7.8 Hz), 9.32 (m, 1H). |
| 254 | 628.3 | ¹HNMR (600 MHz, CDCl₃, 25° C.): 0.86 (t, 3H, J = 6.6 Hz), 1.29 (m, 7H), 1.41 (m, 2H), 1.63 (m, 5H), 1.77 (m, 6H), 2.57 (m, 3H), 2.73 (m, 5H), 2.80 (d, 3H, J = 1.8 Hz), 3.32 (m, 2H), 3.43 (m, 2H), 3.94 (m, 1H), 3.99 (t, 2H, J = 6.6 Hz), 6.97 (d, 2H, J = 9 Hz), 7.75 (dt, 1H, J = 9, 1.8 Hz), 7.79 (dd, 2H, J = 9, 1.2 Hz), 8.22 (dd, 1H, J = 8.4, 1.2 Hz), 8.57 (dd, 1H, J = 9, 1.2 Hz), 9.28 (d, 1H, J = 1.2 Hz). |
| 255 | 655.3 | ¹HNMR (600 MHz, CDCl₃, 25° C.): 0.86 (t, 3H, J = 6.6 Hz), 1.26 (m, 7H), 1.41 (m, 2H), 1.56 (m, 2H), 1.84 (m, 3H), 1.93 (m, 2H), 2.81 (s, 3H), 2.88 (m, 11H), 3.02 (m, 3H), 3.41 (m, 2H), 3.43 (m, 2H), 3.99 (t, 2H, J = 6.6 Hz), 6.99 (d, 2H, J = 9 Hz), 7.63 (dd, 1H, J = 8.4, 1.2 Hz), 7.82 (m, 3H), 7.99 (d, 1H, J = 9 Hz), 8.96 (m, 1H). |
| 256 | 641.3 | ¹HNMR (600 MHz, CDCl₃, 25° C.): 0.86 (t, 3H, J = 6.6 Hz), 1.26 (m, 6H), 1.39 (m, 2H), 1.63 (m, 2H), 1.75 (m, 4H), 1.84 (m, 2H), 2.25 (m, 3H), 2.39 (s, 3H), 2.66 (m, 4H), 2.79 (s, 3H), 2.84 (m, 4H), 3.23 (m, 2H), 3.44 (m, 2H), 3.98 (t, 2H, J = 6 Hz), 6.94 (d, 2H, J = 9 Hz), 7.63 (dd, 1H, J = 8.4, 1.8 Hz), 7.76 (m, 3H), 8.00 (d, 1H, J = 9 Hz), 9.11 (m, 1H). |
| 257 | 657.3 | ¹HNMR (600 MHz, CDCl₃, 25° C.): 0.84 (t, 3H, J = 6.6 Hz), 1.25 (m, 6H), 1.40 (m, 2H), 1.73 (m, 4H), 1.85 (m, 2H), 2.50 (m, 5H), 2.61 (m, 2H), 2.68 (m, 7H), 2.78 (s, 3H), 3.32 (m, 2H), 3.40 (m, 2H), 3.97 (t, 2H, J = 6.6 Hz), 6.95 (d, 2H, J = 9 Hz), 7.74 (dd, 1H, J = 14.4, 7.2 Hz), 7.78 (d, 2H, J = 9 Hz), 8.19 (d, 1H, J = 9 Hz), 8.58 (d, 1H, J = 1.2 Hz), 9.24 (s, 1H). |
| 258 | 695.3 | ¹HNMR (600 MHz, CDCl₃, 25° C.): 0.84 (t, 3H, J = 6.6 Hz), 1.25 (m, 6H), 1.39 (m, 2H), 1.54 (m, 2H), 1.69 (m, 8H), 1.89 (m, 4H), 2.09 (m, 2H), 2.25 (m, 2H), 2.59 (m, 1H), 2.73 (m, 2H), 2.78 (s, 3H), 2.85 (m, 3H), 3.09 (m, 2H), 3.28 (m, 2H), 3.42 (m, 2H), 3.97 (t, 2H, J = 6.6 Hz), 6.94 (d, 2H, J = 9 Hz), 7.73 (dd, 1H, J = 9, 1.8 Hz), 7.76 (d, 2H, J = 9 Hz), 8.19 (d, 1H, J = 3 Hz), 8.55 (d, 1H, J = 1.8 Hz), 9.26 (s, 1H). |
| 259 | 544.2 | ¹HNMR (600 MHz, CDCl₃, 25° C.): 0.86 (t, 3H, J = 7.2 Hz), 1.26 (m, 6H), 1.40 (m, 2H), 1.76 (m, 2H), 2.38 (s, 3H), 2.55 (m, 4H), 2.79 (s, 3H), 3.39 (m, 4H), 3.98 (t, 2H, J = 6.6 Hz), 6.95 (dd, 2H, J = 7.2, 1.8 Hz), 7.80 (dd, 1H, J = 7.2, 2.4 Hz), 7.88 (dd, 2H, J = 9, 1.8 Hz), 8.25 (d, 1H, J = 9 Hz), 8.59 (d, 1H, J = 1.8 Hz), 9.35 (s, 1H). |
| 262 | 688 | ¹HNMR (600 MHz, CDCl₃, 25° C.): 0.85 (t, 3H, J = 7.2 Hz), 1.26 (m, 6H), 1.40 (m, 2H), 1.75 (m, 4H), 1.85 (m, 2H), 1.93 (m, 2H), 2.35 (m, 3H), 2.58 (s, 3H), 2.79 (m, 1H), 2.92 (m, 4H), 3.22 (m, 2H), 3.42 (t, 2H, J = 11.4 Hz), 3.97 (t, 2H, J = 7.2 Hz), 6.95 (d, 2H, J = 9 Hz), 7.23 (m, 1H), 7.33 (t, 2H, J = 7.8 Hz), 7.52 (d, 2H, J = 7.2 Hz), 7.63 (dd, 1H, J = 9, 1.8 Hz), 7.77 (m, 3H), 7.99 (d, 1H, J = 9 Hz), 9.11 (m, 1H) |

TABLE 2-continued

| No  | MS (m/z) | ¹H NMR |
|-----|----------|--------|
| 263 | 704.3 | ¹HNMR (600 MHz, CDCl₃, 25° C.): 0.86 (t, 3H, J = 7.2 Hz), 1.24 (m, 6H), 1.41 (m, 2H), 1.77 (m, 4H), 1.85 (m, 2H), 1.98 (m, 4H), 2.35 (m, 2H), 2.80 (s, 3H), 2.91 (m, 4H), 3.34 (m, 2H), 3.51 (m, 2H), 3.99 (t, 2H, J = 6 Hz), 6.95 (d, 2H, J = 9 Hz), 7.23 (m, 1H), 7.33 (t, 2H, J = 7.8 Hz), 7.52 (d, 2H, J = 7.2 Hz), 7.63 (dd, 1H, J = 9, 1.8 Hz), 7.77 (m, 3H), 7.99 (d, 1H, J = 9 Hz), 9.11 (m, 1H) |
| 264 | 669.3 | ¹HNMR (600 MHz, CDCl₃, 25° C.): 0.83 (t, 3H, J = 7.8 Hz), 1.23 (m, 12H), 1.36 (m, 4H), 1.72 (m, 4H), 1.84 (m, 2H), 2.53 (s, 3H), 2.61 (m, 1H), 2.78 (s, 3H), 2.85 (m, 6H), 3.28 (m, 2H), 3.35 (m, 2H), 3.98 (t, 2H, J = 6.6 Hz), 6.95 (d, 2H, J = 9 Hz), 7.72 (dd, 1H, J = 9, 1.8 Hz), 7.78 (d, 2H, J = 9 Hz), 8.21 (d, 1H, J = 8.4 Hz), 8.59 (d, 1H, J = 1.2 Hz), 9.33 (s, 1H). |
| 265 | 670.3 | ¹HNMR (600 MHz, CDCl₃, 25° C.): 0.87 (m, 3H), 1.23 (m, 14H), 1.44 (m, 2H), 1.61 (m, 3H), 1.78 (m, 6H), 2.49 (m, 1H), 2.67 (m, 4H), 2.80 (s, 3H), 3.33 (m, 4H), 4.00 (m, 2H), 6.97 (m, 2H), 7.80 (m, 3H), 8.23 (m, 1H), 8.59 (m, 1H), 9.31 (m, 1H). |
| 266 | 698 | ¹HNMR (600 MHz, CDCl₃, 25° C.): 0.83 (t, 3H, J = 7.8 Hz), 1.23 (m, 22H), 1.37 (m, 4H), 1.73 (m, 4H), 1.86 (m, 2H), 2.74 (s, 3H), 2.93 (m, 4H), 3.43 (m, 4H), 3.94 (t, 2H, J = 6.6 Hz), 6.92 (d, 2H, J = 9 Hz), 7.63 (dd, 1H, J = 8.4, 1.8 Hz), 7.80 (m, 2H), 8.00 (d, 1H, J = 8.4 Hz), 8.69 (d, 1h, J = 1.8 Hz), 9.00 (s, 1H). |
| 267 | 683.3 | ¹HNMR (600 MHz, CDCl₃, 25° C.): 0.83 (t, 3H, J = 7.2 Hz), 1.24 (m, 14H), 1.44 (m, 2H), 1.75 (m, 4H), 2.11 (m, 2H), 2.63 (s, 3H), 2.79 (m, 4H), 2.89 (m, 2H), 2.99 (m, 4H), 3.07 (m, 2H), 3.28 (m, 2H), 3.43 (t, 2H, J = 10.8 Hz), 3.98 (t, 2H, J = 6.6 Hz), 6.95 (d, 2H, J = 9 Hz), 7.72 (dd, 1H, J = 8.4, 1.2 Hz), 7.76 (d, 2H, J = 9 Hz), 8.20 (d, 1H, J = 8.4 Hz), 8.57 (d, 1H, J = 1.2 Hz), 9.26 (s, 1H). |
| 268 | 699 | ¹HNMR (600 MHz, CDCl₃, 25° C.): 0.84 (t, 3H, J = 7.2 Hz), 1.21 (m, 12H), 1.40 (m, 2H), 1.71 (m, 4H), 1.86 (m, 2H), 2.40 (m, 2H), 2.51 (m, 10H), 2.79 (s, 3H), 3.33 (m, 2H), 3.44 (m, 2H), 3.63 (t, 2H, J = 5.4 Hz), 3.98 (t, 2H, J = 6.6 Hz), 6.96 (d, 2H, J = 9 Hz), 7.77 (dd, 1H, J = 9, 1.8 Hz), 7.79 (d, 2H, J = 9 Hz), 8.20 (d, 1H, J = 9 Hz), 8.57 (d, 1H, J = 1.8 Hz), 9.26 (s, 1H). |
| 269 | 734 | ¹HNMR (600 MHz, CDCl₃, 25° C.): 0.84 (t, 3H, J = 7.2 Hz), 1.24 (m, 12H), 1.42 (m, 2H), 1.54 (m, 2H), 1.71 (m, 12H), 2.06 (m, 2H), 2.27 (m, 2H), 2.58 (m, 1H), 2.67 (m, 2H), 2.79 (s, 3H), 2.81 (m, 4H), 3.09 (m, 2H), 3.30 (m, 2H), 3.44 (t, 2H, J = 12 Hz), 3.98 (t, 2H, J = 6.6 Hz), 6.95 (m, 2H), 7.74 (dd, 1H, J = 9, 2.4 Hz), 7.77 (m, 2H), 8.20 (d, 1H, J = 8.4 Hz), 8.56 (d, 1H, J = 1.8 Hz), 9.26 (s, 1H). |
| 270 | 747 | 1HNMR (600 MHz, CDCl3, 25° C.): 0.85 (t, 3H, J = 7.2 Hz), 1.21 (m, 12H), 1.41 (m, 2H), 1.76 (m, 2H), 1.92 (m, 4H), 2.10 (m, 3H), 2.57 (m, 2H), 2.80 (s, 3H), 3.15 (m, 4H), 3.33 (m, 2H), 3.52 (m, 2H), 3.99 (t, 2H, J = 6.6 Hz), 6.97 (m, 2H), 7.22 (t, 1H, J = 7.2 Hz), 7.31 (t, 2H, J = 7.8 Hz), 7.53 (d, 2H, J = 7.2 Hz), 7.77 (dd, 1H, J = 8.4, 1.8 Hz), 7.80 (d, 2H, J = 9 Hz), 8.22 (d, 1H, J = 9 Hz), 8.55 (s, 1H), 9.24 (m, 1H). |
| 272 | 611.2 | ¹HNMR (600 MHz, CDCl₃, 25° C.): 0.84 (t, 3H, J = 7.2 Hz), 1.22 (m, 8H), 1.40 (m, 2H), 1.75 (m, 2H), 2.06 (m, 3H), 2.56 (m, 6H), 2.67 (m, 1H), 2.88 (m, 2H), 3.10 (m, 2H), 3.25 (m, 7H), 3.96 (t, 2H, J = 12.6 Hz), 6.93 (d, 2H, J = 9 Hz), 7.60 (dd, 1H, J = 9, 2.4 Hz), 7.74 (d, 2H, J = 9 Hz), 7.83 (d, 1H, J = 1.8 Hz), 7.97 (d, 1H, J = 9 Hz), 9.14 (s, 1H). |
| 273 | 639.3 | ¹HNMR (600 MHz, CDCl₃, 25° C.): 0.85 (t, 2H, J = 7.2 Hz), 1.23 (d, 6H, J = 5.4 Hz), 1.31 (m, 9H), 1.41 (m, 2H), 1.75 (m, 2H), 2.00 (m, 4H), 2.47 (m, 3H), 2.57 (s, 3H), 2.59 (m, 3H), 3.00 (m, 1H), 3.19 (m, 2H), 3.30 (m, 4H), 3.99 (t, 2H, J = 6.6 Hz), 6.94 (d, 2H, J = 9 Hz), 7.63 (dd, 1H, J = 8.4, 1.8 Hz), 7.76 (dd, 2H, J = 7.1, 1.8 Hz), 7.89 (d, 1H, J = 1.8 Hz), 8.01 (d, 1H, J = 9 Hz), 9.20 (s, 1H). |
| 274 |  | ¹HNMR (600 MHz, CDCl₃, 25° C.): 0.87 (t, 3H, J = 6.6 Hz), 1.24 (m, 6H), 1.42 (m, 2H), 1.75 (m, 3H), 2.02 (m, 1H), 2.40 (m, 3H), 2.49 (m, 3H), 2.60 (s, 3H), 2.62 (m, 1H), 2.73 (m, 1H), 2.78 (m, 1H), 2.97 (m, 1H), 3.29 (m, 4H), 3.95 (t, 2H, J = 6.6 Hz), 6.90 (d, 2H, J = 9 Hz), 7.27 (m, 1H), 7.33 (m, 4H), 7.65 (dd, 1H, J = 8.4, 1.8 Hz), 7.74 (d, 2H, J = 9 Hz), 7.94 (d, 1H, J = 1.8 Hz), 8.04 (d, 1H, J = 9 Hz), 9.28 (s, 1H). |
| 275 | 701.3 | ¹HNMR (600 MHz, CDCl₃, 25° C.): 0.88 (t, 3H, J = 7.2 Hz), 1.25 (m, 8H), 1.43 (m, 3H), 1.75 (m, 4H), 1.95 (m, 2H), 2.24 (m, 2H), 2.28 (d, 2H, J = 6.2.45 (m, 4H), 2.58 (s, 3H), 2.91 (m, 2H), 3.27 (m, 4H), 3.49 (m, 2H), 3.99 (t, 2H, J = 6.6 Hz), 6.95 (d, 2H, J = 8.4 Hz), 7.25 (m, 1H), 7.31 (m, 4H), 7.64 (dd, 1H, J = 8.4, 1.8 Hz), 7.81 (d, 2H, J = 9 Hz), 7.93 (d, 1H, J = 1.8 Hz), 8.20 (d, 1H, J = 9 Hz), 9.26 (s, 1H). |
| 276 | 628.2 | ¹HNMR (600 MHz, CDCl₃, 25° C.): 0.85 (t, 3H, J = 7.2 Hz), 1.28 (m, 8H), 1.40 (m, 2H), 1.75 (m, 2H), 1.80 (m, 3H), 2.60 (m, 3H), 2.68 (m, 2H), 2.79 (m, 7H), 3.36 (m, 4H), 3.62 (m, 2H), 3.97 (t, 2H, J = 12.6 Hz), 6.94 (d, 2H, J = 9 Hz), 7.79 (dd, 2H, J = 7.2, 2.4 Hz), 7.85 (dd, 1H, J = 9, 1.8 Hz), 8.25 (d, 1H, J = 9 Hz), 8.62 (d, 1H, J = 1.8 Hz), 9.38 (s, 1H). |

TABLE 2-continued

| No | MS (m/z) | ¹H NMR |
|---|---|---|
| 277 | 655.3 | ¹HNMR (600 MHz, CDCl$_3$, 25° C.):<br>0.87 (t, 2H, J = 7.2 Hz), 1.07 (d, 6H, J = 6 Hz), 1.24 (m, 6H), 1.41 (m, 2H), 1.63 (m, 2H), 1.76 (m, 2H), 1.86 (m, 2H), 2.19 (m, 3H), 2.36 (m, 1H), 2.64 (m, 4H), 2.79 (s, 3H), 3.00 (m, 2H), 3.36 (m, 4H), 3.98 (t, 2H, J = 6.6 Hz), 6.94 (d, 2H, J = 9 Hz), 7.79 (d, 2H, J = 9 Hz), 7.84 (dd, 1H, J = 9, 1.2 Hz), 8.26 (d, 1H, J = 9 Hz), 8.63 (d, 1H, J = 1.8 Hz), 9.41 (s, 1H). |
| 278 | 690.3 | ¹HNMR (600 MHz, CDCl$_3$, 25° C.):<br>0.87 (t, 3H, J = 6.6 Hz), 1.24 (m, 6H), 1.42 (m, 2H), 1.75 (m, 3H), 2.04 (m, 2H), 2.43 (m, 3H), 2.57 (m, 3H), 2.80 (s, 3H), 2.87 (m, 1H), 3.01 (m, 1H), 3.38 (m, 4H), 3.65 (m, 2H), 3.96 (t, 2H, J = 6.6 Hz), 6.92 (d, 2H, J = 9 Hz), 7.27 (m, 1H), 7.32 (m, 4H), 7.77 (d, 2H, J = 7.2 Hz), 8.27 (d, 1H, J = 9 Hz), 8.59 (s, 1H), 9.40 (s, 1H). |
| 279 | 717.3 | ¹HNMR (600 MHz, CDCl$_3$, 25° C.):<br>0.85 (t, 3H, J = 7.2 Hz), 1.26 (m, 6H), 1.40 (m, 2H), 1.53 (m, 3H), 1.76 (m, 2H), 1.84 (m, 2H), 2.23 (m, 2H), 2.28 (d, 2H, J = 6.6 Hz), 2.52 (m, 4H), 2.79 (s, 3H), 3.11 (m, 2H), 3.37 (m, 4H), 3.76 (m, 2H), 3.97 (t, 2H, J = 12.6 Hz), 6.95 (dd, 2H, J = 7.2, 1.8 Hz), 7.30 (m, 3H), 7.41 (m, 2H), 7.79 (m, 3H), 8.21 (d, 1H, J = 9 Hz), 8.62 (d, 1H, J = 1.8 Hz), 9.30 (s, 1H). |
| 281 | 625.2 | ¹HNMR (600 MHz, CDCl$_3$, 25° C.):<br>0.87 (t, 3H, J6.6 Hz), 1.27 (m, 6H), 1.41 (m, 4H), 1.60 (m, 4H), 1.77 (m, 2H), 2.46 (m, 9H), 2.58 (s, 3H), 2.60 (m, 2H), 3.82 (m, 4H), 3.98 (t, 2H, J = 6.6 Hz), 6.94 (d, 2H, J = 9 Hz), 7.64 (dd, 1H, J = 9, 1.8 Hz), 7.78 (d, 2H, J = 9 Hz), 7.92 (d, 1H, J = 1.8 Hz), 8.00 (d, 1H, J = 9 Hz), 9.27 (s, 1H). |
| 282 | 642.3 | ¹HNMR (600 MHz, CDCl$_3$, 25° C.):<br>0.85 (t, 3H, J = 7.8 Hz), 1.28 (m, 6H), 1.42 (m, 2H), 1.51 (m, 2H), 1.74 (m, 6H), 2.60 (m, 4H), 2.71 (m, 7H), 2.79 (s, 3H), 3.85 (m, 4H), 3.98 (t, 2H, J = 6.6 Hz), 6.94 (d, 2H, J = 9 Hz), 7.78 (dd, 2H, J = 7.2, 1.8 Hz), 7.83 (dd, 1H, J = 9, 1.8 Hz), 8.25 (d, 1H, J = 8.4 Hz), 8.61 (d, 1H, J = 1.8 Hz), 9.37 (s, 1H). |
| 283 | 697.3 | ¹HNMR (600 MHz, CDCl$_3$, 25° C.):<br>0.83 (t, 3H, J = 7.2 Hz), 1.81 (m, 17H), 1.37 (m, 2H), 1.75 (m, 2H), 1.97 (m, 4H), 2.47 (m, 4H), 2.67 (m, 4H), 2.80 (s, 3H), 3.06 (m, 1H), 3.17 (m, 2H), 3.32 (m, 4H), 3.98 (t, 2H, J = 6.6 Hz), 6.95 (d, 2H, J = 9 Hz), 7.78 (d, 2H, J = 9 Hz), 7.81 (dd, 1H, J = 8.4, 1.2 Hz), 8.25 (d, 1H, J = 9 Hz), 8.63 (d, 1H, J = 1.8 Hz), 9.37 (s, 1H). |
| 284 | 699.3 | ¹HNMR (600 MHz, CDCl$_3$, 25° C.):<br>0.84 (d, 6H, J = 6.6 Hz), 0.91 (d, 3H, J = 6.6 Hz), 1.11 (m, 3H), 1.22 (m, 4H), 1.48 (m, 1H), 1.56 (m, 1H), 1.61 (m, 1H), 1.80 (m, 5H), 2.66 (m, 1H), 2.80 (s, 3H), 2.86 (m, 5H), 3.00 (m, 4H), 3.29 (m, 2H), 3.39 (m, 2H), 3.79 (m, 2H), 4.02 (m, 2H), 6.97 (d, 2H, J = 9 Hz), 7.72 (dd, 1H, J = 8.4, 1.8 Hz), 7.80 (d, 12H, J = 9 Hz), 8.23 (d, 1H, J = 8.4 Hz), 8.61 (d, 1H, J = 1.2 Hz), 9.32 (s, 1H). |
| 285 | 752.3 | ¹HNMR (600 MHz, CDCl$_3$, 25° C.):<br>0.85 (t, 3H, J = 7.2 Hz), 1.24 (m, 14H), 1.44 (m, 2H), 1.78 (m, 9H), 2.39 (s, 3H), 2.45 (m, 3H), 2.77 (m, 8H), 2.80 (s, 3H), 3.15 (m, 2H), 3.20 (m, 2H), 3.49 (m, 2H), 3.99 (t, 2H, J = 6.6 Hz), 6.97 (d, 2H, J = 9 Hz), 7.77 (dd, 1H, J = 9, 1.8 Hz), 7.79 (d, 2H, J = 9 Hz), 8.21 (d, 1H, J = 9 Hz), 8.55 (d, 1H, J = 1.2 Hz), 9.25 (s, 1H). |
| 286 | 739.3 | ¹HNMR (600 MHz, CDCl$_3$, 25° C.):<br>0.84 (t, 3H, J = 7.2 Hz), 1.24 (m, 12H), 1.40 (m, 2H), 1.75 (m, 10H), 2.31 (m, 1H), 2.56 (m, 6H), 2.80 (s, 3H), 2.85 (m, 1H), 3.18 (m, 2H), 3.31 (m, 2H), 3.48 (q, 2H, J = 9 Hz), 3.71 (t, 4H, J = 4.2 Hz), 3.96 (t, 2H, J = 6 Hz), 6.97 (d, 2H, J = 9 Hz), 7.61 (dd, 1H, J = 9, 1.8 Hz), 7.79 (d, 2H, J = 9 Hz), 8.20 (d, 1H, J = 8.4 Hz), 8.54 (d, 1H, J = 1.2 Hz), 9.23 (s, 1H). |
| 287 | 766 | ¹HNMR (600 MHz, CDCl$_3$, 25° C.):<br>0.84 (t, 3H, J = 7.2 Hz), 1.17 (m, 14H), 1.43 (m, 2H), 1.52 (m, 2H), 1.66 (m, 2H), 1.76 (m, 7H), 2.17 (m, 2H), 2.35 (s, 3H), 2.40 (m, 1H), 2.53 (m, 5H), 2.74 (m, 6H), 3.01 (m, 2H), 3.25 (m, 2H), 3.45 (m, 2H), 3.97 (t, 2H, J = 6.6 Hz), 6.94 (d, 2H, J = 9 Hz), 7.77 (m, 3H), 8.20 (d, 1H, J = 9 Hz), 8.55 (d, 1H, J = 1.8 Hz), 9.26 (s, 1H). |
| 288 | 753.3 | ¹HNMR (600 MHz, CDCl$_3$, 25° C.):<br>0.85 (t, 3H, J = 7.2 Hz), 1.24 (m, 18H), 1.77 (m, 14H), 2.44 (m, 2H), 2.67 (m, 2H), 2.81 (m, 7H), 3.06 (q, 1H, J = 14.4 Hz), 3.21 (m, 2H), 3.32 (m, 2H), 3.47 (m, 2H), 3.99 (t, 3H, J = 6 Hz), 6.98 (d, 2H, J = 8.4 Hz), 7.76 (dd, 1H, J = 9, 1.8 Hz), 7.79 (d, 2H, J = 9 Hz), 8.22 (d, 1H, J = 8.4 Hz), 8.56 (s, 1H), 9.25 (s, 1H). |
| 289 | 737.3 | ¹HNMR (600 MHz, CDCl$_3$, 25° C.):<br>0.83 (d, 6H, J = 6.6 Hz), 0.91 (d, 3H, J = 6 Hz), 1.13 (m, 3H), 1.22 (m, 4H), 1.37 (m, 2H), 1.47 (m, 1H), 1.55 (m, 1H), 1.62 (m, 1H), 1.80 (m, 1H), 1.96 (m, 4H), 2.07 (m, 4H), 2.41 (m, 4H), 2.81 (s, 3H), 3.03 (m, 6H), 3.12 (m, 2H), 3.45 (m, 5H), 4.02 (m, 2H), 6.99 (d, 2H, J = 9 Hz), 7.75 (d, 1H, J = 9 Hz), 7.78 (d, 2H, J = 9 Hz), 8.20 (d, 1H, J = 9 Hz), 8.52 (s, 1H), 9.20 (m, 1H). |
| 290 | 755.3 | ¹HNMR (600 MHz, CDCl$_3$, 25° C.):<br>0.82 (m, 3H), 1.26 (m, 16H), 2.07 (m, 12H), 2.33 (m, 4H), 2.50 (m, 2H), 2.80 (m, 5H), 3.24 (m, 6H), 3.48 (m, 2H), 4.08 (m, 2H), 7.08 (m, 1H), 7.56 (m, 1H), 7.64 (m, 1H), 7.76 (m, 1H), 8.63 (m, 1H), 8.57 (m, 1H (, 9.23 (m, 1H). |

TABLE 2-continued

| No | MS (m/z) | ¹H NMR |
|---|---|---|
| 291 | 717.3 | ¹HNMR (600 MHz, CDCl₃, 25° C.): 0.82 (t, 3H, J = 7.2 Hz), 1.22 (m, 12H), 1.40 (m, 2H), 1.77 (m, 6H), 2.66 (m, 1H), 2.79 (s, 3H), 2.86 (m, 6H), 3.01 (m, 4H), 3.27 (m, 2H), 3.36 (m, 2H), 3.78 (t, 2H, J = 4.8 Hz), 4.05 (t, 2H, J = 6.6 Hz), 7.04 (t, 1H, J = 8.4 Hz), 7.55 (dd, 1H, J = 9.6, 1.8 Hz), 7.64 (d, 1H, J = 8.4 Hz), 7.73 (dd, 1H, J = 8.4, 1.2 Hz), 8.23 (d, 1H, J = 9 Hz), 8.60 (s, 1H), 9.32 (s, 1H). |
| 292 | 782.1 | ¹HNMR (600 MHz, CDCl₃, 25° C.): 0.84 (t, 3H, J = 7.2 Hz), 1.23 (m, 16H), 1.40 (m, 2H), 1.76 (m, 6H), 1.93 (m, 4H), 2.45 (m, 2H), 2.66 (m, 2H), 2.74 (m, 4H), 2.80 (s, 3H), 3.17 (m, 2H), 3.31 (m, 2H), 3.46 (m, 2H), 3.68 (m, 3H), 3.98 (t, 2H, J = 6.6 Hz), 6.97 (d, 2H, J = 9 Hz), 7.76 (dd, 1H, J = 8.4, 1.2 Hz), 7.79 (d, 2H, J = 8.4 Hz), 8.21 (d, 1H, J = 9 Hz), 8.55 (s, 1H), 9.24 (s, 1H). |
| 293 | 431 | (400 MHz, DMSO-d₆): 9.20 (s, 1H), 7.84 (d, J = 8.8 Hz, 2H), 7.48 (s, 1H), 7.16 (d, J = 8.8 Hz, 2H), 7.12 (s, 1H), 3.97 (s, 3H), 3.89 (s, 3H), 3.83 (s, 3H), 3.27 (q, J = 7.2 Hz, 4H), 0.60 (t, J = 7.2 Hz, 6H) |
| 294 | 445 | (400 MHz, DMSO-d₆): 9.23 (s, 1H), 7.85 (d, J = 8.8 Hz, 2H), 7.47 (s, 1H), 7.19 (s, 1H), 7.14 (d, J = 8.8 Hz, 2H), 3.97 (s, 3H), 3.89 (s, 3H), 3.83 (s, 3H), 3.83-3, 75 (m, 1H), 3.21 (q, J = 8.Hz, 2H), 1.10-0.98 (br m, 6H) 1.12 (t, J = 7.2 Hz, 3H) |
| 295 | 487.4 | (400 MHz, DMSO-d₆): 9.19 (s, 1H), 7.83 (d, J = 8.8 Hz, 2H), 7.46 (s, 1H), 7.18 (s, 1H), 7.14 (d, J = 8.8 Hz, 2H), 3.96 (s, 3H), 3.88 (s, 3H), 3.82 (s, 3H), 3.19 (t, J = 7.2 Hz, 4H), 1.02 (quint, J = 7.2 Hz, 4H), 1.02-0.76 (m, 4H), 0.67 (t, J = 7.2 Hz, 6H) |
| 296 | 502 | (400 MHz, DMSO-d₆): 9.17 (s, 1H), 7.84 (d, J = 8.8 Hz, 2H), 7.46 (s, 1H), 7.30 (s, 1H), 7.14 (d, J = 8.8 Hz, 2H), 3.97 (s, 3H), 3.89 (s, 3H), 3.83 (s, 3H), 3.29 (q, J = 7.2 Hz, 4H), 2.19 (q, J = 7.2 Hz, 4H), 1.92 (br t, 2H), 0.74 (t, J = 7.2 Hz, 3H), 0.70 (t, J = 7.2 Hz, 6H) |
| 297 | 474 | (400 MHz, DMSO-d₆): 8.70 (s, 1H), 7.90 (d, J = 8.8 Hz, 2H), 7.57 (s, 1H), 7.53-7.50 (br t, 1H), 7.23 (s, 1H), 7.11 (d, J = 8.8 Hz, 2H), 3.90 (s, 3H), 3.88 (s, 3H), 3.88-3.84 (m, 2H), 3.82 (s, 3H), 2.67-2.60 (m, 6H), 1.03 (t, J = 7.2 Hz, 6H) |
| 298 | 488 | (400 MHz, DMSO-d₆): 8.75 (s, 1H), 7.91 (d, J = 8.8 Hz, 2H), 7.41 (s, 1H), 7.26 (s, 1H), 7.12 (d, J = 8.8 Hz, 2H), 6.83 (t, J = 6.8 Hz 1H), 3.92 (s, 3H), 3.87 (s, 3H), 3.82 (s, 3H), 3.66 (q, J = 6.4 Hz 2H), 2.40-2.32 (m, 6H), 1.66-1.58 (m, 2H), 0.86 (t, J = 7.2 Hz, 6H) |
| 299 | 502 | (400 MHz, DMSO-d₆): 8.74 (s, 1H), 7.90 (d, J = 8.8 Hz, 2H), 7.43 (s, 1H), 7.26 (s, 1H), 7.12 (d, J = 8.8 Hz, 2H), 6.87 (t, J = 5.2 Hz, 1H), 3.91 (s, 3H), 3.88 (s, 3H), 3.82 (s, 3H), 3.72-3.66 (m, 2H), 2.38 (q, J = 7.2 Hz, 4H), 2.32-2.28 (m, 2H), 1.55-1.47 (m, 2H), 1.41-1.33 (m, 2H), 0.88 (t, J = 7.2 Hz, 6H) |
| 300 | 502.2 | (400 MHz, DMSO-d₆): 9.18 (s, 1H), 7.81 (d, J = 8.8 Hz, 2H), 7.50 (s, 1H), 7.15 (d, J = 8.8 Hz, 2H), 7.12 (s, 1H), 3.97 (s, 3H), 3.90 (s, 3H), 3.83 (s, 3H), 3.15-3.09 (m, 2H), 2.68 (s, 3H), 2.23 (q, J = 7.2 Hz, 4H), 2.14-2.10 (m, 2H), 1.09-1.01 (m, 2H), 0.78 (t, J = 7.2 Hz, 6H) |
| 301 | 488 | (400 MHz, DMSO-d₆): 9.13 (s, 1H), 7.79 (d, J = 8.8 Hz, 2H), 7.52 (s, 1H), 7.36 (s, 1H), 7.12 (d, J = 8.8 Hz, 2H), 4.45-4.40 (m, 1H), 3.98 (s, 3H), 3.93 (s, 3H), 3.83 (s, 3H), 3.54-3.49 (m, 2H), 3.09 (br s, 4H), 2.46-2.41 (m, 2H), 2.37 (br s, 4H) |
| 302 | 557.2 | (400 MHz, CDCl₃): 9.29 (s, 1H), 7.81 (d, J = 8.8 Hz, 2H), 7.48 (s, 1H), 7.41 (s, 1H), 6.97 (d, J = 8.8 Hz, 2H), 4.06 (s, 3H), 4.01 (s, 3H), 3.87 (s, 3H), 3.25 (br s, 4H), 2.65-2.48 (m, 6H), 2.48-2.38 (m, 6H), 1.70(br s, 2H), 1.11-1.03 (br t, 6H) |
| 303 | 459.4 | (400 MHz, DMSO-d₆): 9.14 (s, 1H), 7.80 (d, J = 8.8 Hz, 2H), 7.51 (s, 1H), 7.38 (br s, 1H), 7.12 (d, J = 8.8 Hz, 2H), 4.71 (d, J = 4.0 Hz 1H), 3.98 (s, 3H), 3.92 (s, 3H), 3.83 (s, 3H), 3.74-3.66 (m, 1H), 3.19-2.94 (br m, 4H), 1.68-1.59 (m, 2H), 1.44-1.34 (br m, 2H) |
| 304 | 473.4 | (400 MHz, DMSO-d₆): 9.08 (br s, 1H), 7.79 (d, J = 8.8 Hz, 2H), 7.48 (s, 1H), 7.33 (s, 1H), 7.12 (d, J = 8.8 Hz, 2H), 4.42-4.35 (br m, 1H), 3.97 (s, 3H), 3.93 (s, 3H), 3.83 (s, 3H), 3.29-3.18 (m, 2H), 3.17-3.10 (m, 1H), 3.09-2.98 (br m, 1H), 2.91 (m, 1H), 2.85-2.77 (br m, 1H), 1.79-1.39 (br m, 3H), 1.14-1.05 (m, 1H) |
| 305 | 445 | (400 MHz, DMSO-d₆): 9.21 (s, 1H), 7.89 (s, 1H), 7.80 (d, J = 8.8 Hz, 2H), 7.53 (s, 1H), 7.11 (d, J = 8.8 Hz, 2H), 5.37 (d, J = 2.0 Hz, 1H), 4.40 (br s, 1H), 3.97 (s, 3H), 3.84 (s, 3H), 3.82 (s, 3H), 3.02 (m, 1H), 2.91-2.85 (m, 1H), 1.95-1.87 (br m, 2H) |
| 306 | 470.2 | (400 MHz, DMSO-d₆): 9.17 (s, 1H), 8.44 (s, 1H), 7.68 (d, J = 8.8 Hz, 2H), 7.45 (s, 1H), 7.08 (d, J = 8.8 Hz, 2H), 4.37 (s, 1H), 3.96 (s, 3H), 3.89 (s, 3H), 3.79 (s, 3H), 3.55 (d, J = 7.2 Hz, 1H), 3.01 (d, J = 9.6 Hz, 1H), 2.39 (s, 1H), 2.25 (d, J = 9.6 Hz, 1H), 2.01 (d, J = 8.8 Hz, 1H), 1.85 (q, J = 8.0 Hz, 2H) |
| 307 | 543 | (400 MHz, DMSO-d₆): 9.14 (s, 1H), 7.83 (d, J = 8.8 Hz, 2H), 7.62 (br s, 1H), 7.49 (s, 1H), 7.14 (d, J = 8.8 Hz, 2H), 3.97 (s, 3H), 3.93 (s, 3H), 3.83 (s, 3H), 3.41 (br s, 2H), 3.22-3.13 (m, 2H), 2.99 (s, 3H), 2.99-2.90 (br m, 2H), 2.84-2.76 (br m, 2H), 2.81 (s, 3H), 2.74-2.65 (m, 2H), 1.79-1.70 (br s, 2H) |
| 308 | 535 | (400 MHz, DMSO-d₆): 9.23 (s, 1H), 7.89 (d, J = 8.8 Hz, 2H), 7.63 (br s, 1H), 7.56 (s, 1H), 7.52 (d, J = 8.0 Hz, 2H), 7.40 (t, J = 7.6 Hz, 2H), 7.26 (t, J = 8.0 Hz, 1H), 7.15 (d, J = 8.8 Hz, 2H), 5.23 (s, 1H), 4.00 (s, 3H), |

TABLE 2-continued

| No | MS (m/z) | $^1$H NMR |
|---|---|---|
| | | 3.94 (s, 3H), 3.84-3.76 (br m, 2H), 3.80 (s, 3H), 2.58-2.48 (br m, 2H), 1.83-1.70 (m, 2H), 1.55-1.46 (br d, 2H) |
| 309 | 577 | (400 MHz, DMSO-d$_6$): 9.19 (br s, 1H), 7.97 (d, J = 8.0 Hz, 2H), 7.83 (d, J = 8.8 Hz, 2H), 7.55 (s, 1H), 7.41 (d, J = 8.0 Hz, 2H), 7.38 (s, 1H), 7.17 (d, J = 8.8 Hz, 2H), 4.00 (s, 3H), 3.98 (s, 3H), 3.86 (s, 3H), 3.80 (s, 3H), 3.50 (m, 2H), 2.97-2.79 (m, 4H), 1.63-1.55 (m, 2H), 1.49-1.35 (br m, 1H) |
| 310 | 576 | (400 MHz, DMSO-d$_6$): 9.18 (br s, 1H), 8.41-8.36 (br m, 1H), 7.83 (t, J = 7.6 Hz, 4H), 7.55 (s, 1H), 7.38 (s, 1H), 7.33 (d, J = 8.0 Hz, 2H), 7.15 (d, J = 8.8 Hz, 2H), 4.00 (s, 3H), 3.98 (s, 3H), 3.81 (s, 3H), 3.54-3.42 (m, 2H), 3.00-2.85 (m, 2H), 2.85-2.74 (m, 2H), 2.79 (d, J = 4.4 Hz, 3H), 1.63-1.54 (br m, 1H) |
| 311 | 549 | (400 MHz, DMSO-d$_6$): 9.17 (br s, 1H), 7.82 (d, J = 8.8 Hz, 2H), 7.54 (s, 1H), 7.38 (s, 1H), 7.20-7.12 (m, 4H), 6.92 (d, J = 8.8 Hz, 2H), 3.99 (s, 3H), 3.97 (s, 3H), 3.81 (s, 3H), 3.75 (s, 3H), 3.47 (m, 2H), 2.96-2.86 (m, 2H), 2.70-2.62 (m, 1H), 1.59-1.50 (br m, 2H), 1.45-1.33 (br m, 1H) |
| 312 | 602.2 | (400 MHz, CDCl$_3$): 9.32-9.20 (br s, 1H), 7.86 (d, J = 8.8 Hz, 2H), 7.51-7.34 (br m, 4H), 7.23 (d, J = 8.0 Hz, 2H), 6.99 (d, J = 8.8 Hz, 2H), 4.07 (s, 3H), 4.05 (s, 3H), 3.86 (s, 3H), 3.83-3.69 (br s, 1H), 3.57-3.47 (m, 4H), 3.21-3.11 (m, 2H), 2.79-2.57 (m, 3H), 1.99-1.49 (br m, 9H) |
| 313 | 505.4 | (400 MHz, DMSO-d$_6$): 9.23 (s, 1H), 7.86 (d, J = 8.8 Hz, 2H), 7.57 (s, 1H), 7.38-7.30 (m, 4H), 7.27-7.22 (m, 1H), 7.15 (d, J = 8.8 Hz, 2H), 7.06 (s, 1H), 3.99 (s, 3H), 3.95 (s, 3H), 3.80 (s, 3H), 3.68-3.59 (m, 1H), 3.30-3.16 (m, 3H), 2.76 (t, J = 9.6 Hz, 1H), 2.40-2.32 (m, 1H), 2.26-2.19 (m, 1H) |
| 314 | 549 | (400 MHz, DMSO-d$_6$): 9.22 (s, 1H), 7.85 (d, J = 8.8 Hz, 2H), 7.56 (s, 1H), 7.15 (d, J = 8.0 Hz, 2H), 7.04 (s, 1H), 6.89 (s, 1H), 6.87 (d, J = 8.8 Hz, 1H), 6.78 (d, J = 8.0 Hz, 1H), 5.99 (s, 2H), 3.98 (s, 3H), 3.94 (s, 3H), 3.81 (s, 3H), 3.62-3.51 (br m, 1H), 3.27-3.14 (m, 3H), 2.73-2.66 (m, 1H), 2.35-2.28 (m, 1H), 2.21-2.13 (m, 1H) |
| 315 | 520.6 | (400 MHz, DMSO-d$_6$): 9.18 (s, 1H), 7.82 (d, J = 8.8 Hz, 2H), 7.54 (s, 1H), 7.27-7.20 (m, 3H), 7.11 (d, J = 8.0 Hz, 2H), 6.96 (d, J = 8.8 Hz, 2H), 6.79 (t, J = 8.0 Hz, 1H), 3.98 (s, 3H), 3.82 (s, 3H), 3.76 (s, 3H), 3.18 (br s, 8H) |
| 316 | 551 | (400 MHz, DMSO-d$_6$): 9.17 (s, 1H), 7.80 (d, J = 8.8 Hz, 2H), 7.54 (s, 1H), 7.32 (s, 1H), 7.11 (d, J = 8.8 Hz, 2H), 6.91 (d, J = 9.2 Hz, 2H), 6.84 (d, J = 9.2 Hz, 2H), 3.99 (s, 3H), 3.84 (s, 3H), 3.82 (s, 3H), 3.70 (s, 3H), 3.28-3.15 (br s, 4H), 3.08-2.95 (br s, 4H) |
| 317 | 592 | (400 MHz, DMSO-d$_6$): 9.18 (s, 1H), 7.84-7.79 (m, 4H), 7.54 (s, 1H), 7.21 (s, 1H), 7.11 (d, J = 8.8 Hz, 2H), 7.02 (d, J = 8.8 Hz, 2H), 6.84 (d, J = 9.2 Hz, 2H), 4.26 (q, J = 7.2 Hz, 2H), 3.98 (s, 3H), 3.82 (s, 3H), 3.74 (s, 3H), 3.38-3.07 (br s, 8H), 1.30 (t, J = 7.2 Hz, 4H) |
| 318 | 564.2 | (400 MHz, DMSO-d$_6$): 9.25 (s, 1H), 7.85 (d, J = 8.8 Hz, 2H), 7.58 (s, 1H), 7.35 (d, J = 9.2 Hz, 2H), 7.23 (s, 1H), 7.08 (d, J = 9.2 Hz, 2H), 7.03 (d, J = 9.2 Hz, 2H), 4.00 (s, 3H), 3.94 (s, 3H), 3.80 (s, 3H), 3.78 (s, 3H), 3.60-3.54 (br s, 2H) |
| 319 | 645 | (400 MHz, DMSO-d$_6$): 9.18 (s, 1H), 7.91 (d, J = 8.8 Hz, 1H), 7.81 (d, J = 8.8 Hz, 2H), 7.76 (d, J = 8.8 Hz, 2H), 7.54 (s, 1H), 7.22 (s, 1H), 7.10 (d, J = 8.8 Hz, 2H), 6.97 (d, J = 8.8 Hz, 2H), 3.98 (s, 3H), 3.82 (s, 3H), 3.79-3.69 (br s, 1H), 3.73 (s, 3H), 3.45-3.07 (br m, 8H), 1.83-1.70 (br d, 4H), 1.65-1.58 (br d, 1H), 1.36-1.23 (m, 4H), 1.19-1.07 (br m, 1 H) |
| 320 | 526 | (400 MHz, DMSO-d$_6$): 9.15 (s, 1H), 7.76 (d, J = 8.8 Hz, 2H), 7.52 (s, 1H), 7.31 (s, 1H), 7.11 (d, J = 8.8 Hz, 2H), 3.98 (s, 3H), 3.94 (s, 3H), 3.83 (s, 3H), 3.28-3.19 (br m, 2H), 2.99-2.87 (br m, 2H), 2.47-2.39 (br s, 4H), 1.56-1.23 (br m, 8H) |
| 321 | 526.5 | (400 MHz, DMSO-d$_6$): 9.18 (s, 1H), 7.78 (d, J = 8.8 Hz, 2H), 7.54 (s, 1H), 7.32 (s, 1H), 7.14 (d, J = 8.8 Hz, 2H), 3.99 (s, 3H), 3.98 (s, 3H), 3.83 (s, 3H), 3.51-3.41 (br t, 2H), 2.89-2.80 (br d, 2H), 2.44 (t, J = 7.2 Hz, 2H), 2.01-1.92 (m, 2H), 1.45-1.30 (br m, 4H) |
| 322 | 542 | (400 MHz, DMSO-d$_6$): 9.17 (s, 1H), 7.77 (d, J = 8.8 Hz, 2H), 7.53 (s, 1H), 7.32 (s, 1H), 7.12 (d, J = 8.8 Hz, 2H), 4.42-4.34 (br s, 1H), 3.98 (s, 3H), 3.93 (s, 3H), 3.83 (s, 3H) 3.33-3.13 (br m, 4H), 3.06 (t, J = 7.2 Hz, 1H), 3.02-2.87 (br m, 2H), 2.87-2.78 (br m, 2H), 2.68-2.58 (br m, 1H), 1.73-1.52 (br m, 5H), 1.37-1.21 (br m, 1H) |
| 323 | 502 | (400 MHz, DMSO-d$_6$): 9.14 (s, 1H), 7.83 (d, J = 8.8 Hz, 2H), 7.54 (s, 1H), 7.50 (s, 1H), 7.14 (d, J = 8.8 Hz, 2H), 3.97 (s, 3H), 3.93 (s, 3H), 3.83 (s, 3H) 3.52 (t, J = 6.0 Hz, 2H), 2.79-2.73 (br m, 2H), 3.19-2.93 (br m, 4H), 2.72-2.66 (br m, 2H), 2.64 (t, J = 6.0 Hz, 2H), 1.79-1.72 (br m, 2H) |
| 324 | 570 | (400 MHz, TFA-d$_1$): Mixture of Diastereomers 8.29, 8.22, 8.16, 7.97 (four s, 1H), 7.70-7.61 (m, 2H), 7.29-7.14 (br m, 2H), 6.99-6.89 (d, 2H), 4.31-3.15 (br m, 22H) 3.13-2.71 (br m, 3H), 2.40-1.86 (m, 2H), 1.05-0.78 (br m, 6H) |
| 325 | 556 | (400 MHz, DMSO-d$_6$): 9.14 (s, 1H), 7.82 (d, J = 8.8 Hz, 2H), 7.51 (s, 1H), 7.34 (s, 1H), 7.14 (d, J = 8.8 Hz, 2H), 4.01 (s, 1H), 3.98 (s, 3H), 3.94 (s, 3H), 3.83 (s, 3H), 3.21-3.13 (br m, 2H), 3.09-2.98 (br m, 2H), 2.89-2.76 (br d, 4H), 2.60-2.50 (br m, 2H), 1.81-1.63 (br m, 2H), 1.60-1.43 (br m, 4H) |

TABLE 2-continued

| No | MS (m/z) | ¹H NMR |
|---|---|---|
| 326 | 514 | (400 MHz, DMSO-d₆): 9.15 (s, 1H), 7.84 (d, J = 8.8 Hz, 2H), 7.70 (s, 1H), 7.49 (s, 1H), 7.14 (d, J = 8.8 Hz, 2H), 4.56 (t, J = 6.0 Hz, 2H), 4.39 (t, J = 6.0 Hz, 2H), 3.98 (s, 6H), 3.83 (s, 3H), 3.63 (quint, J = 6.0 Hz, 1H), 3.30-3.24 (br m, 2H), 3.08-2.76 (br m, 1H), 2.48-2.38 (br m, 3H), 1.78-1.69 (br m, 2H) |
| 327 | 626 | (400 MHz, DMSO-d₆): 9.08 (s, 1H), 7.93 (d, J = 2.4 Hz, 1H), 7.76 (d, J = 8.8 Hz, 2H), 7.51 (s, 1H), 7.45 (d, J = 8.8 Hz, 1H), 7.31 (dd, ³J = 8.8 Hz, 1H), 7.19 (s, 1H), 6.99 (d, J = 8.8 Hz, 2H), 3.96 (s, 3H), 3.91-3.83 (br s, 2H), 3.79 (s, 3H), 3.70-3.53 (br m, 2H), 3.63 (s, 3H), 1.88-1.68 (br m, 2H) |
| 328 | 486 | (400 MHz, DMSO-d₆): 9.12 (s, 1H), 7.81 (d, J = 8.8 Hz, 2H), 7.53 (s, 1H), 7.20 (s, 1H), 7.14 (d, J = 8.8 Hz, 2H), 3.99 (s, 3H), 3.93 (s, 3H), 3.84 (s, 3H), 3.41-3.34 (br m, 2H), 3.28-3.00 (br m, 2H), 2.90 (s, 3H), 2.45-2.37 (br s, 1H) |
| 329 | 558 | (400 MHz, CDCl₃): 9.22 (s, 1H), 7.86 (d, J = 8.8 Hz, 2H), 7.54 (s, 1H), 7.45 (s, 1H), 6.98 (d, J = 8.8 Hz, 2H), 4.05 (s, 3H), 4.01 (s, 3H), 3.88 (s, 3H), 3.34-3.26 (br m, 2H), 3.22-3.11 (br m, 2H), 2.88-2.65 (br m, 8H), 2.54-2.44 (br m, 1H), 1.87-1.78 (br m, 2H), 1.77-1.65 (br m, 2H) |
| 330 | 590 | (400 MHz, CDCl₃): 9.11 (s, 1H), 7.84 (d, J = 8.8 Hz, 2H), 7.46 (s, 1H), 7.40 (s, 1H), 6.99 (d, J = 8.8 Hz, 2H), 4.06 (s, 3H), 4.01 (s, 3H), 3.88 (s, 3H), 3.37-3.25 (br m, 3H), 3.21-3.12 (br m, 2H), 3.07-2.97 (br m, 2H), 2.89-2.76 (br m, 4H), 2.30-2.14 (br m, 3H), 1.90-1.81 (br m, 2H) |
| 331 | 537 | (400 MHz, DMSO-d₆): 9.38 (s, 1H), 8.25 (s, 1H), 8.20 (d, J = 8.0 Hz, 1H), 7.92 (d, J = 8.0 Hz, 1H), 7.83 (d, J = 8.8 Hz, 2H), 7.13 (d, J = 8.8 Hz, 2H), 3.84 (s, 3H), 3.22-3.16 (br m, 2H), 3.09-3.01 (br m, 5H), 2.94 (s, 3H), 2.50-2.40 (br s, 5H), 1.62-1.48 (br m, 5H), 1.44-1.33 (br m, 3H) |
| 332 | 537 | (400 MHz, CDCl₃): 9.27 (br s, 1H), 8.34 (br m, 1H), 8.21 (s, 1H), 7.88 (d, J = 8.8 Hz, 1H), 7.83 (d, J = 8.8 Hz, 2H), 7.02 (d, J = 8.8 Hz, 2H), 4.28-4.20 (br m, 1H), 3.69 (s, 3H), 3.68-3.58 (br t, 2H), 3.44 (t, J = 8.0 Hz, 2H), 3.39-3.27 (br m, 1H), 3.21 (s, 3H), 3.05 (s, 3H), 2.45 (t, J = 8.0 Hz, 2H), 2.09 (quint, J = 8.0 Hz, 2H), 1.88-1.59 (br m, 5H) |
| 333 | 554 | (400 MHz, CDCl₃): 9.35-8.70 (br s, 1H), 8.21 (d, J = 8.8 Hz, 2H), 7.98-7.86 (m, 3H), 7.08 (d, J = 8.8 Hz, 2H), 3.91 (s, 3H), 3.64-3.31 (br m, 4H), 3.21 (s, 3H), 3.12-2.98 (m, 9H), 1.64-1.49 (br s, 8H) |
| 334 | 523 | (400 MHz, CDCl₃): 9.22-9.13 (br s, 1H), 8.70 (s, 1H), 8.18-8.10 (br d, 2H), 7.85 (d, J = 8.8 Hz, 2H), 7.02 (d, J = 8.8 Hz, 2H), 3.89 (s, 3H), 3.58-3.46 (br m, 2H), 3.45-3.33 (br m, 2H), 3.12 (d, J = 4.0 Hz, 3H), 2.82-2.55 (br m, 3H), 2.05-1.40 (br s, 12H) |
| 335 | 469 | (400 MHz, CDCl₃): 9.27 (br s, 1H), 8.42 (d, J = 8.0 Hz, 1H), 8.18 (d, J = 8.0 Hz, 1H), 7.87 (d, J = 8.8 Hz, 2H), 7.44-7.31 (br s, 1H), 7.02 (d, J = 8.8 Hz, 2H), 3.89 (s, 3H), 3.70-3.60 (br m, 2H), 3.40-3.22 (br m, 2H), 3.10 (d, J = 4.0 Hz, 3H), 2.99-2.82 (br m, 4H), 2.65 (s, 3H), 2.01-1.89 (br m, 2H) |
| 336 | 539 | (400 MHz, CDCl₃): 9.31-9.04 (br s, 1H), 8.68 (s, 1H), 8.28-8.07 (br s, 1H), 8.16 (d, J = 8.0 Hz, 1H), 7.85 (d, J = 8.8 Hz, 2H), 7.03 (d, J = 8.8 Hz, 2H), 3.90 (s, 3H), 3.77-3.24 (br m, 6H), 3.11 (d, J = 4.0 Hz, 3H), 2.15-1.78 (br m, 4H), 1.69-1.52 (br m, 5H) |
| 337 | 609 | (400 MHz, CDCl₃): 9.32 (br s, 1H), 8.77 (s, 1H), 8.26-8.15 (br m, 2H), 7.83 (d, J = 8.8 Hz, 2H), 7.01 (d, J = 8.8 Hz, 2H), 3.88 (s, 3H), 3.80-3.52 (br m, 4H), 3.33-3.24 (br m, 2H), 3.07-2.63 (br m, 5H), 2.10-1.49 (br m, 13H), 1.37-1.11 (br m, 6H) |
| 338 | 652.2 | Mixture of Diastereomers in CDCl₃ 9.48, 9.05 (two s, 1H), 8.80, 8.72 (two s, 1H), 8.23-8.12 (br m, d, J = 8.0 Hz, 2H), 7.86, 7.80 (two d, J = 8.8 Hz, 2H), 7.02, 6.99 (two, d, J = 8.8 Hz, 2H), 4.05-3.98 (m, 1H) 3.90, 3.88 (two s, 3H), 3.85-3.77 (m, 2H), 3.74-3.60 (m, 3H), 3.56-3.26 (m, 3H), 3.17-3.06 (m, 1H), 3.04-2.65 (br m, 8H), 2.63-2.28 (br m, 2H), 1.95-1.50 (br m, 5H), 1.32-1.08 (br m, 6H), 0.99-0.84 (br m, 6H) |
| 339 | 727.4 | ¹HNMR (600 MHz, CDCl₃, 25° C.):<br>0.84 (t, 3H, J = 7.2 Hz), 1.22 (m, 16H), 1.40 (m, 2H), 1.75 (m, 2H), 1.85 (m, 4H), 2.73 (m, 1H), 2.80 (s, 3H), 3.01 (m, 6H), 3.21 (m, 6H), 3.42 (m, 2H), 3.90 (m, 2H), 3.99 (t, 2H, J = 6.6 Hz), 6.97 (d, 2H, J = 8.4 Hz), 7.70 (dd, 1H, J = 9, 1.2 Hz), 7.80 (d, 2H, J = 9 Hz), 8.24 (d, 1H, J = 8.4 Hz), 8.63 (s, 1H), 9.37 (s, 1H). |
| 340 | 810.5 | ¹HNMR (600 MHz, CDCl₃, 25° C.):<br>0.84 (t, 3H, J = 6.6 Hz), 1.24 (m, 18H), 1.42 (m, 2H), 1.76 (m, 6H), 1.91 (m, 4H), 2.41 (m, 3H), 2.65 (m, 2H), 2.73 (m, 7H), 2.80 (s, 3H), 3.15 (m, 2H), 3.31 (m, 2H), 3.49 (m, 2H), 3.67 (m, 2H), 3.99 (t, 2H, J = 6.6 Hz), 6.97 (d, 2H, J = 9 Hz), 7.77 (dd, 1H, J = 8.4, 1.2 Hz), 7.79 (d, 2H, J = 9 Hz), 7.21 (d, 1H, J = 8.4 Hz), 8.55 (s, 1H), 9.24 (s, 1H). |
| 341 | 780.5 | ¹HNMR (600 MHz, CDCl₃, 25° C.):<br>0.84 (t, 3H, J = 7.2 Hz), 1.23 (m, 18H), 1.40 (m, 2H), 1.79 (m, 6H), 1.89 (m, 2H), 1.97 (m, 2H), 2.37 (m, 6H), 2.65 (m, 7H), 2.79 (s, 3H), 3.12 (m, 2H), 3.30 (m, 2H), 3.45 (m, 2H), 3.98 (t, 2H, J = 6.6 Hz), 6.96 (d, 2H, J = 9 Hz), 7.66 (dd, 1H, J = 9, 1.8 Hz), 7.78 (d, 2H, J = 9 Hz), 8.20 (d, 1H, J = 8.4 Hz), 8.54 (d, 1H, J = 1.2 Hz), 9.25 (s, 1H). |
| 342 | 765.3 | ¹HNMR (600 MHz, CDCl₃, 25° C.):<br>0.83 (t, 3H, J = 7.2 Hz), 1.23 (m, 18H), 1.40 (m, 2H), 1.75 (m, 3H), 1.90 (m, 9H), 2.39 (m, 3H), 2.80 (m, 3H), 2.82 (m, 4H), 3.29 (m, 6H), 3.48 |

TABLE 2-continued

| No | MS (m/z) | ¹H NMR |
|---|---|---|
| | | (m, 3H), 3.98 (t, 2H, J = 6.6 Hz), 6.98 (d, 2H, J = 8.4 Hz), 7.76 (m, 3H), 8.21 (d, 1H, J = 8.4 Hz), 8.52 (s, 1H), 9.23 (s, 1H). |
| 343 | 781.5 | ¹HNMR (600 MHz, CDCl₃, 25° C.): 0.85 (t, 3H, J = 7.2 Hz), 1.25 (m, 18H), 1.41 (m, 2H), 1.66 (m, 3H), 1.79 (m, 8H), 2.01 (m, 3H), 2.41 (m, 2H), 2.64 (m, 2H), 2.81 (s, 6H), 3.19 (m, 2H), 3.33 (m, 2H), 3.47 (m, 2H), 3.99 (t, 2H, J = 6.6 Hz), 6.97 (d, 2H, J = 8.4 Hz), 7.67 (dd, 1H, J = 9, 1.8 Hz), 7.80 (d, 2H, J = 9 Hz), 8.22 (d, 1H, J = 9 Hz), 8.56 (s, 1H), 9.25 (s, 1H). |
| 344 | 755.3 | ¹HNMR (600 MHz, CDCl₃, 25° C.): 0.84 (t, 3H, J = 7.2 Hz), 1.24 (m, 22H), 1.40 (m, 2H), 1.75 (m, 2H), 1.85 (m, 3H), 2.80 (s, 3H), 3.05 (m, 9H), 3.46 (m, 6H), 3.96 (m, 1H), 4.02 (t, 2H, J = 6.6 Hz), 6.98 (d, 2H, J = 9 Hz), 7.69 (d, 1H, J = 6.6 Hz), 7.81 (d, 2H, J = 8.4 Hz), 8.25 (d, 1H, J = 9 Hz), 8.65 (s, 1H), 9.42 (s, 1H). |
| 345 | 838.5 | ¹HNMR (600 MHz, CDCl₃, 25° C.): 0.85 (t, 3H, J = 7.2 Hz), 1.21 (m, 24H), 1.45 (m, 2H), 1.77 (m, 2H), 1.90 (m, 8H), 2.52 (m, 3H), 2.87 (m, 10H), 3.23 (m, 2H), 3.33 (m, 2H), 3.49 (m, 2H), 3.70 (m, 2H), 3.99 (t, 2H, J = 6.6 Hz), 6.94 (d, 2H, J = 9 Hz), 7.79 (d, 2H, J = 9 Hz), 7.84 (dd, 1H, J = 9, 1.2 Hz), 8.26 (d, 1H, J = 9 Hz), 8.63 (d, 1H, J = 1.8 Hz), 9.41 (s, 1H). |
| 346 | 808.3 | ¹HNMR (600 MHz, CDCl₃, 25° C.): 0.85 (t, 3H, J = 6.6 Hz), 1.22 (m, 24H), 1.77 (m, 2H), 1.98 (m, 2H), 2.10 (m, 6H), 2.56 (s, 3H), 2.60 (m, 3H), 2.82 (s, 3H), 3.07 (m, 7H), 3.33 (m, 4H), 3.51 (m, 2H), 4.00 (t, 2H, J = 6.6 Hz), 7.00 (d, 2H, J = 9 Hz), 7.77 (dd, 1H, J = 8.4, 1.2 Hz), 7.80 (d, 2H, J = 9 Hz), 8.23 (d, 1H, J = 8.4 Hz), 8.53 (s, 1H), 9.23 (s, 1H). |
| 347 | 808.5 | ¹HNMR (600 MHz, CDCl₃, 25° C.): 0.83 (t, 3H, J = 7.2 Hz), 1.22 (m, 22H), 1.40 (m, 2H), 1.75 (m, 8H), 2.20 (m, 5H), 2.39 (m, 3H), 2.48 (m, 2H), 2.80 (m, 4H), 3.21 (m, 7H), 3.43 (m, 2H), 3.98 (t, 2H, J = 6.6 Hz), 6.96 (d, 2H, J = 9 Hz), 7.74 (dd, 1H, J = 9, 1.8 Hz), 7.77 (d, 2H, J = 9 Hz), 8.20 (d, 1H, J = 9 Hz), 8.54 (d, 1H, J = 1.2 Hz), 9.25 (s, 1H) |
| 348 | 809.5 | ¹HNMR (600 MHz, CDCl₃, 25° C.): 0.84 (t, 3H, J = 7.2 Hz), 1.23 (m, 23H), 1.43 (m, 2H), 1.65 (m, 1H), 1.75 (m, 2H), 1.84 (m, 3H), 1.95 (m, 2H), 2.13 (m, 5H), 2.64 (m, 2H), 2.81 (s, 3H), 2.93 (m, 4H), 3.33 (m, 4H), 3.49 (m, 2H), 3.99 (t, 2H, J = 6.6 Hz), 4.14 (m, 1H), 6.98 (d, 2H, J = 9 Hz), 7.66 (dd, 1H, J = 9, 1.2 Hz), 7.79 (d, 2H, J = 9 Hz), 8.21 (d, 1H, J = 9 Hz), 8.54 (s, 1H), 9.23 (s, 1H). |
| 349 | 483.2 | (400 MHz, CDCl₃): 9.36-9.18 (br s, 1H), 8.50-8.32 (br m, 1H), 8.18 (d, J = 8.4 Hz, 1H), 7.92-7.83 (m, 3H), 7.04 (d, J = 8.8 Hz, 2H), 3.89 (s, 3H), 3.60-3.28 (br m, 4H), 3.24-2.95 (br m, 1H), 3.19 (s, 3H), 3.04 (s, 3H), 2.94-2.41 (br m, 5H), 2.11-1.86 (br m, 1H), 1.77-1.52 (br m, 2H) |
| 350 | 554 | (400 MHz, CDCl₃): 9.19 (s, 1H), 8.11 (d, J = 8.0 Hz, 1H), 7.85-7.75 (m, 3H), 7.69 (d, J = 8.8 Hz, 1H), 6.99 (d, J = 8.8 Hz, 2H), 4.25-4.14 (m, 1H), 4.02 (t, J = 6.4 Hz, 2H), 3.57 (t, J = 10.8 Hz, 2H), 3.44 (t, J = 7.2 Hz, 2H), 3.25-3.12 (br m, 2H), 2.62 (s, 3H), 2.45 (t, J = 8.0 Hz, 2H), 2.09 (quint, J = 8.0 Hz, 2H), 1.85-1.56 (br m, 7H), 1.50 (sextet, J = 8.0 Hz, 2H), 0.99 (t, J = 7.4 Hz, 3H) |
| 351 | 571.2 | (400 MHz, DMSO-d₆): 9.23 (s, 1H), 8.05 (d, J = 8.0 Hz, 1H), 7.85-7.78 (m, 4H), 7.12 (d, J = 8.8 Hz, 2H), 4.43-4.38 (m, 1H), 4.06 (t, J = 6.4 Hz, 2H), 3.31-3.17 (br m, 3H), 3.11-2.97 (br m, 3H), 2.63 (s, 3H), 1.75-1.57 (br m, 6H), 1.47-1.27 (br m, 3H), 0.92 (t, J = 7.4 Hz, 3H) |
| 352 | 530.2 | (400 MHz, DMSO-d₆): 9.23 (s, 1H), 8.03 (d, J = 8.8 Hz, 1H), 7.95 (s, 1H), 7.85 (d, J = 8.8 Hz, 2H), 7.80 (d, J = 8.8 Hz, 1H), 7.14 (d, J = 8.8 Hz, 2H), 4.45-4.40 (m, 1H), 4.06 (t, J = 6.4 Hz, 2H), 3.57-3.50 (m, 2H), 3.22-3.15 (br s, 2H), 3.10-3.02 (br s, 2H), 2.77-2.65 (br m, 4H), 2.64-2.58 (br m, 5H), 1.78-1.65 (br m, 4H), 1.46-1.36 (m, 2H), 0.92 (t, J = 7.4 Hz, 3H) |
| 353 | 598.4 | (400 MHz, DMSO-d₆): 9.24 (s, 1H), 8.06 (d, J = 8.8 Hz, 1H), 7.83 (d, J = 8.8 Hz, 1H), 7.75 (d, J = 8.8 Hz, 2H), 7.73 (s, 1H), 7.09 (d, J = 8.8 Hz, 2H), 4.06 (t, J = 6.4 Hz, 2H), 3.75-3.67 (br m, 1H), 3.58-3.51 (br m, 1H), 3.47-3.40 (br m, 1H), 3.32-3.20 (br m, 4H), 3.08-2.73 (br m, 5H), 2.63 (s, 3H), 2.23-2.13 (m, 2H), 1.75-1.51 (br m, 3H), 1.50-1.37 (br m, 2H), 0.92 (t, J = 7.4 Hz, 6H), 0.86 (d, J = 7.4 Hz, 3H) |
| 354 | 647.2 | (400 MHz, DMSO-d₆): 9.17 (s, 1H), 8.09 (t, J = 8.8 Hz, 1H), 8.05 (d, J = 8.8 Hz, 1H), 7.87-7.80 (m, 3H), 7.71 (s, 1H), 7.13 (d, J = 8.8 Hz, 2H), 4.07 (t, J = 6.4 Hz, 2H), 3.80-3.69 (m, 2H), 3.46-3.36 (m, 5H), 2.62 (s, 3H), 1.79-1.65 (br m, 4H), 1.47-1.37 (m, 2H), 0.92 (t, J = 7.4 Hz, 3H) |
| 355 | 586.4 | (400 MHz, DMSO-d₆): 9.23 (s, 1H), 8.05 (d, J = 8.8 Hz, 1H), 7.86-7.79 (m, 4H), 7.13 (d, J = 8.8 Hz, 2H), 4.06 (t, J = 6.4 Hz, 2H), 3.24-3.17 (br s, 2H), 3.13-3.06 (br s, 2H), 2.90-2.77 (br m, 4H), 2.63 (s, 3H), 2.57 (s, 2H), 1.80-1.65 (br m, 6H), 1.62-1.36 (br m, 8H), 0.92 (t, J = 7.4 Hz, 3H) |
| 356 | 542.2 | (400 MHz, DMSO-d₆): 9.23 (s, 1H), 8.05-8.01 (m, 2H), 7.86 (d, J = 8.8 Hz, 2H), 7.80 (d, J = 8.0 Hz, 1H), 7.14 (d, J = 8.8 Hz, 2H), 4.56 (t, J = 6.4 Hz, 2H), 4.43 (t, J = 6.4 Hz, 2H), 4.06 (t, J = 6.4 Hz, 2H), 3.72-3.63 (m, 1H), 3.13-3.06 (br s, 2H), 3.30-3.24 (br s, 2H), 3.06-2.96 (br s, 2H), 2.65 (s, 3H), 2.49-2.39 (br m, 2H), 1.80-1.65 (br m, 4H), 1.41 (sextet, J = 7.4 Hz, 2H), 0.92 (t, J = 7.4 Hz, 3H) |

TABLE 2-continued

| No | MS (m/z) | $^1$H NMR |
|---|---|---|
| 357 | 654 | (400 MHz, DMSO-d$_6$): 9.18 (s, 1H), 8.04 (d, J = 8.0 Hz, 1H), 7.94 (d, J = 2.4 Hz, 1H), 7.81-7.76 (m, 3H), 7.64 (s, 1H), 7.45 (d, J = 8.0 Hz, 1H), 7.31 (dd, $^3$J = 8.0 Hz, $^4$J = 2.4 Hz, 1H), 6.99 (d, J = 8.8 Hz, 2H), 3.98 (t, J = 6.4 Hz, 2H), 3.90-3.33 (br m, 2H), 3.68-3.60 (br m, 2H), 2.36 (s, 3H), 1.86-1.78 (br m, 2H), 1.73-1.65 (m, 2H), 1.41 (sextet, J = 7.4 Hz, 2H), 0.93 (t, J = 7.4 Hz, 3H) |
| 358 | 514 | (400 MHz, CDCl$_3$): 9.05 (s, 1H), 8.27-8.20 (br m, 1H), 7.80 (d, J = 8.8 Hz, 2H), 7.72 (d, J = 8.0 Hz, 1H), 7.68 (s, 1H), 7.02 (d, J = 8.8 Hz, 2H), 4.04 (t, J = 6.4 Hz, 2H), 3.67-3.36 (br m, 6H), 3.09 (s, 3H), 2.70-2.62 (br m, 2H), 2.60 (s, 3H), 1.81 (quint, J = 8.0 Hz, 2H), 1.67-1.46 (br m, 4H), 1.00 (t, J = 7.4 Hz, 3H) |
| 359 | 587 | (400 MHz, DMSO-d$_6$): 9.21(s, 1H), 8.09 (s, 1H), 8.03 (d, J = 8.8 Hz, 1H), 7.89-7.79 (m, 3H), 7.14 (d, J = 8.8 Hz, 2H), 4.07 (t, J = 6.4 Hz, 2H), 3.29-3.17 (br m, 4H), 3.12-2.87 (br m, 5H), 2.77-2.71 (br m, 2H), 2.68-2.59 (br m, 5H), 2.11-2.03 (br m, 2H), 1.99-1.86 (m, 2H), 1.74-1.65 (m, 4H), 1.42 (sxt, J = 7.4 Hz, 2H), 0.92 (t, J = 7.4 Hz, 3H) |
| 360 | 618 | (400 MHz, DMSO-d$_6$): 9.22(s, 1H), 8.06-8.01 (m, 2H), 7.87-7.79 (m, 3H), 7.14 (d, J = 8.8 Hz, 2H), 4.06 (t, J = 6.4 Hz, 2H), 3.28-3.17 (br m, 4H), 3.12-2.88 (br m, 5H), 2.77-2.71 (m, 2H), 2.68-2.59 (br m, 5H), 2.11-2.04 (br m, 2H), 1.99-1.86 (m, 2H), 1.74-1.65 (m, 4H), 1.42 (sxt, J = 7.4 Hz, 2H), 0.92 (t, J = 7.4 Hz, 3H) |
| 361 | 386.2 | (400 MHz, CDCl$_3$): 8.95 (s, 1H), 8.93 (s, 1H), 8.00-7.90 (m, 3H), 7.84 (d, J = 8.8 Hz, 2H), 6.97 (d, J = 8.8 Hz, 2H), 6.52 (br s, 1H), 3.85 (s, 3H), 3.56 (d, J = 5.2 Hz, 3H), 3.07 (d, J = 4.8 Hz, 3H) |
| 362 | 745.4 | $^1$HNMR (600 MHz, CDCl$_3$, 25° C.): 0.82 (t, 3H, J = 7.2 Hz), 1.22 (m, 16H), 1.40 (m, 2H), 1.79 (m, 6H), 2.67 (m, 1H), 2.79 (s, 3H), 2.92 (m, 6H), 3.11 (m, 4H), 3.23 (m, 2H), 3.38 (m, 2H), 3.82 (m, 2H), 4.05 (t, 2H, J = 6.6 Hz), 7.04 (t, 1H, J = 7.8 Hz), 7.54 (dd, 1H, J = 10.2, 2.4 Hz), 7.64 (dd, 1H, J = 9, 1.8 Hz), 7.72 (dd, 1H, J = 9, 1.8 Hz), 8.23 (d, 1H, J = 9 Hz), 8.61 (d, 1H, J = 1.2 Hz), 9.35 (s, 1H). |
| 363 | 783.5 | $^1$HNMR (600 MHz, CDCl$_3$, 25° C.): 0.84 (t, 3H, J = 7.2 Hz), 1.21 (m, 16H), 1.42 (m, 2H), 1.72 (m, 10H), 2.00 (m, 3H), 2.24 (m, 5H), 2.64 (m, 1H), 2.79 (s, 3H), 2.97 (m, 4H), 3.12 (m, 3H), 3.27 (m, 2H), 3.43 (m, 2H), 4.06 (t, 2H, J = 6.6 Hz), 7.03 (t, 1H, J = 8.4 Hz), 7.56 (dd, 1H, J = 10.2, 2.4 Hz), 7.60 (d, 1H, J = 9 Hz), 7.74 (dd, 1H, J = 9, 1.8 Hz), 8.22 (d, 1H, J = 9 Hz), 8.57 (d, 1H, J = 1.2 Hz), 9.29 (s, 1H). |
| 364 | 799.5 | $^1$HNMR (600 MHz, CDCl$_3$, 25° C.): 0.85 (t, 3H, J = 7.2 Hz), 1.22 (m, 17H), 1.43 (m, 2H), 1.63 (m, 3H), 1.78 (m, 11H), 2.34 (m, 2H), 2.52 (m, 2H), 2.73 (m, 4H), 2.81 (s, 3H), 3.12 (m, 2H), 3.29 (m, 2H), 3.46 (m, 2H), 3.93 (m, 1H), 4.07 (t, 2H, J = 6.6 Hz), 7.04 (t, 1H, J = 7.8 Hz), 7.58 (dd, 1H, J = 10.2, 1.8 Hz), 7.62 (d, 1H, J = 8.4 Hz), 7.78 (dd, 1H, J = 9, 1.8 Hz), 8.23 (d, 1H, J = 9 Hz), 8.57 (s, 1H), 9.58 (s, 1H). |
| 365 | 773.5 | $^1$HNMR (600 MHz, CDCl$_3$, 25° C.): 0.82 (t, 3H, J = 7.2 Hz), 1.22 (m, 20H), 1.40 (m, 2H), 1.78 (m, 6H), 2.67 (m, 1H), 2.79 (s, 3H), 2.90 (m, 6H), 3.11 (m, 4H), 3.26 (m, 2H), 3.37 (m, 2H), 3.81 (m, 2H), 4.05 (t, 2H, J = 6.6 Hz), 7.04 (t, 1H, J = 8.4 Hz), 7.54 (dd, 1H, J = 10.2, 2.4 Hz), 7.64 (d, 1H, J = 8.4 Hz), 7.73 (dd, 1H, J = 9, 1.8 Hz), 8.23 (d, 1H, J = 9 Hz), 8.60 (s, 1H), 9.34 (s, 1H). |
| 366 | 811.5 | $^1$HNMR (600 MHz, CDCl$_3$, 25° C.): 0.85 (t, 3H, J = 7.2 Hz), 1.24 (m, 20H), 1.42 (m, 2H), 1.82 (m, 8H), 2.06 (m, 4H), 2.29 (m, 5H), 2.51 (m, 3H), 2.83 (s, 3H), 2.84 (m, 4H), 3.14 (m, 6H)4.10 (t, 2H, J = 6.6 Hz), 7.18 (m, 1H), 7.49 (d, 1H, J = 9 Hz), 7.71 (d, 1H, J = 6 Hz), 7.78 (d, 1H, J = 7.2 Hz), 8.23 (d, 1H, J = 8.4 Hz), 8.51 (s, 1H), 9.18 (m, 1H). |
| 367 | 827.5 | $^1$HNMR (600 MHz, CDCl$_3$, 25° C.): 0.85 (t, 3H, J = 7.2 Hz), 1.22 (m, 20H), 1.40 (m, 2H), 1.63 (m, 3H), 1.77 (m, 11H), 2.34 (m, 2H), 2.52 (m, 2H), 2.73 (m, 4H), 2.81 (s, 3H), 3.12 (m, 2H), 3.29 (m, 2H), 3.46 (m, 2H), 3.93 (m, 1H), 4.07 (t, 2H, J = 6.6 Hz), 7.04 (t, 1H, J = 7.8 Hz), 7.58 (dd, 1H, J = 10.2, 1.8 Hz), 7.62 (d, 1H, J = 9 Hz), 7.78 (dd, 1H, J = 8.4, 1.2 Hz), 8.23 (d, 1H, J = 8.4 Hz), 8.57 (d, 1H, J = 1.8 Hz), 9.28 (s, 1H). |
| 368 | 828.5 | $^1$HNMR (600 MHz, CDCl$_3$, 25° C.): 0.85 (t, 3H, J = 7.2 Hz), 1.20 (m, 21H), 1.43 (m, 2H), 1.81 (m, 6H), 1.92 (m, 4H), 2.42 (m, 2H), 2.72 (m, 8H), 2.81 (s, 3H), 3.14 (m, 8H), 3.30 (m, 2H), 3.50 (m, 2H), 3.66 (t, 2H, J = 5.4 Hz), 4.07 (t, 2H, J = 9 Hz), 7.05 (t, 1H, J = 9.6 Hz), 7.57 (dd, 1H, J = 10.2, 2.4 Hz), 7.63 (d, 1H, J = 9 Hz), 7.78 (dd, 1H, J = 8.4, 1.8 Hz), 8.23 (d, 1H, J = 8.4 Hz), 8.56 (d, 1H, J = 1.2 Hz), 9.27 (s, 1H). |
| 369 | 856.5 | $^1$HNMR (600 MHz, CDCl$_3$, 25° C.): 0.85 (t, 3H, J = 7.2 Hz), 1.22 (m, 23H), 1.44 (m, 2H), 1.81 (m, 10H), 2.51 (m, 2H), 2.67 (m, 2H), 2.79 (m, 7H), 2.81 (s, 3H), 3.21 (m, 2H), 3.31 (m, 2H), 3.49 (m, 2H), 3.69 (t, 2H, J = 5.4 Hz), 4.07 (t, 2H, J = 9 Hz), 7.09 (t, 1H, J = 7.8 Hz), 7.56 (dd, 1H, J = 10.2, 2.4 Hz), 7.64 (d, 1H, J = 9 Hz), 7.78 (dd, 1H, J = 8.4, 1.8 Hz), 8.24 (d, 1H, J = 8.4 Hz), 8.57 (d, 1H, J = 1.2 Hz), 9.27 (s, 1H). |

TABLE 2-continued

| No | MS (m/z) | ¹H NMR |
|---|---|---|
| 370 | 798.5 | ¹HNMR (600 MHz, CDCl₃, 25° C.):<br>0.85 (t, 3H, J = 7.2 Hz), 1.24 (m, 17H), 1.42 (m, 2H), 1.67 (m, 4H), 1.87 (m, 6H), 2.33 (m, 6H), 2.57 (m, 8H), 2.80 (s, 3H), 3.07 (m, 2H), 3.29 (m, 2H), 3.46 (m, 2H), 4.06 (t, 2H, J = 6.6 Hz), 7.03 (t, 1H, J = 8.4 Hz), 7.57 (dd, 1H, J = 10.2, 2.4 Hz), 7.61 (d, 1H, J = 9 Hz), 7.78 (dd, 1H, J = 8.4, 1.8 Hz), 8.22 (d, 1H, J = 9 Hz), 8.56 (d, 1H, J = 1.8 Hz), 9.27 (s, 1H). |
| 371 | 826.5 | ¹HNMR (600 MHz, CDCl₃, 25° C.):<br>0.85 (t, 3H, J = 7.2 Hz), 1.24 (m, 21H), 1.42 (m, 2H), 1.61 (m, 2H), 1.71 (m, 2H), 1.80 (m, 6H), 2.31 (m, 6H), 2.51 (m, 8H), 2.80 (s, 3H), 3.04 (m, 2H), 3.29 (m, 2H), 3.46 (m, 2H), 4.06 (t, 2H, J = 6.6 Hz), 7.02 (t, 1H, J = 8.4 Hz), 7.58 (dd, 1H, J = 10.2, 2.4 Hz), 7.61 (d, 1H, J = 9 Hz), 7.78 (dd, 1H, J = 8.4, 1.8 Hz), 8.22 (d, 1H, J = 9 Hz), 8.57 (d, 1H, J = 1.8 Hz), 9.28 (s, 1H). |
| 372 | 799.5 | ¹HNMR (600 MHz, CDCl₃, 25° C.):<br>0.85 (t, 3H, J = 7.2 Hz), 1.24 (m, 18H), 1.39 (m, 3H), 1.78 (m, 10H), 2.24 (m, 2H), 2.40 (m, 4H), 2.69 (m, 1H), 2.81 (s, 3H), 2.96 (m, 2H), 3.19 (m, 6H), 3.48 (m, 2H), 4.07 (t, 2H, J = 6.6 Hz), 7.05 (d, 1H, J = 8.4 Hz), 7.57 (d, 1H, J = 10.2 Hz), 7.63 (d, 1H, J = 8.4 Hz), 7.75 (d, 1H, J = 9 Hz), 8.23 (d, 1H, J = 9 Hz), 8.58 (s, 1H), 9.27 (s, 1H). |
| 373 | 827.5 | ¹HNMR (600 MHz, CDCl₃, 25° C.):<br>0.84 (t, 3H, J = 7.2 Hz), 1.24 (m, 22H), 1.39 (m, 2H), 1.74 (m, 10H), 2.07 (m, 2H), 2.16 (m, 4H), 2.65 (m, 2H), 2.81 (s, 3H), 3.01 (m, 4H), 3.29 (m, 2H), 3.45 (m, 2H), 3.91 (m, 1H), 4.06 (t, 2H, J = 6.6 Hz), 7.05 (d, 1H, J = 8.4 Hz), 7.57 (d, 1H, J = 10.2 Hz), 7.63 (d, 1H, J = 8.4 Hz), 7.75 (d, 1H, J = 9 Hz), 8.23 (d, 1H, J = 9 Hz), 8.58 (s, 1H), 9.27 (s, 1H). |
| 374 | 781.5 | ¹HNMR (600 MHz, CDCl₃, 25° C.):<br>0.84 (t, 3H, J = 7.2 Hz), 1.24 (m, 18H), 1.46 (m, 2H), 1.85 (m, 10H), 2.26 (m, 2H), 2.42 (m, 6H), 2.78 (s, 3H), 2.97 (m, 2H), 3.20 (m, 6H), 3.45 (m, 2H), 3.99 (t, 2H, J = 6.6 Hz), 6.97 (d, 2H, J = 9 Hz), 7.75 (d, 1H, J = 9.6 Hz), 7.78 (d, 2H, J = 9 Hz), 8.21 (d, 1H, J = 9 Hz), 8.56 (s, 1H), 9.25 (s, 1H). |
| 375 | 809.6 | ¹HNMR (600 MHz, CDCl₃, 25° C.):<br>0.85 (t, 3H, J = 7.2 Hz), 1.21 (m, 22H), 1.44 (m, 2H), 1.86 (m, 10H), 2.26 (m, 2H), 2.41 (m, 4H), 2.80 (s, 3H), 3.01 (m, 2H), 3.20 (m, 7H), 3.48 (m, 2H), 3.99 (t, 2H, J = 6.6 Hz), 4.05 (m, 1H), 6.97 (d, 2H, J = 9 Hz), 7.75 (dd, 1H, J = 8.4, 1.2 Hz), 7.79 (d, 2H, J = 9 Hz), 8.21 (d, 1H, J = 9 Hz), 8.56 (s, 1H), 9.24 (s, 1H). |
| 376 | 783.5 | ¹HNMR (600 MHz, CDCl₃, 25° C.):<br>0.84 (t, 3H, J = 7.2 Hz), 1.22 (m, 24H), 1.40 (m, 2H), 1.76 (m, 2H), 1.86 (m, 4H), 2.67 (m, 2H), 2.79 (s, 3H), 3.21 (m, 7H), 3.33 (m, 7H), 3.94 (m, 2H), 3.99 (t, 2H, J = 6.6 Hz), 6.97 (d, 2H, J = 9 Hz), 7.69 (m, 1H), 7.81 (d, 2H, J = 8.4 Hz), 8.25 (d, 1H, J = 9 Hz), 8.64 (s, 1H), 9.41 (s, 1H). |
| 377 | 821.6 | ¹HNMR (600 MHz, CDCl₃, 25° C.):<br>0.84 (t, 3H, J = 7.2 Hz), 1.23 (m, 24H), 1.38 (m, 2H), 1.77 (m, 2H), 1.87 (m, 10H), 2.23 (m, 2H), 2.32 (m, 2H), 2.69 (m, 2H), 2.81 (s, 3H), 3.08 (m, 5H), 3.32 (m, 5H), 3.49 (m, 2H), 3.99 (t, 2H, J = 6.6 Hz), 6.98 (d, 2H, J = 9 Hz), 7.65 (dd, 1H, J = 8.4, 1.2 Hz), 7.78 (d, 2H, J = 9 Hz), 8.22 (d, 1H, J = 9 Hz), 8.53 (d, 1H, J = 1.2 Hz), 9.23 (s, 1H) |
| 378 | 837.5 | ¹HNMR (600 MHz, CDCl₃, 25° C.):<br>0.85 (t, 3H, J = 7.2 Hz), 1.23 (m, 26H), 1.42 (m, 2H), 1.76 (m, 3H), 1.95 (m, 3H), 2.04 (m, 3H), 2.29 (m, 4H), 2.68 (m, 2H), 2.82 (s, 3H), 3.08 (m, 5H), 3.33 (m, 7H), 4.00 (t, 2H, J = 6 Hz), 4.19 (m, 1H), 7.00 (d, 2H, J = 8.4 Hz), 7.77 (d, 1H, J = 9 Hz), 7.80 (d, 2H, J = 8.4 Hz), 8.22 (d, 1H, J = 9 Hz), 8.53 (s, 1H), 9.27 (s, 1H) |
| 380 | 713.5 | ¹HNMR (400 MHz, CDCl₃, 25° C.): 0.84 (t, 3H, J = 6.8 Hz), 1.25 (m, 12H), 1.38 (m, 2H), 1.76 (m, 2H), 1.86 (m, 4H), 2.69 (m, 1H), 2.79 (s, 3H), 2.90 (m, 6H), 3.09 (m, 6H), 3.25 (m, 2H), 3.39 (m, 2H), 3.82 (m, 2H), 3.99 (t, 2H, J = 8.4 Hz), 6.96 (d, 2H, J = 8.8 Hz), 7.71 (dd, 1H, J = 8.8, 1.6 Hz), 7.80 (d, 2H, J = 8.8 Hz), 8.23 (d, 1H, J = 8.8 Hz), 8.62 (d, 1H, J = 1.2 Hz), 9.35 (s, 1H). |
| 381 | 751.5 | ¹HNMR (400 MHz, CDCl₃, 25° C.): 0.85 (t, 3H, J = 7.2 Hz), 1.23 (m, 12H), 1.43 (m, 3H), 1.61 (m, 2H), 1.76 (m, 8H), 2.03 (m, 6H), 2.20 (m, 2H), 2.33 (m, 2H), 2.67 (m, 1H), 2.80 (s, 3H), 3.05 (m, 4H), 3.15 (m, 2H), 3.31 (m, 2H), 3.44 (m, 2H), 3.99 (t, 2H, J = 6.4 Hz), 6.97 (d, 2H, J = 8.8 Hz), 7.74 (dd, 1H, J = 8.8, 1.6 Hz), 7.79 (d, 2H, J = 8.8 Hz), 8.22 (d, 1H, J = 8.8 Hz), 8.58 (s, 1H), 9.27 (s, 1H). |
| 382 | 767.5 | ¹HNMR (400 MHz, CDCl₃, 25° C.): 0.84 (t, 3H, J = 6.8 Hz), 1.23 (m, 13H), 1.39 (m, 3H), 1.75 (br m, 10H), 2.24 (m, 2H), 2.40 (m, 4H), 2.70 (m, 1H), 2.81 (s, 3H), 2.99 (m, 3H), 3.20 (m, 6H), 3.48 (m, 2H), 3.99 (t, 2H, J = 6.4 Hz), 4.02 (m, 1H), 6.97 (d, 2H, J = 8.8 Hz), 7.74 (dd, 1H, J = 8.8, 1.2 Hz), 7.79 (d, 2H, J = 8.8 Hz), 8.20 (d, 1H, J = 8.8 Hz), 8.57 (s, 1H), 9.23 (s, 1H). |
| 383 | 767.5 | ¹HNMR (400 MHz, CDCl₃, 25° C.): 0.84 (t, 3H, J = 6.8 Hz), 1.25 (m, 13H), 1.42 (m, 3H), 1.67 (m, 1H), 1.80 (br m, 8H), 2.09 (m, 5H), 2.65 (m, 2H), 2.82 (s, 3H), 2.92 (m, 6H), 3.34 (m, 4H), 3.48 (m, 2H), 3.99 (t, 2H, J = 6.8 Hz), 4.14 (m, 1H), 6.99 (d, 2H, J = 8.8 Hz), 7.76 (dd, 1H, J = 8.8, 1.6 Hz), 7.79 (d, 2H, J = 8.8 Hz), 8.21 (d, 1H, J = 8.8 Hz), 8.55 (s, 1H), 9.23 (s, 1H). |

TABLE 2-continued

| No | MS (m/z) | ¹H NMR |
|---|---|---|
| 384 | 696.3 | ¹HNMR (600 MHz, D$_6$-DMSO, 25° C.): 1.13 (m, 6H), 1.40 (m, 2H), 1.48 (br m, 9H), 2.09 (m, 5H), 2.22 (m, 3H), 2.62 (m, 4H), 3.02 (m, 14H), 4.56 (t, 2H, J = 4.8 Hz), 7.11 (m, 1H), 7.18 (m, 1H), 7.75 (m, 1H), 7.79 (m, 3H), 8.03 (m, 1H), 9.21 (m, 1H) |
| 385 | 866.5 | ¹HNMR (600 MHz, D$_6$-DMSO, 25° C.): 0.82 (t, 3H, J = 7.2 Hz), 1.21 (m, 30H), 1.37 (m, 2H), 1.50 (m, 2H), 1.69 (m, 5H), 1.90 (m, 2H), 2.66 (m, 8H), 2.85 (s, 3H), 3.02 (m, 7H), 3.57 (m, 2H), 4.03 (t, 2H, J = 6.6 Hz), 4.65 (m, 1H), 7.13 (d, 2H, J = 8.4 Hz), 7.82 (d, 2H, J = 8.4 Hz), 8.14 (d, 1H, J = 9 Hz), 8.28 (d, 1H, J = 8.4 Hz), 8.48 (s, 1H), 9.38 (m, 1H). |
| 386 | 836.5 | ¹HNMR (600 MHz, D$_6$-DMSO, 25° C.): 0.82 (t, 3H, J = 7.2 Hz), 1.21 (m, 28H), 1.37 (m, 2H), 1.46 (m, 4H), 1.69 (m, 4H), 1.85 (m, 2H), 2.32 (m, 5H), 2.61 (m, 8H), 2.85 (s, 3H), 3.08 (m, 4H), 4.03 (t, 2H, J = 5.4 Hz), 7.11 (d, 2H, J = 8.4 Hz), 7.81 (d, 2H, J = 7.8 Hz), 8.13 (d, 1H, J = 7.8 Hz), 8.27 (d, 1H, J = 9 Hz), 8.49 (s, 1H), 9.37 (m, 1H). |
| 387 | 884.5 | ¹HNMR (600 MHz, D$_6$-DMSO, 25° C.): 0.81 (t, 3H, J = 7.2 Hz), 1.20 (m, 30H), 1.34 (m, 4H), 1.70 (m, 5H), 1.84 (m, 2H), 2.35 (m, 3H), 2.66 (m, 7H), 2.85 (s, 3H), 3.00 (m, 5H), 3.53 (m, 2H), 4.12 (t, 2H, J = 6 Hz), 4.54 (m, 1H), 7.38 (d, 1H, J = 7.2 Hz), 7.73 (m, 2H), 8.14 (d, 1H, J = 8.4 Hz), 8.28 (d, 1H, J = 9 Hz), 8.49 (s, 1H), 9.38 (m, 1H). |
| 388 | 854.5 | ¹HNMR (600 MHz, D$_6$-DMSO, 25° C.): 0.81 (t, 3H, J = 7.2 Hz), 1.20 (m, 28H), 1.34 (m, 2H), 1.46 (m, 4H), 1.62 (m, 4H), 1.70 (m, 2H), 2.20 (m, 6H), 2.41 (m, 3H), 2.52 (m, 4H), 2.85 (s, 3H), 2.90 (m, 2H), 3.07 (m, 2H), 4.13 (t, 2H, J = 6 Hz), 7.36 (t, 1H, J = 7.8 Hz), 7.69 (d, 1H, J = 7.8 Hz), 7.75 (d, 1H, J = 9.6 Hz), 8.13 (d, 1H, J = 9 Hz), 8.27 (d, 1H, J = 9 Hz), 8.49 (s, 1H), 9.37 (m, 1H). |
| 389 | 855.5 | ¹HNMR (600 MHz, D$_6$-DMSO, 25° C.): 0.82 (t, 3H, J = 7.2 Hz), 1.21 (m, 28H), 1.39 (m, 3H), 1.45 (m, 2H), 1.71 (m, 9H), 1.90 (m, 3H), 2.30 (m, 2H), 2.85 (s, 3H), 3.04 (m, 7H), 3.66 (m, 1H), 4.13 (t, 2H, J = 6 Hz), 7.38 (t, 1H, J = 7.8 Hz), 7.72 (m, 1H), 7.78 (d, 1H, J = 10.8 Hz), 8.14 (d, 1H, J = 8.4 Hz), 8.29 (d, 1H, J = 8.4 Hz), 8.50 (s, 1H), 9.38 (s, 1H). |
| 390 | 840.5 | ¹HNMR (600 MHz, D$_6$-DMSO, 25° C.): 0.82 (t, 3H, J = 7.2 Hz), 1.07 (m, 3H), 1.20 (m, 20H), 1.37 (m, 2H), 1.42 (m, 2H), 1.58 (m, 2H), 1.71 (m, 4H), 1.86 (m, 2H), 2.36 (m, 2H), 2.68 (m, 9H), 2.85 (s, 3H), 3.08 (m, 5H), 3.32 (m, 4H), 4.12 (t, 2H, J = 6 Hz), 7.38 (t, 1H, J = 8.4 Hz), 7.73 (d, 1H, J = 7.8 Hz), 7.77 (d, 1H, J = 10.2 Hz), 8.15 (d, 1H, J = 9 Hz), 8.29 (d, 1H, J = 8.4 Hz), 8.49 (s, 1H), 9.38 (s, 1H). |
| 391 | 854.5 | ¹HNMR (600 MHz, D$_6$-DMSO, 25° C.): 0.82 (t, 3H, J = 7.2 Hz), 1.07 (m, 6H), 1.20 (m, 20H), 1.35 (m, 4H), 1.55 (m, 2H), 1.71 (m, 4H), 1.85 (m, 2H), 2.33 (m, 3H), 2.68 (m, 8H), 2.85 (s, 3H), 3.01 (m, 5H), 3.32 (m, 4H), 4.10 (t, 2H, J = 6 Hz), 7.38 (t, 1H, J = 8.4 Hz), 7.72 (d, 1H, J = 8.4 Hz), 7.77 (dd, 1H, J = 10.2, 1.8 Hz), 8.15 (d, 1H, J = 9 Hz), 8.29 (d, 1H, J = 9 Hz), 8.50 (s, 1H), 9.38 (s, 1H). |
| 392 | 840.5 | ¹HNMR (600 MHz, D$_6$-DMSO, 25° C.): 0.82 (t, 3H, J = 7.2 Hz), 1.21 (m, 24H), 1.38 (m, 6H), 1.57 (m, 2H), 1.69 (m, 6H), 2.11 (m, 2H), 2.36 (s, 3H), 2.64 (m, 2H), 2.69 (m, 2H), 2.75 (m, 4H), 2.84 (s, 3H), 2.86 (m, 2H), 3.08 (m, 2H), 4.13 (t, 2H, J = 6 Hz), 7.35 (t, 1H, J = 8.4 Hz), 7.68 (d, 1H, J = 8.4 Hz), 7.76 (dd, 1H, J = 10.8, 1.8 Hz), 8.14 (dd, 1H, J = 8.4, 0.6 Hz), 8.28 (d, 1H, J = 8.4 Hz), 8.50 (s, 1H), 9.38 (s, 1H). |
| 393 | 813.4 | ¹HNMR (600 MHz, D$_6$-DMSO, 25° C.): 0.81 (t, 3H, J = 7.2 Hz), 1.19 (m, 24H), 1.37 (m, 2H), 1.48 (m, 2H), 1.72 (m, 3H), 1.87 (m, 4H), 2.32 (m, 1H), 2.86 (s, 3H), 3.05 (m, 3H), 3.16 (m, 3H), 3.36 (m, 4H), 3.60 (m, 4H), 4.12 (t, 2H, J = 6 Hz), 7.42 (t, 1H, J = 7.8 Hz), 7.76 (m, 3H), 817 (d, 1H, J = 8.4 Hz), 8.30 (d, 1H, J = 8.4 Hz), 8.48 (s, 1H), 9.40 (s, 1H) |
| 394 | 840.5 | ¹HNMR (600 MHz, D$_6$-DMSO, 25° C.): 0.82 (t, 3H, J = 6.6 Hz), 1.09 (t, 3H, J = 6.6 Hz), 1.20 (m, 20H), 1.34 (m, 4H), 1.61 (m, 6H), 1.84 (m, 2H), 2.31 (m, 2H), 2.45 (m, 1H), 2.68 (m, 8H), 2.85 (s, 3H), 3.12 (m, 5H), 3.40 (m, 4H), 4.12 (t, 2H, J = 6 Hz), 7.37 (t, 1H, J = 8.4 Hz), 7.70 (d, 1H, J = 8.4 Hz), 7.76 (dd, 1H, J = 10.2, 1.2 Hz), 8.14 (d, 1H, J = 8.4 Hz), 8.28 (d, 1H, J = 8.4 Hz), 8.51 (s, 1H), 9.38 (s, 1H). |
| 395 | 826.5 | ¹HNMR (600 MHz, D$_6$-DMSO, 25° C.): 0.81 (t, 3H, J = 7.2 Hz), 1.20 (m, 22H), 1.34 (m, 4H), 1.44 (m, 4H), 1.66 (m, 4H), 1.82 (m, 2H), 2.25 (m, 6H), 2.57 (m, 5H), 2.85 (s, 3H), 2.99 (m, 4H), 3.35 (m, 4H), 4.05 (t, 2H, J = 6 Hz), 6.99 (dd, 1H, J = 7.2, 1.8 Hz), 7.08 (d, 1H, J = 9 Hz), 8.08 (m, 1H), 8.15 (d, 1H, J = 8.4 Hz), 8.29 (d, 1H, J = 9 Hz), 8.51 (s, 1H), 9.39 (s, 1H). |
| 396 | 844.5 | ¹HNMR (600 MHz, D$_6$-DMSO, 25° C.): 0.82 (t, 3H, J = 7.2 Hz), 1.21 (m, 24H), 1.32 (m, 4H), 1.66 (m, 4H), 1.80 (m, 4H), 2.25 (m, 4H), 2.77 (m, 6H), 2.85 (s, 3H), 3.05 (m, 5H), 3.35 (m, 2H), 4.28 (m, 2H), 7.82 (m, 2H), 8.18 (d, 1H, J = 8.4 Hz), 8.33 (d, 1H, J = 8.4 Hz), 8.50 (s, 1H), 9.41 (s, 1H). |
| 397 | 844.5 | ¹HNMR (600 MHz, D$_6$-DMSO, 25° C.): 0.80 (t, 3H, J = 7.2 Hz), 1.21 (m, 24H), 1.35 (m, 6H), 1.67 (m, 2H), 1.72 (m, 2H), 1.80 (m, 2H), 2.22 (m, 4H), 2.44 (m, 3H), 2.54 (m, 4H), 2.85 (s, 3H), 2.96 (m, 2H), 3.10 (m, 2H), 3.35 (m, 2H), 4.19 (t, 2H, J = 6.6 Hz), 7.34 (t, 1H, J = 7.2 Hz), 7.93 (m, 1H), 7.16 (d, 1H, J = 9 Hz), 8.29 (d, 1H, J = 9 Hz), 8.52 (s, 1H), 9.38 (s, 1H). |
| 398 | 864.5 | ¹HNMR (600 MHz, D$_6$-DMSO, 25° C.): 0.82 (t, 3H, J = 7.2 Hz), 1.21 (m, 32H), 1.45 (m, 9H), 1.69 (m, 4H), 1.85 (m, 3H), 2.32 (m, 5H), 2.58 (m, 6H), 2.85 (s, 3H), 3.08 (m, 4H), 4.03 (t, 2H, J = 6 Hz), 7.11 (d, 2H, |

TABLE 2-continued

| No | MS (m/z) | ¹H NMR |
|---|---|---|
| | | J = 8.4 Hz), 7.80 (d, 2H, J = 8.4 Hz), 8.13 (d, 1H, J = 8.4 Hz), 8.27 (d, 1H, J = 9 Hz), 8.49 (s, 1H), 9.36 (s, 1H). |
| 399 | 882.5 | ¹HNMR (600 MHz, $D_6$-DMSO, 25° C.): 0.84 (t, 3H, J = 7.2 Hz), 1.21 (m, 32H), 1.33 (m, 7H), 1.73 (m, 4H), 1.90 (m, 4H), 2.32 (m, 4H), 2.58 (m, 6H), 2.85 (m, 5H), 3.09 (m, 4H), 4.14 (m, 2H), 7.39 (m, 1H), 7.73 (m, 2H), 8.15 (m, 1H), 8.27 (m, 1H), 8.49 (s, 1H), 9.38 (s, 1H). |
| 400 | 829.4 | ¹HNMR (600 MHz, $D_6$-DMSO, 25° C.) 0.81 (t, 3H, J = 7.2 Hz), 1.17 (m, 25H), 1.35 (m, 4H), 1.70 (m, 7H), 2.60 (m, 4H), 2.70 (m, 4H), 2.85 (s, 3H), 3.10 (m, 6H), 4.12 (t, 2H, J = 6.6 Hz), 7.40 (t, 1H, J = 6.6 Hz), 7.76 (d, 2H, J = 10.2 Hz), 8.16 (d, 1H, J = 8.4 Hz), 8.29 (d, 1H, J = 8.4 Hz), 8.49 (s, 1H), 9.39 (s, 1H). |
| 401 | 854.4 | ¹HNMR (600 MHz, $D_6$-DMSO, 25° C.): 0.82 (t, 3H, J = 7.2 Hz), 1.24 (m, 22H), 1.35 (m, 2H), 1.44 (m, 2H), 1, 71 (br m, 7H), 1.98 (s, 3H), 2.40 (m, 4H), 2.85 (s, 3H), 3.09 (m, 4H), 3.33 (m, 6H), 3.41 (m, 3H), 4.12 (t, 2H, J = 6.6 Hz), 7.38 (t, 1H, J = 8.4 Hz), 7.74 (d, 1H, J = 7.8 Hz), 7.77 (d, 1H, J = 10.8 Hz), 8.15 (d, 1H, J = 9 Hz), 8.29 (d, 1H, J = 9 Hz), 8.49 (s, 1H), 9.39 (s, 1H). |
| 402 | 842.4 | ¹HNMR (600 MHz, $D_6$-DMSO, 25° C.): 0.82 (t, 3H, J = 7.2 Hz), 1.22 (m, 24H), 1.37 (m, 2H), 1.57 (m, 2H), 1.72 (m, 4H), 1.93 (m, 5H), 2.53 (m, 4H), 2.77 (m, 8H), 3.24 (m, 7H), 4.13 (t, 2H, J = 6.6 Hz), 7.41 (t, 1H, J = 7.8 Hz), 7.79 (d, 2H, J = 9 Hz), 8.36 (m, 2H), 8.68 (s, 1H), 9.41 (s, 1H). |
| 411 | 812.5 | ¹HNMR (600 MHz, $D_6$-DMSO, 25° C.): 0.82 (t, 3H, J = 7.2 Hz), 1.01 (m, 3H), 1.21 (m, 18H), 1.31 (m, 6H), 1.62 (m, 2H), 1.71 (m, 2H), 1.90 (m, 2H), 2.18 (m, 3H), 2.42 (m, 4H), 2.53 (m, 4H), 2.85 (s, 3H), 2.90 (m, 2H), 3.08 (m, 2H), 3.29 (m, 3H), 4.13 (t, 2H, J = 6 Hz), 7.36 (t, 1H, J = 8.4 Hz), 7.70 (d, 1H, J = 8.4 Hz), 7.76 (d, 1H, J = 10.2 Hz), 8.14 (d, 1H, J = 9 Hz), 8.28 (d, 1H, J = 9 Hz), 8.50 (s, 1H), 9.38 (s, 1H). |
| 412 | 826.5 | ¹HNMR (600 MHz, $D_6$-DMSO, 25° C.): 0.82 (t, 3H, J = 6.6 Hz), 1.08 (m, 6H), 1.21 (m, 20H), 1.38 (m, 5H), 1.72 (m, 5H), 1.85 (m, 3H), 2.21 (m, 2H), 2.70 (m, 6H), 2.85 (s, 3H), 3.09 (br m, 6H), 4.13 (t, 2H, J = 6.6 Hz), 7.38 (m, 1H), 7.73 (m, 1H), 7.77 (d, 1H, J = 8.4 Hz), 8.15 (d, 1H, J = 8.4 Hz), 8.29 (d, 1H, J = 9 Hz), 8.50 (s, 1H), 9.38 (s, 1H). |
| 413 | 812.5 | ¹HNMR (600 MHz, $D_6$-DMSO, 25° C.): 0.81 (t, 3H, J = 7.2 Hz), 1.01 (m, 3H), 1.21 (m, 18H), 1.33 (m, 4H), 1.54 (m, 4H), 1.70 (m, 2H), 1.84 (m, 2H), 2.38 (m, 4H), 2.52 (m, 7H), 2.85 (s, 3H), 3.11 (m, 4H), 3.27 (m, 3H), 4.13 (t, 2H, J = 6.6 Hz), 7.37 (t, 1H, J = 8.4 Hz), 7.70 (d, 1H, J = 8.4 Hz), 7.77 (dd, 1H, J = 10.8, 1.8 Hz), 8.13 (dd, 1H, J = 9, 1.2 Hz), 8.28 (d, 1H, J = 8.4 Hz), 8.51 (s, 1H), 9.38 (s, 1H). |
| 414 | 868.5 | ¹HNMR (600 MHz, $D_6$-DMSO, 25° C.): 0.82 (t, 3H, J = 7.2 Hz), 1.01 (m, 3H), 1.21 (m, 28H), 1.35 (m, 6H), 1.64 (m, 2H), 1.72 (m, 2H), 1.81 (m, 2H), 2.22 (m, 6H), 2.57 (m, 5H), 2.85 (s, 3H), 2.95 (m, 2H), 3.08 (m, 2H), 3.29 (m, 1H), 4.12 (t, 2H, J = 6 Hz), 7.37 (t, 1H, J = 8.4 Hz), 7.71 (d, 1H, J = 5.4 Hz), 7.76 (d, 1H, J = 10.2 Hz), 8.14 (d, 1H, J = 8.4 Hz), 8.28 (d, 1H, J = 8.4 Hz), 8.50 (s, 1H), 9.38 (s, 1H). |
| 415 | 882.5 | ¹HNMR (600 MHz, $D_6$-DMSO, 25° C.): (m, 5H), 1.85 (m, 2H), 2.20 (m, 3H), 2.62 (m, 6H), 2.85 (s, 3H), 2.95 (m, 3H), 3.08 (m, 3H), 4.13 (t, 2H, J = 6.6 Hz), 7.37 (t, 1H, J = 7.8 Hz), 7.72 (m, 1H), 7.76 (dd, 1H, J = 10.2, 1.2 Hz), 8.14 (d, 1H, J = 8.4 Hz), 8.29 (d, 1H, J = 8.4 Hz), 8.50 (s, 1H), 9.38 (s, 1H). |
| 416 | 869.5 | ¹HNMR (600 MHz, $D_6$-DMSO, 25° C.): 0.81 (t, 3H, J = 7.2 Hz), 1.20 (m, 32H), 1.35 (m, 5H), 1.60 (m, 2H), 1.71 (m, 2H), 1.89 (m, 2H), 2.38 (m, 3H), 2.54 (m, 6H), 2.85 (s, 3H), 2.95 (m, 2H), 3.12 (m, 4H), 4.12 (t, 2H, J = 6.6 Hz), 7.37 (t, 1H, J = 7.8 Hz), 7.71 (m, 1H), 7.76 (dd, 1H, J = 10.2, 1.8 Hz), 8.14 (d, 1H, J = 8.4 Hz), 8.27 (d, 1H, J = 9 Hz), 8.51 (s, 1H), 9.37 (s, 1H). |
| 417 | 816.5 | ¹HNMR (600 MHz, $D_6$-DMSO, 25° C.): 0.80 (t, 3H, J = 7.2 Hz), 1.20 (m, 18H), 1.35 (m, 6H), 1.63 (m, 2H), 1.72 (m, 5H), 2.18 (m, 6H), 2.38 (m, 4H), 2.55 (m, 2H), 2.85 (s, 3H), 2.90 (m, 2H), 3.11 (m, 2H), 3.28 (m, 2H), 4.19 (t, 2H, J = 6 Hz), 7.33 (t, 1H, J = 7.8 Hz), 7.92 (m, 1H), 8.16 (d, 1H, J = 8.4 Hz), 8.29 (d, 1H, J = 9 Hz), 8.52 (s, 1H), 9.38 (s, 1H). |
| 418 | 830.5 | ¹HNMR (600 MHz, $D_6$-DMSO, 25° C.): 0.80 (t, 3H, J = 7.2 Hz), 1.02 (m, 3H), 1.20 (m, 18H), 1.37 (m, 6H), 1.75 (m, 6H), 2.20 (m, 6H), 2.55 (m, 6H), 2.85 (s, 3H), 2.90 (m, 2H), 3.11 (m, 2H), 3.31 (m, 2H), 4.19 (t, 2H, J = 6.6 Hz), 7.36 (m, 1H), 7.94 (m, 1H), 8.16 (d, 1H, J = 9 Hz), 8.29 (d, 1H, J = 9 Hz), 8.52 (s, 1H), 9.38 (s, 1H). |
| 419 | 844.5 | ¹HNMR (600 MHz, $D_6$-DMSO, 25° C.): 0.80 (t, 3H, J = 7.2 Hz), 1.19 (m, 24H), 1.38 (m, 3H), 1.47 (m, 3H), 1.74 (m, 3H), 1.90 (m, 6H), 2.74 (m, 6H), 2.85 (s, 3H), 2.89 (m, 2H), 3.12 (m, 4H), 3.31 (m, 2H), 4.19 (t, 2H, J = 6.6 Hz), 7.39 (m, 1H), 7.90 (m, 1H), 8.17 (d, 1H, J = 7.2 Hz), 8.30 (d, 1H, J = 7.2 Hz), 8.52 (s, 1H), 9.39 (s, 1H). |
| 420 | 830.4 | ¹HNMR (600 MHz, $D_6$-DMSO, 25° C.): 0.81 (t, 3H, J = 7.2 Hz), 1.09 (m, 3H), 1.21 (m, 20H), 1.39 (m, 5H), 1.65 (m, 4H), 1.72 (m, 2H), 1.84 (m, 2H), 2.44 (m, 4H), 2.55 (m, 5H), 2.85 (s, 3H), 3.16 (m, 4H), 3.31 (m, 2H), 4.20 (t, 2H, J = 6.6 Hz), 7.34 (t, 1H, J = 7.8), 7.91 (m, 1H), 8.16 (d, 1H, J = 9 Hz), 8.29 (d, 1H, J = 8.4 Hz), 8.53 (s, 1H), 9.37 (s, 1H). |
| 421 | 858.5 | ¹HNMR (600 MHz, $D_6$-DMSO, 25° C.): 0.83 (t, 3H, J = 6.6 Hz), 1.22 (m, 33H), 1.66 (m, 6H), 2.15 (m, 6H), 2.61 (m, 4H), 2.86 (m, 7H), 3.09 (m, |

TABLE 2-continued

| No | MS (m/z) | ¹H NMR |
|---|---|---|
| | | 3H), 4.21 (t, 2H, J = 6 Hz), 7.80 (m, 2H), 8.18 (d, 1H, J = 7.8 Hz), 8.33 (d, 1H, J = 8.4 Hz), 8.50 (s, 1H), 9.41 (s, 1H). |
| 422 | 872.5 | ¹HNMR (600 MHz, D$_6$-DMSO, 25° C.): 0.81 (t, 3H, J = 7.2 Hz), 1.20 (m, 34H), 1.77 (m, 5H), 1.99 (m, 6H), 2.68 (m, 4H), 2.85 (m, 8H), 3.15 (m, 3H), 4.19 (t, 2H, J = 6 Hz), 7.41 (m, 1H), 7.93 (m, 1H), 8.18 (m, 1H), 8.32 (m, 1H), 8.51 (s, 1H), 9.40 (s, 1H). |
| 432 | 858.5 | ¹HNMR (600 MHz, D$_6$-DMSO, 25° C.): 0.83 (t, 3H, J = 6.6 Hz), 1.22 (m, 35H), 1.65 (m, 6H), 2.16 (m, 3H), 2.61 (m, 3H), 2.86 (m, 7H), 3.16 (m, 4H), 4.21 (t, 2H, J = 6 Hz), 7.80 (m, 2H), 8.18 (d, 1H, J = 7.8 Hz), 8.33 (d, 1H, J = 8.4 Hz), 8.50 (s, 1H), 9.14 (s, 1H). |
| 433 | 872.5 | ¹HNMR (600 MHz, D$_6$-DMSO, 25° C.): 0.82 (t, 3H, J = 7.2 Hz), 1.20 (m, 36H), 1.66 (m, 4H), 1.90 (m, 5H), 2.74 (m, 5H), 2.86 (m, 6H), 3.04 (m, 4H), 4.21 (t, 2H, J = 6.6 Hz), 7.81 (m, 2H), 8.19 (d, 1H, J = 8.4 Hz), 8.32 (d, 1H, J = 9 Hz), 8.50 (s, 1H), 9.40 (s, 1H). |
| 451 | 794.17 | ¹HNMR (600 MHz, D$_6$-DMSO, 25° C.): 0.84 (t, 3H, J = 7.8 Hz), 1.07 (m, 3H), 1.22 (m, 18H), 1.37 (m, 6H), 1.69 (m, 4H), 1.72 (m, 4H), 1.86 (m, 2H), 2.40 (m, 4H), 2.60 (m, 5H), 2.85 (s, 3H), 3.09 (m, 3H), 3.17 (m, 2H), 4.05 (t, 2H, J = 6 Hz), 7.11 (d, 2H, J = 8.4 Hz), 7.80 (d, 2H, J = 7.2 Hz), 8.14 (d, 1H, J = 8.4 Hz), 8.28 (d, 1H, J = 7.8 Hz), 8.49 (s, 1H), 9.38 (s, 1H). |
| 452 | 808.5 | ¹HNMR (600 MHz, D$_6$-DMSO, 25° C.): 0.84 (t, 3H, J = 7.2 Hz), 1.07 (m, 6H), 1.22 (m, 18H), 1.37 (m, 7H), 1.69 (m, 4H), 1.72 (m, 3H), 2.19 (m, 3H), 2.60 (m, 7H), 2.85 (s, 3H), 2.96 (m, 2H), 3.09 (m, 3H), 4.05 (t, 2H, J = 6.6 Hz), 7.12 (d, 2H, J = 8.4 Hz), 7.81 (d, 2H, J = 7.8 Hz), 8.14 (d, 1H, J = 8.4 Hz), 8.28 (d, 1H, J = 8.4 Hz), 8.49 (s, 1H), 9.37 (s, 1H). |
| 453 | 822.4 | ¹HNMR (600 MHz, D$_6$-DMSO, 25° C.): 0.84 (t, 3H, J = 7.2 Hz), 1.01 (m, 3H), 1.22 (m, 22H), 1.39 (m, 7H), 1.69 (m, 2H), 1.72 (m, 3H), 1.84 (m, 2H), 2.16 (m, 7H), 2.61 (m, 5H), 2.85 (s, 3H), 2.91 (m, 2H), 3.09 (m, 2H), 4.04 (t, 2H, J = 6.6 Hz), 7.11 (d, 2H, J = 8.4 Hz), 7.79 (d, 2H, J = 8.4 Hz), 8.13 (d, 1H, J = 8.4 Hz), 8.27 (d, 1H, J = 9 Hz), 8.50 (s, 1H), 9.37 (s, 1H). |
| 454 | 836.5 | ¹HNMR (600 MHz, D$_6$-DMSO, 25° C.): 0.84 (m, 3H), 1.22 (m, 34H), 1.48 (m, 2H), 1.71 (m, 4H), 1.91 (m, 3H), 2.31 (m, 3H), 2.61 (m, 4H), 2.85 (m, 6H), 3.09 (m, 4H), 4.05 (m, 2H), 7.13 (d, 2H, J = 5.4 Hz), 7.82 (m, 2H), 8.14 (m, 1H), 8.28 (m, 1H), 8.49 (s, 1H), 9.37 (s, 1H). |
| 457 | 878.4 | ¹HNMR (600 MHz, D$_6$-DMSO, 25° C.): 0.84 (t, 3H, J = 7.2 Hz), 0.97 (t, 3H, J = 6.6 Hz), 1.23 (m, 34H), 1.36 (m, 6H), 1.57 (m, 2H), 1.70 (m, 2H), 1.76 (m, 2H), 2.11 (m, 3H), 2.30 (m, 6H), 2.85 (s, 3H), 2.88 (m, 2H), 3.09 (m, 3H), 4.05 (t, 2H, J = 6 Hz), 7.01 (d, 2H, J = 9 Hz), 7.78 (d, 2H, J = 8.4 Hz), 8.12 (dd, 1H, J = 9, 1.2 Hz), 8.27 (d, 1H, J = 8.4 Hz), 8.49 (d, 1H, J = 1.2 Hz), 9.37 (s, 1H). |
| 458 | 878.4 | ¹HNMR (600 MHz, D$_6$-DMSO, 25° C.): 0.84 (t, 3H, J = 7.2 Hz), 0.96 (m, 3H), 1.21 (m, 34H), 1.38 (m, 6H), 1.62 (m, 2H), 1.70 (m, 2H), 1.81 (m, 2H), 2.22 (m, 3H), 2.41 (m, 6H), 2.85 (s, 3H), 2.94 (m, 2H), 3.08 (m, 3H), 4.05 (t, 2H, J = 6 Hz), 7.11 (d, 2H, J = 8.4 Hz), 7.79 (d, 2H, J = 9 Hz), 8.13 (dd, 1H, J = 9, 1.2 Hz), 8.27 (d, 1H, J = 9 Hz), 8.49 (s, 1H), 9.37 (s, 1H). |
| 459 | 890.5 | ¹HNMR (600 MHz, D$_6$-DMSO, 25° C.): 0.29 (d, 4H, J = 9 Hz), 0.83 (t, 3H, J = 7.2 Hz), 1.18 (m, 38H), 1.37 (m, 2H), 1.54 (m, 4H), 1.72 (m, 2H), 1.82 (m, 2H), 2.00 (m, 4H), 2.64 (m, 7H), 2.85 (s, 3H), 4.04 (t, 2H, J = 6 Hz), 7.14 (d, 2H, J = 8.4 Hz), 7.84 (d, 2H, J = 7.8 Hz), 8.16 (d, 1H, J = 9 Hz), 8.30 (d, 1H, J = 8.4 Hz), 8.48 (s, 1H), 9.40 (s, 1H). |
| 460 | 890.5 | ¹HNMR (600 MHz, D$_6$-DMSO, 25° C.): 0.29 (d, 4H, J = 9 Hz), 0.83 (t, 3H, J = 7.2 Hz), 1.18 (m, 38H), 1.39 (m, 2H), 1.54 (m, 4H), 1.72 (m, 2H), 1.82 (m, 2H), 2.00 (m, 4H), 2.64 (m, 7H), 2.85 (s, 3H), 4.06 (t, 2H, J = 6.6 Hz), 7.14 (d, 2H, J = 8.4 Hz), 7.84 (d, 2H, J = 7.8 Hz), 8.16 (d, 1H, J = 8.4 Hz), 8.30 (d, 1H, J = 8.4 Hz), 8.48 (s, 1H), 9.40 (s, 1H). |
| 461 | 892.5 | ¹HNMR (600 MHz, D$_6$-DMSO, 25° C.): 0.84 (m, 3H), 1.22 (m, 38H), 1.70 (m, 8H), 2.35 (m, 7H), 2.60 (m, 5H), 2.84 (m, 4H), 3.12 (m, 6H), 4.05 (m, 2H), 7.12 (m, 2H), 7.82 (m, 2H), 8.15 (m, 1H), 8.29 (m, 1H), 8.49 (s, 1H), 9.37 (s, 1H). |
| 462 | 907.5 | ¹HNMR (600 MHz, D$_6$-DMSO, 25° C.): 0.83 (t, 3H, J = 7.2 Hz), 1.09 (m, 3H), 1.22 (m, 38H), 1.37 (m, 4H), 1.65 (m, 4H), 1.72 (m, 2H), 1.84 (m, 2H), 2.44 (m, 4H), 2.55 (m, 3H), 2.85 (m, 8H), 3.20 (m, 2H), 4.04 (t, 2H, J = 6 Hz), 7.11 (d, 2H, J = 9 Hz), 7.79 (d, 2H, J = 9 Hz), 8.13 (dd, 1H, J = 8.4, 1.2 Hz), 8.27 (d, 1H, J = 9 Hz), 8.50 (s, 1H), 9.36 (s, 1H). |
| 465 | 943.2 | ¹HNMR (600 MHz, D$_6$-DMSO, 25° C.): 0.84 (m, 3H), 1.21 (m, 38H), 1.35 (m, 6H), 1.65 (m, 4H), 1.72 (m, 2H), 1.84 (m, 2H), 2.28 (m, 7H), 2.55 (m, 6H), 2.85 (s, 4H), 3.09 (m, 3H), 4.05 (m, 2H), 7.11 (d, 2H, J = 7.2 Hz), 7.80 (d, 2H, J = 5.4 Hz), 8.13 (d, 1H, J = 6 Hz), 8.28 (d, 1H, J = 7.2 Hz), 8.49 (s, 1H), 9.37 (s, 1H). |
| 466 | 934.5 | ¹HNMR (600 MHz, D$_6$-DMSO, 25° C.): 0.84 (t, 3H, J = 7.2 Hz), 1.09 (m, 3H), 1.22 (m, 40H), 1.37 (m, 4H), 1.65 (m, 4H), 1.72 (m, 3H), 1.84 (m, 2H), 2.44 (m, 4H), 2.55 (m, 4H), 2.85 (m, 8H), 3.10 (m, 2H), 4.05 (t, 2H, J = 6 Hz), 7.12 (m, 2H), 7.81 (m, 2H), 8.14 (m, 1H), 8.28 (m, 1H), 8.50 (s, 1H), 9.37 (s, 1H). |

*LC-MS: (m/z, [M + H]+).
** MS salt: mesylate salt

BIOLOGICAL EXAMPLES

Biological Example 1. Killing Pathogenic Blood Vessels by Targeting PLXDC1/PLXDC2

Pathogenic angiogenesis plays a key role in several major human diseases. In addition to tumor growth and metastasis, angiogenesis is a major pathogenic driving force in several blinding diseases including diabetic retinopathy, age-related macular degeneration (AMD), and retinopathy of prematurity. AMD and diabetic retinopathy are the leading causes of blindness in the elderly and populations at the working age in the United States, respectively. Retinopathy of prematurity is a common reason that causes the loss of vision for newborn babies. Pathogenic blood vessels are blood vessels that exist in the diseased states such tumor blood vessels in tumors and new blood vessels in AMD or diabetic retinopathy that are distinct from healthy blood vessels in the eye (as demonstrated in FIG. 1). PLXDC1 expression was highly enriched in pathogenic blood vessels in a mouse model of CNV (laser-induced choroidal neovascularization (CNV) (FIG. 1A-D), in pathogenic blood vessels in a mouse model of ischemia-induced retinopathy, but not in blood vessels of healthy retina (FIG. 1E-H).

Pathogenic blood vessels differ from healthy blood vessels not only in tissue location and health state, but also in function. Pathogenic blood vessels drive pathogenic processes. For example, tumor blood vessels drive tumor growth and supply tumor with oxygen and nutrients that are essential for its survival. Choroidal neovascularization, the pathogenic blood vessels in AMD, cause blindness due to leakage that kills healthy neurons. While there are current therapeutic strategies for inhibiting the growth of new blood vessels, such as anti-angiogenesis therapies, there are no known strategies for destroying already existing pathogenic blood vessels. The compounds disclosed herein can kill existing pathogenic blood vessels, thus providing an improvement over existing anti-angiogenic therapies.

Two markers of pathogenic blood vessels, PLXDC1 (TEM7) and PLXDC2 are highly specifically expressed in the tumor blood vessels of diverse types of cancer, and in the pathogenic blood vessels in diabetic retinopathy. This highly specific expression in pathogenic blood vessels is especially well documented for TEM7 (=Tumor Endothelial Marker 7), which was first described in 2000. This high enrichment is not present in healthy blood vessels. High PLXDC1 expression has now been identified in choroidal neovascularization (pathogenic angiogenesis in AMD) and ischemia-induced retinopathy (pathogenic angiogenesis in retinopathy of prematurity) (FIG. 1). The striking enrichment of PLXDC1 in the pathogenic blood vessels in several diseases is summarized in the table below:

| Pathogenic angiogenesis | Highly specific expression in pathogenic blood vessels | References |
|---|---|---|
| Tumor blood vessles in diverse types of cancer | Yes | St Croix et al., 2000<br>Carson-Walter et al., 2001<br>Bagley et al., 2011 |
| Diabetic retinopathy | Yes | Yamaji et al., 2008 |
| Choroidal neovascularization | Yes | FIG. 1 |
| Ischemia-induced retinopathy | Yes | FIG. 1 |

Yamaji, Y., et al. (2008). *Invest Ophthalmol Vis Sci* 49, 3151-3157
Bagley et al., (2011) *Microvasc Res.* November; 82(3): 253-62
Carson-Walter E. B. et al., *Cancer Res.* 2001; 61(18): 6649-55.
St Croix, B., et al. (2000). *Science* 289, 1197-1202.

Although PLXDC1/PLXDC2 were known markers of pathogenic blood vessels, it was not known how to effectively target and kill the existing pathogenic blood vessels. In fact, anti-PLXDC1 antibodies have been developed as a potential anti-angiogenic therapy. In Bagley et al., *Microvasc Res.* 2011 November; 82(3):253-62, an anti-PLXDC1 antibody was identified that mediated antibody-dependent cellular cytotoxicity (ADCC) and phagocytosis. Such cancer immunotherapy approaches, however, have not yielded positive therapeutic results. Furthermore, Pigment Epithelium Derived Factor (PEDF), a natural ligand for PLXDC1 and PLXDC2 with anti-angiogenic properties, failed to kill existing PLXDC-expressing blood vessels. This example demonstrates that agents that modulate the PLXDC1/PLXDC2 receptor can effectively kill existing blood vessels.

FIG. 2 demonstrates that compound 369 targeting PLXDC1/PLXDC2 can kill the endothelial cells in an ex vivo model of choroidal neovascularization (see, for example, Shao, Z. et al., PLoS One. 2013 Jul. 26; 8(7): e69552, which is herein incorporated by reference) without affecting the healthy tissue (choroid and RPE).

Biological Example 2: Establishment of an Ex Vivo Primary Tumor Angiogenesis Model This example describes a procedure to prepare a primary tumor angiogenesis model for assessing the efficacy of anti-cancer candidate agents.

Protocol:

1. The day before the experiment, spray all necessary tools with 70% ethanol and sterilize them under UV light overnight, including blade, dissecting and micro-dissecting scissors and biceps. Place 24-well dishes at 4° C. to pre-chill plates and thaw Matrigel 24 hours before tumor dissection.

2. Spray 70% ethanol on working bench. Prepare two sterile petri dishes with 10 mL sterile PBS. Steps 3 and 4 are for mouse tumor models. For fresh human tumor, directly go to step 5.

3. Euthanize the tumor-bearing mice. Spray 70% ethanol on the mouse and remove the tumor using sterilized dissecting tools (avoid the fur). Rinse the tumor in petri dish with sterile PBS to remove ethanol and fur. Transfer the tumor to a new petri dish with PBS for dissection. Place the dish on ice.

4. Using pre-chilled sterile pipet tips to seed regular Matrigel in 24 well plates on ice. Matrigel (30 μL) is dropped in the middle of each well without touching the edge of the well (avoid introducing bubbles if possible).

5. Cut the tumor in halves using the sterile blade. Identify and isolate healthy tumor tissue that is not necrotic and is within the tumor capsule. Cut the healthy tumor tissue into small pieces. For instance, a suitable size for the tumor tissue is 0.5 mm (H)×0.5 mm (L)×0.3 mm (D) with a total volume of 0.075 mm$^3$.

6. Gently transfer and embed each tumor piece in the Matrigel drop in the 24-well plate. Place the embedded piece in the bottom and middle of each Matrigel drop. Keep the plate on ice all the time.

7. After seeding the tumor pieces, plates are incubated in a 37° C. cell culture incubator without medium for 10 minutes in order for the Matrigel to solidify.

8. Endothelial Growth Medium (0.5 mL) is added to each well and incubated at 37° C. with 5% $CO_2$. Wait until the new endothelial cells have grown out of the tumor or are larger than 3 mm in diameter until treatment. This usually takes 4 days for the LL2 Lewis lung cancer model and 7 days for the CT26 colon cancer model. For human tumor models, the growth time is typically 2-3 weeks, depending on the tumor type. Media is changed every 4 days during prolonged culture. Typically, when the tumor tissue grows to 2 mm in diameter, it is good for drug testing. A size of about 3 mm in diameter can make visualization easier.

9. When the assay is ready to be analyzed for cell death (e.g., 48 hours after drug addition), prepare the dye mixture by mixing 6 μL of green dye to stain live cells (5 mg/mL Fluorescein diacetate or FDA in DMSO) with 30 μL of red dye (2.5 mg/mL Propidium iodide or PI in PBS) to stain dead cells in an Eppendorf tube. The FDA dye needs to be stored frozen in a −20° C. freezer because it has a labile ester bond.

10. Add 1 μL of the dye mixture to each well of the 24-well dish. It is usually performed one 24-well dish at a time given the amount of time needed to take pictures (the green dye is not as stable in the cells in the long term).

11. Gently rock the dish a few times to mix the dye with the media in the wells and incubate the dish at 37° C. for 10 min (too long incubation can make the green signal too intense).

12. Wash each well with 0.5 mL of sterile PBS and then add 0.5 mL of phenol red free SFM to each well. Alternatively 0.5 mL of regular Endothelial Cell Growth Media can be added to each well if this well needs to be continuously maintained after the experiment.

13. Look through all wells on an inverted microscope using the 2× objective lens to observe morphological changes.

14. Taking pictures in the red and green channels would allow not only the recording of the result but also more accurate quantitation of the result. To take pictures for all the wells, first pick a well that has robust red and green signals. Take a picture at the red channel using the optimal setting (remember this setting) and then take a picture at the green channel using another optimal setting (remember this setting). The final picture is the merged picture of the red and green channels. Take all other wells in each channel using the same settings so that different wells can be compared.

Cells having green color are live cells and cells having red color are dead cells. A portion of the tumor is yellow, emitted from red cells mixed with green cells. The cell death in the tumor block is likely due to hypoxia in the middle of the tumor that caused cell death over time, which is unrelated to drug treatment. New tumor endothelial cells that are outside of the tumor block in this model allows direct visualization and the quantitation of their growth and killing by an agent (either a compound or a biologic drug) described herein. The samples treated with the compounds show dead endothelial cells in red, whereas the endothelial cells of untreated samples are green. The percent cell death is calculated according the ratio of the red area and total endothelial cell area.

Biological Example 3: Mouse Colon Cancer Model

Drug Testing:

A tumor from xenograft mouse model of colon cancer (CT26.CL25) was grown using the method described herein to establish an ex vivo model of tumor angiogenesis. Treatment did not start until the new tumor endothelial cells had grown for 7 days. After drug treatment was done for two days, cell survival was assessed by a two-color assay using a mixture of fluorescein diacetate (green dye) and propidium iodide (red dye). Green cells represented live cells. Red cells represented dead cells. Orange cells represented a mixture of live and dead cells.

The percent cell death is calculated according the ratio of the red area and total endothelial cell area.

The activity of the tested compounds is provided in Table 3 below. Morphology observations after 48 hours are provided under the column "48 hrs," wherein: "0" indicates all cells have normal endothelial cell morphology (cells are elongated and connect to neighbor cells); "*" indicates 50% or less of cells vesicularize in cell shape; "" indicates more than 50% but less than 100% of endothelial cells vesicularize in cell shape; "*" indicates 100% of endothelial cells vesicularize in cell shape; "****" indicates 100% of endothelial cells vesicularize in cell shape and look flattened in morphology (indicating disintegration of the cell body). Vesicularization in cell shape indicates that the endothelial cells no longer have the elongated shape and no longer connect to neighbor cells.

TABLE 3

| Colon CT26 ex vivo model of tumor angiogenesis | | | |
|---|---|---|---|
| No | 48 hrs | Cell death | Conc. (μm) |
| 42 | 0 | 0% | 40 |
| 43 | *** | 90% | 40 |
| 44 | 0 | 0% | 40 |
| 45 | 0 | 0% | 40 |
| 46 | **** | 100% | 40 |
| 47 | 0 | 10% | 40 |
| 48 | 0 | 10% | 40 |
| 49 | 0 | 10% | 40 |
| 50 | *** | 100% | 40 |
| 51 | *** | 20% | 40 |
| 52 | 0 | 0% | 40 |
| 54 | 0 | 10% | 40 |
| 55 | 0 | 50% | 40 |
| 56 | 0 | 30% | 40 |
| 57 | * | 60% | 40 |
| 58 | * | 50% | 40 |
| 59 | 0 | 50% | 40 |
| 60 | 0 | 5% | 40 |
| 61 | 0 | 20% | 40 |
| 62 | ** | 70% | 40 |
| 63 | *** | 70% | 40 |
| 64 | *** | 100% | 40 |
| 65 | 0 | 0% | 40 |
| 66 | 0 | 0% | 40 |
| 67 | 0 | 0% | 40 |
| 68 | ** | 50% | 40 |
| 69 | 0 | 0% | 40 |
| 70 | 0 | 10% | 40 |
| 71 | 0 | 0% | 40 |
| 72 | 0 | 0% | 40 |
| 73 | 0 | 0% | 40 |
| 74 | *** | 100% | 40 |
| 75 | 0 | 0% | 40 |
| 76 | ** | 100% | 40 |
| 77 | 0 | 40% | 40 |
| 78 | 0 | 0% | 40 |
| 79 | *** | 100% | 10 |

TABLE 3-continued

Colon CT26 ex vivo model of tumor angiogenesis

| No | 48 hrs | Cell death | Conc. (μm) |
|---|---|---|---|
| 80 | *** | 100% | 10 |
| 81 | 0 | 0% | 40 |
| 82 | 0 | 10% | 40 |
| 84 | * | 100% | 40 |
| 85 | 0 | 50% | 40 |
| 86 | *** | 100% | 10 |
| 87 | 0 | 0% | 40 |
| 88 | *** | 60% | 40 |
| 89 | *** | 100% | 10 |
| 90 | 0 | 0% | 40 |
| 91 | *** | 100% | 10 |
| 92 | 0 | 0% | 40 |
| 93 | *** | 100% | 10 |
| 94 | 0 | 0% | 40 |
| 95 | 0 | 0% | 40 |
| 96 | 0 | 0% | 10 |
| 97 | *** | 100% | 10 |
| 98 | *** | 50% | 10 |
| 99 | 0 | 0% | 40 |
| 100 | **** | 100% | 40 |
| 101 | * | 50% | 20 |
| 102 | 0 | 5% | 40 |
| 110 | ** | 10% | 40 |
| 112 | ** | 10% | 40 |
| 116 | * | 50% | 20 |
| 117 | *** | 100% | 20 |
| 118 | *** | 100% | 20 |
| 119 | 0 | 50% | 20 |
| 121 | *** | 40% | 40 |
| 123 | 0 | 20% | 40 |
| 124 | 0 | 20% | 40 |
| 128 | 0 | 10% | 40 |
| 129 | 0 | 0% | 40 |
| 130 | 0 | 40% | 40 |
| 131 | ** | 50% | 40 |
| 132 | * | 40% | 40 |
| 135 | 0 | 30% | 40 |
| 136 | 0 | 30% | 40 |
| 137 | 0 | 40% | 40 |
| 138 | 0 | 20% | 40 |
| 139 | 0 | 40% | 40 |
| 140 | ** | 60% | 40 |
| 144 | 0 | 30% | 40 |
| 145 | 0 | 30% | 40 |
| 146 | 0 | 0% | 40 |
| 147 | 0 | 0% | 40 |
| 148 | 0 | 0% | 40 |
| 149 | * | 20% | 40 |
| 150 | 0 | 10% | 40 |
| 151 | **** | 100% | 40 |
| 152 | ** | 30% | 40 |
| 153 | * | 20% | 40 |
| 154 | * | 30% | 40 |
| 155 | *** | 20% | 40 |
| 156 | 0 | 0% | 40 |
| 157 | **** | 60% | 40 |
| 158 | **** | 100% | 40 |
| 159 | **** | 100% | 40 |
| 160 | **** | 100% | 40 |
| 161 | **** | 100% | 40 |
| 162 | *** | | 40 |
| 163 | **** | 100% | 40 |
| 164 | **** | 100% | 40 |
| 165 | 0 | 10% | 40 |
| 166 | *** | 60% | 40 |
| 191 | 0 | 10% | 40 |
| 192 | 0 | 10% | 40 |
| 201 | * | 10% | 40 |
| 202 | 0 | 10% | 40 |
| 206 | **** | 100% | 40 |
| 207 | **** | 100% | 40 |
| 208 | 0 | 20% | 40 |
| 209 | *** | 90% | 40 |
| 210 | *** | 70% | 40 |
| 211 | **** | 100% | 40 |
| 212 | 0 | 10% | 40 |
| 214 | **** | 100% | 40 |
| 215 | 0 | 20% | 40 |
| 216 | **** | 100% | 40 |
| 218 | *** | 90% | 40 |
| 219 | *** | 90% | 40 |
| 220 | **** | 100% | 40 |
| 221 | **** | 100% | 40 |
| 238 | 0 | 10% | 10 |
| 241 | 0 | 0% | 10 |
| 253 | *** | 80% | 10 |
| 254 | ** | 40% | 10 |
| 255 | 0 | 0% | 10 |
| 256 | *** | 90% | 10 |
| 257 | **** | 100% | 10 |
| 258 | *** | 100% | 10 |
| 259 | *** | 100% | 20 |

Biological Example 4: Mouse Lung Cancer Model

A tumor from xenograft mouse model of lung cancer (LL/2) was grown using the methods described herein to establish an ex vivo model of tumor angiogenesis. Treatment did not start until the new tumor endothelial cells had grown for 5 days. After drug treatment was done for two days, cell survival was assessed by a two-color assay using a mixture of fluorescein diacetate (green dye) and propidium iodide (red dye). Green cells represented live cells. Red cells represented dead cells. Orange cells represented a mixture of live and dead cells. The percent cell death is calculated according the ratio of the red area and total endothelial cell area.

The activity of the tested compounds is provided in Table 4 below. Morphology observations after 48 hours are provided under the column "48 hrs," wherein: "0" indicates all cells have normal endothelial cell morphology (cells are elongated and connect to neighbor cells); "*" indicates 50% or less of cells vesicularize in cell shape; "" indicates more than 50% but less than 100% of endothelial cells vesicularize in cell shape; "*" indicates 100% of endothelial cells vesicularize in cell shape; "****" indicates 100% of endothelial cells vesicularize in cell shape and look flattened in morphology (indicating disintegration of the cell body). Vesicularization in cell shape indicates that the endothelial cells no longer have the elongated shape and no longer connect to neighbor cells.

TABLE 4

Lung LL2 ex vivo model of tumor angiogenesis

| No | 48 hrs | Cell death | Conc. (μm) |
|---|---|---|---|
| 42 | 0 | 30% | 40 |
| 43 | *** | 100% | 40 |
| 44 | ** | 50% | 40 |
| 45 | ** | 10% | 40 |
| 46 | **** | 100% | 40 |
| 47 | 0 | 50% | 40 |
| 48 | ** | 60% | 40 |
| 49 | 0 | 30% | 40 |
| 50 | *** | 90% | 40 |
| 51 | **** | 100% | 40 |
| 52 | ** | 50% | 40 |
| 54 | 0 | 50% | 40 |

TABLE 4-continued

Lung LL2 ex vivo model of tumor angiogenesis

| No | 48 hrs | Cell death | Conc. (µm) |
|---|---|---|---|
| 55 | ** | 70% | 40 |
| 56 | * | 20% | 40 |
| 57 | 0 | 40% | 40 |
| 58 | 0 | 50% | 40 |
| 59 | 0 | 40% | 40 |
| 61 | 0 | 50% | 40 |
| 62 | *** | 30% | 40 |
| 63 | ** | 50% | 40 |
| 64 | *** | 100% | 40 |
| 65 | 0 | 10% | 40 |
| 66 | 0 | 10% | 40 |
| 67 | 0 | 10% | 40 |
| 68 | *** | 80% | 40 |
| 69 | 0 | 20% | 40 |
| 70 | *** | 40% | 40 |
| 71 | * | 10% | 40 |
| 72 | 0 | 20% | 40 |
| 73 | 0 | 10% | 40 |
| 74 | *** | 60% | 40 |
| 75 | ** | 80% | 40 |
| 76 | 0 | 20% | 40 |
| 77 | ** | 80% | 40 |
| 78 | 0 | 40% | 40 |
| 79 | ** | 20% | 20 |
| 80 | *** | 100% | 20 |
| 81 | 0 | 0% | 40 |
| 82 | 0 | 60% | 40 |
| 83 | 0 | 20% | 40 |
| 84 | ** | 100% | 40 |
| 85 | 0 | 80% | 40 |
| 86 | *** | 100% | 20 |
| 87 | 0 | 0% | 40 |
| 88 | 0 | 70% | 40 |
| 89 | *** | 100% | 20 |
| 90 | 0 | 10% | 40 |
| 91 | *** | 80% | 20 |
| 92 | 0 | 10% | 20 |
| 93 | *** | 100% | 20 |
| 94 | 0 | 20% | 40 |
| 95 | 0 | 10% | 40 |
| 96 | 0 | 0% | 20 |
| 97 | ** | 50% | 20 |
| 98 | ** | 10% | 20 |
| 99 | 0 | 10% | 40 |
| 100 | **** | 100% | 40 |
| 101 | *** | 100% | 20 |
| 102 | 0 | 20% | 20 |
| 103 | 0 | 10% | 20 |
| 104 | 0 | 20% | 20 |
| 105 | 0 | 0% | 20 |
| 106 | 0 | 5% | 20 |
| 107 | 0 | 0% | 20 |
| 108 | 0 | 0% | 20 |
| 109 | 0 | 0% | 20 |
| 110 | *** | 95% | 20 |
| 111 | 0 | 30% | 20 |
| 112 | *** | 70% | 20 |
| 113 | 0 | 10% | 20 |
| 114 | 0 | 5% | 20 |
| 115 | 0 | 10% | 20 |
| 116 | *** | 100% | 20 |
| 117 | *** | 100% | 20 |
| 118 | *** | 100% | 20 |
| 119 | *** | 100% | 20 |
| 120 | 0 | 5% | 20 |
| 121 | ** | 50% | 40 |
| 122 | 0 | 10% | 20 |
| 125 | * | 10% | 20 |
| 126 | 0 | 10% | 20 |
| 133 | ** | 10% | 20 |
| 134 | **** |  | 20 |
| 141 | **** | 90% | 20 |
| 142 | **** |  | 20 |
| 143 | 0 | 40% | 40 |
| 151 | **** | 100% | 40 |
| 152 | * | 20% | 20 |
| 154 | * | 30% | 40 |
| 155 | *** | 80% | 40 |
| 156 | ** | 30% | 40 |
| 157 | *** | 100% | 40 |
| 158 | **** | 100% | 40 |
| 159 | **** | 100% | 40 |
| 160 | **** | 100% | 40 |
| 161 | **** | 90% | 40 |
| 162 | *** | 70% | 40 |
| 163 | **** | 95% | 40 |
| 164 | **** | 95% | 40 |
| 165 | * | 10% | 40 |
| 166 | 0 | 10% | 40 |
| 167 | 0 | 40% | 20 |
| 168 | 0 | 10% | 20 |
| 169 | 0 | 40% | 20 |
| 170 | 0 | 10% | 20 |
| 171 | 0 | 40% | 40 |
| 172 | **** | 100% | 40 |
| 173 | ** | 50% | 40 |
| 174 | 0 | 30% | 40 |
| 175 | 0 | 30% | 40 |
| 176 | *** | 100% | 40 |
| 177 | **** | 100% | 40 |
| 178 | **** | 100% | 40 |
| 179 | *** | 60% | 10 |
| 180 | *** | 70% | 10 |
| 181 | **** | 100% | 40 |
| 182 | **** | 100% | 40 |
| 183 | **** | 100% | 10 |
| 184 | 0 | 5% | 10 |
| 185 | * | 30% | 10 |
| 186 | **** | 90% | 10 |
| 187 | 0 | 30% | 40 |
| 191 | 0 | 30% | 40 |
| 192 | *** | 60% | 40 |
| 193 | 0 | 30% | 40 |
| 195 | 0 |  | 40 |
| 196 | 0 | 30% | 40 |
| 197 | 0 | 20% | 40 |
| 198 | 0 | 30% | 40 |
| 199 | 0 | 30% | 40 |
| 200 | 0 | 30% | 40 |
| 201 | 0 | 30% | 40 |
| 202 | ** | 30% | 40 |
| 206 | 0 | 30% | 20 |
| 207 | ** |  | 20 |
| 208 | 0 | 50% | 40 |
| 209 | * | 60% | 40 |
| 210 | 0 | 50% | 40 |
| 211 | **** | 100% | 40 |
| 212 | 0 | 50% | 40 |
| 213 | 0 | 30% | 40 |
| 214 | **** | 100% | 40 |
| 215 | 0 | 30% | 40 |
| 216 | **** | 100% | 40 |
| 217 | 0 | 30% | 40 |
| 218 | **** | 100% | 40 |
| 219 | **** | 60% | 40 |
| 220 | **** | 100% | 40 |
| 221 | **** | 100% | 40 |
| 223 | *** | 30% (rim) | 40 |
| 225 | 0 | 40% | 40 |
| 226 | * | 10% | 40 |
| 227 | 0 | 10% | 40 |
| 228 | 0 | 5% | 40 |
| 229 | 0 | 30% | 40 |
| 230 | *** | 100% | 40 |
| 231 | *** | 100% | 40 |
| 232 | 0 | 10% | 40 |
| 233 | 0 | 5% | 40 |
| 234 | *** | 100% | 40 |
| 235 | 0 | 10% | 40 |
| 236 | 0 | 5% | 40 |
| 237 | *** | 100% | 40 |

TABLE 4-continued

Lung LL2 ex vivo model of tumor angiogenesis

| No | 48 hrs | Cell death | Conc. (μm) |
|---|---|---|---|
| 238 | *** | 100% | 40 |
| 239 | 0 | 40% | 40 |
| 240 | 0 | 30% | 40 |
| 241 | 0 | 40% | 40 |
| 242 | 0 | 30% | 40 |
| 243 | 0 | 20% | 40 |
| 244 | 0 | 20% | 40 |
| 245 | 0 | 40% | 40 |
| 246 | *** | 95% | 20 |
| 247 | *** | 60% | 20 |
| 248 | * | 60% | 20 |
| 249 | *** | 60% | 20 |
| 250 | *** | 90% | 20 |
| 251 | *** | 60% | 20 |
| 253 | **** | 100% | 20 |
| 254 | *** | 100% | 20 |
| 255 | * | 10% | 20 |
| 256 | **** | 100% | 20 |
| 257 | **** | 100% | 20 |
| 258 | **** | 100% | 20 |
| 259 | *** | 95% | 20 |
| 262 | 0 | 20% | 10 |
| 263 | **** | 100% | 10 |
| 264 | * | 20% | 10 |
| 265 | * | 20% | 10 |
| 266 | 0 | 5% | 10 |
| 267 | 0 | 5% | 10 |
| 268 | *** | 50% | 20 |
| 269 | **** | 100% | 20 |
| 270 | * | 50% | 20 |
| 271 | *** | 60% | 20 |
| 272 | * | 20% | 20 |
| 273 | *** | 60% | 20 |
| 274 | 0 | 10% | 20 |
| 275 | 0 | 5% | 20 |
| 276 | *** | 100% | 20 |
| 277 | ** | 60% | 10 |
| 278 | * | 50% | 10 |
| 279 | **** | 100% | 20 |
| 280 | *** | 100% | 20 |
| 281 | ** | 50% | 20 |
| 282 | 0 | 10% | 10 |
| 283 | 0 | 5% | 10 |
| 284 | 0 | 10% | 10 |
| 285 | *** | 60% | 10 |
| 286 | 0 (24 hrs) | 0% (24 hrs) | 20 |
| 287 | * (24 hrs) | 40% (24 hrs) | 20 |
| 288 | *** | 50% | 10 |
| 289 | ** | 20% | 20 |
| 290 | *** | 50% | 10 |
| 291 | * (24 hrs) | 10% (24 hrs) | 20 |
| 292 | * (24 hrs) | 10% (24 hrs) | 20 |
| 294 | * | 50% | 40 |
| 296 | 0 | 20% | 40 |
| 300 | 0 | 20% | 40 |
| 302 | 0 | 70% | 40 |
| 306 | 0 | 40% | 40 |
| 308 | 0 | 20% | 40 |
| 310 | 0 | 10% | 40 |
| 311 | 0 | 30% | 40 |
| 312 | **** | 100% | 40 |
| 317 | 0 | 30% | 40 |
| 318 | 0 | 30% | 40 |
| 320 | 0 | 30% | 40 |
| 321 | 0 | 40% | 40 |
| 322 | 0 | 30% | 40 |
| 323 | 0 | 30% | 40 |
| 324 | 0 | 60% | 40 |
| 325 | * | 30% | 40 |
| 326 | 0 | 30% | 40 |
| 327 | 0 | 20% | 40 |
| 328 | 0 | 30% | 40 |
| 329 | *** | 40% | 40 |
| 330 | *** | 50% | 40 |
| 331 | 0 | 10% | 40 |
| 332 | 0 | 0% | 40 |
| 333 | 0 | 0% | 40 |
| 336 | 0 | 0% | 40 |
| 339 | ** | 50% | 20 |
| 340 | *** | 60% | 20 |
| 341 | *** | 80% | 20 |
| 342 | *** | 60% | 20 |
| 343 | *** | 50% | 20 |
| 344 | * | 10% | 20 |
| 345 | *** | 50% | 20 |
| 346 | * | 20% | 20 |
| 347 | *** | 30% | 20 |
| 348 | * | 20% | 20 |
| 350 | 0 | 20% | 40 |
| 351 | *** | 100% | 40 |
| 352 | *** | 100% | 40 |
| 353 | 0 | 0% | 40 |
| 354 | 0 | 0% | 40 |
| 355 | 0 | 0% | 40 |
| 356 | 0 | 0% | 40 |
| 357 | 0 | 0% | 40 |
| 358 | 0 | 0% | 40 |
| 359 | 0 | 20% | 40 |
| 360 | 0 | 20% | 40 |
| 362 | *** | 20% | 20 |
| 363 | *** | 30% | 20 |
| 364 | *** | 30% | 20 |
| 365 | *** | 20% | 20 |
| 366 | 0 | 10% | 20 |
| 367 | 0 | 5% | 20 |
| 368 | ** | 20% | 20 |
| 369 | * | 20% | 20 |
| 370 | ** | 20% | 20 |
| 371 | *** | 30% | 20 |
| 372 | ** | 20% | 20 |
| 373 | * | 20% | 20 |
| 374 | ** | 20% | 20 |
| 375 | * | 50% | 20 |
| 376 | 0 | 10% | 20 |
| 377 | 0 | 10% | 20 |
| 378 | *** | 30% | 20 |

Certain other compounds described herein also showed activity in causing endothelial cell death in other angiogenesis assays.

Biological Example 5: Ex Vivo Primary Tumor (Colon Cancer) Angiogenesis Model

CT26.CL25 cell line was purchased from ATCC. Frozen vials were thawed and expanded in vitro. Once the cell number reached 6.25 million, tumor cells were inoculated into Balb/c mice.

Tumor-bearing mice were randomized into three (3) groups of up to 10 animals per group when mean tumor volume reached approximately 250-500 mm$^3$. Treatment (single or multiple doses) with test compounds and vehicle was started on the day of randomization. Test compounds or vehicle were formulated with recombinant human serum albumin, oxalic acid and saline as described herein. The test composition or vehicle was administered using an insulin syringe over 10 seconds within 5 minutes of preparing the dosing solution.

All tumor-bearing mice were observed daily for up to 10-days post dosing with photos taken on D0 (dose administration), D1, D3, D5, D7, D8, D10 (where D8 and D10 are optional and dependent on study end date). On the final study day, mice were euthanized, whole mouse photos with shaved tumors facing up were taken of tumor-bearing mice, and the tumors were removed and cut in half. Tumors along with 1 mm of adjacent tissue from all animals in the study were collected for histopathology.

Tumor cell preparation: Cryogenic vials containing CT26.CL25 cells received from ATCC were cultured using a protocol comprising DMEM (Gibco, #11995-065); 10% FBS (VWR, #97068-085); and 1× Pen/Strep (Gibco, #15140-122).

Procedure: On the day of injection, cells were washed in serum-free media, counted and resuspended in cold serum-free media at a concentration of one million (1M) cells per 100 µL. Cells were prepared for injection by withdrawing 100 µL of cell suspension into a 1 mL syringe. The cell suspension and filled syringes were kept on ice.

Mice were prepared for injection using standard approved anesthesia.

Fur Removal: Mice fur was removed using Veet fast acting hair removal gel cream. A thin layer of hair removal cream was applied on the right rear flank area of the mouse. After 30-60 seconds, the cream and fur were wiped away, and wiped once more with water or alcohol if necessary.

One mouse at a time was immobilized and the site of injection was disinfected with an alcohol swab. 100 µL of the cell suspension was subcutaneously injected into the right rear flank of the mouse. During implantation, a new syringe and needle was used for every mouse inoculated. The cells were drawn up into a 1 mL syringe (no needle attached) to a volume of 150 µL, with the 50 µL nearest to the plunger being air and 100 µL of cell suspension. Once the cells were drawn up the needle was attached (without priming the needle). For implant, the skin was lifted or tented using forceps to ensure a subcutaneous injection. The cells were injected, and each mouse was tagged.

Tumor Measurement: The mice were monitored every other day for palpable tumors, or any changes in appearance or behavior and for mice showing any signs of morbidity or mortality. Once tumors were palpable, tumors were measured daily using calipers. Tumor volume was calculated using the following equation: (longest diameter*shortest diameter2)/2.

Once tumors were of the appropriate size (~250-500 mm3) to begin the study, tumors and body weights were measured daily for 7-10 days post-treatment.

Randomization: When average tumor volume reached approximately 250-500 mm$^3$, mice were randomly assigned to treatment groups with up to 10 animals per group. All treatment groups were dosed within 24 hours of randomization according to the protocol shown in the Table below.

Tumor size measurements were taken from Day 0 through Day 7. Mice were photographed every other day starting from Day 0. Body weight was measured daily following randomization and treatment. If body weight loss of >10% was observed, DietGel was given ad libitum. If body weight loss of >20% was observed, the animal was monitored daily for signs of recovery for up to 72 hours. If there were no signs of recovery, the animal was sacrificed for humane reasons as per IACUC protocol regulations.

FIG. 3A-B shows tumor shrinkage and necrosis when mice were treated with certain compounds described herein. FIG. 3A shows that 3 days after injection, all the tumors were shrinking FIG. 3B shows that the tumor shrinkage was maintained 6 days after injection.

Biological Example 6. Preferential Binding to PLXDC1

This example shows that compounds of the disclosure bind to the extracellular domain of PLXDC.

The high affinity interaction between compound 346 (Table 3) and the extracellular domain of PLXDC1 (PLXDC1-ECD). Compound 346 suppressed the endogenous tryptophan fluorescence of PLXDC1-ECD in a dose-dependent manner (FIG. 4A-B). FIG. 4A presents raw data of the tryptophan fluorescence of PLXDC1-ECD as measured in a fluorometer after adding different concentrations of the compound, and FIG. 4B shows the dose-dependent curve of the suppression of tryptophan fluorescence. Tryptophan fluorescence without the compound added is defined as 1. The estimated Kd value is 50 nM.

Biological Example 7. Killing of Tumor Endothelial Cells by PLXDC-Activating Compounds This example investigates the mechanism by which the compounds kill tumor endothelial cells, and demonstrates their killing activities.

Through RNAseq analysis of PLXDC1-expressing endothelial cells killing by PLXDC1-activating compounds, this example identified a transcriptional factor called Gfi1b that specifically induced during PLXDC1-mediated cell killing By linking its promotor to a luciferase reporter gene, this example developed a PLXDC1 receptor activation assay. PLXDC1-activating compounds 346 and 342 (Table 3, labeled as A-Compound-1 and A-Compound-2, respectively) highly activated the promotor activity in PLXDC1-expressing cells, but not in cells without PLXDC1 (FIG.

| Group | Treatment | N | Dose Route | Dose Frequency & Duration | Dose Level | Dose Volume (µL) |
|---|---|---|---|---|---|---|
| 1 | Test compound | 10 | Bolus Injection (administered in 10 seconds) | 2 injections; 2 hours apart | 5 mM (2.5 mM/injection) | 280 µL (140 µL/injection) |
| 2 | Vehicle | 10 | Bolus Injection (administered in 10 seconds) | 2 injections; 2 hours apart | 5 mM (2.5 mM/injection) | 280 µL (140 µL/injection) |

5A). Likewise, these compounds activated the promotor activity in PLXDC2-expressing cells, but not in cells without PLXDC2 (FIG. 5B).

FIG. 5 therefore shows that the compounds activated both PLXDC1 and PLXDC2 and that they preferentially activate PLXDC1 over PLXDC2. One of the compounds, A-Com-2, strongly differentiates between the two receptors. As a control, Fluorouracil, a chemotherapy agent that kills dividing cells by apoptosis does not activate this promoter. This data demonstrates that the cell death mediated by PLXDC1 activation is different from chemotherapy agent-triggered apoptosis.

The killing of human PLXDC1-expressing endothelial cells by the compounds is visualized in FIG. 6. The top three pictures represent control cells and the lower three pictures represent compound-treated cells, showing light microscopy picture (FIG. 6A, left), live cell (middle) and dead cell staining (right). Live cells were stained using Fluorescein diacetate (green signal) and dead cells were stained using propidium iodide (red signal). Quantitation of the killing of human PLXDC1-expressing endothelial cells by the compounds and two antibodies are shown in FIG. 6B. Incubation time of the compounds and antibodies was 24 hours.

Biological Example 8. Specific Killing of Pathogenic Blood Vessels in Ischemia-Induced Retinopathy/Tumor This example examines the expression of the PLXDC proteins on pathogenic blood vessels and normal healthy blood vessels, in different diseases, and confirms that the compounds of the instant disclosure specifically kill the pathogenic blood vessels.

The expression of PLXDC1 in pathogenic blood vessels of ischemia-induced retinopathy was examined and shown in FIG. 1, which shows that PLXDC1 was not expressed in healthy blood vessels. It was then demonstrated that the compounds (e.g., compounds 346) specifically suppressed pathogenic blood vessels in vivo without affecting healthy blood vessels in ischemia-induced retinopathy (FIG. 7). FIG. 7A includes a schematic diagram of the experimental design for ischemia-induced retinopathy. The high oxygen environment caused blood vessel loss (vaso-obliteration). In room air, loss of vessels triggered abnormal angiogenesis that generated pathogenic blood vessels on the top of the retina (marked in yellow in FIG. 7D). Treatment was applied during the return to room air by subcutaneous injection. The lower graph in FIG. 7A shows quantitation of healthy blood vessels, vaso-obliteration and pathogenic blood vessels between the control (n=10) and treated retinas (n=10).

Treatment by PLXDC1-activating compound (compound 346/A-Compound-1) highly suppressed pathogenic blood vessels (two asterisks) while improving the amount of healthy blood vessels (one asterisk). FIG. 7B includes representative images of flat-mounted control retinas (upper two images) and retinas from compound treated mice (lower two images). The same retinas in B with vaso-obliteration areas marked in white color (FIG. 7C). These images illustrate that compound-treated retinas went through vaso-obliteration like the control retinas. The same retinas in B with pathogenic blood vessels marked in yellow color (FIG. 7D). These images illustrate that compound-treated retinas have highly decreased pathogenic blood vessels as compared to the control retinas.

The killing activity was further demonstrated with tumor samples in vivo. Treatment was done at day 0 by bolus IV injection of compound 346 in a tumor animal model. FIG. 8A charts raw data of tumor growth curves of the mice in the control group. FIG. 8B presents raw data of tumor growth curves of the mice in the treatment group. FIG. 8C compares the combined growth data of the control group and the treatment group. Unlike in the control group, compound 346 shrank the tumors significantly.

Tumor morphological changes on live animals due to the treatment by PLXDC1-activating compound were examined Pictures of the whole animals in the experiment described in FIG. 9 show tumor morphological and color changes on day 1 and day 3 (FIG. 9). Tumors in the treatment groups becomes darker in color on day 1 due to the destruction of tumor blood vessels and accumulation of blood in the tumors. Tumors in the treatment groups started to become yellower in color on day 3, consistent with the onset of tumor necrosis due to the lack of tumor blood vessels.

FIG. 10 presents pictures of the whole animals showing tumor morphological and color changes on day 7. tumors in the control group have grown to large sizes, tumors in the treatment groups have highly shrunk in size and become yellow in color.

FIG. 11 shows morphological changes of dissected tumors due to the treatment by the compound. Pictures of the dissected tumors showed tumor morphological and color changes on day 7. While the tumors in the control group are reddish in color, tumors in the treatment groups had highly shrunk in size and become yellow in color, consistent with the lack of tumor blood vessels and tumor necrosis. These data, therefore, demonstrate that the PLXDC1-activating compounds can kill tumor blood vessels in vivo to cause strong tumor necrosis and shrinkage.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:
1. A compound of Formula (I):

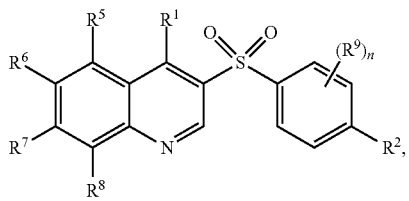

or a pharmaceutically acceptable salt, isotopically enriched analog, stereoisomer, mixture of stereoisomers, or tautomer thereof;
wherein
n is 0, 1, 2, 3 or 4;
$R^1$ is selected from amino, optionally substituted heterocyclyl, optionally substituted cycloheptyl, and optionally substituted heteroaryl;
$R^2$ is selected from H, halo, alkyl, alkenyl, alkynyl, —OH, alkoxy, —CN, —NO$_2$, alkylthio, sulfoxido, sulfonyl, and amino;
$R^5$, $R^7$ and $R^8$ are each independently selected from H, halo, alkyl, alkenyl, alkynyl, hydroxy, alkoxy, alkylthio, sulfoxido, sulfonyl, carboxy, ester, —CN, —NO$_2$, amino, and amido;
$R^6$ is selected from halo, alkyl, hydroxy, alkoxy, alkylthio, sulfoxido, sulfonyl, carboxy, ester, —CN, —NO$_2$, amino, amido, sulfinamido, sulfonamido, heterocyclyl, heteroaryl, poly(ethylene glycol), and methoxypoly(ethylene glycol), or
$R^6$ and $R^7$ together with atoms to which they are attached form a cycloalkyl, heterocyclyl, aryl, or heteroaryl; and
each $R^9$ is independently selected from halo, alkyl, —OH, alkoxy, —CN, and amino;
wherein the compound has at least one of the following:
1) $R^2$ is selected from $C_{2-30}$alkyl, —OH, $C_{1-40}$alkoxy, $C_{1-40}$alkenoxy, $C_{1-40}$alkynoxy, —NO$_2$, alkylthio, sulfoxido, sulfonyl, and amino, where
   a) when $R^2$ is ethyl, then $R^6$ is not methyl or methoxy, and/or
   b) when $R^2$ is methoxy, then $R^6$ is not halo, $C_{1-2}$ alkyl or $C_{1-2}$ alkoxy;
2) $R^1$ is optionally substituted heteroaryl, optionally substituted bridged heterocyclyl, optionally substituted fused heterocyclyl, or optionally substituted cycloheptyl;
3) $R^1$ is heterocyclyl substituted with one halo, amino, hydroxy, alkoxy, —CN, —NO$_2$, alkyl, carboxy, alkylthio, sulfoxido, sulfonyl, sulfinamido, sulfonamido, optionally substituted cycloalkyl, optionally substituted heterocyclyl, optionally substituted heteroaryl, poly(ethylene glycol), or methoxypoly(ethylene glycol),
where if the substituent is alkyl, the alkyl is further substituted with one substituent selected from halo, amino, alkoxy, —CN, —NO$_2$, carboxy, ester, alkylthio, sulfoxido, sulfonyl, sulfinamido, sulfonamido, cycloalkyl, heterocyclyl, poly(ethylene glycol), methoxypoly(ethylene glycol), pyrrolidinyl and piperidinyl; or the alkyl is substituted with at least one —OR$^{31}$, wherein R$^{31}$ is poly(ethylene glycol) or methoxypoly(ethylene glycol);
4) $R^1$ is amino substituted with at least one substituent selected from alkyl, cycloalkyl, heterocyclyl, heteroaryl, poly(ethylene glycol) or methoxypoly(ethylene glycol) and amino,
where the alkyl is substituted with at least one substituent selected from halo, amino, hydroxy, alkoxy, —CN, —NO$_2$, amido, carboxy, ester, alkylthio, sulfoxido, sulfonyl, sulfinamido, sulfonamido, cycloalkyl, heterocyclyl, and heteroaryl;
5) $R^6$ is alkyl substituted with at least one substituent selected from halo, amino, hydroxy, alkoxy, cycloalkoxy, heterocycloalkoxy, aryloxy, heteroaryloxy, poly(ethylene glycol)-oxy, methoxypoly(ethylene glycol)-oxy, —CN, —NO$_2$, oxo, amido, carboxy, ester, alkylthio, sulfoxido, sulfonyl, sulfinamido, sulfonamido, heterocyclyl, cycloalkyl, aryl, heteroaryl, poly(ethylene glycol) and methoxypoly(ethylene glycol).

2. The compound of claim 1, wherein n is 0, 1 or 2.
3. The compound of claim 1, wherein when $R^2$ is $C_{1-6}$ alkyl, $R^6$ is not $C_{1-6}$ alkyl or $C_{1-6}$ alkoxy.
4. The compound of claim 1, wherein $R^1$ is an optionally substituted 5- to 9-membered heterocyclyl, an optionally substituted 5- to 7-membered heterocyclyl, or an optionally substituted 5- to 6-membered heterocyclyl.
5. The compound of claim 1, wherein $R^1$ is an optionally substituted 5- or 6-membered heteroaryl.
6. The compound of claim 1, wherein
$R^1$ is heterocyclyl substituted with at least one substituent selected from oxo, —OH, —OR$^{28}$, —N(R$^{28}$)$_2$, alkyl, aryl, and heterocyclyl,
the alkyl is substituted with at least one substituent selected from —N(R$^{31}$)$_2$, —S(O)$_{0-2}$NR$^{31}$R$^{31}$, —C(O)N(R$^{31}$)$_2$, heterocyclyl, cycloalkyl, pyrrolidinyl, and piperidinyl; or
the alkyl is substituted with at least one —OR$^{31a}$ wherein R$^{31a}$ is poly(ethylene glycol) or methoxypoly(ethylene glycol); and
each R$^{28}$ and R$^{31}$ are independently H or alkyl.
7. The compound of claim 1, wherein $R^1$ is heteroaryl or heterocyclyl substituted with a second heterocyclyl; and
the second heterocyclyl is unsubstituted or substituted with one or more substituents selected from —OH, —C(O)Oalkyl, —C(O)NHalkyl, alkyl, aryl, and heterocyclyl; and
wherein the alkyl and heterocyclyl are each unsubstituted or substituted with one or more substituents selected from —OH, alkyl, and aryl.
8. The compound of claim 1, wherein $R^1$ is

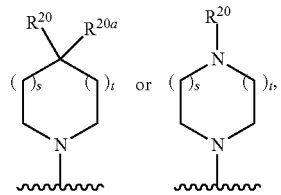

wherein each s and t is independently 0, 1, 2 or 3, provided that the sum of s and t is 1, 2, 3, or 4;
$R^{20}$ is selected from alkyl, cycloalkyl, heterocyclyl, aryl, and heteroaryl; and
$R^{20a}$ is H, NH$_2$, or OH.
9. The compound of claim 1, wherein $R^1$ is heterocyclyl, optionally substituted with a sugar moiety.

10. The compound of claim 1, wherein $R^1$ is —$NR^3R^4$, and $R^3$ is H or alkyl that is unsubstituted or substituted with at least one substituent selected from —OH, —$N(R^{28})_2$, and heteroaryl, and $R^4$ and $R^{28}$ are each independently H or alkyl.
11. The compound of claim 1, wherein $R^1$ is selected from
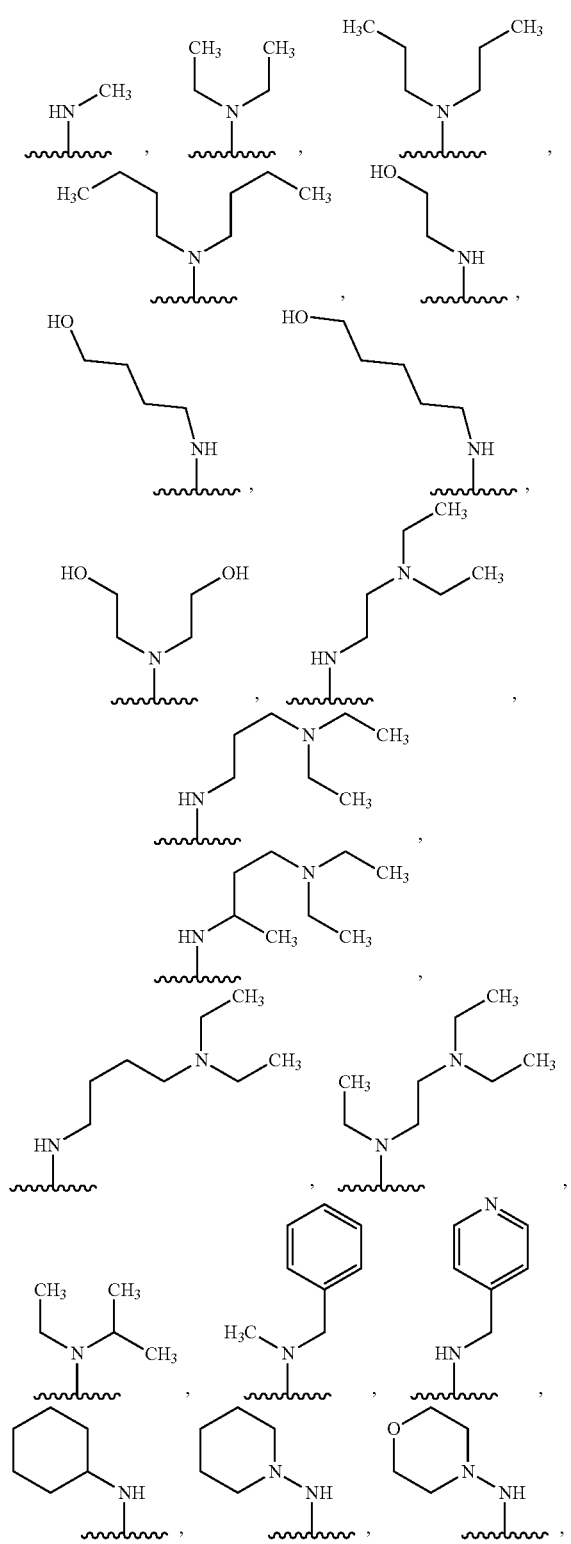
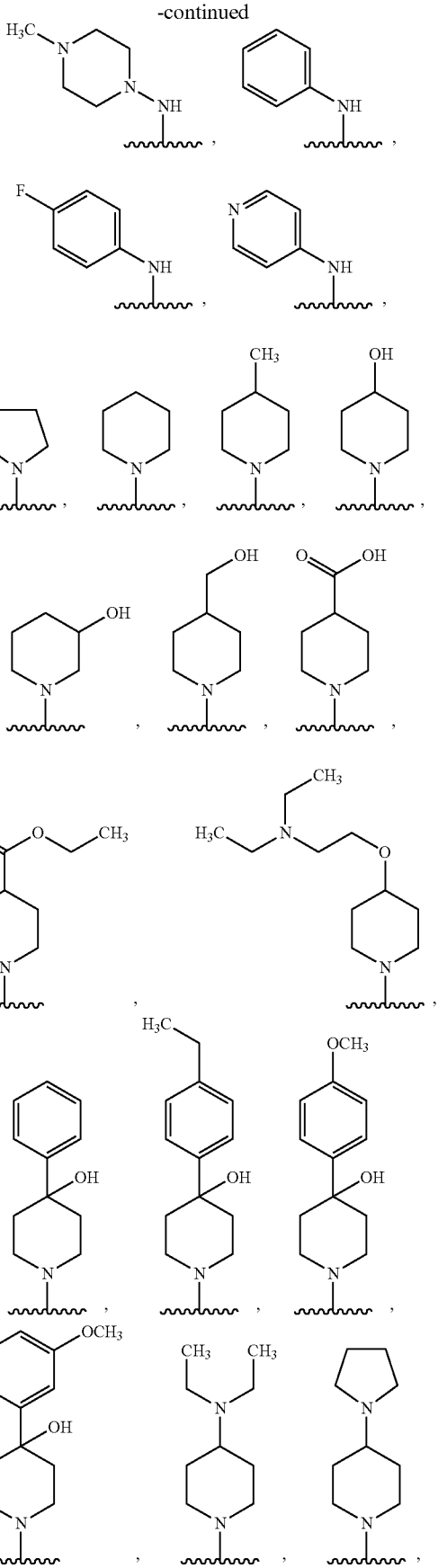

551
-continued
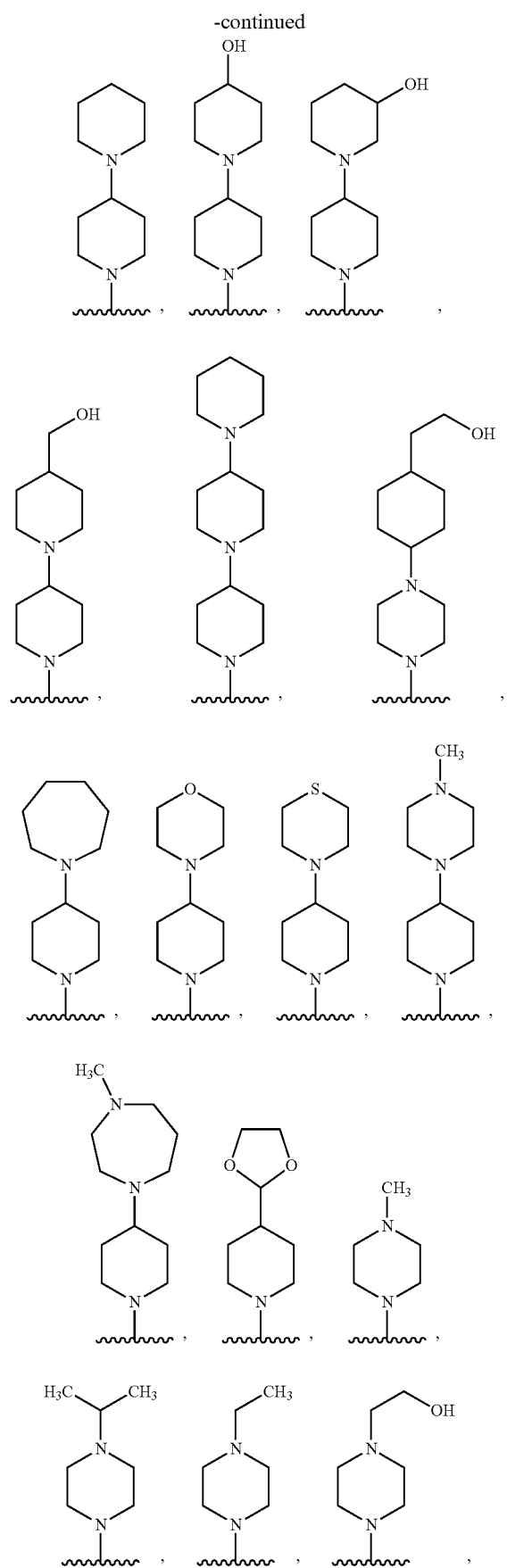
552
-continued
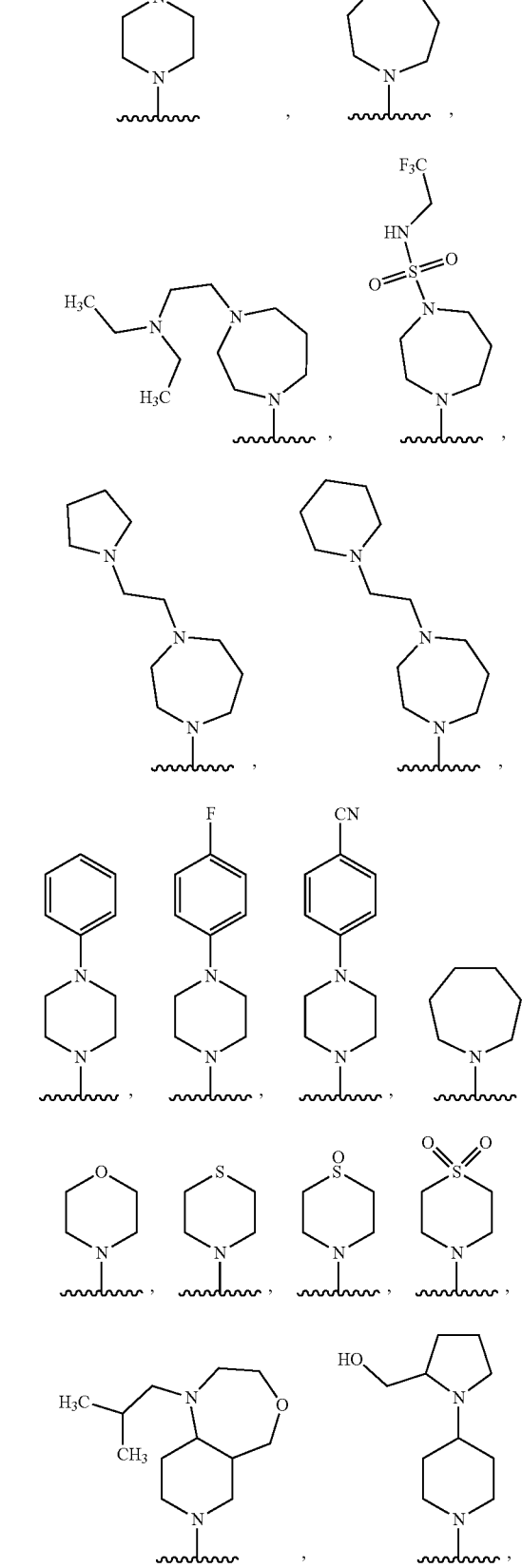

553
-continued
554
-continued
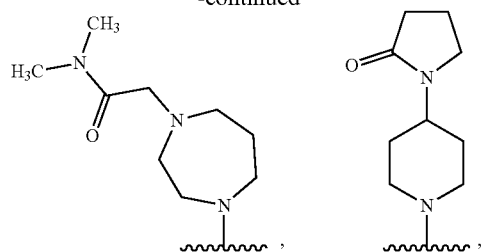
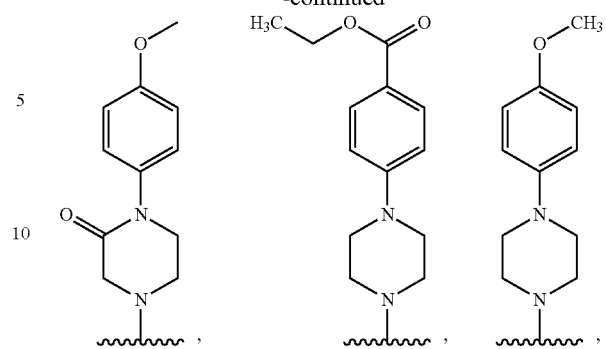
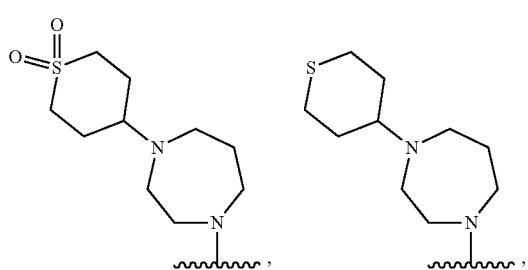
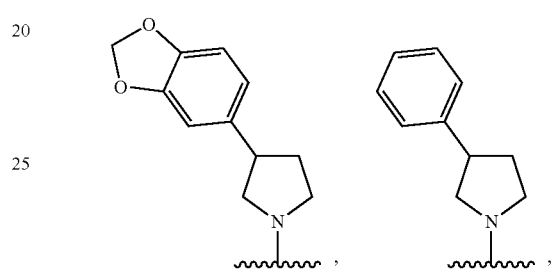
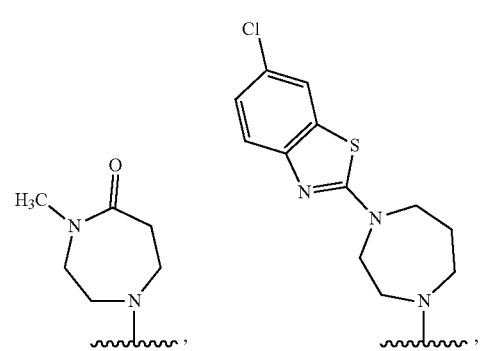
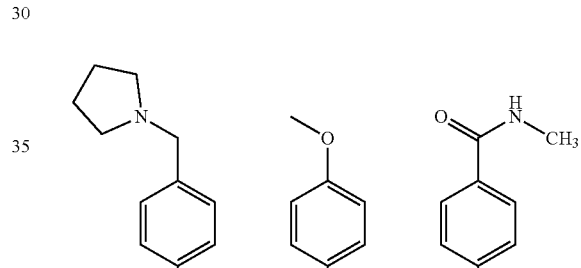
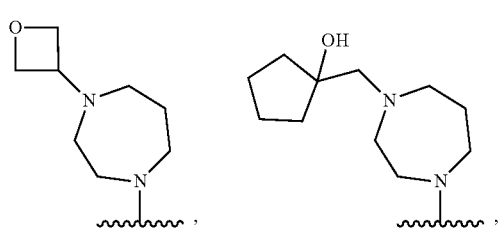
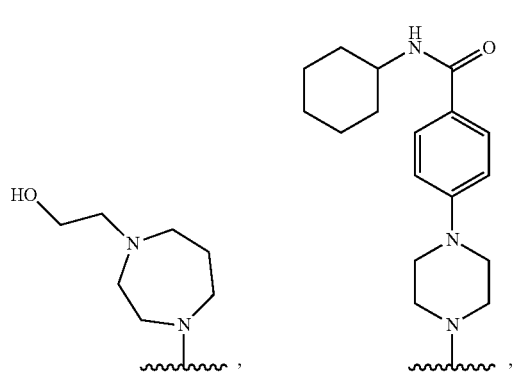
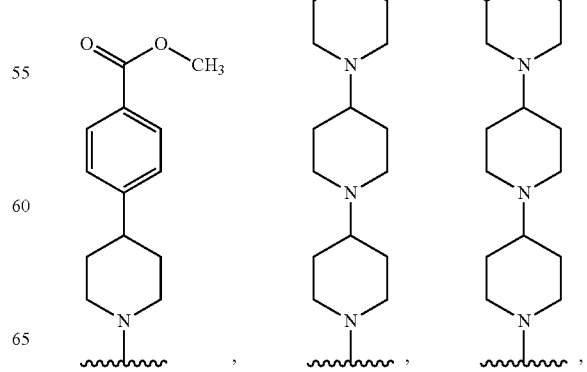

-continued
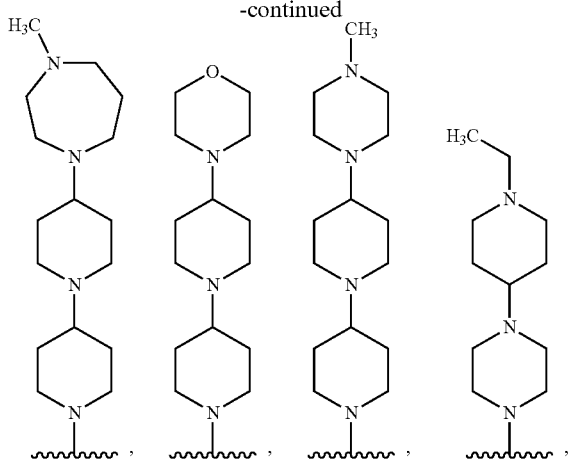
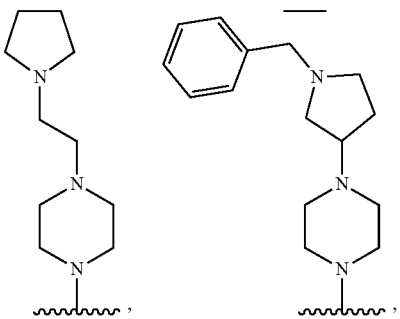
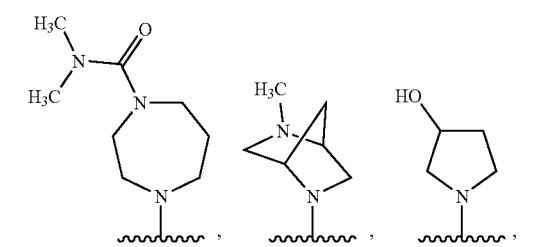
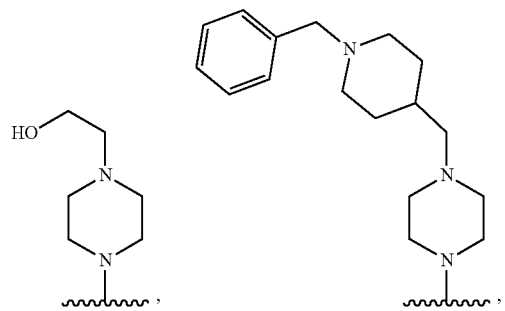
-continued
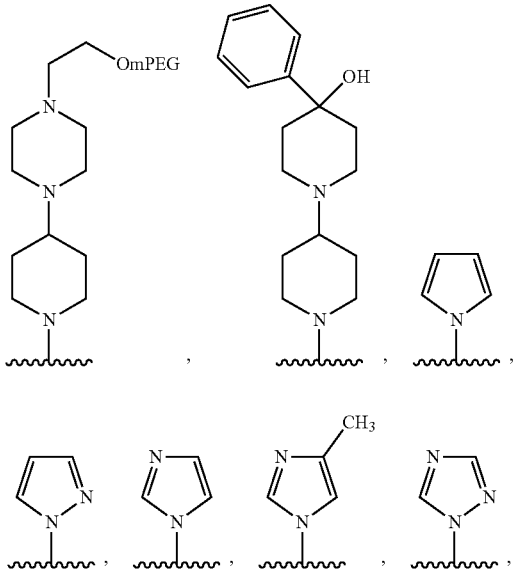
12. The compound of claim 1, wherein $R^1$ is selected from
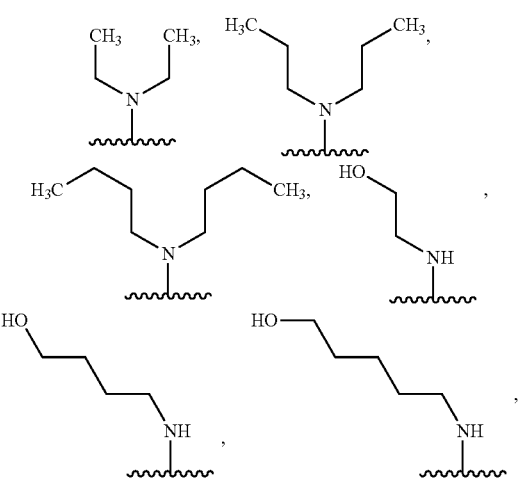

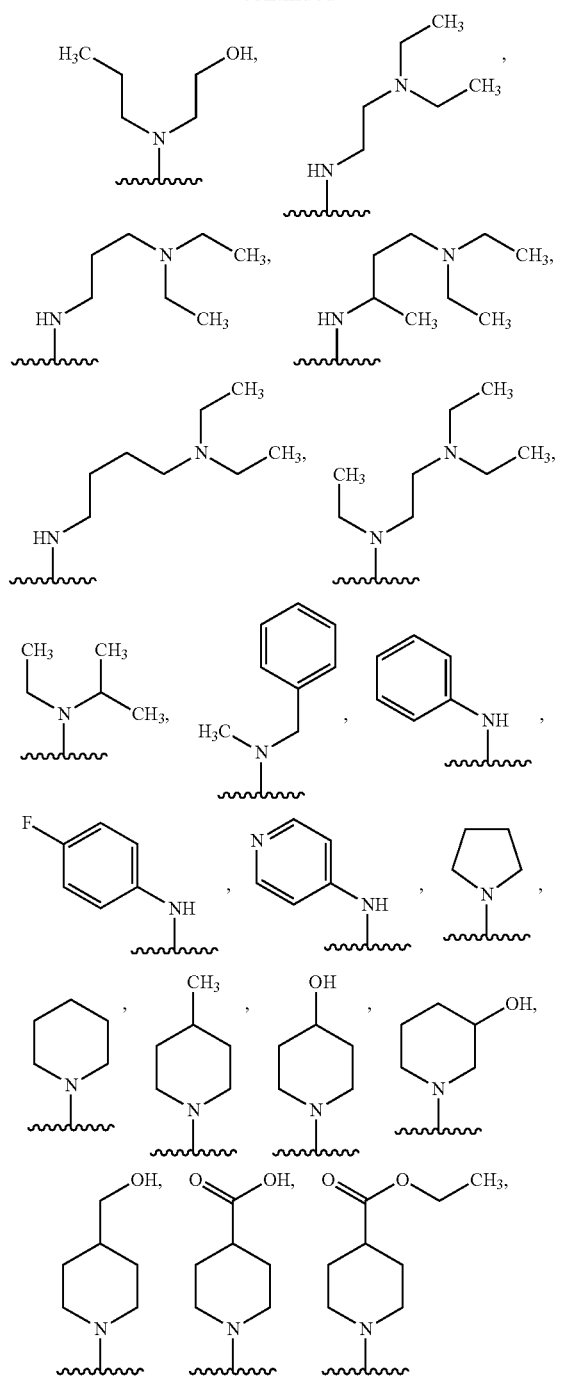
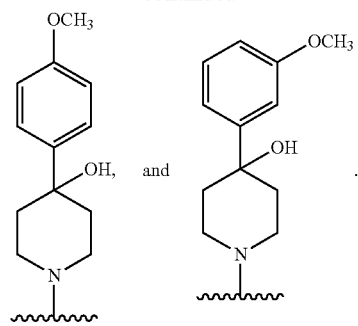
13. The compound of claim 1, wherein $R^1$ is selected from
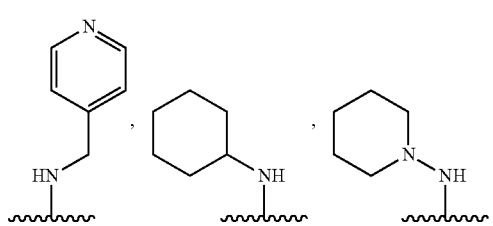
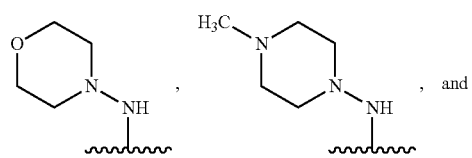
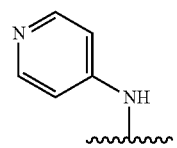
14. The compound of claim 1, wherein $R^1$ is selected from
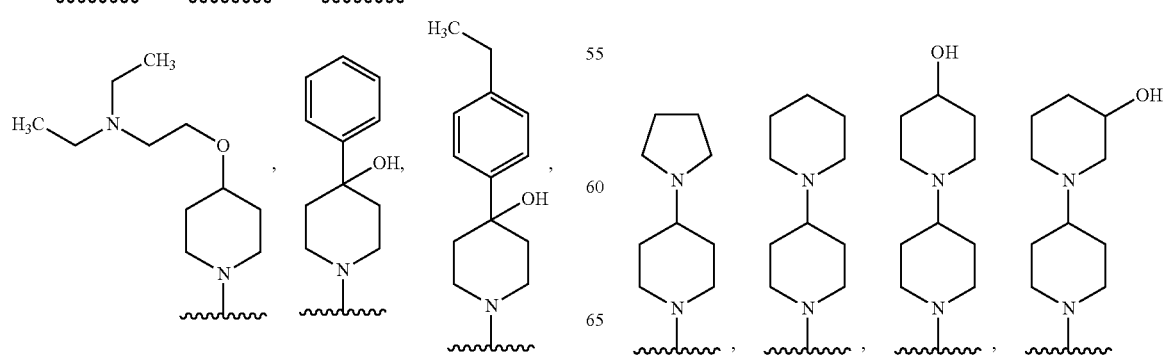

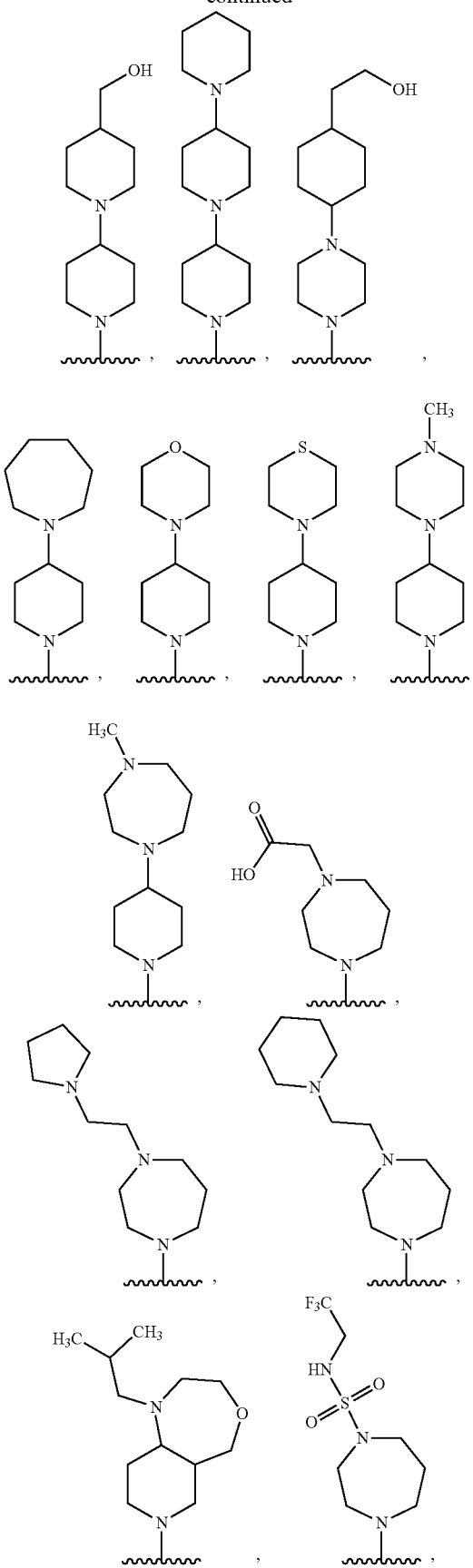
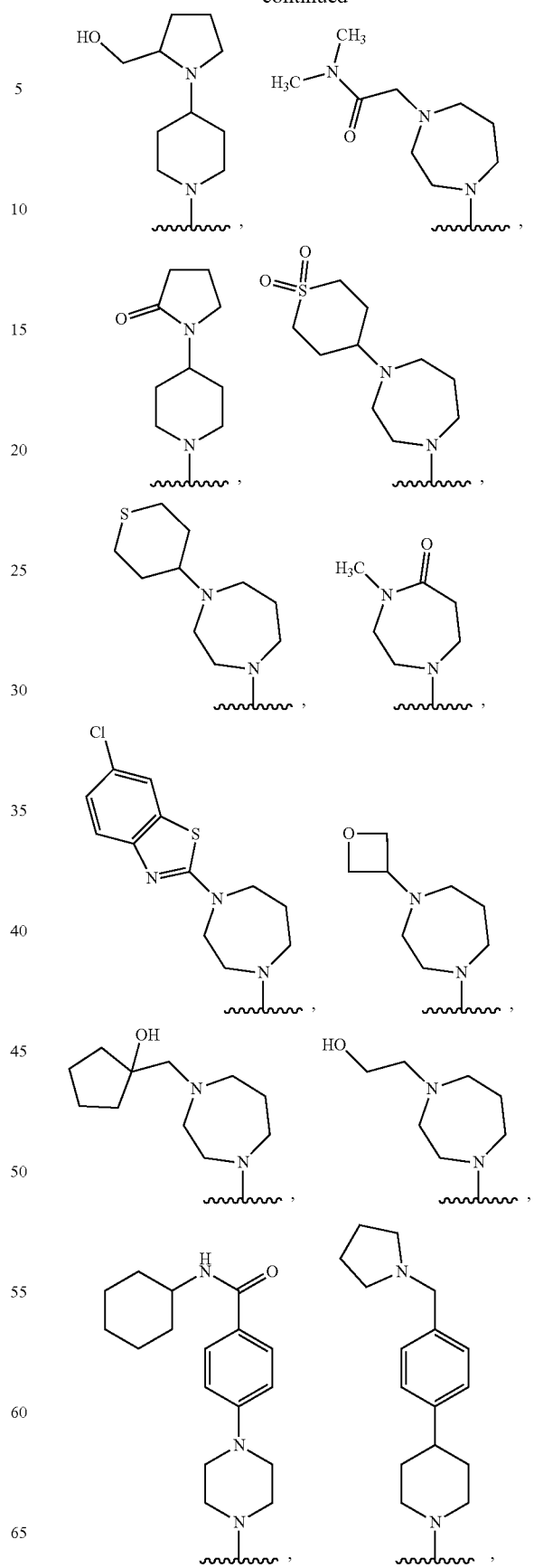

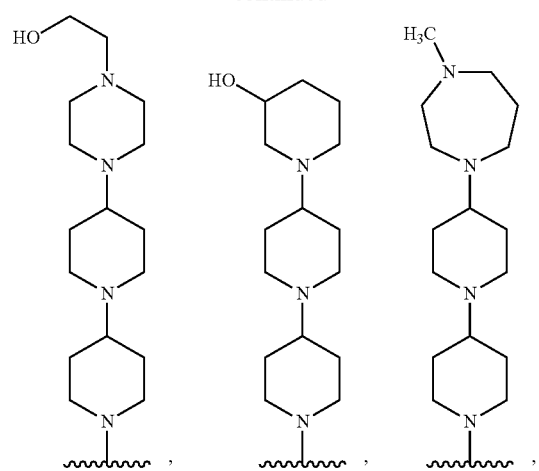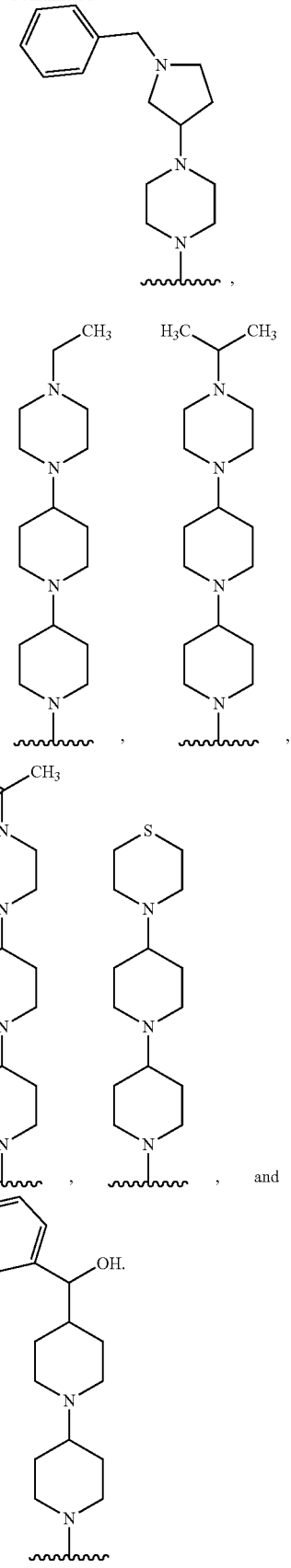

15. The compound of claim 1, wherein $R^1$ is selected from

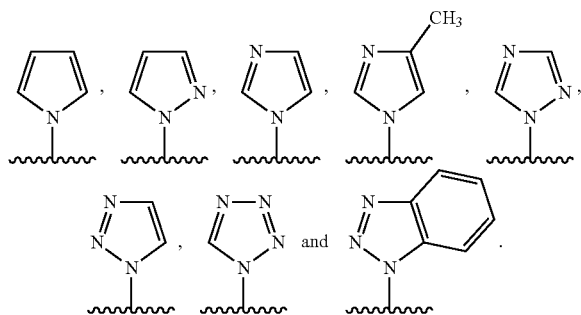

16. The compound of claim 1, wherein $R^2$ is selected from $C_{1-6}$ alkyl, —$NO_2$, —$OR^{18}$, and CN, and $R^{18}$ is selected from $C_{1-16}$ alkyl, $C_{1-6}$ haloalkyl, and $C_{1-6}$ aminoalkyl.

17. The compound of claim 16, wherein $R^2$ is —O$(CH_2)_m CH_3$, wherein m is an integer selected from 1, 2, 3, 4, 5, 6, 7, 8, 9, 10, 11 12, 13, 14, 15, and 16.

18. The compound of claim 1, wherein $R^2$ is amino, substituted with one or more substituents selected from alkyl, cycloalkyl, heterocyclyl, aryl, heteroaryl, and amino.

19. The compound of claim 18, wherein the amino substituent is alkyl substituted with at least one substituent selected from —C(O)OH, —OH, phenyl, and pyridyl, and the phenyl and pyridyl are each independently unsubstituted or substituted with halo, alkyl, or —OH.

20. The compound of claim 1, wherein $R^6$ is selected from halo, alkyl, —$OR^{17}$, —$S(O)_{0-2}R^{16}$, —$C(O)OR^{15}$, —$NO_2$, and —$C(O)NR^{15}R^{15}$;

$R^{15}$ is selected from H, methyl, ethyl, iPr, —$CH_2CH_2NEt_2$, and —$CH_2CH_2OH$;

$R^{16}$ is methyl; and $R^{17}$ is selected from methyl, trifluoromethyl and butyl.

21. The compound of claim 1, wherein $R^6$ is selected from

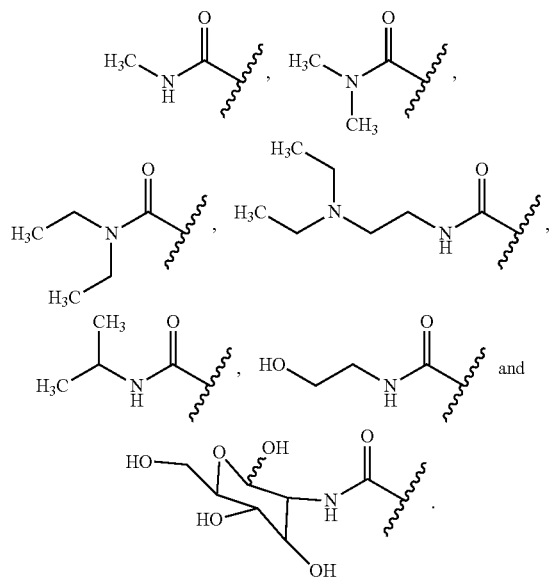

22. The compound of claim 1, wherein $R^5$, $R^7$ and $R^8$ are each H.

23. The compound of claim 1, wherein n is 1 or 2 and each $R^9$ is independently halo.

24. The compound of claim 1, wherein the compound is of Formula (II):

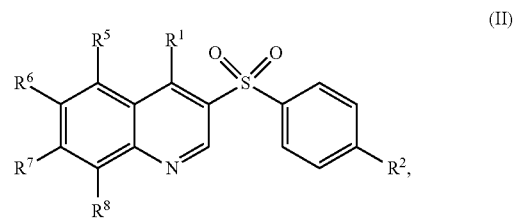

or a pharmaceutically acceptable salt, isotopically enriched analog, stereoisomer, mixture of stereoisomers, or tautomer thereof.

25. The compound of claim 1, wherein the compound is of Formula (III):

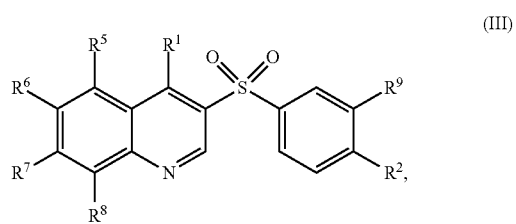

or a pharmaceutically acceptable salt, isotopically enriched analog, stereoisomer, mixture of stereoisomers, or tautomer thereof.

26. The compound of claim 1, wherein the compound is of Formula (IV):

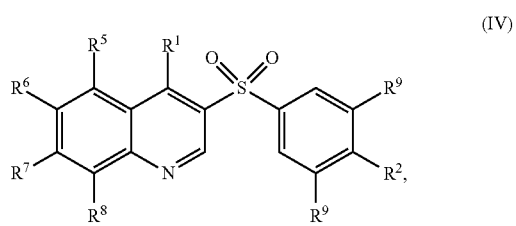

or a pharmaceutically acceptable salt, isotopically enriched analog, stereoisomer, mixture of stereoisomers, or tautomer thereof.

27. The compound of claim 1, wherein the compound is of Formula (V):

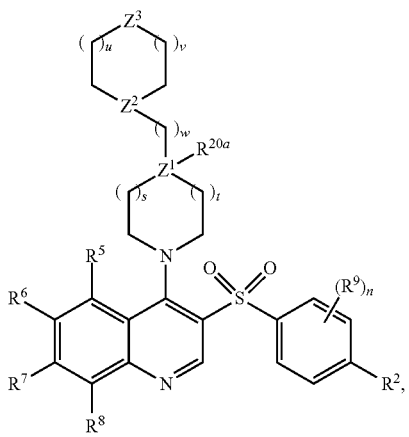

(V)

or a pharmaceutically acceptable salt, isotopically enriched analog, stereoisomer, mixture of stereoisomers, or tautomer thereof, wherein each of s, t, u, and v is independently 0, 1, 2, or 3, provided that the sum of s and t is 1, 2, 3 or 4, and the sum of u and v is 1, 2, 3 or 4;

w is 0, 1, 2, or 3;

$Z^1$ is C or N, when $Z^1$ is C, $R^{20a}$ is selected from H, halo, oxo, —NH$_2$, —OH, —CN, —NO$_2$, —NHR$^{28}$, —N(R$^{28}$)$_2$, —C(O)R$^{28}$, —C(O)OR$^{28}$, —C(O)OH, —OC(O)R$^{28}$, —S(O)$_{0-2}$R$^{28}$, —NHS(O)$_{0-2}$R$^{28}$, —S(O)$_{0-2}$NHR$^{28}$, —NHS(O)$_{0-2}$NHR$^{28}$, —C(O)NH$_2$, —C(O)NHR$^{28}$, —C(O)N(R$^{28}$)$_2$, —NHC(O)R$^{28}$, —OC(O)NHR$^{28}$, —NHC(O)OR$^{28}$, —OC(O)N(R$^{28}$)$_2$, —NR$^{32}$C(O)NH$_2$, —NR$^{32}$C(O)NHR$^{28}$, —NR$^{32}$C(O)N(R$^{28}$)$_2$, poly(ethylene glycol), methoxypoly(ethylene glycol), C$_{1-30}$ alkyl optionally substituted with OH or —C(O)OH, and C$_{1-30}$ heteroalkyl optionally substituted with OH or —C(O)OH, wherein R$^{32}$ is H or C$_{1-4}$ alkyl, and R$^{28}$ is C$_{1-4}$ alkyl;

when $Z^1$ is N, $R^{20a}$ is absent;

$Z^2$ is C or N;

$Z^3$ is CH$_2$, CHR$^{25}$, CR$^{25}$R$^{25}$, or NR$^{25}$, O, or S(O)$_{0-2}$ and R$^{25}$ is selected from H and alkyl.

28. A compound selected from the group consisting of:

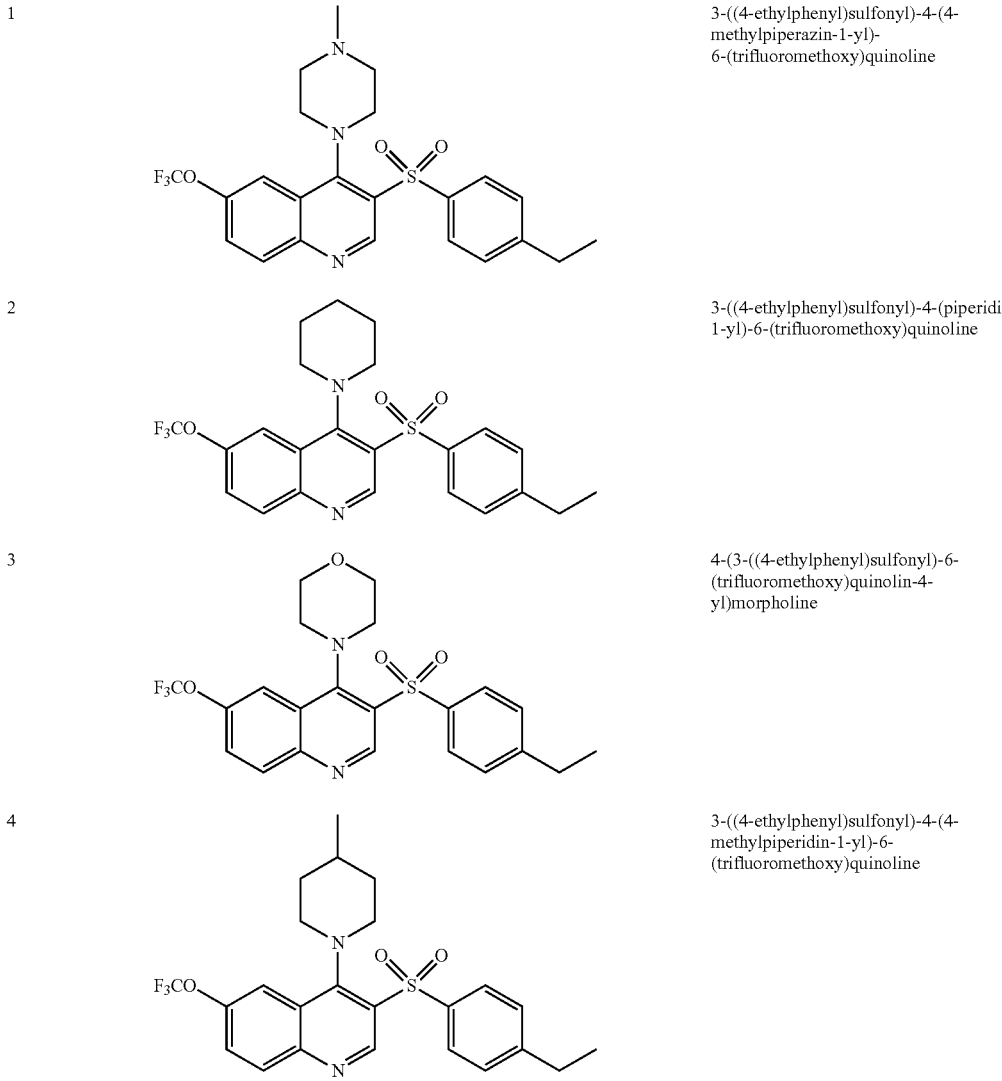

| | | |
|---|---|---|
| 1 | | 3-((4-ethylphenyl)sulfonyl)-4-(4-methylpiperazin-1-yl)-6-(trifluoromethoxy)quinoline |
| 2 | | 3-((4-ethylphenyl)sulfonyl)-4-(piperidin-1-yl)-6-(trifluoromethoxy)quinoline |
| 3 | | 4-(3-((4-ethylphenyl)sulfonyl)-6-(trifluoromethoxy)quinolin-4-yl)morpholine |
| 4 | | 3-((4-ethylphenyl)sulfonyl)-4-(4-methylpiperidin-1-yl)-6-(trifluoromethoxy)quinoline |

| | | |
|---|---|---|
| 5 | 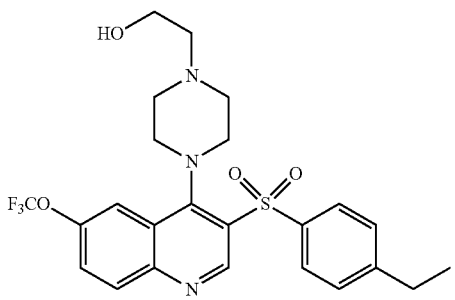 [SMILES: CCc1ccc(S(=O)(=O)c2cnc3ccc(OC(F)(F)F)cc3c2N2CCN(CCO)CC2)cc1] | 2-(4-(3-((4-ethylphenyl)sulfonyl)-6-(trifluoromethoxy)quinolin-4-yl)piperazin-1-yl)ethan-1-ol |
| 6 | 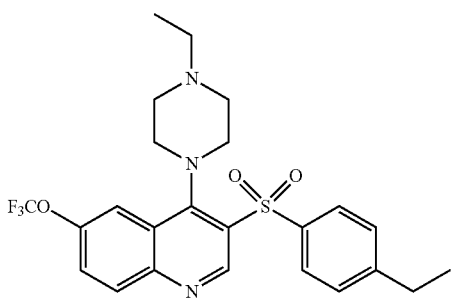 | 3-((4-ethylphenyl)sulfonyl)-4-(4-ethylpiperazin-1-yl)-6-(trifluoromethoxy)quinoline |
| 7 | 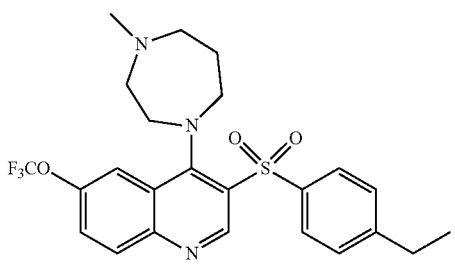 | 3-((4-ethylphenyl)sulfonyl)-4-(4-methyl-1,4-diazepan-1-yl)-6-(trifluoromethoxy)quinoline |
| 8 | 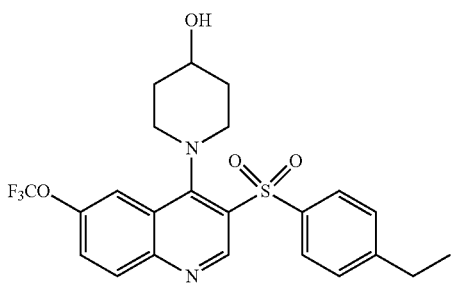 | 1-(3-((4-ethylphenyl)sulfonyl)-6-(trifluoromethoxy)quinolin-4-yl)piperidin-4-ol |
| 9 | 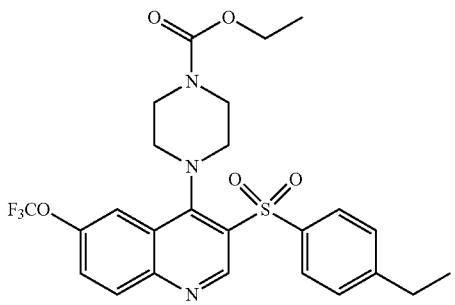 | ethyl 4-(3-((4-ethylphenyl)sulfonyl-6-(trifluoromethoxy)quinolin-4-yl)piperazine-1-carboxylate |

| | | |
|---|---|---|
| 10 | 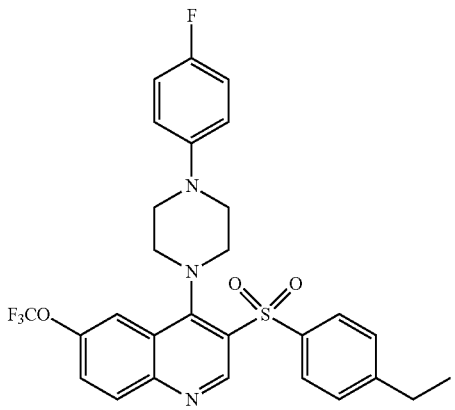 | 3-((4-ethylphenyl)sulfonyl)-4-(4-(4-fluorophenyl)piperazin-1-yl)-6-(trifluoromethoxy)quinoline |
| 11 | 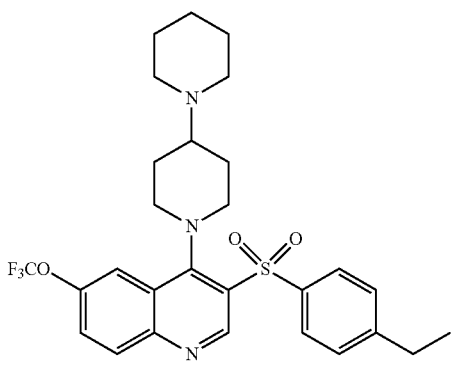 | 4-([1,4'-bipiperidin]-1'-yl)-3-((4-ethylphenyl)sulfonyl)-6-(trifluoromethoxy)quinoline |
| 12 | 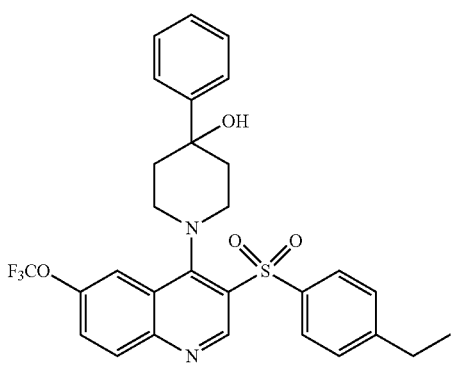 | 1-(3-((4-ethylphenyl)sulfonyl)-6-(trifluoromethoxy)quinolin-4-yl)-4-phenylpiperidin-4-ol |
| 13 | 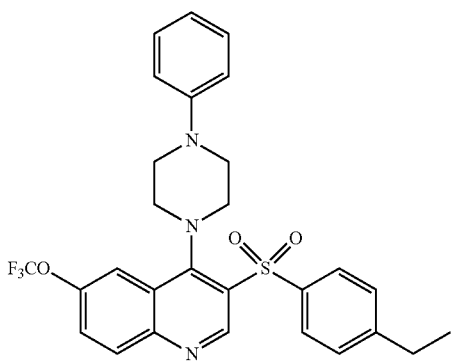 | 3-((4-ethylphenyl)sulfonyl)-4-(4-phenylpiperazin-1-yl)-6-(trifluoromethoxy)quinoline |

-continued
| | | |
|---|---|---|
| 14 | 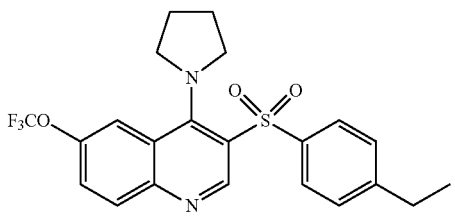 | 3-((4-ethylphenyl)sulfonyl)-4-(pyrrolidin-1-yl)-6-(trifluoromethoxy)quinoline |
| 15 | 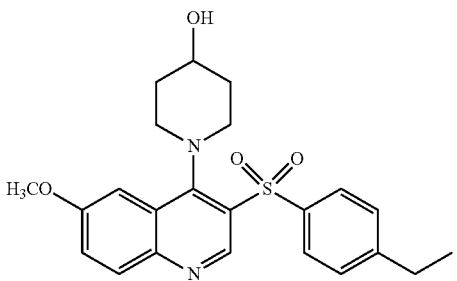 [SMILES: CCc1ccc(S(=O)(=O)c2cnc3ccc(OC(F)(F)F)cc3c2N2CCC(O)CC2)cc1] | 1-(3-((4-ethylphenyl)sulfonyl)-6-methoxyquinolin-4-yl)piperidin-4-ol |
| 16 | 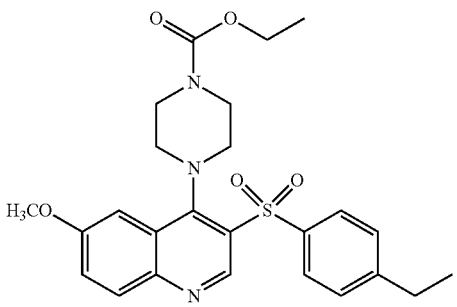 [SMILES: CCOC(=O)N1CCN(c2c(S(=O)(=O)c3ccc(CC)cc3)cnc3ccc(OC(F)(F)F)cc23)CC1] | ethyl 4-(3-((4-ethylphenyl)sulfonyl)-6-methoxyquinolin-4-yl)piperazine-1-carboxylate |
| 17 | 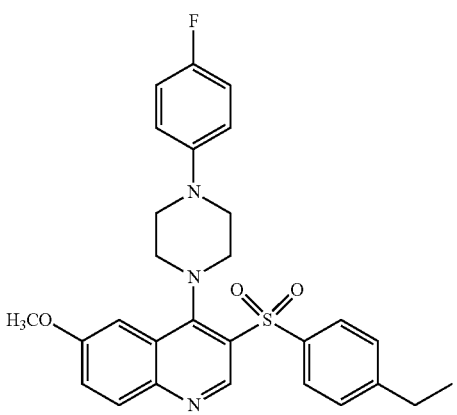 [SMILES: CCc1ccc(S(=O)(=O)c2cnc3ccc(OC(F)(F)F)cc3c2N2CCN(c3ccc(F)cc3)CC2)cc1] | 3-((4-ethylphenyl)sulfonyl)-4-(4-(4-fluorophenyl)piperazin-1-yl)-6-methoxyquinoline |
| 18 | 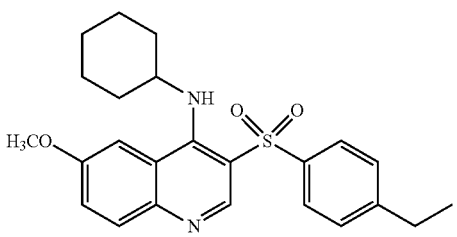 | N-cyclohexyl-3-((4-ethylphenyl)sulfonyl)-6-methoxyquinolin-4-amine |

-continued

| | | |
|---|---|---|
| 19 | 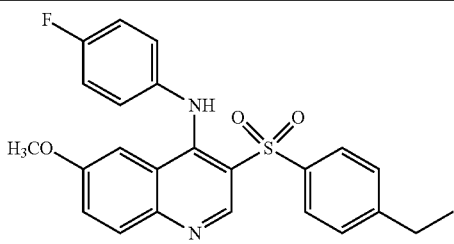 | 3-((4-ethylphenyl)sulfonyl)-N-(4-fluorophenyl)-6-methoxyquinolin-4-amine |
| 20 | 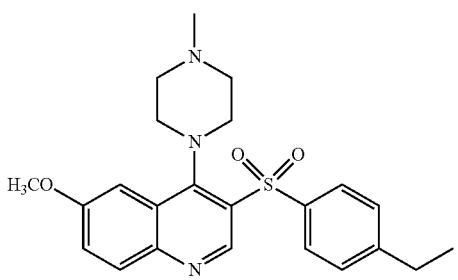 | 3-((4-ethylphenyl)sulfonyl)-6-methoxy-4-(4-methylpiperazin-1-yl)quinoline |
| 21 | 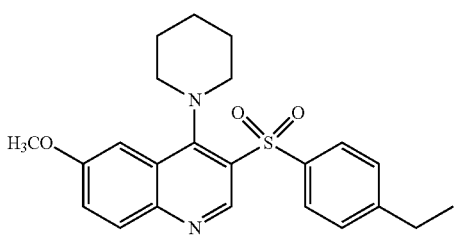 | 3-((4-ethylphenyl)sulfonyl)-6-methoxy-4-(piperidin-1-yl)quinoline |
| 22 | 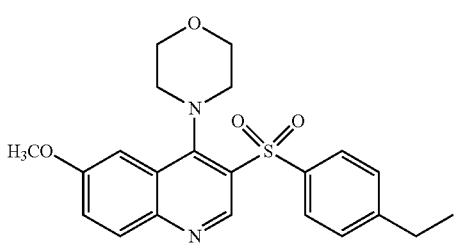 | 4-(3-((4-ethylphenyl)sulfonyl)-6-methoxyquinolin-4-yl)morpholine |
| 23 | 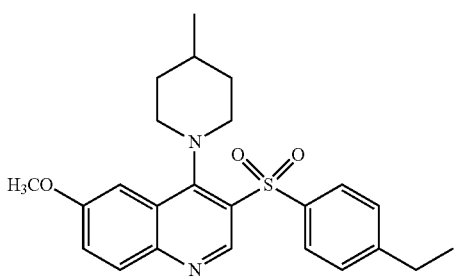 | 3-((4-ethylphenyl)sulfonyl-6-methoxy-4-(4-methylpiperidin-1-yl)quinoline |
| 24 | 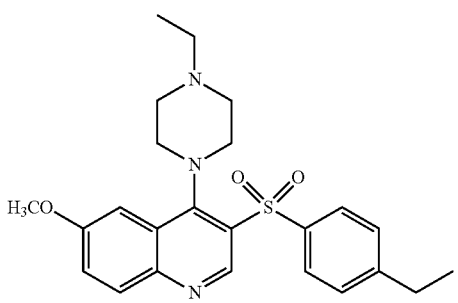 | 3-((4-ethylphenyl)sulfonyl)-4-(4-ethylpiperazin-1-yl)-6-methoxyquinoline |

-continued
| | | |
|---|---|---|
| 25 | 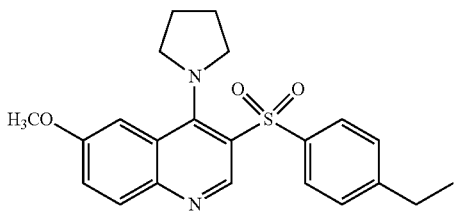 | 3-((4-ethylphenyl)sulfonyl)-6-methoxy-4-(pyrrolidin-1-yl)quinoline |
| 26 | 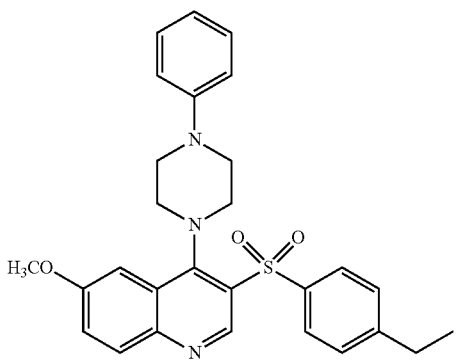 [SMILES: CCc1ccc(S(=O)(=O)c2cnc3ccc(OC(F)(F)F)cc3c2N2CCN(c3ccccc3)CC2)cc1] | 3-((4-ethylphenyl)sulfonyl)-6-methoxy-4-(4-phenylpiperazin-1-yl)quinoline |
| 27 | 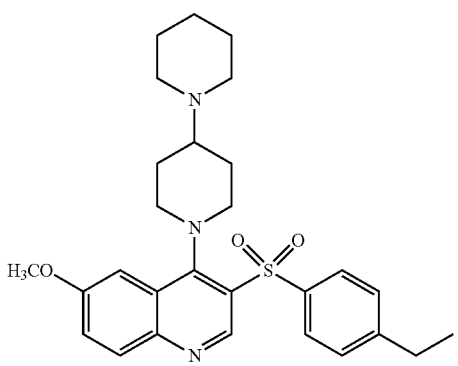 | 4-([1,4'-bipiperidin]-1'-yl)-3-((4-ethylphenyl)sulfonyl)-6-methoxyquinoline |
| 28 | 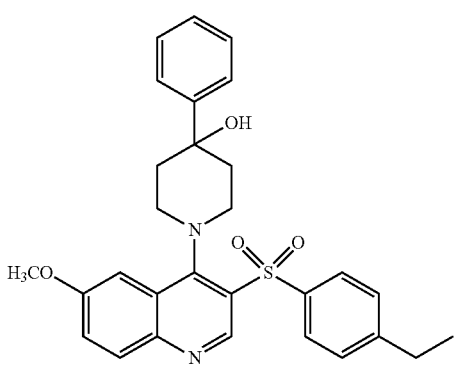 [SMILES: CCc1ccc(S(=O)(=O)c2cnc3ccc(OC)cc3c2N2CCC(O)(c3ccccc3)CC2)cc1] | 1-(3-((4-ethylphenyl)sulfonyl)-6-methoxyquinolin-4-yl)-4-phenylpiperidin-4-ol |
| 29 | 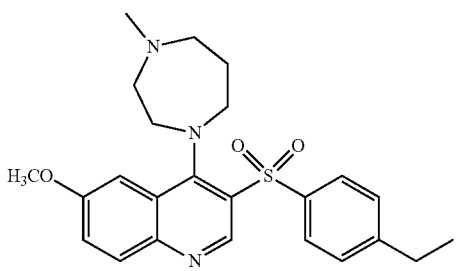 [SMILES: CCc1ccc(S(=O)(=O)c2cnc3ccc(OC)cc3c2N2CCCN(C)CC2)cc1] | 3-((4-ethylphenyl)sulfonyl)-6-methoxy-4-(4-methyl-1,4-diazepan-1-yl)quinoline |

-continued
| | | |
|---|---|---|
| 30 | 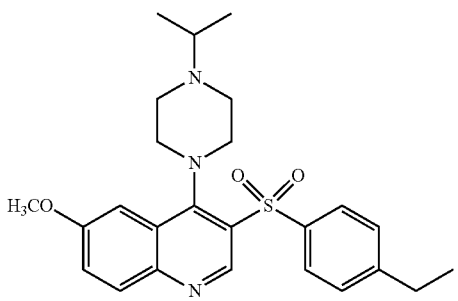 | 3-((4-ethylphenyl)sulfonyl-4-(4-isopropylpiperazin-1-yl)-6-methoxyquinoline |
| 31 | 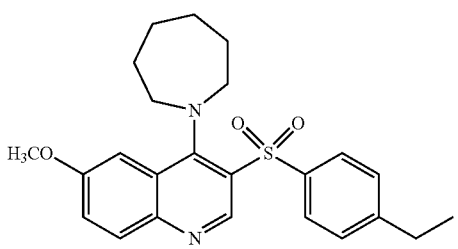 [SMILES: CCc1ccc(S(=O)(=O)c2cnc3ccc(OC)cc3c2N2CCCCCC2)cc1] | 4-(azepan-1-yl)-3-((4-ethylphenyl)sulfonyl)-6-methoxyquinoline |
| 32 | 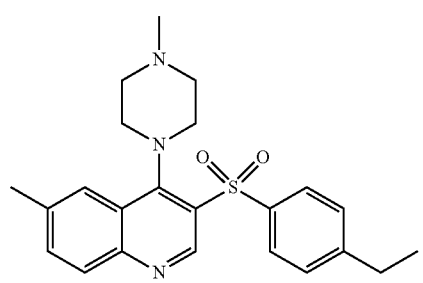 [SMILES: CCc1ccc(S(=O)(=O)c2cnc3ccc(C)cc3c2N2CCN(C)CC2)cc1] | 3-((4-ethylphenyl)sulfonyl)-6-methyl-4-(4-methylpiperazin-1-yl)quinoline |
| 33 | 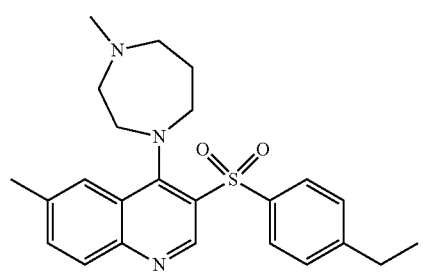 [SMILES: CCc1ccc(S(=O)(=O)c2cnc3ccc(C)cc3c2N2CCCN(C)CC2)cc1] | 3-((4-ethylphenyl)sulfonyl)-6-methyl-4-(4-methyl-1,4-diazepan-1-yl)quinoline |
| 34 | 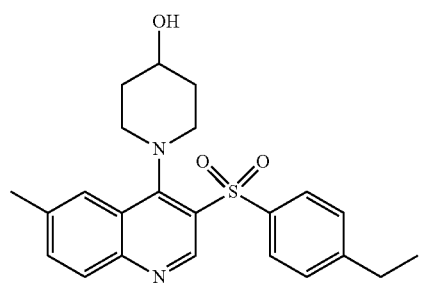 | 1-(3-((4-ethylphenyl)sulfonyl)-6-methylquinolin-4-yl)piperidin-4-ol |

| | | |
|---|---|---|
| 35 | 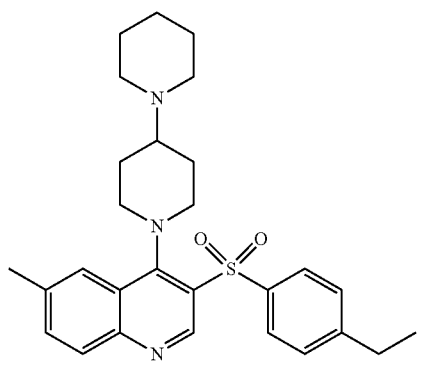 [SMILES: CCc1ccc(S(=O)(=O)c2cnc3ccc(C)cc3c2N2CCC(N3CCCCC3)CC2)cc1] | 4-([1,4'-bipiperidin]-1'-yl)-3-((4-ethylphenyl)sulfonyl)-6-methyl)quinoline |
| 36 | 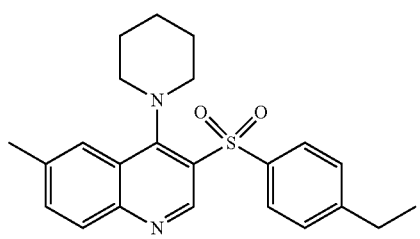 [SMILES: CCc1ccc(S(=O)(=O)c2cnc3ccc(C)cc3c2N2CCCCC2)cc1] | 3-((4-ethylphenyl)sulfonyl)-6-methyl-4-(piperidin-1-yl)quinoline |
| 37 | 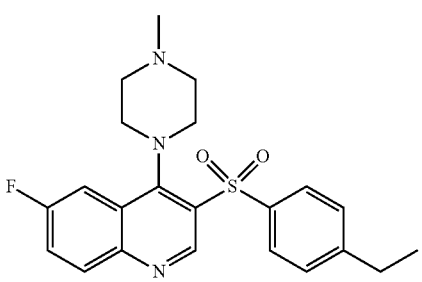 [SMILES: CCc1ccc(S(=O)(=O)c2cnc3ccc(F)cc3c2N2CCN(C)CC2)cc1] | 3-((4-ethylphenyl)sulfonyl)-6-fluoro-4-(4-methylpiperazin-1-yl)quinoline |
| 38 | 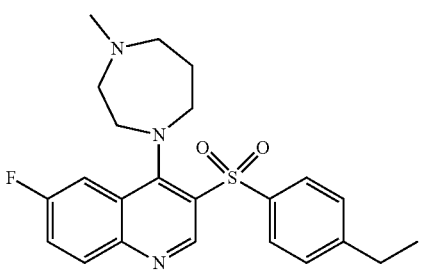 [SMILES: CCc1ccc(S(=O)(=O)c2cnc3ccc(F)cc3c2N2CCCN(C)CC2)cc1] | 3-((4-ethylphenyl)sulfonyl)-6-fluoro-4-(4-methyl-1,4-diazepan-1-yl)quinoline |
| 39 | 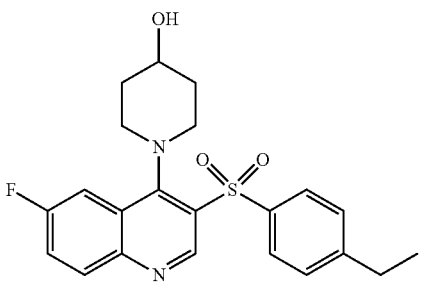 [SMILES: CCc1ccc(S(=O)(=O)c2cnc3ccc(F)cc3c2N2CCC(O)CC2)cc1] | 1-(3-((4-ethylphenyl)sulfonyl)-6-fluoroquinolin-4-yl)piperidin-4-ol |

-continued
| | | |
|---|---|---|
| 40 | 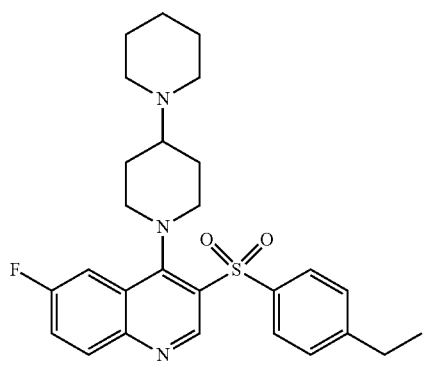 [SMILES: CCc1ccc(S(=O)(=O)c2cnc3ccc(F)cc3c2N2CCC(N3CCCCC3)CC2)cc1] | 4-([1,4'-bipiperidin]-1'-yl)-3-((4-ethylphenyl)sulfonyl)-6-fluoroquinoline |
| 41 | 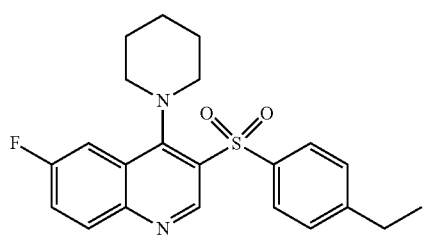 [SMILES: CCc1ccc(S(=O)(=O)c2cnc3ccc(F)cc3c2N2CCCCC2)cc1] | 3-((4-ethylphenyl)sulfonyl-6-fluoro-4-(piperidin-1-yl)quinoline |
| 42 | 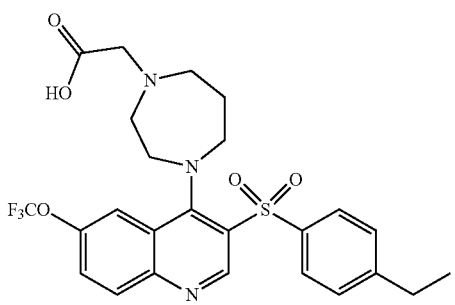 [SMILES: CCc1ccc(S(=O)(=O)c2cnc3ccc(OC(F)(F)F)cc3c2N2CCCN(CC(=O)O)CC2)cc1] | 2-(4-(3-((4-ethylphenyl)sulfonyl-6-(trifluoromethoxy)quinolin-4-yl)-1,4-diazepan-1-yl)acetic acid |
| 43 | 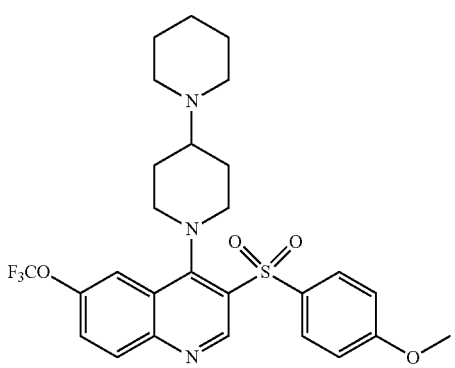 | 4-([1,4'-bipiperidin]-1yl)-3-((4-methoxyphenyl)sulfonyl)-6-(trifluoromethoxy)quinoline |
| 44 | 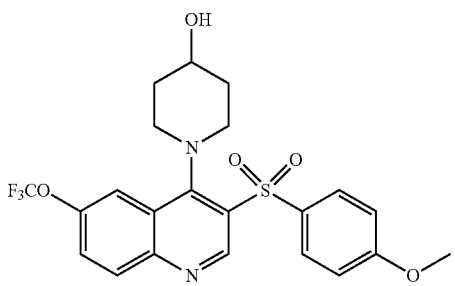 | 1-(3-((4-methoxyphenyl)sulfonyl)-6-(trifluoromethoxy)quinolin-4-yl)piperidin-4-ol |

-continued
| | | |
|---|---|---|
| 45 | 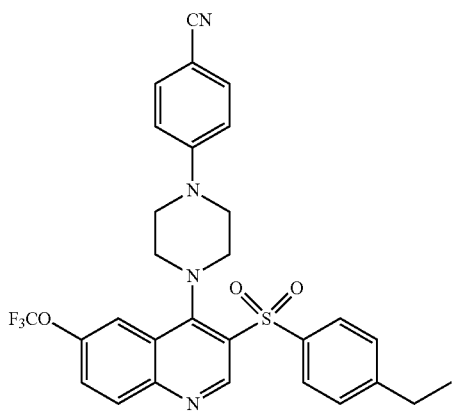 [SMILES: CCc1ccc(S(=O)(=O)c2cnc3ccc(OC(F)(F)F)cc3c2N2CCN(c3ccc(C#N)cc3)CC2)cc1] | 4-(4-(3-((4-ethylphenyl)sulfonyl)-6-(trifluoromethoxy)quinolin-4-yl)piperazin-1-yl)benzonitrile |
| 46 | 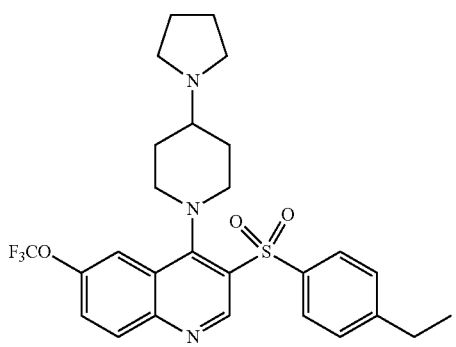 [SMILES: CCc1ccc(S(=O)(=O)c2cnc3ccc(OC(F)(F)F)cc3c2N2CCC(N3CCCC3)CC2)cc1] | 3-((4-ethylphenyl)sulfonyl)-4-(4-(pyrrolidin-1-yl)piperidin-1-yl)-6-(trifluoromethoxy)quinoline |
| 47 | 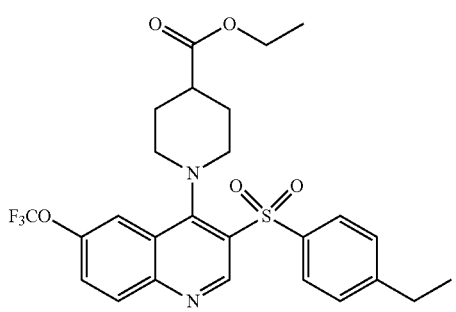 | ethyl)-(3-((4-ethylphenyl)sulfonyl)-6-(trifluoromethoxy)quinolin-4-yl)piperidine-4-carboxylate |
| 48 | 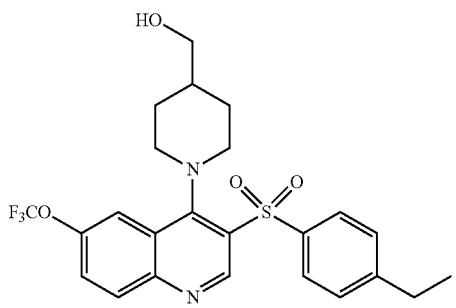 | (1-(3-((4-ethylphenyl)sulfonyl)-6-(trifluoromethoxy)quinolin-4-yl)piperidin-4-yl)methanol |

-continued

| | | |
|---|---|---|
| 49 | 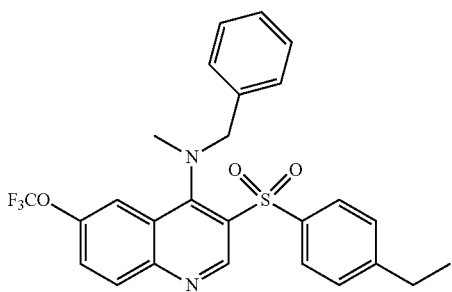 [SMILES: CCc1ccc(S(=O)(=O)c2cnc3ccc(OC(F)(F)F)cc3c2N(C)Cc2ccccc2)cc1] | N-benzyl-3-((4-ethylphenyl)sulfonyl)-N-methyl-6-(trifluoromethoxy)quinolin-4-amine |
| 50 | 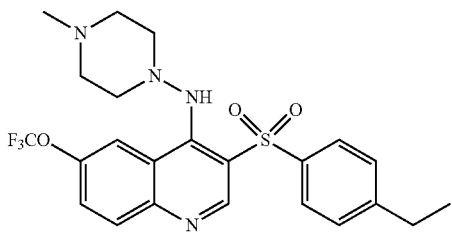 | 3-((4-ethylphenyl)sulfonyl)-N-(4-methylpiperazin-1-yl)-6-(trifluoromethoxy)quinolin-4-amine |
| 51 | 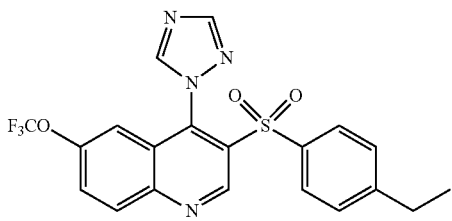 | 3-((4-ethylphenyl)sulfonyl-4-(1H-1,2,4-triazol-1-yl)-6-(trifluoromethoxy)quinoline |
| 52 | 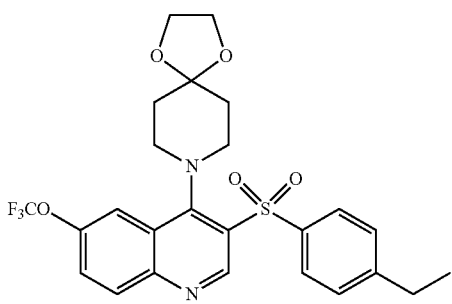 [SMILES: CCc1ccc(S(=O)(=O)c2cnc3ccc(OC(F)(F)F)cc3c2N2CCC3(CC2)OCCO3)cc1] | 8-(3-((4-ethylphenyl)sulfonyl)-6-(trifluoromethoxy)quinolin-4-yl)-1,4-dioxa-8-azaspiro[4,5]decane |
| 53 | 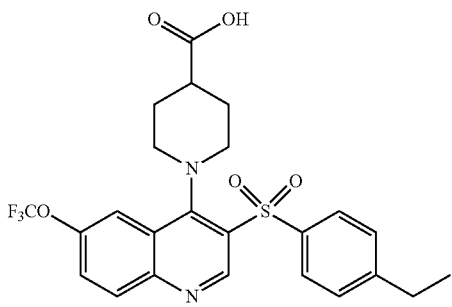 | 1-(3-((4-ethylphenyl)sulfonyl)-6-(trifluoromethoxy)quinolin-4-yl)piperidine-4-carboxylate acid |

| | | |
|---|---|---|
| 54 | 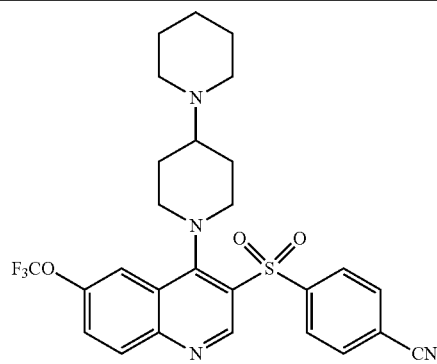 | 4-((4-([1,4'-bipiperidin]-1'-yl)-6-(trifluoromethoxy)quinolin-3-yl)sulfonyl)benzonitrile |
| 55 | 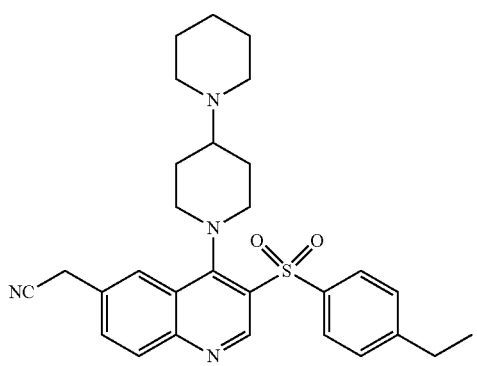 [SMILES: CCc1ccc(S(=O)(=O)c2cnc3ccc(CC#N)cc3c2N2CCC(N3CCCCC3)CC2)cc1] | 2-(4-([1,4'-bipiperidin]-1'-yl-3-((4-ethylphenyl)sulfonyl)quinolin-6-yl)acetonitrile |
| 56 | 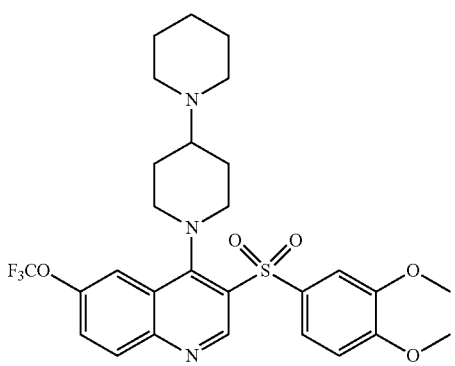 [SMILES: COc1ccc(S(=O)(=O)c2cnc3ccc(OC(F)(F)F)cc3c2N2CCC(N3CCCCC3)CC2)cc1OC] | 4-([1,4'-bipiperidin]-1'-yl)-3-((3,4-dimethoxyphenyl)sulfonyl)-6-(trifluoromethoxy)quinoline |
| 57 | 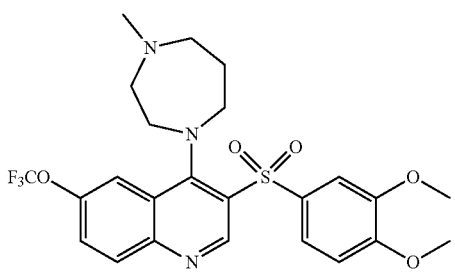 [SMILES: COc1ccc(S(=O)(=O)c2cnc3ccc(OC(F)(F)F)cc3c2N2CCCN(C)CC2)cc1OC] | 3-((3,4-dimethoxyphenyl)sulfonyl)-4-(4-methyl-1,4-diazepan-1-yl)-6-(trifluoromethoxy)quinoline |
| 58 | 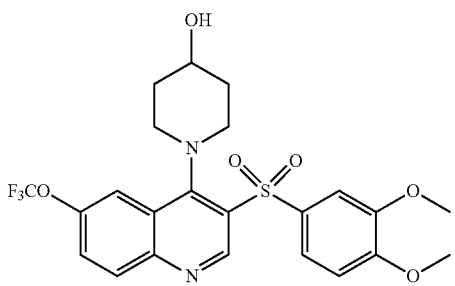 [SMILES: COc1ccc(S(=O)(=O)c2cnc3ccc(OC(F)(F)F)cc3c2N2CCC(O)CC2)cc1OC] | 1-(3-((3,4-dimethoxyphenyl)sulfonyl)-6-(trifluoromethoxy)quinolin-4-yl)piperidin-4-ol |

-continued

| | | |
|---|---|---|
| 59 | 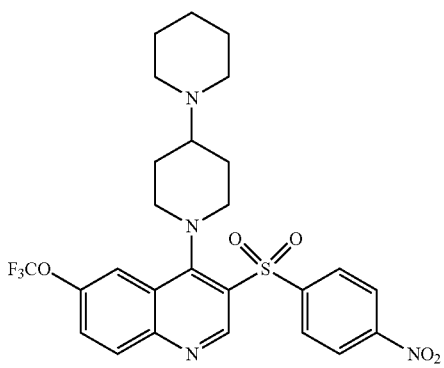 [SMILES: O=[N+]([O-])c1ccc(S(=O)(=O)c2cnc3ccc(OC(F)(F)F)cc3c2N2CCC(N3CCCCC3)CC2)cc1] | 4-([1,4,-bipiperidin]-1'-yl-3-((4-nitrophenyl)sulfonyl-6-(trifluoromethoxy)quinoline |
| 60 | 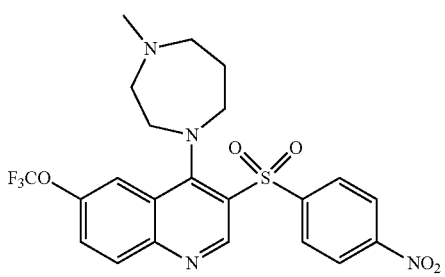 [SMILES: CN1CCCN(c2c(S(=O)(=O)c3ccc([N+](=O)[O-])cc3)cnc3ccc(OC(F)(F)F)cc23)CC1] | 4-(4-methyl-1,4-diaxepan-1-yl)-3-((4-nitrophenyl)sulfonyl-6-(trifluoromethoxy)quinoline |
| 61 | 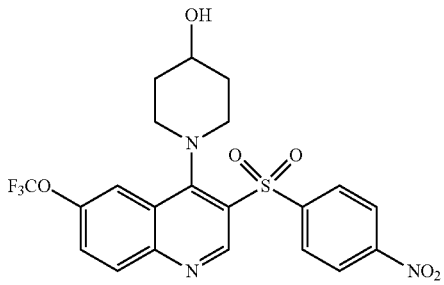 [SMILES: O=[N+]([O-])c1ccc(S(=O)(=O)c2cnc3ccc(OC(F)(F)F)cc3c2N2CCC(O)CC2)cc1] | 1-(3-((4-nitrophenyl)sulfonyl)-6-(trifluoromethoxy)quinolin-4-yl)piperidin-4-ol |
| 62 | 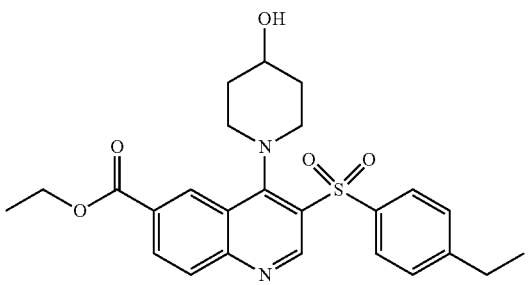 [SMILES: CCOC(=O)c1ccc2ncc(S(=O)(=O)c3ccc(CC)cc3)c(N3CCC(O)CC3)c2c1] | ethyl 3-((4-ethylphenyl)sulfonyl)-4-(4-hydroxypiperidin-1-yl)quinoline-6-carboxylate |
| 63 | 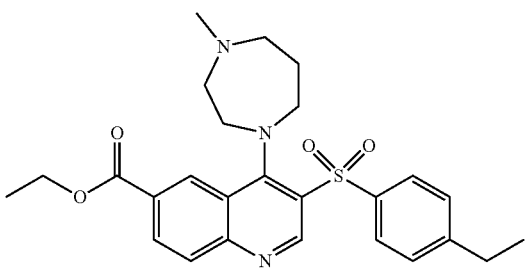 [SMILES: CCOC(=O)c1ccc2ncc(S(=O)(=O)c3ccc(CC)cc3)c(N3CCCN(C)CC3)c2c1] | ethyl 3-((4-ethylphenyl)sulfonyl)-4-(4-methyl-1,4-diazepan-1-yl)quinoline-6-carboxylate |

-continued

| | | |
|---|---|---|
| 64 | 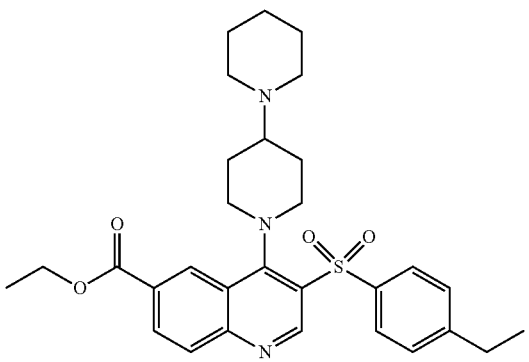 [SMILES: CCOC(=O)c1ccc2ncc(S(=O)(=O)c3ccc(CC)cc3)c(N3CCC(N4CCCCC4)CC3)c2c1] | ethyl 4-([1,4'-bipiperidin]-1'-yl)-3-((4-ethylphenyl)sulfonyl)quinoline-6-carboxylate |
| 65 | 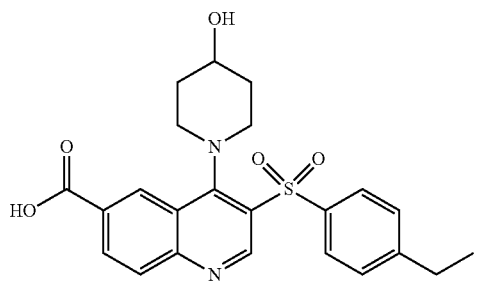 [SMILES: CCc1ccc(S(=O)(=O)c2cnc3ccc(C(=O)O)cc3c2N2CCC(O)CC2)cc1] | 3-((4-ethylphenyl)sulfonyl)-4-(4-hydroxypiperidin-1-yl)quinoline-6-carboxylate acid |
| 66 | 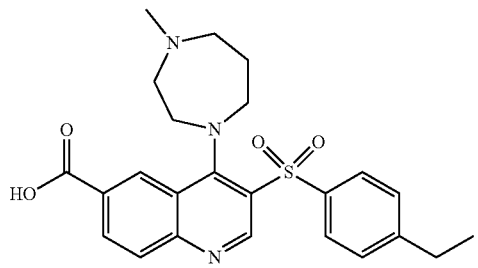 [SMILES: CCc1ccc(S(=O)(=O)c2cnc3ccc(C(=O)O)cc3c2N2CCCN(C)CC2)cc1] | 3-((4-ethylphenyl)sulfonyl)-4-(4-methyl-1,4-diazepan-1-yl)quinoline-6-carboxylate acid |
| 67 | 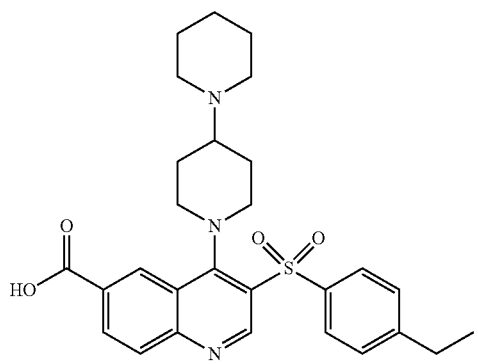 [SMILES: CCc1ccc(S(=O)(=O)c2cnc3ccc(C(=O)O)cc3c2N2CCC(N3CCCCC3)CC2)cc1] | 4-([1,4'-bipiperidin]-1'-yl)-3-((4-ethylphenyl)sulfonyl)quinoline-6-carboxylate acid |
| 68 | 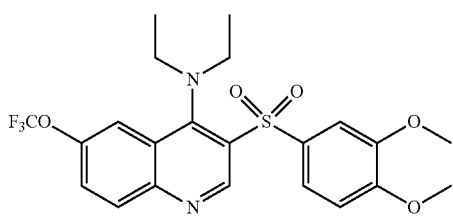 | 3-((3,4-dimethoxyphenyl)sulfonyl)-N,N-diethyl1-6-trifluoromethoxy)quinolin-4-amine |

-continued

| | | |
|---|---|---|
| 69 | 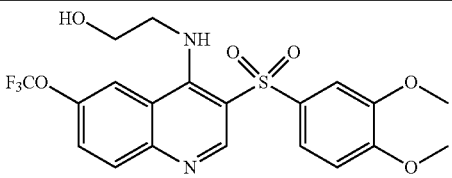 | 2-((3-((3,4-dimethoxyphenyl)sulfonyl)-6-(trifluoromethoxy)quinolin-4-yl)amino)ethan-1-ol |
| 70 | 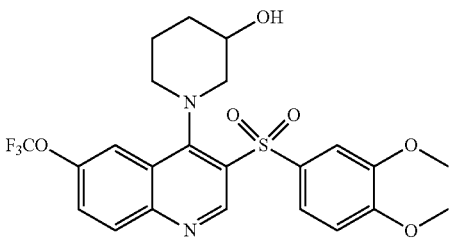 [SMILES: COc1ccc(S(=O)(=O)c2cnc3ccc(OC(F)(F)F)cc3c2N2CCCC(O)C2)cc1OC] | 1-(3-((3,4-dimethoxyphenyl)sulfonyl)-6-(trifluoromethoxy)quinolin-4-yl)piperidin-3-ol |
| 71 | 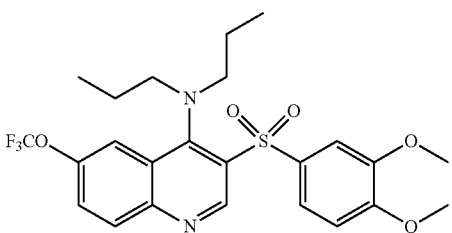 | 3-((3,4-dimethoxyphenyl)sulfonyl)-N,N-dipropyl-6-(trifluoromethoxy)quinolin-4-amine |
| 72 | 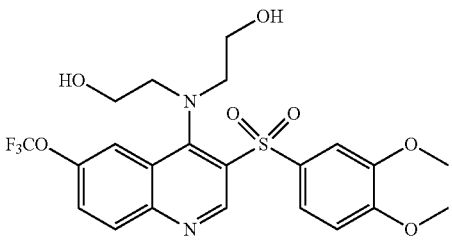 | 2,2'-((3-((3,4-dimethoxyphenyl)sulfonyl)-6-(trifluoromethoxy)quinolin-4-yl)azanediyl)bis(ethan-1-ol) |
| 73 | 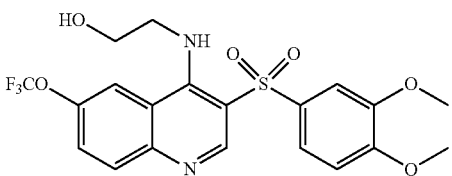 [SMILES: COc1ccc(S(=O)(=O)c2cnc3ccc(OC(F)(F)F)cc3c2NCCO)cc1OC] | 2-((3-((3,4-dimethoxyphenyl)sulfonyl)-6-(trifluoromethoxy)quinolin-4-yl)amino)ethan-1-ol |
| 74 | 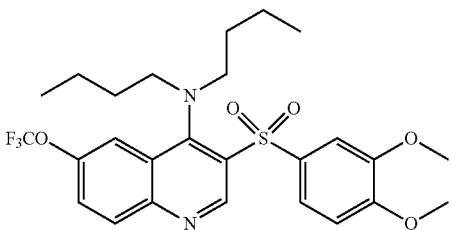 [SMILES: CCCCN(CCCC)c1c(S(=O)(=O)c2ccc(OC)c(OC)c2)cnc2ccc(OC(F)(F)F)cc12] | N,N-dibutyl-3-((3,4-dimethoxyphenyl)sulfonyl)-6-(trifluoromethoxy)quinolin-4-amine |
| 75 | 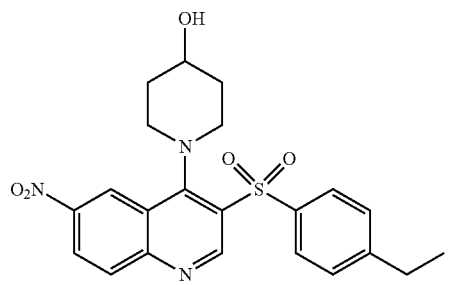 [SMILES: CCc1ccc(S(=O)(=O)c2cnc3ccc([N+](=O)[O-])cc3c2N2CCC(O)CC2)cc1] | 1-(3-((4-ethylphenyl)sulfonyl)-6-nitroquinolin-4-yl)piperidin-4-ol |

| | | -continued |
|---|---|---|
| 76 | 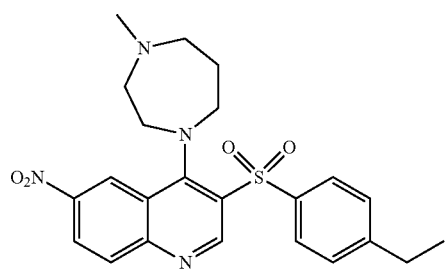 [SMILES: CCc1ccc(S(=O)(=O)c2cnc3ccc([N+](=O)[O-])cc3c2N2CCCN(C)CC2)cc1] | 3-((4-ethylphenyl)sulfonyl-4-(4-methyl-1,4-diazepan-1-yl)-6-nitroquinoline |
| 77 | 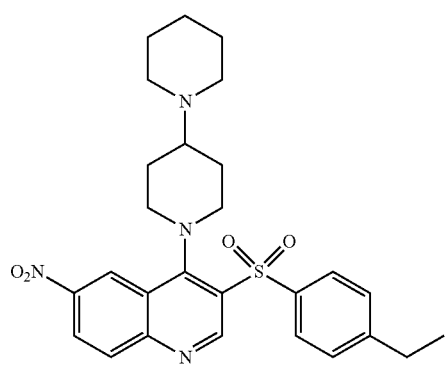 | 4-([1,4'-bipiperidin]-1'-yl)-3-((4-ethylphenyl)sulfonyl)-6-nitroquinoline |
| 78 | 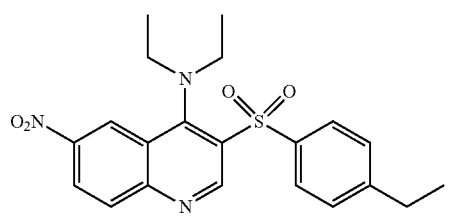 [SMILES: CCc1ccc(S(=O)(=O)c2cnc3ccc([N+](=O)[O-])cc3c2N(CC)CC)cc1] | N,N-diethyl)l-3-((4-ethylphenyl)sulfonyl)-6-nitroquinolin-4-amine |
| 79 | 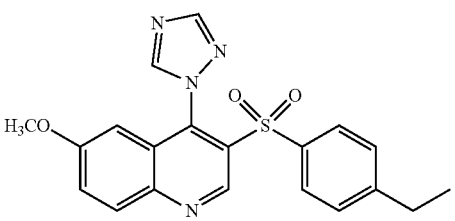 [SMILES: CCc1ccc(S(=O)(=O)c2cnc3ccc(OC)cc3c2-n2cncn2)cc1] | 3-((4-ethylphenyl)sulfonyl)-6-methoxy-4-(1H-1,2,4-triazol-1-yl)quinoline |
| 80 | 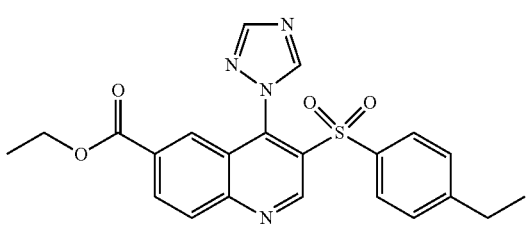 [SMILES: CCOC(=O)c1ccc2ncc(S(=O)(=O)c3ccc(CC)cc3)c(-n3cncn3)c2c1] | ethyl 3-((4-ethylphenyl)sulfonyl)-4-(1H-1,2,4-triazol-1-yl)quinoline-6-carboxylate |
| 81 | 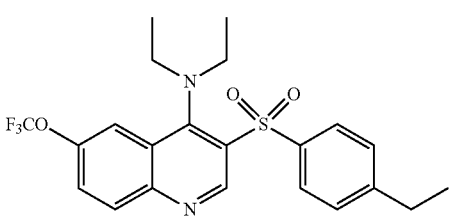 [SMILES: CCc1ccc(S(=O)(=O)c2cnc3ccc(OC(F)(F)F)cc3c2N(CC)CC)cc1] | N,N-diethyl)l-3-((4-ethylphenyl)sulfonyl)-6-(trifluoromethoxy)quinolin-4-amine |

| | | |
|---|---|---|
| 82 | 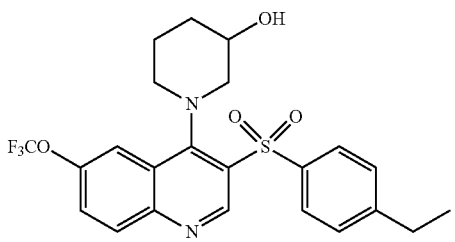 [SMILES: CCc1ccc(S(=O)(=O)c2cnc3ccc(OC(F)(F)F)cc3c2N2CCCC(O)C2)cc1] | 1-(3-((4-ethylphenyl)sulfonyl)-6-(trifluoromethoxy)quinolin-4-yl)piperidin-3-ol |
| 83 | 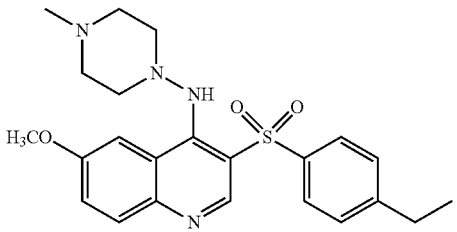 | 3-((4-ethylphenyl)sulfonyl)-6-methoxy-N-(4-methylpiperazin-1-yl)quinolin-4-amine |
| 84 | 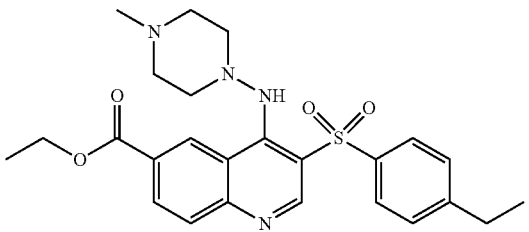 | ethyl 3-((4-ethylphenyl)sulfonyl)-4-((4-methylpiperazin-1-yl)amino)quinoline-6-carboxylate |
| 85 | 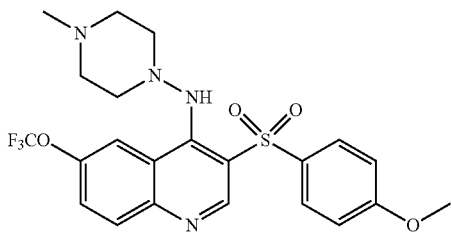 [SMILES: COc1ccc(S(=O)(=O)c2cnc3ccc(OC(F)(F)F)cc3c2NN2CCN(C)CC2)cc1] | 3-((4-methoxyphenyl)sulfonyl)-N-(4-methylpiperazin-1-yl)-6-(trifluoromethoxy)quinolin-4-amine |
| 86 | 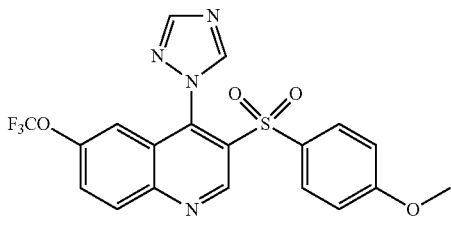 [SMILES: COc1ccc(S(=O)(=O)c2cnc3ccc(OC(F)(F)F)cc3c2-n2cncn2)cc1] | 3-((4-methoxyphenyl)sulfonyl)-4-(1H-1,2,4-triazol-1-yl)-6-(trifluoromethoxy)quinoline |
| 87 | 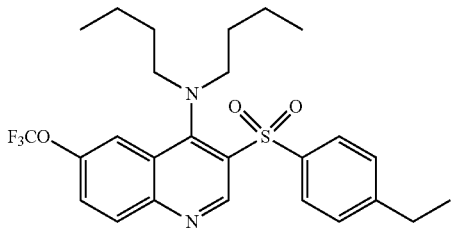 [SMILES: CCCCN(CCCC)c1c(S(=O)(=O)c2ccc(CC)cc2)cnc2ccc(OC(F)(F)F)cc12] | N,N-dibutyl-3-((4-ethylphenyl)sulfonyl)-6-(trifluoromethoxy)quinolin-4-amine |

| | | |
|---|---|---|
| 88 | 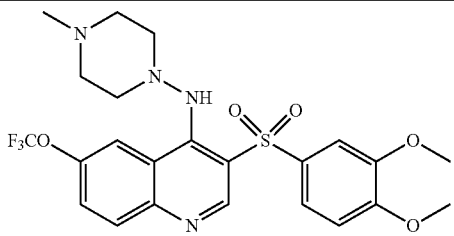 | 3-((3,4-dimethoxyphenyl)sulfonyl)-N-(4-methylpiperazin-1-yl)-6-(trifluoromethoxy)quinolin-4-amine |
| 89 | 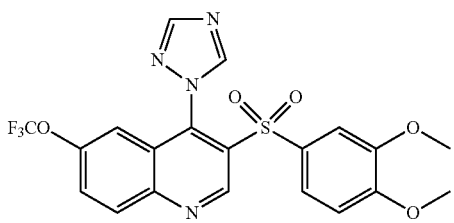 [SMILES: COc1ccc(S(=O)(=O)c2cnc3ccc(OC(F)(F)F)cc3c2-n2cncn2)cc1OC] | 3-((3,4-dimethoxyphenyl)sulfonyl)-4-(1H-1,2,4-triazol-1-yl)-6-(trifluoromethoxy)quinoline |
| 90 | 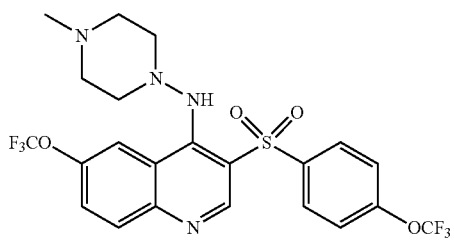 [SMILES: CN1CCN(Nc2c(S(=O)(=O)c3ccc(OC(F)(F)F)cc3)cnc3ccc(OC(F)(F)F)cc23)CC1] | N-(4-methylpiperazin-1-yl)-6-(trifluoromethoxy)-3-((4-(trifluoromethoxy)phenyl)sulfonyl)quinolin-4-amine |
| 91 | 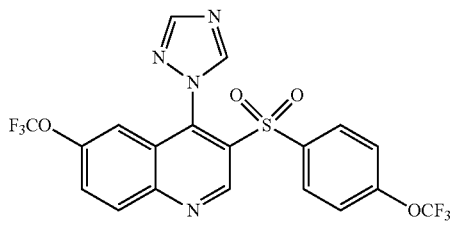 | 4-(1H-1,2,4-triazol-1-yl)-6-(trifluoromethoxy)-3-((4-(trifluoromethoxy)phenyl)sulfonyl)quinoline |
| 92 | 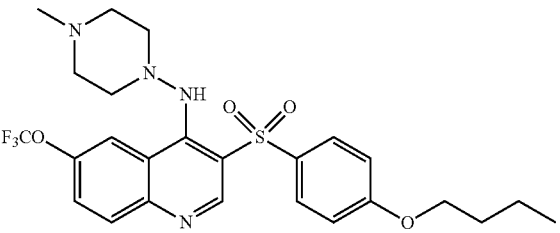 [SMILES: CCCCOc1ccc(S(=O)(=O)c2cnc3ccc(OC(F)(F)F)cc3c2NN2CCN(C)CC2)cc1] | 3-((4-butoxyphenyl)sulfonyl)-N-(4-methylpiperazin-1-yl)-6-(trifluoromethoxy)quinolin-4-amine |
| 93 | 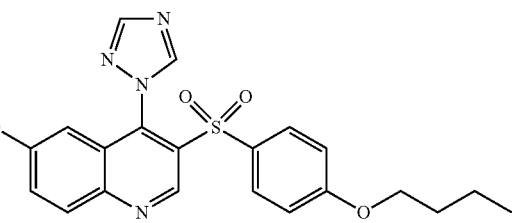 | 3-((4-butoxyphenyl)sulfonyl)-4-(1H-1,2,4-triazol-1-yl)-6-(trifluoromethoxy)quinoline |
| 94 | 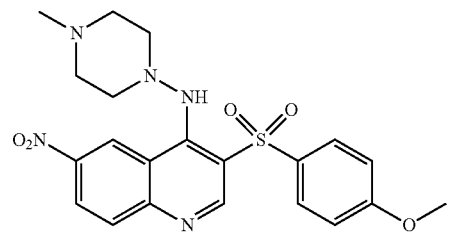 | 3-((4-methoxyphenyl)sulfonyl)-N-(4-methylpiperazin-1-yl)-6-nitroquinolin-4-amine |

-continued

| | | |
|---|---|---|
| 95 | 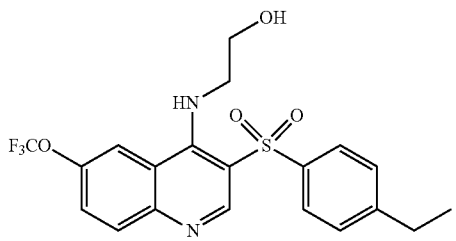 [SMILES: CCc1ccc(S(=O)(=O)c2cnc3ccc(OC(F)(F)F)cc3c2NCCO)cc1] | 2-((3-((4-ethylphenyl)sulfonyl)-6-(trifluoromethoxy)quinolin-4-yl)amino)ethan-1-ol |
| 96 | 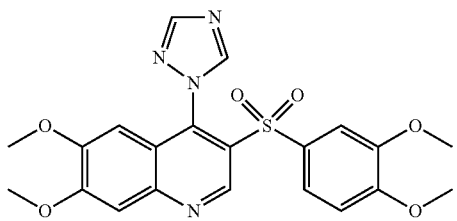 | 3-((3,4-dimethoxyphenyl)sulfonyl)-6,7-dimethoxy-4-(1H-1,2,4-triazol-1-yl)quinoline |
| 97 | 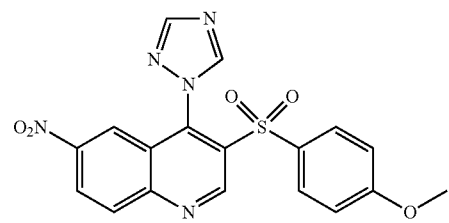 [SMILES: COc1ccc(S(=O)(=O)c2cnc3ccc([N+](=O)[O-])cc3c2-n2cncn2)cc1] | 3-((4-methoxyphenyl)sulfonyl)-6-nitro-4-(1H-1,2,4-triazol-1-yl)quinoline |
| 98 | 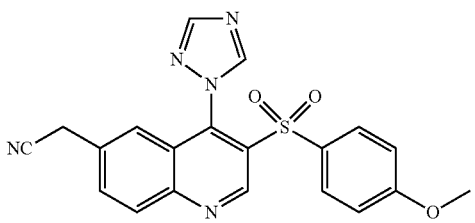 | 2-(3-((4-methoxyphenyl)sulfonyl)-4-(1H-1,2,4-triazol-1-yl)quinolin-6-yl)acetonitrile |
| 99 | 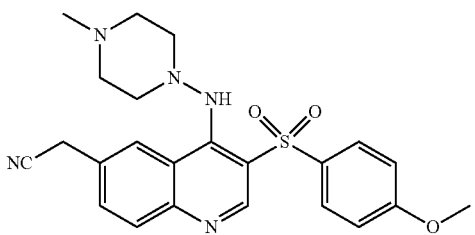 [SMILES: COc1ccc(S(=O)(=O)c2cnc3ccc(CC#N)cc3c2NN2CCN(C)CC2)cc1] | 2-(3-((4-methoxyphenyl)sulfonyl)-4-((4-methylpiperazin-1-yl)amino)quinolin-6-yl)acetonitrile |
| 100 | 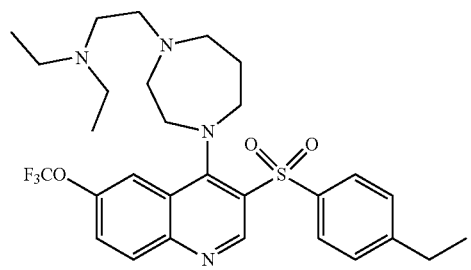 [SMILES: CCc1ccc(S(=O)(=O)c2cnc3ccc(OC(F)(F)F)cc3c2N2CCCN(CCN(CC)CC)CC2)cc1] | N,N-diethyl1-2-(4-(3-((4-ethylphenyl)sulfonyl)-6-(trifluoromethoxy)quinolin-4-yl)-1,4-diazepan-1-yl)ethan-1-amine |

-continued

| | | |
|---|---|---|
| 101 | 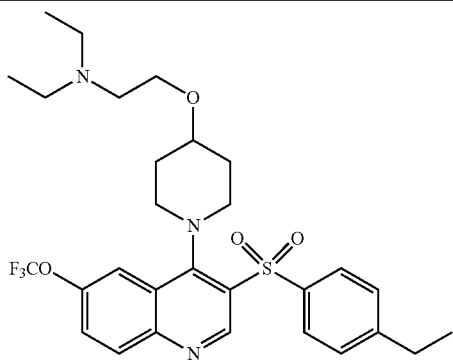 | N,N-diethyl)l-2-((1-(3-((4-ethylphenyl)sulfonyl)-6-(trifluoromethoxy)quinolin-4-yl)piperidin-4-yl)oxy)ethan-1-amine |
| 102 | 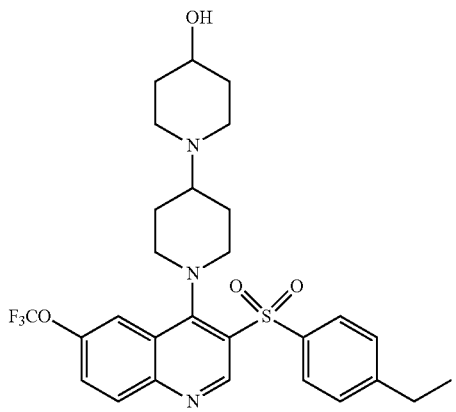 | 1'-(3-((4-ethylphenyl)sulfonyl)-6-(trifluoromethoxy)quinolin-4-yl-[1,4'-bipiperidin]-4-ol |
| 103 | 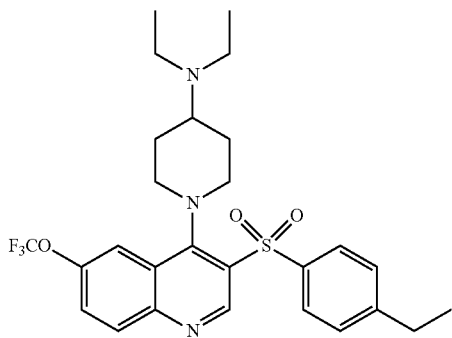 [SMILES: CCc1ccc(S(=O)(=O)c2cnc3ccc(OC(F)(F)F)cc3c2N2CCC(N(CC)CC)CC2)cc1] | N,N-diethyl)l-1-(3-((4-ethylphenyl)sulfonyl-6-(trifluoromethoxy)quinolin-4-yl)piperidin-4-amine |
| 104 | 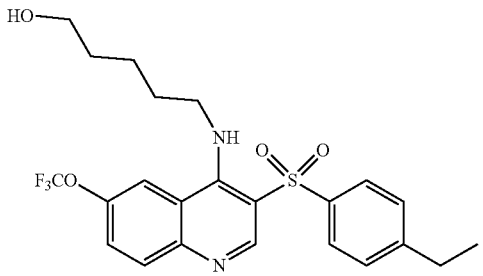 [SMILES: CCc1ccc(S(=O)(=O)c2cnc3ccc(OC(F)(F)F)cc3c2NCCCCCO)cc1] | 5-((3-((4-ethylphenyl)sulfonyl)-6-(trifluoromethoxy)quinolin-4-yl)amino)pentan-1-ol |
| 105 | 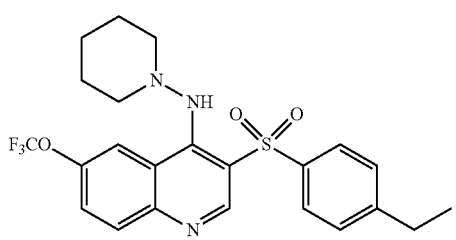 | 3-((4-ethylphenyl)sulfonyl)-N-(piperidin-1-yl)-6-(trifluoromethoxy)quinolin-4-amine |

-continued

| | | |
|---|---|---|
| 106 | 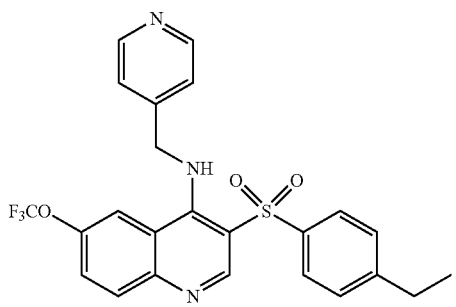 [SMILES: CCc1ccc(S(=O)(=O)c2cnc3ccc(OC(F)(F)F)cc3c2NCc2ccncc2)cc1] | 3-((4-ethylphenyl)sulfonyl)-N-(pyridin-4-ylmethyl)-6-(trifluoromethoxy)quinolin-4-amine |
| 107 | 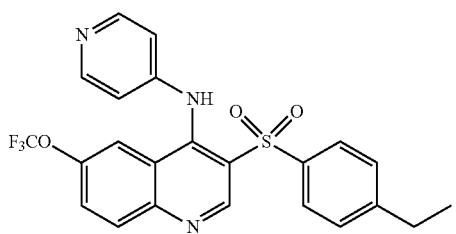 [SMILES: CCc1ccc(S(=O)(=O)c2cnc3ccc(OC(F)(F)F)cc3c2Nc2ccncc2)cc1] | 3-((4-ethylphenyl)sulfonyl)-N-(pyridin-4-yl)-6-(trifluoromethoxy)quinolin-4-amine |
| 108 | 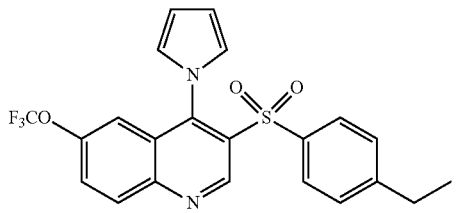 [SMILES: CCc1ccc(S(=O)(=O)c2cnc3ccc(OC(F)(F)F)cc3c2-n2cccc2)cc1] | 3-((4-ethylphenyl)sulfonyl)-4-(1H-pyrrole-1-yl)-6-(trifluoromethoxy)quinoline |
| 109 | 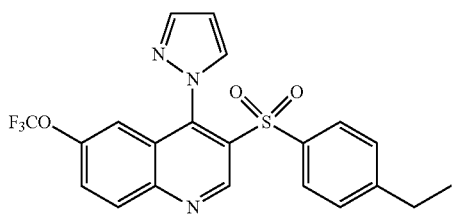 [SMILES: CCc1ccc(S(=O)(=O)c2cnc3ccc(OC(F)(F)F)cc3c2-n2cccn2)cc1] | 3-((4-ethylphenyl)sulfonyl)-4-(1H-pylazol-1-yl)-6-(trifluoromethoxy)quinoline |
| 110 | 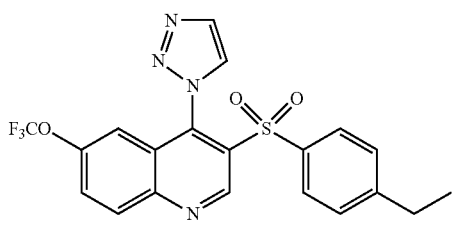 [SMILES: CCc1ccc(S(=O)(=O)c2cnc3ccc(OC(F)(F)F)cc3c2-n2ccnn2)cc1] | 3-((4-ethylphenyl)sulfonyl)-4-(1H-1,2,3-triazol-1-yl)-6-(trifluoromethoxy)quinoline |
| 111 | 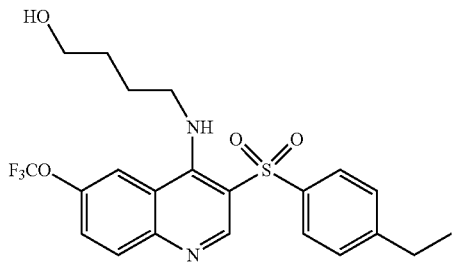 [SMILES: CCc1ccc(S(=O)(=O)c2cnc3ccc(OC(F)(F)F)cc3c2NCCCCO)cc1] | 4-((3-((4-ethylphenyl)sulfonyl)-6-(trifluoromethoxy)quinolin-4-yl)amino)butan-1-ol |

| | | |
|---|---|---|
| 112 | 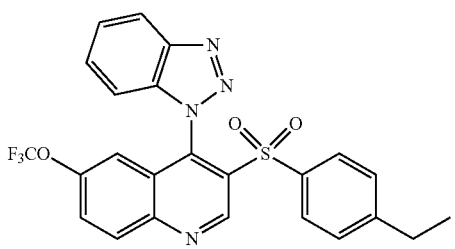 [SMILES: CCc1ccc(S(=O)(=O)c2cnc3ccc(OC(F)(F)F)cc3c2-n2nnc3ccccc32)cc1] | 4-(1H-benzo[d][1,2,3]triazol-1-yl)-3-((4-ethylphenyl)sulfonyl)-6-(trifluoromethoxy)quinoline |
| 113 | 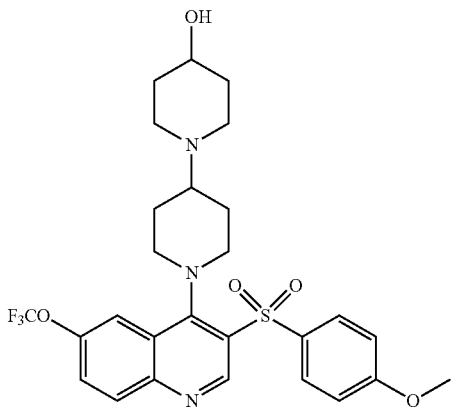 [SMILES: COc1ccc(S(=O)(=O)c2cnc3ccc(OC(F)(F)F)cc3c2N2CCC(N3CCC(O)CC3)CC2)cc1] | 1'-(3-((4-methoxyphenyl)sulfonyl)-6-(trifluoromethoxy)quinolin-4-yl-[1,4'-bipiperidin]-4-ol |
| 114 | 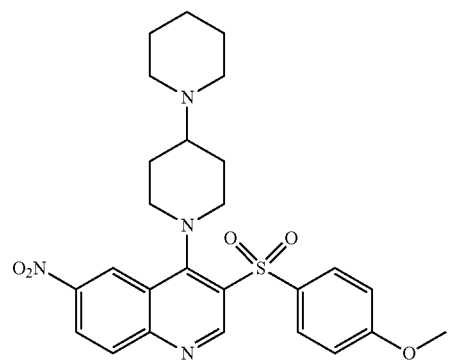 [SMILES: COc1ccc(S(=O)(=O)c2cnc3ccc([N+](=O)[O-])cc3c2N2CCC(N3CCCCC3)CC2)cc1] | 4-([1,4'-bipiperidin]-1'-yl)-3-((4-methoxyphenyl)sulfonyl)-6-nitroquinoline |
| 115 | 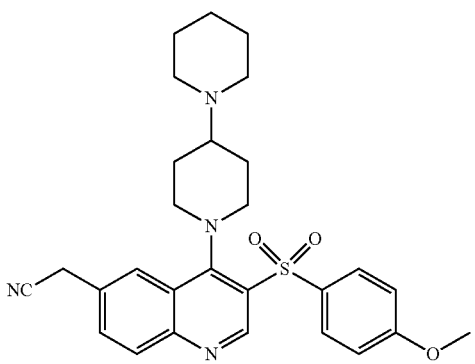 | 2-(4-([1,4'-bipiperidin]-1yl)-3-((4-methoxyphenyl)sulfonyl)quinolin-6-yl)acetonitrile |

| | | |
|---|---|---|
| 116 | 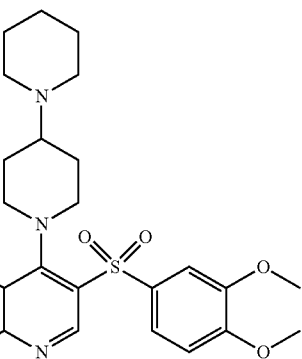 | 4-([1,4'-bipiperidin]-1'-yl)-6-butoxy-3-((3,4-dimethoxyphenyl)sulfonyl)quinoline |
| 117 | 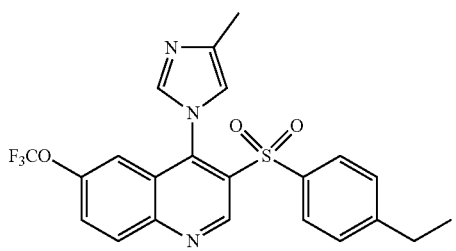 [SMILES: CCc1ccc(S(=O)(=O)c2cnc3ccc(OC(F)(F)F)cc3c2-n2cnc(C)c2)cc1] | 3-((4-ethylphenyl)sulfonyl)-4-(4-methyl-1H-imidazol-1-yl)-6-(trifluoromethoxy)quinoline |
| 118 | 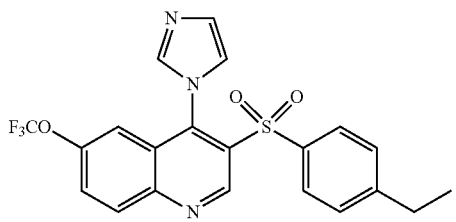 | 3-((4-ethylphenyl)sulfonyl)-4-(1H-imidazol-1-yl)-6-(trifluoromethoxy)quinoline |
| 119 | 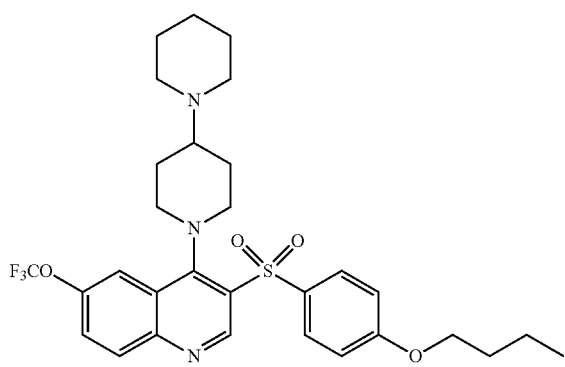 [SMILES: CCCCOc1ccc(S(=O)(=O)c2cnc3ccc(OC(F)(F)F)cc3c2N2CCC(N3CCCCC3)CC2)cc1] | 4-([1,4'-bipiperidin]-1'-yl)-3-((4-butoxyphenyl)sulfonyl)-6-(trifluoromethoxy)quinoline |
| 120 | 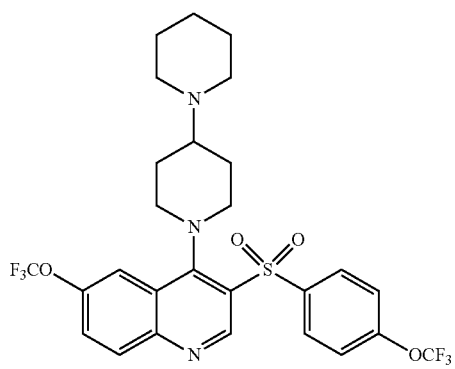 [SMILES: O=S(=O)(c1ccc(OC(F)(F)F)cc1)c1cnc2ccc(OC(F)(F)F)cc2c1N1CCC(N2CCCCC2)CC1] | 4-([1,4'-bipiperidin]-1'-yl)-6-(trifluoromethoxy)-3-((4-(trifluoromethoxy)phenyl)sulfonyl)quinoline |

-continued

| | | |
|---|---|---|
| 121 | 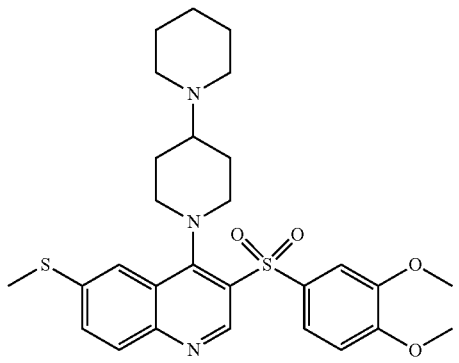 | 4-([1,4'-bipiperidin]-1'-yl)-3-((3,4-dimethoxyphenyl)sulfonyl)-6-(methylthio)quinoline |
| 122 | 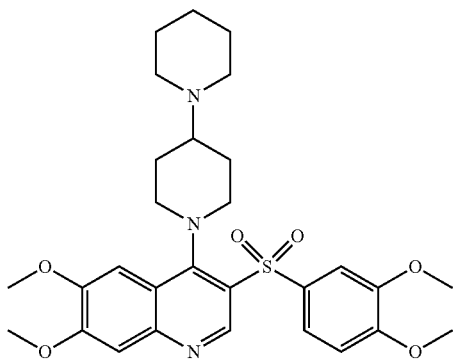 | 4-([1,4'-bipiperidin]-1'-yl)-3-((3,4-dimethoxyphenyl)sulfonyl)-6,7-dimethoxyquinoline |
| 123 | 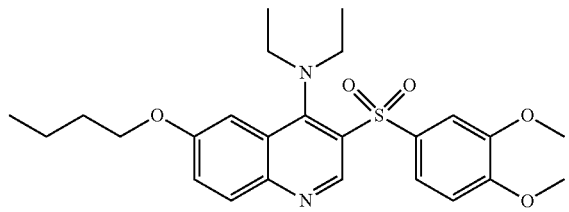 [SMILES: CCCCOc1ccc2ncc(S(=O)(=O)c3ccc(OC)c(OC)c3)c(N(CC)CC)c2c1] | 6-butoxy-3-((3,4-dimethoxyphenyl)sulfonyl)-N,N-diethyl)lquinolin-4-amine |
| 124 | 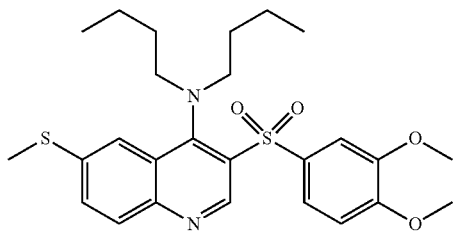 | N,N-dibutyl-3-((3,4-dimethoxyphenyl)sulfonyl)-6-(methythio)quinolin-4-amine |
| 125 | 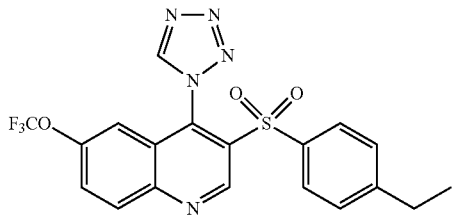 | 3-((4-ethylphenyl)sulfonyl)-4-(1H-tetrazol-1-yl)-6-(trifluorotmethoxy)quinoline |
| 126 | 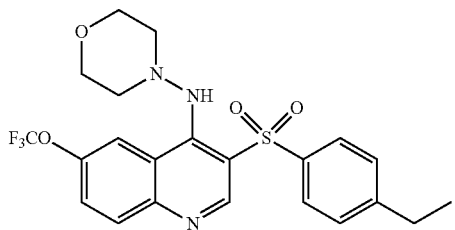 | N-(3-((4-ethylphenyl)sulfonyl)-6-(trifluoromethoxy)quinolin-4-yl)morpholin-4-amine |

| | | |
|---|---|---|
| 127 | 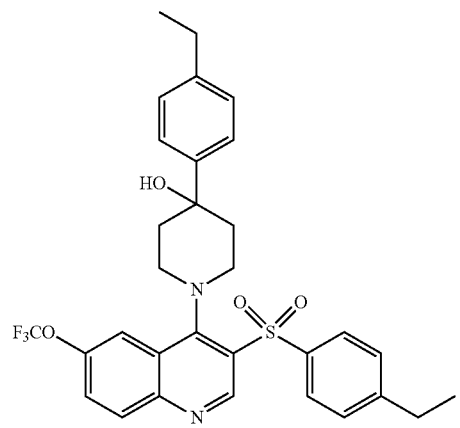 | 4-(4-ethylphenyl)-1-(3-((4-ethylphenyl)sulfonyl)-6-(trifluoromethoxy)quinolin-4-yl)piperidin-4-ol |
| 128 | 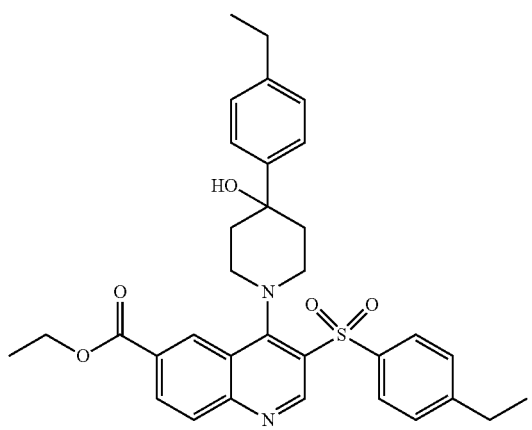 [SMILES: CCOC(=O)c1ccc2ncc(S(=O)(=O)c3ccc(CC)cc3)c(N3CCC(O)(c4ccc(CC)cc4)CC3)c2c1] | ethyl 4-(4-(4-ethylphenyl)-4-hydroxypiperidin-1-yl)-3-((4-ethylphenyl)sulfonyl)quinoline-6-carboxylate |
| 129 | 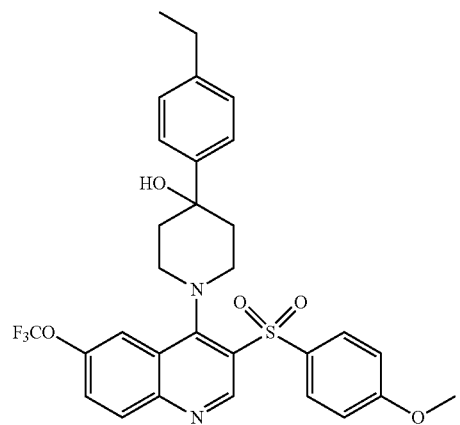 | 4-(4-ethylphenyl)-1-(3-((4-methoxyphenyl)sulfonyl)-6-(trifluoromethoxy)quinolin-4-yl)piperidin-4-ol |

| | | |
|---|---|---|
| 130 | 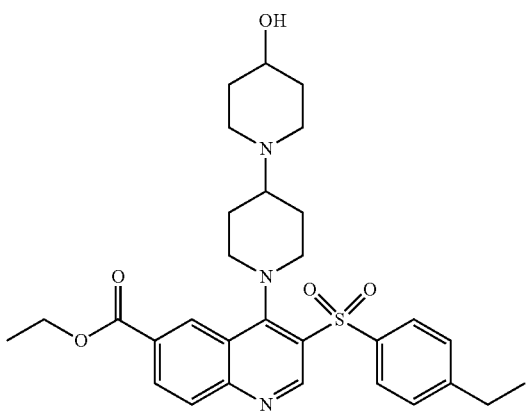 | ethyl 3-((4-ethylphenyl)sulfonyl)-4-(4-hydroxy-[1,4'-bipiperidin]-1'-yl)quinoline-6-carboxylate |
| 131 | 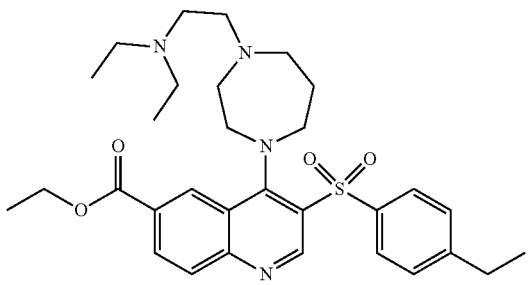 | ethyl 4-(4-(2-(diethyl)lamino)ethyl)-1,4-diazepan-1-yl)-3-((4-ethylphenyl)sulfonyl)quinoline-6-carboxylate |
| 132 | 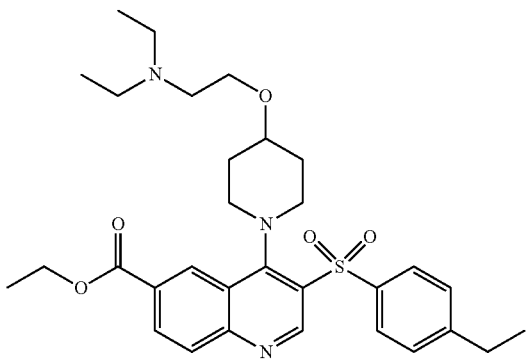 | ethyl 4-(4-(2-(diethyl)laminotethoxy)piperidin-1-yl)-3-((4-ethylphenyl)sulfonyl)quinoline-6-carboxylate |
| 133 | 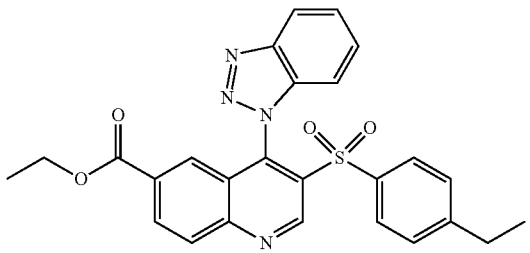 [SMILES: CCOC(=O)c1ccc2ncc(S(=O)(=O)c3ccc(CC)cc3)c(-n3nnc4ccccc43)c2c1] | ethyl 4-(1H-benzo[d][1,2,3]triazol-1-yl)-3-((4-ethylphenyl)sulfonyl)quinoline-6-carboxylate |
| 134 | 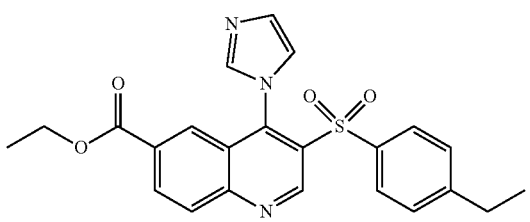 [SMILES: CCOC(=O)c1ccc2ncc(S(=O)(=O)c3ccc(CC)cc3)c(-n3ccnc3)c2c1] | ethyl 3-((4-ethylphenyl)sulfonyl)-4-(1H-imidazol-1-yl)quinoline-6-carboxylate |

-continued

| 135 | 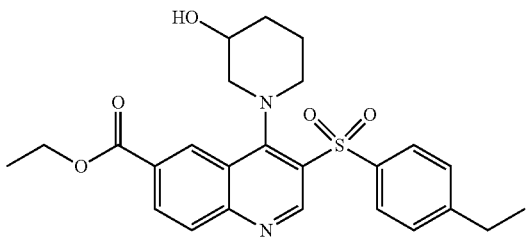 | ethyl 3-((4-ethylphenyl)sulfonyl)-4-(3-hydroxypiperidin-1-yl)quinoline-6-carboxylate |
| 136 | 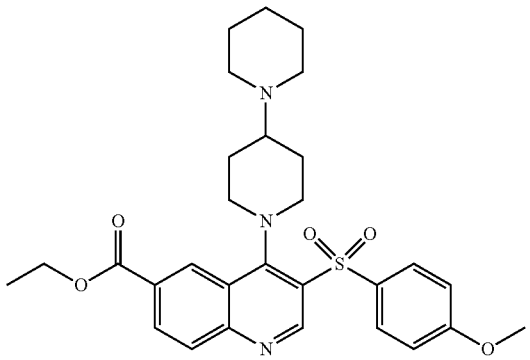 [SMILES: CCOC(=O)c1ccc2ncc(S(=O)(=O)c3ccc(OC)cc3)c(N3CCC(N4CCCCC4)CC3)c2c1] | ethyl 4-([1,4'-bipiperidin]-1'-yl)-3-((4-methoxyphenyl)sulfonyl)quinoline-6-carboxylate |
| 137 | 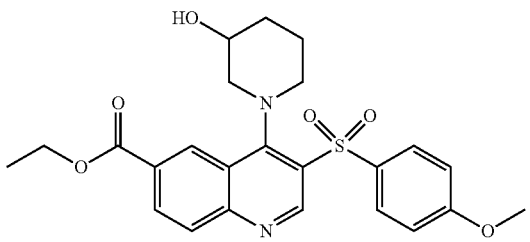 [SMILES: CCOC(=O)c1ccc2ncc(S(=O)(=O)c3ccc(OC)cc3)c(N3CCCC(O)C3)c2c1] | ethyl 4-(3-hydroxypiperidin-1-yl)-3-((4-methoxyphenyl)sulfonyl)quinoline-6-carboxylate |
| 138 | 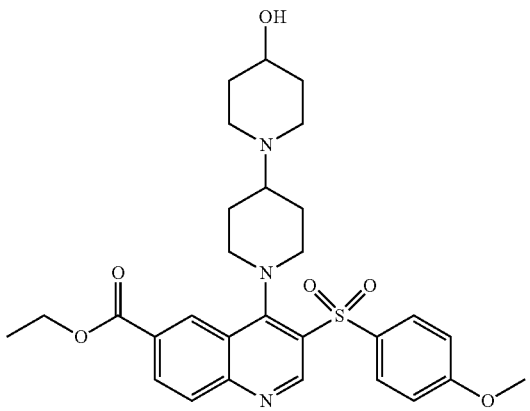 [SMILES: CCOC(=O)c1ccc2ncc(S(=O)(=O)c3ccc(OC)cc3)c(N3CCC(N4CCC(O)CC4)CC3)c2c1] | ethyl 4-(4-hydroxy-[1,4'-bipiperidin]-1'-yl-3-((4-methoxyphenyl)sulfonyl)quinoline-6-carboxylate |
| 139 | 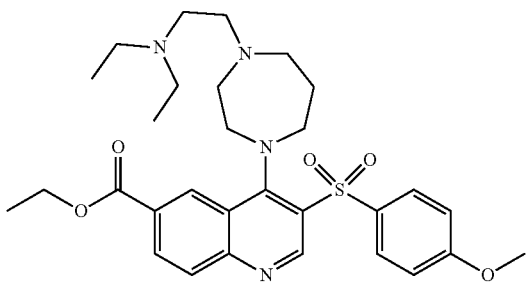 [SMILES: CCOC(=O)c1ccc2ncc(S(=O)(=O)c3ccc(OC)cc3)c(N3CCCN(CCN(CC)CC)CC3)c2c1] | ethyl 4-(4-(2-(diethyl)amino)ethyl)-1,4-diazepan-1-yl)-3-((4-methoxyphenyl)sulfonyl)quinoline-6-carboxylate |

| | | |
|---|---|---|
| 140 | 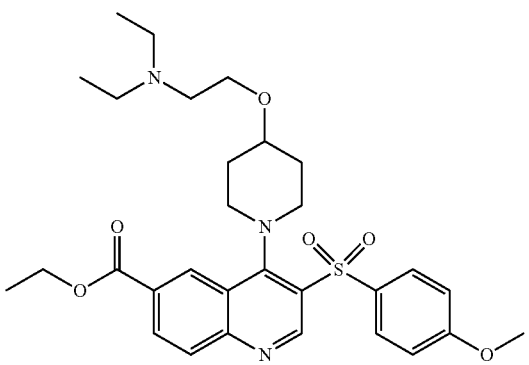 [SMILES: CCOC(=O)c1ccc2ncc(S(=O)(=O)c3ccc(OC)cc3)c(N3CCC(OCCN(CC)CC)CC3)c2c1] | ethyl 4-(4-(2-(diethyl)amino)ethoxy)piperidin-1-yl)-3-((4-methoxyphenyl)sulfonyl)quinoline-6-carboxylate |
| 141 | 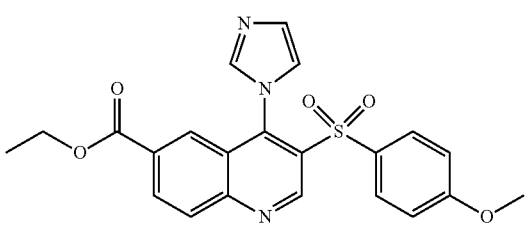 [SMILES: CCOC(=O)c1ccc2ncc(S(=O)(=O)c3ccc(OC)cc3)c(-n3ccnc3)c2c1] | ethyl 4-(1H-imidazol-1-yl)-3-((4-methoxyphenyl)sulfonyl)quinoline-6-carboxylate |
| 142 | 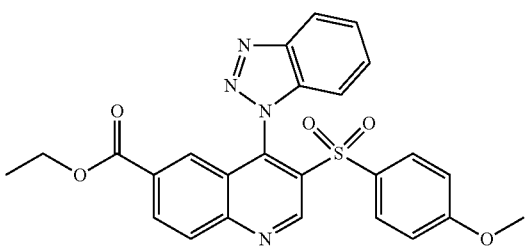 [SMILES: CCOC(=O)c1ccc2ncc(S(=O)(=O)c3ccc(OC)cc3)c(-n3nnc4ccccc43)c2c1] | ethyl 4-(1H-benzo[d][1,2,3]triazol-1-yl)-3-((4-methoxyphenyl)sulfonyl)quinoline-6-carboxylate |
| 143 | 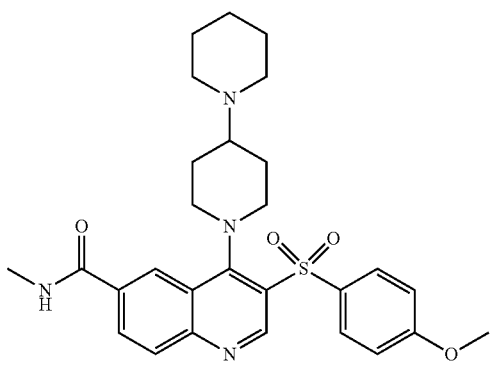 | 4-([1,4'-bipiperidin]-1'-yl)-3-((4-methoxyphenyl)sulfonyl-N-methyl)quinoline-6-carboxamide |
| 144 | 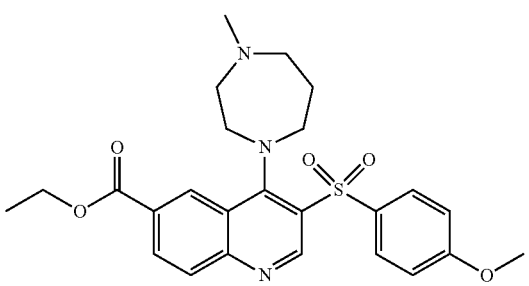 [SMILES: CCOC(=O)c1ccc2ncc(S(=O)(=O)c3ccc(OC)cc3)c(N3CCCN(C)CC3)c2c1] | ethyl 3-((4-methoxyphenyl)sulfonyl)-4-(4-methyl-1,4-diazepan-1-yl)quinoline-6-carboxylate |

-continued
| | | |
|---|---|---|
| 145 | 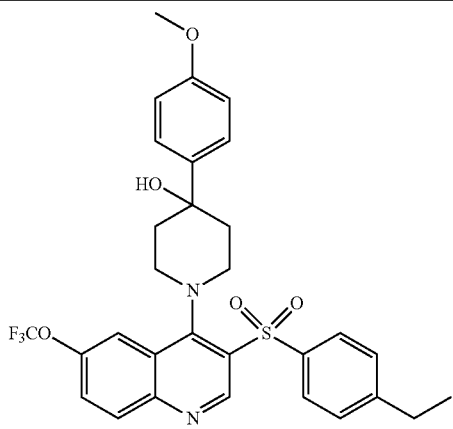 | 1-(3-((4-ethylphenyl)sulfonyl)-6-(trifluoromethoxy)quinolin-4-yl)-4-(4-methoxyphenyl)piperidin-4-ol |
| 146 | 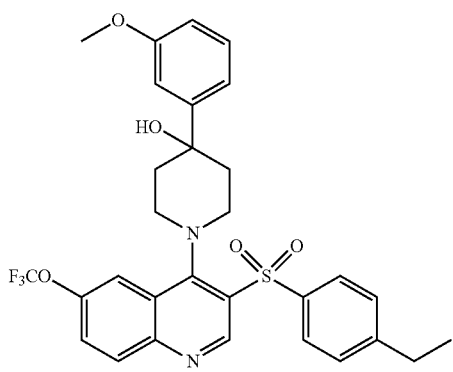 | 1-(3-((4-ethylphenyl)sulfonyl)-6-(trifluoromethoxy)quinolin-4-yl)-4-(3-methoxyphenyl)piperidin-4-ol |
| 147 | 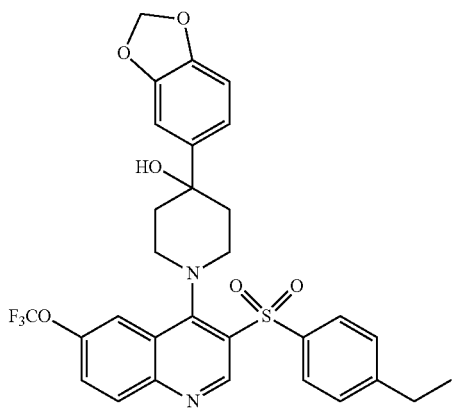 [SMILES: CCc1ccc(S(=O)(=O)c2cnc3ccc(OC(F)(F)F)cc3c2N2CCC(O)(c3ccc4c(c3)OCO4)CC2)cc1] | 4-(benzo[d][1,3]dioxol-5-yl)-1-(3-((4-ethylphenyl)sulfonyl)-6-(trifluoromethoxy)quinolin-4-yl)piperidin-4-ol |
| 148 | 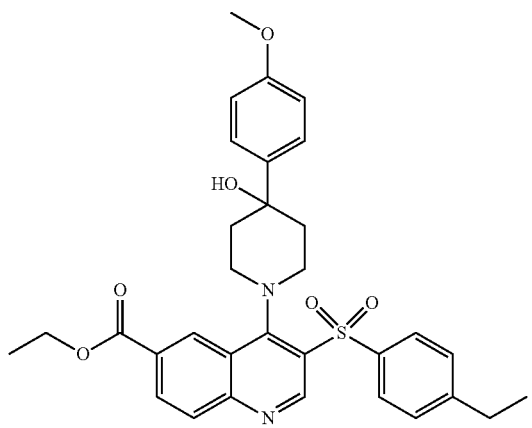 | ethyl 3-((4-ethylphenyl)sulfonyl)-4-(4-hydroxy-4-(4-methoxyphenylpiperidin-1-yl)quinoline-6-carboxylate |

| | | |
|---|---|---|
| 149 | 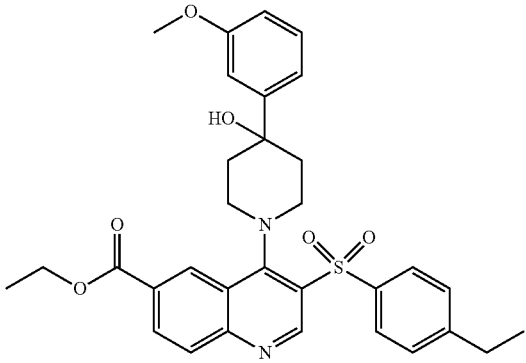 [SMILES: CCOC(=O)c1ccc2ncc(S(=O)(=O)c3ccc(CC)cc3)c(N3CCC(O)(c4cccc(OC)c4)CC3)c2c1] | ethyl 3-((4-ethylphenyl)sulfonyl-4-(4-hydroxy-4-(3-methoxyphenyl)piperidin-1-yl)quinoline-6-carboxylate |
| 150 | 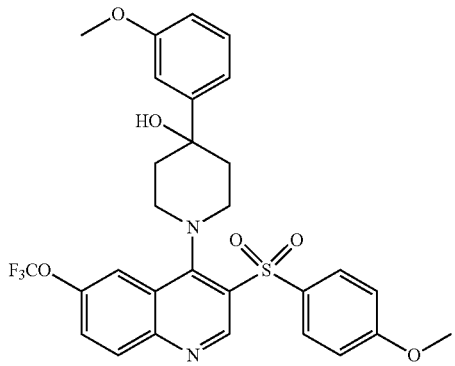 | 4-(3-methoxyphenyl)-1-(3-((4-methoxyphenyl)sulfonyl)-6-(trifluoromethoxy)quinolin-4-yl)piperidin-4-ol |
| 151 | 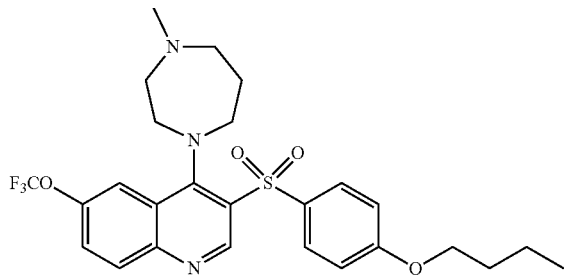 [SMILES: CCCCOc1ccc(S(=O)(=O)c2cnc3ccc(OC(F)(F)F)cc3c2N2CCCN(C)CC2)cc1] | 3-((4-butoxyphenyl)sulfonyl)-4-(4-methyl-1,4-diazepan-1-yl)-6-(trifluoromethoxy)quinoline |
| 152 | 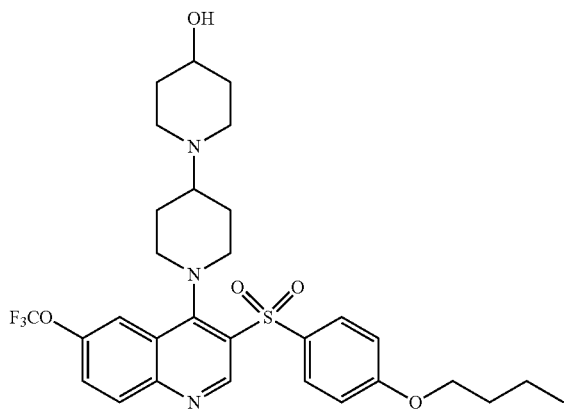 [SMILES: CCCCOc1ccc(S(=O)(=O)c2cnc3ccc(OC(F)(F)F)cc3c2N2CCC(N3CCC(O)CC3)CC2)cc1] | 1'-(3-((4-butoxyphenyl)sulfonyl)-6-(trifluoromethoxy)quinolin-4-yl)-[1,4'-bipiperidin]-4-ol |

| | | |
|---|---|---|
| 153 | 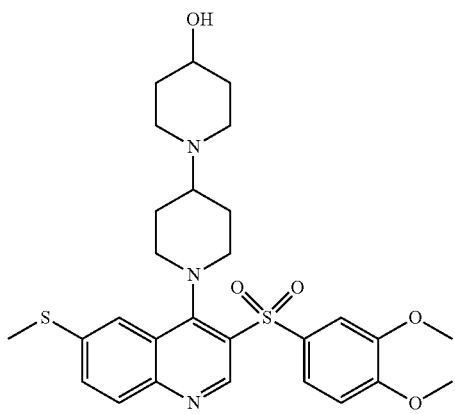 | 1'-(3-((3,4-dimethoxyphenyl)sulfonyl)-6-(methylthio)quinolin-4-yl)-[1,4'-bipiperidin]-4-ol |
| 154 | 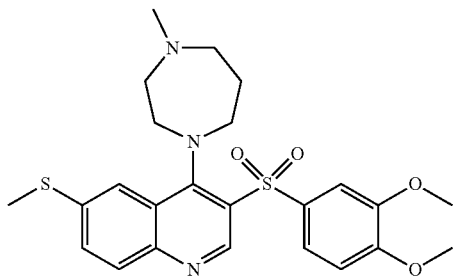 | 3-((3,4-dimethoxyphenyl)sulfonyl)-4-(4-methyl-1,4-diazepan-1-yl)-6-(methylthio)quinoline |
| 155 | 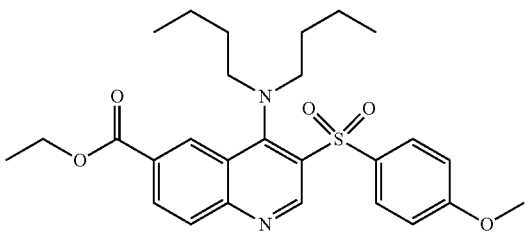 [SMILES: CCCCN(CCCC)c1c(S(=O)(=O)c2ccc(OC)cc2)cnc2ccc(C(=O)OCC)cc12] | ethyl 4-(dibutylamino)-3-((4-methoxyphenyl)sulfonyl)quinoline-6-carboxylate |
| 156 | 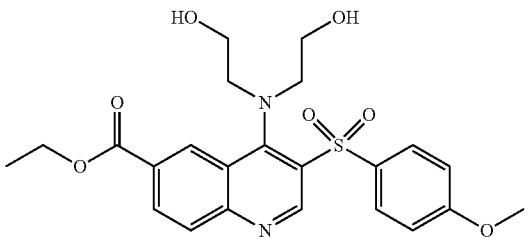 [SMILES: CCOC(=O)c1ccc2ncc(S(=O)(=O)c3ccc(OC)cc3)c(N(CCO)CCO)c2c1] | ethyl 4-(bis(2-hydroxyethyl)amino)-3-((4-methoxyphenyl)sulfonyl)quinoline-6-carboxylate |
| 157 | 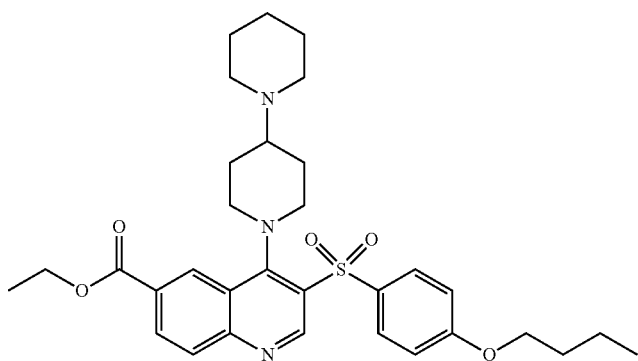 [SMILES: CCCCOc1ccc(S(=O)(=O)c2cnc3ccc(C(=O)OCC)cc3c2N2CCC(N3CCCCC3)CC2)cc1] | ethyl 4-([1,4'-bipiperidin]-1'-yl)-3-((4-butoxyphenyl)sulfonyl)quinoline-6-carboxylate |

-continued
| | | |
|---|---|---|
| 158 | 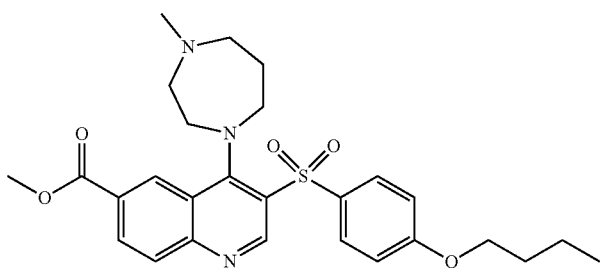 [SMILES: CCCCOc1ccc(S(=O)(=O)c2cnc3ccc(C(=O)OC)cc3c2N2CCCN(C)CC2)cc1] | ethyl 3-((4-butoxyphenyl)sulfonyl)-4-(4-methyl-1,4-diazepan-1-yl)quinoline-6-carboxylate |
| 159 | 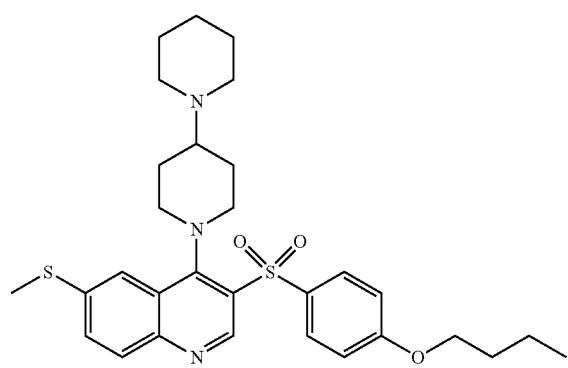 | 4-([1,4'-bipiperidin]-1'-yl)-3-((4-butoxyphenyl)sulfonyl)-6-(methylthio)quinoline |
| 160 | 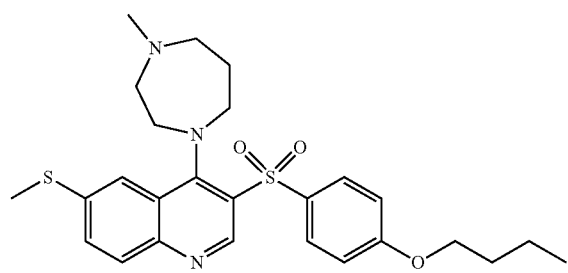 [SMILES: CCCCOc1ccc(S(=O)(=O)c2cnc3ccc(SC)cc3c2N2CCCN(C)CC2)cc1] | 3-((4-butoxyphenyl)sulfonyl)-4-(4-methyl-1,4-diazepan-1-yl)-6-(methylthio)quinoline |
| 161 | 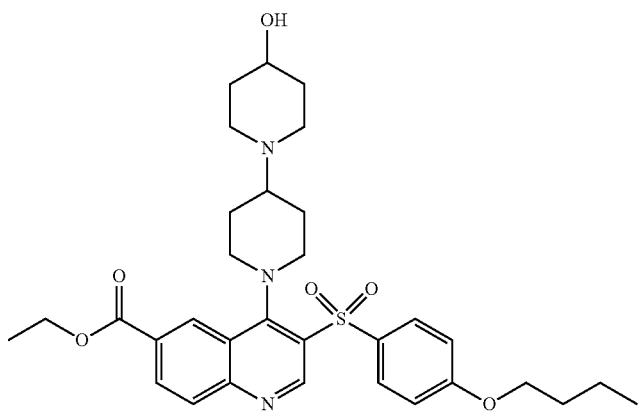 [SMILES: CCCCOc1ccc(S(=O)(=O)c2cnc3ccc(C(=O)OCC)cc3c2N2CCC(N3CCC(O)CC3)CC2)cc1] | ethyl 3-((4-butoxyphenyl)sulfonyl)-4-(4-hydroxy-[1,4'-bipiperidin]-1'-yl)quinoline-6-carboxylate |

| | | |
|---|---|---|
| 162 | 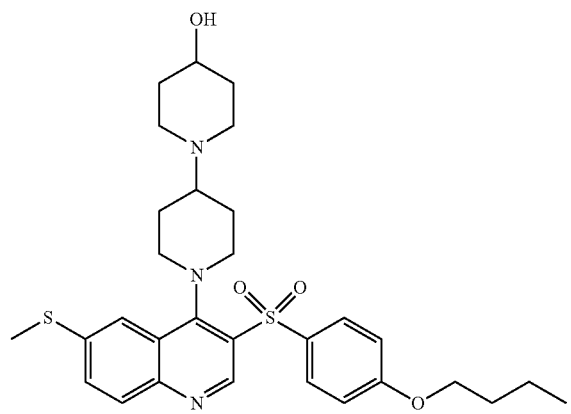 [SMILES: CCCCOc1ccc(S(=O)(=O)c2cnc3ccc(SC)cc3c2N2CCC(N3CCC(O)CC3)CC2)cc1] | 1'-(3-((4-butoxyphenyl)sulfonyl-6-(methylthio)quinolin-4-yl)-[1,4'-bipiperidin]-4-ol |
| 163 | 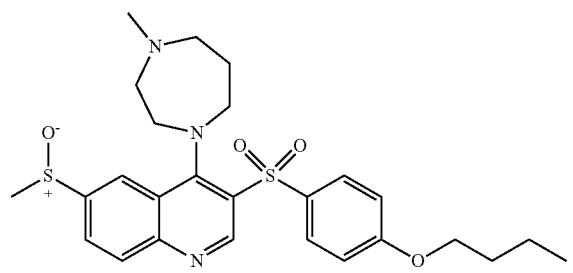 | 3-((4-butoxyphenyl)sulfonyl)-4-(4-methyl-1,4-diazepan-1-yl)-6-(methylsulfinyl)quinoline |
| 164 | 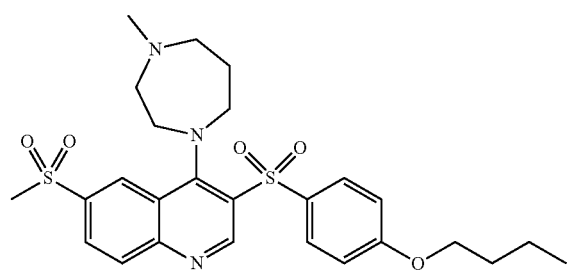 [SMILES: CCCCOc1ccc(S(=O)(=O)c2cnc3ccc(S(C)(=O)=O)cc3c2N2CCCN(C)CC2)cc1] | 3-((4-butoxyphenyl)sulfonyl)-4-(4-methyl-1,4-diazepan-1-yl)-6-(methylsulfonyl)quinoline |
| 165 | 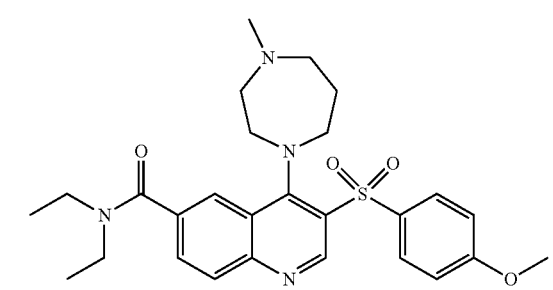 [SMILES: CCN(CC)C(=O)c1ccc2ncc(S(=O)(=O)c3ccc(OC)cc3)c(N3CCCN(C)CC3)c2c1] | N,N-diethyl)l-3-((4-methoxyphenyl)sulfonyl-4-(4-methyl-1,4-diazepan-1-yl)quinoline-6-carboxamide |
| 166 | 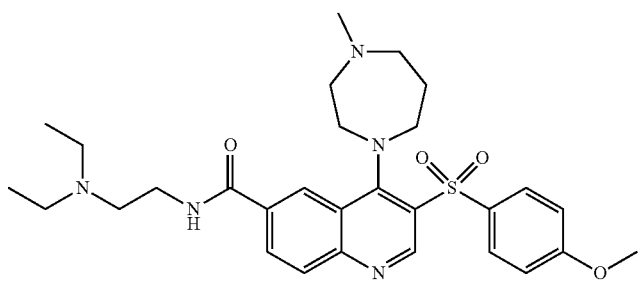 [SMILES: CCN(CC)CCNC(=O)c1ccc2ncc(S(=O)(=O)c3ccc(OC)cc3)c(N3CCCN(C)CC3)c2c1] | N-(2-(diethyl)lamino)ethyl)-3-((4-methoxyphenyl)sulfonyl)-4-(4-methyl-1,4-diazepan-1-yl)quinoline-6-carboxamide |

-continued
| | | |
|---|---|---|
| 167 | 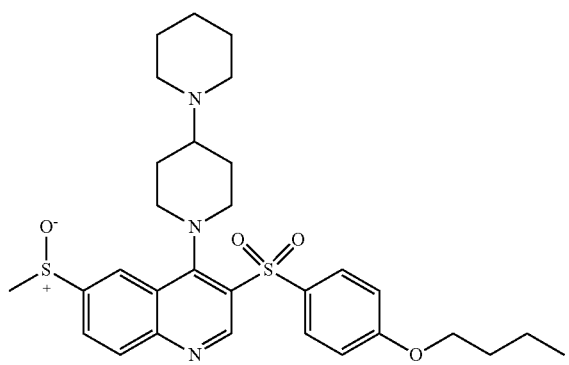 | 4-([1,4'-bipiperidin]-1'-yl)-3-((4-butoxyphenyl)sulfonyl)-6-(methylsulfinyl)quinoline |
| 168 | 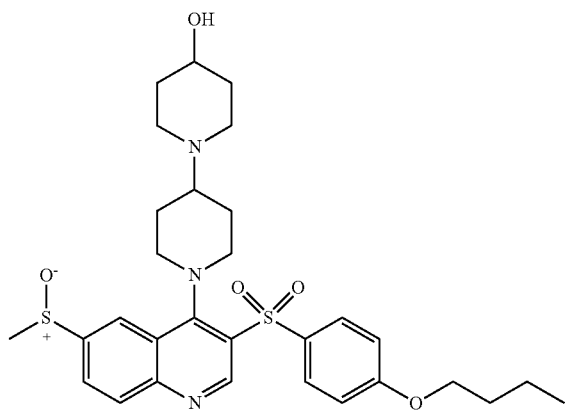 | 1'-(3-((4-butoxyphenyl)sulfonyl)-6-(methylsulfinyl)quinolin-4-yl)-[1,4'-bipiperidin]-4-ol |
| 169 | 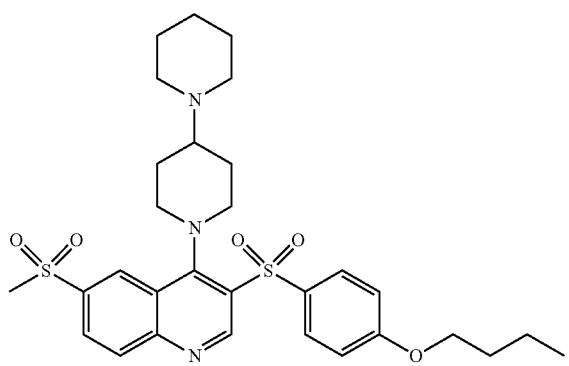 [SMILES: CCCCOc1ccc(S(=O)(=O)c2cnc3ccc(S(C)(=O)=O)cc3c2N2CCC(N3CCCCC3)CC2)cc1] | 4-([1,4'-bipiperidin]-1'-yl)-3-((4-butoxyphenyl)sulfonyl)-6-(methylsulfonyl)quinoline |
| 170 | 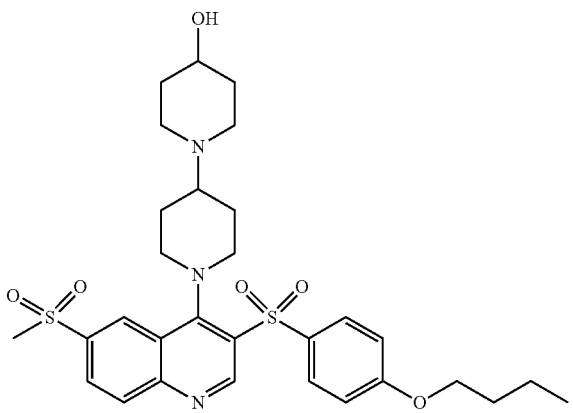 [SMILES: CCCCOc1ccc(S(=O)(=O)c2cnc3ccc(S(C)(=O)=O)cc3c2N2CCC(N3CCC(O)CC3)CC2)cc1] | 1'-(3-((4-butoxyphenyl)sulfonyl)-6-(methylsulfonyl)quinolin-4-yl)-[1,4'-bipiperidin]-4-ol |

| | | |
|---|---|---|
| 171 | 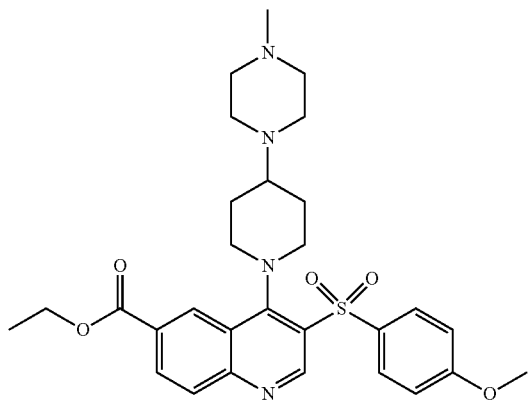 [SMILES: CCOC(=O)c1ccc2ncc(S(=O)(=O)c3ccc(OC)cc3)c(N3CCC(N4CCN(C)CC4)CC3)c2c1] | ethyl 3-((4-methoxyphenyl)sulfonyl)-4-(4-(4-methylpiperazin-1-yl)piperidin-1-yl)quinoline-6-carboxylate |
| 172 | 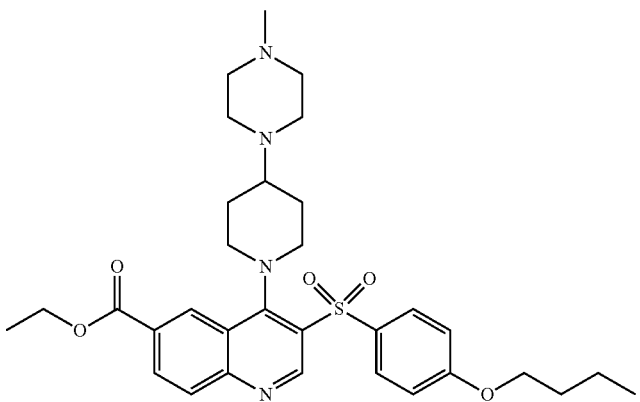 [SMILES: CCCCOc1ccc(S(=O)(=O)c2cnc3ccc(C(=O)OCC)cc3c2N2CCC(N3CCN(C)CC3)CC2)cc1] | ethyl 3-((4-butoxyphenyl)sulfonyl-4-(4-(4-methylpiperazin-1-yl)piperidin-1-yl)quinoline-6-carboxylate |
| 173 | 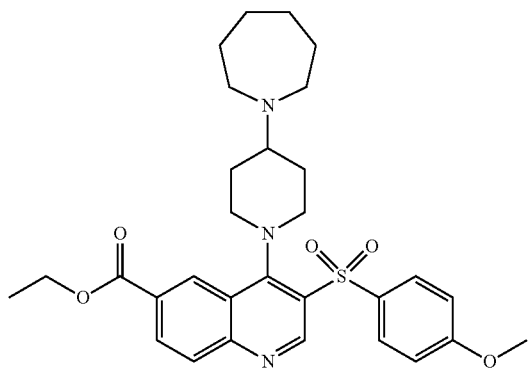 [SMILES: CCOC(=O)c1ccc2ncc(S(=O)(=O)c3ccc(OC)cc3)c(N3CCC(N4CCCCCC4)CC3)c2c1] | ethyl 4-(4-(azepan-1-yl)piperidin-1-yl)-3-((4-ethoxyphenyl)sulfonyl)quinoline-6-carboxylate |
| 174 | 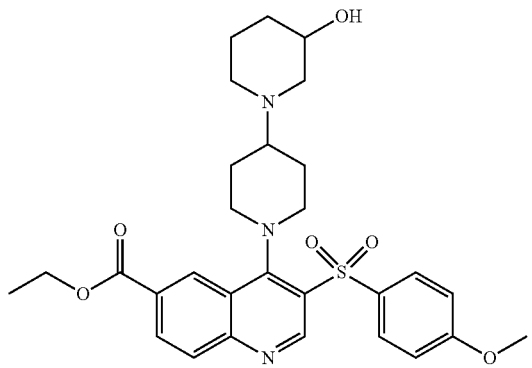 [SMILES: CCOC(=O)c1ccc2ncc(S(=O)(=O)c3ccc(OC)cc3)c(N3CCC(N4CCCC(O)C4)CC3)c2c1] | ethyl 4-(3-hydroxy-[1,4'-bipiperidin]-1'-yl)-3-((4-methoxyphenyl)sulfonyl)quinoline-6-carboxylate |

| | | |
|---|---|---|
| 175 | 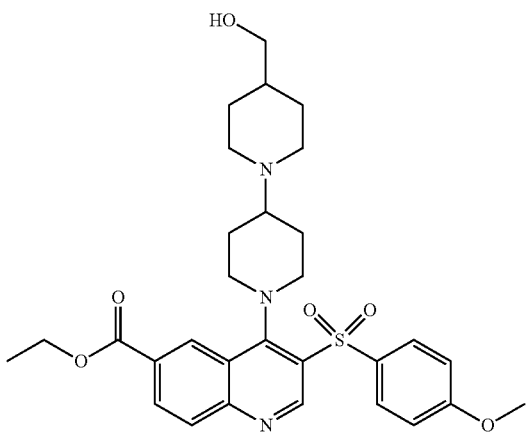 [SMILES: CCOC(=O)c1ccc2ncc(S(=O)(=O)c3ccc(OC)cc3)c(N3CCC(N4CCC(CO)CC4)CC3)c2c1] | ethyl 4-(4-(hydroxymethyl)-[1,4'-bipiperidin]-1'-yl)-3-((4-methoxyphenyl)sulfonyl)quinoline-6-carboxylate |
| 176 | 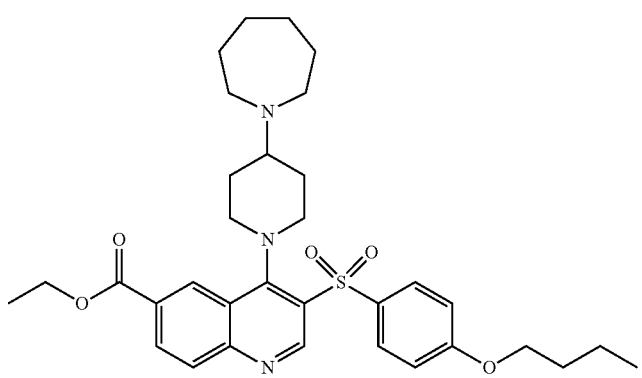 [SMILES: CCCCOc1ccc(S(=O)(=O)c2cnc3ccc(C(=O)OCC)cc3c2N2CCC(N3CCCCCC3)CC2)cc1] | ethyl 4-(4-(azepan-1-yl)piperidin-1-yl)-3-((4-butoxyphenyl)sulfonyl)quinoline-6-carboxylate |
| 177 | 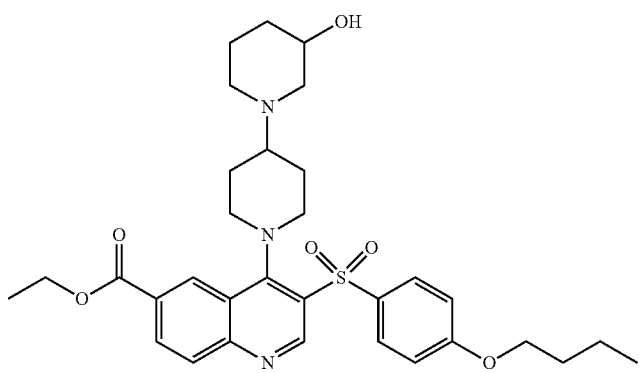 [SMILES: CCCCOc1ccc(S(=O)(=O)c2cnc3ccc(C(=O)OCC)cc3c2N2CCC(N3CCCC(O)C3)CC2)cc1] | ethyl 3-((4-butoxyphenyl)sulfonyl)-4-(3-hydroxy-[1,4'-bipiperidin]-1'-yl)quinoline-6-carboxylate |
| 178 | 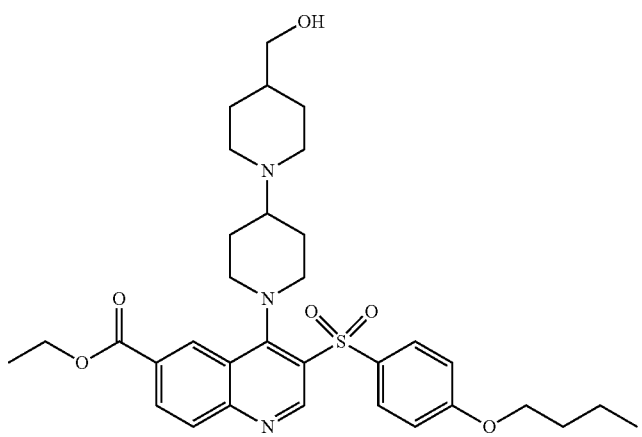 [SMILES: CCCCOc1ccc(S(=O)(=O)c2cnc3ccc(C(=O)OCC)cc3c2N2CCC(N3CCC(CO)CC3)CC2)cc1] | ethyl 3-((4-butoxyphenyl)sulfonyl)-4-(4-(hydroxymethyl)-[1,4'-bipiperidin]-1'-yl)quinoline-6-carboxylate |

| | | |
|---|---|---|
| 179 | 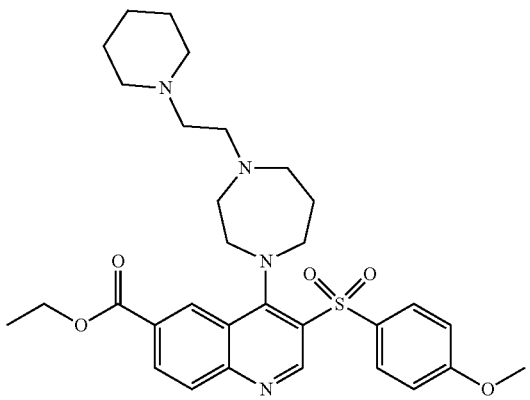 [SMILES: CCOC(=O)c1ccc2ncc(S(=O)(=O)c3ccc(OC)cc3)c(N3CCCN(CCN4CCCCC4)CC3)c2c1] | ethyl 3-((4-methoxyphenyl)sulfonyl)-4-(4-(2-(piperidin-1-yl)ethyl)-1,4-diazepan-1-yl)quinoline-6-carboxylate |
| 180 | 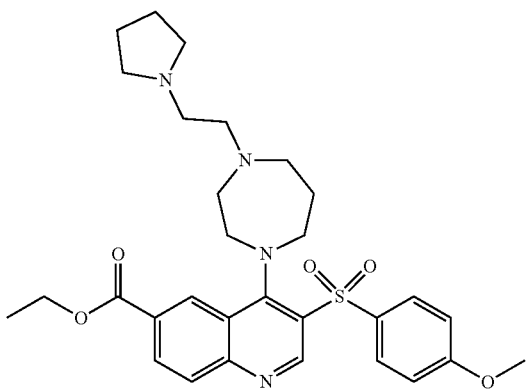 [SMILES: CCOC(=O)c1ccc2ncc(S(=O)(=O)c3ccc(OC)cc3)c(N3CCCN(CCN4CCCC4)CC3)c2c1] | ethyl 3-((4-methoxyphenyl)sulfonyl)-4-(4-(2-(pyrrolidin-1-yl)ethyl)-1,4-diazepan-1-yl)quinoline-6-carboxylate |
| 181 | 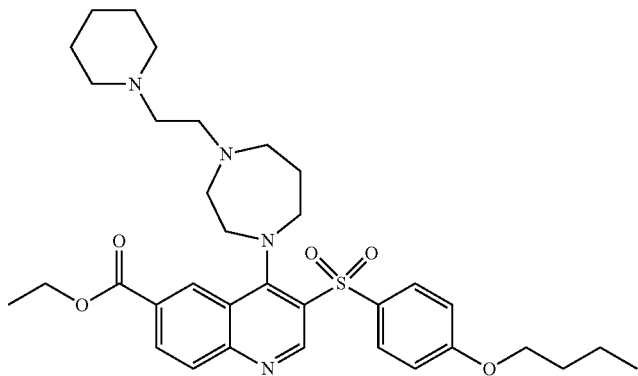 [SMILES: CCCCOc1ccc(S(=O)(=O)c2cnc3ccc(C(=O)OCC)cc3c2N2CCCN(CCN3CCCCC3)CC2)cc1] | ethyl 3-((4-butoxyphenyl)sulfonyl)-4-(4-(2-(piperidin-1-yl)ethyl)-1,4-diazepan-1-yl)quinoline-6-carboxylate |
| 182 | 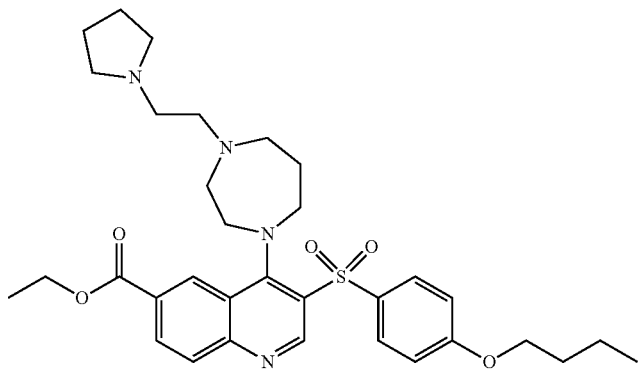 [SMILES: CCCCOc1ccc(S(=O)(=O)c2cnc3ccc(C(=O)OCC)cc3c2N2CCCN(CCN3CCCC3)CC2)cc1] | ethyl 3-((4-butoxyphenyl)sulfonyl)-4-(4-(2-(pyrrolidin-1-yl)ethyl)-1,4-diazepan-1-yl)quinoline-6-carboxylate |

-continued

| | | |
|---|---|---|
| 183 | 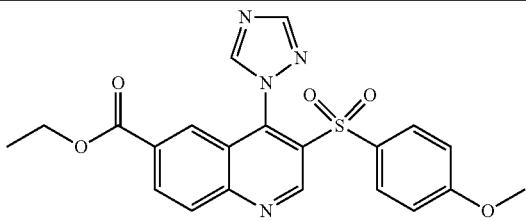 | ethyl 3-((4-methoxyphenyl)sulfonyl)-4-(1H-1,2,4-triazol-1-yl)quinoline-6-carboxylate |
| 184 | 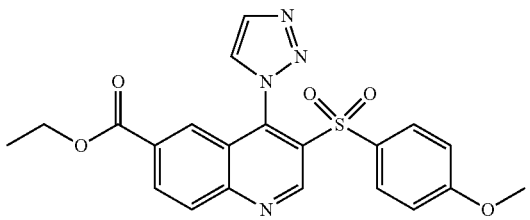 | ethyl 3-((4-methoxyphenyl)sulfonyl)-4-(1H-1,2,3-triazol-1-yl)quinoline-6-carboxylate |
| 185 | 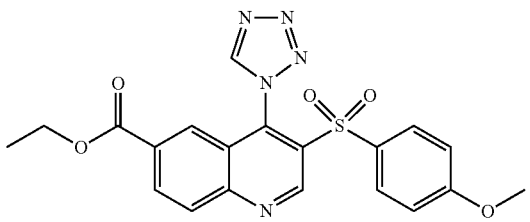 | ethyl 3-((4-methoxyphenyl)sulfonyl)-4-(1H-tetrazol-1-yl)quinoline-6-carboxylate |
| 186 | 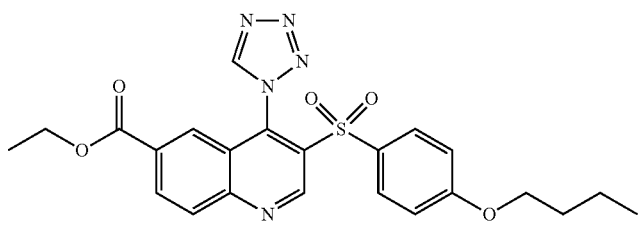 [SMILES: CCCCOc1ccc(S(=O)(=O)c2cnc3ccc(C(=O)OCC)cc3c2-n2cnnn2)cc1] | ethyl 3-((4-butoxyphenyl)sulfonyl)-4-(1H-tetrazol-1-yl)quinoline-6-carboxylate |
| 187 | 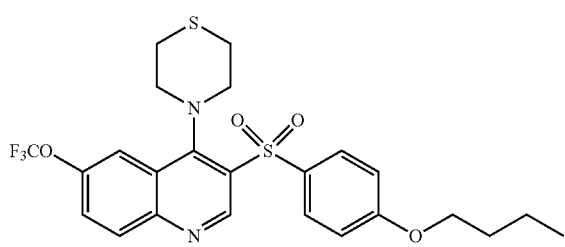 [SMILES: CCCCOc1ccc(S(=O)(=O)c2cnc3ccc(OC(F)(F)F)cc3c2N2CCSCC2)cc1] | 4-(3-((4-butoxyphenyl)sulfonyl)-6-(trifluoromethoxy)quinolin-4-yl)thiomorpholine |
| 188 | 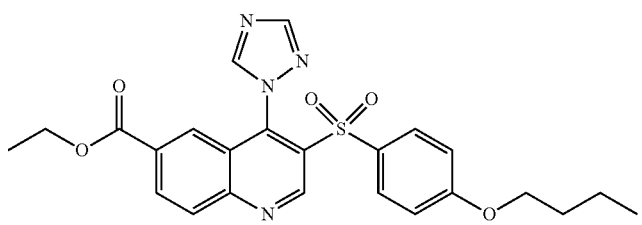 [SMILES: CCCCOc1ccc(S(=O)(=O)c2cnc3ccc(C(=O)OCC)cc3c2-n2cncn2)cc1] | ethyl 3-((4-butoxyphenyl)sulfonyl)-4-(1H-1,2,4-triazol-1-yl)quinoline-6-carboxylate |
| 189 | 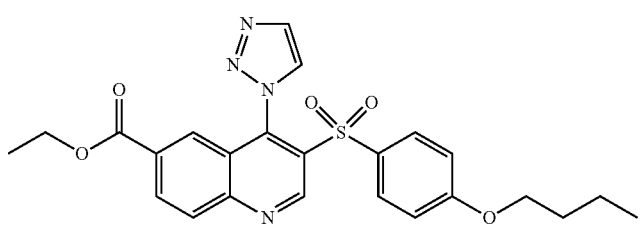 [SMILES: CCCCOc1ccc(S(=O)(=O)c2cnc3ccc(C(=O)OCC)cc3c2-n2ccnn2)cc1] | ethyl 3-((4-butoxyphenyl)sulfonyl)-4-(1H-1,2,3-triazol-1-yl)quinoline-6-carboxylate |

-continued

| | | |
|---|---|---|
| 190 | 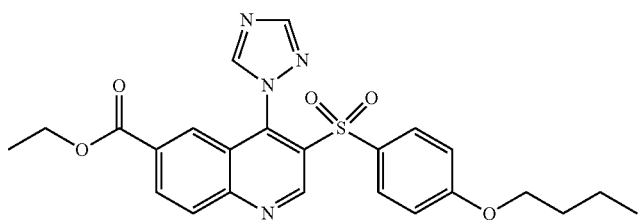 [SMILES: CCCCOc1ccc(S(=O)(=O)c2cnc3ccc(C(=O)OCC)cc3c2-n2cncn2)cc1] | ethyl 3-((4-butoxyphenyl)sulfonyl)-4-(1H-1,2,4-triazol-1-yl)quinoline-6-carboxylate |
| 191 | 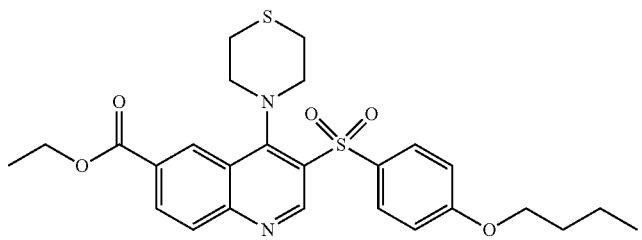 [SMILES: CCCCOc1ccc(S(=O)(=O)c2cnc3ccc(C(=O)OCC)cc3c2N2CCSCC2)cc1] | ethyl 3-((4-butoxyphenyl)sulfonyl)-4-thiomorpholinoquinoline-6-carboxylate |
| 192 | 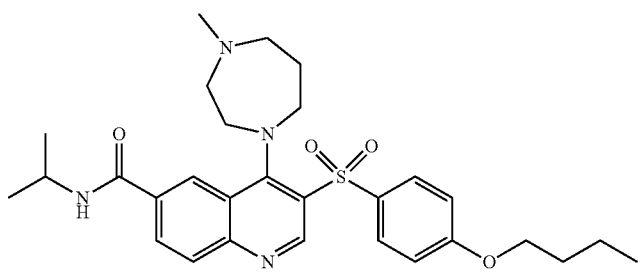 [SMILES: CCCCOc1ccc(S(=O)(=O)c2cnc3ccc(C(=O)NC(C)C)cc3c2N2CCCN(C)CC2)cc1] | 3-((4-butoxyphenyl)sulfonyl)-N-isopropyl-4-(4-methyl-1,4-diazepan-1-yl)quinoline-6-carboxamide |
| 193 | 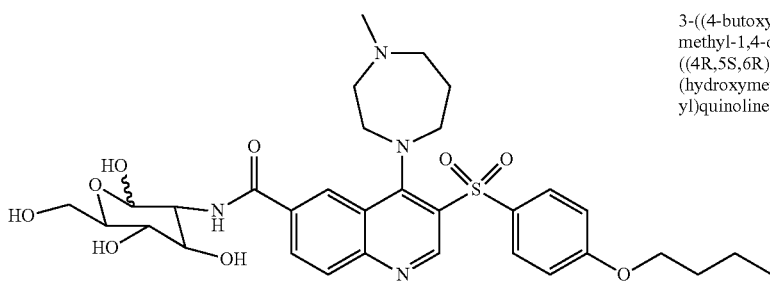 | 3-((4-butoxyphenyl)sulfonyl)-4-(4-methyl-1,4-diazepan-1-yl)-N-((4R,5S,6R)-2,4,5-trihydroxy-6-(hydroxymethyl)tetrahydro-2H-pyran-3-yl)quinoline-6-carboxamide |
| 194 | 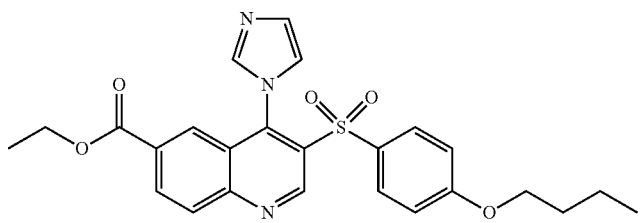 [SMILES: CCCCOc1ccc(S(=O)(=O)c2cnc3ccc(C(=O)OCC)cc3c2-n2ccnc2)cc1] | ethyl 3-((4-butoxyphenyl)sulfonyl)-4-(1H-imidazol-1-yl)quinoline-6-carboxylate |
| 195 | 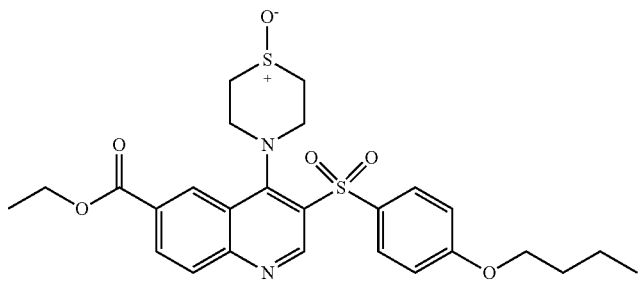 | ethyl 3-((4-butoxyphenyl)sulfonyl)-4-(1-oxidothiomorpholino)quinoline-6-carboxylate |

-continued

| | | |
|---|---|---|
| 196 | 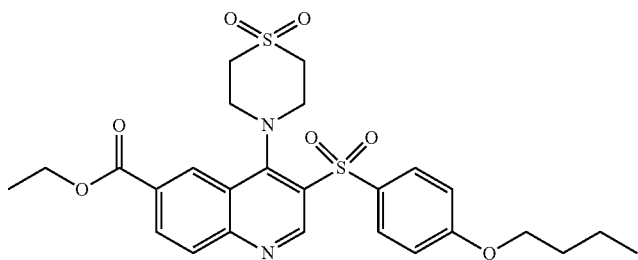 [SMILES: CCCCOc1ccc(S(=O)(=O)c2cnc3ccc(C(=O)OCC)cc3c2N2CCS(=O)(=O)CC2)cc1] | ethyl 3-((4-butoxyphenyl)sulfonyl)-4-(1,1-dioxidothiomorpholino)quinoline-6-carboxylate |
| 197 | 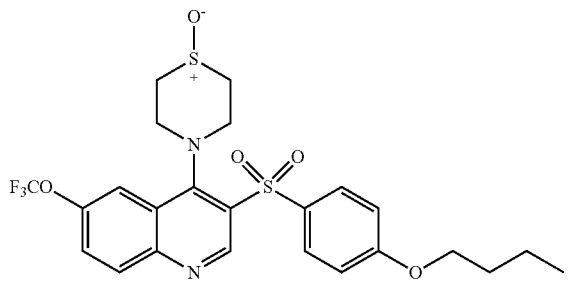 | 4-(3-((4-butoxyphenyl)sulfonyl)-6-(trifluoromethoxy)quinolin-4-yl)thiomorpholine 1-oxide |
| 198 | 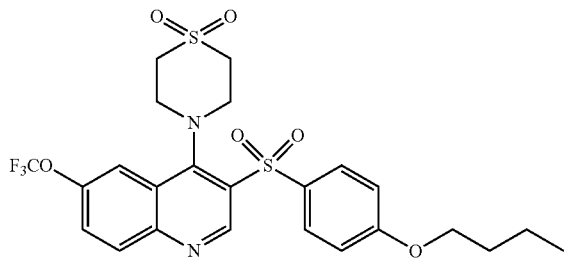 [SMILES: CCCCOc1ccc(S(=O)(=O)c2cnc3ccc(OC(F)(F)F)cc3c2N2CCS(=O)(=O)CC2)cc1] | 4-(3-((4-butoxyphenyl)sulfonyl)-6-(trifluoromethoxy)quinolin-4-yl)thiomorpholine 1,1-dioxide |
| 199 | 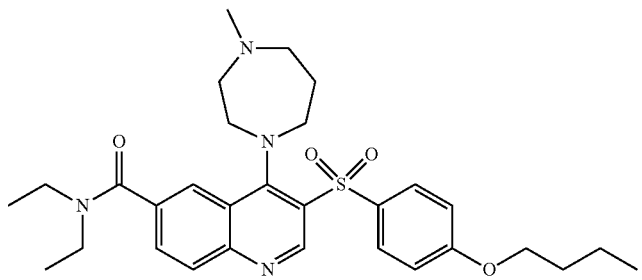 [SMILES: CCCCOc1ccc(S(=O)(=O)c2cnc3ccc(C(=O)N(CC)CC)cc3c2N2CCCN(C)CC2)cc1] | 3-((4-butoxyphenyl)sulfonyl)-N,N-diethyl)-4-(4-methyl-1,4-diazepan-1-yl)quinoline-6-carboxamide |
| 200 | 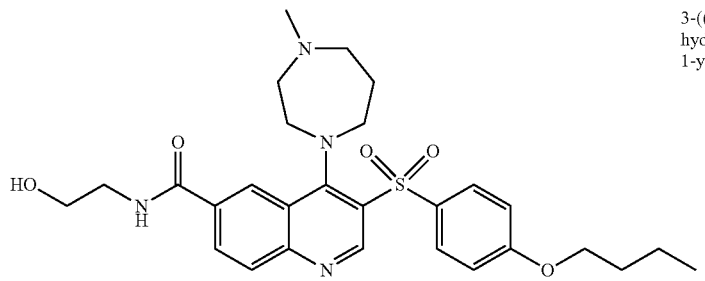 | 3-((4-butoxyphenyl)sulfonyl)-N-(2-hydroxyethyl)-4-(4-methyl-1,4-diazepan-1-yl)quinoline-6-carboxamide |

| | | |
|---|---|---|
| 201 | 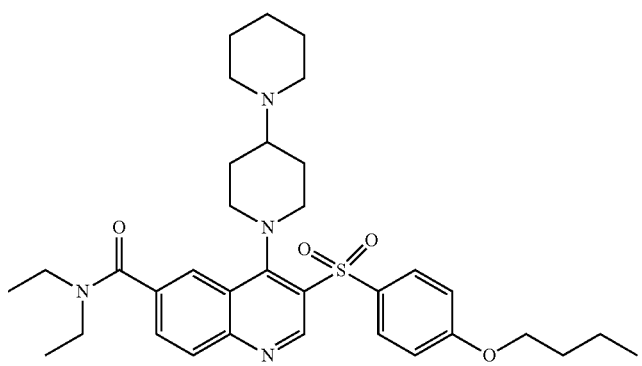 [SMILES: CCCCOc1ccc(S(=O)(=O)c2cnc3ccc(C(=O)N(CC)CC)cc3c2N2CCC(N3CCCCC3)CC2)cc1] | 4-([1,4'-bipiperidin]-1'-yl)-3-((4-butoxyphenyl)sulfonyl)-N,N-diethyl)quinoline-6-carboxamide |
| 202 | 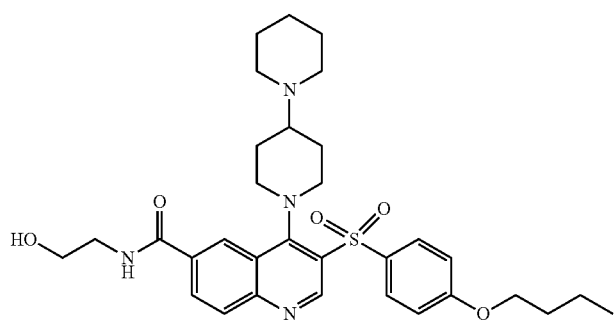 [SMILES: CCCCOc1ccc(S(=O)(=O)c2cnc3ccc(C(=O)NCCO)cc3c2N2CCC(N3CCCCC3)CC2)cc1] | 4-([1,4'-bipiperidin]-1'-yl)-3-((4-butoxyphenyl)sulfonyl)-N-(2-hydroxyethyl)quinoline-6-carboxamide |
| 203 | 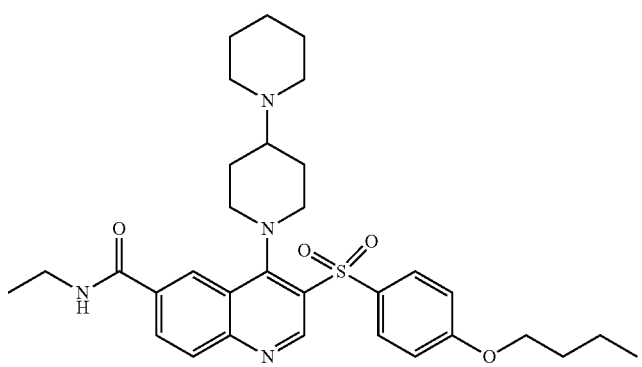 [SMILES: CCCCOc1ccc(S(=O)(=O)c2cnc3ccc(C(=O)NCC)cc3c2N2CCC(N3CCCCC3)CC2)cc1] | 4-([1,4'-bipiperidin]-1'-yl)-3-((4-butoxyphenyl)sulfonyl)-N-ethyl)quinoline-6-carboxamide |
| 204 | 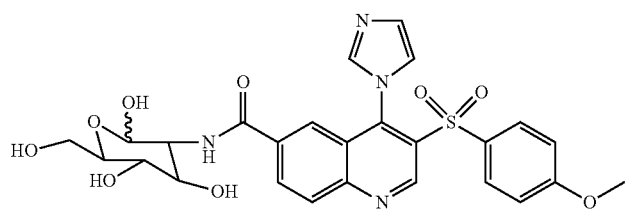 [SMILES: COc1ccc(S(=O)(=O)c2cnc3ccc(C(=O)NC4C(O)OC(CO)C(O)C4O)cc3c2-n2ccnc2)cc1] | 4-(1H-imidazol-1-yl)-3-((4-methoxyphenyl)sulfonyl)-N-((4R,5S,6R)-2,4,5-trihydroxy-6-(hydroxymethyl)tetrahydro-2H-pyran-3-yl)quinoline-6-carboxamide |
| 205 | 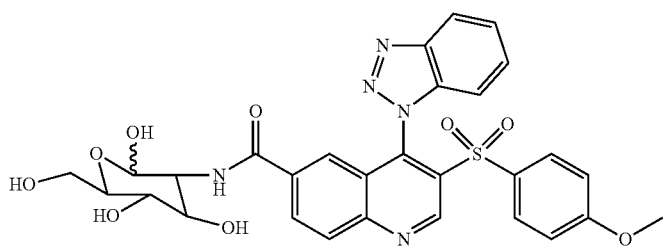 [SMILES: COc1ccc(S(=O)(=O)c2cnc3ccc(C(=O)NC4C(O)OC(CO)C(O)C4O)cc3c2-n2nnc3ccccc32)cc1] | 4-(1H-benzo[d][1,2,3]triazol-1-yl)-3-((4-methoxyphenyl)sulfonyl)-N-((4R,5S,6R)-2,4,5-trihydroxy-6-(hydroxymethyl)tetrahydro-2H-pyran-3-yl)quinoline-6-carboxamide |

| | | |
|---|---|---|
| 206 | 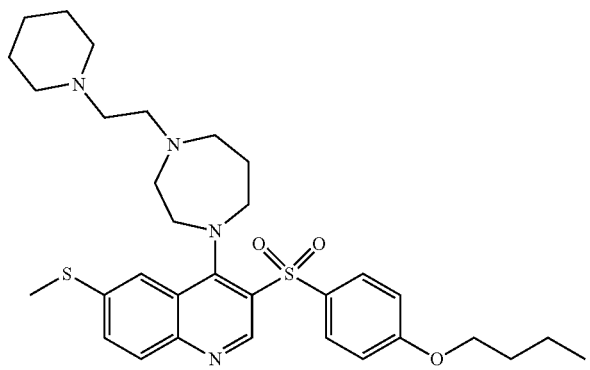 [SMILES: CCCCOc1ccc(S(=O)(=O)c2cnc3ccc(SC)cc3c2N2CCCN(CCN3CCCCC3)CC2)cc1] | 3-((4-butoxyphenyl)sulfonyl)-6-(methylthio)-4-(4-(2-(piperidin-1-yl)ethyl)-1,4-diazepan-1-yl)quinoline |
| 207 | 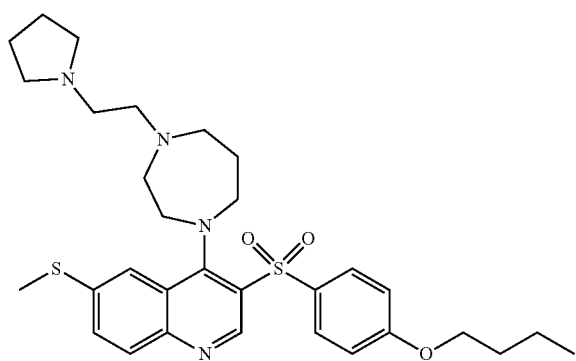 [SMILES: CCCCOc1ccc(S(=O)(=O)c2cnc3ccc(SC)cc3c2N2CCCN(CCN3CCCC3)CC2)cc1] | 3-((4-butoxyphenyl)sulfonyl)-6-(methylthio)-4-(4-(2-(pyrrolidin-1-yl)ethyl)-1,4-diazepan-1-yl)quinoline |
| 208 | 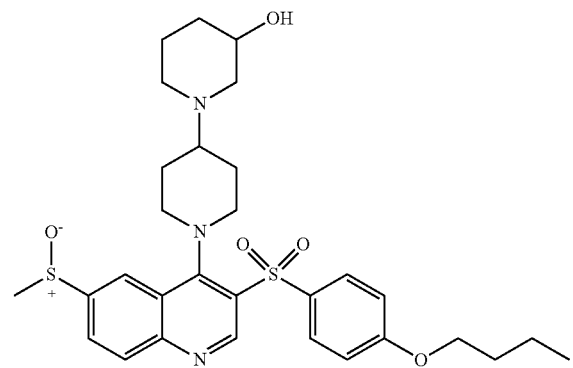 | 1'-(3-((4-butoxyphenyl)sulfonyl)-6-(methylsulfinyl)quinolin-4-yl)-[1,4'-bipiperidin]-3-ol |
| 209 | 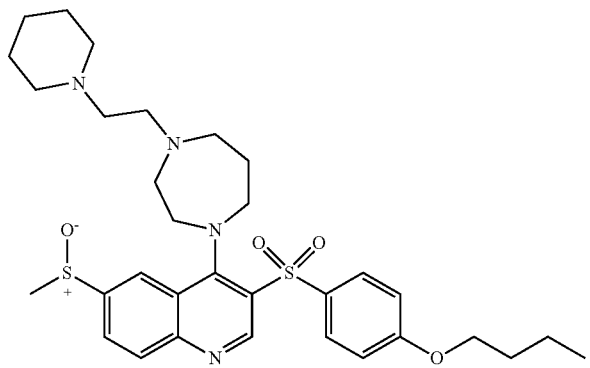 | 3-((4-butoxyphenyl)sulfonyl)-6-(methylsulfinyl)-4-(4-(2-(piperidin-1-yl)ethyl)-1,4-diazepan-1-yl)quinoline |

| | | |
|---|---|---|
| 210 | 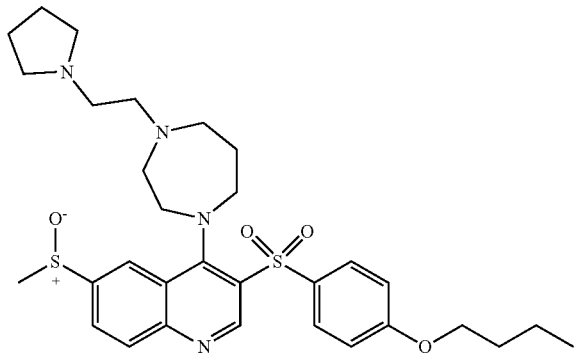 | 3-((4-butoxyphenyl)sulfonyl)-6-(methylsulfinyl)-4-(4-(2-(pyrrolidin-1-yl)ethyl)-1,4-diazepan-1-yl)quinoline |
| 211 | 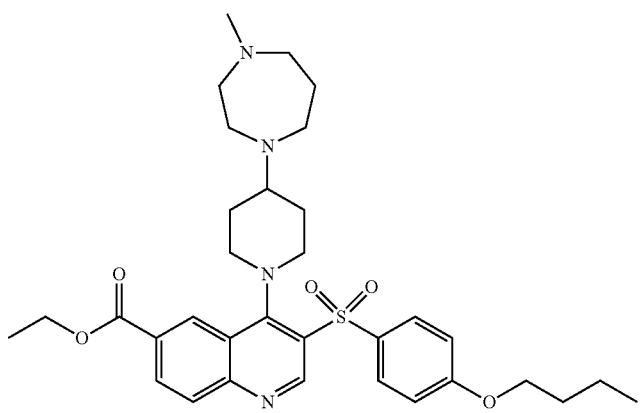 [SMILES: CCCCOc1ccc(S(=O)(=O)c2cnc3ccc(C(=O)OCC)cc3c2N2CCC(N3CCCN(C)CC3)CC2)cc1] | ethyl 3-((4-butoxyphenyl)sulfonyl)-4-(4-(4-methyl-1,4-diazepan-1-yl)piperidin-1-yl)quinoline-6-carboxylate |
| 212 | 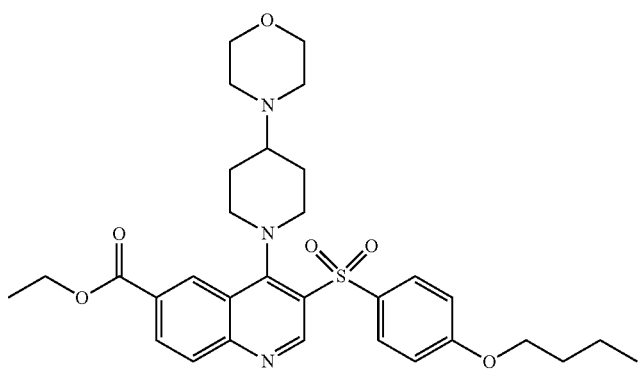 [SMILES: CCCCOc1ccc(S(=O)(=O)c2cnc3ccc(C(=O)OCC)cc3c2N2CCC(N3CCOCC3)CC2)cc1] | ethyl 3-((4-butoxyphenyl)sulfonyl)-4-(4-morpholinopiperidin-1-yl)quinoline-6-carboxylate |
| 213 | 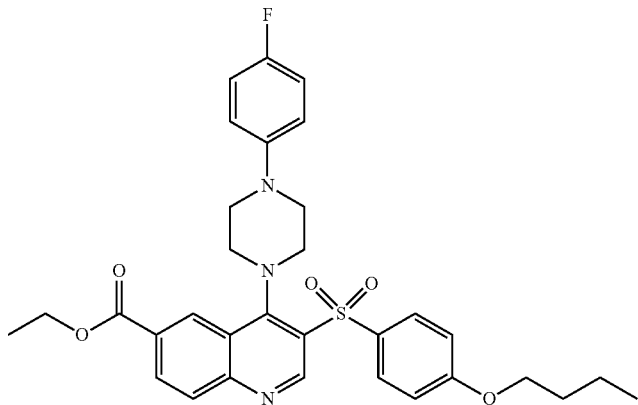 [SMILES: CCCCOc1ccc(S(=O)(=O)c2cnc3ccc(C(=O)OCC)cc3c2N2CCN(c3ccc(F)cc3)CC2)cc1] | ethyl 3-((4-butoxyphenyl)sulfonyl)-4-(4-(4-fluorophenyl)piperazin-1-yl)quinoline-6-carboxylate |

| | | |
|---|---|---|
| 214 | 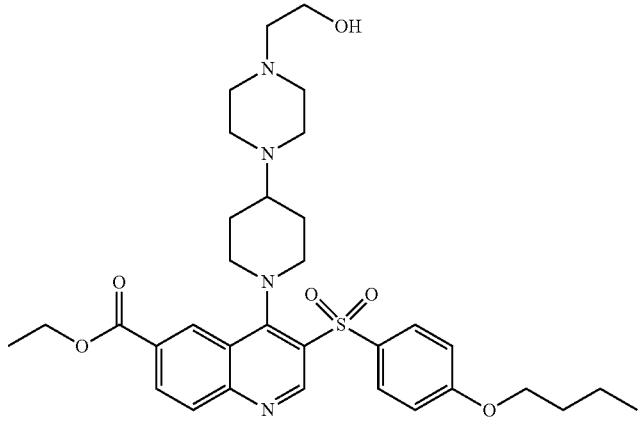 [SMILES: CCCCOc1ccc(S(=O)(=O)c2cnc3ccc(C(=O)OCC)cc3c2N2CCC(N3CCN(CCO)CC3)CC2)cc1] | ethyl 3-((4-butoxyphenyl)sulfonyl)-4-(4-(4-(2-hydroxyethyl)piperazin-1-yl)piperidin-1-yl)quinoline-6-carboxylate |
| 215 | 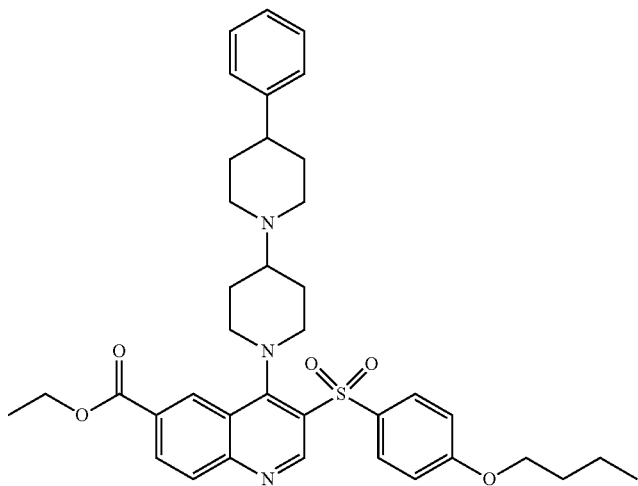 [SMILES: CCCCOc1ccc(S(=O)(=O)c2cnc3ccc(C(=O)OCC)cc3c2N2CCC(N3CCC(c4ccccc4)CC3)CC2)cc1] | ethyl 3-((4-butoxyphenyl)sulfonyl)-4-(4-phenyl-[1,4'-bipiperidin]-1'-yl)quinoline-6-carboxylate |
| 216 | 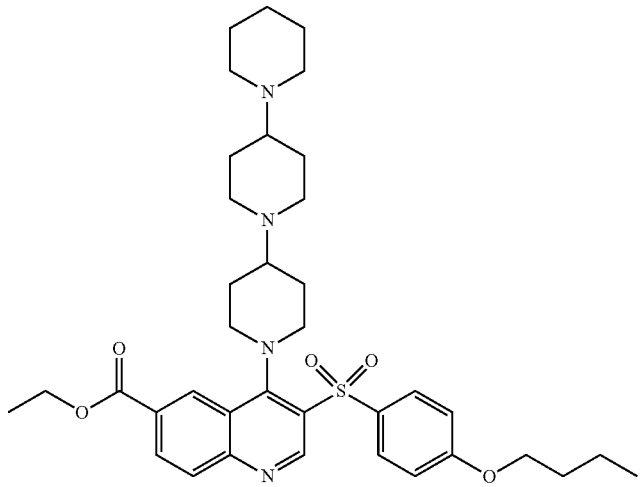 [SMILES: CCCCOc1ccc(S(=O)(=O)c2cnc3ccc(C(=O)OCC)cc3c2N2CCC(N3CCC(N4CCCCC4)CC3)CC2)cc1] | ethyl 4-([1,4':1',4''-terpiperidin]-1''-yl)-3-((4-butoxyphenyl)sulfonyl)quinoline-6-carboxylate |

| | | |
|---|---|---|
| 217 | 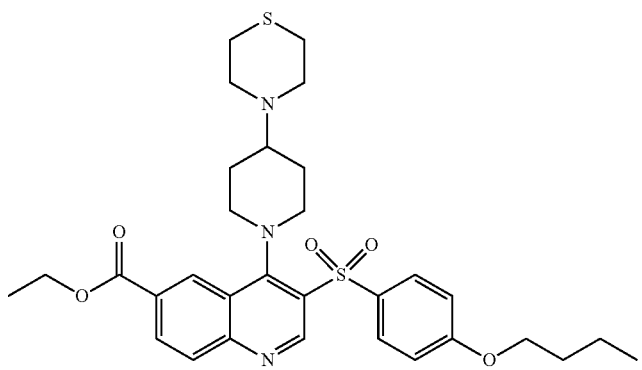 | ethyl 3-((4-butoxyphenyl)sulfonyl)-4-(4-thiomorpholinopiperidin-1-yl)quinoline-6-carboxylate |
| 218 | 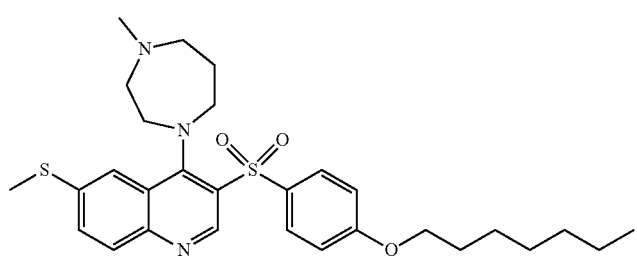 [SMILES: CCCCCCCOc1ccc(S(=O)(=O)c2cnc3ccc(SC)cc3c2N2CCCN(C)CC2)cc1] | 3-((4-(heptyloxy)phenyl)sulfonyl)-4-(4-methyl-1,4-diazepan-1-yl)-6-(methylthio)quinoline |
| 219 | 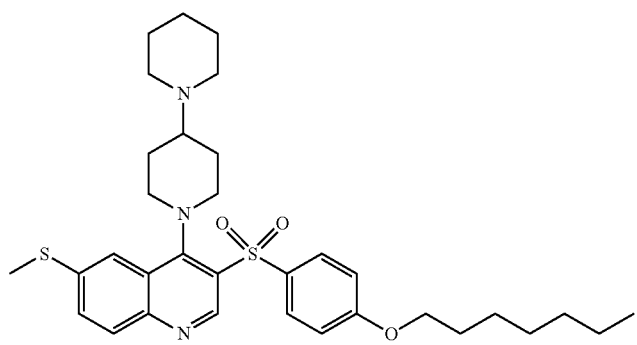 [SMILES: CCCCCCCOc1ccc(S(=O)(=O)c2cnc3ccc(SC)cc3c2N2CCC(N3CCCCC3)CC2)cc1] | 4-([1,4'-bipiperidin]-1'-yl)-3-((4-(heptyloxy)phenyl)sulfonyl)-6-(methylthio)quinoline |
| 220 | 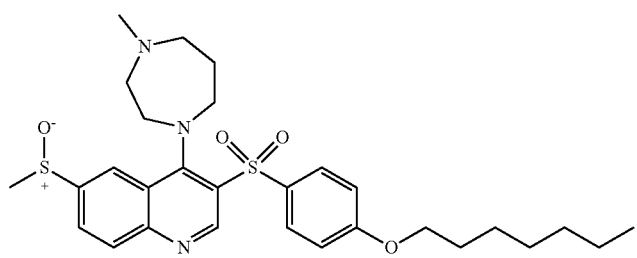 | 3-((4-(heptyloxy)phenyl)sulfonyl)-4-(4-methyl-1,4-diazepan-1-yl)-6-(methylsulfinyl)quinoline |
| 221 | 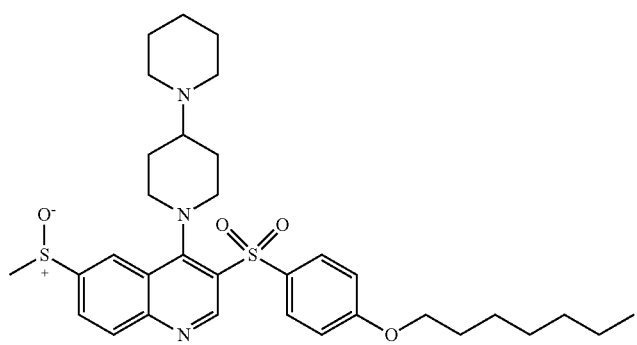 | 4-([1,4'-bipiperidin]-1'-yl)-3-((4-(heptyloxy)phenyl)sulfonyl)-6-(methylsulfinyl)quinoline |

| | | |
|---|---|---|
| 222 | 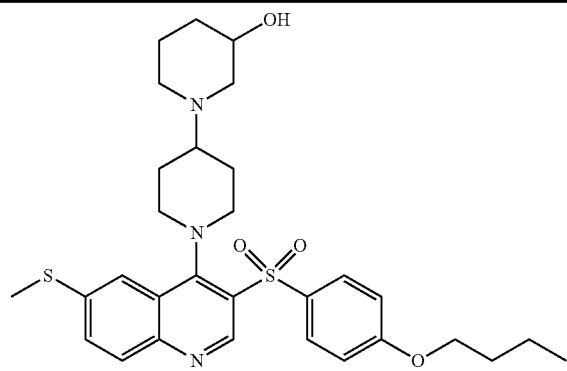 | 1'-(3-((4-butoxyphenyl)sulfonyl)-6-(methylthio)quinolin-4-yl)-[1,4'-bipiperidin]-3-ol |
| 223 | 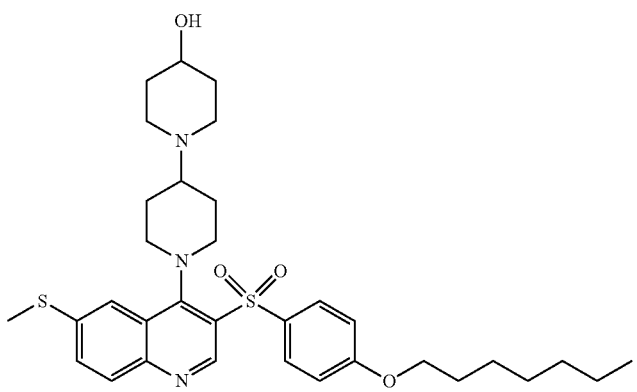 [SMILES: CCCCCCCOc1ccc(S(=O)(=O)c2cnc3ccc(SC)cc3c2N2CCC(N3CCC(O)CC3)CC2)cc1] | 1'-(3-((4-(heptyloxy)phenyl)sulfonyl)-6-(methylthio)quinolin-4-yl-[1,4'-bipiperidin]-4-ol |
| 224 | 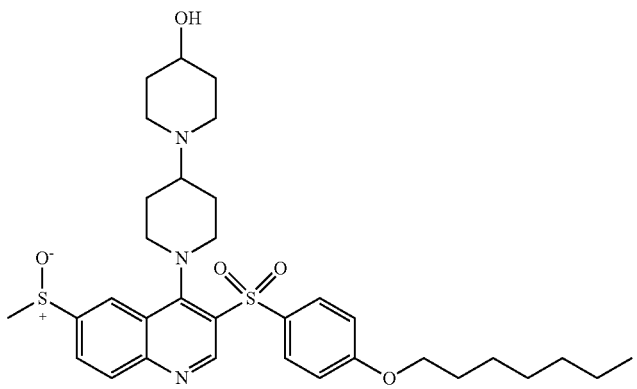 | 1'-(3-((4-(heptyloxy)phenyl)sulfonyl)-6-(methylsulfinyl)quinolin-4-yl)-[1,4'-bipiperidin]-4-ol |
| 225 | 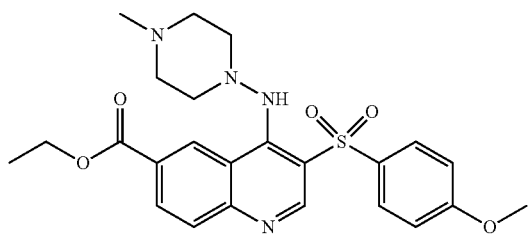 [SMILES: CCOC(=O)c1ccc2ncc(S(=O)(=O)c3ccc(OC)cc3)c(NN3CCN(C)CC3)c2c1] | ethyl 3-((4-methoxyphenyl)sulfonyl)-4-((4-methylpiperazin-1-yl)amino)quinoline-6-carboxylate |
| 226 | 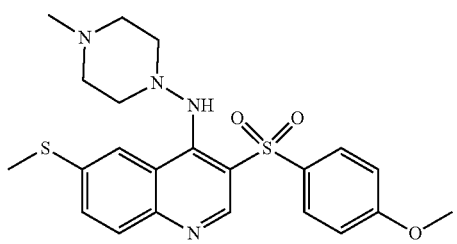 | 3-((4-methoxyphenyl)sulfonyl)-N-(4-methylpiperazin-1-yl)-6-(methylthio)quinolin-4-amine |

| | | |
|---|---|---|
| 227 | 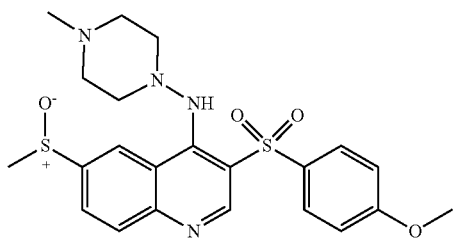 | 3-((4-methoxyphenyl)sulfonyl)-N-(4-methylpiperazin-1-yl)-6-(methylsulfinyl)quinolin-4-amine |
| 228 | 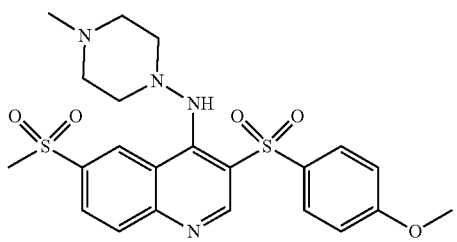 | 3-((4-methoxyphenyl)sulfonyl)-N-(4-methylpiperazin-1-yl)-6-(methylsulfonyl)quinolin-4-amine |
| 229 | 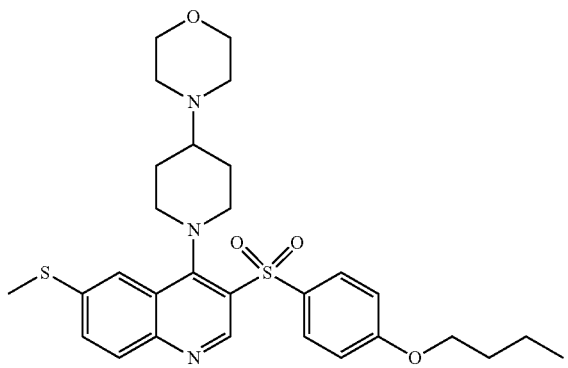 [SMILES: CCCCOc1ccc(S(=O)(=O)c2cnc3ccc(SC)cc3c2N2CCC(N3CCOCC3)CC2)cc1] | 4-(1-(3-((4-butoxyphenyl)sulfonyl)-6-(methylthio)quinolin-4-yl)piperidin-4-yl)morpholine |
| 230 | 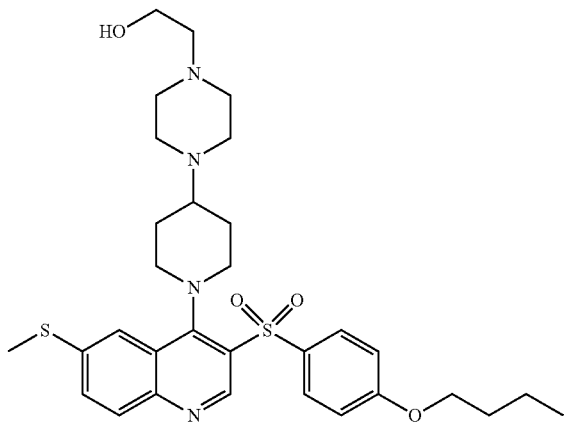 [SMILES: CCCCOc1ccc(S(=O)(=O)c2cnc3ccc(SC)cc3c2N2CCC(N3CCN(CCO)CC3)CC2)cc1] | 2-(4-(1-(3-((4-butoxyphenyl)sulfonyl)-6-(methylthio)quinolin-4-yl)piperidin-4-yl)piperazin-1-yl)ethan-1-ol |

| | | |
|---|---|---|
| 231 | 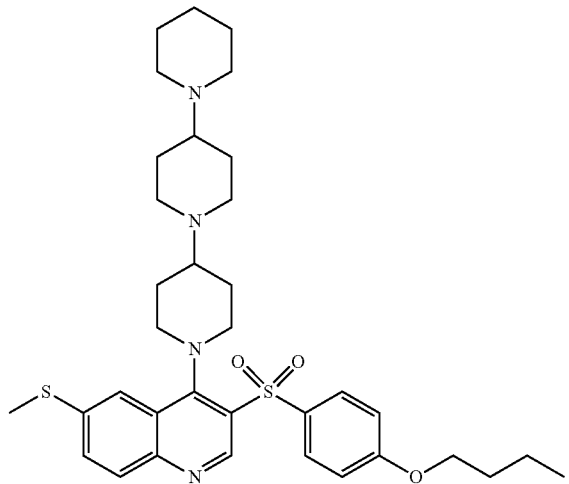 [SMILES: CCCCOc1ccc(S(=O)(=O)c2cnc3ccc(SC)cc3c2N2CCC(N3CCC(N4CCCCC4)CC3)CC2)cc1] | 4-([1,4':1',4"-terpiperidin]-1"-yl)-3-((4-butoxyphenyl)sulfonyl)-6-(methylthio)quinoline |
| 232 | 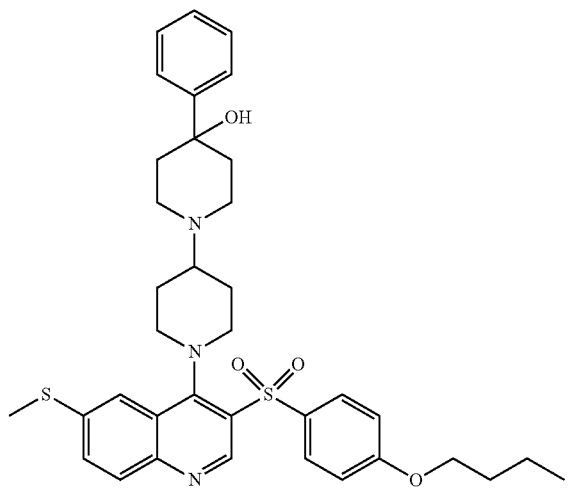 [SMILES: CCCCOc1ccc(S(=O)(=O)c2cnc3ccc(SC)cc3c2N2CCC(N3CCC(O)(c4ccccc4)CC3)CC2)cc1] | 1'-(3-((4-butoxyphenyl)sulfonyl-6-(methylthio)quinolin-4-yl)-4-phenyl-[1,4'-bipiperidin]-4-ol |
| 233 | 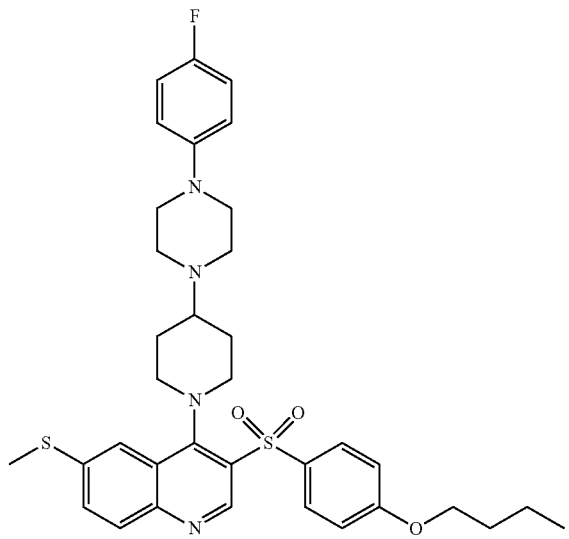 [SMILES: CCCCOc1ccc(S(=O)(=O)c2cnc3ccc(SC)cc3c2N2CCC(N3CCN(c4ccc(F)cc4)CC3)CC2)cc1] | 3-((4-butoxyphenyl)sulfonyl)-4-(4-(4-(4-fluorophenyl)piperazin-1-yl)piperidin-1-yl)-6-(methylthio)quinoline |

| | | |
|---|---|---|
| 234 | 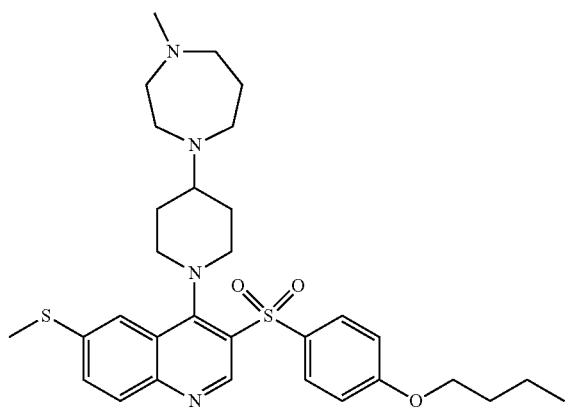 [SMILES: CCCCOc1ccc(S(=O)(=O)c2cnc3ccc(SC)cc3c2N2CCC(N3CCCN(C)CC3)CC2)cc1] | 3-((4-butoxyphenyl)sulfonyl)-4-(4-(4-methyl-1,4-diazepan-1-yl)piperidin-1-yl)-6-(methylthio)quinoline |
| 235 | 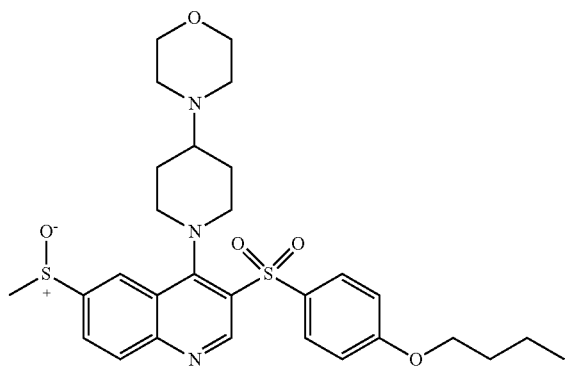 | 4-(1-(3-((4-butoxyphenyl)sulfonyl)-6-(methylsulfinyl)quinolin-4-yl)piperidin-4-yl)morpholine |
| 236 | 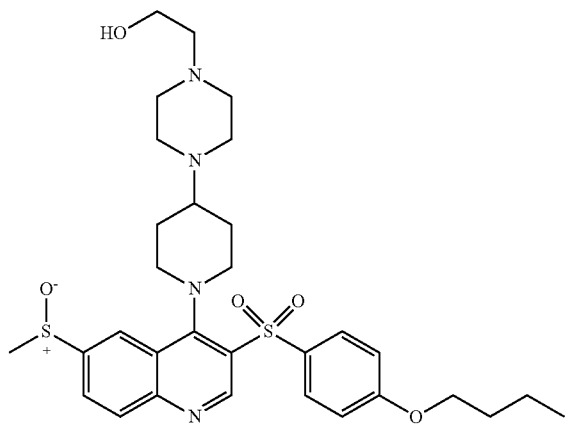 | 2-(4-(1-(3-((4-butoxyphenyl)sulfonyl)-6-(methylsulfinyl)quinolin-4-yl)piperidin-4-yl)piperazin-1-yl)ethan-1-ol |

| | | -continued |
|---|---|---|
| 237 | 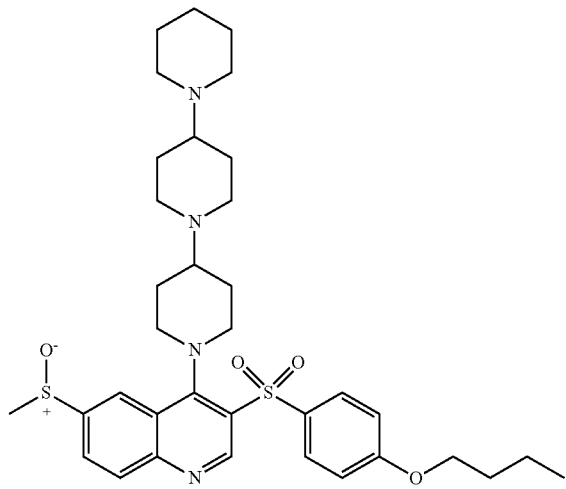 | 4-([1,4':1',4''-terpiperidin]-1''-yl)-3-((4-butoxyphenyl)sulfonyl)-6-(methylsulfinyl)quinoline |
| 238 | 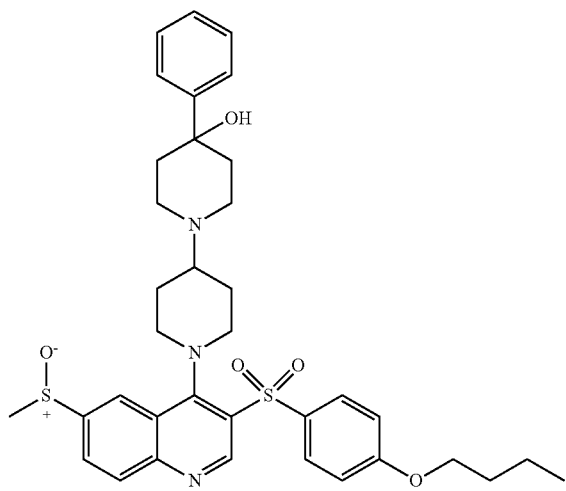 | 1'-(3-((4-butoxyphenyl)sulfonyl)-6-(methylsulfinyl)quinolin-4-yl)-4-phenyl-[1,4'-bipiperidin]-4-ol |
| 239 | 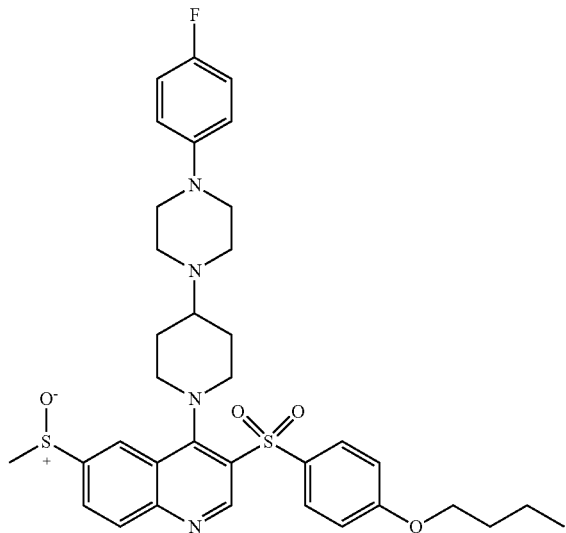 | 3-((4-butoxyphenyl)sulfonyl)-4-(4-(4-(4-fluorophenyl)piperazin-1-yl)piperidin-1-yl)-6-(methylsulfinyl)quinoline |

| | | |
|---|---|---|
| 240 | 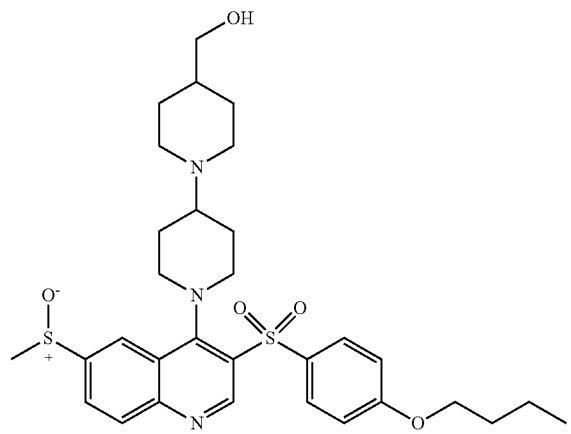 | (1'-(3-((4-butoxyphenyl)sulfonyl)-6-(methylsulfinyl)quinolin-4-yl)-[1,4'-bipiperidin]-4-yl)methanol |
| 241 | 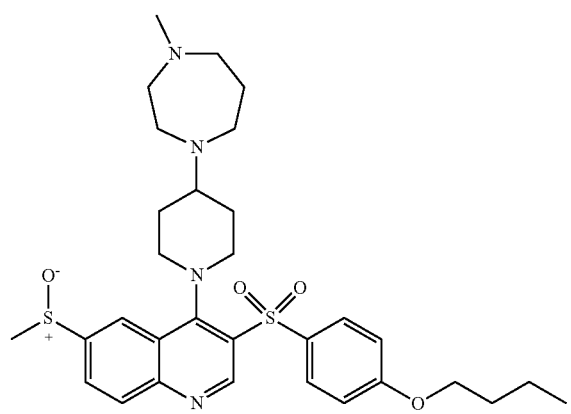 | 3-((4-butoxyphenyl)sulfonyl)-4-(4-(4-methyl-1,4-diazepan-1-yl)piperidin-1-yl)-6-(methylsulfinyl)quinoline |
| 242 | 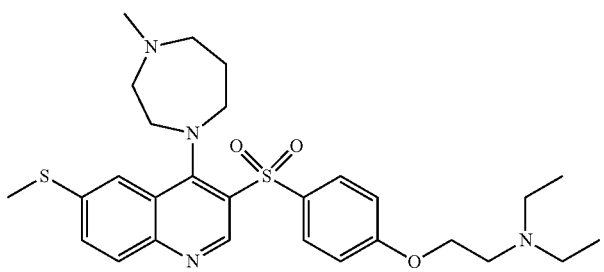 [SMILES: CCN(CC)CCOc1ccc(S(=O)(=O)c2cnc3ccc(SC)cc3c2N2CCCN(C)CC2)cc1] | N,N-diethyl)1-2-(4-((4-(4-methyl-1,4-diazepan-1-yl)-6-(methylthio)quinolin-3-yl)sulfonyl)phenoxy)ethan-1-amine |
| 243 | 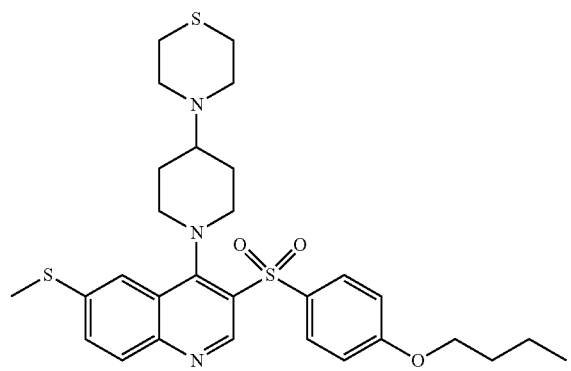 | 4-(1-(3-((4-butoxyphenyl)sulfonyl)-6-(methylthio)quinolin-4-yl)-piperidin-4-yl)thiomoroholine |

| | | |
|---|---|---|
| 244 | 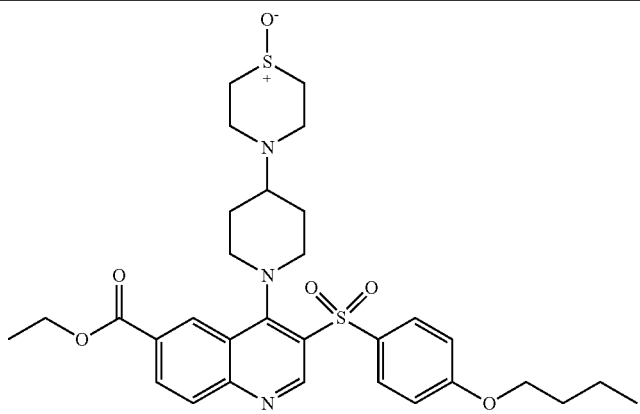 | ethyl 3-((4-butoxyphenyl)sulfonyl)-4-(4-(1-oxidothiomoroholino)piperidin-1-yl)quinoline-6-carboxylate |
| 245 | 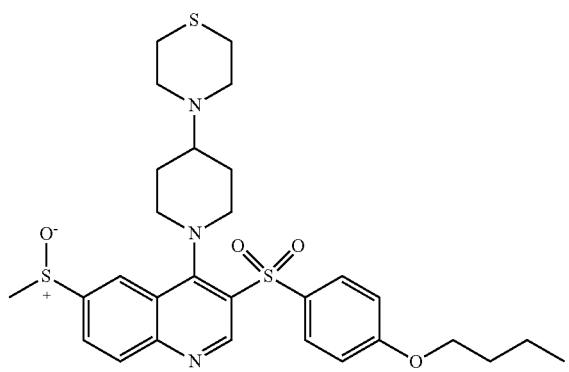 | 4-(1-(3-((4-butoxyphenyl)sulfonyl)-6-(methylsulfinyl)quinolin-4-yl)piperidin-4-yl)thiomorpholine |
| 246 | 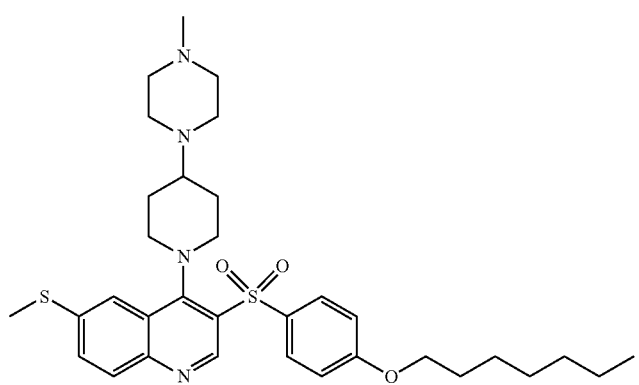 [SMILES: CCCCCCCOc1ccc(S(=O)(=O)c2cnc3ccc(SC)cc3c2N2CCC(N3CCN(C)CC3)CC2)cc1] | 3-((4-(heptyloxy)phenyl)sulfonyl)-4-(4-(4-methylpiperazin-1-yl)piperidin-1-yl)-6-(methylthio)quinoline |
| 247 | 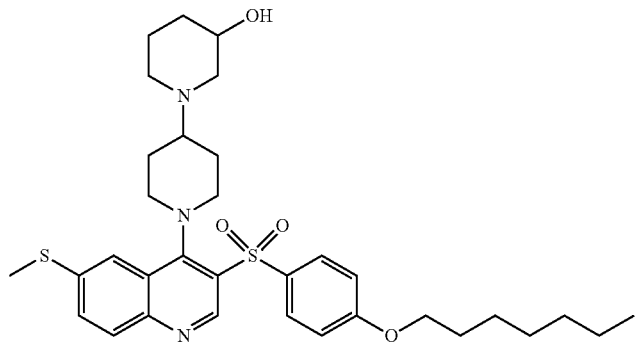 [SMILES: CCCCCCCOc1ccc(S(=O)(=O)c2cnc3ccc(SC)cc3c2N2CCC(N3CCCC(O)C3)CC2)cc1] | 1'-(3-((4-(heptyloxy)phenyl)sulfonyl)-6-(methylthio)quinolin-4-yl)-[1,4'-bipiperidin]-3-ol |

| | | |
|---|---|---|
| 248 | 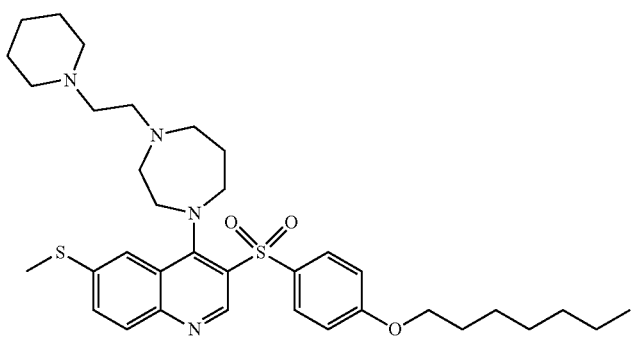 [SMILES: CCCCCCCOc1ccc(S(=O)(=O)c2cnc3ccc(SC)cc3c2N2CCCN(CCN3CCCCC3)CC2)cc1] | 3-((4-(heptyloxy)phenyl)sulfonyl)-6-(methylthio)-4-(4-(2-(piperidin-1-yl)ethyl)-1,4-diazepan-1-yl)quinoline |
| 249 | 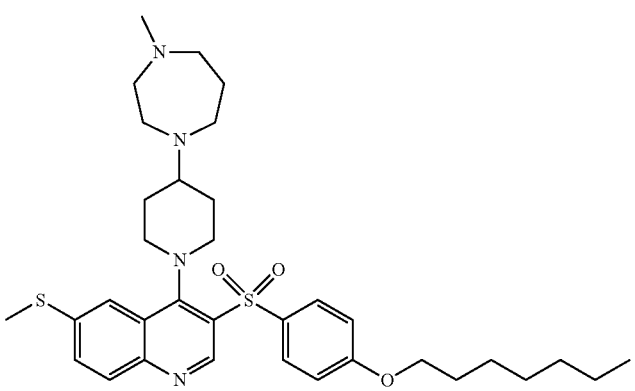 | 3-((4-(heptyloxy)phenyl)sulfonyl)-4-(4-(4-methyl-1,4-diazepan-1-yl)piperidin-1-yl)-6-(methylthio)quinoline |
| 250 | 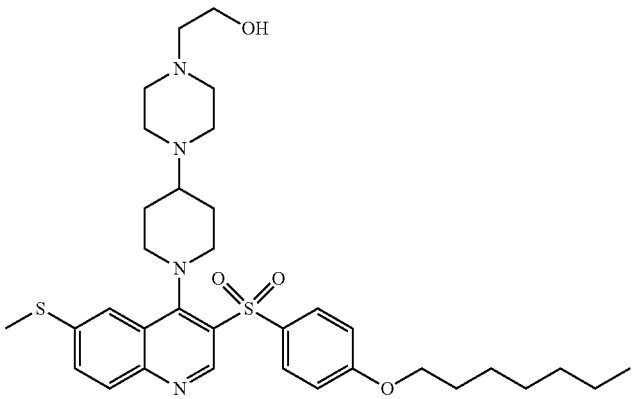 [SMILES: CCCCCCCOc1ccc(S(=O)(=O)c2cnc3ccc(SC)cc3c2N2CCC(N3CCN(CCO)CC3)CC2)cc1] | 2-(4-(1-(3-((4-(heptyloxy)phenyl)sulfonyl)-6-(methylthio)quinolin-4-yl)piperidin-4-yl)piperazin-1-yl)ethan-1-ol |
| 251 | 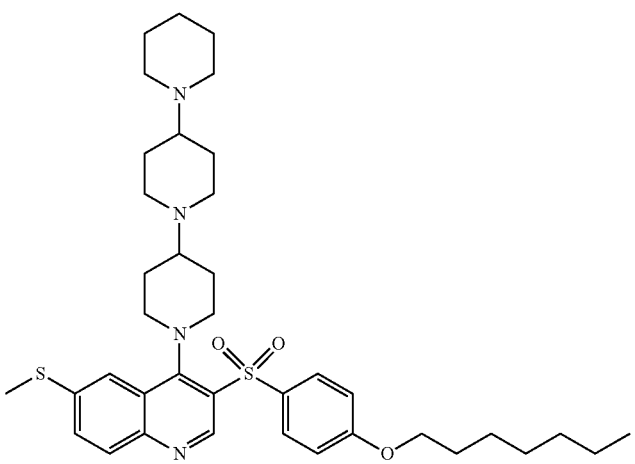 [SMILES: CCCCCCCOc1ccc(S(=O)(=O)c2cnc3ccc(SC)cc3c2N2CCC(N3CCC(N4CCCCC4)CC3)CC2)cc1] | 4-([1,4':1',4''-terpiperidin]-1''-yl)-3-((4-(heptyloxy)phenyl)sulfonyl)-6-(methylthio)quinoline |

-continued
| | | |
|---|---|---|
| 252 | 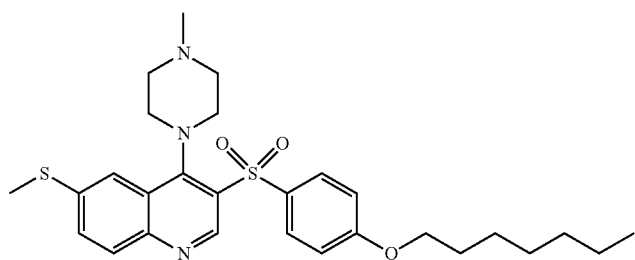 [SMILES: CCCCCCCOc1ccc(S(=O)(=O)c2cnc3ccc(SC)cc3c2N2CCN(C)CC2)cc1] | 3-((4-(heptyloxy)phenyl)sulfonyl)-4-(4-methylpiperazin-1-yl)-6-(methylthio)quinoline |
| 253 | 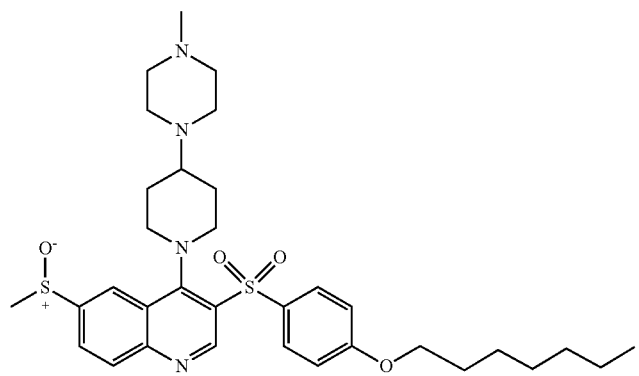 | 3-((4-(heptyloxy)phenyl)sulfonyl-4-(4-(4-methylpiperazin-1-yl)piperidin-1-yl)-6-(methylsulfinyl)quinoline |
| 254 | 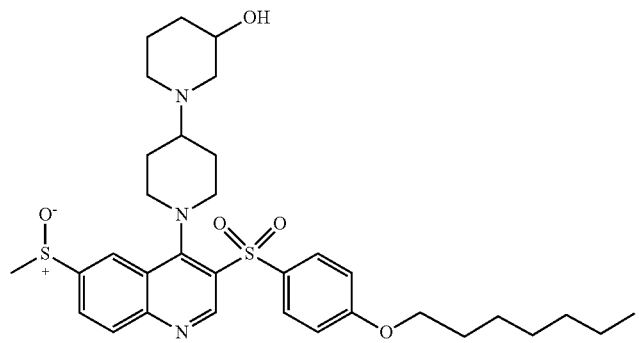 | 1'-(3-((4-(heptyloxy)phenyl)sulfonyl)-6-(methylsulfinyl)quinolin-4-yl)-[1,4'-bipiperidin]-3-ol |
| 255 | 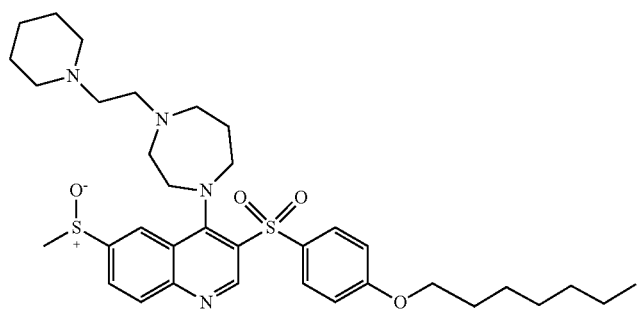 | 3-((4-(heptyloxy)phenyl)sulfonyl)-6-(methylsulfinyl)-4-(2-(piperidin-1-yl)ethyl)-1,4-diazepan-1-yl)quinoline |

| | | |
|---|---|---|
| 256 | 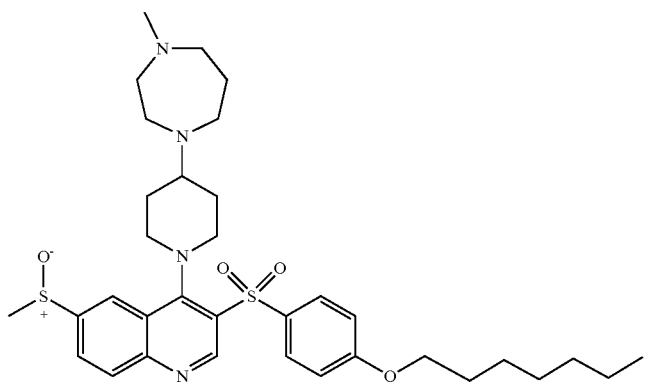 | 3-((4-(heplyloxy)phenyl)sulfonyl)-4-(4-(4-methyl-1,4-diazepan-1-yl)piperidin-1-yl)-6-(methylsulfinyl)quipoline |
| 257 | 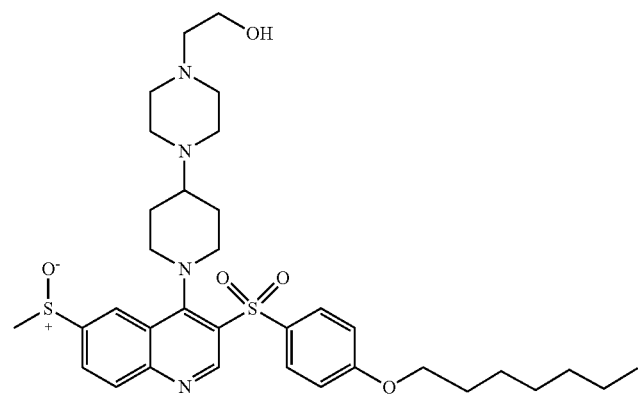 | 2-(4-(1-(3-((4-(heptyloxy)phenyl)sulfonyl)-6-(methylsulfinyl)quinolin-4-yl)piperidin-4-yl)piperazin-1-yl)ethan-1-ol |
| 258 | 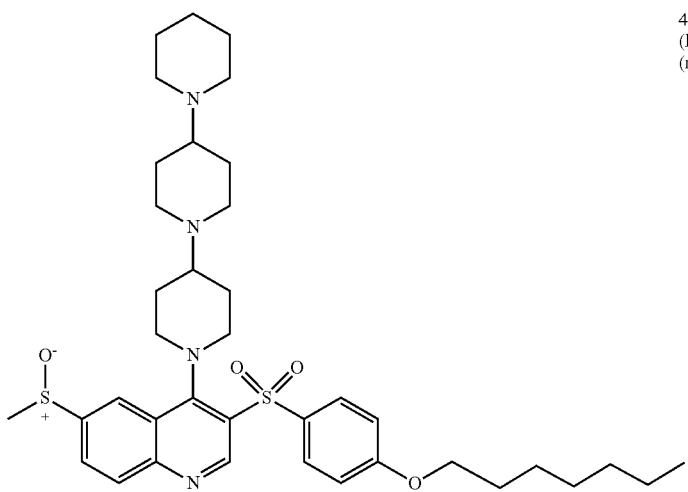 | 4-([1,4':1',4''-terpiperidin]-1''-yl)-3-((4-(heptyloxy)phenyl)sulfonyl)-6-(methylsulfinyl)quinoline |
| 259 | 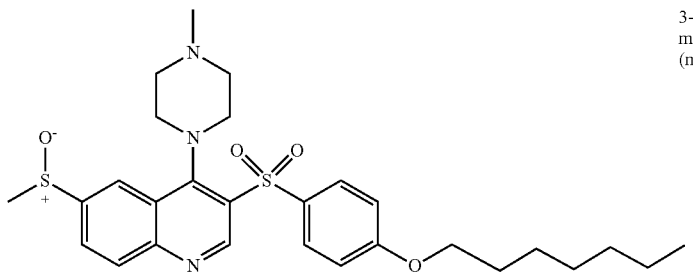 | 3-((4-heptyloxy)phenyl)sulfonyl)-4-(4-methylpiperazin-1-yl)-6-(methylsulfinyl)quinoline |

| | | |
|---|---|---|
| 260 | 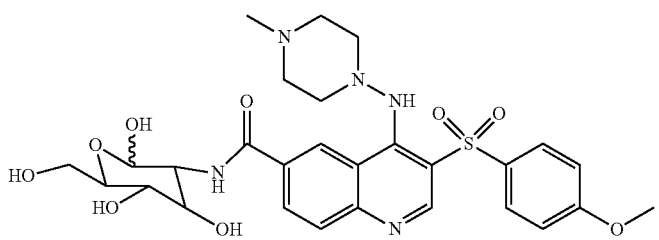 [SMILES: COc1ccc(S(=O)(=O)c2cnc3ccc(C(=O)NC4C(O)OC(CO)C(O)C4O)cc3c2NN2CCN(C)CC2)cc1] | 3-((4-methoxyphenyl)sulfonyl)-4-((4-methylpiperazn-1-yl)amino)-N-((4R,5S,6R)-2,4,5-trihydroxy-6-(hydroxymethyl)tetrahydro-2H-pyran-3-yl)quinoline-6-carboxamide |
| 262 | 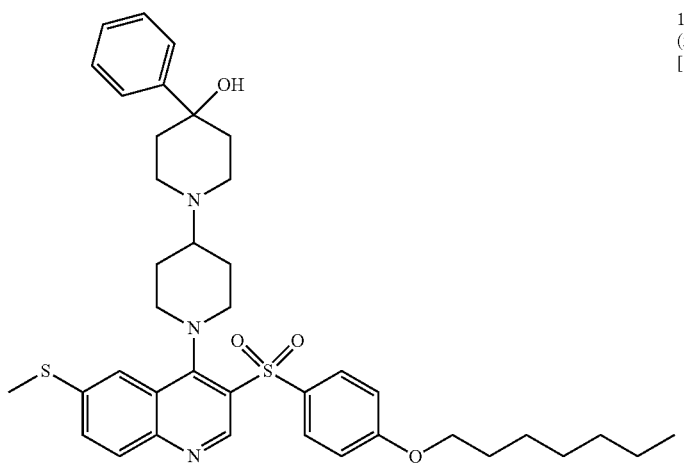 | 1'-(3-((4-(heptyloxy)phenyl)sulfonyl)-6-(methylthio)quinolin-4-yl)-4-phenyl-[1,4'-bipiperidin]-4-ol |
| 263 | 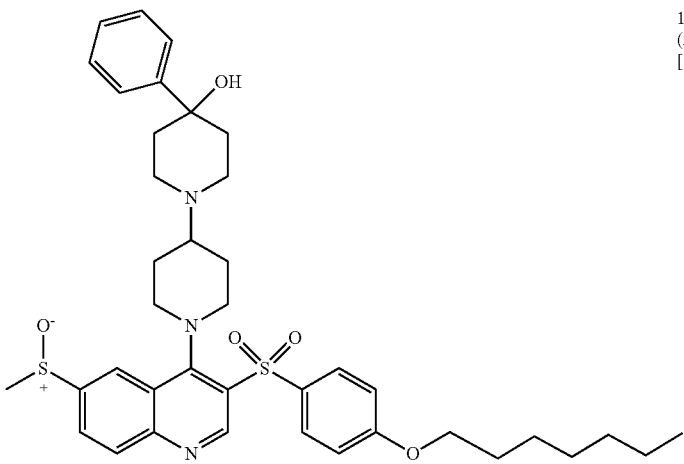 | 1'-(3-((4-(heptyloxy)phenyl)sulfonyl)-6-(methylsulfinyl)quinolin-4-yl)-4-phenyl-[1,4'-bipiperidin]-4-ol |
| 264 | 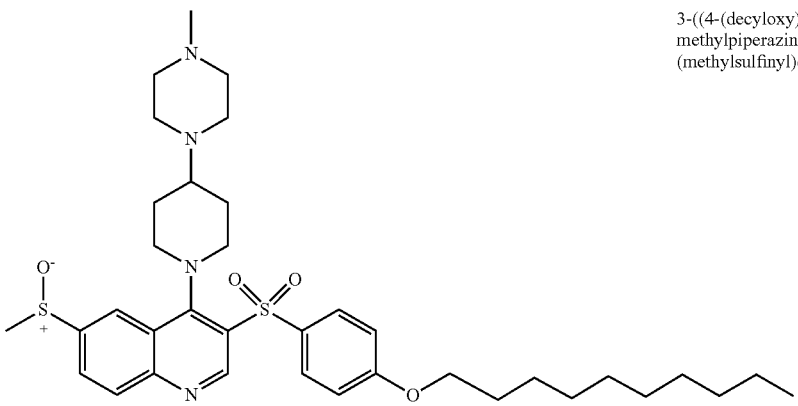 | 3-((4-(decyloxy)phenyl)sulfonyl)-4-(4-(4-methylpiperazin-1-yl)piperidin-1-yl)-6-(methylsulfinyl)quinoline |

| | | |
|---|---|---|
| 265 | 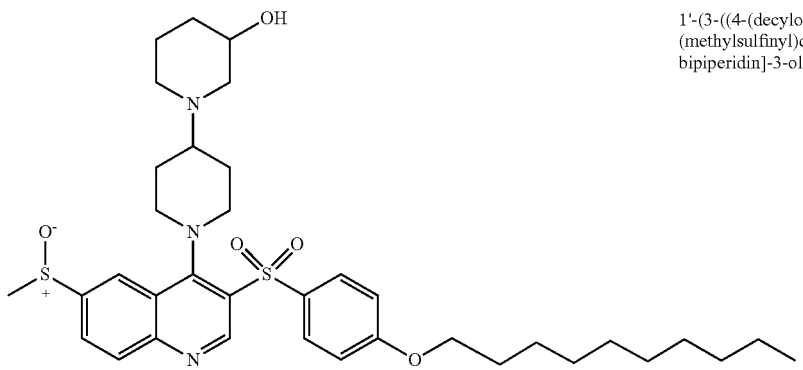 | 1'-(3-((4-(decyloxy)phenyl)sulfonyl)-6-(methylsulfinyl)quinolin-4-yl)-[1,4'-bipiperidin]-3-ol |
| 266 | 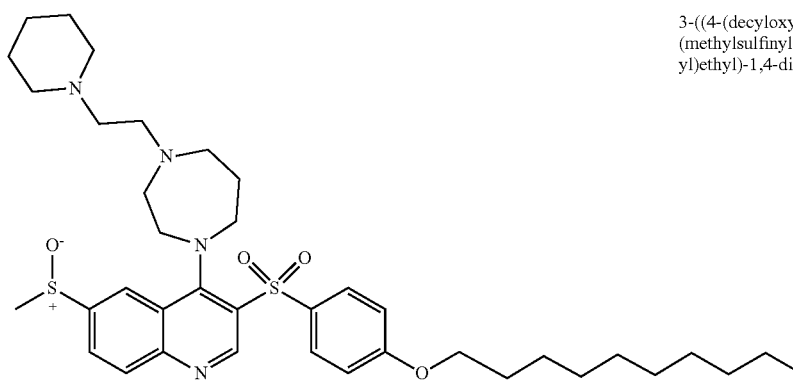 | 3-((4-(decyloxy)phenyl)sulfonyl)-6-(methylsulfinyl)-4-(4-(2-(piperidin-1-yl)ethyl)-1,4-diazepan-1-yl)quinoline |
| 267 | 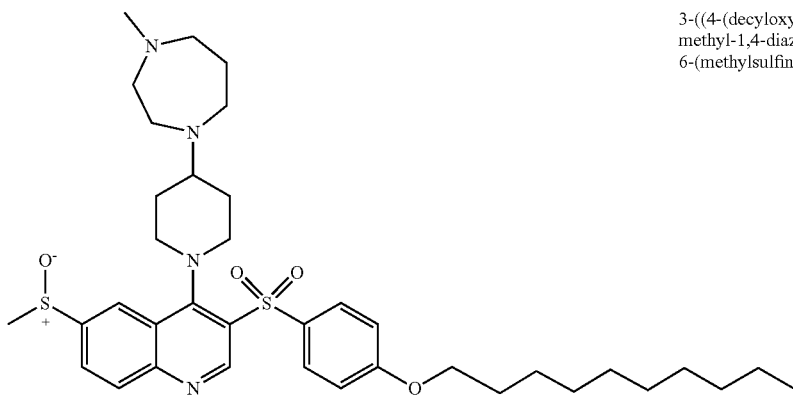 | 3-((4-(decyloxy)phenyl)sulfonyl)-4-(4-(4-methyl-1,4-diazepan-1-yl)piperidin-1-yl)-6-(methylsulfinyl)quinoline |
| 268 | 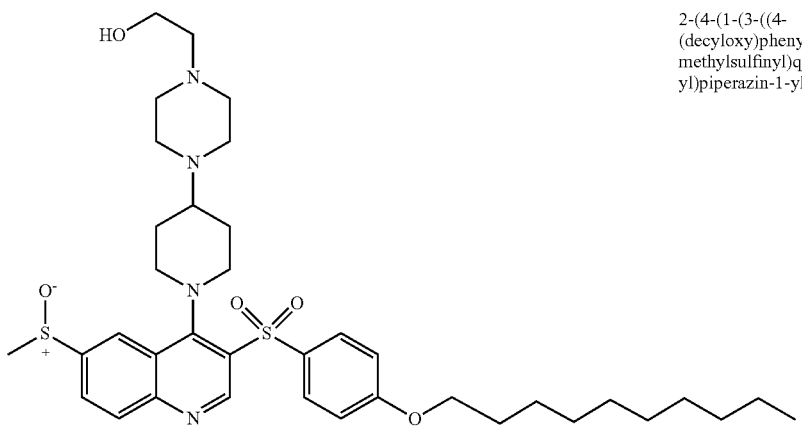 | 2-(4-(1-(3-((4-(decyloxy)phenyl)sulfonyl-6-methylsulfinyl)quinolin-4-yl)piperidin-4-yl)piperazin-1-yl)ethan-1-ol |

| | | |
|---|---|---|
| 269 | 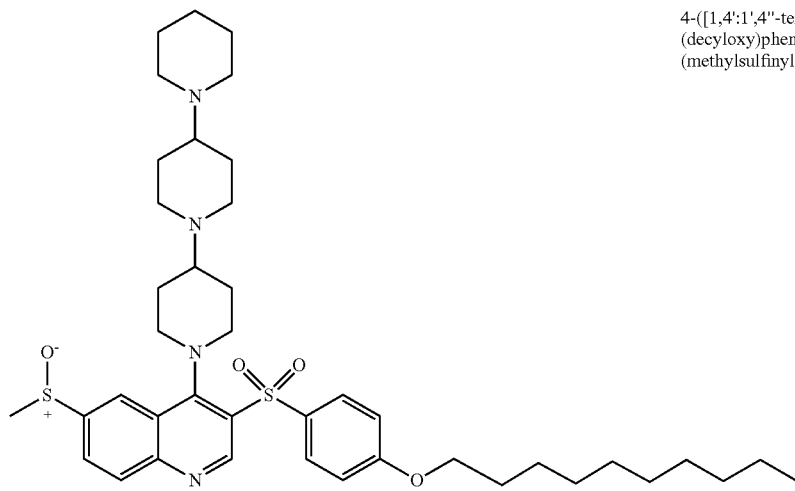 | 4-([1,4':1',4''-terpiperidin]-1''-yl)-3-((4-(decyloxy)phenyl)sulfonyl-6-(methylsulfinyl)quinoline |
| 270 | 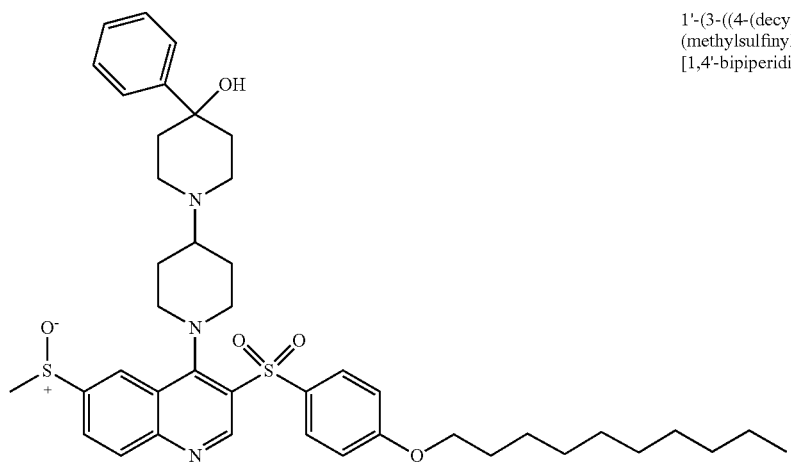 | 1'-(3-((4-(decyloxy)phenyl)sulfonyl)-6-(methylsulfinyl)quinolin-4-yl)-4-phenyl-[1,4'-bipiperidin]-4-ol |
| 271 | 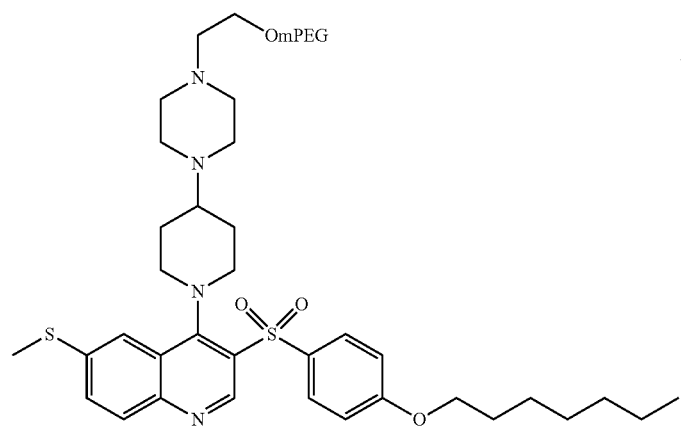 | 3-((4-(heptyloxy)phenyl)sulfonyl)-4-(4-(4-(2-mPEGoxyethyl)piperazin-1-yl)piperidin-1-yl)-6-(methylthio)quinoline |

-continued
272 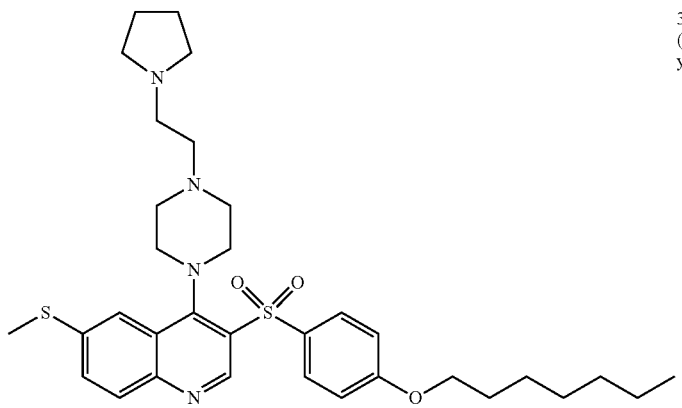 3-((4-(heptyloxy)phenyl)sulfonyl)-6-(methylthio)-4-(4-(2-(pyrrolidin-1-yl)ethyl)piperazin-1-yl)quinoline
273 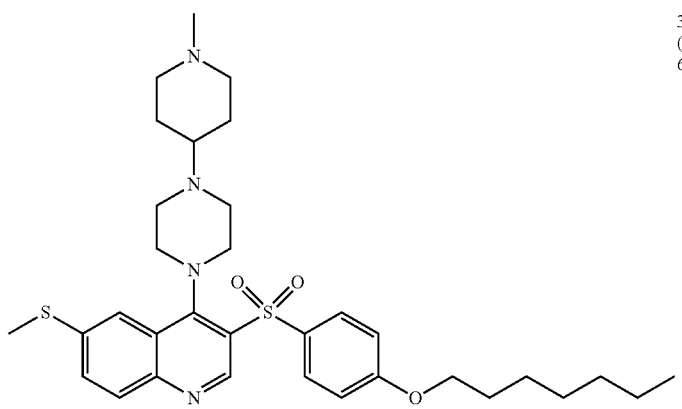 3-((4-(heptyloxy)phenyl)sulfonyl)-4-(4-(1-methylpiperidin-4-yl)piperazin-1-yl)-6-(methylthio)quinoline
274 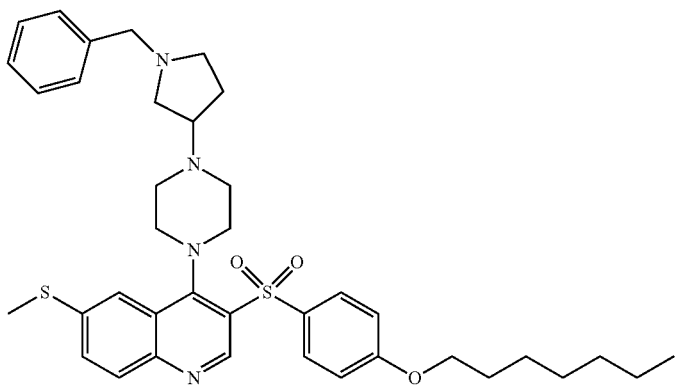 [SMILES: CCCCCCCOc1ccc(S(=O)(=O)c2cnc3ccc(SC)cc3c2N2CCN(C3CCN(Cc4ccccc4)C3)CC2)cc1] 4-(4-(1-benzylpyrrolidin-3-yl)piperazin-1-yl)-3-((4-(heptyloxy)phenyl)sulfonyl)-6-(methylthio)quinoline
275 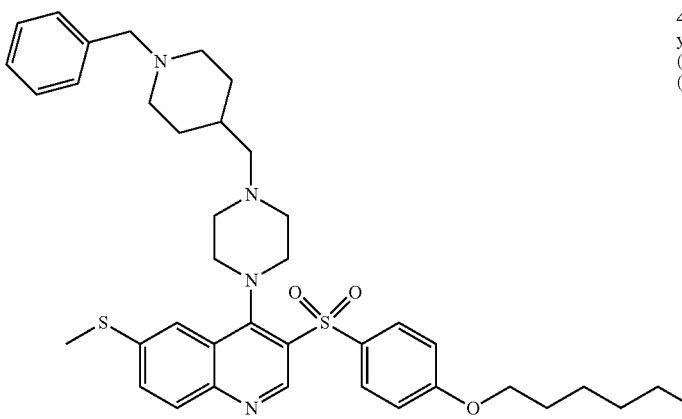 4-(4-((1-benzylpiperidin-4-yl)methyl)piperazin-1-yl)-3-((4-(heptyloxy)phenyl)sulfonyl)-6-(methylthio)quinoline

| | | |
|---|---|---|
| 276 | 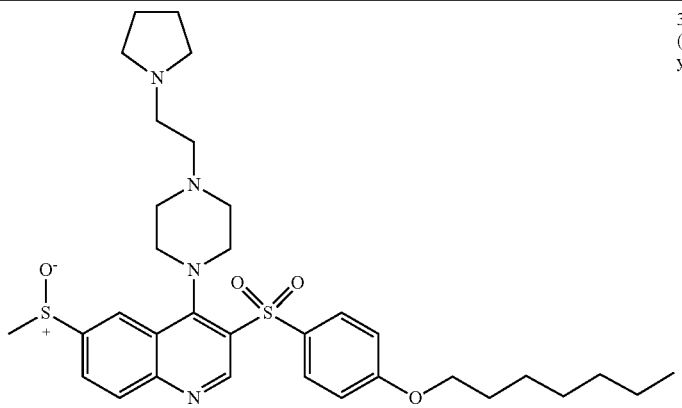 | 3-((4-(heptyloxy)phenyl)sulfonyl)-6-(methylsulfinyl)-4-(4-(2-(pyrrolidin-1-yl)ethyl)piperazin-1-yl)quinoline |
| 277 | 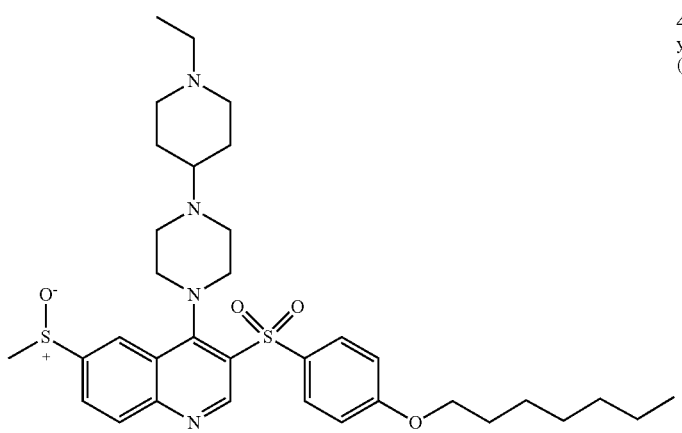 | 4-(4-(1-ethylpiperidin-4-yl)piperazin-1-yl)-3-((4-(heptyloxy)phenyl)sulfonyl)-6-(methylsulfinyl)quinoline |
| 278 | 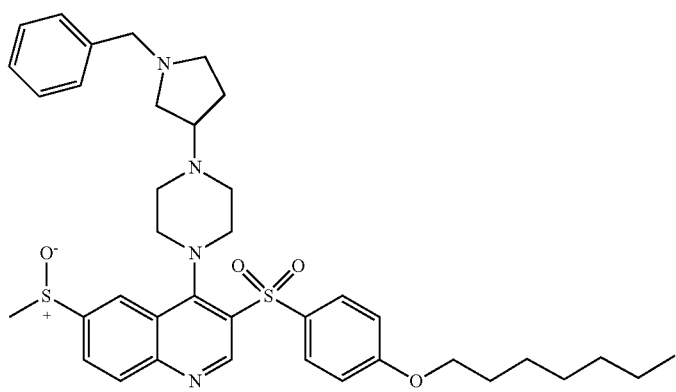 | 4-(4-(1-benzylpyrrolidin-3-yl)piperazin-1-yl)-3-((4-(heptyloxy)phenyl)sulfonyl)-6-(methylsulfinyl)quinoline |
| 279 | 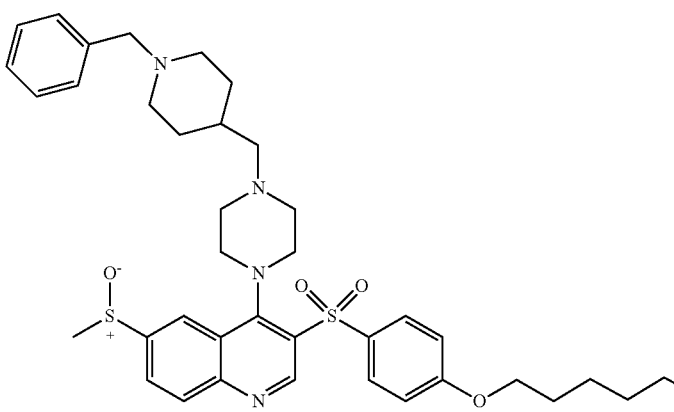 | 4-(4-((1-benzylpiperidin-4-yl)methyl)piperazin-1-yl)-3-((4-(heptyloxy)phenyl)sulfonyl)-6-(methylsulfinyl)quinoline |

| | | |
|---|---|---|
| 280 | 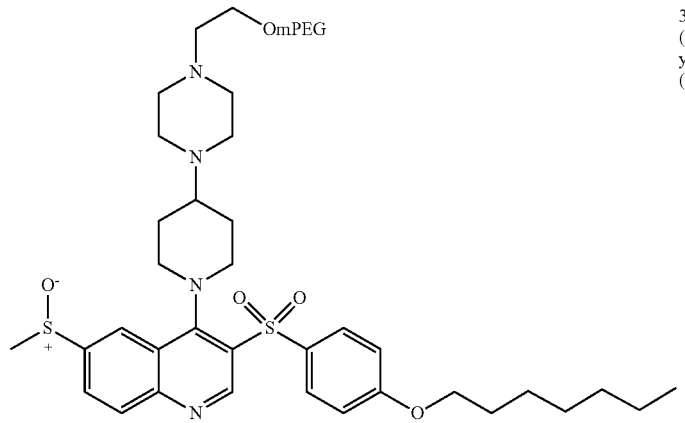 | 3-((4-(heptyloxy)phenyl)sulfonyl)-4-(4-(4-(2-mPEGoxyethyl)piperazin-1-yl)piperidin-1-yl)-6-(methylsulfinyl)quinoline |
| 281 | 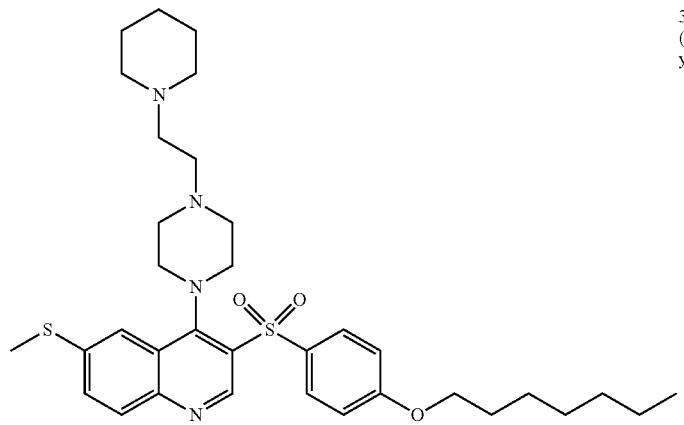 | 3-((4-(heptyloxy)phenyl)sulfonyl)-6-(methylthio)-4-(4-(2-(piperidin-1-yl)ethyl)piperazin-1-yl)quinoline |
| 282 | 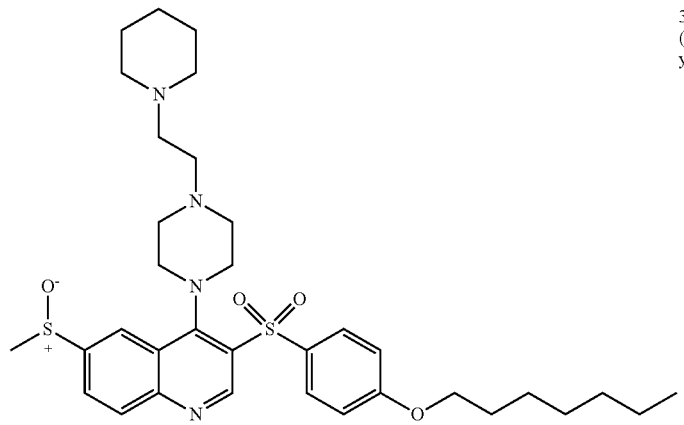 | 3-((4-(heptyloxy)phenyl)sulfonyl)-6-(methylsulfinyl)-4-(4-(2-(piperidin-1-yl)ethyl)piperazin-1-yl)quinoline |

283 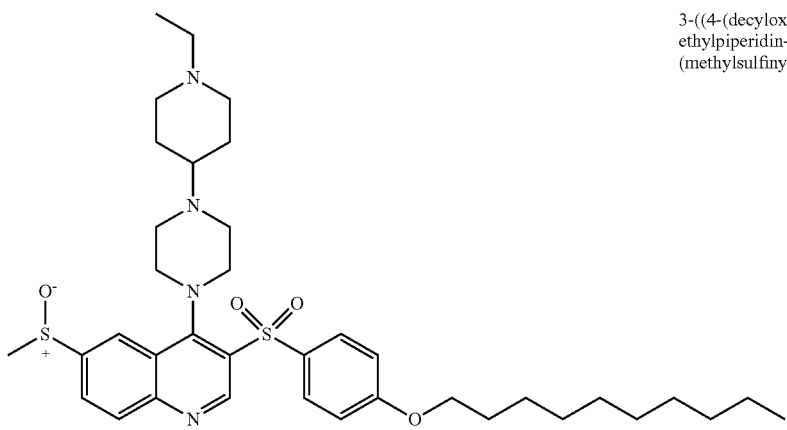 3-((4-(decyloxy)phenyl)sulfonyl)-4-(4-(1-ethylpiperidin-4-yl)piperazin-1-yl)-6-(methylsulfinyl)quinoline
284 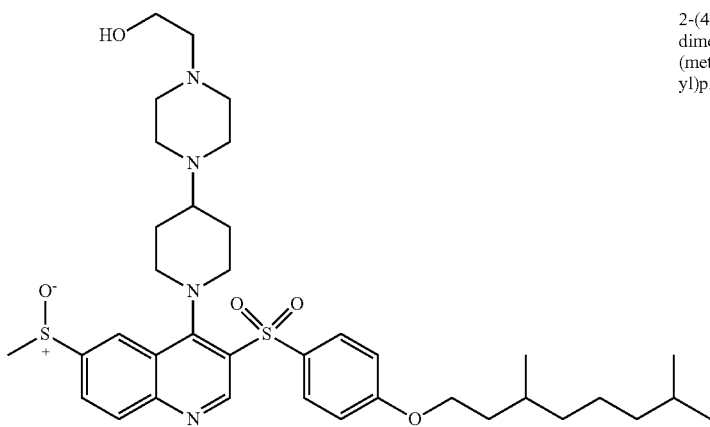 2-(4-(1-(3-((4-((3,7-dimethyloctyl)oxy)phenyl)sulfonyl)-6-(methylsulfinyl)quinolin-4-yl)piperidin-4-yl)piperazin-1-yl)ethan-1-ol
285 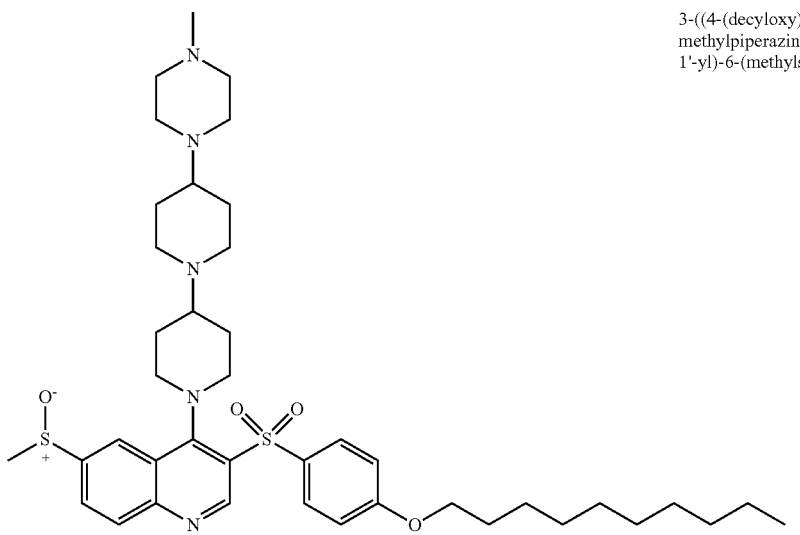 3-((4-(decyloxy)phenyl)sulfonyl)-4-(4-(4-methylpiperazin-1-yl)-[1,4'-bipiperidin]-1'-yl)-6-(methylsulfinyl)quinoline

| | | |
|---|---|---|
| 286 | 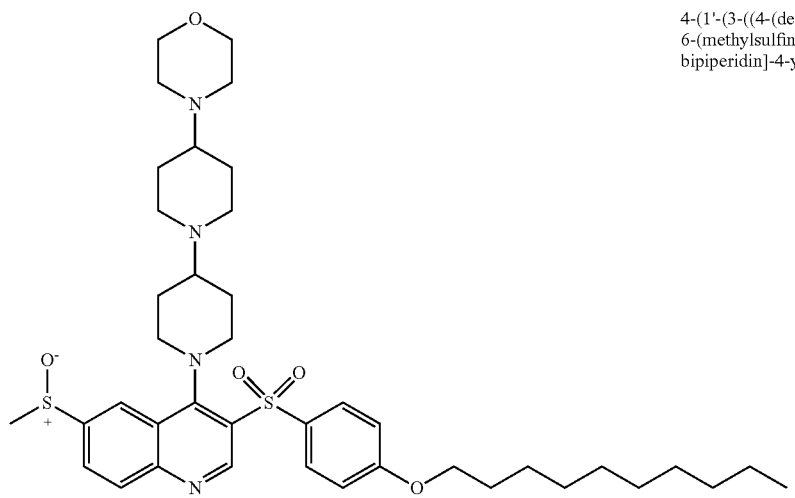 | 4-(1'-(3-((4-(decyloxy)phenyl)sulfonyl)-6-(methylsulfinyl)quinolin-4-yl)-[1,4'-bipiperidin]-4-yl)morpholine |
| 287 | 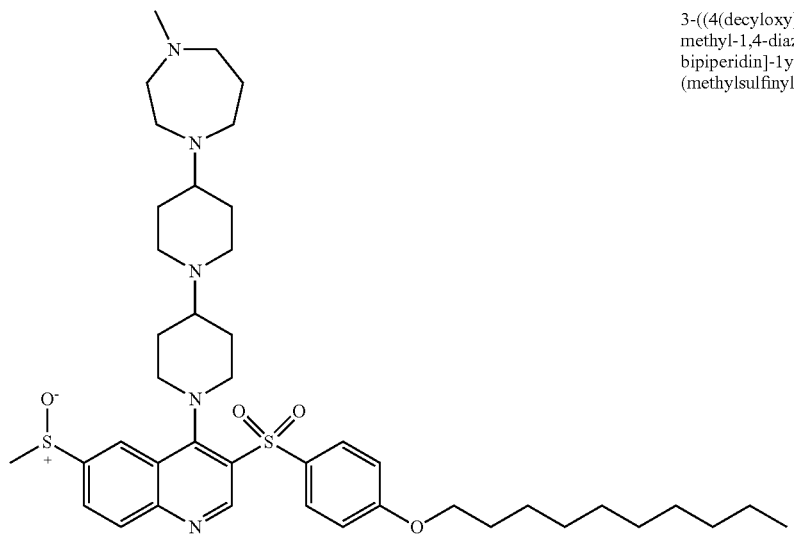 | 3-((4(decyloxy)phenyl)sulfonyl)-4-(4-(4-methyl-1,4-diazepan-1-yl)-[1,4'-bipiperidin]-1yl)-6-(methylsulfinyl)quinoline |
| 288 | 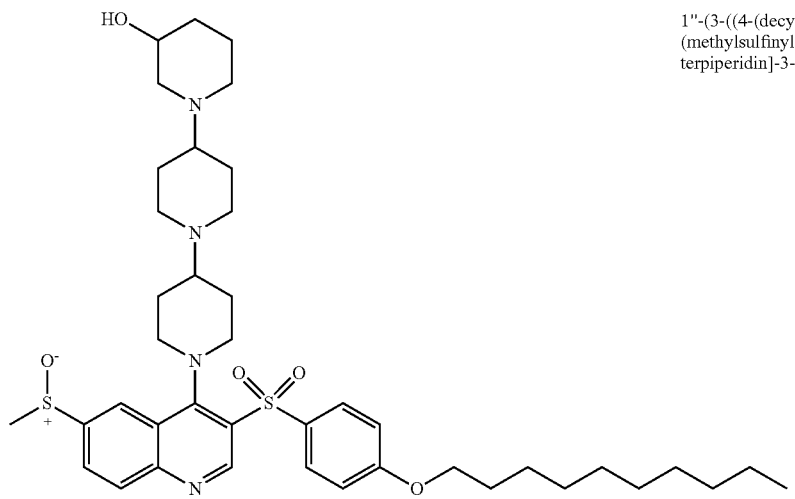 | 1''-(3-((4-(decyloxy)phenyl)sulfonyl)-6-(methylsulfinyl)quinolin-4-yl-[1,4':1',4''-terpiperidin]-3-ol |

| | | |
|---|---|---|
| 289 | 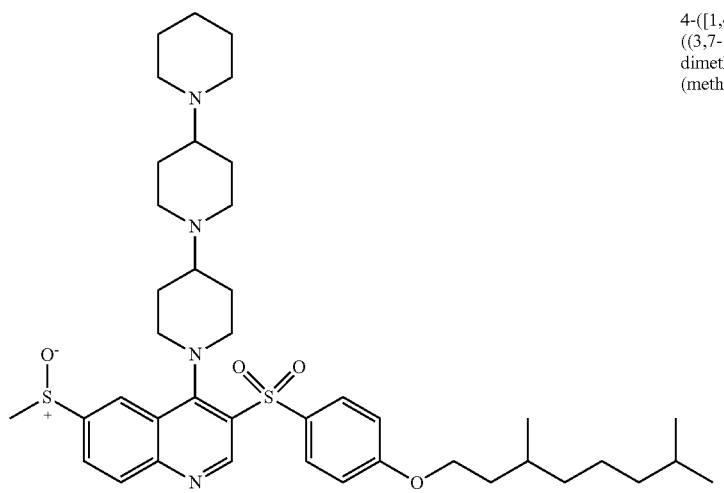 | 4-([1,4':1,4''-terpiperidin]-1''-yl)-3-((4-((3,7-dimethyloctyl)oxy)phenyl)sulfonyl)-6-(methylsulfinyl)quinoline |
| 290 | 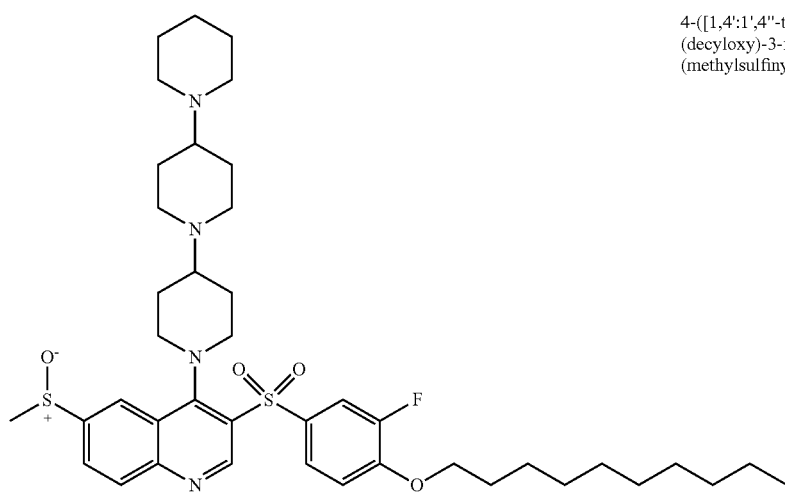 | 4-([1,4':1',4''-terpiperidin]-1''-yl)-3-((4-(decyloxy)-3-fluorophenyl)sulfonyl)-6-(methylsulfinyl)quinoline |
| 291 | 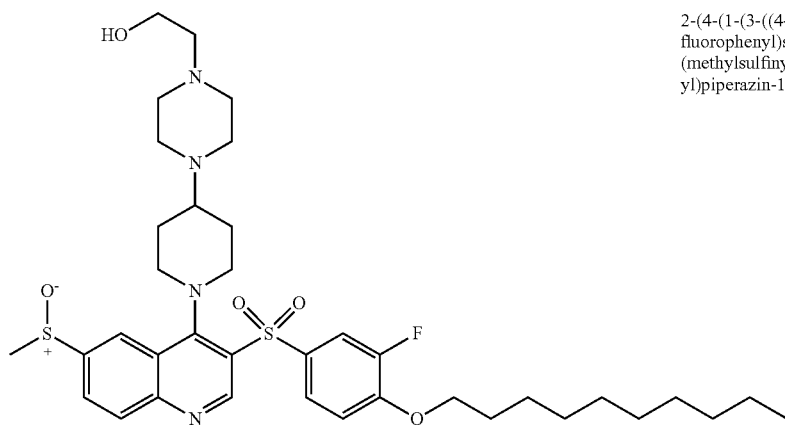 | 2-(4-(1-(3-((4-(decyloxy)-3-fluorophenyl)sulfonyl)-6-(methylsulfinyl)quinolin-4-yl)piperidin-4-yl)piperazin-1-yl)ethan-1-ol |

-continued

| | | |
|---|---|---|
| 292 | 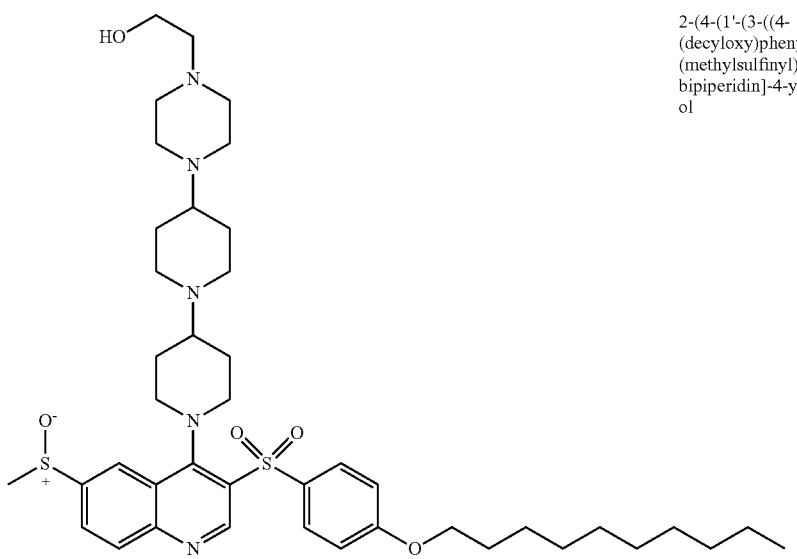 | 2-(4-(1'-(3-((4-(decyloxy)phenyl)sulfonyl-6-(methylsulfinyl)quinolin-4-yl)-[1,4'-bipiperidin]-4-yl)piperazin-1-yl)ethan-1-ol |
| 293 | 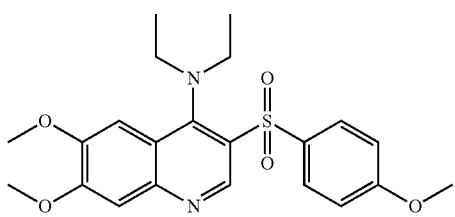 | N,N-diethyl)l-6,7-dimethoxy-3-((4-methoxyphenyl)sulfonyl)quinolin-amine |
| 294 | 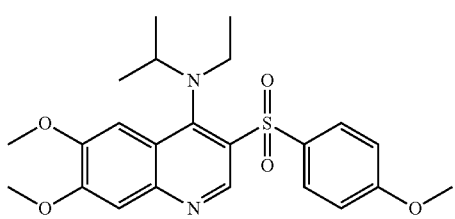 | N-ethyl-N-isopropyl-6,7-dimethoxy-3-((4-methoxyphenyl)sulfonyl)quinolin-4-amine |
| 295 | 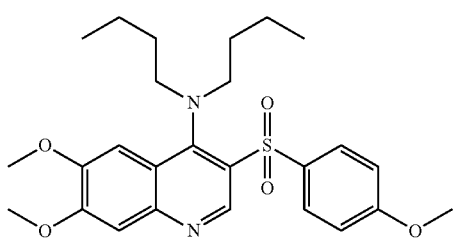 | N,N-dibutyl-6,7-dimethoxy-3-((4-methoxyphenyl)sulfonyl)quinolin-4-amine |
| 296 | 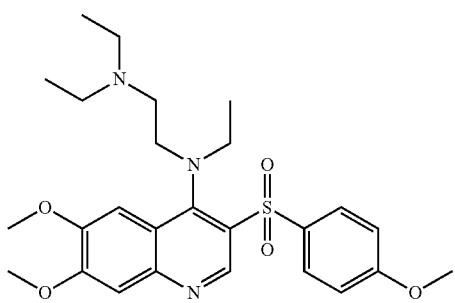 | N1-(6,7-dimethoxy-3-((4-methoxyphenyl)sulfonyl)quinolin-4-yl)-N1,N2,N2-triethylethane-1,2-diamine |

| | | |
|---|---|---|
| 297 | 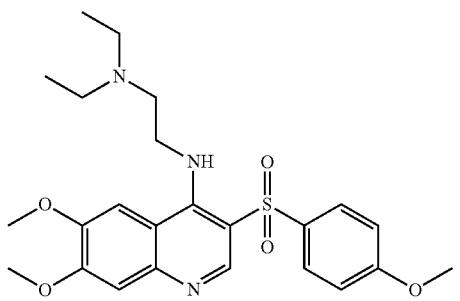 | N1-(6,7-dimethoxy-3-((4-methoxyphenyl)sulfonyl)quinolin-4-yl)-N2,N2-diethyl)ethane-1,2-diamine |
| 298 | 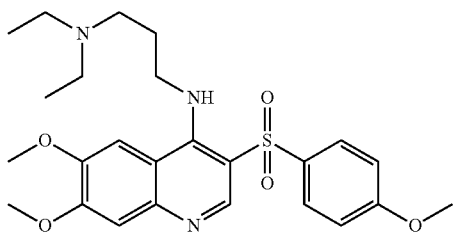 | N1-(6,7-dimethoxy-3-((4-methoxyphenyl)sulfonyl)quinolin-4-yl)-N3,N3-diethyl]propane-1,3-diamine |
| 299 | 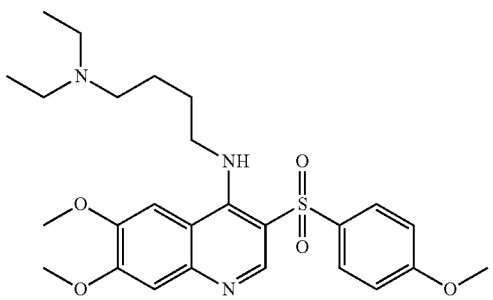 [SMILES: CCN(CC)CCCCNc1c(S(=O)(=O)c2ccc(OC)cc2)cnc2cc(OC)c(OC)cc12] | N1-(6,7-dimethoxy-3-((4-methoxyphenyl)sulfonyl)quinolin-4-yl)-N4,N4-diethyl]butane-1,4-diamine |
| 300 | 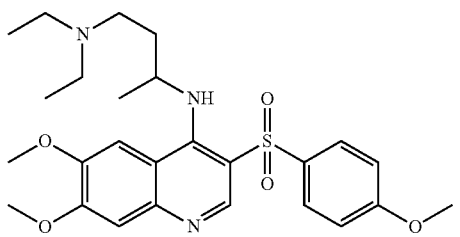 | N3-(6,7-dimethoxy-3-((4-methoxyphenyl)sulfonyl)quinolin-4-yl)-N1,N1-diethyl]butane-1,3-diamine |
| 301 | 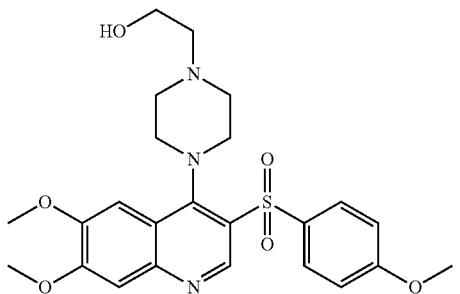 | 2-(4-(6,7-dimethoxy-3-((4-methoxyphenyl)sulfonyl)quinolin-4-yl)piperazin-1-yl)ethan-1-ol |

| | | |
|---|---|---|
| 302 | 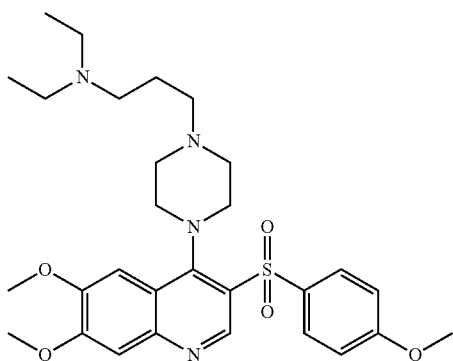 | 3-(4-(6,7-dimethoxy-3-((4-methoxyphenyl)sulfonyl)quinolin-4-yl)piperazin-1-yl)-N,N-diethyl)propan-1-amine |
| 303 | 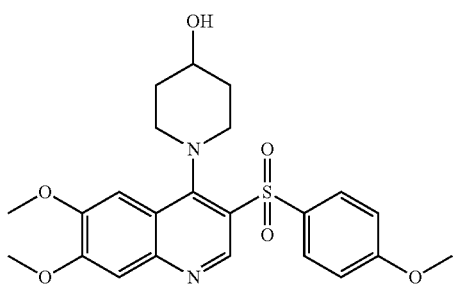 | 1-(6,7-dimethoxy-3-((4-methoxyphenyl)sulfonyl)quinolin-4-yl)piperidin-4-ol |
| 304 | 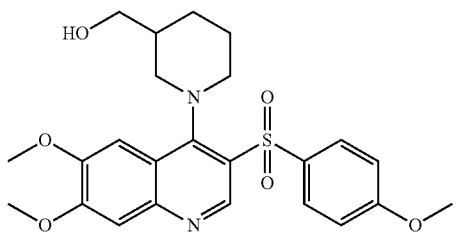 | (1-(6,7-dimethoxy-3-((4-methoxyphenyl)sulfonyl)quinolin-4-yl)piperidin-3-yl)methanol |
| 305 | 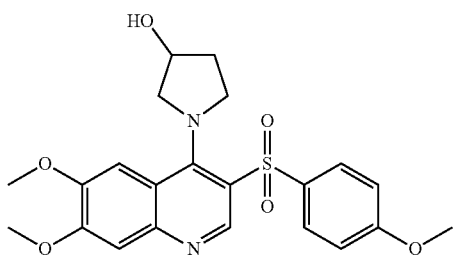 | 1-(6,7-dimethoxy-3-((4-methoxyphenyl)sulfonyl)quinolin-4-yl)pyrrolidin-3-ol |
| 306 | 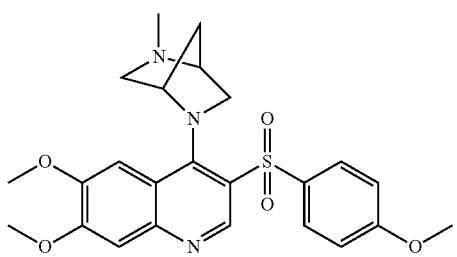 | 6,7-dimethoxy-3-((4-methoxyphenyl)sulfonyl)-4-((1S,4S)-5-methyl-2,5-diazabicyclo[2,2,1]heptan-2-yl)quinoline |

| | | |
|---|---|---|
| 307 | 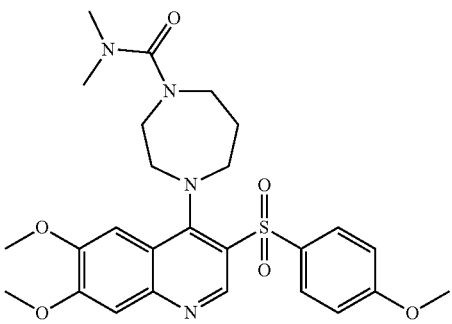 | 4-(6,7-dimethoxy-3-((4-methoxyphenyl)sulfonyl)quinolin-4-yl)-N,N-dimethyl-1,4-diazepane-1-carboxamide |
| 308 | 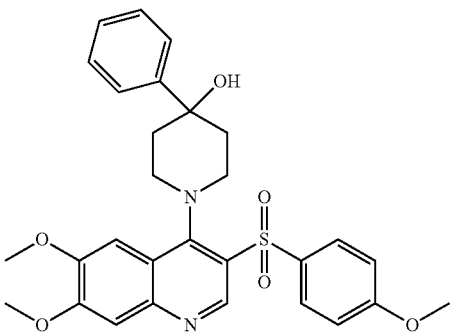 | 1-(6,7-dimethoxy-3-((4-methoxyphenyl)sulfonyl)quinolin-4-yl)-4-phenylpiperidin-4-ol |
| 309 | 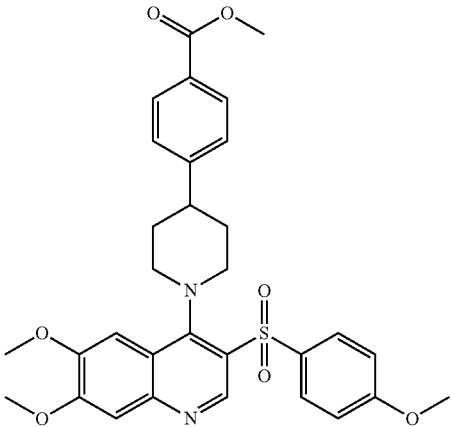 | methyl 4-(1-(6,7-dimethoxy-3-((4-methoxyphenyl)sulfonyl)quinolin-4-yl)piperidin-4-yl)benzoate |
| 310 | 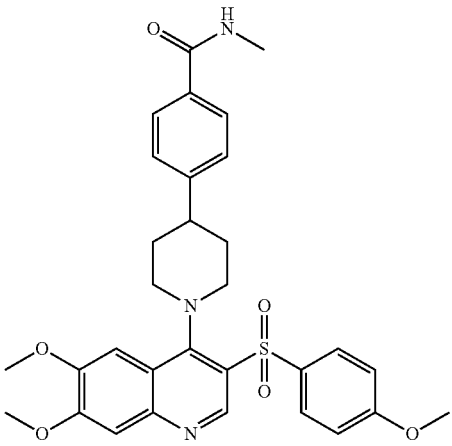 | 4-(1-(6,7-dimethoxy-3-((4-methoxyphenyl)sulfonyl)quinolin-4-yl)piperidin-4-yl)-N-methylbenzamide |

-continued
| | | |
|---|---|---|
| 311 | 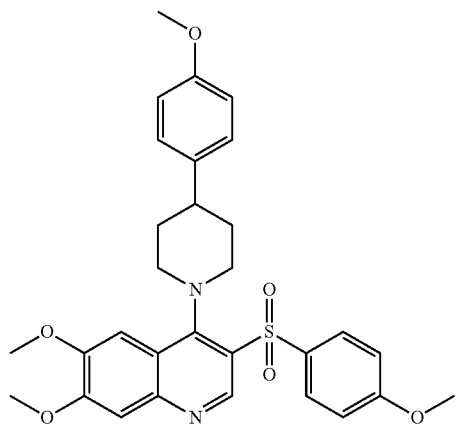 | 6,7-dimethoxy-4-(4-(4-methoxyphenyl)piperidin-1-yl)-3-((4-methoxyphenyl)sulfonyl)quinoline |
| 312 | 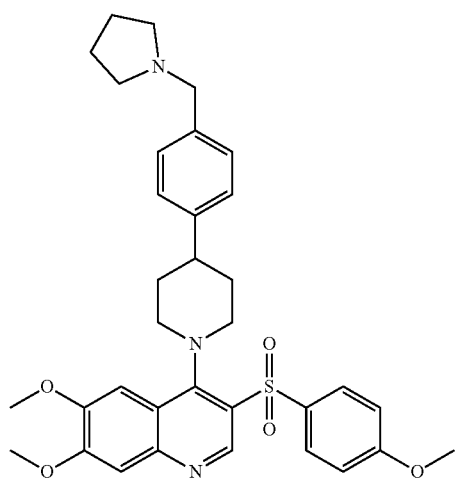 | 6,7-dimethoxy-3-((4-methoxyphenyl)sulfonyl)-4-(4-(4-(pyrrolidin-1-ylmethyl)phenyl)piperidin-1-yl)quinoline |
| 313 | 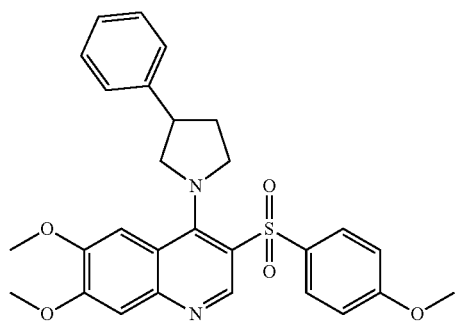 | 6,7-dimethoxy-3-((4-methoxyphenyl)sulfonyl)-4-(3-phenylpyrrolidin-1-yl)quinoline |
| 314 | 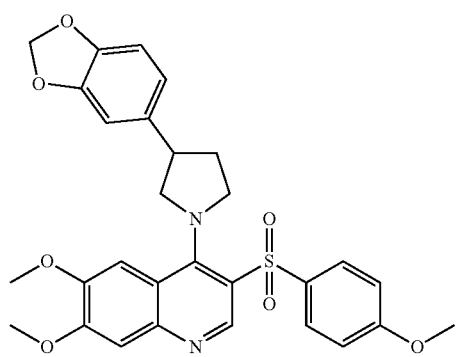 | 4-(3-(benzo[d][1,3]dioxol-5-yl)pyrrolidin-1-yl)-6,7-dimethoxy-3-((4-methoxyphenyl)sulfonyl)quinoline |

| | | |
|---|---|---|
| 315 | 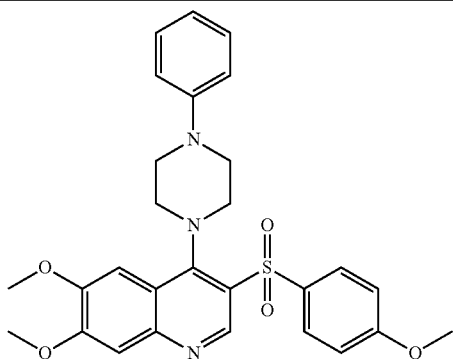 | 6,7-dimethoxy-3-((4-methoxyphenyl)sulfonyl)-4-(4-phenylpiperazin-1-yl)quinoline |
| 316 | 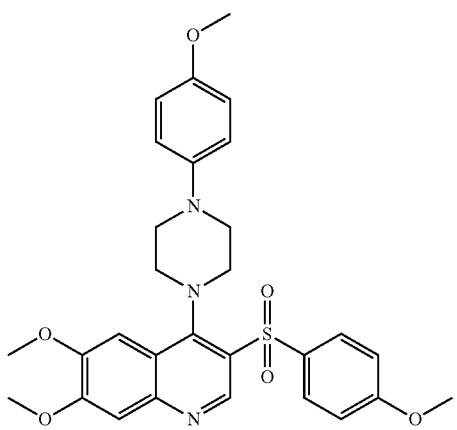 | 6,7-dimethoxy-4-(4-(4-methoxyphenyl)piperazin-1-yl)-3-((4-methoxyphenyl)sulfonyl)quinoline |
| 317 | 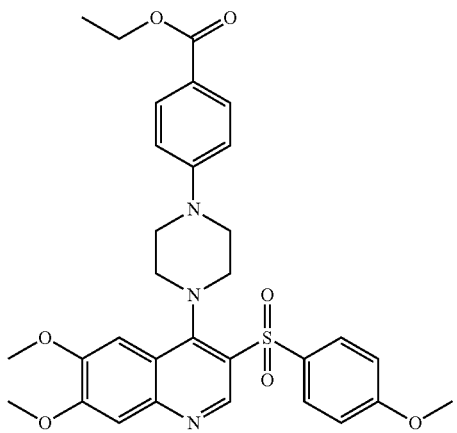 | ethyl 4-(4-(6,7-dimethoxy-3-((4-methoxyphenyl)sulfonyl)quinolin-4-yl)piperazin-1-yl)benzoate |
| 318 | 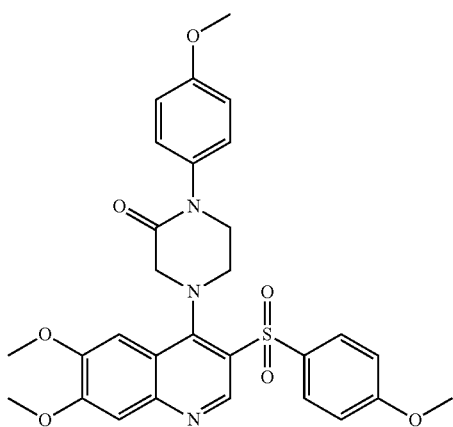 | 4-(6,7-dimethoxy-3-((4-methoxyphenyl)sulfonyl)quinolin-4-yl)-1-(4-methoxyphenyl)piperazin-2-one |

| | | |
|---|---|---|
| 319 | 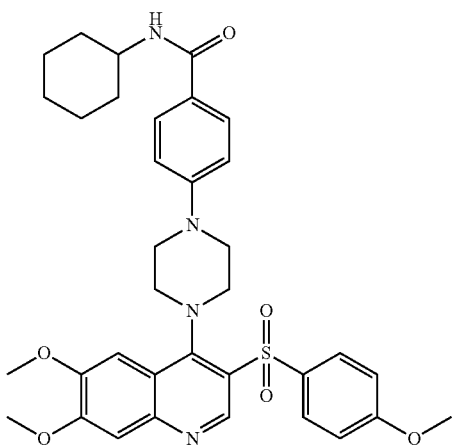 | N-cyclohexyl-4-(4-(6,7-dimethoxy-3-((4-methoxyphenyl)sulfonyl)quinolin-4-yl)piperazin-1-yl)benzamide |
| 320 | 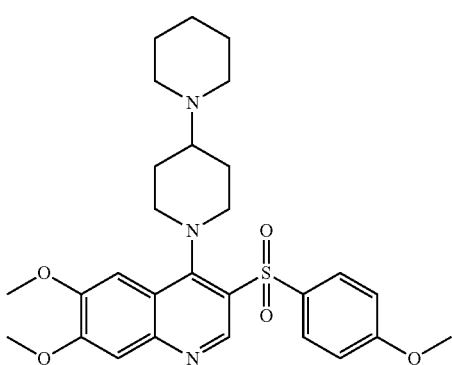 | 4-([1,4'-bipiperidin]-1'-yl)-6,7-dimethoxy-3-((4-methoxyphenyl)sulfonyl)quinoline |
| 321 | 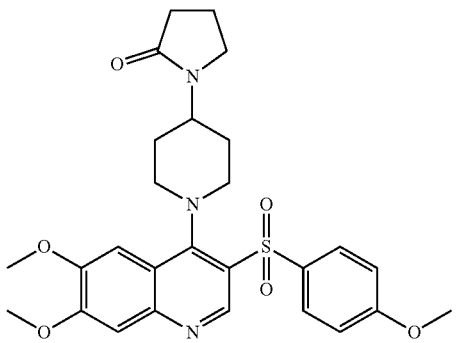 | 1-(1-(6,7-dimethoxy-3-((4-methoxyphenyl)sulfonyl)quinolin-4-yl)piperidin-4-yl)pyrrolidin-2-one |
| 322 | 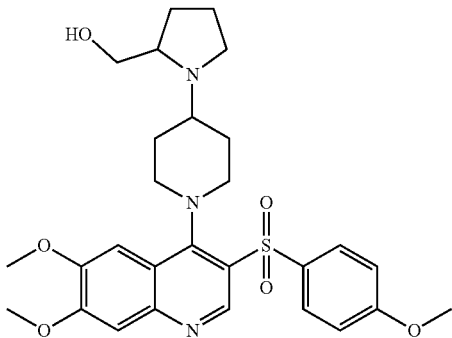 | (1-(1-(6,7-dimethoxy-3-((4-methoxyphenyl)sulfonyl)quinolin-4-yl)piperidin-4-yl)pyrrolidin-2-yl)methanol |

-continued

| | | |
|---|---|---|
| 323 | 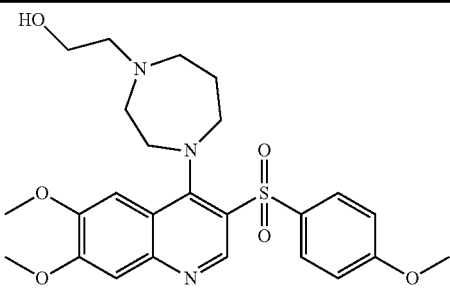 | 2-(4-(6,7-dimethoxy-3-((4-methoxyphenyl)sulfonyl)quinolin-4-yl)-1,4-diazepan-1-yl)ethan-1-ol |
| 324 | 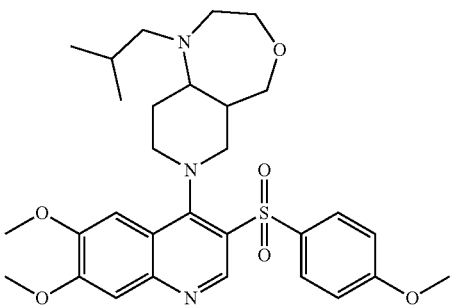 | 7-(6,7-dimethoxy-3-((4-methoxyphenyl)sulfonyl)quinolin-4-yl)-1-isobutyldecahydropyrido[4,3-e][1,4]oxazepine |
| 325 | 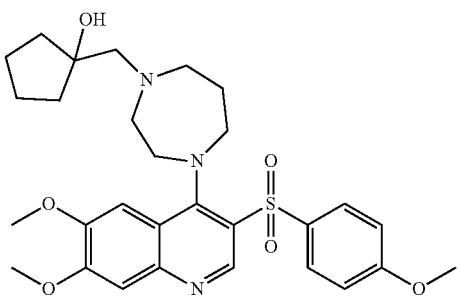 [SMILES: COc1ccc(S(=O)(=O)c2cnc3cc(OC)c(OC)cc3c2N2CCCN(CC3(O)CCCC3)CC2)cc1] | 1-((4-(6,7-dimethoxy-3-((4-methoxyphenyl)sulfonyl)quinolin-4-yl)-1,4-diazepan-1-yl)methyl)cyclopentan-1-ol |
| 326 | 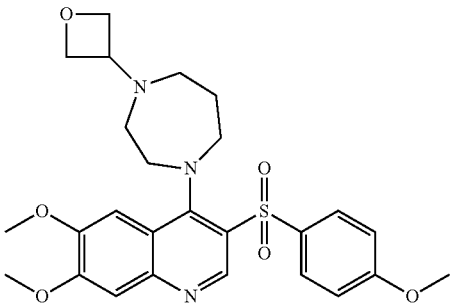 | 6,7-dimethoxy-3-((4-methoxyphenyl)sulfonyl)-4-(4-(oxelan-3-yl)-1,4-diaxepan-1-yl)quinoline |
| 327 | 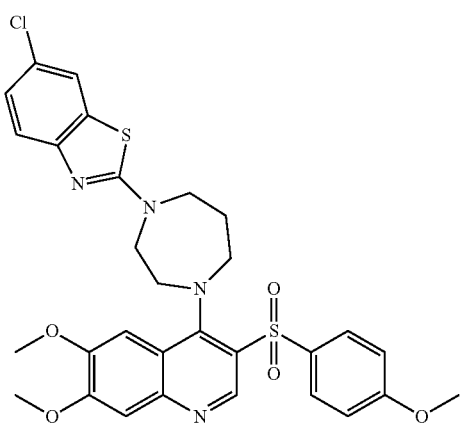 [SMILES: COc1ccc(S(=O)(=O)c2cnc3cc(OC)c(OC)cc3c2N2CCCN(c3nc4ccc(Cl)cc4s3)CC2)cc1] | 6-chloro-2-(4-(6,7-dimethoxy-3-((4-methoxyphenyl)sulfonyl)quinolin-4-yl)-1,4-diazepan-1-yl)benzo[d]thiazole |

| | | -continued | |
|---|---|---|---|
| 328 | 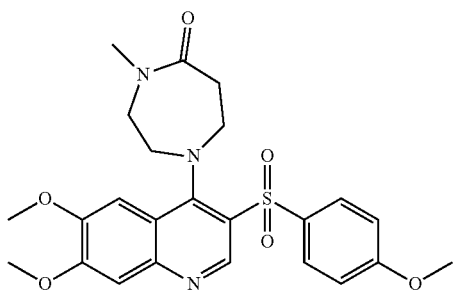 | | 1-(6,7-dimethoxy-3-((4-methoxyphenyl)sulfonyl)quinolin-4-yl)-4-methyl-1,4-diazepan-5-one |
| 329 | 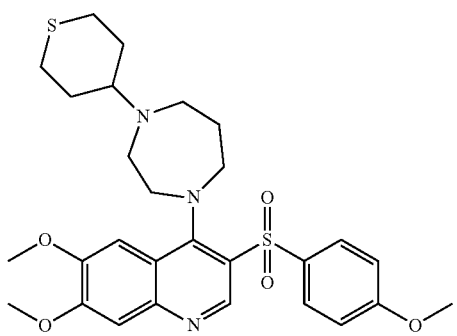 | | 6,7-dimethoxy-3-((4-methoxyphenyl)sulfonyl)-4-(4-(tetrahydro-2H-thiopyran-4-yl)-1,4-diazepan-1-yl)quinoline |
| 330 | 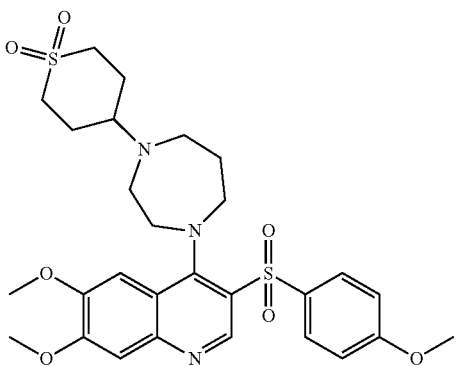 | | 4-(4-(6,7-dimethoxy-3-((4-methoxyphenyl)sulfonyl)quinolin-4-yl)-1,4-diazepan-1-yl)tetrahydro-2H-thiopyran 1,1-dioxide |
| 331 | 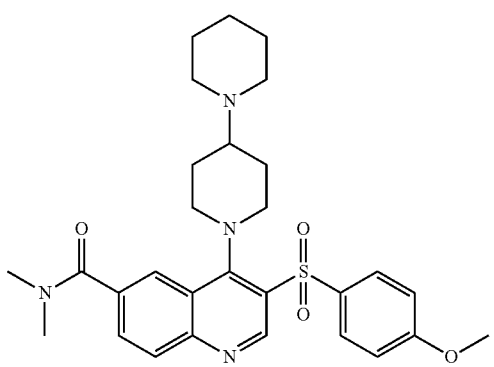 | | 4-([1,4'-bipiperidin]-1'-yl)-3-((4-methoxyphenyl)sulfonyl)-N,N-dimethylquinoline-6-carboxamide |

-continued

| | | |
|---|---|---|
| 332 | 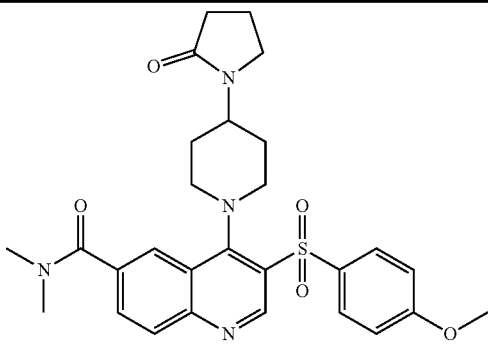 | 3-((4-methoxyphenyl)sulfonyl)-N,N-dimethyl-4-(4-(2-oxopyrrolidin-1-yl)piperidin-1-yl)quinoline-6-carboxamid |
| 333 | 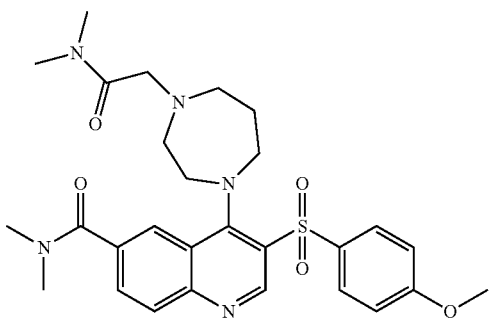 | 4-(4-(2-(dimethylamino)-2-oxoethyl)-1,4-diazepan-1-yl)-3-((4-methoxyphenyl)sulfonyl)-N,N-dimethyl)quinoline-6-carboxamide |
| 334 | 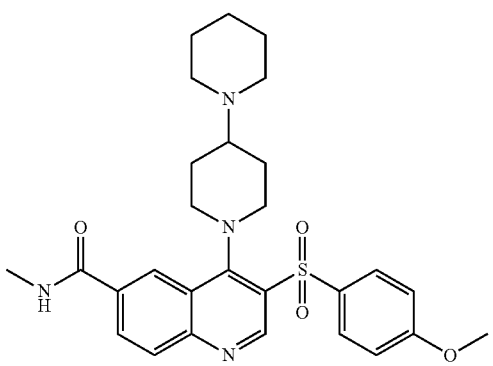 | 4-([1,4'-bipiperidin]-1'-yl)-3-((4-methoxyphenyl)sulfonyl)-N-methylquinoline-6-carboxamide |
| 335 | 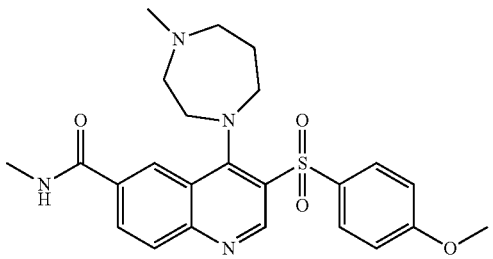 | 3-((4-methoxyphenyl)sulfonyl)-N-methyl-4-(4-methyl-1,4-diazepan-1-yl)quinoline-6-carboxamide |
| 336 | 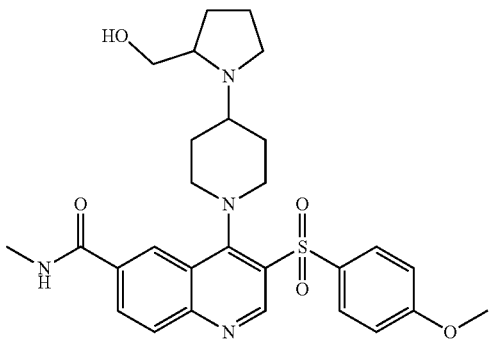 | 4-(4-(2-(hydroxymethyl)pyrrolidin-1-yl)piperidin-1-yl)-3-((4-methoxyphenyl)sulfonyl)-N-methylquinoline-6-carboxamide |

| | | |
|---|---|---|
| 337 | 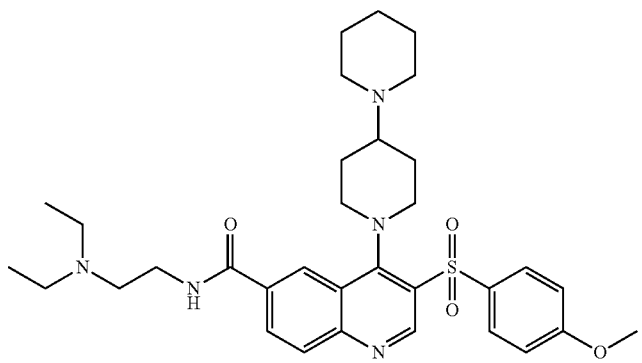 [SMILES: CCN(CC)CCNC(=O)c1ccc2ncc(S(=O)(=O)c3ccc(OC)cc3)c(N3CCC(N4CCCCC4)CC3)c2c1] | 4([1,4'-bipiperidin]-1'-yl)-N-(2-(diethyl)lamino)ethyl)-3-((4-methoxyphenyl)sulfonyl)quinoline-6-carboxamide |
| 338 | 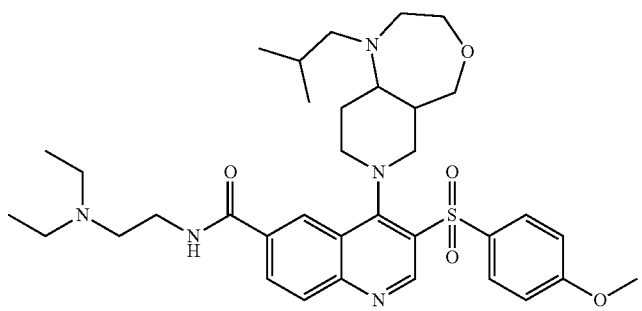 [SMILES: CCN(CC)CCNC(=O)c1ccc2ncc(S(=O)(=O)c3ccc(OC)cc3)c(N3CCC4C(COCCN4CC(C)C)C3)c2c1] | N-(2-(diethyl)lamino)ethyl)-4-(1-isobutyloctahydropyrido[4,3-e][1,4]oxazepin-7(5H)-yl)-3-((4-methoxyphenyl)sulfonyl)quinoline-6-carboxamide |
| 339 | 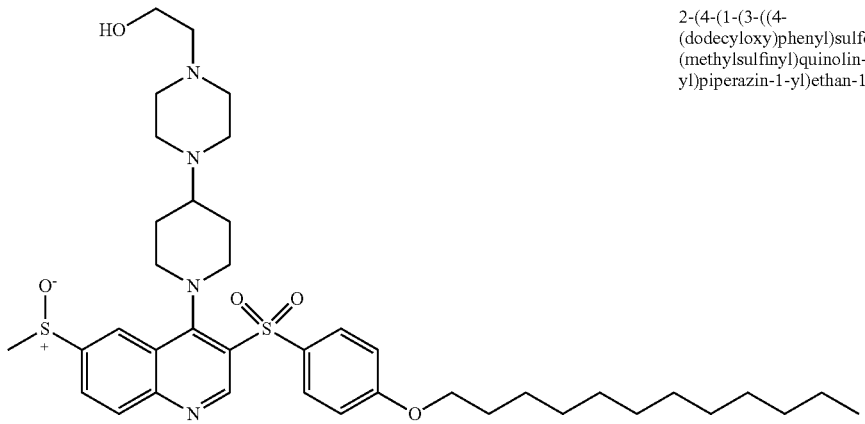 | 2-(4-(1-(3-((4-(dodecyloxy)phenyl)sulfonyl)-6-(methylsulfinyl)quinolin-4-yl)piperidin-4-yl)piperazin-1-yl)ethan-1-ol |
| 340 | 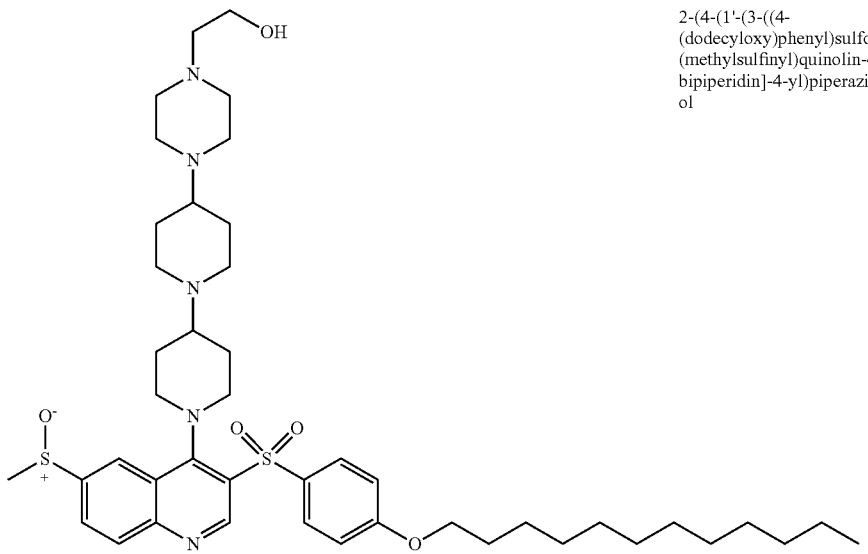 | 2-(4-(1'-(3-((4-(dodecyloxy)phenyl)sulfonyl)-6-(methylsulfinyl)quinolin-4-yl)-[1,4'-bipiperidin]-4-yl)piperazin-1-yl)ethan-1-ol |

-continued
| | | |
|---|---|---|
| 341 | 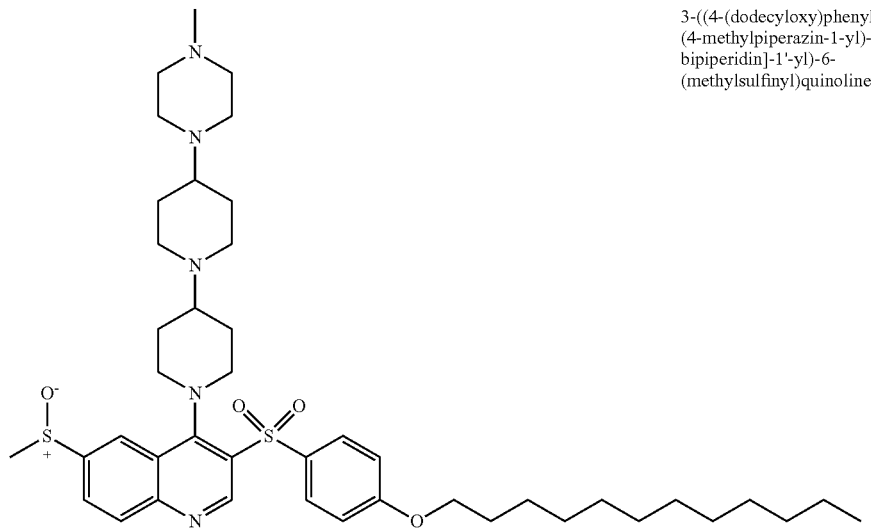 | 3-((4-(dodecyloxy)phenyl)sulfonyl)-4-(4-(4-methylpiperazin-1-yl)-[1,4'-bipiperidin]-1'-yl)-6-(methylsulfinyl)quinoline |
| 342 | 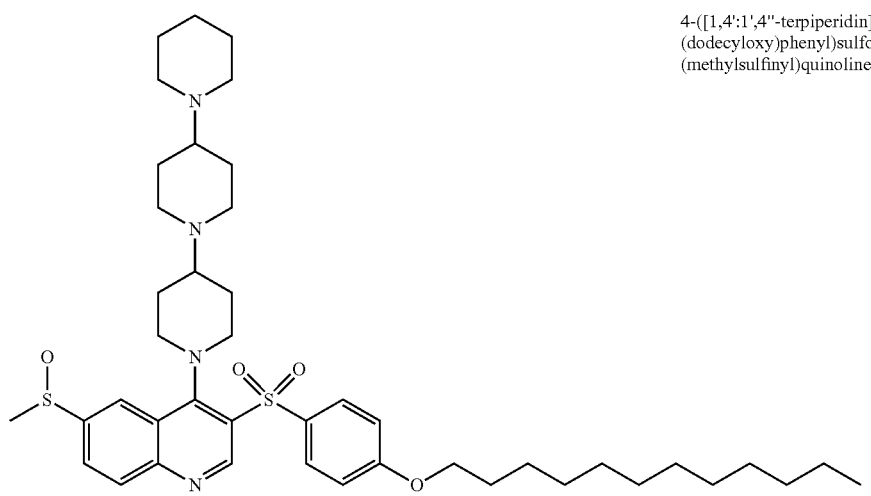 | 4-([1,4':1',4''-terpiperidin]-1''-yl)-3-((4-(dodecyloxy)phenyl)sulfonyl)-6-(methylsulfinyl)quinoline |
| 343 | 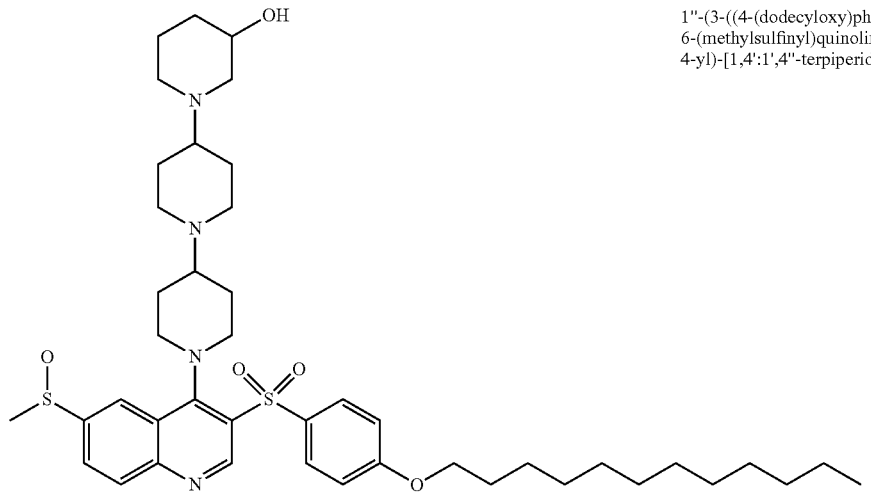 | 1''-(3-((4-(dodecyloxy)phenyl)sulfonyl)-6-(methylsulfinyl)quinolin-4-yl)-[1,4':1',4''-terpiperidin]-3-ol |

| | | |
|---|---|---|
| 344 | 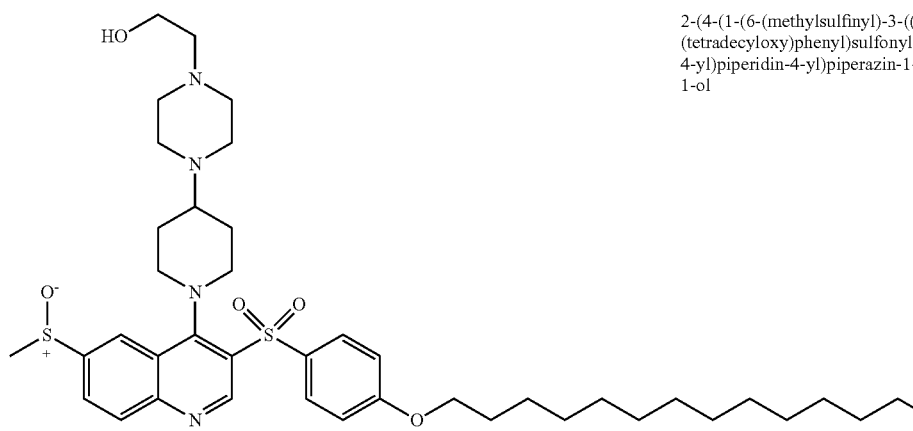 | 2-(4-(1-(6-(methylsulfinyl)-3-((4-(tetradecyloxy)phenyl)sulfonyl)quinolin-4-yl)piperidin-4-yl)piperazin-1-yl)ethan-1-ol |
| 345 | 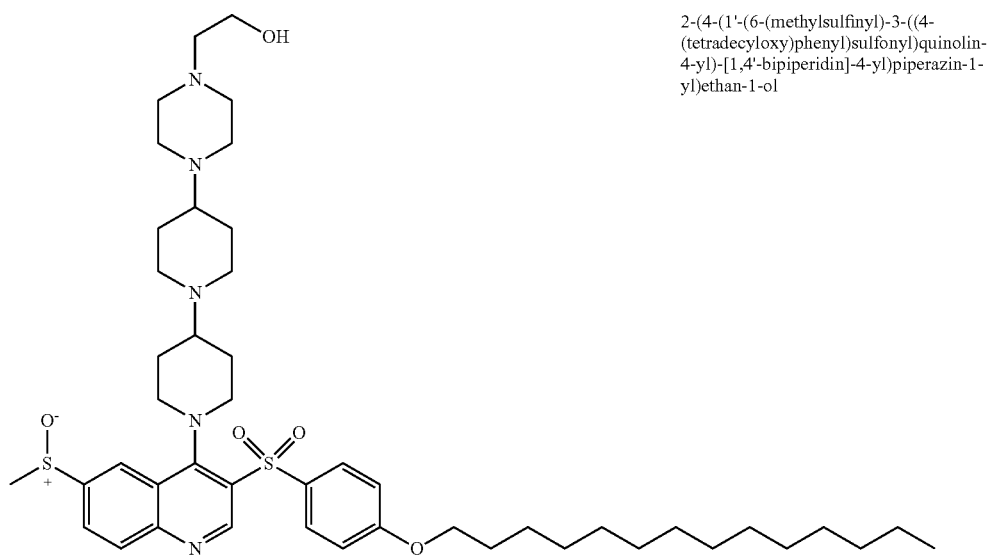 | 2-(4-(1'-(6-(methylsulfinyl)-3-((4-(tetradecyloxy)phenyl)sulfonyl)quinolin-4-yl)-[1,4'-bipiperidin]-4-yl)piperazin-1-yl)ethan-1-ol |
| 346 | 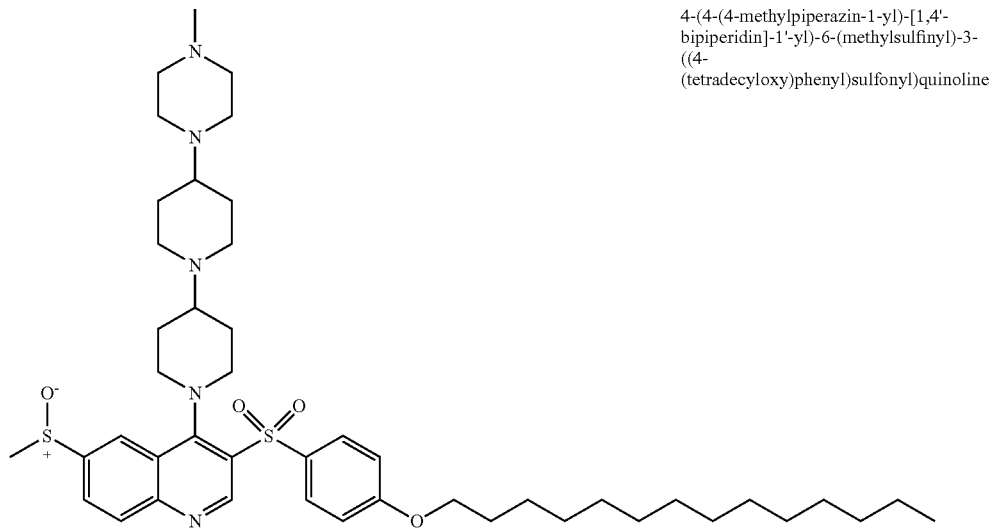 | 4-(4-(4-methylpiperazin-1-yl)-[1,4'-bipiperidin]-1'-yl)-6-(methylsulfinyl)-3-((4-(tetradecyloxy)phenyl)sulfonyl)quinoline |

| | | |
|---|---|---|
| 347 | 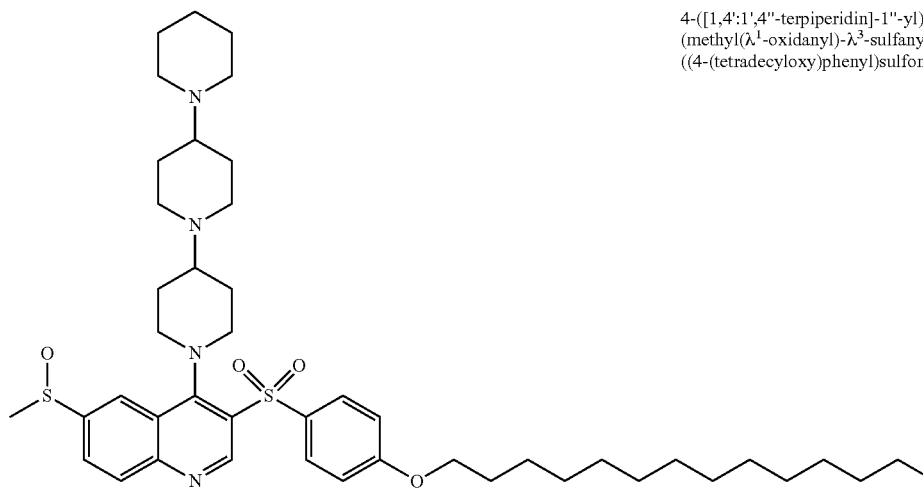 | 4-([1,4':1',4''-terpiperidin]-1''-yl)-6-(methyl(λ¹-oxidanyl)-λ³-sulfanyl)-3-((4-(tetradecyloxy)phenyl)sulfonyl)quinoline |
| 348 | 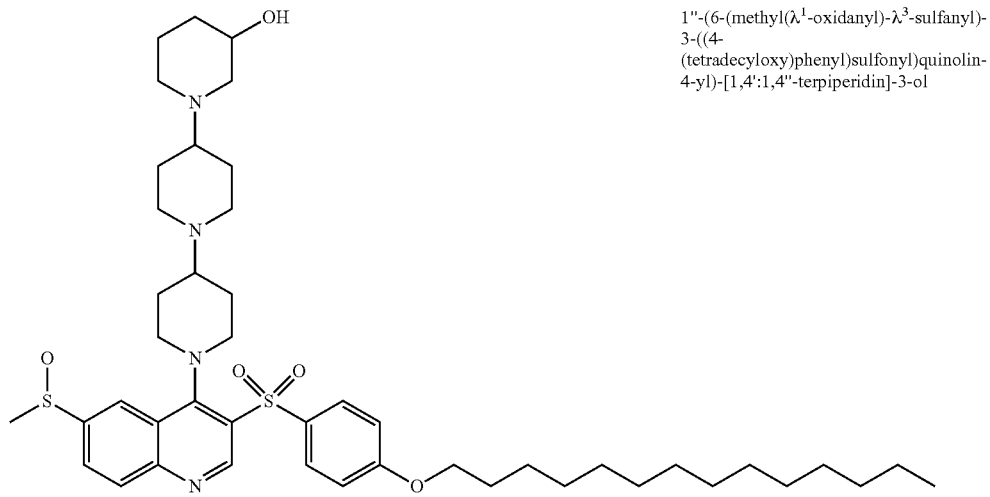 | 1''-(6-(methyl(λ¹-oxidanyl)-λ³-sulfanyl)-3-((4-(tetradecyloxy)phenyl)sulfonyl)quinolin-4-yl)-[1,4':1,4''-terpiperidin]-3-ol |
| 349 | 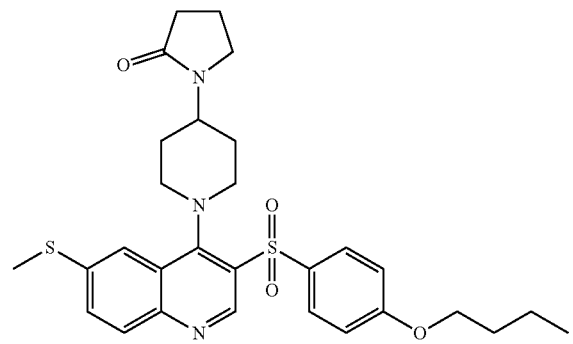 [SMILES: CCCCOc1ccc(S(=O)(=O)c2cnc3ccc(SC)cc3c2N2CCC(N3CCCC3=O)CC2)cc1] | 1-(1-(3-((4-butoxyphenyl)sulfonyl)-6-(methylthio)quinolin-4-yl)piperidin-4-yl)pyrrolidin-2-one |

-continued
| | | |
|---|---|---|
| 350 | 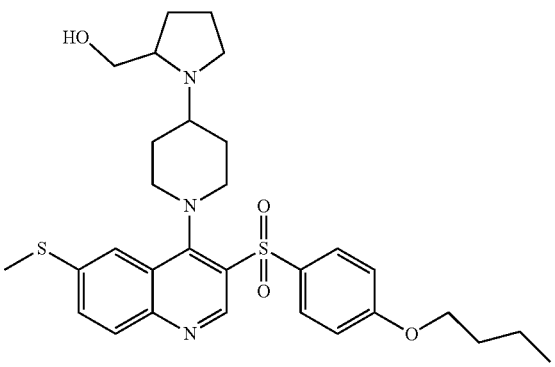 [SMILES: CCCCOc1ccc(S(=O)(=O)c2cnc3ccc(SC)cc3c2N2CCC(N3CCCC3CO)CC2)cc1] | (1-(1-(3-((4-butoxyphenyl)sulfonyl)-6-(methylthio)quinolin-4-yl)piperidin-4-yl)pyrrolidin-2-yl)methanol |
| 351 | 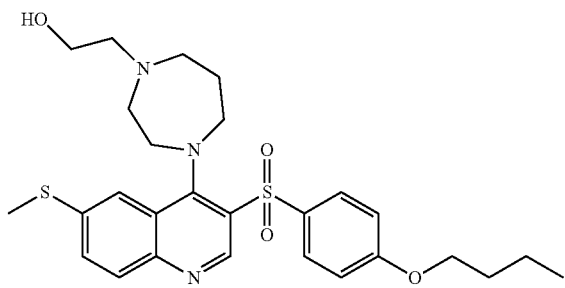 [SMILES: CCCCOc1ccc(S(=O)(=O)c2cnc3ccc(SC)cc3c2N2CCCN(CCO)CC2)cc1] | 2-(4-(3-((4-butoxyphenyl)sulfonyl)-6-(methylthio)quinolin-4-yl)-1,4-diazepan-1-yl)ethan-1-ol |
| 352 | 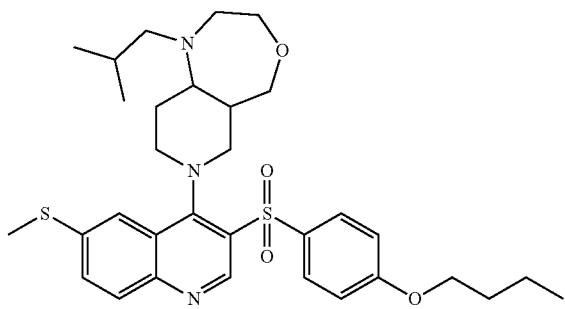 [SMILES: CCCCOc1ccc(S(=O)(=O)c2cnc3ccc(SC)cc3c2N2CCC3C(COCCN3CC(C)C)C2)cc1] | 7-(3-((4-butoxyphenyl)sulfonyl)-6-(methylthio)quinolin-4-yl)-1-isobutyldecahydropyrido[4,3-e][1,4]oxazepine |
| 353 | 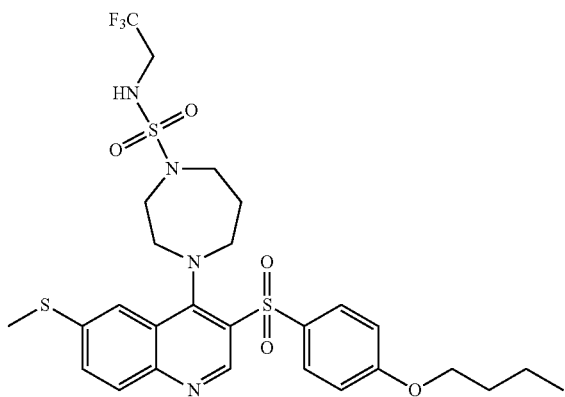 [SMILES: CCCCOc1ccc(S(=O)(=O)c2cnc3ccc(SC)cc3c2N2CCCN(S(=O)(=O)NCC(F)(F)F)CC2)cc1] | 4-(3-((4-butoxyphenyl)sulfonyl)-6-(methylthio)quinolin-4-yl)-N-(2,2,2-trifluoroethyl)-1,4-diazepane-1-sulfonamide |

-continued
| | | |
|---|---|---|
| 354 | 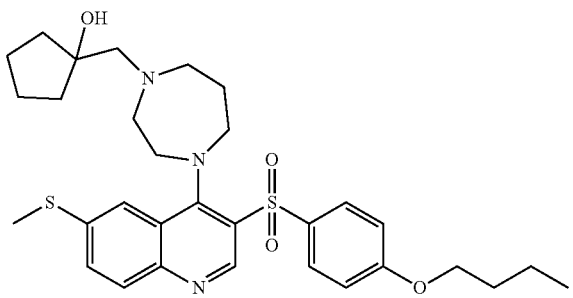 [SMILES: CCCCOc1ccc(S(=O)(=O)c2cnc3ccc(SC)cc3c2N2CCCN(CC3(O)CCCC3)CC2)cc1] | 1-((4-(3-((4-butoxyphenyl)sulfonyl-6-(methylthio)quinolin-4-yl)-1,4-diazepan-1-yl)methyl)cyclopentan-1-ol |
| 355 | 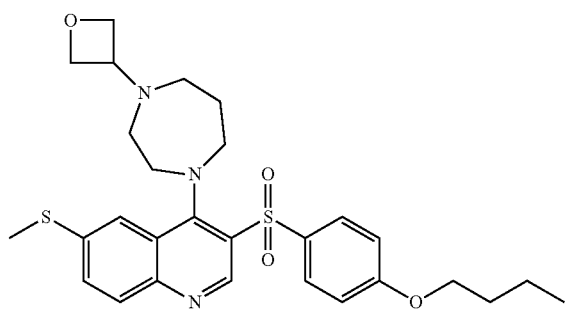 [SMILES: CCCCOc1ccc(S(=O)(=O)c2cnc3ccc(SC)cc3c2N2CCCN(C3COC3)CC2)cc1] | 3-((4-butoxyphenyl)sulfonyl)-6-(methylthio)-4-(4-(oxelan-3-yl)-1,4-diazepan-1-yl)quinoline |
| 356 | 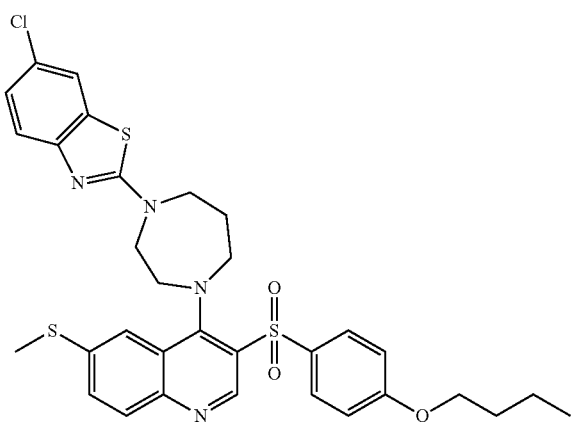 [SMILES: CCCCOc1ccc(S(=O)(=O)c2cnc3ccc(SC)cc3c2N2CCCN(c3nc4ccc(Cl)cc4s3)CC2)cc1] | 2-(4-(3-((4-butoxyphenyl)sulfonyl)-6-(methylthio)quinolin-4-yl)-1,4-diazepan-1-yl)-6-chlorobenzo[d]thiazole |
| 357 | 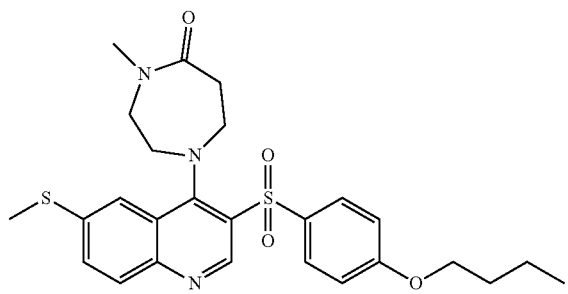 [SMILES: CCCCOc1ccc(S(=O)(=O)c2cnc3ccc(SC)cc3c2N2CCC(=O)N(C)CC2)cc1] | 1-(3-((4-butoxyphenyl)sulfonyl)-6-(methylthio)quinolin-4-yl)-4-methyl-1,4-diazepan-5-one |

-continued

| | | |
|---|---|---|
| 358 | 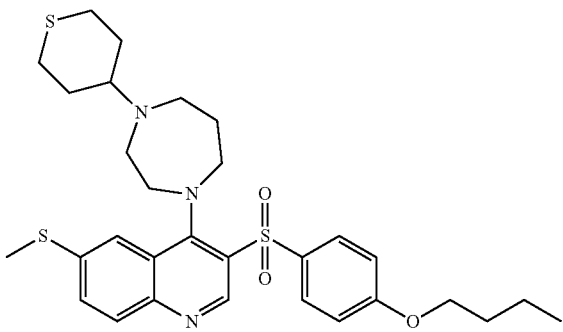 [SMILES: CCCCOc1ccc(S(=O)(=O)c2cnc3ccc(SC)cc3c2N2CCCN(C3CCSCC3)CC2)cc1] | 3-((4-butoxyphenyl)sulfonyl)-6-(methylthio)-4-(4-(tetrahydro-2H-thiopyran-4-yl)-1,4-diaxepan-1-yl)quinoline |
| 359 | 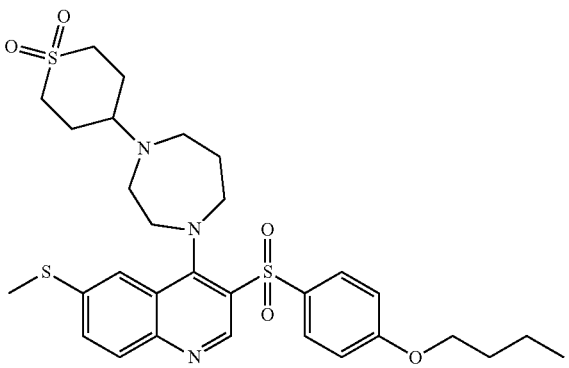 [SMILES: CCCCOc1ccc(S(=O)(=O)c2cnc3ccc(SC)cc3c2N2CCCN(C3CCS(=O)(=O)CC3)CC2)cc1] | 4-(4-(3-((4-butoxyphenyl)sulfonyl)-6-(methylthio)quinolin-4-yl)-1,4-diazepan-1-yl)tetrahydro-2H-thiopyran 1,1-dioxide |
| 360 | 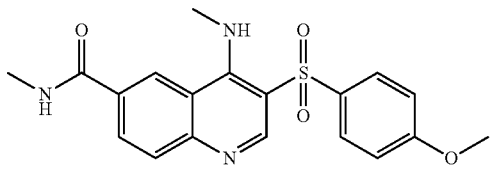 | 3-((4-methoxyphenyl)sulfonyl)-N-methyl-4-methylamino)quinoline-6-carboxamide |
| 361 | 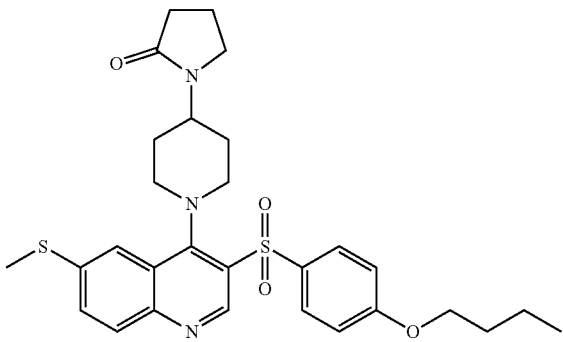 [SMILES: CCCCOc1ccc(S(=O)(=O)c2cnc3ccc(SC)cc3c2N2CCC(N3CCCC3=O)CC2)cc1] | 1-(1-(3-((4-butoxyphenyl)sulfonyl)-6-(methylthio)quinolin-4-yl)piperidin-4-yl)pyrrolidin-2-one |
| 362 | 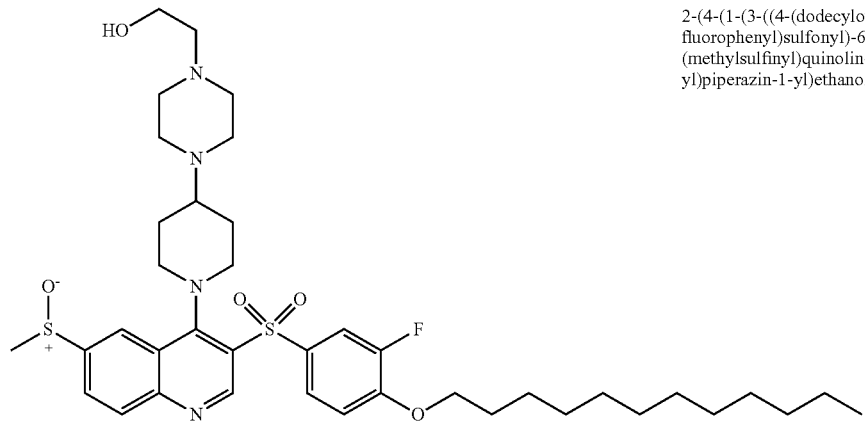 | 2-(4-(1-(3-((4-(dodecyloxy)-3-fluorophenyl)sulfonyl)-6-(methylsulfinyl)quinolin-4-yl)piperidin-4-yl)piperazin-1-yl)ethanol |

| | | |
|---|---|---|
| 363 | 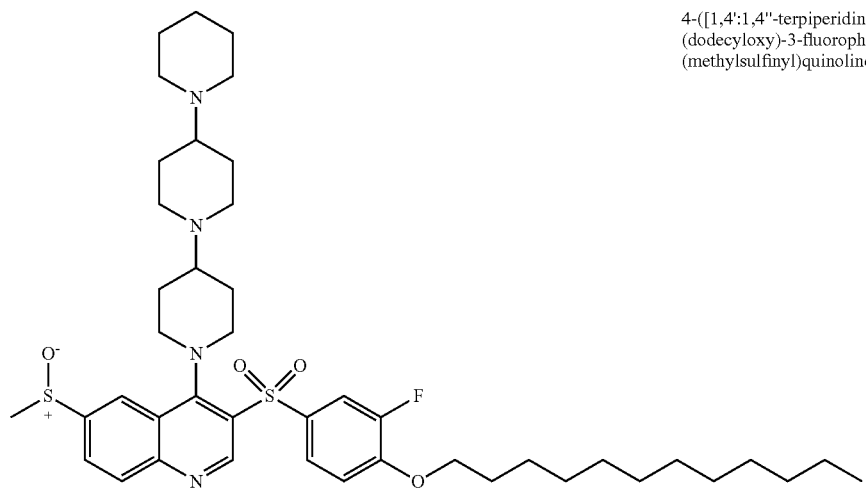 | 4-([1,4':1,4''-terpiperidin]-1''-yl)-3-((4-(dodecyloxy)-3-fluorophenyl)sulfonyl)-6-(methylsulfinyl)quinoline |
| 364 | 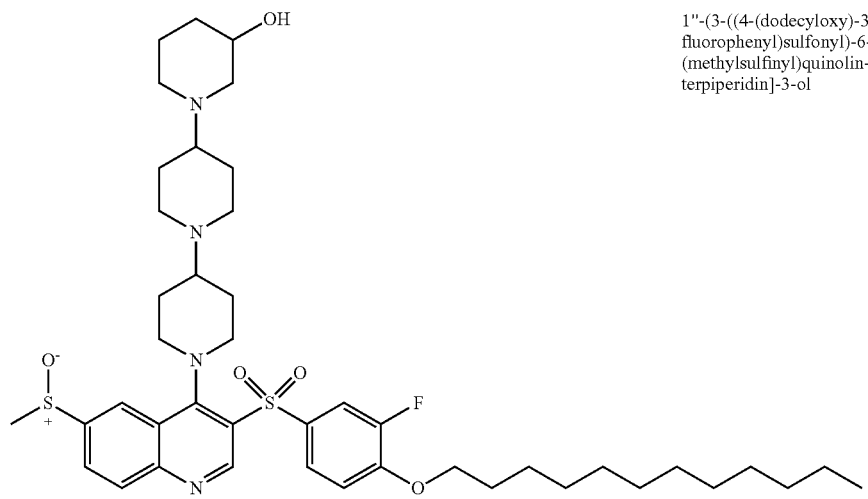 | 1''-(3-((4-(dodecyloxy)-3-fluorophenyl)sulfonyl)-6-(methylsulfinyl)quinolin-4-yl)-[1,4':1',4'']-terpiperidin]-3-ol |
| 365 | 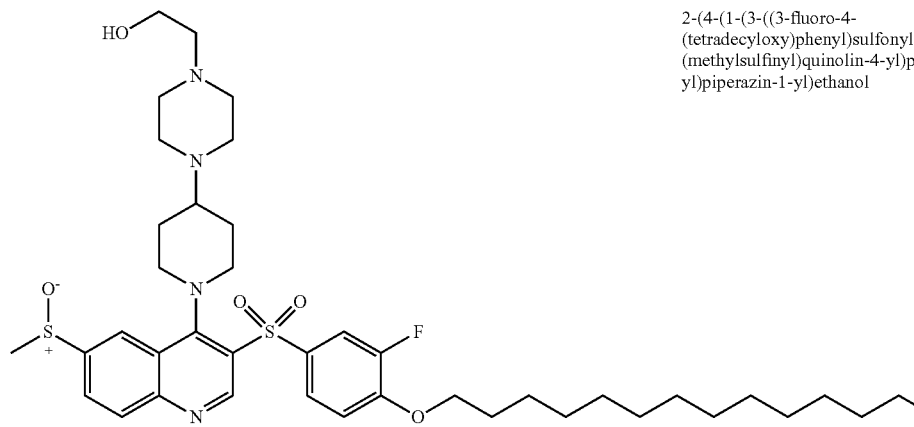 | 2-(4-(1-(3-((3-fluoro-4-(tetradecyloxy)phenyl)sulfonyl)-6-(methylsulfinyl)quinolin-4-yl)piperidin-4-yl)piperazin-1-yl)ethanol |

| | | |
|---|---|---|
| 366 | 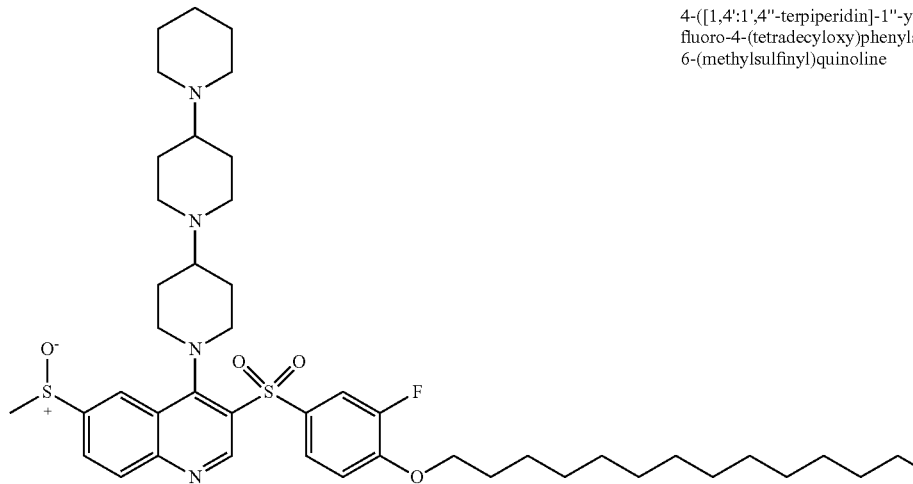 | 4-([1,4':1',4''-terpiperidin]-1''-yl)-3-((3-fluoro-4-(tetradecyloxy)phenylsulfonyl)-6-(methylsulfinyl)quinoline |
| 367 | 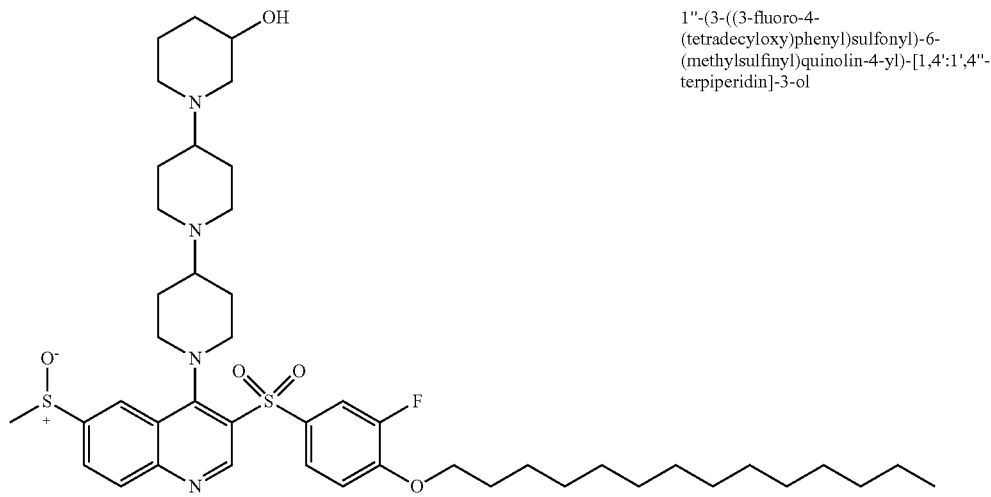 | 1''-(3-((3-fluoro-4-(tetradecyloxy)phenyl)sulfonyl)-6-(methylsulfinyl)quinolin-4-yl)-[1,4':1',4''-terpiperidin]-3-ol |
| 368 | 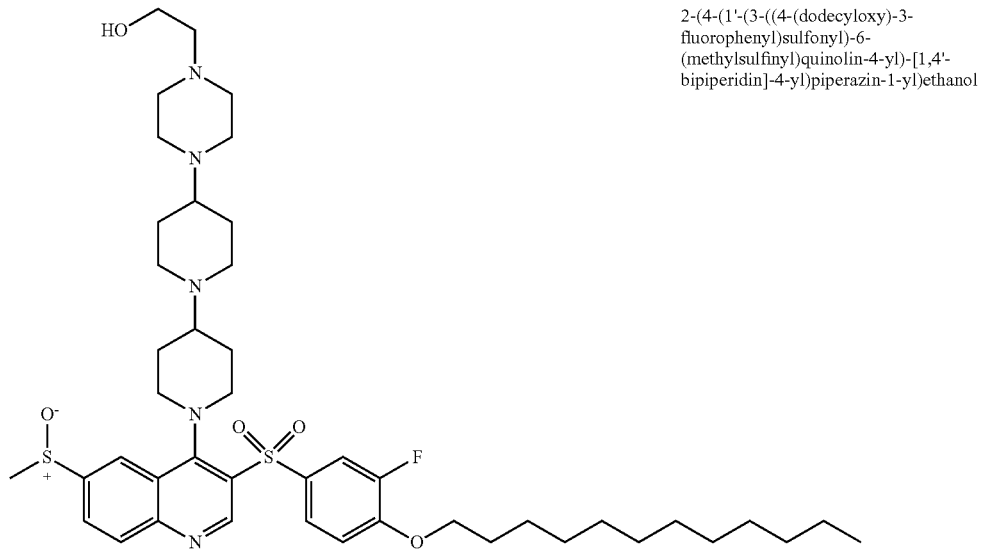 | 2-(4-(1'-(3-((4-(dodecyloxy)-3-fluorophenyl)sulfonyl)-6-(methylsulfinyl)quinolin-4-yl)-[1,4'-bipiperidin]-4-yl)piperazin-1-yl)ethanol |

| | | |
|---|---|---|
| 369 | 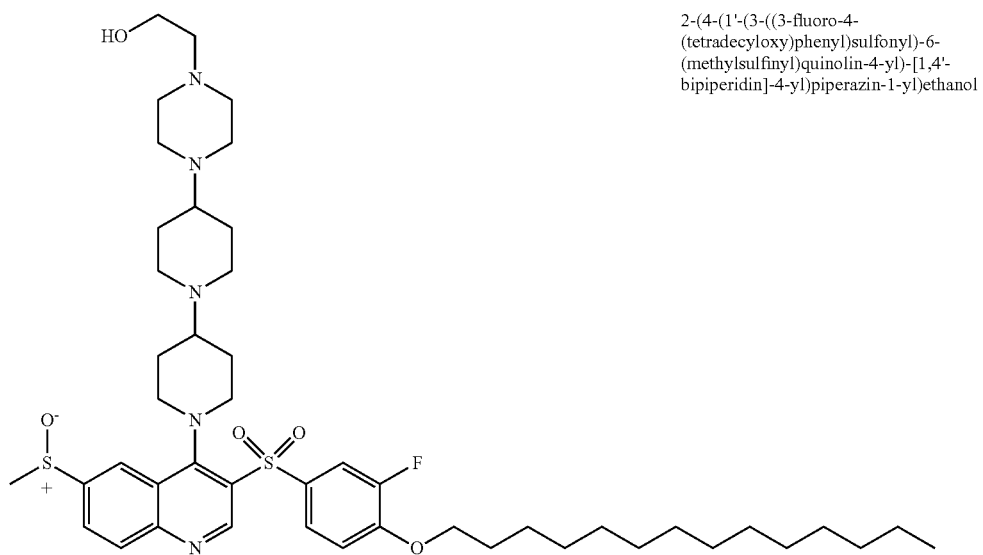 | 2-(4-(1'-(3-((3-fluoro-4-(tetradecyloxy)phenyl)sulfonyl)-6-(methylsulfinyl)quinolin-4-yl)-[1,4'-bipiperidin]-4-yl)piperazin-1-yl)ethanol |
| 370 | 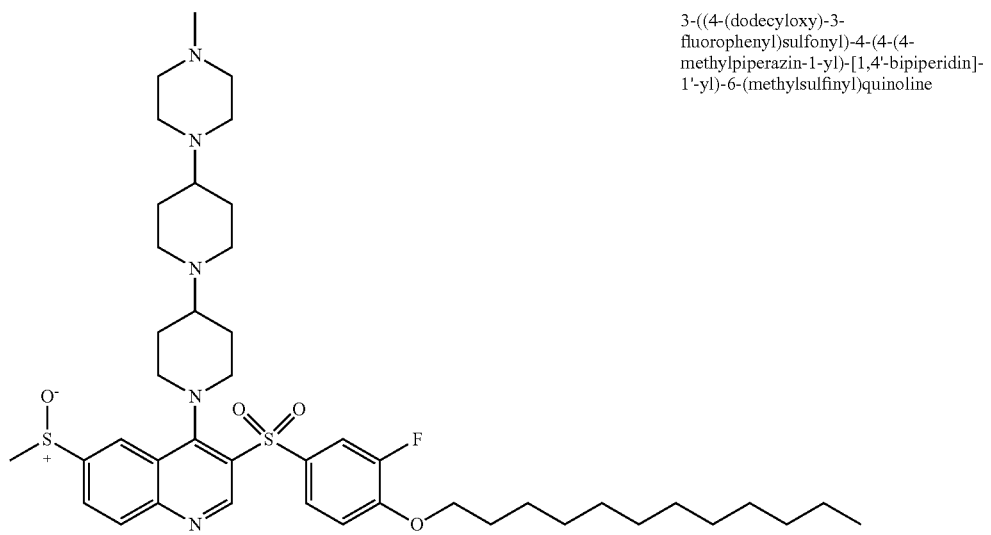 | 3-((4-(dodecyloxy)-3-fluorophenyl)sulfonyl)-4-(4-(4-methylpiperazin-1-yl)-[1,4'-bipiperidin]-1'-yl)-6-(methylsulfinyl)quinoline |
| 371 | 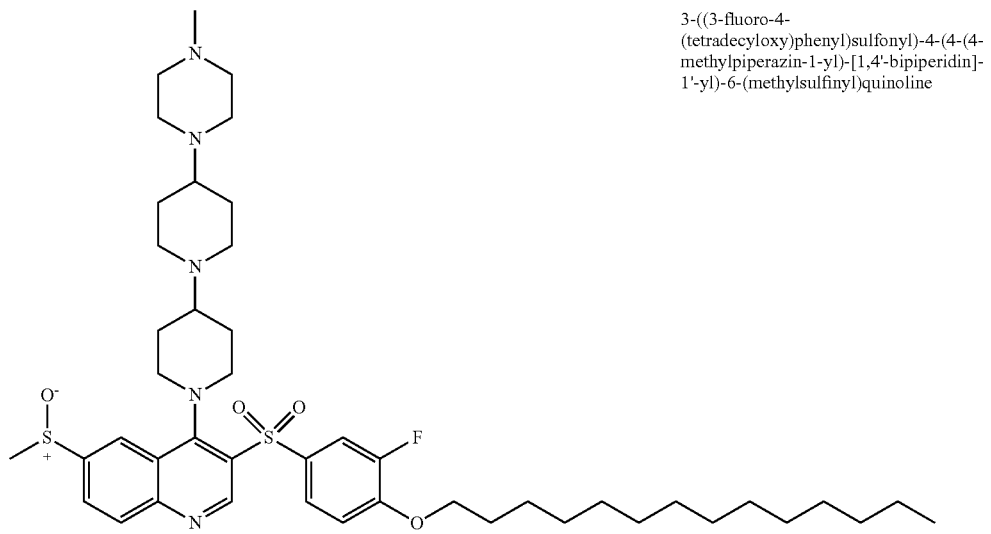 | 3-((3-fluoro-4-(tetradecyloxy)phenyl)sulfonyl)-4-(4-(4-methylpiperazin-1-yl)-[1,4'-bipiperidin]-1'-yl)-6-(methylsulfinyl)quinoline |

| | | |
|---|---|---|
| 372 | 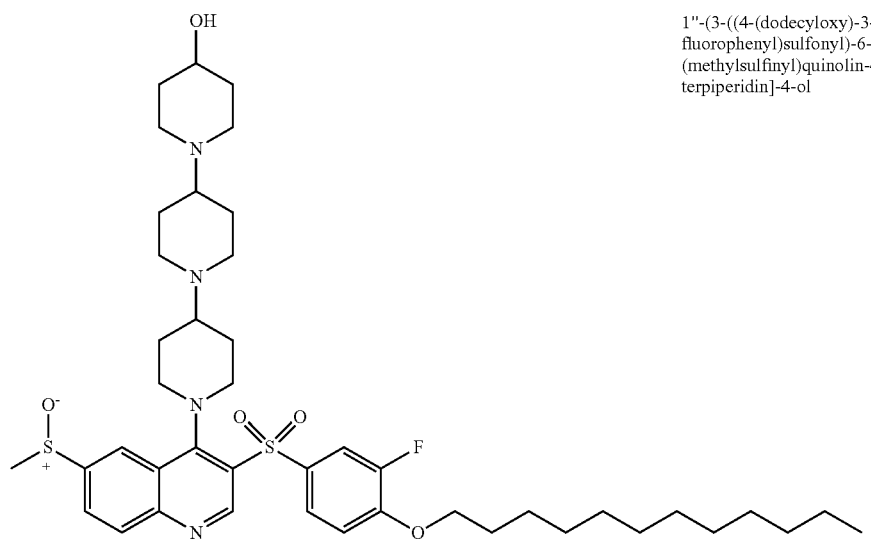 | 1''-(3-((4-(dodecyloxy)-3-fluorophenyl)sulfonyl)-6-(methylsulfinyl)quinolin-4-yl-[1,4':1',4''-terpiperidin]-4-ol |
| 373 | 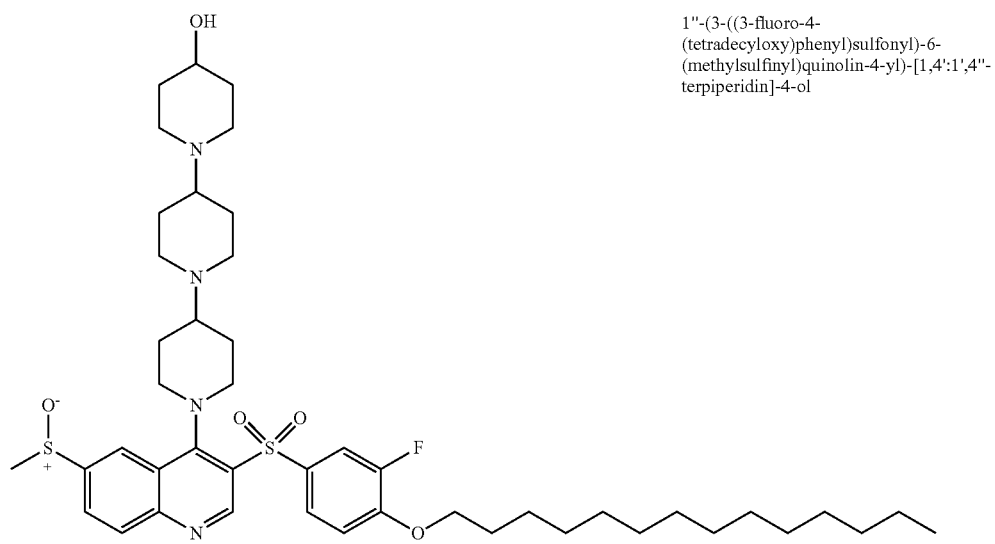 | 1''-(3-((3-fluoro-4-(tetradecyloxy)phenyl)sulfonyl)-6-(methylsulfinyl)quinolin-4-yl)-[1,4':1',4''-terpiperidin]-4-ol |
| 374 | 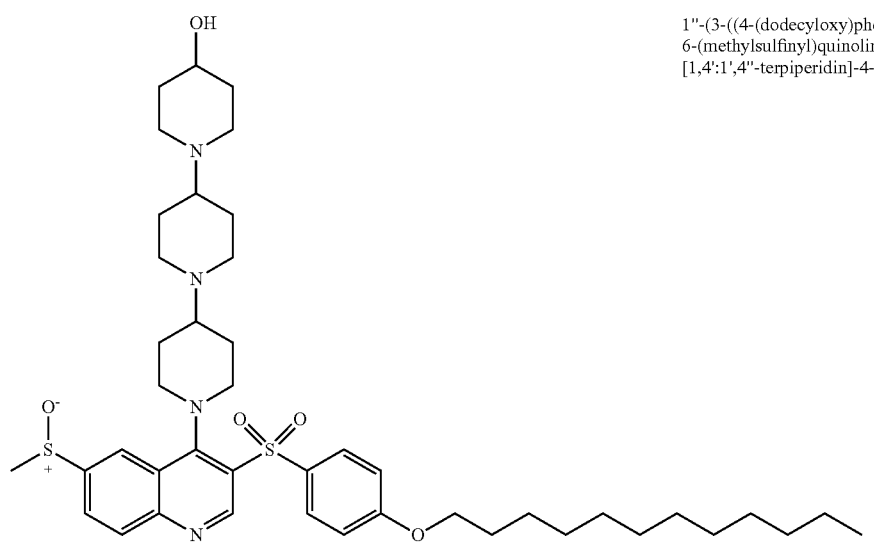 | 1''-(3-((4-(dodecyloxy)phenyl)sulfonyl)-6-(methylsulfinyl)quinolin-4-yl)-[1,4':1',4''-terpiperidin]-4-ol |

| | | |
|---|---|---|
| 375 | 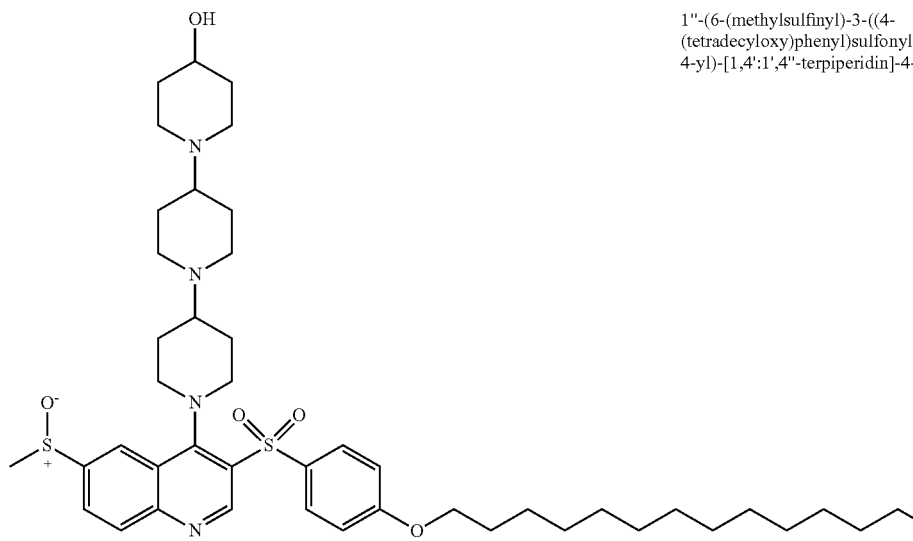 | 1''-(6-(methylsulfinyl)-3-((4-(tetradecyloxy)phenyl)sulfonyl)quinolin-4-yl)-[1,4':1',4''-terpiperidin]-4-ol |
| 376 | 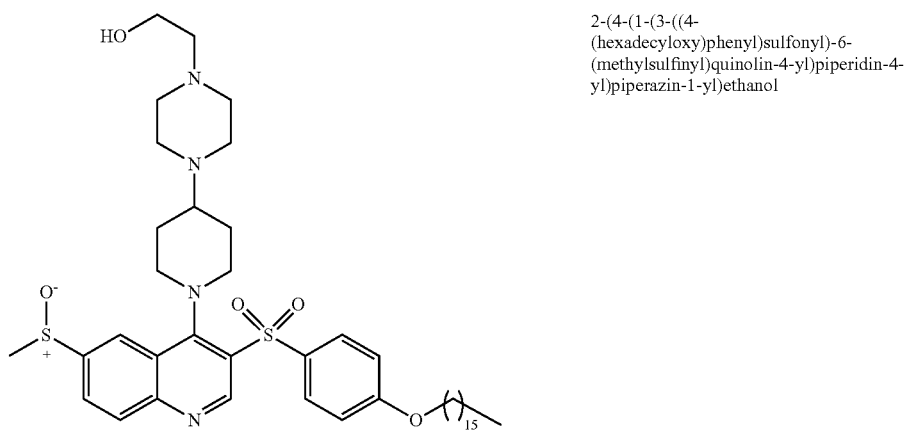 | 2-(4-(1-(3-((4-(hexadecyloxy)phenyl)sulfonyl)-6-(methylsulfinyl)quinolin-4-yl)piperidin-4-yl)piperazin-1-yl)ethanol |
| 377 | 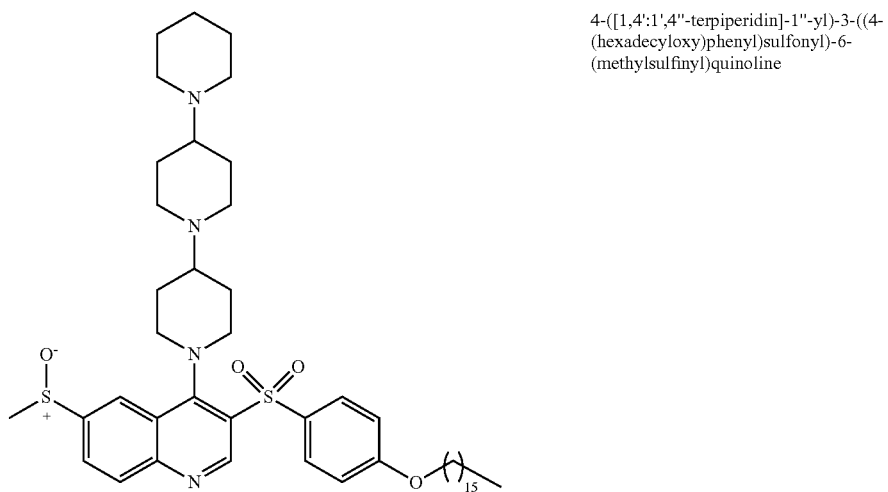 | 4-([1,4':1',4''-terpiperidin]-1''-yl)-3-((4-(hexadecyloxy)phenyl)sulfonyl)-6-(methylsulfinyl)quinoline |

| | | |
|---|---|---|
| 378 | 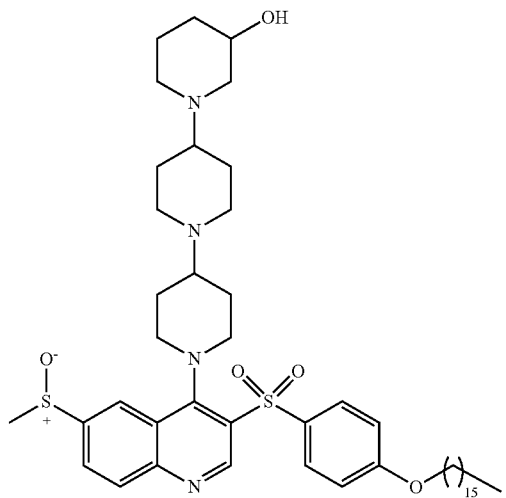 | 1''-(3-((4-(hexadecyloxy)phenyl)sulfonyl)-6-(methylsulfinyl)quinolin-4-yl)-[1,4':1',4''-terpiperidin]-3-ol |
| 379 | 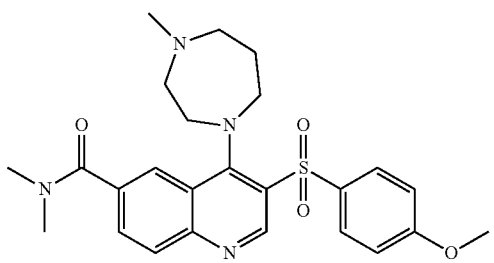 | 3-((4-methoxyphenyl)sulfonyl)-N,N-dimethyl-4-(4-methyl-1,4-diazepan-1-yl)quinoline-6-carboxamide |
| 380 | 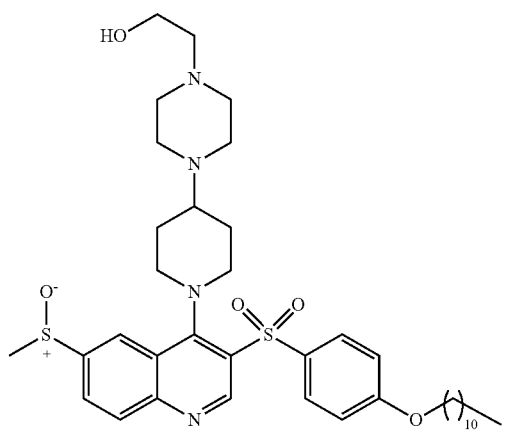 | 2-(4-(1-(6-(methylsulfinyl)-3-((4-(undecyloxy)phenyl)sulfonyl)quinolin-4-yl)piperidin-4-yl)piperazin-1-yl)ethanol |

| | | |
|---|---|---|
| 381 | 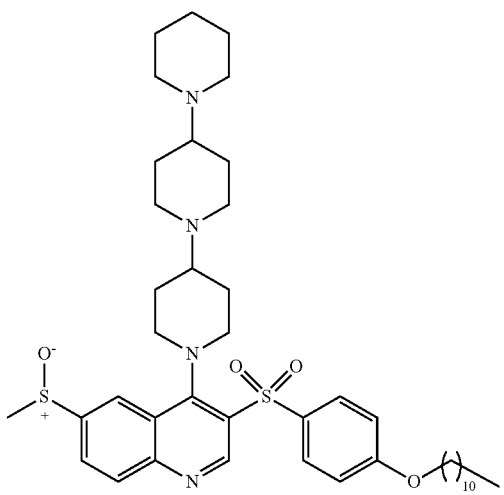 | 4-([1,4':1',4''-terpiperidin]-1''-yl)-6-(methylsulfinyl)-3-((4-(undecyloxy)phenyl)sulfonyl)quinoline |
| 382 | 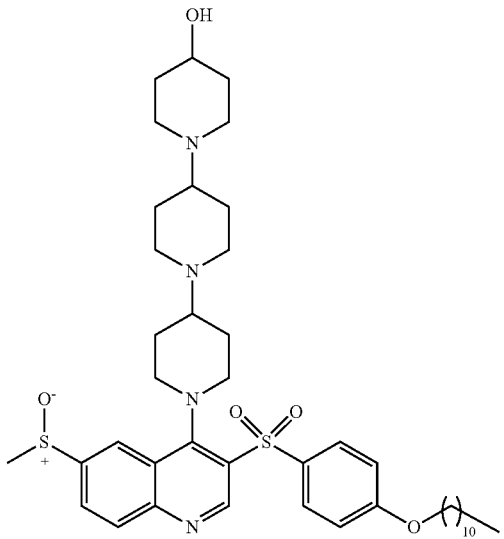 | 1''-(6-(methylsulfinyl)-3-((4-(undecyloxy)phenyl)sulfonyl)quinolin-4-yl)-[1,4,:1',4''-terpiperidin]-4-ol |
| 383 | 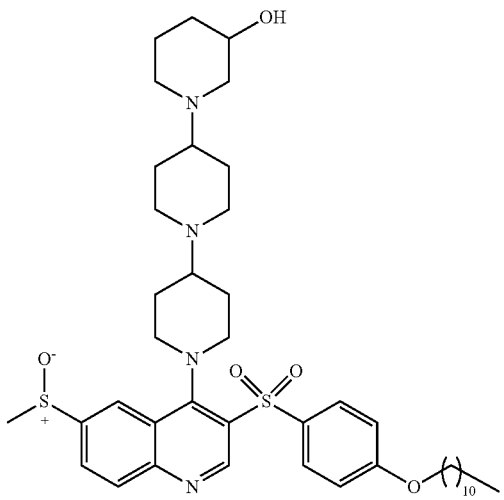 | 1''-(6-(methylsulfinyl)-3-((4-(undecyloxy)phenyl)sulfonyl)quinolin-4-yl)-[1,4':1',4''-terpiperidin]-3-ol |

-continued
| | | |
|---|---|---|
| 384 | 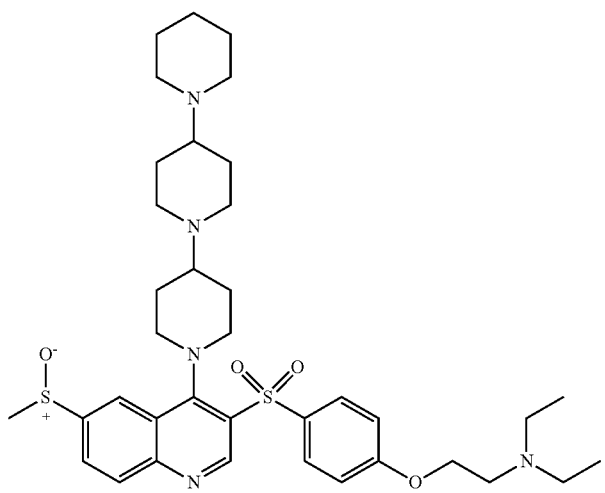 | 2-(4-((4-([1,4':1',4''-terpiperidin]-1''-yl)-6-(methylsulfinyl)quinolin-3-yl)sulfonyl)phenoxy)-N,N-diethyl)ethanamine |
| 385 | 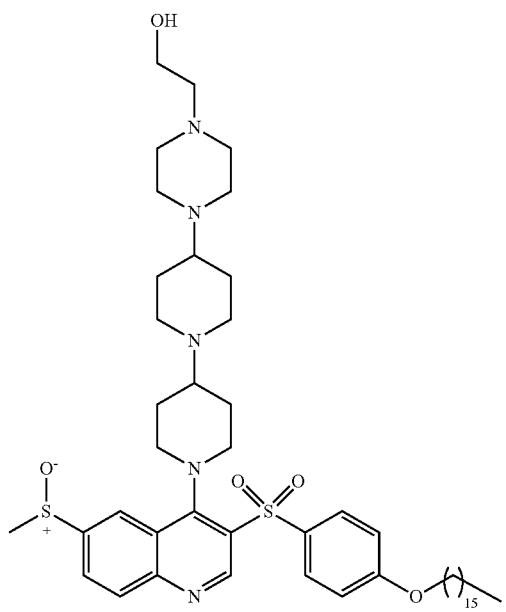 | 2-(4-(1'-(3-((4-(hexadecyloxy)phenyl)sulfonyl)-6-(methylsulfinyl)quinolin-4-yl)-[1,4'-bipiperidin]-4-yl)pipeiazin-1-yl)ethanol |
| 386 | 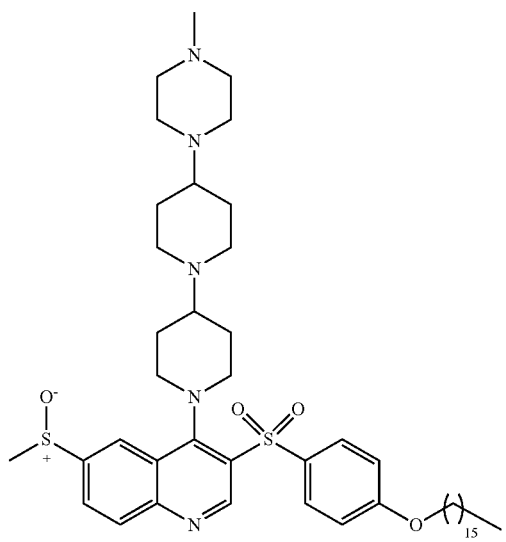 | 3-((4-(hexadecyloxy)phenyl)sulfonyl)-4-(4-(4-methylpiperazin-1-yl)-[1,4'-bipiperidin]-1'-yl)-6-(methylsulfinyl)quinoline |

-continued
| | | |
|---|---|---|
| 387 | 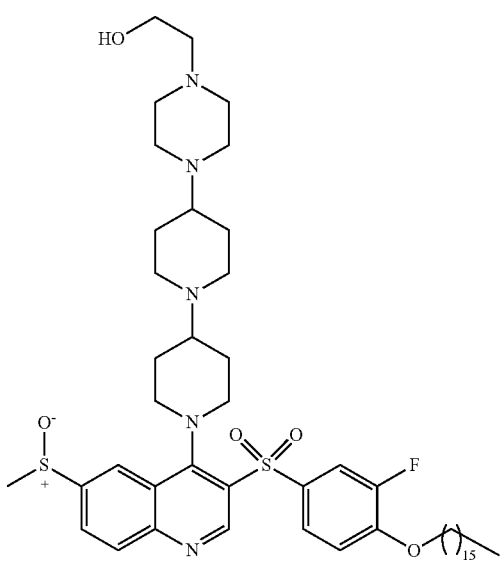 | 2-(4-(1'-(3-((3-fluoro-4-(hexadecyloxy)phenyl)sulfonyl)-6-(methylsulfinyl)quinolin-4-yl-[1,4'-bipiperidin]-4-yl)piperazin-1-yl)ethanol |
| 388 | 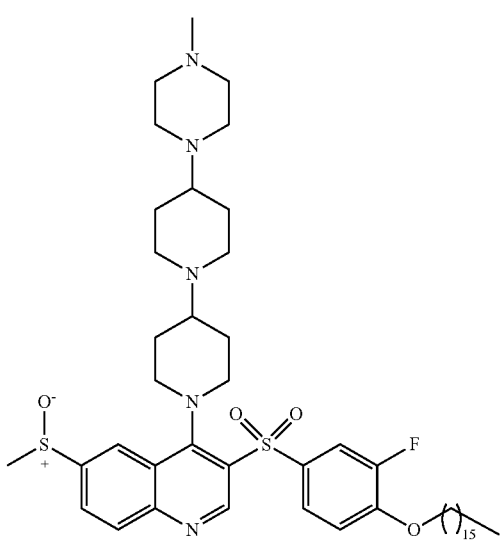 | 3-((3-fluoro-4-(hexadecyloxy)phenyl)sulfonyl)-4-(4-(4-methylpiperazin-1-yl)-[1,4'-bipiperidin]-1'-yl)-6-(methylsulfinyl)quinoline |
| 389 | 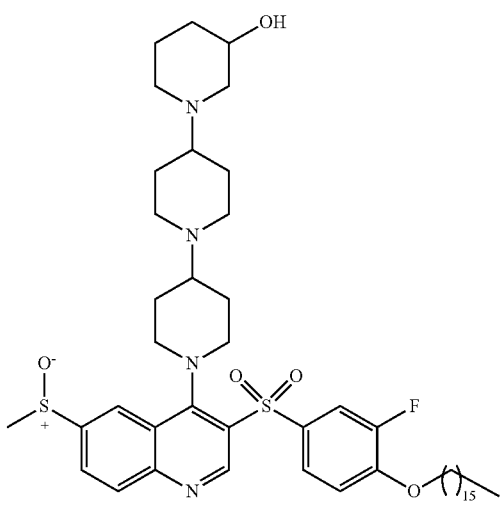 | 1'-(3-((3-fluoro-4-(hexadecyloxy)phenyl)sulfonyl)-6-(methylsulfinyl)quinolin-4-yl)-[1,4':1',4''-terpiperidin]-3-ol |

-continued
| | | |
|---|---|---|
| 390 | 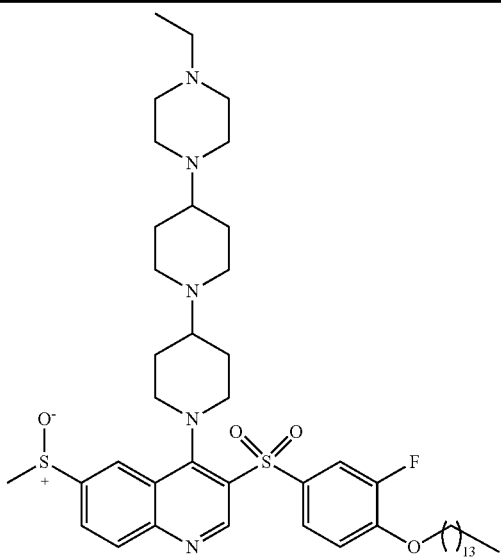 | 4-(4-(4-ethylpiperazin-1-yl)-[1,4'-bipiperidin]-1'-yl)-3-((3-fluoro-4-(tetradecyloxy)phenyl)sulfonyl)-6-(methylsulfinyl)quinoline |
| 391 | 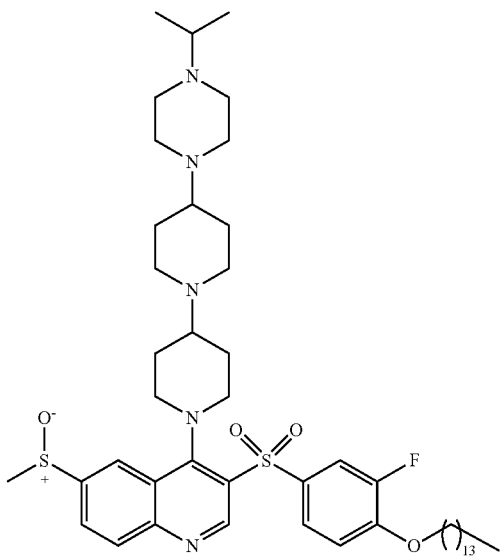 | 3-((3-fluoro-4-(tetradecyloxy)phenyl)sulfonyl)-4-(4-(4-isopropylpiperazin-1-yl)-[1,4'-bipiperidin]-1'-yl)-6-(methylsulfinyl)quinoline |
| 392 | 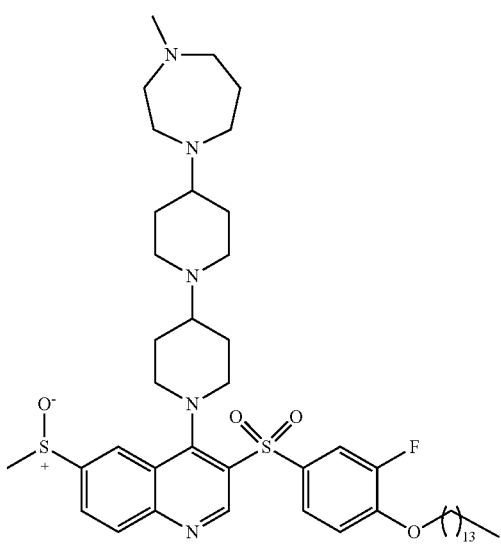 | 3-((3-fluoro-4-(tetradecyloxy)phenyl)sulfonyl)-4-(4-(4-methyl-1,4-diazepan-1-yl)-[1,4'-bipiperidin]-1'-yl)-6-(methylsulfinyl)quinoline |

| | | |
|---|---|---|
| 393 | 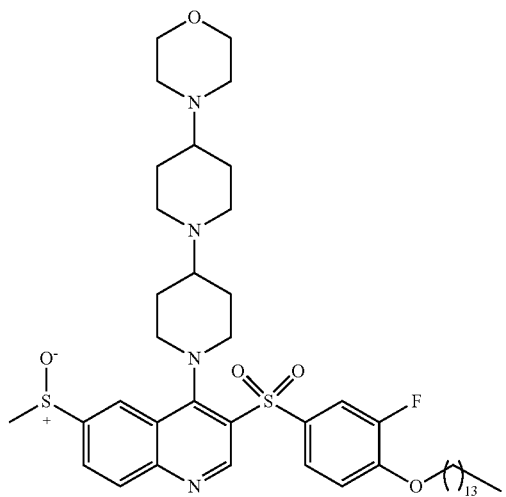 | 4-(1'-(3-((3-fluoro-4-(tetradecyloxy)phenyl)sulfonyl)-6-(methylsulfinyl)quinolin-4-yl)-[1,4'-bipiperidin]-4-yl)quinoline |
| 394 | 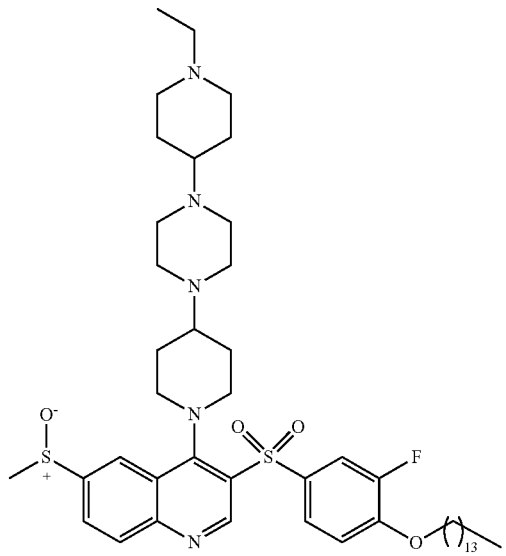 | 4-(4-(4-(1-ethylpiperidin-4-yl)piperazin-1-yl)piperidin-1-yl)-3-((3-fluoro-4-(tetradecyloxy)phenyl)sulfonyl)-6-(methylsulfinyl)quinoline |
| 395 | 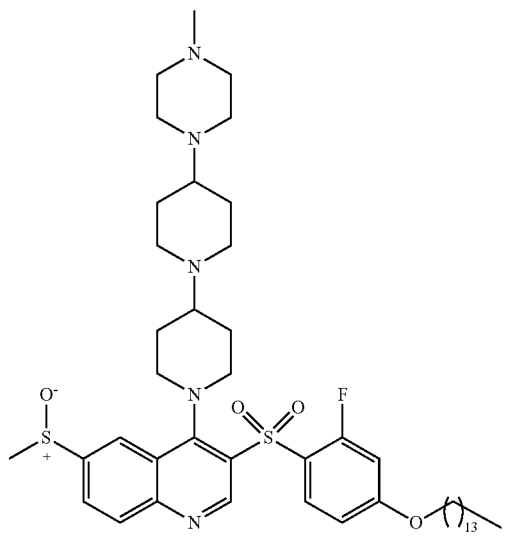 | 3-((2-fluoro-4-(tetradecyloxy)phenyl)sulfonyl)-4-(4-(4-methylpiperazin-1-yl)-[1,4'-bipiperidin]-1'-yl)-6-(methylsulfinyl)quinoline |

-continued
| | | |
|---|---|---|
| 396 | 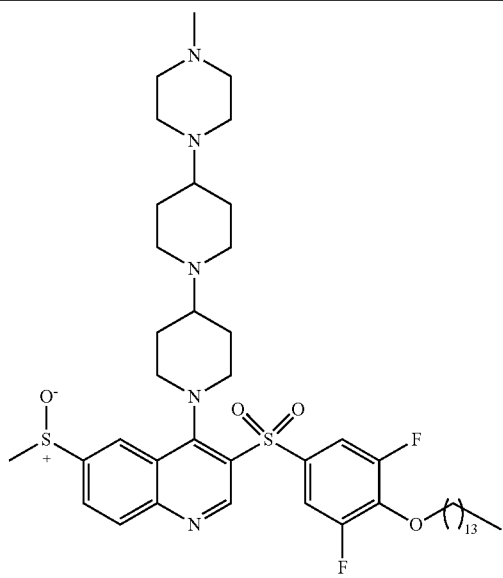 | 3-((3,5-difluoro-4-(tetradecyloxy)phenyl)sulfonyl)-4-(4-(4-methylpiperazin-1-yl)-[1,4'-bipiperidin]-1'-yl)-6-(methylsulfinyl)quinoline |
| 397 | 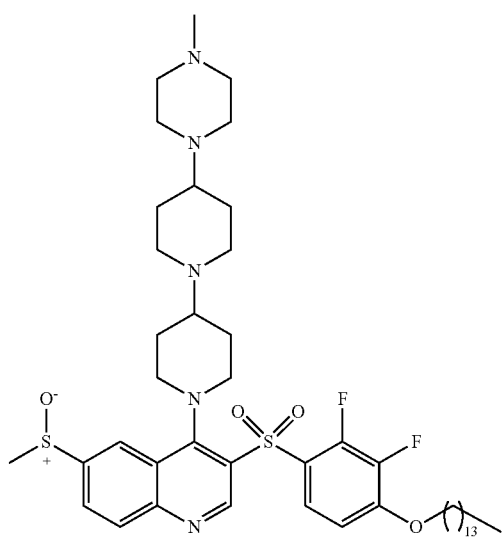 | 3-((2,3-difluoro-4-(tetradecyloxy)phenyl)sulfonyl)-4-(4-(4-methylpiperazin-1-yl)-[1,4'-bipiperidin]-1'-yl)-6-(methylsulfinyl)quinoline |
| 398 | 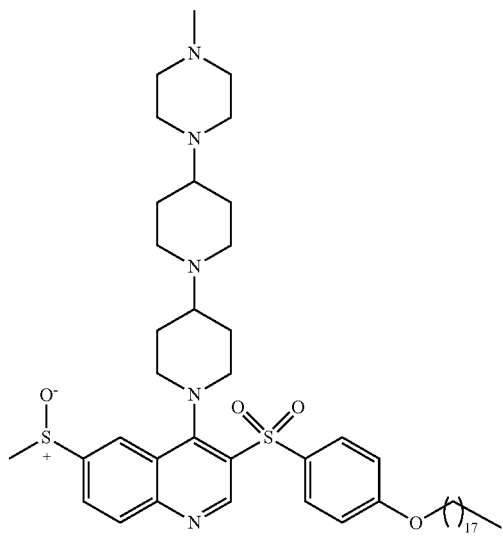 | 4-(4-(4-methylpiperazin-1-yl)-[1,4'-bipiperidin]-1'-yl)-6-(methylsulfinyl)-3-((4-(octadecyloxy)phenyl)sulfonyl)quinoline |

-continued
| | | |
|---|---|---|
| 399 | 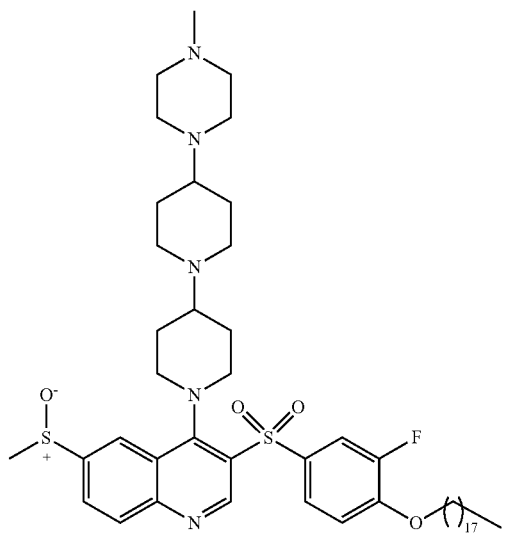 | 3-((3-fluoro-4-(octadecyloxy)phenyl)sulfonyl)-4-(4-(4-methylpiperazin-1-yl)-[1,4'-bipiperidin]-1'-yl)-6-(methylsulfinyl)quinoline |
| 400 | 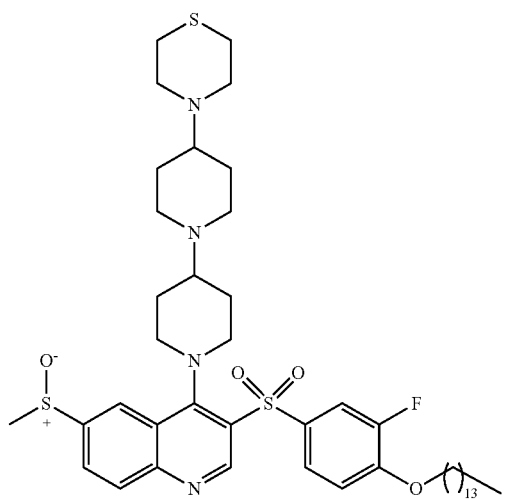 | 4-(1'-(3-((3-fluoro-4-(tetradecyloxy)phenyl)sulfonyl)-6-(methylsulfinyl)quinolin-4-yl)-[1,4'-bipiperidin]-4-yl)thiomorpholine |
| 401 | 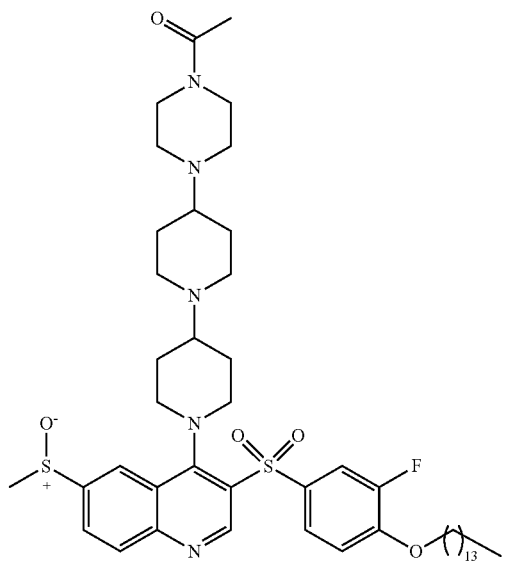 | 1-(4-(1'-(3-((3-fluoro-4-(tetradecyloxy)phenyl)sulfonyl)-6-(methylsulfinyl)quinolin-4-yl)-[1,4'-bipiperidin]-4-yl)piperazin-1-yl)ethanone |

-continued
| | | |
|---|---|---|
| 402 | 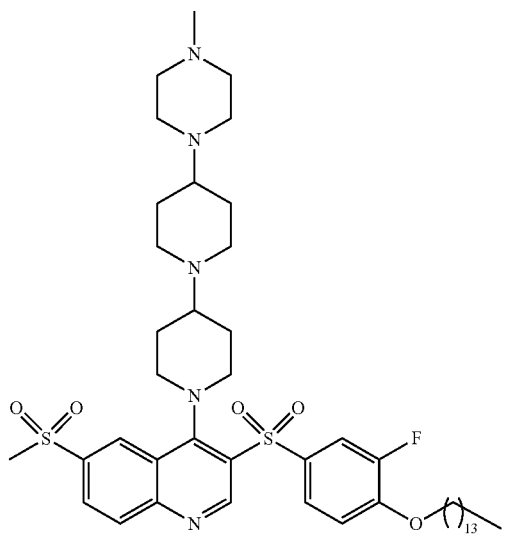 | 3-((3-fluoro-4-(tetradecyloxylphenyl)sulfonyl)-4-(4-(4-methylpiperazin-1-yl)-[1,4'-bipiperidin]-1'-yl)-6-(methylsulfonyl)quinoline |
| 403 | 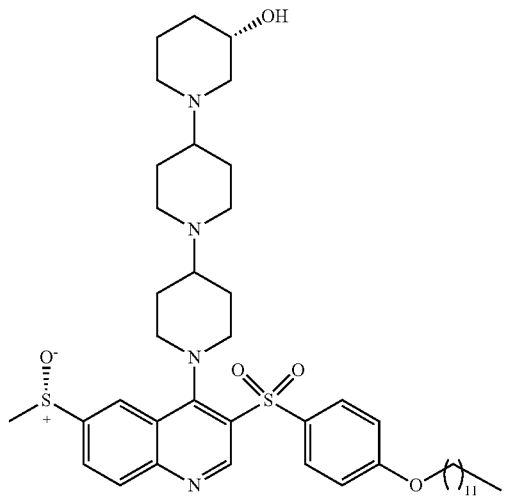 | (S)-1"-(3-((4-(dodecyloxy)phenyl)sulfonyl)-6-((S)-methylsulfinyl)quinolin-4-yl)-[1,4':1',4"-terpiperidin]-3-ol |
| 404 | 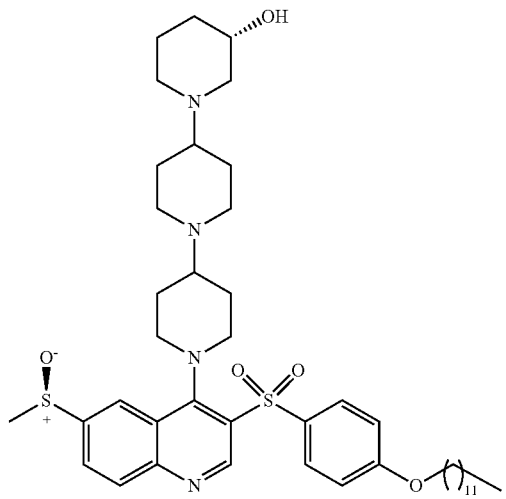 | (S)-1"-(3-((4-(dodecyloxy)phenyl)sulfollyl)-6-((R)-methylsulfinyl)quinolin-4-yl)-[1,4':1',4"-terpiperidin]-3-ol |

-continued
| | | |
|---|---|---|
| 405 | 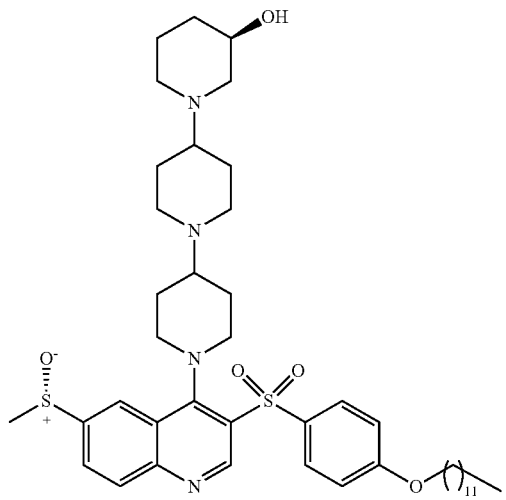 | (R)-1''-(3-((4-(dodecyloxy)phenyl)sulfonyl)-6-((S)-methylsulfinyl)quinolin-4-yl)-[1,4':1',4''-terpiperidin]-3-ol |
| 406 | 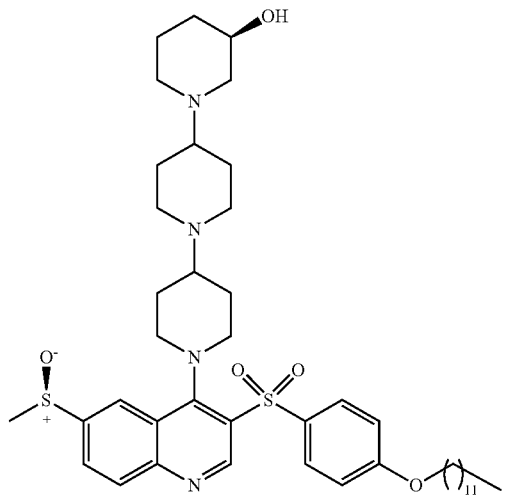 | (R)-1''-(3-((4-(dodecyloxy)phenyl)sulfonyl)-6-((R)-methylsulfinyl)quinolin-4-yl)-[1,4':1',4''-terpiperidin]-3-ol |
| 407 | 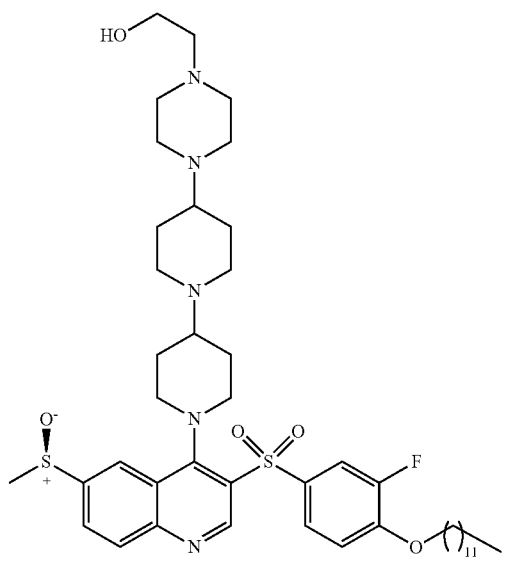 | (R)-2-(4-(1'-(3-((4-(dodecyloxy)-3-fluorophenyl)sulfonyl)-6-(methylsulfinyl)quinolin-4-yl)-[1,4'-bipiperidin]-4-yl)piperazn-1-yl)ethanol |

-continued
| | | |
|---|---|---|
| 408 | 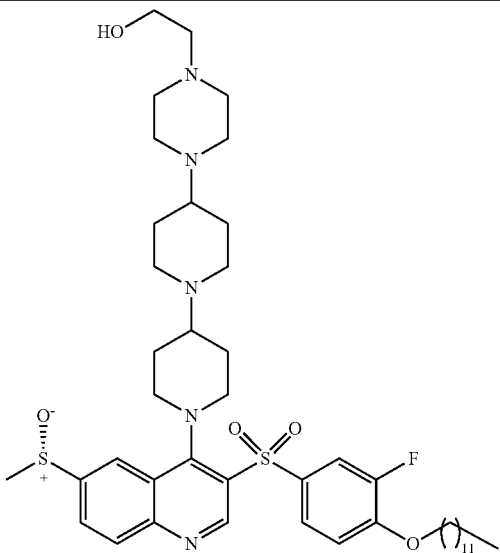 | (S)-2-(4-(1'-(3-((4-(dodecyloxy)-3-fluorophenyl)sulfonyl)-6-(methylsulfinyl)quinolin-4-yl)-[1,4'-bipiperidin]-4-yl)piperazin-1-yl)ethanol |
| 409 | 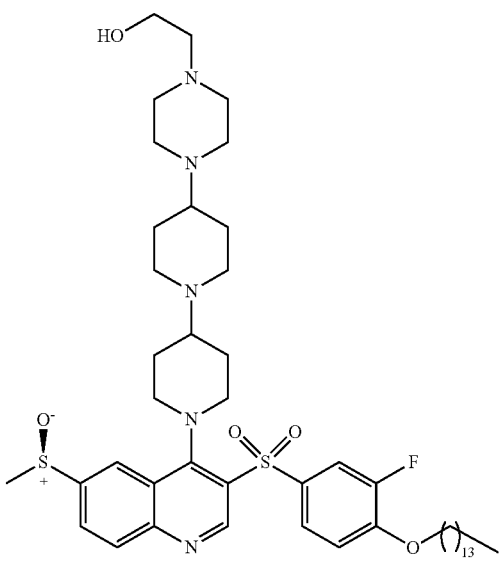 | (R)-2-(4-(1''-(3-((3-fluoro-4-(tetradecyloxy)phenyl)sulfonyl)-6-(methylsulfinyl)quinolin-4-yl)-[1,4'-bipiperidin]-4-yl)piperazin-1-yl)ethanol |
| 410 | 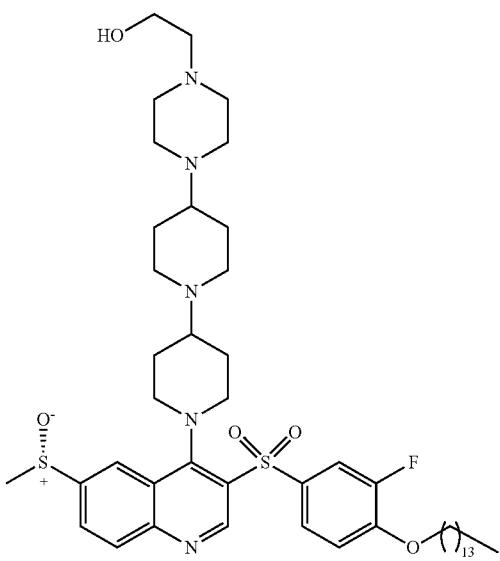 | (S)-2-(4-(1'-(3-((3-fluoro-4-(tetradecyloxy)phenyl)sulfonyl)-6-(methylsulfinyl)quinolin-4-yl)-[1,4'-bipiperidin]-4-yl)piperazin-1-yl)ethanol |

| | | |
|---|---|---|
| 411 | 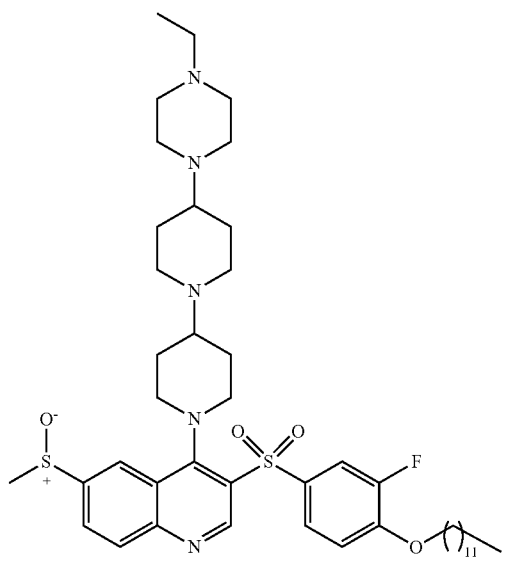 | 3-((4-(dodecyloxy)-3-fluorophenyl)sulfonyl)-4-(4-(4-ethylpiperazin-1-yl)-[1,4'-bipiperidin]-1'-yl)-6-(methylsulfinyl)quinoline |
| 412 | 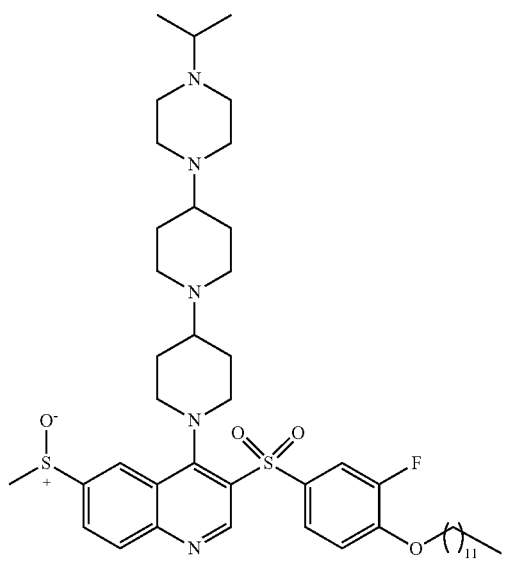 | 3-((4-(dodecyloxy)-3-fluorophenyl)sulfonyl)-4-(4-(4-isopropylpipeiazin-1-yl)-[1,4'-bipiperidin]-1'-yl)-6-(methylsulfinyl)quinoline |

-continued
| | | |
|---|---|---|
| 413 | 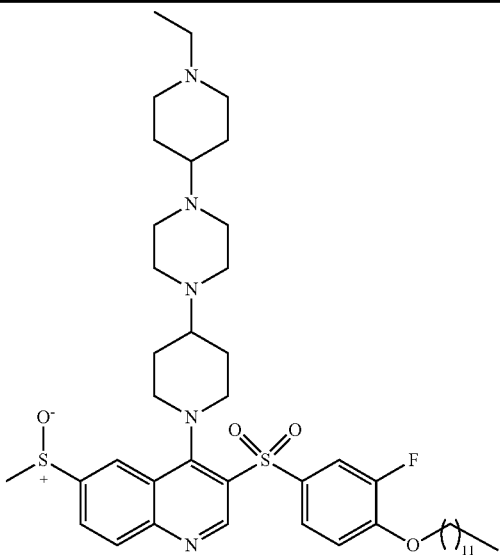 | 3-((4-(dodecyloxy)-3-fluorophenyl)sulfonyl)-4-(4-(4-(1-ethylpiperidin-4-yl)piperazin-1-yl)piperidin-1-yl)-6-(methylsulfinyl)quinoline |
| 414 | 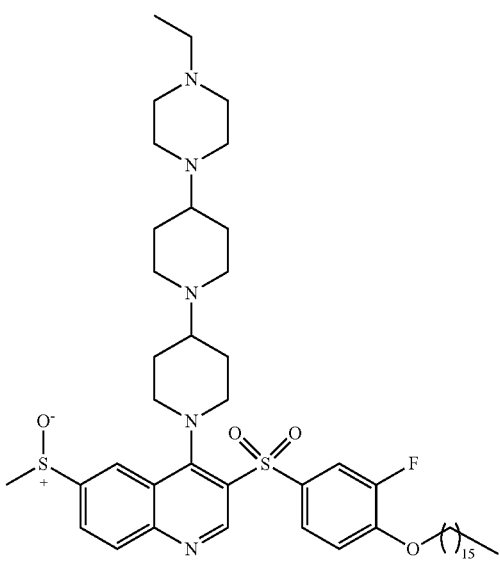 | 4-(4-(4-ethylpiperazin-1-yl)-[1,4'-bipiperidin]-1'-yl)-3-((3-fluoro-4-(hexadecyloxy)phenyl)sulfonyl)-6-(methylsulfinyl)quinoline |
| 415 | 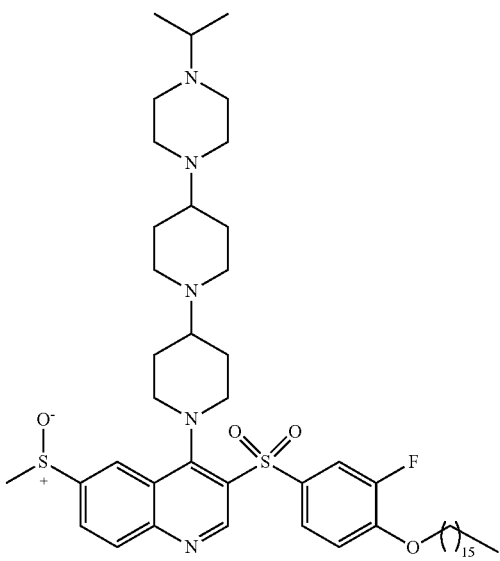 | 3-((3-fluoro-4-(hexadecyloxy)phenyl)sulfonyl)-4-(4-(4-isopropylpiperazin-1-yl)-[1,4'-bipiperidin]-1'-yl)-6-(methylsulfinyl)quinoline |

-continued
| | | |
|---|---|---|
| 416 | 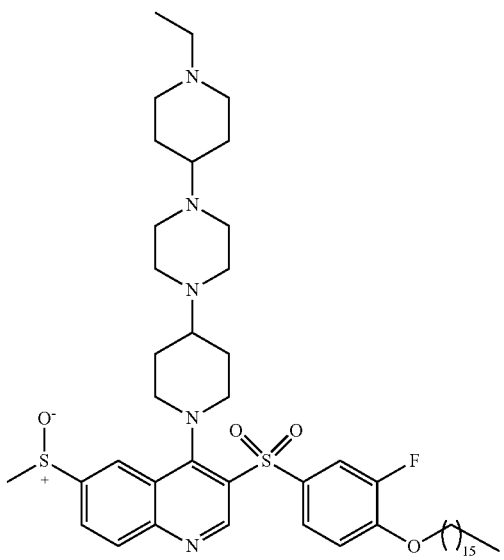 | 4-(4-(4-(1-ethylpiperidin-4-yl)piperazin-1-yl)piperidin-1-yl)-3-((3-fluoro-4-(hexadecyloxy)phenyl)sulfonyl)-6-(methylsulfinyl)quinoline |
| 417 | 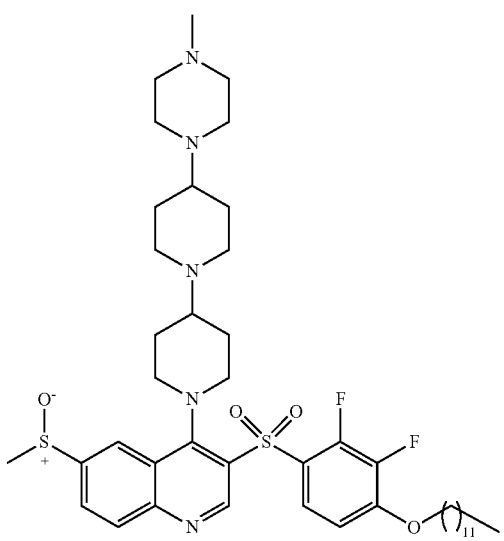 | 3-((4-(dodecyloxy)-2,3-difluorophenyl)sulfonyl)-4-(4-(4-methylpiperazin-1-yl)-[1,4'-bipiperidin]-1'-yl)-6-(methylsulfinyl)quinoline |
| 418 | 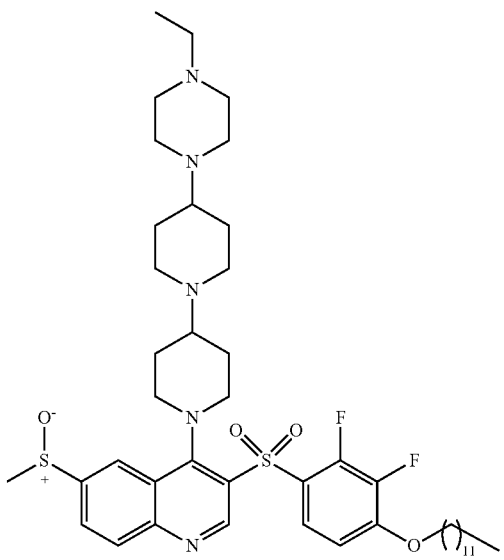 | 3-((4-(dodecyloxy)-2,3-difluorophenyl)sulfonyl)-4-(4-(4-ethylpiperazin-1-yl)-[1,4'-bipiperidin]-1'-yl)-6-(methylsulfinyl)quinoline |

419 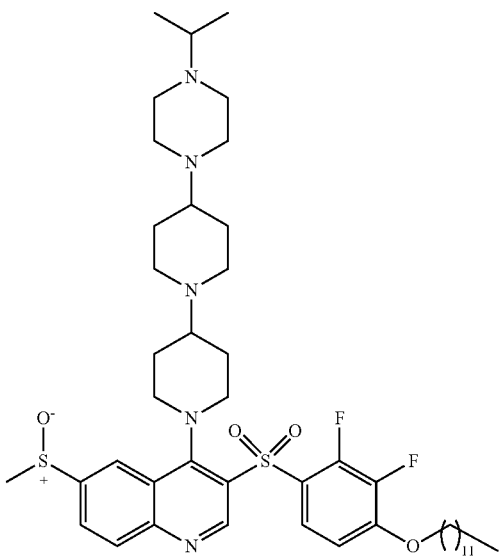 3-((4-(dodecyloxy)-2,3-difluorophenyl)sulfonyl)-4-(4-(4-isopropylpiperazin-1-yl)-[1,4'-bipiperidin]-1'-yl)-6-(methylsulfinyl)quinoline
420 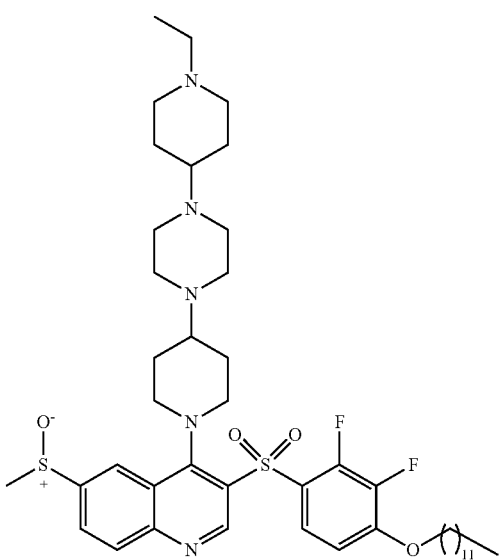 3-((4-(dodecyloxy)-2,3-difluorophenyl)sulfonyl)-4-(4-(4-(1-ethylpiperidin-4-yl)piperazin-1-yl)piperidin-1-yl)-6-(methylsulfinyl)quinoline

| | | |
|---|---|---|
| 421 | 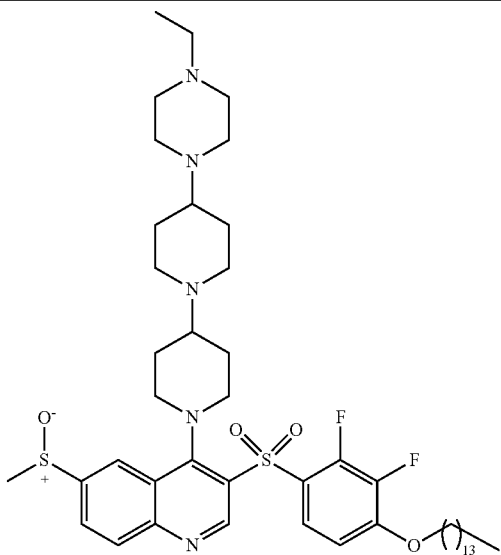 | 3-((2,3-difluoro-4-(tetradecyloxy)phenyl)sulfonyl)-4-(4-(4-ethylpiperazin-1-yl)-[1,4'-bipiperidin]-1'-yl)-6-(methylsulfinyl)quinoline |
| 422 | 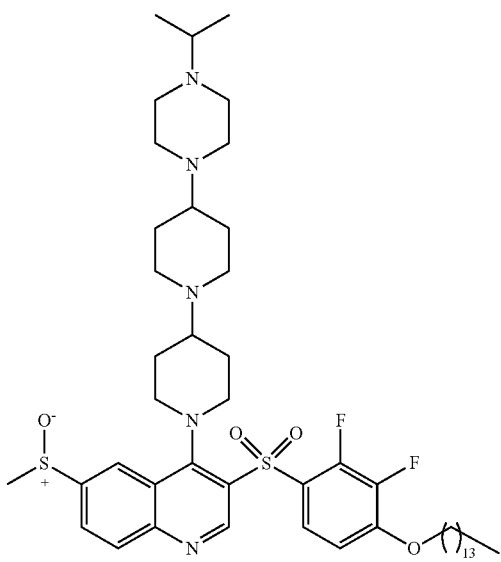 | 3-((2,3-difluoro-4-(tetradecyloxy)phenyl)sulfonyl)-4-(4-(4-isopropylpiperazin-1-yl)-[1,4'-bipiperidin]-1'-yl)-6-(methylsulfinyl)quinoline |
| 423 | 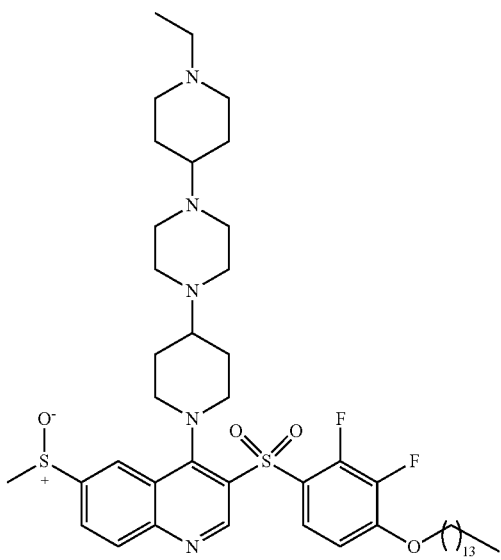 | 3-((2,3-difluoro-4-(tetradecyloxy)phenyl)sulfonyl)-4-(4-(4-(1-ethylpiperidin-4-yl)piperazin-1-yl)piperidin-1-yl)-6-(methylsulfinyl)quinoline |

| | | |
|---|---|---|
| 424 | 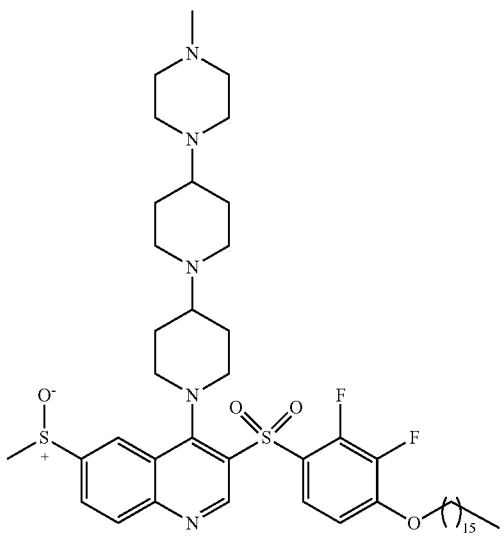 | 3-((2,3-difluoro-4-(hexadecyloxy)phenyl)sulfonyl)-4-(4-(4-methylpiperazin-1-yl)-[1,4'-bipiperidin]-1'-yl)-6-(methylsulfinyl)quinoline |
| 425 | 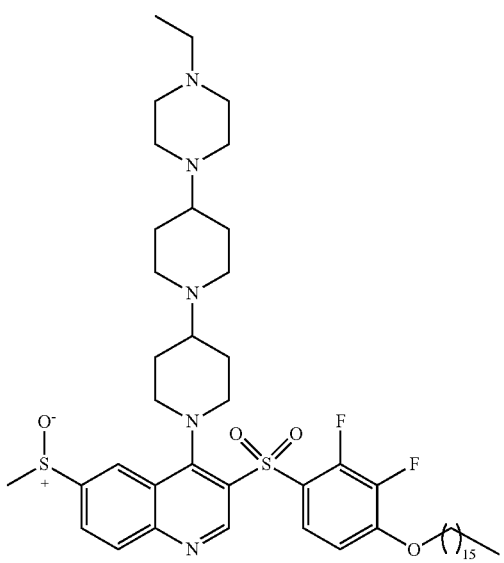 | 3-((2,3-difluoro-4-(hexadecyloxy)phenyl)sulfonyl)-4-(4-(4-ethylpiperazin-1-yl)-[1,4'-bipiperidin]-1'-yl)-6-(methylsulfinyl)quinoline |
| 426 | 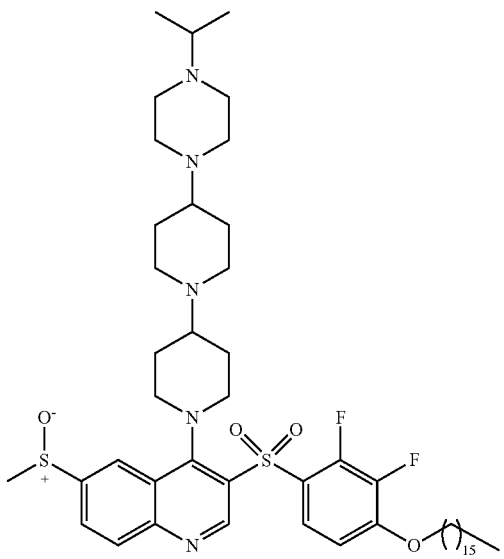 | 3-((2,3-difluoro-4-(hexadecyloxy)phenyl)sulfonyl)-4-(4-(4-isopropylpiperazin-1-yl)-[1,4'-bipiperidin]-1yl)-6-(methylsulfinyl)quinoline |

| | | |
|---|---|---|
| 427 | 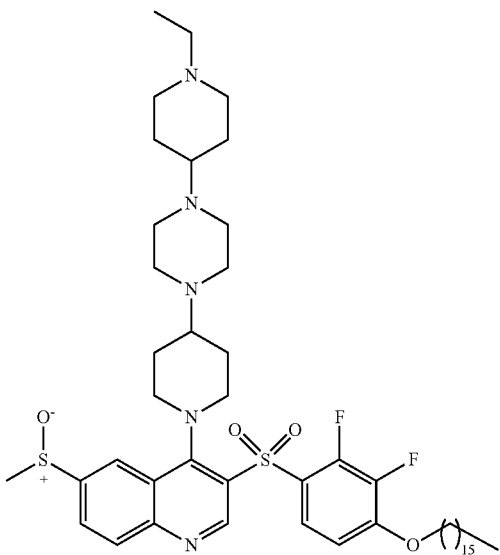 | 3-((2,3-difluoro-4-(hexadecyloxy)phenyl)sulfonyl)-4-(4-(4-(1-ethylpipendin-4-yl)piperazin-1-yl)piperidin-1-yl)-6-(methylsulfinyl)quinoline |
| 428 | 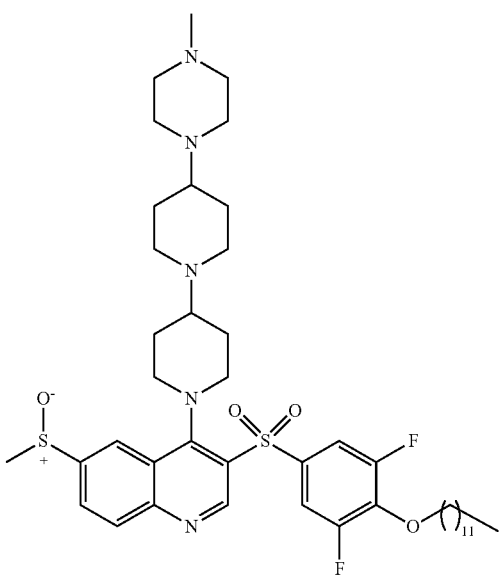 | 3-((4-(dodecyloxy)-3,5-difluorophenyl)sulfonyl)-4-(4-(4-methylpiperazn-1-yl)-[1,4'-bipiperidin]-1'-yl)-6-(methylsulfinyl)quinoline |

| | | |
|---|---|---|
| 429 | 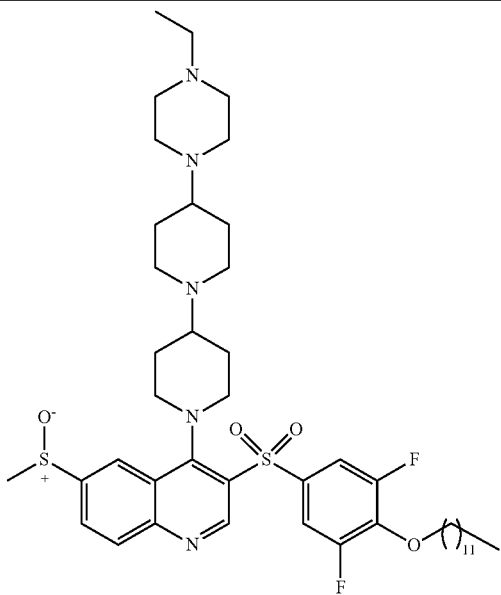 | 3-((4-(dodecyloxy)-3,5-difluorophenyl)sulfonyl)-4-(4-(4-ethylpiperazin-1-yl)-[1,4'-bipiperidin]-1'-yl)-6-(methylsulfinyl)quinoline |
| 430 | 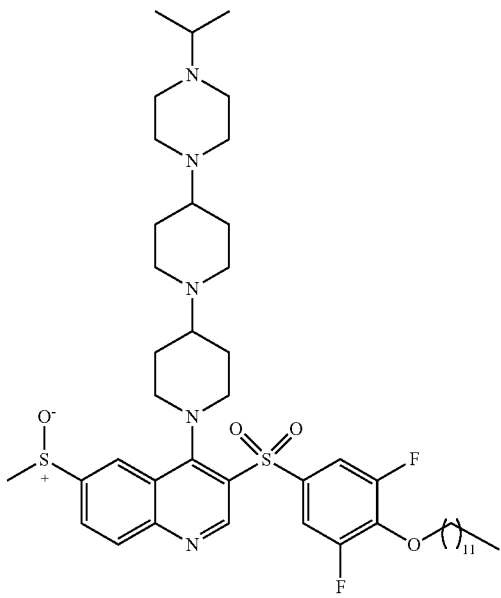 | 3-((4-(dodecyloxy)-3,5-difluorophenyl)sulfonyl)-4-(4-(4-isopropylpiperazin-1-yl)-[1,4'-bipiperidin]-1'-yl)-6-(methylsulfinyl)quinoline |

| | | |
|---|---|---|
| 431 | 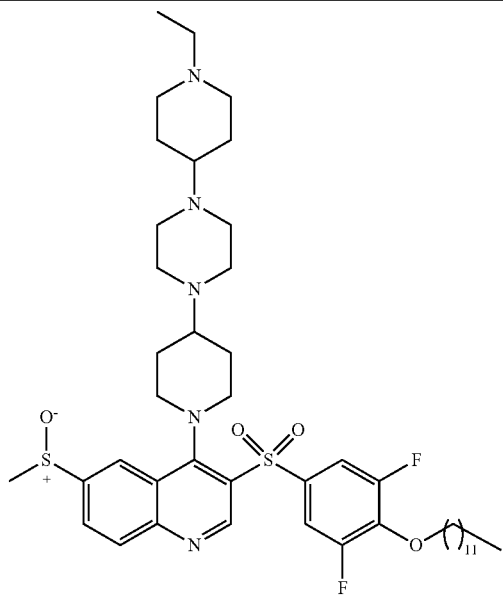 | 3-((4-(dodecyloxy)-3,5-difluorophenyl)sulfonyl)-4-(4-(4-(1-ethylpiperidin-4-yl)piperazin-1-yl)piperidin-1-yl)-6-(methylsulfinyl)quinoline |
| 432 | 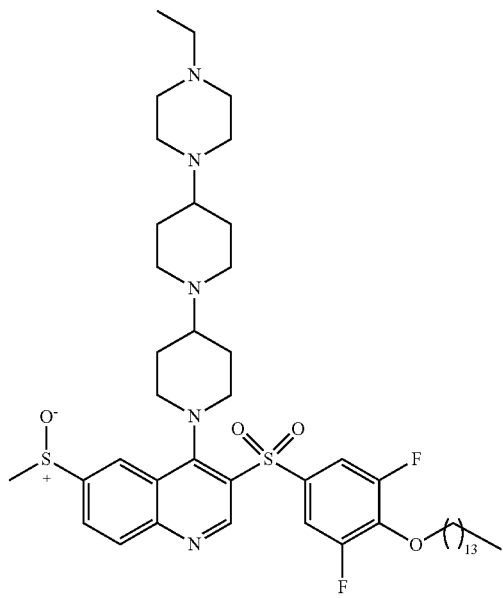 | 3-((3,5-difluoro-4-(tetradecyloxy)phenyl)sulfonyl)-4-(4-(4-ethylpiperazn-1-yl-[1,4'-bipiperidin]-1'-yl)-6-(methylsulfinyl)quinoline |

-continued
| | | |
|---|---|---|
| 433 | 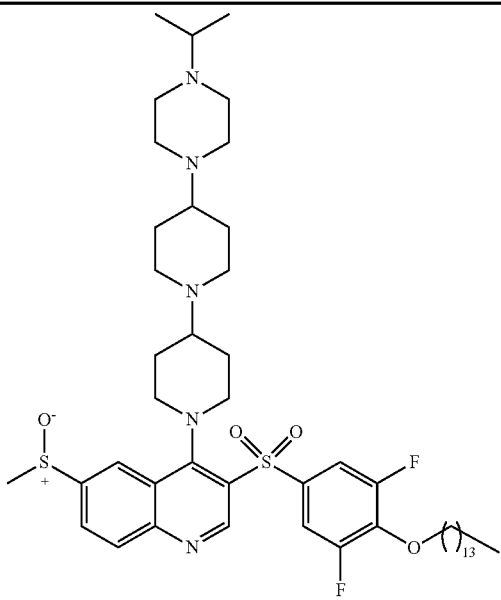 | 3-((3,5-difluoro-4-(tetradecyloxy)phenyl)sulfonyl)-4-(4-(4-isopropylpiperazin-1-yl)-[1,4'-bipiperidin]-1'-yl)-6-(methylsulfinyl)quinoline |
| 434 | 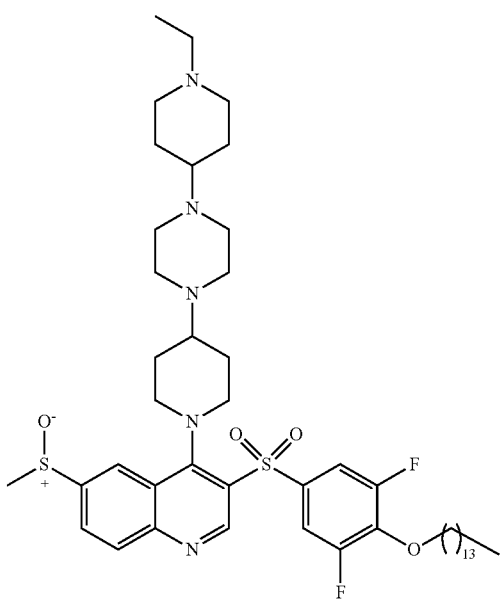 | 3-((3,5-difluoro-4-(tetradecyloxy)phenyl)sulfonyl)-4-(4-(4-(1-ethylpiperidin-4-yl)pipeiaxip-1-yl)piperidin-1-yl)-6-(methylsulfinyl)quinoline |

| | | |
|---|---|---|
| 435 | 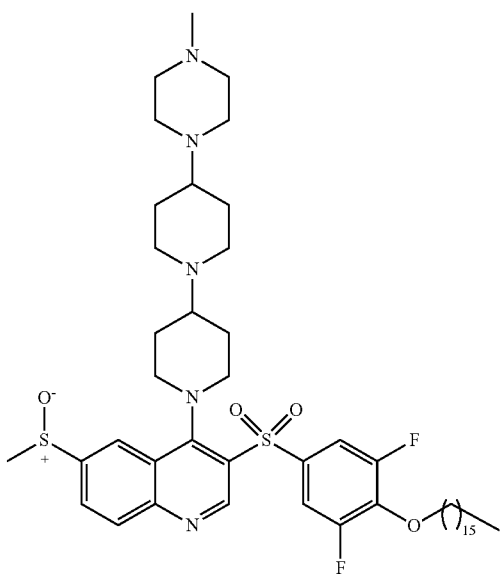 | 3-((3,5-difluoro-4-(hexadecyloxy)phenyl)sulfonyl)-4-(4-(4-methylpiperazin-1-yl)-[1,4'-bipiperidin]-1'-yl)-6-(methylsulfinyl)quinoline |
| 436 | 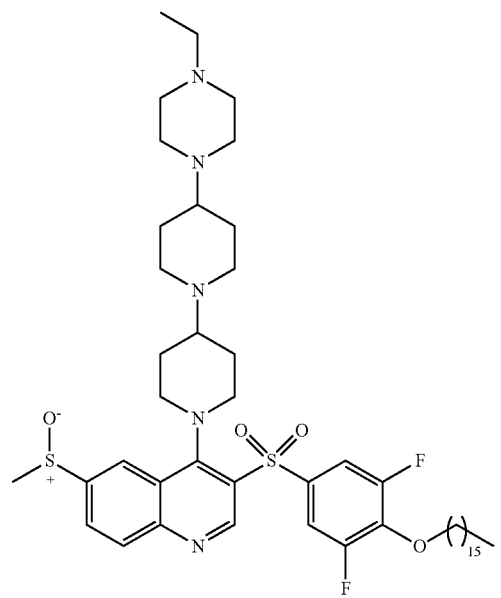 | 3-((3,5-difluoro-4-(hexadecyloxy)phenyl)sulfonyl)-4-(4-(4-ethylpiperazin-1-yl)-[1,4'-bipiperidin]-1'-yl)-6-(methylsulfinyl)quinoline |

| | | |
|---|---|---|
| 437 | 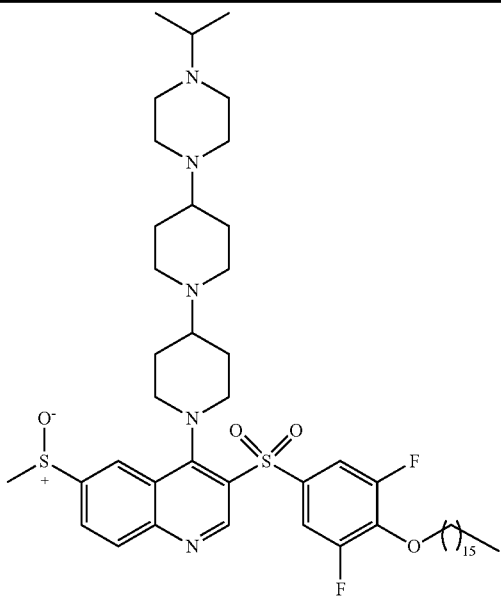 | 3-((3,5-difluoro-4-(hexadecyloxy)phenyl)sulfonyl)-4-(4-(4-isopropylpiperazin-1-yl)-[1,4'-bipiperidin]-1'-yl)-6-(methylsulfinyl)quinoline |
| 438 | 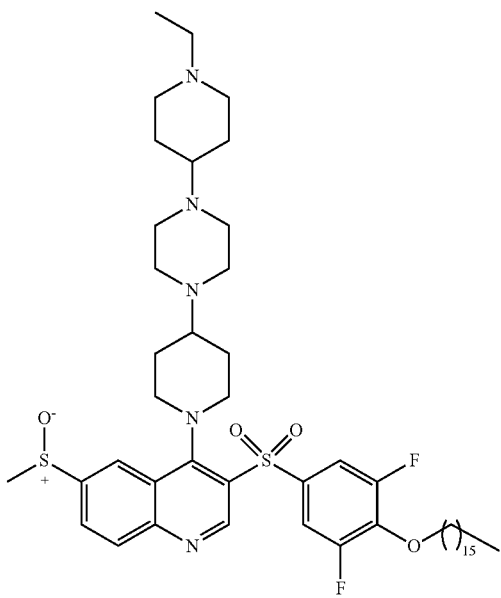 | 3-((3,5-difluoro-4-(hexadecyloxy)phenyl)sulfonyl)-4-(4-(4-(1-ethylpiperidin-4-yl)piperazin-1-yl)piperidin-1-yl)-6-(methylsulfinyl)quinoline |

| | | |
|---|---|---|
| 439 | 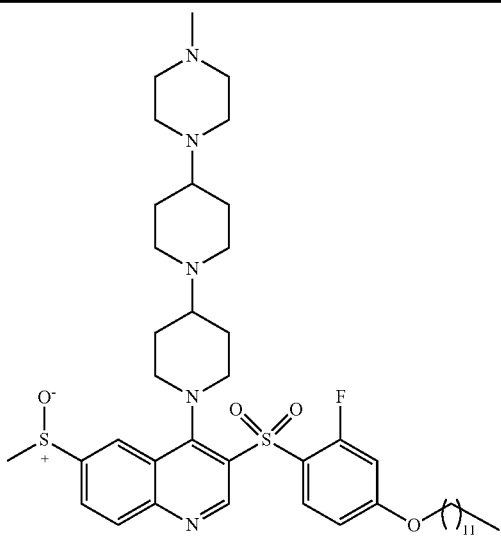 | 3-((4-(dodecyloxy)-2-fluorophenyl)sulfonyl)-4-(4-(4-methylpiperazin-1-yl)-[1,4'-bipiperidin]-1'-yl)-6-(methylsulfinyl)quinoline |
| 440 | 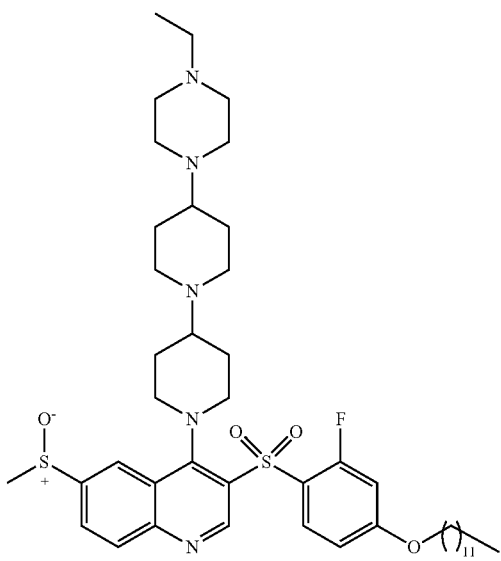 | 3-((4-(dodecyloxy)-2-fluorophenyl)sulfonyl)-4-(4-(4-ethylpiperazin-1-yl)-[1,4'-bipiperidin]-1'-yl)-6-(methylsulfinyl)quinoline |
| 441 | 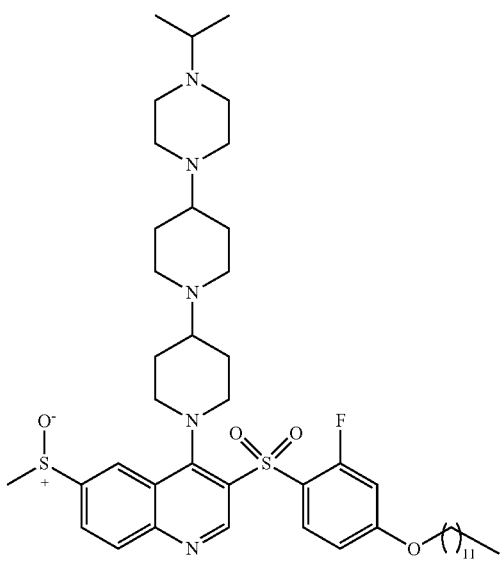 | 3-((4-(dodecyloxy)-2-fluorophenyl)sulfonyl)-4-(4-(4-isopropylpiperazin-1-yl)-[1,4'-bipiperidin]-1'-yl)-6-(methylsulfinyl)quinoline |

-continued
| | | |
|---|---|---|
| 442 | 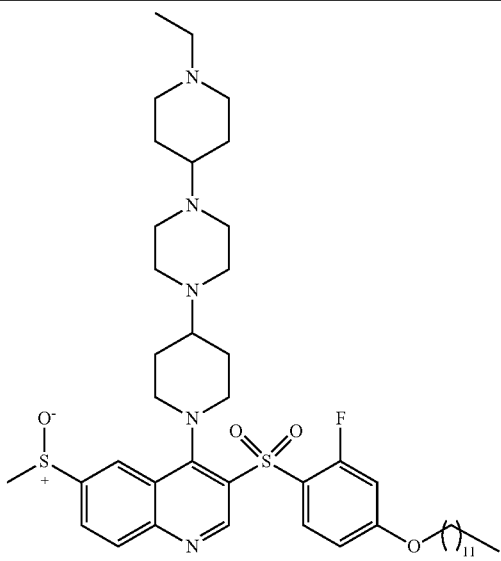 | 3-((4-(dodecyloxy)-2-fluorophenyl)sulfonyl)-4-(4-(4-(1-ethylpiperidin-4-yl)piperazin-1-yl)piperidin-1-yl)-6-(methylsulfinyl)quinoline |
| 443 | 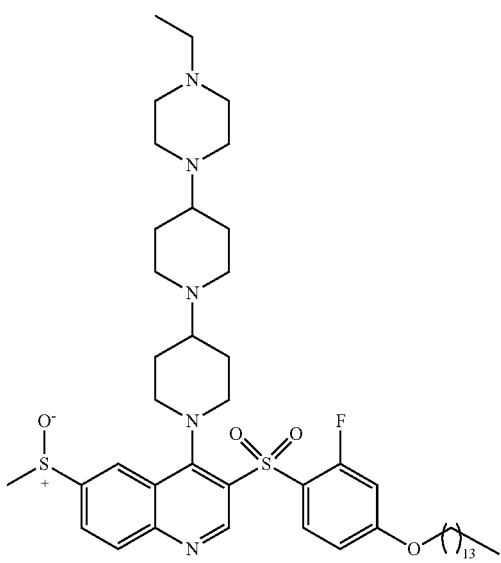 | 4-(4-(4-ethylpiperazin-1-yl)-[1,4'-bipiperidin]-1'-yl)-3-((2-fluoro-4-(tetradecyloxy)phenyl)sulfonyl)-6-(methylsulfinyl)quinoline |
| 444 | 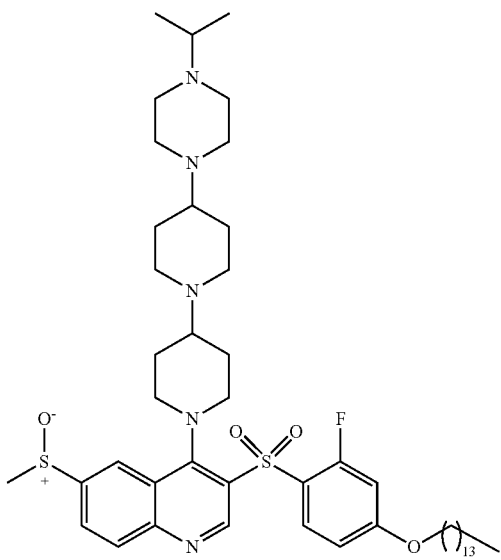 | 3-((2-fluoro-4-(tetradecyloxy)phenyl)sulfonyl)-4-(4-(4-isopropylpiperazin-1-yl)-[1,4'-bipiperidin]-1'-yl)-6-(methylsulfinyl)quinoline |

| | | |
|---|---|---|
| 445 | 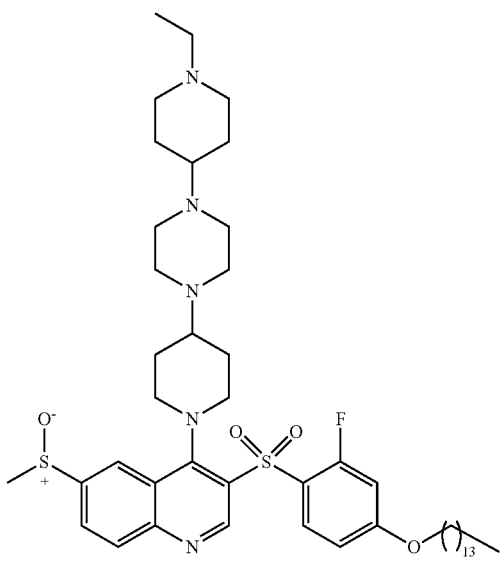 | 4-(4-(4-(1-ethylpiperidin-4-yl)piperazin-1-yl)piperidin-1-yl)-3-((2-fluoro-4-(tetradecyloxy)phenyl)sulfonyl)-6-methylsulfinyl)quinoline |
| 446 | 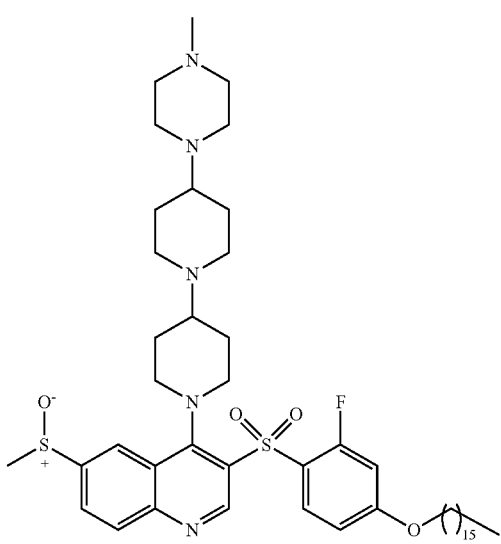 | 3-((2-fluoro-4-(hexadecyloxy)phenyl)sulfonyl-4-(4-(4-methylpiperazin-1-yl)-[1,4'-bipiperidin]-1'-yl)-6-(methylsulfinyl)quinoline |
| 447 | 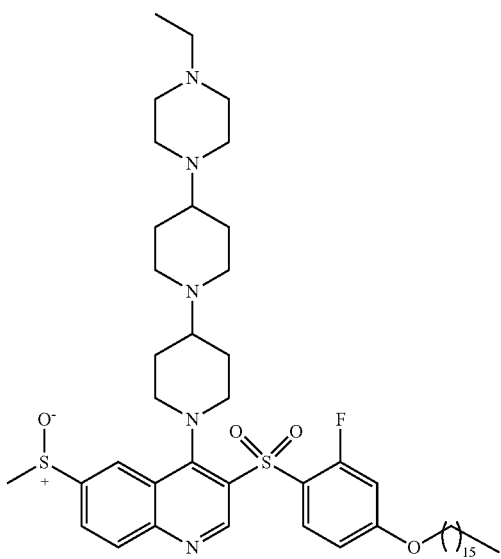 | 4-(4-(4-ethylpiperazin-1-yl)-[1,4'-bipiperidin]-1'-yl)-3-((2-fluoro-4-(hexadecyloxy)phenyl)sulfonyl)-6-(methylsulfinyl)quinoline |

| | | |
|---|---|---|
| 448 | 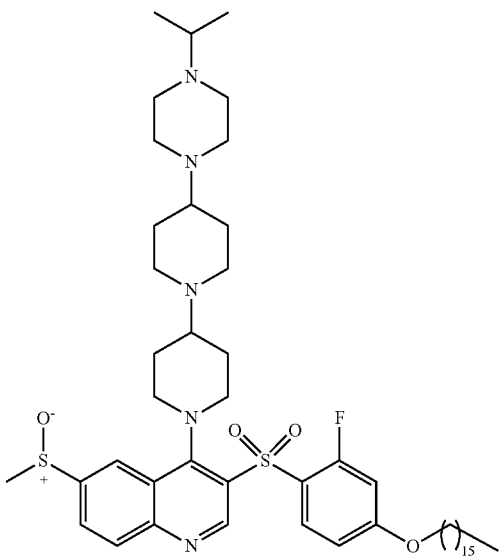 | 3-((2-fluoro-4-(hexadecyloxy)phenyl)sulfonyl)-4-(4-(4-isopropylpiperazin-1-yl)-[1,4'-bipiperidin]-1'-yl)-6-(methylsulfinyl)quinoline |
| 449 | 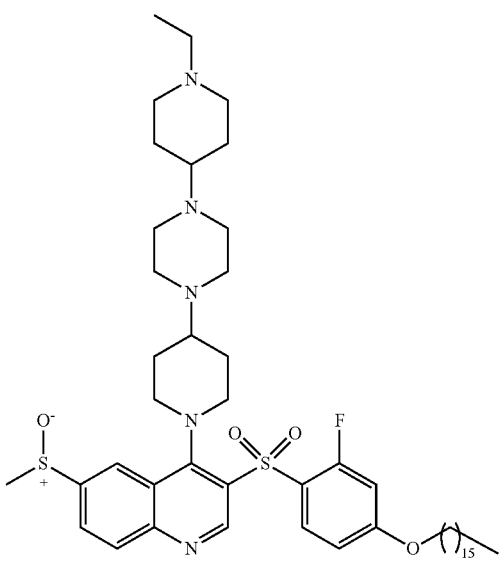 | 4-(4-(4-(1-ethylpiperidin-4-yl)piperazn-1-yl)piperidin-1-yl)-3-((2-fluoro-4-(hexadecyloxy)phenyl)sulfonyl)-6-(methylsulfinyl)quinoline |
| 450 | 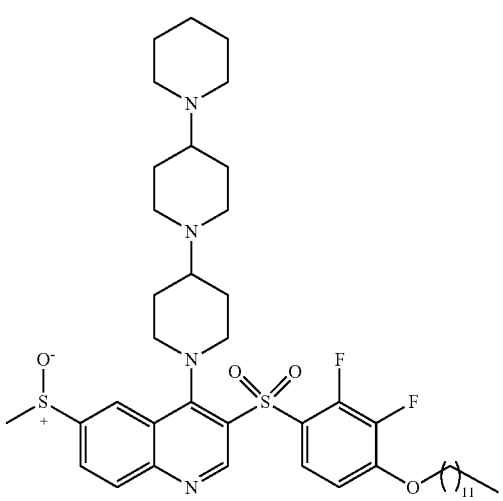 | 4-([1,4':1',4''-terpiperidin]-1''-yl)-3-((4-(dodecyloxy)-2,3-difluorophenyl)sulfonyl-6-(methylsulfinyl)quinoline |

-continued
| | | |
|---|---|---|
| 451 | 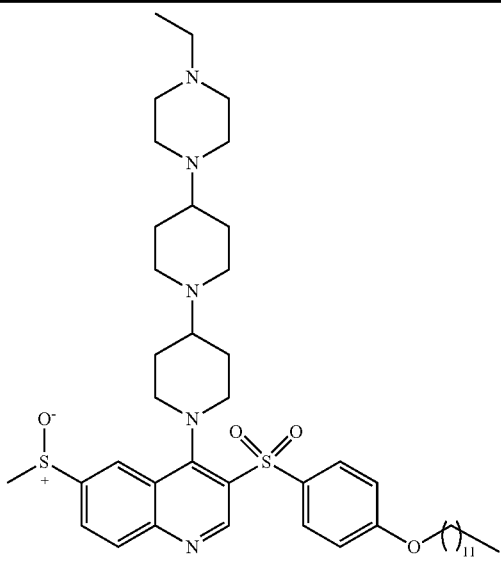 | 3-((4-(dodecyloxy)phenyl)sulfonyl)-4-(4-(4-ethylpiperazin-1-yl)-[1,4'-bipiperidin]-1'-yl)-6-(methylsulfinyl)quinoline |
| 452 | 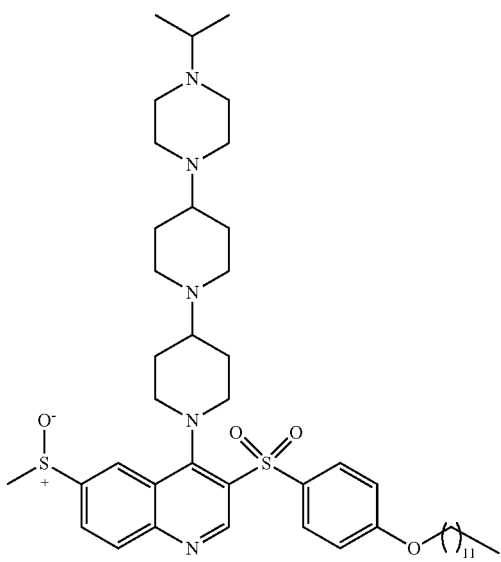 | 3-((4-(dodecyloxy)phenyl)sulfonyl)-4-(4-(4-isopropylpiperazin-1-yl)-[1,4'-bipiperidin]-1'-yl)-6-(methylsulfinyl)quinoline |
| 453 | 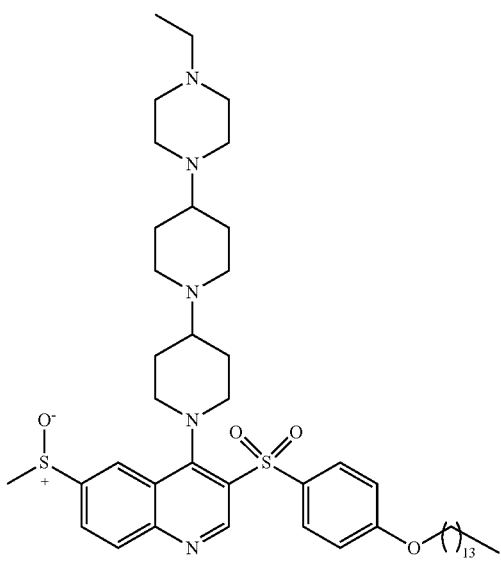 | 4-(4-(4-ethylpiperazin-1-yl)-[1,4'-bipiperidin]-1'-yl)-6-(methylsulfinyl)-3-((4-(tetradecyloxy)phenyl)sulfonyl)quinoline |

| | | |
|---|---|---|
| 454 | 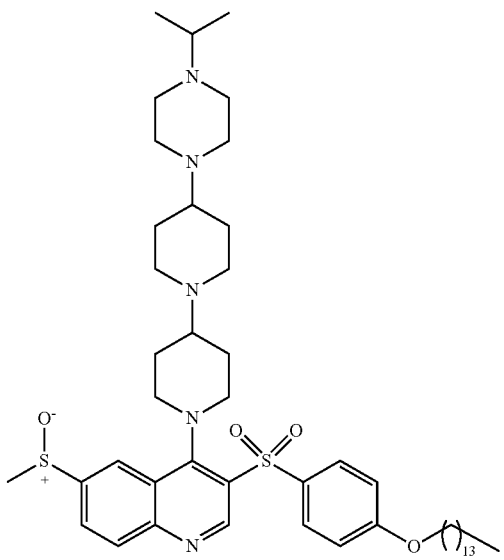 | 4-(4-(4-isopropylpiperazin-1-yl)-[1,4'-bipiperidin]-1'-yl)-6-(methylsulfinyl)-3-((4-(tetradecyloxy)phenyl)sulfonyl)quinoline |
| 455 | 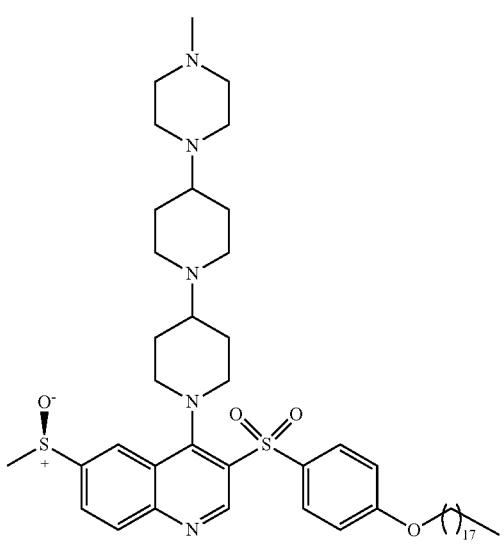 | (R)-4-(4-(4-methylpiperazn-1-yl)-[1,4'-bipiperidin]-1'-yl)-6-(methylsulfinyl)-3-((4-(octadecyloxy)phenyl)sulfonyl)quinoline |
| 456 | 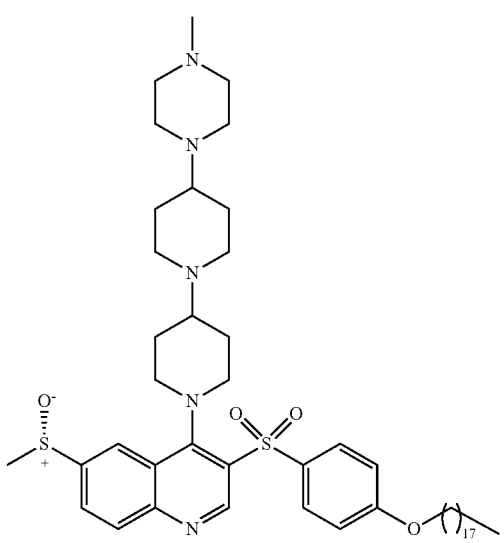 | (S)-4-(4-(4-methylpiperazin-1-yl)-[1,4'-bipiperidin]-1'-yl)-6-(methylsulfinyl)-3-((4-(octadecyloxy)phenyl)sulfonyl)quinoline |

-continued
| | | |
|---|---|---|
| 457 | 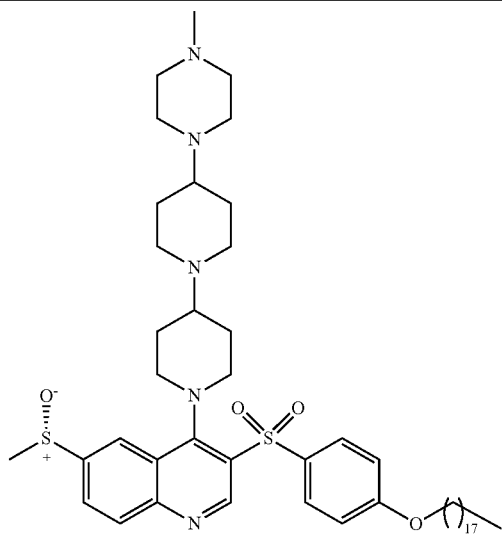 | (R)-4-(4-(4-ethylpiperazin-1-yl)-[1,4'-bipiperidin]-1'-yl)-6-(methylsulfinyl)-3-((4-(octadecyloxy)phenyl)sulfonyl)quinoline |
| 458 | 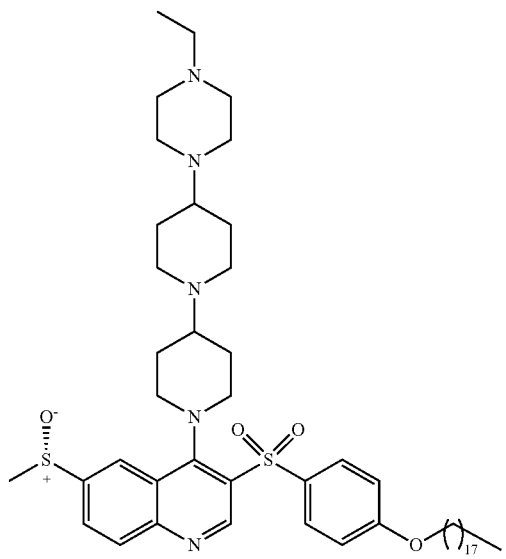 | (S)-4-(4-(4-ethylpiperazn-1-yl)-[1,4'-bipiperidin]-1'-yl)-6-(methylsulfinyl)-3-((4-(octadecyloxy)phenyl)sulfonyl)quinoline |
| 459 | 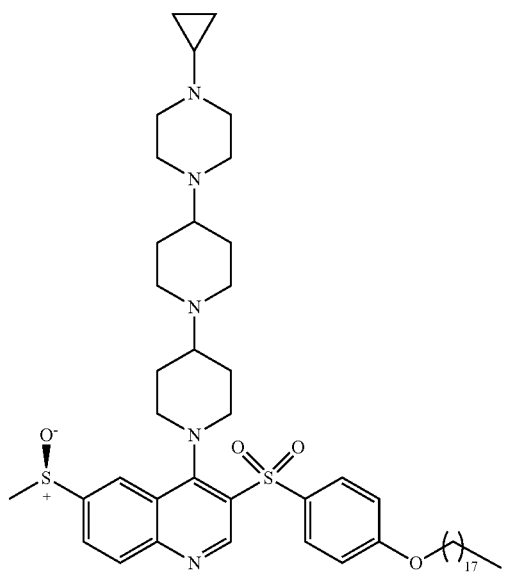 | (R)-4-(4-(4-cyclopropylpiperazin-1-yl)-[1,4'-bipiperidin]-1'-yl)-6-(methylsulfinyl)-3-((4-(octadecyloxy)phenyl)sulfonyl)quinoline |

| | | |
|---|---|---|
| 460 | 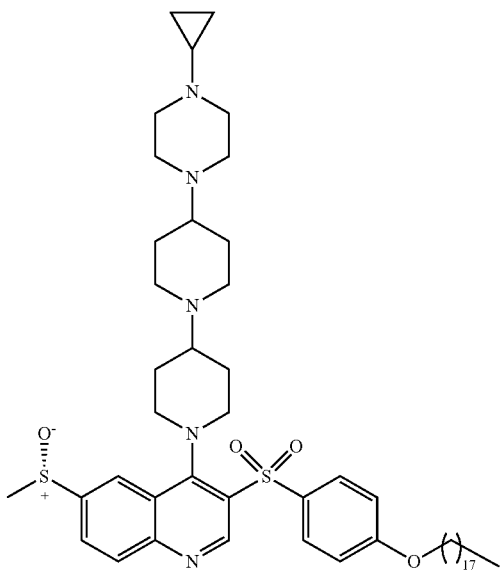 | (S)-4-(4-(4-cyclopropylpiperazin-1-yl)-[1,4'-bipiperidin]-1'-yl)-6-(methylsulfinyl)-3-((4-(octadecyloxy)phenyl)sulfonyl)quinoline |
| 461 | 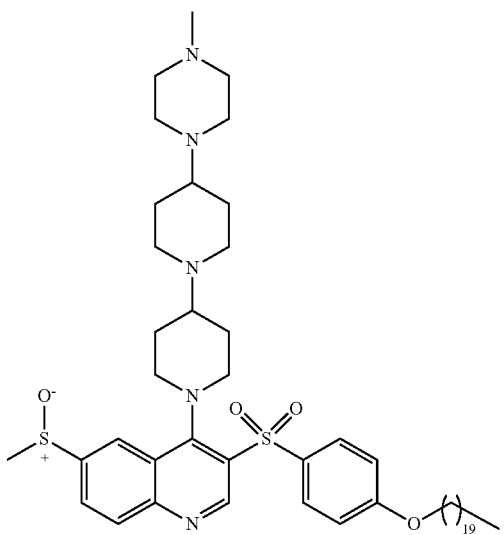 | 3-((4-(icosyloxy)phenyl)sulfonyl)-4-(4-(4-methylpiperazin-1-yl)-[1,4'-bipiperidin]-1'-yl)-6-(methylsulfinyl)quinoline |

-continued
| | | |
|---|---|---|
| 462 | 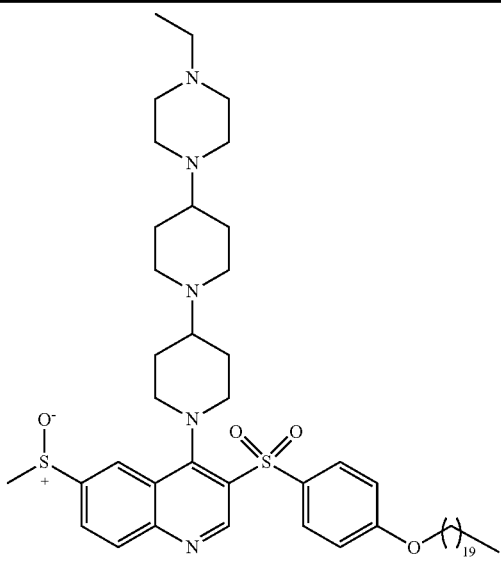 | 4-(4-(4-ethylpiperazin-1-yl)-[1,4'-bipiperidin]-1'-yl)-3-((4-(icosyloxy)phenyl)sulfonyl)-6-(methylsulfinyl)quinoline |
| 463 | 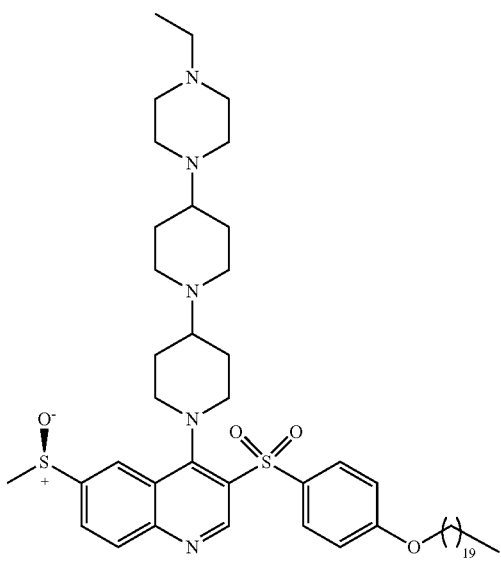 | (R)-4-(4-(4-ethylpiperazin-1-yl)-[1,4'-bipiperidin]-1'-yl)-3-((4-(icosyloxy)phenyl)sulfonyl)-6-(methylsulfinyl)quinoline |
| 464 | 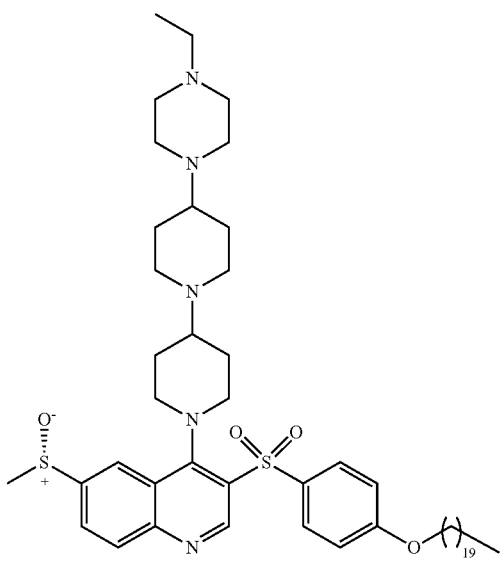 | (S)-4-(4-(4-ethylpiperazin-1-yl)-[1,4'-bipiperidin]-1'-yl)-3-((4-(icosyloxy)phenyl)sulfonyl)-6-(methylsulfinyl)quinoline |

-continued
| | | |
|---|---|---|
| 465 | 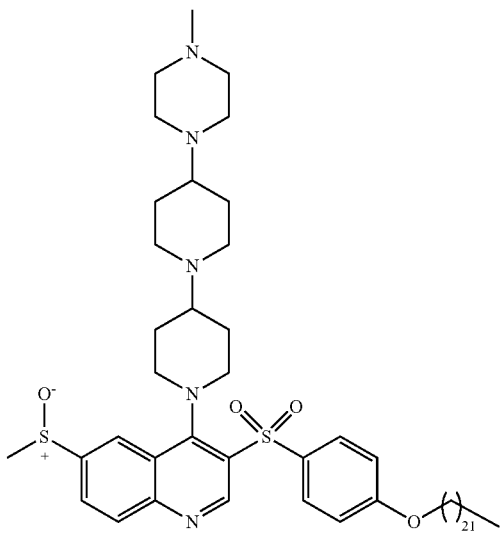 | 3-((4-(docosyloxy)phenyl)sulfonyl)-4-(4-(4-methylpiperazin-1-yl)-[1,4'-bipiperidin]-1'-yl)-6-(methylsulfinyl)quinoline |
| 466 | 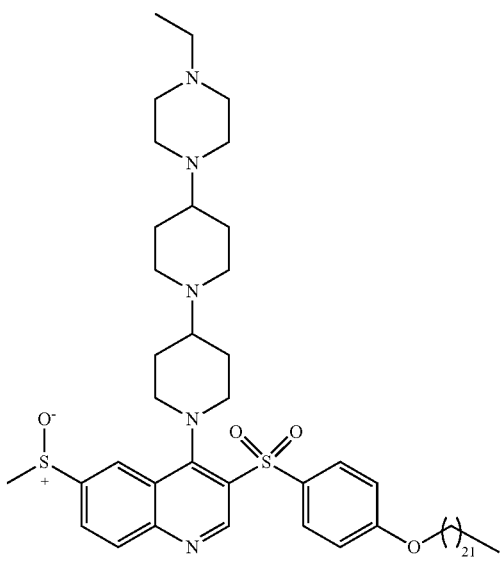 | 3-((4-(docosyloxy)phenyl)sulfonyl)-4-(4-(4-ethylpiperazn-1-yl)-[1,4'-bipiperidin]-1'-yl)-6-(methylsulfinyl)quinoline |
| 467 | 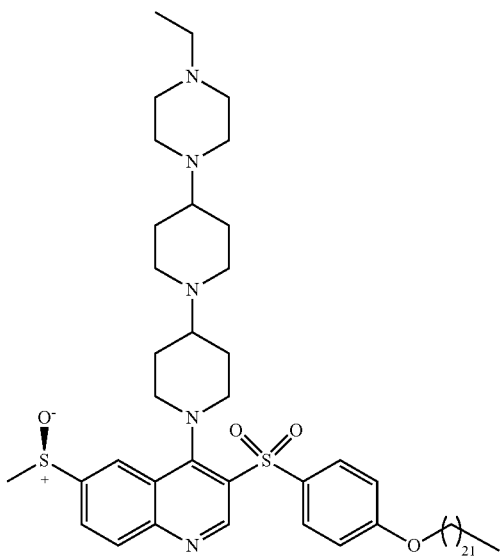 | (R)-3-((4-(docosyloxy)phenyl)sulfonyl)-4-(4-(4-ethylpiperazin-1-yl)-[1,4'-bipiperidin]-1'-yl)-6-(methylsulfinyl)quinoline |

468 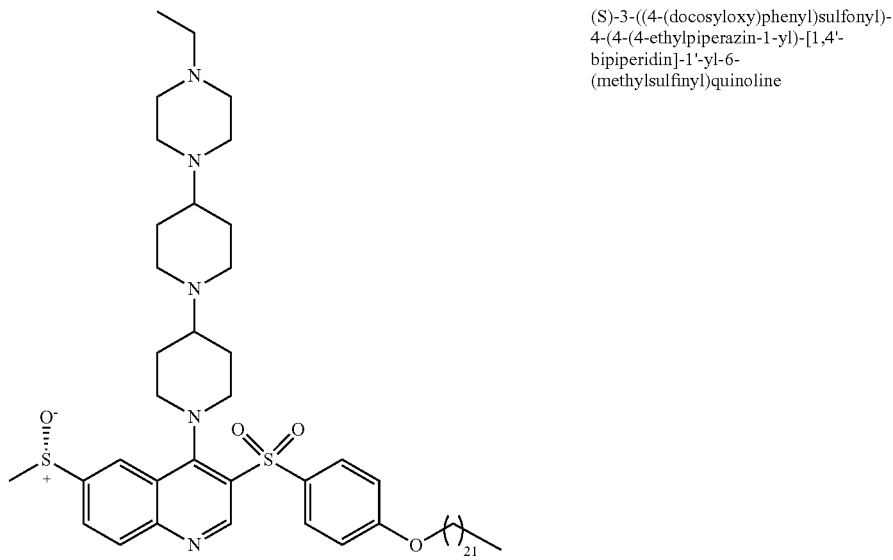 (S)-3-((4-(docosyloxy)phenyl)sulfonyl)-4-(4-(4-ethylpiperazin-1-yl)-[1,4'-bipiperidin]-1'-yl-6-(methylsulfinyl)quinoline
469 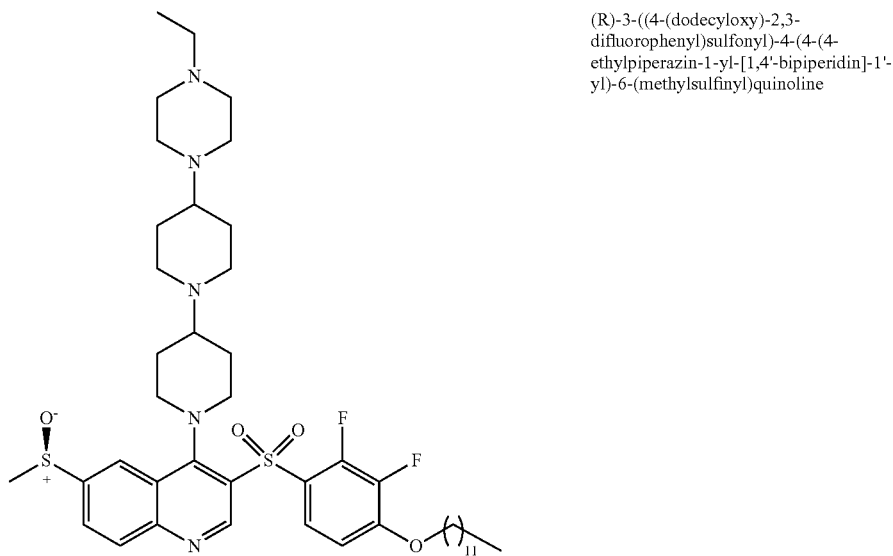 (R)-3-((4-(dodecyloxy)-2,3-difluorophenyl)sulfonyl)-4-(4-(4-ethylpiperazin-1-yl-[1,4'-bipiperidin]-1'-yl)-6-(methylsulfinyl)quinoline -continued
| | | |
|---|---|---|
| 470 | 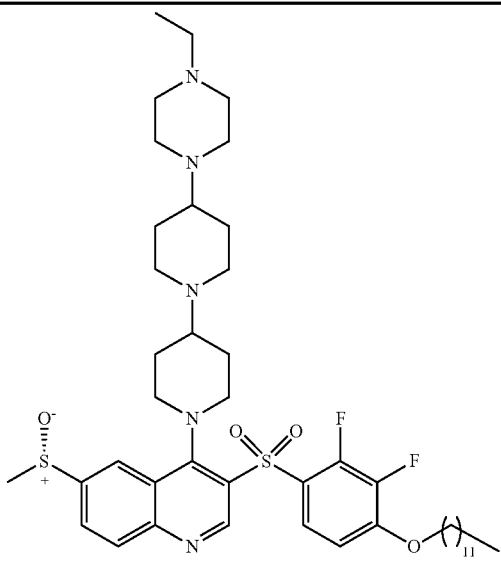 | (S)-3-((4-(dodecyloxy)-2,3-difluorophenyl)sulfonyl)-4-(4-(4-ethylpiperazin-1-yl)-[1,4'-bipiperidin]-1'-yl)-6-(methylsulfinyl)quinoline |
| 471 | 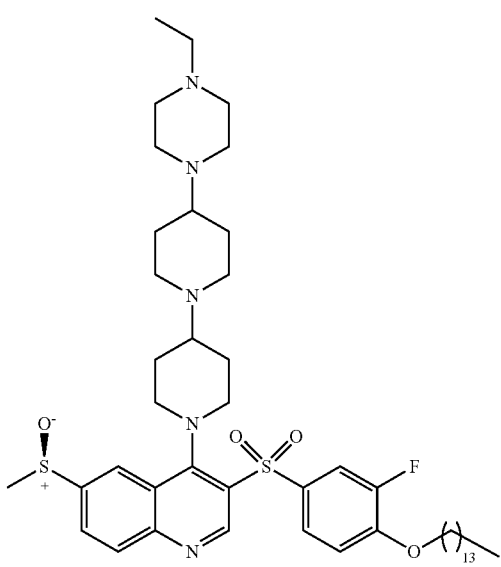 | (R)-4-(4-(4-ethylpiperazin-1-yl)-[1,4'-bipiperidin]-1'-yl)-3-((3-fluoro-4-(tetradecyloxy)phenyl)sulfonyl)-6-(methylsulfinyl)quinoline |
| 472 | 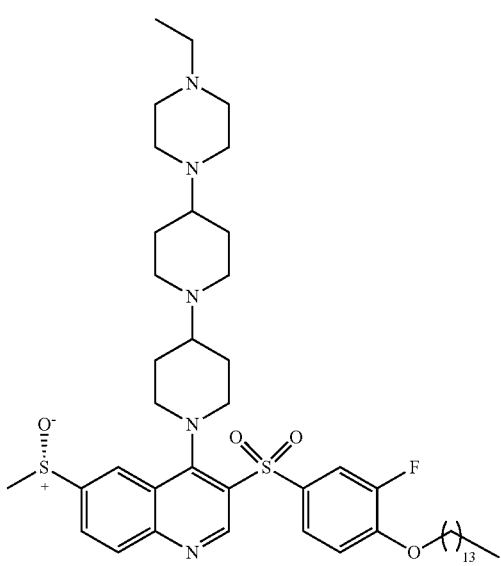 | (S)-4-(4-(4-ethylpiperazin-1-yl-[1,4'-bipiperidin]-1'-yl-3-((3-fluoro-4-(tetradecyloxy)phenyl)sulfonyl)-6-(methylsulfinyl)quinoline |

-continued
| | | |
|---|---|---|
| 473 | 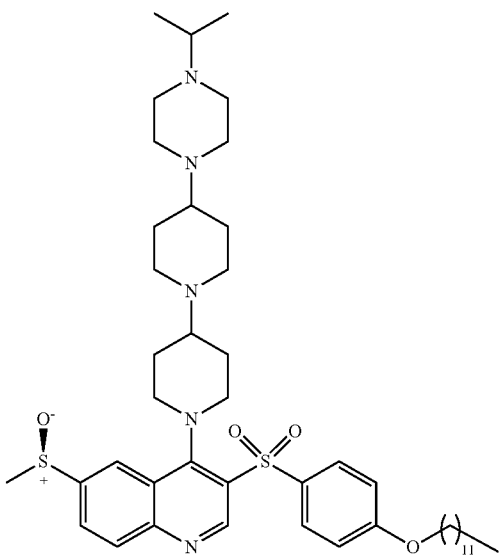 | (R)-3-((4-(dodecyloxy)phenyl)sulfonyl)-4-(4-(4-isopropylpiperazin-1-yl)-[1,4'-bipiperidin]-1'-yl)-6-(methylsulfinyl)quinoline |
| 474 | 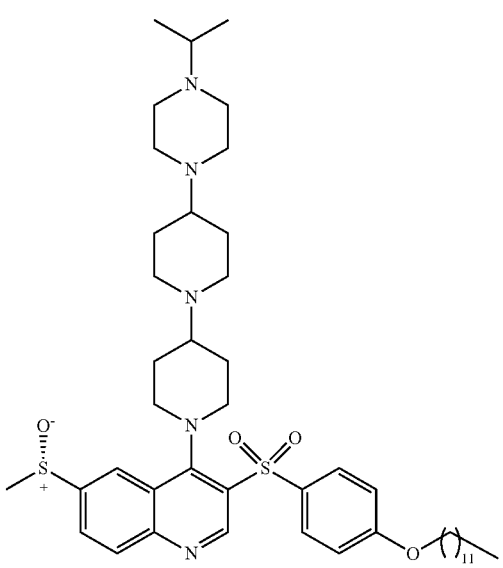 | (S)-3-((4-(dodecyloxy)phenyl)sulfonyl)-4-(4-(4-isopropylpiperazin-1-yl)-[1,4'-bipiperidin]-1'-yl)-6-(methylsutriny)quinoline |
| 475 | 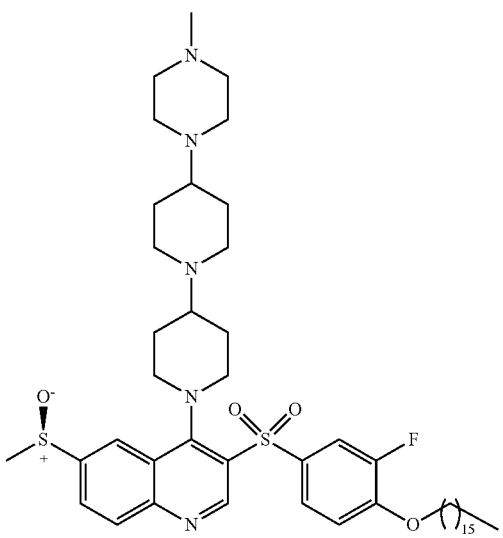 | (R)-3-((3-fluoro-4-(hexadecyloxy)phenyl)sulfonyl)-4-(4-(4-methylpiperazin-1-yl)-[1,4'-bipiperidin]-1'-yl)-6-(methylsulfinyl)quinoline |

| | | |
|---|---|---|
| 476 | 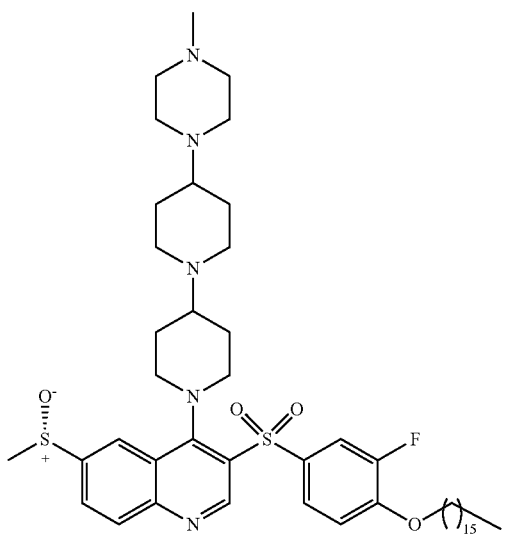 | (S)-3-((3-fluoro-4-(hexadecyloxy)phenyl)sulfonyl)-4-(4-(4-methylpiperazin-1-yl)-[1,4'-bipiperidin]-1'-yl)-6-(methylsulfinyl)quinoline |
| 477 | 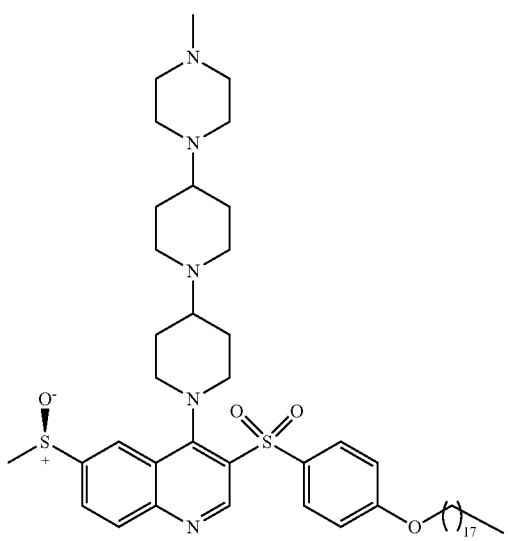 | (R)-4-(4-(4-methylpiperazin-1-yl)-[1,4'-bipiperidin]-1'-yl)-6-(methylsulfinyl)-3-((4-(octadecyloxy)phenyl)sulfonyl)quinoline |
| 478 | 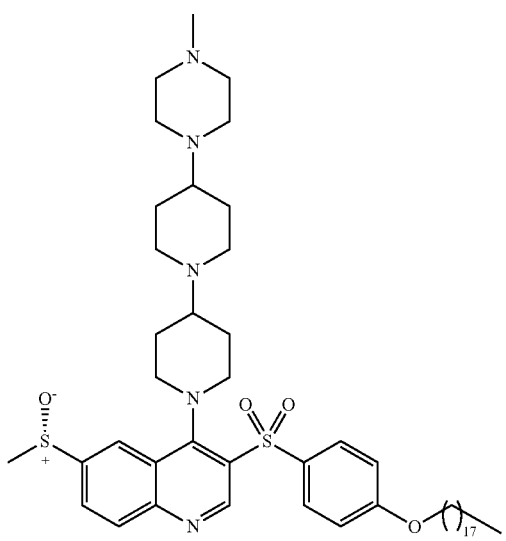 | (S)-4-(4-(4-methylpiperazin-1-yl)-[1,4'-bipiperidin]-1'-yl)-6-(methylsulfinyl-3-((4-(octadecyloxy)phenyl)sulfonyl)quinoline |

| | | |
|---|---|---|
| 479 | 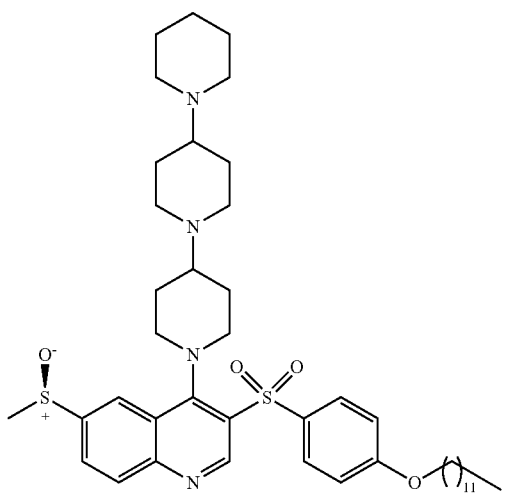 | (R)-4-([1,4':1',4''-terpiperidin]-1''-yl)-3-((4-(dodecyloxy)phenyl)sulfonyl)-6-(methylsulfinyl)quinoline |
| 480 | 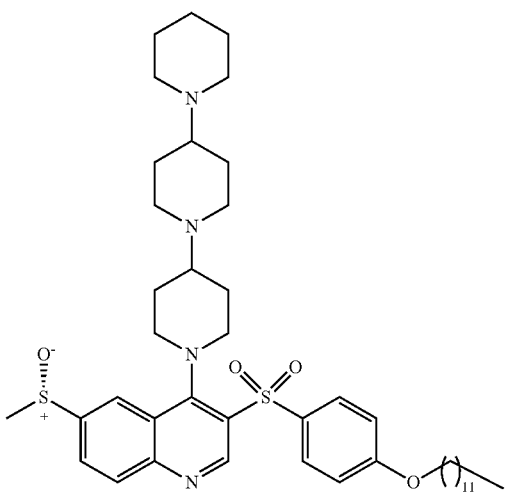 | (S)-4-([1,4':1',4''-terpiperidin]-1''-yl)-3-((4-(dodecyloxy)phenyl)sulfonyl)-6-(methylsulfinyl)quinoline |
| 481 | 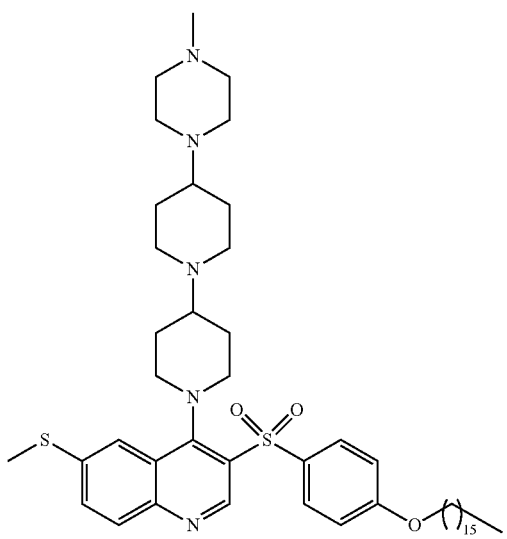 | 3-((4-(hexadecyloxy)phenyl)sulfonyl)-4-(4-(4-methylpiperazin-1-yl)-[1,4'-bipiperidin]-1'-yl)-6-(methylthio)quinoline |

-continued
| | | |
|---|---|---|
| 482 | 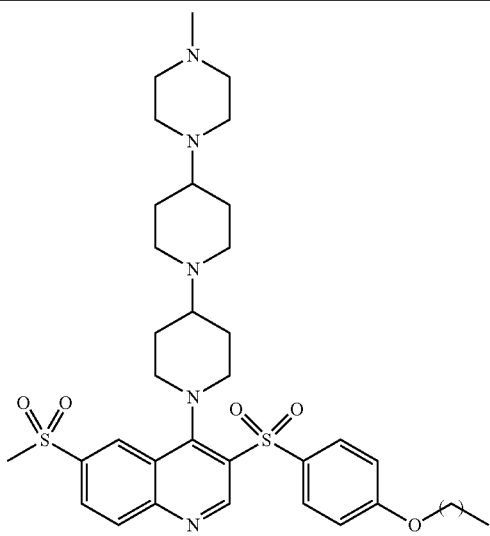 | 3-((4-(hexadecyloxy)phenyl)sulfonyl)-4-(4-(4-methylpiperazin-1-yl)-[1,4'-bipiperidin]-1'-yl)-6-(methylsulfonyl)quinoline |
| 483 | 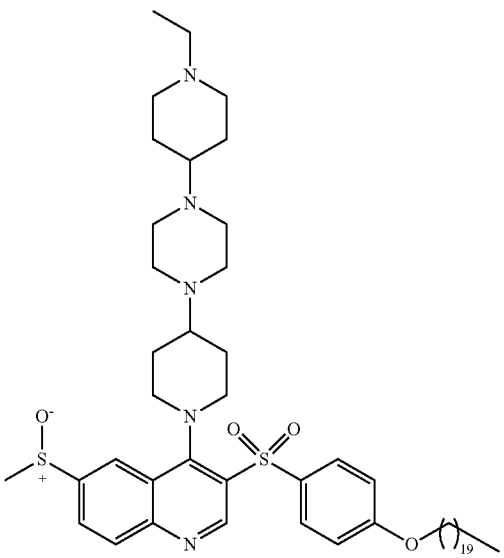 | 4-(4-(4-(1-ethylpiperidin-4-yl)piperazin-1-yl)piperidin-1-yl)-3-((4-(icosyloxy)phenyl)sulfonyl)-6-(methylsulfinyl)quinoline |
| 484 | 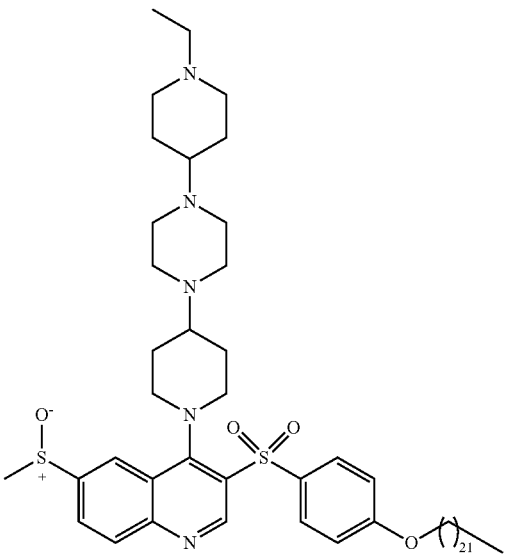 | 3-((4-(docosyloxy)phenyl)sulfonyl)-4-(4-(4-(1-ethylpiperidin-4-yl)piperazin-1-yl)piperidin-1-yl)-6-(methylsulfinyl)quinoline |

-continued
| | | |
|---|---|---|
| 485 | 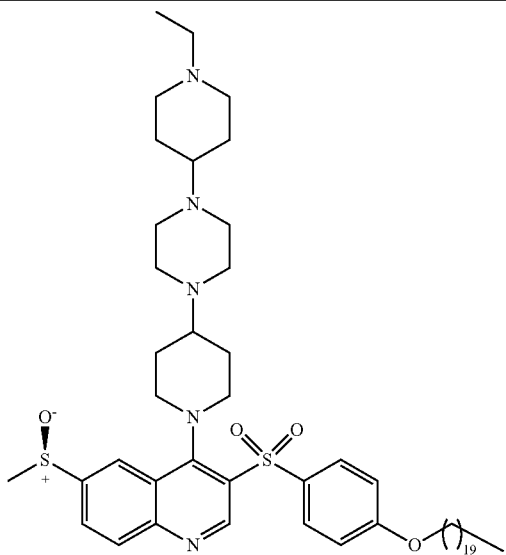 | (R)-4-(4-(4-(1-ethylpiperidin-4-yl)piperazin-1-yl)piperidin-1-yl)-3-((4-(icosyloxy)phenyl)sulfonyl)-6-(methylsulfinyl)quinoline |
| 486 | 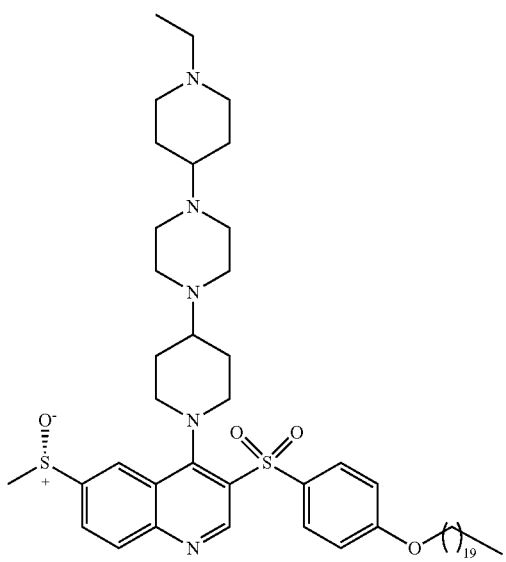 | (S)-4-(4-(4-(1-ethylpiperidin-4-yl)piperazin-1-yl)piperidin-1-yl)-3-((4-(icosyloxy)phenyl)sulfonyl)-6-(methylsulfinyl)quinoline |
| 487 | 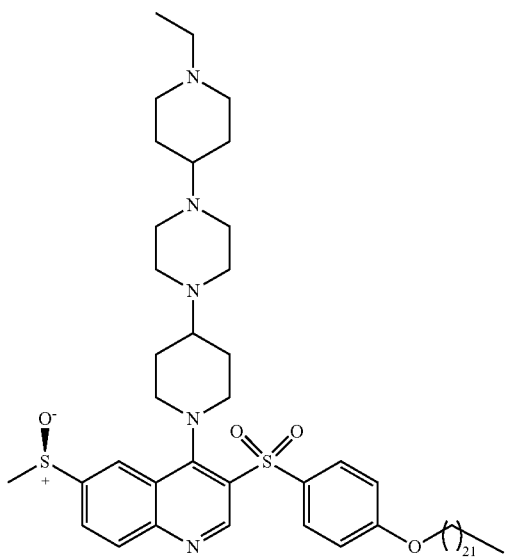 | (R)-3-((4-(docosyloxy)phenyl)sulfonyl)-4-(4-(4-(1-ethylpiperidin-4-yl)piperazin-1-yl)piperidin-1-yl)-6-(methylsulfinyl)quinoline |

| | | |
|---|---|---|
| 488 | 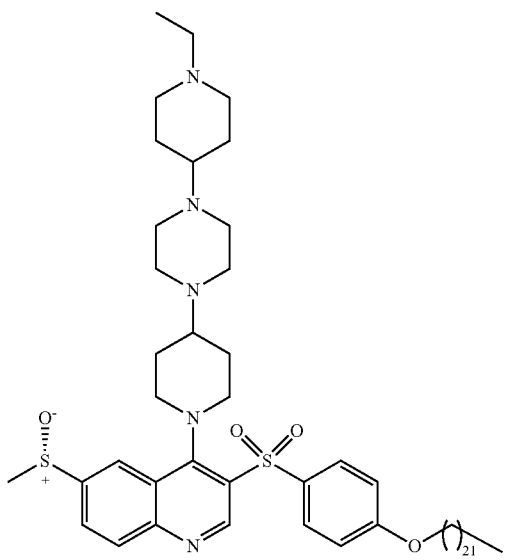 | (S)-3-((4-(docosyloxy)phenyl)sulfonyl)-4-(4-(4-(1-ethylpiperidin-4-yl)piperazin-1-yl)piperidin-1-yl)-6-(methylsulfinyl)quinoline |
| 489 | 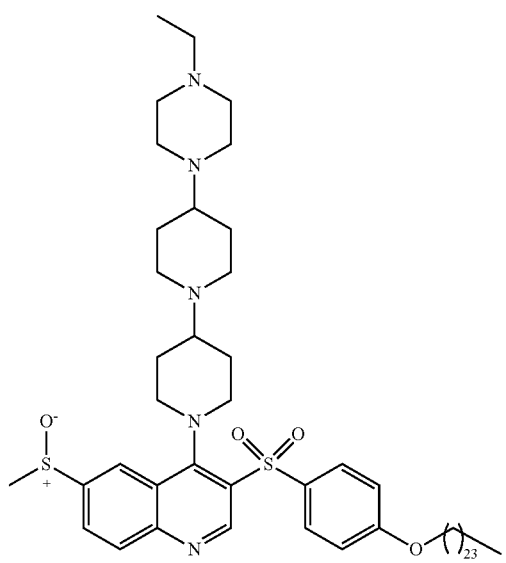 | 4-(4-(4-ethylpiperazin-1-yl)-[1,4'-bipiperidin]-1'-yl)-6-(methylsulfinyl)-3-((4-(tetracosyloxy)phenyl)sulfonyl)quinoline |

-continued
| | | |
|---|---|---|
| 490 | 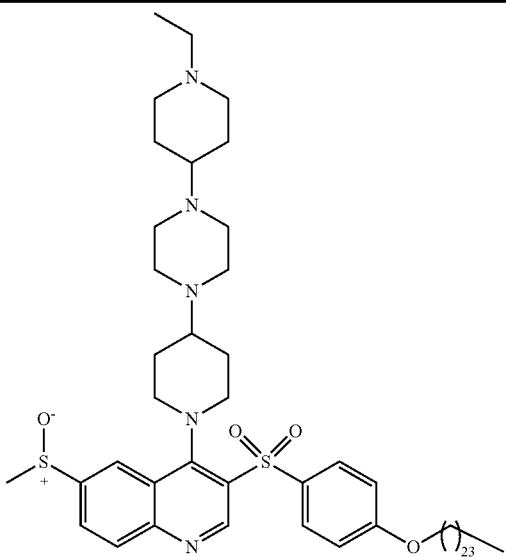 | 4-(4-(4-(1-ethylpiperidin-4-yl)piperazin-1-yl)piperidin-1-yl)-6-(methylsulfinyl)-3-((4-(tetracosyloxy)phenyl)sulfonyl)quinoline |
| 491 | 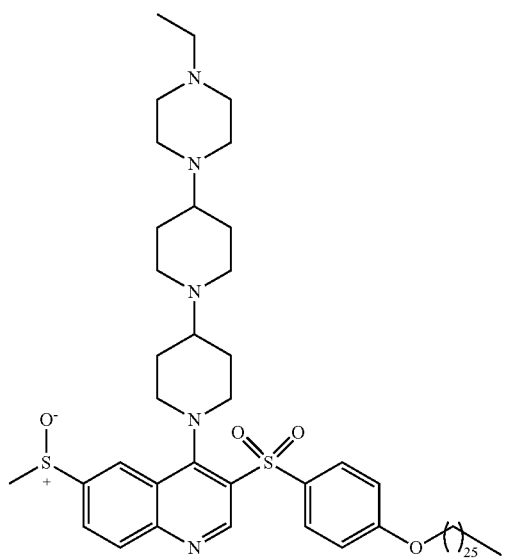 | 4-(4-(4-ethylpiperazin-1-yl)-[1,4'-bipiperidin]-1'-yl)-3-((4-(hexacosyloxy)phenyl)sulfonyl)-6-(methylsulfonyl)quinoline |
| 492 | 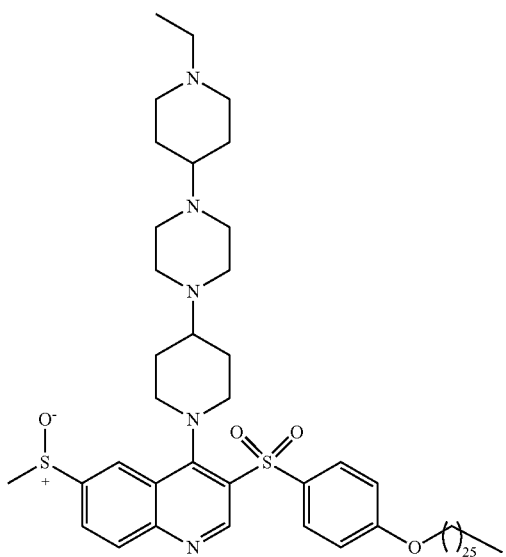 | 4-(4-(4-(1-ethylpiperidin-4-yl)piperazin-1-yl)piperidin-1-yl)-3-((4-(hexacosyloxy)phenyl)sulfonyl)-6-(methylsulfinyl)quinoline |

| | | |
|---|---|---|
| 493 | 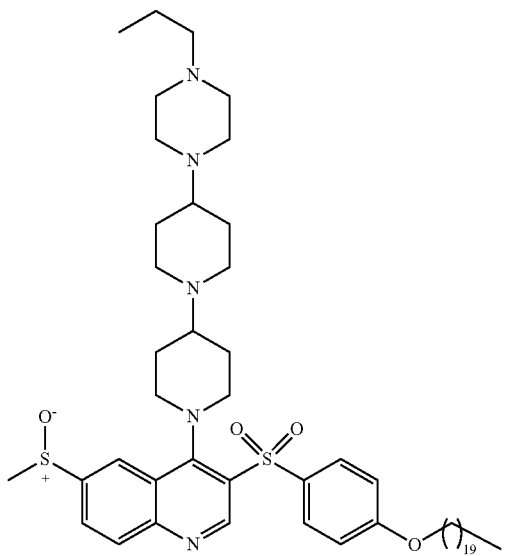 | 3-((4-(icosyloxy)phenyl)sulfonyl)-6-(methylsulfinyl)-4-(4-(4-propylpiperazin-1-yl-[1,4'-bipiperidin]-1'-yl)quinoline |
| 494 | 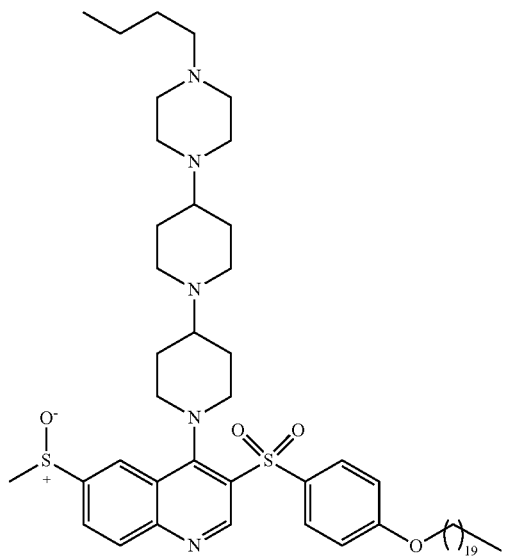 | 4-(4-(4-butylpiperazin-1-yl)-[1,4'-bipiperidin]-1'-yl)-3-((4-(icosyloxy)phenyl)sulfonyl)-6-(methylsulfinyl)quinoline |

-continued
| | | |
|---|---|---|
| 495 | 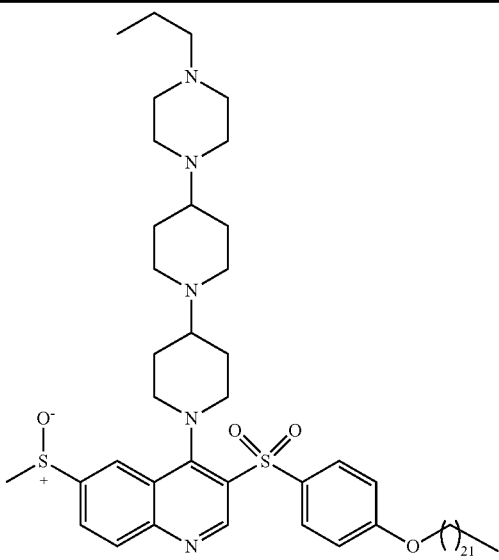 | 3-((4-(docosyloxy)phenyl)sulfonyl)-6-(methylsulfinyl)-4-(4-(4-propylpiperazin-1-yl)-[1,4'-bipiperidin]-1'-yl)quinoline |
| 496 | 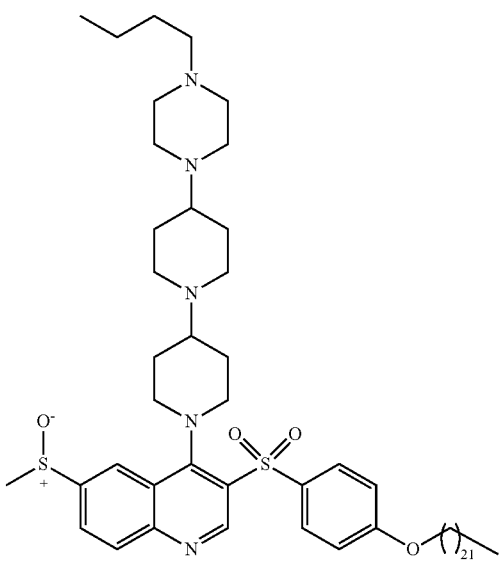 | 4-(4-(4-butylpiperazin-1-yl)-[1,4'-bipiperidin]-1'-yl-3-((4-(docosyloxy)phenyl)sulfonyl)-6-(methylsulfinyl)quinoline |
| 497 | 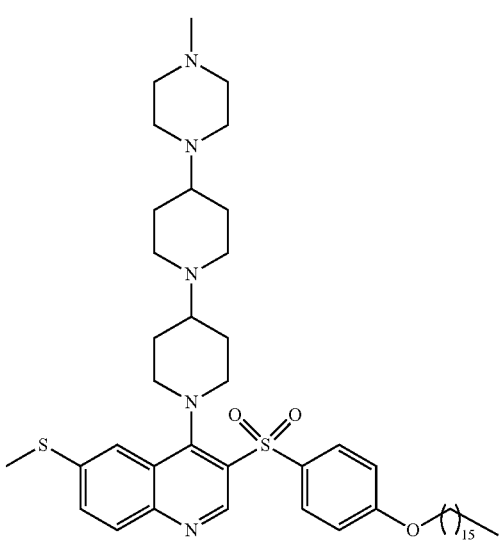 | 3-((4-(hexadecyloxy)phenyl)sulfonyl)-4-(4-(4-methylpiperazin-1-yl)-[1,4'-bipiperidin]-1'-yl)-6-(methylthio)quinoline |

-continued
| | | |
|---|---|---|
| 498 | 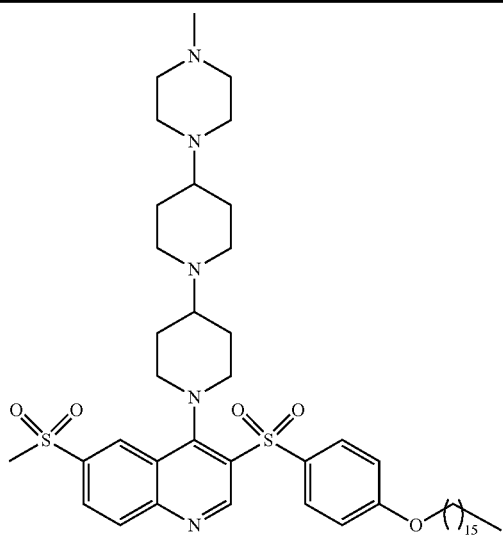 | 3-((4-(hexadecyloxy)phenyl)sulfonyl)-4-(4-(4-methylpiperazin-1-yl)-[1,4'-bipiperidin]-1'-yl)-6-(methylsulfonyl)quinoline |
| 499 | 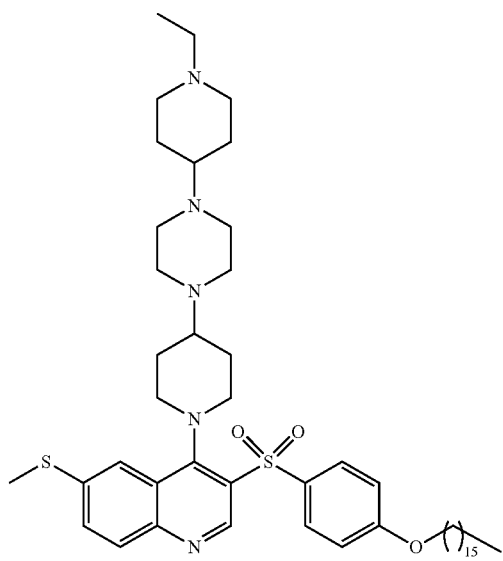 | 4-(4-(4-(1-ethylpiperidin-4-yl)piperazn-1-yl)piperidin-1-yl)-3-((4-(hexadecyloxy)phenyl)sulfonyl)-6-(methylthio)quinoline |
| 500 | 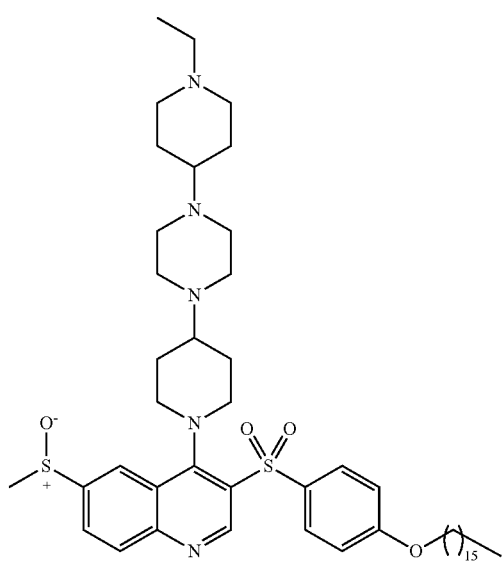 | 4-(4-(4-(1-ethylpiperidin-4-yl)piperazin-1-yl)piperidin-1-yl)-3-((4-(hexadecyloxy)phenyl)sulfonyl)-6-(methylsulfinyl)quinoline |

| | | |
|---|---|---|
| 501 | 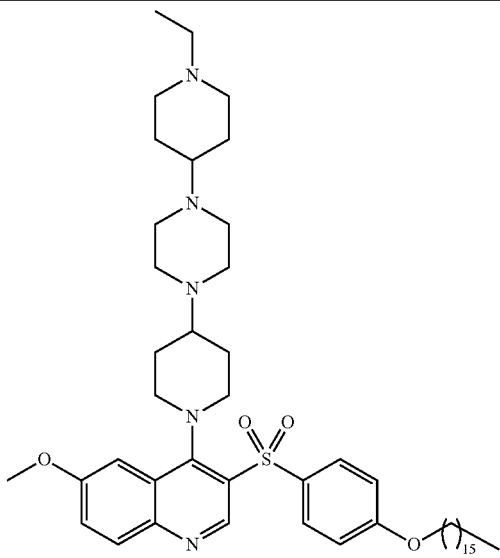 | 4-(4-(4-(1-ethylpiperidin-4-yl)piperazin-1-yl)piperidin-1-yl)-3-((4-(hexadecyloxy)phenyl)sulfonyl)-6-methoxyquinoline |
| 502 | 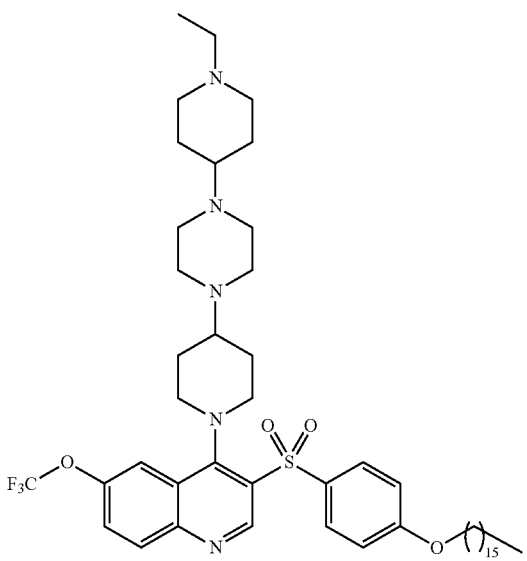 | 4-(4-(4-(1-ethylpiperidin-4-yl)piperazin-1-yl)piperidin-1-yl)-3-((4-(hexadecyloxy)phenyl)sulfonyl)-6-(trifluoromethoxy)quinoline |
| 503 | 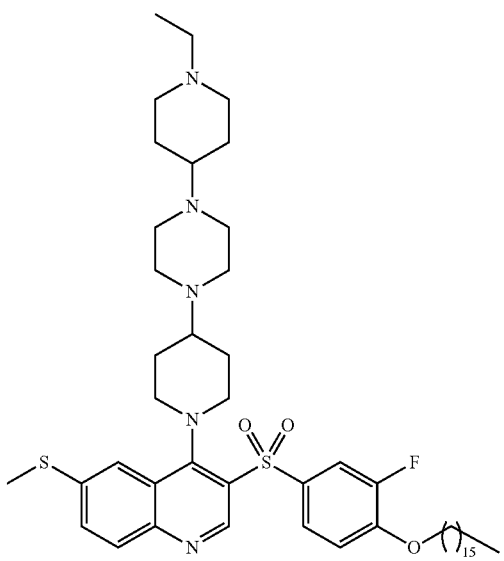 | 4-(4-(4-(1-ethylolneridin-4-yl)piperazin-1-yl)piperidin-1-yl)-3-((3-fluoro-4-(hexadecyloxy)phenyl)sulfonyl)-6-(methylthio)quinoline |

| | | |
|---|---|---|
| 504 | 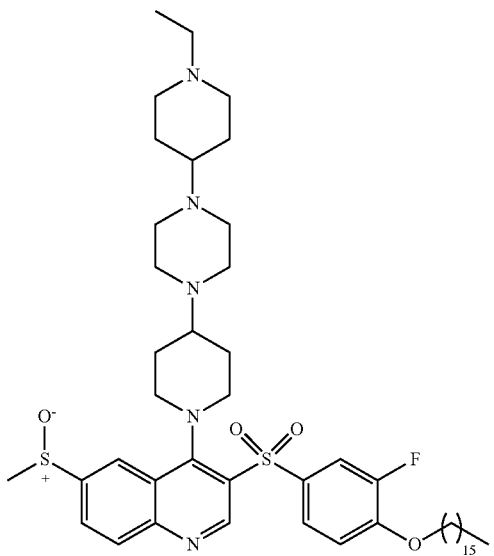 | 4-(4-(4-(1-ethylpiperidin-4-yl)piperazin-1-yl)piperidin-1-yl)-3-((3-fluoro-4-(hexadecyloxy)phenyl)sulfonyl)-6-(methylsulfinyl)quinoline |
| 505 | 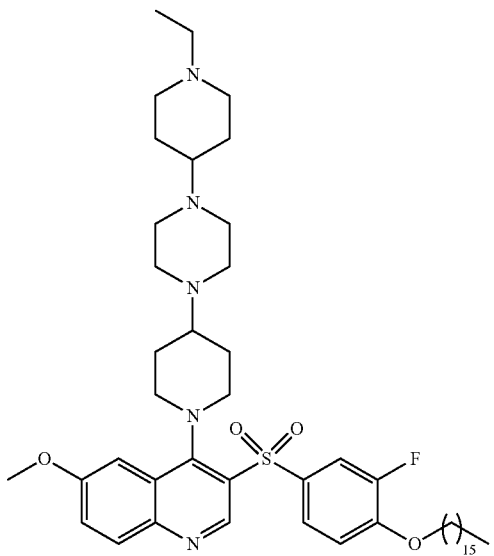 | 4-(4-(4-(1-ethylpiperidin-4-yl)piperazin-1-yl)piperidin-1-yl)-3-((3-fluoro-4-(hexadecyloxy)phenyl)sulfonyl)-6-methoxyquinoline |

-continued
| | | |
|---|---|---|
| 506 | 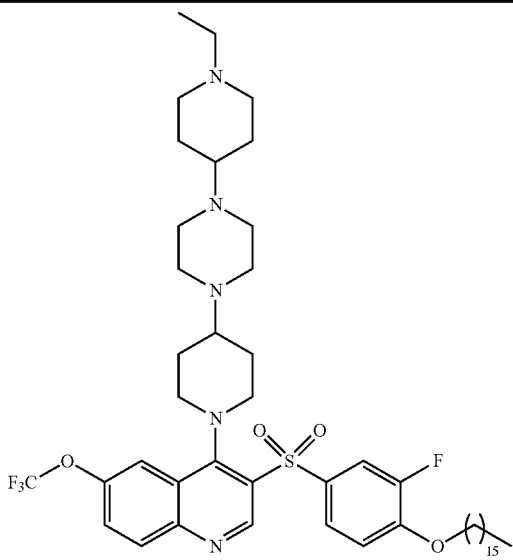 | 4-(4-(4-(1-ethylpiperidin-4-yl)piperazin-1-yl)piperidin-1-yl)-3-((3-fluoro-4-(hexadecyloxy)phenyl)sulfonyl)-6-(trifluoromethoxy)quinoline |
| 507 | 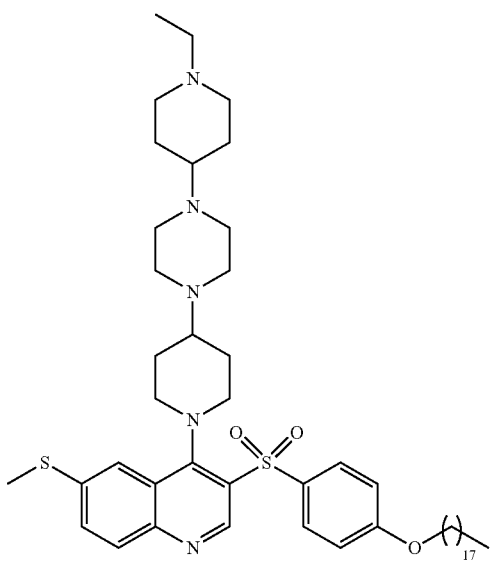 | 4-(4-(4-(1-ethylpiperidin-4-yl)piperazin-1-yl)piperidin-1-yl)-6-(methylthio)-3-((4-(octadecyloxy)phenyl)sulfonyl)quinoline |
| 508 | 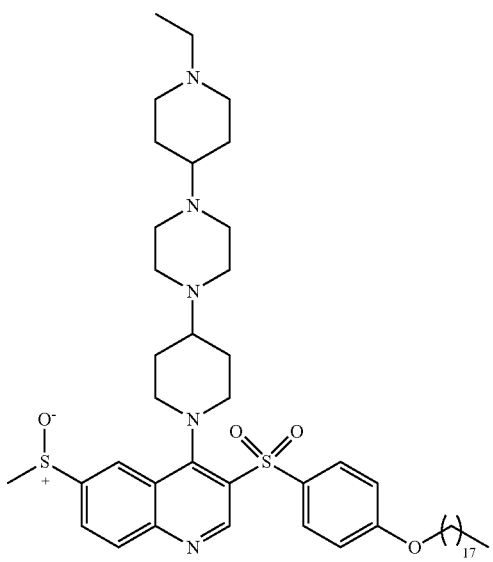 | 4-(4-(4-(1-ethylpiperidin-4-yl)piperazin-1-yl)piperidin-1-yl)-6-(methylsulfinyl)-3-((4-(octadecyloxy)phenyl)sulfonyl)quinoline |

-continued
| | | |
|---|---|---|
| 509 | 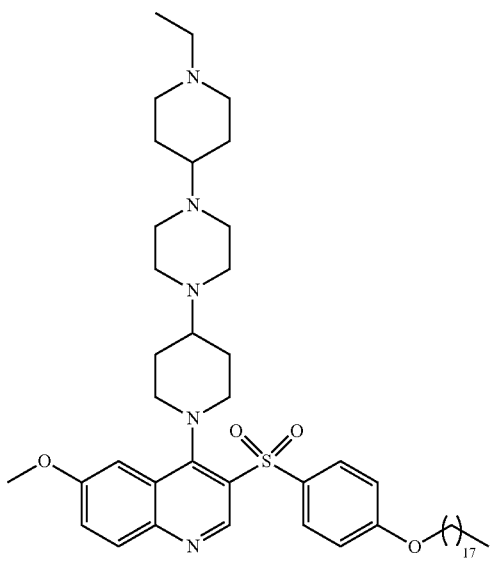 | 4-(4-(4-(1-ethylolneridin-4-yl)piperazin-1-yl)piperidin-1-yl)-6-methoxy-3-((4-(octadecyloxy)phenyl)sulfonyl)quinoline |
| 510 | 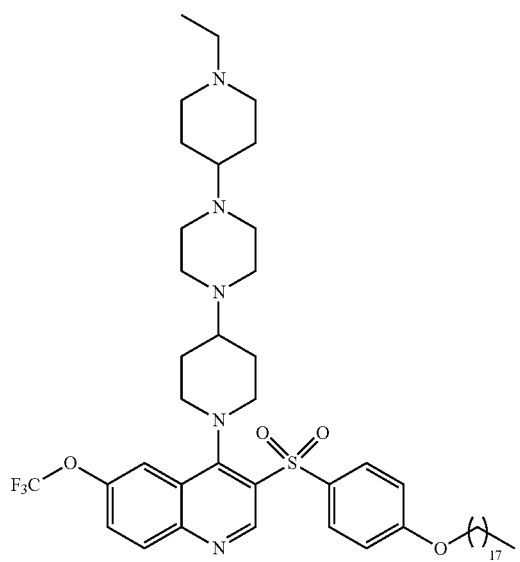 | 4-(4-(4-(1-ethylpiperidin-4-yl)piperazin-1-yl)piperidin-1-yl)-3-((4-(octadecyloxy)phenyl)sulfonyl)-6-(trifluoromethoxy)quinoline |

-continued
| | | |
|---|---|---|
| 511 | 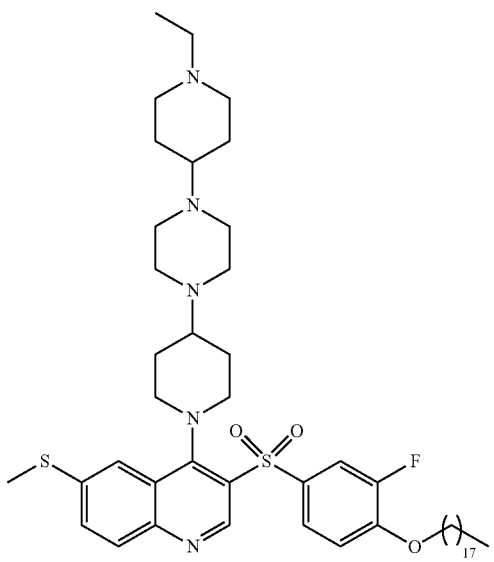 | 4-(4-(4-(1-ethylpiperidin-4-yl)piperazin-1-yl)piperidin-1-yl)-3-((3-fluoro-4-(octadecyloxy)phenyl)sulfonyl)-6-methylthio)quinoline |
| 512 | 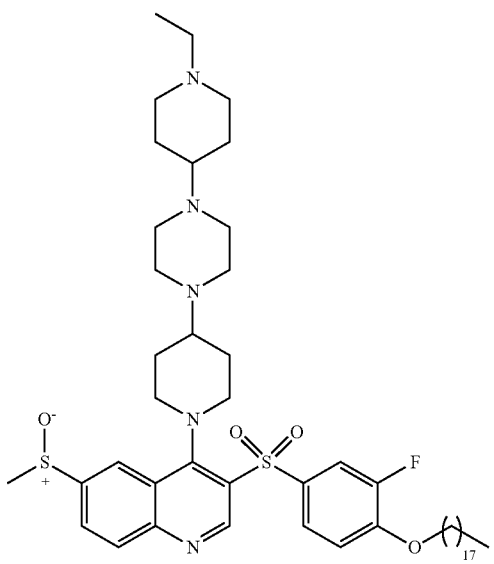 | 4-(4-(4-(1-ethylolneridin-4-yl)piperazin-1-yl)piperidin-1-yl)-3-((3-fluoro-4-(octadecyloxy)phenyl)sulfonyl)-6-(methylsulfinyl)quinoline |

-continued
| | | |
|---|---|---|
| 513 | 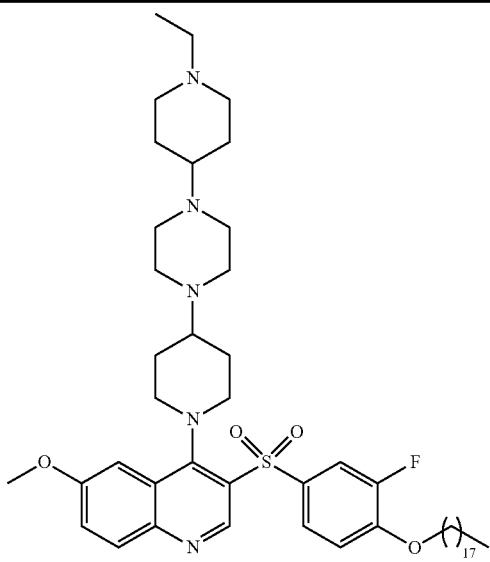 | 4-(4-(4-(1-ethylpiperidin-4-yl)piperazin-1-yl)piperidin-1-yl)-3-((3-fluoro-4-(octadecyloxy)phenyl)sulfonyl)-6-methoxyquinoline |
| 514 | 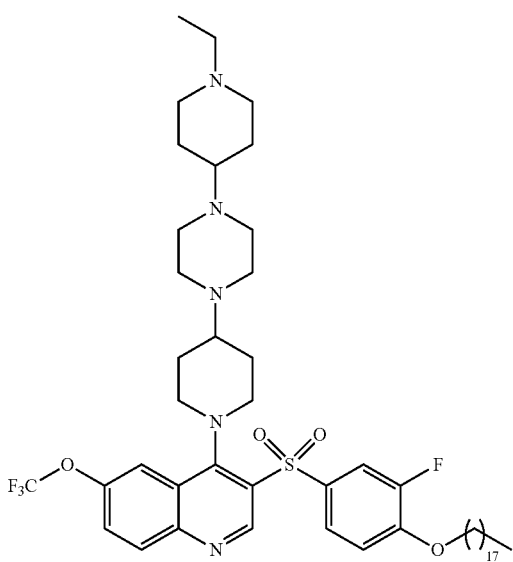 | 4-(4-(4-(1-ethylpiperidin-4-yl)piperazin-1-yl)piperidin-1-yl)-3-((3-fluoro-4-(octadecyloxy)phenyl)sulfonyl)-6-methoxyquinoline |
| 515 | 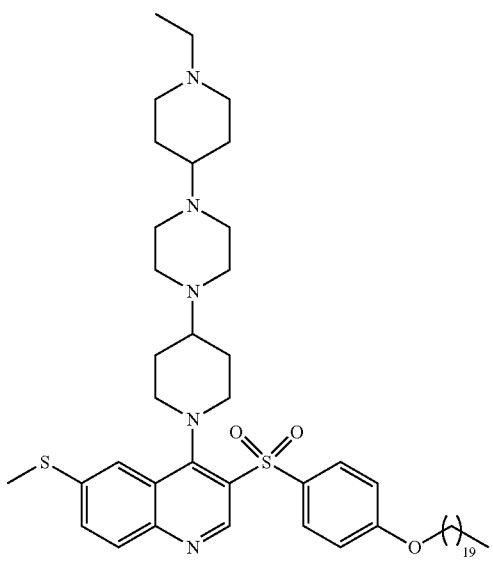 | 4-(4-(4-(1-ethylpiperidin-4-yl)piperazin-1-yl)piperidin-1-yl)-3-((4-(icosyloxy)phenyl)sulfonyl)-6-(methylthio)quinoline |

| | | |
|---|---|---|
| 516 | 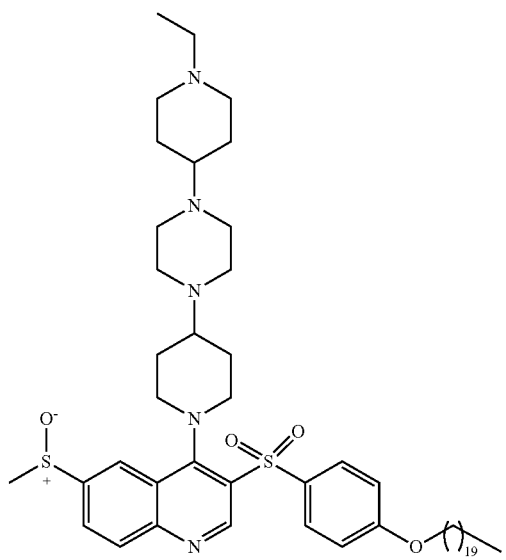 | 4-(4-(4-(1-ethylpiperidin-4-yl)piperazin-1-yl)piperidin-1-yl)-3-((4-(icosyloxy)phenyl)sulfonyl)-6-(methylsulfiny)quinoline |
| 517 | 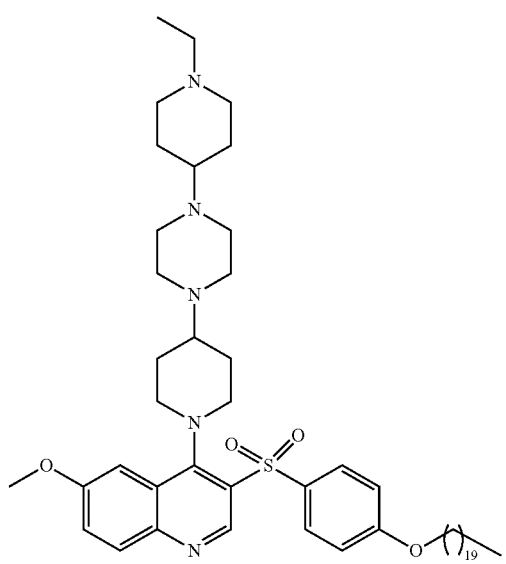 | 4-(4-(4-(1-ethylpiperidin-4-yl)piperazin-1-yl)piperidin-1-yl)-3-((4-(icosyloxy)phenyl)sulfonyl)-6-methoxyquinoline |

-continued
| | | |
|---|---|---|
| 518 | 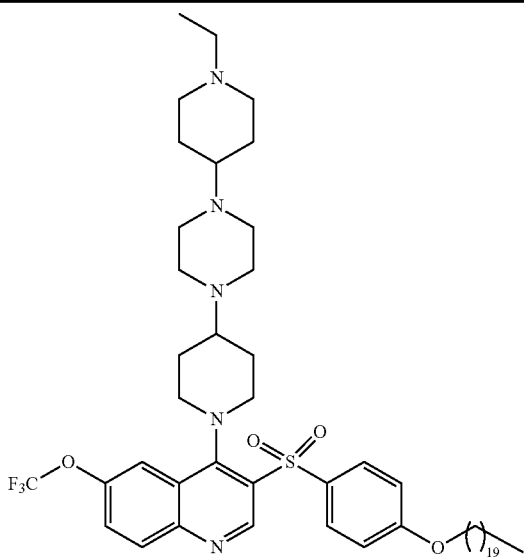 | 4-(4-(4-(1-ethylpiperidin-4-yl)piperazin-1-yl)piperidin-1-yl)-3-((4-(icosyloxy)phenyl)sulfonyl)-6-(trifluoromethoxy)quinoline |
| 519 | 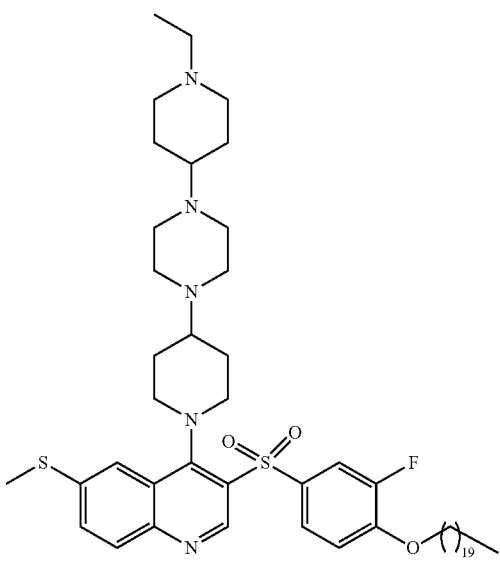 | 4-(4-(4-(1-ethylpiperidin-4-yl)piperazin-1-yl)piperidin-1-yl)-3-((3-fluoro-4-(icosyloxy)phenyl)sulfonyl)-6-(methylthio)quinoline |
| 520 | 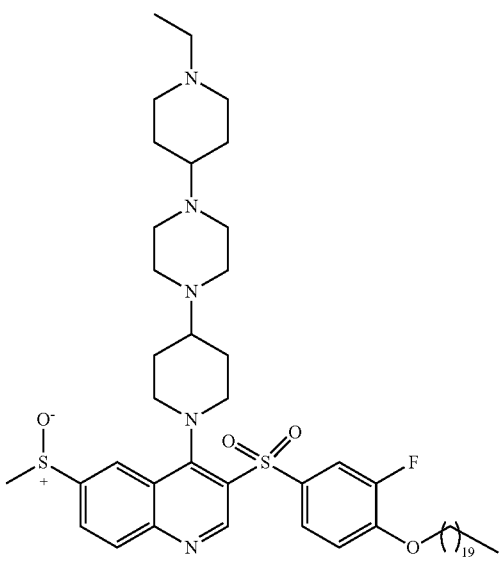 | 4-(4-(4-(1-ethylpiperidin-4-yl)piperazin-1-yl)piperidin-1-yl)-3-((3-fluoro-4-(icosyloxy)phenyl)sulfonyl)-6-(methylsulfinyl)quinoline |

| 521 | 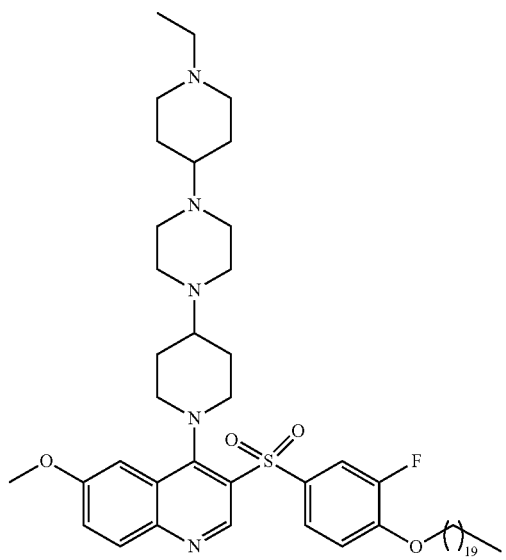 | 4-(4-(4-(1-ethylolneridin-4-yl)piperazin-1-yl)piperidin-1-yl)-3-((3-fluoro-4-(icosyloxy)phenyl)sulfonyl)-6-methoxyquinoline |
| 522 | 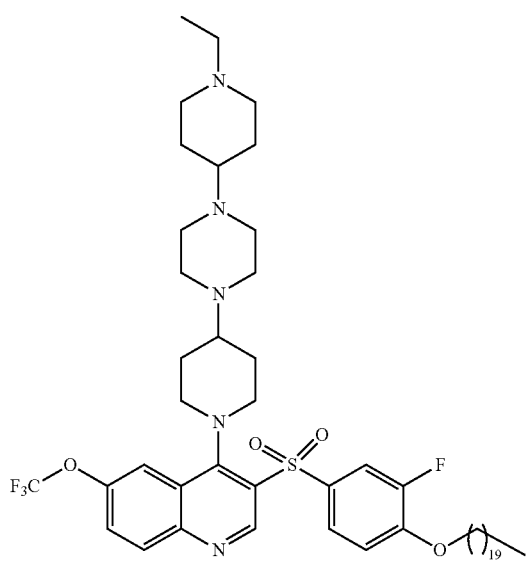 | 4-(4-(4-(I-ethylpiperidin-4-yl)piperazin-1-yl)piperidin-1-yl)-3-((3-fluoro-4-(icosyloxy)phenyl)sulfonyl)-6-(trifluoromethoxy)quinoline |

| | | |
|---|---|---|
| 523 | 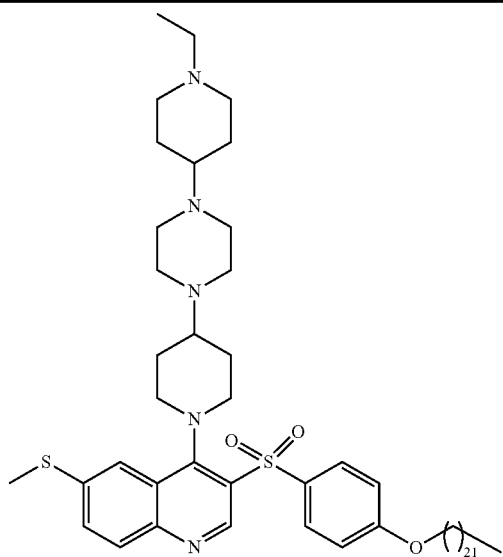 | 3-((4-(docosyloxy)phenyl)sulfonyl)-4-(4-(4-(1-ethylpiperidin-4-yl)piperazin-1-yl)piperidin-1-yl)-6-(methylthio)quinoline |
| 524 | 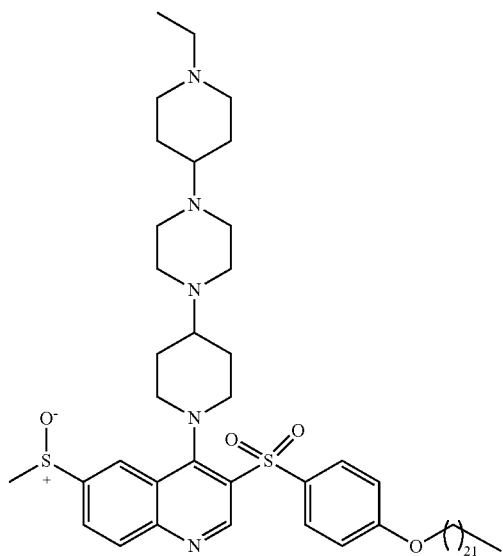 | 3-((4-(docosyloxy)phenyl)sulfonyl)-4-(4-(4-(1-ethylpiperidin-4-yl)piperazin-1-yl)piperidin-1-yl)-6-(methylsulfonyl)quinoline |
| 525 | 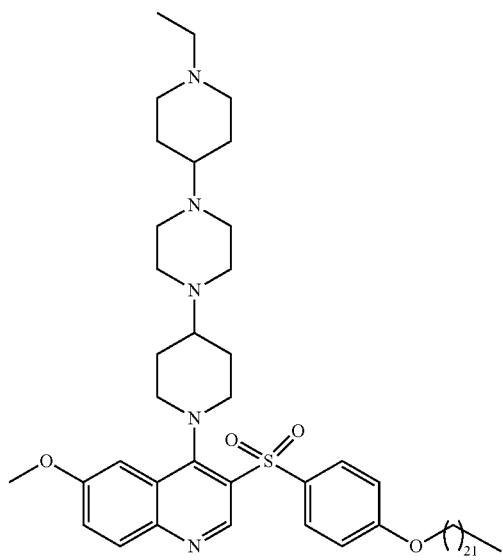 | 3-((4-(docosyloxy)phenyl)sulfonyl-4-(4-(4-(1-ethylpiperidin-4-yl)piperazin-1-yl)piperidin-1-yl)-6-methoxyquinoline |

526 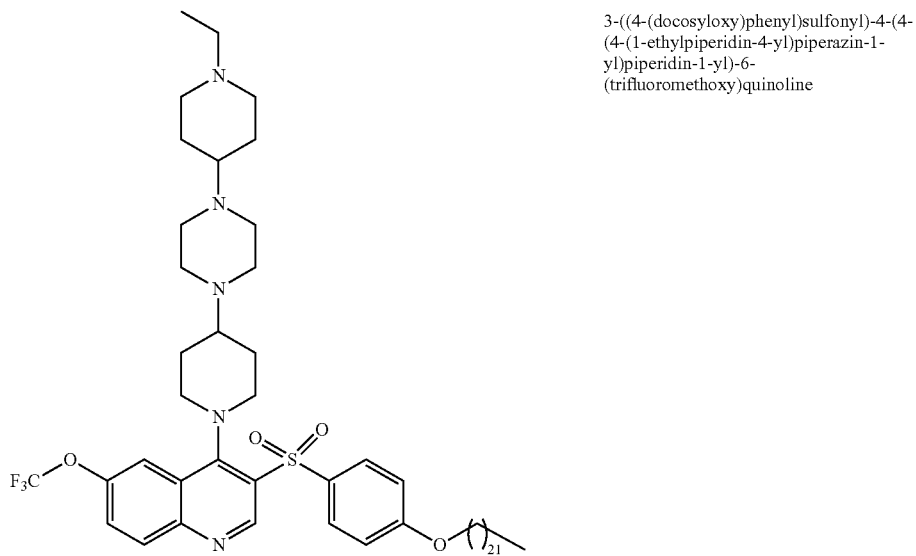 3-((4-(docosyloxy)phenyl)sulfonyl)-4-(4-(4-(1-ethylpiperidin-4-yl)piperazin-1-yl)piperidin-1-yl)-6-(trifluoromethoxy)quinoline
527 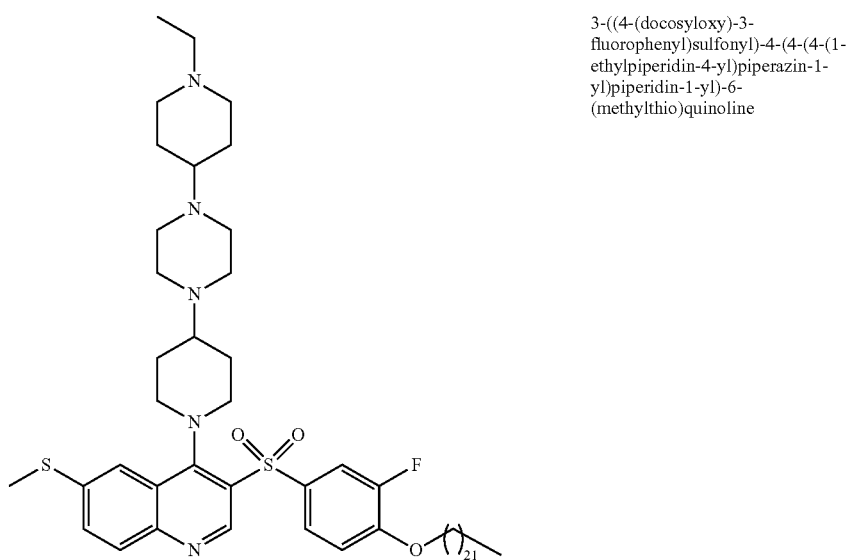 3-((4-(docosyloxy)-3-fluorophenyl)sulfonyl)-4-(4-(4-(1-ethylpiperidin-4-yl)piperazin-1-yl)piperidin-1-yl)-6-(methylthio)quinoline

| | | |
|---|---|---|
| 528 | 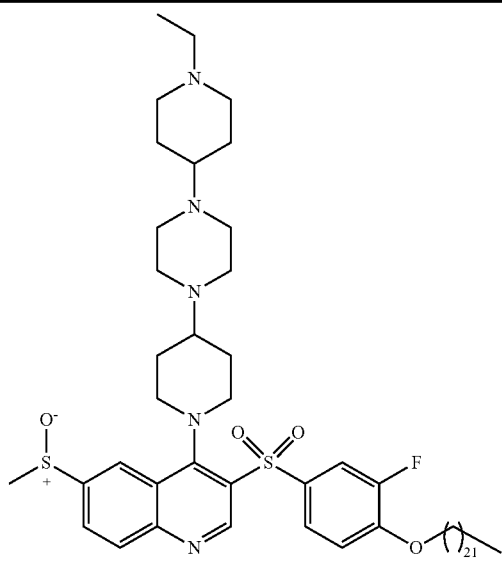 | 3-((4-(docosyloxy)-3-fluorophenyl)sulfonyl-4-(4-(4-(1-ethylpiperidin-4-yl)piperazin-1-yl)piperidin-1-yl)-6-(methylsulfinyl)quinoline |
| 529 | 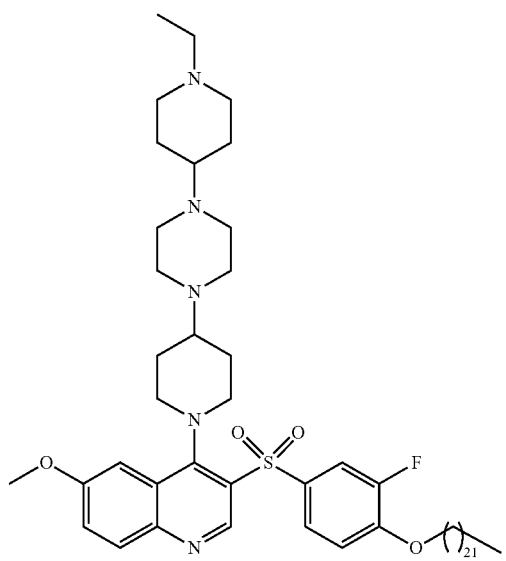 | 3-((4-(docosyloxy)-3-fluorophenyl)sulfonyl-4-(4-(4-(1-ethylpiperidin-4-yl)piperazin-1-yl)piperidin-1-yl)-6-methoxyquinoline |
| 530 | 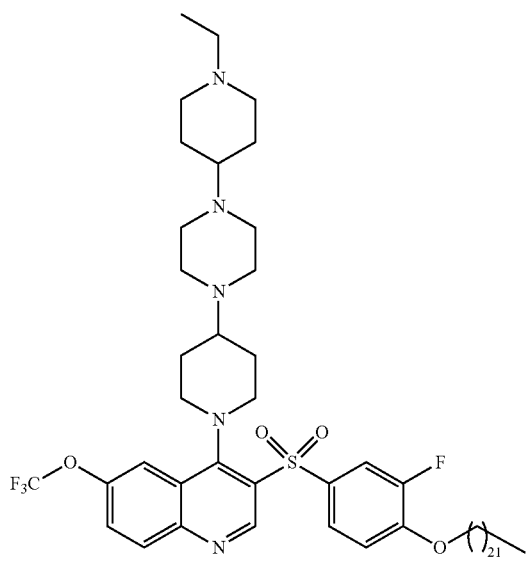 | 3-((4-(docosyloxy)-3-fluorophenyl)sulfonyl)-4-(4-(4-(1-ethylpiperidin-4-yl)piperazin-1-yl)piperidin-1-yl)-6-(trifluoromethoxy)quinoline |

| | | |
|---|---|---|
| 531 | 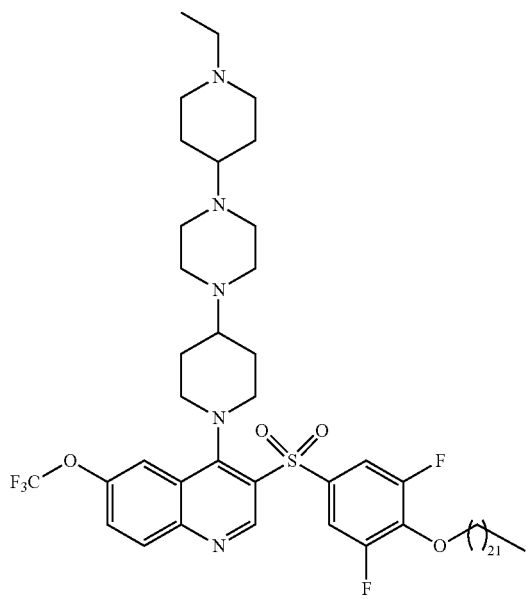 | 3-((4-(docosyloxy)-3,5-difluorophenyl)sulfonyl)-4-(4-(4-(1-ethylpiperidin-4-yl)piperazin-1-yl)piperidin-1-yl)-6-(trifluoromethoxy)quinoline |
| 532 | 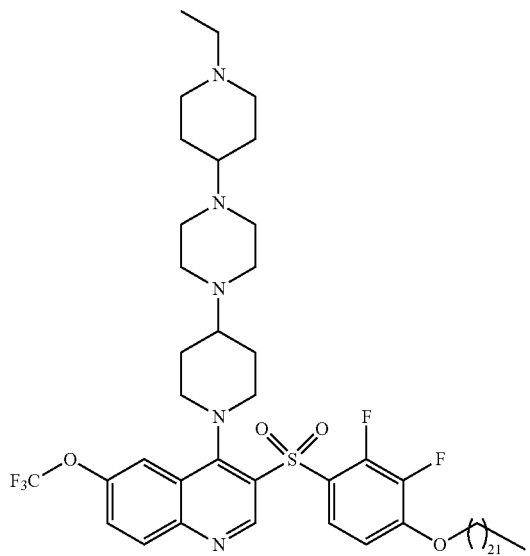 | 3-((4-(docosyloxy)-2,3-difluorophenyl)sulfonyl)-4-(4-(4-(1-ethylpiperidin-4-yl)piperazin-1-yl)piperidin-1-yl)-6-(trifluoromethoxy)quinoline |

| | | |
|---|---|---|
| 533 | 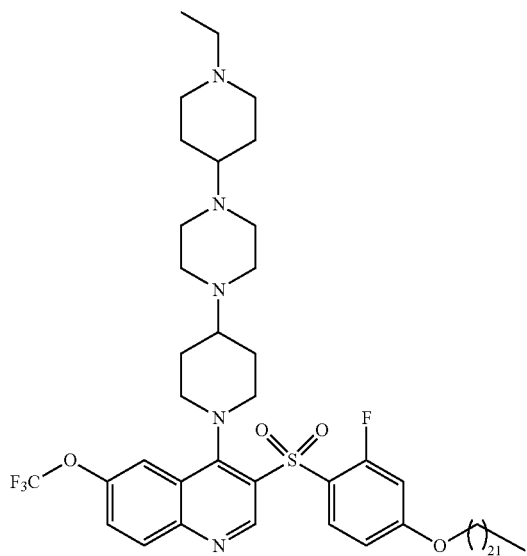 | 3-((4-(docosyloxy)-2-fluorophenyl)sulfonyl)-4-(4-(4-(1-ethylpiperidin-4-yl)piperazin-1-yl)piperidin-1-yl)-6-(trifluoromethoxy)quinoline |
| 534 | 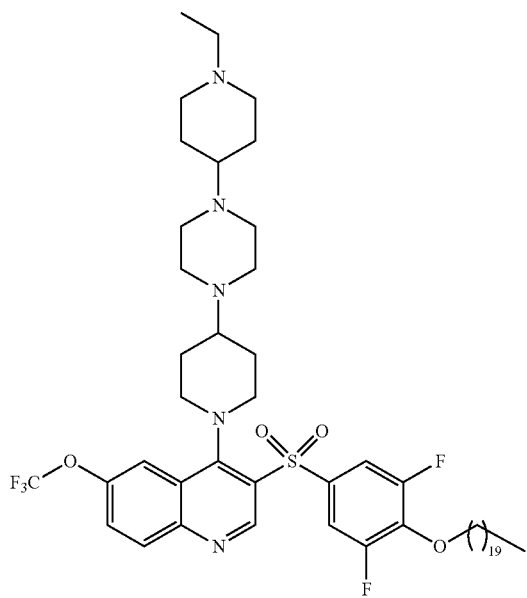 | 3-((3,5-difluoro-4-(icosyloxy)phenyl)sulfonyl)-4-(4-(4-(1-ethylpiperidin-4-yl)piperazin-1-yl)piperidin-1-yl)-6-(trifluoromethoxy)quinoline |

| | | |
|---|---|---|
| 535 | 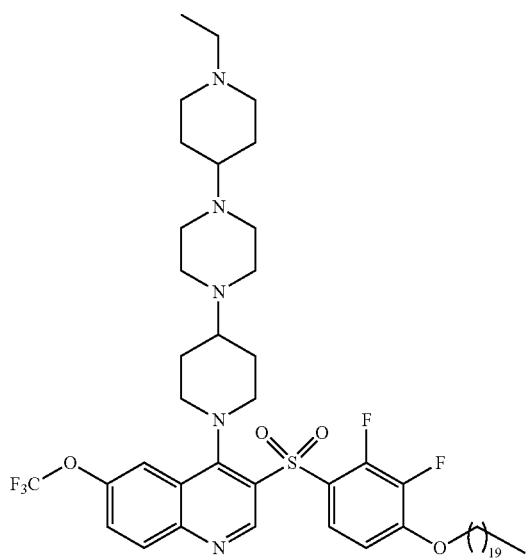 | 3-((2,3-difluoro-4-(icosyloxy)phenyl)sulfonyl)-4-(4-(4-(1-ethylpiperidin-4-yl)piperazin-1-yl)piperidin-1-yl)-6-(trifluoromethoxy)quinoline |
| 536 | 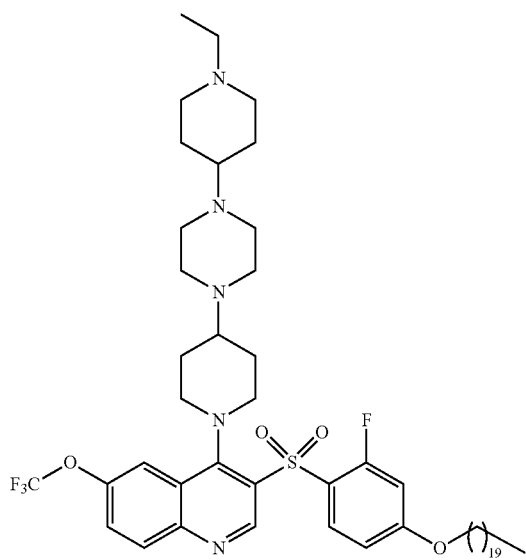 | 4-(4-(4-(1-ethylpiperidin-4-yl)piperazin-1-yl)piperidin-1-yl)-3-((2-fluoro-4-(icosyloxy)phenyl)sulfonyl)-6-(trifluoromethoxy)quinoline |

| | | |
|---|---|---|
| 537 | 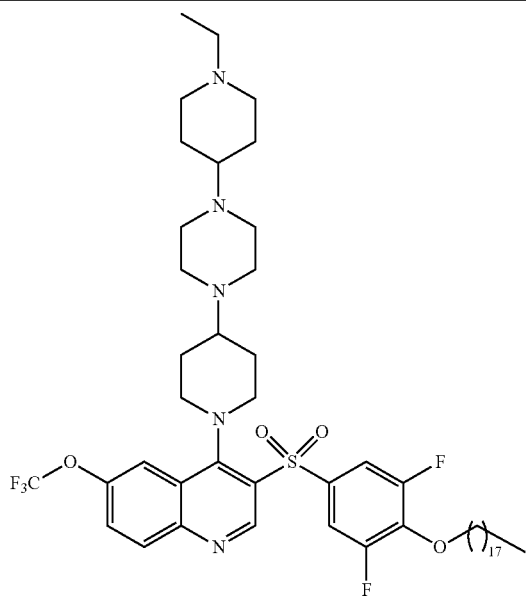 | 3-((3,5-difluoro-4-(octadecyloxy)phenyl)sulfonyl)-4-(4-(4-(1-ethylpiperidin-4-yl)piperazin-1-yl)piperidin-1-yl)-6-(trifluoromethoxy)quinoline |
| 538 | 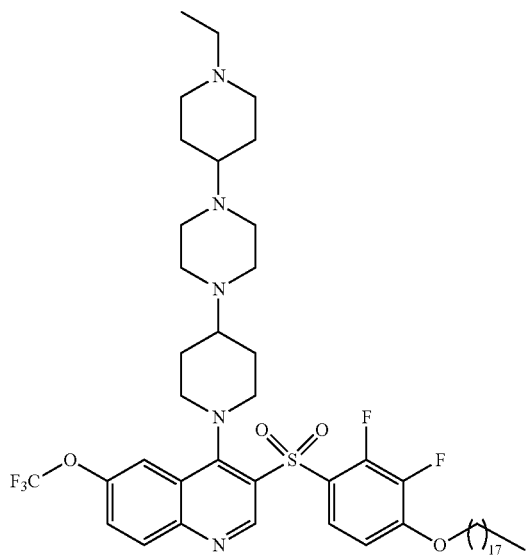 | 3-((2,3-difluoro-4-(octadecyloxy)phenyl)sulfonyl)-4-(4-(4-(1-ethylpiperidin-4-yl)piperazin-1-yl)piperidin-1-yl)-6-(trifluoromethoxy)quinoline |

-continued
| | | |
|---|---|---|
| 539 | 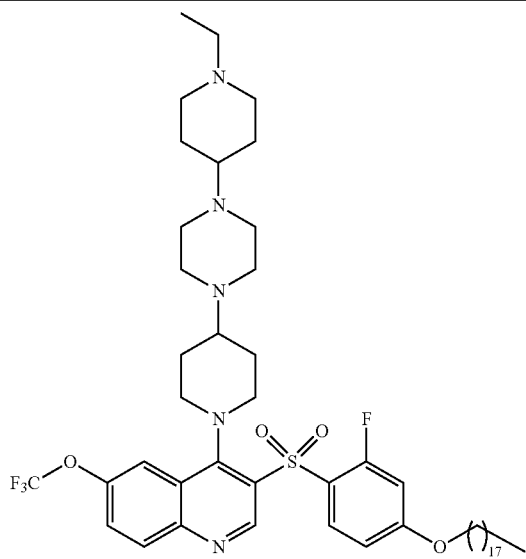 | 4-(4-(4-(1-ethylpiperidin-4-yl)piperazin-1-yl)piperidin-1-yl)-3-((2-fluoro-4-(octadecyloxy)phenyl)sulfonyl)-6-(trifluoromethoxy)quinoline |
| 540 | 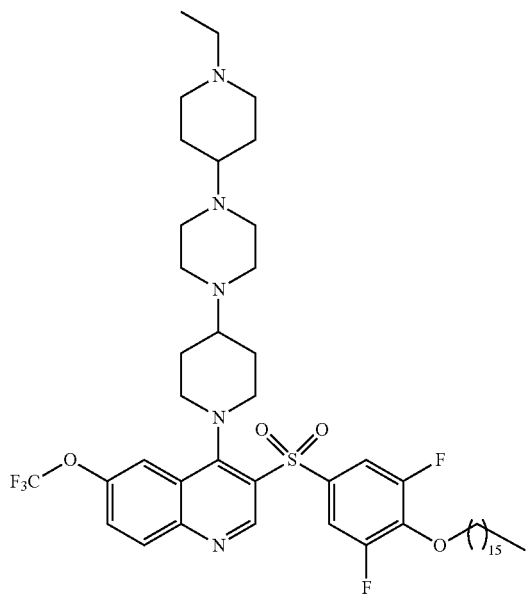 | 3-((3,5-difluoro-4-(hexadecyloxy)phenyl)sulfonyl)-4-(4-(4-(1-ethylpiperidin-4-yl)piperazin-1-yl)piperidin-1-yl)-6-(trifluoromethoxy)quinoline |

-continued
| | | |
|---|---|---|
| 541 | 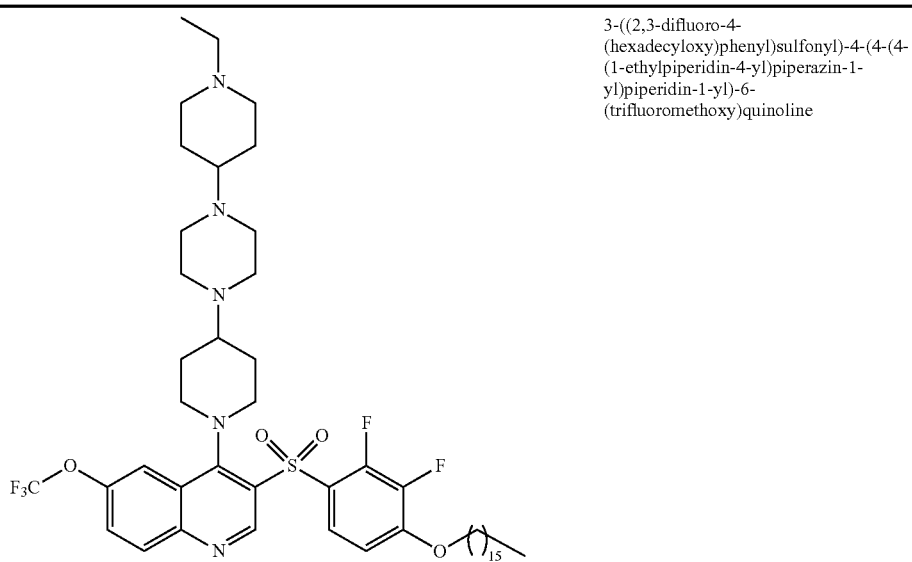 | 3-((2,3-difluoro-4-(hexadecyloxy)phenyl)sulfonyl)-4-(4-(4-(1-ethylpiperidin-4-yl)piperazin-1-yl)piperidin-1-yl)-6-(trifluoromethoxy)quinoline |
| 542 | 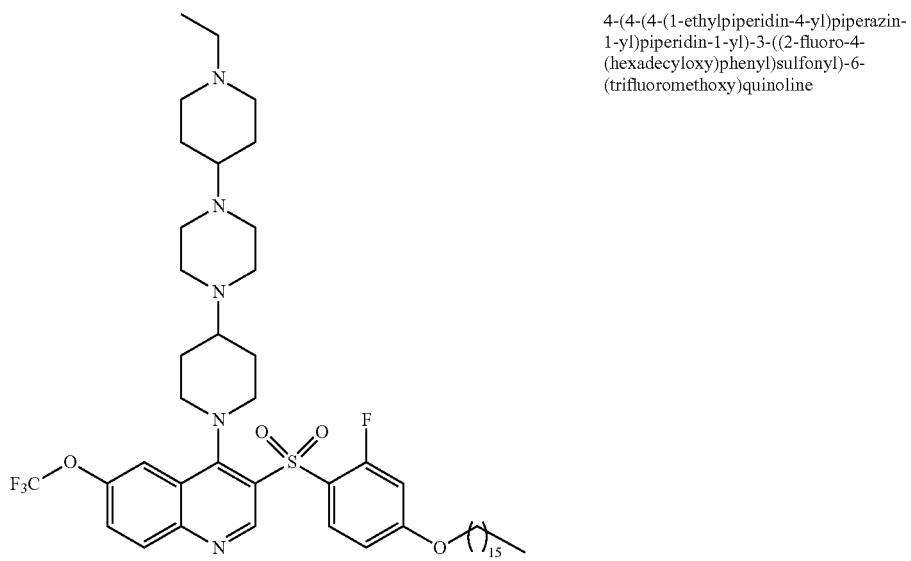 | 4-(4-(4-(1-ethylpiperidin-4-yl)piperazin-1-yl)piperidin-1-yl)-3-((2-fluoro-4-(hexadecyloxy)phenyl)sulfonyl)-6-(trifluoromethoxy)quinoline |
| 543 | 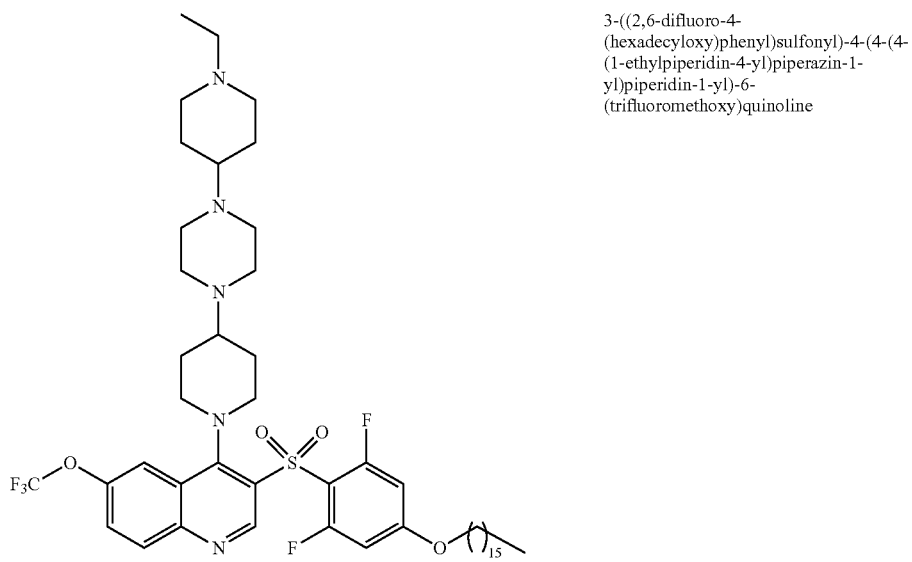 | 3-((2,6-difluoro-4-(hexadecyloxy)phenyl)sulfonyl)-4-(4-(4-(1-ethylpiperidin-4-yl)piperazin-1-yl)piperidin-1-yl)-6-(trifluoromethoxy)quinoline |

-continued
544 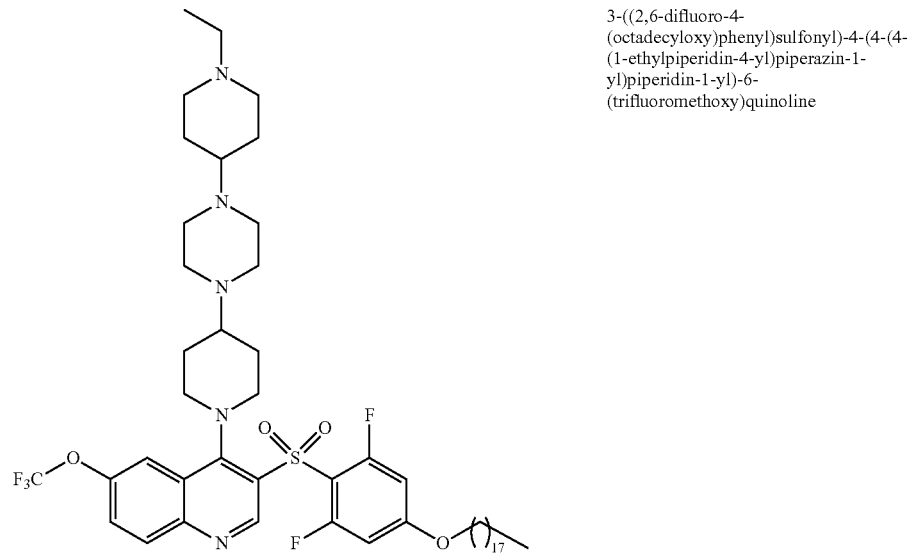 3-((2,6-difluoro-4-(octadecyloxy)phenyl)sulfonyl)-4-(4-(4-(1-ethylpiperidin-4-yl)piperazin-1-yl)piperidin-1-yl)-6-(trifluoromethoxy)quinoline
545 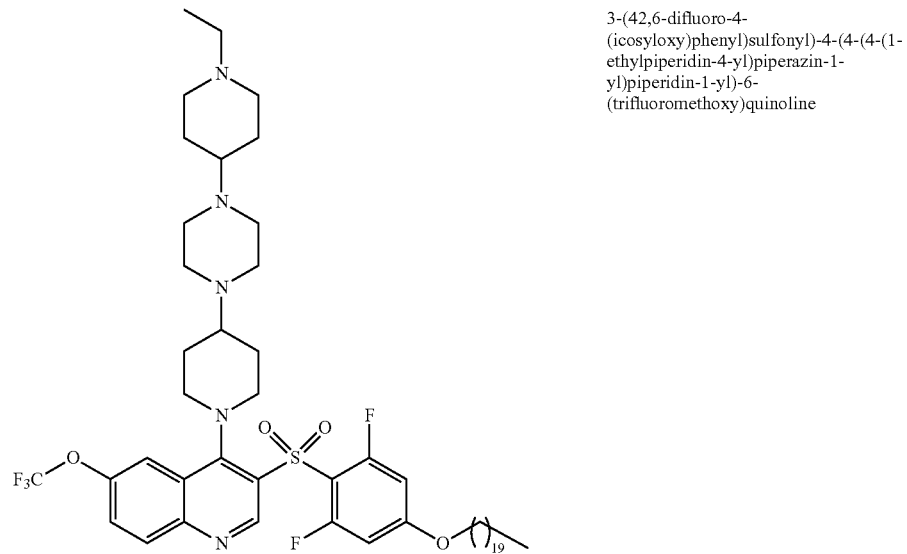 3-(42,6-difluoro-4-(icosyloxy)phenyl)sulfonyl)-4-(4-(4-(1-ethylpiperidin-4-yl)piperazin-1-yl)piperidin-1-yl)-6-(trifluoromethoxy)quinoline -continued
| | | |
|---|---|---|
| 546 | 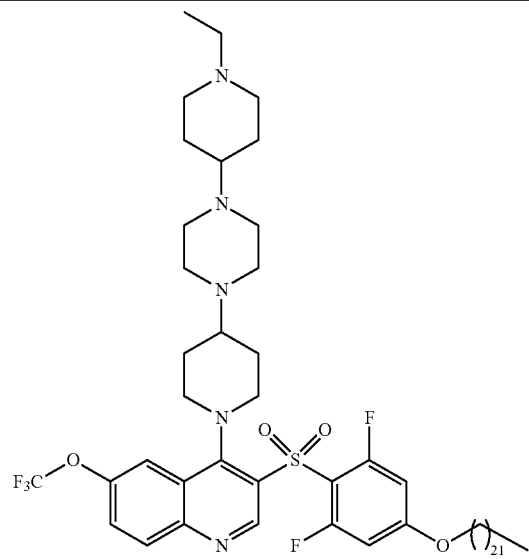 | 3-((4-(docosyloxy)-2,6-difluorophenyl)sulfonyl)-4-(4-(4-(1-ethylpiperidin-4-yl)piperazin-1-yl)piperidin-1-yl)-6-(trifluoromethoxy)quinoline |
| 547 | 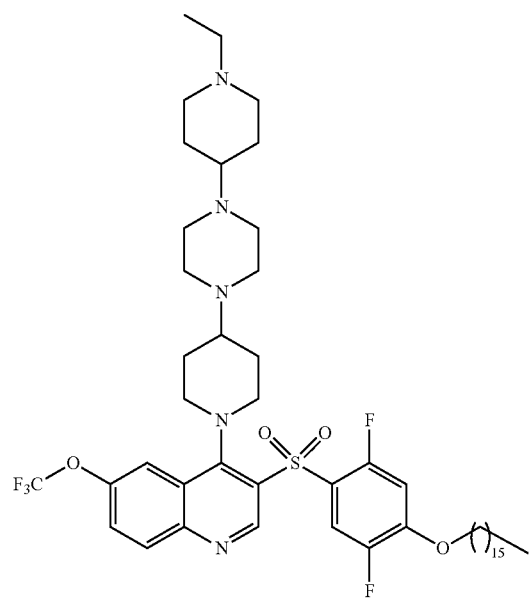 | 3-((2,5-difluoro-4-(hexadecyloxy)phenyl)sulfonyl)-4-(4-(4-(1-ethylpiperidin-4-yl)piperazin-1-yl)piperidin-1-yl)-6-(trifluoromethoxy)quinoline |

-continued
| 548 | 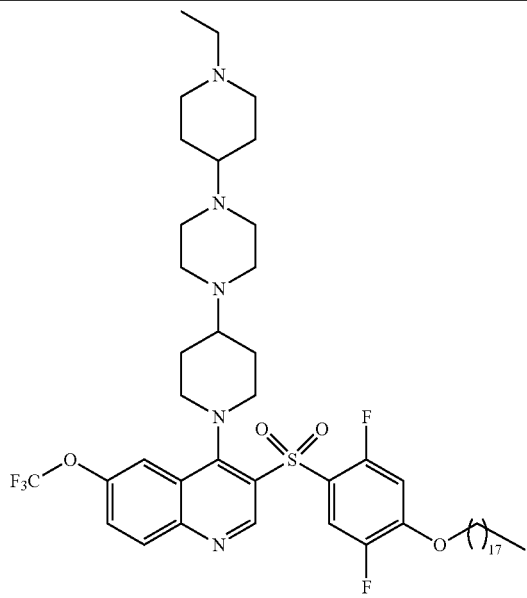 | 3-((2,5-difluoro-4-(octadecyloxy)phenyl)sulfonyl)-4-(4-(4-(1-ethylpiperidin-4-yl)piperazin-1-yl)piperidin-1-yl)-6-(trifluoromethoxy)quinoline |
| --- | --- | --- |
| 549 | 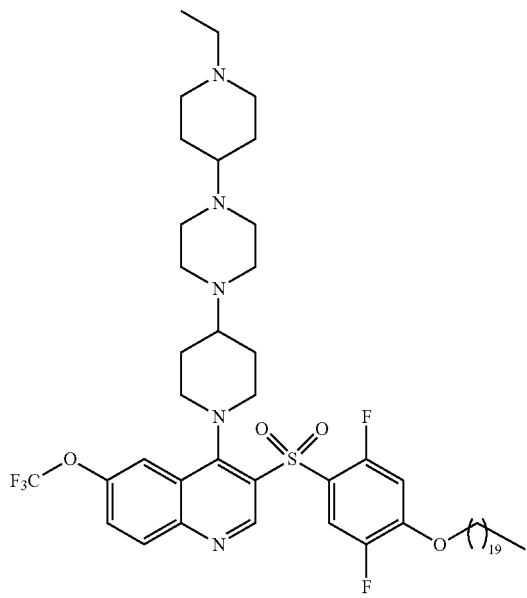 | 3-((2,5-difluoro-4-(icosyloxy)phenyl)sulfonyl-4-(4-(4-(1-ethylpiperidin-4-yl)piperazin-1-yl)piperidin-1-yl)-6-(trifluoromethoxy)quinoline and |

-continued

550

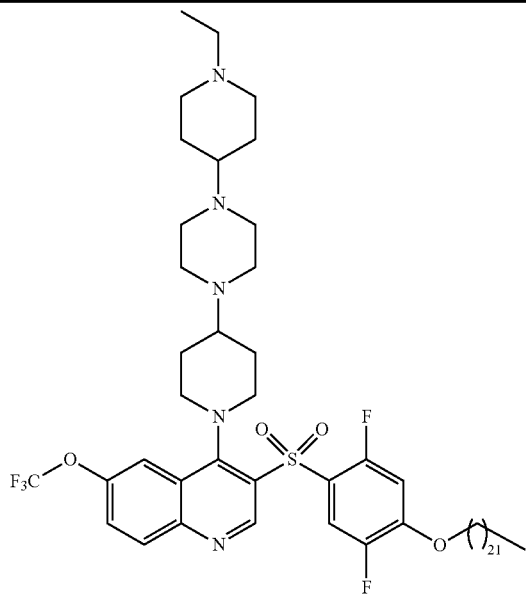

3-((4-(docosyloxy)-2,5-difluorophenyl)sulfonyl)-4-(4-(4-(1-ethylpiperidin-4-yl)piperazin-1-yl)piperidin-1-yl)-6-(trifluoromethoxy)quinoline or a pharmaceutically acceptable salt, isotopically enriched analog, stereoisomer, mixture of stereoisomers, or tautomer thereof.

29. A pharmaceutical composition comprising a compound of claim 1 or a pharmaceutically acceptable salt, isotopically enriched analog, stereoisomer, mixture of stereoisomers, or tautomer thereof.

* * * * *